US011478451B1

(12) United States Patent
Thede et al.

(10) Patent No.: US 11,478,451 B1
(45) Date of Patent: Oct. 25, 2022

(54) MACROCYCLIC CHLORINE SUBSTITUTED INDOLE DERIVATIVES

(71) Applicants: Bayer Aktiengesellschaft, Leverkusen (DE); Bayer Pharma Aktiengesellschaft, Berlin (DE); The Broad Institute, Inc., Cambridge, MA (US)

(72) Inventors: Kai Thede, Leverkusen (DE); Anne Mengel, Leverkusen (DE); Clara Christ, Leverkusen (DE); Joachim Kuhnke, Leverkusen (DE); Sarah Anna Liesa Johannes, Leverkusen (DE); Philipp Buchgraber, Leverkusen (DE); Ulrich Klar, Leverkusen (DE); Ulrike Rauh, Leverkusen (DE); Stefan Kaulfuss, Leverkusen (DE); Amaury Ernesto Fernandez-Montalvan, Leverkusen (DE); Nicolas Werbeck, Leverkusen (DE); Ursula Moenning, Leverkusen (DE); Katrin Nowak-Reppel, Leverkusen (DE); Chris Lemke, Cambridge, MA (US); Michael H. Serrano-Wu, Cambridge, MA (US); David McKinney, Cambridge, MA (US); Mark Fitzgerald, Cambridge, MA (US); Christopher Nasveschuk, Cambridge, MA (US); Kiel Lazarski, Cambridge, MA (US); Steven J. Ferrara, Cambridge, MA (US); Laura Furst, Cambridge, MA (US); Guo Wei, Cambridge, MA (US); Patrick R. McCarren, Cambridge, MA (US); Rebecca Ann Harvey, Lancashire (GB); Daniel Payne, Oldbury (GB); Thomas Pesnot, Macclesfield (GB); Craig Wilson, Buxton (GB)

(73) Assignees: Bayer Aktiengesellschaft, Leverkusen (DE); Bayer Pharma Aktiengesellschaft, Berlin (DE); The Broad Institute, Inc., Cambridge, MA (US)

( * ) Notice: Subject to any disclaimer, the term of this patent is extended or adjusted under 35 U.S.C. 154(b) by 80 days.

(21) Appl. No.: 16/764,565

(22) PCT Filed: Nov. 15, 2018

(86) PCT No.: PCT/EP2018/081370
§ 371 (c)(1),
(2) Date: May 15, 2020

(87) PCT Pub. No.: WO2019/096905
PCT Pub. Date: May 23, 2019

Related U.S. Application Data

(60) Provisional application No. 62/587,925, filed on Nov. 17, 2017.

(51) Int. Cl.
*A61K 31/4162* (2006.01)
*A61K 45/06* (2006.01)
(Continued)

(52) U.S. Cl.
CPC ........ *A61K 31/4162* (2013.01); *A61K 31/496* (2013.01); *A61K 31/5377* (2013.01);
(Continued)

(58) Field of Classification Search
CPC .............. A61K 31/4162; A61K 31/496; A61K 31/5377; A61K 45/06; A61P 35/00; C07D 487/18; C07D 498/18
See application file for complete search history.

(56) References Cited

U.S. PATENT DOCUMENTS 10,981,932 B2    4/2021   Johannes et al.
2015/0336925 A1  11/2015  Lee et al.
(Continued)

FOREIGN PATENT DOCUMENTS

WO    WO-2008/130970 A1    10/2008
WO    WO-2008/131000 A2    10/2008
(Continued)

OTHER PUBLICATIONS

Burke; J. Med. Chem. 2015, 58, 9, 3794-3805. doi: 10.1021/jm501984f (Year: 2015).*
(Continued)

*Primary Examiner* — Daniel R Carcanague
(74) *Attorney, Agent, or Firm* — Foley Hoag LLP; David P. Halstead

(57) ABSTRACT

The present invention relates to macrocyclic indole derivatives of general formula (I):

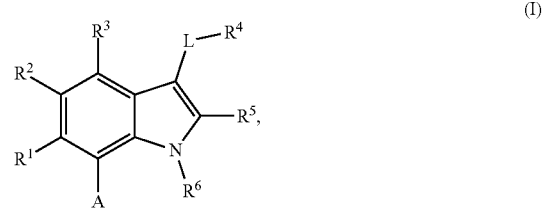

in which $R^1$, $R^2$, $R^3$, $R^4$, $R^5$, $R^6$, A and L are as defined herein, methods of preparing said compounds, intermediate compounds useful for preparing said compounds, pharmaceutical compositions and combinations comprising said compounds, and the use of said compounds for manufacturing pharmaceutical compositions for the treatment or prophylaxis of diseases, in particular of hyperproliferative disorders, as a sole agent or in combination with other active ingredients.

16 Claims, 1 Drawing Sheet
Specification includes a Sequence Listing.

(51) Int. Cl.
*A61P 35/00* (2006.01)
*A61K 31/496* (2006.01)
*C07D 487/18* (2006.01)
*A61K 31/5377* (2006.01)
*C07D 498/18* (2006.01)

(52) U.S. Cl.
CPC .............. *A61K 45/06* (2013.01); *A61P 35/00* (2018.01); *C07D 487/18* (2013.01); *C07D 498/18* (2013.01)

(56) References Cited

U.S. PATENT DOCUMENTS

| | | |
|---|---|---|
| 2016/0106731 A1 | 4/2016 | Lee et al. |
| 2017/0305926 A1 | 10/2017 | Hird et al. |
| 2020/0087322 A1 | 3/2020 | Johannes et al. |
| 2021/0079018 A1 | 3/2021 | Ferrara et al. |
| 2021/0253598 A1 | 8/2021 | Thede et al. |
| 2021/0269456 A1 | 9/2021 | Thede et al. |
| 2021/0277022 A1 | 9/2021 | Thede et al. |
| 2021/0292341 A1 | 9/2021 | Furst et al. |

FOREIGN PATENT DOCUMENTS

| | | |
|---|---|---|
| WO | WO-2014/047427 A2 | 3/2014 |
| WO | WO-2015/031608 A1 | 3/2015 |
| WO | WO-2015/148854 A1 | 10/2015 |
| WO | WO-2017/152076 A1 | 9/2017 |
| WO | WO-2017/182625 A1 | 10/2017 |
| WO | WO-2017/198341 A1 | 11/2017 |
| WO | WO-2018/098534 A1 | 6/2018 |
| WO | WO-2019/096905 A1 | 5/2019 |
| WO | WO-2019/096907 A1 | 5/2019 |
| WO | WO-2019/096909 A1 | 5/2019 |
| WO | WO-2019/096911 A1 | 5/2019 |
| WO | WO-2019/096914 A1 | 5/2019 |
| WO | WO-2019/096922 A1 | 5/2019 |
| WO | WO-2020/151738 A1 | 7/2020 |
| WO | WO-2020/236556 A1 | 11/2020 |

OTHER PUBLICATIONS

Lee; FEBS Letters 2017, 591, 240-251. doi:10.1002/1873-3468.12497 (Year: 2017).*
Zhao; Biochemistry 2018, 57, 32, 4952-4958. doi: 10.1021/acs.biochem.8b00626 (Year: 2018).*
Quinn; Expert Opinion on Investigational Drugs, 2011, 20, 1397-1411. DOI: 10.1517/13543784.2011.609167 (Year: 2011).*
Zhang et al., "Research progress of GSK-3 inhibitors," Progress in Chemistry, 19(4): 614-623 (2007).
Adams et al., "The Bcl-2 apoptotic switch in cancer development and therapy," Oncogene, 26:1324-1337 (2007).
Beroukhim et al., "The Landscape of Somatic Copy-Number Alteration Across Human Cancers," Nature, 463(7283):899-905 (2010).
Glaser et al., "Anti-apoptotic Mcl-1 is essential for the development and sustained growth of acute myeloid leukemia," Genes Dev, 26:120-125 (2012).
Hanahan et al., "Hallmarks of Cancer: The Next Generation," Cell 144(5):646-674 (2011).
International Preliminary Report on Patentability for International Application No. PCT/EP2017/000629 dated Nov. 20, 2018.
International Preliminary Report on Patentability for International Application No. PCT/EP2018/081370 dated May 19, 2020.
International Preliminary Report on Patentability for International Application No. PCT/EP2018/081374 dated May 19, 2020.
International Preliminary Report on Patentability for International Application No. PCT/EP2018/081378 dated May 19, 2020.
International Preliminary Report on Patentability for International Application No. PCT/EP2018/081381 dated May 19, 2020.
International Preliminary Report on Patentability for International Application No. PCT/EP2018/081388 dated May 19, 2020.
International Preliminary Report on Patentability for International Application No. PCT/EP2018/081406 dated May 19, 2020.
International Search Report and Written Opinion for International Application No. PCT/EP2017/000629 dated Sep. 6, 2017.
International Search Report and Written Opinion for International Application No. PCT/EP2018/081370 dated Feb. 13, 2019.
International Search Report and Written Opinion for International Application No. PCT/EP2018/081374 dated Feb. 13, 2019.
International Search Report and Written Opinion for International Application No. PCT/EP2018/081378 dated Jan. 9, 2019.
International Search Report and Written Opinion for International Application No. PCT/EP2018/081381 dated Jan. 15, 2019.
International Search Report and Written Opinion for International Application No. PCT/EP2018/081388 dated Feb. 14, 2019.
International Search Report and Written Opinion for International Application No. PCT/EP2018/081406 dated Feb. 11, 2019.
International Search Report and Written Opinion for International Application No. PCT/US2020/033067 dated Jul. 19, 2020.
Korsmeyer, "BCL-2 Gene Family and the Regulatio of Programmed Cell Death," Cancer Res Suppl, 59(7):1693s-1700s (1999).
Pelz et al., "Discovery of 2-Indole-acylsulfonamide Myeloid Cell Leukemia 1 (Mcl-1) Inhibitors Using Fragment-Based Methods," Journal of Medicinal Chemistry, 59(5):2054-2066 (2016).
Wertz et al., "Sensitivity to antitubulin chemotherapeutics is regulated by MCL1 and FBW7," Nature, 471:110-114 (2011).
Zhou et al., "MCL1 transgenic mice exhibit a high incidence of B-cell lymphoma manifested as a spectrum of histologic subtypes," Blood, 97(12):3902-3909 (2001).

* cited by examiner

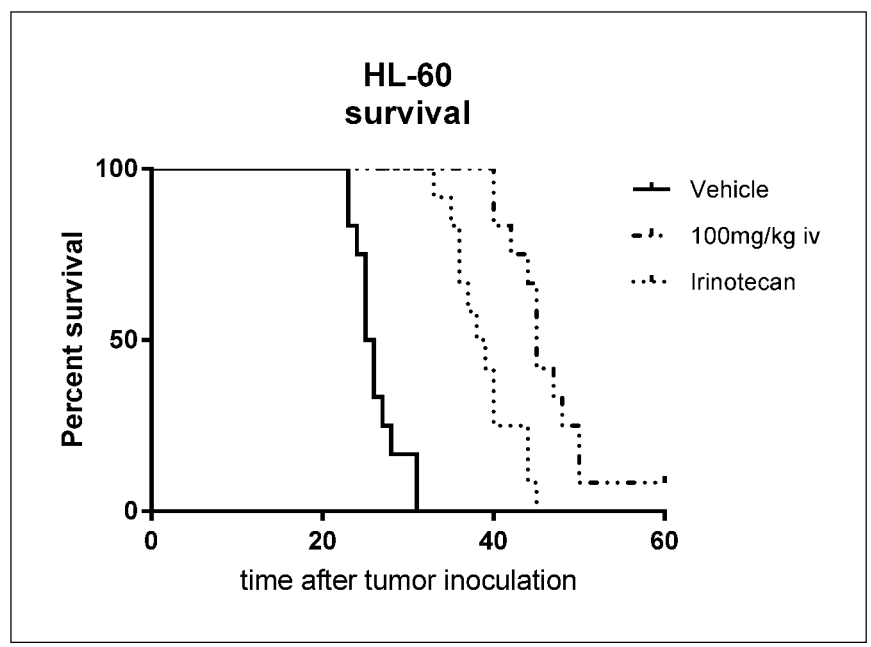

SEQUENCE LISTING

```
<160> NUMBER OF SEQ ID NOS: 5

<210> SEQ ID NO 1
<211> LENGTH: 519
<212> TYPE: PRT
<213> ORGANISM: Artificial Sequence
<220> FEATURE:
<223> OTHER INFORMATION: modified sequence

<400> SEQUENCE: 1

Gly Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110
```

```
Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
        210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Gly
        355                 360                 365

Ser Ser Glu Leu Tyr Arg Gln Ser Leu Glu Ile Ile Ser Arg Tyr Leu
370                 375                 380

Arg Glu Gln Ala Thr Gly Ala Ala Asp Thr Ala Pro Met Gly Ala Ser
385                 390                 395                 400

Gly Ala Thr Ser Arg Lys Ala Leu Glu Thr Leu Arg Arg Val Gly Asp
                405                 410                 415

Gly Val Gln Arg Asn His Glu Thr Ala Phe Gln Gly Met Leu Arg Lys
            420                 425                 430

Leu Asp Ile Lys Asn Glu Asp Val Lys Ser Leu Ser Arg Val Met
        435                 440                 445

Ile His Val Phe Ser Asp Gly Val Thr Asn Trp Gly Arg Ile Val Thr
            450                 455                 460

Leu Ile Ser Phe Gly Ala Phe Val Ala Lys His Leu Lys Thr Ile Asn
465                 470                 475                 480

Gln Glu Ser Cys Ile Glu Pro Leu Ala Glu Ser Ile Thr Asp Val Leu
                485                 490                 495

Val Arg Thr Lys Arg Asp Trp Leu Val Lys Gln Arg Gly Trp Asp Gly
            500                 505                 510

Phe Val Glu Phe Phe His Val
            515
```

```
<210> SEQ ID NO 2
<211> LENGTH: 26
<212> TYPE: PRT
<213> ORGANISM: Artificial Sequence
<220> FEATURE:
<221> NAME/KEY: MOD_RES
<222> LOCATION: 1
<223> OTHER INFORMATION: Biotin-PEG-PEG-PEG-PEG
<220> FEATURE:
<223> OTHER INFORMATION: Modified Sequence
<220> FEATURE:
<221> NAME/KEY: MOD_RES
<222> LOCATION: 8
<223> OTHER INFORMATION: Norvalin
<220> FEATURE:
<221> NAME/KEY: MOD_RES
<222> LOCATION: 26
<223> OTHER INFORMATION: AMIDATION

<400> SEQUENCE: 2

Pro Ala Glu Leu Glu Val Glu Val Ala Thr Gln Leu Arg Arg Phe Gly
1               5                   10                  15

Asp Lys Leu Asn Phe Arg Gln Lys Leu Leu
            20                  25

<210> SEQ ID NO 3
<211> LENGTH: 212
<212> TYPE: PRT
<213> ORGANISM: Artificial Sequence
<220> FEATURE:
<223> OTHER INFORMATION: Modified Sequence
<220> FEATURE:
<221> NAME/KEY: MOD_RES
<222> LOCATION: 212
<223> OTHER INFORMATION: HHHHHH

<400> SEQUENCE: 3

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190
```

Glu Leu Tyr Gly Asn Asn Ala Ala Glu Ser Arg Lys Gly Gln Glu
            195                 200                 205

Arg Phe Asn Arg
        210

<210> SEQ ID NO 4
<211> LENGTH: 25
<212> TYPE: PRT
<213> ORGANISM: Artificial Sequence
<220> FEATURE:
<221> NAME/KEY: MOD_RES
<222> LOCATION: 1
<223> OTHER INFORMATION: Biotin-PEG-PEG-PEG-PEG
<220> FEATURE:
<223> OTHER INFORMATION: Modifed Sequence
<220> FEATURE:
<221> NAME/KEY: MOD_RES
<222> LOCATION: 15
<223> OTHER INFORMATION: Norleucin
<220> FEATURE:
<221> NAME/KEY: MOD_RES
<222> LOCATION: 25
<223> OTHER INFORMATION: AMIDATION

<400> SEQUENCE: 4

Asn Leu Trp Ala Ala Gln Arg Tyr Gly Arg Glu Leu Arg Arg Leu Ser
1               5                   10                  15

Asp Glu Phe Val Asp Ser Phe Lys Lys
            20                  25

<210> SEQ ID NO 5
<211> LENGTH: 211
<212> TYPE: PRT
<213> ORGANISM: Artificial Sequence
<220> FEATURE:
<223> OTHER INFORMATION: Modified Sequence
<220> FEATURE:
<221> NAME/KEY: MOD_RES
<222> LOCATION: 211
<223> OTHER INFORMATION: HHHHHH

<400> SEQUENCE: 5

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

-continued

```
Ser Val Asn Arg Glu Met Ser Pro Leu Val Asp Asn Ile Ala Leu Trp
            165             170                 175

Met Thr Glu Tyr Leu Asn Arg His Leu His Thr Trp Ile Gln Asp Asn
            180             185                 190

Gly Gly Trp Asp Ala Phe Val Glu Leu Tyr Gly Pro Ser Met Arg Pro
            195             200                 205

Leu Phe Asp
    210
```

MACROCYCLIC CHLORINE SUBSTITUTED INDOLE DERIVATIVES

RELATED APPLICATIONS

This application is the U.S. national phase of International Patent Application No. PCT/EP2018/081370, filed Nov. 15, 2018, which claims the benefit of U.S. Provisional Application No. 62/587,925 filed on Nov. 17, 2017. The International Patent Application No. PCT/EP2018/081370 is hereby incorporated by reference in its entirety.

BACKGROUND

The present invention covers macrocyclic indole derivatives of general formula (I) which inhibit the antiapoptotoic activity of MCL-1 by inhibiting its interaction with proapotoic proteins.

Apoptosis, also called programmed cell death, is a natural process which allows a damaged or unwanted cell to die in a controlled manner. Deregulation of this process leads to unrestrained cell proliferation and is thus a hallmark of cancer (Hanahan and Weinberg, 2011).

Apoptosis is highly controlled by proteins of the B-cell lymphoma 2 (BCL-2) family. These proteins are characterized by their conserved regions known as BCL-2 homology (BH) domains (BH1-BH4) (Korsmeyer, 1999) through which they interact with each other. The BCL-2 family can be divided into pro-apoptotic members including BAX, BAK, BAD, BID, BIM, BMF, NOXA, and PUMA, which induce cell death, and anti-apoptotic members such as BCL-2, BCL-XL, BCL-w, Bfl1-AI, and myeloid cell leukemia-1 (MCL-1) which block apoptosis (Adams and Cory, 2007). The relative expression level of these two opponent groups of the BCL-2 family will decide if a cell will go into apoptosis or not.

MCL-1 has been identified as an important therapeutic target in cancer. MCL-1 is highly expressed in a variety of human cancers, and amplification of the MCL-1 locus is one of the most frequent somatic genetic events in human cancer, further pointing to its centrality in the pathogenesis of malignancy (Beroukhim et al., 2010). Its expression has been linked to deregulated anti-apoptotic pathways in cancer, thus leading to increased cancer cell survival, tumor development (Zhou et al., 2001) and resistance to anticancer therapies (Wertz et al., 2011). MCL-1 protein has been shown to mediate survival in models of acute myeloid leukemia (Glaser et al., 2012), lymphomas (Kelly et al., 2014) and multiple myeloma (Zhang et al., 2002). Many chemotherapeutics as well as radiation aim at inducing apoptosis in cancer cells. However, in malignant cells, apoptotic signaling is often deregulated, leading to uncontrolled growth and therapeutic resistance. One key resistance mechanism to apoptosis is to upregulate or genetically amplify MCL-1.

MCI-1 is a major inhibitor of apoptosis in cancer. MCL-1 is the largest member of the anti-apoptotic BCl-2 proteins. Its expression is tightly controlled with a half-life of only 1-4 h. With its BH-3 domain, MCL-1 tightly binds to BH-3 only containing pro-apoptotic proteins such as BAK or BAX and hinders them from inducing pores in the mitochondrial membrane, thereby blocking the intrinsic apoptotic pathway.

Thus, the specific inhibition of the interaction of MCL-1 with BH-3 only containing pro-apoptotic proteins like BAK or BAX represents a very attractive therapeutic principle to induce apoptosis in cancer cells and to address resistance against chemotherapeutics, radiation and new targeted agents. However, from WO 2015/148854, US 2016/0106731, WO 2008/130970, some indole derivatives are known as MCL-1 inhibitors. As there are no inhibitors in the clinic yet, there is still a need for further MCL-1 inhibitors to be provided.

SUMMARY

It has now been found that the compounds of the present invention effectively inhibit the activity of the anti-apoptotic BCL-2 family member Myeloid cell leukemia-1 (MCL-1) protein for which data are given in the biological experimental section, especially the efficacy is unexpectedly enhanced. The compounds of the present invention may therefore be used for the treatment or prophylaxis of hyperproliferative disorders, such as cancer disorders.

In accordance with a first aspect, the present invention provides compounds of general formula (I):

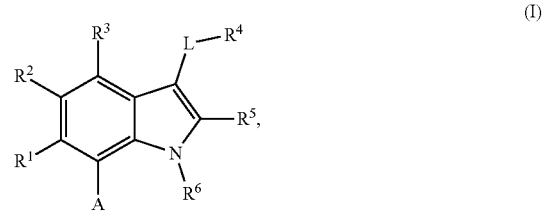

(I)

in which
A is

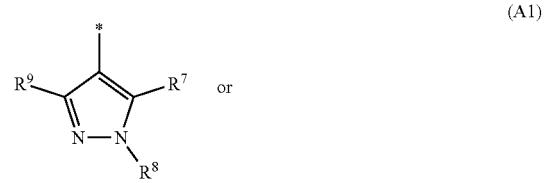

(A1)

or

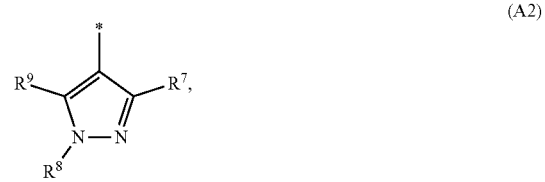

(A2)

wherein $R^6$ and $R^7$, together with two carbon atoms of the pyrazole ring, two carbon atoms of the indole moiety and the nitrogen atom to which $R^6$ is attached, form a 9-membered to 16-membered ring and * is the point of attachment of these moieties to the indole carbon atom bearing the A substituent or

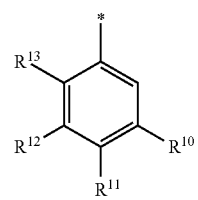

A is (A3) wherein optionally one or two of the groups selected from $CR^{11}$, $CR^{12}$ or $CR^{13}$ may be replaced by a nitrogen atom, wherein $R^6$ and $R^{10}$, together with three carbon atoms of the phenyl ring, two carbon atoms of the indole moiety and the nitrogen atom to which $R^6$ is attached, form a 9-membered to 16-membered ring and * is the point of attachment of these moieties to the indole carbon atom bearing the A substituent;

$R^1$ is a chlorine atom;

$R^2$ and $R^3$ are each a hydrogen atom;

$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a $(C_1$-$C_3)$-haloalkyl-S— group, and a $C_3$-$C_5$-cycloalkyl group;

L is a group —$(CH_2)_m$-E- wherein any $CH_2$ group is unsubstituted or substituted with one or two substituents and each substituent is independently selected from a halogen atom, a cyano group, a hydroxy group, a $C_1$-$C_3$-alkyl group, and a $C_1$-$C_3$-alkoxy group, or two substituents are optionally taken together with their intervening atoms to form a saturated or partially unsaturated 3-membered to 6-membered cycloalkyl ring, or a 3-membered to 8-membered saturated or partially unsaturated heterocyclic ring having 1-2 heteroatoms independently selected from an oxygen atom, a sulfur atom, a —S(O)— group, a —S(O)$_2$— group, and a —$NR^{14}$— group;

E is a bond, an oxygen atom, a sulfur atom, a —S(O)— group, a —S(O)$_2$— group or a —$NR^{14}$— group and constitutes the connecting element to $R^4$;

m is 2, 3, or 4;

$R^5$ is selected from a COOH group, a

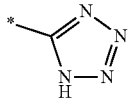

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$($CH_2$)$_s$NHCO($C_1$-$C_6$-alkyl) group, a —C(O)—NHS(O)$_2$($CH_2$)$_s$NHCO($C_3$-$C_6$-cycloalkyl) group, and a —C(O)—NHS(O)$_2$($CH_2$)$_s$NHCO(aryl) group;

s is 0, 1, 2, or 3;

—$R^6$-$R^7$— is selected from #—$(CH_2)_n$—(B)$_t$—$(CH_2)_p$—X—##, #—($C_2$-$C_6$-alkenylene)-(B)$_t$($CH_2$)$_p$—X—##, #—$(CH_2)_n$—(B)$_t$—($C_2$-$C_5$-alkenylene)-X—##, and #—$(CH_2)_q$—(B)—$(CH_2)_r$—(B)—$(CH_2)_v$—X—##, wherein # is the point of attachment with the indole nitrogen atom and ## is the point of attachment with the pyrazole carbon atom bearing the $R^7$ substituent; and wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group, and a (heterocycloalkyl)-($C_1$-$C_3$-alkylene)- group, and where optionally, if two such substituents are bound to the same atom, they may form together a 3-membered to 6-membered spiro ring, and wherein a —CH=CH— group in any alkenylene can be replaced by a 1,2-($C_3$-$C_5$)cycloalkylene group which is unsubstituted or substituted one or two times with a halogen atom or a $C_1$-$C_2$-alkyl group; and where X is an unsubstituted —$CH_2$— group;

—$R^6$-$R^{10}$— is selected from #—$(CH_2)_n$—(B)$_t$—$(CH_2)_p$—X—##, #—($C_2$-$C_6$-alkenylene)-(B)$_t$—$(CH_2)_p$—X—##, #—$(CH_2)_n$—(B)$_t$—($C_2$-$C_5$-alkenylene)-X—##, and #—$(CH_2)_q$—(B)—$(CH_2)_r$—(B)—$(CH_2)_v$—X—##, wherein # is the point of attachment with the indole nitrogen atom and ## is the point of attachment with the carbon atom of the phenyl moiety bearing the $R^{10}$ substituent, and wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group, and a (heterocycloalkyl)-($C_1$-$C_3$-alkylene)- group, wherein a double bond in any alkenylene can be replaced by a 1,2-($C_1$-$C_6$)cycloalkyl group which is unsubstituted or substituted one or two times with a halogen atom or a $C_1$-$C_2$-alkyl group, and where X is an unsubstituted —$CH_2$— group;

n is 2, 3, 4, 5, 6, 7, 8, or 9;

t is 0 or 1;

p is 0, 1, 2, 3, 4, or 5;

q is 2, 3, 4, 5, or 6;

r is 2, 3, 4, 5, or 6;

v is 0, or 1;

wherein the integers selected for variables n, t, p, q, r, and v result in forming a 9-membered to 16-membered ring independently from the selection of variable A1, A2 or A3;

B is independently selected from a —C(O)$NR^{15}$— group, a —$NR^{15}$C(O)— group, a —N($R^{15}$)— group, a —N($R^{15}$)—C(=O)—N($R^{15}$)— group, a —O—C(=O)—N($R^{15}$)— group, a —N($R^{15}$)—C(=O)—O— group, —O—, —S—, —S(O)—, and —S(O)$_2$—:

$R^8$ is selected from a hydrogen atom, a $C_1$-$C_6$-alkyl group, which is unsubstituted or substituted with one or more substituents independently selected from a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group, and a $NR^{20}R^{21}$ group;

a $C_1$-$C_3$-haloalkyl group, a $C_3$-$C_6$-cycloalkyl group, and a $C_1$-$C_6$-alkyl group in which one or two not directly adjacent carbon atoms are independently replaced by a hetero atom selected from —O— and —NH—;

$R^9$ is selected from a hydrogen atom, a $C_1$-$C_4$-alkyl group, a $C_1$-$C_3$-hydroxyalkyl group, a $C_1$-$C_4$-haloalkyl group, a $C_1$-$C_4$-haloalkyl-NH—C(O)—O—($C_1$-$C_3$-alkylene)-group, a $C_2$-$C_6$-haloalkenyl group, a $C_1$-$C_6$-alkyl-O— group, a $C_1$-$C_4$-haloalkoxy group, a $C_1$-$C_6$-alkyl-O—($C_1$-$C_3$-alkylene)- group, a ($C_3$-$C_7$)-cycloalkyl group, a ($C_3$-$C_7$)-cycloalkyl-O—($C_1$-$C_3$-alkylene)- group, a phenyl-O—($C_1$-$C_3$-alkylene)- group, a phenyl-($C_1$-$C_3$-alkylene)-O—($C_1$-$C_3$-alkylene)- group, a R$^{18}$-(phenylene)-(C$_1$-C$_3$-alkylene)-O—(C$_1$-C$_3$-alkylene)- group,
a R$^{18}$-(phenylene)-O—(C$_1$-C$_3$-alkylene)- group,
a R$^{18}$-(phenylene)-(heteroarylene)-O—(C$_1$-C$_3$-alkylene) group,
a (R$^{18}$)-(heterocycloalkylene)-(C$_1$-C$_3$-alkylene)- group,
a (R$^{18}$)-(heterocycloalkylene)-(phenylene)-O—(C$_1$-C$_3$-alkylene)- group,
a (heterocycloalkenyl)-(phenylene)-O—(C$_1$-C$_3$-alkylene)- group,
a (R$^{18}$)-(heteroarylene)-(C$_1$-C$_3$-alkylene)-O—(C$_1$-C$_3$-alkylene)- group,
a (R$^{18}$)-(heteroarylene)-(phenylene)-O—(C$_1$-C$_3$-alkylene)- group,
a (R$^{19}$)—S(O)$_2$-(phenylene)-O—(C$_1$-C$_3$-alkylene)- group,
a (R$^{19}$)—S(O)$_2$—NH-(phenylene)-O—(C$_1$-C$_3$-alkylene)- group,
a (R$^{19}$)—S(O)$_2$—NH-(phenylene)-O—(C$_1$-C$_3$-alkylene)- group,
a (R$^{19}$)—S(O)$_2$—N(C$_1$-C$_6$-alkyl)-(phenylene)-O—(C$_1$-C$_3$-alkylene)- group,
a (R$^{19}$)—S(O)$_2$-(heterocycloalkylene)-(phenylene)-O—(C$_1$-C$_3$-alkylene)- group,
a (R$^{18}$)-(heterocycloalkylene)-(heteroarylene)-O—(C$_1$-C$_3$-alkylene)- group,
a (R$^{19}$)-(heteroarylene)-O—(C$_1$-C$_3$-alkylene)- group,
a (R$^{18}$)-(heteroarylene)-O—(C$_1$-C$_3$-alkylene)- group,
a (R$^{19}$)—S(O)$_2$-(heteroarylene)-O—(C$_1$-C$_3$-alkylene)- group,
a (R$^{19}$)—S(O)$_2$-(heterocycloalkylene)-(heteroarylene)-O—(C$_1$-C$_3$-alkylene)- group,
a NR$^{20}$R$^{21}$—(C$_1$-C$_3$-alkylene)- group,
a (C$_1$-C$_3$-alkyl)-NH—(C$_1$-C$_3$-alkylene)- group,
a (C$_1$-C$_3$-haloalkyl)-(C$_1$-C$_3$-alkylene)-NH—(C$_1$-C$_3$-alkylene)- group,
a (C$_1$-C$_3$-haloalkyl)-NH—(C$_1$-C$_3$-alkylene)- group,
a (C$_1$-C$_3$-alkyl)-NH—C(O)—(C$_1$-C$_3$-alkylene)- group,
a (C$_1$-C$_3$-alkyl)-NR$^{15}$—C(O)—(C$_1$-C$_3$-alkylene)- group,
a (C$_1$-C$_3$-alkyl)-C(O)—NH—(C$_1$-C$_3$-alkylene)- group,
a (C$_1$-C$_3$-alkyl)-C(O)—NR$^{15}$—(C$_1$-C$_3$-alkylene)- group,
a

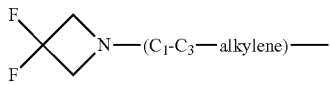

group, and a

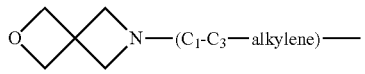

group, wherein the phenyl ring is unsubstituted or substituted with a halogen atom, a hydroxy group or a C$_1$-C$_3$-alkoxy group and
the heterocycloalkyl group is unsubstituted or substituted with an oxo (=O) group or is unsubstituted or substituted with one or more substituents independently selected from a halogen atom, a hydroxy group, a C$_1$-C$_3$-alkyl group and a C$_1$-C$_3$-alkoxy group,
or R$^8$ and R$^9$ together form a 5-membered or 6-membered ring optionally containing one or two heteroatoms selected from —O—, and —NR$^{14}$—;

R$^{11}$ and R$^{13}$ are each independently selected from a hydrogen atom, a halogen atom, a C$_1$-C$_3$-alkyl group and a C$_1$-C$_3$-alkoxy group;
R$^{12}$ is selected from a hydrogen atom, a C$_1$-C$_3$-alkoxy group, a C$_1$-C$_3$-alkyl group, a C$_1$-C$_3$-haloalkyl group, a C$_1$-C$_3$-haloalkoxy group and a NR$^{16}$R$^{17}$ group;
R$^{14}$ is a hydrogen atom or a C$_1$-C$_3$-alkyl group;
R$^{15}$ is independently selected from a hydrogen atom,
a C$_1$-C$_6$-alkyl group,
which is unsubstituted or substituted with one or more substituents selected from a halogen atom, a hydroxy group, a C$_1$-C$_3$-alkyl group, a C$_1$-C$_3$-haloalkyl group, a C$_1$-C$_3$-hydroxyalkyl group, a C$_1$-C$_3$-alkoxy group, a C$_1$-C$_3$-haloalkoxy group, a (C$_1$-C$_3$-alkyl)-C(O)—O— group, a heterocycloalkyl group, an aryl group, a (R$^{18}$)-(heterocycloalkylene)-(arylene)-O— group, a (heterocycloalkyl)-(arylene)-O— group, an aryl-O— group, an aryl-(C$_1$-C$_3$-alkylene)-O— group, a (R$^{19}$)—S(O)$_2$-arylene-O— group, a (R$^{19}$)S(O)$_2$-(heterocycloalkylene)-(arylene)-O— group, an (aryl)-(heteroarylene)-O— group, and an (aryl)-(heteroarylene)-O—(C$_1$-C$_3$-alkylene)- group;
a C$_1$-C$_3$-alkoxy-(C$_1$-C$_6$-alkylen)-O—C(O)— group,
a heterocycloalkyl-(C$_1$-C$_6$-alkylen)-O—C(O)— group,
a phenyl group,
a group

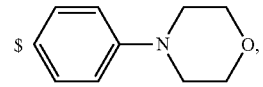

a group

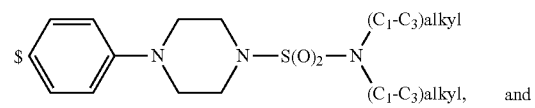

and a group

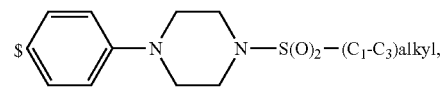

wherein $ is the point of attachment to the nitrogen atom, to which R$^{15}$ is attached,
R$^{16}$ and R$^{17}$ are each independently selected from a hydrogen atom, a C$_1$-C$_6$-alkyl group, a C$_1$-C$_6$-haloalkyl group, a C$_3$-C$_5$-cycloalkyl group, a C$_1$-C$_3$-alkyl-C(O)— group, a C$_1$-C$_3$-alkylS(O)$_2$— group, and a C$_1$-C$_3$-alkyl-O—C(=O)— group;
R$^{18}$ is selected from a hydrogen atom, a hydroxy group, a cyano group, a C$_1$-C$_3$-alkyl group, a C$_1$-C$_6$-hydroxyalkyl group, a C$_1$-C$_3$-alkoxy group, a C(O)OR$^{21}$—(C$_1$-C$_3$-alkylene)- group, a —C(O)OR$^{21}$ group, a —C(O)NR$^{20}$R$^{21}$ group, a (C$_1$-C$_3$-alkyl)-O—(C$_1$-C$_3$-alkylene)-C(O)— group, a (C$_1$-C$_6$-alkyl)-C(O)— group, and a C$_3$-C$_6$-cycloalkyl-C(O)— group;
R$^{19}$ is selected from a C$_1$-C$_3$-alkyl group, a C$_3$-C$_6$-cycloalkyl group, and a NR$^{20}$R$^{21}$ group; and
R$^{20}$ and R$^{21}$ are each independently selected from a hydrogen atom and a C$_1$-C$_6$-alkyl group;

or a tautomer, an N-oxide, or a salt thereof, or a salt of a tautomer, or a salt of an N-oxide, or a mixture of same.

BRIEF DESCRIPTION OF THE DRAWINGS

FIG. 1 (FIG. 1): shows a comparison of survival of immunocompromised mice intravenously injected with human HL-60 with untreated animals (Vehicle) and groups treated with MCL-1 inhibitor of Example 16 or irinotecan (n=12 animals/group).

DETAILED DESCRIPTION

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "unsubstituted or substituted" means that the number of substituents can be equal to or different from zero. Unless otherwise indicated, it is possible that substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

When groups in the compounds according to the invention are substituted, it is possible for said groups to be mono-substituted or poly-substituted with substituent(s), unless otherwise specified. Within the scope of the present invention, the meanings of all groups which occur repeatedly are independent from one another. It is possible that groups in the compounds according to the invention are substituted with one, two, three, four or five identical or different substituents, particularly with one, two or three substituents.

Oxo, an oxo group or an oxo substituent means a doubly attached oxygen atom =O. Oxo may be attached to atoms of suitable valency, for example to a saturated carbon atom or to a sulfur atom. For example, but without limitation, one oxo group is can be attached to a carbon atom, resulting in the formation of a carbonyl group C(=O), or two oxo groups are can be attached to one sulfur atom, resulting in the formation of a sulfonyl group —S(=O)$_2$. The term "ring substituent" means a substituent attached to an aromatic or nonaromatic ring which replaces an available hydrogen atom on the ring.

Should a composite substituent be composed of more than one parts, e.g., ($C_1$-$C_4$-alkoxy)-($C_1$-$C_4$-alkyl)-, it is possible for the position of a given part to be at any suitable position of said composite substituent, i.e. the $C_1$-$C_4$-alkoxy part can be attached to any carbon atom of the $C_1$-$C_4$-alkyl part of said ($C_1$-$C_4$-alkoxy)-($C_1$-$C_4$-alkyl)- group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

The term "comprising" when used in the specification includes "consisting of" but does not have to be the scope indicated by "consisting of.

If within the present text any item is referred to as "as mentioned herein", it means that it may be mentioned anywhere in the present text.

If within the present text any item is referred to as "supra" within the description it indicates any of the respective disclosures made within the specification in any of the preceding pages, or above on the same page.

If within the present text any item is referred to as "infra" within the description it indicates any of the respective disclosures made within the specification in any of the subsequent pages, or below on the same page.

The terms as mentioned in the present text have the following meanings: The term "halogen atom" means a fluorine, chlorine, bromine or iodine atom, particularly a fluorine, chlorine or bromine atom.

The term "$C_1$-$C_8$-alkyl-" means a linear or branched, saturated hydrocarbon group having 1, 2, 3, 4, 5, 6, 7 or 8 carbon atoms, e.g., a methyl-, ethyl-, propyl-, iso-propyl-, n-butyl-, iso-butyl-, sec-butyl-, tert-butyl-, n-pentyl-, iso-pentyl-, 2-methylbutyl-, 1-methylbutyl-, 1-ethylpropyl-, 1,2-dimethylpropyl-, neo-pentyl-, 1,1-dimethylpropyl-, n-hexyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-1,1-dimethylbutyl-, 2,3-dimethylbutyl-, 1,3-dimethylbutyl-, 1,2-dimethylbutyl-, n-heptyl-, 5-methylhexyl-, 4-methylhexyl-, 2-methylhexyl-, 1-methylhexyl-, 2-ethylpentyl-, 1-ethylpentyl-, 3,3-dimethylpentyl-, 2,2-dimethylpentyl-, 1,1-dimethylpentyl-, 2,3-dimethylpentyl-, 1,3-dimethylpentyl-, 1,2-dimethylpentyl-, n-octyl-, 6-methylheptyl-, 4-methylheptyl-, 2-methylheptyl-, 1-methylheptyl-, 2-ethylhexyl-, 1-ethylhexyl-, 3,3-dimethylhexyl-, 2,2-dimethylhexyl-, 1,1-dimethylhexyl-, 2,3-dimethylhexyl-, 1,3-dimethylhexyl-, 1,2-dimethylhexyl-group, or an isomer thereof. Preferably, said group has 1, 2, 3, 4, 5 or 6 carbon atoms ("$C_1$-$C_6$-alkyl-"), e.g., a methyl-, ethyl-, n-propyl-, iso-propyl-, n-butyl-, iso-butyl-, sec-butyl-, tert-butyl-, n-pentyl-, iso-pentyl-, 2-methylbutyl-, 1-methylbutyl-, 1-ethylpropyl-, 1,2-dimethylpropyl-, neo-pentyl-, 1,1-dimethylpropyl-, n-hexyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl- or a 1,2-dimethylbutyl group, or an isomer thereof. More preferably, said group has 1, 2, 3 or 4 carbon atoms ("$C_1$-$C_4$-alkyl-"), e.g., a methyl-, ethyl-, n-propyl-, iso-propyl-, n-butyl-, iso-butyl-, sec-butyl- or tert-butyl- group, 1, 2 or 3 carbon atoms ("$C_1$-$C_3$-alkyl-"), e.g., a methyl-, ethyl-, n-propyl- or iso-propyl group, or 1 or 2 carbon atoms ("$C_1$-$C_2$-alkyl-"), e.g., a methyl group, an ethyl group.

The same definitions can be applied should the alkyl group be placed within a chain as a bivalent "$C_1$-$C_6$-alkylene" moiety. All names as mentioned above then will bear an "ene" added to the end, thus e.g., a "pentyl" becomes a bivalent "pentylene" group. In addition, the term "$C_1$-$C_6$-heteroalkyl" refers to a $C_1$-$C_6$-alkyl group in which one or more of the carbon atoms have been replaced with an atom selected from N, O, S, or P, which are substituted as mentioned herein to satisfy atom valency requirements.

The term "$C_2$-$C_6$-alkylene" means a linear or branched, saturated, divalent hydrocarbon chain (or "tether") having 2, 3, 4, 5 or 6 carbon atoms, e.g., —$CH_2$—$CH_2$— ("ethylene" or "$C_2$-alkylene"), —$CH_2$—$CH_2$—$CH_2$—, —C(H)($CH_3$)—$CH_2$— or —C($CH_3$)$_2$— ("propylene" or "$C_3$-alkylene"), or, for example —$CH_2$—C(H)($CH_3$)—$CH_2$—, —$CH_2$—C $(CH_3)_2$—, —$CH_2$—$CH_2$—$CH_2$—$CH_2$— ("butylene" or "$C_4$-alkylene"), "$C_5$-alkylene", e.g., —$CH_2$—$CH_2$—$CH_2$—$CH_2$—$CH_2$— ("n-pentylene"), or "—$C_6$-alkylene-", e.g., —$CH_2$—$CH_2$—$CH_2$—$CH_2$—$CH_2$—$CH_2$— ("n-hexylene") or a —$C(CH_3)_2$—$C(CH_3)_2$ group.

The term "hydroxy-($C_1$-$C_6$-alkyl)-" means a linear or branched, saturated, hydrocarbon group in which one or more hydrogen atoms of a "$C_1$-$C_6$-alkyl-" as defined supra are each replaced by a hydroxy group, e.g., a hydroxymethyl-, 1-hydroxyethyl-, 2-hydroxyethyl-, 1,2-dihydroxyethyl-, 3-hydroxypropyl-, 2-hydroxypropyl-, 2,3-dihydroxypropyl-, 1,3-dihydroxypropan-2-yl-, 3-hydroxy-2-methylpropyl-, 2-hydroxy-2-methyl-propyl-, or a 1-hydroxy-2-methyl-propyl- group. Particularly the hydroxyalkyl group means a linear or branched, saturated, monovalent hydrocarbon group has 1, 2 or 3 carbon atoms in which 1 hydrogen atom is replaced with a hydroxy group e.g. a hydroxymethyl-, 1-hydroxyethyl-, 2-hydroxyethyl-, 3-hydroxypropyl-, 2-hydroxypropyl-, 1-hydroxypropyl-, 2-hydroxy-2-methyl-ethyl group.

The term "$C_1$-$C_6$-haloalkyl" means a linear or branched, saturated, monovalent hydrocarbon group in which the term "$C_1$-$C_6$-alkyl" is as defined supra and in which one or more of the hydrogen atoms are replaced, identically or differently, with a halogen atom. Preferably, said halogen atom is a fluorine atom. Said $C_1$-$C_6$-haloalkyl, particularly a $C_1$-$C_3$-haloalkyl group is, for example, fluoromethyl-, difluoromethyl-, trifluoromethyl-, 2-fluoroethyl-, 2,2-difluoroethyl-, 2,2,2-trifluoroethyl-, pentafluoroethyl-, 3,3,3-trifluoropropyl- or a 1,3-difluoropropan-2-yl group.

The term "$C_1$-$C_6$-alkoxy" means a linear or branched, saturated, monovalent group of formula ($C_1$-$C_6$-alkyl)-O—, in which the term "$C_1$-$C_6$-alkyl" group is as defined supra, e.g. methoxy-, ethoxy-n-propoxy-, isopropoxy-, n-butoxy-, sec-butoxy-, isobutoxy-, tert-butoxy-, pentyloxy-, isopentyloxy- or a n-hexyloxy group, or an isomer thereof.

The term "$C_1$-$C_6$-alkylthio" or "$C_1$-$C_6$-thioalkyl" means a linear or branched, saturated, monovalent group of formula ($C_1$-$C_6$-alkyl)-S—, in which the term "$C_1$-$C_6$-alkyl" is as defined supra, e.g. methylthio-, ethylthio-, n-propylthio-, isopropylthio-, n-butylthio-, sec-butylthio-, isobutylthio-, tert-butylthio-, pentylthio-, isopentylthio- or a n-hexylthio group, or an isomer thereof.

The term "$C_1$-$C_6$-haloalkoxy" means a linear or branched, saturated, monovalent $C_1$-$C_6$-alkoxy group, as defined supra, in which one or more of the hydrogen atoms is replaced, identically or differently, with a halogen atom. Preferably, said halogen atom in "$C_1$-$C_6$-haloalkoxy-" is fluorine, resulting in a group referred herein as "$C_1$-$C_6$-fluoroalkoxy-". Representative $C_1$-$C_6$-fluoroalkoxy- groups include, for example, —$OCF_3$, —$OCHF_2$, —$OCH_2F$, —$OCF_2CF_3$ and —$OCH_2CF_3$.

The term "$C_1$-$C_6$-haloalkylthio" or "$C_1$-$C_6$-halothioalkyl" or "$C_1$-$C_6$-haloalkyl-S—" means a linear or branched, saturated, monovalent $C_1$-$C_6$-alkylthio group, as defined supra, in which one or more of the hydrogen atoms is replaced, identically or differently, with a halogen atom. Preferably, said halogen atom in "$C_1$-$C_6$-haloalkylthio-" is fluorine.

The term "$C_2$-$C_6$-alkenyl-" means a linear or branched, monovalent hydrocarbon group, which contains one or more double bonds and which has 2, 3, 4, 5 or 6 carbon atoms, preferably 2, 3 or 4 carbon atoms ("$C_2$-$C_4$-alkenyl-") or 2 or 3 carbon atoms ("$C_2$-$C_3$-alkenyl-"), it being understood that in the case in which said alkenyl- group contains more than one double bond, then said double bonds may be isolated from, or conjugated with, each other. Representative alkenyl groups include, for example, an ethenyl-, prop-2-enyl-, (E)-prop-1-enyl-, (Z)-prop-1-enyl-, iso-propenyl-, but-3-enyl-, (E)-but-2-enyl-, (Z)-but-2-enyl-, (E)-but-1-enyl-, (Z)-but-1-enyl-, 2-methylprop-2-enyl-, 1-methylprop-2-enyl-, 2-methylprop-1-enyl-, (E)-1-methylprop-1-enyl-, (Z)-1-methylprop-1-enyl-, buta-1,3-dienyl-, pent-4-enyl-, (E)-pent-3-enyl-, (Z)-pent-3-enyl-, (E)-pent-2-enyl-, (Z)-pent-2-enyl-, (E)-pent-1-enyl-, (Z)-pent-1-enyl-, 3-methylbut-3-enyl-, 2-methylbut-3-enyl-, 1-methylbut-3-enyl-, 3-methylbut-2-enyl-, (E)-2-methylbut-2-enyl-, (Z)-2-methylbut-2-enyl-, (E)-1-methylbut-2-enyl-, (Z)-1-methylbut-2-enyl-, (E)-3-methylbut-1-enyl-, (Z)-3-methylbut-1-enyl-, (E)-2-methylbut-1-enyl-, (Z)-2-methylbut-1-enyl-, (E)-1-methylbut-1-enyl-, (Z)-1-methylbut-1-enyl-, 1,1-dimethylprop-2-enyl-, 1-ethylprop-1-enyl-, 1-propylvinyl-, 1-isopropylvinyl-, (E)-3,3-dimethylprop-1-enyl-, (Z)-3,3-dimethylprop-1-enyl-, penta-1,4-dienyl-, hex-5-enyl-, (E)-hex-4-enyl-, (Z)-hex-4-enyl-, (E)-hex-3-enyl-, (Z)-hex-3-enyl-, (E)-hex-2-enyl-, (Z)-hex-2-enyl-, (E)-hex-1-enyl-, (Z)-hex-1-enyl-, 4-methylpent-4-enyl-, 3-methylpent-4-enyl-, 2-methylpent-4-enyl-, 1-methylpent-4-enyl-, 4-methylpent-3-enyl-, (E)-3-methylpent-3-enyl-, (Z)-3-methylpent-3-enyl-, (E)-2-methylpent-3-enyl-, (Z)-2-methylpent-3-enyl-, (E)-1-methylpent-3-enyl-, (Z)-1-methylpent-3-enyl-, (E)-4-methylpent-2-enyl-, (Z)-4-methylpent-2-enyl-, (E)-3-methylpent-2-enyl-, (Z)-3-methylpent-2-enyl-, (E)-2-methylpent-2-enyl-, (Z)-2-methylpent-2-enyl-, (E)-1-methylpent-2-enyl-, (Z)-1-methylpent-2-enyl-, (E)-4-methylpent-1-enyl-, (Z)-4-methylpent-1-enyl-, (E)-3-methylpent-1-enyl-, (Z)-3-methylpent-1-enyl-, (E)-2-methylpent-1-enyl-, (Z)-2-methylpent-1-enyl-, (E)-1-methylpent-1-enyl-, (Z)-1-methylpent-1-enyl-, 3-ethylbut-3-enyl-2-ethylbut-3-enyl-, 1-ethylbut-3-enyl-, (E)-3-ethylbut-2-enyl-, (Z)-3-ethylbut-2-enyl-, (E)-2-ethylbut-2-enyl-, (Z)-2-ethylbut-2-enyl-, (E)-1-ethylbut-2-enyl-, (Z)-1-ethylbut-2-enyl-, (E)-3-ethylbut-1-enyl-, (Z)-3-ethylbut-1-enyl-, 2-ethylbut-1-enyl-, (E)-1-ethylbut-1-enyl-, (Z)-1-ethylbut-1-enyl-, 2-propylprop-2-enyl-, 1-propylprop-2-enyl-, 2-isopropylprop-2-enyl-, 1-isopropylprop-2-enyl-, (E)-2-propylprop-1-enyl-, (Z)-2-propylprop-1-enyl-, (E)-1-propylprop-1-enyl-, (Z)-1-propylprop-1-enyl-, (E)-2-isopropylprop-1-enyl-, (Z)-2-isopropylprop-1-enyl-, (E)-1-isopropylprop-1-enyl-, (Z)-1-isopropylprop-1-enyl-, hexa-1,5-dienyl- and a 1-(1,1-dimethylethyl-)ethenyl group. Particularly, said group is an ethenyl- or a prop-2-enyl group.

The same definitions can be applied should the alkenyl group be placed within a chain as a bivalent "$C_2$-$C_6$-alkenylene" moiety. All names as mentioned above then will bear a "ene" added to their end, thus e.g., a "pentenyl" becomes a bivalent "pentenylene" group.

The term "$C_2$-$C_6$-haloalkenyl-" means a linear or branched hydrocarbon group in which one or more of the hydrogen atoms of a "$C_2$-$C_6$-alkenyl-" as defined supra are each replaced, identically or differently, by a halogen atom. Preferably, said halogen atom is fluorine, resulting in a group referred herein as "$C_2$-$C_6$-fluoroalkenyl-". Representative $C_2$-$C_6$-fluoroalkenyl- groups include, for example, —$CH=CF_2$, —$CF=CH_2$, —$CF=CF_2$, —$C(CH_3)=CF_2$, —$CH=C(F)$—$CH_3$, —$CH_2$—$CF=CF_2$ and —$CF_2$—$CH=CH_2$.

The term "$C_2$-$C_6$-alkynyl-" means a linear or branched, monovalent hydrocarbon group which contains one or more triple bonds, and which contains 2, 3, 4, 5 or 6 carbon atoms, preferably 2, 3 or 4 carbon atoms ("$C_2$-$C_4$-alkynyl-") or 2 or 3 carbon atoms ("$C_2$-$C_3$-alkynyl-"). Representative $C_2$-$C_6$-alkynyl- groups include, for example, an ethynyl-, prop-1-ynyl-, prop-2-ynyl-, but-1-ynyl-, but-2-ynyl-, but-3-ynyl-, pent-1-ynyl-, pent-2-ynyl, pent-3-ynyl-, pent-4-ynyl-, hex- 1-ynyl-, hex-2-ynyl-, hex-3-ynyl-, hex-4-ynyl-, hex-5-ynyl-, 1-methylprop-2-ynyl-, 2-methylbut-3-ynyl-, 1-methylbut-3-ynyl-, 1-methylbut-2-ynyl-, 3-methylbut-1-ynyl-, 1-ethylprop-2-ynyl-, 3-methylpent-4-ynyl-, 2-methylpent-4-ynyl-, 1-methyl-pent-4-ynyl-, 2-methylpent-3-ynyl-, 1-methyl-pent-3-ynyl-, 4-methylpent-2-ynyl-, 1-methyl-pent-2-ynyl-, 4-methylpent-1-ynyl-, 3-methylpent-1-ynyl-, 2-ethylbut-3-ynyl-, 1-ethylbut-3-ynyl-, 1-ethylbut-2-ynyl-, 1-propylprop-2-ynyl-, 1-isopropylprop-2-ynyl-, 2,2-dimethylbut-3-ynyl-, 1,1-dimethylbut-3-ynyl-, 1,1-dimethylbut-2-ynyl- and a 3,3-dimethylbut-1-ynyl- group. Particularly, said alkynyl- group is an ethynyl-, a prop-1-ynyl- or a prop-2-ynyl- group.

The term "$C_3$-$C_{10}$-cycloalkyl-" means a saturated mono- or bicyclic hydrocarbon ring which contains 3, 4, 5, 6, 7, 8, 9 or 10 carbon atoms ("$C_3$-$C_{10}$-cycloalkyl-"). Said $C_3$-$C_{10}$-cycloalkyl- group may be, for example, a monocyclic hydrocarbon ring, e.g., a cyclopropyl-, cyclobutyl-, cyclopentyl-, cyclohexyl- or cycloheptyl- group, or a bicyclic hydrocarbon ring, such as a decalinyl group. Preferably, said hydrocarbon ring is monocyclic and contains 3, 4, 5, 6 or 7 carbon atoms ("$C_3$-$C_7$-cycloalkyl-"), e.g., a cyclopropyl-, cyclobutyl-, cyclopentyl-, cyclohexyl- or cycloheptyl-group, or 3, 4, 5 or 6 carbon atoms ("$C_3$-$C_6$-cycloalkyl-"), e.g., a cyclopropyl-, cyclobutyl-, cyclopentyl- or a cyclohexyl- group. A cycloalkyl group may be unsubstituted or substituted as defined at the respective part wherein such term is used.

The term "1,2($C_3$-$C_5$)cycloakylene is used in the definition of —$R^6$-$R^7$— and means particularly

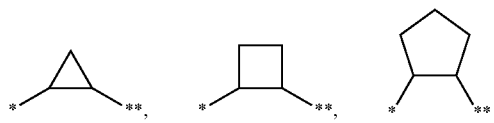

wherein * is the point of attachment of the ring to the adjacent —$CH_2$— group or to the indole nitrogen atom and ** is the point of attachment to the adjacent —$CH_2$— group or to —(B)$_f$—.

The term "$C_4$-$C_8$-cycloalkenyl" means a monovalent, mono- or bicyclic hydrocarbon ring which contains 4, 5, 6, 7 or 8 carbon atoms and one double bond. Particularly, said ring contains 4, 5 or 6 carbon atoms ("$C_4$-$C_6$-cycloalkenyl"). Said $C_4$-$C_8$-cycloalkenyl group is for example, a monocyclic hydrocarbon ring, e.g., a cyclobutenyl-, cyclopentenyl-, cyclohexenyl-, cycloheptenyl- or a cyclooctenyl group, or a bicyclic hydrocarbon ring, e.g., a bicyclo[2.2.1]hept-2-enyl- or a bicyclo[2.2.2]oct-2-enyl group.

The term "4- to 10-membered heterocycloalkyl-" means a saturated mono- or bicyclic hydrocarbon ring which contains 3, 4, 5, 6, 7, 8 or 9 carbon atoms, and which contains 1, 2, 3 or 4 heteroatoms which may be identical or different, said heteroatoms preferably are selected from oxygen, nitrogen or sulfur, and wherein carbon atoms and heteroatoms add up to 4, 5, 6, 7, 8, 9 or 10 ring atoms in total, it being possible for said heterocycloalkyl- group to be attached to the rest of the molecule via any one of the carbon atoms or, if present, a nitrogen atom. "Heterospirocycloalkyl-", "heterobicycloalkyl-" and "bridged heterocycloalkyl-", as defined infra, are also included within the scope of this definition.

Preferably, said "4-membered to 10-membered heterocycloalkyl-" group is monocyclic and contains 3, 4, 5 or 6 carbon atoms, and one or two of the above-mentioned heteroatoms, adding up to 4, 5, 6 or 7 ring atoms in total (a "4-membered to 7-membered monocyclic heterocycloalkyl-"), or contains 3, 4 or 5 carbon atoms, and one or two of the above-mentioned heteroatoms, adding up to 4, 5 or 6 ring atoms in total (a "4-membered to 6-membered monocyclic heterocycloalkyl-"), or contains 3, 4 or 5 carbon atoms, and one or two of the above-mentioned heteroatoms, adding up to 5 or 6 ring atoms in total (a "5-membered to 6-membered monocyclic heterocycloalkyl-"); it being possible for said heterocycloalkyl group to be attached to the rest of the molecule via any one of the carbon atoms or the nitrogen atoms, if present.

Exemplarily, without being limited thereto, said "4-membered to 7-membered monocyclic heterocycloalkyl-", can be a 4-membered ring, a "4-membered heterocycloalkyl-" group, such as an azetidinyl- or an oxetanyl group; or a 5-membered ring, a "5-membered heterocycloalkyl-" group, such as a tetrahydrofuranyl-, dioxolinyl-, pyrrolidinyl-, imidazolidinyl-, pyrazolidinyl- or a pyrrolinyl group; or a 6-membered ring, a "6-membered heterocycloalkyl-" group, such as a tetrahydropyranyl-, piperidinyl-, morpholinyl-, 3-oxomorpholin-4-yl, dithianyl-, thiomorpholinyl- or a piperazinyl group; or a 7-membered ring, a "7-membered heterocycloalkyl-" group, such as an azepanyl-, diazepanyl- or an oxazepanyl group, for example. The heterocycloalkyl groups may be one or more times substituted with $C_1$-$C_3$-alkyl, $C_1$-$C_3$-alkoxy, hydroxy, halogen or a carbonyl group.

The term "5- to 7-membered heterocycloalkenyl" means a monocyclic, unsaturated, nonaromatic heterocycle with 5, 6, or 7 ring atoms in total, which contains one or two double bonds and one or two identical or different ring heteroatoms from the series: N, O, S; it being possible for said heterocycloalkenyl group to be attached to the rest of the molecule via any one of the carbon atoms or, if present, a nitrogen atom.

Said heterocycloalkenyl group is, for example, a 4H-pyranyl-, 3,6-dihydro-2H-pyran-4-yl-, 2H-pyranyl-, dihydropyridinyl-, tetrahydropyridinyl-, 2-oxopyridin-1(2H)-yl-, 2,5-dihydro-1H-pyrrolyl-, [1,3]dioxolyl-, 4H-[1,3,4]thiadiazinyl-, 2,5-dihydrofuranyl-, 2,3-dihydrofuranyl-, 2,5-dihydrothiophenyl-, 2,3-dihydrothiophenyl-, 4,5-dihydrooxazolyl- or a 4H-[1,4]thiazinyl group. Those heterocycloalkenyl groups may be substituted with a hydroxy group or a methoxy group.

The term "heterospirocycloalkyl" means a bicyclic, saturated heterocycle with 6, 7, 8, 9, 10 or 11 ring atoms in total, in which the two rings share one common ring carbon atom, which "heterospirocycloalkyl" contains one or two identical or different ring heteroatoms from the series: N, O, S; it being possible for said heterospirocycloalkyl group to be attached to the rest of the molecule via any one of the carbon atoms, except the spiro carbon atom, or, if present, a nitrogen atom.

Said heterospirocycloalkyl group is, for example, an azaspiro[2.3]hexyl-, azaspiro[3.3]heptyl-, oxaazaspiro[3.3]heptyl-, thiaazaspiro[3.3]heptyl-, oxaspiro[3.3]heptyl-, oxazaspiro[5.3]nonyl-, oxazaspiro[4.3]octyl-, azaspiro[4,5]decyl-, oxazaspiro[5.5]undecyl-, diazaspiro[3.3]heptyl-, thiazaspiro[3.3]heptyl-, thiazaspiro[4.3]octyl- or an azaspiro[5.5]undecyl- group or one of the further homologous scaffolds such as spiro[3.4]-, spiro[4.4]-, spiro[2.4]-, spiro[2.5]-, spiro[2.6]-, spiro[3.5]-, spiro[3.6]-, spiro[4.5]- and spiro[4.6]-.

The term "fused heterocycloalkyl" or "heterobicycloalkyl-" means a bicyclic, saturated heterocycle with 6, 7, 8, 9 or 10 ring atoms in total, in which the two rings share two adjacent ring atoms, which "fused heterocycloalkyl" contains one or two identical or different ring heteroatoms from the series: N, O, S; it being possible for said fused heterocycloalkyl group to be attached to the rest of the molecule via any one of the carbon atoms or, if present, a nitrogen atom.

Said fused heterocycloalkyl or "heterobicycloalkyl-" group is, for example, an azabicyclo[3.3.0]octyl-, azabicyclo[4.3.0]nonyl-, diazabicyclo[4.3.0]nonyl-, oxazabicyclo[4.3.0]nonyl-, and a thiazabicyclo[4.3.0]nonyl or azabicyclo[4.4.0]decyl group.

The term "aryl" means a phenyl-, naphthyl-, 5,6-dihydronaphthyl-, 7,8-dihydronaphthyl-, 5,6,7,8-tetrahydronaphthyl-, indanyl-, or an indenyl group, which is unsubstituted or substituted with one, two, three, four or five substituents, each substituent independently selected from halogen, cyano, $C_1$-$C_3$-alkyl, $C_1$-$C_3$-haloalkyl, $C_1$-$C_3$-alkoxy, $C_1$-$C_3$-thioalkyl, $C_1$-$C_3$-haloalkoxy, $C_1$-$C_3$-halothioalkyl, $C_3$-$C_5$-cycloalkyl, particularly halogen, $C_1$-$C_3$-alkyl, $C_1$-$C_3$-haloalkyl, $C_1$-$C_3$-alkoxy, $C_1$-$C_3$-haloalkoxy.

The term "bridged heterocycloalkyl" means a bicyclic, saturated heterocycle with 7, 8, 9 or 10 ring atoms in total, in which the two rings share two common ring atoms which are not adjacent, which "bridged heterocycloalkyl" contains one or two identical or different ring heteroatoms from the series: N, O, S; it being possible for said bridged heterocycloalkyl group to be attached to the rest of the molecule via any one of the carbon atoms or, if present, a nitrogen atom.

Said bridged heterocycloalkyl group is, for example, an azabicyclo[2.2.1]heptyl-, oxazabicyclo[2.2.1]heptyl-, thiazabicyclo[2.2.1]heptyl-, diazabicyclo[2.2.1]heptyl-, azabicyclo-[2.2.2]octyl-, diazabicyclo[2.2.2]octyl-, oxazabicyclo[2.2.2]octyl-, thiazabicyclo[2.2.2]octyl-, azabicyclo[3.2.1]octyl-, diazabicyclo[3.2.1]octyl-, oxazabicyclo[3.2.1]octyl-, thiazabicyclo[3.2.1]octyl-, azabicyclo[3.3.1]nonyl-, diazabicyclo[3.3.1]nonyl-, oxazabicyclo[3.3.1]nonyl-, thiazabicyclo[3.3.1]nonyl-, azabicyclo[4.2.1]nonyl, diazabicyclo[4.2.1]nonyl-, oxazabicyclo[4.2.1]nonyl-, thiazabicyclo[4.2.1]nonyl-, azabicyclo[3.3.2]decy-1, diazabicyclo[3.3.2]decyl-, oxazabicyclo[3.3.2]decyl-, and a thiazabicyclo[3.3.2]decyl or azabicyclo[4.2.2]decyl group.

The term "aryl" means a phenyl-, naphthyl-, 5,6-dihydronaphthyl-, 7,8-dihydronaphthyl-, 5,6,7,8-tetrahydronaphthyl-, an indanyl-, or an indenyl group, which is unsubstituted or substituted with one, two, three, four or five substituents, each substituent independently selected from halogen, cyano, $C_1$-$C_3$-alkyl, $C_1$-$C_3$-haloalkyl, $C_1$-$C_3$-alkoxy, $C_1$-$C_3$-thioalkyl, $C_1$-$C_3$-haloalkoxy, $C_1$-$C_3$-halothioalkyl, $C_3$-$C_5$-cycloalkyl, particularly halogen, $C_1$-$C_3$-alkyl, $C_1$-$C_3$-haloalkyl, $C_1$-$C_3$-alkoxy, and $C_1$-$C_3$-haloalkoxy.

The term "heteroaryl-" means a monocyclic, bicyclic or tricyclic aromatic ring system having 5, 6, 7, 8, 9, 10, 11, 12, 13 or 14 ring atoms (a "5- to 14-membered heteroaryl-" group), preferably 5, 6, 9 or 10 ring atoms and which contains 1, 2, 3 or 4 heteroatoms which may be identical or different, said heteroatoms being selected from oxygen, nitrogen and sulfur. Said heteroaryl-group can be a 5-membered heteroaryl group, such as, for example, a thienyl-, furanyl-, pyrrolyl-, oxazolyl-, thiazolyl-, imidazolyl-, pyrazolyl-, isoxazolyl-, isothiazolyl-, oxadiazolyl-, triazolyl-, thiadiazolyl- or a tetrazolyl group; or a 6-membered heteroaryl group, such as, for example, a pyridyl-, pyridazinyl-, pyrimidyl-, pyrazinyl- or a triazinyl group; or a benzo-fused 5-membered heteroaryl- group, such as, for example, a benzofuranyl-, benzothienyl-, benzoxazolyl-, benzisoxazolyl-, benzimidazolyl-, benzothiazolyl-, benzotriazolyl-, indazolyl-, indolyl- or a isoindolyl group; or a benzo-fused 6-membered heteroaryl group, such as, for example, a quinolinyl-, quinazolinyl-, isoquinolinyl-, cinnolinyl-, phthalazinyl- or quinoxalinyl-; or another bicyclic group, such as, for example, indolizinyl-, purinyl- or a pteridinyl group; or a tricyclic heteroaryl- group, such as, for example, a carbazolyl-, acridinyl- or a phenazinyl group Preferably, "heteroaryl-" is a monocyclic aromatic ring system having 5 or 6 ring atoms and which contains at least one heteroatom, if more than one, they may be identical or different, said heteroatom being selected from oxygen, nitrogen and sulfur, a ("5- to 6-membered monocyclic heteroaryl-") group, such as, for example, a thienyl-, furanyl-, pyrrolyl-, oxazolyl-, thiazolyl-, imidazolyl-, pyrazolyl-, isoxazolyl-, isothiazolyl-, oxadiazolyl-, triazolyl-, thiadiazolyl-, tetrazolyl-, pyridyl-, pyridazinyl-, pyrimidyl-, pyrazinyl- or a triazinyl- group.

In general, and unless otherwise mentioned, said heteroaryl- groups include all the possible isomeric forms thereof, e.g., the positional isomers thereof. Thus, for some illustrative non-restricting example, the term pyridyl- includes pyridin-2-yl-, pyridin-3-yl- and pyridin-4-yl-; the term thienyl- includes thien-2-yl- and thien-3-yl-. Furthermore, said heteroaryl- groups can be attached to the rest of the molecule via any one of the carbon atoms, or, if applicable, a nitrogen atom, e.g., pyrrol-1-yl-, pyrazol-1-yl- or imidazol-1-yl-.

In general, and unless otherwise mentioned, the heteroaryl or heteroarylene groups include all possible isomeric forms thereof, e.g., tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

Particularly, the heteroaryl group is a pyridyl- or pyrimidyl group or a imidazolyl group. including a hydroxy substitution of the pyridyl group leading e.g. to a 2-hydroxypyridine which is the tautomeric form to a 2-oxo-2(1H)-pyridine.

The term "$C_1$-$C_6$", as used throughout this text, e.g., in the context of the definition of "$C_1$-$C_6$-alkyl-", "$C_1$-$C_6$-haloalkyl-", "$C_1$-$C_6$-alkoxy-" or "$C_1$-$C_6$-haloalkoxy-" is to be understood as meaning an alkyl group having a whole number of carbon atoms from 1 to 6, i.e., 1, 2, 3, 4, 5 or 6 carbon atoms. It is to be understood further that said term "$C_1$-$C_6$" is to be interpreted as disclosing any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$; preferably $C_1$-$C_2$, $C_1$-$C_3$, $C_1$-$C_4$, $C_1$-$C_5$, $C_1$-$C_6$ more preferably $C_1$-$C_4$, in the case of "$C_1$-$C_6$-haloalkyl-" or "$C_1$-$C_6$-haloalkoxy-" even more preferably $C_1$-$C_2$.

Similarly, as used herein, the term "$C_2$-$C_6$", as used throughout this text, e.g., in the context of the definitions of "$C_2$-$C_6$-alkenyl-" and "$C_2$-$C_6$-alkynyl-", is to be understood as meaning an alkenyl- group or an alkynyl group having a whole number of carbon atoms from 2 to 6, i.e., 2, 3, 4, 5 or 6 carbon atoms. It is to be understood further that said term "$C_2$-$C_6$" is to be interpreted as disclosing any sub-range comprised therein, e.g., $C_2$-$C_6$, $C_3$-$C_5$, $C_3$-$C_4$, $C_2$-$C_3$, $C_2$-$C_4$, $C_2$—C; preferably $C_2$-$C_3$.

Further, as used herein, the term "$C_3$-$C_7$", as used throughout this text, e.g., in the context of the definition of "$C_3$-$C_7$-cycloalkyl-", is to be understood as meaning a cycloalkyl- group having a whole number of carbon atoms of 3 to 7, i.e., 3, 4, 5, 6 or 7 carbon atoms. It is to be understood further that said term "$C_3$-$C_7$" is to be interpreted as disclosing any sub-range comprised therein, e.g., $C_3$-$C_6$, $C_4$-$C_5$, $C_3$-$C_5$, $C_3$-$C_4$, $C_4$-$C_6$, $C_5$-$C_7$; preferably $C_3$-$C_6$.

As used herein, the term "leaving group" refers to an atom or a group of atoms that is displaced in a chemical reaction as stable species taking with it the bonding electrons, e.g., typically forming an anion. Preferably, a leaving group is selected from the group comprising: halo, in particular a chloro, bromo or iodo, (methylsulfonyl)oxy-, [(4-methylphenyl)sulfonyl]oxy-, [(trifluoromethyl)sulfonyl]oxy-, [(nonafluorobutyl)sulfonyl]oxy-, [(4-bromophenyl)sulfonyl]oxy-, [(4-nitrophenyl)sulfonyl]oxy-, [(2-nitrophenyl)sulfonyl]oxy-, [(4-isopropylphenyl)sulfonyl]oxy-, [(2,4,6-triisopropylphenyl)sulfonyl]oxy-, [(2,4,6-trimethylphenyl)sulfonyl]oxy-, [(4-tert-butylphenyl)sulfonyl]oxy-, (phenylsulfonyl)oxy-, and a [(4-methoxyphenyl)sulfonyl]oxy group.

As used herein, the term "protective group" is a protective group attached to an oxygen or nitrogen atom in intermediates used for the preparation of compounds of the general formula (I). Such groups are introduced e.g., by chemical modification of the respective hydroxy or amino group in order to obtain chemoselectivity in a subsequent chemical reaction. Protective groups for hydroxy and amino groups are described for example in T. W. Greene and P. G. M. Wuts in *Protective Groups in Organic Synthesis*, $4^{th}$ edition, Wiley 2006; more specifically, protective groups for amino groups can be selected from substituted sulfonyl groups, such as a mesyl-, tosyl- or a phenylsulfonyl group, acyl groups such as a benzoyl-, acetyl- or a tetrahydropyranoyl group, or carbamate based groups, such as a tert-butoxycarbonyl group (Boc). Protective groups for hydroxy groups can be selected from acyl groups such as a benzoyl-, acetyl, pivaloyl- or a tetrahydropyranoyl group, or can include silicon, as in e.g., a tert-butyldimethylsilyl-, tert-butyldiphenylsilyl-, triethylsilyl- or a triisopropylsilyl group.

The term "substituent" refers to a group "substituted" on, e.g., an alkyl-, haloalkyl-, cycloalkyl-, heterocyclyl-, heterocycloalkenyl-, cycloalkenyl-, aryl, or a heteroaryl group at any atom of that group, replacing one or more hydrogen atoms therein. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g. substituted with an H) or substituted.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valencies, etc., and to give compounds which are not inherently unstable. For example, any carbon atom will be bonded to two, three, or four other atoms, consistent with the four valence electrons of carbon.

By "subject" is meant a mammal, including, but not limited to, a human or non-human mammal, such as a bovine, equine, canine, ovine, rodent, or feline.

It is possible for the compounds of general formula (I) to exist as isotopic variants. The invention therefore includes one or more isotopic variant(s) of the compounds of general formula (I), particularly deuterium-containing compounds of general formula (I).

The invention also includes all suitable isotopic variations of a compound of the invention.

The term "isotopic variant" of a compound or a reagent is defined as a compound exhibiting an unnatural proportion of one or more of the isotopes that constitute such a compound.

The expression "unnatural proportion" in relation to an isotope means a proportion of such isotope which is higher than its natural abundance. The natural abundances of isotopes to be applied in this context are described in "Isotopic Compositions of the Elements 1997", Pure Appl. Chem., 70(1), 217-235, 1998.

An isotopic variation of a compound of the invention is defined as one in which at least one atom is replaced by an atom having the same atomic number but an atomic mass different from the atomic mass usually or predominantly found in nature.

Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S $^{36}$S, $^{18}$F, $^{36}$Cl, $^{82}$Br, $^{123}$I, $^{124}$I, $^{129}$I and $^{131}$I, respectively. Accordingly, recitation of "hydrogen" or "H" should be understood to encompass $^1$H (protium), $^2$H (deuterium), and $^3$H (tritium) unless otherwise specified. Certain isotopic variations of a compound of the invention, for example, those in which one or more radioactive isotopes such as 3H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

With respect to the treatment and/or prophylaxis of the disorders specified herein, the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3$H or $^{14}$C, are incorporated are useful, e.g., in drug and/or substrate tissue distribution studies. These isotopes are particularly preferred for the ease of their incorporation and detectability. Positron-emitting isotopes such as $^{18}$F or $^{11}$C may be incorporated into a compound of general formula (I). These isotopic variants of the compounds of general formula (I) are useful for in vivo imaging applications. Deuterium-containing and $^{13}$C-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g., Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g., Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g., lower number of doses or lower dosage to achieve the desired effect) and/or may produce lower metabolite loads.

A compound of general formula (I) may have multiple potential sites of vulnerability to metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g., cytochrome $P_{450}$.

For example, in some embodiments, the present invention concerns a deuterium-containing compound of general formula (I), e.g.:

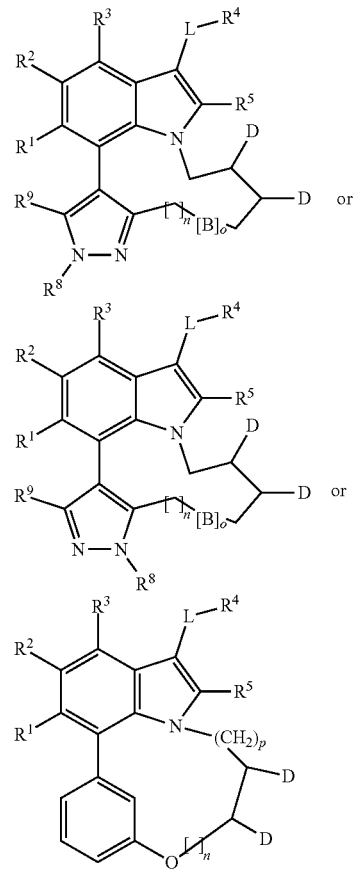

Such deuterium-containing compounds can be prepared by methods well-known to the person skilled in the art. Particularly, such deuterium-containing compounds can be prepared from the corresponding olefins, which are available by methods known to the person skilled in the art, such as ring closing metathesis reactions, as discussed e.g., in the general description of the synthesis of compounds of general formula (I), infra, in the context of Schemes 2c and 2j, respectively.

Where the plural form of the word compounds, salts, polymorphs, hydrates, solvates and the like, is used herein, this is taken to mean also a single compound, salt, polymorph, isomer, hydrate, solvate or the like. The terms "a" or "an," as used in herein means one or more.

By "stable compound' or "stable structure" is meant a compound that is sufficiently robust to survive isolation to a useful degree of purity from a reaction mixture, and formulation into an efficacious therapeutic agent.

Compounds of the present invention, as well as the corresponding macrocyclic intermediates of formula (II), are typically chiral merely as a result of restricted rotation around at least one single bond, which is due to limited comformational flexibility of their macrocyclic core as a whole or even of open chain precursors. Hence, compounds of the present invention as well as the corresponding macrocyclic intermediates of formula (II), can exist as atropisomers. Atropisomers represent a subclass of conformers which arise from restricted rotation around a single bond. The conformers (called atropisomers) can be isolated as separated species (IUPAC Gold book, http://qoldbook.iupac.orq/A00511.html; Pure and Appl. Chem., 2009, 68, 2193-2222). This induced chirality belongs to the axial type of chirality. The compounds of the present invention as well as the corresponding macrocyclic intermediates of formula (II), furthermore optionally contain one or more asymmetric centers, depending upon the location and nature of the various substituents desired. It is possible that one or more asymmetric carbon atoms are present in the (R) or (S) configuration, which can result in racemic mixtures in the case of a single asymmetric center, and in diastereomeric mixtures in the case of multiple asymmetric centers. Hence, compounds of the present invention, as well as the corresponding macrocyclic intermediates of formula (II), featuring the abovementioned atropisomerism and an additional asymmetric centre can also exist as diasteromeric mixtures as described supra.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

If only one isomer (enantiomer) displays the desired biological activity, and the second isomer (enantiomer) is inactive, the preferred isomer is the one which produces the more desirable biological activity. Should one isomer (enantiomer/diastereomer) display better activity than the other isomer (enantiomer/diastreromer) the preferred isomer is the one which produces the better biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials, enantioselective catalytic reactions, and other suitable methods.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, in any ratio. Isolation of a single stereoisomer, e.g., a single enantiomer or a single diastereomer, of a compound of the present invention may be achieved by any suitable method, such as chromatography, especially chiral chromatography, for example.

Further, it is possible for the compounds of the present invention to exist as tautomers. For example, any compound of the present invention which contains an pyrazol moiety as a heteroaryl group for example can exist as a 1H tautomer, or a 2H tautomer, or even a mixture in any amount of the two tautomers, namely:

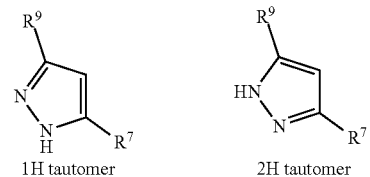

1H tautomer      2H tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

An embodiment of the invention are the compounds of formula (I) and a tautomer, an N-oxide, or a salt thereof, or a salt of a tautomer, or a salt of an N-oxide, or a mixture of same.

Another embodiment of the invention are the compounds of formula (I) and a tautomer, or a salt thereof, or a salt of a tautomer, or a mixture of same.

The present invention also includes useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention form a crystal that contains molecules of polar solvents, in particular water, methanol or ethanol, for example, as structural element of the crystal lattice of the compounds. The molecules of polar solvents, in particular water, may be present in a stoichiometric or non-stoichiometric ratio with the molecules of the compound. In the case of stoichiometric solvates, e.g., a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g., as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19. It includes any physiologically acceptable salt as referred to below.

Physiologically acceptable salts of the compounds according to the invention encompass acid addition salts of mineral acids, carboxylic acids and sulfonic acids, for example salts of hydrochloric acid, hydrobromic acid, hydroiodic acid, sulfuric acid, bisulfuric acid, phosphoric acid, nitric acid or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalenedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

A "pharmaceutically acceptable anion" refers to the deprotonated form of a conventional acid, such as, for example, a hydroxide, a carboxylate, a sulfate, a halide, a phosphate, or a nitrate.

Physiologically acceptable salts of the compounds according to the invention also comprise salts of conventional bases, such as, by way of example and by preference, alkali metal salts (for example lithium, sodium and potassium salts), alkaline earth metal salts (for example calcium, strontium and magnesium salts) and ammonium salts derived from ammonia or organic amines with 1 to 16 C atoms, such as, by way of example and by preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, dimethylglucamine, ethylglucamine, 1,6-hexadiamine, glucosamine, sarcosine, serinol, tris(hydroxymethyl) aminomethane, aminopropanediol, Sovak base, and 1-amino-2,3,4-butanetriol.

Additionally, the compounds according to the invention may form salts with a quaternary ammonium ion obtainable, e.g., by quaternisation of a basic nitrogen-containing group with agents such as lower alkylhalides, such as alkylchlorides, e.g. methylchloride, ethylchloride, propylchloride and butylchloride; such as alkylbromides, e.g. methylbromide, ethylbromide, propylbromide and butylbromide; and such as alkyliodides; e.g. methyliodide, ethyliodide, propyliodide and butyliodide; dialkylsulfates such as dimethylsulfate, diethylsulfate, dibutylsulfate and diamylsulfates, long chain halides such as e.g. decylchloride, laurylchloride, myristylchloride and stearylchloride, decylbromide, laurylbromide, myristylbromide and stearylbromide, decyliodide, lauryliodide, myristyliodide and stearyliodide, aralkylhalides such as benzylchloride, benzylbromide, benzyliodide and phenethylbromides and others. Examples of suitable quaternary ammonium ions are tetramethylammonium, tetraethylammonium, tetra(n-propyl)ammonium, tetra (n-butyl)ammonium, or N-benzyl-N,N,N-trimethylammonium.

The present invention includes all possible salts of the compounds of the present invention as single salts, or as any mixture of said salts, in any ratio.

Unless specified otherwise, suffixes to chemical names or structural formulae relating to salts, such as "hydrochloride", "trifluoroacetate", "sodium salt", or "x HCl", "x $CF_3COOH$", "x $Na^+$", for example, mean a salt form, the stoichiometry of which salt form not being specified.

Solvates and hydrates of disclosed intermediates or example compounds, or salts thereof, which have been obtained, by the preparation and/or purification processes described herein, may be formed in any ratio.

Furthermore, the present invention includes all possible crystalline forms, or polymorphs, of the compounds of the present invention, either as a single polymorph, or as a mixture of more than one polymorph, in any ratio.

Moreover, the present invention also includes prodrugs of the compounds according to the invention. The term "prodrugs" designates compounds which themselves can be biologically active or inactive, but are converted (for example metabolically or hydrolytically) into compounds according to the invention during their residence time in the body. For example, a prodrug may be in the form of an in vivo hydrolysable ester of the specified compound. Derivatives of the compounds of formula (I) and the salts thereof which are converted into a compound of formula (I) or a salt thereof in a biological system (bioprecursors or pro-drugs) are covered by the invention. Said biological system may be, for example, a mammalian organism, particularly a human subject. The bioprecursor is, for example, converted into the compound of formula (I) or a salt thereof by metabolic processes.

DESCRIPTION

In accordance with a first aspect, the present invention provides compounds of formula (I) in which
A is

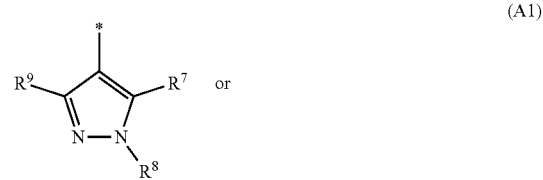

(A1)

or

(A2)

wherein $R^6$ and $R^7$, together with two carbon atoms of the pyrazole ring, two carbon atoms of the indole moiety and the nitrogen atom to which $R^6$ is attached, form a 9-membered to 16-membered ring and * is the point of attachment of these moieties to the indole carbon atom bearing the A substituent or
A is

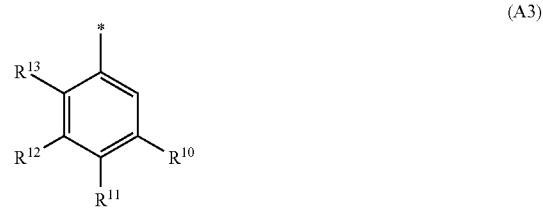

(A3)

wherein optionally one or two of the groups selected from $CR^{11}$, $CR^{12}$ or $CR^{13}$ may be replaced by a nitrogen atom,
wherein $R^6$ and $R^{10}$, together with three carbon atoms of the phenyl ring, two carbon atoms of the indole moiety and the nitrogen atom to which $R^6$ is attached, form a 9-membered to 16-membered ring and * is the point of attachment of these moieties to the indole carbon atom bearing the A substituent;

$R^1$ is a chlorine atom, $R^2$ and $R^3$ are each a hydrogen atom;

$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a $(C_1$-$C_3)$-haloalkyl-S— group, and a $C_3$-$C_5$-cycloalkyl group;

L is a group —$(CH_2)_m$-E- wherein any $CH_2$ group is unsubstituted or substituted with one or two substituents and each substituent is independently selected from a halogen atom, a cyano group, a hydroxy group, a $C_1$-$C_3$-alkyl group, and a $C_1$-$C_3$-alkoxy group, or two substituents are optionally taken together with their intervening atoms to form a saturated or partially unsaturated 3-membered to 6-membered cycloalkyl ring, or a 3-membered to 8-membered saturated or partially unsaturated heterocyclic ring having 1-2 heteroatoms independently selected from an oxygen atom, a sulfur atom, a —S(O)— group, a —S(O)$_2$— group, and a —NR$^{14}$— group;

E is a bond, an oxygen atom, a sulfur atom, a —S(O)— group, a —S(O)$_2$— group or a —NR$^{14}$— group and constitutes the connecting element to $R^4$;

m is 2, 3, or 4;

$R^5$ is selected from a COOH group, a

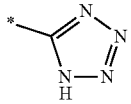

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl) group, and a —C(O)—NHS(O)$_2$(CH$_2$)$_s$NHCO(aryl) group;

s is 0, 1, 2, or 3;

—$R^6$-$R^7$— is selected from $^{\#}$—(CH$_2$)$_n$—(B)$_t$—(CH$_2$)$_p$—X—$^{\#\#}$, $^{\#}$—(C$_2$-C$_6$-alkenylene)-(B)$_t$—(CH$_2$)$_p$—X—$^{\#\#}$, $^{\#}$—(CH$_2$)$_n$—(B)$_t$—(C$_2$-C$_5$-alkenylene)-X—$^{\#\#}$, and $^{\#}$—(CH$_2$)$_q$—(B)—(CH$_2$)$_r$—(B)—(CH$_2$)$_v$—X—$^{\#\#}$,
wherein $^{\#}$ is the point of attachment with the indole nitrogen atom and $^{\#\#}$ is the point of attachment with the pyrazole carbon atom bearing the $R^7$ substituent; and
wherein one or more —CH$_2$— groups may be unsubstituted or substituted with one or more substituents independently selected from a halogen atom, a hydroxy group, a NR$^{16}$R$^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group, and a (heterocycloalkyl)-($C_1$-$C_3$-alkylene)- group, and wherein optionally, if two such substituents are bound to the same atom, they may form together a 3-membered to 6-membered spiro ring, and wherein a —CH=CH— group in any alkenylene can be replaced by a 1,2-($C_3$-$C_5$)cycloalkylene group which is unsubstituted or substituted one or two times with a halogen atom or a $C_1$-$C_2$-alkyl group; and where X is an unsubstituted —CH$_2$— group;

—$R^6$-$R^{10}$— is selected from $^{\#}$—(CH$_2$)$_n$—(B)$_t$—(CH$_2$)$_p$—X—$^{\#\#}$, $^{\#}$—(C$_2$-C$_6$-alkenylene)-(B)$_t$—(CH$_2$)$_p$—X—$^{\#\#}$, $^{\#}$—(CH$_2$)$_n$—(B)$_t$—(C$_2$-C$_5$-alkenylene)-X—$^{\#\#}$, and $^{\#}$—(CH$_2$)$_q$—(B)—(CH$_2$)$_r$—(B)—(CH$_2$)$_v$—X—$^{\#\#}$,
wherein $^{\#}$ is the point of attachment with the indole nitrogen atom and $^{\#\#}$ is the point of attachment with the carbon atom of the phenyl moiety bearing the $R^{10}$ substituent,
or more —CH$_2$— groups may be unsubstituted or substituted with one or more substituents independently selected from a halogen atom, a hydroxy group, a NR$^{16}$R$^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group, and a (heterocycloalkyl)-($C_1$-$C_3$-alkylene)- group,
wherein a double bond in any alkenylene can be replaced by a 1,2-($C_1$-$C_6$)cycloalkyl group which is unsubstituted or substituted one or two times with a halogen atom or a $C_1$-$C_2$-alkyl group, and where X is an unsubstituted —CH$_2$— group;

n is 2, 3, 4, 5, 6, 7, 8, or 9;

t is 0 or 1;

p is 0, 1, 2, 3, 4, or 5;

q is 2, 3, 4, 5, or 6;

r is 2, 3, 4, 5, or 6;

v is 0, or 1;

wherein the integers selected for variables n, t, p, q, r, and v result in forming a 9-membered to 16-membered ring independently from the selection of variable A1, A2 or A3;

B is independently selected from a —C(O)NR$^{15}$— group, a —NR$^{15}$C(O)— group, a —N(R$^{15}$)— group, a —N(R$^{15}$)—C(=O)—N(R$^{15}$)— group, a —O—C(=O)—N(R$^{15}$)— group, a —N(R$^{15}$)—C(=O)—O— group, —O—, —S—, —S(O)—, and —S(O)$_2$—;

$R^8$ is selected from a hydrogen atom,
a $C_1$-$C_6$-alkyl group, which is unsubstituted or substituted with one or more substituents independently selected from a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group, and a NR$^{20}$R$^{21}$ group;
a $C_1$-$C_3$-haloalkyl group,
a $C_3$-$C_6$-cycloalkyl group, and
a $C_1$-$C_6$-alkyl group in which one or two not directly adjacent carbon atoms are independently replaced by a hetero atom selected from —O— and —NH—;

$R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$)-cycloalkyl-O—($C_1$-$C_3$-alkylene)- group,
a phenyl-O—($C_1$-$C_3$-alkylene)- group,
a phenyl-($C_1$-$C_3$-alkylene)-O—($C_1$-$C_3$-alkylene)- group,
a $R^{18}$-(phenylene)-($C_1$-$C_3$-alkylene)-O—($C_1$-$C_3$-alkylene)- group, a $R^{18}$-(phenylene)-O—($C_1$-$C_3$-alkylene)- group,
a $R^{18}$-(phenylene)-(heteroarylene)-O—($C_1$-$C_3$-alkylene) group,
a ($R^{18}$)-(heterocycloalkylene)-($C_1$-$C_3$-alkylene)- group,
a ($R^{18}$)-(heterocycloalkylene)-(phenylene)-O—($C_1$-$C_3$-alkylene)- group,
a (heterocycloalkenyl)-(phenylene)-O—($C_1$-$C_3$-alkylene)- group,
a ($R^{18}$)-(heteroarylene)-($C_1$-$C_3$-alkylene)-O—($C_1$-$C_3$-alkylene)- group,
a ($R^{18}$)-(heteroarylene)-(phenylene)-O—($C_1$-$C_3$-alkylene)- group,
a ($R^{19}$)—S(O)$_2$-(phenylene)-O—($C_1$-$C_3$-alkylene)- group,
a ($R^{19}$)—S(O)$_2$—NH-(phenylene)-O—($C_1$-$C_3$-alkylene)- group,
a ($R^{19}$)—S(O)$_2$—NH-(phenylene)-O—($C_1$-$C_3$-alkylene)- group,
a ($R^{19}$)—S(O)$_2$—N($C_1$-$C_6$-alkyl)-(phenylene)-O—($C_1$-$C_3$-alkylene)- group,
a ($R^{19}$)—S(O)$_2$-(heterocycloalkylene)-(phenylene)-O—($C_1$-$C_3$-alkylene)- group,
a ($R^{18}$)-(heterocycloalkylene)-(heteroarylene)-O—($C_1$-$C_3$-alkylene)- group,
a ($R^{19}$)-(heteroarylene)-O—($C_1$-$C_3$-alkylene)- group,
a ($R^{18}$)-(heteroarylene)-O—($C_1$-$C_3$-alkylene)- group,
a ($R^{19}$)—S(O)$_2$-(heteroarylene)-O—($C_1$-$C_3$-alkylene)- group,
a ($R^{19}$)—S(O)$_2$-(heterocycloalkylene)-(heteroarylene)-O—($C_1$-$C_3$-alkylene)- group,
a $NR^{20}R^{21}$—($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-NH—C(O)—($C_1$-$C_3$-alkylene)- group,
a ($C_1$-$C_3$-alkyl)-$NR^{15}$—C(O)—($C_1$-$C_3$-alkylene)- group,
a ($C_1$-$C_3$-alkyl)-C(O)—NH—($C_1$-$C_3$-alkylene)- group,
a ($C_1$-$C_3$-alkyl)-C(O)—$NR^{15}$—($C_1$-$C_3$-alkylene)- group,
a

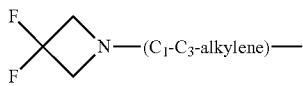

group, and a

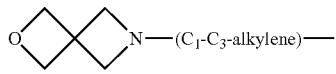

group, wherein the phenyl ring is unsubstituted or substituted with a halogen atom, a hydroxy group, or a $C_1$-$C_3$-alkoxy group and
the heterocycloalkyl group is unsubstituted or substituted with an oxo (═O) group or is unsubstituted or substituted with one or more substituents independently selected from a halogen atom, a hydroxy group, a $C_1$-$C_3$-alkyl group, and a $C_1$-$C_3$-alkoxy group,
or $R^8$ and $R^9$ together form a 5-membered or 6-membered ring optionally containing one or two heteroatoms selected from —O—, and —$NR^{14}$—;

$R^{11}$ and $R^{13}$ are each independently selected from a hydrogen atom, a halogen atom, a $C_1$-$C_3$-alkyl group, and a $C_1$-$C_3$-alkoxy group;
$R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group and a $NR^{16}R^{17}$ group;
$R^{14}$ is a hydrogen atom or a $C_1$-$C_3$-alkyl group;
$R^{15}$ is independently selected from a hydrogen atom,
  a $C_1$-$C_6$-alkyl group
    which is unsubstituted or substituted with one or more substituents selected from a halogen atom, a hydroxy group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a ($C_1$-$C_3$-alkyl)-C(O)—O— group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$-(heterocycloalkylene)-(arylene)-O— group, an (aryl)-(heteroarylene)-O— group, and an (aryl)-(heteroarylene)-O—($C_1$-$C_3$-alkylene)- group;
  a $C_1$-$C_3$-alkoxy-($C_1$-$C_6$-alkylen)-O—C(O)— group,
  a heterocycloalkyl-($C_1$-$C_6$-alkylen)-O—C(O)— group,
  a phenyl group,
  a group,

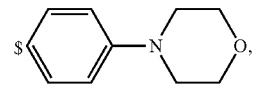

a group

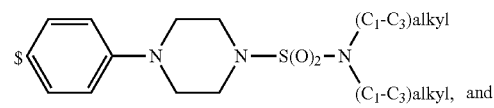

a group

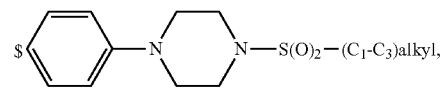

wherein $ is the point of attachment to the nitrogen atom, to which $R^{15}$ is attached,
$R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group, and a $C_1$-$C_3$-alkyl-O—C(═O)— group;
$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a C(O)O$R^{21}$—($C_1$-$C_3$-alkylene)- group, a —C(O)O$R^{21}$ group, a —C(O)$NR^{20}R^{21}$ group, a ($C_1$-$C_3$-alkyl)-O—($C_1$-$C_3$-alkylene)-C(O)— group, a ($C_1$-$C_6$-alkyl)-C(O)— group, and a $C_3$-$C_6$-cycloalkyl-C(O)— group;
$R^{19}$ is selected from a $C_1$-$C_3$-alkyl group, a $C_3$-$C_6$-cycloalkyl group, and a $NR^{20}R^{21}$ group; and
$R^{20}$ and $R^{21}$ are each independently selected from a hydrogen atom and a $C_1$-$C_6$-alkyl group;

or a tautomer, an N-oxide, or a salt thereof, or a salt of a tautomer, or a salt of an N-oxide, or a mixture of same.

Further Embodiments of the First Aspect of the Present Invention

In accordance with a further aspect, the present invention provides compounds of formula (I) in which
A is

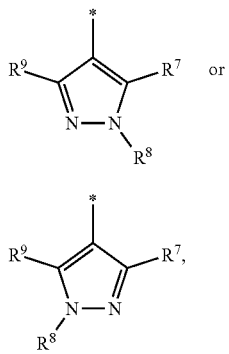

(A1)

(A2)

wherein $R^6$ and $R^7$, together with two carbon atoms of the pyrazole ring, two carbon atoms of the indole moiety and the nitrogen atom to which $R^6$ is attached, form a 9- to 16-membered ring and * is the point of attachment of these moieties to the indole carbon atom bearing the A substituent;
or
A is

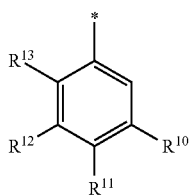

(A3)

wherein optionally one or two of the groups selected from $CR^{11}$, $CR^{12}$ or $CR^{13}$ may be replaced by a nitrogen atom,
wherein $R^6$ and $R^{10}$, together with three carbon atoms of the phenyl ring, two carbon atoms of the indole moiety and the nitrogen atom to which $R^6$ is attached, form a 9-membered to 16-membered ring and * is the point of attachment of these moieties to the indole carbon atom bearing the A substituent;
$R^1$ is a chlorine atom,
$R^2$ and $R^3$ are each a hydrogen atom;
$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a $(C_1$-$C_3)$-haloalkyl-S— group, and a $C_3$-$C_5$-cycloalkyl group;
L is a group —$(CH_2)_m$-E- wherein any $CH_2$ group is unsubstituted or substituted with one or two substituents and each substituent is independently selected from a halogen atom, a cyano group, a hydroxy group, a $C_1$-$C_3$-alkyl group, and a $C_1$-$C_3$-alkoxy group, or two substituents are optionally taken together with their intervening atoms to form a saturated or partially unsaturated 3-membered to 6-membered cycloalkyl ring, or a 3-membered to 8-membered saturated or partially unsaturated heterocyclic ring having 1-2 heteroatoms independently selected from an oxygen atom, a sulfur atom, a —S(O)— group, a —S(O)$_2$— group, and a —NR$^{14}$— group;
E is a bond, an oxygen atom, a sulfur atom, a —S(O)— group, a —S(O)$_2$— group or a —NR$^{14}$— group and constitutes the connecting element to $R^4$;
m is 2, 3, or 4;
$R^5$ is selected from a COOH group, a

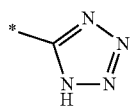

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl)- group, and a —C(O)—NHS(O)$_2$(CH$_2$)$_s$NHCO(aryl) group;
s is 0, 1, 2, or 3;
—$R^6$-$R^7$— is selected from $^\#$—(CH$_2$)$_n$—(B)$_t$—(CH$_2$)$_p$—X—$^{\#\#}$, $^\#$—(C$_2$-$C_6$-alkenylene)-(B)$_t$—(CH$_2$)$_p$—X—$^{\#\#}$, $^\#$—(CH$_2$)$_n$—(B)$_t$—(C$_2$-$C_5$-alkenylene)-X—$^{\#\#}$, and $^\#$—(CH$_2$)$_q$—(B)—(CH$_2$)$_r$—(B)—(CH$_2$)$_v$—X—$^{\#\#}$,
wherein $^\#$ is the point of attachment with the indole nitrogen atom and $^{\#\#}$ is the point of attachment with the pyrazole carbon atom bearing the $R^7$ substituent; and
wherein one or more —CH$_2$— groups may be unsubstituted or substituted with one or more substituents independently selected from a halogen atom, a hydroxy group, a NR$^{16}$R$^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group, and a (heterocycloalkyl)-($C_1$-$C_3$-alkylene)- group, and wherein optionally, if two such substituents are bound to the same atom, they may form together a 3-membered to 6-membered spiro ring, and
wherein a —CH=CH— group in any alkenylene can be replaced by a 1,2-($C_3$-$C_5$)cycloalkylene group which is unsubstituted or substituted one or two times with a halogen atom or a $C_1$-$C_2$-alkyl group; and where
X is an unsubstituted —CH$_2$— group;
—$R^6$-$R^{10}$— is selected from $^\#$—(CH$_2$)$_n$—(B)$_t$—(CH$_2$)$_p$—X—$^{\#\#}$, $^\#$—(C$_2$-$C_6$-alkenylene)-(B)$_t$—(CH$_2$)$_p$—X—$^{\#\#}$, $^\#$—(CH$_2$)$_n$—(B)$_t$—(C$_2$-$C_5$-alkenylene)-X—$^{\#\#}$ and $^\#$—(CH$_2$)$_q$—(B)—(CH$_2$)$_r$—(B)—(CH$_2$)$_v$—X—$^{\#\#}$,
wherein $^\#$ is the point of attachment with the indole nitrogen atom and $^{\#\#}$ is the point of attachment with the carbon atom of the phenyl moiety bearing the $R^{10}$ substituent,
or more —CH$_2$— groups may be unsubstituted or substituted with one or more substituents independently selected from a halogen atom, a hydroxy group, a NR$^{16}$R$^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group and a (heterocycloalkyl)-($C_1$-$C_3$-alkylene)- group,
wherein a double bond in any alkenylene can be replaced by a 1,2-($C_1$-$C_6$)cycloalkyl group which is unsubstituted or substituted one or two times with a halogen atom or a $C_1$-$C_2$-alkyl group, and where
X is an unsubstituted —$CH_2$— group;
n is 2, 3, 4, 5, 6, 7, 8, or 9;
t is 0 or 1;
p is 0, 1, 2, 3, 4, or 5;
q is 2, 3, 4, 5, or 6;
r is 2, 3, 4, 5, or 6;
v is 0, or 1;
wherein the integers selected for variables n, t, p, q, r, and v result in forming a 9-membered to 16-membered ring independently from the selection of variable A1, A2 or A3;
B is independently selected from a —C(O)$NR^{15}$— group, a —$NR^{15}$C(O)— group, a —N($R^{15}$)— group, a —N($R^{15}$)—C(=O)—N($R^{15}$)— group, a —O—C(=O)—N($R^{15}$)— group, a —N($R^{15}$)—C(=O)—O— group, —O—, —S—, —S(O)—, and —S(O)$_2$—:
$R^8$ is selected from a hydrogen atom,
 a $C_1$-$C_6$-alkyl group, which is unsubstituted or substituted with one or more substituents independently selected from
  a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group, and a $NR^{20}R^{21}$ group;
and
 a $C_3$-$C_6$-cycloalkyl group;
$R^9$ is selected from a hydrogen atom,
 a $C_1$-$C_4$-alkyl group,
 a $C_1$-$C_3$-hydroxyalkyl group,
 a $C_1$-$C_4$-haloalkyl group,
 a $C_1$-$C_4$-haloalkyl-NH—C(O)—O—($C_1$-$C_3$-alkylene)- group,
 a $C_2$-$C_6$-haloalkenyl group,
 a $C_1$-$C_6$-alkyl-O— group,
 a $C_1$-$C_4$-haloalkoxy group,
 a $C_1$-$C_6$-alkyl-O—($C_1$-$C_3$-alkylene)- group,
 a ($C_3$-$C_7$)-cycloalkyl group,
 a ($C_3$-$C_7$)-cycloalkyl-O—($C_1$-$C_3$-alkylene)- group,
 a phenyl-O—($C_1$-$C_3$-alkylene)- group,
 a phenyl-($C_1$-$C_3$-alkylene)-O—($C_1$-$C_3$-alkylene)- group,
 a $R^{18}$-(phenylene)-($C_1$-$C_3$-alkylene)-O—($C_1$-$C_3$-alkylene)- group,
 a $R^{18}$-(phenylene)-O—($C_1$-$C_3$-alkylene)- group,
 a $R^{18}$-(phenylene)-(heteroarylene)-O—($C_1$-$C_3$-alkylene) group,
 a ($R^{18}$)-(heterocycloalkylene)-($C_1$-$C_3$-alkylene)- group,
 a ($R^{18}$)-(heterocycloalkylene)-(phenylene)-O—($C_1$-$C_3$-alkylene)- group,
 a (heterocycloalkenyl)-(phenylene)-O—($C_1$-$C_3$-alkylene)- group,
 a ($R^{18}$)-(heteroarylene)-($C_1$-$C_3$-alkylene)-O—($C_1$-$C_3$-alkylene)- group,
 a ($R^{18}$)-(heteroarylene)-(phenylene)-O—($C_1$-$C_3$-alkylene)- group,
 a ($R^{19}$)—S(O)$_2$-(phenylene)-O—($C_1$-$C_3$-alkylene)- group,
 a ($R^{19}$)—S(O)$_2$—NH-(phenylene)-O—($C_1$-$C_3$-alkylene)- group,
 a ($R^{19}$)—S(O)$_2$—NH-(phenylene)-O—($C_1$-$C_3$-alkylene)- group,
 a ($R^{19}$)—S(O)$_2$—N($C_1$-$C_6$-alkyl)-(phenylene)-O—($C_1$-$C_3$-alkylene)- group,
 a ($R^{19}$)—S(O)$_2$-(heterocycloalkylene)-(phenylene)-O—($C_1$-$C_3$-alkylene)- group,
 a ($R^{18}$)-(heterocycloalkylene)-(heteroarylene)-O—($C_1$-$C_3$-alkylene)- group,
 a ($R^{19}$)-(heteroarylene)-O—($C_1$-$C_3$-alkylene)- group,
 a ($R^{18}$)-(heteroarylene)-O—($C_1$-$C_3$-alkylene)- group,
 a ($R^{19}$)—S(O)$_2$-(heteroarylene)-O—($C_1$-$C_3$-alkylene)- group,
 a ($R^{19}$)—S(O)$_2$-(heterocycloalkylene)-(heteroarylene)-O—($C_1$-$C_3$-alkylene)- group,
 a $NR^{20}R^{21}$—($C_1$-$C_3$-alkylene)- group,
 a ($C_1$-$C_3$-alkyl)-NH—($C_1$-$C_3$-alkylene)- group,
 a ($C_1$-$C_3$-haloalkyl)-($C_1$-$C_3$-alkylene)-NH—($C_1$-$C_3$-alkylene)- group,
 a ($C_1$-$C_3$-haloalkyl)-NH—($C_1$-$C_3$-alkylene)- group,
 a ($C_1$-$C_3$-alkyl)-NH—C(O)—($C_1$-$C_3$-alkylene)- group,
 a ($C_1$-$C_3$-alkyl)-$NR^{15}$—C(O)—($C_1$-$C_3$-alkylene)- group,
 a ($C_1$-$C_3$-alkyl)-C(O)—NH—($C_1$-$C_3$-alkylene)- group,
 a ($C_1$-$C_3$-alkyl)-C(O)—$NR^{15}$—($C_1$-$C_3$-alkylene)- group,
 a

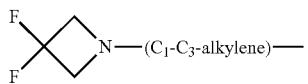

group, and a

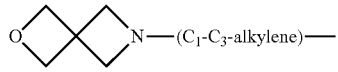

group, wherein the phenyl ring is unsubstituted or substituted with a halogen atom, a hydroxy group, or a $C_1$-$C_3$-alkoxy group and
 the heterocycloalkyl group is unsubstituted or substituted with an oxo (=O) group or is unsubstituted or substituted with one or more substituents independently selected from a halogen atom, a hydroxy group, a $C_1$-$C_3$-alkyl group, and a $C_1$-$C_3$-alkoxy group,
or $R^8$ and $R^9$ together form a 5-membered or 6-membered ring optionally containing one or two heteroatoms selected from —O—, and —$NR^{14}$—;
$R^{11}$ and $R^{13}$ are each independently selected from a hydrogen atom, a halogen atom, a $C_1$-$C_3$-alkyl group, and a $C_1$-$C_3$-alkoxy group;
$R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group, and a $NR^{16}R^{17}$ group;
$R^{14}$ is a hydrogen atom or a $C_1$-$C_3$-alkyl group;
$R^{15}$ is independently selected from a hydrogen atom,
 a $C_1$-$C_6$-alkyl group
  which is unsubstituted or substituted with one or more substituents selected from a halogen atom, a hydroxy group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a ($C_1$-$C_3$-alkyl)-C(O)—O— group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$-(heterocycloalkylene)-(arylene)-O— group, an (aryl)-(heteroarylene)-O— group, and an (aryl)-(heteroarylene)-O—($C_1$-$C_3$-alkylene)- group;
 a $C_1$-$C_3$-alkoxy-($C_1$-$C_6$-alkylen)-O—C(O)— group,
 a heterocycloalkyl-($C_1$-$C_6$-alkylen)-O—C(O)— group, a phenyl group,
a group

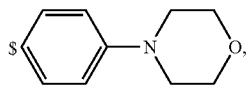

a group

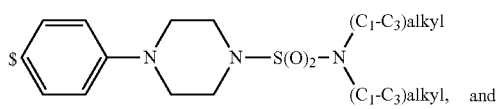

a group

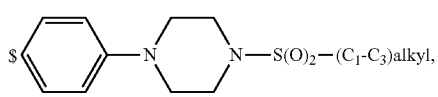

wherein $ is the point of attachment to the nitrogen atom, to which $R^{15}$ is attached, $R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group, and a $C_1$-$C_3$-alkyl-O—C(=O)— group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a C(O)OR$^{21}$—($C_1$-$C_3$-alkylene)- group, a —C(O)OR$^{21}$ group, a —C(O)NR$^{20}$R$^{21}$ group, a ($C_1$-$C_3$-alkyl)-O—($C_1$-$C_3$-alkylene)-C(O)— group, a ($C_1$-$C_6$-alkyl)-C(O)— group, and a $C_3$-$C_6$-cycloalkyl-C(O)— group;

$R^{19}$ is selected from a $C_1$-$C_3$-alkyl group, a $C_3$-$C_6$-cycloalkyl group, and a NR$^{20}$R$^{21}$ group; and $R^{20}$ and $R^{21}$ are each independently selected from a hydrogen atom and a $C_1$-$C_6$-alkyl group;

or a tautomer, an N-oxide, or a salt thereof, or a salt of a tautomer, or a salt of an N-oxide, or a mixture of same.

In accordance with a further aspect, the present invention provides compounds of general formula (I) in which A is

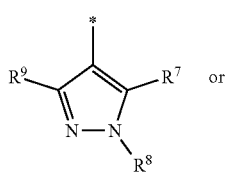
(A1)

or

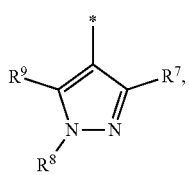
(A2)

wherein $R^6$ and $R^7$, together with two carbon atoms of the pyrazole ring, two carbon atoms of the indole moiety and the nitrogen atom to which $R^6$ is attached, form a 9-membered to 16-membered ring and * is the point of attachment of these moieties to the indole carbon atom bearing the A substituent $R^1$ is a chlorine atom;
$R^2$ and $R^3$ are each a hydrogen atom;
$R^4$ is selected from an aryl group and a heteroaryl group, each of which is unsubstituted or substituted with one, two, or three, substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group, and a $C_3$-$C_5$-cycloalkyl group;

L is a group —(CH$_2$)$_m$-E- wherein any CH$_2$ group is unsubstituted or substituted with one or two substituents and each substituent is independently selected from a halogen atom, a cyano group, a hydroxy group, a $C_1$-$C_3$-alkyl group and a $C_1$-$C_3$-alkoxy group, or two substituents are optionally taken together with their intervening atoms to form a saturated or partially unsaturated 3-membered to 6-membered cycloalkyl ring, or a 3-membered to 8-membered saturated or partially unsaturated heterocyclic ring having 1-2 heteroatoms independently selected from an oxygen atom, a sulfur atom, a —S(O)— group, a —S(O)$_2$— group, and a —NR$^{14}$— group;

E is a bond, an oxygen atom, a sulfur atom, a —S(O)— group, a —S(O)$_2$— group or a —NR$^{14}$— group and constitutes the connecting element to $R^4$;

$R^5$ is selected from a COOH group, a

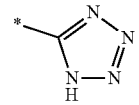

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl) group, and a —C(O)—NHS(O)$_2$(CH$_2$)$_s$NHCO(aryl) group;

s is 0, 1, 2, or 3;

—R$^6$-R$^7$— is selected from $^{\#}$—(CH$_2$)$_n$—(B)$_t$—(CH$_2$)$_p$—X—$^{\#\#}$, $^{\#}$—(C$_2$-C$_6$-alkenylene)-(B)$_t$—(CH$_2$)$_p$—X—$^{\#\#}$, $^{\#}$—(CH$_2$)$_n$—(B)$_t$—(C$_2$-C$_5$-alkenylene)-X—$^{\#\#}$, and $^{\#}$—(CH$_2$)$_q$—(B)—(CH$_2$)$_r$—(B)—(CH$_2$)$_v$—X—$^{\#\#}$, wherein $^{\#}$ is the point of attachment with the indole nitrogen atom and $^{\#\#}$ is the point of attachment with the pyrazole carbon atom bearing the $R^7$ substituent; and wherein one or more —CH$_2$— groups may be unsubstituted or substituted with one or more substituents independently selected from a halogen atom, a hydroxy group, a NR$^{16}$R$^{17}$ group, a $C_1$-$C_3$-alkyl group, a $C_1$-$C_3$-haloalkyl group, a $C_1$-$C_3$-alkoxy group, and a $C_1$-$C_3$-haloalkoxy group, and wherein optionally if two such substituents are bound to the same atom they may form together a 3- to 6-membered spiro ring, and wherein a —CH=CH— group in any alkenylene can be replaced by a 1,2-($C_3$-$C_5$)cycloalkylene group which is unsubstituted or substituted one or two times with a halogen atom or a $C_1$-$C_2$-alkyl group, and where X is an unsubstituted —CH$_2$— group;
n is 2, 3, 4, 5, 6, 7, 8, or 9;
p is 0, 1, 2, 3, 4, or 5;

t is 0 or 1;
wherein the integers selected for variables n, t, and p, result in forming a 9-membered to 16-membered ring independently from the selection of variable A1, or A2;
B is independently selected from a —C(O)NR$^{15}$— group, a —NR$^{15}$C(O)— group, a —N(R$^{15}$)— group, a —N(R$^{15}$)—C(=O)—N(R$^{15}$)— group, a —O—C(=O)—N(R$^{15}$)— group, a —N(R$^{15}$)—C(=O)—O— group, —O—, —S—, —S(O)—, and —S(O)$_2$—:
R$^8$ is selected from
 a hydrogen atom,
 a C$_1$-C$_6$-alkyl group, which is unsubstituted or substituted with one or more substituents independently selected from
  a halogen atom, a hydroxy group, a C$_1$-C$_3$-alkoxy group, a C$_1$-C$_3$-haloalkoxy group, a C$_3$-C$_6$-cycloalkyl group, a heterocycloalkyl group, and a NR$^{20}$R$^{21}$ group;
 and
 a C$_3$-C$_6$-cycloalkyl group;
R$^9$ is selected from a hydrogen atom,
 a C$_1$-C$_4$-alkyl group,
 a C$_1$-C$_3$-hydroxyalkyl group,
 a C$_1$-C$_4$-haloalkyl group,
 a C$_1$-C$_4$-haloalkyl-NH—C(O)—O—(C$_1$-C$_3$-alkylene)- group,
 a C$_2$-C$_6$-haloalkenyl group,
 a C$_1$-C$_6$-alkyl-O-group,
 a C$_1$-C$_4$-haloalkoxy group,
 a C$_1$-C$_6$-alkyl-O—(C$_1$-C$_3$-alkylene)- group,
 a (C$_3$-C$_7$)-cycloalkyl group,
 a (C$_3$-C$_7$-cycloalkyl)-O—(C$_1$-C$_3$-alkylene)- group,
 a phenyl-O—(C$_1$-C$_3$-alkylene)- group,
 a phenyl-(C$_1$-C$_3$-alkylene)-O—(C$_1$-C$_3$-alkylene)- group,
 a (R$^{18}$)-(phenylene)-O—(C$_1$-C$_3$-alkylene)- group,
 a (R$^{18}$)-(phenylene)-(C$_1$-C$_3$-alkylene)-O—(C$_1$-C$_3$-alkylene)- group,
 a (R$^{18}$)-(phenylene)-(heteroarylene)-O—(C$_1$-C$_3$-alkylene) group,
 a (R$^{18}$)-(heterocycloalkylene)-(C$_1$-C$_6$-alkylene)- group,
 a (R$^{18}$)-(heterocycloalkylene)-(phenylene)-O—(C$_1$-C$_3$-alkylene)- group,
 a (heterocycloalkenyl)-(phenylene)-O—(C$_1$-C$_3$-alkylene)- group,
 a (R$^{18}$)-(heteroarylene)-(C$_1$-C$_3$-alkylene)-O—(C$_1$-C$_3$-alkylene)- group,
 a (R$^{18}$)-(heteroarylene)-(phenylene)-O—(C$_1$-C$_3$-alkylene)- group,
 a (R$^{18}$)-(phenylene)-(C$_1$-C$_3$-alkylene)-O—(C$_1$-C$_3$-alkylene)- group,
 a (R$^{19}$)—S(O)$_2$-(phenylene)-O—(C$_1$-C$_3$-alkylene)- group,
 a (R$^{19}$)—S(O)$_2$—NH-(phenylene)-O—(C$_1$-C$_3$-alkylene)- group,
 a (R$^{19}$)—S(O)$_2$—N(C$_1$-C$_6$-alkyl)-(phenylene)-O—(C$_1$-C$_3$-alkylene)- group,
 a (R$^{19}$)—S(O)$_2$-(heterocycloalkylene)-(phenylene)-O—(C$_1$-C$_3$-alkylene)- group,
 a (R$^{18}$)-(heterocycloalkylene)-(heteroarylene)-O—(C$_1$-C$_3$-alkylene)- group,
 a (R$^{19}$)-(heteroarylene)-O—(C$_1$-C$_3$-alkylene)- group,
 a (R$^{19}$)—S(O)$_2$-(heteroarylene)-O—(C$_1$-C$_3$-alkylene)- group,
 a (R$^{19}$)—S(O)$_2$-(heterocycloalkylene)-(heteroarylene)-O—(C$_1$-C$_3$-alkylene)- group,
 a NR$^{20}$R$^{21}$—(C$_1$-C$_3$-alkylene)- group,
 a (C$_1$-C$_3$-alkyl)-NH—(C$_1$-C$_3$-alkylene)- group,
 a (C$_1$-C$_3$-haloalkyl)-(C$_1$-C$_3$-alkylene)-NH—(C$_1$-C$_3$-alkylene)- group,
 a (C$_1$-C$_3$-haloalkyl)-NH—(C$_1$-C$_3$-alkylene)- group,
 a (C$_1$-C$_3$-alkyl)-NH—C(O)—(C$_1$-C$_3$-alkylene)- group,
 a (C$_1$-C$_3$-alkyl)-NR$^{15}$—C(O)—(C$_1$-C$_3$-alkylene)- group,
 a (C$_1$-C$_3$-alkyl)-C(O)—NH—(C$_1$-C$_3$-alkylene)- group,
 a (C$_1$-C$_3$-alkyl)-C(O)—NR$^{15}$—(C$_1$-C$_3$-alkylene)- group,
 a
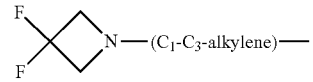
group, and a
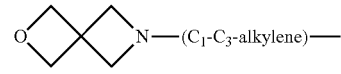
group, wherein the phenyl ring is optionally substituted with a halogen atom, a hydroxy group, or a C$_1$-C$_3$-alkoxy group and
 the heterocycloalkyl group is optionally substituted with an oxo (=O) group or is optionally substituted with one or more substituents independently selected from a halogen atom, and a C$_1$-C$_3$-alkyl group;
or R$^8$ and R$^9$ together form a 5-membered or 6-membered ring optionally containing one or two heteroatoms selected from of —O—, and —NR$^{14}$—;
R$^{14}$ is a hydrogen atom or a C$_1$-C$_3$-alkyl group;
R$^{15}$ is independently selected from a hydrogen atom,
 a C$_1$-C$_6$-alkyl group
  which is optionally substituted with one or more substituents selected from a halogen atom, a hydroxy group, a C$_1$-C$_3$-alkyl group, a C$_1$-C$_3$-haloalkyl group, a C$_1$-C$_3$-hydroxyalkyl group, a C$_1$-C$_3$-alkoxy group, a C$_1$-C$_3$-haloalkoxy group, a (C$_1$-C$_3$-alkyl)-C(O)—O— group, a heterocycloalkyl group, an aryl group, a (R$^{18}$)-(heterocycloalkylene)-(arylene)-O— group, an aryl-O— group, an aryl-(C$_1$-C$_3$-alkylene)-O— group, a (R$^{19}$)—S(O)$_2$— arylene-O— group, a (R$^{19}$)S(O)$_2$-heterocycloalkylene-arylene-O— group, and an aryl-heteroarylene-O— group;
 a C$_1$-C$_3$-alkoxy-(C$_1$-C$_6$-alkylen)-O—C(O)— group,
 a heterocycloalkyl-(C$_1$-C$_6$-alkylen)-O—C(O)— group,
 a phenyl group,
 a group
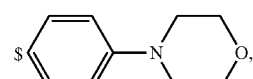
 a group
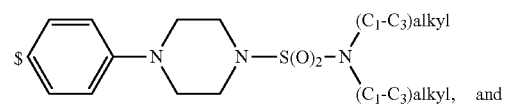
 a group
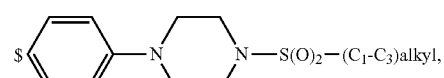

wherein $ is the point of attachment to the nitrogen atom, to which R$^{15}$ is attached;

R$^{16}$ and R$^{17}$ are each independently selected from a hydrogen atom, a C$_1$-C$_6$-alkyl group, a C$_1$-C$_6$-haloalkyl group, a C$_3$-C$_5$-cycloalkyl group, a C$_1$-C$_3$-alkyl-C(O)— group, a C$_1$-C$_3$-alkylS(O)$_2$— group, and a C$_1$-C$_3$-alkyl-O—C(=O)— group;

R$^{18}$ is selected from a hydrogen atom, a hydroxy group, a cyano group, a C$_1$-C$_3$-alkyl group, a C$_1$-C$_6$-hydroxyalkyl group, a C$_1$-C$_3$-alkoxy group, a C(O)OR$^{21}$—(C$_1$-C$_3$-alkylene)- group, a —C(O)OR$^{21}$ group, a —C(O)NR$^{20}$R$^{21}$ group, a (C$_1$-C$_3$-alkyl)-O—(C$_1$-C$_3$-alkylene)-C(O)— group, (C$_1$-C$_6$-alkyl)-C(O)— group, and a C$_3$-C$_6$-cycloalkyl-C(O)— group;

R$^{19}$ is selected from a C$_1$-C$_3$-alkyl group, a C$_3$-C$_6$-cycloalkyl group, and a NR$^{20}$R$^{21}$ group; and R$^{20}$ and R$^{21}$ are each independently selected from a hydrogen atom and a C$_1$-C$_6$-alkyl group;

or a tautomer, an N-oxide, or a salt thereof, or a salt of a tautomer, or a salt of an N-oxide, or a mixture of same.

In accordance with a further aspect, the present invention provides compounds of general formula (I) in which A is

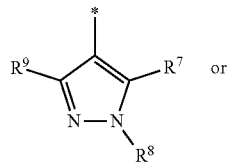

(A1)

or

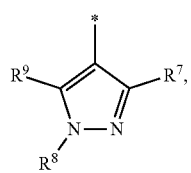

(A2)

wherein R$^6$ and R$^7$, together with two carbon atoms of the pyrazole ring, two carbon atoms of the indole moiety and the nitrogen atom to which R$^6$ is attached, form a 9-membered to 16-membered ring and * is the point of attachment of these moieties to the indole carbon atom bearing the A substituent R$^1$ is a chlorine atom;

R$^2$ and R$^3$ are each a hydrogen atom;

R$^4$ is selected from an aryl group and a heteroaryl group, each of which is unsubstituted or substituted with one, two, or three, substituents and each substituent is independently selected from a halogen atom, a cyano group, a C$_1$-C$_3$-alkyl group, a C$_1$-C$_3$-haloalkyl group, a C$_1$-C$_3$-alkoxy group, a C$_1$-C$_3$-thioalkyl group, a C$_1$-C$_3$-haloalkoxy group, and a (C$_1$-C$_3$)-haloalkyl-S— group, and a C$_3$-C$_5$-cycloalkyl group;

L is a group —(CH$_2$)$_m$-E- wherein any CH$_2$ group is unsubstituted or substituted with one or two substituents and each substituent is independently selected from a halogen atom, a cyano group, a hydroxy group, a C$_1$-C$_3$-alkyl group and a C$_1$-C$_3$-alkoxy group, or two substituents are optionally taken together with their intervening atoms to form a saturated or partially unsaturated 3-membered to 6-membered cycloalkyl ring, or a 3-membered to 8-membered saturated or partially unsaturated heterocyclic ring having 1-2 heteroatoms independently selected from an oxygen atom, a sulfur atom, a —S(O)— group, a —S(O)$_2$— group and a —NR$^{14}$— group;

E is a bond, an oxygen atom, a sulfur atom, a —S(O)— group, a —S(O)$_2$— group or a —NR$^{14}$— group and constitutes the connecting element to R$^4$;

R$^5$ is selected from a COOH group, a

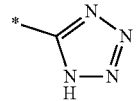

group, a —C(O)—NHS(O)$_2$(C$_1$-C$_6$-alkyl) group, a —C(O)—NHS(O)$_2$(C$_3$-C$_6$-cycloalkyl) group, a —C(O)—NHS(O)$_2$(aryl) group, a —C(O)—NHS(O)$_2$(CH$_2$)$_s$NHCO(C$_1$-C$_6$-alkyl) group, a —C(O)—NHS(O)$_2$(CH$_2$)$_s$NHCO(C$_3$-C$_6$-cycloalkyl) group and a —C(O)—NHS(O)$_2$(CH$_2$)$_s$NHCO(aryl) group;

s is 0, 1, 2, or 3;

—R$^6$-R$^7$— is selected from $^{\#}$—(CH$_2$)$_n$—(B)$_t$—(CH$_2$)$_p$—X—$^{\#\#}$, $^{\#}$—(C$_2$-C$_6$-alkenylene)-(B)$_t$—(CH$_2$)$_p$—X—$^{\#\#}$, $^{\#}$—(CH$_2$)$_n$—(B)$_t$—(C$_2$-C$_5$-alkenylene)-X—$^{\#\#}$, and $^{\#}$—(CH$_2$)$_q$—(B)—(CH$_2$)$_r$—(B)—(CH$_2$)$_v$—X—$^{\#\#}$, wherein $^{\#}$ is the point of attachment with the indole nitrogen atom and $^{\#\#}$ is the point of attachment with the pyrazole carbon atom bearing the R$^7$ substituent; and wherein one or more —CH$_2$— groups may be unsubstituted or substituted with one or more substituents independently selected from a halogen atom, a hydroxy group, a NR$^{16}$R$^{17}$ group, a C$_1$-C$_3$-alkyl group, a C$_1$-C$_3$-haloalkyl group, a C$_1$-C$_3$-alkoxy group, and a C$_1$-C$_3$-haloalkoxy group, and wherein optionally if two such substituents are bound to the same atom they may form together a 3-membered to 6-membered spiro ring, and wherein a —CH=CH— group in any alkenylene can be replaced by a 1,2-cyclopropylene group or a 1,2-cyclobutylene group, and where X is an unsubstituted —CH$_2$— group;

n is 2, 3, 4, 5, 6, 7, 8, or 9;

p is 0, 1, 2, 3, 4, or 5;

t is 0 or 1;

wherein the integers selected for variables n, t, and p, result in forming a 9-membered to 16-membered ring independently from the selection of variable A1, or A2;

B is independently selected from a —C(O)NR$^{15}$— group, a —NR$^{15}$C(O)— group, a —N(R$^{15}$)— group, a —N(R$^{15}$)—C(=O)—N(R$^{15}$)— group, a —O—C(=O)—N(R$^{15}$)— group, a —N(R$^{15}$)—C(=O)—O— group, —O—, —S—, —S(O)—, and —S(O)$_2$—;

R$^8$ is selected from a hydrogen atom,
  a C$_1$-C$_6$-alkyl group, which is unsubstituted or substituted with one or more substituents independently selected from
    a halogen atom, a hydroxy group, a C$_1$-C$_3$-alkoxy group, a C$_1$-C$_3$-haloalkoxy group,
    a C$_3$-C$_6$-cycloalkyl group, a heterocycloalkyl group, and a NR$^{20}$R$^{21}$ group;

R$^9$ is selected from a hydrogen atom,
  a C$_1$-C$_4$-alkyl group,
  a C$_1$-C$_3$-hydroxyalkyl group,
  a C$_1$-C$_4$-haloalkyl group,
  a C$_1$-C$_4$-haloalkyl-NH—C(O)—O—(C$_1$-C$_3$-alkylene)- group,
  a C$_2$-C$_6$-haloalkenyl group, a $C_1$-$C_6$-alkyl-O-group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$-cycloalkyl)-O—($C_1$-$C_3$-alkylene)- group,
a phenyl-O—($C_1$-$C_3$-alkylene)- group,
a phenyl-($C_1$-$C_3$-alkylene)-O—($C_1$-$C_3$-alkylene)- group,
a ($R^{18}$)-(phenylene)-O—($C_1$-$C_3$-alkylene)- group,
a ($R^{18}$)-(phenylene)-($C_1$-$C_3$-alkylene)-O—($C_1$-$C_3$-alkylene)- group,
a ($R^{18}$)-(phenylene)-(heteroarylene)-O—($C_1$-$C_3$-alkylene) group,
a ($R^{18}$)-(heterocycloalkylene)-($C_1$-$C_6$-alkylene)- group,
a ($R^{18}$)-(heterocycloalkylene)-(phenylene)-O—($C_1$-$C_3$-alkylene)- group,
a (heterocycloalkenyl)-(phenylene)-O—($C_1$-$C_3$-alkylene)- group,
a ($R^{18}$)-(heteroarylene)-($C_1$-$C_3$-alkylene)-O—($C_1$-$C_3$-alkylene)- group,
a ($R^{18}$)-(heteroarylene)-(phenylene)-O—($C_1$-$C_3$-alkylene)- group,
a ($R^{18}$)-(phenylene)-($C_1$-$C_3$-alkylene)-O—($C_1$-$C_3$-alkylene)- group,
a ($R^{19}$)—S(O)$_2$-(phenylene)-O—($C_1$-$C_3$-alkylene)- group,
a ($R^{19}$)—S(O)$_2$—NH-(phenylene)-O—($C_1$-$C_3$-alkylene)- group,
a ($R^{19}$)—S(O)$_2$—N($C_1$-$C_6$-alkyl)-(phenylene)-O—($C_1$-$C_3$-alkylene)- group,
a ($R^{19}$)—S(O)$_2$-(heterocycloalkylene)-(phenylene)-O—($C_1$-$C_3$-alkylene)- group,
a ($R^{18}$)-(heterocycloalkylene)-(heteroarylene)-O—($C_1$-$C_3$-alkylene)- group,
a ($R^{19}$)-(heteroarylene)-O—($C_1$-$C_3$-alkylene)- group,
a ($R^{19}$)—S(O)$_2$-(heteroarylene)-O—($C_1$-$C_3$-alkylene)- group,
a ($R^{19}$)—S(O)$_2$-(heterocycloalkylene)-(heteroarylene)-O—($C_1$-$C_3$-alkylene)- group,
a $NR^{20}R^{21}$—($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-NH—C(O)—($C_1$-$C_3$-alkylene)- group,
a ($C_1$-$C_3$-alkyl)-$NR^{15}$—C(O)—($C_1$-$C_3$-alkylene)- group,
a ($C_1$-$C_3$-alkyl)-C(O)—NH—($C_1$-$C_3$-alkylene)- group,
a ($C_1$-$C_3$-alkyl)-C(O)—$NR^{15}$—($C_1$-$C_3$-alkylene)- group,
a

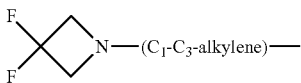

group, and a

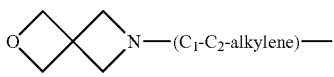

group, wherein the phenyl ring is optionally substituted with a halogen atom, a hydroxy group, or a $C_1$-$C_3$-alkoxy group and
the heterocycloalkyl group is optionally substituted with an oxo (═O) group or optionally substituted with one or more substituents independently selected from a halogen atom, and a $C_1$-$C_3$-alkyl group;
or $R^8$ and $R^9$ together form a 5-membered or 6-membered ring optionally containing one or two heteroatoms selected from of —O—, and —$NR^{14}$—;
$R^{14}$ is a hydrogen atom or a $C_1$-$C_3$-alkyl group;
$R^{15}$ is independently selected from a hydrogen atom,
a $C_1$-$C_6$-alkyl group,
which is optionally substituted with one or more substituents selected from a halogen atom, a hydroxy group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a ($C_1$-$C_3$-alkyl)-C(O)—O— group, a heterocycloalkyl group, an aryl group, a ($R^{18}$)-(heterocycloalkylene)-(arylene)-O— group, an aryl-O— group, an aryl-($C_1$-$C_3$-alkylene)-O— group, a ($R^{19}$)—S(O)$_2$— arylene-O— group, a ($R^{19}$)S(O)$_2$-heterocycloalkylene-arylene-O— group, and an aryl-heteroarylene-O— group;
a $C_1$-$C_3$-alkoxy-($C_1$-$C_6$-alkylen)-O—C(O)— group,
a heterocycloalkyl-($C_1$-$C_6$-alkylen)-O—C(O)— group,
a phenyl group,
a group

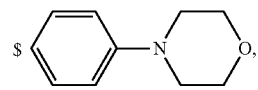

a group

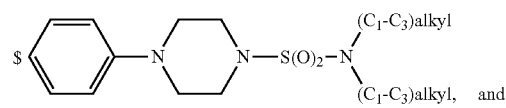

a group

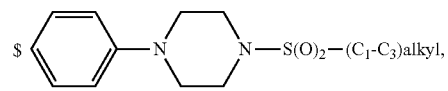

wherein $ is the point of attachment to the nitrogen atom, to which $R^{15}$ is attached;
$R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group, and a $C_1$-$C_3$-alkyl-O—C(═O)— group;
$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a C(O)$OR^{21}$—($C_1$-$C_3$-alkylene)- group, a —C(O)$OR^{21}$ group, a —C(O)$NR^{20}R^{21}$ group, a ($C_1$-$C_3$-alkyl)-O—($C_1$-$C_3$-alkylene)-C(O)— group, ($C_1$-$C_6$-alkyl)-C(O)— group, and a $C_3$-$C_6$-cycloalkyl-C(O)— group;
$R^{19}$ is selected from a $C_1$-$C_3$-alkyl group, a $C_3$-$C_6$-cycloalkyl group, and a $NR^{20}R^{21}$ group; and
$R^{20}$ and $R^{21}$ are each independently selected from a hydrogen atom and a $C_1$-$C_6$-alkyl group;
or a tautomer, an N-oxide, or a salt thereof, or a salt of a tautomer, or a salt of an N-oxide, or a mixture of same.

In accordance with a further aspect, the present invention provides compounds of general formula (I) in which A is

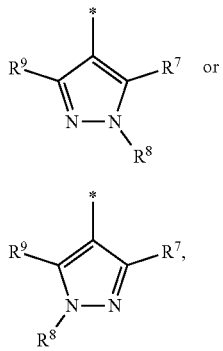

wherein $R^6$ and $R^7$, together with two carbon atoms of the pyrazole ring, two carbon atoms of the indole moiety and the nitrogen atom to which $R^6$ is attached, form a 10-membered to 12-membered ring and * is the point of attachment of these moieties to the indole carbon atom bearing the A substituent $R^1$ is a chlorine atom;

$R^2$ and $R^3$ are each a hydrogen atom;

$R^4$ is selected from an aryl group and a heteroaryl group, each of which is unsubstituted or substituted with one, two, or three, substituents and each substituent is independently selected from a halogen atom, a $C_1$-$C_3$-alkyl group, and a $C_1$-$C_3$-haloalkyl group;

L is a group —$(CH_2)_m$-E-;

E is a bond or an oxygen atom and constitutes the connecting element to $R^4$;

m is 2, 3, or 4;

$R^5$ is a COOH group;

—$R^6$-$R^7$— is selected from $^\#$—$(CH_2)_n$—$(B)_t$—$(CH_2)_p$—X—$^{\#\#}$, and $^\#$—$(C_2$-$C_6$-alkenylene)-$(B)_t$—$(CH_2)_p$—X—$^{\#\#}$, and wherein a double bond in any alkenylene can be replaced by an unsubstituted a 1,2-($C_3$-$C_5$-cycloalkyl) group, wherein $^\#$ is the point of attachment with the indole nitrogen atom and $^{\#\#}$ is the point of attachment with the pyrazole carbon atom bearing the $R^7$ substituent; and wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, and a $C_1$-$C_3$-alkoxy group, and wherein optionally if two such substituents are bound to the same atom they may form together a 3-membered to 6-membered spiro ring; and wherein a —CH=CH— group in any alkenylene can be replaced by a 1,2-($C_3$-$C_5$)cycloalkylene group which is unsubstituted or substituted one or two times with a halogen atom or a $C_1$-$C_2$-alkyl group, and where X is an unsubstituted —$CH_2$— group;

n is 3, 4, 5, or 6;

t is 0 or 1;

p is 0;

wherein the integers selected for variables n, t, and p, result in forming a 10-membered to 12-membered ring independently from the selection of variable A1 or A2;

B is independently selected from a —$N(R^{15})$— group and —O— group;

$R^8$ is selected from a hydrogen atom and,
a $C_1$-$C_4$-alkyl group, which is unsubstituted or substituted with one or more substituents independently selected from a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group, and a $NR^{20}R^{21}$ group;

$R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_2$-$C_6$-haloalkenyl group,
a $C_1$-$C_6$-alkyl-O—($C_1$-$C_3$-alkylene)- group,
a ($C_3$-$C_7$-cycloalkyl) group,
a phenyl-O—($C_1$-$C_3$-alkylene)- group,
a ($R^{18}$)-(phenylene)-O—($C_1$-$C_3$-alkylene)- group,
a ($R^{18}$)-(heterocycloalkylene)-($C_1$-$C_3$-alkylene)- group,
a ($R^{18}$)-(heteroarylene)-O—($C_1$-$C_3$-alkylene)- group,
a ($R^{19}$)—$S(O)_2$-(heteroarylene)-O—($C_1$-$C_3$-alkylene)- group,
a $NR^{20}R^{21}$—($C_1$-$C_3$-alkylene)- group, and
a ($C_1$-$C_3$-alkyl)-NH—($C_1$-$C_3$-alkylene)- group,
wherein the phenyl group is unsubstituted or substituted with a halogen atom, a hydroxy group, or a $C_1$-$C_3$-alkoxy group and
the heterocycloalkylene group is unsubstituted or substituted with a substituent independently selected from an oxo (=O) group and a $C_1$-$C_3$-alkyl group;

or $R^8$ and $R^9$ together form 6-membered ring optionally containing one or two oxygen atoms;

$R^{15}$ is selected from a hydrogen atom,
a $C_1$-$C_5$-alkyl group, which is optionally substituted with one or more substituents selected from a halogen atom, a hydroxy group, a $C_1$-$C_3$-alkyl group, a $C_1$-$C_3$-haloalkyl group, a $C_1$-$C_3$-hydroxyalkyl group, a $C_1$-$C_3$-alkoxy group, a ($C_1$-$C_3$-alkyl)-C(O)—O— group, a heterocycloalkyl group, a phenyl group, and a benzyl group;

a $C_1$-$C_3$-alkoxy-($C_1$-$C_6$-alkylen)-O—C(O)— group,
a heterocycloalkyl-($C_1$-$C_6$-alkylen)-O—C(O)— group,
a phenyl group,
a group

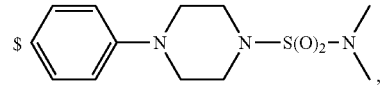

a group

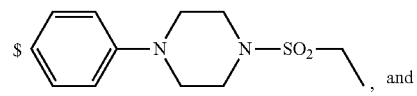
, and a group

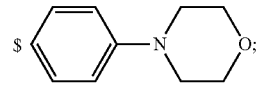

wherein $ is the point of attachment to the nitrogen atom, to which $R^{15}$ is attached, $R^{16}$ and $R^{17}$ are each independently selected from a hydrogen atom, a $C_1$-$C_6$-alkyl group, and a $C_1$-$C_6$-haloalkyl group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a C(O)OR$^{21}$—($C_1$-$C_3$-alkylene)- group, a —C(O)OR$^{21}$ group, a —C(O)NR$^{20}$R$^{21}$ group, a ($C_1$-$C_3$-alkyl)-O—($C_1$-$C_3$-alkylene)-C(O)— group, a ($C_1$-$C_3$-alkyl)-C(O)— group, and a $C_3$-$C_6$-cycloalkyl-C(O)— group;

$R^{19}$ is selected from a $C_1$-$C_3$-alkyl group, a $C_3$-$C_6$-cycloalkyl group, and a NR$^{20}$R$^{21}$ group; and $R^{20}$ and $R^{21}$ are each independently selected from a hydrogen atom, and a $C_1$-$C_3$-alkyl group;

or a tautomer, an N-oxide, or a salt thereof, or a salt of a tautomer, or a salt of an N-oxide, or a mixture of same.

In accordance with a further aspect, the present invention provides compounds of general formula (I) in which A is

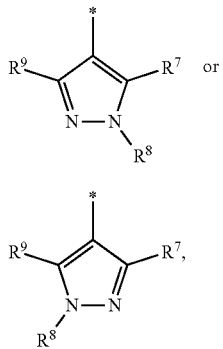

(A1)

(A2)

wherein $R^6$ and $R^7$, together with two carbon atoms of the pyrazole ring, two carbon atoms of the indole moiety and the nitrogen atom to which $R^6$ is attached, form a 10-membered to 12-membered ring and * is the point of attachment of these moieties to the indole carbon atom bearing the A substituent $R^1$ is a chlorine atom;

$R^2$ and $R^3$ are each a hydrogen atom;

$R^4$ is selected from an aryl group and a heteroaryl group, each of which is unsubstituted or substituted with one, two, or three, substituents and each substituent is independently selected from a halogen atom, a $C_1$-$C_3$-alkyl group, and a $C_1$-$C_3$-haloalkyl group;

L is a group —(CH$_2$)$_m$-E-;

E is a bond or an oxygen atom and constitutes the connecting element to $R^4$;

m is 2, 3, or 4;

$R^5$ is a COOH group;

—$R^6$-$R^7$— is selected from $^\#$—(CH$_2$)$_n$—(B)$_t$—(CH$_2$)$_p$—X—$^{\#\#}$, and $^\#$—(C$_2$-C$_6$-alkenylene)-(B)$_t$—(CH$_2$)$_p$—X—$^{\#\#}$, wherein $^\#$ is the point of attachment with the indole nitrogen atom and $^{\#\#}$ is the point of attachment with the pyrazole carbon atom bearing the $R^7$ substituent; and wherein one or more —CH$_2$— groups may be unsubstituted or substituted with one or more substituents independently selected from a halogen atom, a hydroxy group, a NR$^{16}$R$^{17}$ group, a $C_1$-$C_3$-alkyl group, a $C_1$-$C_3$-haloalkyl group, and a $C_1$-$C_3$-alkoxy group; and wherein optionally if two such substituents are bound to the same atom they may form together a 3-membered to 6-membered spiro ring; and wherein a —CH=CH— group in any alkenylene can be replaced by a 1,2-(C$_3$-C$_5$)cycloalkylene group which is unsubstituted or substituted one or two times with a halogen atom or a $C_1$-$C_2$-alkyl group; and where X is an unsubstituted —CH$_2$— group;

n is 3, 4, 5, or 6;

t is 0 or 1;

p is 0;

wherein the integers selected for variables n, t, and p, result in forming a 10-membered to 12-membered ring independently from the selection of variable A1 or A2;

B is independently selected from a —N(R$^{15}$)— group and —O— group;

$R^8$ is selected from a hydrogen atom and, a $C_1$-$C_4$-alkyl group, which is unsubstituted or substituted with one or more substituents independently selected from a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group, and a NR$^{20}$R$^{21}$ group;

$R^9$ is selected from a hydrogen atom, a $C_1$-$C_4$-alkyl group, a $C_1$-$C_3$-hydroxyalkyl group, a $C_1$-$C_4$-haloalkyl group, a $C_2$-$C_6$-haloalkenyl group, a $C_1$-$C_6$-alkyl-O—(C$_1$-$C_3$-alkylene)- group, a (C$_3$-$C_7$-cycloalkyl) group, a phenyl-O—(C$_1$-$C_3$-alkylene)- group, a (R$^{18}$)-(phenylene)-O—(C$_1$-$C_3$-alkylene)- group, a (R$^{18}$)-(heterocycloalkylene)-(C$_1$-$C_3$-alkylene)- group, a (R$^{18}$)-(heteroarylene)-O—(C$_1$-$C_3$-alkylene)- group, a (R$^{19}$)—S(O)$_2$-(heteroarylene)-O—(C$_1$-$C_3$-alkylene)- group, a NR$^{20}$R$^{21}$—(C$_1$-$C_3$-alkylene)- group, and a (C$_1$-$C_3$-alkyl)-NH—(C$_1$-$C_3$-alkylene)- group, wherein the phenyl group is unsubstituted or substituted with a halogen atom, a hydroxy group, or a $C_1$-$C_3$-alkoxy group and the heterocycloalkylene group is unsubstituted or substituted with a substituent independently selected from an oxo (=O) group and a $C_1$-$C_3$-alkyl group; or $R^8$ and $R^9$ together form 6-membered ring optionally containing one or two oxygen atoms;

$R^{15}$ is selected from a hydrogen atom, a $C_1$-$C_5$-alkyl group, which is optionally substituted with one or more substituents selected from a halogen atom, a hydroxy group, a $C_1$-$C_3$-alkyl group, a $C_1$-$C_3$-haloalkyl group, a $C_1$-$C_3$-hydroxyalkyl group, a $C_1$-$C_3$-alkoxy group, a (C$_1$-$C_3$-alkyl)-C(O)—O— group, a heterocycloalkyl group, a phenyl group, and a benzyl group;

a $C_1$-$C_3$-alkoxy-(C$_1$-$C_6$-alkylen)-O—C(O)— group, a heterocycloalkyl-(C$_1$-$C_6$-alkylen)-O—C(O)— group, a phenyl group, a group

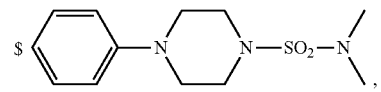

a group

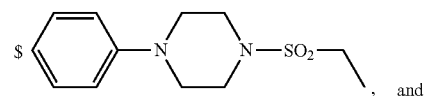

, and a group

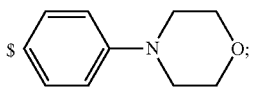 [SMILES: c1ccc(N2CCOCC2)cc1]

$R^{16}$ and $R^{17}$ are each independently selected from a hydrogen atom, a $C_1$-$C_6$-alkyl group, and a $C_1$-$C_6$-haloalkyl group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a $C(O)OR^{21}$—($C_1$-$C_3$-alkylene)- group, a —$C(O)OR^{21}$ group, a —$C(O)NR^{20}R^{21}$ group, a ($C_1$-$C_3$-alkyl)-O—($C_1$-$C_3$-alkylene)-C(O)— group, a ($C_1$-$C_3$-alkyl)-C(O)— group, and a $C_3$-$C_6$-cycloalkyl-C(O)— group;

$R^{19}$ is selected from a $C_1$-$C_3$-alkyl group, a $C_3$-$C_6$-cycloalkyl group, and a $NR^{20}R^{21}$ group; and $R^{20}$ and $R^{21}$ are each independently selected from a hydrogen atom and a $C_1$-$C_3$-alkyl group;

or a tautomer, an N-oxide, or a salt thereof, or a salt of a tautomer, or a salt of an N-oxide, or a mixture of same.

In accordance with a further aspect, the present invention provides compounds of general formula (I) in which A is

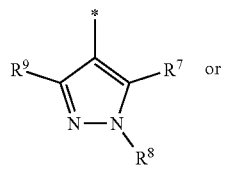

(A1)

(A2)

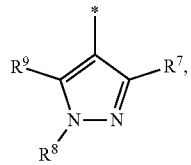

wherein $R^6$ and $R^7$, together with two carbon atoms of the pyrazole ring, two carbon atoms of the indole moiety and the nitrogen atom to which $R^6$ is attached, form a 10-membered or 11-membered ring and * is the point of attachment of these moieties to the indole carbon atom bearing the A substituent $R^1$ is a chlorine atom;

$R^2$ and $R^3$ are each a hydrogen atom;

$R^4$ is an aryl group which is unsubstituted or substituted with a halogen atom;

L is a group —$(CH_2)_m$-E-;

E is an oxygen atom and constitutes the connecting element to $R^4$;

m is 3;

$R^5$ is a COOH group;

—$R^6$-$R^7$— is selected from #—$(CH_2)_n$—(B)$_t$—$(CH_2)_p$—X—##, and #—($C_2$-$C_6$-alkenylene)-(B)$_t$—$(CH_2)_p$—X—##, and wherein # is the point of attachment with the indole nitrogen atom and ## is the point of attachment with the pyrazole carbon atom bearing the $R^7$ substituent, and wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, and a $C_1$-$C_3$-alkoxy group, and wherein optionally if two such substituents are bound to the same atom they may form together a 3-membered to 6-membered spiro ring, and wherein a —CH=CH— group in any alkenylene can be replaced by a 1,2-($C_3$-$C_5$)cycloalkylene group and where X is an unsubstituted —$CH_2$— group;

n is 3, 4, 5, or 6;

t is 0 or 1;

p is 0;

wherein the integers selected for variables n, t, and p, result in forming a 10-membered to 11-membered ring independently from the selection of variable A1 or A2;

B is independently selected from —O— and —N($R^{15}$)—;

$R^8$ is selected from a hydrogen atom and,
a $C_1$-$C_4$-alkyl group, which is unsubstituted or substituted with one or more substituents independently selected from a halogen atom, a hydroxy group, a $C_3$-$C_6$-cycloalkyl group, and a heterocycloalkyl group;

$R^9$ is a $C_1$-$C_4$-alkyl group,
a $C_1$-$C_3$-hydroxyalkyl group,
a $C_1$-$C_3$-haloalkyl group,
a $C_1$-$C_3$-alkyl-O— group,
a $C_1$-$C_3$-haloalkoxy group,
a $C_1$-$C_3$-alkyl-O—($C_1$-$C_3$-alkylene)- group,
a ($C_3$-$C_6$)-cycloalkyl group,
a $R^{18}$-(phenylene)-O—($C_1$-$C_3$-alkylene)- group,
a $NR^{20}R^{21}$—($C_1$-$C_3$-alkylene)- group, and
a ($C_1$-$C_3$-alkyl)-NH—($C_1$-$C_3$-alkylene)- group;

$R^{15}$ is selected from a hydrogen atom, a $C_1$-$C_3$-alkyl group, a $C_1$-$C_3$-haloalkyl group, a $C_1$-$C_5$-hydroxyalkyl group, a ($C_1$-$C_3$-alkyoxy)-($C_1$-$C_3$-alkylene)- group, a ($C_1$-$C_3$-alkyl)-C(O)—O—($C_1$—$C_4$)alkylene- group, a ($C_1$-$C_3$-alkyoxy)-($C_1$-$C_3$-alkylene)-O—C(O)— group, a heterocycloalkyl-($C_1$-$C_3$-alkylene)-O—C(O)— group, and a heterocycloalkyl-($C_1$-$C_3$-alkylene)- group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a —$C(O)OR^{21}$ group, a —$C(O)NR^{20}R^{21}$ group, and ($C_1$-$C_6$-alkyl)-C(O)— group;

$R^{20}$ and $R^{21}$ are each independently selected from a hydrogen atom, and a $C_1$-$C_3$-alkyl group;

or a tautomer, or a salt thereof or a salt of a tautomer or a mixture of same.

In accordance with a further aspect, the present invention provides compounds of general formula (I) in which A is

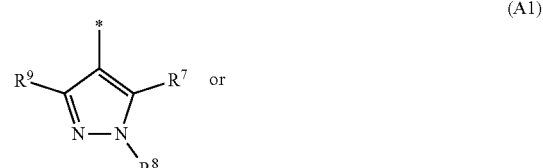

(A1)

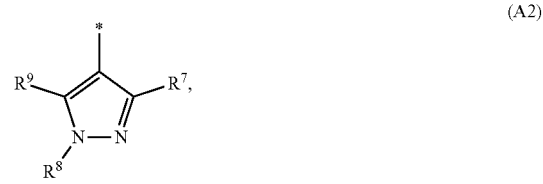

(A2)

wherein R⁶ and R⁷, together with two carbon atoms of the pyrazole ring, two carbon atoms of the indole moiety and the nitrogen atom to which R⁶ is attached, form a 10-membered or 11-membered ring and * is the point of attachment of these moieties to the indole carbon atom bearing the A substituent;
R¹ is a chlorine atom;
R² and R³ are each a hydrogen atom;
R⁴ is an aryl group which is unsubstituted or substituted with a halogen atom;
L is a group —(CH₂)$_m$-E-;
E is an oxygen atom and constitutes the connecting element to R⁴;
m is 3;
R⁵ is a COOH group;
—R⁶-R⁷— is selected from #—(CH₂)$_n$—(B)$_t$—(CH₂)$_p$—X—##, and #—(C₂-C₆-alkenylene)-(B)$_t$—(CH₂)$_p$—X—##, and
  wherein # is the point of attachment with the indole nitrogen atom and ## is the point of attachment with the pyrazole carbon atom bearing the R⁷ substituent, and
  wherein one or more —CH₂— groups may be unsubstituted or substituted with one or more substituents independently selected from a halogen atom, a hydroxy group, a NR¹⁶R¹⁷ group, a C₁-C₃-alkyl group, a C₁-C₃-haloalkyl group, and a C₁-C₃-alkoxy group;
  and wherein optionally if two such substituents are bound to the same atom they may form together a 3-membered to 6-membered spiro ring, and
  wherein a —CH=CH— group in any alkenylene can be replaced by a 1,2-(C₃-C₅)cycloalkylene group and where
X is an unsubstituted —CH₂— group;
n is 3 or 4;
t is 1;
p is 0
  wherein the integers selected for variables n, t, and p, result in forming a 10-membered to 11-membered ring independently from the selection of variable A1 or A2;
B is independently selected from —O— and —N(R¹⁵)—;
R⁸ is selected from a hydrogen atom and,
  a C₁-C₄-alkyl group, which is unsubstituted or substituted with one or more substituents independently selected from a halogen atom, a hydroxy group, a C₃-C₆-cycloalkyl group, and a heterocycloalkyl group;
R⁹ is a C₁-C₄-alkyl group,
  a C₁-C₃-hydroxyalkyl group,
  a C₁-C₃-haloalkyl group,
  a C₁-C₃-alkyl-O— group,
  a C₁-C₃-haloalkoxy group,
  a C₁-C₃-alkyl-O—(C₁-C₃-alkylene)- group,
  a (C₃-C₆)-cycloalkyl group,
  a R¹⁸-(phenylene)-O—(C₁-C₃-alkylene)- group,
  a NR²⁰R²¹—(C₁-C₃-alkylene)- group, and
  a (C₁-C₃-alkyl)-NH—(C₁-C₃-alkylene)- group;
R¹⁵ is selected from a hydrogen atom, a C₁-C₃-alkyl group, a C₁-C₃-haloalkyl group, a C₁-C₅-hydroxyalkyl group, a (C₁-C₃-alkyoxy)-(C₁-C₃-alkylene)- group, a (C₁-C₃-alkyl)-C(O)—O—(C₁-C₄)alkylene- group, a (C₁-C₃-alkyoxy)-(C₁-C₃-alkylene)-O—C(O)— group, a heterocycloalkyl-(C₁-C₃-alkylene)-O—C(O)— group, and a heterocycloalkyl-(C₁-C₃-alkylene)- group;
R¹³ is selected from a hydrogen atom, a hydroxy group, a cyano group, a C₁-C₃-alkyl group, a C₁-C₆-hydroxyalkyl group, a C₁-C₃-alkoxy group, a —C(O)OR²¹ group, a —C(O)NR²⁰R²¹ group, and (C₁-C₆-alkyl)-C(O)— group;

R²⁰ and R²¹ are each independently selected from a hydrogen atom, and a C₁-C₃-alkyl group;
or a tautomer, or a salt thereof or a salt of a tautomer or a mixture of same.

In accordance with a further aspect, the present invention provides compounds of general formula (I) in which A is

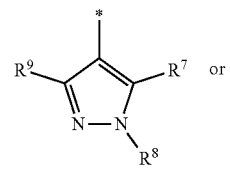

(A1)

or

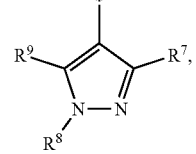

(A2)

wherein R⁶ and R⁷, together with two carbon atoms of the pyrazole ring, two carbon atoms of the indole moiety and the nitrogen atom to which R⁶ is attached, form a 10-membered or 11-membered ring and * is the point of attachment of these moieties to the indole carbon atom bearing the A substituent
R¹ is a chlorine atom;
R² and R³ are each a hydrogen atom;
R⁴ is an aryl group which is unsubstituted or substituted with a halogen atom;
L is a group —(CH₂)$_m$-E-;
E is an oxygen atom and constitutes the connecting element to R⁴;
m is 3;
R⁵ is a COOH group;
—R⁶-R⁷— is selected from #—(CH₂)$_n$—(B)$_t$—(CH₂)$_p$—X—##, and #—(C₂-C₆-alkenylene)-(B)$_t$—(CH₂)$_p$—X—##, and
  wherein # is the point of attachment with the indole nitrogen atom and ## is the point of attachment with the pyrazole carbon atom bearing the R⁷ substituent, and
  wherein one or more —CH₂— groups may be unsubstituted or substituted with one or more substituents independently selected from a halogen atom, a hydroxy group, a NR¹⁶R¹⁷ group, a C₁-C₃-alkyl group, a C₁-C₃-haloalkyl group, and a C₁-C₃-alkoxy group,
  and wherein optionally if two such substituents are bound to the same atom they may form together a 3-membered to 6-membered spiro ring, and
  wherein a —CH=CH— group in any alkenylene can be replaced by a 1,2-(C₃-C₅)cycloalkylene group and where
X is an unsubstituted —CH₂— group;
n is 3 or 4;
t is 1;
p is 0;
  wherein the integers selected for variables n, t, and p, result in forming a 10-membered to 11-membered ring independently from the selection of variable A1 or A2;
B is independently selected from —O— and —N(R¹⁵)—;
R⁸ is selected from a hydrogen atom and, a C$_1$-C$_4$-alkyl group, which is unsubstituted or substituted with one or more substituents independently selected from a halogen atom, a hydroxy group, a C$_3$-C$_6$-cycloalkyl group and a heterocycloalkyl group;

R$^9$ is a C$_1$-C$_4$-alkyl group,
a C$_1$-C$_3$-hydroxyalkyl group,
a C$_1$-C$_3$-haloalkyl group,
a C$_1$-C$_3$-alkyl-O— group,
a C$_1$-C$_3$-haloalkoxy group,
a C$_1$-C$_3$-alkyl-O—(C$_1$-C$_3$-alkylene)- group,
a (C$_3$-C$_6$)-cycloalkyl group,
a R$^{18}$-(phenylene)-O—(C$_1$-C$_3$-alkylene)- group,
a NR$^{20}$R$^{21}$—(C$_1$-C$_3$-alkylene)- group, and
a (C$_1$-C$_3$-alkyl)-NH—(C$_1$-C$_3$-alkylene)- group;

R$^{15}$ is selected from a hydrogen atom, a C$_1$-C$_3$-alkyl group, a C$_1$-C$_3$-haloalkyl group, a C$_1$-C$_5$-hydroxyalkyl group, a (C$_1$-C$_3$-alkyoxy)-(C$_1$-C$_3$-alkylene)- group, a (C$_1$-C$_3$-alkyl)-C(O)—O—(C$_1$-C$_4$)alkylene- group, a (C$_1$-C$_3$-alkyoxy)-(C$_1$-C$_3$-alkylene)-O—C(O)— group, a heterocycloalkyl-(C$_1$-C$_3$-alkylene)-O—C(O)— group, and a heterocycloalkyl-(C$_1$-C$_3$-alkylene) group;

R$^{18}$ is selected from a hydrogen atom, a hydroxy group, a cyano group, a C$_1$-C$_3$-alkyl group, a C$_1$-C$_6$-hydroxyalkyl group, a C$_1$-C$_3$-alkoxy group, a —C(O)OR$^{21}$ group, a —C(O)NR$^{20}$R$^{21}$ group, and (C$_1$-C$_6$-alkyl)-C(O)— group;

R$^{20}$ and R$^{21}$ are each independently selected from a hydrogen atom and a C$_1$-C$_3$-alkyl group;

or a tautomer, or a salt thereof, or a salt of a tautomer, or a mixture of same.

In accordance with a further aspect, the present invention provides compounds of general formula (I) in which A is

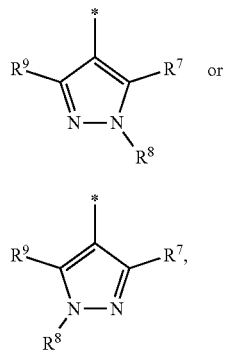

(A1)

(A2)

wherein R$^6$ and R$^7$, together with two carbon atoms of the pyrazole ring, two carbon atoms of the indole moiety and the nitrogen atom to which R$^6$ is attached, form a 10- or 11-membered ring and * is the point of attachment of these moieties to the indole carbon atom bearing the A substituent;

R$^1$ is a chlorine atom;
R$^2$ and R$^3$ are each a hydrogen atom;
R$^4$ is an aryl group which is unsubstituted or substituted with a halogen atom;
L is a group —(CH$_2$)$_m$-E-;
E is an oxygen atom and constitutes the connecting element to R$^4$;
m is 3;
R$^5$ is a COOH group;
—R$^6$-R$^7$— is selected from $^{\#}$—(CH$_2$)$_n$—(B)$_t$—(CH$_2$)$_p$—X—$^{\#\#}$ and $^{\#}$—(C$_2$-C$_6$-alkenylene)-(B)$_t$—(CH$_2$)$_p$—X—$^{\#\#}$, and wherein $^{\#}$ is the point of attachment with the indole nitrogen atom and $^{\#\#}$ is the point of attachment with the pyrazole carbon atom bearing the R$^7$ substituent, and
wherein a —CH═CH— group in any alkenylene can be replaced by a 1,2-(C$_3$-C$_5$)cycloalkylene group and where X is an unsubstituted —CH$_2$— group;
n is 3 or 4;
t is 1;
p is 0;
wherein the integers selected for variables n, t, and p, result in forming a 10-membered to 11-membered ring independently from the selection of variable A1 or A2;
B is independently selected from —O— and —N(R$^{15}$)—;
R$^8$ is selected from a hydrogen atom and,
a C$_1$-C$_4$-alkyl group, which is unsubstituted or substituted with one or more substituents independently selected from a halogen atom, a hydroxy group, a C$_3$-C$_6$-cycloalkyl group and a heterocycloalkyl group;
R$^9$ is a C$_1$-C$_4$-alkyl group,
a C$_1$-C$_3$-hydroxyalkyl group,
a C$_1$-C$_3$-haloalkyl group,
a C$_1$-C$_3$-alkyl-O— group,
a C$_1$-C$_3$-haloalkoxy group,
a C$_1$-C$_3$-alkyl-O—(C$_1$-C$_3$-alkylene)- group,
a (C$_3$-C$_6$)-cycloalkyl group,
a R$^{18}$-(phenylene)-O—(C$_1$-C$_3$-alkylene)- group,
a NR$^{20}$R$^{21}$—(C$_1$-C$_3$-alkylene)- group, and
a (C$_1$-C$_3$-alkyl)-NH—(C$_1$-C$_3$-alkylene)- group;
R$^{15}$ is selected from a hydrogen atom, a C$_1$-C$_3$-alkyl group, a C$_1$-C$_3$-haloalkyl group, a C$_1$-C$_5$-hydroxyalkyl group, a (C$_1$-C$_3$-alkyoxy)-(C$_1$-C$_3$-alkylene)- group, a (C$_1$-C$_3$-alkyl)-C(O)—O—(C$_1$-C$_4$)alkylene- group, a (C$_1$-C$_3$-alkyoxy)-(C$_1$-C$_3$-alkylene)-O—C(O)— group, a heterocycloalkyl-(C$_1$-C$_3$-alkylene)-O—C(O)— group, and a heterocycloalkyl-(C$_1$-C$_3$-alkylene) group;
R$^{18}$ is selected from a hydrogen atom, a hydroxy group, a cyano group, a C$_1$-C$_3$-alkyl group, a C$_1$-C$_6$-hydroxyalkyl group, a C$_1$-C$_3$-alkoxy group, a —C(O)OR$^{21}$ group, a —C(O)NR$^{20}$R$^{21}$ group, and (C$_1$-C$_6$-alkyl)-C(O)— group;
R$^{20}$ and R$^{21}$ are each independently selected from a hydrogen atom and a C$_1$-C$_3$-alkyl group;
or a tautomer, an N-oxide, or a salt thereof, or a salt of a tautomer, or a salt of an N-oxide, or a mixture of same.

In accordance with a further aspect, the present invention provides compounds of general formula (I) in which A is

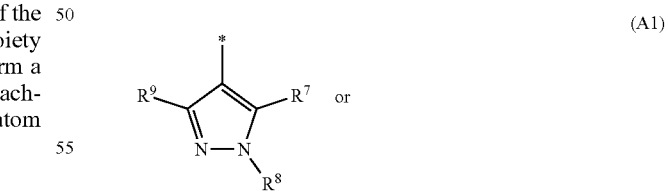

(A1)

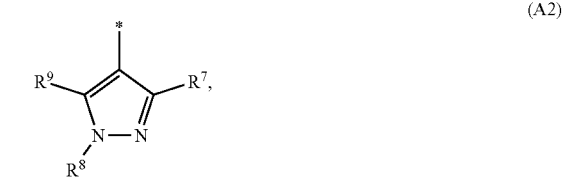

(A2)

wherein R$^6$ and R$^7$, together with two carbon atoms of the pyrazole ring, two carbon atoms of the indole moiety and the nitrogen atom to which R$^6$ is attached, form a 10- or 11-membered ring and * is the point of attachment of these moieties to the indole carbon atom bearing the A substituent $R^1$ is a chlorine atom;
$R^2$ and $R^3$ are each a hydrogen atom;
$R^4$ is an aryl group which is unsubstituted or substituted with a halogen atom;
L is a group —$(CH_2)_m$-E-;
E is an oxygen atom and constitutes the connecting element to $R^4$;
m is 3;
$R^5$ is a COOH group;
—$R^6$-$R^7$— is selected from #—$(CH_2)_n$—(B)$_t$—$(CH_2)_p$—X—##, and #—($C_2$-$C_6$-alkenylene)-(B)$_t$—$(CH_2)_p$—X—##, and wherein # is the point of attachment with the indole nitrogen atom and ## is the point of attachment with the pyrazole carbon atom bearing the $R^7$ substituent, and wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, and a $C_1$-$C_3$-alkoxy group, and wherein optionally if two such substituents are bound to the same atom they may form together a 3-membered to 6-membered spiro ring, and wherein a —CH=CH— group in any alkenylene can be replaced by a 1,2-($C_3$-$C_5$)cycloalkylene group, and where X is an unsubstituted —$CH_2$— group;
n is 3 or 4;
t is 1;
p is 0
wherein the integers selected for variables n, t, and p, result in forming a 10-membered to 11-membered ring independently from the selection of variable A1 or A2;
B is independently selected from —O— and —N($R^{15}$)—;
$R^8$ is selected from a hydrogen atom and,
a $C_1$-$C_4$-alkyl group, which is unsubstituted or substituted with one or more substituents independently selected from a halogen atom, a hydroxy group, a $C_3$-$C_6$-cycloalkyl group, and a heterocycloalkyl group;
$R^9$ is a $C_1$-$C_4$-alkyl group,
$R^{15}$ is selected from a hydrogen atom, a $C_1$-$C_3$-alkyl group, a $C_1$-$C_3$-haloalkyl group, a $C_1$-$C_5$-hydroxyalkyl group, a ($C_1$-$C_3$-alkyoxy)-($C_1$-$C_3$-alkylene)- group, a ($C_1$-$C_3$-alkyl)-C(O)—O—($C_1$-$C_4$)alkylene- group, a ($C_1$-$C_3$-alkyoxy)-($C_1$-$C_3$-alkylene)-O—C(O)— group, a heterocycloalkyl-($C_1$-$C_3$-alkylene)-O—C(O)— group, and a heterocycloalkyl-($C_1$-$C_3$-alkylene) group;
$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a —C(O)O$R^{21}$ group, a —C(O)N$R^{20}R^{21}$ group, and ($C_1$-$C_6$-alkyl)-C(O)— group;
$R^{20}$ and $R^{21}$ are each independently selected from a hydrogen atom and a $C_1$-$C_3$-alkyl group;
or a tautomer, an N-oxide, or a salt thereof, or a salt of a tautomer, or a salt of an N-oxide, or a mixture of same.

In accordance with a further aspect, the present invention provides compounds of general formula (I) in which A is

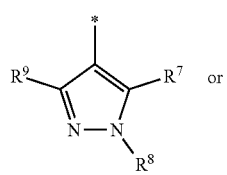

(A1)

or

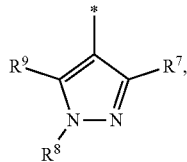

(A2)

wherein $R^6$ and $R^7$, together with two carbon atoms of the pyrazole ring, two carbon atoms of the indole moiety and the nitrogen atom to which $R^6$ is attached, form a 10- or 11-membered ring and * is the point of attachment of these moieties to the indole carbon atom bearing the A substituent;

$R^1$ is a chlorine atom;
$R^2$ and $R^3$ are each a hydrogen atom;
$R^4$ is an aryl group which is unsubstituted or substituted with a halogen atom;
L is a group —$(CH_2)_m$-E-;
E is an oxygen atom and constitutes the connecting element to $R^4$;
m is 3;
$R^5$ is a COOH group;
—$R^6$-$R^7$— is #—$(CH_2)_n$—(B)$_t$—$(CH_2)_p$—X—## and wherein # is the point of attachment with the indole nitrogen atom and * is the point of attachment with the pyrazole carbon atom bearing the $R^7$ substituent and wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, and a $C_1$-$C_3$-alkoxy group, and wherein optionally if two such substituents are bound to the same atom they may form together a 3-membered to 6-membered spiro ring, and wherein a —CH=CH— group in any alkenylene can be replaced by a 1,2-($C_3$-$C_5$)cycloalkylene group and where X is an unsubstituted —$CH_2$— group;
n is 3 or 4;
t is 1;
p is 0;
wherein the integers selected for variables n, t, and p, result in forming a 10-membered to 11-membered ring independently from the selection of variable A1 or A2;
B is independently selected from —O— and —N($R^{15}$)—;
$R^8$ is selected from a hydrogen atom and,
a $C_1$-$C_4$-alkyl group, which is unsubstituted or substituted with one or more substituents independently selected from a halogen atom, a hydroxy group, a $C_3$-$C_6$-cycloalkyl group, and a heterocycloalkyl group;
$R^9$ is a $C_1$-$C_4$-alkyl group;
$R^{15}$ is selected from a hydrogen atom, a $C_1$-$C_3$-alkyl group, a $C_1$-$C_3$-haloalkyl group, a $C_1$-$C_5$-hydroxyalkyl group, a ($C_1$-$C_3$-alkyoxy)-($C_1$-$C_3$-alkylene)- group, a ($C_1$-$C_3$-alkyl)-C(O)—O—($C_1$-$C_4$)alkylene- group, a ($C_1$-$C_3$-alkyoxy)-($C_1$-$C_3$-alkylene)-O—C(O)— group, a heterocycloalkyl-($C_1$-$C_3$-alkylene)-O—C(O)— group, and a heterocycloalkyl-($C_1$-$C_3$-alkylene) group;
$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a —C(O)O$R^{21}$ group, a —C(O)N$R^{20}R^{21}$ group, and ($C_1$-$C_6$-alkyl)-C(O)— group;
$R^{20}$ and $R^{21}$ are each independently selected from a hydrogen atom and a $C_1$-$C_3$-alkyl group;

or a tautomer, an N-oxide, or a salt thereof, or a salt of a tautomer, or a salt of an N-oxide, or a mixture of same.

In accordance with a further aspect, the present invention provides compounds of general formula (I) in which
A is

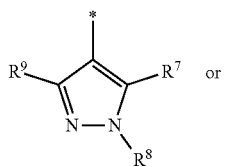
(A1)

or

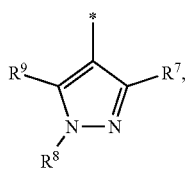
(A2)

wherein $R^6$ and $R^7$, together with two carbon atoms of the pyrazole ring, two carbon atoms of the indole moiety and the nitrogen atom to which $R^6$ is attached, form a 10- or 11-membered ring and * is the point of attachment of these moieties to the indole carbon atom bearing the A substituent;

$R^1$ is a chlorine atom;

$R^2$ and $R^3$ are each a hydrogen atom;

$R^4$ is an aryl group which is unsubstituted or substituted with a halogen atom;

L is a group —$(CH_2)_m$-E-;

E is an oxygen atom and constitutes the connecting element to $R^4$;

m is 3;

$R^5$ is a COOH group;

—$R^6$-$R^7$— is $^{\#}$—$(C_2$-$C_6$-alkenylene)-(B)$_t$—$(CH_2)_p$—X—$^{\#\#}$ and wherein $^{\#}$ is the point of attachment with the indole nitrogen atom and * is the point of attachment with the pyrazole carbon atom bearing the $R^7$ substituent, and wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, and a $C_1$-$C_3$-alkoxy group, and wherein optionally if two such substituents are bound to the same atom they may form together a 3-membered to 6-membered spiro ring, and wherein a —CH=CH— group in any alkenylene can be replaced by a 1,2-($C_3$-$C_5$)cycloalkylene group and where X is an unsubstituted —$CH_2$— group;

n is 3 or 4;

t is 1;

p is 0;

wherein the integers selected for variables n, t, and p, result in forming a 10-membered to 11-membered ring independently from the selection of variable A1 or A2;

B is independently selected from —O— and —$N(R^{15})$—;

$R^8$ is selected from a hydrogen atom and,
a $C_1$-$C_4$-alkyl group, which is unsubstituted or substituted with one or more substituents independently selected from a halogen atom, a hydroxy group, a $C_3$-$C_6$-cycloalkyl group, and a heterocycloalkyl group;

$R^9$ is a $C_1$-$C_4$-alkyl group;

$R^{15}$ is selected from a hydrogen atom, a $C_1$-$C_3$-alkyl group, a $C_1$-$C_3$-haloalkyl group, a $C_1$-$C_5$-hydroxyalkyl group, a ($C_1$-$C_3$-alkyoxy)-($C_1$-$C_3$-alkylene)- group, a ($C_1$-$C_3$-alkyl)-C(O)—O—($C_1$-$C_4$)alkylene- group, a ($C_1$-$C_3$-alkyoxy)-($C_1$-$C_3$-alkylene)-O—C(O)— group, a heterocycloalkyl-($C_1$-$C_3$-alkylene)-O—C(O)— group, and a heterocycloalkyl-($C_1$-$C_3$-alkylene) group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a —C(O)OR$^{21}$ group, a —C(O)NR$^{20}$R$^{21}$ group, and ($C_1$-$C_6$-alkyl)-C(O)— group;

$R^{20}$ and $R^{21}$ are each independently selected from a hydrogen atom and a $C_1$-$C_3$-alkyl group;

or a tautomer, an N-oxide, or a salt thereof, or a salt of a tautomer, or a salt of an N-oxide, or a mixture of same.

In accordance with a further aspect, the present invention provides compounds of general formula (I) in which
A is

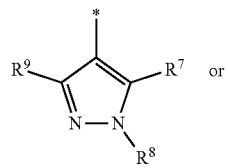
(A1)

or

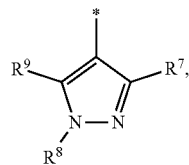
(A2)

wherein $R^6$ and $R^7$, together with two carbon atoms of the pyrazole ring, two carbon atoms of the indole moiety and the nitrogen atom to which $R^6$ is attached, form a 10- or 11-membered ring and * is the point of attachment of these moieties to the indole carbon atom bearing the A substituent;

$R^1$ is a chlorine atom;

$R^2$ and $R^3$ are each a hydrogen atom;

$R^4$ is an aryl group which is unsubstituted or substituted with a halogen atom;

L is a group —$(CH_2)_m$-E-;

E is an oxygen atom and constitutes the connecting element to $R^4$;

m is 3;

$R^5$ is a COOH group;

—$R^6$-$R^7$— is selected from $^{\#}$—$(CH_2)_n$—(B)$_t$—$(CH_2)_p$—X—$^{\#\#}$ and $^{\#}$—$(C_2$-$C_6$-alkenylene)-(B)$_t$—$(CH_2)_p$—X—$^{\#\#}$, and wherein $^{\#}$ is the point of attachment with the indole nitrogen atom and $^{\#\#}$ is the point of attachment with the pyrazole carbon atom bearing the $R^7$ substituent, and wherein a —CH=CH— group in any alkenylene can be replaced by a 1,2-($C_3$-$C_5$)cycloalkylene group and where X is an unsubstituted —$CH_2$— group;

n is 3 or 4;

t is 1;

p is 0;

wherein the integers selected for variables n, t, and p, result in forming a 10-membered to 11-membered ring independently from the selection of variable A1 or A2;

B is independently selected from —O— and —N(R$^{15}$)—;
R$^8$ is selected from a hydrogen atom and,
  a C$_1$-C$_4$-alkyl group, which is unsubstituted or substituted with one or more substituents independently selected from a halogen atom, a hydroxy group, a C$_3$-C$_6$-cycloalkyl group, and a heterocycloalkyl group;
R$^9$ is a C$_1$-C$_4$-alkyl group;
R$^{15}$ is selected from a hydrogen atom, a C$_1$-C$_3$-alkyl group, a C$_1$-C$_3$-haloalkyl group, a C$_1$-C$_5$-hydroxyalkyl group, a (C$_1$-C$_3$-alkyoxy)-(C$_1$-C$_3$-alkylene)- group, a (C$_1$-C$_3$-alkyl)-C(O)—O—(C$_1$-C$_4$)alkylene- group, a (C$_1$-C$_3$-alkyoxy)-(C$_1$-C$_3$-alkylene)-O—C(O)— group, a heterocycloalkyl-(C$_1$-C$_3$-alkylene)-O—C(O)— group, and a heterocycloalkyl-(C$_1$-C$_3$-alkylene) group;
R$^{18}$ is selected from a hydrogen atom, a hydroxy group, a cyano group, a C$_1$-C$_3$-alkyl group, a C$_1$-C$_6$-hydroxyalkyl group, a C$_1$-C$_3$-alkoxy group, a —C(O)OR$^{21}$ group, a —C(O)NR$^{20}$R$^{21}$ group, and (C$_1$-C$_6$-alkyl)-C(O)— group;
R$^{20}$ and R$^{21}$ are each independently selected from a hydrogen atom and a C$_1$-C$_3$-alkyl group;
or a tautomer, an N-oxide, or a salt thereof, or a salt of a tautomer, or a salt of an N-oxide, or a mixture of same.

In accordance with a further aspect, the present invention provides compounds of general formula (I) in which A is

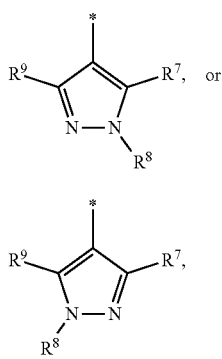

(A1)

or (A2)

wherein R$^6$ and R$^7$, together with two carbon atoms of the pyrazole ring, two carbon atoms of the indole moiety and the nitrogen atom to which R$^6$ is attached, form a 10-membered or 11-membered ring and * is the point of attachment of these moieties to the indole carbon atom bearing the A substituent
R$^1$ is a chlorine atom;
R$^2$ and R$^3$ are each a hydrogen atom;
R$^4$ is an aryl group which is unsubstituted or substituted with a halogen atom;
L is a group —(CH$_2$)$_m$-E-;
E is an oxygen atom and constitutes the connecting element to R$^4$;
m is 3;
R$^5$ is a COOH group;
—R$^6$-R$^7$— is selected from $^\#$—(CH$_2$)$_n$—(B)$_t$—(CH$_2$)$_p$—X—$^{\#\#}$ and $^\#$—(C$_2$-C$_6$-alkenylene)-(B)$_t$—(CH$_2$)$_p$—X—$^{\#\#}$, and
  wherein $^\#$ is the point of attachment with the indole nitrogen atom and $^{\#\#}$ is the point of attachment with the pyrazole carbon atom bearing the R$^7$ substituent, and
  wherein one or more —CH$_2$— groups may be unsubstituted or substituted with one or more substituents independently selected from a halogen atom, a hydroxy group, a NR$^{16}$R$^{17}$ group, a C$_1$-C$_3$-alkyl group, a C$_1$-C$_3$-haloalkyl group, and a C$_1$-C$_3$-alkoxy group, an
  and wherein optionally if two such substituents are bound to the same atom they may form together a 3-membered to 6-membered spiro ring, and
  wherein a —CH═CH— group in any alkenylene can be replaced by a 1,2-(C$_3$-C$_5$)cycloalkylene group, and where
X is an unsubstituted —CH$_2$— group;
n is 3 or 4;
t is 1;
p is 0;
  wherein the integers selected for variables n, t, and p, result in forming a 10-membered to 11-membered ring independently from the selection of variable A1 or A2;
B is independently selected from —O— and —N(R$^{15}$)—;
R$^8$ is selected from a hydrogen atom and,
  a C$_1$-C$_4$-alkyl group, which is unsubstituted or substituted with one or more substituents independently selected from a halogen atom, a hydroxy group, a C$_3$-C$_6$-cycloalkyl group, and a heterocycloalkyl group;
R$^9$ is a C$_1$-C$_2$-alkyl group;
R$^{15}$ is selected from a hydrogen atom, a C$_1$-C$_3$-alkyl group, a C$_1$-C$_3$-haloalkyl group, a C$_1$-C$_5$-hydroxyalkyl group, a (C$_1$-C$_3$-alkyoxy)-(C$_1$-C$_3$-alkylene)- group, a (C$_1$-C$_3$-alkyl)-C(O)—O—(C$_1$-C$_4$)alkylene- group, a (C$_1$-C$_3$-alkyoxy)-(C$_1$-C$_3$-alkylene)-O—C(O)— group, a heterocycloalkyl-(C$_1$-C$_3$-alkylene)-O—C(O)— group, and a heterocycloalkyl-(C$_1$-C$_3$-alkylene) group;
R$^{18}$ is selected from a hydrogen atom, a hydroxy group, a cyano group, a C$_1$-C$_3$-alkyl group, a C$_1$-C$_6$-hydroxyalkyl group, a C$_1$-C$_3$-alkoxy group, a —C(O)OR$^{21}$ group, a —C(O)NR$^{20}$R$^{21}$ group, and (C$_1$-C$_6$-alkyl)-C(O)— group;
R$^{20}$ and R$^{21}$ are each independently selected from a hydrogen atom and a C$_1$-C$_3$-alkyl group;
or a tautomer, an N-oxide, or a salt thereof, or a salt of a tautomer, or a salt of an N-oxide, or a mixture of same.

In accordance with a further aspect, the present invention provides compounds of general formula (I) in which A is

(A1)

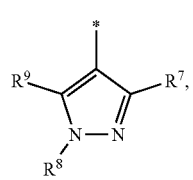

(A2)

wherein R$^6$ and R$^7$, together with two carbon atoms of the pyrazole ring, two carbon atoms of the indole moiety and the nitrogen atom to which R$^6$ is attached, form a 11-membered ring and * is the point of attachment of these moieties to the indole carbon atom bearing the A substituent;
R$^1$ is a chlorine atom;
R$^2$ and R$^3$ are each a hydrogen atom;

R⁴ is a naphtyl group, which is unsubstituted or substituted with a halogen atom;
L is a group —(CH₂)₃—O—;
R⁵ is a COOH group;
—R⁶-R⁷— is selected from #—(CH₂)ₙ—(B)ₜ—(CH₂)ₚ—X—## and #—(C₂-C₆-alkenylene)-(B)ₜ—(CH₂)ₚ—X—##,
and
wherein # is the point of attachment with the indole nitrogen atom and ## is the point of attachment with the pyrazole carbon atom bearing the R⁷ substituent and
wherein one or more —CH₂— groups may be unsubstituted or substituted with one or more halogen atoms or a hydroxy group,
and wherein a —CH=CH— group in any alkenylene can be replaced by a

group or a

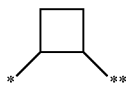

group wherein * is the point of attachment of the ring to the adjacent —CH₂— group or to the indole nitrogen atom and ** is the point of attachment to the adjacent —CH₂— group or to —(B)ₜ— and
wherein optionally if two such substituents are bound to the same atom they may form together a 3-membered to 6-membered spiro ring, and where
X is an unsubstituted —CH₂— group;
n is 4;
t is 1;
p is 0;
wherein the integers selected for variables n, t, and p, result in forming a 11-membered ring independently from the selection of variable A1 or A2;
B is independently selected from —O— and —N(R¹⁵)—;
R⁸ is a C₁-C₃-alkyl group, which is unsubstituted or substituted with a heterocycloalkyl group;
R⁹ is a C₁-C₃-alkyl group;
R¹⁵ is selected from a hydrogen atom, a C₁-C₃-alkyl group, a C₁-C₃-haloalkyl group, a C₁-C₅-hydroxyalkyl group, a (C₁-C₃-alkyoxy)-(C₁-C₃-alkylene)- group, a (C₁-C₃-alkyl)-C(O)—O—(C₁-C₄)alkylene- group, a (C₁-C₃-alkyoxy)-(C₁-C₃-alkylene)-O—C(O)— group, a heterocycloalkyl-(C₁-C₃-alkylene)-O—C(O)— group, and a heterocycloalkyl-(C₁-C₃-alkylene) group;
or a tautomer, an N-oxide, or a salt thereof, or a salt of a tautomer, or a salt of an N-oxide, or a mixture of same.

In accordance with a further aspect, the present invention provides compounds of general formula (I) in which
A is

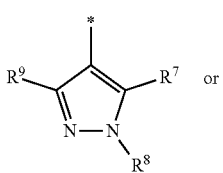

(A1) or

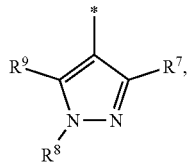

(A2)

wherein R⁶ and R⁷, together with two carbon atoms of the pyrazole ring, two carbon atoms of the indole moiety and the nitrogen atom to which R⁶ is attached, form a 11-membered ring and * is the point of attachment of these moieties to the indole carbon atom bearing the A substituent;
R¹ is a chlorine atom;
R² and R³ are each a hydrogen atom;
R⁴ is a naphtyl group, which is unsubstituted or substituted with a halogen atom;
L is a —(CH₂)₃—O— group;
R⁵ is a COOH group;
—R⁶-R⁷— is selected from #—(CH₂)ₙ—(B)ₜ—(CH₂)ₚ—X—## and #—(C₂-C₆-alkenylene)-(B)ₜ—(CH₂)ₚ—X—##,
and
wherein # is the point of attachment with the indole nitrogen atom and ## is the point of attachment with the pyrazole carbon atom bearing the R⁷ substituent and
wherein one or more —CH₂— groups may be unsubstituted or substituted with one or more halogen atoms or a hydroxy group,
and wherein a —CH=CH— group in any alkenylene can be replaced by a

group or a

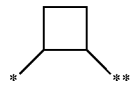

group wherein * is the point of attachment of the ring to the adjacent —CH₂— group or to the indole nitrogen atom and ** is the point of attachment to the adjacent —CH₂— group or to —(B)ₜ—, and
wherein optionally if two such substituents are bound to the same atom they may form together a 3-membered to 6-membered spiro ring, and where
X is an unsubstituted —CH₂— group;
n is 4;
t is 1;
p is 0;
wherein the integers selected for variables n, t, and p, result in forming a 11-membered ring independently from the selection of variable A1 or A2;
B is independently selected from —O— and —N(R¹⁵)—;
R⁸ is a C₁-C₃-alkyl group, which is unsubstituted or substituted with a heterocycloalkyl group;
R⁹ is a C₁-C₃-alkyl group;
R¹⁵ is selected from a hydrogen atom, a C₁-C₃-alkyl group, a C₁-C₃-haloalkyl group, a C₁-C₅-hydroxyalkyl group, a (C₁-C₃-alkyoxy)-(C₁-C₃-alkylene)- group, a (C₁-C₃-alkyl)-C(O)—O—($C_1$-$C_4$)alkylene- group, a ($C_1$-$C_3$-alkyoxy)-($C_1$-$C_3$-alkylene)-O—C(O)— group, a heterocycloalkyl-($C_1$-$C_3$-alkylene)-O—C(O)— group, and a heterocycloalkyl-($C_1$-$C_3$-alkylene) group;

or a tautomer, or a salt thereof, or a salt of a tautomer, or a mixture of same.

In accordance with a further aspect, the present invention provides compounds of general formula (I) in which A is

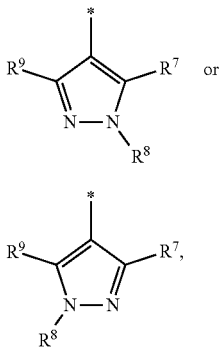

wherein $R^6$ and $R^7$, together with two carbon atoms of the pyrazole ring, two carbon atoms of the indole moiety and the nitrogen atom to which $R^6$ is attached, form a 11-membered or 12-membered ring and * is the point of attachment of these moieties to the indole carbon atom bearing the A substituent;

$R^1$ is a chlorine atom;

$R^2$ and $R^3$ are each a hydrogen atom;

$R^4$ is a naphtyl group, which is unsubstituted or substituted with a halogen atom;

L is a —(CH$_2$)$_3$—O— group;

$R^5$ is a COOH group;

—$R^6$-$R^7$— is selected from $^\#$—(CH$_2$)$_n$—(B)$_t$—(CH$_2$)$_p$—X—$^{\#\#}$ and $^\#$—(C$_2$-C$_6$-alkenylene)-(B)$_t$—(CH$_2$)$_p$—X—$^{\#\#}$, and wherein $^\#$ is the point of attachment with the indole nitrogen atom and $^{\#\#}$ is the point of attachment with the pyrazole carbon atom bearing the $R^7$ substituent and wherein one or more —CH$_2$— groups may be unsubstituted or substituted with one or more halogen atoms or a hydroxy group, and wherein a —CH═CH— group in any alkenylene can be replaced by a

group or a

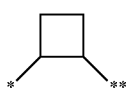

group wherein * is the point of attachment of the ring to the adjacent —CH$_2$— group or to the indole nitrogen atom and ** is the point of attachment to the adjacent —CH$_2$— group or to —(B)$_t$— and wherein optionally if two such substituents are bound to the same atom they may form together a 3-membered to 6-membered spiro ring, and where X is an unsubstituted —CH$_2$— group;

n is 4;

t is 1;

p is 0 or 1;

wherein the integers selected for variables n, t, and p, result in forming a 11-membered or 12-membered ring independently from the selection of variable A1 or A2;

B is independently selected from —O— and —N($R^{15}$)—;

$R^8$ is a $C_1$-$C_3$-alkyl group, which is unsubstituted or substituted with a heterocycloalkyl group;

$R^9$ is a $C_1$-$C_3$-alkyl group;

$R^{15}$ is selected from a hydrogen atom, a $C_1$-$C_3$-alkyl group, a $C_1$-$C_3$-haloalkyl group, a $C_1$-$C_5$-hydroxyalkyl group, a ($C_1$-$C_3$-alkyoxy)-($C_1$-$C_3$-alkylene)- group, a ($C_1$-$C_3$-alkyl)-C(O)—O—($C_1$-$C_4$)alkylene- group, a ($C_1$-$C_3$-alkyoxy)-($C_1$-$C_3$-alkylene)-O—C(O)— group, a heterocycloalkyl-($C_1$-$C_3$-alkylene)-O—C(O)— group, and a heterocycloalkyl-($C_1$-$C_3$-alkylene) group;

or a tautomer, an N-oxide, or a salt thereof, or a salt of a tautomer, or a salt of an N-oxide, or a mixture of same.

In accordance with a further aspect, the present invention provides compounds of general formula (I) in which A is

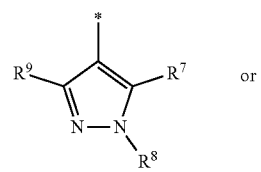

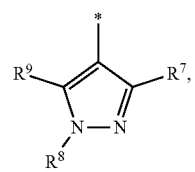

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is a chlorine atom;

$R^2$ and $R^3$ are each a hydrogen atom;

$R^4$ is a naphtyl group, which is unsubstituted or substituted with a halogen atom;

L is a —(CH$_2$)$_3$—O— group;

$R^5$ is a COOH group;

—$R^6$-$R^7$— is $^\#$—(CH$_2$)$_n$—(B)$_t$—(CH$_2$)$_p$—X—$^{\#\#}$ and wherein $^\#$ is the point of attachment with the indole nitrogen atom and * is the point of attachment with the pyrazole carbon atom bearing the $R^7$ substituent and wherein one or more —CH$_2$— groups may be unsubstituted or substituted with one or more halogen atoms or a hydroxy group, and wherein a —CH═CH— group in any alkenylene can be replaced by a

group or a

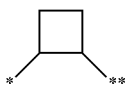

group wherein * is the point of attachment of the ring to the adjacent —CH$_2$— group or to the indole nitrogen atom and ** is the point of attachment to the adjacent —CH$_2$— group or to —(B)$_t$— and
 wherein optionally if two such substituents are bound to the same atom they may form together a 3- to 6-membered spiro ring, and where
X is an unsubstituted —CH$_2$— group;
n is 4;
t is 1;
p is 0;
 wherein the integers selected for variables n, t, and p, result in forming a 11-membered ring independently from the selection of variable A1 or A2;
B is independently selected from —O— and —N(R$^{15}$)—;
R$^8$ is a C$_1$-C$_3$-alkyl group, which is unsubstituted or substituted with a heterocycloalkyl group;
R$^9$ is a C$_1$-C$_3$-alkyl group;
R$^{15}$ is selected from a hydrogen atom, a C$_1$-C$_3$-alkyl group, a C$_1$-C$_3$-haloalkyl group, a C$_1$-C$_5$-hydroxyalkyl group, a (C$_1$-C$_3$-alkyoxy)-(C$_1$-C$_3$-alkylene)- group, a (C$_1$-C$_3$-alkyl)-C(O)—O—(C$_1$-C$_4$)alkylene- group, a (C$_1$-C$_3$-alkyoxy)-(C$_1$-C$_3$-alkylene)-O—C(O)— group, a heterocycloalkyl-(C$_1$-C$_3$-alkylene)-O—C(O)— group, and a heterocycloalkyl-(C$_1$-C$_3$-alkylene) group;
or a tautomer, an N-oxide, or a salt thereof, or a salt of a tautomer, or a salt of an N-oxide, or a mixture of same.

In accordance with a further aspect, the present invention provides compounds of general formula (I) in which
A is

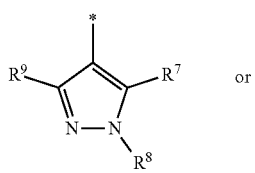

(A1)

or

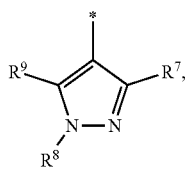

(A2)

wherein R$^6$ and R$^7$, together with two carbon atoms of the pyrazole ring, two carbon atoms of the indole moiety and the nitrogen atom to which R$^6$ is attached, form a 11-membered ring and * is the point of attachment of these moieties to the indole carbon atom bearing the A substituent;
R$^1$ is a chlorine atom;
R$^2$ and R$^3$ are each a hydrogen atom;
R$^4$ is a naphtyl group, which is unsubstituted or substituted with a halogen atom;
L is a —(CH$_2$)$_3$—O— group;
R$^5$ is a COOH group;

—R$^6$-R$^7$— is $^\#$—(C$_2$-C$_6$-alkenylene)-(B)$_t$—(CH$_2$)$_p$—X—$^{\#\#}$ and wherein $^\#$ is the point of attachment with the indole nitrogen atom and * is the point of attachment with the pyrazole carbon atom bearing the R$^7$ substituent and
 wherein one or more —CH$_2$— groups may be unsubstituted or substituted with one or more halogen atoms or a hydroxy group,
 and wherein a —CH=CH— group in any alkenylene can be replaced by a

group or a

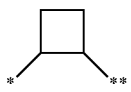

group wherein * is the point of attachment of the ring to the adjacent —CH$_2$— group or to the indole nitrogen atom and ** is the point of attachment to the adjacent —CH$_2$— group or to —(B)$_t$—, and
 wherein optionally if two such substituents are bound to the same atom they may form together a 3-membered to 6-membered spiro ring, and where
X is an unsubstituted —CH$_2$— group;
n is 4;
t is 1;
p is 0
 wherein the integers selected for variables n, t, and p, result in forming a 11-membered ring independently from the selection of variable A1 or A2;
B is independently selected from —O— and —N(R$^{15}$)—;
R$^8$ is a C$_1$-C$_3$-alkyl group, which is unsubstituted or substituted with a heterocycloalkyl group;
R$^9$ is a C$_1$-C$_3$-alkyl group;
R$^{15}$ is selected from a hydrogen atom, a C$_1$-C$_3$-alkyl group, a C$_1$-C$_3$-haloalkyl group, a C$_1$-C$_5$-hydroxyalkyl group, a (C$_1$-C$_3$-alkyoxy)-(C$_1$-C$_3$-alkylene)- group, a (C$_1$-C$_3$-alkyl)-C(O)—O—(C$_1$-C$_4$)alkylene- group, a (C$_1$-C$_3$-alkyoxy)-(C$_1$-C$_3$-alkylene)-O—C(O)— group, a heterocycloalkyl-(C$_1$-C$_3$-alkylene)-O—C(O)— group, and a heterocycloalkyl-(C$_1$-C$_3$-alkylene) group;
or a tautomer, an N-oxide, or a salt thereof, or a salt of a tautomer, or a salt of an N-oxide, or a mixture of same.

In accordance with a further aspect, the present invention provides compounds of general formula (I) in which
A is

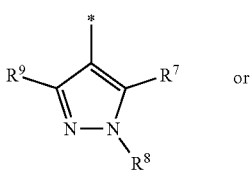

(A1)

or

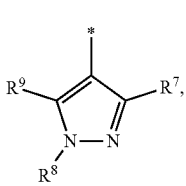

(A2)

wherein R$^6$ and R$^7$, together with two carbon atoms of the pyrazole ring, two carbon atoms of the indole moiety and the nitrogen atom to which R⁶ is attached, form a 11-membered ring and * is the point of attachment of these moieties to the indole carbon atom bearing the A substituent;

R¹ is a chlorine atom;

R² and R³ are each a hydrogen atom;

R⁴ is a naphtyl group, which is unsubstituted or substituted with a halogen atom;

L is a —(CH₂)₃—O— group;

R⁵ is a COOH group;

—R⁶-R⁷— is selected from #—(CH₂)ₙ—(B)ₜ—(CH₂)ₚ—X—## and #—(C₂-C₆-alkenylene)-(B)ₜ—(CH₂)ₚ—X—##, and wherein # is the point of attachment with the indole nitrogen atom and ## is the point of attachment with the pyrazole carbon atom bearing the R⁷ substituent, and and wherein a —CH=CH— group in any alkenylene can be replaced by a

group or a

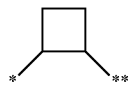

group wherein * is the point of attachment of the ring to the adjacent —CH₂— group or to the indole nitrogen atom and ** is the point of attachment to the adjacent —CH₂— group or to —(B)ₜ—, and wherein optionally if two such substituents are bound to the same atom they may form together a 3-membered to 6-membered spiro ring, and where X is an unsubstituted —CH₂— group;

n is 4;

t is 1;

p is 0;

wherein the integers selected for variables n, t, and p, result in forming a 11-membered ring independently from the selection of variable A1 or A2;

B is independently selected from —O— and —N(R¹⁵)—;

R⁸ is a C₁-C₃-alkyl group, which is unsubstituted or substituted with a heterocycloalkyl group;

R⁹ is a C₁-C₃-alkyl group;

R¹⁵ is selected from a hydrogen atom, a C₁-C₃-alkyl group, a C₁-C₃-haloalkyl group, a C₁-C₅-hydroxyalkyl group, a (C₁-C₃-alkyoxy)-(C₁-C₃-alkylene)- group, a (C₁-C₃-alkyl)-C(O)—O—(C₁-C₄)alkylene- group, a (C₁-C₃-alkyoxy)-(C₁-C₃-alkylene)-O—C(O)— group, a heterocycloalkyl-(C₁-C₃-alkylene)-O—C(O)— group, and a heterocycloalkyl-(C₁-C₃-alkylene) group;

or a tautomer, an N-oxide, or a salt thereof, or a salt of a tautomer, or a salt of an N-oxide, or a mixture of same.

In accordance with a further aspect, the present invention provides compounds of general formula (I):

in which

A is

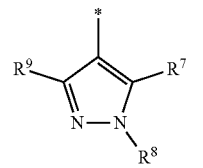 (A1)

or

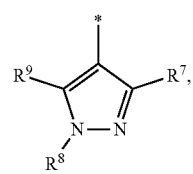 (A2)

wherein R⁶ and R⁷, together with two carbon atoms of the pyrazole ring, two carbon atoms of the indole moiety and the nitrogen atom to which R⁶ is attached, form a 11-membered ring and * is the point of attachment of these moieties to the indole carbon atom bearing the A substituent;

R¹ is a chlorine atom;

R² and R³ are a hydrogen atom;

R⁴ is a naphtyl group, which is unsubstituted or substituted with a fluorine atom;

L is a —(CH₂)₃—O— group;

R⁵ is a COOH group;

—R⁶-R⁷— is selected from #—(CH₂)₄—NH—CH₂—##, #—(CH₂)₄—N(CH₂)₂O—CH₃)—CH₂—##, #—(CH₂)₄—N[C(O)—O—(CH₂)₂—O—CH₃]—CH₂—##, #—(CH₂)₄—N[C(O)—O—(CH₂)₂-(oxetan-4-yl)]-CH₂—##, #—(CH₂)₄—N[(CH₂)₂-(oxetan-4-yl)]-CH₂—##, #—(CH₂)₄—N[(CH₂)₂—(N-morpholinyl)]-CH₂—##, #—(CH₂)₂—N(CH₂CHF₂)—(CH₂)₃—##, #—(CH₂)₂—N[(CH₂)₂CHF₂]—(CH₂)₃—##, #—(CH₂)₂—N[(CH₂)₄—O—C(O)—CH₃]—(CH₂)₃—##, #—(CH₂)₄—N[(CH₂)₂—C(CH₃)₂—OH]—CH₂—##, #—(CH₂)₂—N[(CH₂)₄—OH]—(CH₂)₃—##, #—(CH₂)₄—N[(CH₂)₃—OH]—CH₂—##, #—(CH₂)₂—O—CH₂—##, #—(CH₂)₂—O—(CH₂)₃—##, #—(CH₂)₂—CF₂—CH₂—N(CH₃)—CH₂—##, #—CH₂—CF₂—(CH₂)₂—N(CH₃)—CH₂—##, #—(CH₂)₂CH(OH)—CH₂—O—CH₂—##, #—CH₂—CH=CH—CH₂—O—CH₂—##, #—CH₂—CH=CH—CH₂—N(CH₃)—CH₂—##, and

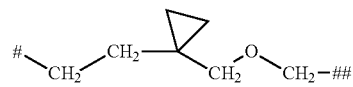

and wherein # is the point of attachment with the indole nitrogen atom and ## is the point of attachment with the pyrazole carbon atom bearing the R⁷ substituent R⁸ is selected from a methyl group, an ethyl, and a propyl group which is substituted with a morpholino group;

R⁹ is a methyl group or an ethyl group;

or a tautomer or a salt thereof or a salt of a tautomer or a mixture of same.

In accordance with a further aspect, the present invention provides compounds of general formula (I):

in which
A is

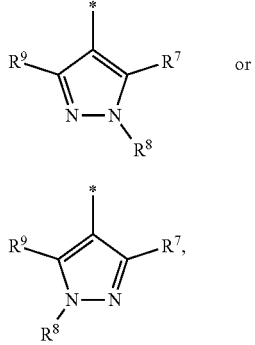

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;
$R^1$ is a chlorine atom;
$R^2$ and $R^3$ are a hydrogen atom;
$R^4$ is a naphtyl group, which is unsubstituted or substituted with a fluorine atom;
L is a —$(CH_2)_3$—O— group;
$R^5$ is a COOH group;
—$R^6$-$R^7$— is selected from #—$(CH_2)_3$—N($CH_3$)—$CH_2$—##, #—$(CH_2)_3$—NH—$CH_2$—##, #—$(CH_2)_4$—N($CH_3$)—$CH_2$—##, #—$(CH_2)_4$—NH—$CH_2$—##, #—$(CH_2)_4$—N($CH_2CF_3$)—$CH_2$—##, #—$(CH_2)_4$—N($CH_2CHF_2$)—$CH_2$—##, #—$(CH_2)_4$—N($CH_2)_2$O—$CH_3$)—$CH_2$—##, #—$(CH_2)_4$—N[C(O)—O—$(CH_2)_2$O—$CH_3$]—$CH_2$—##, #—$(CH_2)_4$—N[C(O)—O—$(CH_2)_2$-(oxetan-4-yl)]-$CH_2$—##, #—$(CH_2)_4$—N[$(CH_2)_2$-(oxetan-4-yl)]-$CH_2$—##, #—$(CH_2)_4$—N[$(CH_2)_2$—(N-morpholinyl)]-$CH_2$—##, #—$(CH_2)_2$—N($CH_2CHF_2$)—$(CH_2)_3$—##, #—$(CH_2)_2$—N[$(CH_2)_2CHF_2$]—$(CH_2)_3$—##, #—$(CH_2)_2$—N[$(CH_2)_4$—O—C(O)—$CH_3$]—$(CH_2)_3$—##, #—$(CH_2)_4$—N[$(CH_2)_2$—C($CH_3)_2$—OH]—$CH_2$—##, #—$(CH_2)_2$—N[$(CH_2)_4$—OH]—$(CH_2)_3$—##, #—$(CH_2)_4$—N[$(CH_2)_3$—OH]—$CH_2$—##, #—$(CH_2)_4$O—$CH_2$—##, #—$(CH_2)_2$O—$CH_2$—##, #—$(CH_2)_2$—O—$(CH_2)_3$—##, #—$(CH_2$-$)_6$##, #—$(CH_2)_2$—$CF_2$—$CH_2$—O—$CH_2$—##, #—$CH_2$—$CF_2$—$(CH_2)_2$O—$CH_2$—##, #—$CH_2$—$CF_2$—$CF_2$—$CH_2$—O—$CH_2$—##, #—$(CH_2)_2$—$CF_2$—$CH_2$—N($CH_3$)—$CH_2$—##, #—$CH_2$—$CF_2$—$(CH_2)_2$—N($CH_3$)—$CH_2$—##, #—$(CH_2)_2$CH(OH)—$CH_2$—O—$CH_2$—##, #—$CH_2$—CH=CH—$CH_2$—O—$CH_2$—##, #—$CH_2$—CH=CH—$CH_2$—N($CH_3$)—$CH_2$—##,

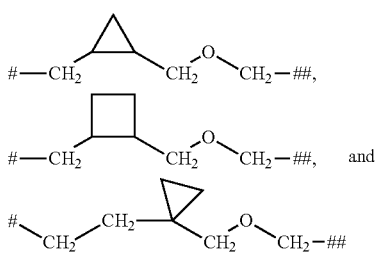

and wherein # is the point of attachment with the indole nitrogen atom and ## is the point of attachment with the pyrazole carbon atom bearing the $R^7$ substituent
$R^8$ is selected from a methyl group, an ethyl, and a propyl group which is substituted with a morpholino group;
$R^9$ is a methyl group or an ethyl group;
or a tautomer, an N-oxide, or a salt thereof, or a salt of a tautomer, or a salt of an N-oxide, or a mixture of same.

In accordance with a further aspect, the present invention provides compounds of general formula (I):
in which
A is

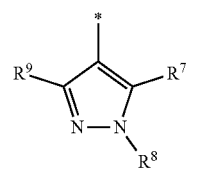

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;
$R^1$ is a chlorine atom;
$R^2$ and $R^3$ are a hydrogen atom;
$R^4$ is a naphtyl group which is unsubstituted or substituted with a fluorine atom;
L is a —$(CH_2)_3$—O— group;
$R^5$ is a COOH group;
—$R^6$-$R^7$— is selected from #—$(CH_2)_3$—N($CH_3$)—$CH_2$—##, #—$(CH_2)_3$—NH—$CH_2$—##, #—$(CH_2)_4$—N($CH_3$)—$CH_2$—##, #—$(CH_2)_4$—NH—$CH_2$—##, #—$(CH_2)_4$—N($CH_2CF_3$)—$CH_2$—##, #—$(CH_2)_4$—N($CH_2CHF_2$)—$CH_2$—##, #—$(CH_2)_4$—N($(CH_2)_2$O—$CH_3$)—$CH_2$—##, #—$(CH_2)_4$—N[C(O)—O—$(CH_2)_2$O—$CH_3$]—$CH_2$—##, #—$(CH_2)_4$—N[C(O)—O—$(CH_2)_2$-(oxetan-4-yl)]-$CH_2$—##, #—$(CH_2)_4$—N[$(CH_2)_2$-(oxetan-4-yl)]-$CH_2$—##, #—$(CH_2)_4$—N[$(CH_2)_2$—(N-morpholinyl)]-$CH_2$—##, #—$(CH_2)_2$—N($CH_2CHF_2$)—$(CH_2)_3$—##, #—$(CH_2)_2$—N[$(CH_2)_2CHF_2$]—$(CH_2)_3$—##, #—$(CH_2)_2$—N[$(CH_2)_4$—O—C(O)—$CH_3$]—$(CH_2)_3$—##, #—$(CH_2)_4$—N[$(CH_2)_2$—C($CH_3)_2$—OH]—$CH_2$—##, #—$(CH_2)_2$—N[$(CH_2)_4$—OH]—$(CH_2)_3$—##, and #—$(CH_2)_4$—N[$(CH_2)_3$—OH]—$CH_2$—##, and wherein * is the point of attachment with the indole nitrogen atom and ## is the point of attachment with the pyrazole carbon atom bearing the $R^7$ substituent;
$R^8$ is selected from a methyl group, an ethyl, and a propyl group which is substituted with a morpholino group;
$R^9$ is a methyl group or an ethyl group;
or a tautomer, an N-oxide, or a salt thereof, or a salt of a tautomer, or a salt of an N-oxide, or a mixture of same.

In accordance with a further aspect, the present invention provides compounds of general formula (I):

in which
A is

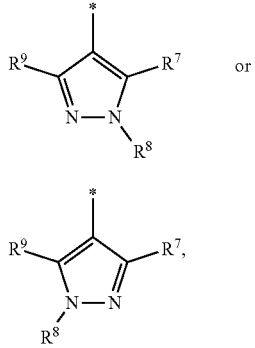

(A1)

or (A2)

wherein R⁶ and R⁷, together with two carbon atoms of the pyrazole ring, two carbon atoms of the indole moiety and the nitrogen atom to which R⁶ is attached, form a 11-membered ring and * is the point of attachment of these moieties to the indole carbon atom bearing the A substituent;

$R^1$ is a chlorine atom;

$R^2$ and $R^3$ are a hydrogen atom;

$R^4$ is a naphtyl group which is unsubstituted or substituted with a fluorine atom;

L is a —(CH$_2$)$_3$—O— group;

$R^5$ is a COOH group;

—R⁶-R⁷— is selected from #—(CH$_2$)$_4$O—CH$_2$—##, #—(CH$_2$)$_2$O—CH$_2$—##, #—(CH$_2$)$_2$—O—(CH$_2$)$_3$—##, #—(CH$_2$)$_2$—CF$_2$—CH$_2$—O—CH$_2$—##, #—CH$_2$—CF$_2$—(CH$_2$)$_2$O—CH$_2$—##, #—CH$_2$—CF$_2$—CF$_2$—CH$_2$—O—CH$_2$—##, #—(CH$_2$)$_2$—CF$_2$—CH$_2$—N(CH$_3$)—CH$_2$—##, #—CH$_2$—CF$_2$—(CH$_2$)$_2$—N(CH$_3$)—CH$_2$—##, #—(CH$_2$)$_2$CH(OH)—CH$_2$—O—CH$_2$—##, #—CH$_2$—CH=CH—CH$_2$—O—CH$_2$—##, #—CH$_2$—CH=CH—CH$_2$—N(CH$_3$)—CH$_2$—##,

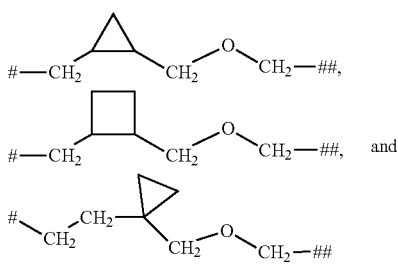

and wherein # is the point of attachment with the indole nitrogen atom and ## is the point of attachment with the pyrazole carbon atom bearing the R⁷ substituent $R^8$ is selected from a methyl group, an ethyl, and a propyl group which is substituted with a morpholino group;

$R^9$ is a methyl group or an ethyl group;

or a tautomer, an N-oxide, or a salt thereof, or a salt of a tautomer, or a salt of an N-oxide, or a mixture of same.

In accordance with a further aspect, the present invention provides compounds of general formula (I):

in which
A is

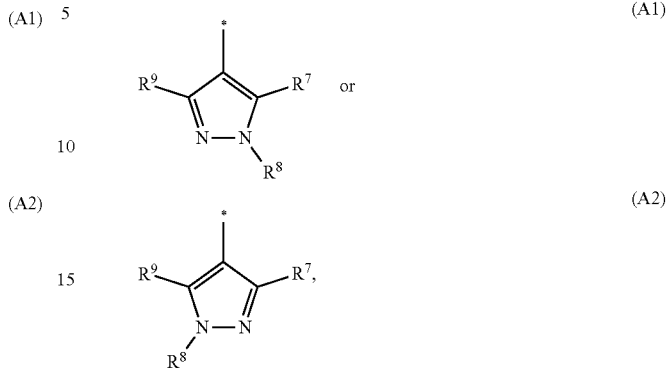

(A1)

or (A2)

wherein R⁶ and R⁷, together with two carbon atoms of the pyrazole ring, two carbon atoms of the indole moiety and the nitrogen atom to which R⁶ is attached, form a 11-membered ring and * is the point of attachment of these moieties to the indole carbon atom bearing the A substituent;

$R^1$ is a chlorine atom;

$R^2$ and $R^3$ are a hydrogen atom;

$R^4$ is a naphtyl group, which is unsubstituted or substituted with a fluorine atom;

L is a —(CH$_2$)$_3$—O— group;

$R^5$ is a COOH group;

—R⁶-R⁷— is #—(CH$_2$-)$_6$##, and wherein # is the point of attachment with the indole nitrogen atom and ## is the point of attachment with the pyrazole carbon atom bearing the R⁷ substituent $R^8$ is selected from a methyl group, an ethyl, and a propyl group which is substituted with a morpholino group;

$R^9$ is a methyl group or an ethyl group;

or a tautomer, an N-oxide, or a salt thereof, or a salt of a tautomer, or a salt of an N-oxide, or a mixture of same.

In accordance with a further aspect, the present invention provides compounds of general formula (I):
in which
A is

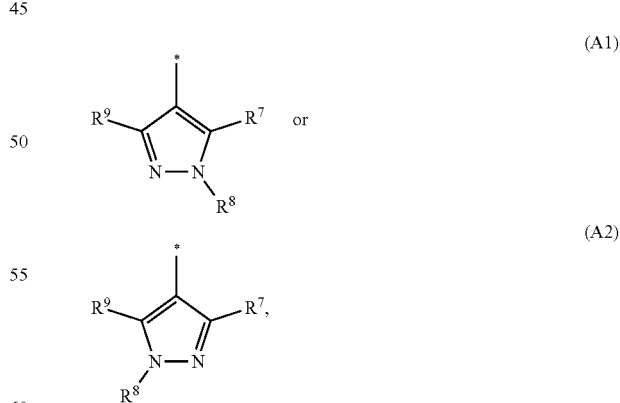

(A1)

or (A2)

wherein R⁶ and R⁷, together with two carbon atoms of the pyrazole ring, two carbon atoms of the indole moiety and the nitrogen atom to which R⁶ is attached, form a 11-membered ring and * is the point of attachment of these moieties to the indole carbon atom bearing the A substituent;

R$^1$ is a chlorine atom;
R$^2$ and R$^3$ are a hydrogen atom;
R$^4$ is a naphtyl group which is unsubstituted or substituted with a fluorine atom;
L is a —(CH$_2$)$_3$—O— group;
R$^5$ is a COOH group;
—R$^6$-R$^7$— is selected from $^\#$—(CH$_2$)$_3$—N(CH$_3$)—CH$_2$—$^{\#\#}$, $^\#$—(CH$_2$)$_3$—NH—CH$_2$—$^{\#\#}$, $^\#$—(CH$_2$)$_4$—N(CH$_3$)—CH$_2$—$^{\#\#}$, $^\#$—(CH$_2$)$_4$—NH—CH$_2$—$^{\#\#}$, $^\#$—(CH$_2$)$_4$—N(CH$_2$CF$_3$)—CH$_2$—$^{\#\#}$, $^\#$—(CH$_2$)$_4$—N(CH$_2$CHF$_2$)—CH$_2$—$^{\#\#}$, $^\#$—(CH$_2$)$_4$—N(CH$_2$)$_2$O—CH$_3$]—CH$_2$—$^{\#\#}$, $^\#$—(CH$_2$)$_4$—N[C(O)—O—(CH$_2$)$_2$O—CH$_3$]—CH$_2$—$^{\#\#}$, $^\#$—(CH$_2$)$_4$—N[C(O)—O—(CH$_2$)$_2$-(oxetan-4-yl)]-CH$_2$—$^{\#\#}$, $^\#$—(CH$_2$)$_4$—N[(CH$_2$)$_2$-(oxetan-4-yl)]-CH$_2$—$^{\#\#}$, $^\#$—(CH$_2$)$_4$—N[(CH$_2$)$_2$—(N-morpholinyl)]-CH$_2$—$^{\#\#}$, $^\#$—(CH$_2$)$_2$—N(CH$_2$CHF$_2$)—(CH$_2$)$_3$—$^{\#\#}$, $^\#$—(CH$_2$)$_2$—N[(CH$_2$)$_2$CHF$_2$]—(CH$_2$)$_3$—$^{\#\#}$, $^\#$—(CH$_2$)$_2$—N[(CH$_2$)$_4$—O—C(O)—CH$_3$]—(CH$_2$)$_3$—$^{\#\#}$, $^\#$—(CH$_2$)$_4$—N[(CH$_2$)$_2$—C(CH$_3$)$_2$—OH]—CH$_2$—$^{\#\#}$, $^\#$—(CH$_2$)$_2$—N[(CH$_2$)$_4$—OH]—(CH$_2$)$_3$—$^{\#\#}$, $^\#$—(CH$_2$)$_4$—N[(CH$_2$)$_3$—OH]—CH$_2$—$^{\#\#}$, $^\#$—(CH$_2$)$_4$O—CH$_2$—$^{\#\#}$, $^\#$—(CH$_2$)$_2$O—CH$_2$—$^{\#\#}$, $^\#$—(CH$_2$)$_2$—O—(CH$_2$)$_3$—$^{\#\#}$, $^\#$—(CH$_2$-)$_6$$^{\#\#}$, $^\#$—(CH$_2$)$_2$—CF$_2$—CH$_2$—O—CH$_2$—$^{\#\#}$, $^\#$—CH$_2$—CF$_2$—(CH$_2$)$_2$O—CH$_2$—$^{\#\#}$, $^\#$—CH$_2$—CF$_2$—CF$_2$—CH$_2$—O—CH$_2$—$^{\#\#}$, $^\#$—(CH$_2$)$_2$—CF$_2$—CH$_2$—N(CH$_3$)—CH$_2$—$^{\#\#}$, $^\#$—CH$_2$—CF$_2$—(CH$_2$)$_2$—N(CH$_3$)—CH$_2$—$^{\#\#}$, $^\#$—(CH$_2$)$_2$CH(OH)—CH$_2$—O—CH$_2$—$^{\#\#}$ and

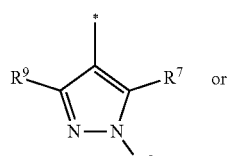

and wherein $^\#$ is the point of attachment with the indole nitrogen atom and $^{\#\#}$ is the point of attachment with the pyrazole carbon atom bearing the R$^7$ substituent;
R$^8$ is selected from a methyl group, an ethyl, and a propyl group which is substituted with a morpholino group;
R$^9$ is a methyl group or an ethyl group;
or a tautomer, an N-oxide, or a salt thereof, or a salt of a tautomer, or a salt of an N-oxide, or a mixture of same.

In accordance with a further aspect, the present invention provides compounds of general formula (I):
in which
A is

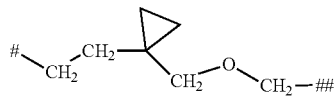 (A1)

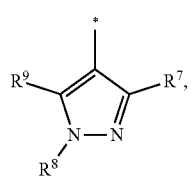 (A2)

wherein R$^6$ and R$^7$, together with two carbon atoms of the pyrazole ring, two carbon atoms of the indole moiety and the nitrogen atom to which R$^6$ is attached, form a 11-membered ring and * is the point of attachment of these moieties to the indole carbon atom bearing the A substituent;
R$^1$ is a chlorine atom;
R$^2$ and R$^3$ are a hydrogen atom;
R$^4$ is a naphtyl group which is unsubstituted or substituted with a fluorine atom;
L is a —(CH$_2$)$_3$—O— group;
R$^5$ is a COOH group;
—R$^6$-R$^7$— is selected from $^\#$—(CH$_2$)$_3$—N(CH$_3$)—CH$_2$—$^{\#\#}$, $^\#$—(CH$_2$)$_3$—NH—CH$_2$—$^{\#\#}$, $^\#$—(CH$_2$)$_4$—N(CH$_3$)—CH$_2$—$^{\#\#}$, $^\#$—(CH$_2$)$_4$—NH—CH$_2$—$^{\#\#}$, $^\#$—(CH$_2$)$_4$—N(CH$_2$CF$_3$)—CH$_2$—$^{\#\#}$, $^\#$—(CH$_2$)$_4$—N(CH$_2$CHF$_2$)—CH$_2$—$^{\#\#}$, $^\#$—(CH$_2$)$_4$—N[(CH$_2$)$_2$O—CH$_3$]—CH$_2$—$^{\#\#}$, $^\#$—(CH$_2$)$_4$—N[C(O)—O—(CH$_2$)$_2$O—CH$_3$]—CH$_2$—$^{\#\#}$, $^\#$—(CH$_2$)$_4$—N[C(O)—O—(CH$_2$)$_2$-(oxetan-4-yl)]-CH$_2$—$^{\#\#}$, $^\#$—(CH$_2$)$_4$—N[(CH$_2$)$_2$-(oxetan-4-yl)]-CH$_2$—$^{\#\#}$, $^\#$—(CH$_2$)$_4$—N[(CH$_2$)$_2$—(N-morpholinyl)]-CH$_2$—$^{\#\#}$, $^\#$—(CH$_2$)$_2$—N(CH$_2$CHF$_2$)—(CH$_2$)$_3$—$^{\#\#}$, $^\#$—(CH$_2$)$_2$—N[(CH$_2$)$_2$CHF$_2$]—(CH$_2$)$_3$—$^{\#\#}$, $^\#$—(CH$_2$)$_2$—N[(CH$_2$)$_4$—O—C(O)—CH$_3$]—(CH$_2$)$_3$—$^{\#\#}$, $^\#$—(CH$_2$)$_4$—N[(CH$_2$)$_2$—C(CH$_3$)$_2$—OH]—CH$_2$—$^{\#\#}$, $^\#$—(CH$_2$)$_2$—N[(CH$_2$)$_4$—OH]—(CH$_2$)$_3$—$^{\#\#}$, $^\#$—(CH$_2$)$_4$—N[(CH$_2$)$_3$—OH]—CH$_2$—$^{\#\#}$, $^\#$—(CH$_2$)$_4$O—CH$_2$—$^{\#\#}$, $^\#$—(CH$_2$)$_2$O—CH$_2$—$^{\#\#}$, $^\#$—(CH$_2$)$_2$—O—(CH$_2$)$_3$—$^{\#\#}$, $^\#$—(CH$_2$-)$_6$$^{\#\#}$, $^\#$—(CH$_2$)$_2$—CF$_2$—CH$_2$—O—CH$_2$—$^{\#\#}$, $^\#$—CH$_2$—CF$_2$—(CH$_2$)$_2$O—CH$_2$—$^{\#\#}$, $^\#$—CH$_2$—CF$_2$—CF$_2$—CH$_2$—O—CH$_2$—$^{\#\#}$, $^\#$—(CH$_2$)$_2$—CF$_2$—CH$_2$—N(CH$_3$)—CH$_2$—$^{\#\#}$, $^\#$—CH$_2$—CF$_2$—(CH$_2$)$_2$—N(CH$_3$)—CH$_2$—$^{\#\#}$, $^\#$—(CH$_2$)$_2$CH(OH)—CH$_2$—O—CH$_2$—$^{\#\#}$ and

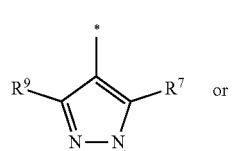

and wherein $^\#$ is the point of attachment with the indole nitrogen atom and $^{\#\#}$ is the point of attachment with the pyrazole carbon atom bearing the R$^7$ substituent;
R$^8$ is selected from a methyl group, a morpholin-4-yl-ethyl-group and a morpholin-4-yl-propyl group;
R$^9$ is a methyl group or an ethyl group;
or a tautomer, an N-oxide, or a salt thereof, or a salt of a tautomer, or a salt of an N-oxide, or a mixture of same.

In accordance with a further aspect, the present invention provides compounds of general formula (I):
in which
A is (A1)

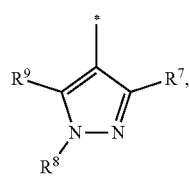 (A2)

wherein R$^6$ and R$^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;
$R^1$ is a chlorine atom;
$R^2$ and $R^3$ are a hydrogen atom;
$R^4$ is a naphtyl group which is unsubstituted or substituted with a fluorine atom;
L is a group —$(CH_2)_3$—O—;
$R^5$ is a COOH group;
—$R^6$-$R^7$— is selected #—$CH_2$—CH=CH—$CH_2$—O—$CH_2$—##, #—$CH_2$—CH=CH—$CH_2$—N($CH_3$)—$CH_2$—##,

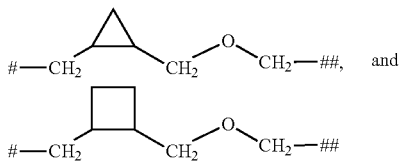

and wherein # is the point of attachment with the indole nitrogen atom and * is the point of attachment with the pyrazole carbon atom bearing the $R^7$ substituent
$R^8$ is selected from a methyl group, an ethyl, a morpholin-4-yl-ethyl- group, and a morpholin-4-yl-propyl- group;
$R^9$ is a methyl group or an ethyl group;
or a tautomer, an N-oxide, or a salt thereof, or a salt of a tautomer, or a salt of an N-oxide, or a mixture of same.

In another aspect the invention provides compounds of formula (I)
in which
A is (A1)

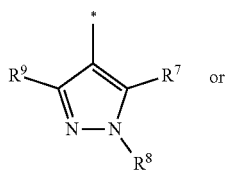

or (A2)

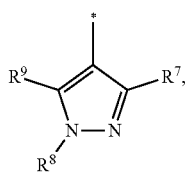

wherein $R^6$ and $R^7$, together with two carbon atoms of the pyrazole ring, two carbon atoms of the indole moiety and the nitrogen atom to which $R^6$ is attached, form a 9- to 16-membered ring and * is the point of attachment of these moieties to the indole carbon atom bearing the A substituent;
or
A is (A3)

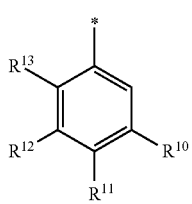

wherein optionally one or two of the groups selected from $CR^{11}$, $CR^{12}$ or $CR^{13}$ may be replaced by a nitrogen atom,
wherein $R^6$ and $R^{10}$, together with three carbon atoms of the phenyl ring, two carbon atoms of the indole moiety and the nitrogen atom to which $R^6$ is attached, form a 9- to 16-membered ring and * is the point of attachment of these moieties to the indole carbon atom bearing the A substituent;
$R^1$ is a chlorine atom,
$R^2$ and $R^3$ are each a hydrogen atom;
$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a $(C_1$-$C_3)$-haloalkyl-S— group, and a $C_3$-$C_5$-cycloalkyl group;
L is a group —$(CH_2)_m$-E- wherein any $CH_2$ group is unsubstituted or substituted with one or two substituents and each substituent is independently selected from a halogen atom, a cyano group, a hydroxy group, a $C_1$-$C_3$-alkyl group, and a $C_1$-$C_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a —S(O)$_2$— group, and a —$NR^{14}$— group;
E is a bond, an oxygen atom, a sulfur atom, a —S(O)— group, a —S(O)$_2$— group or a —$NR^{14}$— group and constitutes the connecting element to $R^4$;
m is 2, 3, or 4;
$R^5$ is selected from a COOH group, a

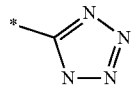

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$($CH_2$)$_s$NHCO ($C_1$-$C_6$-alkyl) group, a —C(O)—NHS(O)$_2$($CH_2$)$_s$NHCO ($C_3$-$C_6$-cycloalkyl) group, and a —C(O)—NHS(O)$_2$ ($CH_2$)$_s$NHCO(aryl) group;
—$R^6$-$R^7$— is selected from #—$(CH_2)_n$—(B)$_t$—$(CH_2)_p$—X—##, #—$(C_2$-$C_6$-alkenylene)-(B)$_t$—$(CH_2)_p$—X—##, #—$(CH_2)_n$—(B)$_t$—$(C_2$-$C_5$-alkenylene)-X—##, and #—$(CH_2)_q$—(B)—$(CH_2)_r$—(B)—$(CH_2)_v$—X—##,
wherein # is the point of attachment with the indole nitrogen atom and ## is the point of attachment with the pyrazole carbon atom bearing the $R^7$ substituent; and
wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group, and a (heterocycloalkyl)-($C_1$-$C_3$-alkylene)- group, and
wherein a double bond in any alkenylene can be replaced by a 1,2-($C_1$-$C_6$)cycloalkyl group which is unsubstituted or substituted one or two times with a halogen atom or a $C_1$-$C_2$-alkyl group; and where X is an unsubstituted —$CH_2$— group;
—$R^6$-$R^{10}$— is selected from #—$(CH_2)_n$—(B)$_t$—$(CH_2)_p$—X—##, #—($C_2$-$C_6$-alkenylene)-(B)$_t$—$(CH_2)_p$—X—##, #—$(CH_2)_n$—(B)$_t$—($C_2$-$C_5$-alkenylene)-X—##, and #—$(CH_2)_q$—(B)—$(CH_2)_r$—(B)—$(CH_2)_v$—X—##,
wherein # is the point of attachment with the indole nitrogen atom and ## is the point of attachment with the carbon atom of the phenyl moiety bearing the $R^{10}$ substituent, and
wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group, and a (heterocycloalkyl)-($C_1$-$C_3$-alkylene)- group,
wherein a —CH=CH— group in any alkenylene can be replaced by a 1,2-($C_3$-$C_5$)cycloalkylene group which is unsubstituted or substituted one or two times with a halogen atom or a $C_1$-$C_2$-alkyl group, and where
X is an unsubstituted —$CH_2$— group;
n is 2, 3, 4, 5, 6, 7, 8, or 9;
t is 0 or 1;
p is 0, 1, 2, 3, 4, or 5;
q is 2, 3, 4, 5, or 6;
r is 2, 3, 4, 5, or 6;
v is 0, or 1;
s is 0, 1, 2, or 3;
wherein the integers selected for variables n, t, p, q, r, and v result in forming a 9- to 16-membered ring independently from the selection of variable A1, A2 or A3;
B is independently selected from a —C(O)$NR^{15}$— group, a —$NR^{15}$C(O)— group, a —N($R^{15}$)— group, a —N($R^{15}$)—C(=O)—N($R^{15}$)— group, a —O—C(=O)—N($R^{15}$)— group, a —N($R^{15}$)—C(=O)—O— group, —O—, —S—, —S(O)—, and —S(O)$_2$—:
$R^8$ is selected from a hydrogen atom,
a $C_1$-$C_6$-alkyl group, which is unsubstituted or substituted with one or more substituents independently selected from
a halogen atom, a hydroxy group, a $C_1$-$C_3$-alkoxy group, a $C_1$-$C_3$-haloalkoxy group,
a $C_3$-$C_6$-cycloalkyl group, a heterocycloalkyl group, and a $NR^{20}R^{21}$ group, and
a $C_3$-$C_6$-cycloalkyl group,
$R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$)-cycloalkyl-O—($C_1$-$C_3$-alkylene)- group,
a phenyl-O—($C_1$-$C_3$-alkylene)- group,
a phenyl-($C_1$-$C_3$-alkylene)-O—($C_1$-$C_3$-alkylene)- group,
a $R^{18}$-(phenylene)-($C_1$-$C_3$-alkylene)-O—($C_1$-$C_3$-alkylene)- group,
a $R^{18}$-(phenylene)-O—($C_1$-$C_3$-alkylene)- group,
a $R^{18}$-(phenylene)-(heteroarylene)-O—($C_1$-$C_3$-alkylene) group,
a ($R^{18}$)-(heterocycloalkylene)-($C_1$-$C_3$-alkylene)- group,
a ($R^{18}$)-(heterocycloalkylene)-(phenylene)-O—($C_1$-$C_3$-alkylene)- group,
a (heterocycloalkenyl)-(phenylene)-O—($C_1$-$C_3$-alkylene)- group,
a ($R^{18}$)-(heteroarylene)-($C_1$-$C_3$-alkylene)-O—($C_1$-$C_3$-alkylene)- group,
a ($R^{18}$)-(heteroarylene)-(phenylene)-O—($C_1$-$C_3$-alkylene)- group,
a ($R^{19}$)—S(O)$_2$-(phenylene)-O—($C_1$-$C_3$-alkylene)- group,
a ($R^{19}$)—S(O)$_2$—NH-(phenylene)-O—($C_1$-$C_3$-alkylene)- group,
a ($R^{19}$)—S(O)$_2$—NH-(phenylene)-O—($C_1$-$C_3$-alkylene)- group,
a ($R^{19}$)—S(O)$_2$—N($C_1$-$C_6$-alkyl)-(phenylene)-O—($C_1$-$C_3$-alkylene)- group,
a ($R^{19}$)—S(O)$_2$-(heterocycloalkylene)-(phenylene)-O—($C_1$-$C_3$-alkylene)- group,
a ($R^{18}$)-(heterocycloalkylene)-(heteroarylene)-O—($C_1$-$C_3$-alkylene)- group,
a ($R^{19}$)-(heteroarylene)-O—($C_1$-$C_3$-alkylene)- group,
a ($R^{18}$)-(heteroarylene)-O—($C_1$-$C_3$-alkylene)- group,
a ($R^{19}$)—S(O)$_2$-(heteroarylene)-O—($C_1$-$C_3$-alkylene)- group,
a ($R^{19}$)—S(O)$_2$-(heterocycloalkylene)-(heteroarylene)-O—($C_1$-$C_3$-alkylene)- group,
a $NR^{20}R^{21}$—($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-NH—C(O)—($C_1$-$C_3$-alkylene)- group,
a ($C_1$-$C_3$-alkyl)-$NR^{15}$—C(O)—($C_1$-$C_3$-alkylene)- group,
a ($C_1$-$C_3$-alkyl)-C(O)—NH—($C_1$-$C_3$-alkylene)- group,
a ($C_1$-$C_3$-alkyl)-C(O)—$NR^{15}$—($C_1$-$C_3$-alkylene)- group,
a

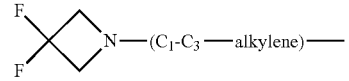

group, and a

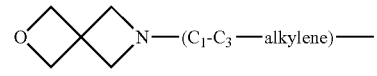

group, wherein the phenyl ring is unsubstituted or substituted with a halogen atom, a hydroxy group, or a $C_1$-$C_3$-alkoxy group and
the heterocycloalkyl group is unsubstituted or substituted with an oxo (=O) group or is unsubstituted or substituted with one or more substituents independently selected from a halogen atom, a hydroxy group, a $C_1$-$C_3$-alkyl group, and a $C_1$-$C_3$-alkoxy group,
or $R^8$ and $R^9$ together form a 5- or 6-membered ring optionally containing one or two heteroatoms selected from —O—, and —$NR^{14}$—;
$R^{11}$ and $R^{13}$ are each independently selected from a hydrogen atom, a halogen atom, a $C_1$-$C_3$-alkyl group, and a $C_1$-$C_3$-alkoxy group;
$R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group, and a $NR^{16}R^{17}$ group;
$R^{14}$ is a hydrogen atom or a $C_1$-$C_3$-alkyl group;
$R^{15}$ is independently selected from a hydrogen atom, a $C_1$-$C_6$-alkyl group
which is unsubstituted or substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$-(heterocycloalkylene)-(arylene)-O— group, an (aryl)-(heteroarylene)-O— group, and an (aryl)-(heteroarylene)-O—($C_1$-$C_3$-alkylene)- group;

a phenyl group,
a group

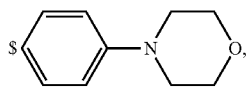

a group

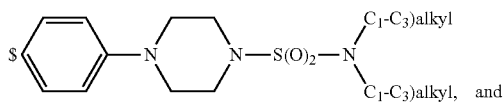

a group

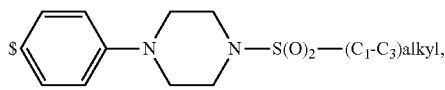

wherein $ is the point of attachment to the nitrogen atom, to which $R^{15}$ is attached,
$R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group, and a $C_1$-$C_3$-alkyl-O—C(=O)— group;
$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a C(O)OR$^{21}$—($C_1$-$C_3$-alkylene)- group, a —C(O)OR$^{21}$ group, a —C(O)NR$^{20}$R$^{21}$ group, a ($C_1$-$C_3$-alkyl)-O—($C_1$-$C_3$-alkylene)-C(O)— group, a ($C_1$-$C_6$-alkyl)-C(O)— group, and a $C_3$-$C_6$-cycloalkyl-C(O)— group;
$R^{19}$ is selected from a $C_1$-$C_3$-alkyl group, a $C_3$-$C_6$-cycloalkyl group, and a NR$^{20}$R$^{21}$ group; and
$R^{20}$ and $R^{21}$ are each independently selected from a hydrogen atom and a $C_1$-$C_6$-alkyl group;
or a tautomer, an N-oxide, or a salt thereof, or a salt of a tautomer, or a salt of an N-oxide, or a mixture of same.

In accordance with a further aspect, the present invention provides compounds of general formula (I): in which
A is

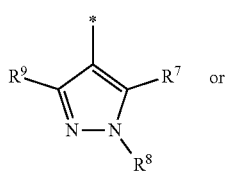

(A1)

or

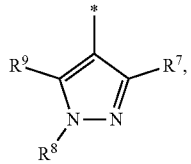

(A2)

wherein $R^6$ and $R^7$, together with two carbon atoms of the pyrazole ring, two carbon atoms of the indole moiety and the nitrogen atom to which $R^6$ is attached, form a 9- to 16-membered ring and * is the point of attachment of these moieties to the indole carbon atom bearing the A substituent;
$R^1$ is a chlorine atom;
$R^2$ and $R^3$ are each a hydrogen atom;
$R^4$ is selected from an aryl group and a heteroaryl group, each of which is unsubstituted or substituted with one, two, or three, substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, and a ($C_1$-$C_3$)-haloalkyl-S— group, and a $C_3$-$C_5$-cycloalkyl group;
L is a group —(CH$_2$)$_m$-E- wherein any CH$_2$ group is unsubstituted or substituted with one or two substituents and each substituent is independently selected from a halogen atom, a cyano group, a hydroxy group, a $C_1$-$C_3$-alkyl group and a $C_1$-$C_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a —S(O)$_2$— group, and a —NR$^{14}$— group;
E is a bond, an oxygen atom, a sulfur atom, a —S(O)— group, a —S(O)$_2$— group or a —NR$^{14}$— group and constitutes the connecting element to $R^4$;
$R^5$ is selected from a COOH group, a

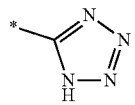

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl) group and a —C(O)—NHS(O)$_2$(CH$_2$)$_s$NHCO(aryl) group;
s is 0, 1, 2, or 3;
—$R^6$-$R^7$— is selected from $^{\#}$—(CH$_2$)$_n$—(B)$_t$—(CH$_2$)$_p$—X—$^{\#\#}$, $^{\#}$—($C_2$-$C_6$-alkenylene)-(B)$_t$—(CH$_2$)$_p$—X—$^{\#\#}$, $^{\#}$—(CH$_2$)$_n$—(B)$_t$($C_2$-$C_5$-alkenylene)-X—$^{\#\#}$, and $^{\#}$—(CH$_2$)$_q$—(B)—(CH$_2$)$_r$—(B)—(CH$_2$)$_v$—X—$^{\#\#}$,
wherein $^{\#}$ is the point of attachment with the indole nitrogen atom and $^{\#\#}$ is the point of attachment with the pyrazole carbon atom bearing the $R^7$ substituent; and
wherein one or more —CH$_2$— groups may be unsubstituted or substituted with one or more substituents independently selected from a halogen atom, a hydroxy group, a NR$^{16}$R$^{17}$ group, a C$_1$-C$_3$-alkyl group, a C$_1$-C$_3$-haloalkyl group, a C$_1$-C$_3$-alkoxy group, and a C$_1$-C$_3$-haloalkoxy group, and wherein a double bond in any alkenylene can be replaced by a 1,2-(C$_3$-C$_5$)cycloalkylene group which is unsubstituted or substituted one or two times with a halogen atom or a C$_1$-C$_2$-alkyl group, and wherein X is an unsubstituted —CH$_2$— group;

n is 2, 3, 4, 5, 6, 7, 8, or 9;

p is 0, 1, 2, 3, 4, or 5;

t is 0 or 1;

wherein the integers selected for variables n, t, and p, result in forming a 9- to 16-membered ring independently from the selection of variable A1, or A2;

B is independently selected from a —C(O)NR$^{15}$— group, a —NR$^{15}$C(O)— group, a —N(R$^{15}$)— group, a —N(R$^{15}$)—C(=O)—N(R$^{15}$)— group, a —O—C(=O)—N(R$^{15}$)— group, a —N(R$^{15}$)—C(=O)—O— group, —O—, —S—, —S(O)—, and —S(O)$_2$—;

R$^8$ is a hydrogen atom, a C$_1$-C$_6$-alkyl group, which is unsubstituted or substituted with one or more substituents independently selected from a halogen atom, a hydroxy group, a C$_1$-C$_3$-alkoxy group, a C$_1$-C$_3$-haloalkoxy group, a C$_3$-C$_6$-cycloalkyl group, a heterocycloalkyl group, and a NR$^{20}$R$^{21}$ group;

a C$_1$-C$_3$-haloalkyl group, a C$_3$-C$_6$-cycloalkyl group, and a C$_1$-C$_6$-alkyl group in which one or two not directly adjacent carbon atoms are independently replaced by a hetero atom selected from —O— and —NH—;

R$^9$ is selected from a hydrogen atom, a C$_1$-C$_4$-alkyl group, a C$_1$-C$_3$-hydroxyalkyl group, a C$_1$-C$_4$-haloalkyl group, a C$_1$-C$_4$-haloalkyl-NH—C(O)—O—(C$_1$-C$_3$-alkylene)- group, a C$_2$-C$_6$-haloalkenyl group, a C$_1$-C$_6$-alkyl-O-group, a C$_1$-C$_4$-haloalkoxy group, a C$_1$-C$_6$-alkyl-O—(C$_1$-C$_3$-alkylene)- group, a (C$_3$-C$_7$)-cycloalkyl group, a (C$_3$-C$_7$)-cycloalkyl)-O—(C$_1$-C$_3$-alkylene)- group, a phenyl-O—(C$_1$-C$_3$-alkylene)- group, a phenyl-(C$_1$-C$_3$-alkylene)-O—(C$_1$-C$_3$-alkylene)- group, a (R$^{18}$)-(phenylene)-O—(C$_1$-C$_3$-alkylene)- group, a (R$^{18}$)-(phenylene)-(C$_1$-C$_3$-alkylene)-O—(C$_1$-C$_3$-alkylene)- group, a (R$^{18}$)-(phenylene)-(heteroarylene)-O—(C$_1$-C$_3$-alkylene) group, a (R$^{18}$)-(heterocycloalkylene)-(C$_1$-C$_6$-alkylene)- group, a (R$^{18}$)-(heterocycloalkylene)-(phenylene)-O—(C$_1$-C$_3$-alkylene)- group, a (heterocycloalkenyl)-(phenylene)-O—(C$_1$-C$_3$-alkylene)- group, a (R$^{18}$)-(heteroarylene)-(C$_1$-C$_3$-alkylene)-O—(C$_1$-C$_3$-alkylene)- group, a (R$^{18}$)-(heteroarylene)-(phenylene)-O—(C$_1$-C$_3$-alkylene)- group, a (R$^{18}$)-(phenylene)-(C$_1$-C$_3$-alkylene)-O—(C$_1$-C$_3$-alkylene)- group, a (R$^{19}$)—S(O)$_2$-(phenylene)-O—(C$_1$-C$_3$-alkylene)- group, a (R$^{19}$)—S(O)$_2$—NH-(phenylene)-O—(C$_1$-C$_3$-alkylene)- group, a (R$^{19}$)—S(O)$_2$—N(C$_1$-C$_6$-alkyl)-(phenylene)-O—(C$_1$-C$_3$-alkylene)- group, a (R$^{19}$)—S(O)$_2$-(heterocycloalkylene)-(phenylene)-O—(C$_1$-C$_3$-alkylene)- group, a (R$^{18}$)-(heterocycloalkylene)-(heteroarylene)-O—(C$_1$-C$_3$-alkylene)- group, a (R$^{19}$)-(heteroarylene)-O—(C$_1$-C$_3$-alkylene)- group, a (R$^{19}$)—S(O)$_2$-(heteroarylene)-O—(C$_1$-C$_3$-alkylene)- group, a (R$^{19}$)—S(O)$_2$-(heterocycloalkylene)-(heteroarylene)-O—(C$_1$-C$_3$-alkylene)- group, a NR$^{20}$R$^{21}$—(C$_1$-C$_3$-alkylene)- group, a (C$_1$-C$_3$-alkyl)-NH—(C$_1$-C$_3$-alkylene)- group, a (C$_1$-C$_3$-haloalkyl)-(C$_1$-C$_3$-alkylene)-NH—(C$_1$-C$_3$-alkylene)- group, a (C$_1$-C$_3$-haloalkyl)-NH—(C$_1$-C$_3$-alkylene)- group, a (C$_1$-C$_3$-alkyl)-NH—C(O)—(C$_1$-C$_3$-alkylene)- group, a (C$_1$-C$_3$-alkyl)-NR$^{15}$—C(O)—(C$_1$-C$_3$-alkylene)- group, a (C$_1$-C$_3$-alkyl)-C(O)—NH—(C$_1$-C$_3$-alkylene)- group, a (C$_1$-C$_3$-alkyl)-C(O)—NR$^{15}$—(C$_1$-C$_3$-alkylene)- group, a

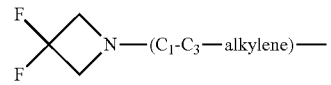

group, and a

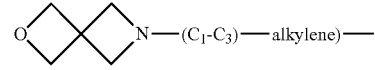

group, wherein the phenyl ring is optionally substituted with a halogen atom, a hydroxy group, or a C$_1$-C$_3$-alkoxy group and the heterocycloalkyl group is optionally substituted with an oxo (=O) group or is optionally substituted with one or more substituents independently selected from a halogen atom, and a C$_1$-C$_3$-alkyl group;

or R$^8$ and R$^9$ together form a 5- or 6-membered ring optionally containing one or two heteroatoms selected from of —O—, and —NR$^{14}$—;

R$^{14}$ is a hydrogen atom or a C$_1$-C$_3$-alkyl group;

R$^{15}$ is independently selected from a hydrogen atom, a C$_1$-C$_6$-alkyl group which is optionally substituted with one or more substituents selected from a halogen atom, a C$_1$-C$_3$-alkyl group, a C$_1$-C$_3$-haloalkyl group, a C$_1$-C$_3$-hydroxyalkyl group, a C$_1$-C$_3$-alkoxy group, a C$_1$-C$_3$-haloalkoxy group, a heterocycloalkyl group, an aryl group, a (R$^{18}$)-(heterocycloalkylene)-(arylene)-O— group, an aryl-O— group, an aryl-(C$_1$-C$_3$-alkylene)-O— group, a (R$^{19}$)—S(O)$_2$— arylene-O— group, a (R$^{19}$)S(O)$_2$-heterocycloalkylene-arylene-O— group, and an aryl-heteroarylene-O— group;

a phenyl group, a group

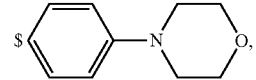

a group

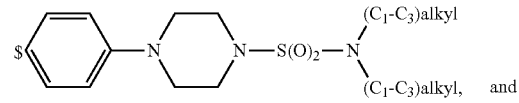

a group

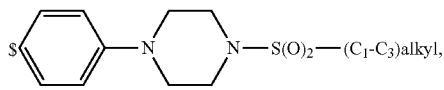

wherein $ is the point of attachment to the nitrogen atom, to which R$^{15}$ is attached;

R$^{16}$ and R$^{17}$ are each independently selected from a hydrogen atom, a C$_1$-C$_6$-alkyl group, a C$_1$-C$_6$-haloalkyl group, a C$_3$-C$_5$-cycloalkyl group, a C$_1$-C$_3$-alkyl-C(O)— group, a C$_1$-C$_3$-alkylS(O)$_2$— group, and a C$_1$-C$_3$-alkyl-O—C(=O)— group;

R$^{18}$ is selected from a hydrogen atom, a hydroxy group, a cyano group, a C$_1$-C$_3$-alkyl group, a C$_1$-C$_6$-hydroxyalkyl group, a C$_1$-C$_3$-alkoxy group, a C(O)OR$^{21}$—(C$_1$-C$_3$-alkylene)- group, a —C(O)OR$^{21}$ group, a —C(O)NR$^{20}$R$^{21}$ group, a (C$_1$-C$_3$-alkyl)-O—(C$_1$-C$_3$-alkylene)-C(O)— group, (C$_1$-C$_6$-alkyl)-C(O)— group, and a C$_3$-C$_6$-cycloalkyl-C(O)— group;

R$^{19}$ is selected from a C$_1$-C$_3$-alkyl group, a C$_3$-C$_6$-cycloalkyl group, and a NR$^{20}$R$^{21}$ group; and R$^{20}$ and R$^{21}$ are each independently selected from a hydrogen atom and a C$_1$-C$_6$-alkyl group;

or a tautomer, an N-oxide, or a salt thereof, or a salt of a tautomer, or a salt of an N-oxide, or a mixture of same.

In accordance with a further aspect, the present invention provides compounds of general formula (I): in which A is (A1)

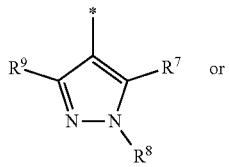

or (A2)

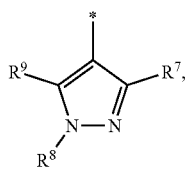

wherein R$^6$ and R$^7$, together with two carbon atoms of the pyrazole ring, two carbon atoms of the indole moiety and the nitrogen atom to which R$^6$ is attached, form a 9- to 16-membered ring and * is the point of attachment of these moieties to the indole carbon atom bearing the A substituent;

R$^1$ is a chlorine atom;

R$^2$ and R$^3$ are each a hydrogen atom;

R$^4$ is selected from an aryl group and a heteroaryl group, each of which is unsubstituted or substituted with one, two, or three, substituents and each substituent is independently selected from a halogen atom, a cyano group, a C$_1$-C$_3$-alkyl group, a C$_1$-C$_3$-haloalkyl group, a C$_1$-C$_3$-alkoxy group, a C$_1$-C$_3$-thioalkyl group, a C$_1$-C$_3$-haloalkoxy group, and a (C$_1$-C$_3$)-haloalkyl-S— group, and a C$_3$-C$_5$-cycloalkyl group;

L is a group —(CH$_2$)$_m$-E- wherein any CH$_2$ group is unsubstituted or substituted with one or two substituents and each substituent is independently selected from a halogen atom, a cyano group, a hydroxy group, a C$_1$-C$_3$-alkyl group and a C$_1$-C$_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a —S(O)$_2$— group, and a —NR$^{14}$— group;

E is a bond, an oxygen atom, a sulfur atom, a —S(O)— group, a —S(O)$_2$— group or a —NR$^{14}$— group and constitutes the connecting element to R$^4$;

R$^5$ is selected from a COOH group, a

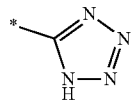

group, a —C(O)—NHS(O)$_2$(C$_1$-C$_6$-alkyl) group, a —C(O)—NHS(O)$_2$(C$_3$-C$_6$-cycloalkyl) group, a —C(O)—NHS(O)$_2$(aryl) group, a —C(O)—NHS(O)$_2$(CH$_2$)$_s$NHCO(C$_1$-C$_6$-alkyl) group, a —C(O)—NHS(O)$_2$(CH$_2$)$_s$NHCO(C$_3$-C$_6$-cycloalkyl) group, and a —C(O)—NHS(O)$_2$(CH$_2$)$_s$NHCO(aryl) group;

—R$^6$-R$^7$— is selected from $^\#$—(CH$_2$)$_n$—(B)$_t$—(CH$_2$)$_p$—X—$^{\#\#}$, $^\#$—(C$_2$-C$_6$-alkenylene)-(B)$_t$—(CH$_2$)$_p$—X—$^{\#\#}$, $^\#$—(CH$_2$)$_n$—(B)$_t$—(C$_2$-C$_5$-alkenylene)-X—$^{\#\#}$, and $^\#$—(CH$_2$)$_q$—(B)—(CH$_2$)$_r$—(B)—(CH$_2$)$_v$—X—$^{\#\#}$, wherein $^\#$ is the point of attachment with the indole nitrogen atom and $^{\#\#}$ is the point of attachment with the pyrazole carbon atom bearing the R$^7$ substituent; and wherein one or more —CH$_2$— groups may be unsubstituted or substituted with one or more substituents independently selected from a halogen atom, a hydroxy group, a NR$^{16}$R$^{17}$ group, a C$_1$-C$_3$-alkyl group, a C$_1$-C$_3$-haloalkyl group, a C$_1$-C$_3$-alkoxy group, and a C$_1$-C$_3$-haloalkoxy group, and wherein a double bond in any alkenylene can be replaced by a 1,2-cyclopropylene group or a 1,2-cyclobutylene group which are unsubstituted or substituted one or two times with a halogen atom or a C$_1$-C$_2$-alkyl group, and wherein X is an unsubstituted —CH$_2$— group;

n is 2, 3, 4, 5, 6, 7, 8, or 9;

p is 0, 1, 2, 3, 4, or 5;

t is 0 or 1;

wherein the integers selected for variables n, t, and p, result in forming a 9- to 16-membered ring independently from the selection of variable A1, or A2;

B is independently selected from a —C(O)NR$^{15}$— group, a —NR$^{15}$C(O)— group, a —N(R$^{15}$)— group, a —N(R$^{15}$)—C(=O)—N(R$^{15}$)— group, a —O—C(=O)—N(R$^{15}$)— group, a —N(R$^{15}$)—C(=O)—O— group, —O—, —S—, —S(O)—, and —S(O)$_2$—;

R$^8$ is a hydrogen atom, a C$_1$-C$_6$-alkyl group, which is unsubstituted or substituted with one or more substituents independently selected from a halogen atom, a hydroxy group, a C$_1$-C$_3$-alkoxy group, a C$_1$-C$_3$-haloalkoxy group, a C$_3$-C$_6$-cycloalkyl group, a heterocycloalkyl group and a NR$^{20}$R$^{21}$ group;

a C$_1$-C$_3$-haloalkyl group, a C$_3$-C$_6$-cycloalkyl group, a C$_1$-C$_6$-alkyl group in which one or two not directly adjacent carbon atoms are independently replaced by a hetero atom selected from —O— and —NH—;

$R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O-group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$-cycloalkyl)-O—($C_1$-$C_3$-alkylene)- group,
a phenyl-O—($C_1$-$C_3$-alkylene)- group,
a phenyl-($C_1$-$C_3$-alkylene)-O—($C_1$-$C_3$-alkylene)- group,
a ($R^{18}$)-(phenylene)-O—($C_1$-$C_3$-alkylene)- group,
a ($R^{18}$)-(phenylene)-($C_1$-$C_3$-alkylene)-O—($C_1$-$C_3$-alkylene)- group,
a ($R^{18}$)-(phenylene)-(heteroarylene)-O—($C_1$-$C_3$-alkylene) group,
a ($R^{18}$)-(heterocycloalkylene)-($C_1$-$C_6$-alkylene)- group,
a ($R^{18}$)-(heterocycloalkylene)-(phenylene)-O—($C_1$-$C_3$-alkylene)- group,
a (heterocycloalkenyl)-(phenylene)-O—($C_1$-$C_3$-alkylene)- group,
a ($R^{18}$)-(heteroarylene)-($C_1$-$C_3$-alkylene)-O—($C_1$-$C_3$-alkylene)- group,
a ($R^{18}$)-(heteroarylene)-(phenylene)-O—($C_1$-$C_3$-alkylene)- group,
a ($R^{18}$)-(phenylene)-($C_1$-$C_3$-alkylene)-O—($C_1$-$C_3$-alkylene)- group,
a ($R^{19}$)—S(O)$_2$-(phenylene)-O—($C_1$-$C_3$-alkylene)- group,
a ($R^{19}$)—S(O)$_2$—NH-(phenylene)-O—($C_1$-$C_3$-alkylene)- group,
a ($R^{19}$)—S(O)$_2$—N($C_1$-$C_6$-alkyl)-(phenylene)-O—($C_1$-$C_3$-alkylene)- group,
a ($R^{19}$)—S(O)$_2$-(heterocycloalkylene)-(phenylene)-O—($C_1$-$C_3$-alkylene)- group,
a ($R^{18}$)-(heterocycloalkylene)-(heteroarylene)-O—($C_1$-$C_3$-alkylene)- group,
a ($R^{19}$)-(heteroarylene)-O—($C_1$-$C_3$-alkylene)- group,
a ($R^{19}$)—S(O)$_2$-(heteroarylene)-O—($C_1$-$C_3$-alkylene)- group,
a ($R^{19}$)—S(O)$_2$-(heterocycloalkylene)-(heteroarylene)-O—($C_1$-$C_3$-alkylene)- group,
a $NR^{20}R^{21}$—($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-NH—C(O)—($C_1$-$C_3$-alkylene)- group,
a ($C_1$-$C_3$-alkyl)-$NR^{15}$—C(O)—($C_1$-$C_3$-alkylene)- group,
a ($C_1$-$C_3$-alkyl)-C(O)—NH—($C_1$-$C_3$-alkylene)- group,
a ($C_1$-$C_3$-alkyl)-C(O)—$NR^{15}$—($C_1$-$C_3$-alkylene)- group,
a

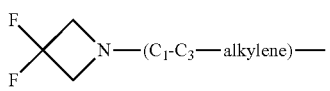

group, and a

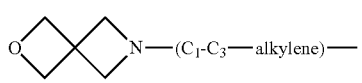

group, wherein the phenyl ring is optionally substituted with a halogen atom, a hydroxy group or a $C_1$-$C_3$-alkoxy group and
the heterocycloalkyl group is optionally substituted with an oxo (=O) group or is optionally substituted with one or more substituents independently selected from a halogen atom, and a $C_1$-$C_3$-alkyl group;
or $R^8$ and $R^9$ together form a 5- or 6-membered ring optionally containing one or two heteroatoms selected from of —O—, and —$NR^{14}$—;
$R^{14}$ is a hydrogen atom or a $C_1$-$C_3$-alkyl group;
$R^{15}$ is independently selected from a hydrogen atom,
a $C_1$-$C_6$-alkyl group
which is optionally substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a ($R^{18}$)-(heterocycloalkylene)-(arylene)-O— group, an aryl-O— group, an aryl-($C_1$-$C_3$-alkylene)-O— group, a ($R^{19}$)—S(O)$_2$— arylene-O— group, a ($R^{19}$)S(O)$_2$-heterocycloalkylene-arylene-O— group and an aryl-heteroarylene-O— group;
a phenyl group,
a group

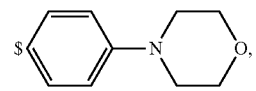

a group

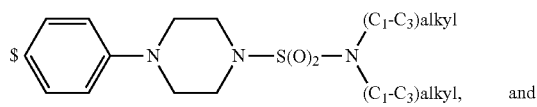

a group

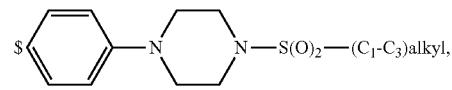

wherein $ is the point of attachment to the nitrogen atom, to which $R^{15}$ is attached,
$R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group, and a $C_1$-$C_3$-alkyl-O—C(=O)— group;
$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a C(O)$OR^{21}$—($C_1$-$C_3$-alkylene)- group, a —C(O)$OR^{21}$ group, a —C(O)$NR^{20}R^{21}$ group, a ($C_1$-$C_3$-alkyl)-O—($C_1$-$C_3$-alkylene)-C(O)— group, ($C_1$-$C_6$-alkyl)-C(O)— group, and a $C_3$-$C_6$-cycloalkyl-C(O)— group;
$R^{19}$ is selected from a $C_1$-$C_3$-alkyl group, a $C_3$-$C_6$-cycloalkyl group, and a $NR^{20}R^{21}$ group; and
$R^{20}$ and $R^{21}$ are each independently selected from a hydrogen atom and a $C_1$-$C_6$-alkyl group;

or a tautomer, an N-oxide, or a salt thereof, or a salt of a tautomer, or a salt of an N-oxide, or a mixture of same.

In accordance with a further aspect, the present invention provides compounds of general formula (I): in which
A is

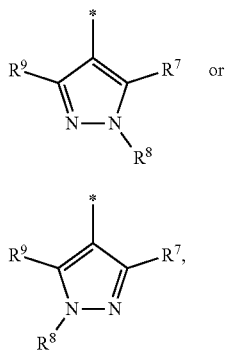

wherein $R^6$ and $R^7$, together with two carbon atoms of the pyrazole ring, two carbon atoms of the indole moiety and the nitrogen atom to which $R^6$ is attached, form a 10- to 12-membered ring and * is the point of attachment of these moieties to the indole carbon atom bearing the A substituent;
$R^1$ is a chlorine atom;
$R^2$ and $R^3$ are each a hydrogen atom;
$R^4$ is selected from an aryl group and a heteroaryl group, each of which is unsubstituted or substituted with one, two, or three, substituents and each substituent is independently selected from a halogen atom, a $C_1$-$C_3$-alkyl group, and a $C_1$-$C_3$-haloalkyl group;
L is a group —$(CH_2)_m$-E-;
E is a bond or an oxygen atom and constitutes the connecting element to $R^4$;
m is 2, 3, or 4;
$R^5$ is a COOH group;
—$R^6$-$R^7$— is selected from $^{\#}$—$(CH_2)_n$—$(B)_t$—$(CH_2)_p$—X—$^{\#\#\#}$ and $^{\#}$—$(C_2$-$C_6$-alkenylene)-$(B)_t$—$(CH_2)_p$—X—$^{\#\#\#}$, and
wherein a double bond in any alkenylene can be replaced by an unsubstituted a 1,2-($C_3$-$C_5$-cycloalkyl) group,
wherein $^{\#}$ is the point of attachment with the indole nitrogen atom and $^{\#\#\#}$ is the point of attachment with the pyrazole carbon atom bearing the $R^7$ substituent; and
wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, and a $C_1$-$C_3$-alkoxy group, and
wherein a —CH═CH— group in any alkenylene can be replaced by a 1,2-($C_1$-$C_6$)cycloalkylene group which is unsubstituted or substituted one or two times with a halogen atom or a $C_1$-$C_2$-alkyl group, and where
X is an unsubstituted —$CH_2$— group;
n is 3, 4, 5, or 6;
t is 0 or 1;
p is 0;
wherein the integers selected for variables n, t, and p, result in forming a 10- to 12-membered ring independently from the selection of variable A1 or A2;
B is independently selected from a —$N(R^{15})$— group and —O— group;

$R^8$ is selected from a hydrogen atom and,
a $C_1$-$C_4$-alkyl group, which is unsubstituted or substituted with one or more substituents independently selected from a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group, and a $NR^{20}R^{21}$ group;
$R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_2$-$C_6$-haloalkenyl group,
a $C_1$-$C_6$-alkyl-O—($C_1$-$C_3$-alkylene)- group,
a ($C_3$-$C_7$-cycloalkyl) group,
a phenyl-O—($C_1$-$C_3$-alkylene)- group,
a ($R^{18}$)-(phenylene)-O—($C_1$-$C_3$-alkylene)- group,
a ($R^{13}$)-(heterocycloalkylene)-($C_1$-$C_3$-alkylene)- group,
a ($R^{18}$)-(heteroarylene)-O—($C_1$-$C_3$-alkylene)- group,
a ($R^{19}$)—$S(O)_2$-(heteroarylene)-O—($C_1$-$C_3$-alkylene)- group,
a $NR^{20}R^{21}$—($C_1$-$C_3$-alkylene)- group, and
a ($C_1$-$C_3$-alkyl)-NH—($C_1$-$C_3$-alkylene)- group,
wherein the phenyl group is unsubstituted or substituted with a halogen atom, a hydroxy group, or a $C_1$-$C_3$-alkoxy group and
the heterocycloalkylene group is unsubstituted or substituted with a substituent independently selected from an oxo (═O) group and a $C_1$-$C_3$-alkyl group; or
$R^8$ and $R^9$ together form 6-membered ring optionally containing one or two oxygen atoms;
$R^{15}$ is selected from a hydrogen atom, a $C_1$-$C_3$-alkyl group, a $C_1$-$C_3$-haloalkyl group, a phenyl group, a benzyl group, a group

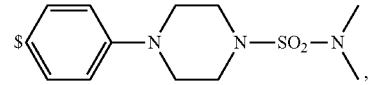

a group

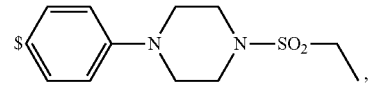

and a group

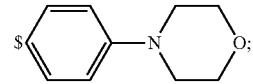

$R^{16}$ and $R^{17}$ are each independently selected from a hydrogen atom, a $C_1$-$C_6$-alkyl group, a $C_1$-$C_6$-haloalkyl group;
$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a $C(O)OR^{21}$—($C_1$-$C_3$-alkylene)- group, a —$C(O)OR^{21}$ group, a —$C(O)NR^{20}R^{21}$ group, a ($C_1$-$C_3$-alkyl)-O—($C_1$-$C_3$-alkylene)-$C(O)$— group, a ($C_1$-$C_3$-alkyl)-$C(O)$— group, and a $C_3$-$C_6$-cycloalkyl-$C(O)$— group;
$R^{19}$ is selected from a $C_1$-$C_3$-alkyl group, a $C_3$-$C_6$-cycloalkyl group, and a $NR^{20}R^{21}$ group; and
$R^{20}$ and $R^{21}$ are each independently selected from a hydrogen atom and a $C_1$-$C_3$-alkyl group;

or a tautomer, an N-oxide, or a salt thereof, or a salt of a tautomer, or a salt of an N-oxide, or a mixture of same.

In accordance with a further aspect, the present invention provides compounds of general formula (I): in which A is

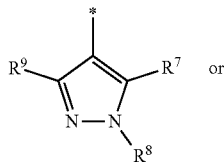

(A1)

or

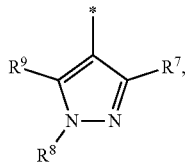

(A2)

wherein $R^6$ and $R^7$, together with two carbon atoms of the pyrazole ring, two carbon atoms of the indole moiety and the nitrogen atom to which $R^6$ is attached, form a 10- or 11-membered ring and * is the point of attachment of these moieties to the indole carbon atom bearing the A substituent;

$R^1$ is a chlorine atom;

$R^2$ and $R^3$ are each a hydrogen atom;

$R^4$ is selected from an aryl group and a heteroaryl group, each of which is unsubstituted or substituted with one or two substituents and each substituent is independently selected from a halogen atom and a $C_1$-$C_3$-alkyl group;

L is a group —$(CH_2)_m$-E-;

E is an oxygen atom and constitutes the connecting element to $R^4$, m is 3;

$R^5$ is a COOH group;

—$R^6$-$R^7$— is selected from $^{\#}$—$CH_2)_n$—(B)$_t$—$(CH_2)_p$—X—$^{\#\#}$ and $^{\#}$—$(C_2$-$C_6$-alkenylene)-(B)$_t$—$(CH_2)_p$—X—$^{\#\#}$, and wherein $^{\#}$ is the point of attachment with the indole nitrogen atom and $^{\#\#}$ is the point of attachment with the pyrazole carbon atom bearing the $R^7$ substituent and wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, and a $C_1$-$C_3$-alkoxy group, and wherein a double bond in any alkenylene can be replaced by a 1,2-cyclopropylene group or a 1,2-cyclobutylene group and wherein X is an unsubstituted —$CH_2$— group;

n is 3 or 4;

t is 1;

p is 0 wherein the integers selected for variables n, t, and p, result in forming a 10- to 11-membered ring independently from the selection of variable A1 or A2;

B is independently selected from —O— and —N($R^{15}$)—;

$R^8$ is selected from a hydrogen atom and, a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group;

$R^9$ is a $C_1$-$C_4$-alkyl group, a $C_1$-$C_3$-hydroxyalkyl group, a $C_1$-$C_3$-haloalkyl group, a $C_1$-$C_3$-alkyl-O— group, a $C_1$-$C_3$-haloalkoxy group, a $C_1$-$C_3$-alkyl-O—($C_1$-$C_3$-alkylene)- group, a ($C_3$-$C_6$)-cycloalkyl group, a $R^{18}$-(phenylene)-O—($C_1$-$C_3$-alkylene)- group, a $NR^{20}R^{21}$—($C_1$-$C_3$-alkylene)- group, and a ($C_1$-$C_3$-alkyl)-NH—($C_1$-$C_3$-alkylene)- group;

$R^{15}$ is selected from a hydrogen atom, a $C_1$-$C_3$-alkyl group and a $C_1$-$C_3$-haloalkyl group;

or a tautomer, or a salt thereof or a salt of a tautomer or a mixture of same.

In accordance with a further aspect, the present invention provides compounds of general formula (I): in which A is (A1)

(A2)

wherein $R^6$ and $R^7$, together with two carbon atoms of the pyrazole ring, two carbon atoms of the indole moiety and the nitrogen atom to which $R^6$ is attached, form a 10- or 11-membered ring and * is the point of attachment of these moieties to the indole carbon atom bearing the A substituent;

$R^1$ is a chlorine atom;

$R^2$ and $R^3$ are each a hydrogen atom;

$R^4$ is an aryl group, which is unsubstituted or substituted with a halogen atom;

L is a group —$(CH_2)_m$-E-;

E is an oxygen atom and constitutes the connecting element to $R^4$;

m is 3;

$R^5$ is a COOH group;

—$R^6$-$R^7$— is selected from $^{\#}$—$CH_2)_n$—(B)$_t$—$(CH_2)_p$—X—$^{\#\#}$ and $^{\#}$—$(C_2$-$C_6$-alkenylene)-(B)$_t$—$(CH_2)_p$—X—$^{\#\#}$, and wherein $^{\#}$ is the point of attachment with the indole nitrogen atom and $^{\#\#}$ is the point of attachment with the pyrazole carbon atom bearing the $R^7$ substituent and wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, and a $C_1$-$C_3$-alkoxy group, and wherein a double bond in any alkenylene can be replaced by a 1,2-cyclopropylene group or a 1,2-cyclobutylene group and wherein X is an unsubstituted —$CH_2$— group;

n is 3 or 4;

t is 1;

p is 0 wherein the integers selected for variables n, t, and p, result in forming a 10- to 11-membered ring independently from the selection of variable A1 or A2;

B is independently selected from —O— and —N($R^{15}$)—;
$R^8$ is selected from a hydrogen atom and,
  a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group;
$R^9$ is a $C_1$-$C_4$-alkyl group,
  a $C_1$-$C_3$-hydroxyalkyl group,
  a $C_1$-$C_3$-haloalkyl group,
  a $C_1$-$C_3$-alkyl-O— group,
  a $C_1$-$C_3$-haloalkoxy group,
  a $C_1$-$C_3$-alkyl-O—($C_1$-$C_3$-alkylene)- group,
  a ($C_3$-$C_6$)-cycloalkyl group,
  a $R^{18}$-(phenylene)-O—($C_1$-$C_3$-alkylene)- group,
  a $NR^{20}R^{21}$—($C_1$-$C_3$-alkylene)- group, and
  a ($C_1$-$C_3$-alkyl)-NH—($C_1$-$C_3$-alkylene)- group;
$R^{15}$ is selected from a hydrogen atom, a $C_1$-$C_3$-alkyl group and a $C_1$-$C_3$-haloalkyl group;
or a tautomer, or a salt thereof or a salt of a tautomer or a mixture of same.

In accordance with a further aspect, the present invention provides compounds of general formula (I): in which
A is

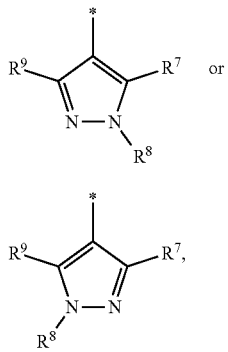

(A1)

(A2)

wherein $R^6$ and $R^7$, together with two carbon atoms of the pyrazole ring, two carbon atoms of the indole moiety and the nitrogen atom to which $R^6$ is attached, form a 10- or 11-membered ring and * is the point of attachment of these moieties to the indole carbon atom bearing the A substituent;
$R^1$ is a chlorine atom;
$R^2$ and $R^3$ are each a hydrogen atom;
$R^4$ is selected from an aryl group and a heteroaryl group, each of which is unsubstituted or substituted with one or two substituents and each substituent is independently selected from a halogen atom and a $C_1$-$C_3$-alkyl group;
L is a group —$(CH_2)_m$-E-;
E is an oxygen atom and constitutes the connecting element to $R^4$;
m is 3;
$R^5$ is a COOH group;
—$R^6$-$R^7$— is selected from $^{\#}$—$(CH_2)_n$—$(B)_t$—$(CH_2)_p$—X—$^{\#\#}$ and $^{\#}$—$(C_2$-$C_6$-alkenylene)-$(B)_t$—$(CH_2)_p$—X—$^{\#\#}$, and
  wherein $^{\#}$ is the point of attachment with the indole nitrogen atom and $^{\#\#}$ is the point of attachment with the pyrazole carbon atom bearing the $R^7$ substituent and wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, and a $C_1$-$C_3$-alkoxy group, and
  wherein a double bond in any alkenylene can be replaced by a 1,2-cyclopropylene group or a 1,2-cyclobutylene group, and
  wherein X is an unsubstituted —$CH_2$— group;
n is 3 or 4;
t is 1;
p is 0
  wherein the integers selected for variables n, t, and p, result in forming a 10- to 11-membered ring independently from the selection of variable A1 or A2;
B is independently selected from —O— and —N($R^{15}$)—;
$R^8$ is selected from a hydrogen atom and,
  a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group;
$R^9$ is a $C_1$-$C_4$-alkyl group,
$R^{15}$ is selected from a hydrogen atom, a $C_1$-$C_3$-alkyl group and a $C_1$-$C_3$-haloalkyl group;
or a tautomer, or a salt thereof or a salt of a tautomer or a mixture of same.

In accordance with a further aspect, the present invention provides compounds of general formula (I): in which
A is

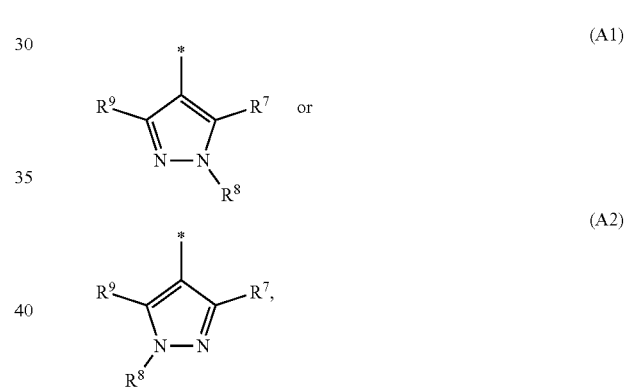

(A1)

(A2)

wherein $R^6$ and $R^7$, together with two carbon atoms of the pyrazole ring, two carbon atoms of the indole moiety and the nitrogen atom to which $R^6$ is attached, form a 10- or 11-membered ring and * is the point of attachment of these moieties to the indole carbon atom bearing the A substituent;
$R^1$ is a chlorine atom;
$R^2$ and $R^3$ are each a hydrogen atom;
$R^4$ is an aryl group, which is unsubstituted or substituted with a halogen atom;
L is a group —$(CH_2)_m$-E-;
E is an oxygen atom and constitutes the connecting element to $R^4$;
m is 3;
$R^5$ is a COOH group;
—$R^6$-$R^7$— is selected from $^{\#}$—$(CH_2)_n$—$(B)_t$—$(CH_2)_p$—X—$^{\#\#}$ and $^{\#}$—$(C_2$-$C_6$-alkenylene)-$(B)_t$—$(CH_2)_p$—X—$^{\#\#}$, and
  wherein $^{\#}$ is the point of attachment with the indole nitrogen atom and $^{\#\#}$ is the point of attachment with the pyrazole carbon atom bearing the $R^7$ substituent and wherein one or more —$CH_2$— groups may be unsubstituted or substituted with one or more substituents independently selected from a halogen atom, a hydroxy group, a NR$^{16}$R$^{17}$ group, a C$_1$-C$_3$-alkyl group, a C$_1$-C$_3$-haloalkyl group, and a C$_1$-C$_3$-alkoxy group, and wherein a double bond in any alkenylene can be replaced by a 1,2-cyclopropylene group or a 1,2-cyclobutylene group, and wherein X is an unsubstituted —CH$_2$— group;

n is 3 or 4;

t is 1;

p is 0 wherein the integers selected for variables n, t, and p, result in forming a 10- to 11-membered ring independently from the selection of variable A1 or A2;

B is independently selected from —O— and —N(R$^{15}$)—;

R$^8$ is selected from a hydrogen atom and,
a C$_1$-C$_4$-alkyl group, which is unsubstituted or substituted with one or more substituents independently selected from a halogen atom, a hydroxy group, a C$_3$-C$_6$-cycloalkyl group, and a heterocycloalkyl group;

R$^9$ is a C$_1$-C$_4$-alkyl group;

R$^{15}$ is selected from a hydrogen atom, a C$_1$-C$_3$-alkyl group and a C$_1$-C$_3$-haloalkyl group;

or a tautomer, or a salt thereof or a salt of a tautomer or a mixture of same.

In accordance with a further aspect, the present invention provides compounds of general formula (I): in which
A is

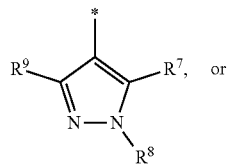

(A1)

or

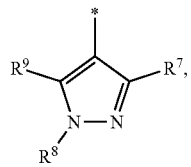

(A2)

wherein R$^6$ and R$^7$, together with two carbon atoms of the pyrazole ring, two carbon atoms of the indole moiety and the nitrogen atom to which R$^6$ is attached, form a 10- or 11-membered ring and * is the point of attachment of these moieties to the indole carbon atom bearing the A substituent;

R$^1$ is a chlorine atom;

R$^2$ and R$^3$ are a hydrogen atom;

R$^4$ is a naphtyl group, which is unsubstituted or substituted with a fluorine atom;

L is a group —(CH$_2$)$_3$—O—;

R$^5$ is a COOH group;

—R$^6$-R$^7$— is selected from $^{\#}$—(CH$_2$)$_n$—(B)$_t$—(CH$_2$)$_p$—X—$^{\#\#}$ and $^{\#}$—(C$_2$-C$_6$-alkenylene)-(B)$_t$—(CH$_2$)$_p$—X—$^{\#\#}$, and wherein $^{\#}$ is the point of attachment with the indole nitrogen atom and $^{\#\#}$ is the point of attachment with the pyrazole carbon atom bearing the R$^7$ substituent wherein a —CH=CH— group in any alkenylene can be replaced by a 1,2-cyclopropylene group or a 1,2-cyclobutylene group and wherein one or more —CH$_2$— groups may be unsubstituted or substituted with one or two substituents independently selected from a halogen atom, a hydroxy group and a C$_1$-C$_3$-alkyl group, and wherein X is an unsubstituted —CH$_2$— group;

n is 3 or 4;

t is 1;

p is 1 or 2 wherein the integers selected for variables n, t, and p, result in forming a 10- or 11-membered ring independently from the selection of variable A1 or A2;

B is independently selected from —O— and —N(R$^{15}$)—;

R$^8$ is selected from a methyl group and a 2-morpholinoethyl group;

R$^9$ is selected from a methyl group and an ethyl group;

R$^{15}$ is selected from a hydrogen atom, a methyl group, a 2,2-difluoroethyl group, and a 2,2,2-trifluoroethyl group;

or a tautomer, or a salt thereof or a salt of a tautomer or a mixture of same.

In accordance with a further aspect, the present invention provides compounds of general formula (I):
in which
A is

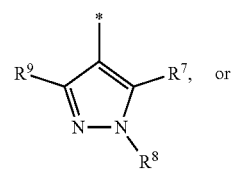

(A1)

or

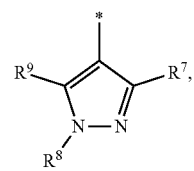

(A2)

wherein R$^6$ and R$^7$, together with two carbon atoms of the pyrazole ring, two carbon atoms of the indole moiety and the nitrogen atom to which R$^6$ is attached, form a 11-membered ring and * is the point of attachment of these moieties to the indole carbon atom bearing the A substituent;

R$^1$ is a chlorine atom;

R$^2$ and R$^3$ are each a hydrogen atom;

R$^4$ is a naphtyl group, which is unsubstituted or substituted with a halogen atom;

L is a group —(CH$_2$)$_3$—O—;

R$^5$ is a COOH group;

—R$^6$-R$^7$— is selected from $^{\#}$—(CH$_2$)$_n$—(B)$_t$—(CH$_2$)$_p$—X—$^{\#\#}$ and $^{\#}$—(C$_2$-C$_6$-alkenylene)-(B)$_t$—(CH$_2$)$_p$—X—$^{\#\#}$, and wherein $^{\#}$ is the point of attachment with the indole nitrogen atom and $^{\#\#}$ is the point of attachment with the pyrazole carbon atom bearing the R$^7$ substituent, and wherein one or more —CH$_2$— groups may be unsubstituted or substituted with one or more halogen atoms, and wherein a —CH=CH— group in any alkenylene can be replaced by a

group or a

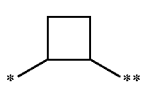

group wherein * is the point of attachment of the ring to the adjacent —$CH_2$— group or to the indole nitrogen atom and ** is the point of attachment to the adjacent —$CH_2$— group or to —(B)$_t$—, and
  wherein X is an unsubstituted —$CH_2$— group;
n is 4;
t is 1;
p is 0
  wherein the integers selected for variables n, t, and p, result in forming a 11-membered ring independently from the selection of variable A1 or A2;
B is independently selected from —O— and —N($R^{15}$)—;
$R^8$ is a $C_1$-$C_3$-alkyl group, which is unsubstituted or substituted with a heterocycloalkyl group;
$R^9$ is a $C_1$-$C_3$-alkyl group;
$R^{15}$ is selected from a hydrogen atom, a $C_1$-$C_3$-alkyl group, and a $C_1$-$C_3$-haloalkyl group;
or a tautomer, or a salt thereof or a salt of a tautomer or a mixture of same.

In accordance with a further aspect, the present invention provides compounds of general formula (I) in which:
A is

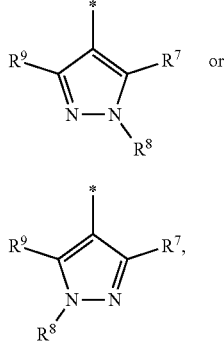

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;
$R^1$ is a chlorine atom;
$R^2$ and $R^3$ are a hydrogen atom;
$R^4$ is a naphtyl group, which is unsubstituted or substituted with a halogen atom;
L is a group —($CH_2$)$_3$—O—;
$R^5$ is a COOH group;
—$R^6$-$R^7$— is selected from $^\#$—($CH_2$)$_n$—(B)$_t$—($CH_2$)$_p$—X—$^{\#\#}$ and $^\#$—($C_2$-$C_6$-alkenylene)-(B)—($CH_2$)$_p$—X—$^{\#\#}$, wherein $^\#$ is the point of attachment with the indole nitrogen atom and $^{\#\#}$ is the point of attachment with the pyrazole carbon atom bearing the $R^7$ substituent and wherein one or more —$CH_2$— groups may be unsubstituted or substituted with one or more halogen atoms, wherein a —CH=CH— group in any alkenylene can be replaced by a 1,2-($C_3$-$C_5$-cycloalkylene) group and said 1,2-($C_3$-$C_5$-cycloalkylene) is unsubstituted;
  wherein X is an unsubstituted —$CH_2$— group;
n is 3 or 4;
t is 1;
p is 1 or 2 wherein the integers selected for variables n, t, and p, result in forming a 11-membered ring independently from the selection of variable A1 or A2;
B is independently selected from —O— and —N($R^{15}$)—;
$R^8$ is a $C_1$-$C_3$-alkyl group, which is unsubstituted or substituted with a heterocycloalkyl group;
$R^9$ is a $C_1$-$C_3$-alkyl group;
$R^{15}$ is selected from a hydrogen atom, a $C_1$-$C_3$-alkyl group, a $C_1$-$C_3$-haloalkyl group;
or a tautomer, or a salt thereof or a salt of a tautomer or a mixture of same.

In accordance with a further aspect, the present invention provides compounds of general formula (I) in which:
A is

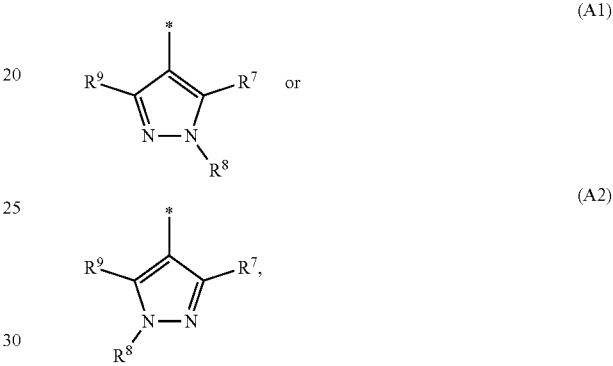

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;
$R^1$ is a chlorine atom;
$R^2$ and $R^3$ are a hydrogen atom;
$R^4$ is a naphtyl group, which is unsubstituted or substituted with a halogen atom;
L is a group —($CH_2$)$_3$—O—;
$R^5$ is a COOH group;
—$R^6$-$R^7$— is $^\#$—($CH_2$)$_n$—(B)$_t$—($CH_2$)$_p$—X—$^{\#\#}$, and
  wherein $^\#$ is the point of attachment with the indole nitrogen atom and $^{\#\#}$ is the point of attachment with the pyrazole carbon atom bearing the $R^7$ substituent, and
  wherein one or more —$CH_2$— groups may be unsubstituted or substituted with one or more halogen atoms, and
  wherein X is an unsubstituted —$CH_2$— group;
n is 3 or 4;
t is 1;
p is 1 or 2;
  wherein the integers selected for variables n, t, and p, result in forming a 11-membered ring independently from the selection of variable A1 or A2;
B is independently selected from —O— and —N($R^{15}$)—;
$R^8$ is a $C_1$-$C_3$-alkyl group, which is unsubstituted or substituted with a heterocycloalkyl group;
$R^9$ is a $C_1$-$C_3$-alkyl group;
$R^{15}$ is selected from a hydrogen atom, a $C_1$-$C_3$-alkyl group, and a $C_1$-$C_3$-haloalkyl group
or a tautomer, or a salt thereof or a salt of a tautomer or a mixture of same.

In accordance with a further aspect, the present invention provides compounds of general formula (I):
in which
A is

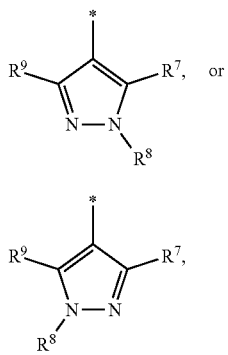

(A1)

(A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is a chlorine atom;
$R^2$ and $R^3$ are a hydrogen atom;
$R^4$ is a naphtyl group, which is unsubstituted or substituted with a halogen atom;
L is a group —$(CH_2)_3$—O—;
$R^5$ is a COOH group;
—$R^6$-$R^7$— is $^\#$—$(C_2$-$C_6$-alkenylene)-$(B)_t$—$(CH_2)_p$—X—$^{\#\#}$, and
  wherein $^\#$ is the point of attachment with the indole nitrogen atom and $^{\#\#}$ is the point of attachment with the pyrazole carbon atom bearing the $R^7$ substituent, and
  wherein one or more —$CH_2$— groups may be unsubstituted or substituted with one or more halogen atoms, and
  wherein a —CH═CH— group in any alkenylene can be replaced by a 1,2-($C_3$-$C_5$-cycloalkylene) group and said 1,2-($C_3$-$C_5$-cycloalkylene) is unsubstituted, and
  wherein X is an unsubstituted —$CH_2$— group;
n is 3 or 4;
t is 1;
p is 1 or 2
  wherein the integers selected for variables n, t, and p, result in forming a 11-membered ring independently from the selection of variable A1 or A2;
B is independently selected from —O— and —N($R^{15}$)—;
$R^8$ is a $C_1$-$C_3$-alkyl group, which is unsubstituted or substituted with a heterocycloalkyl group;
$R^9$ is a $C_1$-$C_3$-alkyl group;
$R^{15}$ is selected from a hydrogen atom, a $C_1$-$C_3$-alkyl group, and a $C_1$-$C_3$-haloalkyl group;
or a tautomer, or a salt thereof or a salt of a tautomer or a mixture of same.

In accordance with a further aspect, the present invention provides compounds of general formula (I):
in which
A is (A1)

(A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is a chlorine atom;
$R^2$ and $R^3$ are a hydrogen atom;
$R^4$ is a naphtyl group, which is unsubstituted or substituted with a fluorine atom;
L is a group —$(CH_2)_3$—O—;
$R^5$ is a COOH group;
—$R^6$-$R^7$— is selected from $^\#$—$(CH_2)_n$—$(B)_t$—$(CH_2)_p$—X—$^{\#\#}$ and $^\#$—$(C_2$-$C_6$-alkenylene)-$(B)_t$—$(CH_2)_p$—X—$^{\#\#}$, and
  wherein $^\#$ is the point of attachment with the indole nitrogen atom and $^{\#\#}$ is the point of attachment with the pyrazole carbon atom bearing the $R^7$ substituent, and
  wherein one or more —$CH_2$— groups may be unsubstituted or substituted with one or two fluorine atoms, and
  and wherein a —CH═CH— group in any alkenylene can be replaced by a

group or a

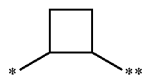

group wherein * is the point of attachment of the ring to the adjacent —$CH_2$— group or to the indole nitrogen atom and ** is the point of attachment to the adjacent —$CH_2$— group or to —$(B)_t$— and
  wherein X is an unsubstituted —$CH_2$— group;
n is 3 or 4;
t is 1;
p is 1 or 2;
  wherein the integers selected for variables n, t, and p, result in forming a 11-membered ring independently from the selection of variable A1 or A2;
B is independently selected from —O— and —N($R^{15}$)—;

R⁸ is a $C_1$-$C_3$-alkyl group, which is unsubstituted or substituted with a heterocycloalkyl group;
R⁹ is a $C_1$-$C_3$-alkyl group;
R¹⁵ is selected from a hydrogen atom, a $C_1$-$C_3$-alkyl group, a $C_1$-$C_3$-haloalkyl group;
or a tautomer, or a salt thereof or a salt of a tautomer or a mixture of same.

In accordance with a further aspect, the present invention provides compounds of general formula (I) in which A is

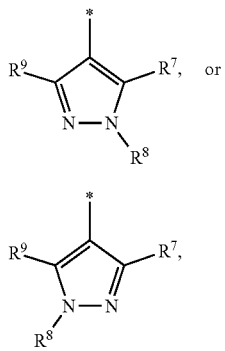

(A1)

or (A2)

wherein R⁶ and R⁷, together with two carbon atoms of the pyrazole ring, two carbon atoms of the indole moiety and the nitrogen atom to which R⁶ is attached, form a 11-membered ring and * is the point of attachment of these moieties to the indole carbon atom bearing the A substituent;
R¹ is a chlorine atom;
R² and R³ are each a hydrogen atom;
R⁴ is a naphtyl group, which is unsubstituted or substituted with a fluorine atom;
L is a group —$(CH_2)_3$—O—;
R⁵ is a COOH group;
—R⁶-R⁷— is selected from #—$(CH_2)_n$—$(B)_t$—$(CH_2)_p$—X—## and #—$(C_2$-$C_6$-alkenylene)-$(B)_t$—$(CH_2)_p$—X—##, and
wherein # is the point of attachment with the indole nitrogen atom and ## is the point of attachment with the pyrazole carbon atom bearing the R⁷ substituent and
wherein one or more —$CH_2$— groups may be unsubstituted or substituted with one or more fluorine atoms, and wherein a —CH=CH— group in any alkenylene can be replaced by a

group or a

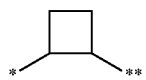

group wherein * is the point of attachment of the ring to the adjacent —$CH_2$— group or to the indole nitrogen atom and ** is the point of attachment to the adjacent —$CH_2$— group or to —$(B)_t$— and
wherein X is an unsubstituted —$CH_2$— group;
n is 4;
t is 1;
p is 0;
wherein the integers selected for variables n, t, and p, result in forming a 11-membered ring independently from the selection of variable A1 or A2;
B is independently selected from —O— and —$N(R^{15})$—;
R⁸ is a $C_1$-$C_3$-alkyl group, which is unsubstituted or substituted with a morpholino or 4-methyl-piperazino group;
R⁹ is a $C_1$-$C_2$-alkyl group;
R¹⁵ is selected from a hydrogen atom, a $C_1$-$C_3$-alkyl group, and a $C_1$-$C_3$-haloalkyl group;
or a tautomer, or a salt thereof or a salt of a tautomer or a mixture of same.

In accordance with a further aspect, the present invention provides compounds of general formula (I) in which:
A is

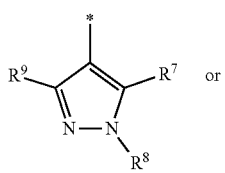

(A1)

or

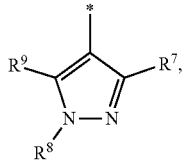

(A2)

wherein R⁶ and R⁷, together with two carbon atoms of the pyrazole ring, two carbon atoms of the indole moiety and the nitrogen atom to which R⁶ is attached, form a 11-membered ring and * is the point of attachment of these moieties to the indole carbon atom bearing the A substituent;
R¹ is a chlorine atom;
R² and R³ are each a hydrogen atom;
R⁴ is a naphtyl group, which is unsubstituted or substituted with a fluorine atom;
L is a group —$(CH_2)_3$—O—;
R⁵ is a COOH group;
—R⁶-R⁷— is #—$(CH_2)_n$—$(B)_t(CH_2)_p$—X—##, and wherein # is the point of attachment with the indole nitrogen atom and * is the point of attachment with the pyrazole carbon atom bearing the R⁷ substituent and
wherein one or more —$CH_2$— groups may be unsubstituted or substituted with one or more fluorine atoms,
wherein X is an unsubstituted —$CH_2$— group;
n is 4;
t is 1;
p is 0;
wherein the integers selected for variables n, t, and p, result in forming a 11-membered ring independently from the selection of variable A1 or A2;
B is independently selected from —O— and —$N(R^{15})$—;
R⁸ is a methyl group;
R⁹ is a $C_1$-$C_2$-alkyl group;
R¹⁵ is selected from a hydrogen atom, a methyl group, and a $CH_2CF_3$— and a $CH_2CHF_2$ group;
or a tautomer, or a salt thereof or a salt of a tautomer or a mixture of same.

In accordance with a further aspect, the present invention provides compounds of general formula (I) in which A is

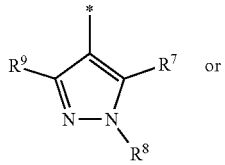

(A1)

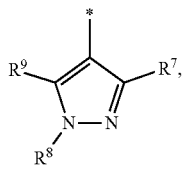

(A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;
$R^1$ is a chlorine atom;
$R^2$ and $R^3$ are each a hydrogen atom;
$R^4$ is a 6-fluoro-naphtyl group;
L is a group —$(CH_2)_3$—O—;
$R^5$ is a COOH group;
—$R^6$-$R^7$— is $^\#$—$(CH_2)_n$—$(B)_t(CH_2)_p$—X—$^{\#\#}$, and wherein
$^\#$ is the point of attachment with the indole nitrogen atom and * is the point of attachment with the pyrazole carbon atom bearing the $R^7$ substituent and
wherein one or more —$CH_2$— groups may be unsubstituted or substituted with one or more fluorine atoms,
wherein X is an unsubstituted —$CH_2$— group;
n is 4;
t is 1;
p is 0;
wherein the integers selected for variables n, t, and p, result in forming a 11-membered ring independently from the selection of variable A1 or A2;
B is —O—;
$R^8$ is a methyl group;
$R^9$ is a $C_1$-$C_2$-alkyl group;
or a tautomer, or a salt thereof or a salt of a tautomer or a mixture of same.

In accordance with a further aspect, the present invention provides compounds of general formula (I) in which
A is

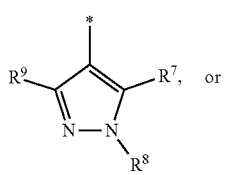

(A1)

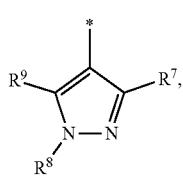

(A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;
$R^1$ is a chlorine atom;
$R^2$ and $R^3$ are each a hydrogen atom;
$R^4$ is a 6-fluoro-naphtyl group;
L is a group —$(CH_2)_3$—O—;
$R^5$ is a COOH group;
—$R^6$-$R^7$— is $^\#$—$(CH_2)_n$—$(B)_t(CH_2)_p$—X—$^{\#\#}$, and wherein
$^\#$ is the point of attachment with the indole nitrogen atom and * is the point of attachment with the pyrazole carbon atom bearing the $R^7$ substituent and
wherein one or more —$CH_2$— groups may be unsubstituted or substituted with one or more fluorine atoms,
wherein X is an unsubstituted —$CH_2$— group;
n is 4;
t is 1;
p is 0;
wherein the integers selected for variables n, t, and p, result in forming a 11-membered ring independently from the selection of variable A1 or A2;
B is —$NR^{15}$—;
$R^8$ is a methyl group;
$R^9$ is a $C_1$-$C_2$-alkyl group;
$R^{15}$ is selected from a hydrogen atom, a methyl group, and a $CH_2CF_3$— and a $CH_2CHF_2$ group;
or a tautomer, or a salt thereof or a salt of a tautomer or a mixture of same.

In accordance with a further aspect, the present invention provides compounds of general formula (I) in which:
A is

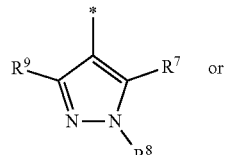

(A1)

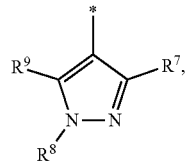

(A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;
$R^1$ is a chlorine atom;
$R^2$ and $R^3$ are each a hydrogen atom;
$R^4$ is a naphtyl group, which is unsubstituted or substituted with a fluorine atom;
L is a group —$(CH_2)_3$—O—;
$R^5$ is a COOH group;
—$R^6$-$R^7$— is $^\#$—$(CH_2)_n$—$(B)_t(CH_2)_p$—X—$^{\#\#}$, and wherein
$^\#$ is the point of attachment with the indole nitrogen atom and ## is the point of attachment with the pyrazole carbon atom bearing the $R^7$ substituent;
B is —$NR^{15}$— or —O—;
n is 4;
t is 1;
p is 0;
wherein the integers selected for variables n, t, and p, result in forming a 11-membered ring independently from the selection of variable A1 or A2;
$R^8$ is methyl or —$(CH_2)_2$-morpholino;
$R^9$ is methyl or ethyl;
$R^{15}$ is methyl or —$CH_2$—$CF_3$;
or a tautomer, or a salt thereof or a salt of a tautomer or a mixture of same.

In accordance with a further aspect, the present invention provides compounds of general formula (I):
in which
A is

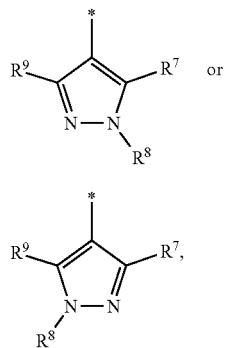

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent
$R^1$ is a chlorine atom;
$R^2$ and $R^3$ are a hydrogen atom;
$R^4$ is a naphtyl group, which is unsubstituted or substituted with a fluorine atom;
L is a group —$(CH_2)_3$—O—;
$R^5$ is a COOH group;
—$R^6$-$R^7$— is selected from #—$(CH_2)_3$—$N(CH_3)$—$CH_2$—##, #—$(CH_2)_3$—NH—$CH_2$—##, #—$(CH_2)_4$—$N(CH_3)$—$CH_2$—##, #—$(CH_2)_4$—$N(CH_2CF_3)$—$CH_2$—##, #—$(CH_2)_4$—$N(CH_2CHF_2)$—$CH_2$—*, #—$CH_2$—CH=CH—$CH_2$—O—$CH_2$—##, #—$CH_2$—CH=CH—$CH_2$—$N(CH_3)$—$CH_2$—##, #—$(CH_2)_4O$—$CH_2$—##, #—$(CH_2)_6$—##, #—$(CH_2)_2$—$CF_2$—$CH_2$—O—$CH_2$—##, #—$CH_2$—$CF_2$—$(CH_2)_2O$—$CH_2$—##, #—$CH_2$—$CF_2$—$CF_2$—$CH_2$—O—$CH_2$—##,

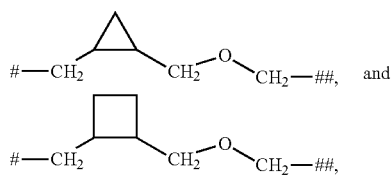

and wherein # is the point of attachment with the indole nitrogen atom and ## is the point of attachment with the pyrazole carbon atom bearing the $R^7$ substituent
n is 3 or 4;
t is 1;
p is 1 or 2;
wherein the integers selected for variables n, t, and p, result in forming a 11-membered ring independently from the selection of variable A1 or A2;
B is independently selected from —O— and —$N(R^{15})$—;
$R^8$ is selected from a methyl group, an ethyl group and a propyl group which is substituted with a morpholino group;
$R^9$ is a methyl group or an ethyl group;
$R^{15}$ is selected from a hydrogen atom, a methyl group, a 2,2-difluoroethyl group and a 2,2,2-trifluoroethyl group;
or a tautomer or a salt thereof or a salt of a tautomer or a mixture of same.

In some embodiments, the present invention includes compounds of general formula (I) selected from
(rac)-(11Z)-4-chloro-1,3-dimethyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid,
rac-4-chloro-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid,
4-chloro-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1),
4-chloro-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2),
(rac)-4-chloro-3-ethyl-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid,
4-chloro-3-ethyl-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid (enantiomer 1),
4-chloro-3-ethyl-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid (enantiomer 2),
(rac)-4-chloro-3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid,
4-chloro-3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (enantiomer 1),
4-chloro-3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (enantiomer 2),
(rac)-4-chloro-2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid,
(+)-4-chloro-2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid-N-ethylethanamine salt (enantiomer 1), (−)-4-chloro-2,3,14-trimethyl-7-[3-(naphthalen-1-yloxy)
propyl]-10,11,12,13,14,15-hexahydro-2H-pyrazolo[3',4':
8,9][1,6]diazacycloundecino[10,11,1-hi]indole-8-carbox-
ylic acid-N-ethylethanamine salt (enantiomer 2), (rac)-4-chloro-7-{3-[(6-fluoronaphthalen-1-yl)oxy]propyl}-
2,3-dimethyl-2,10,11,12,13,15-hexahydropyrazolo[4',3':
9,10][1,6]oxazacycloundecino[8,7,6-hi]indole-8-carbox-
ylic acid, (+)-4-chloro-7-{3-[(6-fluoronaphthalen-1-yl)oxy]propyl}-
2,3-dimethyl-2,10,11,12,13,15-hexahydropyrazolo[4',3':
9,10][1,6]oxazacycloundecino[8,7,6-hi]indole-8-carbox-
ylic acid-N-ethylethanamine salt (enantiomer 1), (−)-4-chloro-7-{3-[(6-fluoronaphthalen-1-yl)oxy]propyl}-
2,3-dimethyl-2,10,11,12,13,15-hexahydropyrazolo[4',3':
9,10][1,6]oxazacycloundecino[8,7,6-hi]indole-8-carbox-
ylic acid (enantiomer 1), (−)-4-chloro-7-{3-[(6-fluoronaphthalen-1-yl)oxy]propyl}-
2,3-dimethyl-2,10,11,12,13,15-hexahydropyrazolo[4',3':
9,10][1,6]oxazacycloundecino[8,7,6-hi]indole-8-carbox-
ylic acid-N-ethylethanamine salt (enantiomer 2), (rac)-(11Z)-4-chloro-3-ethyl-2-methyl-7-[3-(naphthalen-1-
yloxy)propyl]-2,10,13,15-tetrahydropyrazolo[4',3':9,10]
[1,6]oxazacycloundecino[8,7,6-hi]indole-8-carboxylic
acid (rac)-4-chloro-3-ethyl-2-methyl-7-[3-(naphthalen-1-yloxy)
propyl]-2,10,11,12,13,15-hexahydropyrazolo[4',3':9,10]
[1,6]oxazacycloundecino[8,7,6-hi]indole-8-carboxylic
acid, 4-chloro-3-ethyl-2-methyl-7-[3-(naphthalen-1-yloxy)pro-
pyl]-2,10,11,12,13,15-hexahydropyrazolo[4',3':9,10][1,6]
oxazacycloundecino[8,7,6-hi]indole-8-carboxylic acid
(enantiomer 1), 4-chloro-3-ethyl-2-methyl-7-[3-(naphthalen-1-yloxy)pro-
pyl]-2,10,11,12,13,15-hexahydropyrazolo[4',3':9,10][1,6]
oxazacycloundecino[8,7,6-hi]indole-8-carboxylic acid
(enantiomer 2), (rac)-4-chloro-3-ethyl-2,14-dimethyl-7-[3-(naphthalen-1-
yloxy)propyl]-10,11,12,13,14,15-hexahydro-2H-pyra-
zolo[3',4':8,9][1,6]diazacycloundecino[10,11,1-hi]indole-
8-carboxylic acid, 4-chloro-3-ethyl-2,14-dimethyl-7-[3-(naphthalen-1-yloxy)
propyl]-10,11,12,13,14,15-hexahydro-2H-pyrazolo[3',4':
8,9][1,6]diazacycloundecino[10,11,1-hi]indole-8-carbox-
ylic acid (enantiomer 1), 4-chloro-3-ethyl-2,14-dimethyl-7-[3-(naphthalen-1-yloxy)
propyl]-10,11,12,13,14,15-hexahydro-2H-pyrazolo[3',4':
8,9][1,6]diazacycloundecino[10,11,1-hi]indole-8-carbox-
ylic acid (enantiomer 2), (rac)-4-chloro-2,3-dimethyl-7-[3-(naphthalen-1-yloxy)pro-
pyl]-2,10,11,12,13,15-hexahydropyrazolo[4',3':9,10][1,6]
oxazacycloundecino[8,7,6-hi]indole-8-carboxylic acid, 4-chloro-2,3-dimethyl-7-[3-(naphthalen-1-yloxy)propyl]-2,
10,11,12,13,15-hexahydropyrazolo[4',3':9,10][1,6]oxaza-
cycloundecino[8,7,6-hi]indole-8-carboxylic acid-N-ethy-
lethanamine salt (enantiomer 1), 4-chloro-2,3-dimethyl-7-[3-(naphthalen-1-yloxy)propyl]-2,
10,11,12,13,15-hexahydropyrazolo[4',3':9,10][1,6]oxaza-
cycloundecino[8,7,6-hi]indole-8-carboxylic acid-N-ethy-
lethanamine salt (enantiomer 2), (rac)-12-chloro-10,11-dimethyl-1-[3-(naphthalen-1-yloxy)
propyl]-4,5,6,7,8,10-hexahydropyrazolo[3',4':7,8][1,5]di-
azecino[9,10,1-hi]indole-2-carboxylic acid-formic acid
salt, (rac)-12-chloro-7,10,11-trimethyl-1-[3-(naphthalen-1-
yloxy)propyl]-4,5,6,7,8,10-hexahydropyrazolo[3',4':7,8]
[1,5]diazecino[9,10,1-hi]indole-2-carboxylic acid, (rac)-4-chloro-7-{3-[(6-fluoronaphthalen-1-yl)oxy]propyl}-
2,3,14-trimethyl-10,11,12,13,14,15-hexahydro-2H-pyra-
zolo[3',4':8,9][1,6]diazacycloundecino[10,11,1-hi]indole-
8-carboxylic acid, (+)-4-chloro-7-{3-[(6-fluoronaphthalen-1-yl)oxy]propyl}-
2,3,14-trimethyl-10,11,12,13,14,15-hexahydro-2H-pyra-
zolo[3',4':8,9][1,6]diazacycloundecino[10,11,1-hi]indole-
8-carboxylic acid-N-ethylethanamine salt (enantiomer 1), (−)-4-chloro-7-{3-[(6-fluoronaphthalen-1-yl)oxy]propyl}-
2,3,14-trimethyl-10,11,12,13,14,15-hexahydro-2H-pyra-
zolo[3',4':8,9][1,6]diazacycloundecino[10,11,1-hi]indole-
8-carboxylic acid-N-ethylethanamine salt (enantiomer 2), (rac)-4-chloro-3-ethyl-7-{3-[(6-fluoronaphthalen-1-yl)oxy]
propyl}-1-methyl-1,10,11,12,13,15-hexahydropyrazolo
[4',3':9,10][1,6]oxazacycloundecino[8,7,6-hi]indole-8-
carboxylic acid (+)-4-chloro-3-ethyl-7-{3-[(6-fluoronaphthalen-1-yl)oxy]
propyl}-1-methyl-1,10,11,12,13,15-hexahydropyrazolo
[4',3':9,10][1,6]oxazacycloundecino[8,7,6-hi]indole-8-
carboxylic acid (enantiomer 1), (−)-4-chloro-3-ethyl-7-{3-[(6-fluoronaphthalen-1-yl)oxy]
propyl}-1-methyl-1,10,11,12,13,15-hexahydropyrazolo
[4',3':9,10][1,6]oxazacycloundecino[8,7,6-hi]indole-8-
carboxylic acid (enantiomer 2), (rac)-4-chloro-3-ethyl-7-{3-[(6-fluoronaphthalen-1-yl)oxy]
propyl}-2-methyl-2,10,11,12,13,15-hexahydropyrazolo
[4',3':9,10][1,6]oxazacycloundecino[8,7,6-hi]indole-8-
carboxylic acid, (+)-4-chloro-3-ethyl-7-{3-[(6-fluoronaphthalen-1-yl)oxy]
propyl}-2-methyl-2,10,11,12,13,15-hexahydropyrazolo
[4',3':9,10][1,6]oxazacycloundecino[8,7,6-hi]indole-8-
carboxylic acid-N-ethylethanamine salt (enantiomer 1), (−)-4-chloro-3-ethyl-7-{3-[(6-fluoronaphthalen-1-yl)oxy]
propyl}-2-methyl-2,10,11,12,13,15-hexahydropyrazolo
[4',3':9,10][1,6]oxazacycloundecino[8,7,6-hi]indole-8-
carboxylic acid-N-ethylethanamine salt (enantiomer 2), (rac)-4-chloro-3-ethyl-7-{3-[(6-fluoronaphthalen-1-yl)oxy]
propyl}-1,14-dimethyl-10,11,12,13,14,15-hexahydro-
1H-pyrazolo[3',4':8,9][1,6]diazacycloundecino[10,11,1-
hi]indole-8-carboxylic acid, 4-chloro-3-ethyl-7-{3-[(6-fluoronaphthalen-1-yl)oxy]pro-
pyl}-1,14-dimethyl-10,11,12,13,14,15-hexahydro-1H-
pyrazolo[3',4':8,9][1,6]diazacycloundecino[10,11,1-hi]
indole-8-carboxylic acid (enantiomer 1), 4-chloro-3-ethyl-7-{3-[(6-fluoronaphthalen-1-yl)oxy]pro-
pyl}-1,14-dimethyl-10,11,12,13,14,15-hexahydro-1H-
pyrazolo[3',4':8,9][1,6]diazacycloundecino[10,11,1-hi]
indole-8-carboxylic acid (enantiomer 2), (rac)-(11Z)-4-chloro-3-ethyl-14-methyl-1-[2-(morpholin-4-
yl)ethyl]-7-{3-[(naphthalen-1-yl)oxy]propyl}-10,13,14,
15-tetrahydro-1H-pyrazolo[3',4':8,9][1,6]diazacycloun-
decino [10,11,1-hi]indole-8-carboxylic acid, (11Z)-4-chloro-3-ethyl-14-methyl-1-[2-(morpholin-4-yl)
ethyl]-7-{3-[(naphthalen-1-yl)oxy]propyl}-10,13,14,15-
tetrahydro-1H-pyrazolo[3',4':8,9][1,6]diazacyclounde-
cino [10,11,1-hi]indole-8-carboxylic acid-ammonia salt
(enantiomer 1), (11Z)-4-chloro-3-ethyl-14-methyl-1-[2-(morpholin-4-yl)
ethyl]-7-{3-[(naphthalen-1-yl)oxy]propyl}-10,13,14,15-
tetrahydro-1H-pyrazolo[3',4':8,9][1,6]diazacyclounde-
cino [10,11,1-hi]indole-8-carboxylic acid-ammonia salt
(enantiomer 2), (rac)-4-chloro-3-ethyl-14-methyl-1-[2-(morpholin-4-yl)
ethyl]-7-{3-[(naphthalen-1-yl)oxy]propyl}-10,11,12,13,
14,15-hexahydro-1H-pyrazolo[3',4':8,9][1,6]diazacy-
cloundecino [10,11,1-hi]indole-8-carboxylic acid, 4-chloro-3-ethyl-14-methyl-1-[2-(morpholin-4-yl)ethyl]-7-{3-[(naphthalen-1-yl)oxy]propyl}-10,11,12,13,14,15-hexahydro-1H-pyrazolo[3',4':8,9][1,6]diazacycloundecino[10,11,1-hi]indole-8-carboxylic acid (enantiomer 1), 4-chloro-3-ethyl-14-methyl-1-[2-(morpholin-4-yl)ethyl]-7-{3-[(naphthalen-1-yl)oxy]propyl}-10,11,12,13,14,15-hexahydro-1H-pyrazolo[3',4':8,9][1,6]diazacycloundecino[10,11,1-hi]indole-8-carboxylic acid (enantiomer 2), (rac)-4-chloro-3-methyl-2-[3-(4-methylpiperazin-1-yl)propyl]-7-{3-[(naphthalen-1-yl)oxy]propyl}-2,10,11,12,13,15-hexahydropyrazolo[4',3':9,10][1,6]oxazacycloundecino [8,7,6-hi]indole-8-carboxylic acid, (+)-4-chloro-3-methyl-2-[3-(4-methylpiperazin-1-yl)propyl]-7-{3-[(naphthalen-1-yl)oxy]propyl}-2,10,11,12,13,15-hexahydropyrazolo[4',3':9,10][1,6]oxazacycloundecino [8,7,6-hi]indole-8-carboxylic acid (enantiomer 1), (−)-4-chloro-3-methyl-2-[3-(4-methylpiperazin-1-yl)propyl]-7-{3-[(naphthalen-1-yl)oxy]propyl}-2,10,11,12,13,15-hexahydropyrazolo[4',3':9,10][1,6]oxazacycloundecino [8,7,6-hi]indole-8-carboxylic acid (enantiomer 2), (rac)-4-chloro-3-ethyl-2-methyl-7-{3-[(naphthalen-1-yl)oxy]propyl}-10,11,12,13,14,15-hexa-hydro-2H-pyrazolo[4',3':4,5]azacycloundecino[3,2,1-hi]indole-8-carboxylic acid, (+)-4-chloro-3-ethyl-2-methyl-7-{3-[(naphthalen-1-yl)oxy]propyl}-10,11,12,13,14,15-hexahydro-2H-pyrazolo[4',3':4,5]azacycloundecino[3,2,1-hi]indole-8-carboxylic acid-N-ethylethanamine salt—(enantiomer 1), (−)4-chloro-3-ethyl-2-methyl-7-{3-[(naphthalen-1-yl)oxy]propyl}-10,11,12,13,14,15-hexahydro-2H-pyrazolo[4',3':4,5]azacycloundecino[3,2,1-hi]indole-8-carboxylic acid-N-ethylethanamine salt—(enantiomer 2), (rac)-4-chloro-3-ethyl-7-{3-[(6-fluoronaphthalen-1-yl)oxy]propyl}-2-methyl-10,11,12,13,14,15-hexahydro-2H-pyrazolo[4',3':4,5]azacycloundecino[3,2,1-hi]indole-8-carboxylic acid, (rac)-4-chloro-12,12-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, 4-chloro-12,12-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid-N-ethylethanamine salt—(enantiomer 1), 4-chloro-12,12-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid-N-ethylethanamine salt—(enantiomer 2), (rac)-4-chloro-7-{3-[(6-fluoronaphthalen-1-yl)oxy]propyl}-2,3-dimethyl-14-(2,2,2-trifluoroethyl)-10,11,12,13,14,15-hexahydro-2H-pyrazolo[3',4':8,9][1,6]diazacycloundecino [10,11,1-hi]indole-8-carboxylic acid, 4-chloro-7-{3-[(6-fluoronaphthalen-1-yl)oxy]propyl}-2,3-dimethyl-14-(2,2,2-trifluoroethyl)-10,11,12,13,14,15-hexahydro-2H-pyrazolo[3',4':8,9][1,6]diazacycloundecino[10,11,1-hi]indole-8-carboxylic acid—(enantiomer 1), 4-chloro-7-{3-[(6-fluoronaphthalen-1-yl)oxy]propyl}-2,3-dimethyl-14-(2,2,2-trifluoroethyl)-10,11,12,13,14,15-hexahydro-2H-pyrazolo[3',4':8,9][1,6]diazacycloundecino[10,11,1-hi]indole-8-carboxylic acid—(enantiomer 2), (rac) 4-chloro-3-ethyl-7-{3-[(6-fluoronaphthalen-1-yl)oxy]propyl}-2-methyl-14-(2,2,2-trifluo-roethyl)-10,11,12,13,14,15-hexahydro-2H-pyrazolo[3',4':8,9][1,6]diazacycloundecino[10,11,1-hi]indole-8-carboxylic acid, (rac)-4-chloro-14-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino [10,11,1-hi]indole-8-carboxylic acid, (9aS,11aR)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]oxazacycloundecino [8,7,6-hi]indole-14-carboxylic acid-stereoisomer 1, (9aR,11aS)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]oxazacycloundecino [8,7,6-hi]indole-14-carboxylic acid—stereoisomer 2, (9aS,10aR or 9aR,10aS)-3-chloro-4,5-dimethyl-14-{3-[(naphthalen-1-yl)oxy]propyl}-5,7,9a,10,10a,11-hexahydro-9H-cyclopropa[3,4]pyrazolo[4',3':9,10][1,6]-oxazacycloundecino[8,7,6-hi]indole-13-carboxylic acid—stereoisomer 1, (9aR,10aS or 9aS,10aR)-3-chloro-4,5-dimethyl-14-{3-[(naphthalen-1-yl)oxy]propyl}-5,7,9a,10,10a,11-hexahydro-9H-cyclopropa[3,4]pyrazolo[4',3':9,10][1,6]-oxazacycloundecino[8,7,6-hi]indole-13-carboxylic acid—stereoisomer 2, (rac)-4-chloro-11,11,12,12-tetrafluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, (rac)-4-chloro-11,11-difluoro-2,3-dimethyl-7-[3-(1-naphthyloxy)propyl]-2,10,11,12,13,15-hexahydropyrazolo[4',3':9,10][1,6]oxazacycloundecino[8,7,6-hi]indole-8-carboxylic acid 4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (enantiomer 1), (+)-4-chloro-3-ethyl-7-{3-[(6-fluoronaphthalen-1-yl)oxy]propyl}-2-methyl-10,11,12,13,14,15-hexahydro-2H-pyrazolo[4',3':4,5]azacycloundecino[3,2,1-hi]indole-8-carboxylic acid—N-ethylethanamine salt (enantiomer 1), (−)-4-chloro-3-ethyl-7-{3-[(6-fluoronaphthalen-1-yl)oxy]propyl}-2-methyl-10,11,12,13,14,15-hexahydro-2H-pyrazolo[4',3':4,5]azacycloundecino[3,2,1-hi]indole-8-carboxylic acid—N-ethylethanamine salt (enantiomer 2), (rac)-4'-chloro-3'-ethyl-2'-methyl-7'-{3-[(naphthalen-1-yl)oxy]propyl}-2',10',11',15'-tetrahydro-13'H-spiro[cyclopropane-1,12'-pyrazolo[4',3':9,10][1,6]oxazacycloundecino [8,7,6-hi]indole]-8'-carboxylic acid, (−)-4'-chloro-3'-ethyl-2'-methyl-7'-{3-[(naphthalen-1-yl)oxy]propyl}-2',10',11',15'-tetrahydro-13'H-spiro[cyclopropane-1,12'-pyrazolo[4',3':9,10][1,6]oxazacycloundecino[8,7,6-hi]indole]-8'-carboxylic acid—N-ethylethanamine salt (enantiomer 1), (+)-4'-chloro-3'-ethyl-2'-methyl-7'-{3-[(naphthalen-1-yl)oxy]propyl}-2',10',11',15'-tetrahydro-13'H-spiro[cyclopropane-1,12'-pyrazolo[4',3':9,10][1,6]oxazacycloundecino[8,7,6-hi]indole]-8'-carboxylic acid—N-ethylethanamine salt (enantiomer 2), (+)-4-chloro-14-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino [10,11,1-hi]indole-8-carboxylic acid-N-ethylethanamine salt, (−)-4-chloro-14-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino [10,11,1-hi]indole-8-carboxylic acid N-ethylethanamine salt, (rac)-4-chloro-14-(2,2-difluoroethyl)-7-{3-[(6-fluoronaphthalen-1-yl)oxy]propyl}-2,3-dimethyl-10,11,12,13,14,15-hexahydro-2H-pyrazolo[3',4':8,9][1,6]diazacycloundecino [10,11,1-hi]indole-8-carboxylic acid, (9aS,11aR)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]-oxazacycloundecino[8,7,6-hi]indole-14-carboxylic acid, (9aR,11aS)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]-oxazacycloundecino[8,7,6-hi]indole-14-carboxylic acid, (9aS,11aR)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]-oxazacycloundecino[8,7,6-hi]indole-14-carboxylic acid, (9aR,11aS)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]-oxazacycloundecino[8,7,6-hi]indole-14-carboxylic acid, (9aS,10aR or 9aR,10aS)-3-chloro-4,5-dimethyl-14-{3-[(naphthalen-1-yl)oxy]propyl}-5,7,9a,10,10a,11-hexahydro-9H-cyclopropa[3,4]pyrazolo[4',3':9,10][1,6]-oxazacycloundecino[8,7,6-hi]indole-13-carboxylic acid, (9aS,10aR or 9aR,10aS)-3-chloro-4,5-dimethyl-14-{3-[(naphthalen-1-yl)oxy]propyl}-5,7,9a,10,10a,11-hexahydro-9H-cyclopropa[3,4]pyrazolo[4',3':9,10][1,6]-oxazacycloundecino[8,7,6-hi]indole-13-carboxylic acid, (rac)-4-chloro-3-ethyl-12,12-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (−)-4-chloro-3-ethyl-12,12-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-12,12-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (rac)-11-chloro-9,10-dimethyl-1-{3-[(naphthalen-1-yl)oxy]propyl}-4,5,7,9-tetrahydropyrazolo[4',3':7,8][1,4]oxazonino[6,5,4-hi]indole-2-carboxylic acid, 11-chloro-9,10-dimethyl-1-{3-[(naphthalen-1-yl)oxy]propyl}-4,5,7,9-tetrahydropyrazolo[4',3':7,8][1,4]oxazonino[6,5,4-hi]indole-2-carboxylic acid, 11-chloro-9,10-dimethyl-1-{3-[(naphthalen-1-yl)oxy]propyl}-4,5,7,9-tetrahydropyrazolo[4',3':7,8][1,4]oxazonino[6,5,4-hi]indole-2-carboxylic acid, (rac)-4-Chloro-12,12-difluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid, 4-chloro-12,12-difluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid-N-ethylethanamine salt, 4-chloro-12,12-difluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid, (rac)-4-Chloro-11,11-difluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid, 4-chloro-11,11-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid N-ethylethanamine salt, 4-chloro-11,11-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid N-ethylethanamine salt, (rac)-4-chloro-3-ethyl-11,11-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (−)-4-chloro-3-ethyl-11,11-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-11,11-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, 4-chloro-3-ethyl-7-{3-[(6-fluoronaphthalen-1-yl)oxy]propyl}-12-hydroxy-2-methyl-2,10,11,12,13,15-hexahydropyrazolo[4',3':9,10][1,6]oxazacycloundecino[8,7,6-hi]indole-8-carboxylic acid—N-ethylethanamine salt (stereoisomer 1), 4-chloro-3-ethyl-7-{3-[(6-fluoronaphthalen-1-yl)oxy]propyl}-12-hydroxy-2-methyl-2,10,11,12,13,15-hexahydropyrazolo[4',3':9,10][1,6]oxazacycloundecino[8,7,6-hi]indole-8-carboxylic acid—N-ethylethanamine salt (stereoisomer 2), 4-chloro-3-ethyl-7-{3-[(6-fluoronaphthalen-1-yl)oxy]propyl}-12-hydroxy-2-methyl-2,10,11,12,13,15-hexahydropyrazolo[4',3':9,10][1,6]oxazacycloundecino[8,7,6-hi]indole-8-carboxylic acid—N-ethylethanamine salt (stereoisomer 3), 4-chloro-3-ethyl-7-{3-[(6-fluoronaphthalen-1-yl)oxy]propyl}-12-hydroxy-2-methyl-2,10,11,12,13,15-hexahydropyrazolo[4',3':9,10][1,6]oxazacycloundecino[8,7,6-hi]indole-8-carboxylic acid—N-ethylethanamine salt (stereoisomer 4), (rac)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid, (+)-(9aS or R,10aR or S)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid N-ethylethanamine salt, (−)-(9aS or R,10aR or S)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid N-ethylethanamine salt, (rac)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid, (+)-(9aS,10aR)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid, (−)-(9aS,10aR)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid, (rac)-4'-chloro-3'-ethyl-7'-{3-[(6-fluoronaphthalen-1-yl)oxy]propyl}-2'-methyl-2',10',11',15'-tetrahydro-13'H- spiro[cyclopropane-1,12'-pyrazolo[4',3':9,10][1,6]-oxazacycloundecino[8,7,6-hi]indole]-8'-carboxylic acid,
(−)-4'-chloro-3'-ethyl-7'-{3-[(6-fluoronaphthalen-1-yl)oxy]propyl}-2'-methyl-2',10',11',15'-tetrahydro-13'H-spiro[cyclopropane-1,12'-pyrazolo[4',3':9,10][1,6]oxazacycloundecino-[8,7,6-hi]indole]-8'-carboxylic acid—N-ethylethanamine salt,
(+)-4'-chloro-3'-ethyl-7'-{3-[(6-fluoronaphthalen-1-yl)oxy]propyl}-2'-methyl-2',10',11',15'-tetrahydro-13'H-spiro[cyclopropane-1,12'-pyrazolo[4',3':9,10][1,6]oxazacycloundecino-[8,7,6-hi]indole]-8'-carboxylic acid—N-ethylethanamine salt,
(rac)-12-chloro-11-ethyl-1-{3-[(6-fluoronaphthalen-1-yl)oxy]propyl}-7,10-dimethyl-4,5,6,7,8,10-hexahydropyrazolo[3',4':7,8][1,5]diazecino[9,10,1-hi]indole-2-carboxylic acid
(+) 12-chloro-11-ethyl-1-{3-[(6-fluoronaphthalen-1-yl)oxy]propyl}-7,10-dimethyl-4,5,6,7,8,10-hexahydropyrazolo[3',4':7,8][1,5]diazecino[9,10,1-hi]indole-2-carboxylic acid N-ethylethanamine salt,
(−)-12-chloro-11-ethyl-1-{3-[(6-fluoronaphthalen-1-yl)oxy]propyl}-7,10-dimethyl-4,5,6,7,8,10-hexahydropyrazolo[3',4':7,8][1,5]diazecino[9,10,1-hi]indole-2-carboxylic acid-salt,
(rac)-4-chloro-3-ethyl-7-{3-[(6-fluoronaphthalen-1-yl)oxy]propyl}-2,12-dimethyl-10,11,12,13,14,15-hexahydro-2H-pyrazolo[3',4':8,9][1,4]diazacycloundecino[10,11,1-hi]indole-8-carboxylic acid,
(+)-4-chloro-3-ethyl-7-{3-[(6-fluoronaphthalen-1-yl)oxy]propyl}-2,12-dimethyl-10,11,12,13,14,15-hexahydro-2H-pyrazolo[3',4':8,9][1,4]diazacycloundecino[10,11,1-hi]indole-8-carboxylic acid,
(−)-4-chloro-3-ethyl-7-{3-[(6-fluoronaphthalen-1-yl)oxy]propyl}-2,12-dimethyl-10,11,12,13,14,15-hexahydro-2H-pyrazolo[3',4':8,9][1,4]diazacycloundecino[10,11,1-hi]indole-8-carboxylic acid,
(rac)-4-chloro-12-(2,2-difluoroethyl)-3-ethyl-7-{3-[(6-fluoro-1-naphthyl)oxy]propyl}-2-methyl-10,11,12,13,14,15-hexahydro-2H-pyrazolo[3',4':8,9][1,4]diazacycloundecino [10,11,1-hi]indole-8-carboxylic acid,
(+)-4-chloro-12-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,4]diazacycloundecino [10,11,1-hi]indole-8-carboxylic acid N-ethylethanamine salt,
(−)-4-chloro-12-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,4]diazacycloundecino [10,11,1-hi]indole-8-carboxylic acid-N-ethylethanamine salt,
(rac)- 12-(4-acetoxybutyl)-4-chloro-3-ethyl-7-{3-[(6-fluoro-1-naphthyl)oxy]propyl}-2-methyl-10,11,12,13,14,15-hexahydro-2H-pyrazolo[3',4':8,9][1,4]diazacycloundecino[10,11,1-hi]indole-8-carboxylic acid,
(rac)-4-chloro-3-ethyl-7-{3-[(6-fluoro-1-naphthyl)oxy]propyl}-12-(4-hydroxybutyl)-2-methyl-10,11,12,13,14,15-hexahydro-2H-pyrazolo[3',4':8,9][1,4]diazacycloundecino[10,11,1-hi]indole-8-carboxylic acid,
(rac)-4-chloro-3-ethyl-7-{3-[(6-fluoro-1-naphthyl)oxy]propyl}-2-methyl-12-(2,2,3,3-tetrafluoropropyl)-10,11,12,13,14,15-hexahydro-2H-pyrazolo[3',4':8,9][1,4]diazacycloundecino[10,11,1-hi]indole-8-carboxylic acid,
(rac)-4-chloro-3-ethyl-7-{3-[(6-fluoro-1-naphthyl)oxy]propyl}-2-methyl-2,10,11,13,14,15-hexahydropyrazolo[4',3':7,8][1,4]oxazacycloundecino[6,5,4-hi]indole-8-carboxylic acid
(rac)-4-chloro-3-ethyl-7-{3-[(6-fluoro-1-naphthyl)oxy]propyl}-1-methyl-1,10,11,13,14,15-hexahydropyrazolo[4',3':7,8][1,4]oxazacycloundecino[6,5,4-hi]indole-8-carboxylic acid,
(rac)-4-Chloro-3-ethyl-12,12-difluoro-7-{3-[(6-fluoro-1-naphthyl)oxy]propyl}-2,14-dimethyl-10,11,12,13,14,15-hexahydro-2H-pyrazolo[3',4':8,9][1,6]diazacycloundecino[10,11,1-hi]indol-14-ium-8-carboxylate,
4-chloro-3-ethyl-12,12-difluoro-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid,
4-chloro-3-ethyl-12,12-difluoro-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid,
rac-4-chloro-3-ethyl-11,11-difluoro-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino [10,11,1-hi]indole-8-carboxylic acid,
rac-4-chloro-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylic acid,
rac-4-chloro-3-ethyl-7-{3-[(6-fluoronaphthalen-1-yl)oxy]propyl}-14-(2-methoxyethyl)-2-methyl-10,11,12,13,14,15-hexahydro-2H-pyrazolo[3',4':8,9][1,6]diazacycloundecino[10,11,1-hi]indole-8-carboxylic acid,
4-chloro-3-ethyl-7-{3-[(6-fluoronaphthalen-1-yl)oxy]propyl}-14-(2-methoxyethyl)-2-methyl-10,11,12,13,14,15-hexahydro-2H-pyrazolo[3',4':8,9][1,6]diazacycloundecino[10,11,1-hi]indole-8-carboxylic acid,
4-chloro-3-ethyl-7-{3-[(6-fluoronaphthalen-1-yl)oxy]propyl}-14-(2-methoxyethyl)-2-methyl-10,11,12,13,14,15-hexahydro-2H-pyrazolo[3',4':8,9][1,6]diazacycloundecino[10,11,1-hi]indole-8-carboxylic acid N-ethylethanamine salt,
rac-4-chloro-3-ethyl-7-{3-[(6-fluoronaphthalen-1-yl)oxy]propyl}-14-[(2-methoxyethoxy)carbonyl]-2-methyl-10,11,12,13,14,15-hexahydro-2H-pyrazolo[3',4':8,9][1,6]diazacycloundecino[10,11,1-hi]indole-8-carboxylic acid,
rac-4-chloro-3-ethyl-7-{3-[(6-fluoronaphthalen-1-yl)oxy]propyl}-2-methyl-14-[2-(oxan-4-yl)ethyl]-10,11,12,13,14,15-hexahydro-2H-pyrazolo[3',4':8,9][1,6]diazacycloundecino [10,11,1-hi]indole-8-carboxylic acid,
4-chloro-3-ethyl-7-{3-[(6-fluoronaphthalen-1-yl)oxy]propyl}-2-methyl-14-[2-(oxan-4-yl)ethyl]-10,11,12,13,14,15-hexahydro-2H-pyrazolo[3',4':8,9][1,6]diazacycloundecino[10,11,1-hi]indole-8-carboxylic acid N-ethylethanamine salt,
4-chloro-3-ethyl-7-{3-[(6-fluoronaphthalen-1-yl)oxy]propyl}-2-methyl-14-[2-(oxan-4-yl)ethyl]-10,11,12,13,14,15-hexahydro-2H-pyrazolo[3',4':8,9][1,6]diazacycloundecino[10,11,1-hi]indole-8-carboxylic acid-N-ethylethanamine (1/1),
rac-4-chloro-3-ethyl-7-{3-[(6-fluoronaphthalen-1-yl)oxy]propyl}-2-methyl-14-{[2-(oxan-4-yl)ethoxy]carbonyl}-10,11,12,13,14,15-hexahydro-2H-pyrazolo[3',4':8,9][1,6]diaza cycloundecino[10,11,1-hi]indole-8-carboxylic acid,
rac-4-chloro-3-ethyl-7-{3-[(6-fluoronaphthalen-1-yl)oxy]propyl}-14-(3-hydroxypropyl)-2-methyl-10,11,12,13,14,15-hexahydro-2H-pyrazolo[3',4':8,9][1,6]diazacycloundecino [10,11,1-hi]indole-8-carboxylic acid,
4-chloro-3-ethyl-7-{3-[(6-fluoronaphthalen-1-yl)oxy]propyl}-14-(3-hydroxy-3-methylbutyl)-2-methyl-10,11,12, 13,14,15-hexahydro-2H-pyrazolo[3',4':8,9][1,6]diazacycloundecino [10,11,1-hi]indole-8-carboxylic acid (enantiomer 1),
4-chloro-3-ethyl-7-{3-[(6-fluoronaphthalen-1-yl)oxy]propyl}-14-(3-hydroxy-3-methylbutyl)-2-methyl-10,11,12,13,14,15-hexahydro-2H-pyrazolo[3',4':8,9][1,6]diazacycloundecino [10,11,1-hi]indole-8-carboxylic acid (enantiomer 2),
4-chloro-3-ethyl-7-{3-[(6-fluoronaphthalen-1-yl)oxy]propyl}-2-methyl-14-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid (enantiomer 1), and
4-chloro-3-ethyl-7-{3-[(6-fluoronaphthalen-1-yl)oxy]propyl}-2-methyl-14-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid (enantiomer 2), or a tautomer, an N-oxide, or a salt thereof, or a salt of a tautomer, or a salt of an N-oxide, or a mixture of same.

In some embodiments, the present invention includes compounds of general formula (I) selected from:

(rac)-(11Z)-4-chloro-1,3-dimethyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid,
rac-4-chloro-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid,
4-chloro-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1),
4-chloro-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2),
(rac)-4-chloro-3-ethyl-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid,
4-chloro-3-ethyl-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid (enantiomer 1),
4-chloro-3-ethyl-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid (enantiomer 2),
(rac)-4-chloro-3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid,
4-chloro-3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid—N-ethylethanamine salt (enantiomer 1),
4-chloro-3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid—N-ethylethanamine salt (enantiomer 2),
(rac)-4-chloro-2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid,
(+)-4-chloro-2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid—N-ethylethanamine salt (enantiomer 1),
(−)-4-chloro-2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid—N-ethylethanamine salt (enantiomer 2),
(rac)-4-chloro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid,
(+)-4-chloro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid-N-ethylethanamine salt (enantiomer 1),
(−)-4-chloro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid (enantiomer 1),
(−)-4-chloro-7-{3-[(6-fluoronaphthalen-1-yl)oxy]propyl}-2,3-dimethyl-2,10,11,12,13,15-hexahydropyrazolo[4',3':9,10][1,6]oxazacyclound,ecino[8,7,6-hi]indole-8-carboxylic acid-N-ethylethanamine salt (enantiomer 2)
(rac)-(11Z)-4-chloro-3-ethyl-2-methyl-7-[3-(naphthalen-1-yloxy)propyl]-2,10,13,15-tetrahydropyrazolo[4',3':9,10][1,6]oxazacycloundecino[8,7,6-hi]indole-8-carboxylic acid,
(rac)-4-chloro-3-ethyl-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid,
4-chloro-3-ethyl-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (enantiomer 1),
4-chloro-3-ethyl-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (enantiomer 2),
(rac)-4-chloro-3-ethyl-2,14-dimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid,
4-chloro-3-ethyl-2,14-dimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid (enantiomer 1),
4-chloro-3-ethyl-2,14-dimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid (enantiomer 2),
(rac)-4-chloro-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid,
4-chloro-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (enantiomer 1),
4-chloro-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (enantiomer 2),
(rac)-12-chloro-10,11-dimethyl-1-[3-(naphthalen-1-yloxy)propyl]-4,5,6,7,8,10-hexahydropyrazolo[3',4':7,8][1,5]diazecino[9,10,1-hi]indole-2-carboxylic acid—formic acid salt, (rac)-12-chloro-7,10,11-trimethyl-1-[3-(naphthalen-1-yloxy)propyl]-4,5,6,7,8,10-hexahydropyrazolo[3',4':7,8][1,5]diazecino[9,10,1-hi]indole-2-carboxylic acid, (rac)-4-chloro-7-{3-[(6-fluoronaphthalen-1-yl)oxy]propyl}-2,3,14-trimethyl-10,11,12,13,14,15-hexahydro-2H-pyrazolo[3',4':8,9][1,6]diazacycloundecino[10,11,1-hi]indole-8-carboxylic acid, (+)-4-chloro-7-{3-[(6-fluoronaphthalen-1-yl)oxy]propyl}-2,3,14-trimethyl-10,11,12,13,14,15-hexahydro-2H-pyrazolo[3',4':8,9][1,6]diazacycloundecino[10,11,1-hi]indole-8-carboxylic acid-N-ethylethanamine salt (enantiomer 1), (−)-4-chloro-7-{3-[(6-fluoronaphthalen-1-yl)oxy]propyl}-2,3,14-trimethyl-10,11,12,13,14,15-hexahydro-2H-pyrazolo[3',4':8,9][1,6]diazacycloundecino[10,11,1-hi]indole-8-carboxylic acid—N-ethylethanamine salt (enantiomer 2), (rac)-4-chloro-3-ethyl-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid (enantiomer 1), (−)-4-chloro-3-ethyl-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid (enantiomer 2), (rac)-4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 1), (−)-4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 2), (rac)-4-chloro-3-ethyl-7-{3-[(6-fluoronaphthalen-1-yl)oxy]propyl}-1,14-dimethyl-10,11,12,13,14,15-hexahydro-1H-pyrazolo[3',4':8,9][1,6]diazacycloundecino[10,11,1-hi]indole-8-carboxylic acid, 4-chloro-3-ethyl-7-{3-[(6-fluoronaphthalen-1-yl)oxy]propyl}-1,14-dimethyl-10,11,12,13,14,15-hexahydro-1H-pyrazolo[3',4':8,9][1,6]diazacycloundecino[10,11,1-hi]indole-8-carboxylic acid (enantiomer 1), 4-chloro-3-ethyl-7-{3-[(6-fluoronaphthalen-1-yl)oxy]propyl}-1,14-dimethyl-10,11,12,13,14,15-hexahydro-1H-pyrazolo[3',4':8,9][1,6]diazacycloundecino[10,11,1-hi]indole-8-carboxylic acid (enantiomer 2), (rac)-(11Z)-4-chloro-3-ethyl-14-methyl-1-[2-(morpholin-4-yl)ethyl]-7-{3-[(naphthalen-1-yl)oxy]propyl}-10,13,14,15-tetrahydro-1H-pyrazolo[3',4':8,9][1,6]diazacycloundecino[10,11,1-hi]indole-8-carboxylic acid, (11Z)-4-chloro-3-ethyl-14-methyl-1-[2-(morpholin-4-yl)ethyl]-7-{3-[(naphthalen-1-yl)oxy]propyl}-10,13,14,15-tetrahydro-1H-pyrazolo[3',4':8,9][1,6]diazacycloundecino[10,11,1-hi]indole-8-carboxylic acid—ammonia salt (enantiomer 1), (11Z)-4-chloro-3-ethyl-14-methyl-1-[2-(morpholin-4-yl)ethyl]-7-{3-[(naphthalen-1-yl)oxy]propyl}-10,13,14,15-tetrahydro-1H-pyrazolo[3',4':8,9][1,6]diazacycloundecino[10,11,1-hi]indole-8-carboxylic acid—ammonia salt (enantiomer 2), (rac)-4-chloro-3-ethyl-14-methyl-1-[2-(morpholin-4-yl)ethyl]-7-{3-[(naphthalen-1-yl)oxy]propyl}-10,11,12,13,14,15-hexahydro-1H-pyrazolo[3',4':8,9][1,6]diazacycloundecino[10,11,1-hi]indole-8-carboxylic acid, 4-chloro-3-ethyl-14-methyl-1-[2-(morpholin-4-yl)ethyl]-7-{3-[(naphthalen-1-yl)oxy]propyl}-10,11,12,13,14,15-hexahydro-1H-pyrazolo[3',4':8,9][1,6]diazacycloundecino[10,11,1-hi]indole-8-carboxylic acid (enantiomer 1), 4-chloro-3-ethyl-14-methyl-1-[2-(morpholin-4-yl)ethyl]-7-{3-[(naphthalen-1-yl)oxy]propyl}-10,11,12,13,14,15-hexahydro-1H-pyrazolo[3',4':8,9][1,6]diazacycloundecino[10,11,1-hi]indole-8-carboxylic acid (enantiomer 2), (rac)-4-chloro-3-methyl-2-[3-(4-methylpiperazin-1-yl)propyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, (+)-4-chloro-3-methyl-2-[3-(4-methylpiperazin-1-yl)propyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 1), (−)-4-chloro-3-methyl-2-[3-(4-methylpiperazin-1-yl)propyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (enantiomer 2), (rac)-4-chloro-3-ethyl-2-methyl-7-{3-[(naphthalen-1-yl)oxy]propyl}-10,11,12,13,14,15-hexahydro-2H-pyrazolo[4',3':4,5]azacycloundecino[3,2,1-hi]indole-8-carboxylic acid, (+)-4-chloro-3-ethyl-2-methyl-7-{3-[(naphthalen-1-yl)oxy]propyl}-10,11,12,13,14,15-hexahydro-2H-pyrazolo[4',3':4,5]azacycloundecino[3,2,1-hi]indole-8-carboxylic acid-N-ethylethanamine salt—Enantiomer 1, (−) 4-chloro-3-ethyl-2-methyl-7-{3-[(naphthalen-1-yl)oxy]propyl}-10,11,12,13,14,15-hexahydro-2H-pyrazolo[4',3':4,5]azacycloundecino[3,2,1-hi]indole-8-carboxylic acid-N-ethylethanamine salt—Enantiomer 2, (rac)-4-chloro-3-ethyl-7-{3-[(6-fluoronaphthalen-1-yl)oxy]propyl}-2-methyl-10,11,12,13,14,15-hexahydro-2H-pyrazolo[4',3':4,5]azacycloundecino[3,2,1-hi]indole-8-carboxylic acid, (rac)-4-chloro-12,12-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, 4-chloro-12,12-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid-N-ethylethanamine salt—Enantiomer 1, 4-chloro-12,12-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid-N-ethylethanamine salt—Enantiomer 2, (rac)-4-chloro-7-{3-[(6-fluoronaphthalen-1-yl)oxy]propyl}-2,3-dimethyl-14-(2,2,2-trifluoroethyl)-10,11,12,13,14,15-hexahydro-2H-pyrazolo[3',4':8,9][1,6]diazacycloundecino[10,11,1-hi]indole-8-carboxylic acid, 4-chloro-7-{3-[(6-fluoronaphthalen-1-yl)oxy]propyl}-2,3-dimethyl-14-(2,2,2-trifluoroethyl)-10,11,12,13,14,15-hexahydro-2H-pyrazolo[3',4':8,9][1,6]diazacycloundecino[10,11,1-hi]indole-8-carboxylic acid Enantiomer 1, 4-chloro-7-{3-[(6-fluoronaphthalen-1-yl)oxy]propyl}-2,3-dimethyl-14-(2,2,2-trifluoroethyl)-10,11,12,13,14,15-hexahydro-2H-pyrazolo[3',4':8,9][1,6]diazacycloundecino[10,11,1-hi]indole-8-carboxylic acid—Enantiomer 2, (rac) 4-chloro-3-ethyl-7-{3-[(6-fluoronaphthalen-1-yl)oxy]propyl}-2-methyl-14-(2,2,2-trifluoroethyl)-10,11,12,13, 14,15-hexahydro-2H-pyrazolo[3',4':8,9][1,6]diazacycloundecino[10,11,1-hi]indole-8-carboxylic acid,
(rac)-4-chloro-14-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylic acid,
(9aS,11aR)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]oxazacycloundecino[8,7,6-hi]indole-14-carboxylic acid- Stereoisomer 1,
(9aR,11aS)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]oxazacycloundecino[8,7,6-hi]indole-14-carboxylic acid—Stereoisomer 2,
(9aS,10aR or 9aR,10aS)-3-chloro-4,5-dimethyl-14-{3-[(naphthalen-1-yl)oxy]propyl}-5,7,9a,10,10a,11-hexahydro-9H-cyclopropa[3,4]pyrazolo[4',3':9,10][1,6]oxazacycloundecino[8,7,6-hi]indole-13-carboxylic acid—Stereoisomer 1,
(9aR,10aS or 9aS,10aR)-3-chloro-4,5-dimethyl-14-{3-[(naphthalen-1-yl)oxy]propyl}-5,7,9a,10,10a,11-hexahydro-9H-cyclopropa[3,4]pyrazolo[4',3':9,10][1,6]oxazacycloundecino[8,7,6-hi]indole-13-carboxylic acid—Stereoisomer 2,
(rac)-4-chloro-11,11,12,12-tetrafluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid and
(rac)-4-chloro-11,11-difluoro-2,3-dimethyl-7-[3-(1-naphthyloxy)propyl]-2,10,11,12,13,15-hexahydropyrazolo[4',3':9,10][1,6]oxazacycloundecino[8,7,6-hi]indole-8-carboxylic acid or a tautomer, an N-oxide, or a salt thereof, or a salt of a tautomer, or a salt of an N-oxide, or a mixture of same.

In some embodiments, the present invention includes compounds of general formula (I) selected from:

4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (enantiomer 1),
(+)-4-chloro-3-ethyl-7-{3-[(6-fluoronaphthalen-1-yl)oxy]propyl}-2-methyl-10,11,12,13,14,15-hexahydro-2H-pyrazolo[4',3':4,5]azacycloundecino[3,2,1-hi]indole-8-carboxylic acid—N-ethylethanamine salt (enantiomer 1),
(−)-4-chloro-3-ethyl-7-{3-[(6-fluoronaphthalen-1-yl)oxy]propyl}-2-methyl-10,11,12,13,14,15-hexahydro-2H-pyrazolo[4',3':4,5]azacycloundecino[3,2,1-hi]indole-8-carboxylic acid—N-ethylethanamine salt (enantiomer 2),
(rac)-4'-chloro-3'-ethyl-2'-methyl-7'-{3-[(naphthalen-1-yl)oxy]propyl}-2',10',11',15'-tetrahydro-13'H-spiro[cyclopropane-1,12'-pyrazolo[4',3':9,10][1,6]oxazacycloundecino [8,7,6-hi]indole]-8'-carboxylic acid,
(−)-4'-chloro-3'-ethyl-2'-methyl-7'-{3-[(naphthalen-1-yl)oxy]propyl}-2',10',11',15'-tetrahydro-13'H-spiro[cyclopropane-1,12'-pyrazolo[4',3':9,10][1,6]oxazacycloundecino[8,7,6-hi]indole]-8'-carboxylic acid—N-ethylethanamine salt (enantiomer 1),
(+)-4'-chloro-3'-ethyl-2'-methyl-7'-{3-[(naphthalen-1-yl)oxy]propyl}-2',10',11',15'-tetrahydro-13'H-spiro[cyclopropane-1,12'-pyrazolo[4',3':9,10][1,6]oxazacycloundecino[8,7,6-hi]indole]-8'-carboxylic acid—N-ethylethanamine salt (enantiomer 2),
(+)-4-chloro-14-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino [10,11,1-hi]indole-8-carboxylic acid-N-ethylethanamine salt,
(−)-4-chloro-14-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino [10,11,1-hi]indole-8-carboxylic acid N-ethylethanamine salt,
(rac)-4-chloro-14-(2,2-difluoroethyl)-7-{3-[(6-fluoronaphthalen-1-yl)oxy]propyl}-2,3-dimethyl-10,11,12,13,14,15-hexahydro-2H-pyrazolo[3',4':8,9][1,6]diazacycloundecino [10,11,1-hi]indole-8-carboxylic acid,
(9aS,11aR)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]-oxazacycloundecino[8,7,6-hi]indole-14-carboxylic acid,
(9aR,11aS)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]-oxazacycloundecino[8,7,6-hi]indole-14-carboxylic acid,
(9aS,11aR)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]-oxazacycloundecino[8,7,6-hi]indole-14-carboxylic acid,
(9aR,11aS)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]-oxazacycloundecino[8,7,6-hi]indole-14-carboxylic acid,
(9aS,10aR or 9aR,10aS)-3-chloro-4,5-dimethyl-14-{3-[(naphthalen-1-yl)oxy]propyl}-5,7,9a,10,10a,11-hexahydro-9H-cyclopropa[3,4]pyrazolo[4',3':9,10][1,6]-oxazacycloundecino[8,7,6-hi]indole-13-carboxylic acid,
(9aS,10aR or 9aR,10aS)-3-chloro-4,5-dimethyl-14-{3-[(naphthalen-1-yl)oxy]propyl}-5,7,9a,10,10a,11-hexahydro-9H-cyclopropa[3,4]pyrazolo[4',3':9,10][1,6]-oxazacycloundecino[8,7,6-hi]indole-13-carboxylic acid,
(rac)-4-chloro-3-ethyl-12,12-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid,
(−)-4-chloro-3-ethyl-12,12-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid,
(+)-4-chloro-3-ethyl-12,12-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid,
(rac)-11-chloro-9,10-dimethyl-1-{3-[(naphthalen-1-yl)oxy]propyl}-4,5,7,9-tetrahydropyrazolo[4',3':7,8][1,4]oxazonino[6,5,4-hi]indole-2-carboxylic acid,
11-chloro-9,10-dimethyl-1-{3-[(naphthalen-1-yl)oxy]propyl}-4,5,7,9-tetrahydropyrazolo[4',3':7,8][1,4]oxazonino[6,5,4-hi]indole-2-carboxylic acid,
11-chloro-9,10-dimethyl-1-{3-[(naphthalen-1-yl)oxy]propyl}-4,5,7,9-tetrahydropyrazolo[4',3':7,8][1,4]oxazonino[6,5,4-hi]indole-2-carboxylic acid,
(rac)-4-Chloro-12,12-difluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid,
4-chloro-12,12-difluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid-N-ethylethanamine salt,
4-chloro-12,12-difluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid, (rac)-4-Chloro-11,11-difluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid, 4-chloro-11,11-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid N-ethylethanamine salt, 4-chloro-11,11-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid N-ethylethanamine salt, (rac)-4-chloro-3-ethyl-11,11-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (−)-4-chloro-3-ethyl-11,11-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-11,11-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, 4-chloro-3-ethyl-7-{3-[(6-fluoronaphthalen-1-yl)oxy]propyl}-12-hydroxy-2-methyl-2,10,11,12,13,15-hexahydropyrazolo[4',3':9,10][1,6]oxazacycloundecino[8,7,6-hi]indole-8-carboxylic acid—N-ethylethanamine salt (stereoisomer 1), 4-chloro-3-ethyl-7-{3-[(6-fluoronaphthalen-1-yl)oxy]propyl}-12-hydroxy-2-methyl-2,10,11,12,13,15-hexahydropyrazolo[4',3':9,10][1,6]oxazacycloundecino[8,7,6-hi]indole-8-carboxylic acid—N-ethylethanamine salt (stereoisomer 2), 4-chloro-3-ethyl-7-{3-[(6-fluoronaphthalen-1-yl)oxy]propyl}-12-hydroxy-2-methyl-2,10,11,12,13,15-hexahydropyrazolo[4',3':9,10][1,6]oxazacycloundecino[8,7,6-hi]indole-8-carboxylic acid—N-ethylethanamine salt (stereoisomer 3), 4-chloro-3-ethyl-7-{3-[(6-fluoronaphthalen-1-yl)oxy]propyl}-12-hydroxy-2-methyl-2,10,11,12,13,15-hexahydropyrazolo[4',3':9,10][1,6]oxazacycloundecino[8,7,6-hi]indole-8-carboxylic acid—N-ethylethanamine salt (stereoisomer 4), (rac)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid, (+)-(9aS or R,10aR or S)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid N-ethylethanamine salt, (−)-(9aS or R,10aR or S)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid N-ethylethanamine salt, (rac)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid, (+)-(9aS,10aR)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid, (−)-(9aS,10aR)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid, (rac)-4'-chloro-3'-ethyl-7'-{3-[(6-fluoronaphthalen-1-yl)oxy]propyl}-2'-methyl-2',10',11',15'-tetrahydro-13'H-spiro[cyclopropane-1,12'-pyrazolo[4',3':9,10][1,6]-oxazacycloundecino[8,7,6-hi]indole]-8'-carboxylic acid, (−)-4'-chloro-3'-ethyl-7'-{3-[(6-fluoronaphthalen-1-yl)oxy]propyl}-2'-methyl-2',10',11',15'-tetrahydro-13'H-spiro[cyclopropane-1,12'-pyrazolo[4',3':9,10][1,6]oxazacycloundecino-[8,7,6-hi]indole]-8'-carboxylic acid—N-ethylethanamine salt, (+)-4'-chloro-3'-ethyl-7'-{3-[(6-fluoronaphthalen-1-yl)oxy]propyl}-2'-methyl-2',10',11',15'-tetrahydro-13'H-spiro[cyclopropane-1,12'-pyrazolo[4',3':9,10][1,6]oxazacycloundecino-[8,7,6-hi]indole]-8'-carboxylic acid—N-ethylethanamine salt, (rac)-12-chloro-11-ethyl-1-{3-[(6-fluoronaphthalen-1-yl)oxy]propyl}-7,10-dimethyl-4,5,6,7,8,10-hexahydropyrazolo[3',4':7,8][1,5]diazecino[9,10,1-hi]indole-2-carboxylic acid (+) 12-chloro-11-ethyl-1-{3-[(6-fluoronaphthalen-1-yl)oxy]propyl}-7,10-dimethyl-4,5,6,7,8,10-hexahydropyrazolo[3',4':7,8][1,5]diazecino[9,10,1-hi]indole-2-carboxylic acid N-ethylethanamine salt, (−)-12-chloro-11-ethyl-1-{3-[(6-fluoronaphthalen-1-yl)oxy]propyl}-7,10-dimethyl-4,5,6,7,8,10-hexahydropyrazolo[3',4':7,8][1,5]diazecino[9,10,1-hi]indole-2-carboxylic acid-salt, (rac)-4-chloro-3-ethyl-7-{3-[(6-fluoronaphthalen-1-yl)oxy]propyl}-2,12-dimethyl-10,11,12,13,14,15-hexahydro-2H-pyrazolo[3',4':8,9][1,4]diazacycloundecino[10,11,1-hi]indole-8-carboxylic acid, (+)-4-chloro-3-ethyl-7-{3-[(6-fluoronaphthalen-1-yl)oxy]propyl}-2,12-dimethyl-10,11,12,13,14,15-hexahydro-2H-pyrazolo[3',4':8,9][1,4]diazacycloundecino[10,11,1-hi]indole-8-carboxylic acid, (−)-4-chloro-3-ethyl-7-{3-[(6-fluoronaphthalen-1-yl)oxy]propyl}-2,12-dimethyl-10,11,12,13,14,15-hexahydro-2H-pyrazolo[3',4':8,9][1,4]diazacycloundecino[10,11,1-hi]indole-8-carboxylic acid, (rac)-4-chloro-12-(2,2-difluoroethyl)-3-ethyl-7-{3-[(6-fluoro-1-naphthyl)oxy]propyl}-2-methyl-10,11,12,13,14,15-hexahydro-2H-pyrazolo[3',4':8,9][1,4]diazacycloundecino [10,11,1-hi]indole-8-carboxylic acid, (+)-4-chloro-12-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,4]diazacycloundecino [10,11,1-hi]indole-8-carboxylic acid N-ethylethanamine salt, (−)-4-chloro-12-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,4]diazacycloundecino [10,11,1-hi]indole-8-carboxylic acid-N-ethylethanamine salt, (rac)- 12-(4-acetoxybutyl)-4-chloro-3-ethyl-7-{3-[(6-fluoro-1-naphthyl)oxy]propyl}-2-methyl-10,11,12,13,14,15-hexahydro-2H-pyrazolo[3',4':8,9][1,4]diazacycloundecino[10,11,1-hi]indole-8-carboxylic acid, (rac)-4-chloro-3-ethyl-7-{3-[(6-fluoro-1-naphthyl)oxy]propyl}-12-(4-hydroxybutyl)-2-methyl-10,11,12,13,14,15-hexahydro-2H-pyrazolo[3',4':8,9][1,4]diazacycloundecino[10,11,1-hi]indole-8-carboxylic acid, (rac)-4-chloro-3-ethyl-7-{3-[(6-fluoro-1-naphthyl)oxy]propyl}-2-methyl-12-(2,2,3,3-tetrafluoropropyl)-10,11,12, 13,14,15-hexahydro-2H-pyrazolo[3',4':8,9][1,4]diazacycloundecino[10,11,1-hi]indole-8-carboxylic acid,
(rac)-4-chloro-3-ethyl-7-{3-[(6-fluoro-1-naphthyl)oxy]propyl}-2-methyl-2,10,11,13,14,15-hexahydropyrazolo[4',3':7,8][1,4]oxazacycloundecino[6,5,4-hi]indole-8-carboxylic acid,
(rac)-4-chloro-3-ethyl-7-{3-[(6-fluoro-1-naphthyl)oxy]propyl}-1-methyl-1,10,11,13,14,15-hexahydropyrazolo[4',3':7,8][1,4]oxazacycloundecino[6,5,4-hi]indole-8-carboxylic acid,
(rac)-4-Chloro-3-ethyl-12,12-difluoro-7-{3-[(6-fluoro-1-naphthyl)oxy]propyl}-2,14-dimethyl-10,11,12,13,14,15-hexahydro-2H-pyrazolo[3',4':8,9][1,6]diazacycloundecino[10,11,1-hi]indol-14-ium-8-carboxylate,
4-chloro-3-ethyl-12,12-difluoro-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid,
4-chloro-3-ethyl-12,12-difluoro-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid,
rac-4-chloro-3-ethyl-11,11-difluoro-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino [10,11,1-hi]indole-8-carboxylic acid,
rac-4-chloro-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylic acid,
rac-4-chloro-3-ethyl-7-{3-[(6-fluoronaphthalen-1-yl)oxy]propyl}-14-(2-methoxyethyl)-2-methyl-10,11,12,13,14,15-hexahydro-2H-pyrazolo[3',4':8,9][1,6]diazacycloundecino[10,11,1-hi]indole-8-carboxylic acid,
4-chloro-3-ethyl-7-{3-[(6-fluoronaphthalen-1-yl)oxy]propyl}-14-(2-methoxyethyl)-2-methyl-10,11,12,13,14,15-hexahydro-2H-pyrazolo[3',4':8,9][1,6]diazacycloundecino[10,11,1-hi]indole-8-carboxylic acid,
4-chloro-3-ethyl-7-{3-[(6-fluoronaphthalen-1-yl)oxy]propyl}-14-(2-methoxyethyl)-2-methyl-10,11,12,13,14,15-hexahydro-2H-pyrazolo[3',4':8,9][1,6]diazacycloundecino[10,11,1-hi]indole-8-carboxylic acid N-ethylethanamine salt,
rac-4-chloro-3-ethyl-7-{3-[(6-fluoronaphthalen-1-yl)oxy]propyl}-14-[(2-methoxyethoxy)carbonyl]-2-methyl-10,11,12,13,14,15-hexahydro-2H-pyrazolo[3',4':8,9][1,6]diazacycloundecino[10,11,1-hi]indole-8-carboxylic acid,
rac-4-chloro-3-ethyl-7-{3-[(6-fluoronaphthalen-1-yl)oxy]propyl}-2-methyl-14-[2-(oxan-4-yl)ethyl]-10,11,12,13,14,15-hexahydro-2H-pyrazolo[3',4':8,9][1,6]diazacycloundecino [10,11,1-hi]indole-8-carboxylic acid,
4-chloro-3-ethyl-7-{3-[(6-fluoronaphthalen-1-yl)oxy]propyl}-2-methyl-14-[2-(oxan-4-yl)ethyl]-10,11,12,13,14,15-hexahydro-2H-pyrazolo[3',4':8,9][1,6]diazacycloundecino[10,11,1-hi]indole-8-carboxylic acid N-ethylethanamine salt,
4-chloro-3-ethyl-7-{3-[(6-fluoronaphthalen-1-yl)oxy]propyl}-2-methyl-14-[2-(oxan-4-yl)ethyl]-10,11,12,13,14,15-hexahydro-2H-pyrazolo[3',4':8,9][1,6]diazacycloundecino[10,11,1-hi]indole-8-carboxylic acid-N-ethylethanamine (1/1),
rac-4-chloro-3-ethyl-7-{3-[(6-fluoronaphthalen-1-yl)oxy]propyl}-2-methyl-14-{[2-(oxan-4-yl)ethoxy]carbonyl}-10,11,12,13,14,15-hexahydro-2H-pyrazolo[3',4':8,9][1,6]diaza cycloundecino[10,11,1-hi]indole-8-carboxylic acid,
rac-4-chloro-3-ethyl-7-{3-[(6-fluoronaphthalen-1-yl)oxy]propyl}-14-(3-hydroxypropyl)-2-methyl-10,11,12,13,14,15-hexahydro-2H-pyrazolo[3',4':8,9][1,6]diazacycloundecino [10,11,1-hi]indole-8-carboxylic acid,
4-chloro-3-ethyl-7-{3-[(6-fluoronaphthalen-1-yl)oxy]propyl}-14-(3-hydroxy-3-methylbutyl)-2-methyl-10,11,12,13,14,15-hexahydro-2H-pyrazolo[3',4':8,9][1,6]diazacycloundecino [10,11,1-hi]indole-8-carboxylic acid (enantiomer 1),
4-chloro-3-ethyl-7-{3-[(6-fluoronaphthalen-1-yl)oxy]propyl}-14-(3-hydroxy-3-methylbutyl)-2-methyl-10,11,12,13,14,15-hexahydro-2H-pyrazolo[3',4':8,9][1,6]diazacycloundecino [10,11,1-hi]indole-8-carboxylic acid (enantiomer 2),
4-chloro-3-ethyl-7-{3-[(6-fluoronaphthalen-1-yl)oxy]propyl}-2-methyl-14-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid (enantiomer 1) and
4-chloro-3-ethyl-7-{3-[(6-fluoronaphthalen-1-yl)oxy]propyl}-2-methyl-14-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid (enantiomer 2)
or a tautomer, an N-oxide, or a salt thereof, or a salt of a tautomer, or a salt of an N-oxide, or a mixture of same.

In some embodiments, the present invention includes compounds of general formula (I) selected from:
(rac)-4-chloro-3-ethyl-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid,
4-chloro-3-ethyl-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid (enantiomer 1),
4-chloro-3-ethyl-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid (enantiomer 2),
(rac)-4-chloro-3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid,
4-chloro-3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid—N-ethylethanamine salt (enantiomer 1) and
4-chloro-3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid—N-ethylethanamine salt (enantiomer 2)
or a tautomer, an N-oxide, or a salt thereof, or a salt of a tautomer, or a salt of an N-oxide, or a mixture of same.

In some embodiments, the present invention includes compounds of general formula (I) selected from:
(rac)-4-chloro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid,
(+)-4-chloro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid-N-ethylethanamine salt (enantiomer 1), (−)-4-chloro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid (enantiomer 1), (−)-4-chloro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid-N-ethylethanamine salt (enantiomer 2), (rac)-(11Z)-4-chloro-3-ethyl-2-methyl-7-[3-(naphthalen-1-yloxy)propyl]-2,10,13,15-tetrahydropyrazolo[4',3':9,10][1,6]oxazacycloundecino[8,7,6-hi]indole-8-carboxylic acid, (rac)-4-chloro-3-ethyl-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, 4-chloro-3-ethyl-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (enantiomer 1), 4-chloro-3-ethyl-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (enantiomer 2), (rac)-4-chloro-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, 4-chloro-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (enantiomer 1), 4-chloro-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (enantiomer 2), (rac)-4-chloro-3-ethyl-7-{3-[(6-fluoronaphthalen-1-yl)oxy]propyl}-1,14-dimethyl-10,11,12,13,14,15-hexahydro-1H-pyrazolo[3',4':8,9][1,6]diazacycloundecino[10,11,1-hi]indole-8-carboxylic acid, 4-chloro-3-ethyl-7-{3-[(6-fluoronaphthalen-1-yl)oxy]propyl}-1,14-dimethyl-10,11,12,13,14,15-hexahydro-1H-pyrazolo[3',4':8,9][1,6]diazacycloundecino[10,11,1-hi]indole-8-carboxylic acid (enantiomer 1), 4-chloro-3-ethyl-7-{3-[(6-fluoronaphthalen-1-yl)oxy]propyl}-1,14-dimethyl-10,11,12,13,14,15-hexahydro-1H-pyrazolo[3',4':8,9][1,6]diazacycloundecino[10,11,1-hi]indole-8-carboxylic acid (enantiomer 2), (rac)-4-chloro-3-ethyl-7-{3-[(6-fluoronaphthalen-1-yl)oxy]propyl}-2-methyl-10,11,12,13,14,15-hexahydro-2H-pyrazolo[4',3':4,5]azacycloundecino[3,2,1-hi]indole-8-carboxylic acid, (rac)-4-chloro-7-{3-[(6-fluoronaphthalen-1-yl)oxy]propyl}-2,3-dimethyl-14-(2,2,2-trifluoroethyl)-10,11,12,13,14,15-hexahydro-2H-pyrazolo[3',4':8,9][1,6]diazacycloundecino [10,11,1-hi]indole-8-carboxylic acid, 4-chloro-7-{3-[(6-fluoronaphthalen-1-yl)oxy]propyl}-2,3-dimethyl-14-(2,2,2-trifluoroethyl)-10,11,12,13,14,15-hexahydro-2H-pyrazolo[3',4':8,9][1,6]diazacycloundecino[10,11,1-hi]indole-8-carboxylic acid—(enantiomer 1), 4-chloro-7-{3-[(6-fluoronaphthalen-1-yl)oxy]propyl}-2,3-dimethyl-14-(2,2,2-trifluoroethyl)-10,11,12,13,14,15-hexahydro-2H-pyrazolo[3',4':8,9][1,6]diazacycloundecino[10,11,1-hi]indole-8-carboxylic acid—(enantiomer 2), (+)-4-chloro-3-ethyl-7-{3-[(6-fluoronaphthalen-1-yl)oxy]propyl}-2-methyl-10,11,12,13,14,15-hexahydro-2H-pyrazolo[4',3':4,5]azacycloundecino[3,2,1-hi]indole-8-carboxylic acid—N-ethylethanamine salt (enantiomer 1)

(−)-4-chloro-3-ethyl-7-{3-[(6-fluoronaphthalen-1-yl)oxy]propyl}-2-methyl-10,11,12,13,14,15-hexahydro-2H-pyrazolo[4',3':4,5]azacycloundecino[3,2,1-hi]indole-8-carboxylic acid—N-ethylethanamine salt (enantiomer 2), (rac)-4-chloro-3-ethyl-11,11-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (−)-4-chloro-3-ethyl-11,11-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-11,11-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (rac)-4-chloro-3-ethyl-7-{3-[(6-fluoronaphthalen-1-yl)oxy]propyl}-2,12-dimethyl-10,11,12,13,14,15-hexahydro-2H-pyrazolo[3',4':8,9][1,4]diazacycloundecino[10,11,1-hi]indole-8-carboxylic acid, (+)-4-chloro-3-ethyl-7-{3-[(6-fluoronaphthalen-1-yl)oxy]propyl}-2,12-dimethyl-10,11,12,13,14,15-hexahydro-2H-pyrazolo[3',4':8,9][1,4]diazacycloundecino[10,11,1-hi]indole-8-carboxylic acid, (−)-4-chloro-3-ethyl-7-{3-[(6-fluoronaphthalen-1-yl)oxy]propyl}-2,12-dimethyl-10,11,12,13,14,15-hexahydro-2H-pyrazolo[3',4':8,9][1,4]diazacycloundecino[10,11,1-hi]indole-8-carboxylic acid, (rac)-4-Chloro-3-ethyl-12,12-difluoro-7-{3-[(6-fluoro-1-naphthyl)oxy]propyl}-2,14-dimethyl-10,11,12,13,14,15-hexahydro-2H-pyrazolo[3',4':8,9][1,6]diazacycloundecino[10,11,1-hi]indol-14-ium-8-carboxylate, 4-chloro-3-ethyl-12,12-difluoro-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid, 4-chloro-3-ethyl-12,12-difluoro-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid, rac-4-chloro-3-ethyl-7-{3-[(6-fluoronaphthalen-1-yl)oxy]propyl}-14-[(2-methoxyethoxy)carbonyl]-2-methyl-10,11,12,13,14,15-hexahydro-2H-pyrazolo[3',4':8,9][1,6]diazacycloundecino[10,11,1-hi]indole-8-carboxylic acid and rac-4-chloro-3-ethyl-7-{3-[(6-fluoronaphthalen-1-yl)oxy]propyl}-2-methyl-14-{[2-(oxan-4-yl)ethoxy]carbonyl}-10,11,12,13,14,15-hexahydro-2H-pyrazolo[3',4':8,9][1,6]diaza cycloundecino[10,11,1-hi]indole-8-carboxylic acid or a tautomer, an N-oxide, or a salt thereof, or a salt of a tautomer, or a salt of an N-oxide, or a mixture of same.

In some embodiments, the present invention includes compounds of general formula (I) selected from:

(rac)-4-chloro-2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid, (+)-4-chloro-2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid—N-ethylethanamine salt (enantiomer 1), (−)-4-chloro-2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid—N-ethylethanamine salt (enantiomer 2), (rac)-4-chloro-7-{3-[(6-fluoronaphthalen-1-yl)oxy]propyl}-2,3,14-trimethyl-10,11,12,13,14,15-hexahydro-2H-pyrazolo[3',4':8,9][1,6]diazacycloundecino[10,11,1-hi]indole-8-carboxylic acid, (+)-4-chloro-7-{3-[(6-fluoronaphthalen-1-yl)oxy]propyl}-2,3,14-trimethyl-10,11,12,13,14,15-hexahydro-2H-pyrazolo[3',4':8,9][1,6]diazacycloundecino[10,11,1-hi]indole-8-carboxylic acid-N-ethylethanamine salt (enantiomer 1), (−)-4-chloro-7-{3-[(6-fluoronaphthalen-1-yl)oxy]propyl}-2,3,14-trimethyl-10,11,12,13,14,15-hexahydro-2H-pyrazolo[3',4':8,9][1,6]diazacycloundecino[10,11,1-hi]indole-8-carboxylic acid—N-ethylethanamine salt (enantiomer 2), (rac)-4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 1), (−)-4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 2), (rac)-4-chloro-3-ethyl-14-methyl-1-[2-(morpholin-4-yl)ethyl]-7-{3-[(naphthalen-1-yl)oxy]propyl}-10,11,12,13,14,15-hexahydro-1H-pyrazolo[3',4':8,9][1,6]diazacycloundecino [10,11,1-hi]indole-8-carboxylic acid, 4-chloro-3-ethyl-14-methyl-1-[2-(morpholin-4-yl)ethyl]-7-{3-[(naphthalen-1-yl)oxy]propyl}-10,11,12,13,14,15-hexahydro-1H-pyrazolo[3',4':8,9][1,6]diazacycloundecino[10,11,1-hi]indole-8-carboxylic acid (enantiomer 1), 4-chloro-3-ethyl-14-methyl-1-[2-(morpholin-4-yl)ethyl]-7-{3-[(naphthalen-1-yl)oxy]propyl}-10,11,12,13,14,15-hexahydro-1H-pyrazolo[3',4':8,9][1,6]diazacycloundecino[10,11,1-hi]indole-8-carboxylic acid (enantiomer 2), (rac)-4-chloro-14-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino [10,11,1-hi]indole-8-carboxylic acid, 4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (enantiomer 1), (+)-4-chloro-14-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino [10,11,1-hi]indole-8-carboxylic acid-N-ethylethanamine salt, (−)-4-chloro-14-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino [10,11,1-hi]indole-8-carboxylic acid N-ethylethanamine salt, (rac)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid, (+)-(9aS or R,10aR or S)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid N-ethylethanamine salt, (−)-(9aS or R,10aR or S)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid N-ethylethanamine salt, (rac)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid, (+)-(9aS,10aR)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid, (−)-(9aS,10aR)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid, (rac)-4'-chloro-3'-ethyl-7'-{3-[(6-fluoronaphthalen-1-yl)oxy]propyl}-2'-methyl-2',10',11',15'-tetrahydro-13'H-spiro[cyclopropane-1,12'-pyrazolo[4',3':9,10][1,6]-oxazacycloundecino[8,7,6-hi]indole]-8'-carboxylic acid, (−)-4'-chloro-3'-ethyl-7'-{3-[(6-fluoronaphthalen-1-yl)oxy]propyl}-2'-methyl-2',10',11',15'-tetrahydro-13'H-spiro[cyclopropane-1,12'-pyrazolo[4',3':9,10][1,6]oxazacycloundecino-[8,7,6-hi]indole]-8'-carboxylic acid—N-ethylethanamine salt, (+)-4'-chloro-3'-ethyl-7'-{3-[(6-fluoronaphthalen-1-yl)oxy]propyl}-2'-methyl-2',10',11',15'-tetrahydro-13'H-spiro[cyclopropane-1,12'-pyrazolo[4',3':9,10][1,6]oxazacycloundecino-[8,7,6-hi]indole]-8'-carboxylic acid—N-ethylethanamine salt, (rac)-4-chloro-12-(2,2-difluoroethyl)-3-ethyl-7-{3-[(6-fluoro-1-naphthyl)oxy]propyl}-2-methyl-10,11,12,13,14,15-hexahydro-2H-pyrazolo[3',4':8,9][1,4]diazacycloundecino [10,11,1-hi]indole-8-carboxylic acid, (+)-4-chloro-12-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,4]diazacycloundecino [10,11,1-hi]indole-8-carboxylic acid N-ethylethanamine salt, (−)-4-chloro-12-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,4]diazacycloundecino [10,11,1-hi]indole-8-carboxylic acid-N-ethylethanamine salt, rac-4-chloro-3-ethyl-7-{3-[(6-fluoronaphthalen-1-yl)oxy]propyl}-14-(2-methoxyethyl)-2-methyl-10,11,12,13,14,15-hexahydro-2H-pyrazolo[3',4':8,9][1,6]diazacycloundecino[10,11,1-hi]indole-8-carboxylic acid, 4-chloro-3-ethyl-7-{3-[(6-fluoronaphthalen-1-yl)oxy]propyl}-14-(2-methoxyethyl)-2-methyl-10,11,12,13,14,15-hexahydro-2H-pyrazolo[3',4':8,9][1,6]diazacycloundecino[10,11,1-hi]indole-8-carboxylic acid, 4-chloro-3-ethyl-7-{3-[(6-fluoronaphthalen-1-yl)oxy]propyl}-14-(2-methoxyethyl)-2-methyl-10,11,12,13,14,15-hexahydro-2H-pyrazolo[3',4':8,9][1,6]diazacycloundecino[10,11,1-hi]indole-8-carboxylic acid N-ethylethanamine salt, rac-4-chloro-3-ethyl-7-{3-[(6-fluoronaphthalen-1-yl)oxy]propyl}-2-methyl-14-[2-(oxan-4-yl)ethyl]-10,11,12,13,14,15-hexahydro-2H-pyrazolo[3',4':8,9][1,6]diazacycloundecino [10,11,1-hi]indole-8-carboxylic acid, 4-chloro-3-ethyl-7-{3-[(6-fluoronaphthalen-1-yl)oxy]propyl}-2-methyl-14-[2-(oxan-4-yl)ethyl]-10,11,12,13,14,15-hexahydro-2H-pyrazolo[3',4':8,9][1,6]diazacycloundecino[10,11,1-hi]indole-8-carboxylic acid N-ethylethanamine salt, 4-chloro-3-ethyl-7-{3-[(6-fluoronaphthalen-1-yl)oxy]propyl}-2-methyl-14-[2-(oxan-4-yl)ethyl]-10,11,12,13,14, 15-hexahydro-2H-pyrazolo[3',4':8,9][1,6]diazacycloundecino[10,11,1-hi]indole-8-carboxylic acid-N-ethylethanamine (1/1), 4-chloro-3-ethyl-7-{3-[(6-fluoronaphthalen-1-yl)oxy]propyl}-14-(3-hydroxy-3-methylbutyl)-2-methyl-10,11,12,13,14,15-hexahydro-2H-pyrazolo[3',4':8,9][1,6]diazacycloundecino [10,11,1-hi]indole-8-carboxylic acid (enantiomer 1)

4-chloro-3-ethyl-7-{3-[(6-fluoronaphthalen-1-yl)oxy]propyl}-14-(3-hydroxy-3-methylbutyl)-2-methyl-10,11,12,13,14,15-hexahydro-2H-pyrazolo[3',4':8,9][1,6]diazacycloundecino [10,11,1-hi]indole-8-carboxylic acid (enantiomer 2), 4-chloro-3-ethyl-7-{3-[(6-fluoronaphthalen-1-yl)oxy]propyl}-2-methyl-14-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid (enantiomer 1) and 4-chloro-3-ethyl-7-{3-[(6-fluoronaphthalen-1-yl)oxy]propyl}-2-methyl-14-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid (enantiomer 2)

or a tautomer, an N-oxide, or a salt thereof, or a salt of a tautomer, or a salt of an N-oxide, or a mixture of same.

In some embodiments, the present invention includes compounds of general formula (I) selected from:

(+)-4-chloro-2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid—N-ethylethanamine salt (enantiomer 1), (rac)-4-chloro-7-{3-[(6-fluoronaphthalen-1-yl)oxy]propyl}-2,3,14-trimethyl-10,11,12,13,14,15-hexahydro-2H-pyrazolo[3',4':8,9][1,6]diazacycloundecino[10,11,1-hi]indole-8-carboxylic acid, (+)-4-chloro-7-{3-[(6-fluoronaphthalen-1-yl)oxy]propyl}-2,3,14-trimethyl-10,11,12,13,14,15-hexahydro-2H-pyrazolo[3',4':8,9][1,6]diazacycloundecino[10,11,1-hi]indole-8-carboxylic acid-N-ethylethanamine salt (enantiomer 1), (rac)-4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 1), 4-chloro-3-ethyl-14-methyl-1-[2-(morpholin-4-yl)ethyl]-7-{3-[(naphthalen-1-yl)oxy]propyl}-10,11,12,13,14,15-hexahydro-1H-pyrazolo[3',4':8,9][1,6]diazacycloundecino[10,11,1-hi]indole-8-carboxylic acid (enantiomer 1), 4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (enantiomer 1), (+)-4-chloro-14-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino [10,11,1-hi]indole-8-carboxylic acid-N-ethylethanamine salt, (rac)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid, (+)-(9aS or R,10aR or S)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid N-ethylethanamine salt, (+)-(9aS,10aR)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid, (−)-4'-chloro-3'-ethyl-7'-{3-[(6-fluoronaphthalen-1-yl)oxy]propyl}-2'-methyl-2',10',11',15'-tetrahydro-13'H-spiro[cyclopropane-1,12'-pyrazolo[4',3':9,10][1,6]oxazacycloundecino-[8,7,6-hi]indole]-8'-carboxylic acid—N-ethylethanamine salt, (+)-4-chloro-12-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,4]diazacycloundecino [10,11,1-hi]indole-8-carboxylic acid N-ethylethanamine salt, 4-chloro-3-ethyl-7-{3-[(6-fluoronaphthalen-1-yl)oxy]propyl}-14-(2-methoxyethyl)-2-methyl-10,11,12,13,14,15-hexahydro-2H-pyrazolo[3',4':8,9][1,6]diazacycloundecino[10,11,1-hi]indole-8-carboxylic acid, 4-chloro-3-ethyl-7-{3-[(6-fluoronaphthalen-1-yl)oxy]propyl}-2-methyl-14-[2-(oxan-4-yl)ethyl]-10,11,12,13,14,15-hexahydro-2H-pyrazolo[3',4':8,9][1,6]diazacycloundecino[10,11,1-hi]indole-8-carboxylic acid N-ethylethanamine salt, 4-chloro-3-ethyl-7-{3-[(6-fluoronaphthalen-1-yl)oxy]propyl}-14-(3-hydroxy-3-methylbutyl)-2-methyl-10,11,12,13,14,15-hexahydro-2H-pyrazolo[3',4':8,9][1,6]diazacycloundecino [10,11,1-hi]indole-8-carboxylic acid (enantiomer 1) and 4-chloro-3-ethyl-7-{3-[(6-fluoronaphthalen-1-yl)oxy]propyl}-2-methyl-14-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid (enantiomer 1)

or a tautomer, an N-oxide, or a salt thereof, or a salt of a tautomer, or a salt of an N-oxide, or a mixture of same.

In some embodiments, the present invention includes compounds of general formula (I) selected from:

(+)-4-chloro-2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid—N-ethylethanamine salt (enantiomer 1), (rac)-4-chloro-7-{3-[(6-fluoronaphthalen-1-yl)oxy]propyl}-2,3,14-trimethyl-10,11,12,13,14,15-hexahydro-2H-pyrazolo[3',4':8,9][1,6]diazacycloundecino[10,11,1-hi]indole-8-carboxylic acid, (+)-4-chloro-7-{3-[(6-fluoronaphthalen-1-yl)oxy]propyl}-2,3,14-trimethyl-10,11,12,13,14,15-hexahydro-2H-pyrazolo[3',4':8,9][1,6]diazacycloundecino[10,11,1-hi]indole-8-carboxylic acid-N-ethylethanamine salt (enantiomer 1), (rac)-4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 1) and 4-chloro-3-ethyl-14-methyl-1-[2-(morpholin-4-yl)ethyl]-7-{3-[(naphthalen-1-yl)oxy]propyl}-10,11,12,13,14,15-hexahydro-1H-pyrazolo[3',4':8,9][1,6]diazacycloundecino[10,11,1-hi]indole-8-carboxylic acid (enantiomer 1)

or a tautomer, an N-oxide, or a salt thereof, or a salt of a tautomer, or a salt of an N-oxide, or a mixture of same.

In some embodiments, the present invention includes compounds of general formula (I) selected from:
- 4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (enantiomer 1),
- (+)-4-chloro-14-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino [10,11,1-hi]indole-8-carboxylic acid-N-ethylethanamine salt,
- (rac)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid,
- (+)-(9aS or R,10aR or S)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid N-ethylethanamine salt,
- (+)-(9aS,10aR)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid,
- (−)-4'-chloro-3'-ethyl-7'-{3-[(6-fluoronaphthalen-1-yl)oxy]propyl}-2'-methyl-2',10',11',15'-tetrahydro-13'H-spiro[cyclopropane-1,12'-pyrazolo[4',3':9,10][1,6]oxazacycloundecino-[8,7,6-hi]indole]-8'-carboxylic acid—N-ethylethanamine salt,
- (+)-4-chloro-12-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,4]diazacycloundecino [10,11,1-hi]indole-8-carboxylic acid N-ethylethanamine salt,
- 4-chloro-3-ethyl-7-{3-[(6-fluoronaphthalen-1-yl)oxy]propyl}-14-(2-methoxyethyl)-2-methyl-10,11,12,13,14,15-hexahydro-2H-pyrazolo[3',4':8,9][1,6]diazacycloundecino[10,11,1-hi]indole-8-carboxylic acid,
- 4-chloro-3-ethyl-7-{3-[(6-fluoronaphthalen-1-yl)oxy]propyl}-2-methyl-14-[2-(oxan-4-yl)ethyl]-10,11,12,13,14,15-hexahydro-2H-pyrazolo[3',4':8,9][1,6]diazacycloundecino[10,11,1-hi]indole-8-carboxylic acid N-ethylethanamine salt,
- 4-chloro-3-ethyl-7-{3-[(6-fluoronaphthalen-1-yl)oxy]propyl}-14-(3-hydroxy-3-methylbutyl)-2-methyl-10,11,12,13,14,15-hexahydro-2H-pyrazolo[3',4':8,9][1,6]diazacycloundecino [10,11,1-hi]indole-8-carboxylic acid (enantiomer 1) and
- 4-chloro-3-ethyl-7-{3-[(6-fluoronaphthalen-1-yl)oxy]propyl}-2-methyl-14-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid (enantiomer 1)

or a tautomer, an N-oxide, or a salt thereof, or a salt of a tautomer, or a salt of an N-oxide, or a mixture of same.

In some embodiments, the present invention includes compounds of general formula (I) selected from:
- 4-chloro-3-ethyl-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid (enantiomer 1),
- (+)-4-chloro-2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid—N-ethylethanamine salt (enantiomer 1),
- (+)-4-chloro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid-N-ethylethanamine salt (enantiomer 1),
- (−)-4-chloro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid (enantiomer 1),
- 4-chloro-3-ethyl-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (enantiomer 1),
- (+)-4-chloro-7-{3-[(6-fluoronaphthalen-1-yl)oxy]propyl}-2,3,14-trimethyl-10,11,12,13,14,15-hexahydro-2H-pyrazolo[3',4':8,9][1,6]diazacycloundecino[10,11,1-hi]indole-8-carboxylic acid-N-ethylethanamine salt (enantiomer 1),
- (+)-4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 1),
- 4-chloro-3-ethyl-7-{3-[(6-fluoronaphthalen-1-yl)oxy]propyl}-1,14-dimethyl-10,11,12,13,14,15-hexahydro-1H-pyrazolo[3',4':8,9][1,6]diazacycloundecino[10,11,1-hi]indole-8-carboxylic acid (enantiomer 1),
- 4-chloro-3-ethyl-14-methyl-1-[2-(morpholin-4-yl)ethyl]-7-{3-[(naphthalen-1-yl)oxy]propyl}-10,11,12,13,14,15-hexahydro-1H-pyrazolo[3',4':8,9][1,6]diazacycloundecino[10,11,1-hi]indole-8-carboxylic acid (enantiomer 1) and
- 4-chloro-7-{3-[(6-fluoronaphthalen-1-yl)oxy]propyl}-2,3-dimethyl-14-(2,2,2-trifluoroethyl)-10,11,12,13,14,15-hexahydro-2H-pyrazolo[3',4':8,9][1,6]diazacycloundecino[10,11,1-hi]indole-8-carboxylic acid Enantiomer 1 or a tautomer, an N-oxide, or a salt thereof, or a salt of a tautomer, or a salt of an N-oxide, or a mixture of same.

In some embodiments, the present invention includes compounds of general formula (I) selected from example 01-example 68, or a tautomer, an N-oxide, or a salt thereof, or a salt of a tautomer, or a salt of an N-oxide, or a mixture of same.

In some embodiments, the present invention includes compounds of general formula (I) selected from example 69-example 143, or a tautomer, an N-oxide, or a salt thereof, or a salt of a tautomer, or a salt of an N-oxide, or a mixture of same.

In some embodiments, the present invention includes compounds of general formula (I) selected from example 01-example 143, or a tautomer, an N-oxide, or a salt thereof, or a salt of a tautomer, or a salt of an N-oxide, or a mixture of same.

In some embodiments, the present invention includes the most effective isomer of the compounds of general formula (I) as provided in any list above if several isomers of the same structure are encompassed or a tautomer, an N-oxide, or a salt thereof, or a salt of a tautomer, or a salt of an N-oxide, or a mixture of same.

In some embodiments, the present invention includes all intermediate compounds leading to a compound of general formula (I) as disclosed in the example section and their use for the synthesis of the compound of formula (I), starting from Intermediate 1 and ending up with intermediate 138, or a tautomer, an N-oxide, or a salt thereof, or a salt of a tautomer, or a salt of an N-oxide, or a mixture of same.

In some embodiments, the present invention includes all intermediate compounds leading to a compound of general formula (I) as disclosed in the example section and their use for the synthesis of the compound of formula (I), starting from Intermediate 139 and ending up with intermediate 229, or a tautomer, an N-oxide, or a salt thereof, or a salt of a tautomer, or a salt of an N-oxide, or a mixture of same.

In some embodiments, the present invention includes all intermediate compounds leading to a compound of general formula (I) as disclosed in the example section and their use for the synthesis of the compound of formula (I), starting from Intermediate 1 and ending up with intermediate 229, or a tautomer, an N-oxide, or a salt thereof, or a salt of a tautomer, or a salt of an N-oxide, or a mixture of same.

In some embodiments, the present invention includes compounds of formula (I), supra, in which $R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group, and a $C_3$-$C_5$-cycloalkyl group or a tautomer, an N-oxide, or a salt thereof, or a salt of a tautomer, or a salt of an N-oxide, or a mixture of same.

In some embodiments, the present invention includes compounds of formula (I), supra, in which $R^4$ is selected from an aryl group and a heteroaryl group, each of which is unsubstituted or substituted with one, two, or three, substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, and a ($C_1$-$C_3$)-haloalkyl-S— group, and a $C_3$-$C_5$-cycloalkyl group; or a tautomer, an N-oxide, or a salt thereof, or a salt of a tautomer, or a salt of an N-oxide, or a mixture of same In some embodiments, the present invention includes compounds of formula (I), supra, in which $R^4$ is selected from an aryl group and a heteroaryl group, each of which is unsubstituted or substituted with one, two, or three, substituents and each substituent is independently selected from a halogen atom, a $C_1$-$C_3$-alkyl group, and a $C_1$-$C_3$-haloalkyl group or a tautomer, an N-oxide, or a salt thereof, or a salt of a tautomer, or a salt of an N-oxide, or a mixture of same.

In some embodiments, the present invention includes compounds of formula (I), supra, in which $R^4$ is selected from an aryl group and a heteroaryl group, each of which is unsubstituted or substituted with one or two substituents and each substituent is independently selected from a halogen atom, and a $C_1$-$C_3$-alkyl group or a tautomer, an N-oxide, or a salt thereof, or a salt of a tautomer, or a salt of an N-oxide, or a mixture of same.

In some embodiments, the present invention includes compounds of formula (I), supra, in which $R^4$ is selected from an aryl group, each of which is unsubstituted or substituted with one, two or three substituents and each substituent is independently selected from a halogen atom, and a $C_1$-$C_3$-alkyl group or a tautomer, an N-oxide, or a salt thereof, or a salt of a tautomer, or a salt of an N-oxide, or a mixture of same.

In some embodiments, the present invention includes compounds of formula (I), supra, in which $R^4$ is an aryl group, which is unsubstituted or substituted with one or two substituents and each substituent is independently selected from a halogen atom, and a $C_1$-$C_3$-alkyl group or a tautomer, an N-oxide, or a salt thereof, or a salt of a tautomer, or a salt of an N-oxide, or a mixture of same.

In some embodiments, the present invention includes compounds of formula (I), supra, in which $R^4$ is an aryl group, which is unsubstituted or substituted with a halogen atom; or a tautomer, an N-oxide, or a salt thereof, or a salt of a tautomer, or a salt of an N-oxide, or a mixture of same.

In some embodiments, the present invention includes compounds of formula (I), supra, in which $R^4$ is an aryl group, which is unsubstituted or substituted with one substituent which is a halogen atom or a tautomer, an N-oxide, or a salt thereof, or a salt of a tautomer, or a salt of an N-oxide, or a mixture of same.

In some embodiments, the present invention includes compounds of formula (I), supra, in which $R^4$ is a aryl group, which is unsubstituted or substituted with a fluorine or a chlorine atom or a tautomer, an N-oxide, or a salt thereof, or a salt of a tautomer, or a salt of an N-oxide, or a mixture of same.

In some embodiments, the present invention includes compounds of formula (I), supra, in which $R^4$ is a aryl group, which is unsubstituted or substituted with a fluorine atom or a tautomer, an N-oxide, or a salt thereof, or a salt of a tautomer, or a salt of an N-oxide, or a mixture of same.

In some embodiments, the present invention includes compounds of formula (I), supra, in which $R^4$ is a naphtyl group, which is unsubstituted or substituted with a halogen atom or a tautomer, an N-oxide, or a salt thereof, or a salt of a tautomer, or a salt of an N-oxide, or a mixture of same.

In some embodiments, the present invention includes compounds of formula (I), supra, in which $R^4$ is a naphtyl group, which is unsubstituted or substituted with a fluorine atom or a chlorine atom or tautomer, an N-oxide, or a salt thereof or a salt of a tautomer or a salt of an N-oxide or a mixture of same.

In some embodiments, the present invention includes compounds of formula (I), supra, in which $R^4$ is a naphtyl group, which is substituted with a fluorine atom or a tautomer, an N-oxide, or a salt thereof, or a salt of a tautomer, or a salt of an N-oxide, or a mixture of same.

In some embodiments, the present invention includes compounds of formula (I), supra, in which $R^4$ is a naphtyl group, which is substituted with a chlorine atom or a tautomer, an N-oxide, or a salt thereof, or a salt of a tautomer, or a salt of an N-oxide, or a mixture of same.

In some embodiments, the present invention includes compounds of formula (I), supra, in which $R^4$ is a naphtyl group, which is unsubstituted or a tautomer, an N-oxide, or a salt thereof, or a salt of a tautomer, or a salt of an N-oxide, or a mixture of same.

In some embodiments, the present invention includes compounds of formula (I), supra, in which $R^4$ is a naphtyl group, which is unsubstituted or substituted with a chlorine atom or a tautomer, an N-oxide, or a salt thereof, or a salt of a tautomer, or a salt of an N-oxide, or a mixture of same.

In some embodiments, the present invention includes compounds of formula (I), supra, in which $R^4$ is a naphtyl group, which is unsubstituted or substituted with a fluorine atom or a tautomer, an N-oxide, or a salt thereof, or a salt of a tautomer, or a salt of an N-oxide, or a mixture of same.

In further embodiments the present invention includes compounds of formula (I), supra, in which $R^4$ is selected from 1-naphthyl group, a 4-chloro-3,5-dimethyl-phenyl-1-yl group, a 5,6,7,8-tetrahydronaphthalene-1-yl group, a 6-fluoro-naphthyl group, and a 6-chloro-naphthyl group.

In some embodiments, the present invention includes compounds of formula (I), supra, in which $R^4$ is a napht-1-yl group or a 6-fluoro-napht-1-yl group or a tautomer, an N-oxide, or a salt thereof, or a salt of a tautomer, or a salt of an N-oxide, or a mixture of same.

In some embodiments, the present invention includes compounds of formula (I), supra, in which $R^4$ is a napht-1-yl group or a tautomer, an N-oxide, or a salt thereof, or a salt of a tautomer, or a salt of an N-oxide, or a mixture of same.

In some embodiments, the present invention includes compounds of formula (I), supra, in which $R^4$ is a 6-fluoro-naphth-1-yl group or a tautomer, an N-oxide, or a salt thereof, or a salt of a tautomer, or a salt of an N-oxide, or a mixture of same.

In further embodiments the present invention includes compounds of formula (I), supra, in which $R^4$ is selected from a naphth-1-yl group, a 6-fluoro-naphthyl group and a 6-chloro-naphth-1-yl group In further embodiments the present invention includes compounds of formula (I), supra, in which $R^4$ is selected from a 1-naphthyl group, a 4-chloro-3,5-dimethyl-phenyl-1-yl group, and a 5,6,7,8-tetrahydronaphthalene-1-yl group, or a tautomer, an N-oxide, or a salt thereof, or a salt of a tautomer, or a salt of an N-oxide, or a mixture of same.

In further embodiments, the present invention includes compounds of formula (I), supra, in which $R^4$ is a halogen substituted naphthyl group, particularly 6-halo-naphthyl group, more particularly a 6-chloro-naphthyl group or a 6-fluoro-naphthyl group or a tautomer, an N-oxide, or a salt thereof, or a salt of a tautomer, or a salt of an N-oxide, or a mixture of same.

In further embodiments, the present invention includes compounds of formula (I), supra, in which $R^4$ is a halogen substituted naphthyl group, particularly 6-halo-naphthyl group, more particularly a 6-fluoro-naphthyl group or a tautomer, an N-oxide, or a salt thereof, or a salt of a tautomer, or a salt of an N-oxide, or a mixture of same.

In other embodiments, the present invention includes compounds of formula (I), supra, in which $R^4$ has one, two or three optional substituents.

In other embodiments, the present invention includes compounds of formula (I), supra, in which $R^4$ has one substituent.

In other embodiments, the present invention includes compounds of formula (I), supra, in which L is a group —$(CH_2)_m$-E- which is unsubstituted or substituted with one or two substituents and each substituent is independently selected from a halogen atom, a cyano group, a hydroxy group, a $C_1$-$C_3$-alkyl group, and a $C_1$-$C_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a —S(O)$_2$— group, and a —$NR^{14}$— group, or a tautomer, an N-oxide, or a salt thereof, or a salt of a tautomer, or a salt of an N-oxide, or a mixture of same.

In other embodiments, the present invention includes compounds of formula (I), supra, in which L is a group —$(CH_2)_m$-E- which is unsubstituted or substituted with one or two substituents and each substituent is independently selected from a halogen atom, a cyano group, a hydroxy group, a $C_1$-$C_3$-alkyl group, and a $C_1$-$C_3$-alkoxy group, or two substituents are optionally taken together with their intervening atoms to form a saturated or partially unsaturated 3-membered to 6-membered cycloalkyl ring, or a 3-membered to 8-membered saturated or partially unsaturated heterocyclic ring having 1-2 heteroatoms independently selected from an oxygen atom, a sulfur atom, a —S(O)— group, a —S(O)$_2$— group, and a —$NR^{14}$— group, or a tautomer, an N-oxide, or a salt thereof, or a salt of a tautomer, or a salt of an N-oxide, or a mixture of same.

In other embodiments, the present invention includes compounds of formula (I), supra, in which L is a —$(CH_2)_m$-E- group which is unsubstituted or substituted with a $C_1$-$C_3$-alkyl group or a tautomer, an N-oxide, or a salt thereof, or a salt of a tautomer, or a salt of an N-oxide, or a mixture of same.

In other embodiments, the present invention includes compounds of formula (I), supra, in which L is an unsubstituted group —$(CH_2)_m$-E- or a tautomer, an N-oxide, or a salt thereof, or a salt of a tautomer, or a salt of an N-oxide, or a mixture of same.

In further embodiments the present invention includes compounds of formula (I), supra, in which E is an oxygen atom and constitutes the connecting element to $R^4$, or a tautomer, an N-oxide, or a salt thereof, or a salt of a tautomer, or a salt of an N-oxide, or a mixture of same.

In other embodiments, the present invention includes compounds of formula (I), supra, in which L is an unsubstituted group —$(CH_2)_m$-E- and E is an oxygen atom or a tautomer, an N-oxide, or a salt thereof, or a salt of a tautomer, or a salt of an N-oxide, or a mixture of same.

In other embodiments, the present invention includes compounds of formula (I), supra, in which L-$R^4$ is an unsubstituted group —$(CH_2)_m$-E-$R^4$ in which m is 3, E is an oxygen atom and $R^4$ is a halogen substituted naphthyl group or a tautomer, an N-oxide, or a salt thereof, or a salt of a tautomer, or a salt of an N-oxide, or a mixture of same.

In other embodiments, the present invention includes compounds of formula (I), supra, in which L-$R^4$ is an unsubstituted group —$(CH_2)_m$-E-$R^4$ in which m is 3, E is an oxygen atom and $R^4$ is a fluorine substituted naphthyl group or a tautomer, an N-oxide, or a salt thereof, or a salt of a tautomer, or a salt of an N-oxide, or a mixture of same.

In other embodiments, the present invention includes compounds of formula (I), supra, in which L-$R^4$ is an unsubstituted group —$(CH_2)_m$-E-$R^4$ in which m is 3, E is an oxygen atom and $R^4$ is 6-fluoro-naphthyl group or a tautomer, an N-oxide, or a salt thereof, or a salt of a tautomer, or a salt of an N-oxide, or a mixture of same.

In yet further embodiments, the present invention includes compounds of formula (I), supra, in which $R^5$ is a COOH group, a

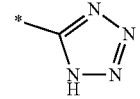

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$($CH_2$)$_s$NHCO($C_1$-$C_6$-alkyl) group, a —C(O)—NHS(O)$_2$($CH_2$)$_s$NHCO($C_3$-$C_6$-cycloalkyl) group, and a —C(O)—NHS(O)$_2$($CH_2$)$_s$NHCO(aryl) group; and s is 0, 1, 2, or 3; or a tautomer, an N-oxide, or a salt thereof, or a salt of a tautomer, or a salt of an N-oxide, or a mixture of same.

In yet further embodiments, the present invention includes compounds of formula (I), supra, in which $R^5$ is a COOH group, a

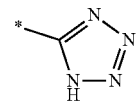

group, a —C(O)—NHS(O)$_2$($C_1$-$C_6$-alkyl) group, a —C(O)—NHS(O)$_2$($C_3$-$C_6$-cycloalkyl) group, a —C(O)—

NHS(O)$_2$(aryl) group, a —C(O)—NHS(O)$_2$(CH$_2$)$_s$NHCO (C$_1$-C$_6$-alkyl) group, a —C(O)—NHS(O)$_2$(CH$_2$)$_s$NHCO (C$_3$-C$_6$-cycloalkyl) group, and a —C(O)—NHS(O)$_2$(CH$_2$)$_s$NHCO(aryl) group and s is 0, 1, 2, or 3, or a tautomer, an N-oxide, or a salt thereof, or a salt of a tautomer, or a salt of an N-oxide, or a mixture of same.

In further embodiments, the present invention includes compounds of formula (I), supra, in which R$^5$ is a COOH group, or a

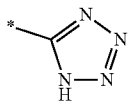

group, or a tautomer, an N-oxide, or a salt thereof, or a salt of a tautomer, or a salt of an N-oxide, or a mixture of same.

In further embodiments, the present invention includes compounds of formula (I), supra, in which R$^5$ is a COOH group, or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from $^\#$—(CH$_2$)$_n$—(B)$_t$—(CH$_2$)$_p$—X—$^{\#\#}$, $^\#$—(C$_2$-C$_6$-alkenylene)-(B)$_t$—(CH$_2$)$_p$—X—$^{\#\#}$, $^\#$—(CH$_2$)$_n$—(B)$_t$-(C$_2$-C$_5$-alkenylene)-X—$^{\#\#}$, and $^\#$—(CH$_2$)$_q$—(B)—(CH$_2$)$_r$—(B)—(CH$_2$)$_v$—X—$^{\#\#}$, wherein $^\#$ is the point of attachment with the indole nitrogen atom and $^{\#\#}$ is the point of attachment with the pyrazole carbon atom bearing the R$^7$ substituent; and wherein one or more —CH$_2$— groups may be unsubstituted or substituted with one or more substituents independently selected from a halogen atom, a hydroxy group, a NR$^{16}$R$^{17}$ group, a C$_1$-C$_3$-alkyl group, a C$_1$-C$_3$-haloalkyl group, a C$_1$-C$_3$-alkoxy group, a C$_1$-C$_3$-haloalkoxy group, a C$_3$-C$_6$-cycloalkyl group, and a (heterocycloalkyl)-(C$_1$-C$_3$-alkylene)- group, and wherein optionally, if two such substituents are bound to the same atom, they may form together a 3- to 6-membered spiro ring, and wherein a —CH═CH— group in any alkenylene can be replaced by a 1,2-(C$_3$-C$_5$)cycloalkylene group which is unsubstituted or substituted one or two times with a halogen atom or a C$_1$-C$_2$-alkyl group; or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from $^\#$—(CH$_2$)$_n$—(B)$_t$—(CH$_2$)$_p$—X—$^{\#\#}$, $^\#$—(C$_2$-C$_6$-alkenylene)-(B)$_t$—(CH$_2$)$_p$—X—$^{\#\#}$, $^\#$—(CH$_2$)$_n$—(B)$_t$-(C$_2$-C$_5$-alkenylene)-X—$^{\#\#}$, and $^\#$—(CH$_2$)$_q$—(B)—(CH$_2$)$_r$—(B)—(CH$_2$)$_v$—X—$^{\#\#}$, wherein $^\#$ is the point of attachment with the indole nitrogen atom and $^{\#\#}$ is the point of attachment with the pyrazole carbon atom bearing the R$^7$ substituent; and wherein one or more —CH$_2$— groups may be unsubstituted or substituted with one or more substituents independently selected from a halogen atom, a hydroxy group, a NR$^{16}$R$^{17}$ group, a C$_1$-C$_3$-alkyl group, a C$_1$-C$_3$-haloalkyl group, a C$_1$-C$_3$-alkoxy group, a C$_1$-C$_3$-haloalkoxy group, and wherein optionally if two such substituents are bound to the same atom they may form together a 3- to 6-membered spiro ring, and wherein a —CH═CH— group in any alkenylene can be replaced by a 1,2-(C$_3$-C$_5$)cycloalkylene group which is unsubstituted or substituted one or two times with a halogen atom or a C$_1$-C$_2$-alkyl group, or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from $^\#$—(CH$_2$)$_n$—(B)$_t$—(CH$_2$)$_p$—X—$^{\#\#}$ and $^\#$—(C$_2$-C$_6$-alkenylene)-(B)$_t$—(CH$_2$)$_p$—X—$^{\#\#}$, and wherein a double bond in any alkenylene can be replaced by an unsubstituted a 1,2-(C$_3$-C$_5$-cycloalkyl) group, wherein $^\#$ is the point of attachment with the indole nitrogen atom and $^{\#\#}$ is the point of attachment with the pyrazole carbon atom bearing the R$^7$ substituent; and wherein one or more —CH$_2$— groups may be unsubstituted or substituted with one or more substituents independently selected from a halogen atom, a hydroxy group, a NR$^{16}$R$^{17}$ group, a C$_1$-C$_3$-alkyl group, a C$_1$-C$_3$-haloalkyl group, and a C$_1$-C$_3$-alkoxy group, and wherein optionally if two such substituents are bound to the same atom they may form together a 3-membered to 6-membered spiro ring wherein a —CH═CH— group in any alkenylene can be replaced by a 1,2-(C$_3$-C$_5$)cycloalkylene group which is unsubstituted or substituted one or two times with a halogen atom or a C$_1$-C$_2$-alkyl group, or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from $^\#$—(CH$_2$)$_n$—(B)$_t$—(CH$_2$)$_p$—X—$^{\#\#}$, $^\#$—(C$_2$-C$_6$-alkenylene)-(B)$_t$—(CH$_2$)$_p$—X—$^{\#\#}$, and wherein $^\#$ is the point of attachment with the indole nitrogen atom and $^{\#\#}$ is the point of attachment with the pyrazole carbon atom bearing the R$^7$ substituent and wherein one or more —CH$_2$— groups may be unsubstituted or substituted with one or more substituents independently selected from a halogen atom, a hydroxy group, a NR$^{16}$R$^{17}$ group, a C$_1$-C$_3$-alkyl group, a C$_1$-C$_3$-haloalkyl group, and a C$_1$-C$_3$-alkoxy group, and and wherein optionally if two such substituents are bound to the same atom they may form together a 3-membered to 6-membered spiro ring, and wherein a —CH═CH— group in any alkenylene can be replaced by a 1,2-(C$_3$-C$_5$)cycloalkylene group or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from $^\#$—(CH$_2$)$_n$—(B)$_t$—(CH$_2$)$_p$—X—$^{\#\#}$, $^\#$—(C$_2$-C$_6$-alkenylene)-(B)$_t$—(CH$_2$)$_p$—X—$^{\#\#}$, and wherein $^\#$ is the point of attachment with the indole nitrogen atom and $^{\#\#}$ is the point of attachment with the pyrazole carbon atom bearing the R$^7$ substituent and wherein one or more —CH$_2$— groups may be unsubstituted or substituted with one or more halogen atoms or a hydroxy group, and wherein a —CH═CH— group in any alkenylene can be replaced by a

group or a

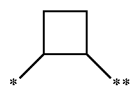

group wherein * is the point of attachment of the ring to the adjacent —CH$_2$— group or to the indole nitrogen atom and ** is the point of attachment to the adjacent —CH$_2$— group or to —(B)$_t$— and wherein optionally if two such substituents are bound to the same atom they may form together a 3-membered to 6-membered spiro ring, or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from $^{\#}$—(CH$_2$)$_n$—(B)$_t$—(CH$_2$)$_p$—X—$^{\#\#}$, $^{\#}$—(C$_2$-C$_6$-alkenylene)-(B)$_t$—(CH$_2$)$_p$—X—$^{\#\#}$, $^{\#}$—(CH$_2$)$_n$—(B)$_t$—(C$_2$-C$_5$-alkenylene)-X—$^{\#\#}$, and $^{\#}$—(CH$_2$)$_q$—(B)—(CH$_2$)$_r$—(B)—(CH$_2$)$_v$—X—$^{\#\#}$, wherein $^{\#}$ is the point of attachment with the indole nitrogen atom and $^{\#\#}$ is the point of attachment with the pyrazole carbon atom bearing the R$^7$ substituent; and wherein one or more —CH$_2$— groups may be unsubstituted or substituted with one or more substituents independently selected from a halogen atom, a hydroxy group, a NR$^{16}$R$^{17}$ group, a C$_1$-C$_3$-alkyl group, a C$_1$-C$_3$-haloalkyl group, a C$_1$-C$_3$-alkoxy group, a C$_1$-C$_3$-haloalkoxy group, a C$_3$-C$_6$-cycloalkyl group, and a (heterocycloalkyl)-(C$_1$-C$_3$-alkylene)- group, and wherein a —CH=CH— group in any alkenylene can be replaced by a 1,2-(C$_3$-C$_6$)cycloalkylene group which is unsubstituted or substituted one or two times with a halogen atom or a C$_1$-C$_2$-alkyl group; and wherein X is an unsubstituted —CH$_2$— group;

or a tautomer, an N-oxide, or a salt thereof, or a salt of a tautomer, or a salt of an N-oxide, or a mixture of same.

In further embodiments, the present invention includes compounds of formula (I), supra, in which —R$^6$-R$^7$— is selected from $^{\#}$—(CH$_2$)$_n$—(B)$_t$—(CH$_2$)$_p$—X—$^{\#\#}$, $^{\#}$—(C$_2$-C$_6$-alkenylene)-(B)$_t$—(CH$_2$)$_p$—X—$^{\#\#}$, $^{\#}$—(CH$_2$)$_n$—(B)$_t$—(C$_2$-C$_5$-alkenylene)-X—$^{\#\#}$, and $^{\#}$—(CH$_2$)$_q$—(B)—(CH$_2$)$_r$—(B)—(CH$_2$)$_v$—X—$^{\#\#}$, wherein $^{\#}$ is the point of attachment with the indole nitrogen atom and $^{\#\#}$ is the point of attachment with the pyrazole carbon atom bearing the R$^7$ substituent; and wherein one or more —CH$_2$— groups may be unsubstituted or substituted with one or more substituents independently selected from a halogen atom, a hydroxy group, a NR$^{16}$R$^{17}$ group, a C$_1$-C$_3$-alkyl group, a C$_1$-C$_3$-haloalkyl group, a C$_1$-C$_3$-alkoxy group, and a C$_1$-C$_3$-haloalkoxy group, and wherein a —CH=CH— group in any alkenylene can be replaced by a 1,2-(C$_3$-C$_6$)cycloalkylene group which is unsubstituted or substituted one or two times with a halogen atom or a C$_1$-C$_2$-alkyl group, and wherein X is an unsubstituted —CH$_2$— group;

or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from $^{\#}$—(CH$_2$)$_n$—(B)$_t$—(CH$_2$)$_p$—X—$^{\#\#}$, $^{\#}$—(C$_2$-C$_6$-alkenylene)-(B)$_t$—(CH$_2$)$_p$—X—$^{\#\#}$, and wherein a double bond in any alkenylene can be replaced by an unsubstituted a 1,2-(C$_3$-C$_5$-cycloalkyl) group, and wherein $^{\#}$ is the point of attachment with the indole nitrogen atom and $^{\#\#}$ is the point of attachment with the pyrazole carbon atom bearing the R$^7$ substituent; and wherein one or more —CH$_2$— groups may be unsubstituted or substituted with one or more substituents independently selected from a halogen atom, a hydroxy group, a NR$^{16}$R$^{17}$ group, a C$_1$-C$_3$-alkyl group, a C$_1$-C$_3$-haloalkyl group, and a C$_1$-C$_3$-alkoxy group, and wherein a —CH=CH— group in any alkenylene can be replaced by a 1,2-(C$_3$-C$_6$)cycloalkylene group which is unsubstituted or substituted one or two times with a halogen atom or a C$_1$-C$_2$-alkyl group, and wherein X is an unsubstituted —CH$_2$— group;

or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from CH$_2$)$_n$—(B)$_t$—(CH$_2$)$_p$—X—$^{\#\#}$, $^{\#}$—(C$_2$-C$_6$-alkenylene)-(B)$_t$—(CH$_2$)$_p$—X—$^{\#\#}$, and wherein $^{\#}$ is the point of attachment with the indole nitrogen atom and $^{\#\#}$ is the point of attachment with the pyrazole carbon atom bearing the R$^7$ substituent and wherein one or more —CH$_2$— groups may be unsubstituted or substituted with one or more substituents independently selected from a halogen atom, a hydroxy group, a NR$^{16}$R$^{17}$ group, a C$_1$-C$_3$-alkyl group, a C$_1$-C$_3$-haloalkyl group, and a C$_1$-C$_3$-alkoxy group, and wherein a —CH=CH— group in any alkenylene can be replaced by a 1,2-cyclopropylene group or a 1,2-cyclobutylene group and wherein X is an unsubstituted —CH$_2$— group;

or a tautomer or a salt thereof or a salt of a tautomer or a mixture of same.

In other embodiments, the present invention includes compounds of formula (I), supra, in which —R$^6$-R$^7$— is selected from $^{\#}$—(CH$_2$)$_n$—(B)$_t$—(CH$_2$)$_p$—X—$^{\#\#}$ and $^{\#}$—(C$_2$-C$_6$-alkenylene)-(B)$_t$—(CH$_2$)$_p$—X—$^{\#\#}$, and wherein $^{\#}$ is the point of attachment with the indole nitrogen atom and $^{\#\#}$ is the point of attachment with the pyrazole carbon atom bearing the R$^7$ substituent and wherein one or more —CH$_2$— groups may be unsubstituted or substituted with one or more a halogen atoms, and wherein a —CH=CH— group in any alkenylene can be replaced by a 1,2-cyclopropylene group or a 1,2-cyclobutylene group and wherein X is an unsubstituted —CH$_2$— group;

or a tautomer or a salt thereof or a salt of a tautomer or a mixture of same.

In other embodiments, the present invention includes compounds of formula (I), supra, in which —R$^6$-R$^7$— is selected from $^{\#}$—(CH$_2$)$_n$—(B)$_t$—(CH$_2$)$_p$—X—$^{\#\#}$ and $^{\#}$—(C$_2$-C$_6$-alkenylene)-(B)$_t$—(CH$_2$)$_p$—X—$^{\#\#}$, and wherein $^{\#}$ is the point of attachment with the indole nitrogen atom and $^{\#\#}$ is the point of attachment with the pyrazole carbon atom bearing the R$^7$ substituent and wherein one or more —CH$_2$— groups may be unsubstituted or substituted with one or more a halogen atoms, and wherein a —CH=CH— group in any alkenylene can be replaced by the groups

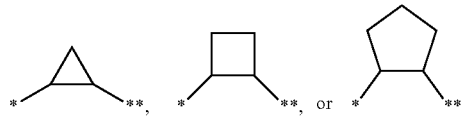

and wherein X is an unsubstituted —CH$_2$— group;

or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from $^{\#}$—(CH$_2$)$_n$—(B)$_t$—(CH$_2$)$_p$—X—$^{\#\#}$ and $^{\#}$—(C$_2$-C$_6$-alkenylene)-(B)$_t$—(CH$_2$)$_p$—X—$^{\#\#}$, wherein $^{\#}$ is the point of attachment with the indole nitrogen atom and $^{\#\#}$ is the point of attachment with the pyrazole carbon atom bearing the $R^7$ substituent, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^\#$—$(CH_2)_n$—$(B)_t$—$(CH_2)_p$—X—$^{\#\#}$, wherein $^\#$ is the point of attachment with the indole nitrogen atom and * is the point of attachment with the pyrazole carbon atom bearing the $R^7$ substituent, and A is A1 or A2, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^\#$—$(CH_2)_n$—$(B)_t$—$(CH_2)_p$—X—$^{\#\#}$, wherein $^\#$ is the point of attachment with the indole nitrogen atom and $^{\#\#}$ is the point of attachment with the pyrazole carbon atom bearing the $R^7$ substituent, and A is A1 or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^\#$—$(CH_2)_n$—$(B)_t$—$(CH_2)_p$—X—$^{\#\#}$, wherein $^\#$ is the point of attachment with the indole nitrogen atom and $^{\#\#}$ is the point of attachment with the pyrazole carbon atom bearing the $R^7$ substituent, and A is A2, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^\#$—$(C_2$-$C_6$-alkenylene)-$(B)_t$—$(CH_2)_p$—X—$^{\#\#}$, wherein $^\#$ is the point of attachment with the indole nitrogen atom and $^{\#\#}$ is the point of attachment with the pyrazole carbon atom bearing the $R^7$ substituent, and A is A1 or A2, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^\#$—$(C_2$-$C_6$-alkenylene)-$(B)_t$—$(CH_2)_p$—X—$^{\#\#}$, wherein $^\#$ is the point of attachment with the indole nitrogen atom and $^{\#\#}$ is the point of attachment with the pyrazole carbon atom bearing the $R^7$ substituent, and A is A1, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^\#$—$(C_2$-$C_6$-alkenylene)-$(B)_t$—$(CH_2)_p$—X—$^{\#\#}$, wherein $^\#$ is the point of attachment with the indole nitrogen atom and $^{\#\#}$ is the point of attachment with the pyrazole carbon atom bearing the $R^7$ substituent, and A is A2, or a tautomer, an N-oxide, or a salt thereof, or a salt of a tautomer, or a salt of an N-oxide, or a mixture of same.

In other embodiments, the present invention includes compounds of formula (I), supra, in which $R^6$-$R^7$— is selected from $^\#$—$(CH_2)_n$—$(B)_t$—$(CH_2)_p$—X—$^{\#\#}$, and wherein $^\#$ is the point of attachment with the indole nitrogen atom and $^{\#\#}$ is the point of attachment with the pyrazole carbon atom bearing the $R^7$ substituent and wherein one or more —$CH_2$— groups may be unsubstituted or substituted with one or more fluorine atoms or a hydroxy group, wherein X is an unsubstituted —$CH_2$— group or a tautomer, an N-oxide, or a salt thereof, or a salt of a tautomer, or a salt of an N-oxide, or a mixture of same.

In other embodiments, the present invention includes compounds of formula (I), supra, in which $R^6$-$R^7$— is selected from $^\#$—$(CH_2)_n$—$(B)_t$—$(CH_2)_p$—X—$^{\#\#}$, and wherein $^\#$ is the point of attachment with the indole nitrogen atom and $^{\#\#}$ is the point of attachment with the pyrazole carbon atom bearing the $R^7$ substituent and wherein one or more —$CH_2$— groups may be unsubstituted or substituted with one or more fluorine atoms, wherein X is an unsubstituted —$CH_2$— group or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is selected from $^\#$—$(CH_2)_3$—$N(CH_3)$—$CH_2$—$^{\#\#}$, $^\#$—$(CH_2)_3$—NH—$CH_2$—$^{\#\#}$, $^\#$—$(CH_2)_4$—$N(CH_3)$—$CH_2$—$^{\#\#}$, $^\#$—$(CH_2)_4$—NH—$CH_2$—$^{\#\#}$, $^\#$—$(CH_2)_4$—$N(CH_2CF_3)$—$CH_2$—$^{\#\#}$, $^\#$—$(CH_2)_4$—$N(CH_2CHF_2)$—$CH_2$—$^{\#\#}$, $^\#$—$(CH_2)_4$—$N[(CH_2)_2$—O—$CH_3]$—$CH_2$—$^{\#\#}$, $^\#$—$(CH_2)_4$—$N[C(O)$—O—$(CH_2)_2$—O—$CH_3]$—$CH_2$—$^{\#\#}$, $^\#$—$(CH_2)_4$—$N[C(O)$—O—$(CH_2)_2$-(oxetan-4-yl)]-$CH_2$—$^{\#\#}$, $^\#$—$(CH_2)_4$—$N[(CH_2)_2$-(oxetan-4-yl)]-$CH_2$—$^{\#\#}$, $^\#$—$(CH_2)_4$—$N[(CH_2)_2$—(N-morpholinyl)]-$CH_2$—$^{\#\#}$, $^\#$—$(CH_2)_2$—$N(CH_2CHF_2)$—$(CH_2)_3$—$^{\#\#}$, $^\#$—$(CH_2)_2$—$N[(CH_2)_2CHF_2]$—$(CH_2)_3$—$^{\#\#}$, $^\#$—$(CH_2)_2$—$N[(CH_2)_4$—O—$C(O)$—$CH_3]$—$(CH_2)_3$—$^{\#\#}$, $^\#$—$(CH_2)_2$—$N[(CH_2)_4$—OH]—$(CH_2)_3$—$^{\#\#}$, $^\#$—$(CH_2)_4$—$N[(CH_2)_2$—$C(CH_3)_2$OH]—$CH_2$—$^{\#\#}$, $^\#$—$(CH_2)_4$—$N[(CH_2)_3$—OH]—$CH_2$—$^{\#\#}$, $^\#$—$(CH_2)_4O$—$CH_2$—$^{\#\#}$, $^\#$—$(CH_2)_2O$—$CH_2$—$^{\#\#}$, $^\#$—$(CH_2)_2$—O—$(CH_2)_3$—$^{\#\#}$, $^\#$—$(CH_2)_6$—$^{\#\#}$, $^\#$—$(CH_2)_2$—$CF_2$—$CH_2$—O—$CH_2$—$^{\#\#}$, $^\#$—$CH_2$—$CF_2$—$(CH_2)_2O$—$CH_2$—$^{\#\#}$, $^\#$—$CH_2$—$CF_2$—$CF_2$—$CH_2$—O—$CH_2$—$^{\#\#}$, $^\#$—$(CH_2)_2$—$CF_2$—$CH_2$—$N(CH_3)$—$CH_2$—$^{\#\#}$, $^\#$—$CH_2$—$CF_2$—$(CH_2)_2$—$N(CH_3)$—$CH_2$—$^{\#\#}$, $^\#$—$(CH_2)_2CH(OH)$—$CH_2$—O—$CH_2$—$^{\#\#}$, $^\#$—$CH_2$—CH=CH—$CH_2O$—$CH_2$—$^{\#\#}$, $^\#$—$CH_2$—CH=CH—$CH_2$—$N(CH_3)$—$CH_2$—$^{\#\#}$,

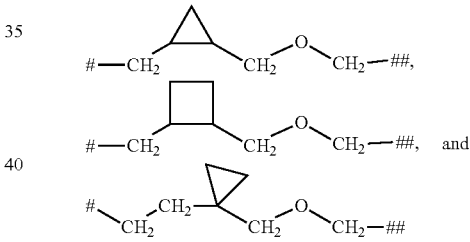

and wherein $^\#$ is the point of attachment with the indole nitrogen atom and $^{\#\#}$ is the point of attachment with the pyrazole carbon atom bearing the $R^7$ substituent or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is selected from $^\#$—$(CH_2)_3$—$N(CH_3)$—$CH_2$—$^{\#\#}$, $^\#$—$(CH_2)_3$—NH—$CH_2$—$^{\#\#}$, $^\#$—$(CH_2)_4$—$N(CH_3)$—$CH_2$—$^{\#\#}$, $^\#$—$(CH_2)_4$—NH—$CH_2$—$^{\#\#}$, $^\#$—$(CH_2)_4$—$N(CH_2CF_3)$—$CH_2$—$^{\#\#}$, $^\#$—$(CH_2)_4$—$N(CH_2CHF_2)$—$CH_2$—$^{\#\#}$, $^\#$—$(CH_2)_4$—$N[(CH_2)_2$-(oxetan-4-yl)]-$CH_2$—$^{\#\#}$, $^\#$—$(CH_2)_4$—$N[(CH_2)_2$—(N-morpholinyl)]-$CH_2$—$^{\#\#}$, $^\#$—$(CH_2)_2$—$N(CH_2CHF_2)$—$(CH_2)_3$—$^{\#\#}$, $^\#$—$(CH_2)_2$—$N[(CH_2)_2CHF_2]$—$(CH_2)_3$—$^{\#\#}$, $^\#$—$(CH_2)_2$—$N[(CH_2)_4$—O—$C(O)$—$CH_3]$—$(CH_2)_3$—$^{\#\#}$, $^\#$—$(CH_2)_4$—$N[(CH_2)_2$—$C(CH_3)_2OH]$—$CH_2$—$^{\#\#}$, $^\#$—$(CH_2)_2$—$N[(CH_2)_4$—OH]—$(CH_2)_3$—$^{\#\#}$, $^\#$—$(CH_2)_4$—$N[(CH_2)_3$—OH]—$CH_2$—$^{\#\#}$, $^\#$—$(CH_2)_2$—$CF_2$—$CH_2$—$N(CH_3)$—$CH_2$—$^{\#\#}$, and $^\#$—$CH_2$—$CF_2$—$(CH_2)_2$—$N(CH_3)$—$CH_2$—$^{\#\#}$, and wherein $^\#$ is the point of attachment with the indole nitrogen atom and $^{\#\#}$ is the point of attachment with the pyrazole carbon atom bearing the $R^7$ substituent or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is selected from #—$(CH_2)_4$O—$CH_2$—##, #—$(CH_2)_2$O—$CH_2$—##, #—$(CH_2)_2$—O—$(CH_2)_3$—##, #—$(CH_2)_2$—$CF_2$—$CH_2$—O—$CH_2$—##, #—$CH_2$—$CF_2$—$CF_2$—$CH_2$—O—$CH_2$—##, #—$(CH_2)_2$CH(OH)—$CH_2$—O—$CH_2$—##, #—$CH_2$CH=CH—$CH_2$O$CH_2$—##, #—$CH_2$—CH=CH—$CH_2$—N($CH_3$)—$CH_2$—##,

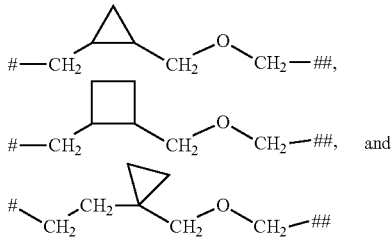

and wherein # is the point of attachment with the indole nitrogen atom and ## is the point of attachment with the pyrazole carbon atom bearing the $R^7$ substituent or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is #—$(CH_2-)_6$##, and wherein # is the point of attachment with the indole nitrogen atom and ## is the point of attachment with the pyrazole carbon atom bearing the $R^7$ substituent or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is selected from #—$(CH_2)_3$—N($CH_3$)—$CH_2$—##, #—$(CH_2)_3$—NH—$CH_2$—##, #—$(CH_2)_4$—N($CH_3$)—$CH_2$—##, #—$(CH_2)_4$—N($CH_2CF_3$)—$CH_2$—##, #—$(CH_2)_4$—N($CH_2CHF_2$)—$CH_2$—##, #—$CH_2$—CH=CH—$CH_2$—O—$CH_2$—##, #—$CH_2$—CH=CH—$CH_2$—N($CH_3$)—$CH_2$—##, #—$(CH_2)_4$O—$CH_2$—##, #—$(CH_2-)_6$##, #—$(CH_2)_2$—$CF_2$—$CH_2$—O—$CH_2$—##, #—$CH_2$—$CF_2$—$(CH_2)_2$O—$CH_2$—##, #—$CH_2$—$CF_2$—$CF_2$—$CH_2$—O—$CH_2$—##,

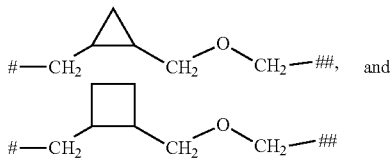

or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is selected from #—$(CH_2)_3$—N($CH_3$)—$CH_2$—##, #—$(CH_2)_3$—NH—$CH_2$—##, #—$(CH_2)_4$—N($CH_3$)—$CH_2$—##, #—$(CH_2)_4$—NH—$CH_2$—##, #—$(CH_2)_4$—N($CH_2CF_3$)—$CH_2$—##, #—$(CH_2)_4$—N($CH_2CHF_2$)—$CH_2$—##, #—$(CH_2)_4$—N($CH_2)_2$O—$CH_3$)—$CH_2$—##, #—$(CH_2)_4$—N[C(O)—O—$(CH_2)_2$O—$CH_3$]—$CH_2$—##, #—$(CH_2)_4$—N[C(O)—O—$(CH_2)_2$-(oxetan-4-yl)]-$CH_2$—##, #—$(CH_2)_4$—N[$(CH_2)_2$-(oxetan-4-yl)]-$CH_2$—##, #—$(CH_2)_4$—N[$(CH_2)_2$-(N-morpholinyl)]-$CH_2$—##, #—$(CH_2)_2$—N($CH_2CHF_2$)—$(CH_2)_3$—##, #—$(CH_2)_2$—N[$(CH_2)_2CHF_2$]—$(CH_2)_3$—##, #—$(CH_2)_2$—N[$(CH_2)_4$—O—C(O)—$CH_3$]—$(CH_2)_3$—##, #—$(CH_2)_4$—N[$(CH_2)_2$—C($CH_3)_2$OH]—$CH_2$—##, #—$(CH_2)_2$—N[$(CH_2)_4$—OH]—$(CH_2)_3$—##, #—$(CH_2)_4$—N[$(CH_2)_3$—OH]—$CH_2$—##, #—$(CH_2)_4$O—$CH_2$—##, #—$(CH_2)_2$O—$CH_2$—##, #—$(CH_2)_2$—O—$(CH_2)_3$—##, #—$(CH_2-)_6$##, #—$CH_2$—CH=CH—$CH_2$—O—$CH_2$—##, #—$CH_2$—CH=CH—$CH_2$—N($CH_3$)—$CH_2$—##,

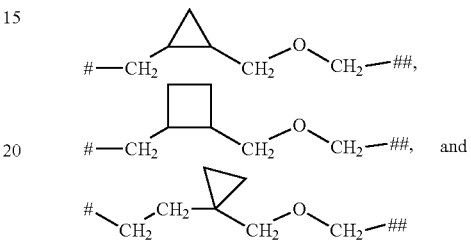

and wherein # is the point of attachment with the indole nitrogen atom and ## is the point of attachment with the pyrazole carbon atom bearing the $R^7$ substituent or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is selected from #—$(CH_2)_3$—N($CH_3$)—$CH_2$—##, #—$(CH_2)_3$—NH—$CH_2$—##, #—$(CH_2)_4$—N($CH_3$)—$CH_2$—##, #—$(CH_2)_4$—N($CH_2CF_3$)—$CH_2$—##, #—$(CH_2)_4$—N($CH_2CHF_2$)—$CH_2$—##, #—$CH_2$—CH=CH—$CH_2$—O—$CH_2$—##, #—$CH_2$—CH=CH—$CH_2$—N($CH_3$)—$CH_2$—##, #—$(CH_2)_4$O—$CH_2$—##, #—$(CH_2-)_6$##, #—$(CH_2)_2$—$CF_2$—$CH_2$—O—$CH_2$—##,

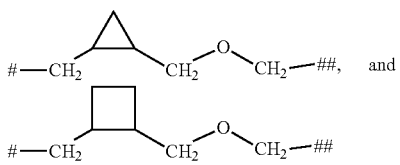

or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is selected from #—$(CH_2)_3$—N($CH_3$)—$CH_2$—##, #—$(CH_2)_3$—NH—$CH_2$—##, #—$(CH_2)_4$—N($CH_3$)—$CH_2$—##, #—$(CH_2)_4$—NH—$CH_2$—#, —$(CH_2)_4$—N($CH_2CF_3$)—$CH_2$—##, #—$(CH_2)_4$—N($CH_2CHF_2$)—$CH_2$—##, #—$(CH_2)_4$—N($CH_2)_2$O—$CH_3$)—$CH_2$—##, #—$(CH_2)_4$—N[C(O)—O—$(CH_2)_2$O—$CH_3$]—$CH_2$—##, #—$(CH_2)_4$—N[C(O)—O—$(CH_2)_2$-(oxetan-4-yl)]-$CH_2$—##, #—$(CH_2)_4$—N[$(CH_2)_2$-(oxetan-4-yl)]-$CH_2$—##, #—$(CH_2)_4$—N[$(CH_2)_2$-(N-morpholinyl)]-$CH_2$—##, #—$(CH_2)_2$—N($CH_2CHF_2$)—$(CH_2)_3$—##, #—$(CH_2)_2$—N[$(CH_2)_2CHF_2$]—$(CH_2)_3$—##, #—$(CH_2)_2$—N[$(CH_2)_4$—O—C(O)—$CH_3$]—$(CH_2)_3$—##, #—$(CH_2)_4$—N[$(CH_2)_2$—C($CH_3)_2$OH]—$CH_2$—##, #—$(CH_2)_2$—N[$(CH_2)_4$—OH]—$(CH_2)_3$—##, #—$(CH_2)_4$—N[$(CH_2)_3$—OH]—$CH_2$—##, #—$(CH_2)_4$O—$CH_2$—##, #—$(CH_2)_2$O—$CH_2$—##,

—(CH$_2$)$_2$—O—(CH$_2$)$_3$—##, #—(CH$_2$—)$_6$##, #—(CH$_2$)$_2$—CF$_2$—CH$_2$—O—CH$_2$—##, #—CH$_2$—CF$_2$—(CH$_2$)$_2$O—CH$_2$—##, #—CH$_2$—CF$_2$—CF$_2$—CH$_2$—O—CH$_2$—##, #—(CH$_2$)$_2$—CF$_2$—CH$_2$—N(CH$_3$)—CH$_2$—##, #—CH$_2$—CF$_2$—(CH$_2$)$_2$—N(CH$_3$)—CH$_2$—##, #—(CH$_2$)$_2$CH(OH)—CH$_2$—O—CH$_2$—##,

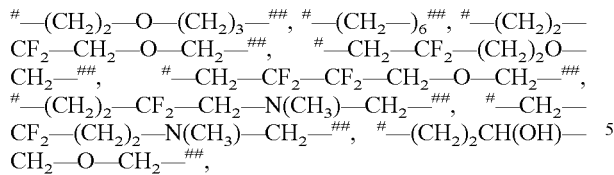

and wherein # is the point of attachment with the indole nitrogen atom and ## is the point of attachment with the pyrazole carbon atom bearing the R$^7$ substituent or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from #—(CH$_2$)$_3$—N(CH$_3$)—CH$_2$—##, #—(CH$_2$)$_3$—NH—CH$_2$—##, #—(CH$_2$)$_4$—N(CH$_3$)—CH$_2$—##, #—(CH$_2$)$_4$—NH—CH$_2$—##, #—(CH$_2$)$_4$—N(CH$_2$CF$_3$)—CH$_2$—##, #—(CH$_2$)$_4$—N(CH$_2$CHF$_2$)—CH$_2$—##, #—(CH$_2$)$_4$—N(CH$_2$)$_2$O—CH$_3$)—CH$_2$—##, #—(CH$_2$)$_4$—N[C(O)—O—(CH$_2$)$_2$O—CH$_3$]—CH$_2$—##, #—(CH$_2$)$_4$—N[C(O)—O—(CH$_2$)$_2$-(oxetan-4-yl)]-CH$_2$—##, #—(CH$_2$)$_4$—N[(CH$_2$)$_2$-(oxetan-4-yl)]-CH$_2$—##, #—(CH$_2$)$_4$—N[(CH$_2$)$_2$—(N-morpholinyl)]-CH$_2$—##, #—(CH$_2$)$_2$—N(CH$_2$CHF$_2$)—(CH$_2$)$_3$—##, #—(CH$_2$)$_2$—N[(CH$_2$)$_2$CHF$_2$]—(CH$_2$)$_3$—##, #—(CH$_2$)$_2$—N[(CH$_2$)$_4$—O—C(O)—CH$_3$]—(CH$_2$)$_3$—##, #—(CH$_2$)$_4$—N[(CH$_2$)$_2$—C(CH$_3$)$_2$OH]—CH$_2$—##, #—(CH$_2$)$_2$—N[(CH$_2$)$_4$—OH]—(CH$_2$)$_3$—##, #—(CH$_2$)$_4$—N[(CH$_2$)$_3$—OH]—CH$_2$—##, #—(CH$_2$)$_4$O—CH$_2$—##, #—(CH$_2$)$_2$O—CH$_2$—##, #—(CH$_2$)$_2$—O—(CH$_2$)$_3$—##, #—(CH$_2$—)$_6$##, #—(CH$_2$)$_2$—CF$_2$—CH$_2$—O—CH$_2$—##, #—CH$_2$—CF$_2$—(CH$_2$)$_2$O—CH$_2$—##, #—CH$_2$—CF$_2$—CF$_2$—CH$_2$—O—CH$_2$—##, #—(CH$_2$)$_2$—CF$_2$—CH$_2$—N(CH$_3$)—CH$_2$—##, #—CH$_2$—CF$_2$—(CH$_2$)$_2$—N(CH$_3$)—CH$_2$—##, and #—(CH$_2$)$_2$CH(OH)—CH$_2$—O—CH$_2$—##, and wherein # is the point of attachment with the indole nitrogen atom and ## is the point of attachment with the pyrazole carbon atom bearing the R$^7$ substituent or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from #—(CH$_2$)$_3$—N(CH$_3$)—CH$_2$—##, #—(CH$_2$)$_3$—NH—CH$_2$—##, #—(CH$_2$)$_4$—N(CH$_3$)—CH$_2$—##, #—(CH$_2$)$_4$—N(CH$_2$CF$_3$)—CH$_2$—##, #—(CH$_2$)$_4$—N(CH$_2$CHF$_2$)—CH$_2$—##, #—(CH$_2$)$_4$O—CH$_2$—##, #—(CH$_2$-)$_6$##, #—(CH$_2$)$_2$—CF$_2$—CH$_2$—O—CH$_2$—##,

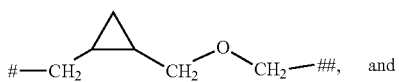

and

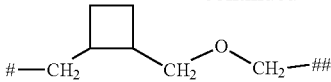

or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from #—(CH$_2$)$_3$—N(CH$_3$)—CH$_2$—##, #—(CH$_2$)$_3$—NH—CH$_2$—##, #—(CH$_2$)$_4$—N(CH$_3$)—CH$_2$—##, #—(CH$_2$)$_4$—N(CH$_2$CF$_3$)—CH$_2$—##, #—(CH$_2$)$_4$—N(CH$_2$CHF$_2$)—CH$_2$—##, #—(CH$_2$)$_4$O—CH$_2$—##, #—(CH$_2$-)$_6$##, and #—(CH$_2$)$_2$—CF$_2$—CH$_2$—O—CH$_2$—##, or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected #—CH$_2$—CH=CH—CH$_2$—O—CH$_2$—##, #—CH$_2$—CH=CH—CH$_2$—N(CH$_3$)—CH$_2$—##,

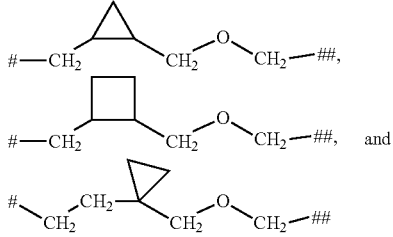

and wherein # is the point of attachment with the indole nitrogen atom and ## is the point of attachment with the pyrazole carbon atom bearing the R$^7$ substituent or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from #—CH$_2$—CH=CH—CH$_2$—O—CH$_2$—##, #—CH$_2$—CH=CH—CH$_2$—N(CH$_3$)—CH$_2$—##,

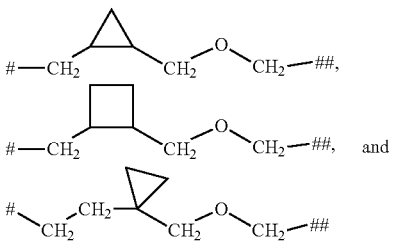

or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from #—(CH$_2$)$_3$—N(CH$_3$)—CH$_2$—##, #—(CH$_2$)$_3$—NH—CH$_2$—##, #—(CH$_2$)$_4$—N(CH$_3$)—CH$_2$—##, #—(CH$_2$)$_4$—N(CH$_2$CF$_3$)—CH$_2$—##, #—(CH$_2$)$_4$—N(CH$_2$CHF$_2$)—CH$_2$—##, and #—CH$_2$—CH=CH—CH$_2$—N(CH$_3$)—CH$_2$—##, or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is selected from #—CH$_2$—CH=CH—CH$_2$—O—CH$_2$—##, #—(CH$_2$)$_4$O—CH$_2$—##, #—(CH$_2$)$_2$—CF$_2$—CH$_2$—O—CH$_2$—##,

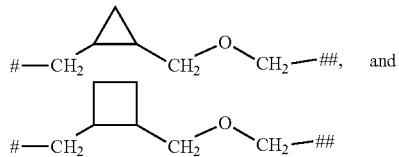

or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is —(CH$_2$-)$_6$ or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^{10}$— is selected from #—(CH$_2$)$_n$—(B)$_t$—(CH$_2$)$_p$—X—##, #—(C$_2$-C$_6$-alkenylene)-(B)$_t$—(CH$_2$)$_p$—X—##, #—(CH$_2$)$_n$—(B)$_r$—(C$_2$-C$_5$-alkenylene)-X—##, and #—(CH$_2$)$_q$—(B)—(CH$_2$)$_r$—(B)—(CH$_2$)$_v$—X—##,
wherein # is the point of attachment with the indole nitrogen atom and ## is the point of attachment with the carbon atom of the phenyl moiety bearing the R$^{10}$ substituent,
or more —CH$_2$— groups may be unsubstituted or substituted with one or more substituents independently selected from a halogen atom, a hydroxy group, a NR$^{16}$R$^{17}$ group, a C$_1$-C$_3$-alkyl group, a C$_1$-C$_3$-haloalkyl group, a C$_1$-C$_3$-alkoxy group, a C$_1$-C$_3$-haloalkoxy group, a C$_3$-C$_6$-cycloalkyl group, and a (heterocycloalkyl)-(C$_1$-C$_3$-alkylene)- group,
wherein a double bond in any alkenylene can be replaced by a 1,2-(C$_1$-C$_6$)cycloalkyl group which is unsubstituted or substituted one or two times with a halogen atom or a C$_1$-C$_2$-alkyl group, and
wherein X is an unsubstituted —CH$_2$— group;
or a tautomer, an N-oxide, or a salt thereof, or a salt of a tautomer, or a salt of an N-oxide, or a mixture of same.

In further embodiments, the present invention includes compounds of formula (I), supra, in which B is independently selected from a —C(O)NR$^{15}$— group, a —NR$^{15}$C(O)— group, a —N(R$^{15}$)— group, a —N(R$^{15}$)—C(=O)—N(R$^{15}$)— group, a —O—C(=O)—N(R$^{15}$)— group, a —N(R$^{15}$)—C(=O)—O— group, —O—, —S—, —S(O)—, and —S(O)$_2$—, or a tautomer, an N-oxide, or a salt thereof, or a salt of a tautomer, or a salt of an N-oxide, or a mixture of same.

In further embodiments, the present invention includes compounds of formula (I), supra, in which B is independently selected from a —C(O)NR$^{15}$— group, a —NR$^{15}$C(O)— group, a —N(R$^{15}$)- group, —O—, —S—, —S(O)—, and —S(O)$_2$—, or a tautomer, an N-oxide, or a salt thereof, or a salt of a tautomer, or a salt of an N-oxide, or a mixture of same.

In further embodiments, the present invention includes compounds of formula (I), supra, in which B is independently selected from a —N(R$^{15}$)— group, —O—, —S—, —S(O)—, and —S(O)$_2$—, or a tautomer, an N-oxide, or a salt thereof, or a salt of a tautomer, or a salt of an N-oxide, or a mixture of same.

In further embodiments, the present invention includes compounds of formula (I), supra, in which B is independently selected from a —C(O)NR$^{15}$— group, a —NR$^{15}$C(O)— group, a —N(R$^{15}$)- group, —O—, and —S— or a tautomer, an N-oxide, or a salt thereof, or a salt of a tautomer, or a salt of an N-oxide, or a mixture of same.

In further embodiments, the present invention includes compounds of formula (I), supra, in which B is independently selected from —O—, —S—, and a —N(R$^{15}$)— group or a tautomer, an N-oxide, or a salt thereof, or a salt of a tautomer, or a salt of an N-oxide, or a mixture of same.

In further embodiments, the present invention includes compounds of formula (I), supra, in which B is independently selected from —O— and a —N(R$^{15}$)— group or a tautomer, an N-oxide, or a salt thereof, or a salt of a tautomer, or a salt of an N-oxide, or a mixture of same.

In further embodiments, the present invention includes compounds of formula (I), supra, in which B is a —NR$^{15}$— group or a tautomer, an N-oxide, or a salt thereof, or a salt of a tautomer, or a salt of an N-oxide, or a mixture of same.

In further embodiments, the present invention includes compounds of formula (I), supra, in which B is an oxygen atom or a tautomer, an N-oxide, or a salt thereof, or a salt of a tautomer, or a salt of an N-oxide, or a mixture of same.

In yet further embodiments, the present invention includes compounds of formula (I), supra, in which B is —NR$^{15}$— and R$^{15}$ is selected from a hydrogen atom, a C$_1$-C$_3$-alkyl group, a C$_1$-C$_3$-haloalkyl group, a C$_1$-C$_4$-hydroxyalkyl group, a (C$_1$-C$_3$-alkyoxy)-(C$_1$-C$_3$-alkylene)- group, a (C$_1$-C$_3$-alkyl)-C(O)—O—(C$_1$-C$_4$)alkylene- group, a (C$_1$-C$_3$-alkyoxy)-(C$_1$-C$_3$-alkylene)-O—C(O)— group, a heterocycloalkyl-(C$_1$-C$_3$-alkylene)-O—C(O)— group, and a heterocycloalkyl-(C$_1$-C$_3$-alkylene) group; or a tautomer, an N-oxide, or a salt thereof, or a salt of a tautomer, or a salt of an N-oxide, or a mixture of same.

In further embodiments, the present invention includes compounds of formula (I), supra, in which B is —NR$^{15}$—, particularly —NH—, —N(C$_1$-C$_3$-alkyl)-, or —N(C$_1$-C$_3$-haloalkyl), more particularly —NH—, —N(CH$_3$)—, N(CH$_2$—CF$_3$)—, or —N(CH$_2$CHF$_2$) or a tautomer, an N-oxide, or a salt thereof, or a salt of a tautomer, or a salt of an N-oxide, or a mixture of same.

In other embodiments, the present invention includes compounds of formula (I), supra, in which A is A1, or a tautomer, an N-oxide, or a salt thereof, or a salt of a tautomer, or a salt of an N-oxide, or a mixture of same.

In further embodiments, the present invention includes compounds of formula (I), supra, in which A is A2, or a tautomer, an N-oxide, or a salt thereof, or a salt of a tautomer, or a salt of an N-oxide, or a mixture of same.

In yet other embodiments, the present invention includes compounds of formula (I), supra, in which A is A3, or a tautomer, an N-oxide, or a salt thereof, or a salt of a tautomer, or a salt of an N-oxide, or a mixture of same.

In yet other embodiments, the present invention includes compounds of formula (I), supra, in which A is A3 and the macrocyclic ring is a 9- membered-, a 10-membered-, a 11-membered-, a 12-membered-, a 13-membered-, a 14-membered-, a 15-membered- or a 16-membered ring, particularly a 9- membered-, a 10-membered-, a 11-membered-, or a 12-membered ring, more particularly a 12-membered ring or a tautomer, an N-oxide, or a salt thereof, or a salt of a tautomer, or a salt of an N-oxide, or a mixture of same.

In further embodiments, the present invention includes compounds of formula (I), supra, in which A is A1 or A2, or a tautomer, an N-oxide, or a salt thereof, or a salt of a tautomer, or a salt of an N-oxide, or a mixture of same.

In other embodiments, the present invention includes compounds of formula (I), supra, in which A is A1 or A2 and the macrocyclic ring is a 9- membered-, a 10-membered-, a 11-membered-, a 12-membered-, a 13-membered-, a 14-membered-, a 15-membered- or a 16-membered ring, particularly a 9- to 12-membered ring or a 12- or a 13-membered ring, more particularly a 10-to 11-membered ring, even more particularly a 11-membered ring or a tautomer, an N-oxide, or a salt thereof, or a salt of a tautomer, or a salt of an N-oxide, or a mixture of same.

In other embodiments, the present invention includes compounds of formula (I), supra, in which A is A1 or A2, which together with the indole moiety and the $R^6$-$R^7$ form a 9- membered-, a 10-membered-, a 11-membered- or a 12-membered macrocyclic ring or a tautomer, an N-oxide, or a salt thereof, or a salt of a tautomer, or a salt of an N-oxide, or a mixture of same.

In yet other embodiments, the present invention includes compounds of formula (I), supra, in which A is A1, which together with the indole moiety and the $R^6$-$R^7$ form a 9- membered-, a 10-membered-, a 11-membered- or a 12-membered macrocyclic ring or a tautomer, an N-oxide, or a salt thereof, or a salt of a tautomer, or a salt of an N-oxide, or a mixture of same.

In yet other embodiments, the present invention includes compounds of formula (I), supra, in which A is A2, which together with the indole moiety and the $R^6$-$R^7$ form a 9- membered-, a 10-membered-, a 11-membered- or a 12-membered macrocyclic ring or a tautomer, an N-oxide, or a salt thereof, or a salt of a tautomer, or a salt of an N-oxide, or a mixture of same.

In yet other embodiments, the present invention includes compounds of formula (I), supra, in which A is A1 or A2, which together with the indole moiety and the $R^6$-$R^7$ form a 10-membered- or a 11-membered macrocyclic ring or a tautomer, an N-oxide, or a salt thereof, or a salt of a tautomer, or a salt of an N-oxide, or a mixture of same.

In yet other embodiments, the present invention includes compounds of formula (I), supra, in which A is A1 or A2, which together with the indole moiety and the $R^6$-$R^7$ form a 11-membered macrocyclic ring or a tautomer, an N-oxide, or a salt thereof, or a salt of a tautomer, or a salt of an N-oxide, or a mixture of same.

In yet other embodiments, the present invention includes compounds of formula (I), supra, in which A is A1 and $R^8$ and $R^9$ are $C_1$-$C_3$-alkyl, $R^8$ is particularly methyl and $R^9$ is methyl or ethyl or a tautomer, an N-oxide, or a salt thereof, or a salt of a tautomer, or a salt of an N-oxide, or a mixture of same.

In yet other embodiments, the present invention includes compounds of formula (I), supra, in which A is A2 and $R^8$ and $R^9$ are $C_1$-$C_3$-alkyl, $R^8$ is particularly methyl and $R^9$ is methyl or ethyl or a tautomer, an N-oxide, or a salt thereof, or a salt of a tautomer, or a salt of an N-oxide, or a mixture of same.

In yet other embodiments, the present invention includes compounds of formula (I), supra, in which A is A2 and $R^8$ and $R^9$ are $C_1$-$C_3$-alkyl, $R^8$ is particularly methyl and $R^9$ is ethyl or a tautomer, an N-oxide, or a salt thereof, or a salt of a tautomer, or a salt of an N-oxide, or a mixture of same.

In other embodiments, the present invention includes compounds of formula (I), supra, in which A is A1 or A2 and $R^8$ and $R^9$ are $C_1$-$C_3$-alkyl, $R^8$ is particularly methyl, morpholinoethyl or morpholinopropyl and $R^9$ is methyl or ethyl or a tautomer, an N-oxide, or a salt thereof, or a salt of a tautomer, or a salt of an N-oxide, or a mixture of same.

In further embodiments, the present invention includes compounds of formula (I), supra, in which A is A1 or A2 and $R^8$ and $R^9$ are independently selected from $C_1$-$C_3$-alkyl or a —($C_1$-$C_3$-alkyl)-heterocyclyl or a tautomer, an N-oxide, or a salt thereof, or a salt of a tautomer, or a salt of an N-oxide, or a mixture of same.

In yet other embodiments, the present invention includes compounds of formula (I), supra, in which A is A1 or A2 and $R^8$ and $R^9$ are $C_1$-$C_3$-alkyl, $R^8$ is particularly methyl and $R^9$ is methyl or ethyl or a tautomer, an N-oxide, or a salt thereof, or a salt of a tautomer, or a salt of an N-oxide, or a mixture of same.

The integers selected for variables n, t, p, q, r, and v may result in different ring sizes but still the rings obtained have to fulfill the rule that only rings of a ring size of 9 members up to a ring size of 16 members including 9 and 16 members are encompassed.

In some embodiments, the present invention includes compounds of formula (I), supra, in which
n is 2, 3, 4, 5, 6, 7, 8, or 9;
t is 0 or 1;
p is 0, 1, 2, 3, 4, or 5;
q is 2, 3, 4, 5, or 6;
r is 2, 3, 4, 5, or 6;
v is 0, or 1; and
s is 0, 1, 2, or 3;

In some embodiments, the present invention includes compounds of formula (I), supra, in which
n is 2, 3, 4, 5, 6, 7, 8, or 9;
p is 0, 1, 2, 3, 4, or 5;
t is 0 or 1; and
s is 0, 1, 2, or 3;

In some embodiments, the present invention includes compounds of formula (I), supra, in which
n is 2, 3, 4, 5, 6, 7, 8, or 9;
t is 0 or 1;
p is 0, 1, 2, 3, 4, 5, or 6;
q is 2, 3, 4, 5, or 6;
r is 2, 3, 4, 5, or 6; and
v is 0, 1, or 2;

In further embodiments, the present invention includes compounds of formula (I), supra, in which
n is 2, 3, 4, 5, 6;
t is 0 or 1;
p is 0, 1, or 2;
q is 2;
r is 2; and
v is 0 or 1.

In further embodiments, the present invention includes compounds of formula (I), supra, in which
n is 2, 3, 4, 5, 6;
t is 1;
p is 1;
q is 2;
r is 2; and
v is 0 or 1.

In further embodiments, the present invention includes compounds of formula (I), supra, in which
n is 2,3,4,5;
t is 0, 1; and
p is 0,1,2,3,4.

In further embodiments, the present invention includes compounds of formula (I), supra, in which
n is 3, 4, 5, or 6;
t is 0 or 1; and
p is 0 or 1.

In further embodiments, the present invention includes compounds of formula (I), supra, in which
n is 3, 4, 5, or 6;
t is 0 or 1; and
p is 0

In further embodiments, the present invention includes compounds of formula (I), supra, in which
n is 3 or 4;
t is 1; and
p is 1 or 2

In further embodiments, the present invention includes compounds of formula (I), supra, in which
n is 3 or 4;
t is 1; and
p is 0;

In further embodiments, the present invention includes compounds of formula (I), supra, in which
n is 2, 3 or 4;
t is 0,1; and
p is 0,1,2;

In further embodiments, the present invention includes compounds of formula (I), supra, in which
n is 2 or 3;
t is 0,1; and
p is 0 or 2

In further embodiments, the present invention includes compounds of formula (I), supra, in which
n 4;
t is 1; and
p is 0

The limitations relating to A1 and A2 are independent from the limitations relating to A3.

In further embodiments, the present invention includes compounds of formula (I), supra, in which $R^8$ is selected from $R^8$ is a hydrogen atom,
a $C_1$-$C_6$-alkyl group, which is unsubstituted or substituted with one or more substituents independently selected from a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group and a $NR^{20}R^{21}$ group;
a $C_1$-$C_3$-haloalkyl group,
a $C_3$-$C_6$-cycloalkyl group,
a $C_1$-$C_6$-alkyl group in which one or two not directly adjacent carbon atoms are independently replaced by a hetero atom selected from —O— and —NH—;

In further embodiments, the present invention includes compounds of formula (I), supra, in which $R^8$ is selected from a hydrogen atom
  a $C_1$-$C_6$-alkyl group, which is unsubstituted or substituted with one or more substituents independently selected from
    a halogen atom, a hydroxy group, a $C_1$-$C_3$-alkoxy group, a $C_1$-$C_3$-haloalkoxy group,
    a $C_3$-$C_6$-cycloalkyl group, a heterocycloalkyl group, and a $NR^{20}R^{21}$ group; and
  a $C_3$-$C_6$-cycloalkyl group, or a tautomer, an N-oxide, or a salt thereof, or a salt of a tautomer, or a salt of an N-oxide, or a mixture of same.

In further embodiments, the present invention includes compounds of formula (I), supra, in which $R^8$ is selected from a hydrogen atom and, a $C_1$-$C_4$-alkyl group($CH_3$), which is unsubstituted or substituted with one or more substituents independently selected from a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group, and a $NR^{20}R^{21}$ group; or a tautomer, an N-oxide, or a salt thereof, or a salt of a tautomer, or a salt of an N-oxide, or a mixture of same.

In further embodiments, the present invention includes compounds of formula (I), supra, in which $R^8$ is selected from a hydrogen atom and, a $C_1$-$C_4$-alkyl group($CH_3$), which is unsubstituted or substituted with one or more substituents independently selected from a halogen atom, a hydroxy group, a $C_3$-$C_6$-cycloalkyl group, and a heterocycloalkyl group or a tautomer, an N-oxide, or a salt thereof, or a salt of a tautomer, or a salt of an N-oxide, or a mixture of same.

In further embodiments, the present invention includes compounds of formula (I), supra, in which $R^8$ is a $C_1$-$C_6$-alkyl group which is unsubstituted or substituted with one or more heterocycloalkyl groups or a tautomer, an N-oxide, or a salt thereof, or a salt of a tautomer, or a salt of an N-oxide, or a mixture of same.

In further embodiments, the present invention includes compounds of formula (I), supra, in which $R^8$ is a $C_1$-$C_6$-alkyl group which is unsubstituted or substituted with a heterocycloalkyl group or a tautomer, an N-oxide, or a salt thereof, or a salt of a tautomer, or a salt of an N-oxide, or a mixture of same.

In further embodiments, the present invention includes compounds of formula (I), supra, in which $R^8$ is a $C_1$-$C_6$-alkyl group which is unsubstituted or substituted with a morpholino group or a tautomer, an N-oxide, or a salt thereof, or a salt of a tautomer, or a salt of an N-oxide, or a mixture of same.

In further embodiments, the present invention includes compounds of formula (I), supra, in which $R^8$ is a $C_1$-$C_3$-alkyl group which is unsubstituted or substituted with a morpholino group or a tautomer, an N-oxide, or a salt thereof, or a salt of a tautomer, or a salt of an N-oxide, or a mixture of same.

In further embodiments, the present invention includes compounds of formula (I), supra, in which $R^8$ is morpholin-4-yl-ethyl- group or a morpholin-4-yl-propyl- group or a tautomer, an N-oxide, or a salt thereof, or a salt of a tautomer, or a salt of an N-oxide, or a mixture of same.

In further embodiments, the present invention includes compounds of formula (I), supra, in which $R^8$ is a methyl group or a tautomer, an N-oxide, or a salt thereof, or a salt of a tautomer, or a salt of an N-oxide, or a mixture of same.

In further embodiments, the present invention includes compounds of formula (I), supra, in which
  $R^9$ is selected from a hydrogen atom,
    a $C_1$-$C_4$-alkyl group,
    a $C_1$-$C_3$-hydroxyalkyl group,
    a $C_1$-$C_4$-haloalkyl group,
    a $C_1$-$C_4$-haloalkyl-NH—C(O)—O—($C_1$-$C_3$-alkylene)- group,
    a $C_2$-$C_6$-haloalkenyl group,
    a $C_1$-$C_6$-alkyl-O— group,
    a $C_1$-$C_4$-haloalkoxy group,
    a $C_1$-$C_6$-alkyl-O—($C_1$-$C_3$-alkylene)- group,
    a ($C_3$-$C_7$)-cycloalkyl group,
    a ($C_3$-$C_7$)-cycloalkyl-O—($C_1$-$C_3$-alkylene)- group,
    a phenyl-O—($C_1$-$C_3$-alkylene)- group,
    a phenyl-($C_1$-$C_3$-alkylene)-O—($C_1$-$C_3$-alkylene)- group,
    a $R^{13}$-(phenylene)-($C_1$-$C_3$-alkylene)-O—($C_1$-$C_3$-alkylene)- group,
    a $R^{13}$-(phenylene)-O—($C_1$-$C_3$-alkylene)- group,
    a $R^{13}$-(phenylene)-(heteroarylene)-O—($C_1$-$C_3$-alkylene) group,
    a ($R^{13}$)-(heterocycloalkylene)-($C_1$-$C_3$-alkylene)- group, a (R$^{13}$)-(heterocycloalkylene)-(phenylene)-O—(C$_1$-C$_3$-alkylene)- group,
a (heterocycloalkenyl)-(phenylene)-O—(C$_1$-C$_3$-alkylene)- group,
a (R$^{13}$)-(heteroarylene)-(C$_1$-C$_3$-alkylene)-O—(C$_1$-C$_3$-alkylene)- group,
a (R$^{13}$)-(heteroarylene)-(phenylene)-O—(C$_1$-C$_3$-alkylene)- group,
a (R$^{19}$)—S(O)$_2$-(phenylene)-O—(C$_1$-C$_3$-alkylene)- group,
a (R$^{19}$)—S(O)$_2$—NH-(phenylene)-O—(C$_1$-C$_3$-alkylene)- group,
a (R$^{19}$)—S(O)$_2$—NH-(phenylene)-O—(C$_1$-C$_3$-alkylene)- group,
a (R$^{19}$)—S(O)$_2$—N(C$_1$-C$_6$-alkyl)-(phenylene)-O—(C$_1$-C$_3$-alkylene)- group,
a (R$^{19}$)—S(O)$_2$-(heterocycloalkylene)-(phenylene)-O—(C$_1$-C$_3$-alkylene)- group,
a (R$^{13}$)-(heterocycloalkylene)-(heteroarylene)-O—(C$_1$-C$_3$-alkylene)- group,
a (R$^{19}$)-(heteroarylene)-O—(C$_1$-C$_3$-alkylene)- group,
a (R$^{13}$)-(heteroarylene)-O—(C$_1$-C$_3$-alkylene)- group,
a (R$^{19}$)—S(O)$_2$-(heteroarylene)-O—(C$_1$-C$_3$-alkylene)- group,
a (R$^{19}$)—S(O)$_2$-(heterocycloalkylene)-(heteroarylene)-O—(C$_1$-C$_3$-alkylene)- group,
a NR$^{20}$R$^{21}$—(C$_1$-C$_3$-alkylene)- group,
a (C$_1$-C$_3$-alkyl)-NH—(C$_1$-C$_3$-alkylene)- group,
a (C$_1$-C$_3$-haloalkyl)-(C$_1$-C$_3$-alkylene)-NH—(C$_1$-C$_3$-alkylene)- group,
a (C$_1$-C$_3$-haloalkyl)-NH—(C$_1$-C$_3$-alkylene)- group,
a (C$_1$-C$_3$-alkyl)-NH—C(O)—(C$_1$-C$_3$-alkylene)- group,
a (C$_1$-C$_3$-alkyl)-NR$^{15}$—C(O)—(C$_1$-C$_3$-alkylene)- group,
a (C$_1$-C$_3$-alkyl)-C(O)—NH—(C$_1$-C$_3$-alkylene)- group,
a (C$_1$-C$_3$-alkyl)-C(O)—NR$^{15}$—(C$_1$-C$_3$-alkylene)- group,
a

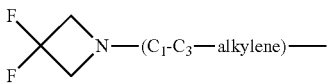

group, and a

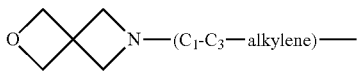

group, wherein the phenyl ring is unsubstituted or substituted with a halogen atom, a hydroxy group, or a C$_1$-C$_3$-alkoxy group and
the heterocycloalkyl group is unsubstituted or substituted with an oxo (=O) group or is unsubstituted or substituted with one or more substituents independently selected from a halogen atom, a hydroxy group, a C$_1$-C$_3$-alkyl group, and a C$_1$-C$_3$-alkoxy group,
or R$^8$ and R$^9$ together form a 5- or 6-membered ring optionally containing one or two heteroatoms selected from —O—, and —NR$^{14}$—;
and wherein
R$^{19}$ is selected from a hydrogen atom, a hydroxy group, a cyano group, a C$_1$-C$_3$-alkyl group, a C$_1$-C$_6$-hydroxyalkyl group, a C$_1$-C$_3$-alkoxy group, a C(O)OR$^{21}$—(C$_1$-C$_3$-alkylene)- group, a —C(O)OR$^{21}$ group, a —C(O)NR$^{20}$R$^{21}$ group, a (C$_1$-C$_3$-alkyl)-O—(C$_1$-C$_3$-alkylene)-C(O)— group, a (C$_1$-C$_6$-alkyl)-C(O)— group, and a C$_3$-C$_6$-cycloalkyl-C(O)— group;
wherein R$^{19}$ is selected from a C$_1$-C$_3$-alkyl group, a C$_3$-C$_6$-cycloalkyl group, and a NR$^{20}$R$^{21}$ group; and
wherein R$^{20}$, R$^{21}$ are independently selected from a hydrogen atom or a C$_1$-C$_6$-alkyl group;
or a tautomer, an N-oxide, or a salt thereof, or a salt of a tautomer, or a salt of an N-oxide, or a mixture of same.

In further embodiments, the present invention includes compounds of formula (I), supra, in which
R$^9$ is selected from
a hydrogen atom,
a C$_1$-C$_4$-alkyl group,
a C$_1$-C$_3$-hydroxyalkyl group,
a C$_1$-C$_4$-haloalkyl group,
a C$_1$-C$_4$-haloalkyl-NH—C(O)—O—(C$_1$-C$_3$-alkylene)- group,
a C$_2$-C$_6$-haloalkenyl group,
a C$_1$-C$_6$-alkyl-O— group,
a C$_1$-C$_4$-haloalkoxy group,
a C$_1$-C$_6$-alkyl-O—(C$_1$-C$_3$-alkylene)- group,
a (C$_3$-C$_7$)-cycloalkyl group,
a (C$_3$-C$_7$)-cycloalkyl-O—(C$_1$-C$_3$-alkylene)- group,
a phenyl-O—(C$_1$-C$_3$-alkylene)- group,
a phenyl-(C$_1$-C$_3$-alkylene)-O—(C$_1$-C$_3$-alkylene)- group,
a R$^{18}$-(phenylene)-(C$_1$-C$_3$-alkylene)-O—(C$_1$-C$_3$-alkylene)- group,
a R$^{18}$-(phenylene)-O—(C$_1$-C$_3$-alkylene)- group,
a R$^{13}$-(phenylene)-(heteroarylene)-O—(C$_1$-C$_3$-alkylene) group,
a (R$^{18}$)-(heterocycloalkylene)-(C$_1$-C$_3$-alkylene)- group,
a (R$^{18}$)-(heterocycloalkylene)-(phenylene)-O—(C$_1$-C$_3$-alkylene)- group,
a (heterocycloalkenyl)-(phenylene)-O—(C$_1$-C$_3$-alkylene)- group,
a (R$^{18}$)-(heteroarylene)-(C$_1$-C$_3$-alkylene)-O—(C$_1$-C$_3$-alkylene)- group,
a (R$^{18}$)-(heteroarylene)-(phenylene)-O—(C$_1$-C$_3$-alkylene)- group,
a (R$^{19}$)—S(O)$_2$-(phenylene)-O—(C$_1$-C$_3$-alkylene)- group,
a (R$^{19}$)—S(O)$_2$—NH-(phenylene)-O—(C$_1$-C$_3$-alkylene)- group,
a (R$^{19}$)—S(O)$_2$—NH-(phenylene)-O—(C$_1$-C$_3$-alkylene)- group,
a (R$^{19}$)—S(O)$_2$—N(C$_1$-C$_6$-alkyl)-(phenylene)-O—(C$_1$-C$_3$-alkylene)- group,
a (R$^{19}$)—S(O)$_2$-(heterocycloalkylene)-(phenylene)-O—(C$_1$-C$_3$-alkylene)- group,
a (R$^{18}$)-(heterocycloalkylene)-(heteroarylene)-O—(C$_1$-C$_3$-alkylene)- group,
a (R$^{19}$)-(heteroarylene)-O—(C$_1$-C$_3$-alkylene)- group,
a (R$^{18}$)-(heteroarylene)-O—(C$_1$-C$_3$-alkylene)- group,
a (R$^{19}$)—S(O)$_2$-(heteroarylene)-O—(C$_1$-C$_3$-alkylene)- group,
a (R$^{19}$)—S(O)$_2$-(heterocycloalkylene)-(heteroarylene)-O—(C$_1$-C$_3$-alkylene)- group,
a NR$^{20}$R$^{21}$—(C$_1$-C$_3$-alkylene)- group,
a (C$_1$-C$_3$-alkyl)-NH—(C$_1$-C$_3$-alkylene)- group,
a (C$_1$-C$_3$-haloalkyl)-(C$_1$-C$_3$-alkylene)-NH—(C$_1$-C$_3$-alkylene)- group,
a (C$_1$-C$_3$-haloalkyl)-NH—(C$_1$-C$_3$-alkylene)- group,
a (C$_1$-C$_3$-alkyl)-NH—C(O)—(C$_1$-C$_3$-alkylene)- group,
a (C$_1$-C$_3$-alkyl)-NR$^{15}$—C(O)—(C$_1$-C$_3$-alkylene)- group,
a (C$_1$-C$_3$-alkyl)-C(O)—NH—(C$_1$-C$_3$-alkylene)- group,
a (C$_1$-C$_3$-alkyl)-C(O)—NR$^{15}$—(C$_1$-C$_3$-alkylene)- group, a

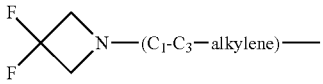

group, and a

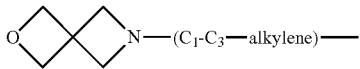

group,
wherein the phenyl ring is unsubstituted or substituted with a halogen atom, a hydroxy group, or a $C_1$-$C_3$-alkoxy group and
the heterocycloalkyl group is unsubstituted or substituted with an oxo (=O) group or is unsubstituted or substituted with one or more substituents independently selected from a halogen atom, a hydroxy group, a $C_1$-$C_3$-alkyl group, and a $C_1$-$C_3$-alkoxy group,
or $R^8$ and $R^9$ together form a 5- or 6-membered ring optionally containing one or two heteroatoms selected from —O—, and —$NR^{14}$—;
or a tautomer, an N-oxide, or a salt thereof, or a salt of a tautomer, or a salt of an N-oxide, or a mixture of same.

In further embodiments, the present invention includes compounds of formula (I), supra, in which $R^9$ is selected from
a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O-group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$-cycloalkyl)-O—($C_1$-$C_3$-alkylene)- group,
a phenyl-O—($C_1$-$C_3$-alkylene)- group,
a phenyl-($C_1$-$C_3$-alkylene)-O—($C_1$-$C_3$-alkylene)- group,
a ($R^{13}$)-(phenylene)-O—($C_1$-$C_3$-alkylene)- group,
a ($R^{13}$)-(phenylene)-($C_1$-$C_3$-alkylene)-O—($C_1$-$C_3$-alkylene)- group,
a ($R^{13}$)-(phenylene)-(heteroarylene)-O—($C_1$-$C_3$-alkylene) group,
a ($R^{13}$)-(heterocycloalkylene)-($C_1$-$C_6$-alkylene)- group,
a ($R^{13}$)-(heterocycloalkylene)-(phenylene)-O—($C_1$-$C_3$-alkylene)- group,
a (heterocycloalkenyl)-(phenylene)-O—($C_1$-$C_3$-alkylene)- group,
a ($R^{13}$)-(heteroarylene)-($C_1$-$C_3$-alkylene)-O—($C_1$-$C_3$-alkylene)- group,
a ($R^{13}$)-(heteroarylene)-(phenylene)-O—($C_1$-$C_3$-alkylene)- group,
a ($R^{18}$)-(phenylene)-($C_1$-$C_3$-alkylene)-O—($C_1$-$C_3$-alkylene)- group,
a ($R^{19}$)-S(O)$_2$-(phenylene)-O—($C_1$-$C_3$-alkylene)- group,
a ($R^{19}$)—S(O)$_2$—NH-(phenylene)-O—($C_1$-$C_3$-alkylene)- group,
a ($R^{19}$)—S(O)$_2$—N($C_1$-$C_6$-alkyl)-(phenylene)-O—($C_1$-$C_3$-alkylene)- group,
a ($R^{19}$)—S(O)$_2$-(heterocycloalkylene)-(phenylene)-O—($C_1$-$C_3$-alkylene)- group,
a ($R^{18}$)-(heterocycloalkylene)-(heteroarylene)-O—($C_1$-$C_3$-alkylene)- group,
a ($R^{19}$)-(heteroarylene)-O—($C_1$-$C_3$-alkylene)- group,
a ($R^{19}$)—S(O)$_2$-(heteroarylene)-O—($C_1$-$C_3$-alkylene)- group,
a ($R^{19}$)—S(O)$_2$-(heterocycloalkylene)-(heteroarylene)-O—($C_1$-$C_3$-alkylene)- group,
a $NR^{20}R^{21}$—($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-NH—C(O)—($C_1$-$C_3$-alkylene)- group,
a ($C_1$-$C_3$-alkyl)-$NR^{15}$—C(O)—($C_1$-$C_3$-alkylene)- group,
a ($C_1$-$C_3$-alkyl)-C(O)—NH—($C_1$-$C_3$-alkylene)- group,
a ($C_1$-$C_3$-alkyl)-C(O)—$NR^{15}$—($C_1$-$C_3$-alkylene)- group,
a

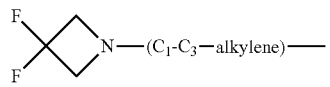

group, and a

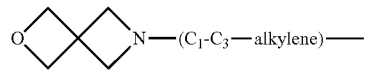

group, wherein the phenyl ring is optionally substituted with a halogen atom, a hydroxy group, or a $C_1$-$C_3$-alkoxy group and
the heterocycloalkyl group is optionally substituted with an oxo (=O) group or is optionally substituted with one or more substituents independently selected from a halogen atom, and a $C_1$-$C_3$-alkyl group;
or $R^8$ and $R^9$ together form a 5- or 6-membered ring optionally containing one or two heteroatoms selected from of —O—, and —$NR^{14}$—;
or a tautomer, an N-oxide, or a salt thereof, or a salt of a tautomer, or a salt of an N-oxide, or a mixture of same.

In further embodiments, the present invention includes compounds of formula (I), supra, in which $R^9$ is selected from
a hydrogen atom,
a $C_1$-$C_4$-alkyl group,
a $C_1$-$C_3$-hydroxyalkyl group,
a $C_1$-$C_4$-haloalkyl group,
a $C_2$-$C_6$-haloalkenyl group,
a $C_1$-$C_6$-alkyl-O-group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$-cycloalkyl)-O—($C_1$-$C_3$-alkylene)- group,
a phenyl-O—($C_1$-$C_3$-alkylene)- group,
a ($R^{18}$)-(phenylene)-O—($C_1$-$C_3$-alkylene)- group,
a ($R^{18}$)-(heterocycloalkylene)-($C_1$-$C_6$-alkylene)- group,
a ($R^{19}$)—S(O)$_2$-(phenylene)-O—($C_1$-$C_3$-alkylene)- group,
a ($R^{19}$)—S(O)$_2$—NH-(phenylene)-O—($C_1$-$C_3$-alkylene)- group, a ($R^{19}$)-(heteroarylene)-O—($C_1$-$C_3$-alkylene)- group,
a ($R^{19}$)—S(O)$_2$-(heteroarylene)-O—($C_1$-$C_3$-alkylene)- group,
a NR$^{20}$R$^{21}$—($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-NH—C(O)—($C_1$-$C_3$-alkylene)- group,
a ($C_1$-$C_3$-alkyl)-NR$^{15}$—C(O)—($C_1$-$C_3$-alkylene)- group,
a ($C_1$-$C_3$-alkyl)-C(O)—NH—($C_1$-$C_3$-alkylene)- group,
a ($C_1$-$C_3$-alkyl)-C(O)—NR$^{15}$—($C_1$-$C_3$-alkylene)- group,
wherein the phenyl ring is optionally substituted with a halogen atom, a hydroxy group, or a $C_1$-$C_3$-alkoxy group and
the heterocycloalkyl group is optionally substituted with an oxo (=O) group or is optionally substituted with one or more substituents independently selected from a halogen atom, and a $C_1$-$C_3$-alkyl group;
or a tautomer, an N-oxide, or a salt thereof, or a salt of a tautomer, or a salt of an N-oxide, or a mixture of same.

In further embodiments, the present invention includes compounds of formula (I), supra, in which $R^9$ is selected from
a $C_1$-$C_4$-haloalkyl-NH—C(O)—O—($C_1$-$C_3$-alkylene)- group,
a phenyl-($C_1$-$C_3$-alkylene)-O—($C_1$-$C_3$-alkylene)- group,
a ($R^{18}$)-(phenylene)-($C_1$-$C_3$-alkylene)-O—($C_1$-$C_3$-alkylene)- group,
a ($R^{18}$)-(phenylene)-(heteroarylene)-($C_1$-$C_3$-alkylene) group,
a ($R^{18}$)-(heterocycloalkylene)-(phenylene)-O—($C_1$-$C_3$-alkylene)- group,
a (heterocycloalkenyl)-(phenylene)-O—($C_1$-$C_3$-alkylene)- group,
a ($R^{18}$)-(heteroarylene)-($C_1$-$C_3$-alkylene)-O—($C_1$-$C_3$-alkylene)- group,
a ($R^{18}$)-(heteroarylene)-(phenylene)-O—($C_1$-$C_3$-alkylene)- group,
a ($R^{18}$)-(phenylene)-($C_1$-$C_3$-alkylene)-O—($C_1$-$C_3$-alkylene)- group,
a ($R^{19}$)—S(O)$_2$—N($C_1$-$C_6$-alkyl)-(phenylene)-O—($C_1$-$C_3$-alkylene)- group,
a ($R^{19}$)—S(O)$_2$-(heterocycloalkylene)-(phenylene)-O—($C_1$-$C_3$-alkylene)- group,
a ($R^{18}$)-(heterocycloalkylene)-(heteroarylene)-O—($C_1$-$C_3$-alkylene)- group,
a ($R^{19}$)—S(O)$_2$-(heterocycloalkylene)-(heteroarylene)-O—($C_1$-$C_3$-alkylene)- group,
a

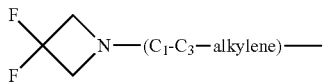

group, and a

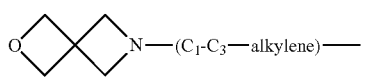

group, wherein the phenyl ring is optionally substituted with a halogen atom, a hydroxy group, or a $C_1$-$C_3$-alkoxy group and
the heterocycloalkyl group is optionally substituted with an oxo (=O) group or is optionally substituted with one or more substituents independently selected from a halogen atom, and a $C_1$-$C_3$-alkyl group;
or $R^8$ and $R^9$ together form a 5- or 6-membered ring optionally containing one or two heteroatoms selected from of —O—, and —NR$^{14}$—;
or a tautomer, an N-oxide, or a salt thereof, or a salt of a tautomer, or a salt of an N-oxide, or a mixture of same.

In further embodiments, the present invention includes compounds of formula (I), supra, in which
$R^9$ is selected from
a hydrogen atom,
a $C_1$-$C_4$-alkyl group,
a $C_1$-$C_3$-hydroxyalkyl group,
a $C_1$-$C_4$-haloalkyl group,
a $C_2$-$C_6$-haloalkenyl group,
a $C_1$-$C_6$-alkyl-O—($C_1$-$C_3$-alkylene)- group,
a ($C_3$-$C_7$-cycloalkyl) group,
a phenyl-O—($C_1$-$C_3$-alkylene)- group,
a ($R^{18}$)-(phenylene)-O—($C_1$-$C_3$-alkylene)- group,
a ($R^{18}$)-(heterocycloalkylene)-($C_1$-$C_3$-alkylene)- group,
a ($R^{18}$)-(heteroarylene)-O—($C_1$-$C_3$-alkylene)- group,
a ($R^{19}$)—S(O)$_2$-(heteroarylene)-O—($C_1$-$C_3$-alkylene)- group,
a NR$^{20}$R$^{21}$—($C_1$-$C_3$-alkylene)- group, and
a ($C_1$-$C_3$-alkyl)-NH—($C_1$-$C_3$-alkylene)- group,
wherein the phenyl group is unsubstituted or substituted with a halogen atom, a hydroxy group, or a $C_1$-$C_3$-alkoxy group and
the heterocycloalkylene group is unsubstituted or substituted with a substituent independently selected from an oxo (=O) group and a $C_1$-$C_3$-alkyl group;
or $R^8$ and $R^9$ together form 6-membered ring optionally containing one or two oxygen atoms;
or a tautomer, an N-oxide, or a salt thereof, or a salt of a tautomer, or a salt of an N-oxide, or a mixture of same.

In further embodiments, the present invention includes compounds of formula (I), supra, in which
$R^9$ is a $C_1$-$C_4$-alkyl group,
a $C_1$-$C_3$-hydroxyalkyl group,
a $C_1$-$C_3$-haloalkyl group,
a $C_1$-$C_3$-alkyl-O— group,
a $C_1$-$C_3$-haloalkoxy group,
a $C_1$-$C_3$-alkyl-O—($C_1$-$C_3$-alkylene)- group,
a ($C_3$-$C_6$)-cycloalkyl group,
a $R^{18}$-(phenylene)-O—($C_1$-$C_3$-alkylene)- group,
a NR$^{20}$R$^{21}$—($C_1$-$C_3$-alkylene)- group, and
a ($C_1$-$C_3$-alkyl)-NH—($C_1$-$C_3$-alkylene)- group;
or a tautomer, an N-oxide, or a salt thereof, or a salt of a tautomer, or a salt of an N-oxide, or a mixture of same.

In further embodiments, the present invention includes compounds of formula (I), supra, in which $R^9$ is a $C_1$-$C_4$-alkyl group,
a $C_1$-$C_3$-hydroxyalkyl group,
a $C_1$-$C_3$-haloalkyl group,
a $C_1$-$C_3$-alkyl-O—($C_1$-$C_3$-alkylene)- group,
a $R^{18}$-(phenylene)-O—($C_1$-$C_3$-alkylene)- group,
a NR$^{20}$R$^{21}$—($C_1$-$C_3$-alkylene)- group, and
a ($C_1$-$C_3$-alkyl)-NH—($C_1$-$C_3$-alkylene)- group;
or a tautomer, an N-oxide, or a salt thereof, or a salt of a tautomer, or a salt of an N-oxide, or a mixture of same.

In further embodiments, the present invention includes compounds of formula (I), supra, in which $R^9$ is a $C_1$-$C_4$-alkyl group;
or a tautomer, an N-oxide, or a salt thereof, or a salt of a tautomer, or a salt of an N-oxide, or a mixture of same.

In further embodiments, the present invention includes compounds of formula (I), supra, in which $R^9$ is a $C_1$-$C_3$-alkyl group;
or a tautomer, an N-oxide, or a salt thereof, or a salt of a tautomer, or a salt of an N-oxide, or a mixture of same.

In further embodiments, the present invention includes compounds of formula (I), supra, in which $R^9$ is a methyl group or an ethyl group;
or a tautomer, an N-oxide, or a salt thereof, or a salt of a tautomer, or a salt of an N-oxide, or a mixture of same.

In further embodiments, the present invention includes compounds of formula (I), supra, in which $R^9$ is an ethyl group;
or a tautomer, an N-oxide, or a salt thereof, or a salt of a tautomer, or a salt of an N-oxide, or a mixture of same.

In further embodiments, the present invention includes compounds of formula (I), supra, in which $R^8$ is a methyl group and $R^9$ is an ethyl group or a tautomer, an N-oxide, or a salt thereof, or a salt of a tautomer, or a salt of an N-oxide, or a mixture of same.

In further embodiments, the present invention includes compounds of formula (I), supra, in which $R^8$ and $R^9$ together form a 5- or 6-membered ring optionally containing one or two heteroatoms selected from —O—, and —$NR^{14}$—, or a tautomer, an N-oxide, or a salt thereof, or a salt of a tautomer, or a salt of an N-oxide, or a mixture of same.

In further embodiments, the present invention includes compounds of formula (I), supra, in which $R^8$ and $R^9$ together form a 5- or 6-membered ring optionally containing one or two oxygen atoms, or a tautomer, an N-oxide, or a salt thereof, or a salt of a tautomer, or a salt of an N-oxide, or a mixture of same.

In further embodiments, the present invention includes compounds of formula (I), supra, in which $R^8$ and $R^9$ together form a 6-membered ring optionally containing one or two oxygen atoms, or a tautomer, an N-oxide, or a salt thereof, or a salt of a tautomer, or a salt of an N-oxide, or a mixture of same.

In further embodiments, the present invention includes compounds of formula (I), supra, in which $R^8$ and $R^9$ together form a 6-membered ring optionally containing one oxygen atoms, or a tautomer, an N-oxide, or a salt thereof, or a salt of a tautomer, or a salt of an N-oxide, or a mixture of same.

In further embodiments, the present invention includes compounds of formula (I), supra, in which $R^8$ and $R^9$ together are *—($CH_2$-$)_3$—O—**, *—($CH_2$)$_2$O—$CH_2$—**, —($CH_2$)$_4$—, wherein * means the point of attachment at the pyrazol nitrogen atom ($R^8$ site) whereas ** means the point of attachment to the carbon atom ($R^9$ site) of the pyrazol. or a tautomer, an N-oxide, or a salt thereof, or a salt of a tautomer, or a salt of an N-oxide, or a mixture of same.

In further embodiments, the present invention includes compounds of formula (I), supra, in which $R^{12}$ is a methoxy group, or a tautomer, an N-oxide, or a salt thereof, or a salt of a tautomer, or a salt of an N-oxide, or a mixture of same.

In further embodiments, the present invention includes compounds of formula (I), supra, in which $R^{12}$ is hydrogen or a methoxy group, or a tautomer, an N-oxide, or a salt thereof, or a salt of a tautomer, or a salt of an N-oxide, or a mixture of same.

In further embodiments, the present invention includes compounds of formula (I), supra, in which $R^{13}$ is hydrogen or a methyl group, or a tautomer, an N-oxide, or a salt thereof, or a salt of a tautomer, or a salt of an N-oxide, or a mixture of same.

In further embodiments, the present invention includes compounds of formula (I), supra,
in which $R^{15}$ is independently selected from a hydrogen atom,
a $C_1$-$C_6$-alkyl group
which is unsubstituted or substituted with one or more substituents selected from a halogen atom, a hydroxy group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a ($C_1$-$C_3$-alkyl)-C(O)—O— group, a heterocycloalkyl group, a heterocycloalkyl-($C_1$-$C_3$-alkylene) group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$-(heterocycloalkylene)-(arylene)-O— group, an (aryl)-(heteroarylene)-O— group, and an (aryl)-(heteroarylene)-O—($C_1$-$C_3$-alkylene)- group;
a $C_1$-$C_3$-alkoxy-($C_1$-$C_6$-alkylene)-O—C(O)— group,
a heterocycloalkyl-($C_1$-$C_6$-alkylene)-O—C(O)— group,
a phenyl group,
a group

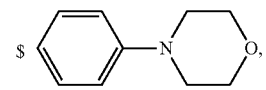

a group

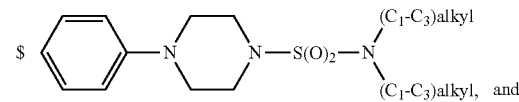

a group

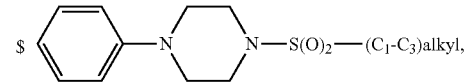

wherein $ is the point of attachment to the nitrogen atom, to which $R^{15}$ is attached, or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is independently selected from
a $C_1$-$C_6$-alkyl group which is unsubstituted or substituted with one or more substituents selected from
a ($C_1$-$C_3$-alkyl)-C(O)—O— group,
a heterocycloalkyl-($C_1$-$C_3$-alkylene) group;
a $C_1$-$C_3$-alkoxy-($C_1$-$C_6$-alkylene)-O—C(O)— group, and
a heterocycloalkyl-($C_1$-$C_6$-alkylene)-O—C(O)— group,
or a tautomer, an N-oxide, or a salt thereof, or a salt of a tautomer, or a salt of an N-oxide, or a mixture of same.

In further embodiments, the present invention includes compounds of formula (I), supra, in which
$R^{15}$ is independently selected from a hydrogen atom,
a $C_1$-$C_6$-alkyl group
which is unsubstituted or substituted with one or more substituents selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$- haloalkoxy group, a heterocycloalkyl group, an aryl group, a (R$^{18}$)-(heterocycloalkylene)-(arylene)-O— group, a (heterocycloalkyl)-(arylene)-O— group, an aryl-O— group, an aryl-(C$_1$-C$_3$-alkylene)-O— group, a (R$^{19}$)—S(O)$_2$-arylene-O— group, a (R$^{19}$)S(O)$_2$-(heterocycloalkylene)-(arylene)-O— group, an (aryl)-(heteroarylene)-O— group, and an (aryl)-(heteroarylene)-O—(C$_1$-C$_3$-alkylene)- group;

a phenyl group,
a group

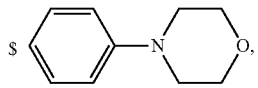

a group

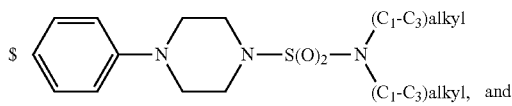

a group

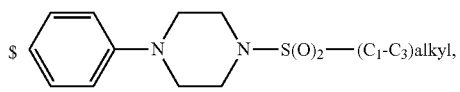

wherein $ is the point of attachment to the nitrogen atom, to which R$^{15}$ is attached, or a tautomer, an N-oxide, or a salt thereof, or a salt of a tautomer, or a salt of an N-oxide, or a mixture of same.

In further embodiments, the present invention includes compounds of formula (I), supra, in which R$^{15}$ is independently selected from R$^{15}$ is independently selected from a hydrogen atom,
a C$_1$-C$_6$-alkyl group
which is optionally substituted with one or more substituents selected from a halogen atom, a C$_1$-C$_3$-alkyl group, a C$_1$-C$_3$-haloalkyl group, a C$_1$-C$_3$-hydroxyalkyl group, a C$_1$-C$_3$-alkoxy group, a C$_1$-C$_3$-haloalkoxy group, a (C$_1$-C$_3$-alkyl)-C(O)—O— group, a heterocycloalkyl group, a heterocycloalkyl-(C$_1$-C$_3$-alkylene) group, an aryl group, a (R$^{18}$)-(heterocycloalkylene)-(arylene)-O— group, an aryl-O— group, an aryl-(C$_1$-C$_3$-alkylene)-O— group, a (R$^{19}$)—S(O)$_2$— arylene-O-group, a (R$^{19}$)S(O)$_2$-heterocycloalkylene-arylene-O— group and an aryl-heteroarylene-O-group;

a C$_1$-C$_3$-alkoxy-(C$_1$-C$_6$-alkylene)-O—C(O)— group,
a heterocycloalkyl-(C$_1$-C$_6$-alkylene)-O—C(O)— group,
a phenyl group,
a group

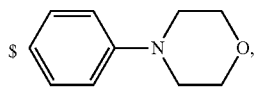

a group

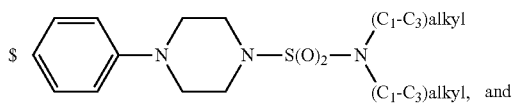

a group

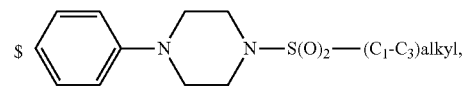

wherein $ is the point of attachment to the nitrogen atom, to which R$^{15}$ is attached, or a tautomer, an N-oxide, or a salt thereof, or a salt of a tautomer, or a salt of an N-oxide, or a mixture of same.

In further embodiments, the present invention includes compounds of formula (I), supra, in which R$^{15}$ is independently selected from a hydrogen atom, a C$_1$-C$_6$-alkyl group
which is optionally substituted with one or more substituents selected from a halogen atom, a C$_1$-C$_3$-alkyl group, a C$_1$-C$_3$-haloalkyl group, a C$_1$-C$_3$-hydroxyalkyl group, a C$_1$-C$_3$-alkoxy group, a C$_1$-C$_3$-haloalkoxy group, a heterocycloalkyl group, an aryl group, a (R$^{18}$)-(heterocycloalkylene)-(arylene)-O— group, an aryl-O— group, an aryl-(C$_1$-C$_3$-alkylene)-O— group, a (R$^{19}$)—S(O)$_2$-arylene-O— group, a (R$^{19}$)S(O)$_2$-heterocycloalkylene-arylene-O— group and an aryl-heteroarylene-O— group;

a phenyl group,
a group

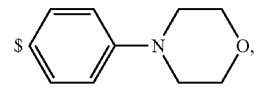

a group

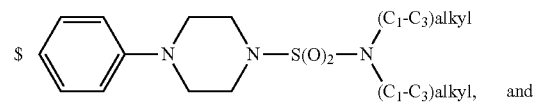

a group

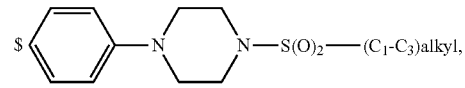

wherein $ is the point of attachment to the nitrogen atom, to which R$^{15}$ is attached, or a tautomer, an N-oxide, or a salt thereof, or a salt of a tautomer, or a salt of an N-oxide, or a mixture of same.

In further embodiments, the present invention includes compounds of formula (I), supra, in which R$^{15}$ is independently selected from R$^{15}$ is selected from a hydrogen atom,
a C$_1$-C$_3$-alkyl group, which is optionally substituted with one or more substituents selected from a halogen atom, a C$_1$-C$_3$-alkyl group, a C$_1$-C$_3$-haloalkyl group, a C$_1$—C$_3$-hydroxyalkyl group, a C$_1$-C$_3$-alkoxy group, a (C$_1$-C$_3$-alkyl)-C(O)—O— group, a heterocycloalkyl group, a heterocycloalkyl-(C$_1$-C$_3$-alkylene) group, a phenyl group,
a benzyl group;
a C$_1$-C$_3$-alkoxy-(C$_1$-C$_6$-alkylene)-O—C(O)— group,
a heterocycloalkyl-(C$_1$-C$_6$-alkylene)-O—C(O)— group,
a phenyl group, a group

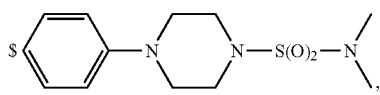

a group

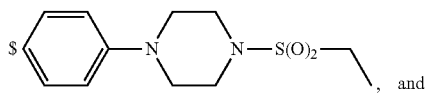, and a group

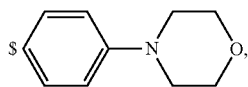

wherein $ is the point of attachment to the nitrogen atom, to which $R^{15}$ is attached,
or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is selected from a hydrogen atom, a $C_1$-$C_3$-alkyl group, a $C_1$-$C_3$-haloalkyl group, e.g. a phenyl group, a benzyl group, a group

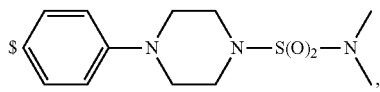

a group

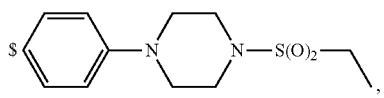

and a group

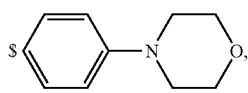 [SMILES: c1ccc(N2CCOCC2)cc1]

or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is selected from
$R^{15}$ is selected from a hydrogen atom, a $C_1$-$C_3$-alkyl group, a $C_1$-$C_3$-haloalkyl group, a $C_1$-$C_4$-hydroxyalkyl group, a ($C_1$-$C_3$-alkyoxy)-($C_1$-$C_3$-alkylene)- group, a ($C_1$-$C_3$-alkyl)-C(O)—O—($C_1$-$C_4$)alkylene- group, a ($C_1$-$C_3$-alkyoxy)-($C_1$-$C_3$-alkylene)-O—C(O)— group, a heterocycloalkyl-($C_1$-$C_3$-alkylene)-O—C(O)— group, and a heterocycloalkyl-($C_1$-$C_3$-alkylene) group;
or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is selected from a hydrogen atom, a $C_1$-$C_3$-alkyl group and a $C_1$-$C_3$-haloalkyl group;
or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is selected from
$R^{15}$ is selected from a hydrogen atom, a —$(CH_2)_2O$—$CH_3$ group, a —C(O)—O—$(CH_2)_2O$—$CH_3$ group,
a —C(O)—O—$(CH_2)_2$-(oxetan-4-yl) group, a —$(CH_2)_2$-(oxetan-4-yl)- group, a —$(CH_2)_2$—(N-morpholinyl) group, ($CH_2CHF_2$), a —$(CH_2)_2CHF_2$ group, a —$(CH_2)_4$—O—C(O)—$CH_3$ group, a —$(CH_2)_2$—C($CH_3$)$_2$—OH group, a —$(CH_2)_4$—OH group, a —$(CH_2)_3$—OH group, and —$CH_3$ group, or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is selected from a hydrogen atom, a methyl group, a 2,2-difluoroethyl group, and a 2,2,2-trifluoroethyl group;
or a tautomer, an N-oxide, or a salt thereof, or a salt of a tautomer, or a salt of an N-oxide, or a mixture of same.

In yet further embodiments, the present invention includes compounds of formula (I), supra, in which $R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group, and a $C_1$-$C_3$-alkyl-O—C(═O)— group; or a tautomer, an N-oxide, or a salt thereof, or a salt of a tautomer, or a salt of an N-oxide, or a mixture of same.

In yet further embodiments, the present invention includes compounds of formula (I), supra, in which $R^{16}$ and $R^{17}$ are each independently selected from a hydrogen atom, a $C_1$-$C_6$-alkyl group, and a $C_1$-$C_6$-haloalkyl group or a tautomer, an N-oxide, or a salt thereof, or a salt of a tautomer, or a salt of an N-oxide, or a mixture of same.

In further embodiments, the present invention includes compounds of formula (I), supra, in which $R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a C(O)OR$^{21}$—($C_1$-$C_3$-alkylene)- group, a —C(O)OR$^{21}$ group, a —C(O)NR$^{20}$R$^{21}$ group, a ($C_1$-$C_3$-alkyl)-O—($C_1$-$C_3$-alkylene)-C(O)— group, a ($C_1$-$C_6$-alkyl)-C(O)— group, and a $C_3$-$C_6$-cycloalkyl-C(O)— group;
or a tautomer, an N-oxide, or a salt thereof, or a salt of a tautomer, or a salt of an N-oxide, or a mixture of same.

In yet further embodiments, the present invention includes compounds of formula (I), supra, in which $R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a —C(O)OR$^{21}$ group, a —C(O)NR$^{20}$R$^{21}$ group, and ($C_1$-$C_6$-alkyl)-C(O)— group;
or a tautomer, an N-oxide, or a salt thereof, or a salt of a tautomer, or a salt of an N-oxide, or a mixture of same.

In further embodiments, the present invention includes compounds of formula (I), supra, wherein $R^{19}$ is selected from a $C_1$-$C_3$-alkyl group, a $C_3$-$C_6$-cycloalkyl group, and a NR$^{20}$R$^{21}$ group; and
or a tautomer, an N-oxide, or a salt thereof, or a salt of a tautomer, or a salt of an N-oxide, or a mixture of same.

In further embodiments, the present invention includes compounds of formula (I), supra, wherein $R^{19}$ is a $C_1$-$C_3$- alkyl group, or a tautomer, an N-oxide, or a salt thereof, or a salt of a tautomer, or a salt of an N-oxide, or a mixture of same.

In further embodiments, the present invention includes compounds of formula (I), supra, in which $R^{20}$ and $R^{21}$ are each independently selected from a hydrogen atom and a $C_1$-$C_6$-alkyl group;
or a tautomer, an N-oxide, or a salt thereof, or a salt of a tautomer, or a salt of an N-oxide, or a mixture of same.

In further embodiments, the present invention includes compounds of formula (I), supra, in which $R^{20}$ and $R^{21}$ are each independently selected from a hydrogen atom and a $C_1$-$C_3$-alkyl group; or a tautomer, an N-oxide, or a salt thereof, or a salt of a tautomer, or a salt of an N-oxide, or a mixture of same.

Furthermore it is understood that the invention includes any subcombination of the disclosed single embodiments herein for certain residues or subcombination of residues of formula (I).

The present invention includes any sub-combination within any embodiments or aspects of the present invention of compounds of general formula (I), supra.

The present invention includes any sub-combination within any embodiments or aspects of the present invention of compounds or intermediate compounds of general formula (I or II). The present invention includes the compounds of general formula (I) which are disclosed in the Example Section of this text, infra.

General Synthesis of Compounds of General Formula (I) of the Present Invention

A. General Synthesis Route

Scheme 1

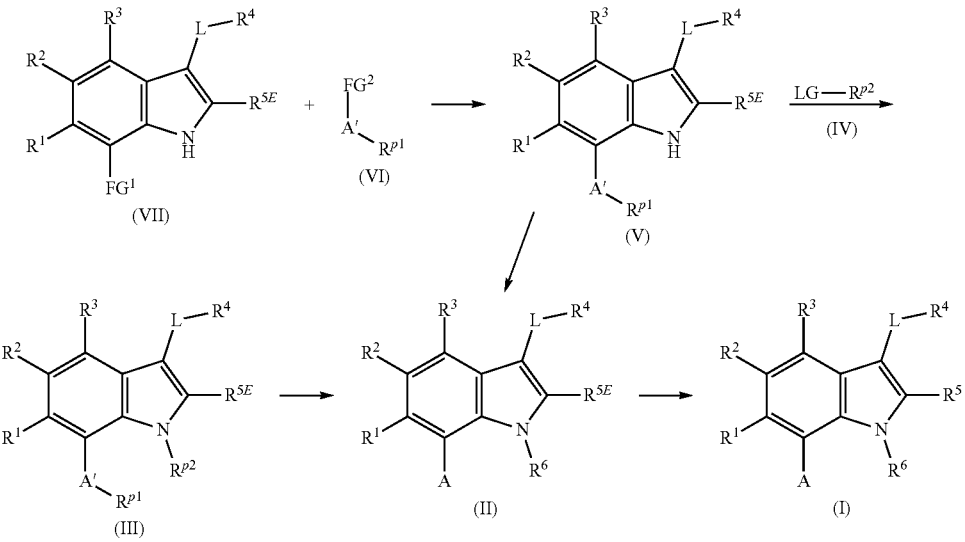

In further embodiments, the present invention includes compounds of formula (I), or a tautomer, an N-oxide, or a salt thereof or a salt of a tautomer or a N-oxide or a mixture of same.

In further embodiments, the present invention includes compounds of formula (I), or a salt thereof.

In further embodiments, the present invention includes compounds of formula (I), or a tautomer or a salt thereof or a salt of a tautomer or a mixture of same.

In further embodiments, the present invention includes compounds of formula (I), which are salts.

One embodiment of the present invention is a salt of a compound of formula (I) such as e.g. an ammonium salt, a diethylamine salt, a formic acid salt, and a trifluoroacetic acid salt.

In further embodiments, the present invention includes compounds of formula (I), which are a tautomer, or a salt of a tautomer or a mixture of same In further embodiments, the present invention includes compounds of formula (I), which are a an N-oxide, or a salt of an N-oxide or a mixture of same In further embodiments of the first aspect, the present invention provides combinations of two or more of the above mentioned embodiments under the heading "further embodiments of the first aspect of the present invention".

Compounds of general formula (I) can be synthesized according to the general synthesis route depicted in Scheme 1, encompassing a Suzuki coupling of starting materials of formulae (VII) and (VI) to give intermediates of formula (V), elaboration of the macrocylic core by attachment of a group $R^{p2}$ to the indole nitrogen present in compounds of formula (V), by reaction with compounds of formula (IV), in which LG represents a leaving group as defined herein and $R^{p2}$ is discussed below, followed by (or together in one step with) macrocyclisation of the resulting intermediates of formula (III), e.g. by intramolecular nucleophilic substitution, to give macrocyclic intermediates of formula (II). Dependent inter alia on the nature of $R^{p1}$ and $R^{p2}$, which together give rise to a group $^{\#}\text{---}(CH_2)_n\text{---}(B)_t\text{---}(CH_2)_p\text{---}X\text{---}^{\#\#}$, $^{\#}\text{---}(CH_2)_n\text{---}(B)_t\text{---}(CH_2)_p\text{---}X\text{---}^{\#\#}$, $^{\#}\text{---}(C_2\text{-}C_6\text{-alkenylene})\text{-}(B)_t\text{---}(CH_2)_p\text{---}X\text{---}^{\#\#}$, $^{\#}\text{---}(CH_2)_n\text{---}(B)_t\text{---}(C_2\text{-}C_5\text{-alkenylene})\text{-}X\text{---}^{\#\#}$ or $^{\#}\text{---}(CH_2)_q\text{---}(B)\text{---}(CH_2)_r\text{---}(B)\text{---}(CH_2)_v\text{---}X\text{---}^{\#\#}$, which groups are as defined for the compounds of general formula (I) after elaboration into the compounds of the present invention, the conversion of compounds of formula (V) into said macrocyclic intermediates of formula (II) may proceed with or without the intermediacy of intermediates of formula (III); e.g. directly from the compounds of formula (V) to the macrocyclic intermediates of formula (II) without requiring the use of compounds of formula (IV); for details see e.g. the Schemes 2a-2j, infra. Finally, conversion of $R^{5E}$ into $R^5$, e.g. by ester saponification, optionally followed by conversion of the resulting carboxylic acid into an acylsulfonamide according to methods known to the person skilled in the art (see for example: *Bioorg. Med. Chem. Lett.* 2006, 16, 3639-3641; *Bioorg. Med Chem. Lett.* 2012, 22, 713-717; *Org. Lett.* 2012, 14(2), 556-559), yields the compounds of formula (I).

Said general synthesis route commences with a well-known Suzuki coupling of compounds of formula (VII), in which $R^1$, $R^2$, $R^3$, $R^4$ and L are as defined for the compounds of general formula (I), and in which $R^{5E}$ represents a group suitable to act as a precursor of a —C(=O)OH or a tetrazol-5-yl group, preferably a group —C(=O)O—$C_{1-4}$-alkyl, with compounds of formula (VI), in which A', together with the group $R^{p1}$ attached to it, represents a group suitable to act as precursor of a group A as defined for the compounds of general formula (I), to give compounds of formula (V). The group $R^4$, constituting the terminus of the side chain attached to C-3 of the indole core in formula (VII), can alternatively be established on later stage (see e.g. Scheme 2i and its discussion for details). Examples of groups A' are exemplified further below in this chapter.

In formulae (VI) and (VII), $FG^1$ in combination with $FG^2$ represents a pair of functional groups together enabling a Suzuki coupling; either $FG^1$ represents bromo, iodo or a trifluoromethanesulfonyl- group and $FG^2$ represents a group —B($OR^B$)$_2$, or vice versa. Said group —B($OR^B$)$_2$ may be a boronic acid moiety ($R^B$=—H) or an alkyl ester of the boronic acid, e.g. its isopropyl ester ($R^B$=$C_1$-$C_4$-alkyl, e.g. —CH(CH$_3$)$_2$), or an ester derived from a diol such as pinacol in which the boronic acid intermediate forms a cyclic boronic ester, preferably a 4,4,5,5-tetramethyl-1,3,2-dioxaborolane ($R^B$—$R^B$=$C_2$-$C_6$-alkylene, preferably —C(CH$_3$)$_2$—C(CH$_3$)$_2$—). Many boronic acids and their esters are commercially available and their synthesis is well-known to the person skilled in the art; see e.g. D. G. Hall, Boronic Acids, 2005 WILEY-VCH Verlag GmbH & Co. KGaA, Weinheim, ISBN 3-527-30991-8 and references cited therein, and Journal of Medicinal Chemistry, 2015, 58, 2180-2194. Alternatively to boronic acid derivatives, also tetrafluoroborates, in which —BF$_4^-$ replaces the —B($OR^B$)$_2$ moiety, can also be employed.

Said Suzuki coupling reaction can be catalysed by palladium catalysts, exemplified by but not limited to by Pd(0) catalysts such as tetrakis(triphenylphosphine)palladium(0) [Pd(PPh$_3$)$_4$], tris(dibenzylideneacetone)di-palladium(0) [Pd$_2$(dba)$_3$] in combination with a ligand, e.g. a phosphine such as triphenylphosphine, or by Pd(II) catalysts such as dichlorobis(triphenylphosphine)-palladium(II) [Pd(PPh$_3$)$_2$Cl$_2$], dichloropalladium-tricyclohexylphosphine (1:2), palladium(II) acetate in combination with a ligand, e.g. a phosphine such as triphenylphosphine, chloro(2-dicyclohexylphosphino-2',4',6'-triisopropyl-1,1'-biphenyl)[2-(2'-amino-1,1'-biphenyl)]palladium(II), (2-dicyclohexylphosphino-2',4',6'-triisopropyl-1,1'-biphenyl)[2-(2'-amino-1,1'-biphenyl)]palladium(II) methanesulfonate, or by [1,1'-bis(diphenylphosphino)ferrocene]-palladium dichloride, in free form [Pd(dppf)Cl$_2$] or as dichloromethane adduct [Pd(dppf)Cl$_2$×CH$_2$Cl$_2$].

The reaction is preferably carried out in solvents such as 1,2-dimethoxyethane, 1,4-dioxane, DMF, THF, toluene or n-propanol, or mixtures thereof, optionally also in mixture with water, and in the presence of a base such as aqueous potassium carbonate, aqueous sodium carbonate or aqueous potassium phosphate.

The reaction is performed at temperatures ranging from room temperature (i.e. 20° C.) to the boiling point of the solvent. Additionally, the reaction can be performed at temperatures above the boiling point using pressure tubes and a microwave oven. (for a review on Suzuki couplings see: D. G. Hall, Boronic Acids, 2005 WILEY-VCH Verlag GmbH & Co. KGaA, Weinheim, ISBN 3-527-30991-8 and references cited therein).

The reaction is preferably completed after 1 to 36 hours of reaction time.

Synthetic approaches to starting materials of formulae (VI) and (VII) are discussed in context of chapter D, infra.

Compounds of formula (II) can be obtained using various methods described in more detail below, e.g. by reacting compounds of formula (V) with compounds of formula (IV) in which LG represents a leaving group, preferably bromo or iodo, and in which $R^{p2}$ represents a group suitable to act as a precursor for the group $R^6$ as defined for the compounds of general formula (I). The following paragraphs outline more specific examples of said conversion of compounds of formulae (Va), (Vb), (Ve), (Vh) and (Vj), all of them constituting sub-compartments of formula (V), into compounds of (IIa), (IIc), (IIe), (IIf), (IIh) and (IIj), all of them constituting sub-compartments of formula (II), some of which with the intermediacy of compounds of formulae (IIIb), (IIIc), (IIIf) and (IIIh), all of them constituting sub-compartments of formula (III), as discussed in the context of Scheme 1.

Said macrocyclic intermediates of formula (II) can finally be converted into the compounds of general formula (I) as described in further detail in context with Scheme 3, infra.
B. More Specific Synthesis Routes for Establishing the Macrocyclic Core, Schemes 2a-2i:

Examples for $R^{p1}$ and $R^{p2}$ groups, as referred to in the general Synthesis Route of Scheme 1 above, are listed below and are put into their synthetic context in the more specific synthesis routes for establishing the macrocyclic core as present in advanced macrocyclic intermediates of formula (II), from compounds of formula (V), described further below. $R^{p1}$ groups are exemplified by but not limited to groups such as —C(=O)H, —X—OH, —X—(CH$_2$)$_b$—OH, —X—(CH$_2$)$_b$-LG$^2$, —X—(CH$_2$)$_b$-LG$^3$, —X—(CH$_2$)$_c$—OH, —X—(CH$_2$)$_c$—O—(CH$_2$)$_d$—CH=CH$_2$, —CH=CH—(CH$_2$)$_g$—OH, —(CH$_2$)$_{g+2}$-LG$^{10}$, —X—(CH$_2$)$_c$—NR$^{15}$(PG$^2$),

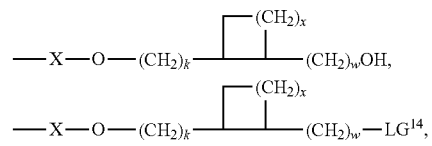

—X—O—(CH$_2$)$_k$—(CF$_2$)$_y$—(CH$_2$)$_z$—OH and —X—O—(CH$_2$)$_k$—(CF$_2$)$_y$—(CH$_2$)$_z$-LG$^{14}$, in which LG$^2$, LG$^3$ and LG$^{10}$, independently from each other, represent a leaving group as defined supra, preferably chloro, bromo or iodo, in which LG$^{14}$ represents a leaving group as defined supra, preferably chloro, bromo or iodo, or an alkylsulfonate or an arylsulfonate, preferably methanesulfonate, in which $R^{15}$ is as defined for the compounds of general formula (I), in which PG$^2$ represents a protective group, and in which indices "b", "c", "d", "g", "k", "w", "x", "y" and "z" are as defined infra, and $R^{p2}$ groups are exemplified by but not limited to groups such as —(CH$_2$)$_a$—N(R$^{15}$)—PG$^1$,

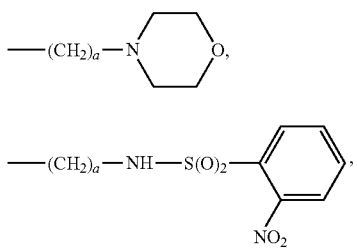

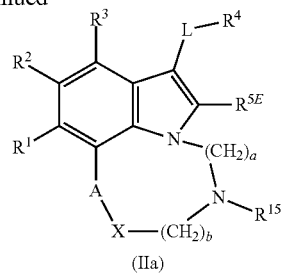

(IIa)

—$(CH_2)_e$—CH=$CH_2$, —$(CH_2)_f$-$LG^9$ or a hydrogen atom, in which $R^{15}$ is as defined for the compounds of general formula (I), $PG^1$ represents a hydrogen atom or a protective group, $LG^9$ represents a leaving group as defined supra, preferably chloro, bromo or iodo, and indices "a", "e" and "f" are as defined infra.

The reader is referred to the fact that the indices "a", "b", "c", "d", "e", "f", "g", "h", "i", "j", "k", "w", "x", "y" and "z" used within and in the context of the following Schemes 2a-2j have been introduced independently from the corresponding indices "n", "p", "q", "r", "t" and "v" used in the claims, in order to reflect diversity of chemotypes encompassed within the general formula (I), and of the various synthesis routes useful for their preparation. Said diversity encompasses inter alia

- the fact that whilst A contributes two carbon atoms to the macrocyclic core if being derived from pyrazole, A contributes three carbon atoms to the macrocyclic core if being derived from benzene;
- the fact that inherently unstable formaldehyde aminals or hemiaminals result when "t" represents an integer 1 and a nitrogen or oxygen atom (but not a carbon atom), which is encoded for by $(B)_t$, is separated from the core indole nitrogen only by one carbon atom;
- the fact that certain parts of precursor groups of —$R^6$-$R^7$ and —$R^6$-$R^{10}$, such as olefinic double bonds, have been drawn explicitly in some of the Schemes for the sake of chemical clarity, mandating independent indices for the remaining parts of said precursor groups.

Scheme 2a

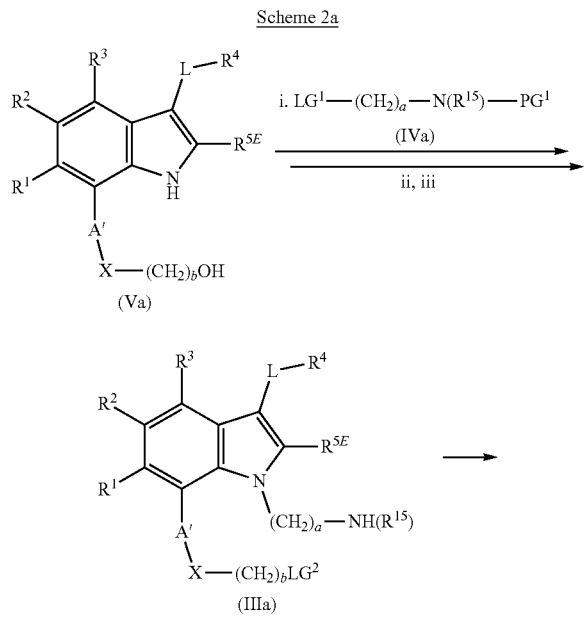

According to Scheme 2a, compounds of formula (IIa), in which $R^7$ (which is a feature of group A as defined for the compounds of general formula (I)) and $R^6$ together form a $^{\#\#}$—X—$(CH_2)_b$—$N(R^{15})$—$(CH_2)_a$—$^{\#}$ group, in which $^{\#}$ represents the point of attachment to the indole nitrogen atom and $^{\#\#}$ represents the point of attachment to the pyrazole carbon atom bearing the $R^7$ substituent, can be obtained from compounds of formula (Va), in which X, $R^1$, $R^2$, $R^3$, $R^4$ and L are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, and in which $R^{P2}$ represents a hydrogen atom and $R^{P1}$ (see General Synthesis Route, Scheme 1) represents a —X—$(CH_2)_b$—OH group (in which the index "b" represents an integer selected from 0, 1, 2, 3, 4, 5, 6 and 7), by (i) reacting with compounds of formula (IVa), in which $R^{15}$ is as defined for the compounds of general formula (I), the index "a" represents an integer selected from 2, 3, 4, 5, 6, 7, 8, 9 and 10, with the proviso that the sum of the integers representing indices "a" and "b" is at least 2 and does not exceed 9, $LG^1$ represents a leaving group and $PG^1$ represents a hydrogen atom or a protective group, followed by (ii) conversion of said —X—$(CH_2)_b$—OH group into a —X—$(CH_2)_b$-$LG^2$ group, and (iii), if $PG^1$ represents a protective group, cleavage of said protective group, to give compounds of formula (IIIa), in which $R^{P1}$ represents a —X—$(CH_2)_b$-$LG^2$ group (in which in turn $LG^2$ represents a leaving group, preferably bromo), and in which $R^{P2}$ represents a —$(CH_2)_a$—$NH(R^{15})$ group. Dependent on the reaction and/or work-up conditions, compounds of the formula (IIIa) can be isolated as free bases or as salts, e.g. salts with hydrochloric acid. Subsequently, said compounds of formula (IIIa) can be subjected to an intramolecular nucleophilic substitution, giving rise to the corresponding macrocyclic intermediates of formula (IIa).

The abovementioned sequence of transformations can be advantageously accomplished by (step i) deprotonating a compound of formula (Va) with a suitable base, such as cesium carbonate, potassium tert-butoxide, or sodium hydride, in a suitable solvent, such as DMF, acetonitrile or THF, followed by addition of a compound of formula (IVa); subsequently (step ii) by halogenation of said —X—$(CH_2)_b$—OH group, e.g. by treatment with tetrabromomethane and triphenylphosphine in a halogenated hydrocarbon, such as dichloromethane, as a solvent, and (step iii), if $PG^1$ represents a protective group, by an appropriate deprotection method (see e.g. T. W. Greene and P. G. M. Wuts in Protective Groups in Organic Synthesis, 4$^{th}$ edition, Wiley 2006), such as the cleavage of a tert-butoxycarbonyl group by hydrogen chloride in dioxane or by trifluoroacetic acid. The subsequent macrocyclization is favorably accomplished by reacting a compound of formula (IIIa) in the presence of a base such as an alkali carbonate or an alkali phosphate, preferably cesium carbonate, in a dipolar aprotic solvent such as dimethylformamide (DMF), dimethylacetamide or N-methyl pyrrolidin-2-one, preferably DMF, at a temperature between 20° C. and 120° C., preferably between 50° C. and 80° C.

Scheme 2b

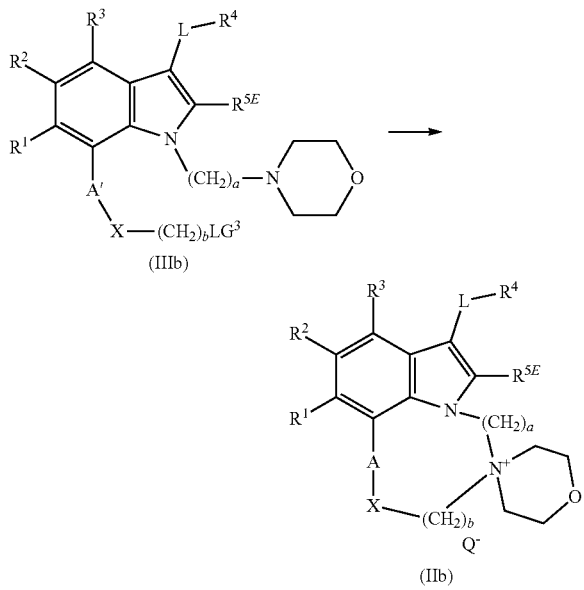

In an analogous fashion, and as outlined in Scheme 2b, compounds of formula (IIb), in which $R^7$ (which is a feature of group A as defined for the compounds of general formula (I)) and $R^6$ together form a

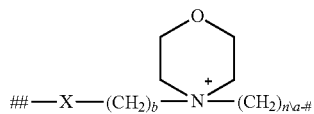

group, in which $^\#$ represents the point of attachment to the indole nitrogen atom and $^{\#\#}$ represents the point of attachment to the pyrazole carbon atom bearing the $R^7$ substituent, and in which Q- represents an anion corresponding to a leaving group, preferably a halide ion such as a bromide ion, can be obtained from compounds of formula (IIIb), in which $R^1$, $R^2$, $R^3$, $R^4$ and L are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, in which $R^{P1}$ (see General Synthesis Route, Scheme 1) represents a —X—$(CH_2)_b$-$LG^3$ group (in which the index "b" represents an integer selected from 0, 1, 2, 3, 4, 5, 6 and 7, and LG represents a leaving group, preferably bromo), and in which $R^{P2}$ (see General Synthesis Route, Scheme 1) represents a

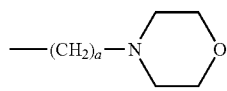

group (in which the index "a" represents an integer selected from 2, 3, 4, 5, 6, 7, 8, 9 and 10), by subjection to an intramolecular nucleophilic substitution, with the proviso that the sum of the integers representing indices "a" and "b" is at least 2 and does not exceed 9. Compounds of formula (IIIb) can be prepared in analogy to the approach outlined in Scheme 2a, supra.

Said intramolecular nucleophilic substitution can be favorably accomplished by reacting a compound of formula (IIIb) in the presence of a base such as an alkali carbonate or an alkali phosphate, preferably potassium carbonate, in a dipolar aprotic solvent such as dimethylformamide (DMF), dimethylacetamide (DMA) or N-methyl pyrrolidin-2-one, preferably DMA, at a temperature between 20° C. and 120° C., preferably between 40° C. and 70° C.

Scheme 2c

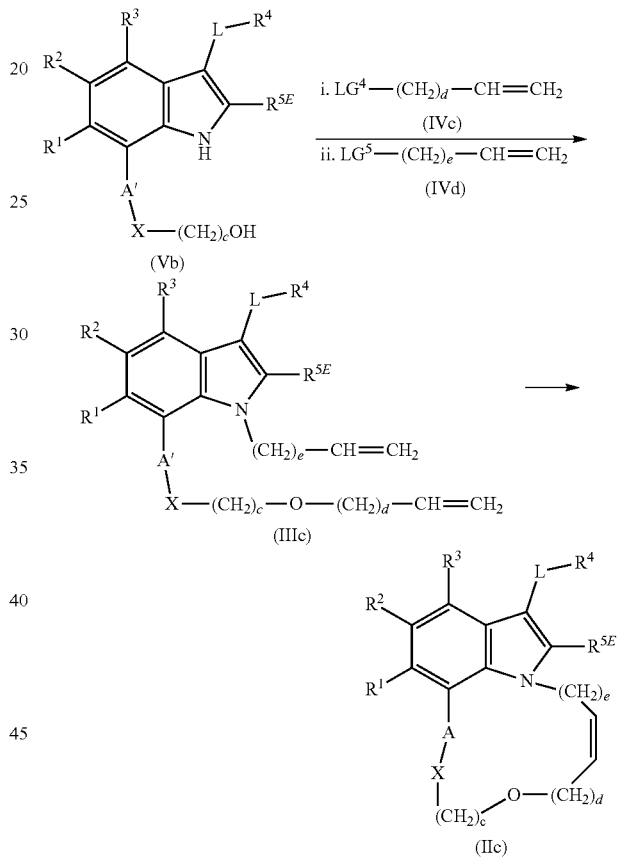

According to Scheme 2c, compounds of formula (IIc), in which $R^7$ (which is a feature of group A as defined for the compounds of general formula (I)) and $R^6$ together form a $^{\#\#}$—X—$(CH_2)_c$—O—$(CH_2)_d$—CH=CH—$(CH_2)_e$—$^\#$ group, in which $^\#$ represents the point of attachment to the indole nitrogen atom and $^{\#\#}$ represents the point of attachment to the pyrazole carbon atom bearing the $R^7$ substituent, can be obtained from compounds of formula (Vb), in which $R^1$, $R^2$, $R^3$, $R^4$, L and X are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, in which $R^{P2}$ represents a hydrogen atom and $R^{P1}$ (see General Synthesis Route, Scheme 1) represents a —X—$(CH_2)_c$—OH group, in which index "c" represents an integer selected from 0, 1 and 2, by reacting with compounds of formula (IVc), followed by compounds of formula (IVd), in which indices "d" and "e", independently from each other, represent an integer selected from 1, 2, 3, 4, 5 and 6, with the proviso that the sum of the integers representing indices "c", "d" and "e" does not exceed 7, and $LG^4$ and $LG^5$, independently from each other, represent a leaving group, to give compounds of formula (IIIc), in which $R^{p1}$ represents a —X—$(CH_2)_c$—O—$(CH_2)_d$—CH=$CH_2$ group, and in which $R^{p2}$ represents a —$(CH_2)_e$—CH=$CH_2$ group. Subsequently, said compounds of formula (IIIc) can be subjected to a ring closing metathesis (RCM) reaction (see e.g. Chem. Rev., 2009, 109 (8), pp 3783-3816), giving rise to the corresponding macrocyclic intermediates of formula (IIc).

The abovementioned sequence of transformations can be advantageously accomplished by deprotonating a compound of formula (Vb) with one equivalent of a suitable base, such as sodium hydride or cesium carbonate, in a suitable solvent, such as THF, dimethylformamide (DMF) or dimethylacetamide (DMA), followed by addition of a compound of formula (IVc), followed by the addition of one further equivalent of a suitable base, such as sodium hydride or cesium carbonate, followed by addition of a compound of formula (IVd). Whenever indices "d" and "e" are identical, said base can be added in one portion, followed by one reagent of formula (IVc) or (IVd). The subsequent macrocyclization is favorably accomplished by reacting a compound of formula (IIIc) in the presence of a catalyst suitable for the performance of a ring closing metathesis exemplified by but not limited to (1,3-bis(2,4,6-trimethylphenyl)-2-imidazolidinylidene)dichloro(phenylmethylene)(tricyclohexyl-phosphine)ruthenium or (1,3-bis-(2,4,6-trimethylphenyl)-2-imidazolidinylidene)dichloro(o-isopropoxyphenyl-methylene)ruthenium, in a halogenated hydrocarbon such as dichloromethane, chloroform, or 1,2-dichloroethane, preferably dichloromethane, at a temperature between 0° C. and 50° C., preferably between 20° C. and 30° C., using pressure tubes and a microwave oven if needed.

Scheme 2c, can be prepared in one synthetic step from compounds of formula (Vb), in which $R^1$, $R^2$, $R^3$, $R^4$, L and X are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, in which $R^{p2}$ represents a hydrogen atom and $R^{p1}$ (see General Synthesis Route, Scheme 1) represents a —X—$(CH_2)_c$—OH group, in which in turn index "c" represents an integer selected from 0, 1 or 2, by reacting with compounds of formula (IVe), in which indices "d" and "e", independently from each other, represent an integer selected from 1, 2, 3, 4, 5 and 6, with the proviso that the sum of the integers representing indices "c", "d" and "e" does not exceed 87 and $LG^6$ and $LG^7$ represent, independently from each other, a leaving group, preferably chloro, bromo or iodo, giving rise to the corresponding macrocyclic intermediates of formula (IIc). If compounds of formula (IVe) are being employed as (Z)-alkenes, macrocyclic compounds of formulas (IIc) can be obtained as single (Z) double bond isomers.

Said reaction can be advantageously accomplished by reacting a compound of formula (Vb) with a compound of formula (IVe) in the presence of a base such as an alkali carbonate or an alkali phosphate, preferably cesium carbonate, preferably in the presence of an alkali iodide, preferably sodium iodide (to convert $LG^6$ and/or $LG^7$ into iodo in situ), in a solvent such as e.g. dimethylformamide (DMF), 1,2-dimethoxyethane, bis-(2-methoxymethyl) ether or acetonitrile, at a temperature between 0° C. and 100° C., preferably between 15° C. and 75° C.

In a preferred embodiment of the invention, said reaction is performed in the presence of one to three equivalents (relative to the compound of formula (IVe) of sodium iodide, in a solvent selected from acetonitrile and bis-(2-methoxymethyl) ether, initially at a temperature between 15° C. and 40° C. for a period of 2 to 30 hours, followed by a temperature between 50° C. and 80° C., for a period of 2 to 8 hours.

Scheme 2d

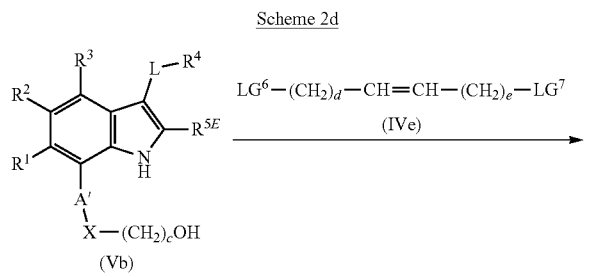

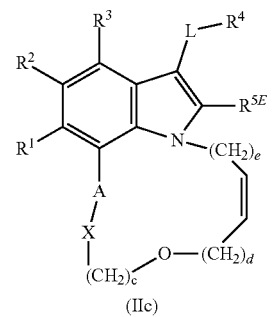

Scheme 2e

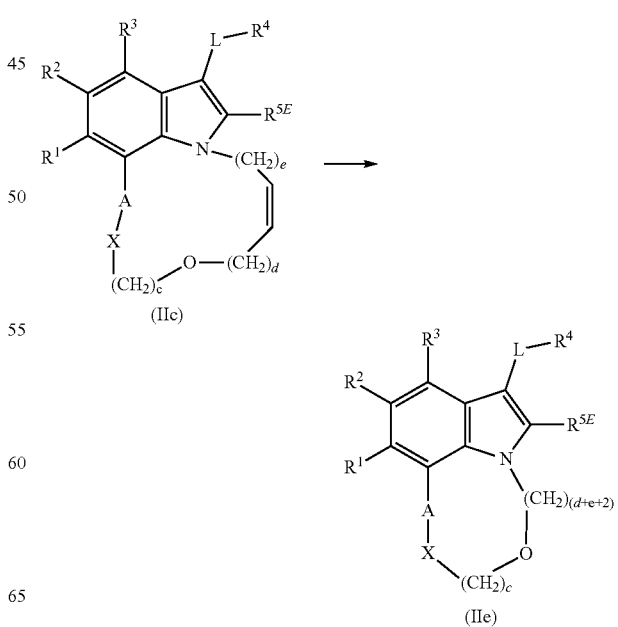

In an alternative approach outlined in Scheme 2d, compounds of the formula (IIc), as defined above in context of According to Scheme 2e, Compounds of formula (IIe), in which R$^7$ (which is a feature of group A as defined for the compounds of general formula (I)) and R$^6$ together form a $^{\#\#}$—X—(CH$_2$)$_c$—O—(CH$_2$)$_{(d+e+2)}$—$^{\#}$ group, in which $^{\#}$ represents the point of attachment to the indole nitrogen atom and $^{\#\#}$ represents the point of attachment to the pyrazole carbon atom bearing the R$^7$ substituent, can be obtained from compounds of formula (IIc), in which R$^1$, R$^2$, R$^3$, R$^4$, L and X are as defined for the compounds of general formula (I), in which R$^{5E}$ represents a group suitable to act as a precursor of a —C(=O)OH or a tetrazol-5-yl group, preferably a group —C(=O)O—C$_{1-4}$-alkyl, and in which R$^7$ and R$^6$ together form a —X—(CH$_2$)$_c$—O—(CH$_2$)$_d$—CH=CH—(CH$_2$)$_e$— group as defined in context of Schemes 2c and 2d, by hydrogenation of the olefinic double bond.

Said hydrogenation of the olefinic double bond can be advantageously accomplished by catalytic hydrogenation which is well known to the person skilled in the art, e.g. by reacting a solution of a compound of formula (IIc) in a solvent such as e.g. methanol, ethanol, THF or ethyl acetate, with an atmosphere of hydrogen under ambient or elevated pressure, in the presence of a hydrogenation catalyst such as e.g. palladium on carbon.

Scheme 2f

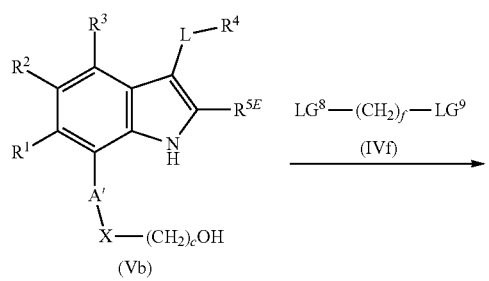

(Vb)

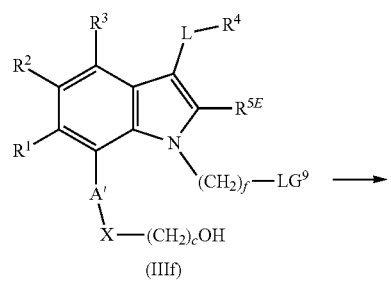

(IIIf)

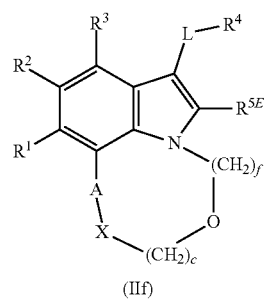

(IIf)

According to Scheme 2f, compounds of the formula (IIf), in which R$^7$ (which is a feature of group A as defined for the compounds of general formula (I)) and R$^6$ together form a $^{\#\#}$—X—(CH$_2$)$_c$—O—(CH$_2$)$_f$—$^{\#}$ group, in which $^{\#}$ represents the point of attachment to the indole nitrogen atom and $^{\#\#}$ represents the point of attachment to the pyrazole carbon atom bearing the R$^7$ substituent, can be obtained from compounds of formula (Vb), in which R$^1$, R$^2$, R$^3$, R$^4$, L and X are as defined for the compounds of general formula (I), in which R$^{5E}$ represents a group suitable to act as a precursor of a —C(=O)OH or a tetrazol-5-yl group, preferably a group —C(=O)O—C$_{1-4}$-alkyl, in which R$^{p2}$ represents a hydrogen atom and R$^{p1}$ (see General Synthesis Route, Scheme 1) represents a —X—(CH$_2$)$_c$—OH group, in which in turn index "c" represents an integer selected from 0, 1 or 2, by reacting with compounds of formula (IVf), in which index "f" represents an integer selected from 2, 3, 4, 5, 6, 7, 8 and 9, with the proviso that the sum of the integers representing indices "c" and "f" is at least 3 and does not exceed 9, and in which LG$^8$ and LG$^9$ represent, independently from each other, a leaving group, preferably bromo or iodo, giving rise to the corresponding macrocyclic intermediates of formula (IIf). Dependent on the reaction conditions and the choice of leaving groups LG$^8$ and LG$^9$, intermediate compounds of formula (IIIf) can be isolated and subsequently cyclised to the corresponding macrocyclic intermediates of formula (IIf).

Said reaction can be advantageously accomplished in one step by reacting a compound of formula (Vb) with a compound of formula (IVf), in which both LG$^8$ and LG$^9$ represent iodo, in the presence of a base such as e.g. an alkali carbonate or an alkali phosphate, preferably cesium carbonate, in a solvent such as e.g. dimethylformamide (DMF) or dimethylsulfoxide (DMSO), at a temperature between 0° C. and 100° C., preferably between 15° C. and 50° C.

Scheme 2g

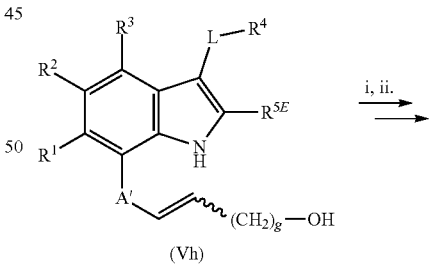

(Vh)

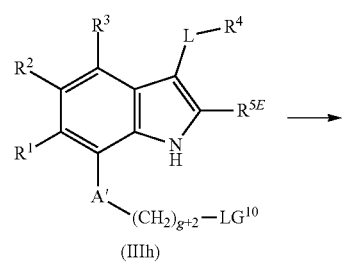

(IIIh)

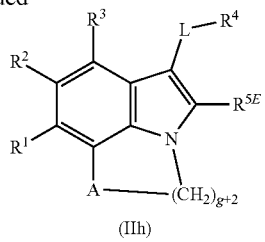

(IIh)

As outlined in Scheme 2 g, compounds of formula (IIh), in which $R^7$ (which is a feature of group A as defined for the compounds of general formula (I)) and $R^6$ together form a $-(CH_2)_{g+2}-$ group, can be obtained from compounds of formula (Vh), in which $R^1$, $R^2$, $R^3$, $R^4$ and L are as defined for the compounds of general formula (I), in which $R^{5E}$ represents a group suitable to act as a precursor of a $-C(=O)OH$ or a tetrazol-5-yl group, preferably a group $-C(=O)O-C_{1-4}$-alkyl, and in which $R^{p2}$ represents a hydrogen atom and $R^{p1}$ (see General Synthesis Route, Scheme 1) represents a $-CH=CH-(CH_2)_g-OH$ group (in which the index "g" represents an integer selected from 2, 3, 4, 5, 6, 7, 8 and 9), by (i) conversion of said $-CH=CH-(CH_2)_g-OH$ group into a $-(CH_2)_{g+2}-OH$ group by means of catalytic hydrogenation, and (ii) conversion of said $-(CH_2)_{g+2}-OH$ group into a $-(CH_2)_{g+2}-LG^{10}$ group, to give compounds of formula (IIIh), in which $R^{p1}$ represents a $-(CH_2)_{g+2}-LG^{10}$ group (in which in turn $LG^{10}$ represents a leaving group, preferably bromo), and in which $R^{p2}$ represents a hydrogen atom. Subsequently, said compounds of formula (IIIh) can be subjected to an intramolecular nucleophilic substitution, giving rise to the corresponding macrocyclic intermediates of formula (IIh).

The abovementioned sequence of transformations can be advantageously accomplished by (step i) hydrogenating a compound of formula (Vh) in an atmosphere of hydrogen at a pressure between 1 and 20 bar, in ethanol as a solvent and in the presence of a palladium on charcoal hydrogenation catalyst, followed (step ii) by halogenation of the resulting $-(CH_2)_{g+2}-OH$ group, e.g. by treatment with tetrabromomethane and triphenylphosphine in a halogenated hydrocarbon, such as e.g. dichloromethane, as a solvent. The subsequent macrocyclization can be favorably accomplished by reacting a compound of formula (IIIh) in the presence of a base such as e.g. potassium tert-butoxide, in an ethereal solvent such as e.g. 1,4-dioxane, THF or 1,2-dimethoxyethane, preferably 1,4-dioxane, at a temperature between 20° C. and 120° C., preferably between 60° C. and 100° C., using pressure tubes and a microwave oven if needed.

Starting materials of the formula (Vh) are available in analogy to Scheme 1, e.g. by employing a compound of formula (VI), in which $FG^2$ represents a halogen atom such as e.g. bromine, and in which $R^{p1}$ represents a $-(CH_2)-OH$ group, which can be (a) oxidized by methods well known to the person skilled in the art, such as e.g. a Swern oxidation, to the corresponding aldehyde (in which $R^{p1}$ represents a $-C(=O)H$ group), followed by (b) reacting said aldehyde in a well-known Wittig or Wadsworth-Horner-Emmons olefination reaction with a suitable phosphonium salt, and (c) subsequently establishing the terminal hydroxy group from a precursor group present in said phosphonium salt, e.g. by removal of a protective group or reduction of a corresponding carboxylic acid ester to give the corresponding hydroxyalkenyl compound of formula (VI) in which $R^{p1}$ represents a $-CH=CH-(CH_2)_g-OH$ group, and finally (d) a Suzuki coupling with a compound of formula (VII) as outlined in Scheme 1.

Scheme 2h

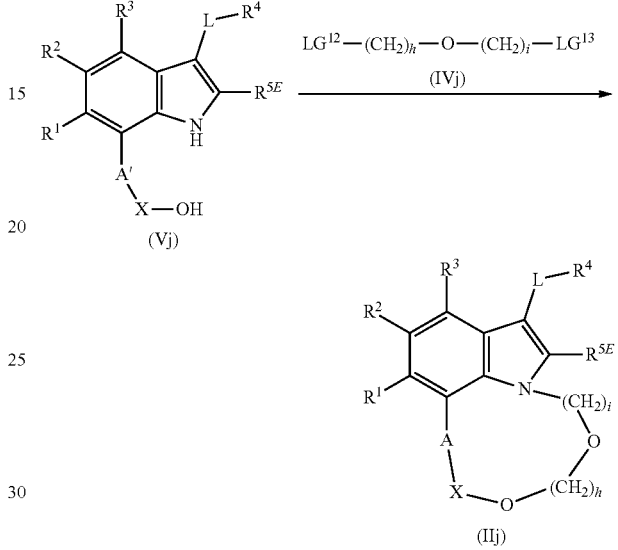

As outlined in Scheme 2h, compounds of formula (IIj), in which $R^7$ (which is a feature of group A as defined for the compounds of general formula (I)) and $R^6$ together form an $^{\#\#}-X-O-(CH_2)_h-O-(CH_2)_i-^\#$ group, in which $^\#$ represents the point of attachment to the indole nitrogen atom and $^{\#\#}$ represents the point of attachment to the pyrazole carbon atom bearing the $R^7$ substituent, can be obtained from compounds of formula (Vj), in which $R^1$, $R^2$, $R^3$, $R^4$, L and X are as defined for the compounds of general formula (I), in which $R^{5E}$ represents a group suitable to act as a precursor of a $-C(=O)OH$ or a tetrazol-5-yl group, preferably a group $-C(=O)O-C_{1-4}$-alkyl, in which $R^{p2}$ represents a hydrogen atom and $R^{p1}$ (see general Synthesis Route, Scheme 1) represents a group $-X-CH_2OH$, which is a hydroxymethyl group, by reaction with compounds of formula (IVj), in which the indices "h" and "i", independently from each other, represent an integer selected from 2, 3, 4, 5 and 6, with the proviso that the sum of the integers representing indices "h" and "i" does not exceed 8, and in which $LG^{12}$ and $LG^{13}$, independently from each other, represent a leaving group, preferably iodo), to directly give the corresponding macrocyclic intermediates of formula (IIj). If said indices "h" and "i" are different from each other, regioisomeric mixtures (inverse arrangement of "h" and "i" in the reaction product) may result which may be separated by methods known to the person skilled in the art, such as e.g. preparative HPLC.

Said reaction can be favorably accomplished by reacting a compound of formula (Vj) with a compound of formula (IVj) in the presence of a base such as e.g. an alkali carbonate or an alkali phosphate, preferably cesium carbonate, in a solvent such bis-(2-methoxyethyl) ether, at a temperature between 15° C. and 100° C., preferably between 15° C. and 80° C.

Scheme 2i

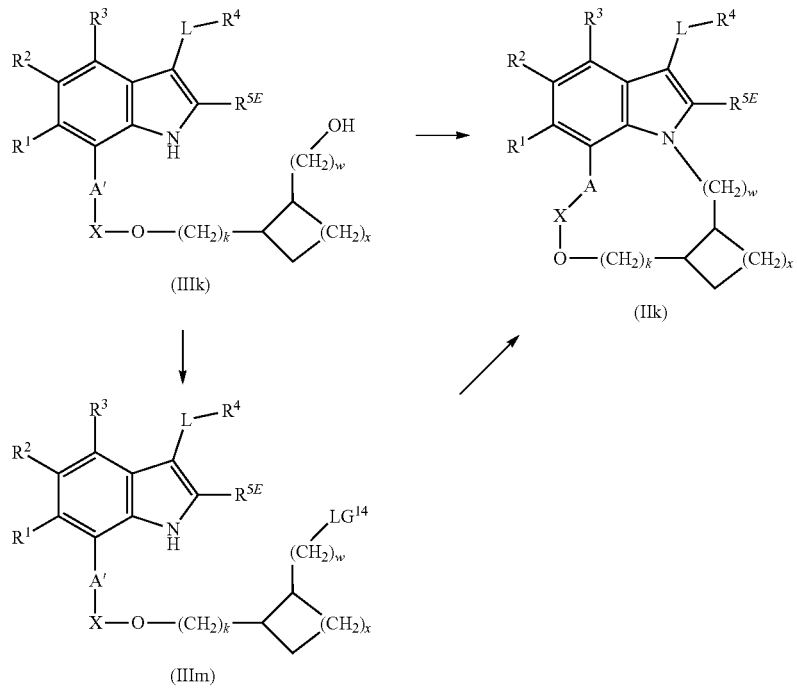

As outlined in Scheme 2i, compounds of formula (IIk), in which $R^7$ (which is a feature of group A as defined for the compounds of general formula (I)) and $R^6$ together form a

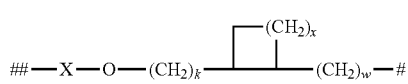

group, in which # represents the point of attachment to the indole nitrogen atom and ## represents the point of attachment to the pyrazole carbon atom bearing the $R^7$ substituent, can be obtained from compounds of formula (IIIk), in which $R^1$, $R^2$, $R^3$, $R^4$, X and L are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, and in which $R^{P2}$ represents a hydrogen atom and $R^{P1}$ (see General Synthesis Route, Scheme 1) represents a

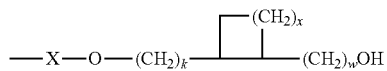

group (in which the index "x" represents an integer selected from 0, 1 and 2, and index "k" represents an integer selected from 1, 2, 3, 4, 5 and 6, in which the index "w" represents an integer selected from 1, 2, 3, 4, 5 and 6, with the proviso that the sum of the integers representing indices "k" and "w" does not exceed 7, by (i) conversion of said

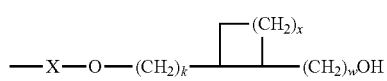

group of the a compound of general formula (IIIk) into a group

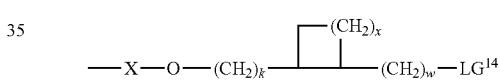

to yield a compound of general formula (IIIm), in which $LG^{14}$ represents a leaving group as defined supra, preferably chloro, bromo or iodo, or an alkylsulfonate or an arylsulfonate, preferably methanesulfonate, and (ii) subsequent cyclisation to yield a compound of general formula (IIk).

Alternatively a compound of general formula (IIIk) can be cyclized to deliver a compound of general formula (IIk).

The abovementioned sequence of transformations can be advantageously accomplished by (step i), reacting a compound of formula (IIIk) in the presence of a base such as e.g. a trialkylamine, preferably triethylamine, in a solvent such as e.g. dichloromethane, at a temperature between 0° C. and 40° C., with an arylsulfonyl chloride, or alkylsulfonyl chloride or alkylsulfonyl anhydride, preferably methanesulfonyl chloride, at a temperature between 0° C. and 40° C., preferably at room temperature, followed by (step ii), reacting a compound of formula (IIIm) in the presence of a base such as e.g. cesium carbonate, in a solvent such as e.g. N,N-dimethylformamide, at a temperature between 40° C. and 150° C., preferably between 80° C. and 130° C.

The macrocyclisation of a compound of formula (IIIk) to deliver a compound of general formula (IIk) can be favorably accomplished by reacting a compound of formula (IIIk) in the presence of triphenylphosphine and di-tert-butyl azodicarboxylate, in a solvent such as e.g. tetrahydrofuran, at a temperature between −10° C. and 40° C., preferably at a temperature between −10° C. and room temperature.

Starting materials of the formula (IIIk) are available in analogy to Scheme 1. Specific examples are given in the Experimental section, infra.

Scheme 2j

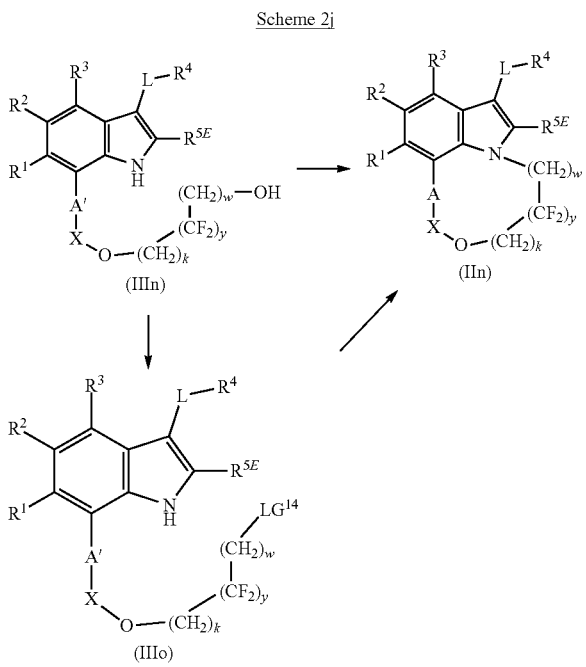

As outlined in Scheme 2j, compounds of formula (IIn), in which $R^7$ (which is a feature of group A as defined for the compounds of general formula (I)) and $R^6$ together form a $^{\#\#}$—X—O—(CH$_2$)$_k$—(CF$_2$)$_y$—(CH$_2$)$_z$—$^\#$ group, in which $^\#$ represents the point of attachment to the indole nitrogen atom and $^{\#\#}$ represents the point of attachment to the pyrazole carbon atom bearing the $R^7$ substituent, can be obtained from compounds of formula (IIIn), in which $R^1$, $R^2$, $R^3$, $R^4$, X and L are as defined for the compounds of general formula (I), in which $R^{5E}$ represents a group suitable to act as a precursor of a —C(=O)OH or a tetrazol-5-yl group, preferably a group —C(=O)O—C$_{1-4}$-alkyl, and in which $R^{p2}$ represents a hydrogen atom and $R^{p1}$ (see General Synthesis Route, Scheme 1) represents a *—X—O—(CH$_2$)$_k$—(CF$_2$)$_y$—(CH$_2$)$_z$—OH group (in which the index "k" represents an integer selected from 1, 2, 3, 4, 5 and 6, and index "y" represents an integer selected from 1, 2, 3, 4, 5 and 6, and index "z" represents an integer selected from 1, 2, 3, 4, 5 and 6, with the proviso that the sum of the integers representing indices "k", "y" and "z" does not exceed 9, by (i) conversion of said $^{\#\#}$—X—O—(CH$_2$)$_k$—(CF$_2$)$_y$—(CH$_2$)$_z$—OH group of the a compound of general formula (IIIn) into a group $^{\#\#}$—X—O—(CH$_2$)$_k$—(CF$_2$)$_y$—(CH$_2$)$_z$-LG$^{14}$ to yield a compound of general formula (IIIo), in which LG$^{14}$ represents a leaving group as defined supra, preferably chloro, bromo or iodo, or an alkylsulfonate or an arylsulfonate, preferably methanesulfonate, and (ii) subsequent cyclisation to yield a compound of general formula (IIn).

Alternatively a compound of general formula (IIIn) can be cyclised to deliver a compound of general formula (IIn).

The abovementioned sequence of transformations can be advantageously accomplished by (step i), reacting a compound of formula (IIIn) in the presence of a base such as e.g. a trialkylamine, preferably triethylamine, in a solvent such as e.g. dichloromethane, at a temperature between 0° C. and 40° C., with an arylsulfonyl chloride, or alkylsulfonyl chloride or alkylsulfonyl anhydride, preferably methanesulfonyl chloride, at a temperature between 0° C. and 40° C., preferably at room temperature, followed by (step ii), reacting a compound of formula (IIIo) in the presence of a base such as e.g. cesium carbonate, in a solvent such as e.g. N,N-dimethylformamide, at a temperature between 40° C. and 150° C., preferably between 80° C. and 130° C.

The macrocyclisation of a compound of formula (IIIn) to deliver a compound of general formula (IIn) can be favorably accomplished by reacting a compound of formula (IIIn) in the presence of triphenylphosphine and di-tert-butyl azodicarboxylate, in a solvent such as e.g. tetrahydrofuran, at a temperature between −10° C. and 40° C., preferably at a temperature between −10° C. and room temperature.

Starting materials of the formula (IIIn) are available in analogy to Scheme 1. Specific examples are given in the Experimental section, infra.

Scheme 2k

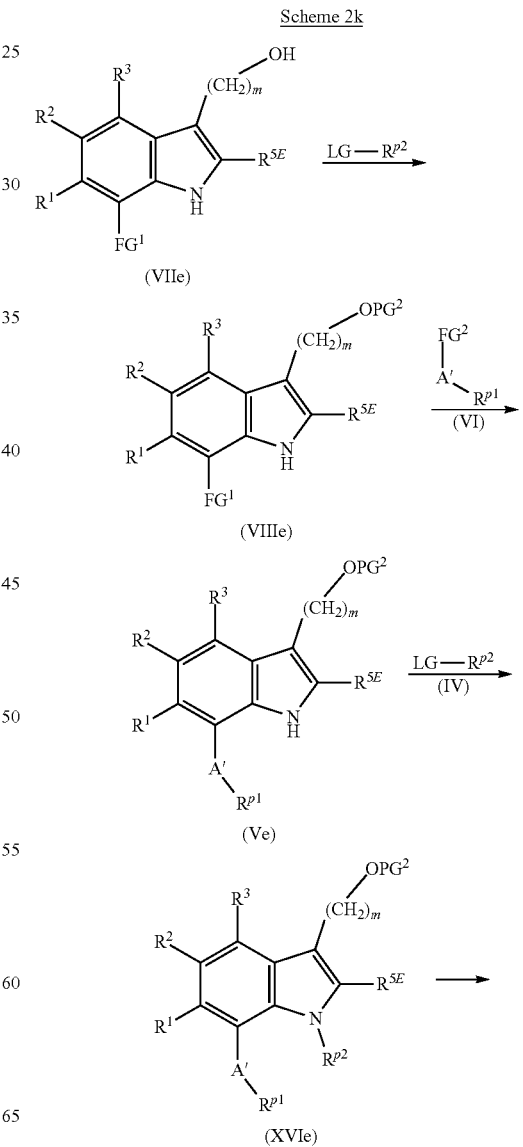

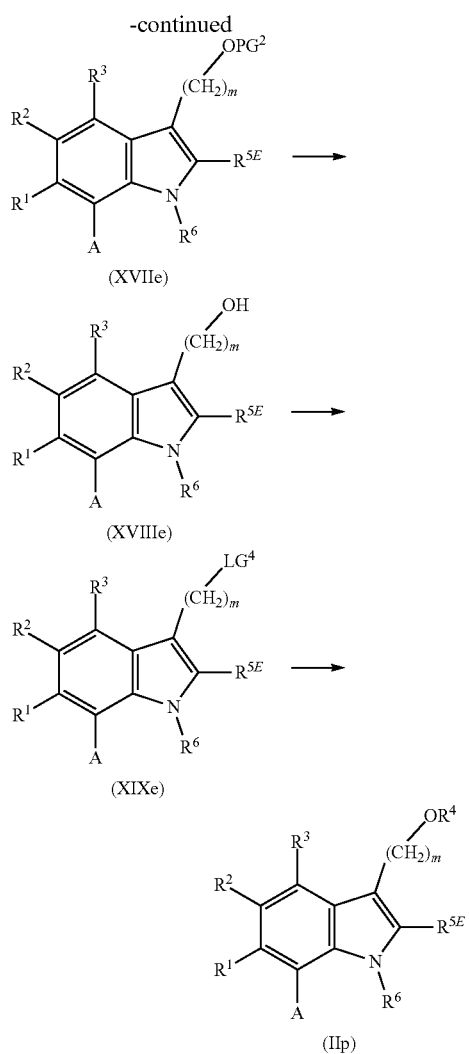

(XVIIe)

(XVIIIe)

(XIXe)

(IIp)

Scheme 2k outlines a modified general synthesis route for certain macrocyclic intermediates of general formula (IIp), constituting a sub-compartment of formula (II), supra, in which E represents an oxygen atom, which employs indole starting materials of formula (VIIe), in turn constituting a sub-compartment of formula (VII), supra. The approach differs from the ones described in the preceding Schemes in that the group $R^4$ is only introduced on late stage, after elaboration of the macrocyclic core, and hence is particularly useful for preparing multiple compounds of the present invention with many different $R^4$ groups.

As shown in Scheme 2i, indole starting materials of formula (VIIe), in which $R^1$, $R^2$, $R^3$, and m are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, and in which $FG^1$ represents bromo, iodo, a trifluoromethanesulfonyl- group or a group —B(OR$^B$)$_2$, preferably a group —B(OR$^B$)$_2$, are protected at their free hydroxy group attached to —(CH$_2$)$_m$— with PG$^2$, a protective group for hydroxy groups as defined herein, such as e.g. tert-butyldimethylsilyl-, by reaction with a suitable reagent such as e.g. tert-butylchlorodimethylsilane, in the presence of a base such as e.g. imidazole, using a halogenated aliphatic hydrocarbon, such as e.g. dichloromethane, as a solvent, to give indole derivatives of formula (VIIf). It is well possible to elaborate said —B(OR$^B$)$_2$ group, if not present already in the compounds of formula (VIIe), from bromo upon introduction of the protective group PG$^2$. Specific examples are given in the Experimental Section, infra.

In formulae (VI), (VIIe) and (VIIIe), FG$^1$ in combination with FG$^2$ represents a pair of functional groups together enabling a Suzuki coupling; either FG$^1$ represents bromo, iodo or a trifluoromethanesulfonyl- group and FG$^2$ represents a group —B(OR$^B$)$_2$, or vice versa. Said group —B(OR$^B$)$_2$ may be a boronic acid moiety (R$^B$=—H) or an alkyl ester of the boronic acid, e.g. its isopropyl ester (R$^B$=C$_1$-C$_4$-alkyl, e.g. —CH(CH$_3$)$_2$), or an ester derived from a diol such as e.g. pinacol in which the boronic acid intermediate forms a cyclic boronic ester, preferably a 4,4,5,5-tetramethyl-1,3,2-dioxaborolane (R$^B$—R$^B$=C$_2$-C$_6$-alkylene, preferably —C(CH$_3$)$_2$—C(CH$_3$)$_2$—).

Said indole derivatives of formula (VIIe) can, in analogy to the methods discussed in the context of Scheme 1, be reacted in a well-known Suzuki coupling with compounds of formula (VI), in which FG$^2$ is as discussed above and in and in which A', together with the group R$^{P1}$ attached to it, represents a group suitable to act as precursor of a group A as defined for the compounds of general formula (I), to give compounds of formula (Ve). Said indole starting materials of formula (VIIe) are well known to the person skilled in the art and can be prepared as described infra.

In subsequent steps, the macrocyclic core can be elaborated using approaches such as e.g. those outlined and discussed in the context of Scheme 1 and Schemes 2a-2h to deliver compounds of general formula (XVIIe)

Said macrocyclic intermediate compounds of formula (XVIIe) can be subsequently subjected to a cleavage of the protective group PG$^2$, according to methods known to the person skilled in the art (see e.g. T. W. Greene and P. G. M. Wuts in Protective Groups in Organic Synthesis, 4$^{th}$ edition, Wiley 2006), to give compounds of the formula (XVIIIe). The hydroxy group present in said compounds of the formula (XVIIIe) can then be converted into LG$^4$, representing a leaving group as defined herein, by methods known to the person skilled in the art, such as e.g. the reaction with tetrabromomethane in the presence of triphenylphosphane, in a suitable solvent such as e.g. a halogenated aliphatic hydrocarbon, e.g. dichloromethane, or by reaction with an arylsulfonyl chloride, or alkylsulfonyl chloride or alkylsulfonyl anhydride, such as e.g. methanesulfonyl chloride, giving rise to compounds of the formula (XIXe). The group $R^4$ can finally be introduced by reaction of said compounds of the formula (XIXe) with a compound of the formula $R^4$—OH, in which $R^4$ is as defined for the compounds of formula (I), in the presence of a base, such as e.g. sodium hydride or cesium carbonate, in a solvent such as e.g. tetrahydrofuran or N,N-dimethylformamide (DMF), to give compounds of formula (IIp).

Alternatively, the compounds of formula (IIp) can be obtained by reacting an alcohol $R^4$—OH, in which $R^4$ is as defined for the compounds of formula (I) and a compound of formula (XVIIIe) in the presence of triphenylphosphine and diisopropyl azodicarboxylate or di-tert-butyl azodicarboxylate, in a solvent such as e.g. tetrahydrofuran, at a temperature between −10° C. and 40° C., preferably at a temperature between −10° C. and room temperature.

Specific examples are given in the Experimental section, infra.

Scheme 2z

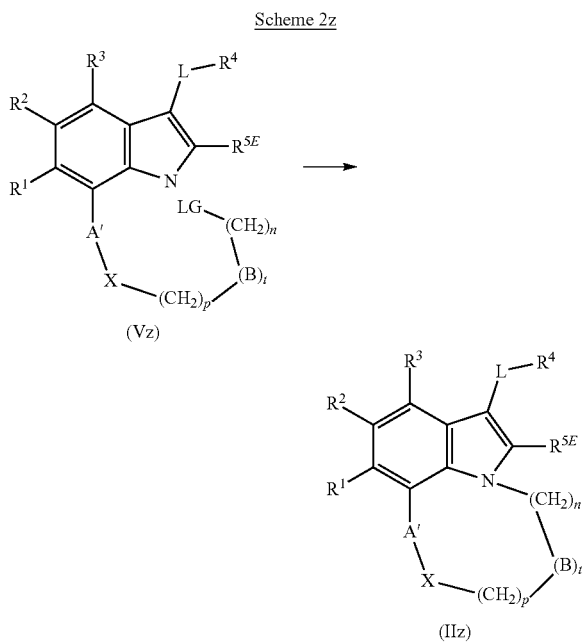

According to Scheme 2z, compounds of formula (IIz), in which $R^7$ (which is a feature of group A as defined for the compounds of general formula (I)) and $R^6$ together form a #—$(CH_2)_n$—$(B)_t$—$(CH_2)_p$—X—## group, in which B, t, n, p and X are as defined for the compounds of the general formula (I) and wherein one or more $CH_2$ groups may be unsubstituted or substituted with one or more substituents as defined for the compounds of the general formula (I) and wherein optionally if two such substituents are bound to the same atom they may form together a 3- to 6-membered spiro ring as described for the compounds of the general formula (I), # represents the point of attachment to the indole nitrogen atom and ## represents the point of attachment to the pyrazole carbon atom bearing the $R^7$ substituent, can be obtained from compounds of formula (Vz), in which $R^1$, $R^2$, $R^3$, $R^4$, B, t, n, p and L are as defined for the compounds of general formula (I), in which $R^{5E}$ represents a group suitable to act as a precursor of a —C(=O)OH group such as e.g. an ester group, or a tetrazol-5-yl group, preferably a —C(=O)O—$C_{1-4}$-alkyl group, in which $R^{P2}$ represents a hydrogen atom and $R^{P1}$ (see General Synthesis Route, Scheme 1) represents a —X—$(CH_2)_p$—$(B)_t$—$(CH_2)_n$-LG group, in which LG represents a suitable leaving group, preferably in which LG represents —OH, —Br, —$OSO_2CF_3$ or —$OSO_2CH_3$, more preferably in which LG represents —OH, by direct alkylation of the indole nitrogen atom, such as e.g. by nucleophilic substitution or preferably by reacting in a so-called Mitsunobu reaction (see e.g. O. Mitsunobu, Synthesis 1981, 1, 1-28) with an azodicarboxylate of the formula $C_1$-$C_4$-alkyl-$O_2$C—N=N—$CO_2$—$C_1$-$C_4$-alkyl, preferably diisopropyl azodicarboxylate or di-tert-butyl azodicarboxylate, and a phosphine $(R^P)_3P$, in which the three groups $R^P$ are independently selected from each other from $C_1$-$C_4$-alkyl, phenyl, and furan-2-yl, wherein phenyl is optionally substituted one or two times with $C_1$-$C_3$-alkyl, $C_1$-$C_3$-alkoxy, or halogen; giving rise to the corresponding macrocyclic intermediates of formula (IIz). Optionally, cyanomethylene phosphoranes of the formula NC—C=$PR^P_3$ can be used, wherein the three groups $R^P$ are as defined above, preferably wherein the three groups $R^P$ are selected from $C_1$-$C_4$-alkyl, more preferably wherein the three groups $R^P$ are n-butyl. Cyanomethylene phosphoranes are easily accessible to a skilled person via literature procedures (see e.g. T. Tsunoda, Tetrahedron Lett. 1994, 35, 5081) and/or commercially available.

Said reaction can be advantageously accomplished in a solvent selected from an acyclic or cyclic ether, such as e.g. tetrahydrofurane, tetrahydropyrane, 1,2-dimethoxyethane, bis-(2-methoxymethyl) ether, diethyl ether, or in a dipolar aprotic solvent, such as e.g. N,N-dimethylformamide, N,N-dimethylacetamide or acetonitrile, or an aliphatic halogenated hydrocarbon of the formula $C_1$-$C_3$-haloalkyl-H, such as e.g. dichloromethane, chloroform, or 1,2-dichloroethane, at a temperature in a range from 0° C. to 60° C. Preferably, the reaction is carried out in tetrahydrofurane at room temperature, that is, in a temperature range from 20° C. to 25° C.

Phosphines $(R^P)_3P$ and azodicarboxylates of the formula $C_1$-$C_4$-alkyl-$O_2$C—N=N—$CO_2$—$C_1$-$C_4$-alkyl are widely commercially available.

Specific examples are given in the Experimental section, infra.

In a further embodiment, the present invention relates to a process for the preparation for a compound of formula (I) as defined in any embodiment supra or according to any of claims 1-6 or a tautomer, or a salt thereof, or a salt of a tautomer, or a mixture of same, said process comprising (i) providing a compound of formula (IIz)

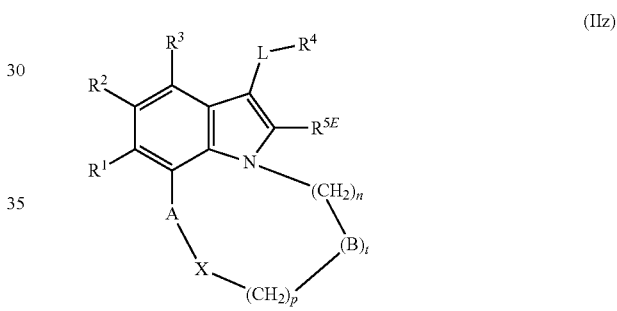

wherein

A, X, $R^1$, $R^2$, $R^3$, $R^4$, B, t, n, p and L are as defined for the compounds of general formula (I) supra $R^{5E}$ is a group suitable to act as a precursor of a —C(=O) OH group, preferably wherein $R^{5E}$ is an ester group, more preferably wherein $R^{5E}$ is a-C(=O)O—$C_{1-4}$-alkyl group, more preferably wherein $R^{5E}$ is a C(=O) $OCH_2CH_3$ group;

(ii) converting $R^{5E}$ to $R^E$, preferably by ester saponification, wherein providing a compound of formula (IIz) in step (i) optionally comprises converting a compound of formula (Vz)

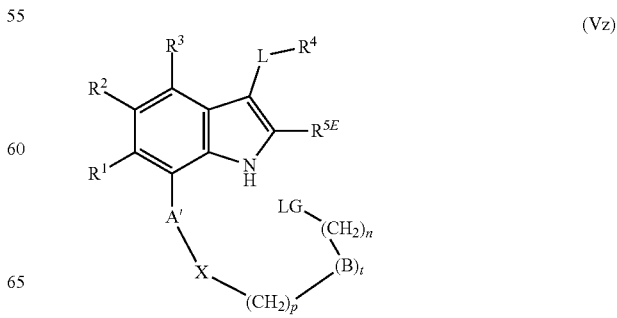

wherein
A' is A
LG is a suitable leaving group, preferably wherein LG is selected from —OH, —Br, —OSO$_2$CF$_3$ or —OSO$_2$CH$_3$, more preferably wherein LG is —OH;
into a compound of formula (IIz), preferably by a ring closure reaction, more preferably by a Mitsunobu reaction.

In a further embodiment, the present invention relates to a process for the preparation of a compound of formula (IIz) or a tautomer, or a salt thereof, or a salt of a tautomer, or a mixture of same,

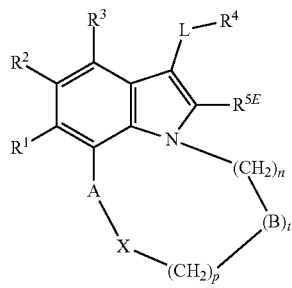

(IIz)

wherein
A, X, R$^1$, R$^2$, R$^3$, R$^4$, B, t, n, p and L are as defined for the compounds of general formula (I) supra;
R$^{5E}$ is a group suitable to act as a precursor of a —C(=O)OH group, preferably wherein R$^{5E}$ is an ester group, more preferably wherein R$^{5E}$ is a —C(=O)O—C$_{1-4}$-alkyl group, more preferably wherein R$^{5E}$ is a C(=O)OCH$_2$CH$_3$ group;
said process comprising converting a compound of formula (Vz)

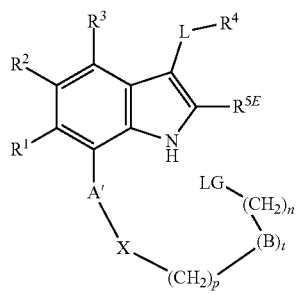

(Vz)

wherein
A' is A
LG is a suitable leaving group, preferably wherein LG is selected from —OH, —Br, —OSO$_2$CF$_3$ or —OSO$_2$CH$_3$, more preferably wherein LG is —OH
into a compound of formula (IIz), preferably by a ring closure reaction, more preferably by a Mitsunobu reaction.

In a further preferred embodiment, the present invention relates to a process for the preparation for a compound of formula (I) or a tautomer, or a salt thereof, or a salt of a tautomer, or a mixture of same, wherein
A is

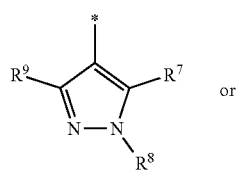

(A1)

or

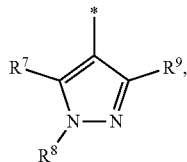

(A2)

wherein R$^6$ and R$^7$, together with two carbon atoms of the pyrazole ring, two carbon atoms of the indole moiety and the nitrogen atom to which R$^6$ is attached, form a 10-membered or 11-membered ring and $^{\#\#}$ is the point of attachment of these moieties to the indole carbon atom bearing the A substituent R$^1$ is a chlorine atom;
R$^2$ and R$^3$ are each a hydrogen atom;
R$^4$ is an aryl group, which is unsubstituted or substituted with a halogen atom;
L is a group —(CH$_2$)$_m$-E-;
E is an oxygen atom and constitutes the connecting element to R$^4$,
m is 3;
R$^5$ is a COOH group;
—R$^6$-R$^7$— is $^{\#}$—(CH$_2$)$_n$—(B)$_t$(CH$_2$)$_p$—X—$^{\#\#}$, and wherein $^{\#}$ is the point of attachment with the indole nitrogen atom and $^{\#\#}$ is the point of attachment with the pyrazole carbon atom bearing the R$^7$ substituent and
wherein one or more —CH$_2$— groups may be unsubstituted or substituted with one or more substituents independently selected from a halogen atom, a hydroxy group, a NR$^{16}$R$^{17}$ group, a C$_1$-C$_3$-alkyl group, a C$_1$-C$_3$-haloalkyl group, and a C$_1$-C$_3$-alkoxy group, and and wherein optionally if two such substituents are bound to the same atom they may form together a 3-membered to 6-membered spiro ring, and
X is an unsubstituted —CH$_2$— group;
n is 3 or 4;
t is 1;
p is 0
wherein the integers selected for variables n, t, and p, result in forming a 10-membered to 11-membered ring independently from the selection of variable A1 or A2;
B is independently selected from —O— and —N(R$^{15}$)—;
R$^8$ is selected from a hydrogen atom and,
a C$_1$-C$_4$-alkyl group, which is unsubstituted or substituted with one or more substituents independently selected from a halogen atom, a hydroxy group, a C$_3$-C$_6$-cycloalkyl group and a heterocycloalkyl group;
R$^9$ is a C$_1$-C$_4$-alkyl group,
a C$_1$-C$_3$-hydroxyalkyl group,
a C$_1$-C$_3$-haloalkyl group,
a C$_1$-C$_3$-alkyl-O— group,
a C$_1$-C$_3$-haloalkoxy group,
a C$_1$-C$_3$-alkyl-O—(C$_1$-C$_3$-alkylene)- group,
a (C$_3$-C$_6$)-cycloalkyl group,
a R$^{18}$-(phenylene)-O—(C$_1$-C$_3$-alkylene)- group,
a NR$^{20}$R$^{21}$—(C$_1$-C$_3$-alkylene)- group, and
a (C$_1$-C$_3$-alkyl)-NH—(C$_1$-C$_3$-alkylene)- group;
R$^{15}$ is selected from a hydrogen atom, a C$_1$-C$_3$-alkyl group, a C$_1$-C$_3$-haloalkyl group, a C$_1$-C$_5$-hydroxyalkyl group, a (C$_1$-C$_3$-alkyoxy)-(C$_1$-C$_3$-alkylene)- group, a (C$_1$-C$_3$-alkyl)-C(O)—(C$_1$-C$_4$)alkylene- group, a (C$_1$-C$_3$-alkyoxy)-(C$_1$-C$_3$-alkylene)-O—C(O)— group, a heterocycloalkyl-(C$_1$-C$_3$-alkylene)-O—C(O)— group, and a heterocycloalkyl-(C$_1$-C$_3$-alkylene) group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a —C(O)OR$^{21}$ group, a —C(O)NR$^{20}$R$^{21}$ group, and ($C_1$-$C_6$-alkyl)-C(O)— group; and $R^{20}$ and $R^{21}$ are each independently selected from a hydrogen atom and a $C_1$-$C_3$-alkyl group, said process comprising
(i) providing a compound of formula (IIz)

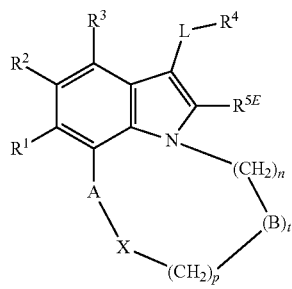

wherein
$R^{5E}$ is a group suitable to act as a precursor of a —C(=O)OH group, preferably wherein $R^{5E}$ is an ester group, more preferably wherein $R^{5E}$ is a —C(=O)O—$C_{1-4}$-alkyl group, more preferably wherein $R^{5E}$ is a C(=O)OCH$_2$CH$_3$ group;

(ii) converting $R^{5E}$ to $R^5$, preferably by ester saponification wherein providing a compound of formula (IIz) in step (i) optionally comprises converting a compound of formula (Vz)

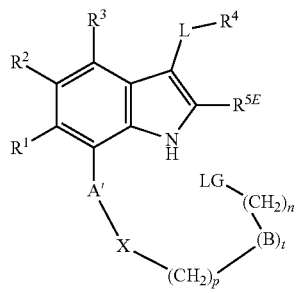

wherein
$R^6$ is H;
$R^7$ is LG-(CH$_2$)$_n$—(B)$_t$—(CH$_2$)$_p$—X—$^{\#\#}$, wherein $^{\#\#}$ is the point of attachment with the pyrazole carbon atom bearing the $R^7$ substituent, wherein one or more —CH$_2$— groups may be unsubstituted or substituted with one or more substituents independently selected from a halogen atom, a hydroxy group, a NR$^{16}$R$^{17}$ group, a $C_1$-$C_3$-alkyl group, a $C_1$-$C_3$-haloalkyl group, and a $C_1$-$C_3$-alkoxy group, and wherein optionally if two such substituents are bound to the same atom they may form together a 3-membered to 6-membered spiro ring;

A' is A;
LG is a suitable leaving group, preferably wherein LG is selected from —OH, —Br, —OSO$_2$CF$_3$ or —OSO$_2$CH$_3$, more preferably wherein LG is —OH;

into a compound of formula (IIz), preferably by a ring closure reaction, more preferably by a Mitsunobu reaction.

In a further preferred embodiment, the present invention relates to a process for the preparation of a compound of formula (IIz) or a tautomer, or a salt thereof, or a salt of a tautomer, or a mixture of same,

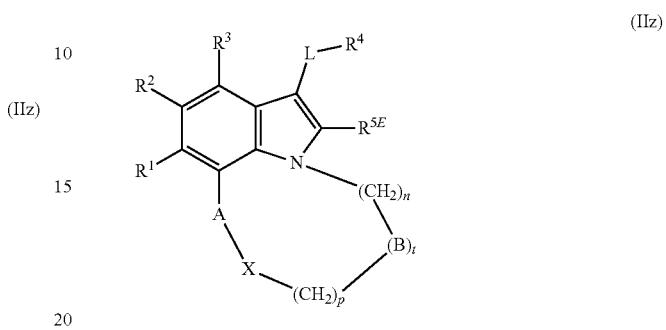

wherein
$R^{5E}$ is a group suitable to act as a precursor of a —C(=O)OH group, preferably wherein $R^{5E}$ is an ester group, more preferably wherein $R^{5E}$ is a —C(=O)O—$C_{1-4}$-alkyl group, more preferably wherein $R^{5E}$ is a C(=O)OCH$_2$CH$_3$ group;
A is

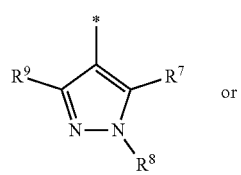

or

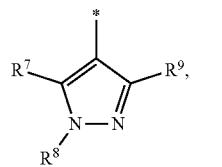

wherein $R^6$ and $R^7$, together with two carbon atoms of the pyrazole ring, two carbon atoms of the indole moiety and the nitrogen atom to which $R^6$ is attached, form a 10-membered or 11-membered ring and $^{\#\#}$ is the point of attachment of these moieties to the indole carbon atom bearing the A substituent;

$R^1$ is a chlorine atom;
$R^2$ and $R^3$ are each a hydrogen atom;
$R^4$ is an aryl group, which is unsubstituted or substituted with a halogen atom;
L is a group —(CH$_2$)$_m$-E-;
E is an oxygen atom and constitutes the connecting element to $R^4$, m is 3;
$R^5$ is a COOH group;
—$R^6$-$R^7$— is $^{\#}$—(CH$_2$)$_n$—(B)$_t$(CH$_2$)$_p$—X—$^{\#\#}$, wherein $^{\#}$ is the point of attachment with the indole nitrogen atom and $^{\#\#}$ is the point of attachment with the pyrazole carbon atom bearing the $R^7$ substituent and
wherein one or more —CH$_2$— groups may be unsubstituted or substituted with one or more substituents independently selected from a halogen atom, a hydroxy group, a NR$^{16}$R$^{17}$ group, a $C_1$-$C_3$-alkyl group, a $C_1$-$C_3$-haloalkyl group, and a $C_1$-$C_3$-alkoxy group, and wherein optionally if two such substituents are bound to the same atom they may form together a 3-membered to 6-membered spiro ring;

X is an unsubstituted —$CH_2$— group;

n is 3 or 4;

t is 1;

p is 0 wherein the integers selected for variables n, t, and p, result in forming a 10-membered to 11-membered ring independently from the selection of variable A1 or A2;

B is independently selected from —O— and —$N(R^{15})$—;

$R^8$ is selected from a hydrogen atom and,
a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group;

$R^9$ is a $C_1$-$C_4$-alkyl group,
a $C_1$-$C_3$-hydroxyalkyl group,
a $C_1$-$C_3$-haloalkyl group,
a $C_1$-$C_3$-alkyl-O— group,
a $C_1$-$C_3$-haloalkoxy group,
a $C_1$-$C_3$-alkyl-O—($C_1$-$C_3$-alkylene)- group,
a ($C_3$-$C_6$)-cycloalkyl group,
a $R^{18}$-(phenylene)-O—($C_1$-$C_3$-alkylene)- group,
a $NR^{20}R^{21}$—($C_1$-$C_3$-alkylene)- group, and
a ($C_1$-$C_3$-alkyl)-NH—($C_1$-$C_3$-alkylene)- group;

$R^{15}$ is selected from a hydrogen atom, a $C_1$-$C_3$-alkyl group, a $C_1$-$C_3$-haloalkyl group, a $C_1$-$C_5$-hydroxyalkyl group, a ($C_1$-$C_3$-alkyoxy)-($C_1$-$C_3$-alkylene)- group, a ($C_1$-$C_3$-alkyl)-C(O)—O—($C_1$-$C_4$)alkylene- group, a ($C_1$-$C_3$-alkyoxy)-($C_1$-$C_3$-alkylene)-O—C(O)— group, a heterocycloalkyl-($C_1$-$C_3$-alkylene)-O—C(O)— group, and a heterocycloalkyl-($C_1$-$C_3$-alkylene) group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a —$C(O)OR^{21}$ group, a —$C(O)NR^{20}R^{21}$ group, and ($C_1$-$C_6$-alkyl)-C(O)— group;

$R^{20}$ and $R^{21}$ are each independently selected from a hydrogen atom and a $C_1$-$C_3$-alkyl group;

said process comprising converting a compound of formula (Vz)

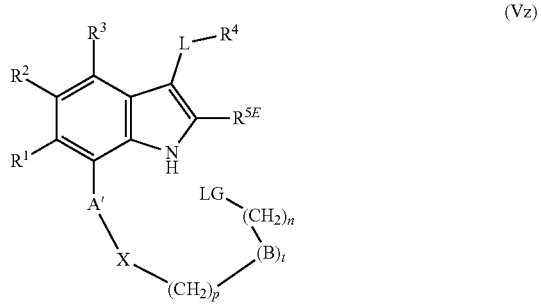

(Vz)

wherein $R^6$ is H;

$R^7$ is LG-$(CH_2)_n$—$(B)_t$—$(CH_2)_p$—X—##, wherein ## is the point of attachment with the pyrazole carbon atom bearing the $R^7$ substituent, wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, and a $C_1$-$C_3$-alkoxy group, and wherein optionally if two such substituents are bound to the same atom they may form together a 3-membered to 6-membered spiro ring;

A' is A

LG is a suitable leaving group, preferably wherein LG is selected from —OH, —Br, —$OSO_2CF_3$ or —$OSO_2CH_3$, more preferably wherein LG is —OH,
into a compound of formula (IIz), preferably by a ring closure reaction, more preferably by a Mitsunobu reaction.

In a further preferred embodiment, the Mitsunobu reaction supra comprises the reaction of a compound of formula (Vz), supra, with an azodicarboxylate of the formula $C_1$-$C_4$-alkyl-$O_2C$—N=N—$CO_2$—$C_1$-$C_4$-alkyl, preferably diisopropyl azodicarboxylate or di-tert-butyl azodicarboxylate, and a phosphine $(R^P)_3P$, in which the three groups $R^P$ are independently selected from each other from $C_1$-$C_4$-alkyl, phenyl, and furan-2-yl, wherein phenyl is optionally substituted one or two times with $C_1$-$C_3$-alkyl, $C_1$-$C_3$-alkoxy, or halogen.

In a further preferred embodiment, the Mitsunobu reaction described above comprises the use of cyanomethylene phosphoranes of the formula NC—C=$P(R^P)_3$, wherein the three groups $R^P$ are independently selected from each other from $C_1$-$C_4$-alkyl, phenyl, and furan-2-yl, wherein phenyl is optionally substituted one or two times with $C_1$-$C_3$-alkyl, $C_1$-$C_3$-alkoxy, or halogen.

In a further preferred embodiment, the three groups $R^P$ in cyanomethylene phosphoranes of the formula NC—C=P $(R^P)_3$ are selected from $C_1$-$C_4$-alkyl, more preferably the three groups $R^P$ are n-butyl.

In a further preferred embodiment, the Mitsunobu reaction is carried out in a solvent selected from an acyclic or cyclic ether, preferably wherein the solvent is selected from tetrahydrofurane, tetrahydropyrane, 1,2-dimethoxyethane, bis-(2-methoxymethyl) ether and diethyl ether.

In a further preferred embodiment, the Mitsunobu reaction is carried out in a dipolar aprotic solvent, preferably wherein the solvent is selected from N,N-dimethylformamide, N,N-dimethylacetamide and acetonitrile.

In a further preferred embodiment, the Mitsunobu reaction is carried out in an aliphatic halogenated hydrocarbon of the formula $C_1$-$C_3$-haloalkyl-H, preferably wherein the solvent is selected from dichloromethane, chloroform and 1,2-dichloroethane.

In a further preferred embodiment, the Mitsunobu reaction is carried out at a temperature in a range from 0° C. to 60° C. Preferably, the reaction is carried out in tetrahydrofurane at room temperature, that is, in a temperature range from 20° C. to 25° C.

C. Conversion into Compounds of Formula (I), Scheme 3:

Scheme 3

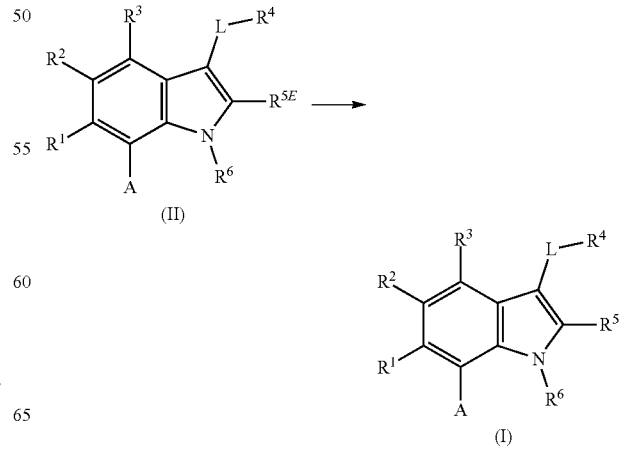

According to Scheme 3, compounds of formula (II) (such as the compounds of the formulae (IIa), (IIb), (IIc), (IIe), (IIf), (IIh), (IIj), (IIk), (IIn) and (IIp)), in which $R^1$, $R^2$, $R^3$, $R^4$, $R^6$, A and L are as defined for the compounds of general formula (I), and in which $R^{5E}$ represents a group suitable to act as a precursor of a —C(=O)OH or a tetrazol-5-yl group, preferably a carboxylic ester group, such as e.g. a —C(=O)O—$C_{1-4}$-alkyl group or a benzyl ester, can be readily converted into compounds of formula (I) by transforming group $R^{5E}$ into group $R^5$ as defined for the compounds of general formula (I), preferably by reacting with an alkali hydroxide, such as e.g. potassium hydroxide, sodium hydroxide, lithium hydroxide, preferably lithium hydroxide, in a mixture of water with THF and/or an aliphatic alcohol of the formula $C_1$-$C_3$-alkyl-OH, preferably methanol or ethanol, at a temperature between 0° C. and 100° C., and subsequent usual workup as known by the person skilled in the art and as for example disclosed in the experimental section.

Said compounds of general formula (I) may be obtained as free acids or converted into pharmaceutically acceptable salts thereof, such as e.g. alkali salts, e.g. sodium or potassium salts, earth alkali salts, e.g. magnesium or calcium salts, and ammonium salts, e.g. ammonium ($NH_4^+$), diethylammonium (herein also referred to as N-ethylethanamine salts) or triethylammonium salts, by methods known to the person skilled in the art. Compounds of the invention featuring a basic nitrogen atom, such as e.g. some of those obtainable from macrocyclic intermediates of formula (IIc), can be isolated as salts with a counteranion of the basic nitrogen, such as e.g. trifluoroacetate, and the like, or as inner carboxylate salts. Further, compounds of formula (I) in which $R^5$ represents a free carboxylic acid group can be optionally converted into an acylsulfonamide according to methods known to the person skilled in the art (see for example: *Bioorg. Med Chem. Lett.* 2006, 16, 3639-3641; *Bioorg. Med Chem. Lett.* 2012, 22, 713-717; *Org. Lett.* 2012, 14(2), 556-559).

Further, single enantiomers of said compounds of general formula (I) may be obtained by methods known to the person skilled in the art, such as e.g. preparative HPLC on a chiral stationary phase, as described supra, and as exemplified in the Experimental Section, infra.

D. Synthesis Routes to Starting Materials of Formulae (VI) and (VII); Schemes 4a-4b:

As outlined in Schemes 4a and 4b below, several approaches, which are intended to illustrate but not to limit the synthetic routes available to the person skilled in the art for this purpose, can be followed in order to prepare starting materials of the formula (VI), as defined in the context of Scheme 1, supra, i.e. in which A', together with the group $R^{p1}$ attached to it, represents a group suitable to act as precursor of a group A as defined for the compounds of general formula (I), and in which $FG^2$, in combination with the group $FG^1$ present in formula (VII), represents a pair of functional groups together enabling a Suzuki coupling; either $FG^1$ represents bromo, iodo or a trifluoromethanesulfonyl- group and $FG^2$ represents a group —$B(OR^B)_2$ as defined supra, or vice versa. Preferably, $FG^2$ represents bromo. Conversion of compounds, in which $FG^2$ represents bromo, into compounds in which $FG^2$ represents a group —$B(OR^B)_2$, is possible on various steps of the outlined synthesis routes using methods well known to the person skilled in the art.

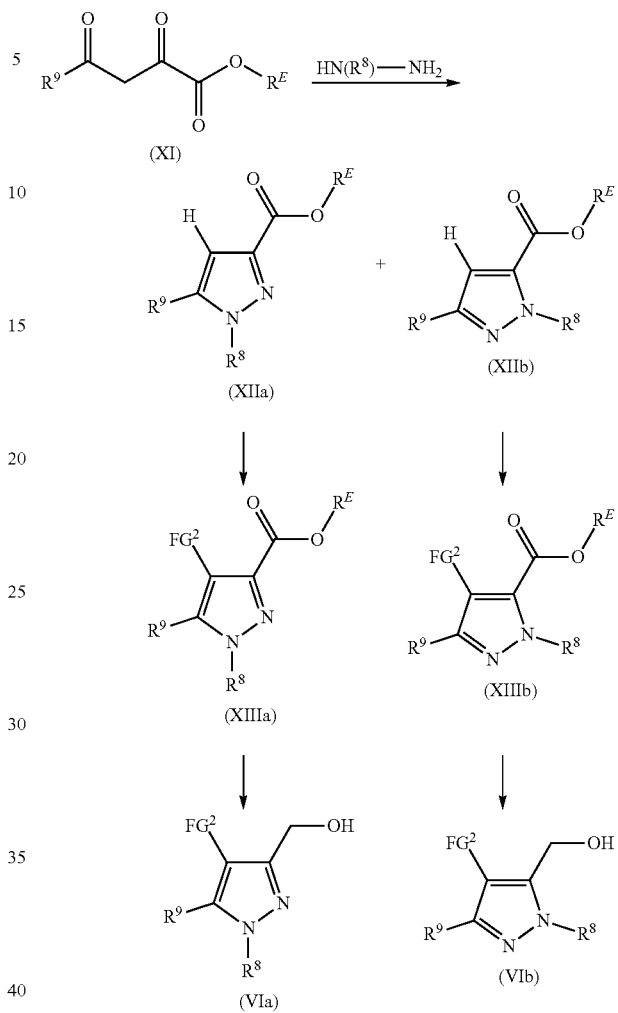

Scheme 4a

Scheme 4a illustrates the synthesis route enabling the preparation of compounds of formula (VI), in which A' is derived from pyrazole, namely compounds of formulae (VIa) and (VIb), both of them constituting sub-compartments for formula (VI).

Said compounds of formulae (VIa) and (VIb) can be prepared from well-known α,γ-diketoesters of formula (XI), in which $R^9$ is as defined for the compounds of general formula (I), and in which $R^E$ represents a $C_1$-$C_6$-alkyl group, by reaction with hydrazines $HN(R^8)$—$NH_2$, in which $R^8$ is as defined for the compounds of general formula (I), to give regioisomeric mixtures of pyrazole derivatives of formulae (XIIa) and (XIIb), which can be separated on this step or on one of the steps described below. If unsubstituted hydrazine ($R^8$=H) is used, $R^8$ groups different from a hydrogen atom can be introduced into compounds of formulae (XIIa) and (XIIb) e.g. by suitable alkylating agents such as e.g. a $C_1$-$C_6$-alkyl halide or a di($C_1$-$C_6$-alkyl)sulfate in the presence of a base, such as e.g. sodium carbonate, in a solvent such as dichloromethane or N,N-dimethylformamide.

Said pyrazole derivatives of formulae (XIIa) and (XIIb) can subsequently reacted with reagents suitable to introduce $FG^2$, such as e.g. N-halo succinimides or solutions of elemental halogens, to give pyrazole derivatives of formulae (XIIIa) and (XIIIb); preferably, N-bromo succinimide in a halogenated hydrocarbon, such as e.g. 1,2-dichloroethane, as a solvent, or bromine in a solvent such as e.g. glacial acetic acid or a halogenated hydrocarbon, such as e.g. dichloromethane, can be used. Said pyrazole derivatives of formulae (XIIIa) and (XIIIb) can be subsequently reduced by a suitable reducing agent not interfering with the groups $FG^2$, such as e.g. lithium borohydride, in a solvent such as e.g. tetrahydrofuran, to give pyrazolyl methanols of formulae (VIa) and (VIb). Specific examples are given in the Experimental section, infra. It is readily recognised by the person skilled in the art that the —$CH_2OH$ group present in said pyrazolyl methanols of formulae (VIa) and (VIb) can be converted in various other $R^{p1}$ groups (see formula (VI)).

Compounds of formulae (XIV) and (XV) are commercially available, and known to the person skilled in the art, in considerable variety. Using known methods, groups $R^{11}$, $R^{12}$ and $R^{13}$ can be broadly modified using known methods at various stages of the synthesis. Protective groups as present in compounds of formula (XIV), and methods of their removal, are well known to the person skilled in the art, see e.g. T. W. Greene and P. G. M. Wuts in Protective Groups in Organic Synthesis, $4^{th}$ edition, Wiley 2006.

Indole based starting materials of formula (VII), in which $R^1$, $R^2$, $R^3$, $R^4$ and L are as defined for the compounds of general formula (I), in which $R^{5E}$ represents a group suitable to act as a precursor of a —C(=O)OH or a tetrazol-5-yl Scheme 4b

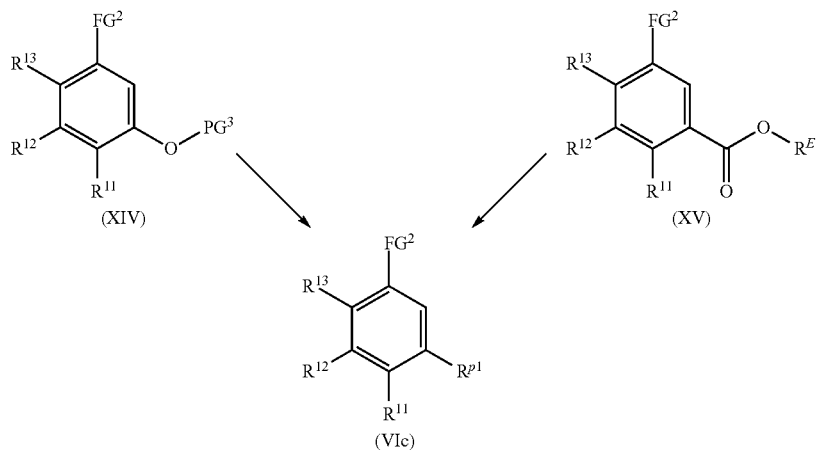

Scheme 4b illustrates synthesis routes enabling the preparation of compounds of formula (VI), in which A' is derived from phenyl, pyridinyl, pyrimidinyl or pyridazinyl, namely compounds of formula (VIc), constituting yet another subcompartment of formula (VI).

Starting from compounds of formula (XIV), in which $R^{11}$, $R^{12}$, and $R^{13}$ are as defined for the compounds of general formula (I), and wherein one or two of the groups selected from $CR^{11}$, $CR^{12}$ or $CR^{13}$ may be replaced by a nitrogen atom, and in which $FG^2$, in combination with the group $FG^1$ present in formula (VII), represents a pair of functional groups together enabling a Suzuki coupling; either $FG^1$ represents bromo, iodo or a trifluoromethanesulfonyl- group and $FG^2$ represents a group —$B(OR^B)_2$ as defined supra, or vice versa, and in which $PG^3$ represents a protective group, compounds of formula (VIc), in which $R^{p1}$ represents a hydroxy group, can be readily obtained. Likewise, compounds of formula (XV), in which $R^{11}$, $R^{12}$, and $R^{13}$ are as defined for the compounds of general formula (I), and wherein one or two of the groups selected from $CR^{11}$, $CR^{12}$ or $CR^{13}$ may be replaced by a nitrogen atom, and in which $FG^2$, in combination with the group $FG^1$ present in formula (VII), represents a pair of functional groups together enabling a Suzuki coupling; either $FG^1$ represents bromo, iodo or a trifluoromethanesulfonyl- group and $FG^2$ represents a group —$B(OR^B)_2$ as defined supra, or vice versa, and $R^E$ represents a-$C_1$-$C_6$-alkyl group, can be converted into compounds of formula (VIc), in which $R^{p1}$ represents a —$CH_2$—OH group, a —C(=O)H group, or a —$CH_2$-$LG^5$ group, in which $LG^5$ represents a leaving group, preferably bromo, in analogy to methods known to the person skilled in the art.

group, preferably a group —C(=O)O—$C_{1-4}$-alkyl, and in which $FG^1$ represents bromo, iodo, a trifluoromethanesulfonyl- group or a group —$B(OR^B)_2$, preferably a group —$B(OR^B)_2$, can be prepared using methods well known to the person skilled in the art, see e.g. Journal of Medicinal Chemistry, 2015, 58, 2180-2194. Said group —$B(OR^B)_2$ may be a boronic acid moiety ($R^B$=—H) or an alkyl ester of the boronic acid, e.g. its isopropyl ester ($R^B$=$C_1$-$C_4$-alkyl, e.g. —$CH(CH_3)_2$), or an ester derived from a diol such as e.g. pinacol in which the boronic acid intermediate forms a cyclic boronic ester, preferably a 4,4,5,5-tetramethyl-1,3,2-dioxaborolane ($R^B$—$R^B$=$C_2$-$C_6$-alkylene, preferably —$C(CH_3)_2$—$C(CH_3)_2$—). Alternatively to boronic acid derivatives, also tetrafluoroborates, in which —$BF_4$— replaces the —$B(OR^B)_2$ moiety, can also be employed.

Modification of any of the substituents, such as e.g. $R^1$, $R^2$, $R^3$, $R^4$, $R^5$, $R^{5E}$, $R^6$, $R^7$, $R^8$, $R^9$, $R^{10}$, $R^{11}$, $R^{12}$, $R^{13}$, $R^{15}$, $R^{p1}$ and $R^{p2}$ can be achieved before and/or after the exemplified transformation. However, also other routes may be used to synthesise the target compounds, in accordance with common general knowledge of a person skilled in the art of organic synthesis. Also, suitable and optionally protected precursor groups of said substituents can be carried through the synthesis routes described in context of the Schemes above, to be elaborated into the actual substituents as defined for the general formula (I) on late stage, as exemplified in the Experimental Section below.

Said modifications can be such as e.g. the introduction of protective groups, cleavage of protective groups, reduction or oxidation of functional groups, formation or cleavage of esters or carboxamides, halogenation, metalation, substitution or other reactions known to a person skilled in the art. These transformations include those which introduce a functionality which allows for further interconversion of substituents. Appropriate protective groups and their introduction and cleavage are well-known to a person skilled in the art (see for example T. W. Greene and P. G. M. Wuts in Protective Groups in Organic Synthesis, 4$^{th}$ edition, Wiley 2006). Further, it is possible that two or more successive steps may be performed without work-up being performed between said steps, e.g. a "one-pot" reaction, as it is well-known to a person skilled in the art.

In accordance with a further aspect, the present invention provides a method of preparing a compound of general formula (I) according to any one of claims 1 to 5, said method comprising the step of allowing an intermediate compound of general formula (II)

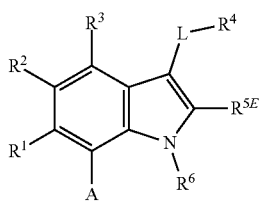

(II)

in which $R^1$, $R^2$, $R^3$, $R^4$, $R^6$, A and L are as defined for the compound of general formula (I) according to any one of claims 1 to 5, and $R^{5E}$ represents a carboxylic ester group or a benzyl ester to react with an alkali hydroxide in a mixture of water with THF and/or an aliphatic alcohol of formula $C_1$-$C_3$-alkyl-OH, at a temperature between 0° C. and 100° C. including 0° C. and 100° C., to transform the group $R^{5E}$ into a group $R^5$ as defined for the compounds of general formula (I), and subsequently optionally to convert the free acid group $R^5$ into a pharmaceutically acceptable salts thereof to obtain a compound of general formula (I)

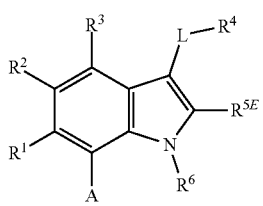

(I)

in which $R^1$, $R^2$, $R^3$, $R^4$, $R^5$, $R^6$, A and L are as defined for the compound of general formula (I) according to any one of claims 1 to 6 or a stereoisomer, a tautomer, an N-oxide, a hydrate, a solvate, or a salt thereof, or a mixture of same and subsequently optionally separating enantiomers by means of preparative HPLC on a chiral stationary phase.

In accordance with a further aspect, the present invention covers a method of preparing compounds of general formula (I) according to any one of claims 1 to 5, said method comprising the step of allowing an intermediate compound of general formula (II)

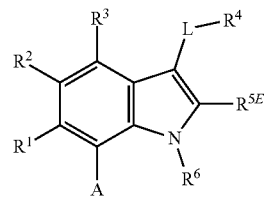

(II)

in which $R^1$, $R^2$, $R^3$, $R^4$, $R^6$, A and L are as defined for the compound of general formula (I) according to any one of claims 1 to 5, and $R^{5E}$ represents a carboxylic ester group or a benzyl ester to react with an alkali hydroxide such as e.g. potassium hydroxide, sodium hydroxide, lithium hydroxide, preferably lithium hydroxide, in a mixture of water with THF and/or an aliphatic alcohol of the formula $C_1$-$C_3$-alkyl-OH, preferably methanol or ethanol, at a temperature between 0° C. and 100° C., preferably between 20° C. and 60° C., to transform the group $R^{5E}$ into a group $R^5$ as defined for the compounds of general formula (I), and subsequently optionally to convert the free acid group $R^5$ into a pharmaceutically acceptable salts thereof to obtain a compound of general formula (I)

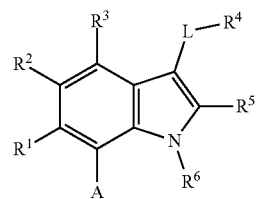

(I)

in which $R^1$, $R^2$, $R^3$, $R^4$, $R^5$, $R^6$, A and L are as defined for the compound of general formula (I) according to any one of claims 1 to 5 or a stereoisomer, a tautomer, an N-oxide, a hydrate, a solvate, or a salt thereof, or a mixture of same and subsequently optionally separating enantiomers by means of preparative HPLC on a chiral stationary phase.

The present invention provides methods of preparing compounds of the present invention of general formula (I), said methods comprising the steps as described in the Experimental Section herein.

In accordance with a further aspect, the present invention provides intermediate compounds which are useful for the preparation of the compounds of general formula (I), supra.

Particularly, the invention provides the intermediate compounds of general formula (II)

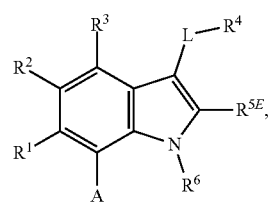

(II)

in which $R^1$, $R^2$, $R^3$, $R^4$, $R^6$, A and L are as defined for the compound of general formula (I) according to any one of claims 1 to 5, and $R^{5E}$ represents a carboxylic ester group or a benzyl group.

In accordance with another aspect, the present invention provides the use of said intermediate compounds for the preparation of a compound of general formula (I) as defined supra.

In accordance with another aspect, the present invention provides a method of using the intermediate compound of general formula (II) for the preparation of a compound of general formula (I).

The present invention provides the intermediate compounds which are disclosed in the Example Section of this text, infra.

The present invention provides any sub-combination within any embodiment or aspect of the present invention of intermediate compounds of general formula (II), supra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Methods and Administration

Compounds of general formula (I) of the present invention demonstrate a valuable pharmacological spectrum of action and pharmacokinetic profile, both of which could not have been predicted. Compounds of the present invention have surprisingly been found to effectively inhibit MCL-1 activity, and it is possible therefore that said compounds can be used for the treatment or prophylaxis of diseases, preferably hyperproliferative disorders in humans and animals.

As used herein, "prophylaxis" includes a use of the compound that, in a statistical sample, reduces the occurrence of the disorder or condition in the treated sample relative to an untreated control sample, or delays the onset or reduces the severity of one or more symptoms of the disorder or condition relative to the untreated control sample, when administered to prior to the onset of the disorder or condition.

Compounds of the present invention can be utilized to inhibit, block, reduce, and/or decrease cell proliferation and/or cell division, and/or induce apoptosis. Disclosed methods include administering to a mammal in need thereof, including a human, an amount of a compound of general formula (I) of the present invention, or a pharmaceutically acceptable salt, isomer, polymorph, metabolite, hydrate, solvate or ester thereof, which is effective to treat the disorder. Hyperproliferative disorders include, but are not limited to, for example: psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancers include, but are not limited to, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypothalmic glioma, cerebellar and cerebral astrocytoma, medulloblastoma, ependymoma, as well as neuroectodermal and pineal tumours.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Tumours of the digestive tract include, but are not limited to, anal, colon, colorectal, oesophageal, gallbladder, gastric, pancreatic, rectal, small-intestine, and salivary gland cancers.

Tumours of the urinary tract include, but are not limited to, bladder, penile, kidney, renal pelvis, ureter, urethral and human papillary renal cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, basal cell carcinoma, squamous cell carcinoma, Kaposi's sarcoma, malignant melanoma, Merkel cell skin cancer, and non-melanoma skin cancer.

Head-and-neck cancers include, but are not limited to, laryngeal, hypopharyngeal, nasopharyngeal, oropharyngeal cancer, lip and oral cavity cancer and squamous cell.

Lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute myeloid leukemia, acute lymphoblastic leukemia, chronic lymphocytic leukemia, chronic myelogenous leukemia, and hairy cell leukemia.

The present invention also provides methods of treating angiogenic disorders including diseases associated with excessive and/or abnormal angiogenesis.

Inappropriate and ectopic expression of angiogenesis can be deleterious to an organism. A number of pathological conditions are associated with the growth of extraneous blood vessels. These include, for example, diabetic retinopathy, ischemic retinal-vein occlusion, and retinopathy of prematurity [Aiello et al., New Engl. J. Med., 1994, 331, 1480; Peer et al., Lab. Invest., 1995, 72, 638], age-related macular degeneration (AMD) [Lopez et al., Invest. Opthhalmol. Vis. Sci., 1996, 37, 855], neovascular glaucoma, psoriasis, retrolental fibroplasias, angiofibroma, inflammation, rheumatoid arthritis (RA), restenosis, in-stent restenosis, and vascular graft restenosis. In addition, the increased blood supply associated with cancerous and neoplastic tissue encourages growth, leading to rapid tumour enlargement and metastasis. Moreover, the growth of new blood and lymph vessels in a tumour provides an escape route for rapidly dividing cells, encouraging metastasis and the consequence spread of the cancer. Thus, compounds of general formula (I) of the present invention can be utilized to treat and/or prevent any of the aforementioned angiogenesis disorders, for example by inhibiting and/or reducing blood vessel formation; by inhibiting, blocking, reducing, and/or decreasing endothelial cell proliferation, or other pathways involved in angiogenesis, as well as causing cell death or apoptosis of such cell types.

These disorders have been well characterized in humans, but also exist with a similar etiology in other mammals, and can be treated by administering pharmaceutical compositions of the present invention.

By "subject" is meant a mammal, including, but not limited to, a human or non-human mammal, such as a bovine, equine, canine, ovine, or feline.

The term "treating" or "treatment" as stated throughout this document is used conventionally, for example the management or care of a subject for the purpose of combating, alleviating, reducing, relieving, and/or improving the condition of a disease or disorder, such as a carcinoma.

The compounds of the present invention can be used in particular in therapy and prevention, i.e., prophylaxis, of tumour growth and metastases, especially in solid tumours of all indications and stages with or without pre-treatment of the tumour growth.

Generally, the use of chemotherapeutic agents and/or anti-cancer agents in combination with a compound or pharmaceutical composition of the present invention may serve to:
1. yield better efficacy in reducing the growth of a tumour or even eliminate the tumour as compared to administration of either agent alone,
2. provide for the administration of lesser amounts of the administered chemotherapeutic agents,
3. provide for a chemotherapeutic treatment that is well tolerated in the patient with fewer deleterious pharmacological complications than observed with single agent chemotherapies and certain other combined therapies,
4. provide for treating a broader spectrum of different cancer types in mammals, especially humans,
5. provide for a higher response rate among treated patients,
6. provide for a longer survival time among treated patients compared to standard chemotherapy treatments,
7. provide a longer time for tumour progression, and/or
8. yield efficacy and tolerability results at least as good as those of the agents used alone, compared to known instances where other cancer agent combinations produce antagonistic effects.

In addition, the compounds of general formula (I) of the present invention can also be used in combination with radiotherapy and/or surgical intervention.

In some embodiments of the present invention, the compounds of general formula (I) of the present invention may be used to sensitize a cell to radiation, i.e., treatment of a cell with a compound of the present invention prior to radiation treatment of the cell renders the cell more susceptible to DNA damage and cell death than the cell would be in the absence of any treatment with a compound of the present invention. In some embodiments, the cell is treated with at least one compound of general formula (I) of the present invention.

Thus, the present invention also provides a method of killing a cell, wherein a cell is administered one or more compounds of the present invention in combination with conventional radiation therapy.

The present invention also provides a method of rendering a cell more susceptible to cell death, wherein the cell is treated with one or more compounds of general formula (I) of the present invention prior to the treatment of the cell to cause or induce cell death. In some embodiments, after the cell is treated with one or more compounds of general formula (I) of the present invention, the cell is treated with at least one compound, or at least one method, or a combination thereof, in order to cause DNA damage for the purpose of inhibiting the function of the normal cell or killing the cell.

In other embodiments of the present invention, a cell is killed by treating the cell with at least one DNA damaging agent, i.e., after treating a cell with one or more compounds of general formula (I) of the present invention to sensitize the cell to cell death, the cell is treated with at least one DNA damaging agent to kill the cell. DNA damaging agents useful in the present invention include, but are not limited to, chemotherapeutic agents (e.g., cis platin), ionizing radiation (X-rays, ultraviolet radiation), carcinogenic agents, and mutagenic agents.

In other embodiments, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In some embodiments, a compound of general formula (I) of the present invention is administered to a cell prior to the radiation or other induction of DNA damage in the cell. In some embodiments, a compound of general formula (I) of the present invention is administered to a cell concomitantly with the radiation or other induction of DNA damage in the cell. In some embodiments, a compound of general formula (I) of the present invention is administered to a cell immediately after radiation or other induction of DNA damage in the cell has begun.

In some embodiments, the cell is in vitro. In some embodiments, the cell is in vivo.

Thus in some embodiments, the present invention includes a method of inhibiting proliferation of a cell and/or the induction of apoptosis in a cell, comprising contacting the cell with a compound of formula (I) according to any one of claims 1-6.

Another aspect of the invention is a method for controlling cancer (e.g., through treatment and/or prophylaxis) in a subject (e.g., human, other mammal, such as rat, etc.) by administering an effective amount of at least one compound of general formula (I), or a pharmaceutically acceptable salt, polymorph, metabolite, hydrate, solvate or ester thereof to the subject.

In some embodiments, the subject may be administered a medicament, comprising at least one compound of general formula (I) and one or more pharmaceutically acceptable carriers, excipients, and/or diluents.

Furthermore in some embodiments, the present invention includes a method of using a compound of general formula (I) for the treatment of diseases.

Particularly in some embodiments, the present invention includes a method of treating a hyperproliferative disease, more particularly cancer, comprising administering an effective amount of at lest one compound of general formula (I) according to any one of claims 1-6.

In some embodiments, the method of treatment and/or prophylaxis of a hyperproliferative disorder in a subject may comprise administering to the subject an effective amount of a compound of general formula (I). The hyperproliferative disorder may be, for example, cancer (e.g., breast cancer;

esophageal cancer, leukemia, liver cancer, lung cancer; lymphoma, melanoma; and multiple myeloma, etc.).

A method of inhibiting dihydroorotate dehydrogenase activity in a cancer cell is also provided, wherein the method comprises contacting a cancer cell with a compound of general formula (I). The cancer cell may be in vitro or in vivo.

Furthermore in some embodiments, the present invention includes a method of treating cancer, particularly breast cancer; endomesophagealetrial cancer, leukemia, liver cancer, lung cancer; lymphoma, melanoma; and multiple myeloma comprising administering an effective amount of at least one compound of formula (I) according to any one of claims 1-6.

Furthermore in some embodiments, the present invention includes a method of treating cancer, particularly breast cancer; endomesophagealetrial cancer, leukemia, liver cancer, lung cancer (including non small cell lung cancer and small cell lung cancer); lymphoma, melanoma; and multiple myeloma comprising administering an effective amount of at least one compound of formula (I) according to any one of claims 1-6.

Furthermore in some embodiments, the present invention includes a method of treating cancer, particularly multiple myeloma, acute monocytic leukemia, melanoma and lung cancer. comprising administering an effective amount of at least one compound of formula (I) according to any one of claims 1-6.

In some embodiments the present invention provides for compounds of general formula (I) for use in a method of treating cancer, particularly where the cancer disease is breast cancer; esophageal cancer, leukemia, liver cancer, lung cancer; lymphoma, melanoma; and multiple myeloma.

Furthermore in some embodiments, the present invention includes a method of treating cancer, particularly breast cancer; esophageal cancer, leukemia, liver cancer, lung cancer; lymphoma, melanoma; and multiple myeloma comprising administering an effective amount of at least one compound of formula (I) according to any one of claims 1-6.

Furthermore in some embodiments, the present invention includes a method of treating cancer, particularly breast cancer; esophageal cancer, liver cancer, lung cancer; lymphoma including non-Hodgkin-lymphoma type, diffuse large B-cell lymphoma subtype including GC-DLBCL* and ABC-DLBCL subtypes, and mantle cell lymphoma; acute leukemia, acute myeloid leukemia type, acute monocytic leukemia; melanoma; multiple myeloma; ovarian cancer; pancreas cancer. GC-DLBCL means Germinal B-cell Diffuse Large B-Cell Lymphoma and  ABC-DLBCL means Activated B-cell Diffuse Large B-Cell Lymphoma comprising administering an effective amount of at least one compound of formula (I) according to any one of claims 1-6.

Furthermore in some embodiments, the present invention includes a method of treating cancer, particularly breast cancer; esophageal cancer, leukemia, liver cancer, lung cancer; lymphoma, melanoma; and multiple myeloma comprising administering an effective amount of at least one compound of formula (I) according to any one of claims 1-6. Furthermore in accordance with another aspect, the present invention provides a compound of formula (I) for use of treating diseases.

In some embodiments, the present invention includes a compound of general formula (I) for use in a method of inhibiting proliferation of a cell and/or the induction of apoptosis in a cell, comprising contacting the cell with a compound of formula (I) according to any one of claims 1-6.

Furthermore in some embodiments, the present invention includes a method of treating [lymphoma] in a subject, the method comprising administering to the subject an effective amount of a compound of formula (I).

Particularly in some embodiments, the present invention includes compounds of general formula (I) for use in a method of treating a hyperproliferative disease, more particularly wherein the hyperproliferative disease is cancer, and yet even more particularly wherein the cancer disease breast cancer; esophageal cancer, leukemia, liver cancer, lung cancer; lymphoma, melanoma; and multiple myeloma.

Particularly in some embodiments, the present invention includes compounds of general formula (I) for use in a method of treating a hyperproliferative disease, more particularly wherein the hyperproliferative disease is cancer, and yet even more particularly wherein the cancer disease breast cancer; esophageal cancer, leukemia, liver cancer, lung cancer (including non-small cell lung cancer and small cell lung cancer); lymphoma, melanoma; and multiple myeloma.

In yet some embodiments, the present invention includes compounds of general formula (I) for use in a method of treating a hyperproliferative disease, more particularly wherein the hyperproliferative disease is cancer, and yet even more particularly wherein the cancer disease is breast cancer; esophageal cancer, liver cancer, lung cancer; lymphoma including non-Hodgkin-lymphoma type, diffuse large B-cell lymphoma subtype including GC-DLBCL* and ABC-DLBCL subtypes, and mantle cell lymphoma; acute leukemia, acute myeloid leukemia type, acute monocytic leukemia; melanoma; multiple myeloma; ovarian cancer; pancreas cancer. GC-DLBCL means Germinal B-cell Diffuse Large B-Cell Lymphoma and  ABC-DLBCL means Activated B-cell Diffuse Large B-Cell Lymphoma In some embodiments, the present invention includes use of the compounds of general formula (I) for the manufacture of a medicament for the treatment of a hyperproliferative disease, particularly cancer and more particularly breast cancer; esophageal cancer, leukemia, liver cancer, lung cancer; lymphoma, melanoma; and multiple myeloma.

In some embodiments, the present invention includes use of the compounds of general formula (I) for the manufacture of a medicament for the treatment of a hyperproliferative disease, particularly cancer and more particularly breast cancer; esophageal cancer, leukemia, liver cancer, lung cancer (including non small cell lung cancer and small cell lung cancer); lymphoma, melanoma; and multiple myeloma.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, or otic route or as an implant or stent.

For these administration routes, it is possible for the compounds according to the invention to be administered in suitable administration forms.

For oral administration, it is possible to formulate the compounds according to the invention into dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatin capsules), sugar-coated tablets, granules, pellets, powders, emulsions, suspensions, aerosols or solutions. It is possible to incorporate the compounds according to the invention in crystalline and/or amorphous and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation (inter alia powder inhalers, nebulizers), nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia,

- fillers and carriers (for example, cellulose, microcrystalline cellulose (such as, for example, Avicel®), lactose, mannitol, starch, calcium phosphate (such as, for example, Di-Cafos®)),
- ointment bases (for example petroleum jelly, paraffins, triglycerides, waxes, wool wax, wool wax alcohols, lanolin, hydrophilic ointment, polyethylene glycols),
- bases for suppositories (for example, polyethylene glycols, cacao butter, hard fat),
- solvents (for example, water, ethanol, isopropanol, glycerol, propylene glycol, medium chain-length triglycerides, fatty oils, liquid polyethylene glycols, paraffins),
- surfactants, emulsifiers, dispersants or wetters (for example, sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®),
- buffers, acids and bases (for example, phosphates, carbonates, citric acid, acetic acid, hydrochloric acid, sodium hydroxide solution, ammonium carbonate, trometamol, triethanolamine),
- isotonicity agents (for example, glucose, sodium chloride),
- adsorbents (for example, highly-disperse silicas),
- viscosity-increasing agents, gel formers, thickeners and/or binders (for example, polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatin),
- disintegrants (for example, modified starch, carboxymethylcellulose-sodium, sodium starch glycolate (such as, for example, Explotab®), cross- linked polyvinylpyrrolidone, croscarmellose-sodium (such as, for example, AcDiSol®)),
- flow regulators, lubricants, glidants and mould release agents (for example, magnesium stearate, stearic acid, talc, highly-disperse silicas (such as, for example, Aerosil®)),
- coating materials (for example, sugar, shellac) and film formers for films or diffusion membranes which dissolve rapidly or in a modified manner (for example, polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)),
- capsule materials (for example, gelatin, hydroxypropylmethylcellulose),
- synthetic polymers (for example, polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers),
- plasticizers (for example, polyethylene glycols, propylene glycol, glycerol, triacetine, triacetyl citrate, dibutyl phthalate),
- penetration enhancers,
- stabilisers (for example, antioxidants such as, for example, ascorbic acid, ascorbyl palmitate, sodium ascorbate, butylhydroxyanisole, butylhydroxytoluene, propyl gallate),
- preservatives (for example, parabens, sorbic acid, thiomersal, benzalkonium chloride, chlorhexidine acetate, sodium benzoate),
- colourants (for example, inorganic pigments such as, for example, iron oxides, titanium dioxide), and
- flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In some embodiments, the present invention includes pharmaceutical combinations, in particular medicaments, comprising at least one compound of general formula (I) of the present invention and at least one or more further active ingredients, in particular for the treatment and/or prophylaxis of a hyperproliferative disorder, particularly cancer.

Particularly, the present invention includes a pharmaceutical combination, which comprises:
- one or more first active ingredients, in particular compounds of general formula (I) as defined supra, and
- one or more further active ingredients, in particular for the treatment and/or prophylaxis of hyperproliferative disorder, particularly cancer.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent, or in combination with one or more other pharmaceutically active ingredients where the combination causes no unacceptable adverse effects. The present invention also includes such pharmaceutical combinations. For example, the compounds of the present invention can be combined with known anti-cancer agents.

Examples of anti-cancer agents include:

131I-chTNT, abarelix, abiraterone, aclarubicin, adotrastuzumab emtansine, afatinib, aflibercept, aldesleukin, alemtuzumab, Alendronic acid, alitretinoin, altretamine, amifostine, aminoglutethimide, Hexyl aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, lasocholine, lenalidomide, lenograstim, lentinan, letrozole, leuprorelin, levamisole, levonorgestrel, levothyroxine sodium, lisuride, lobaplatin, lomustine, Ionidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Based upon standard laboratory techniques known to evaluate compounds useful for the treatment of hyperproliferative diseases, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 40 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 3000 mg of active ingredient, and can be administered one or more times per day or less than once a day. The average daily dosage for administration by injection, including intravenous, intramuscular, subcutaneous and parenteral injections, and use of infusion techniques will preferably be from about 0.01 to about 200 mg/kg of total body weight. The average daily rectal dosage regimen will preferably be from about 0.01 to about 200 mg/kg of total body weight. The average daily vaginal dosage regimen will preferably be from about 0.01 to about 200 mg/kg of total body weight. The average daily topical dosage regimen will preferably be from about 0.1 to about 200 mg administered between one to four times daily. The transdermal concentration will preferably be that required to maintain a daily dose of from about 0.01 to about 200 mg/kg. The average daily inhalation dosage regimen will preferably be from about 0.01 to about 100 mg/kg of total body weight.

In one embodiment the average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from abut 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Experimental Section

Experimental Section—NMR Spectra

To the extent NMR peak forms and multiplicities are specified, they are stated as they appear in the spectra, possible higher order effects have not been considered.

The $^1$H-NMR data of selected examples are listed in the form of $^1$H-NMR peaklists. For each signal peak the δ value in ppm is given, followed by the signal intensity, reported in round brackets. The δ value-signal intensity pairs from different peaks are separated by commas. Therefore, a peaklist is described by the general form: $\delta_1$ (intensity$_1$), $\delta_2$ (intensity$_2$), ..., $\delta_i$ (intensity$_i$), ..., $\delta_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of target compounds (also the subject of the invention), and/or peaks of impurities. The peaks of stereoisomers, and/or peaks of impurities are typically displayed with a lower intensity compared to the peaks of the target compounds (e.g., with a purity of >90%). Such stereoisomers and/or impurities may be typical for the particular manufacturing process, and therefore their peaks may help to identify the reproduction of our manufacturing process on the basis of "by-product fingerprints". An expert who calculates the peaks of the target compounds by known methods (MestReC, ACD simulation, or by use of empirically evaluated expectation values), can isolate the peaks of target compounds as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within Patent Applications" (cf. Research Disclosure Database Number 605005, 2014, 1 Aug. 2014, or http://www.researchdisclosure.com/searching-disclosures). In the peak picking routine, as described in the Research Disclosure Database Number 605005, the parameter "MinimumHeight" can be adjusted between 1% and 4%. Depending on the chemical structure and/or depending on the concentration of the measured compound it may be reasonable to set the parameter "MinimumHeight"<1%.

Experimental Section—Abbreviations

The following table lists the abbreviations used in this paragraph and in the Intermediates and Examples section as far as they are not explained within the text body. Other abbreviations have their meanings customary per se to the skilled person. A comprehensive list of the abbreviations utilized by organic chemists of ordinary skill in the art appears presented in the first issue of each volume of the Journal of Organic Chemistry; this list is typically presented in a table titled "Standard List of Abbreviations". In case of doubt, the abbreviations and/or their meaning according to the following table shall prevail.

TABLE 1

Abbreviations

| Abbreviation | Meaning |
| --- | --- |
| br. | Broad signal (NMR) |
| BPR | Back Pressure Regulator |
| d | doublet (NMR) |
| DAD | Diode array detector |
| dd | doublet of doublet (NMR) |
| dt | doublet of triplet (NMR) |
| DMF | N,N-dimethylformamide |
| DMSO | dimethylsulfoxide |

TABLE 1-continued

Abbreviations

| Abbreviation | Meaning |
|---|---|
| EDC | N-[3-(dimethylamino)propyl]-N'-ethylcarbodiimide hydrochloride |
| ESI | electrospray (ES) ionisation |
| h, hr, hrs | hour, hours |
| HCl | hydrogen chloride, hydrochloric acid |
| HMBC | heteronuclear multiple bond correlation |
| HPLC | high performance liquid chromatography |
| HSQC | heteronuclear single quantum coherence |
| LC-MS | liquid chromatography-mass spectrometry |
| m | multiplet (NMR) |
| min | minute(s) |
| MS | mass spectrometry |
| MWD | Multiple wavelength detector |
| NHS | N-Hydroxysuccinimide |
| NMR | nuclear magnetic resonance spectroscopy: chemical shifts ($\delta$) are given in ppm. The chemical shifts were corrected by setting the DMSO signal to 2.50 ppm using dmso-d6 unless otherwise stated. |
| q | quartet (NMR) |
| rt, RT | room temperature |
| $R_t$, Rt | retention time |
| s | singulet (NMR) |
| SFC | Supercritical Fluid Chromatography |
| t | triplet (NMR) |
| td | triplet of doublet (NMR) |
| TFA | trifluoroacetic acid |
| THF | tetrahydrofuran |
| TLC | thin layer chromatography |
| UPLC | ultra performance liquid chromatography |
| UV | ultraviolet |
| tt | triplet of triplet (NMR) |
| $\delta$ | chemical shift |
| XPhos Pd G2 | chloro(2-dicyclohexylphosphino-2',4',6'-triisopropyl-1,1'-biphenyl)[2-(2'-amino-1,1'-biphenyl)]palladium(II) (Cas No: 1310584-14-5) |
| XPhos Pd G3 | (2-dicyclohexylphosphino-2',4',6'-triisopropyl-1,1'-biphenyl)[2-(2'-amino-1,1'-biphenyl)]palladium(II)methanesulfonate (Cas No: 1445085-55-1) |

Other abbreviations have their meanings customary per se to the skilled person.

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art. Reactions were set up and started, e.g. by the addition of reagents, at temperatures as specified in the protocols; if no temperature is specified, the respective working step was performed at ambient temperature, i.e. between 18 and 25° C.

"Silicone filter" or "water resistant filter" refers to filter papers which are made hydrophobic (impermeable to water) by impregnation with a silicone. With the aid of these filters, water can be separated from water-immiscible organic solvents by means of a filtration (i.e. filter paper type MN 617 WA, Macherey-Nagel).

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be removed by trituration using a suitable solvent or solvent mixture. In some cases, the compounds may be purified by chromatography, particularly flash column chromatography, using for example prepacked silica gel cartridges, e.g. Biotage SNAP cartridges KP-Sil® or KP-NH® in combination with a Biotage autopurifier system (SP4® or Isolera Four®) and eluents such as gradients of hexane/ethyl acetate or DCM/ethanol. In flash column chromatography, unmodified ("regular") silica gel may be used as well as aminophase functionalized silica gel. As used herein, "Biotage SNAP cartridge silica" refers to the use of regular silica gel; "Biotage SNAP cartridge $NH_2$ silica" refers to the use of aminophase functionalized silica gel. If reference is made to flash column chromatography or to flash chromatography in the experimental section without specification of a stationary phase, regular silica gel was used. Further, column chromatography can also be used advantageously in the reversed-phase mode, using materials such as C18 siliga gel as stationary phase, and using eluents such as gradients of water and acetonitrile which may contain additives such as trifluoroacetic acid, formic acid, diethylamine or aqueous ammonia. If reference is made to reversed phase column chromatography in the experimental section without specification of a stationary phase, C18 siliga gel was used.

In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid, diethylamine or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

UPLC-MS Standard Procedures

Analytical UPLC-MS was performed as described below. The masses (m/z) are reported from the positive mode electrospray ionisation unless the negative mode is indicated (ESI–).

Analytical UPLC Methods:

Method 1:

Instrument: Waters Acquity UPLCMS SingleQuad; Column: Acquity UPLC BEH C18 1.7 µm, 50×2.1 mm; eluent A: water+0.1 vol % formic acid (99%), eluent B: acetonitrile; gradient: 0-1.6 min 1-99% B, 1.6-2.0 min 99% B; flow 0.8 mL/min; temperature: 60° C.; DAD scan: 210-400 nm.

Method 2:

Instrument: Waters Acquity UPLCMS SingleQuad; Column: Acquity UPLC BEH C18 1.7 µm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; DAD scan: 210-400 nm.

Method 3:

Column: CSH C18 1.7 µm 2.1×50 mm, Waters Acquity Binary pump (Flow 0.8 mL/min), Waters Acquity Autosampler, Waters Acquity QDA, Waters Acquity PDA, Run Time: 4.60 mins, Solvents: A) 0.1% formic acid in water, B) Acetonitrile+0.1% formic acid, Gradient: 2-95% B in 4.00 mins, hold at 95% B 4.60 min Method 4:

Instrument: Waters Acquity UPLC H-Class system; Column: XBridge C8 2.5 µm 2.1×50 mm; eluent A: water, eluent B: acetonitrile, eluent C: 2 vol % ammonia (28%) in water, eluent D: 2 vol % formic acid in water; gradient: 0-4.0 min 50-95% B with 5% D throughout, 4.0-4.6 min 95% B; flow 0.8 ml/min; temperature: 40° C.; PDA: 215-350 nm.

Method 5:

Instrument: Waters Acquity UPLC H-Class system; Column: Acquity CSH C18 1.7 µm 2.1×50 mm; eluent A: water, eluent B: acetonitrile, eluent C: 2 vol % ammonia (28%) in water, eluent D: 2 vol % formic acid in water; gradient: 0-4.0 min 50-95% B with 5% C throughout, 4.0-4.6 min 95% B; flow 0.8 ml/min; temperature: 40° C.; PDA: 215-350 nm.

Method 6:

Instrument: Waters Alliance HT; Column: Waters Cortecs 30 mm×3 mm×2.7 µm; eluent A: Water (MilliQ)+0.01 vol % formic acid, eluent B: acetonitrile+0.01 vol % formic acid; gradient: 0-1.7 min 3-95% B, 1.7-2.2 min 95% B; 2.3-2.5 3% B; flow: 1.75 mL/mn; temperature: 45° C.; DAD scan: 200-500 nm.

Method 7:

Instrument: Waters Alliance HT; Column: Waters Cortecs 30 mm×3 mm×2.7 µm; eluent A: Water (MilliQ)+0.01 vol % formic acid, eluent B: acetonitrile+0.01 vol % formic acid; gradient: 0-6.8 min 5-95% B, 6.8-7.3 min 95% B; 7.3-7.5 5% B; flow: 1.75 mL/mn; temperature: 45° C.; DAD scan: 200-500 nm.

Method 8:

Instrument: Waters Acquity; Column: Waters Acquity BEH C18 50 mm×2.1 mm×1.7 µm; eluent A: Water (MilliQ)+0.01 vol % formic acid, eluent B: acetonitrile+0.01 vol % formic acid; gradient: 0-0.3 min 3-4% B, 0.3-1.5 min 4-95% B, 1.5-1.9 min 95% B; 1.9-2.0 min 5% B; flow: 0.65 mL/min; temperature: 50° C.; DAD scan: 200-500 nm, Preparative HPLC Methods:

Method P1: Instrument: pump: Labomatic HD-5000 or HD-3000, head HDK 280, low pressure gradient module ND-B1000; manual injection valve: Rheodyne 3725i038; detector: Knauer Azura UVD 2.15; collector: Labomatic Labocol Vario-4000; column: Chromatorex RP C-18 10 µm, 125×30 mm; Eluent acidic: solvent A: water+0.1 vol-% formic acid, solvent B: acetonitrile; 0.00-0.50 min 30% B (150 mL/min), 0.50-6.00 min 30-70% B (150 mL/min), 6.00-6.10 min 70-100% B (150 mL/min), 6.10-8.00 min 100% B (150 mL/min)

Method P2:

Instrument: Pump: Labomatic HD-5000 or HD-3000, Head HDK 280, low pressure gradient module ND-B1000; Manual injection valve: Rheodyne 3725i038; Detector: Knauer Azura UVD 2.15; Collector: Labomatic Labocol Vario-4000; Column: Chromatorex RP C-18 10 µm, 125×30 mm; solvent A: water+0.1 vol-% formic acid, solvent B: acetonitrile; gradient: 0.00-0.50 min 65% B (150 mL/min), 0.50-6.00 min 65-100% B (150 mL/min), 6.00-8.00 min 100% B (150 mL/min), UV-Detection.

Method P3: Instrument: pump: Labomatic HD-5000 or HD-3000, head HDK 280, low pressure gradient module ND-B1000; manual injection valve: Rheodyne 3725i038; detector: Knauer Azura UVD 2.15; collector: Labomatic Labocol Vario-4000; column: Chromatorex RP C-18 10 µm, 125×30 mm; Eluent basic: solvent A: water+0.2 vol-% aqueous ammonia (32%), solvent B: acetonitrile; 0.00-0.50 min 15% B (150 mL/min), 0.50-6.00 min 15-55% B (150 mL/min), 6.00-6.10 min 55-100% B (150 mL/min), 6.10-8.00 min 100% B (150 mL/min)

Specific Optial Rotation Methods:

Method 01: Instrument: JASCO P2000 Polarimeter; wavelength 589 nm; temperature: 20° C.; integration time 10 s; path length 100 mm.

Intermediates

Intermediate 1 tert-butyl (4-bromobutyl)methylcarbamate

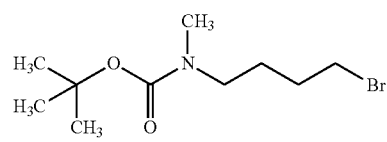

Tert-butyl (4-hydroxybutyl)methylcarbamate (CAS 99207-32-6, 10.6 g, 95% purity, 49.3 mmol) and triphenylphosphane (17.5 g, 66.6 mmol) were provided in 200 mL of dichloromethane at 0° C. and tetrabromomethane (21.5 g, 64.1 mmol) was added slowly and in portions. The mixture was stirred overnight at room temperature (rt) and concentrated under reduced pressure. The residue was triturated with hexane, the solid material was isolated by filtration and dried under reduced pressure to give the title compound (15.5 g).

$^1$H-NMR (400 MHz, DMSO-d6) δ[ppm]: 1.388 (16.00), 2.748 (0.68), 3.157 (0.57), 3.174 (1.09), 3.192 (0.55), 3.532 (0.81), 3.549 (1.66), 3.565 (0.80), 7.698 (1.28).

Intermediate 2 di-tert-butyl (4-bromobutyl)-2-imidodicarbonate

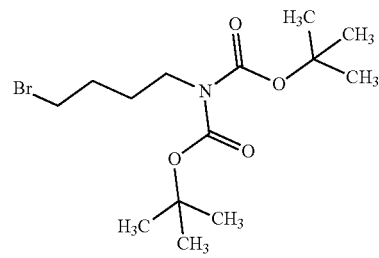 [SMILES: CC(C)(C)OC(=O)N(CCCCBr)C(=O)OC(C)(C)C]

Di-tert-butyl 2-imidodicarbonate (CAS 51779-32-9, 27.0 g, 124 mmol) was solved in 510 mL DMF and 500 mL THF and sodium hydride (4.97 g, 60% purity, 124 mmol) was added portionswise to the reaction mixture. After complete addition it was stirred at 65° C. for 2 hours. Then it was cooled to room temperature and 1,4-dibromobutane (CAS 110-52-1, 65 mL, 550 mmol) was added dropwise into the reaction mixture. It was stirred at 65° C. for 3 hours. Under cooling the mixture was diluted with methyl tert. butyl ether and water. The layers were separated and the aqueous layer was extracted with ether twice. The organic layers were dried using a water resistant filter. The clear filtrate was concentrated under reduced pressure. The crude product was purified using a 340 g silica column (Gradient: hexane/ethyl acetate 0-60) to provide the target compound in 95% purity: 41.6 g.

¹H-NMR (400 MHz, DMSO-d6): δ [ppm]=1.45 (s, 18H), 1.56-1.66 (m, 2H), 1.71-1.82 (m, 2H), 3.46-3.52 (m, 2H), 3.52-3.56 (m, 2H).

Intermediate 3

5-((2-bromo-3-chlorophenyl)diazenyl)-6-ethoxy-6-oxohexanoic acid

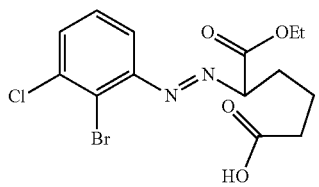 [SMILES: CCOC(=O)C(CCCC(=O)O)/N=N/c1cccc(Cl)c1Br]

To a stirred solution of 2-bromo-3-chloro-aniline (CAS 96558-73-5, 50 g, 242 mmol) in aqueous hydrochloric acid (2.5 M, 500 mL) was added sodium nitrite (17 g, 247 mmol) in water (100 mL) drop-wise at 0° C. over 0.5 hour. After addition, the mixture was stirred at 0° C. for 0.5 hour. Then sodium acetate (84 g, 1.02 mol) in water (500 mL) was added into the reaction mixture, followed by ethyl 2-oxo-cyclopentanecarboxylate (40 g, 256 mmol). The mixture was stirred at 0° C. for 0.5 hour and then it was warmed to 25° C. and stirred for 1 hour. Dichloromethane (800 mL) was added into the reaction mixture. Two layers were separated and the aqueous layer was extracted with dichloromethane (300 mL×3). The combined organic layer was washed with water (300 mL×3), dried over sodium sulfate, filtered and concentrated by evaporation in vacuum to give 5-((2-bromo-3-chlorophenyl)diazenyl)-6-ethoxy-6-oxohexanoic acid (108 g, crude) as black oil, which was used directly for the next step.

Intermediate 4 ethyl 7-bromo-6-chloro-3-(3-ethoxy-3-oxopropyl)-1H-indole-2-carboxylate

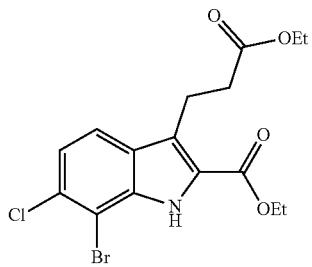 [SMILES: CCOC(=O)CCc1c(C(=O)OCC)[nH]c2c(Br)c(Cl)ccc12]

To a stirred solution of 5-((2-bromo-3-chlorophenyl)diazenyl)-6-ethoxy-6-oxohexanoic acid (see Intermediate 3, 108 g, crude) in ethanol (600 mL) was added conc. sulphuric acid (150 mL) drop-wise. After addition, the reaction mixture was stirred at reflux for 16 hours. LC-MS indicated the reaction completed. After cooling to room temperature, the mixture was added to water (3 L) with stirring and the formed solid was collected by filtration. The solid was then added to dichloromethane (800 mL) and the mixture was stirred for 1 hour and then filtered. The filtrate was filtered through a short plug of silica gel and the silica gel was washed with dichloromethane. The combined filtrate and washings were concentrated under reduced pressure. The residue was slurried with petrol ether (500 mL) and then filtered. The filter cake was dried in vacuum to give ethyl 7-bromo-6-chloro-3-(3-ethoxy-3-oxo-propyl)-1H-indole-2-carboxylate (62 g) as a gray solid.

¹H-NMR (400 MHz, DMSO-d6): δ=11.61 (s, 1H), 7.79 (d, 1H), 7.33 (d, 1H), 4.44-4.38 (m, 2H), 4.06-4.03 (m, 2H), 3.33-3.30 (m, 2H), 2.66-2.62 (m, 2H), 1.41 (t, 3H), 1.15 (t, 3H).

Intermediate 5 ethyl 7-bromo-6-chloro-3-(3-hydroxypropyl)-1H-indole-2-carboxylate

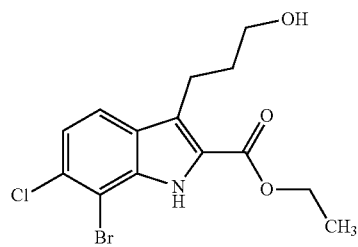 [SMILES: CCOC(=O)c1[nH]c2c(Br)c(Cl)ccc2c1CCCO]

The reactions were performed as two batches in parallel: to a stirred solution of ethyl 7-bromo-6-chloro-3-(3-ethoxy-3-oxo-propyl)-1H-indole-2-carboxylate (see Intermediate 4, 51 g, 127 mmol) in THF (250 mL) was boran dimethylsulfide (10 M, 17 mL) drop-wise over 0.5 hour at 25° C. under nitrogen. After addition, the reaction mixture was stirred at 50° C. for 16 hours. The reactions were performed as two batches in parallel and the combined reaction mixture (two batches) was quenched by methanol (40 mL) drop-wise at 0° C. After addition, the mixture was stirred at 25° C. for 0.5 hour, and then concentrated by evaporation in vacuum. The residue was slurried with petrol ether (400 mL) and filtered. The cake was dried in vacuum to afford ethyl 7-bromo-6-chloro-3-(3-hydroxypropyl)-1H-indole-2-carboxylate (81 g, 85% purity) as a white solid.

¹H-NMR: (400 MHz, DMSO-d6): δ=11.45 (s, 1H), 7.74 (d, 1H), 7.29 (d, 1H), 4.47 (t, 1H), 4.38-4.35 (m, 2H), 3.42-3.41 (m, 2H), 3.04-3.02 (m, 2H), 1.73-1.39 (m, 2H), 1.37 (t, 3H).

LC-MS (Method 1): Rt=0.945 min; m/z=360.0 (M+H)⁺

The title compound was prepared as described in J. Med. Chem. 2015, 58, 3794-3805.

Intermediate 6 ethyl 7-bromo-6-chloro-3-[3-(naphthalen-1-yloxy)propyl]-1H-indole-2-carboxylate

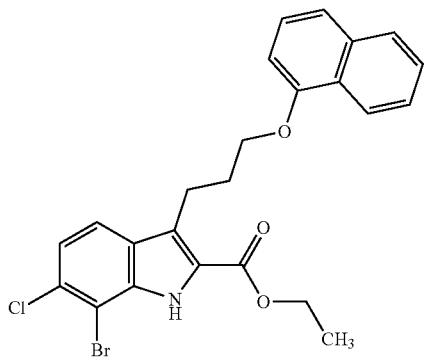 [SMILES: CCOC(=O)c1[nH]c2c(Br)c(Cl)ccc2c1CCCOc1cccc2ccccc12]

To a mixture of ethyl 7-bromo-6-chloro-3-(3-hydroxypropyl)-1H-indole-2-carboxylate (see Intermediate 5, 6.62 g, 18.4 mmol), naphthalen-1-ol (3.21 g, 99% purity, 22.0 mmol) and triphenylphosphine (5.84 g, 22.0 mmol) in THF (150 mL) was added diisopropyl azodicarboxylate (4.4 mL, 22 mmol) at 10° C. and the mixture was stirred for 24 hours at room temperature. For work-up, the mixture was diluted with ethyl acetate and was washed with aqueous sodium bicarbonate solution and brine. The organic phase was dried over sodium sulfate, filtered and the filtrate was concentrated under reduced pressure. The crude product was purified by flash chromatography (hexane/dichloromethane gradient 20→100% dichloromethane) to give, after trituration with methanol, the title compound (3.5 g).

Intermediate 7 ethyl 6-chloro-3-[3-(naphthalen-1-yloxy)propyl]-7-(4,4,5,5-tetramethyl-1,3,2-dioxaborolan-2-yl)-1H-indole-2-carboxylate

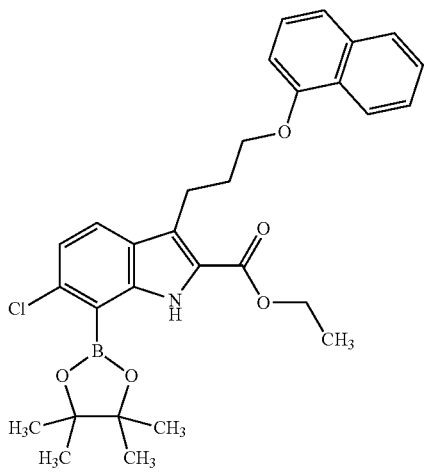 [SMILES: CCOC(=O)c1[nH]c2c(B3OC(C)(C)C(C)(C)O3)c(Cl)ccc2c1CCCOc1cccc2ccccc12]

To a degassed mixture of ethyl 7-bromo-6-chloro-3-[3-(naphthalen-1-yloxy)propyl]-1H-indole-2-carboxylate (see Intermediate 6, 5.50 g, 11.3 mmol) and 4,4,4',4',5,5,5',5'-octamethyl-2,2'-bi-1,3,2-dioxaborolane (8.61 g, 33.9 mmol) in 1,4-dioxane (97 mL) was added potassium acetate (4.44 g, 45.2 mmol) and to the mixture was added 1,1'-Bis(diphenylphosphino)ferrocene-palladium(II)chloride (827 mg, 1.13 mmol), and the reaction mixture was purged with argon for 10 minutes. The mixture was stirred for 24 hours at 80° C. For work-up the mixture was concentrated and the residue was purified by flash chromatography (Biotage SNAP cartridge silica, hexanes/ethyl acetate gradient, 7%→25% ethyl acetate) to give the title compound (1.5 g).

Intermediate 8 ethyl 7-bromo-6-chloro-3-{3-[(6-fluoronaphthalen-1-yl)oxy]propyl}-1H-indole-2-carboxylate

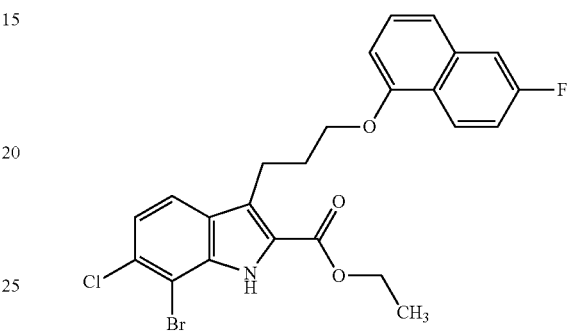

Triphenylphospane (1.60 g, 6.10 mmol) was dissolved in 20 mL of THF and 6-fluoronaphthalen-1-ol (CAS 804498-72-4, 989 mg, 6.10 mmol) was added. The mixture was cooled to −10° C. and diisopropyl azodicarboxylate (1.2 mL, 6.1 mmol) was added dropwise. After complete addition, the mixture was stirred for 10 minutes. Ethyl 7-bromo-6-chloro-3-(3-hydroxypropyl)-1H-indole-2-carboxylate (see Intermediate 5, 2.00 g, 5.55 mmol) was dissolved in 20 mL of THF and was added dropwise. The mixture was allowed to warm to rt and was stirred overnight. The reaction mixture was concentrated under reduced pressure and the residue was triturated with methanol. The remaining solids were isolated by filtration. In a second preparation triphenylphospane (1.60 g, 6.10 mmol) was dissolved in 20 mL of THF and 6-fluoronaphthalen-1-ol (CAS 804498-72-4, 989 mg, 6.10 mmol) was added. The mixture was cooled to −10° C. and diisopropyl azodicarboxylate (1.2 mL, 6.1 mmol) was added dropwise. After complete addition, the mixture was stirred for 10 minutes. Ethyl 7-bromo-6-chloro-3-(3-hydroxypropyl)-1H-indole-2-carboxylate (see Intermediate 5, 2.00 g, 5.55 mmol) was dissolved in 20 mL of THF and was added dropwise. The mixture was allowed to warm to rt and was stirred for 3 days. The reaction mixture was concentrated under reduced pressure and the residue was triturated with methanol. The remaining solids were isolated by filtration. In a third preparation triphenylphospane (1.60 g, 6.10 mmol) was dissolved in 20 mL of THF and 6-fluoronaphthalen-1-ol (CAS 804498-72-4, 989 mg, 6.10 mmol) was added. The mixture was cooled to −10° C. and diisopropyl azodicarboxylate (1.2 mL, 6.1 mmol) was added dropwise. After complete addition, the mixture was stirred for 10 minutes. Ethyl 7-bromo-6-chloro-3-(3-hydroxypropyl)-1H-indole-2-carboxylate (see Intermediate 5, 2.00 g, 5.55 mmol) was dissolved in 20 mL of THF and was added dropwise. The mixture was allowed to warm to rt and was stirred overnight. The reaction mixture was concentrated under reduced pressure and the residue was triturated with methanol. The remaining solids were isolated by filtration. Combined with the products of the other preparations the crude material was purified by flash chromatography using silica gel (hexane/ethyl acetate gradient). The obtained material was triturated with a mixture of tert.-butyl methyl ether and petroleum ether and the remaining solids were isolated by filtration and dried to give the title compound (2.4 g). The filtrate was concentrated and triturated with methanol. The remaining solids were isolated by filtration and dried to give a second batch of the title compound (1.88 g).

LC-MS (Method 1): R$_t$=1.80 min; MS (ESIneg): m/z=502 [M−H]$^-$ $^1$H-NMR (400 MHz, DMSO-d6) δ[ppm]: 1.191 (0.89), 1.208 (1.68), 1.226 (0.79), 1.275 (7.17), 1.286 (1.82), 1.293 (16.00), 1.303 (2.45), 1.310 (7.38), 1.321 (1.00), 2.177 (1.63), 2.194 (2.33), 2.211 (1.65), 2.227 (0.56), 2.518 (5.40), 2.523 (3.59), 3.280 (2.10), 3.299 (3.61), 3.317 (2.70), 4.147 (2.35), 4.162 (4.59), 4.176 (2.33), 4.190 (0.84), 4.269 (2.24), 4.286 (7.10), 4.304 (6.99), 4.322 (2.10), 5.759 (0.86), 6.834 (1.79), 6.842 (1.91), 6.848 (1.61), 6.856 (1.91), 7.168 (5.12), 7.189 (5.66), 7.240 (0.68), 7.249 (0.72), 7.261 (0.61), 7.271 (0.61), 7.316 (1.23), 7.322 (1.37), 7.333 (1.19), 7.339 (2.17), 7.345 (2.33), 7.360 (1.21), 7.367 (1.37), 7.391 (0.51), 7.412 (3.59), 7.418 (3.89), 7.426 (8.20), 7.438 (0.54), 7.579 (0.51), 7.600 (0.49), 7.624 (2.17), 7.630 (2.17), 7.650 (2.14), 7.656 (2.07), 7.721 (4.87), 7.743 (4.59), 7.757 (0.58), 7.778 (0.47), 8.046 (1.89), 8.061 (1.98), 8.069 (1.91), 8.084 (1.82), 11.517 (3.28).

On larger scale the title compound could be obtained in a similar manner with slightly modified reaction conditions in two batches: To a stirred solution of ethyl 7-bromo-6-chloro-3-(3-hydroxypropyl)-1H-indole-2-carboxylate (see Intermediate 6, 2000 g) and N,N-diethylethanamine (1.77 kg) in dichloromethane (20.0 L) was added methanesulfonyl chloride (1.30 kg) dropwise over 3 hours at 0-5° C. under an atmosphere of nitrogen. After addition, the reaction mixture was stirred at 25° C. for 16 hours. The mixture was washed with water (8 L) and concentrated to give a brown solid (3.99 kg, crude). This material (697 g) was added to a stirred solution of 6-fluoronaphthalen-1-ol (CAS 804498-72-4, 214 g) and potassium carbonate (428 g) in acetonitrile (5400 mL) under an atmosphere of nitrogen, and the reaction mixture was stirred at 85° C. for 16 hours. The mixture was filtered, and the solution was concentrated. The residue was purified by silica gel chromatography (petrol ether/dichloromethane=3/1) to obtain a crude material, which was then slurried in petrol ether/dichloromethane (800/200 mL) at 20° C. for 16 hours, and was filtered to obtain the title compound (262 g).

Intermediate 9 ethyl 6-chloro-3-{3-[(6-fluoronaphthalen-1-yl)oxy]propyl}-7-(4,4,5,5-tetramethyl-1,3,2-dioxa-borolan-2-yl)-1H-indole-2-carboxylate

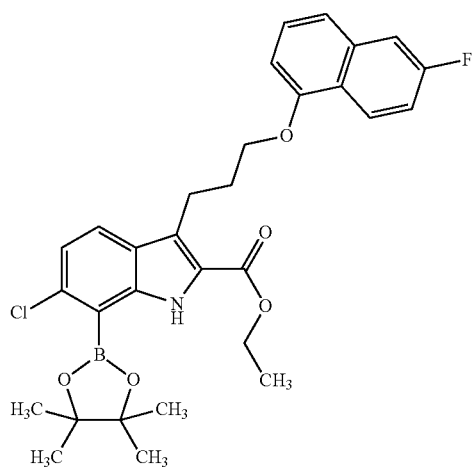 [SMILES: CCOC(=O)c1[nH]c2c(B3OC(C)(C)C(C)(C)O3)c(Cl)ccc2c1CCCOc1cccc2cc(F)ccc12]

Ethyl-7-bromo-6-chloro-3-{3-[(6-fluoronaphthalen-1-yl)oxy]propyl}-1H-indole-2-carboxylate (see Intermediate 8, 200 mg, 396 μmol) was dissolved in 3 mL of DMF. 4,4,4',4',5,5,5',5'-Octamethyl-2,2'-bi-1,3,2-dioxaborolane (CAS 78183-34-3151 mg, 594 μmol), potassium acetate (117 mg, 1.19 mmol) and [1,1'-Bis(diphenylphosphino)ferrocene]dichloro-palladium(II) (32.4 mg, 39.6 μmol) were added. The mixture was purged with argon for 10 minutes. The tube was sealed and stirred at 95° C. for 12 hours. After cooling to rt the mixture was filtered and purified by preparative HPLC (Method P3) to give the title compound (34 mg, 12% yield).

LC-MS (Method 1): R$_t$=1.90 min; MS (ESIpos): m/z=552 [M+H]$^+$ $^1$H-NMR (400 MHz, DMSO-d6) δ[ppm]: 1.257 (2.02), 1.275 (4.69), 1.292 (2.08), 1.324 (2.13), 1.373 (2.56), 1.383 (16.00), 2.202 (0.58), 2.219 (0.41), 2.518 (1.69), 2.522 (1.13), 3.301 (0.50), 3.320 (1.26), 4.144 (0.54), 4.159 (1.11), 4.173 (0.52), 4.235 (0.54), 4.252 (1.83), 4.270 (1.80), 4.288 (0.51), 5.758 (0.73), 6.824 (0.49), 6.832 (0.50), 6.838 (0.42), 6.846 (0.53), 7.045 (1.22), 7.067 (1.18), 7.319 (0.49), 7.326 (0.53), 7.408 (0.98), 7.414 (1.04), 7.422 (2.36), 7.622 (0.57), 7.629 (0.58), 7.648 (0.58), 7.655 (0.57), 7.839 (0.81), 7.861 (0.72), 8.010 (0.44), 8.024 (0.47), 8.033 (0.47), 8.047 (0.45), 9.978 (0.64).

On larger scale the title compound could be obtained in a similar manner with slightly modified reaction conditions: To a stirred solution of 4,4,4',4',5,5,5',5'-octamethyl-2,2'-bi-1,3,2-dioxaborolane (CAS 78183-34-3151 mg, 91.7 g), sodium carbonate (76.6 g) and [1,1'-bis(diphenylphosphino)ferrocene]dichloro-palladium(II) (4.40 g) in 1,4-dioxane (700 mL) was added ethyl-7-bromo-6-chloro-3-{3-[(6-fluoronaphthalen-1-yl)oxy]propyl}-1H-indole-2-carboxylate (see Intermediate 8, 70 g) under an atmosphere of nitrogen, and the reaction mixture was stirred at 100° C. for 40 hours. The residue was slurried in a mixture of ethanol and dichloromethane (300 and 50 mL) at 20° C. for 16 hours, then recrystallized in dichloromethane (80 mL) from 50° C. to 0° C. for 3 hours, and filtered to obtain the title compound (84.8 g). The filtrate was purified by silica gel column chromatography (petrol ether/ethyl acetate/dichloromethane=20/0/0-20/1/1) to obtain the title compound (21.2 g).

Intermediate 10 ethyl-7-bromo-3-(3-{[tert-butyl(dimethyl)silyl]oxy}propyl)-6-chloro-1H-indole-2-carboxylate

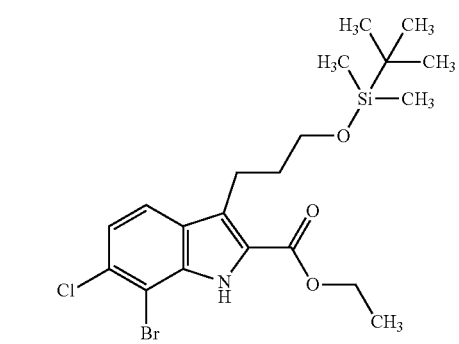 [SMILES: CCOC(=O)c1[nH]c2c(Br)c(Cl)ccc2c1CCCO[Si](C)(C)C(C)(C)C]

Ethyl-7-bromo-6-chloro-3-(3-hydroxypropyl)-1H-indole-2-carboxylate (see Intermediate 5, 20.0 g, 55.5 mmol) was dissolved in 400 mL of tetrahydrofuran and 1H-imidazole (5.66 g, 83.2 mmol), N,N-dimethylpyridin-4-amine (339 mg, 2.77 mmol) and tert-butyl(chloro)dimethylsilane (CAS 18162-48-6, 10.0 g, 66.5 mmol) were added. The mixture was stirred at room temperature for 3 hours, was poured into water and extracted with dichloromethane. The combined organic layers were dried using sodium sulfate, were filtered and were concentrated under reduced pressure. The crude material was purified by flash chromatography using silica gel (gradient hexane/ethyl acetate) to give the title compound (23.7 g, 87% yield).

LC-MS (Method 1): $R_t$=1.94 min; MS (ESIpos): m/z=474 [M+H]$^+$ $^1$H-NMR (400 MHz, DMSO-d6) δ[ppm]: −0.008 (0.46), 0.007 (0.55), 0.842 (0.87), 0.849 (16.00), 0.856 (1.01), 1.326 (1.22), 1.344 (2.74), 1.361 (1.25), 3.027 (0.47), 3.574 (0.45), 3.590 (1.01), 3.605 (0.44), 4.327 (1.21), 4.345 (1.19), 7.256 (0.94), 7.277 (1.00), 7.680 (0.97), 7.701 (0.83).

Intermediate 11 ethyl 3-(3-{[tert-butyl(dimethyl)silyl]oxy}propyl)-6-chloro-7-(4,4,5,5-tetramethyl-1,3,2-dioxa-borolan-2-yl)-1H-indole-2-carboxylate

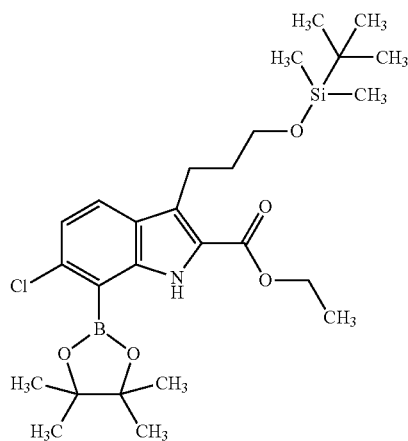 [SMILES: CCOC(=O)c1[nH]c2c(B3OC(C)(C)C(C)(C)O3)c(Cl)ccc2c1CCCO[Si](C)(C)C(C)(C)C]

Ethyl-7-bromo-3-(3-{[tert-butyl(dimethyl)silyl]oxy}propyl)-6-chloro-1H-indole-2-carboxylate (see Intermediate 10, 13.7 g, 28.8 mmol), 4,4,4',4',5,5,5',5'-octamethyl-2,2'-bi-1,3,2-dioxaborolane (CAS 78183-34-3, 8.79 g, 34.6 mmol), potassium acetate (5.66 g, 57.7 mmol) and 1,1'-bis(diphenylphosphino)-ferrocenpalladium(II)chloride (1.18 g, 1.44 mmol) in 30 mL of dried and degassed 1,4-dioxane were stirred for 3 days at 90° C., were filtered and were purified by flash chromatography using silica gel (gradient hexane/ethyl acetate) to give the title compound (7.90 g, 50% yield).

$^1$H-NMR (400 MHz, DMSO-d6) δ[ppm]: −0.007 (0.60), 0.007 (0.48), 0.844 (1.28), 0.850 (16.00), 0.857 (0.99), 1.281 (0.56), 1.325 (1.24), 1.342 (2.82), 1.360 (1.64), 1.373 (12.47), 3.044 (0.49), 3.568 (0.46), 3.584 (1.00), 3.600 (0.44), 4.318 (1.18), 4.336 (1.16), 7.120 (0.94), 7.141 (0.98), 7.791 (0.66), 7.812 (0.60), 9.956 (0.51).

Intermediate 12 ethyl 4-bromo-1,3-dimethyl-1H-pyrazole-5-carboxylate

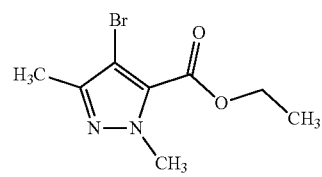

N-Bromosuccinimide (11.2 g, 62.4 mmol) was added to a solution of ethyl 1,3-dimethyl-1H-pyrazole-5-carboxylate (5.00 g, 29.7 mmol, CAS No: 5744-40-1) in 1,2-dichloroethane (100 mL) and the mixture was stirred for 15 h at 65-80° C. followed by 3 days at room temperature. For work-up, the mixture was diluted with ethyl acetate, washed with water and the organic phase was filtrated through a silicone filter and concentrated. The residue was purified by flash chromatography (Biotage SNAP cartridge silica, hexanes/dichloromethane gradient, 0%→100% dichloromethane) to give the title compound (6.69 g, 89% yield).

LC-MS (Method 2): $R_t$=1.15 min; MS (ESIpos): m/z=247 [M+H]$^+$ $^1$H-NMR (400 MHz, DMSO-d6) δ[ppm]: 1.308 (4.21), 1.325 (8.89), 1.343 (4.18), 2.155 (14.47), 3.862 (1.45), 4.008 (16.00), 4.302 (1.34), 4.320 (4.19), 4.337 (4.07), 4.355 (1.24).

Intermediate 13

(4-bromo-1,3-dimethyl-1H-pyrazol-5-yl)methanol

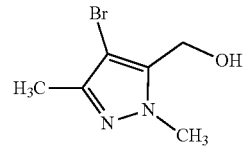

Lithium aluminium hydride (27 mL, 1.0 M in THF, 27 mmol) was added dropwise at 0° C. to a solution of ethyl 4-bromo-1,3-dimethyl-1H-pyrazole-5-carboxylate (see Intermediate 12, 6.69 g, 27.1 mmol) in THF (220 mL) and the mixture was stirred at 0° C. for 1.5 h. The reaction was quenched by dropwise addition of water (5.4 mL) followed by aqueous sodium hydroxide (5.4 mL, 2 M, 11 mmol) and again water (5.4 mL). The mixture was then filtrated through a pad of celite, eluted with THF and the filtrate was concentrated. The residue was purified by flash chromatography (Biotage SNAP cartridge silica 100 g, hexanes/ethyl acetate gradient, 20%→80% ethyl acetate) to give the title compound (3.77 g, 67% yield).

$^1$H-NMR (400 MHz, DMSO-d6) δ[ppm]: 2.083 (14.56), 3.334 (16.00), 4.422 (2.80), 4.435 (2.81), 5.311 (0.59), 5.325 (1.50), 5.337 (0.56).

Intermediate 14 ethyl 4-bromo-1,5-dimethyl-1H-pyrazole-3-carboxylate

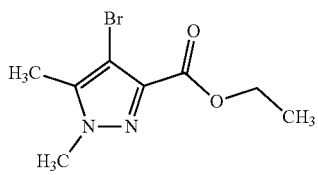

N-Bromosuccinimide (16.3 g, 90.5 mmol) was added to a solution of ethyl 1,5-dimethyl-1H-pyrazole-3-carboxylate (7.25 g, 43.1 mmol, CAS No 5744-51-4) in 1,2-dichloroethane (150 mL) and the mixture was stirred for 15 h at 80° C. For work-up, the mixture was diluted with dichloromethane, washed with water and the organic phase was filtrated through a silicone filter and concentrated. The residue was purified by flash chromatography (Biotage SNAP cartridge silica 340 g, hexanes/dichloromethane gradient, 0→100% dichloromethane) to give the title compound (6.49 g, 61% yield).

$^1$H-NMR (400 MHz, DMSO-d6) δ[ppm]: 1.261 (4.14), 1.278 (8.78), 1.296 (4.21), 2.268 (14.94), 2.518 (0.74), 2.523 (0.49), 3.857 (16.00), 4.229 (1.31), 4.247 (4.03), 4.264 (3.94), 4.282 (1.24).

Intermediate 15

(4-bromo-1,5-dimethyl-1H-pyrazol-3-yl)methanol

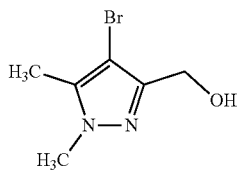

Lithium borohydride (711 mg, 32.6 mmol) was added to a solution of ethyl 4-bromo-1,5-dimethyl-1H-pyrazole-3-carboxylate (see Intermediate 14, 6.45 g, 26.1 mmol in THF (150 mL) and the mixture was stirred for 1 h at room temperature and 7 h at 60° C. The reaction was quenched by addition of saturated aqueous ammonium chloride solution and the mixture was extracted with ethyl acetate. The organic phase was filtrated through a silicone filter and concentrated. The residue was purified by flash chromatography (hexanes/ethyl acetate gradient, 50%→100% ethyl acetate) to give the title compound (4.07 g, 76% yield).

$^1$H-NMR (400 MHz, DMSO-d6) δ[ppm]: 2.205 (16.00), 2.518 (0.43), 3.330 (10.35), 4.285 (3.97), 4.299 (4.13), 4.933 (1.00), 4.946 (2.22), 4.960 (0.93).

Intermediate 16 ethyl 5-ethyl-1-methyl-1H-pyrazole-3-carboxylate

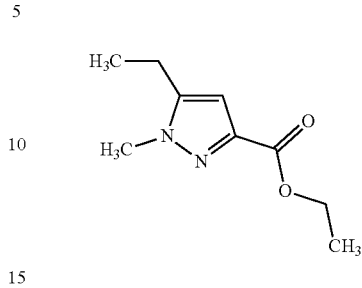

Ethyl 2,4-dioxohexanoate (CAS 13246-52-1, 5.00 g, 29.0 mmol) was dissolved in 20 mL of acetic acid. Under ice cooling methylhydrazine (1.5 mL, 29.0 mmol) was added and the mixture was stirred at rt for 23 hours. Methylhydrazine (0.5 mL, 10.0 mmol) was added and stirring was continued at rt for 24 hours. The reaction mixture was poured into ice water and extracted with ethyl acetate. The combined organic layers were washed with brine, dried using a water resistant filter and concentrated under reduced pressure. The crude material was purified using silica gel (gradient hexaneethyl acetate) to obtain the title compound (2.13 g, 40% yield).

LC-MS (Method 1): $R_t$=0.92 min; MS (ESIpos): m/z=183 [M+H]$^+$ $^1$H-NMR (400 MHz, DMSO-d6) δ[ppm]: 1.170 (6.09), 1.188 (12.55), 1.208 (6.57), 1.245 (7.14), 1.263 (16.00), 1.280 (7.23), 2.601 (1.10), 2.602 (1.08), 2.619 (3.24), 2.621 (3.35), 2.638 (3.29), 2.640 (3.34), 2.657 (1.02), 2.659 (1.03), 3.331 (8.78), 4.200 (1.95), 4.218 (6.25), 4.236 (6.29), 4.254 (1.95), 5.759 (0.98), 6.518 (4.92).

Intermediate 17 ethyl 4-bromo-5-ethyl-1-methyl-1H-pyrazole-3-carboxylate

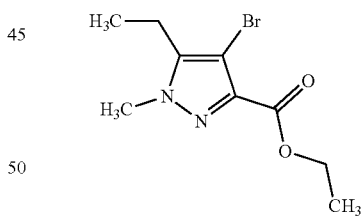

Ethyl 5-ethyl-1-methyl-1H-pyrazole-3-carboxylate (see Intermediate 16, 2.10 g, 11.5 mmol) was dissolved in 15 mL of acetic acid. A solution of bromine in acetic acid (23 mL, 1.0 M, 23 mmol) was added dropwise and the reaction mixture was stirred for 18 hours at rt. The mixture was poured into ice water and aqueous sodium thiosulfate solution (10%) was added. The mixture was extracted with ethyl acetate and the combined organic layers were washed with brine, dried using a water resistant filter and concentrated under reduced pressure to obtain 2.97 g of the title compound. The crude material was used without further purification in the next step.

LC-MS (Method 1): $R_t$=1.08 min; MS (ESIpos): m/z=261 [M+H]$^+$

¹H-NMR (400 MHz, DMSO-d6) δ[ppm]: 1.077 (2.69), 1.096 (6.29), 1.115 (2.81), 1.260 (3.48), 1.278 (7.87), 1.295 (3.68), 1.907 (1.63), 2.518 (0.62), 2.523 (0.41), 2.673 (0.89), 2.692 (2.71), 2.711 (2.65), 2.730 (0.75), 3.894 (16.00), 4.231 (1.11), 4.249 (3.60), 4.266 (3.59), 4.284 (1.10).

Intermediate 18

(4-bromo-5-ethyl-1-methyl-1H-pyrazol-3-yl)methanol

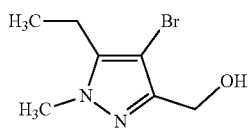

Ethyl 4-bromo-5-ethyl-1-methyl-1H-pyrazole-3-carboxylate (see Intermediate 17, 2.97 g) was dissolved in 45 mL of THF and lithium borohydride (310 mg, 14.2 mmol) was added portionwise. This mixture was stirred for 20 hours at rt and for 22 hours at 60° C. Lithium borohydride (50 mg, 2.3 mmol) was added and stirring was continued for 24 hours at rt and 3 hours at 60° C. The reaction mixture was diluted with saturated aqueous ammonia chloride solution and extracted with ethyl acetate. The combined organic layers were washed with brine, dried using a water resistant filter and concentrated under reduced pressure to obtain the title compound (2.18 g).

The crude material was used without further purification in the next step.

LC-MS (Method 1): $R_t$=0.79 min; MS (ESIpos): m/z=219 [M+H]⁺

¹H-NMR (400 MHz, DMSO-d6) δ[ppm]: 1.068 (3.21), 1.087 (7.19), 1.105 (3.37), 2.518 (0.44), 2.609 (1.02), 2.628 (3.36), 2.647 (3.29), 2.666 (1.04), 3.761 (16.00), 4.287 (4.77), 4.301 (4.91), 4.941 (1.34), 4.955 (2.69), 4.969 (1.21).

Intermediate 19

(4-bromo-3-ethyl-1-methyl-1H-pyrazol-5-yl)methanol

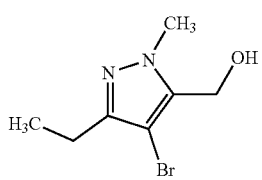

To a solution of ethyl 4-bromo-3-ethyl-1-methyl-1H-pyrazole-5-carboxylate (CAS, 128537-28-0, 200 g, 766 mmol, 1 eq) in 200 mL THF was added lithiumborohydride (83 g, 3.83 mol, 5 eq) slowly. The mixture was stirred at 60° C. for 3 h. The reaction mixture was quenched by addition of water (2000 mL) at 20° C., and then extracted with ethyl acetate (1000 mL) three times. The combined organic layers were washed with brine (800 mL), dried over sodium sulfate, filtered and concentrated under reduced pressure to give a residue. The residue was purified by triturating with PE (2000 mL) for 3 times to give the target compound (112 g, 99% purity) as a white solid.

¹H-NMR (400 MHz, Methanol-d4) δ [ppm]=4.60 (s, 2H), 3.86 (s, 3H), 2.58 (q, 2H), 1.20 (t, 3H).

Intermediate 20 ethyl 5-ethyl-1-[2-(morpholin-4-yl)ethyl]-1H-pyrazole-3-carboxylate

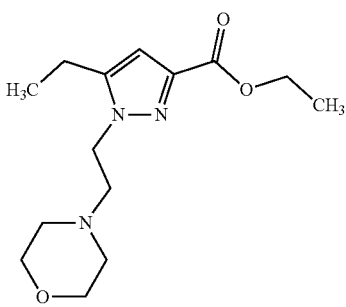 [SMILES: CCOC(=O)c1cc(CC)n(CCN2CCOCC2)n1]

To a mixture of ethyl 2,4-dioxohexanoate (CAS 13246-52-1, 3.00 g, 17.1 mmol) in acetic acid (24 mL) was added 4-(2-hydrazinylethyl)morpholine (CAS 2154-24-7, 2.53 g, 17.1 mmol) at 0° C. and the reaction mixture was stirred at 100° C. for 3 h. Upon cooling, the mixture was concentrated. The residue was diluted with ethyl acetate and the organic phase was washed with saturated aqueous sodium bicarbonate solution and brine. The organic phase was dried over sodium sulfate. After filtration and removal of the solvents the crude product was purified by flash chromatography (hexane/ethyl acetate gradient, 50%→100% ethyl acetate) to give the title compound (1.96 g).

¹H-NMR (400 MHz, DMSO-d6) δ[ppm]: 1.192 (5.34), 1.211 (12.80), 1.230 (6.02), 1.249 (7.04), 1.267 (16.00), 1.285 (7.15), 2.385 (2.88), 2.396 (3.98), 2.408 (3.12), 2.518 (1.26), 2.523 (0.85), 2.642 (3.19), 2.658 (5.49), 2.661 (5.21), 2.663 (4.60), 2.669 (1.00), 2.675 (2.92), 2.680 (3.82), 2.682 (3.66), 2.700 (1.08), 3.519 (4.16), 3.530 (5.19), 3.542 (4.09), 4.175 (2.39), 4.192 (4.57), 4.207 (3.68), 4.225 (6.71), 4.242 (6.56), 4.260 (1.95), 6.511 (5.60).

Intermediate 21 ethyl 3-ethyl-1-[2-(morpholin-4-yl)ethyl]-1H-pyrazole-5-carboxylate

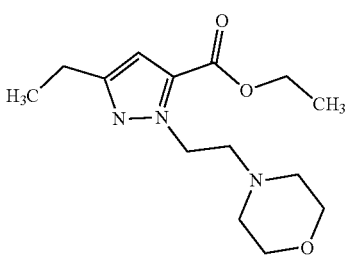

The title compound was isolated as a side product in the synthesis of ethyl 5-ethyl-1-[2-(morpholin-4-yl)ethyl]-1H-pyrazole-3-carboxylate (see Intermediate 20).

¹H-NMR (500 MHz, DMSO-d6) δ[ppm]: 0.000 (5.34), 1.145 (7.12), 1.155 (0.41), 1.160 (16.00), 1.175 (7.30), 1.283 (6.71), 1.298 (14.69), 1.312 (7.24), 1.906 (0.75), 2.367 (2.57), 2.376 (3.50), 2.384 (2.63), 2.529 (1.62), 2.544 (4.72), 2.559 (4.59), 2.574 (1.47), 2.602 (2.50), 2.615 (4.09), 2.629 (2.56), 3.329 (3.25), 3.501 (3.51), 3.510 (4.71), 3.519 (3.52), 4.255 (2.16), 4.269 (6.47), 4.284 (6.75), 4.298 (2.08), 4.507 (2.42), 4.520 (4.07), 4.534 (2.37), 6.653 (7.25).

Intermediate 22 ethyl 4-bromo-3-ethyl-1-[2-(morpholin-4-yl)ethyl]-1H-pyrazole-5-carboxylate

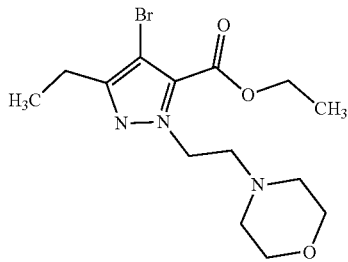

A solution of bromine in acetic acid (8.2 mL, 1.0 M, 8.2 mmol) was added to a solution of ethyl 3-ethyl-1-[2-(morpholin-4-yl)ethyl]-1H-pyrazole-5-carboxylate (770 mg, 2.74 mmol; see Intermediate 21) in acetic acid (16 mL) at 0° C., and the mixture was stirred for 4 h at room temperature. For work-up, the reaction was poured into ice water followed by the addition of a saturated aqueous sodium thiosulfate solution and the pH of the mixture was adjusted to pH>7 by the addition of saturated aqueous sodium bicarbonate solution. The mixture was extracted with ethyl acetate and the combined organic phases were dried over sodium sulfate. After filtration and removal of the solvents the crude product was purified by flash chromatography (hexane/ethyl acetate gradient, 0%→100% ethyl acetate) to give the title compound (810 mg).

LC-MS (Method 2): Rt=1.28 min; MS (ESIpos): m/z=360 [M+H]⁺

¹H-NMR (400 MHz, CDCl₃): δ [ppm]=4.61 (t, 2H), 4.39 (q, 2H), 3.75-3.53 (m, 4H), 2.71 (t, 2H), 2.64 (q, 2H), 2.51-2.36 (m, 4H), 1.59 (s, 2H), 1.43 (t, 3H), 1.23 (t, 3H).

Intermediate 23

{4-bromo-3-ethyl-1-[2-(morpholin-4-yl)ethyl]-1H-pyrazol-5-yl}methanol

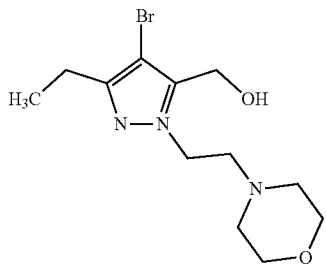

To a solution of ethyl 4-bromo-3-ethyl-1-[2-(morpholin-4-yl)ethyl]-1H-pyrazole-5-carboxylate (810 mg, 2.25 mmol; see Intermediate 22) in THF (9 mL) was added a solution of lithium borohydride in THF (1.3 mL, 2.0 M, 2.7 mmol) and the mixture was stirred at 60° C. for 24 hours. For work-up, sodium sulfate hydrate was added and the mixture was stirred for 1 hour at room temperature. The mixture was filtrated and the filtrate was concentrated under reduced pressure and the crude product was purified by flash chromatography (dichloromethane/acetone gradient, 0%→40% acetone) to give the title compound (650 mg).

Intermediate 24 ethyl-1-(3-{[tert-butyl(dimethyl)silyl]oxy}propyl)-5-methyl-1H-pyrazole-3-carboxylate

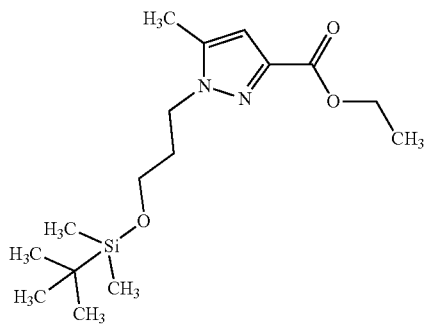 [SMILES: CCOC(=O)c1cc(C)n(CCCO[Si](C)(C)C(C)(C)C)n1]

Ethyl-5-methyl-1H-pyrazole-3-carboxylate (CAS 4027-57-0, 10.0 g, 64.9 mmol) and 3-bromopropoxy-(tert-butyl)-dimethylsilane (CAS 89031-84-5, 17 mL, 71 mmol) were dissolved in 100 mL of DMF and cesium carbonate (52.8 g, 162 mmol) was added. The mixture was stirred at 80° C. overnight. The reaction mixture was poured into water and extracted with ethyl acetate. The combined organic layers were dried using sodium sulfate, were filtered and were concentrated under reduced pressure. The crude material was purified by flash chromatography using silica gel (gradient hexane/ethyl acetate) to give the title compound (6.10 g, 27% yield).

LC-MS (Method 1): Rt=1.55 min; MS (ESIpos): m/z=327 [M+H]⁺

¹H-NMR (400 MHz, DMSO-d6) δ[ppm]: 0.000 (0.86), 0.003 (0.63), 0.018 (0.49), 0.835 (1.24), 0.839 (1.08), 0.846 (16.00), 0.854 (0.89), 1.221 (1.41), 1.239 (3.08), 1.256 (1.41), 1.890 (0.56), 2.257 (3.58), 3.517 (0.60), 3.532 (1.20), 3.547 (0.58), 4.091 (0.56), 4.109 (0.95), 4.126 (0.53), 4.176 (0.45), 4.194 (1.43), 4.211 (1.40), 4.229 (0.42), 6.484 (1.06), 6.486 (1.06).

Intermediate 25 ethyl-4-bromo-1-(3-{[tert-butyl(dimethyl)silyl]oxy}propyl)-5-methyl-1H-pyrazole-3-carboxylate

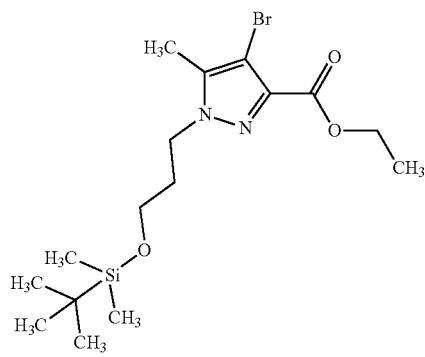 [SMILES: CCOC(=O)c1nn(CCCO[Si](C)(C)C(C)(C)C)c(C)c1Br]

Ethyl-1-(3-{[tert-butyl(dimethyl)silyl]oxy}propyl)-5-methyl-1H-pyrazole-3-carboxylate (see Intermediate 24, 6.10 g, 18.7 mmol) and 1-bromopyrrolidine-2,5-dione (CAS 128-08-5, 4.99 g, 28.0 mmol) were dissolved in 80 mL of DMF and the mixture was stirred at rt overnight. Water was added and the mixture was extracted with ethyl acetate. The combined organic layers were washed with a solution of saturated aqueous sodium bicarbonate and brine, was dried using sodium sulfate, was filtered and was concentrated under reduced pressure. The crude material was purified by flash chromatography using silica gel (gradient hexane/ethyl acetate) to give the title compound (3.66 g, 48% yield).

LC-MS (Method 1): $R_t$=1.66 min; MS (ESIpos): m/z=405 $[M+H]^+$ $^1$H-NMR (400 MHz, DMSO-d6) δ[ppm]: 0.000 (0.52), 0.015 (0.41), 0.833 (0.90), 0.840 (16.00), 0.847 (0.76), 1.242 (1.43), 1.260 (3.27), 1.278 (1.46), 1.893 (0.48), 2.264 (5.14), 3.533 (0.52), 3.547 (1.01), 3.562 (0.49), 4.176 (0.48), 4.194 (0.85), 4.212 (0.69), 4.230 (1.39), 4.248 (1.37), 4.266 (0.41).

Intermediate 26

[4-bromo-1-(3-{[tert-butyl(dimethyl)silyl]oxy}propyl)-5-methyl-1H-pyrazol-3-yl]methanol

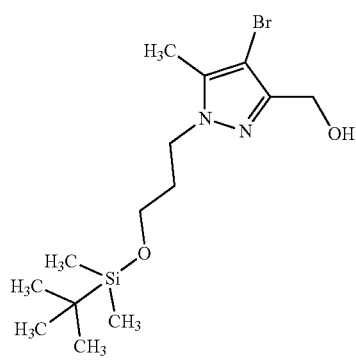 [SMILES: Cc1c(Br)c(CO)nn1CCCO[Si](C)(C)C(C)(C)C]

Ethyl-4-bromo-1-(3-{[tert-butyl(dimethyl)silyl]oxy}propyl)-5-methyl-1H-pyrazole-3-carboxylate (see Intermediate 25, 3.66 g, 9.03 mmol) was dissolved in 80 mL of THF and lithium borohydride solution (2.9 mL, 4M in THF, 11.74 mmol) was added. The reaction mixture was stirred at 50° C. for 3 hours and at rt for 72 hours. The mixture was diluted with aqueous saturated ammonia chloride solution and extracted with ethyl acetate. The combined organic layers were dried using sodium sulfate, filtered and concentrated under reduced pressure to give the title compound (3.12 g). The crude material was used without further purification.

LC-MS (Method 1): $R_t$=1.45 min; MS (ESIpos): m/z=363 $[M+H]^+$ $^1$H-NMR (400 MHz, DMSO-d6) δ[ppm]: 0.000 (0.58), 0.015 (0.44), 0.836 (0.99), 0.843 (16.00), 0.850 (0.92), 1.846 (0.51), 2.190 (5.40), 3.514 (0.61), 3.528 (1.13), 3.543 (0.53), 4.029 (0.53), 4.047 (0.83), 4.064 (0.50), 4.273 (1.54), 4.287 (1.60), 4.916 (0.47), 4.930 (1.08), 4.944 (0.44).

Intermediate 27

4-bromo-5-ethyl-1-methyl-1H-pyrazole-3-carbaldehyde

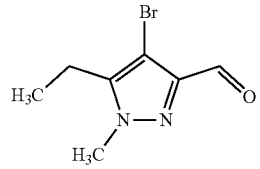

Ethanedioyl dichloride (CAS 79-37-8, 9.0 mL, 100 mmol) was dissolved in 170 mL of dichloromethane under an argon atmosphere. The mixture was cooled to −72° C. and DMSO (14.6 mL, 205 mmol) was added dropwise. After 15 minutes of stirring a mixture of (4-bromo-5-ethyl-1-methyl-1H-pyrazol-3-yl)methanol (see Intermediate 18, 15.0 g, 68.5 mmol) in 120 mL of dichloromethane and triethylamine (57 mL, 410 mmol) were added dropwise. The reaction mixture was allowed to warm to rt over a period of 1.5 hours. Water was added and the mixture was extracted with dichloromethane. The combined organic layers were washed with brine, dried using sodium sulfate, filtered and concentrated under reduced pressure to give the title compound (16.6 g). The crude material was used without further purification.

LC-MS (Method 1): $R_t$=0.94 min; MS (ESIpos): m/z=217 $[M+H]^+$ $^1$H-NMR (400 MHz, DMSO-d6) δ[ppm]: 1.094 (2.90), 1.113 (6.29), 1.132 (2.93), 1.178 (0.45), 2.101 (0.72), 2.539 (5.77), 2.691 (0.90), 2.710 (2.83), 2.729 (2.74), 2.748 (0.82), 3.958 (16.00), 9.800 (5.92).

Intermediate 28 ethyl (5E)-6-(4-bromo-5-ethyl-1-methyl-1H-pyrazol-3-yl)hex-5-enoate

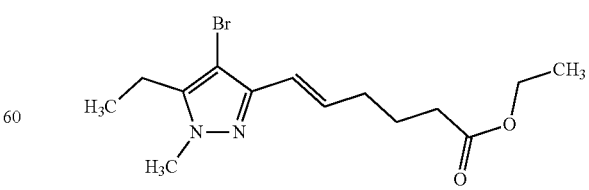

4-Bromo-5-ethyl-1-methyl-1H-pyrazole-3-carbaldehyde (see Intermediate 27 12.9 g, 59.4 mmol), (5-ethoxy-5-oxopentyl)(triphenyl)phosphanium bromide (CAS 118026-77-0, 35.0 g, 74.3 mmol) and potassium carbonate (10.3 g, 74.3 mmol) were stirred in 500 mL of 2-propanol under reflux overnight. The reaction mixture was filtered and concentrated under reduced pressure. The crude material was purified by flash chromatography using silica gel (gradient hexane/ethyl acetate) to give 2.40 g of the title compound and 1.90 g of the Z-isomer (see Intermediate 29).

LC-MS (Method 1): Rt=1.34 min; MS (ESIpos): m/z=329 [M+H]$^+$ $^1$H-NMR (400 MHz, DMSO-d6) δ[ppm]: 1.053 (0.76), 1.063 (3.17), 1.068 (1.10), 1.082 (7.55), 1.090 (0.95), 1.100 (4.00), 1.109 (0.42), 1.152 (4.38), 1.169 (9.61), 1.187 (4.68), 1.649 (1.28), 1.667 (1.95), 1.686 (1.41), 1.704 (0.42), 2.108 (1.26), 2.142 (0.53), 2.145 (0.55), 2.162 (1.43), 2.179 (1.40), 2.197 (0.48), 2.200 (0.47), 2.285 (1.89), 2.304 (3.63), 2.322 (1.80), 2.518 (0.82), 2.523 (0.53), 2.609 (0.90), 2.628 (3.04), 2.639 (0.43), 2.647 (3.01), 2.666 (0.98), 3.765 (16.00), 3.772 (1.46), 3.783 (1.23), 4.017 (1.36), 4.034 (4.07), 4.052 (4.04), 4.070 (1.28), 4.395 (0.67), 4.651 (0.67), 6.159 (0.57), 6.162 (1.20), 6.166 (0.57), 6.199 (0.84), 6.202 (1.69), 6.206 (0.85), 6.352 (0.62), 6.369 (1.35), 6.387 (0.60), 6.392 (0.44), 6.409 (0.90), 6.427 (0.41).

Intermediate 29 ethyl (5Z)-6-(4-bromo-5-ethyl-1-methyl-1H-pyrazol-3-yl)hex-5-enoate

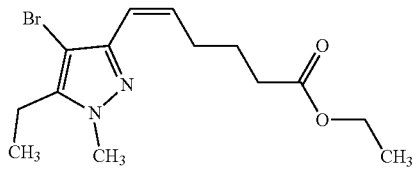 [SMILES: CCOC(=O)CCC/C=C\c1nn(C)c(CC)c1Br]

The title compound was isolated in the synthesis of Intermediate 28.

LC-MS (Method 1): Rt=1.42 min; MS (ESIpos): m/z=329 [M+H]$^+$ $^1$H-NMR (400 MHz, DMSO-d6) δ [ppm]: 1.073 (2.98), 1.092 (6.99), 1.110 (3.15), 1.132 (4.31), 1.139 (0.58), 1.150 (9.34), 1.154 (0.78), 1.168 (4.54), 1.642 (1.44), 1.660 (2.13), 1.679 (1.50), 1.698 (0.45), 2.080 (0.54), 2.277 (1.98), 2.295 (3.48), 2.314 (1.72), 2.518 (0.85), 2.520 (0.85), 2.523 (0.81), 2.539 (1.42), 2.543 (1.45), 2.558 (1.39), 2.562 (1.42), 2.576 (0.48), 2.580 (0.49), 2.624 (0.89), 2.643 (2.97), 2.662 (2.97), 2.681 (0.87), 3.800 (16.00), 3.999 (1.30), 4.017 (3.99), 4.034 (3.89), 4.052 (1.21), 5.659 (0.51), 5.677 (1.06), 5.687 (0.56), 5.696 (0.49), 5.706 (1.21), 5.724 (0.56), 6.092 (0.70), 6.096 (1.43), 6.100 (0.68), 6.121 (0.59), 6.125 (1.20), 6.129 (0.60).

Intermediate 30

6-(4-bromo-5-ethyl-1-methyl-1H-pyrazol-3-yl)hex-5-en-1-ol

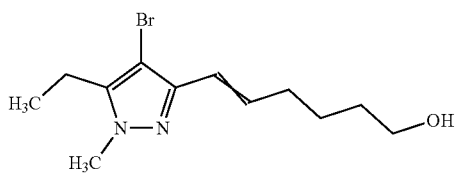 [SMILES: CCc1c(Br)c(C=CCCCCO)nn1C]

Ethyl-(5E)-6-(4-bromo-5-ethyl-1-methyl-1H-pyrazol-3-yl)hex-5-enoate (see Intermediate 28, 2.40 g, 7.29 mmol) and ethyl-(5Z)-6-(4-bromo-5-ethyl-1-methyl-1H-pyrazol-3-yl)hex-5-enoate (see Intermediate 29, 1.90 g, 5.77 mmol) were dissolved in 100 mL of THF and lithium borohydride solution (7.2 mL, 2.0 M in THF, 29 mmol) was added. The reaction mixture was stirred at rt for 72 hours. The mixture was diluted with aqueous saturated ammonia chloride solution and extracted with ethyl acetate. The combined organic layers were dried using sodium sulfate, filtered and concentrated under reduced pressure to give 3.60 g of the title compound as a mixture of the E- and Z-isomer. The crude material was used without further purification in the next step.

LC-MS (Method 1): Rt=1.11 and 1.19 min; MS (ESIpos): m/z=329 [M+H]$^+$ $^1$H-NMR (400 MHz, DMSO-d6) δ[ppm]: 1.053 (0.89), 1.062 (3.45), 1.068 (1.43), 1.075 (3.69), 1.081 (8.36), 1.093 (7.29), 1.100 (4.51), 1.112 (3.19), 1.352 (0.67), 1.397 (0.62), 1.406 (1.16), 1.417 (2.55), 1.423 (3.08), 1.428 (4.19), 1.434 (4.61), 1.445 (3.19), 1.465 (0.52), 2.081 (0.44), 2.108 (1.26), 2.147 (1.04), 2.151 (1.10), 2.164 (1.16), 2.167 (1.03), 2.181 (0.51), 2.518 (1.29), 2.523 (1.25), 2.525 (1.25), 2.529 (1.17), 2.543 (1.20), 2.547 (1.06), 2.561 (0.47), 2.607 (1.01), 2.626 (3.93), 2.644 (5.76), 2.663 (3.68), 2.682 (0.86), 3.363 (0.77), 3.378 (2.37), 3.392 (3.15), 3.406 (2.21), 3.421 (0.50), 3.722 (0.59), 3.762 (16.00), 3.772 (1.25), 3.783 (1.19), 3.806 (15.16), 4.322 (1.24), 4.335 (2.55), 4.348 (1.19), 4.361 (1.33), 4.374 (2.68), 4.387 (1.28), 4.395 (0.75), 4.651 (0.69), 5.670 (0.49), 5.689 (1.02), 5.699 (0.55), 5.706 (0.48), 5.717 (1.19), 5.736 (0.56), 6.063 (0.66), 6.067 (1.35), 6.071 (0.72), 6.092 (0.57), 6.096 (1.12), 6.100 (0.63), 6.154 (0.57), 6.158 (1.19), 6.161 (0.64), 6.194 (0.79), 6.198 (1.67), 6.201 (0.91), 6.384 (0.62), 6.402 (1.27), 6.419 (0.60), 6.424 (0.46), 6.442 (0.95), 6.459 (0.42), 6.549 (1.16), 7.015 (0.46), 7.033 (0.49).

Intermediate 31 ethyl 6-chloro-7-[5-(hydroxymethyl)-1,3-dimethyl-1H-pyrazol-4-yl]-3-[3-(naphthalen-1-yloxy)-propyl]-1H-indole-2-carboxylate

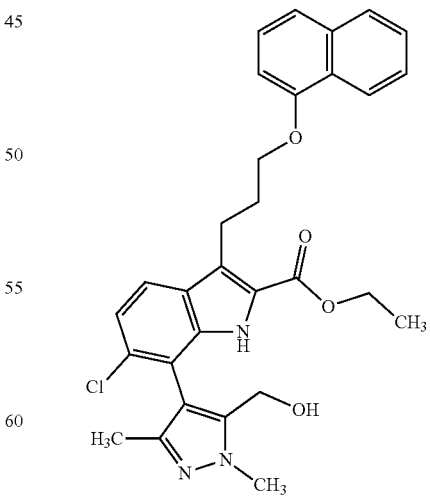

To a solution of ethyl 6-chloro-3-[3-(naphthalen-1-yloxy) propyl]-7-(4,4,5,5-tetramethyl-1,3,2-dioxaborolan-2-yl)-1H-indole-2-carboxylate (see Intermediate 7, 3.00 g, 5.62 mmol) and (4-bromo-1,3-dimethyl-1H-pyrazol-5-yl)methanol (see intermediate 13, 960 mg, 4.68 mmol) in 1,4-dioxane (54 mL) were added an aqueous 2-molar solution of potassium carbonate (5.9 mL, 2.0 M, 12 mmol) and palladium-triphenylphosphine (1:4) (541 mg, 468 µmol) and the mixture was purged with argon for 3 minutes. The reaction was stirred at 110° C. for 3 h in a microwave reactor (divided in 3 portions). For work-up the combined reaction mixtures were concentrated under reduced pressure and the residue was purified by flash chromatography (hexane/ethyl acetate gradient, 25%→100% ethyl acetate) to give the title product (550 mg).

LC-MS (Method 2): Rt=1.54 min; MS (ESIpos): m/z=532 [M+H]$^+$

Intermediate 32

(rac)-ethyl (11Z)-4-chloro-1,3-dimethyl-7-[3-(naphthalen-1-yloxy)propyl]-1,10,13,15-tetrahydropyrazolo[4',3':9,10][1,6]oxazacycloundecino[8,7,6-hi]indole-8-carboxylate

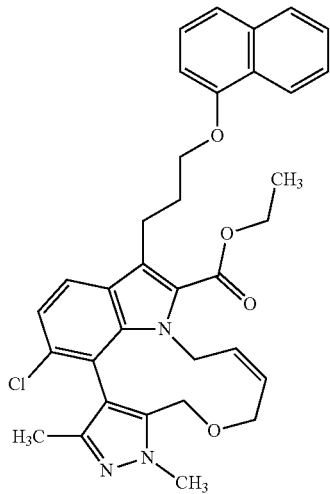 [SMILES: CCOC(=O)c1c(CCCOc2cccc3ccccc23)c2ccc(Cl)c3c2n1C/C=C\COCc1c-3c(C)nn1C]

To a mixture of ethyl 6-chloro-7-[5-(hydroxymethyl)-1,3-dimethyl-1H-pyrazol-4-yl]-3-[3-(naphthalen-1-yloxy)propyl]-1H-indole-2-carboxylate (see Intermediate 31, 550 mg, 1.03 mmol) in acetonitrile (11 mL) was added caesium carbonate (1.70 g, 5.17 mmol) and the mixture was stirred for 10 minutes. (2Z)-1,4-dichlorobut-2-ene (CAS 110-57-6, 130 µL, 1.1 mmol) and sodium iodide (313 mg, 2.07 mmol) were added and the reaction mixture was stirred for 18 h at 40° C. For work-up, the mixture was poured into water and the mixture was extracted with ethyl acetate. The combined organic phases were washed with brine and the organic phase was dried over sodium sulfate, filtered and concentrated under reduced pressure. The crude product was purified by flash chromatography (dichloromethane/acetone gradient 0→40% acetone) to give title compound (200 mg).

LC-MS (Method 2): Rt=1.71 min; MS (ESIpos): m/z=584 [M+H]$^+$ $^1$H-NMR (400 MHz, DMSO-d6) δ[ppm]: 1.066 (1.25), 1.172 (0.59), 1.263 (4.98), 1.281 (10.78), 1.298 (5.03), 1.670 (16.00), 1.988 (0.99), 2.229 (0.91), 2.247 (1.29), 2.263 (0.96), 2.323 (0.57), 2.327 (0.78), 2.331 (0.56), 2.518 (3.28), 2.523 (2.24), 2.665 (0.56), 2.669 (0.77), 2.673 (0.53), 3.288 (0.72), 3.307 (1.42), 3.347 (0.78), 3.364 (0.40), 3.482 (0.68), 3.513 (1.26), 3.544 (0.85), 3.744 (0.73), 3.755 (0.82), 3.776 (0.66), 3.787 (0.68), 3.877 (15.25), 4.088 (2.02), 4.122 (2.15), 4.222 (2.11), 4.231 (1.35), 4.239 (3.94), 4.248 (2.55), 4.253 (1.70), 4.266 (1.93), 4.271 (0.74), 4.284 (0.68), 4.289 (1.81), 4.307 (1.70), 4.316 (0.88), 4.325 (0.52), 4.334 (0.86), 4.524 (0.59), 4.550 (0.72), 4.564 (0.74), 4.591 (0.87), 4.693 (2.19), 4.727 (2.02), 4.787 (0.59), 4.814 (1.04), 4.840 (0.55), 4.926 (0.96), 4.964 (0.83), 5.126 (0.42), 5.143 (0.68), 5.154 (0.66), 5.759 (0.72), 6.910 (1.87), 6.927 (2.02), 7.274 (3.98), 7.295 (4.14), 7.375 (1.34), 7.395 (2.63), 7.414 (2.17), 7.450 (2.78), 7.463 (0.75), 7.470 (1.56), 7.479 (1.46), 7.483 (1.61), 7.486 (0.82), 7.500 (1.60), 7.505 (1.90), 7.510 (1.57), 7.526 (1.56), 7.530 (1.60), 7.543 (0.79), 7.547 (0.68), 7.814 (3.67), 7.836 (3.20), 7.858 (1.78), 7.876 (1.68), 7.879 (1.48), 8.138 (1.60), 8.158 (1.51).

Intermediate 33

(rac)-ethyl 4-chloro-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

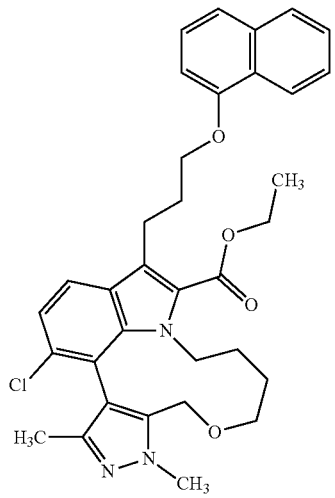 [SMILES: CCOC(=O)c1c(CCCOc2cccc3ccccc23)c2ccc(Cl)c3c2n1CCCCOCc1c-3c(C)nn1C]

A mixture of (rac)-ethyl (11Z)-4-chloro-1,3-dimethyl-7-[3-(naphthalen-1-yloxy)propyl]-1,10,13,15-tetrahydropyrazolo[4',3':9,10][1,6]oxazacycloundecino[8,7,6-hi]indole-8-carboxylate (see Intermediate 32, 100 mg, 171 µmol) and chloro[tris(triphenyl-λ$^5$-phosphanyl)]rhodium (318 mg, 342 µmol) in ethanol (13 mL) was stirred under an atmosphere of hydrogen at room temperature for 24 hours. For work-up, the reaction mixture was concentrated under reduced pressure. The residue was purified by flash chromatography (hexane/ethyl acetate gradient, 12%→100% ethyl acetate) to give the title compound (55 mg).

LC-MS (Method 2): Rt=1.74 min; MS (ESIpos): m/z=586 [M+H]⁺

¹H-NMR (400 MHz, DMSO-d6) δ[ppm]: 1.021 (0.98), 1.035 (1.52), 1.050 (1.15), 1.066 (0.70), 1.145 (0.42), 1.154 (1.10), 1.172 (2.15), 1.190 (1.45), 1.233 (1.31), 1.256 (5.47), 1.274 (11.35), 1.291 (5.29), 1.739 (16.00), 1.907 (0.87), 1.988 (3.11), 2.209 (1.15), 2.225 (0.87), 2.318 (0.42), 2.323 (1.01), 2.327 (1.43), 2.331 (1.01), 2.518 (6.13), 2.523 (4.47), 2.660 (0.56), 2.665 (1.12), 2.669 (1.52), 2.673 (1.10), 2.678 (0.54), 2.837 (0.80), 2.847 (0.54), 2.865 (0.82), 3.229 (0.47), 3.245 (0.61), 3.262 (0.89), 3.282 (0.49), 3.307 (0.61), 3.361 (0.63), 3.415 (0.40), 3.430 (0.87), 3.445 (0.75), 3.459 (0.82), 3.866 (15.35), 3.943 (0.47), 3.964 (0.73), 3.978 (0.56), 3.999 (0.58), 4.018 (0.73), 4.035 (0.75), 4.166 (1.96), 4.183 (0.51), 4.200 (3.95), 4.212 (2.32), 4.218 (2.53), 4.228 (2.74), 4.245 (1.94), 4.260 (0.77), 4.263 (0.75), 4.277 (1.87), 4.295 (1.73), 4.304 (1.03), 4.313 (0.56), 4.322 (1.01), 4.376 (0.42), 4.388 (0.91), 4.401 (0.51), 4.411 (0.47), 4.424 (0.80), 4.638 (2.20), 4.671 (2.01), 5.759 (8.00), 6.897 (1.87), 6.915 (2.01), 7.236 (4.37), 7.258 (4.68), 7.371 (1.94), 7.391 (3.20), 7.410 (2.78), 7.450 (3.25), 7.471 (2.08), 7.481 (1.12), 7.486 (1.24), 7.498 (2.15), 7.502 (1.96), 7.512 (2.20), 7.518 (3.16), 7.523 (2.29), 7.532 (2.06), 7.536 (2.39), 7.549 (1.50), 7.554 (1.17), 7.565 (0.87), 7.573 (0.80), 7.596 (0.96), 7.613 (0.80), 7.622 (0.84), 7.625 (0.87), 7.642 (0.61), 7.645 (0.61), 7.796 (3.70), 7.818 (3.46), 7.859 (1.68), 7.865 (1.12), 7.878 (1.78), 7.882 (1.47), 8.179 (1.36), 8.184 (1.43), 8.203 (1.33).

Intermediate 34 ethyl 6-chloro-7-[5-ethyl-3-(hydroxymethyl)-1-methyl-1H-pyrazol-4-yl]-3-{3-[(6-fluoro-naphthalen-1-yl)oxy]propyl}-1H-indole-2-carboxylate

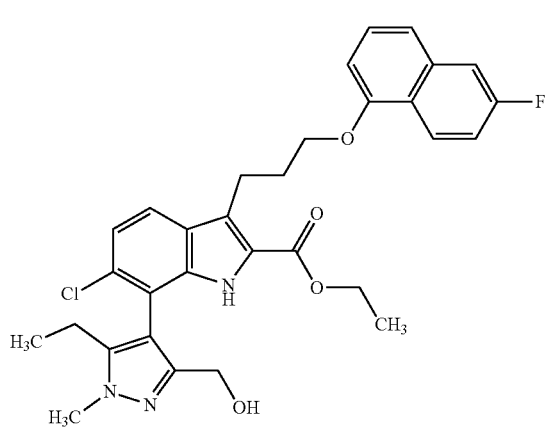 [SMILES: CCOC(=O)c1[nH]c2c(-c3c(CO)nn(C)c3CC)c(Cl)ccc2c1CCCOc1cccc2cc(F)ccc12]

Because of the limited reaction size in a microwave tube this experiment was partioned in two portions. They were combined for work up. The starting material was impure and contains 49% ethyl 6-chloro-3-{3-[(6-fluoro-1-naphthyl)oxy]propyl}-1H-indole-2-carboxylate. Ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 9, 4.69 g, 33% purity, 2.80 mmol) and (4-bromo-5-ethyl-1-methyl-1H-pyrazol-3-yl)methanol (see Intermediate 18, 614 mg, 2.80 mmol) were suspended in 1,4-dioxane and nitrogen was bubbled through this mixture for 5 min. Afterwords XPhos Pd G3 (285 mg, 337 μmol) and the aqueous potassiumphosphate-solution (4.5 mL, 1.5 M, 6.7 mmol) were added and again nitrogen was passed through the suspension for 5 min. The reaction mixture was heated for 20 min. at 100° C. in the microwave. The mixture was filtered through celite under vacuo and the filter cake was washed with ethyl acetate. The clear filtrate was diluted with ethyl acetate and water. The layers were separated and the aqueous layer was extracted with ethyl acetate once. The combined organic layers were washed with brine and dried using a water resistant filter. The crude product was purified using a 50 g-silica column (Gradient: hexane/ethyl acetate/ethanol). The received product was further purified by flash chromatography using a 25 g silica ultra column (gradient dichloromethane/acetone 0-50%) to obtain the title compound (364.9 mg, 85% purity).

¹H-NMR (400 MHz, DMSO-d6): δ [ppm]=0.86 (t, 3H), 1.25 (t, 3H), 2.14-2.27 (m, 2H), 2.35-2.47 (m, 2H), 3.26-3.33 (m, 2H), 3.83 (s, 3H), 4.01-4.08 (m, 1H), 4.16-4.26 (m, 4H), 4.29 (d, 1H), 4.84 (t, 1H), 6.85-6.93 (m, 1H), 7.17 (d, 1H), 7.36-7.48 (m, 3H), 7.64-7.73 (m, 2H), 8.27 (dd, 1H), 10.76 (s, 1H)

LC-MS (Method 2): R_t=1.61 min; MS (ESIpos): m/z=564 [M+H]⁺

Intermediate 35 ethyl 1-{4-[(tert-butoxycarbonyl)(methyl)amino]butyl}-6-chloro-7-[5-ethyl-3-(hydroxymethyl)-1-methyl-1H-pyrazol-4-yl]-3-{3-[(6-fluoronaphthalen-1-yl)oxy]propyl}-1H-indole-2-carboxylate

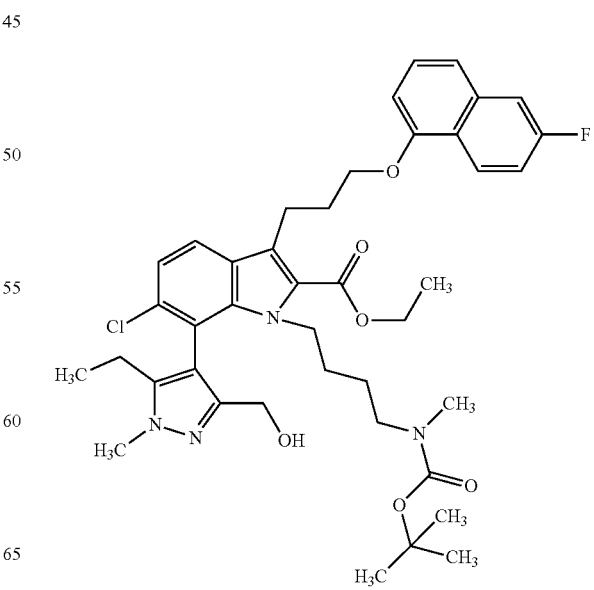

Ethyl-6-chloro-7-[5-ethyl-3-(hydroxymethyl)-1-methyl-1H-pyrazol-4-yl]-3-{3-[(6-fluoronaphthalen-1-yl)oxy]propyl}-1H-indole-2-carboxylate (see Intermediate 34, 360 mg) was dissolved in 3.7 mL DMF and cesium carbonate (624 mg, 1.91 mmol) was added. This mixture was prestirred for 10 min. Afterwords tert-butyl (4-bromobutyl)methylcarbamate (see Intermediate 1, 255 mg, 957 μmol) was added and the mixture was stirred at rt for 10 days. The reaction mixture was diluted with ethyl acetate and water. The aqueous layer was extracted with ethyl acetate twice. The combined organic layers were dried using a water resistant filter. The clear filtrate was concentrated under reduced pressure. The crude material was purified using a 25 g-silica ultra column (gradient ethyl acetate/ethanol 0-5%) to obtain the desired product (225.8 mg, 92% purity).

$^1$H-NMR (400 MHz, DMSO-d6): δ [ppm]=1.17 (t, 3H), 1.21-1.41 (m, 12H), 1.99 (s, 3H), 2.11-2.31 (m, 3H), 2.61-2.72 (m, 3H), 2.90 (br d, 2H), 3.25 (br t, 2H), 3.83 (s, 3H), 3.92-4.07 (m, 4H), 4.14 (br s, 1H), 4.17-4.31 (m, 5H), 4.72 (t, 1H), 6.84-6.94 (m, 1H), 7.22 (d, 1H), 7.35-7.49 (m, 3H), 7.67 (dd, 1H), 7.75 (d, 1H), 8.25 (dd, 1H).

LC-MS (Method 2): $R_t$=1.76 min; MS (ESIpos): m/z=749 [M+H]$^+$

Intermediate 36 ethyl-7-[3-(bromomethyl)-5-ethyl-1-methyl-1H-pyrazol-4-yl]-1-{4-[(tert-butoxycarbonyl)-(methyl)amino]butyl}-6-chloro-3-{3-[(6-fluoronaphthalen-1-yl)oxy]propyl}-1H-indole-2-carboxylate

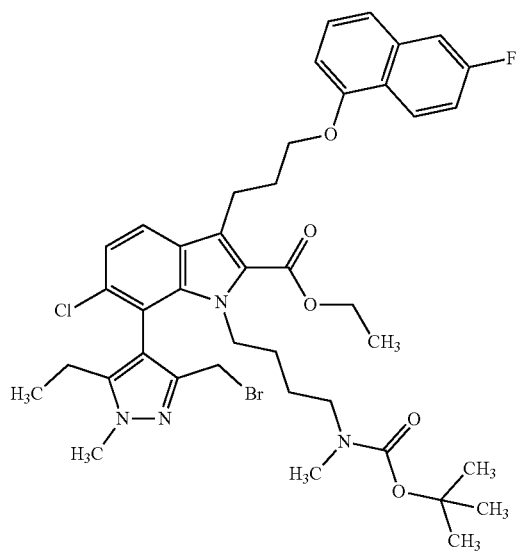 [SMILES: CCOC(=O)c1c(CCCOc2cccc3cc(F)ccc23)c2ccc(Cl)c(-c3c(CBr)nn(C)c3CC)c2n1CCCCN(C)C(=O)OC(C)(C)C]

Ethyl 1-{4-[(tert-butoxycarbonyl)(methyl)amino]butyl}-6-chloro-7-[5-ethyl-3-(hydroxymethyl)-1-methyl-1H-pyrazol-4-yl]-3-{3-[(6-fluoronaphthalen-1-yl)oxy]propyl}-1H-indole-2-carboxylate (see Intermediate 35, 225 mg) was dissolved in 5.8 mL dichloromethane and cooled to 0° C. At this temperature triphenylphosphine (118 mg, 450 μmol) was added. After 10 min of stirring under cooling tetrabromomethane (149 mg, 450 μmol) was added to the mixture. The ice bath was removed and it was stirred 2 hours at rt. The reaction mixture was directly loaded on isolute and it was purified using a 10 g silica column (gradient hexane/ethyl acetate 20-80%) to obtain the title compound (180.7 mg, 99% purity).

$^1$H-NMR (400 MHz, DMSO-d6): δ [ppm]=0.93-1.13 (m, 5H), 1.21-1.31 (m, 9H), 1.31-1.40 (m, 4H), 2.14-2.23 (m, 2H), 2.24-2.36 (m, 1H), 2.55 (br d, 1H), 2.67 (br dd, 3H), 2.81-3.05 (m, 2H), 3.26 (br t, 2H), 3.88 (s, 3H), 3.93 (br s, 1H), 4.03 (q, 2H), 4.17-4.30 (m, 6H), 6.89 (dd, 1H), 7.26 (d, 1H), 7.36-7.42 (m, 1H), 7.43-7.48 (m, 2H), 7.67 (dd, 1H), 7.82 (d, 1H), 8.24 (dd, 1H).

LC-MS (Method 2): $R_t$=1.89 min; MS (ESIpos): m/z=811 [M+H]$^+$

Intermediate 37 ethyl 7-[3-(bromomethyl)-5-ethyl-1-methyl-1H-pyrazol-4-yl]-6-chloro-3-{3-[(6-fluoronaphthalen-1-yl)oxy]propyl}-1-[4-(methylamino)butyl]-1H-indole-2-carboxylate-hydrochloric acid salt

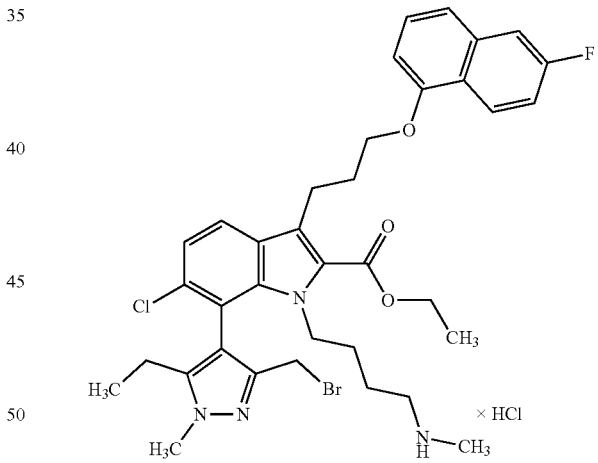

Ethyl 7-[3-(bromomethyl)-5-ethyl-1-methyl-1H-pyrazol-4-yl]-1-{4-[(tert-butoxycarbonyl)(methyl)-amino]butyl}-6-chloro-3-{3-[(6-fluoronaphthalen-1-yl)oxy]propyl}-1H-indole-2-carboxylate (see Intermediate 36, 175 mg) was dissolved in 2.2 mL methanol and the hydrochloric acid in dioxane (270 μL, 4.0 M, 1.1 mmol) was added. The mixture was stirred at 40° C. for 2 hours. The reaction mixture was concentrated under reduced pressure to provide the desired product (162 mg, 95% purity).

$^1$H-NMR (400 MHz, DMSO-d6): δ [ppm]=0.97 (td, 3H), 1.08-1.24 (m, 3H), 1.26-1.37 (m, 4H), 2.14-2.32 (m, 3H), 2.53-2.69 (m, 3H), 3.23-3.33 (m, 2H), 3.88-4.05 (m, 5H), 4.19-4.33 (m, 5H), 4.39 (s, 1H), 6.85-6.94 (m, 1H), 7.28 (d, 1H), 7.40 (td, 1H), 7.44-7.49 (m, 2H), 7.68 (dd, 1H), 7.84 (dd, 1H), 8.24 (dd, 1H), 8.44 (br s, 2H).—2H missing, underneath DMSO/water signal.

Intermediate 38

(rac)-ethyl 4-chloro-3-ethyl-7-{3-[(6-fluoronaphtha-len-1-yl)oxy]propyl}-2,14-dimethyl-10,11,12,13,14, 15-hexahydro-2H-pyrazolo[3',4':8,9][1,6]diazacycloundecino[10,11,1-hi]indole-8-carboxylate

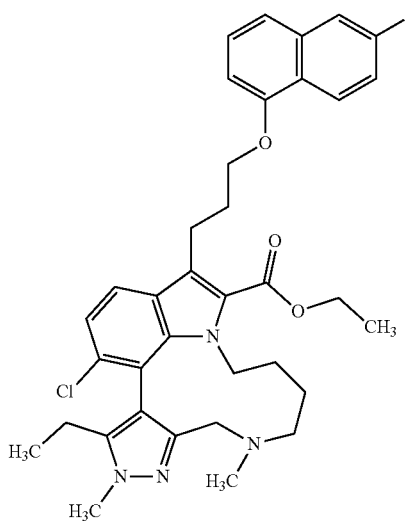

Ethyl 7-[3-(bromomethyl)-5-ethyl-1-methyl-1H-pyrazol-4-yl]-6-chloro-3-{3-[(6-fluoronaphthalen-1-yl)oxy]propyl}-1-[4-(methylamino)butyl]-1H-indole-2-carboxylate-hydrochloric acid salt (see Intermediate 37, 160 mg) was dissolved in 1.0 mL DMF and cesium carbonate (348.2 mg, 1.07 mmol) was added. This mixture was stirred at 60° C. overnight. The reaction mixture was diluted with ethyl acetate and water. The aqueous layer was extracted with ethyl acetate twice. The combined organic layers were dried using a water resistant filter. The clear filtrate was directly absorbed with isolute to purify the crude material by flash chromatography using an 11 g amino column (gradient hexane/ethyl acetate 0-50%) to obtain the title compound (29.7 mg, 100% purity).

¹H-NMR (400 MHz, DMSO-d6): δ [ppm]=0.74-0.82 (m, 3H), 0.83-0.97 (m, 1H), 0.98-1.10 (m, 1H), 1.11-1.30 (m, 5H), 1.76-1.86 (m, 1H), 1.96-2.01 (m, 3H), 2.03-2.26 (m, 4H), 2.34-2.45 (m, 1H), 3.16-3.31 (m, 3H), 3.45-3.53 (m, 1H), 3.81 (s, 3H), 3.86-3.97 (m, 1H), 4.08-4.35 (m, 5H), 6.83-6.92 (m, 1H), 7.19-7.26 (m, 1H), 7.36-7.48 (m, 3H), 7.64-7.70 (m, 1H), 7.70-7.76 (m, 1H), 8.24-8.34 (m, 1H).

LC-MS (Method 2): $R_t$=1.83 min; MS (ESIpos): m/z=632 [M+H]⁺

Intermediate 39 ethyl 6-chloro-7-{3-ethyl-5-(hydroxymethyl)-1-[2-(morpholin-4-yl)ethyl]-1H-pyrazol-4-yl}-3-[3-(naphthalen-1-yloxy)propyl]-1H-indole-2-carboxylate

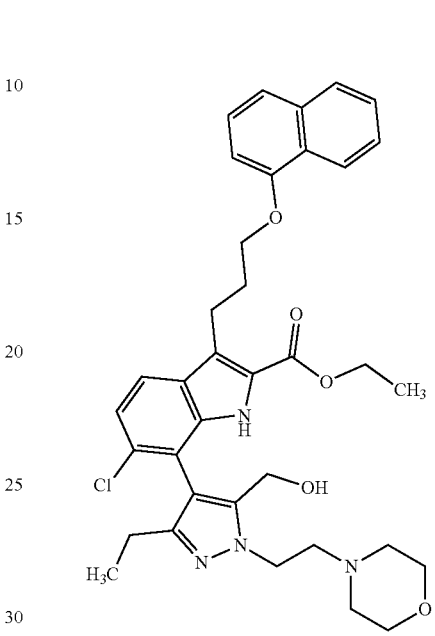

The following procedure was performed three times, each reaction with a third of the given amount of material. {4-bromo-3-ethyl-1-[2-(morpholin-4-yl)ethyl]-1H-pyrazol-5-yl}methanol (see Intermediate 23, 1.00 g, 3.14 mmol) and ethyl 6-chloro-3-[3-(naphthalen-1-yloxy)propyl]-7-(4,4,5,5-tetramethyl-1,3,2-dioxaborolan-2-yl)-1H-indole-2-carboxylate (see Intermediate 7, 2.01 g, 3.77 mmol) were dissolved in 1,4 dioxane (39 mL, 460 mmol). The mixture then was purged with argon for three minutes. Afterwards XPhos Pd G3 (326 mg, 98% purity, 377 μmol) and an aqueous solution of potassium phosphate (15 mL, 0.50 M, 7.5 mmol) were added and the mixture heated to 100° C. for one hour in a microwave reactor. After cooling the mixture was diluted with ethyl acetate and washed with a saturated aqueous sodium chloride solution. After drying of the organic phase with sodium sulphate and filtration the filtrate was evaporated to dryness and subjected to flash chromatography (Biotage SNAP cartridge silica, dichloromethane/acetone gradient, 6%→40% acetone) to give the title compound (1.22 g).

LC-MS (Method 2): Rt=1.63 min; MS (ESIpos): m/z=646 [M+H]⁺

¹H-NMR (400 MHz, DMSO-d6) δ[ppm]: 0.920 (6.67), 0.939 (16.00), 0.958 (7.01), 1.066 (1.33), 1.112 (1.56), 1.131 (3.72), 1.138 (0.41), 1.150 (1.56), 1.156 (0.48), 1.239 (6.83), 1.256 (15.78), 1.274 (6.96), 2.084 (0.45), 2.202 (1.09), 2.223 (1.50), 2.231 (1.20), 2.238 (1.21), 2.250 (1.37), 2.268 (1.62), 2.287 (2.23), 2.306 (2.16), 2.321 (1.13), 2.325 (1.00), 2.332 (0.51), 2.340 (2.18), 2.359 (2.24), 2.378 (1.62), 2.397 (1.92), 2.408 (1.29), 2.415 (1.28), 2.426 (1.66), 2.438 (3.04), 2.453 (2.73), 2.460 (1.86), 2.465 (1.60), 2.479 (2.40), 2.518 (2.52), 2.523 (1.51), 2.632 (0.54), 2.648 (1.10), 2.665 (0.89), 2.669 (0.68), 2.673 (0.45), 2.773 (1.49), 2.789 (3.27), 2.807 (1.78), 3.306 (1.46), 3.344 (1.45), 3.530 (0.94), 3.542 (1.28), 3.559 (4.13), 3.571 (7.38), 3.583 (3.99), 4.055 (1.25), 4.088

(1.46), 4.199 (2.08), 4.214 (3.80), 4.223 (1.21), 4.233 (2.35), 4.250 (3.53), 4.252 (4.11), 4.268 (3.81), 4.270 (4.02), 4.280 (0.72), 4.289 (2.39), 4.297 (1.23), 4.305 (0.96), 4.314 (1.72), 4.331 (0.99), 4.349 (0.80), 4.359 (1.40), 4.392 (1.15), 4.450 (0.64), 4.461 (0.64), 5.628 (0.74), 5.759 (3.80), 6.908 (2.16), 6.925 (2.34), 7.167 (5.23), 7.188 (5.20), 7.375 (1.81), 7.395 (3.29), 7.414 (2.82), 7.452 (3.20), 7.473 (1.79), 7.484 (0.61), 7.489 (0.84), 7.501 (2.02), 7.506 (1.81), 7.508 (0.94), 7.513 (2.16), 7.519 (4.36), 7.525 (2.15), 7.532 (1.90), 7.537 (2.16), 7.549 (0.86), 7.553 (0.55), 7.711 (4.17), 7.732 (3.74), 7.860 (1.87), 7.868 (1.06), 7.879 (2.00), 7.884 (1.61), 8.208 (1.68), 8.213 (1.59), 8.226 (0.87), 8.230 (1.48), 8.232 (1.59), 10.637 (2.11).

Intermediate 40

(rac)-ethyl (11Z)-4-chloro-3-ethyl-1-[2-(morpholin-4-yl)ethyl]-7-[3-(naphthalen-1-yloxy)propyl]-1,10,13,15-tetrahydropyrazolo[4',3':9,10][1,6]oxazacycloundecino[8,7,6-hi]indole-8-carboxylate

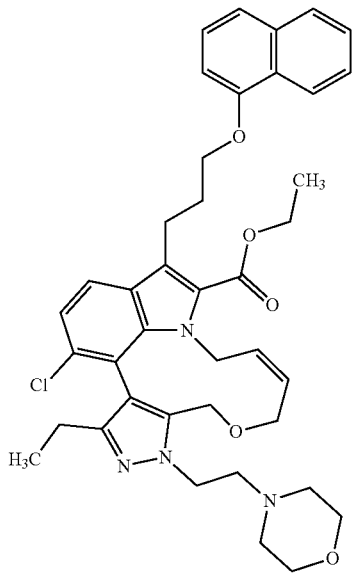

Ethyl-6-chloro-7-{3-ethyl-5-(hydroxymethyl)-1-[2-(morpholin-4-yl)ethyl]-1H-pyrazol-4-yl}-3-[3-(naphthalen-1-yloxy)propyl]-1H-indole-2-carboxylate (see Intermediate 39, 610 mg, 945 µmol) was dissolved in acetonitrile (10 mL). After addition of cesium carbonate (1.54 g, 4.73 mmol) and stirring of the mixture for 10 minutes (2Z)-1,4-dichlorobut-2-ene (CAS 110-57-6, 130 µL, 95% purity, 1.1 mmol) and sodium iodide (286 mg, 99% purity, 1.89 mmol) were added an stirring was continued for 18 hours at room temperature. After addition of water the slurry was extracted three times with ethyl acetate. After washing of the combined organic phases with saturated aqueous sodium chloride solution, drying of the organic matter with sodium sulphate and filtration the filtrate was evaporated to dryness and subjected to flash chromatography (Biotage SNAP cartridge silica, hexane/ethyl acetate gradient, 6%→60% ethyl acetate) to give the title compound (0.33 g).

¹H-NMR (600 MHz, DMSO-d6) δ[ppm]: 0.000 (7.62), 0.785 (6.85), 0.797 (14.67), 0.809 (7.31), 1.123 (1.06), 1.135 (2.37), 1.148 (1.18), 1.274 (7.81), 1.286 (16.00), 1.297 (7.60), 2.005 (1.39), 2.017 (3.57), 2.018 (3.44), 2.029 (3.44), 2.031 (3.17), 2.042 (1.17), 2.227 (0.56), 2.238 (1.18), 2.249 (1.74), 2.259 (1.78), 2.269 (1.18), 2.280 (0.56), 2.383 (1.75), 2.386 (1.95), 2.389 (2.43), 2.392 (2.31), 2.400 (2.31), 2.474 (0.64), 2.487 (1.84), 2.520 (3.32), 2.524 (3.25), 2.526 (2.57), 2.614 (0.62), 2.618 (0.81), 2.620 (0.61), 2.652 (0.56), 2.736 (0.53), 2.745 (0.69), 2.748 (0.74), 2.757 (1.33), 2.766 (0.97), 2.769 (1.01), 2.778 (0.73), 2.835 (0.69), 2.847 (1.53), 2.859 (0.93), 2.868 (1.06), 2.881 (0.50), 3.276 (0.41), 3.288 (0.64), 3.298 (1.13), 3.310 (1.67), 3.317 (1.26), 3.324 (1.41), 3.330 (1.66), 3.364 (0.45), 3.555 (4.83), 3.562 (7.27), 3.570 (4.39), 3.583 (1.50), 3.604 (2.12), 3.625 (1.31), 3.756 (1.07), 3.763 (1.25), 3.777 (1.01), 3.785 (0.89), 4.121 (2.97), 4.144 (2.93), 4.211 (0.49), 4.224 (3.06), 4.234 (6.85), 4.239 (2.00), 4.245 (3.54), 4.252 (2.71), 4.257 (1.14), 4.263 (2.83), 4.270 (0.80), 4.275 (1.18), 4.280 (1.19), 4.290 (1.80), 4.301 (3.32), 4.308 (0.70), 4.313 (2.53), 4.320 (1.59), 4.325 (1.03), 4.331 (2.03), 4.341 (1.71), 4.353 (1.10), 4.363 (0.97), 4.376 (0.46), 4.459 (0.61), 4.592 (0.90), 4.609 (1.09), 4.619 (1.18), 4.637 (1.33), 4.761 (2.81), 4.784 (2.71), 4.802 (0.92), 4.805 (0.86), 4.822 (1.61), 4.841 (0.86), 4.936 (1.45), 4.961 (1.30), 5.121 (0.57), 5.128 (0.60), 5.140 (1.01), 5.147 (1.03), 5.159 (0.53), 5.166 (0.50), 5.763 (3.22), 6.904 (3.09), 6.917 (3.26), 7.271 (5.39), 7.285 (5.72), 7.381 (2.19), 7.395 (4.01), 7.408 (3.02), 7.454 (3.93), 7.468 (2.68), 7.474 (1.29), 7.476 (1.38), 7.485 (1.99), 7.487 (2.72), 7.490 (1.37), 7.499 (2.08), 7.501 (1.88), 7.515 (1.90), 7.517 (2.18), 7.529 (2.91), 7.531 (2.33), 7.540 (1.31), 7.542 (1.26), 7.820 (5.13), 7.834 (4.66), 7.863 (2.93), 7.877 (2.68), 8.147 (2.68), 8.161 (2.51).

Intermediate 41

(rac)-ethyl 4-chloro-3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylate

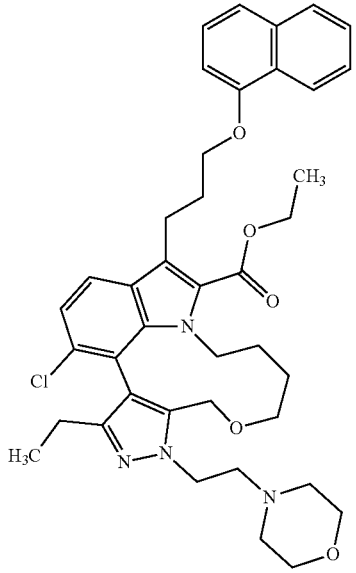 [SMILES: CCOC(=O)c1c(CCCOc2cccc3ccccc23)c2ccc(Cl)c3c2n1CCCCOCc1c-3c(CC)nn1CCN1CCOCC1]

A mixture of (rac)-ethyl (11Z)-4-chloro-3-ethyl-1-[2-(morpholin-4-yl)ethyl]-7-[3-(naphthalen-1-yloxy)propyl]-1,10,13,15-tetrahydropyrazolo[4',3':9,10][1,6]oxazacycloundecino[8,7,6-hi]indole-8-carboxylate (see Intermediate 40, 258 mg, 370 µmol) and tris(triphenyl-lambda⁵-phosphanyl)rhodium(1+) chloride (687 mg, 740 µmol) in ethanol (50 mL) was stirred for three hours at normal pressure under a hydrogen atmosphere. Then the reaction mixture was evaporated to dryness and subjected to flash chromatography (Biotage SNAP cartridge silica, dichloromethane/ethanol gradient, 0%→15% ethanol) to give the title compound (191 mg).

LC-MS (Method 2): $R_t$=1.76 min; MS (ESIpos): m/z=700 $[M+H]^+$ $^1$H-NMR (400 MHz, DMSO-d6) δ[ppm]: 0.798 (0.51), 0.814 (0.70), 0.823 (6.69), 0.842 (15.65), 0.861 (6.91), 0.904 (0.60), 0.975 (0.51), 0.998 (0.73), 1.020 (0.89), 1.035 (4.75), 1.041 (0.95), 1.053 (7.45), 1.070 (4.56), 1.145 (0.57), 1.232 (2.12), 1.257 (7.76), 1.275 (16.00), 1.292 (7.41), 1.906 (2.03), 2.070 (1.52), 2.089 (4.82), 2.108 (4.66), 2.127 (1.39), 2.195 (1.14), 2.210 (1.62), 2.228 (1.20), 2.318 (0.79), 2.322 (1.77), 2.327 (2.66), 2.332 (2.06), 2.337 (1.93), 2.354 (1.43), 2.366 (2.22), 2.377 (1.20), 2.518 (7.76), 2.523 (5.48), 2.660 (0.63), 2.664 (1.43), 2.669 (1.96), 2.673 (1.43), 2.678 (0.63), 2.716 (0.41), 2.730 (1.17), 2.746 (2.15), 2.762 (2.63), 2.779 (1.01), 2.793 (0.51), 2.905 (0.41), 2.922 (0.89), 2.933 (0.63), 2.940 (0.63), 2.951 (0.95), 3.230 (0.57), 3.246 (0.82), 3.264 (1.17), 3.284 (0.70), 3.299 (0.79), 3.352 (0.79), 3.370 (0.41), 3.404 (0.57), 3.417 (0.67), 3.422 (1.74), 3.435 (2.03), 3.439 (1.96), 3.452 (2.19), 3.457 (0.89), 3.469 (1.01), 3.481 (0.44), 3.526 (4.37), 3.537 (7.51), 3.549 (4.34), 3.996 (0.54), 4.017 (0.89), 4.032 (0.67), 4.052 (0.48), 4.189 (3.49), 4.202 (3.07), 4.206 (2.79), 4.211 (3.14), 4.223 (4.18), 4.230 (3.52), 4.238 (1.08), 4.247 (3.90), 4.265 (3.55), 4.283 (3.33), 4.292 (0.79), 4.301 (2.50), 4.310 (1.43), 4.318 (0.79), 4.328 (1.39), 4.342 (1.27), 4.355 (2.34), 4.368 (1.27), 4.379 (0.57), 4.392 (0.95), 4.404 (0.41), 4.667 (2.41), 4.701 (2.19), 5.759 (1.20), 6.887 (2.44), 6.904 (2.66), 7.225 (6.08), 7.247 (5.99), 7.367 (2.15), 7.388 (3.83), 7.407 (3.23), 7.450 (3.83), 7.471 (2.31), 7.483 (0.95), 7.487 (1.17), 7.501 (2.44), 7.504 (2.19), 7.513 (2.50), 7.519 (4.53), 7.525 (2.66), 7.532 (2.41), 7.537 (2.76), 7.549 (1.52), 7.554 (1.14), 7.565 (0.67), 7.573 (0.60), 7.591 (0.48), 7.596 (0.70), 7.608 (0.48), 7.612 (0.57), 7.622 (0.70), 7.625 (0.70), 7.642 (0.44), 7.645 (0.44), 7.789 (4.91), 7.810 (4.37), 7.859 (2.15), 7.866 (1.30), 7.877 (2.34), 7.882 (1.84), 8.189 (1.84), 8.193 (1.84), 8.211 (1.71), 8.213 (1.74).

Intermediate 42 ethyl 6-chloro-7-[3-(hydroxymethyl)-1,5-dimethyl-1H-pyrazol-4-yl]-3-[3-(naphthalen-1-yloxy)-propyl]-1H-indole-2-carboxylate

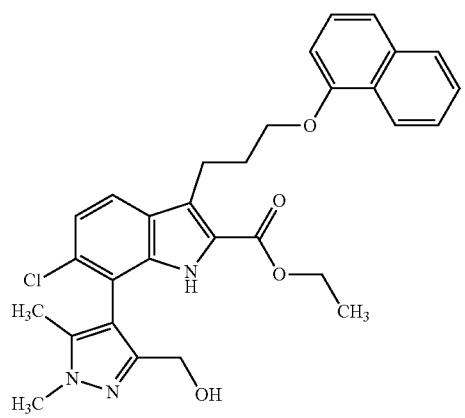 [SMILES: CCOC(=O)c1[nH]c2c(-c3c(CO)nn(C)c3C)c(Cl)ccc2c1CCCOc1cccc2ccccc12]

Ethyl 6-chloro-3-[3-(naphthalen-1-yloxy)propyl]-7-(4,4,5,5-tetramethyl-1,3,2-dioxaborolan-2-yl)-1H-indole-2-carboxylate (see Intermediate 7, 2.00 g) and (4-bromo-1,5-dimethyl-1H-pyrazol-3-yl)methanol (see Intermediate 15, 691 mg, 3.37 mmol) were provided in 15 mL of 1,4-dioxane and 5 mL of water and the mixture was purged with argon for 5 minutes. XPhos Pd G3 (342 mg, 405 μmol) and potassium phosphate (1.72 g, 8.09 mmol) were added and the mixture was purged with argon for 5 minutes and stirred for 2 hours at 100° C. in a microwave reactor. The reaction mixture was poured into water and extracted with dichloromethane. The combined organic layers were dried over sodium sulfate, filtered and concentrated under reduced pressure. The crude material was purified by flash chromatography using amino-functionalized silica gel (gradient dichloromethane/acetone) to obtain the title compound (965 mg).

LC-MS (Method 1): $R_t$=1.58 min; MS (ESIpos): m/z=532 $[M+H]^+$ $^1$H-NMR (400 MHz, DMSO-d6) δ[ppm]: 1.066 (16.00), 1.241 (2.07), 1.258 (4.56), 1.277 (2.12), 1.996 (7.13), 2.198 (0.50), 2.205 (0.53), 2.215 (0.60), 2.234 (0.48), 2.518 (2.20), 2.523 (1.49), 3.306 (0.66), 3.800 (6.99), 3.941 (2.70), 4.199 (0.64), 4.214 (1.41), 4.226 (0.83), 4.243 (1.39), 4.258 (1.25), 4.261 (1.26), 4.276 (0.49), 4.279 (0.48), 4.288 (0.64), 4.317 (0.44), 5.182 (0.52), 5.759 (3.82), 6.915 (0.79), 6.932 (0.85), 7.162 (1.56), 7.183 (1.59), 7.378 (0.58), 7.398 (1.10), 7.417 (0.90), 7.454 (1.18), 7.475 (0.62), 7.504 (0.64), 7.509 (0.62), 7.515 (0.70), 7.522 (1.48), 7.528 (0.73), 7.534 (0.67), 7.538 (0.73), 7.693 (1.36), 7.715 (1.22), 7.862 (0.68), 7.880 (0.64), 7.885 (0.58), 8.215 (0.59), 8.220 (0.57), 8.239 (0.58), 10.884 (0.64).

Intermediate 43 ethyl 1-{4-[(tert-butoxycarbonyl)(methyl)amino] butyl}-6-chloro-7-[3-(hydroxymethyl)-1,5-dimethyl-1H-pyrazol-4-yl]-3-[3-(naphthalen-1-yloxy) propyl]-1H-indole-2-carboxylate

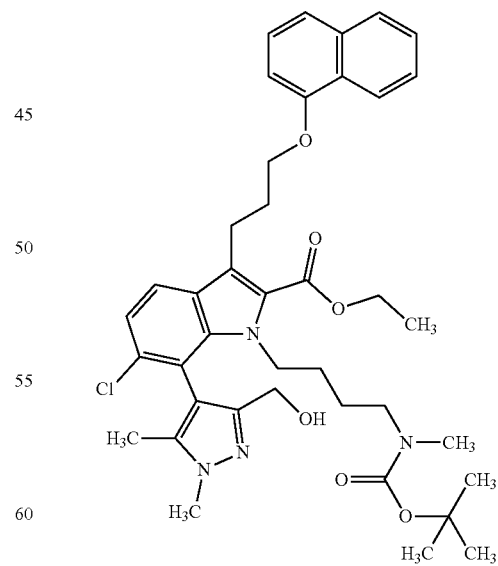

Ethyl 6-chloro-7-[3-(hydroxymethyl)-1,5-dimethyl-1H-pyrazol-4-yl]-3-[3-(naphthalen-1-yloxy)-propyl]-1H-indole-2-carboxylate (see Intermediate 42, 1.70 g, 3.20 mmol) was dissolved in 30 mL of DMF and tert-butyl (4-bromobutyl)methylcarbamate (see Intermediate 1, 1.70 g) and cesium carbonate (5.21 g, 16.0 mmol) were added. The mixture was stirred at rt overnight. Tert-butyl (4-bromobutyl)-methylcarbamate (see Intermediate 1, 800 mg, 3.01 mmol) was added again and stirring was continued at rt for 24 hours. The mixture was poured into water and was extracted with dichloromethane. The combined organic layers were dried over sodium sulfate, filtered and concentrated under reduced pressure. The crude material was purified by flash chromatography using silica gel (gradient dichloromethane/acetone) to obtain the title compound (1.40 g, 59% yield).

LC-MS (Method 1): $R_f$=1.74 min; MS (ESIpos): m/z=717 $[M+H]^+$ $^1$H-NMR (400 MHz, DMSO-d6) δ[ppm]: 1.015 (1.36), 1.067 (10.06), 1.254 (9.83), 1.271 (12.35), 1.289 (6.61), 1.357 (6.37), 1.380 (4.33), 2.013 (3.27), 2.083 (1.28), 2.171 (1.54), 2.190 (2.19), 2.204 (2.78), 2.669 (3.62), 2.673 (3.65), 2.729 (10.42), 2.886 (12.52), 3.242 (1.79), 3.262 (2.82), 3.279 (1.83), 3.725 (1.05), 3.804 (16.00), 3.940 (1.83), 3.977 (0.57), 4.012 (0.56), 4.126 (1.64), 4.149 (2.84), 4.161 (2.63), 4.179 (1.10), 4.191 (1.02), 4.211 (2.08), 4.226 (4.16), 4.234 (3.02), 4.240 (2.88), 4.252 (4.08), 4.270 (3.66), 4.288 (1.59), 4.302 (0.58), 4.693 (2.03), 4.706 (3.80), 4.719 (2.02), 5.758 (6.16), 6.918 (2.20), 6.937 (2.41), 7.204 (4.51), 7.225 (4.72), 7.382 (1.63), 7.403 (3.35), 7.421 (2.64), 7.457 (3.74), 7.478 (2.07), 7.492 (0.51), 7.497 (0.79), 7.509 (2.11), 7.514 (3.82), 7.525 (4.53), 7.533 (4.43), 7.539 (3.29), 7.551 (1.55), 7.556 (1.24), 7.563 (0.99), 7.572 (0.80), 7.596 (1.09), 7.613 (0.99), 7.625 (1.50), 7.630 (0.94), 7.639 (0.46), 7.643 (0.79), 7.742 (4.21), 7.764 (3.85), 7.863 (2.05), 7.866 (1.92), 7.873 (1.30), 7.880 (1.66), 7.886 (1.98), 7.951 (1.72), 8.212 (1.72), 8.219 (1.63), 8.236 (1.91).

Intermediate 44 ethyl 7-[3-(bromomethyl)-1,5-dimethyl-1H-pyrazol-4-yl]-1-{4-[(tert-butoxycarbonyl)(methyl)-amino]butyl}-6-chloro-3-[3-(naphthalen-1-yloxy)propyl]-1H-indole-2-carboxylate

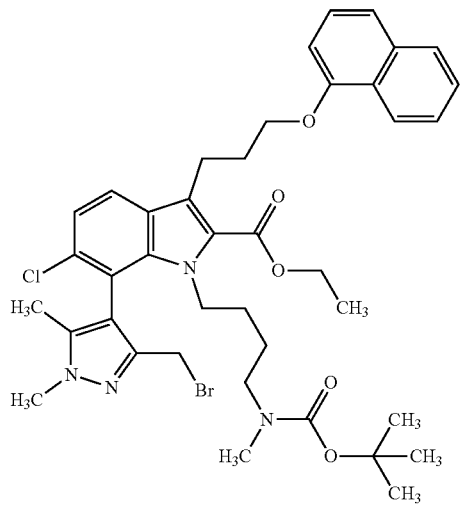 [SMILES: CCOC(=O)c1c(CCCOc2cccc3ccccc23)c2ccc(Cl)c(-c3c(CBr)nn(C)c3C)c2n1CCCCN(C)C(=O)OC(C)(C)C]

Ethyl-1-{4-[(tert-butoxycarbonyl)(methyl)amino]butyl}-6-chloro-7-[3-(hydroxymethyl)-1,5-di-methyl-1H-pyrazol-4-yl]-3-[3-(naphthalen-1-yloxy)propyl]-1H-indole-2-carboxylate (see Intermediate 43, 930 mg, 1.30 mmol) was dissolved in 25 mL of dichloromethane. Triphenylphosphane (816 mg, 3.11 mmol) was added at 0° C. After 10 minutes of stirring tetrabromomethane (946 mg, 2.85 mmol) was added and the mixture was stirred for 3 hours at rt. The mixture was concentrated and the crude product was purified by flash chromatography using silica gel (gradient hexane/ethyl acetate) to obtain the title compound (298 mg).

LC-MS (Method 1): $R_f$=1.86 min; MS (ESIpos): m/z=779 $[M+H]^+$ $^1$H-NMR (400 MHz, DMSO-d6) δ[ppm]: 1.154 (4.24), 1.171 (9.06), 1.189 (4.64), 1.249 (2.08), 1.257 (2.32), 1.266 (1.63), 1.275 (2.84), 1.285 (1.28), 1.292 (1.51), 1.302 (0.63), 1.352 (1.80), 1.986 (16.00), 2.043 (0.72), 2.201 (0.63), 2.218 (0.62), 2.326 (0.42), 2.518 (1.84), 2.522 (1.23), 2.664 (1.38), 2.668 (1.44), 3.256 (0.58), 3.275 (0.86), 3.294 (0.58), 3.845 (5.24), 3.896 (1.10), 3.998 (1.10), 4.017 (3.27), 4.034 (3.30), 4.052 (1.10), 4.211 (1.05), 4.226 (1.55), 4.242 (2.10), 4.257 (0.94), 4.270 (0.91), 4.275 (0.99), 4.292 (0.46), 6.908 (0.62), 6.925 (0.65), 7.247 (1.50), 7.268 (1.62), 7.378 (0.52), 7.398 (0.97), 7.417 (0.82), 7.454 (1.00), 7.475 (0.56), 7.503 (0.59), 7.508 (0.60), 7.513 (0.75), 7.520 (1.42), 7.527 (0.89), 7.533 (0.70), 7.537 (0.69), 7.809 (1.57), 7.830 (1.41), 7.864 (0.74), 7.869 (0.45), 7.879 (0.57), 7.884 (0.50), 8.195 (0.53), 8.201 (0.54), 8.219 (0.54).

Intermediate 45 ethyl 7-[3-(bromomethyl)-1,5-dimethyl-1H-pyrazol-4-yl]-6-chloro-1-[4-(methylamino)butyl]-3-[3-(naphthalen-1-yloxy)propyl]-1H-indole-2-carboxylate-hydrochloric acid salt

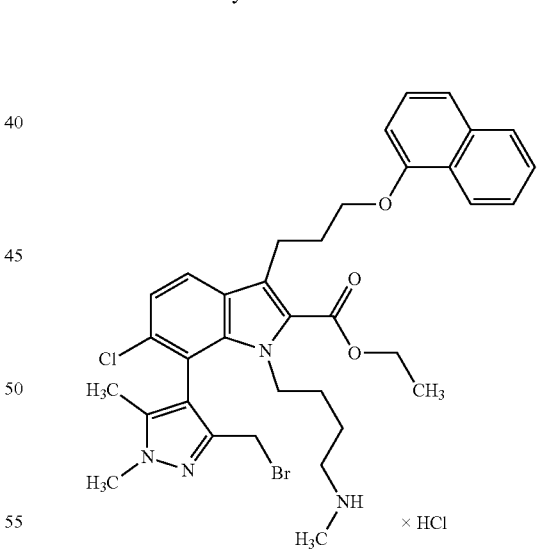

Ethyl-7-[3-(bromomethyl)-1,5-dimethyl-1H-pyrazol-4-yl]-1-{4-[(tert-butoxycarbonyl)(methyl)-amino]butyl}-6-chloro-3-[3-(naphthalen-1-yloxy)propyl]-1H-indole-2-carboxylate (see Intermediate 44, 610 mg) was dissolved in 20 mL of ethanol and a solution of hydrogen chloride in 1,4-dioxane (20 mL, 4.0 M, 82 mmol) was added. The mixture was stirred at rt overnight and was concentrated under reduced pressure to obtain the title compound (640 mg) which was used without further purification.

LC-MS (Method 1): $R_t$=1.36 min; MS (ESIpos): m/z=679 [M+H]$^+$ $^1$H-NMR (400 MHz, DMSO-d6) δ[ppm]: 1.035 (7.79), 1.052 (16.00), 1.065 (1.35), 1.070 (8.54), 1.106 (0.51), 1.136 (0.63), 1.268 (0.63), 1.279 (2.49), 1.286 (1.28), 1.296 (5.04), 1.314 (2.41), 2.057 (5.12), 2.183 (0.53), 2.201 (0.72), 2.218 (0.60), 2.226 (1.04), 2.462 (2.10), 2.475 (5.21), 2.518 (6.01), 2.523 (4.10), 2.627 (0.68), 3.272 (0.65), 3.291 (0.92), 3.309 (0.58), 3.385 (0.41), 3.410 (2.63), 3.428 (8.13), 3.445 (8.04), 3.462 (2.58), 3.488 (0.48), 3.499 (0.41), 3.565 (1.06), 3.699 (1.47), 3.713 (1.01), 3.761 (1.06), 3.889 (6.13), 4.226 (0.87), 4.241 (2.03), 4.257 (1.28), 4.265 (1.11), 4.271 (1.16), 4.276 (1.25), 4.288 (1.11), 4.293 (1.16), 4.357 (0.56), 4.367 (2.37), 4.601 (0.53), 6.924 (0.82), 6.942 (0.89), 7.267 (1.42), 7.288 (1.50), 7.387 (0.58), 7.407 (1.16), 7.426 (0.92), 7.462 (1.25), 7.483 (0.68), 7.507 (0.72), 7.511 (0.65), 7.519 (0.80), 7.525 (1.52), 7.531 (0.80), 7.538 (0.72), 7.543 (0.77), 7.826 (1.18), 7.830 (0.77), 7.847 (1.09), 7.851 (0.72), 7.868 (0.77), 7.887 (0.72), 7.891 (0.63), 8.194 (0.65), 8.199 (0.65), 8.217 (0.60), 8.413 (0.51).

Intermediate 46

(rac)-ethyl 4-chloro-2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylate

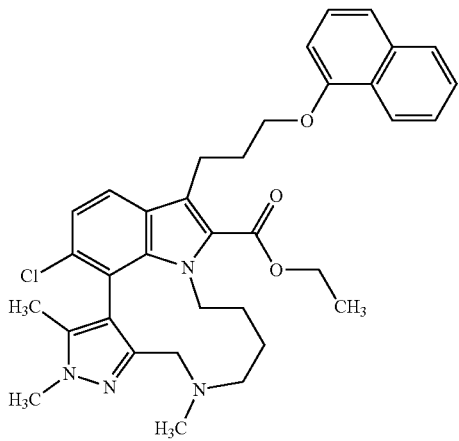 [SMILES: CCOC(=O)c1c(CCCOc2cccc3ccccc23)c2ccc(Cl)c3c2n1CCCCN(C)Cc1nn(C)c(C)c1-3]

Ethyl 6-chloro-7-[3-(chloromethyl)-1,5-dimethyl-1H-pyrazol-4-yl]-1-[4-(methylamino)butyl]-3-[3-(naphthalen-1-yloxy)propyl]-1H-indole-2-carboxylate-hydrochloric acid salt (see Intermediate 45, 831 mg) was dissolved in 21 mL of DMF and cesium carbonate (1.71 g, 5.25 mmol) was added. The mixture was stirred at 65° C. for 72 hours. The reaction mixture was poured into water and the precipitated material was isolated by filtration to give the title compound (730 mg) which was used without further purification.

Intermediate 47 ethyl 6-chloro-3-{3-[(6-fluoronaphthalen-1-yl)oxy]propyl}-7-[3-(hydroxymethyl)-1,5-dimethyl-1H-pyrazol-4-yl]-1H-indole-2-carboxylate

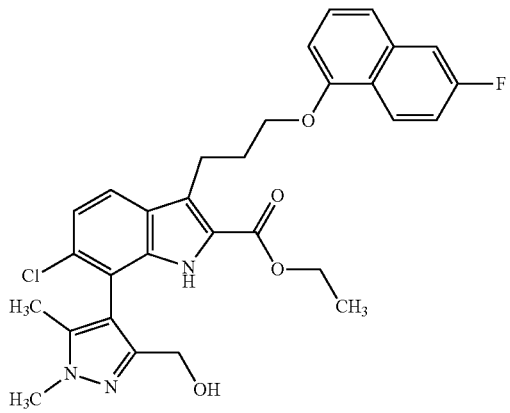 [SMILES: CCOC(=O)c1[nH]c2c(-c3c(CO)nn(C)c3C)c(Cl)ccc2c1CCCOc1cccc2cc(F)ccc12]

Ethyl-6-chloro-3-{3-[(6-fluoronaphthalen-1-yl)oxy]propyl}-7-(4,4,5,5-tetramethyl-1,3,2-dioxa-borolan-2-yl)-1H-indole-2-carboxylate (see Intermediate 9, 2.00 g, 3.62 mmol), (4-bromo-1,5-dimethyl-1H-pyrazol-3-yl)methanol (see Intermediate 15, 929 mg, 4.53 mmol) and potassium phosphate (2.31 g, 10.9 mmol) in 15 mL of 1,4-dioxane and 5 mL of water were purged with argon for 5 minutes. XPhos Pd G3 (1.07 g, 1.27 mmol) was added and the mixture was stirred for 1 hour at 100° C. in a microwave reactor. The reaction mixture was diluted with ethyl acetate and filtered. Water was added to the filtrate. The filtrate was extracted with ethyl acetate and the combined organic layers were washed with water, were dried over sodium sulfate, were filtered and were concentrated under reduced pressure. The crude product was purified by flash chromatography using silica gel (gradient dichloromethane/acetone) to obtain the title compound (943 mg, 46% yield).

LC-MS (Method 1): $R_t$=1.57 min; MS (ESIpos): m/z=550 [M+H]$^+$ $^1$H-NMR (400 MHz, DMSO-d6) δ[ppm]: 1.230 (3.92), 1.248 (8.81), 1.265 (4.02), 1.994 (12.76), 2.084 (16.00), 2.194 (0.79), 2.205 (1.37), 2.210 (1.07), 2.230 (0.82), 2.518 (2.62), 2.523 (1.71), 3.298 (1.04), 3.317 (1.92), 3.725 (0.73), 3.789 (0.58), 3.800 (12.81), 4.039 (0.67), 4.053 (0.68), 4.069 (0.82), 4.082 (0.78), 4.198 (1.14), 4.204 (0.79), 4.213 (2.90), 4.231 (2.61), 4.234 (2.52), 4.248 (2.15), 4.251 (2.07), 4.266 (0.72), 4.269 (0.63), 4.284 (0.95), 4.293 (0.89), 4.299 (0.40), 4.313 (0.73), 4.322 (0.67), 5.173 (0.69), 5.184 (1.15), 5.197 (0.65), 5.759 (0.99), 6.890 (0.99), 6.899 (1.10), 6.912 (1.05), 7.167 (3.24), 7.189 (3.35), 7.369 (0.72), 7.376 (0.83), 7.391 (1.05), 7.398 (1.12), 7.414 (0.69), 7.421 (0.88), 7.440 (2.25), 7.444 (2.33), 7.453 (4.45), 7.648 (1.22), 7.655 (1.24), 7.674 (1.22), 7.681 (1.24), 7.691 (2.33), 7.712 (2.11), 8.235 (1.05), 8.249 (1.10), 8.258 (1.08), 8.273 (1.00), 10.888 (1.88).

Intermediate 48

(rac)-ethyl (11Z)-4-chloro-7-{3-[(6-fluoronaphthalen-1-yl)oxy]propyl}-2,3-dimethyl-2,10,13,15-tetrahydropyrazolo[4',3':9,10][1,6]oxazacycloundecino[8,7,6-hi]indole-8-carboxylate

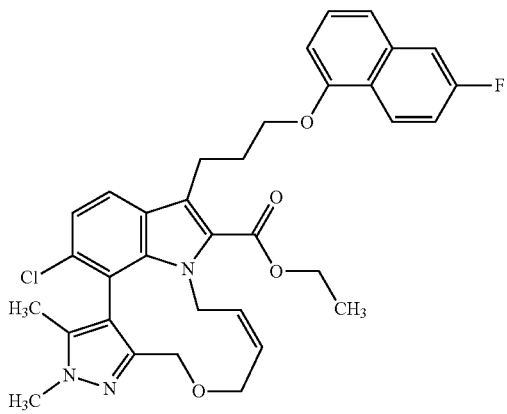 [SMILES: CCOC(=O)c1c(CCCOc2cccc3cc(F)ccc23)c2ccc(Cl)c3c2n1C/C=C\COCc1nn(C)c(C)c1-3]

To a mixture of ethyl 6-chloro-3-{3-[(6-fluoronaphthalen-1-yl)oxy]propyl}-7-[3-(hydroxymethyl)-1,5-dimethyl-1H-pyrazol-4-yl]-1H-indole-2-carboxylate (see Intermediate 47, 590 mg, 1.07 mmol) in 15 mL of acetonitrile cesium carbonate (1.75 g, 5.36 mmol) was added and the mixture was stirred at rt for 10 minutes. (2Z)-1,4-dichlorobut-2-ene (CAS 110-57-6, 170 µL, 1.61 mmol) and sodium iodide (322 mg, 2.15 mmol) were added and the reaction mixture was stirred overnight at 70° C. The mixture was poured into water and was extracted with dichloromethane. The combined organic layers were dried over sodium sulfate, filtered and concentrated under reduced pressure. The crude product was purified by flash chromatography (gradient dichloromethane/acetone) to give the title compound (355 mg).

LC-MS (Method 1): $R_t$=1.67 min; MS (ESIpos): m/z=602 [M+H]$^+$ $^1$H-NMR (400 MHz, DMSO-d6) δ[ppm]: 1.173 (0.48), 1.190 (0.85), 1.209 (0.69), 1.227 (1.09), 1.253 (4.25), 1.270 (9.28), 1.288 (4.39), 1.792 (15.22), 1.835 (0.53), 2.080 (16.00), 2.219 (1.82), 2.238 (1.18), 2.518 (6.12), 3.259 (0.83), 3.278 (1.34), 3.310 (1.71), 3.556 (0.69), 3.568 (0.85), 3.585 (1.13), 3.599 (0.99), 3.721 (1.02), 3.750 (1.57), 3.778 (0.78), 3.832 (0.78), 3.854 (14.22), 4.146 (2.05), 4.164 (0.60), 4.179 (2.61), 4.200 (0.95), 4.217 (2.61), 4.231 (3.42), 4.245 (3.00), 4.262 (1.82), 4.286 (1.71), 4.304 (1.59), 4.313 (0.90), 4.322 (0.58), 4.330 (0.81), 4.349 (2.70), 4.381 (1.92), 4.610 (0.60), 4.638 (0.69), 4.650 (0.90), 4.676 (0.95), 4.818 (1.09), 4.855 (0.81), 4.979 (0.53), 5.000 (0.99), 5.007 (1.04), 5.027 (0.60), 5.248 (0.44), 5.261 (0.53), 5.273 (0.83), 5.286 (0.78), 5.755 (1.41), 6.887 (1.20), 6.897 (1.55), 6.909 (1.34), 7.255 (3.14), 7.276 (3.44), 7.352 (0.78), 7.359 (0.85), 7.375 (1.45), 7.381 (1.52), 7.396 (1.04), 7.403 (1.02), 7.415 (0.42), 7.440 (3.42), 7.449 (5.33), 7.645 (1.45), 7.651 (1.57), 7.671 (1.55), 7.677 (1.55), 7.739 (0.42), 7.785 (3.00), 7.807 (2.82), 8.185 (1.22), 8.199 (1.34), 8.208 (1.29), 8.222 (1.20).

Intermediate 49

(rac)-ethyl 4-chloro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylate (rac)-Ethyl (11Z)-4-chloro-7-{3-[(6-fluoronaphthalen-1-yl)oxy]propyl}-2,3-dimethyl-2,10,13,15-tetra-hydropyrazolo[4',3':9,10][1,6]oxazacycloundecino[8,7,6-hi]indole-8-carboxylate (see Intermediate 48, 1.40 g) was dissolved in a mixture of 120 mL of ethanol and 50 mL of THF. Tris(triphenylphosphine)rhodium(I) chloride (4.32 g, 4.65 mmol) was added and the mixture was stirred under hydrogen atmosphere until complete conversion. The catalyst was filtered off and the filtrate was concentrated under reduced pressure. The crude material was purified by flash chromatography twice using silica gel (gradient dichloromethane/acetone and hexane/ethyl acetate) to give the title compound (470 mg).

LC-MS (Method 1): $R_t$=1.71 min; MS (ESIpos): m/z=604 [M+H]$^+$ $^1$H-NMR (400 MHz, DMSO-d6) δ[ppm]: 0.922 (0.42), 0.931 (0.43), 0.944 (0.41), 1.154 (0.95), 1.172 (1.96), 1.185 (1.08), 1.189 (1.35), 1.197 (0.97), 1.209 (0.70), 1.220 (0.42), 1.232 (0.47), 1.252 (5.02), 1.270 (10.57), 1.288 (5.18), 1.776 (15.54), 1.987 (1.94), 2.185 (0.95), 2.202 (1.34), 2.219 (0.99), 2.331 (0.57), 2.518 (2.57), 2.523 (1.81), 2.673 (0.57), 3.110 (0.72), 3.125 (0.66), 3.215 (0.46), 3.231 (0.63), 3.249 (0.97), 3.268 (0.59), 3.275 (0.62), 3.295 (1.31), 3.313 (1.73), 3.821 (16.00), 3.845 (0.47), 3.854 (0.76), 3.865 (0.46), 3.879 (0.50), 4.017 (0.46), 4.035 (0.46), 4.162 (0.53), 4.182 (1.20), 4.193 (3.12), 4.200 (2.79), 4.212 (2.30), 4.217 (2.63), 4.224 (3.66), 4.235 (1.04), 4.244 (1.81), 4.262 (0.69), 4.282 (1.73), 4.299 (1.62), 4.309 (0.95), 4.317 (0.49), 4.327 (0.93), 4.421 (2.34), 4.453 (1.89), 5.759 (3.08), 6.871 (1.27), 6.878 (1.31), 6.886 (1.13), 6.893 (1.34), 7.216 (4.00), 7.238 (3.94), 7.375 (0.88), 7.381 (0.97), 7.397 (1.38), 7.403 (1.49), 7.413 (0.58), 7.419 (1.00), 7.426 (1.16), 7.434 (2.51), 7.441 (2.74), 7.448 (5.79), 7.462 (0.46), 7.646 (1.55), 7.653 (1.58), 7.672 (1.55), 7.679 (1.51), 7.749 (3.55), 7.771 (3.27), 8.206 (1.32), 8.221 (1.36), 8.230 (1.35), 8.244 (1.28).

Intermediate 50 ethyl 6-chloro-7-[5-ethyl-3-(hydroxymethyl)-1-methyl-1H-pyrazol-4-yl]-3-[3-(naphthalen-1-yloxy)propyl]-1H-indole-2-carboxylate

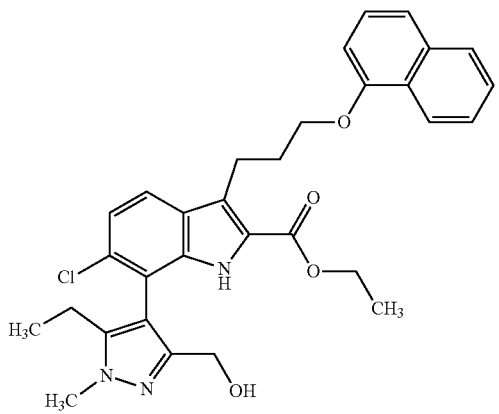 [SMILES: CCOC(=O)c1[nH]c2c(-c3c(CO)nn(C)c3CC)c(Cl)ccc2c1CCCOc1cccc2ccccc12]

Because of the limited reaction size in a microwave tube this experiment was partioned in ten portions. They were combined for work up. Ethyl 6-chloro-3-[3-(naphthalen-1-yloxy)propyl]-7-(4,4,5,5-tetramethyl-1,3,2-dioxaborolan-2-yl)-1H-indole-2-carboxylate (see Intermediate 7, 5.00 g, 9.37 mmol) and (4-bromo-5-ethyl-1-methyl-1H-pyrazol-3-yl)methanol (see Intermediate 18, 4.10 g, 18.7 mmol) were suspended in 80 mL 1,4-dioxane and 37 mL aqueous potassiumphosphate-solution (0.50 M) under argon atmosphere. Afterwords XPhos Pd G2 (737 mg, 937 µmol) was added and again the suspension was flushed with argon. The reaction mixture was heated for 30 min. at 120° C. in the microwave. The mixture was diluted with ethyl acetate and water. The layers were separated and the aqueous layer was extracted with ethyl acetate. The combined organic layers were washed with brine and dried over sodium sulfate. The crude product was purified using a silica column, gradient hexane/ethyl acetate 0-100% and dichloromethane/ethanol 0-10%, to obtain the titled product (1.49 g, 90% purity).

$^1$H-NMR (400 MHz, DMSO-d6) δ[ppm]: 0.845 (3.40), 0.864 (8.05), 0.882 (3.59), 1.066 (0.74), 1.086 (1.19), 1.105 (0.52), 1.156 (0.97), 1.240 (5.03), 1.258 (11.11), 1.276 (5.10), 2.197 (0.90), 2.214 (1.17), 2.234 (0.93), 2.360 (0.76), 2.378 (1.43), 2.397 (1.42), 2.401 (1.40), 2.420 (1.37), 2.439 (0.74), 2.458 (0.52), 2.518 (2.83), 2.523 (2.11), 2.627 (0.52), 2.646 (0.50), 3.298 (1.16), 3.320 (2.11), 3.642 (0.50), 3.760 (2.49), 3.831 (16.00), 4.029 (1.14), 4.043 (1.23), 4.059 (1.49), 4.073 (1.49), 4.204 (1.40), 4.215 (2.57), 4.218 (3.23), 4.225 (2.52), 4.230 (1.83), 4.233 (1.59), 4.245 (3.56), 4.248 (3.06), 4.255 (1.45), 4.263 (2.71), 4.266 (2.51), 4.280 (0.86), 4.284 (0.76), 4.287 (0.97), 4.301 (0.83), 4.822 (1.57), 4.833 (1.97), 4.836 (1.81), 4.847 (1.42), 4.955 (0.50), 6.917 (1.69), 6.934 (1.78), 7.157 (4.44), 7.179 (4.39), 7.379 (1.37), 7.399 (2.56), 7.418 (2.19), 7.456 (2.47), 7.476 (1.38), 7.498 (0.60), 7.511 (1.75), 7.517 (2.26), 7.526 (3.58), 7.535 (2.42), 7.541 (1.85), 7.553 (0.62), 7.693 (2.64), 7.714 (2.42), 7.863 (1.42), 7.867 (1.07), 7.873 (0.73), 7.881 (1.00), 7.887 (1.21), 8.231 (1.30), 8.238 (1.07), 8.244 (0.54), 8.247 (0.59), 8.250 (0.71), 8.253 (0.98), 8.255 (1.14), 10.758 (2.49).

Intermediate 51

(rac)-ethyl (11Z)-4-chloro-3-ethyl-2-methyl-7-[3-(naphthalen-1-yloxy)propyl]-2,10,13,15-tetrahydropyrazolo[4',3':9,10][1,6]oxazacycloundecino[8,7,6-hi]indole-8-carboxylate

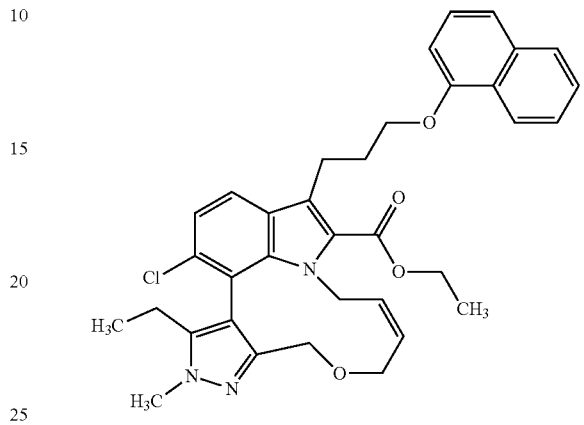

In a microwave tube ethyl 6-chloro-7-[5-ethyl-3-(hydroxymethyl)-1-methyl-1H-pyrazol-4-yl]-3-[3-(naphthalen-1-yloxy)propyl]-1H-indole-2-carboxylate (see Intermediate 50, 750 mg, 1.37 mmol) was dissolved in 20 mL acetonitrile, cesium carbonate (2.24 g, 6.87 mmol) was added and the mixture was stirred for 10 minutes. (2Z)-1,4-dichlorobut-2-ene (CAS 110-57-6, 220 µL, 2.1 mmol) and sodium iodide (412 mg, 2.75 mmol) were added and the reaction mixture was heated overnight at 65° C. in a microwave. The mixture was poured into water and the mixture was extracted with ethyl acetate. The organic layer was washed with brine and dried over sodium sulfate, filtered and concentrated under reduced pressure. The crude product was purified by flash chromatography, gradient hexane/ethyl acetate (0-100%) to give the titled compound (372 mg.)

$^1$H-NMR (400 MHz, DMSO-d6) δ[ppm]: 0.787 (3.14), 0.806 (7.38), 0.825 (3.21), 1.066 (1.02), 1.154 (1.82), 1.172 (3.76), 1.190 (1.94), 1.230 (0.50), 1.236 (0.47), 1.247 (0.60), 1.260 (4.74), 1.278 (10.37), 1.295 (4.74), 1.907 (0.52), 1.987 (5.83), 2.148 (0.72), 2.166 (1.60), 2.185 (2.19), 2.204 (1.82), 2.222 (1.50), 2.241 (1.22), 2.332 (0.92), 2.336 (0.42), 2.518 (4.88), 2.523 (3.49), 3.273 (0.67), 3.292 (1.40), 3.312 (1.87), 3.362 (0.42), 3.559 (0.60), 3.572 (0.72), 3.589 (0.90), 3.602 (0.80), 3.734 (0.82), 3.763 (1.22), 3.792 (0.70), 3.888 (16.00), 3.994 (0.40), 3.999 (0.55), 4.017 (1.42), 4.035 (1.45), 4.053 (0.52), 4.159 (1.99), 4.191 (2.62), 4.207 (0.77), 4.216 (1.57), 4.225 (1.87), 4.232 (3.19), 4.242 (1.87), 4.251 (2.42), 4.259 (0.67), 4.269 (2.02), 4.275 (0.80), 4.287 (0.77), 4.293 (1.87), 4.302 (0.42), 4.311 (1.72), 4.320 (0.97), 4.329 (0.57), 4.338 (1.00), 4.350 (2.52), 4.382 (1.94), 4.615 (0.52), 4.643 (0.60), 4.654 (0.80), 4.682 (0.87), 4.806 (0.92), 4.843 (0.65), 4.990 (0.47), 4.997 (0.50), 5.017 (0.92), 5.024 (0.90), 5.044 (0.50), 5.050 (0.47), 5.283 (0.42), 5.296 (0.65), 5.309 (0.62), 6.908 (1.69), 6.925 (1.84), 7.252 (4.09), 7.273 (3.96), 7.376 (1.42), 7.396 (2.59), 7.415 (2.22), 7.454 (2.72), 7.475 (1.62), 7.483 (0.90), 7.496 (1.67), 7.500 (1.55), 7.503 (0.97), 7.512 (1.99), 7.514 (2.34), 7.518 (2.47), 7.520 (2.04), 7.532 (1.67), 7.535 (1.87), 7.549 (0.82), 7.553 (0.62), 7.789 (3.54), 7.811 (3.34), 7.861 (1.67), 7.867 (1.17), 7.879 (1.77), 7.884 (1.40), 8.180 (1.32), 8.184 (1.35), 8.202 (1.30), 8.204 (1.27).

245

Intermediate 52

(rac)-ethyl 4-chloro-3-ethyl-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

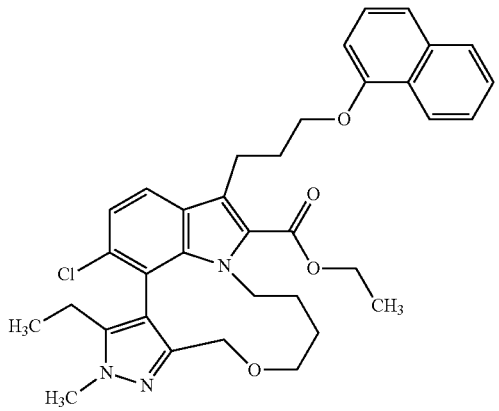 [SMILES: CCOC(=O)c1c(CCCOc2cccc3ccccc23)c2ccc(Cl)c3c2n1CCCCOCc1nn(C)c(CC)c1-3]

(rac)-Ethyl-(11Z)-4-chloro-3-ethyl-2-methyl-7-[3-(naphthalen-1-yloxy)propyl]-2,10,13,15-tetra-hydropyrazolo[4',3':9,10][1,6]oxazacycloundecino[8,7,6-hi]indole-8-carboxylate (see Intermediate 51, 269 mg, 450 µmol) was dissolved in 65 mL THF. Tris(triphenylphosphine)-rhodium (I) chloride (292 mg, 315 µmol) was added and the mixture was vigorously stirred under hydrogen atmosphere for 7 hours. It was concentrated under reduced pressure. The crude material was purified by flash chromatography using a silica column, gradient hexane/ethyl acetate 0-100% (240 mg).

$^1$H-NMR (400 MHz, CHLOROFORM-d) δ [ppm]: 0.896 (2.88), 0.915 (7.02), 0.934 (2.97), 1.142 (0.42), 1.232 (0.52), 1.252 (0.53), 1.363 (4.32), 1.381 (9.52), 1.399 (4.62), 1.421 (0.71), 1.428 (0.71), 1.449 (0.54), 1.567 (7.69), 2.200 (0.58), 2.209 (0.42), 2.219 (1.39), 2.228 (1.31), 2.238 (1.27), 2.247 (1.33), 2.256 (0.43), 2.266 (0.56), 2.297 (0.64), 2.313 (0.96), 2.331 (0.96), 2.347 (0.68), 3.272 (0.42), 3.279 (0.58), 3.288 (0.91), 3.306 (0.96), 3.316 (0.49), 3.322 (0.85), 3.342 (0.54), 3.350 (0.58), 3.370 (0.83), 3.388 (0.55), 3.461 (0.50), 3.469 (0.55), 3.485 (0.45), 3.920 (16.00), 3.995 (0.59), 4.019 (0.41), 4.187 (0.96), 4.202 (1.94), 4.215 (0.97), 4.287 (0.51), 4.294 (1.07), 4.303 (0.71), 4.311 (0.98), 4.321 (1.87), 4.329 (0.58), 4.338 (1.65), 4.343 (0.82), 4.357 (0.63), 4.361 (1.62), 4.371 (2.21), 4.378 (1.60), 4.387 (0.71), 4.396 (0.58), 4.403 (2.57), 4.659 (2.15), 4.691 (1.79), 6.767 (1.44), 6.784 (1.55), 7.006 (0.45), 7.162 (3.17), 7.183 (3.63), 7.284 (0.48), 7.346 (1.31), 7.367 (2.25), 7.386 (1.95), 7.428 (2.12), 7.449 (1.26), 7.471 (0.61), 7.475 (0.51), 7.478 (0.62), 7.482 (0.45), 7.490 (0.80), 7.502 (2.15), 7.506 (1.52), 7.512 (1.71), 7.514 (1.74), 7.520 (1.54), 7.526 (2.18), 7.537 (0.55), 7.540 (0.41), 7.544 (0.43), 7.590 (3.21), 7.611 (2.95), 7.656 (0.45), 7.660 (0.50), 7.677 (0.41), 7.686 (0.47), 7.690 (0.52), 7.707 (0.44), 7.815 (1.16), 7.819 (0.76), 7.827 (1.04), 7.831 (0.76), 7.838 (0.97), 8.366 (0.97), 8.377 (0.82), 8.385 (0.55), 8.390 (0.92).

246

Intermediate 53 ethyl 1-{4-[(tert-butoxycarbonyl)(methyl)amino]butyl}-6-chloro-7-[5-ethyl-3-(hydroxymethyl)-1-methyl-1H-pyrazol-4-yl]-3-[3-(naphthalen-1-yloxy)propyl]-1H-indole-2-carboxylate

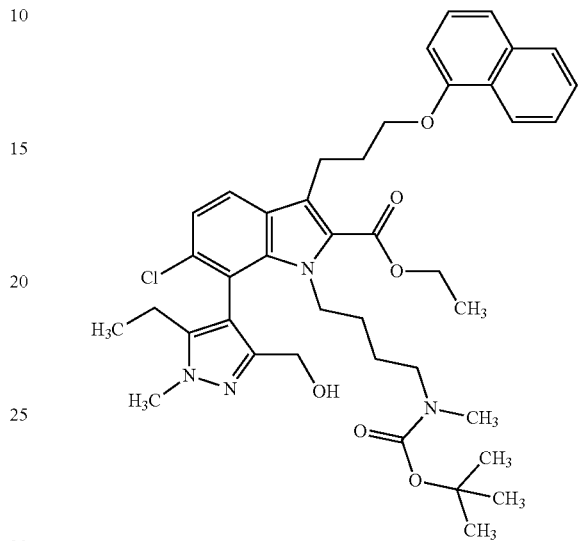

Ethyl-6-chloro-7-[5-ethyl-3-(hydroxymethyl)-1-methyl-1H-pyrazol-4-yl]-3-[3-(naphthalen-1-yloxy)propyl]-1H-indole-2-carboxylate (see Intermediate 50, 1.35 g, 2.47 mmol) was dissolved in 27 mL N,N-dimethylacetamide and cesium carbonate (4.03 g, 12.4 mmol) was added. This suspension was stirred for 10 min. at room temperature. Now tert-butyl (4-bromobutyl)-methylcarbamate (see Intermediate 1, 1.32 g, 4.94 mmol) dissolved in 6.5 mL N,N-dimethylacetamide was added. The mixture was stirred at rt for 72 hours. The mixture was poured into water and the mixture was extracted with ethyl acetate. The organic layer was washed with brine and dried over sodium sulfate, filtered and concentrated under reduced pressure. The crude product was purified by flash chromatography, gradient hexane/ethyl acetate (0-100%) to give the titled compound (1.26 g).

$^1$H-NMR (400 MHz, DMSO-d6) δ[ppm]: 0.875 (0.66), 0.894 (0.49), 0.946 (2.43), 1.067 (1.89), 1.086 (3.46), 1.104 (1.77), 1.115 (0.54), 1.154 (0.77), 1.172 (1.46), 1.190 (0.83), 1.251 (4.74), 1.268 (11.83), 1.286 (7.23), 1.356 (4.60), 1.987 (2.31), 2.152 (0.46), 2.168 (1.23), 2.188 (1.63), 2.205 (1.43), 2.219 (1.29), 2.238 (1.23), 2.256 (1.37), 2.275 (1.06), 2.318 (0.51), 2.322 (1.09), 2.327 (1.46), 2.332 (1.06), 2.336 (0.51), 2.518 (5.20), 2.523 (3.57), 2.608 (0.43), 2.627 (1.43), 2.646 (1.71), 2.665 (3.46), 2.669 (3.51), 2.673 (2.91), 2.678 (2.20), 2.689 (1.91), 2.927 (0.71), 3.238 (1.46), 3.259 (2.09), 3.276 (1.40), 3.760 (7.00), 3.818 (1.11), 3.833 (16.00), 3.999 (0.80), 4.017 (0.97), 4.035 (0.94), 4.053 (0.54), 4.111 (0.57), 4.141 (0.77), 4.178 (2.23), 4.189 (2.37), 4.208 (2.74), 4.225 (3.74), 4.240 (2.14), 4.247 (3.43), 4.265 (2.97), 4.287 (2.17), 4.301 (1.80), 4.705 (1.94), 4.717 (2.86), 4.731 (1.74), 4.941 (0.43), 4.955 (0.89), 6.916 (1.83), 6.935 (1.86), 7.202 (5.26), 7.223 (5.77), 7.381 (1.80), 7.402 (3.34), 7.421 (2.80), 7.458 (3.49), 7.479 (1.89), 7.494 (0.49), 7.499 (0.86), 7.511 (2.17), 7.517 (3.34), 7.527 (4.77), 7.535 (4.03), 7.541 (2.74), 7.547 (1.40), 7.549 (1.31), 7.553 (1.46), 7.558 (1.17), 7.565 (1.49), 7.566 (1.11), 7.572 (1.20), 7.591 (0.94), 7.596 (1.74), 7.601

(0.43), 7.606 (0.66), 7.608 (0.91), 7.612 (1.43), 7.615 (1.29), 7.622 (1.66), 7.625 (1.74), 7.630 (0.94), 7.632 (0.89), 7.638 (0.60), 7.642 (1.03), 7.645 (1.09), 7.649 (0.46), 7.742 (4.77), 7.764 (4.37), 7.865 (2.00), 7.868 (1.51), 7.874 (1.03), 7.882 (1.46), 7.888 (1.69), 8.211 (1.63), 8.219 (1.40), 8.226 (0.80), 8.236 (1.60).

Intermediate 54 ethyl 1-{4-[(tert-butoxycarbonyl)(methyl)amino]butyl}-6-chloro-7-[3-(chloromethyl)-5-ethyl-1-methyl-1H-pyrazol-4-yl]-3-[3-(naphthalen-1-yloxy)propyl]-1H-indole-2-carboxylate

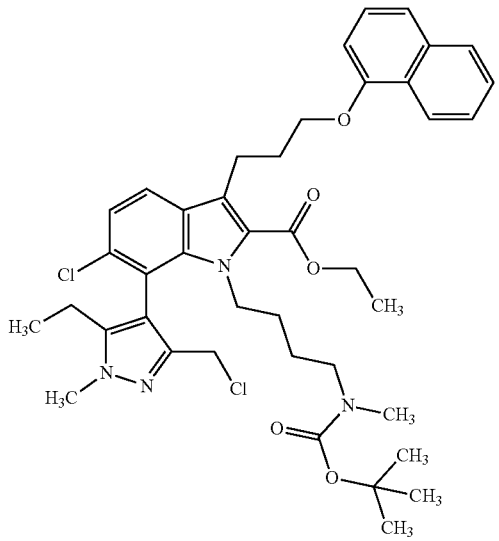 [SMILES: CCOC(=O)c1c(CCCOc2cccc3ccccc23)c2ccc(Cl)c(-c3c(CCl)nn(C)c3CC)c2n1CCCCN(C)C(=O)OC(C)(C)C]

Ethyl 1-{4-[(tert-butoxycarbonyl)(methyl)amino]butyl}-6-chloro-7-[5-ethyl-3-(hydroxymethyl)-1-methyl-1H-pyrazol-4-yl]-3-[3-(naphthalen-1-yloxy)propyl]-1H-indole-2-carboxylate (see Intermediate 53, 1.05 g, 1.44 mmol) with tetrachloromethane (550 µL, 5.7 mmol) and pyridine (460 µL, 5.7 mmol) was dissolved in 13 mL acetonitrile at 0° C. Now triphenylphosphine (1.51 g, 5.74 mmol) was added and the mixture was stirred at rt for 2 hours. The reaction mixture was concentrated under reduced pressure and the residue was washed with toluene two times. The crude product was purified by flash chromatography, gradient hexane/ethyl acetate (0-80%) to give the titled compound (542 mg).

$^1$H-NMR (400 MHz, CHLOROFORM-d) δ [ppm]: 1.074 (1.95), 1.228 (0.81), 1.252 (1.53), 1.261 (0.90), 1.270 (2.51), 1.287 (1.21), 1.371 (6.89), 1.388 (16.00), 1.406 (10.87), 1.434 (6.69), 1.565 (13.47), 2.056 (3.20), 2.288 (0.42), 2.304 (1.24), 2.320 (1.68), 2.339 (1.33), 2.355 (0.48), 2.396 (0.53), 2.414 (0.84), 2.433 (1.24), 2.453 (1.09), 2.471 (0.44), 2.769 (11.74), 3.332 (1.67), 3.351 (2.76), 3.370 (1.45), 3.951 (5.27), 4.075 (0.40), 4.105 (0.50), 4.123 (1.05), 4.140 (1.12), 4.158 (0.67), 4.207 (2.19), 4.223 (4.55), 4.238 (2.01), 4.326 (1.93), 4.331 (1.23), 4.344 (5.18), 4.362 (6.58), 4.380 (1.54), 4.429 (0.92), 4.459 (0.53), 5.310 (2.34), 6.784 (2.02), 6.801 (2.17), 7.006 (0.48), 7.177 (1.78), 7.198 (1.97), 7.352 (1.79), 7.373 (3.17), 7.392 (2.78), 7.433 (3.06), 7.454 (1.71), 7.488 (0.69), 7.501 (2.41), 7.504 (2.72), 7.506 (2.42), 7.514 (3.53), 7.522 (2.42), 7.525 (2.85), 7.528 (2.81), 7.539 (0.72), 7.644 (3.57), 7.666 (3.28), 7.817 (1.74), 7.822 (1.19), 7.830 (1.28), 7.835 (1.08), 7.841 (1.47), 8.357 (1.22), 8.368 (1.03), 8.381 (1.18).

Intermediate 55 ethyl 6-chloro-7-[3-(chloromethyl)-5-ethyl-1-methyl-1H-pyrazol-4-yl]-1-[4-(methylamino)butyl]-3-[3-(naphthalen-1-yloxy)propyl]-1H-indole-2-carboxylate-hydrochlochloric acid salt

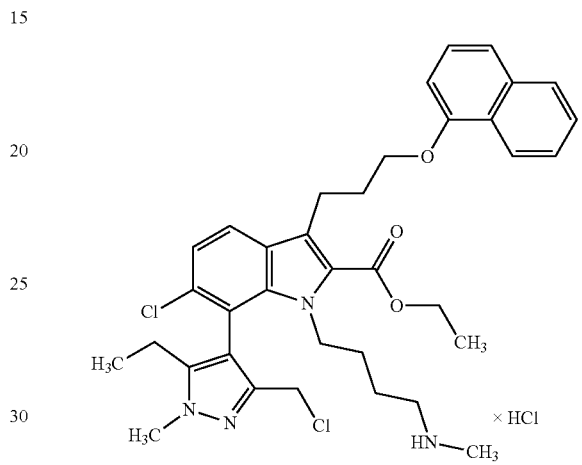

Ethyl-1-{4-[(tert-butoxycarbonyl)(methyl)amino]butyl}-6-chloro-7-[3-(chloromethyl)-5-ethyl-1-methyl-1H-pyrazol-4-yl]-3-[3-(naphthalen-1-yloxy)propyl]-1H-indole-2-carboxylate (see Intermediate 54, 650 mg, 867 µmol) was dissolved in 16 mL ethanol and the hydrochloric acid in 1,4-dioxane (7.6 mL, 4.0 M, 30 mmol) was added. The mixture was stirred at rt overnight. The mixture was concentrated under reduced pressure to obtain the pure product (617 mg).

$^1$H-NMR (400 MHz, DMSO-d6) δ[ppm]: 1.014 (3.36), 1.033 (7.61), 1.051 (3.42), 1.207 (0.82), 1.229 (1.13), 1.240 (1.10), 1.281 (0.49), 1.298 (0.57), 1.343 (5.40), 1.360 (12.36), 1.378 (5.79), 2.248 (0.92), 2.266 (1.23), 2.285 (0.98), 2.299 (0.53), 2.318 (0.72), 2.338 (0.96), 2.356 (1.10), 2.375 (0.82), 2.384 (0.47), 2.389 (0.94), 2.393 (1.39), 2.398 (0.90), 2.538 (3.25), 2.552 (10.19), 2.584 (4.69), 2.589 (3.23), 2.614 (0.82), 2.632 (1.08), 2.651 (1.00), 2.670 (0.84), 2.690 (1.00), 2.707 (1.23), 2.726 (1.25), 2.731 (1.41), 2.735 (1.51), 2.740 (1.19), 3.336 (1.21), 3.357 (1.66), 3.373 (1.21), 3.524 (0.57), 3.526 (0.41), 3.534 (0.49), 3.537 (0.57), 3.553 (0.51), 3.555 (0.45), 3.566 (0.45), 3.742 (0.45), 3.744 (0.47), 3.766 (0.51), 3.768 (0.43), 3.780 (0.41), 3.985 (16.00), 4.013 (1.04), 4.033 (1.58), 4.051 (0.86), 4.291 (1.39), 4.306 (2.86), 4.320 (2.52), 4.337 (4.66), 4.355 (4.42), 4.373 (1.25), 4.459 (7.94), 6.988 (1.76), 7.004 (1.90), 7.332 (4.15), 7.354 (4.46), 7.451 (1.41), 7.472 (2.70), 7.491 (2.27), 7.527 (2.70), 7.548 (1.49), 7.555 (0.57), 7.559 (0.72), 7.572 (1.62), 7.576 (1.43), 7.585 (1.74), 7.591 (2.99), 7.597 (1.76), 7.605 (1.58), 7.609 (1.84), 7.622 (0.78), 7.626 (0.53), 7.894 (3.83), 7.916

(3.46), 7.934 (1.58), 7.941 (0.96), 7.953 (1.70), 7.957 (1.37), 8.257 (1.37), 8.262 (1.37), 8.280 (1.29), 8.282 (1.33), 8.524 (0.86).

Intermediate 56

(rac)-ethyl 4-chloro-3-ethyl-2,14-dimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylate

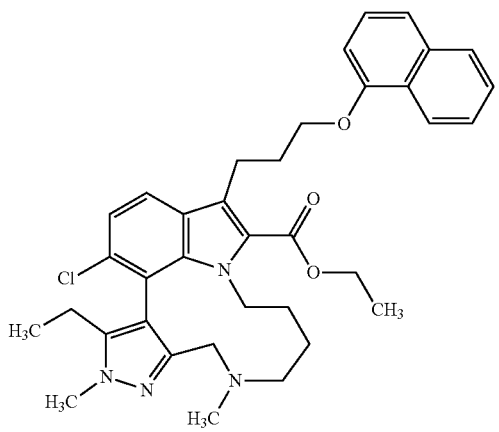 [SMILES: CCOC(=O)c1c(CCCOc2cccc3ccccc23)c2ccc(Cl)c3c2n1CCCCN(C)Cc1nn(C)c(CC)c1-3]

Ethyl 6-chloro-7-[3-(chloromethyl)-5-ethyl-1-methyl-1H-pyrazol-4-yl]-1-[4-(methylamino)butyl]-3-[3-(naphthalen-1-yloxy)propyl]-1H-indole-2-carboxylate-hydrochloric acid salt (see Intermediate 55, 617 mg, 96% purity, 863 µmol) was dissolved in 30 mL N,N-dimethylacetamide and sodium iodide (194 mg, 1.29 mmol) was added. After short stirring cesium carbonate (1.41 g, 4.32 mmol) was added and the mixture was heated overnight at 65° C. in a heating block. The mixture was poured into water and the mixture was extracted with ethyl acetate. The organic layer was washed with brine and dried over sodium sulfate, filtered and concentrated under reduced pressure. (622 mg, contains some N,N-dimethylacetamide).

$^1$H-NMR (400 MHz, CHLOROFORM-d) δ [ppm]: 0.887 (1.18), 0.906 (2.86), 0.925 (1.23), 1.363 (2.09), 1.381 (4.50), 1.398 (2.17), 1.629 (0.43), 2.093 (10.78), 2.125 (1.92), 2.214 (0.58), 2.222 (0.53), 2.233 (0.51), 2.241 (0.53), 2.316 (0.46), 2.333 (0.59), 2.350 (0.45), 2.950 (10.16), 3.022 (16.00), 3.315 (0.44), 3.393 (0.40), 3.428 (0.43), 3.461 (0.49), 3.564 (0.44), 3.902 (5.98), 3.915 (0.93), 4.203 (0.72), 4.219 (1.36), 4.235 (0.61), 4.297 (0.51), 4.307 (0.40), 4.315 (0.55), 4.324 (0.80), 4.342 (0.85), 4.357 (0.80), 4.374 (0.68), 5.309 (2.01), 6.767 (0.65), 6.786 (0.67), 7.169 (1.36), 7.190 (1.54), 7.340 (0.51), 7.360 (0.86), 7.379 (0.71), 7.426 (0.94), 7.446 (0.55), 7.497 (0.81), 7.499 (0.86), 7.502 (0.90), 7.511 (1.02), 7.517 (0.70), 7.520 (0.90), 7.523 (0.85), 7.591 (1.46), 7.612 (1.11), 7.812 (0.55), 7.816 (0.43), 7.825 (0.51), 7.835 (0.44), 8.367 (0.48).

Intermediate 57

(rac)-ethyl (11Z)-4-chloro-2,3-dimethyl-7-[3-(naphthalen-1-yloxy)propyl]-2,10,13,15-tetrahydropyrazolo[4',3':9,10][1,6]oxazacycloundecino[8,7,6-hi]indole-8-carboxylate To a mixture of ethyl 6-chloro-7-[3-(hydroxymethyl)-1,5-dimethyl-1H-pyrazol-4-yl]-3-[3-(naphthalen-1-yloxy)propyl]-1H-indole-2-carboxylate (see Intermediate 42, 298 mg, 560 µmol) in 10 mL of acetonitrile cesium carbonate (912 mg, 2.80 mmol) was added and the mixture was stirred for 10 minutes. (2Z)-1,4-dichlorobut-2-ene (CAS 110-57-6, 88 µL, 840 µmol) and sodium iodide (168 mg, 1.12 mmol) were added and the reaction mixture was stirred overnight at 70° C. The mixture was poured into water and extracted with dichloromethane. The combined organic layers were dried over sodium sulfate, filtered and concentrated under reduced pressure. The crude product was purified by flash chromatography using silica gel (gradient hexane/ethyl acetate/ ethanol) to give the title compound (240 mg, 71% yield).

LC-MS (Method 1): $R_t$=1.71 min; MS (ESIpos): m/z=584 [M+H]$^+$ $^1$H-NMR (400 MHz, DMSO-d6) δ[ppm]: 0.794 (0.49), 1.005 (0.44), 1.083 (0.44), 1.262 (4.91), 1.279 (10.71), 1.297 (4.96), 1.798 (15.86), 2.209 (0.95), 2.226 (1.31), 2.243 (0.98), 2.518 (2.75), 2.522 (1.85), 2.673 (0.55), 3.198 (0.44), 3.253 (0.44), 3.269 (0.65), 3.287 (1.06), 3.307 (1.17), 3.561 (0.65), 3.574 (0.76), 3.591 (0.98), 3.604 (0.87), 3.728 (0.84), 3.756 (1.31), 3.785 (0.71), 3.859 (16.00), 4.158 (2.04), 4.190 (2.67), 4.207 (0.55), 4.220 (1.66), 4.224 (1.88), 4.235 (3.46), 4.242 (1.77), 4.251 (3.03), 4.260 (0.60), 4.269 (1.91), 4.276 (0.74), 4.287 (0.68), 4.293 (1.96), 4.311 (1.83), 4.320 (0.95), 4.329 (0.57), 4.338 (0.98), 4.355 (2.73), 4.386 (2.04), 4.619 (0.57), 4.645 (0.65), 4.657 (0.84), 4.684 (0.93), 4.827 (0.98), 4.865 (0.71), 4.996 (0.52), 5.003 (0.52), 5.023 (0.98), 5.030 (0.95), 5.050 (0.55), 5.056 (0.49), 5.262 (0.41), 5.275 (0.44), 5.289 (0.74), 5.301 (0.68), 5.758 (3.35), 6.915 (1.85), 6.932 (1.96), 7.252 (4.03), 7.273 (4.14), 7.378 (1.42), 7.398 (2.67), 7.417 (2.24), 7.453 (2.81), 7.474 (1.58), 7.482

(0.79), 7.495 (1.55), 7.499 (1.42), 7.511 (1.94), 7.514 (2.32), 7.517 (2.51), 7.531 (1.61), 7.535 (1.80), 7.548 (0.76), 7.552 (0.57), 7.790 (3.76), 7.811 (3.33), 7.860 (1.74), 7.866 (1.12), 7.879 (1.80), 7.883 (1.44), 8.173 (1.42), 8.178 (1.44), 8.198 (1.36).

Intermediate 58

(rac)-ethyl 4-chloro-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate

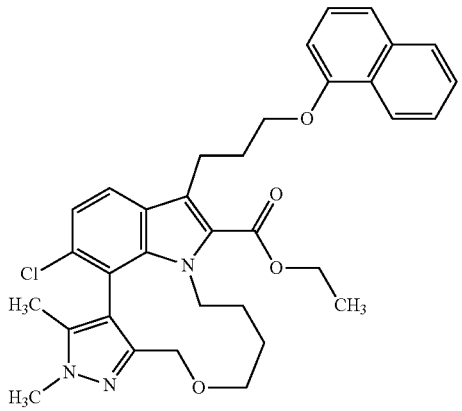 [SMILES: CCOC(=O)c1c(CCCOc2cccc3ccccc23)c2ccc(Cl)c3c2n1CCCCOCc1nn(C)c(C)c1-3]

(rac)-Ethyl (11Z)-4-chloro-2,3-dimethyl-7-[3-(naphthalen-1-yloxy)propyl]-2,10,13,15-tetrahydropyrazolo[4',3':9,10][1,6]oxazacycloundecino[8,7,6-hi]indole-8-carboxylate (see Intermediate 57, 250 mg, 428 µmol) was dissolved in 47 mL of ethanol. Tris(triphenylphosphine)rhodium(I) chloride (795 mg, 856 µmol) was added and the mixture was stirred under hydrogen atmosphere at rt for 4 hours. The catalyst was filtered off and the filtrate was concentrated under reduced pressure. The crude material was purified by flash chromatography using silica gel (gradient hexane/ethyl acetate) (176 mg, 66% yield).

LC-MS (Method 1): $R_t$=1.74 min; MS (ESIpos): m/z=586 [M+H]$^+$ $^1$H-NMR (400 MHz, DMSO-d6) δ[ppm]: 0.928 (0.44), 1.154 (0.84), 1.172 (1.82), 1.189 (1.45), 1.199 (1.01), 1.256 (5.16), 1.274 (11.26), 1.291 (5.46), 1.779 (15.98), 1.987 (1.84), 2.187 (0.91), 2.203 (1.28), 2.220 (0.93), 2.336 (0.47), 2.518 (5.90), 2.522 (3.93), 2.673 (1.01), 3.110 (0.71), 3.125 (0.66), 3.219 (0.47), 3.236 (0.64), 3.253 (0.93), 3.273 (0.54), 3.310 (2.06), 3.821 (16.00), 3.847 (0.47), 3.858 (0.76), 3.866 (0.52), 3.882 (0.49), 4.016 (0.42), 4.035 (0.39), 4.165 (0.49), 4.189 (3.15), 4.202 (3.29), 4.211 (2.46), 4.220 (4.30), 4.229 (2.36), 4.247 (1.84), 4.267 (0.74), 4.284 (1.72), 4.303 (1.60), 4.311 (0.98), 4.320 (0.52), 4.329 (0.96), 4.417 (2.36), 4.449 (1.94), 5.759 (4.79), 6.896 (1.84), 6.913 (2.02), 7.220 (3.88), 7.241 (4.25), 7.371 (1.50), 7.391 (2.75), 7.410 (2.26), 7.453 (2.85), 7.474 (1.67), 7.493 (0.49), 7.498 (0.74), 7.511 (1.82), 7.516 (2.61), 7.526 (3.69), 7.535 (2.92), 7.540 (1.97), 7.552 (0.79), 7.557 (0.52), 7.759 (3.71), 7.780 (3.29), 7.861 (1.55), 7.871 (0.84), 7.879 (1.13), 7.885 (1.33), 8.207 (1.35), 8.214 (1.13), 8.222 (0.64), 8.231 (1.25).

Intermediate 59 ethyl 1-{3-[(tert-butoxycarbonyl)amino]propyl}-6-chloro-7-[3-(hydroxymethyl)-1,5-dimethyl-1H-pyrazol-4-yl]-3-[3-(naphthalen-1-yloxy)propyl]-1H-indole-2-carboxylate

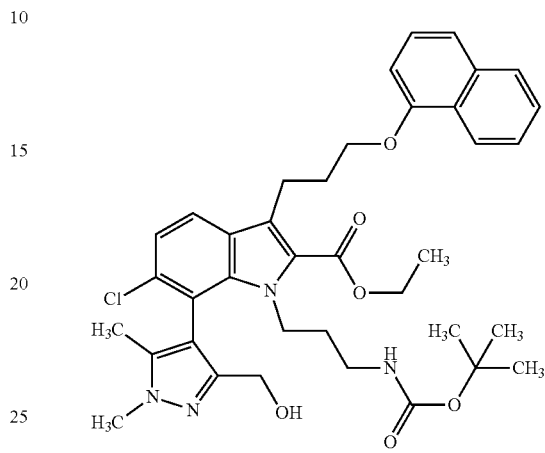

Ethyl 6-chloro-7-[3-(hydroxymethyl)-1,5-dimethyl-1H-pyrazol-4-yl]-3-[3-(naphthalen-1-yloxy)-propyl]-1H-indole-2-carboxylate (see Intermediate 42, 2.00 g) was dissolved in 20 mL of DMF and tert-butyl 3-bromopropyl) carbamate (827 mg, 3.47 mmol, CAS 83948-53-2) and cesium carbonate (2.57 g, 7.89 mmol) were added. The mixture was stirred at rt overnight. Tert-butyl 3-bromopropyl)carbamate (375 mg, 1.57 mmol, CAS 83948-53-2) was added and stirring was continued at rt for 12 hours. The mixture was poured into water and was extracted with dichloromethane. The combined organic layers were dried over sodium sulfate, filtered and concentrated under reduced pressure. The crude material was purified by flash chromatography using silica gel (gradient dichloromethane/acetone) to obtain the title compound (1.42 g).

LC-MS (Method 1): $R_t$=1.69 min; MS (ESIpos): m/z=689 [M+H]$^+$ $^1$H-NMR (400 MHz, DMSO-d6) δ[ppm]: 1.066 (5.53), 1.263 (3.12), 1.281 (6.81), 1.299 (3.42), 1.355 (16.00), 1.367 (3.83), 2.004 (9.62), 2.084 (2.82), 2.171 (0.61), 2.190 (0.87), 2.205 (7.35), 2.408 (0.49), 2.424 (0.63), 2.444 (0.51), 2.518 (7.59), 2.522 (5.02), 2.728 (4.39), 2.888 (5.63), 3.243 (0.77), 3.264 (1.07), 3.280 (0.71), 3.725 (7.15), 3.826 (6.04), 3.938 (0.97), 4.078 (0.45), 4.092 (0.65), 4.108 (1.15), 4.123 (1.24), 4.150 (1.13), 4.162 (1.15), 4.180 (0.53), 4.193 (0.55), 4.213 (0.91), 4.228 (1.92), 4.239 (1.20), 4.254 (1.72), 4.256 (1.92), 4.271 (1.68), 4.275 (1.64), 4.285 (2.29), 4.299 (2.19), 4.674 (1.09), 4.686 (1.60), 4.700 (1.05), 4.932 (0.61), 4.946 (1.24), 4.960 (0.55), 6.625 (0.65), 6.927 (1.13), 6.944 (1.19), 7.200 (1.72), 7.221 (1.80), 7.383 (0.87), 7.404 (1.70), 7.423 (1.42), 7.458 (1.76), 7.479 (0.95), 7.513 (1.15), 7.517 (1.60), 7.527 (1.94), 7.537 (1.62), 7.541 (1.38), 7.553 (0.41), 7.738 (1.98), 7.759 (1.80), 7.865 (0.97), 7.868 (0.69), 7.879 (0.65), 7.882 (0.63), 7.888 (0.87), 7.951 (0.71), 8.218 (0.87), 8.229 (0.65), 8.242 (0.81).

Intermediate 60 ethyl 1-{3-[(tert-butoxycarbonyl)amino]propyl}-6-chloro-7-[3-(chloromethyl)-1,5-dimethyl-1H-pyrazol-4-yl]-3-[3-(naphthalen-1-yloxy)propyl]-1H-indole-2-carboxylate

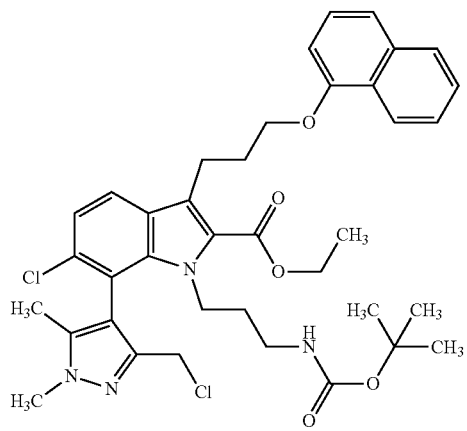 [SMILES: CCOC(=O)c1c(CCCOc2cccc3ccccc23)c2ccc(Cl)c(-c3c(CCl)nn(C)c3C)c2n1CCCNC(=O)OC(C)(C)C]

Ethyl 1-{3-[(tert-butoxycarbonyl)amino]propyl}-6-chloro-7-[3-(hydroxymethyl)-1,5-dimethyl-1H-pyrazol-4-yl]-3-[3-(naphthalen-1-yloxy)propyl]-1H-indole-2-carboxylate (see Intermediate 59, 1.42 g), tetrachloromethane (800 µL, 8.24 mmol) and pyridine (670 µL, 8.24 mmol) were dissolved in 50 mL of acetonitrile. Triphenylphosphine (2.16 g, 8.24 mmol) was added, the mixture was stirred at rt for 5 hours and was concentrated under reduced pressure. The crude material was purified by flash chromatography using silica gel (gradient hexane/ethyl acetate) to give the title compound (1.05 g).

LC-MS (Method 1): $R_t$=1.80 min; MS (ESIpos): m/z=707 [M+H]$^+$ $^1$H-NMR (400 MHz, DMSO-d6) δ[ppm]: 1.117 (1.47), 1.266 (3.00), 1.284 (6.57), 1.301 (3.56), 1.356 (16.00), 1.402 (1.89), 1.442 (0.45), 2.054 (8.45), 2.084 (2.86), 2.182 (0.66), 2.201 (0.91), 2.219 (0.73), 2.442 (0.63), 2.460 (0.77), 2.518 (13.03), 2.522 (9.12), 3.254 (0.80), 3.276 (1.22), 3.292 (0.91), 3.372 (0.98), 3.875 (5.80), 4.211 (1.19), 4.226 (2.06), 4.240 (1.22), 4.246 (1.15), 4.256 (1.43), 4.264 (1.64), 4.274 (1.47), 4.282 (1.43), 4.292 (1.36), 4.299 (0.52), 4.321 (2.24), 4.342 (1.54), 4.372 (0.52), 6.676 (0.70), 6.690 (0.38), 6.914 (1.12), 6.932 (1.26), 7.237 (1.71), 7.257 (1.82), 7.377 (0.87), 7.397 (1.68), 7.416 (1.40), 7.454 (1.78), 7.475 (0.98), 7.494 (0.42), 7.506 (1.08), 7.513 (1.54), 7.522 (2.41), 7.526 (1.15), 7.530 (2.13), 7.537 (2.03), 7.545 (2.03), 7.547 (2.72), 7.549 (2.79), 7.555 (2.45), 7.558 (1.92), 7.565 (2.93), 7.573 (2.59), 7.591 (2.10), 7.595 (3.46), 7.601 (0.94), 7.609 (1.99), 7.612 (3.00), 7.615 (2.66), 7.622 (3.60), 7.625 (3.56), 7.632 (1.89), 7.638 (1.36), 7.641 (2.27), 7.645 (2.13), 7.649 (0.98), 7.795 (1.96), 7.816 (1.78), 7.861 (1.01), 7.870 (0.52), 7.879 (0.80), 7.885 (0.87), 8.203 (0.87), 8.210 (0.77), 8.219 (0.45), 8.227 (0.84).

Intermediate 61 ethyl 1-(3-aminopropyl)-6-chloro-7-[3-(chloromethyl)-1,5-dimethyl-1H-pyrazol-4-yl]-3-[3-(naphthalen-1-yloxy)propyl]-1H-indole-2-carboxylate-hydrochloric acid salt

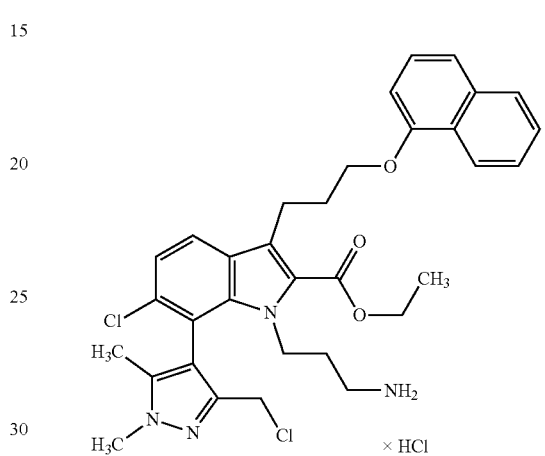

Ethyl-1-{3-[(tert-butoxycarbonyl)amino]propyl}-6-chloro-7-[3-(chloromethyl)-1,5-dimethyl-1H-pyrazol-4-yl]-3-[3-(naphthalen-1-yloxy)propyl]-1H-indole-2-carboxylate (see Intermediate 60, 1.05 g, 1.48 mmol) was dissolved in 25 mL of ethanol and a solution of hydrogen chloride in 1,4-dioxane (0.7 mL, 4 M, 2.97 mmol) was added. The mixture was stirred at rt for 3 days and was concentrated under reduced pressure to obtain the title compound (955 mg).

LC-MS (Method 1): $R_t$=1.49 min; MS (ESIpos): m/z=607 [M+H]$^+$ $^1$H-NMR (400 MHz, DMSO-d6) δ[ppm]: 1.033 (5.03), 1.051 (9.90), 1.064 (1.26), 1.068 (5.20), 1.283 (1.70), 1.300 (3.79), 1.318 (1.76), 2.080 (5.37), 2.183 (0.56), 2.198 (0.67), 2.212 (0.47), 2.522 (0.84), 3.275 (0.46), 3.296 (0.65), 3.313 (0.43), 3.410 (1.65), 3.427 (4.95), 3.444 (4.99), 3.461 (1.57), 3.563 (4.85), 3.882 (5.87), 3.919 (0.76), 3.964 (16.00), 4.227 (0.55), 4.242 (1.10), 4.257 (0.60), 4.268 (0.49), 4.285 (1.18), 4.301 (1.05), 4.303 (1.04), 4.336 (0.65), 4.366 (1.28), 4.402 (1.28), 4.432 (0.63), 6.930 (0.68), 6.948 (0.72), 7.272 (1.41), 7.294 (1.46), 7.388 (0.49), 7.409 (0.94), 7.428 (0.78), 7.463 (1.01), 7.483 (0.54), 7.516 (0.64), 7.520 (1.11), 7.530 (1.53), 7.534 (0.77), 7.539 (1.45), 7.545 (1.88), 7.547 (1.41), 7.553 (1.20), 7.556 (1.16), 7.563 (1.52), 7.571 (1.34), 7.589 (1.06), 7.594 (1.88), 7.599 (0.46), 7.607 (1.00), 7.611 (1.56), 7.613 (1.41), 7.620 (1.86), 7.623 (1.85), 7.636 (0.65), 7.640 (1.13), 7.643 (1.08), 7.648 (0.46), 7.831 (1.30), 7.853 (1.26), 7.868 (1.01), 7.872 (0.95), 7.879 (0.97), 7.883 (1.14), 7.886 (1.18), 7.891 (1.13), 8.216 (0.49), 8.240 (0.47).

Intermediate 62

(rac)-ethyl 12-chloro-10,11-dimethyl-1-[3-(naphthalen-1-yloxy)propyl]-4,5,6,7,8,10-hexahydropyrazolo[3',4':7,8][1,5]diazecino[9,10,1-hi]indole-2-carboxylate

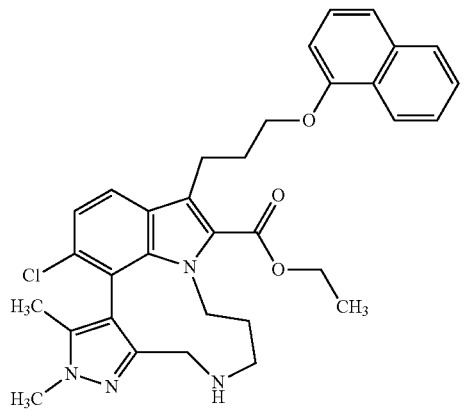 [SMILES: CCOC(=O)c1c(CCCOc2cccc3ccccc23)c2ccc(Cl)c3c2n1CCCNCc1nn(C)c(C)c1-3]

Ethyl 1-(3-aminopropyl)-6-chloro-7-[3-(chloromethyl)-1,5-dimethyl-1H-pyrazol-4-yl]-3-[3-(naph-thalen-1-yloxy)propyl]-1H-indole-2-carboxylate-hydrochloric acid salt (see Intermediate 61, 955 mg) was dissolved in 20 mL of DMF and cesium carbonate (2.42 g, 7.41 mmol) was added. The mixture was stirred at 65° C. for 72 hours and was poured into water. The precipitated material was isolated by filtration to give the title compound (625 mg).

LC-MS (Method 2): $R_t$=1.66 min; MS (ESIpos): m/z=571 [M+H]$^+$ $^1$H-NMR (400 MHz, DMSO-d6) δ[ppm]: 1.182 (0.39), 1.207 (0.53), 1.223 (0.74), 1.240 (5.23), 1.258 (11.02), 1.276 (5.69), 1.452 (0.53), 1.866 (0.42), 1.882 (0.53), 1.918 (16.00), 1.945 (0.85), 1.959 (1.02), 1.967 (0.95), 1.997 (0.88), 2.011 (0.88), 2.040 (0.42), 2.163 (1.17), 2.179 (1.59), 2.196 (1.24), 2.322 (1.09), 2.326 (1.55), 2.331 (1.20), 2.522 (11.73), 2.664 (1.13), 2.668 (1.59), 3.034 (1.55), 3.069 (1.73), 3.182 (0.42), 3.199 (0.64), 3.216 (0.81), 3.233 (1.06), 3.252 (0.67), 3.601 (1.87), 3.635 (1.77), 3.713 (0.64), 3.730 (0.92), 3.793 (14.80), 3.812 (1.13), 3.823 (0.95), 3.880 (0.53), 3.912 (0.71), 3.940 (0.60), 4.166 (0.67), 4.184 (1.48), 4.194 (2.08), 4.211 (3.71), 4.225 (2.23), 4.229 (2.72), 4.243 (2.26), 4.261 (1.98), 4.270 (0.99), 4.278 (0.74), 4.288 (0.92), 4.430 (0.74), 4.465 (0.71), 6.904 (1.91), 6.922 (2.01), 7.180 (3.60), 7.201 (3.96), 7.376 (1.41), 7.396 (2.65), 7.415 (2.19), 7.453 (3.00), 7.474 (1.84), 7.488 (0.81), 7.492 (1.06), 7.505 (2.01), 7.509 (2.01), 7.514 (2.26), 7.522 (3.89), 7.529 (2.47), 7.534 (2.23), 7.539 (2.23), 7.551 (1.41), 7.555 (1.20), 7.565 (0.99), 7.572 (0.85), 7.595 (1.13), 7.612 (0.95), 7.621 (1.09), 7.624 (1.13), 7.641 (0.71), 7.644 (0.71), 7.733 (3.32), 7.754 (3.11), 7.861 (1.91), 7.868 (1.24), 7.879 (1.80), 7.884 (1.59), 8.195 (1.38), 8.201 (1.48), 8.219 (1.55).

Intermediate 63

(rac)-ethyl 12-chloro-7,10,11-trimethyl-1-[3-(naphthalen-1-yloxy)propyl]-4,5,6,7,8,10-hexahydropyrazolo[3',4':7,8][1,5]diazecino[9,10,1-hi]indole-2-carboxylate

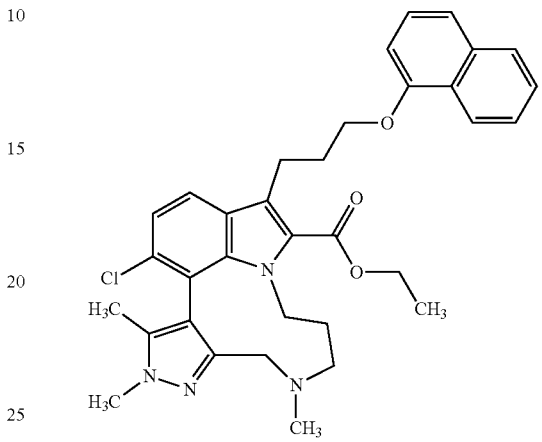

(rac)-Ethyl-12-chloro-10,11-dimethyl-1-[3-(naphthalen-1-yloxy)propyl]-4,5,6,7,8,10-hexahydropyrazolo[3',4':7,8][1,5]diazecino[9,10,1-hi]indole-2-carboxylate (see Intermediate 62, 100 mg) was stirred in an argon atmosphere in 2 mL of ethanol. Acetic acid (20 μL, 350 μmol) and formaldehyde (66 μL, 37% purity, 880 μmol) were added. After 15 minutes sodium cyanoborohydride (22.0 mg, 350 μmol) was added and the mixture was stirred overnight at rt. The reaction mixture was extracted with ethyl acetate. The combined organic layers were dried over sodium sulfate, filtered and concentrated under reduced pressure. The crude product was purified by flash chromatography using silica gel (gradient dichloromethane/acetone) to obtain the title compound (57.6 mg).

LC-MS (Method 2): $R_t$=1.79 min; MS (ESIpos): m/z=585 [M+H]$^+$ $^1$H-NMR (400 MHz, DMSO-d6) δ[ppm]: 1.256 (4.82), 1.273 (10.58), 1.291 (4.89), 1.381 (0.42), 1.553 (0.47), 1.746 (0.60), 1.814 (12.10), 1.965 (16.00), 1.985 (0.75), 2.020 (0.77), 2.084 (13.96), 2.162 (1.03), 2.179 (1.53), 2.196 (1.07), 2.379 (0.43), 2.407 (0.72), 2.439 (0.47), 2.454 (0.47), 2.460 (0.57), 2.518 (3.59), 2.523 (2.65), 3.064 (1.42), 3.095 (1.92), 3.215 (2.70), 3.231 (0.72), 3.247 (2.37), 3.268 (0.50), 3.306 (0.98), 3.358 (0.70), 3.769 (0.68), 3.791 (16.00), 3.824 (1.02), 4.168 (1.05), 4.178 (1.95), 4.182 (1.79), 4.196 (1.64), 4.206 (0.92), 4.214 (0.93), 4.223 (1.95), 4.232 (0.90), 4.241 (1.99), 4.251 (1.97), 4.259 (0.83), 4.268 (1.80), 4.277 (0.75), 4.286 (0.58), 4.295 (0.70), 4.463 (0.58), 4.475 (0.58), 4.496 (0.53), 4.511 (0.50), 5.759 (1.40), 6.872 (1.69), 6.889 (1.87), 7.125 (3.79), 7.146 (3.87), 7.365 (1.38), 7.385 (2.45), 7.404 (2.02), 7.448 (2.54), 7.468 (1.43), 7.490 (0.43), 7.495 (0.67), 7.508 (1.74), 7.512 (1.65), 7.516 (1.97), 7.524 (3.52), 7.532 (2.15), 7.535 (1.85), 7.540 (1.84), 7.544 (0.67), 7.547 (0.83), 7.552 (1.08), 7.555 (0.78), 7.565 (0.82), 7.572 (0.63), 7.591 (0.57), 7.596 (0.95), 7.609 (0.55), 7.613 (0.83), 7.622 (0.97), 7.625 (0.97), 7.630 (0.53), 7.642 (0.58), 7.645 (0.57), 7.701 (3.49), 7.722 (3.09), 7.859 (1.53), 7.868 (0.82), 7.876 (1.25), 7.882 (1.23), 8.202 (1.32), 8.208 (1.17), 8.218 (0.65), 8.226 (1.18).

Intermediate 64 ethyl 1-{4-[(tert-butoxycarbonyl)(methyl)amino]butyl}-6-chloro-3-{3-[(6-fluoronaphthalen-1-yl)oxy]propyl}-7-[3-(hydroxymethyl)-1,5-dimethyl-1H-pyrazol-4-yl]-1H-indole-2-carboxylate

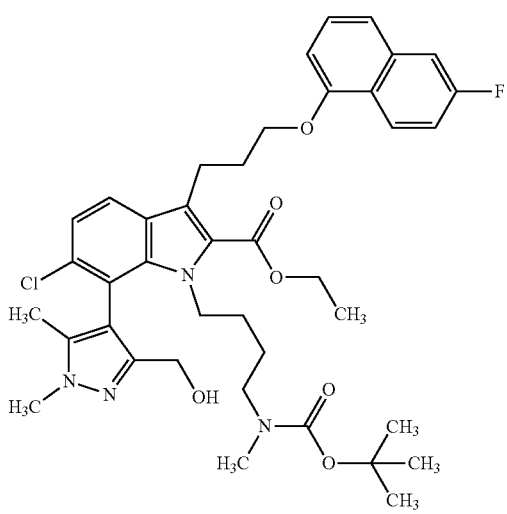

Ethyl 6-chloro-3-{3-[(6-fluoronaphthalen-1-yl)oxy]propyl}-7-[3-(hydroxymethyl)-1,5-dimethyl-1H-pyrazol-4-yl]-1H-indole-2-carboxylate (see Intermediate 47, 740 mg, 1.35 mmol) was dissolved in 10 mL of DMF and tert-butyl (4-bromobutyl)methylcarbamate (see Intermediate 1, 716 mg, 2.69 mmol) and cesium carbonate (2.19 g, 6.73 mmol) were added. The mixture was stirred at rt overnight. Tert-butyl (4-bromobutyl)-methylcarbamate (Intermediate 1, 200 mg, 0.75 mmol) was added and stirring was continued at rt for 6 hours. The mixture was poured into water and was extracted with dichloromethane. The combined organic layers were dried over sodium sulfate, filtered and concentrated under reduced pressure. The crude material was purified by flash chromatography using silica gel (gradient dichloromethane/acetone) to obtain the title compound (618 mg).

LC-MS (Method 1): $R_t$=1.73 min; MS (ESIpos): m/z=735 [M+H]$^+$ $^1$H-NMR (400 MHz, DMSO-d6) δ[ppm]: 0.806 (0.47), 1.008 (0.97), 1.200 (0.50), 1.246 (6.62), 1.264 (11.36), 1.282 (5.46), 1.355 (4.49), 1.380 (2.48), 1.387 (0.85), 1.995 (2.67), 2.084 (16.00), 2.165 (1.25), 2.183 (1.66), 2.202 (1.32), 2.220 (0.66), 2.318 (0.63), 2.323 (1.32), 2.327 (1.85), 2.332 (1.32), 2.336 (0.60), 2.518 (5.80), 2.523 (4.27), 2.660 (2.76), 2.665 (3.39), 2.669 (3.95), 2.673 (3.45), 2.728 (8.03), 2.888 (10.23), 3.233 (1.44), 3.252 (2.13), 3.271 (1.38), 3.804 (15.72), 3.976 (0.44), 4.122 (1.19), 4.143 (2.26), 4.155 (2.07), 4.174 (0.91), 4.187 (0.85), 4.211 (1.76), 4.226 (4.17), 4.244 (4.17), 4.261 (3.04), 4.279 (1.00), 4.693 (2.01), 4.706 (3.48), 4.719 (1.82), 5.758 (1.69), 6.897 (1.19), 6.906 (1.57), 6.918 (1.22), 7.211 (5.46), 7.233 (5.36), 7.383 (1.19), 7.390 (1.38), 7.405 (1.66), 7.412 (1.85), 7.427 (1.35), 7.434 (1.44), 7.447 (3.89), 7.450 (4.14), 7.459 (7.12), 7.529 (0.56), 7.533 (0.41), 7.536 (0.56), 7.545 (1.00), 7.547 (1.35), 7.549 (1.25), 7.555 (1.22), 7.565 (1.57), 7.573 (1.35), 7.591 (1.13), 7.596 (2.01), 7.601 (0.47), 7.606 (0.78), 7.609 (1.10), 7.613 (1.69), 7.615 (1.44), 7.622 (1.95), 7.625 (1.98), 7.630 (1.13), 7.632 (1.04), 7.638 (0.78), 7.642 (1.25), 7.645 (1.32), 7.649 (0.78), 7.653 (2.16), 7.660 (2.07), 7.680 (2.01), 7.686 (2.01), 7.742 (4.71), 7.763 (4.24), 7.951 (1.19), 8.234 (1.63), 8.249 (1.73), 8.257 (1.69), 8.272 (1.57).

Intermediate 65 ethyl 1-{4-[(tert-butoxycarbonyl)(methyl)amino]butyl}-6-chloro-7-[3-(chloromethyl)-1,5-dimethyl-1H-pyrazol-4-yl]-3-{3-[(6-fluoronaphthalen-1-yl)oxy]propyl}-1H-indole-2-carboxylate

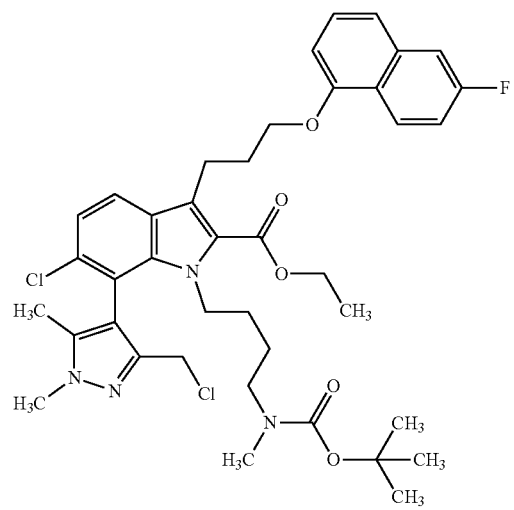 [SMILES: CCOC(=O)c1c(CCCOc2cccc3cc(F)ccc23)c2ccc(Cl)c(-c3c(CCl)nn(C)c3C)c2n1CCCCN(C)C(=O)OC(C)(C)C]

Ethyl-1-{4-[(tert-butoxycarbonyl)(methyl)amino]butyl}-6-chloro-3-{3-[(6-fluoronaphthalen-1-yl)-oxy]propyl}-7-[3-(hydroxymethyl)-1,5-dimethyl-1H-pyrazol-4-yl]-1H-indole-2-carboxylate (see Intermediate 64, 615 mg), tetrachloromethane (320 μL, 3.35 mmol) and pyridine (270 μL, 3.35 mmol) were dissolved in 20 mL of acetonitrile. Triphenylphosphane (878 mg, 3.35 mmol) was added and the mixture was stirred at rt for 5 hours. The reaction mixture was concentrated under reduced pressure and the crude product was purified by flash chromatography using silica gel (gradient dichloromethane/acetone) to obtain the title compound (420 mg).

LC-MS (Method 1): $R_t$=1.84 min; MS (ESIpos): m/z=753 [M+H]$^+$ $^1$H-NMR (400 MHz, DMSO-d6) δ[ppm]: 1.017 (0.97), 1.252 (8.76), 1.269 (9.56), 1.287 (4.86), 1.352 (4.84), 1.385 (1.33), 1.957 (0.41), 2.040 (2.43), 2.057 (2.35), 2.084 (7.96), 2.176 (1.35), 2.195 (1.80), 2.212 (1.38), 2.322 (1.16), 2.327

(1.60), 2.332 (1.19), 2.518 (8.70), 2.523 (5.44), 2.665 (3.87), 2.669 (4.20), 2.673 (3.29), 2.905 (0.77), 3.245 (1.66), 3.264 (2.46), 3.282 (1.69), 3.805 (0.72), 3.850 (16.00), 4.211 (1.96), 4.226 (3.76), 4.240 (2.43), 4.253 (3.04), 4.270 (2.85), 4.288 (1.05), 4.341 (5.11), 5.759 (1.11), 6.887 (1.35), 6.896 (1.58), 6.908 (1.44), 7.252 (4.70), 7.273 (5.06), 7.374 (1.11), 7.380 (1.30), 7.397 (1.71), 7.403 (1.88), 7.418 (1.24), 7.425 (1.35), 7.442 (3.68), 7.447 (3.95), 7.455 (7.21), 7.547 (0.50), 7.555 (0.44), 7.565 (0.53), 7.572 (0.47), 7.596 (0.66), 7.613 (0.58), 7.622 (0.66), 7.625 (0.72), 7.642 (0.53), 7.645 (0.58), 7.652 (2.07), 7.658 (2.10), 7.678 (2.02), 7.684 (1.99), 7.803 (4.42), 7.825 (4.03), 8.225 (1.66), 8.240 (1.77), 8.248 (1.80), 8.263 (1.60).

Intermediate 66 ethyl 6-chloro-7-[3-(chloromethyl)-1,5-dimethyl-1H-pyrazol-4-yl]-3-{3-[(6-fluoronaphthalen-1-yl)oxy]propyl}-1-[4-(methylamino)butyl]-1H-indole-2-carboxylate-hydrochloric acid salt

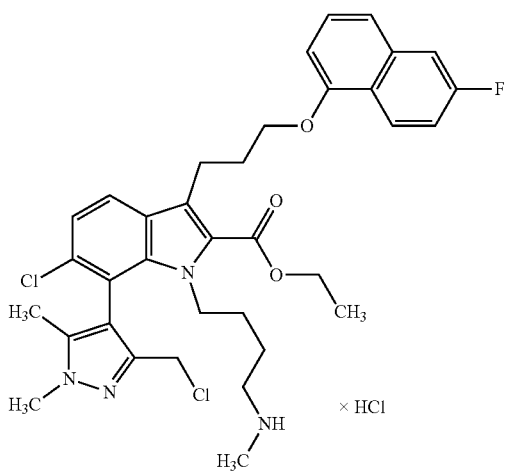 [SMILES: CCOC(=O)c1c(CCCOc2cccc3cc(F)ccc23)c2ccc(Cl)c(-c3c(CCl)nn(C)c3C)c2n1CCCCNC]

Ethyl 1-{4-[(tert-butoxycarbonyl)(methyl)amino]butyl}-6-chloro-7-[3-(chloromethyl)-1,5-dimethyl-1H-pyrazol-4-yl]-3-{3-[(6-fluoronaphthalen-1-yl)oxy]propyl}-1H-indole-2-carboxylate (see Intermediate 65, 420 mg) was dissolved in 10 mL of ethanol and a solution of hydrogen chloride in 1,4-dioxane (10 mL, 4.0 M, 40 mmol) was added. The mixture was stirred at rt overnight. The mixture was concentrated under reduced pressure to obtain the title compound (411 mg) which was used without further purification.

LC-MS (Method 1): $R_t$=1.35 min; MS (ESIpos): m/z=653 [M+H]$^+$ $^1$H-NMR (400 MHz, DMSO-d6) δ[ppm]: 1.035 (0.91), 1.052 (2.25), 1.070 (1.20), 1.109 (0.79), 1.128 (0.87), 1.142 (0.95), 1.164 (0.83), 1.230 (0.43), 1.246 (0.46), 1.253 (0.56), 1.272 (4.44), 1.289 (9.47), 1.307 (4.38), 2.059 (12.40), 2.178 (0.83), 2.194 (1.07), 2.214 (0.85), 2.457 (3.08), 2.471 (6.84), 2.518 (3.99), 2.523 (2.87), 2.604 (0.83), 2.620 (1.14), 2.635 (0.79), 3.262 (1.07), 3.282 (1.47), 3.299 (1.01), 3.411 (0.76), 3.428 (1.55), 3.445 (2.13), 3.565 (16.00), 3.663 (0.41), 3.675 (0.46), 3.677 (0.48), 3.699 (0.45), 3.701 (0.41), 3.805 (0.41), 3.893 (12.94), 4.109 (0.43), 4.136 (0.46), 4.225 (1.26), 4.240 (2.54), 4.249 (1.32), 4.253 (1.69), 4.266 (1.98), 4.271 (2.13), 4.283 (2.01), 4.289 (1.82), 4.301 (0.66), 4.306 (0.52), 4.364 (6.26), 6.901 (1.05), 6.911 (1.28), 6.923 (1.08), 7.271 (3.45), 7.293 (3.58), 7.379 (0.77), 7.386 (0.81), 7.401 (1.10), 7.408 (1.16), 7.423 (0.77), 7.430 (0.97), 7.450 (2.62), 7.453 (2.71), 7.463 (4.55), 7.595 (0.43), 7.622 (0.45), 7.660 (1.32), 7.666 (1.30), 7.686 (1.28), 7.692 (1.26), 7.823 (2.92), 7.844 (2.60), 8.226 (1.12), 8.241 (1.18), 8.249 (1.14), 8.264 (1.05), 8.485 (0.70).

Intermediate 67

(rac)-ethyl 4-chloro-7-{3-[(6-fluoronaphthalen-1-yl)oxy]propyl}-2,3,14-trimethyl-10,11,12,13,14,15-hexahydro-2H-pyrazolo[3',4':8,9][1,6]diazacycloundecino[10,11,1-hi]indole-8-carboxylate

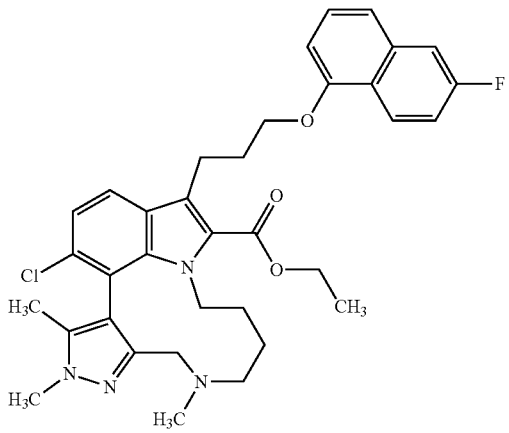 [SMILES: CCOC(=O)c1c(CCCOc2cccc3cc(F)ccc23)c2ccc(Cl)c3c2n1CCCCN(C)Cc1nn(C)c(C)c1-3]

Ethyl-6-chloro-7-[3-(chloromethyl)-1,5-dimethyl-1H-pyrazol-4-yl]-3-{3-[(6-fluoronaphthalen-1-yl)oxy]propyl}-1-[4-(methylamino)butyl]-1H-indole-2-carboxylate-hydrochloric acid salt (see Intermediate 66, 384 mg) was dissolved in 10 mL of DMF and cesium carbonate (957 mg, 2.94 mmol) was added. The mixture was stirred at 65° C. for 72 hours and was poured into water. The precipitated material was isolated by filtration and was purified by flash chromatography using silica gel (gradient dichloromethane/ethanol) to give the title compound (163 mg, 64% purity) which was used without further purification.

LC-MS (Method 1): $R_t$=1.42 min; MS (ESIpos): m/z=617 [M+H]$^+$

Intermediate 68 ethyl 6-chloro-7-[3-ethyl-5-(hydroxymethyl)-1-methyl-1H-pyrazol-4-yl]-3-{3-[(6-fluoro-naphthalen-1-yl)oxy]propyl}-1H-indole-2-carboxylate

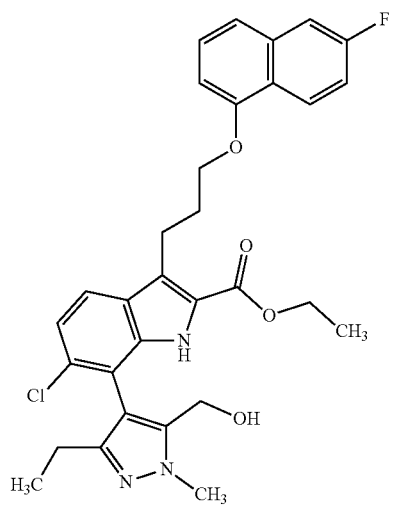 [SMILES: CCOC(=O)c1[nH]c2c(-c3c(CC)nn(C)c3CO)c(Cl)ccc2c1CCCOc1cccc2cc(F)ccc12]

The reaction was performed in four identical preparations using a quarter of all materials. Ethyl-6-chloro-3-{3-[(6-fluoronaphthalen-1-yl)oxy]propyl}-7-(4,4,5,5-tetramethyl-1,3,2-dioxa-borolan-2-yl)-1H-indole-2-carboxylate (see Intermediate 9, 4.00 g, 7.25 mmol) and 4-bromo-3-ethyl-1-methyl-1H-pyrazol-5-yl)methanol (see Intermediate 19, 1.67 g, 7.61 mmol) were dissolved in 88 mL of THF. Aqueous potassium phosphate solution (29 mL, 0.50 M, 14 mmol) was added and the mixture was purged with argon for 10 minutes. XPhos Pd G3 (285 mg, 362 μmol) was added and the mixture was purged with argon for 10 minutes, was stirred for 20 minutes at 110° C. in a microwave reactor and was concentrated under reduced pressure. The residue was purified by flash chromatography using silica gel (gradient dichloromethane/acetone) to give the title compound (2.72 g, 66% yield).

LC-MS (Method 2): $R_t$=1.62 min; MS (ESIpos): m/z=564 [M+H]$^+$ $^1$H-NMR (400 MHz, DMSO-d6) δ[ppm]: 0.929 (0.88), 0.948 (2.01), 0.967 (0.89), 1.066 (16.00), 1.232 (0.88), 1.250 (1.94), 1.268 (0.90), 2.083 (1.23), 2.327 (0.41), 2.518 (0.50), 3.879 (2.74), 3.938 (2.61), 4.212 (0.49), 4.242 (0.46), 4.244 (0.52), 4.259 (0.52), 4.262 (0.55), 7.164 (0.69), 7.185 (0.70), 7.438 (0.45), 7.444 (0.46), 7.452 (0.95), 7.700 (0.53), 7.721 (0.48).

Intermediate 69

(rac)-ethyl-(11Z)-4-chloro-3-ethyl-7-{3-[(6-fluoronaphthalen-1-yl)oxy]propyl}-1-methyl-1,10,13,15-tetrahydropyrazolo[4',3':9,10][1,6]oxazacycloundecino[8,7,6-hi]indole-8-carboxylate

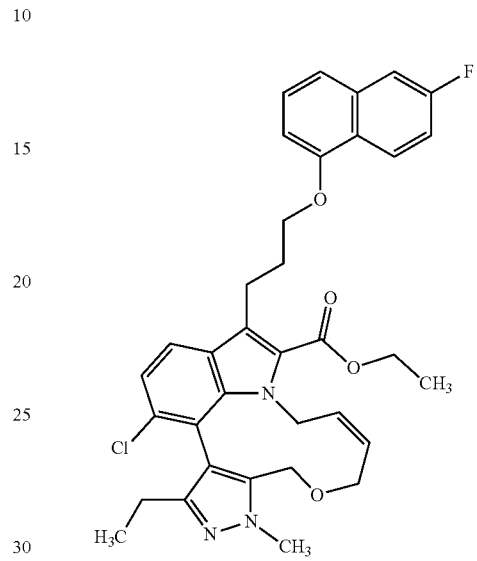

To a mixture of ethyl 6-chloro-7-[3-ethyl-5-(hydroxymethyl)-1-methyl-1H-pyrazol-4-yl]-3-{3-[(6-fluoronaphthalen-1-yl)oxy]propyl}-1H-indole-2-carboxylate (see Intermediate 68, 2.20 g, 3.90 mmol) in 50 mL of acetonitrile cesium carbonate (6.35 g, 19.5 mmol) was added and the mixture was stirred at rt for 10 minutes. (2Z)-1,4-dichlorobut-2-ene (CAS 110-57-6, 450 μL, 4.29 mmol) and sodium iodide (1.17 g, 7.80 mmol) were added and the reaction mixture was stirred for 23 hours at 45° C. The mixture was concentrated under reduced pressure and the residue was purified by flash chromatography using silica gel (gradient dichloromethane/ethanol) to give the title compound (2.01 g, 84% yield).

LC-MS (Method 2): Rt=1.78 min; MS (ESIpos): m/z=616 [M+H]$^+$ $^1$H-NMR (400 MHz, DMSO-d6) δ[ppm]: 0.783 (1.71), 0.802 (3.87), 0.821 (1.85), 1.231 (0.46), 1.248 (0.46), 1.257 (1.87), 1.274 (3.90), 1.292 (1.87), 1.989 (0.86), 2.007 (1.22), 2.026 (0.83), 2.233 (0.45), 2.249 (0.62), 2.265 (0.46), 2.729 (13.26), 2.888 (16.00), 3.300 (0.61), 3.314 (0.66), 3.506 (0.52), 3.888 (5.80), 4.087 (0.79), 4.122 (0.84), 4.217 (0.94), 4.231 (1.38), 4.245 (1.25), 4.262 (0.74), 4.286 (0.70), 4.304 (0.66), 4.689 (0.86), 4.723 (0.80), 4.777 (0.45), 4.910 (0.41), 6.874 (0.51), 6.882 (0.58), 6.895 (0.57), 7.273 (1.38), 7.294 (1.50), 7.353 (0.55), 7.359 (0.61), 7.433 (1.17), 7.437 (1.28), 7.446 (2.35), 7.643 (0.61), 7.650 (0.66), 7.670 (0.62), 7.676 (0.65), 7.814 (1.31), 7.835 (1.22), 7.951 (2.22), 8.145 (0.53), 8.160 (0.57), 8.168 (0.57), 8.183 (0.53).

Intermediate 70

(rac)-ethyl 4-chloro-3-ethyl-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylate

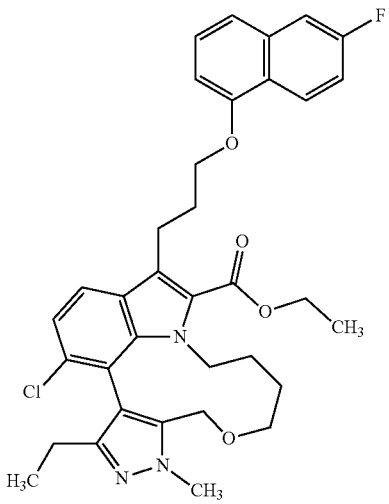 [SMILES: CCOC(=O)c1c(CCCOc2cccc3cc(F)ccc23)c2ccc(Cl)c3c2n1CCCCOCc1c-3c(CC)nn1C]

(Rac)-ethyl-(11Z)-4-chloro-3-ethyl-7-{3-[(6-fluoronaphthalen-1-yl)oxy]propyl}-1-methyl-1,10,13,15-tetrahydropyrazolo[4',3':9,10][1,6]oxazacycloundecino[8,7,6-hi]indole-8-carboxylate (see Intermediate 69, 2.01 g, 3.26 mmol) was dissolved in a mixture of 120 mL of ethanol and 20 mL of THF. Tris(triphenylphosphine)rhodium(I) chloride (6.06 g, 6.52 mmol) was added and the mixture was stirred under hydrogen atmosphere for 5 hours. The catalyst was filtered off and the filtrate was concentrated under reduced pressure. The crude material was purified by flash chromatography using silica gel (gradient dichloromethane/acetone) to give the title compound (1.51 g, 75% yield).

LC-MS (Method 2): $R_t$=1.80 min; MS (ESIpos): m/z=618 [M+H]$^+$ $^1$H-NMR (400 MHz, DMSO-d6) δ[ppm]: 0.833 (4.65), 0.852 (10.63), 0.870 (4.91), 0.879 (0.47), 1.018 (0.93), 1.033 (1.37), 1.046 (1.16), 1.149 (0.64), 1.166 (0.88), 1.186 (0.61), 1.202 (0.54), 1.232 (1.51), 1.252 (5.53), 1.270 (11.21), 1.287 (5.20), 2.052 (0.82), 2.064 (0.74), 2.071 (1.91), 2.083 (2.06), 2.089 (1.90), 2.102 (1.82), 2.108 (0.72), 2.120 (0.72), 2.191 (0.90), 2.208 (1.28), 2.225 (0.97), 2.322 (0.70), 2.326 (0.98), 2.332 (0.70), 2.518 (4.43), 2.522 (2.90), 2.664 (0.70), 2.668 (0.95), 2.673 (0.70), 2.836 (0.79), 2.847 (0.52), 2.853 (0.51), 2.865 (0.82), 3.223 (0.44), 3.240 (0.64), 3.257 (0.97), 3.277 (0.56), 3.287 (0.59), 3.306 (1.24), 3.445 (0.82), 3.459 (0.74), 3.473 (0.75), 3.879 (16.00), 3.946 (0.46), 3.953 (0.43), 3.967 (0.72), 3.981 (0.56), 3.988 (0.47), 4.174 (2.04), 4.181 (0.79), 4.199 (2.06), 4.207 (4.63), 4.216 (2.04), 4.225 (2.68), 4.234 (0.67), 4.243 (1.82), 4.261 (1.05), 4.278 (1.72), 4.296 (1.65), 4.305 (0.97), 4.314 (0.52), 4.323 (0.95), 4.348 (0.39), 4.361 (0.87), 4.373 (0.51), 4.382 (0.46), 4.395 (0.77), 4.631 (2.21), 4.665 (2.00), 6.864 (1.29), 6.871 (1.34), 6.878 (1.19), 6.885 (1.39), 7.230 (4.11), 7.251 (4.24), 7.362 (0.88), 7.369 (0.98), 7.384 (1.37), 7.391 (1.49), 7.407 (1.06), 7.413 (1.11), 7.430 (2.54), 7.438 (2.80), 7.445 (6.04), 7.459 (0.47), 7.646 (1.59), 7.652 (1.62), 7.672 (1.59), 7.678 (1.55), 7.787 (3.66), 7.809 (3.34), 8.202 (1.37), 8.217 (1.42), 8.225 (1.37), 8.240 (1.31).

Intermediate 71

(rac)-ethyl-(11Z)-4-chloro-3-ethyl-7-{3-[(6-fluoronaphthalen-1-yl)oxy]propyl}-2-methyl-2,10,13,15-tetrahydropyrazolo[4',3':9,10][1,6]oxazacycloundecino[8,7,6-hi]indole-8-carboxylate

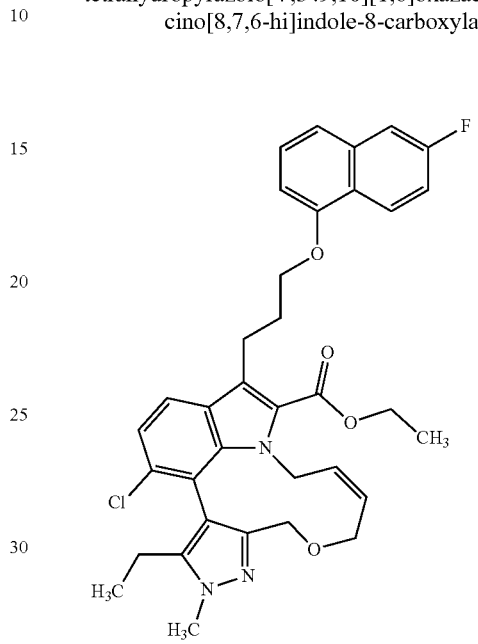

To a mixture of ethyl-6-chloro-7-[5-ethyl-3-(hydroxymethyl)-1-methyl-1H-pyrazol-4-yl]-3-{3-[(6-fluoronaphthalen-1-yl)oxy]propyl}-1H-indole-2-carboxylate (see Intermediate 34, 1.00 g, 1.77 mmol) in 23 mL of acetonitrile cesium carbonate (2.89 g, 8.86 mmol) was added and the mixture was stirred for 10 minutes. (2Z)-1,4-dichlorobut-2-ene (CAS 110-57-6, 210 μL, 2.0 mmol) and sodium iodide (531 mg, 3.55 mmol) were added and the reaction mixture was stirred for 23 hours at 45° C. and was concentrated under reduced pressure. The residue was purified by flash chromatography using silica gel (gradient dichloromethane/ethanol) to give the title compound (894 mg, 82% yield).

LC-MS (Method 2): $R_t$=1.73 min; MS (ESIpos): m/z=616 [M+H]$^+$ $^1$H-NMR (400 MHz, DMSO-d6) δ[ppm]: 0.784 (3.24), 0.803 (7.54), 0.822 (3.46), 0.884 (0.85), 0.901 (1.69), 0.920 (0.90), 0.991 (0.68), 1.009 (0.61), 1.171 (0.55), 1.232 (0.90), 1.254 (5.04), 1.272 (10.81), 1.290 (5.00), 2.065 (2.17), 2.091 (0.53), 2.145 (0.77), 2.163 (1.69), 2.182 (2.30), 2.201 (1.86), 2.219 (1.51), 2.238 (1.27), 2.332 (0.92), 2.336 (0.42), 2.419 (0.48), 2.437 (0.50), 2.518 (5.08), 2.522 (3.53), 2.673 (0.92), 3.266 (0.75), 3.283 (1.45), 3.302 (1.47), 3.557 (0.64), 3.570 (0.77), 3.586 (0.96), 3.600 (0.85), 3.700 (0.75), 3.731 (0.85), 3.760 (1.58), 3.788 (0.70), 3.887 (16.00), 4.151 (2.06), 4.183 (2.59), 4.203 (0.50), 4.216 (1.60), 4.220 (1.88), 4.231 (3.33), 4.238 (1.82), 4.247 (3.02), 4.265 (1.88), 4.271 (0.70), 4.283 (0.68), 4.289 (1.84), 4.299 (0.42), 4.307 (1.67), 4.316 (0.92), 4.325 (0.55), 4.334 (0.94), 4.349 (2.65), 4.381 (2.04), 4.611 (0.55), 4.637 (0.66), 4.649 (0.85), 4.676 (0.94), 4.798 (1.01), 4.836 (0.70), 4.969 (0.53), 4.976 (0.50), 4.997 (0.99), 5.003 (0.96), 5.024 (0.53), 5.029 (0.48), 5.270 (0.44), 5.283 (0.70), 5.296 (0.68), 6.883 (1.25), 6.891 (1.34), 6.896

(1.14), 6.905 (1.38), 7.258 (4.16), 7.280 (4.08), 7.355 (0.83), 7.362 (0.99), 7.378 (1.34), 7.385 (1.45), 7.400 (0.96), 7.406 (1.05), 7.417 (0.42), 7.438 (2.76), 7.443 (2.96), 7.451 (5.94), 7.464 (0.44), 7.648 (1.56), 7.655 (1.62), 7.674 (1.58), 7.681 (1.56), 7.789 (3.51), 7.810 (3.29), 8.193 (1.32), 8.207 (1.42), 8.215 (1.38), 8.231 (1.34).

Intermediate 72

(rac)-ethyl 4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylate

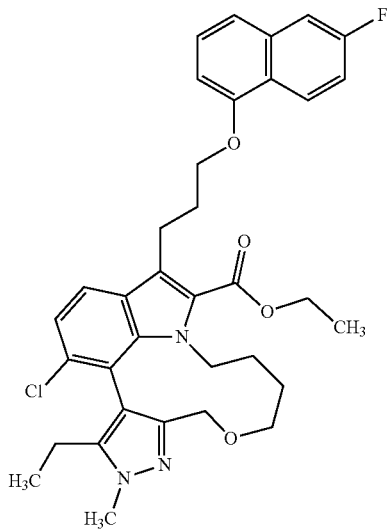 [SMILES: CCOC(=O)c1c(CCCOc2cccc3cc(F)ccc23)c2ccc(Cl)c3c2n1CCCCOCc1nn(C)c(CC)c1-3]

(Rac)-ethyl-(11Z)-4-chloro-3-ethyl-7-{3-[(6-fluoronaphthalen-1-yl)oxy]propyl}-2-methyl-2,10,13,15-tetrahydropyrazolo[4',3':9,10][1,6]oxazacycloundecino[8,7,6-hi]indole-8-carboxylate (see Intermediate 71, 890 mg, 1.44 mmol) was dissolved in a mixture of 53 mL of ethanol and 8.9 mL of THF. Tris(triphenylphosphine)rhodium(I) chloride (2.68 g, 2.89 mmol) was added and the mixture was stirred under hydrogen atmosphere for 7 hours. The catalyst was filtered off and the filtrate was concentrated under reduced pressure. The crude material was purified by flash chromatography using silica gel (gradient dichloromethane/acetone) to give the title compound (748 mg, 84% yield).

LC-MS (Method 2): $R_f$=1.78 min; MS (ESIpos): m/z=618 [M+H]$^+$ $^1$H-NMR (400 MHz, DMSO-d6) δ[ppm]: 0.784 (3.12), 0.803 (7.26), 0.821 (3.31), 0.896 (0.51), 0.913 (0.44), 1.165 (0.48), 1.192 (0.88), 1.206 (1.03), 1.218 (1.02), 1.228 (1.28), 1.250 (5.13), 1.267 (10.43), 1.285 (5.17), 2.084 (6.65), 2.117 (0.73), 2.135 (1.49), 2.156 (1.79), 2.176 (1.64), 2.194 (1.50), 2.213 (1.49), 2.331 (0.55), 2.518 (3.12), 2.522 (1.96), 3.122 (0.71), 3.136 (0.70), 3.146 (0.47), 3.235 (0.68), 3.253 (1.09), 3.280 (1.17), 3.299 (0.80), 3.314 (1.11), 3.849 (16.00), 3.868 (0.87), 3.893 (0.52), 4.159 (0.71), 4.175 (1.03), 4.189 (3.22), 4.198 (2.86), 4.208 (2.44), 4.220 (3.33), 4.226 (2.54), 4.243 (1.73), 4.262 (0.75), 4.281 (1.63), 4.299 (1.58), 4.308 (0.90), 4.317 (0.50), 4.325 (0.88), 4.420 (2.35), 4.451 (1.90), 6.862 (1.29), 6.868 (1.34), 6.877 (1.21), 6.884 (1.38), 7.212 (3.67), 7.233 (3.85), 7.375 (0.87), 7.381 (0.99), 7.397 (1.45), 7.403 (1.59), 7.409 (0.73), 7.419 (1.02), 7.430 (2.49), 7.440 (2.78), 7.446 (5.73), 7.461 (0.58), 7.646 (1.59), 7.652 (1.63), 7.672 (1.57), 7.678 (1.55), 7.747 (3.41), 7.768 (3.11), 8.210 (1.32), 8.224 (1.37), 8.233 (1.36), 8.248 (1.28).

Intermediate 73 ethyl 1-{4-[(tert-butoxycarbonyl)(methyl)amino]butyl}-6-chloro-7-[3-ethyl-5-(hydroxymethyl)-1-methyl-1H-pyrazol-4-yl]-3-{3-[(6-fluoronaphthalen-1-yl)oxy]propyl}-1H-indole-2-carboxylate

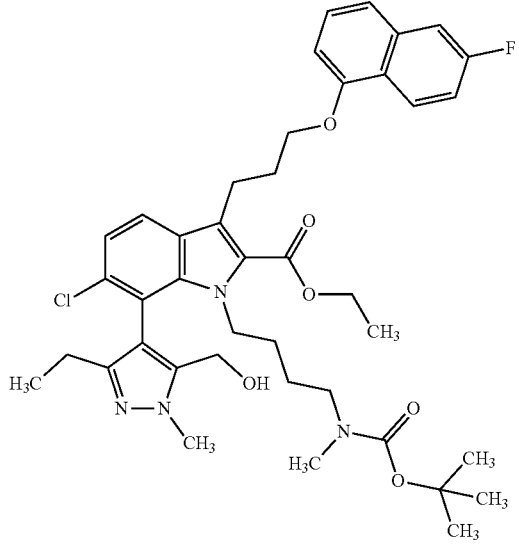 [SMILES: CCOC(=O)c1c(CCCOc2cccc3cc(F)ccc23)c2ccc(Cl)c(-c3c(CC)nn(C)c3CBr)c2n1CCCCN(C)C(=O)OC(C)(C)C]

Ethyl-6-chloro-7-[3-ethyl-5-(hydroxymethyl)-1-methyl-1H-pyrazol-4-yl]-3-{3-[(6-fluoro-naphthalen-1-yl)oxy]propyl}-1H-indole-2-carboxylate (see Intermediate 68, 2.48 g, 4.40 mmol) was dissolved in 25 mL DMF and treated with the cesiumcarbonate (4.30 g, 13.2 mmol). It was stirred for 10 minutes at room temperature under nitrogen atmosphere. Then the tert-butyl (4-bromobutyl)methylcarbamate (Intermediate 1, 1.76 g, 6.60 mmol) was added and it was stirred at room temperature for 2 days. The reaction mixture was diluted with water and ethyl acetate, extracted three times, washed once with water and brine, filtered through a silicone coated filter and concentrated under reduced pressure. The crude product was purified by flash chromatography twice (50 g column, silica, SNAP ultra, methylene chloride/ethanol 0%-10% ethanol; second time: hexane/ethyl acetate 50%-100%/ethyl acetate/ethanol 0%-10% ethanol) to provide the desired compound in 94% purity: 2.4 g ¹H-NMR (400 MHz, DMSO-d6): δ [ppm]=0.98 (t, 3H), 1.05-1.44 (m, 13H), 1.99 (s, 5H), 2.06-2.32 (m, 4H), 2.66 (br s, 2H), 2.83-2.98 (m, 2H), 3.25 (br t, 2H), 3.88 (s, 3H), 4.07-4.36 (m, 7H), 5.18 (br t, 1H), 6.90 (dd, 1H), 7.23 (d, 1H), 7.35-7.49 (m, 3H), 7.67 (dd, 1H), 7.77 (d, 1H), 8.25 (dd, 1H).

¹H-NMR (400 MHz, DMSO-d6): δ [ppm]=1.00 (br t, 3H), 1.09-1.40 (m, 15H), 2.11-2.31 (m, 4H), 2.67 (dd, 4H), 2.80-3.04 (m, 2H), 3.26 (br t, 2H), 3.90 (s, 3H), 3.92-4.11 (m, 2H), 4.17-4.31 (m, 4H), 4.38-4.60 (m, 2H), 6.90 (dd, 1H), 7.26 (d, 1H), 7.35-7.49 (m, 3H), 7.67 (dd, 1H), 7.82 (d, 1H), 8.24 (dd, 1H).—no OH signal detected.

Intermediate 74 ethyl 7-[5-(bromomethyl)-3-ethyl-1-methyl-1H-pyrazol-4-yl]-1-{4-[(tert-butoxycarbonyl)-(methyl)amino]butyl}-6-chloro-3-{3-[(6-fluoronaphthalen-1-yl)oxy]propyl}-1H-indole-2-carboxylate Intermediate 75 ethyl 7-[5-(bromomethyl)-3-ethyl-1-methyl-1H-pyrazol-4-yl]-6-chloro-3-{3-[(6-fluoronaphthalen-1-yl)oxy]propyl}-1-[4-(methylamino)butyl]-1H-indole-2-carboxylate-hydrochloric acid salt

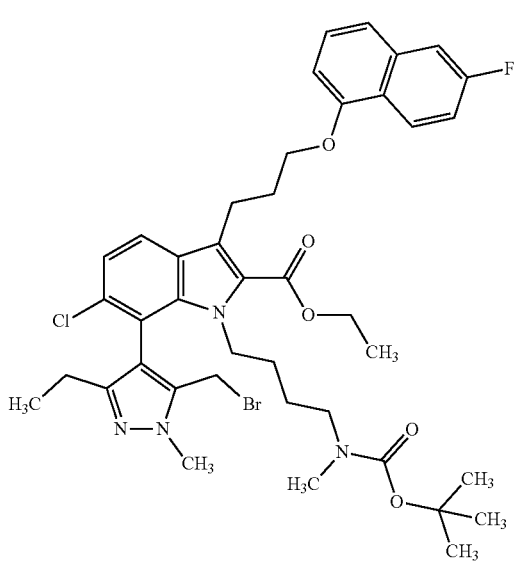

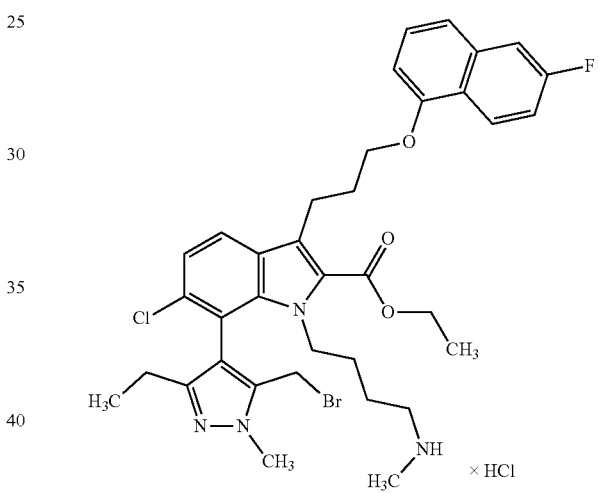

Ethyl-1-{4-[(tert-butoxycarbonyl)(methyl)amino]butyl}-6-chloro-7-[3-ethyl-5-(hydroxymethyl)-1-methyl-1H-pyrazol-4-yl]-3-{3-[(6-fluoronaphthalen-1-yl)oxy]propyl}-1H-indole-2-carboxylate (see Intermediate 73, 2.40 g) was dissolved in 62 mL dichloromethane and cooled with an ice bath. Then triphenylphosphine (1.26 g, 4.80 mmol) was added and it was stirred 10 minutes at this temperature under nitrogen atmosphere. Tetrabromomethane (1.59 g, 4.80 mmol) was added and it was stirred at room temperature over night. The reaction mixture was concentrated under reduced pressure and purified by flash chromatography (50 g column, silica, SNAP ultra; hexane/ethyl acetate 0%-60%) to provide the desired and analytically pure target compound: 1.7 g.

Ethyl-7-[5-(bromomethyl)-3-ethyl-1-methyl-1H-pyrazol-4-yl]-1-{4-[(tert-butoxycarbonyl)-(methyl)amino]butyl}-6-chloro-3-{3-[(6-fluoronaphthalen-1-yl)oxy]propyl}-1H-indole-2-carboxylate (see Intermediate 74, 1.69 g, 2.08 mmol) was dissolved in 21 mL methanol and treated with the hydrogenchloride in dioxane (2.6 mL, 4.0 M, 10 mmol). It was stirred at 40° C. for 2 hours under nitrogen atmosphere. The reaction mixture was concentrated under reduced pressure. The 84% pure crude product was used without further purification: 1.7 g.

¹H-NMR (400 MHz, DMSO-d6): δ [ppm]=0.99 (t, 3H), 1.09-1.25 (m, 4H), 1.29 (t, 3H), 2.08-2.22 (m, 3H), 2.29 (dd, 1H), 2.46 (t, 2H), 2.57-2.66 (m, 2H), 3.28 (br t, 2H), 3.80-3.92 (m, 1H), 3.97 (s, 3H), 4.03-4.16 (m, 1H), 4.17-

4.34 (m, 4H), 4.52-4.82 (m, 3H), 6.83-6.97 (m, 1H), 7.28 (d, 1H), 7.35-7.51 (m, 3H), 7.67 (dd, 1H), 7.84 (d, 1H), 8.23 (dd, 1H), 8.58 (br d, 2H).

Intermediate 76 ethyl 4-chloro-3-ethyl-7-{3-[(6-fluoronaphthalen-1-yl)oxy]propyl}-1,14-dimethyl-10,11,12,13,14,15-hexahydro-1H-pyrazolo[3',4':8,9][1,6]diazacycloundecino[10,11,1-hi]indole-8-carboxylate

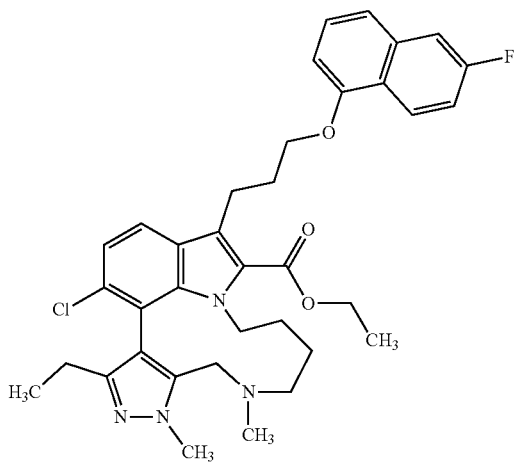 [SMILES: CCOC(=O)c1c(CCCOc2cccc3cc(F)ccc23)c2ccc(Cl)c3c2n1CCCCN(C)Cc1c-3c(CC)nn1C]

ethyl 7-[5-(bromomethyl)-3-ethyl-1-methyl-1H-pyrazol-4-yl]-6-chloro-3-{3-[(6-fluoronaphthalen-1-yl)oxy]propyl}-1-[4-(methylamino)butyl]-1H-indole-2-carboxylate-hydrochloric acid salt (see Intermediate 75, 1.67 g) was dissolved in 11 mL DMF and treated with cesium carbonate (3.63 g, 11.2 mmol). It was stirred at 60° C. over night under nitrogen atmosphere. The reaction mixture was diluted with water and ethyl acetate. The aqueous layer was extracted with ethyl acetate three times. The combined organic layers were washed with water and brine once, filtered through a silicone coated filter and concentrated under reduced pressure. The crude was purified by flash chromatography. (28 g column, aminophase; hexane/ethyl acetate 0%-50% ethyl acetate) to provide the desired target compound in 73% purity: 399 mg $^1$H-NMR (400 MHz, DMSO-d6): δ [ppm]=0.67-1.32 (m, 11H), 1.88-2.26 (m, 7H), 2.35-2.46 (m, 1H), 3.15 (d, 1H), 3.19-3.27 (m, 1H), 3.28-3.39 (m, 1H), 3.67 (d, 1H), 3.86 (s, 3H), 3.88-3.98 (m, 1H), 4.16-4.36 (m, 4H), 4.40-4.52 (m, 1H), 6.88 (dd, 1H), 7.23 (d, 1H), 7.35-7.49 (m, 3H), 7.67 (dd, 1H), 7.78 (d, 1H), 8.26 (dd, 1H).

LC-MS (Method 2): $R_t$=1.85 min; MS (ESIpos): m/z=632 [M+H]$^+$

Intermediate 77 ethyl 6-chloro-7-{3-ethyl-5-[(methylamino)methyl]-1-[2-(morpholin-4-yl)ethyl]-1H-pyrazol-4-yl}-3-{3-[(naphthalen-1-yl)oxy]propyl}-1H-indole-2-carboxylate

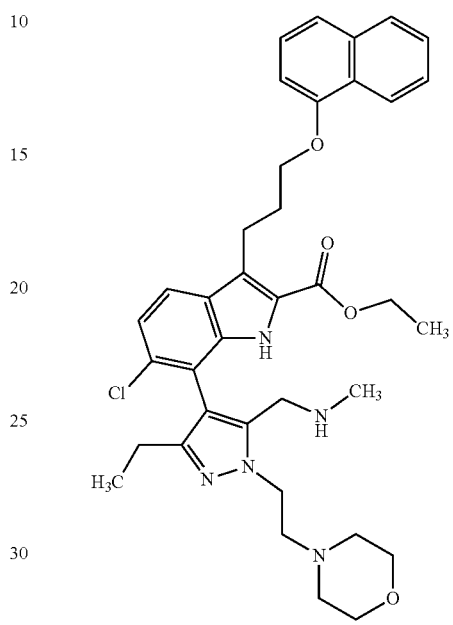

Ethyl-6-chloro-7-{3-ethyl-5-(hydroxymethyl)-1-[2-(morpholin-4-yl)ethyl]-1H-pyrazol-4-yl}-3-{3-[(naphthalen-1-yl)oxy]propyl}-1H-indole-2-carboxylate (see Intermediate 39, 3.60 g, 5.58 mmol) was dissolved in THF, N,N-diisopropylethylamine (1.9 mL, 11.2 mmol) and methanesulfonyl chloride (520 µL, 6.70 mmol) were added and the mixture was stirred for 30 minutes at room temperature. Methanamine (CAS 74-89-5, 28 mL, 2.0 M, 55.8 mmol) was added and the mixture was stirred for 2 hours at room temperature. The reaction mixture was concentrated under reduced pressure and the crude material was purified by flash chromatography using silica gel (gradient dichloromethane/ethanol) to give the title compound (2.34 g, 64% yield).

LC-MS (Method 2): $R_t$=1.72 min; MS (ESIneg): m/z=656 [M−H]$^-$ $^1$H-NMR (400 MHz, DMSO-d6) δ[ppm]: 0.927 (6.80), 0.946 (16.00), 0.965 (7.07), 1.249 (6.80), 1.267 (14.87), 1.285 (6.97), 2.125 (10.62), 2.197 (0.47), 2.214 (1.35), 2.231 (2.06), 2.243 (1.59), 2.249 (1.60), 2.261 (3.05), 2.271 (1.37), 2.280 (3.41), 2.292 (1.66), 2.299 (3.74), 2.306 (1.45), 2.318 (2.42), 2.322 (0.84), 2.327 (0.96), 2.332 (0.70), 2.337 (0.87), 2.434 (1.25), 2.450 (1.92), 2.469 (2.92), 2.518 (3.16), 2.523 (2.42), 2.525 (1.99), 2.544 (0.56), 2.665 (0.63), 2.669 (0.89), 2.673 (0.67), 2.679 (0.47), 2.695 (0.96), 2.708 (0.63), 2.714 (0.80), 2.728 (1.56), 2.741 (0.63), 2.813 (0.62), 2.831 (1.03), 2.846 (1.12), 2.864 (0.69), 2.878 (0.44), 2.952 (0.84), 2.984 (0.90), 3.340 (2.79), 3.347 (2.35), 3.361 (1.33), 3.501 (0.89), 3.508 (1.10), 3.518 (1.02), 3.530 (1.89), 3.537 (1.77), 3.546 (1.93), 3.552 (1.50), 3.585 (1.50), 3.592 (1.86), 3.601 (1.77), 3.608 (1.87), 3.620 (1.02), 3.636 (2.30), 3.668 (1.46), 4.177 (0.73), 4.188 (2.20), 4.203 (4.48), 4.209 (3.45), 4.212 (2.91), 4.218 (3.66), 4.226 (2.55), 4.236 (3.58), 4.244 (0.89), 4.254 (3.39), 4.258 (1.40), 4.271 (1.32), 4.276 (2.78), 4.285 (0.64), 4.294 (2.45), 4.303 (1.25), 4.311 (0.70), 4.321 (1.20), 5.759 (3.21), 6.877 (2.36), 6.894 (2.56), 7.176 (6.25), 7.198 (6.15), 7.357 (1.92), 7.378 (3.42), 7.397 (2.93), 7.433 (4.18), 7.447 (1.99), 7.450 (2.69), 7.454 (2.86), 7.467 (1.87), 7.471 (1.85), 7.489 (1.73), 7.492 (1.86), 7.506 (1.22), 7.509 (2.50), 7.513 (2.10), 7.527 (1.23), 7.530 (1.12), 7.705 (5.11), 7.727 (4.74), 7.845 (2.43), 7.865 (2.13), 8.087 (2.22), 8.106 (1.93), 8.108 (2.03).

Intermediate 78

(rac)-ethyl-(11Z)-4-chloro-3-ethyl-14-methyl-1-[2-(morpholin-4-yl)ethyl]-7-{3-[(naphthalen-1-yl)oxy]propyl}-10,13,14,15-tetrahydro-1H-pyrazolo[3',4':8,9][1,6]diazacycloundecino[10,11,1-hi]indole-8-carboxylate

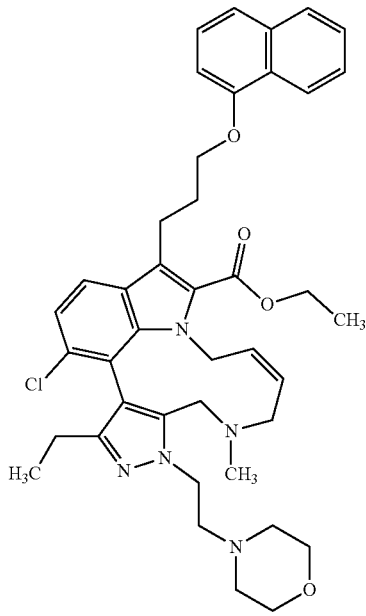 [SMILES: CCOC(=O)c1c(CCCOc2cccc3ccccc23)c2ccc(Cl)c3c2n1C/C=C\CN(C)Cc1c-3c(CC)nn1CCN1CCOCC1]

To a mixture of ethyl 6-chloro-7-{3-ethyl-5-[(methylamino)methyl]-1-[2-(morpholin-4-yl)ethyl]-1H-pyrazol-4-yl}-3-{3-[(naphthalen-1-yl)oxy]propyl}-1H-indole-2-carboxylate (see Intermediate 77, 350 mg, 532 µmol) in 6.8 mL of acetonitrile cesium carbonate (866 mg, 2.66 mmol) was added and the mixture was stirred for 10 minutes at rt. (2Z)-1,4-dichlorobut-2-ene (CAS 110-57-6, 62 µL, 580 µmol) was added and the reaction mixture was stirred for 72 hours. The mixture was concentrated under reduced pressure and the residue was purified by flash chromatography using silica gel (gradient dichloromethane/acetone) to give the title compound (170 mg, 45% yield).

LC-MS (Method 2): $R_t$=1.85 min; MS (ESIpos): m/z=710 [M+H]$^+$ $^1$H-NMR (400 MHz, DMSO-d6) δ[ppm]: 0.755 (6.78), 0.774 (15.94), 0.792 (7.12), 1.137 (0.80), 1.262 (7.37), 1.279 (16.00), 1.298 (7.46), 1.967 (1.29), 1.984 (3.30), 1.988 (3.21), 2.003 (3.02), 2.007 (2.90), 2.022 (1.02), 2.084 (0.89), 2.227 (1.29), 2.246 (1.76), 2.261 (1.33), 2.327 (1.88), 2.331 (1.51), 2.336 (0.83), 2.359 (15.75), 2.385 (1.76), 2.397 (2.47), 2.408 (1.33), 2.518 (7.12), 2.523 (4.78), 2.669 (1.94), 2.673 (1.70), 2.687 (0.62), 2.692 (0.65), 2.705 (1.26), 2.718 (0.96), 2.723 (1.02), 2.736 (0.74), 2.773 (0.74), 2.791 (1.73), 2.810 (1.54), 2.822 (1.14), 2.840 (1.51), 2.955 (1.05), 2.986 (1.23), 3.022 (0.77), 3.140 (2.28), 3.173 (2.44), 3.267 (0.49), 3.281 (1.02), 3.299 (2.25), 3.555 (4.96), 3.567 (8.88), 3.578 (4.78), 3.686 (2.22), 3.719 (2.00), 4.198 (0.55), 4.216 (3.55), 4.232 (4.59), 4.243 (4.19), 4.261 (3.30), 4.272 (2.03), 4.278 (1.33), 4.290 (3.48), 4.299 (0.80), 4.308 (2.96), 4.317 (1.45), 4.325 (0.77), 4.335 (1.42), 4.353 (0.40), 4.509 (1.33), 4.527 (1.51), 4.546 (1.42), 4.560 (1.39), 4.577 (1.51), 4.706 (0.83), 4.736 (1.39), 4.764 (0.71), 4.867 (1.26), 4.904 (1.08), 5.272 (0.49), 5.292 (0.89), 5.319 (0.49), 6.902 (2.59), 6.919 (2.84), 7.253 (6.17), 7.274 (6.69), 7.372 (2.10), 7.393 (3.85), 7.412 (3.27), 7.451 (3.92), 7.472 (2.96), 7.490 (2.19), 7.493 (2.19), 7.497 (1.14), 7.510 (3.51), 7.515 (3.42), 7.530 (2.16), 7.534 (2.47), 7.547 (1.20), 7.551 (0.92), 7.784 (5.43), 7.805 (4.99), 7.858 (2.34), 7.877 (2.53), 7.881 (2.03), 8.161 (2.10), 8.164 (2.19), 8.180 (1.79), 8.183 (2.07).

Intermediate 79

(rac)-ethyl-4-chloro-3-ethyl-14-methyl-1-[2-(morpholin-4-yl)ethyl]-7-{3-[(naphthalen-1-yl)oxy]-propyl}-10,11,12,13,14,15-hexahydro-1H-pyrazolo[3',4':8,9][1,6]diazacyclo-undecino[10,11,1-hi]indole-8-carboxylate

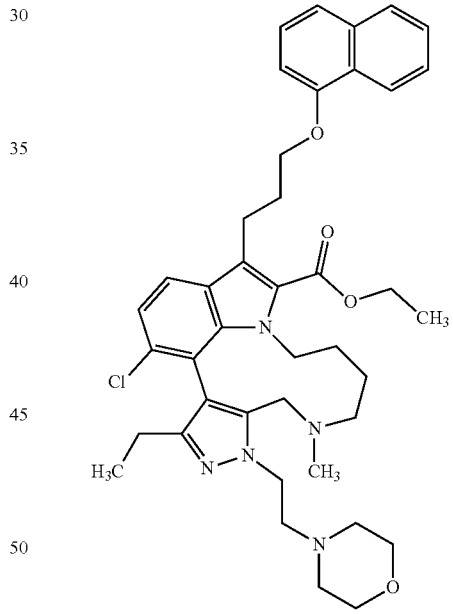

(Rac)-ethyl-(11Z)-4-chloro-3-ethyl-14-methyl-1-[2-(morpholin-4-yl)ethyl]-7-{3-[(naphthalen-1-yl)oxy]propyl}-10,13,14,15-tetrahydro-1H-pyrazolo[3',4':8,9][1,6]diazacycloundecino[10,11,1-hi]indole-8-carboxylate (see Intermediate 78, 168 mg, 237 µmol) was dissolved in a mixture of 8.7 mL of ethanol and 1.4 mL of THF. Tris (triphenylphosphine)rhodium(I) chloride (439 mg, 473 µmol) was added and the mixture was stirred under hydrogen atmosphere for 6 hours. The catalyst was filtered off and the filtrate was concentrated under reduced pressure. The crude material was purified by flash chromatography using silica gel (gradient dichloromethane/ethanol) to give the title compound (136 mg, 81% yield).

LC-MS (Method 2): R$_t$=1.88 min; MS (ESIpos): m/z=712 [M+H]$^+$ $^1$H-NMR (400 MHz, DMSO-d6) δ[ppm]: 0.717 (0.59), 0.745 (0.70), 0.798 (0.62), 0.814 (0.86), 0.824 (6.83), 0.843 (15.69), 0.862 (7.02), 0.904 (0.70), 0.982 (0.62), 1.035 (2.03), 1.052 (4.88), 1.070 (2.50), 1.098 (0.82), 1.127 (0.55), 1.231 (1.13), 1.258 (7.69), 1.276 (16.00), 1.294 (7.45), 1.902 (3.98), 1.985 (0.62), 2.013 (0.90), 2.049 (1.13), 2.067 (1.21), 2.086 (2.54), 2.105 (2.65), 2.108 (2.65), 2.127 (2.50), 2.149 (14.05), 2.164 (1.48), 2.183 (1.48), 2.203 (1.83), 2.220 (1.37), 2.327 (2.34), 2.331 (1.72), 2.336 (0.86), 2.362 (1.44), 2.378 (1.60), 2.390 (2.69), 2.401 (1.48), 2.431 (0.98), 2.518 (8.23), 2.523 (5.62), 2.669 (2.30), 2.673 (1.68), 2.678 (0.74), 2.701 (0.55), 2.706 (0.55), 2.720 (1.21), 2.732 (0.94), 2.738 (1.01), 2.751 (0.74), 2.768 (0.74), 2.786 (1.64), 2.804 (0.90), 2.817 (0.86), 3.130 (1.91), 3.163 (1.99), 3.223 (0.62), 3.240 (0.82), 3.258 (1.21), 3.278 (0.66), 3.362 (0.78), 3.379 (0.43), 3.422 (0.90), 3.435 (0.94), 3.440 (0.86), 3.452 (0.86), 3.546 (4.64), 3.558 (8.04), 3.570 (4.57), 3.719 (2.07), 3.752 (1.91), 3.933 (0.51), 3.967 (0.94), 3.994 (0.59), 4.183 (0.98), 4.201 (2.73), 4.206 (2.26), 4.219 (4.68), 4.228 (4.02), 4.236 (3.04), 4.246 (3.20), 4.264 (1.29), 4.283 (2.54), 4.291 (0.51), 4.300 (2.34), 4.310 (1.33), 4.318 (0.70), 4.327 (1.33), 4.344 (0.86), 4.356 (1.17), 4.369 (1.09), 4.389 (1.37), 4.406 (0.94), 4.423 (1.01), 4.441 (0.51), 4.465 (0.94), 4.500 (0.86), 6.900 (2.46), 6.917 (2.69), 7.218 (5.70), 7.239 (5.74), 7.372 (2.07), 7.392 (3.63), 7.411 (2.97), 7.455 (3.71), 7.476 (2.15), 7.493 (0.55), 7.497 (0.86), 7.509 (2.30), 7.514 (2.26), 7.517 (3.04), 7.525 (5.00), 7.534 (3.16), 7.536 (2.69), 7.541 (2.65), 7.553 (1.01), 7.558 (0.66), 7.773 (5.07), 7.795 (4.53), 7.863 (2.11), 7.871 (1.13), 7.880 (1.68), 7.886 (1.83), 8.216 (1.87), 8.222 (1.64), 8.232 (0.90), 8.240 (1.76).

Intermediate 80 ethyl-7-[1-(3-{[tert-butyl(dimethyl)silyl]oxy}propyl)-3-(hydroxymethyl)-5-methyl-1H-pyrazol-4-yl]-6-chloro-3-{3-[(naphthalen-1-yl)oxy]propyl}-1H-indole-2-carboxylate

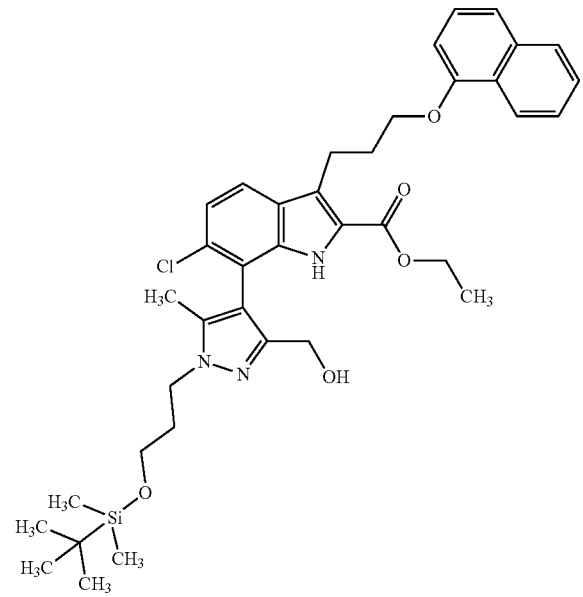 [SMILES: CCOC(=O)c1[nH]c2c(-c3c(CO)nn(CCCO[Si](C)(C)C(C)(C)C)c3C)c(Cl)ccc2c1CCCOc1cccc2ccccc12]

Ethyl-6-chloro-3-{3-[(naphthalen-1-yl)oxy]propyl}-7-(4,4,5,5-tetramethyl-1,3,2-dioxaborolan-2-yl)-1H-indole-2-carboxylate (see Intermediate 7, 4.41 g, 8.26 mmol) and 4-bromo-1-(3-{[tert-butyl(dimethyl)silyl]oxy}propyl)-5-methyl-1H-pyrazol-3-yl]methanol (see Intermediate 26, 3.00 g, 8.26 mmol) in 15 mL of 1,4-dioxane and 5 mL of water were purged with argon for five minutes. Potassium phosphate (4.21 g, 19.8 mmol) was added and the mixture was purged with argon for 5 minutes. XPhos Pd G3 (839 mg, 991 μmol) was added and the mixture was stirred for 50 minutes at 100° C. in a microwave reactor. The layers of the reaction mixture were separated and the organic layer was concentrated under reduced pressure. The residue was purified twice by flash chromatography using silica gel (gradient dichloromethane/ethyl acetate) to give the title compound (2.20 g, 38% yield).

LC-MS (Method 1): R$_t$=1.93 min; MS (ESIpos): m/z=690 [M+H]$^+$ $^1$H-NMR (400 MHz, DMSO-d6) δ[ppm]: 0.846 (16.00), 1.140 (0.50), 1.206 (1.24), 1.224 (2.73), 1.242 (1.26), 1.955 (1.23), 1.975 (4.22), 2.182 (0.45), 2.485 (1.26), 2.490 (0.82), 3.275 (0.49), 4.101 (0.49), 4.116 (0.53), 4.168 (0.45), 4.183 (0.84), 4.197 (0.48), 4.207 (0.77), 4.209 (0.82), 4.224 (0.73), 4.227 (0.70), 4.274 (0.42), 6.881 (0.48), 6.899 (0.51), 7.133 (0.81), 7.154 (0.83), 7.365 (0.66), 7.384 (0.53), 7.420 (0.72), 7.469 (0.41), 7.480 (0.44), 7.486 (0.83), 7.493 (0.44), 7.500 (0.40), 7.504 (0.42), 7.664 (0.76), 7.686 (0.68), 7.828 (0.42), 7.847 (0.40).

Intermediate 81

(rac)-ethyl-(11Z)-2-(3-{[tert-butyl(dimethyl)silyl]oxy}propyl)-4-chloro-3-methyl-7-{3-[(naphthalen-1-yl)oxy]propyl}-2,10,13,15-tetrahydropyrazolo[4',3':9,10][1,6]oxazacycloundecino[8,7,6-hi]indole-8-carboxylate

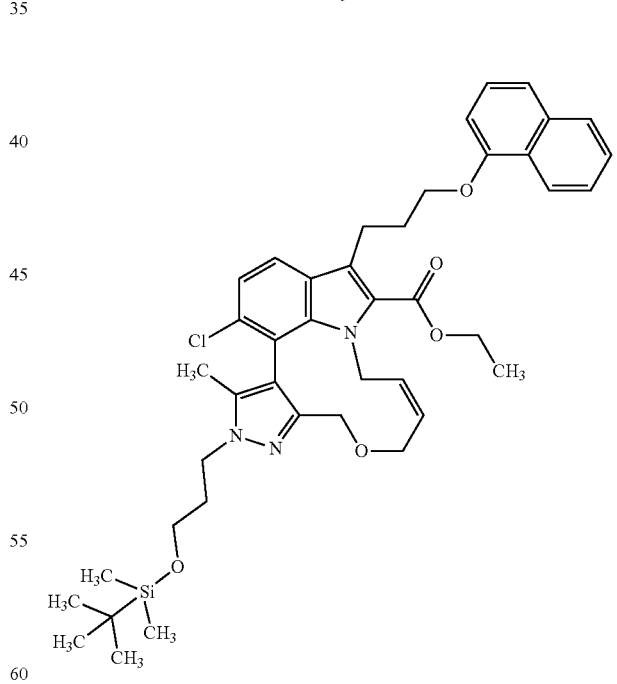

To a mixture of ethyl-7-[1-(3-{[tert-butyl(dimethyl)silyl]oxy}propyl)-3-(hydroxymethyl)-5-methyl-1H-pyrazol-4-yl]-6-chloro-3-{3-[(naphthalen-1-yl)oxy]propyl}-1H-indole-2-carboxylate (see Intermediate 80, 2.20 g, 3.19 mmol) in 100 mL of acetonitrile cesium carbonate (5.19 g, 15.9 mmol), sodium iodide (955 mg, 6.37 mmol) and (2Z)-1,4- dichlorobut-2-ene (CAS 110-57-6, 500 μL, 4.78 mmol) were added. The reaction mixture was stirred for 72 hours at 70° C. The mixture was filtered and was concentrated under reduced pressure. The residue was purified by flash chromatography using silica gel (gradient hexane/ethyl acetate) to give the title compound (1.60 g, 68% yield).

$^1$H-NMR (400 MHz, DMSO-d6) δ[ppm]: 0.000 (0.47), 0.016 (0.47), 0.834 (0.86), 0.841 (16.00), 0.847 (0.89), 1.148 (0.60), 1.237 (1.15), 1.255 (2.57), 1.272 (1.19), 1.777 (3.62), 1.963 (1.14), 2.494 (0.72), 2.499 (0.49), 3.550 (0.54), 3.562 (0.58), 3.577 (0.41), 4.149 (0.62), 4.182 (0.81), 4.189 (0.45), 4.196 (0.42), 4.201 (0.47), 4.211 (0.85), 4.219 (0.41), 4.228 (0.66), 4.246 (0.43), 4.272 (0.43), 4.333 (0.64), 4.365 (0.46), 6.888 (0.42), 6.906 (0.46), 7.231 (0.90), 7.253 (0.98), 7.372 (0.61), 7.391 (0.50), 7.428 (0.63), 7.488 (0.51), 7.491 (0.56), 7.770 (0.85), 7.791 (0.78).

Intermediate 82

(rac)-ethyl 2-(3-{[tert-butyl(dimethyl)silyl]oxy}propyl)-4-chloro-3-methyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate

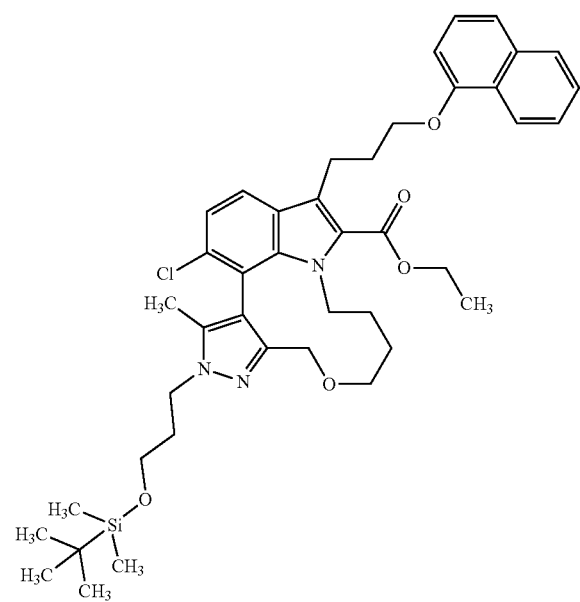 [SMILES: CCOC(=O)c1c(CCCOc2cccc3ccccc23)c2ccc(Cl)c3c2n1CCCCOCc1nn(CCCO[Si](C)(C)C(C)(C)C)c(C)c1-3]

(Rac)-ethyl-(11Z)-2-(3-{[tert-butyl(dimethyl)silyl]oxy}propyl)-4-chloro-3-methyl-7-{3-[(naphthalen-1-yl)oxy]propyl}-2,10,13,15-tetrahydropyrazolo[4',3':9,10][1,6]oxazacycloundecino[8,7,6-hi]indole-8-carboxylate (see Intermediate 81, 1.60 g, 2.16 mmol) was dissolved in a mixture of 90 mL of ethanol and 30 mL of THF. Tris(triphenylphosphine)rhodium(I) chloride (1.00 g, 1.08 mmol) was added and the mixture was stirred under hydrogen atmosphere until complete conversion. The catalyst was filtered off and the filtrate was concentrated under reduced pressure. The crude material was purified by flash chromatography using silica gel (gradient hexane/ethyl acetate) to give the title compound (1.48 g, 92% yield).

$^1$H-NMR (400 MHz, DMSO-d6) δ[ppm]: 0.000 (0.65), 0.015 (0.46), 0.835 (1.33), 0.842 (16.00), 0.849 (0.95), 1.132 (1.69), 1.150 (3.49), 1.168 (1.88), 1.232 (1.24), 1.249 (2.56), 1.267 (1.26), 1.755 (3.80), 1.965 (6.17), 2.496 (0.51), 3.288 (0.43), 3.526 (0.46), 3.537 (0.47), 3.977 (0.46), 3.995 (1.36), 4.012 (1.31), 4.031 (0.42), 4.154 (0.55), 4.178 (1.00), 4.188 (0.80), 4.196 (0.55), 4.206 (0.73), 4.212 (0.79), 4.223 (0.50), 4.263 (0.41), 4.400 (0.55), 4.431 (0.46), 6.869 (0.46), 6.887 (0.49), 7.200 (0.94), 7.221 (0.95), 7.365 (0.63), 7.384 (0.49), 7.429 (0.66), 7.491 (0.57), 7.500 (0.85), 7.509 (0.60), 7.515 (0.43), 7.739 (0.86), 7.760 (0.76).

Intermediate 83

(rac)-ethyl 4-chloro-2-(3-hydroxypropyl)-3-methyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate

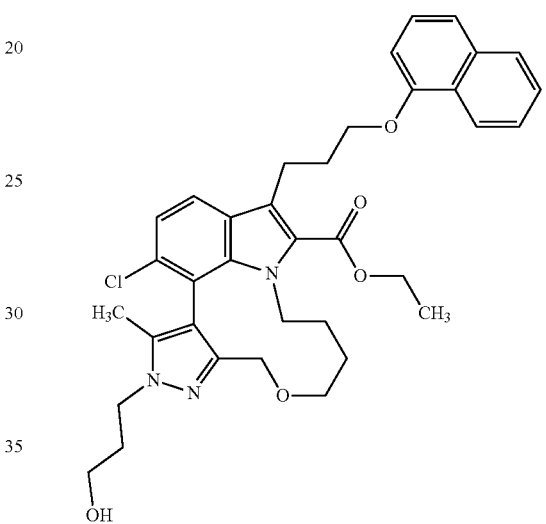

(Rac)-ethyl-2-(3-{[tert-butyl(dimethyl)silyl]oxy}propyl)-4-chloro-3-methyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate (see Intermediate 82, 1.48 g, 1.99 mmol) was dissolved in 50 mL of THF and a solution of N,N,N-tributylbutan-1-aminium fluoride in THF (2.2 mL, 1.0 M, 2.2 mmol) was added. The reaction mixture was stirred overnight at room temperature. The mixture was poured into water and was extracted with ethyl acetate. The combined organic layers were washed with brine and dried over sodium sulfate, were filtered and were concentrated under reduced pressure. The crude material was purified by flash chromatography using silica gel (gradient dichloromethane/ethanol) to give the titled compound (1.13 g, 90 yield).

LC-MS (Method 1): R$_t$=1.66 min; MS (ESIpos): m/z=630 [M+H]$^+$ $^1$H-NMR (400 MHz, DMSO-d6) δ[ppm]: 0.000 (4.51), 0.883 (5.79), 0.996 (0.42), 1.004 (0.42), 1.017 (0.42), 1.212 (0.75), 1.220 (0.96), 1.232 (1.00), 1.245 (0.94), 1.257 (0.67), 1.269 (0.52), 1.301 (5.05), 1.319 (11.09), 1.337 (5.41), 1.834 (16.00), 1.958 (1.19), 1.974 (1.78), 1.989 (1.30), 2.006 (0.40), 2.231 (0.82), 2.247 (1.19), 2.265 (0.88), 2.562 (3.88), 2.568 (2.71), 3.139 (0.71), 3.153 (0.63), 3.267 (0.44), 3.284 (0.61), 3.301 (0.88), 3.321 (0.50), 3.338 (0.59), 3.357 (1.80), 3.412 (1.13), 3.427 (2.42), 3.440 (2.44), 3.455 (0.94), 3.911 (0.71), 3.921 (0.42), 3.935 (0.46), 4.191 (0.92), 4.208 (1.98), 4.217 (2.15), 4.224 (1.50), 4.233 (2.40), 4.246 (4.07), 4.268

(2.24), 4.277 (4.41), 4.295 (1.88), 4.312 (1.04), 4.330 (1.73), 4.348 (1.63), 4.356 (0.92), 4.365 (0.48), 4.374 (0.92), 4.462 (2.36), 4.493 (1.92), 4.643 (1.48), 4.655 (3.59), 4.668 (1.40), 5.803 (2.53), 6.940 (1.84), 6.958 (1.98), 7.265 (4.03), 7.286 (4.22), 7.416 (1.40), 7.436 (2.63), 7.455 (2.09), 7.498 (2.67), 7.519 (1.52), 7.543 (0.56), 7.555 (1.63), 7.561 (2.59), 7.571 (3.45), 7.580 (2.92), 7.586 (1.75), 7.598 (0.58), 7.805 (3.51), 7.826 (3.26), 7.906 (1.50), 7.916 (0.77), 7.924 (1.04), 7.930 (1.27), 8.252 (1.34), 8.259 (1.06), 8.268 (0.61), 8.277 (1.21).

Intermediate 84

(rac)-ethyl 4-chloro-3-methyl-7-{3-[(naphthalen-1-yl)oxy]propyl}-2-(3-oxopropyl)-2,10,11,12,13,15-hexahydropyrazolo[4',3':9,10][1,6]oxazacycloundecino[8,7,6-hi]indole-8-carboxylate

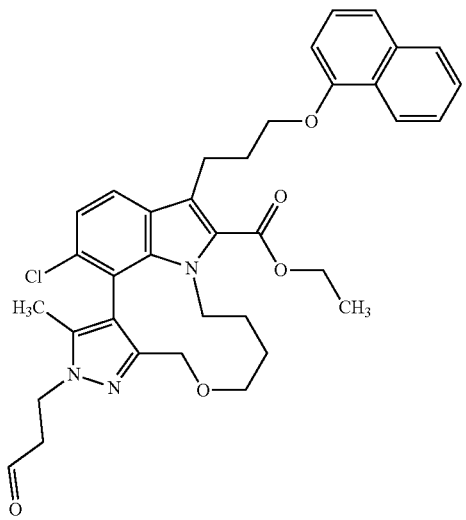 [SMILES: CCOC(=O)c1c(CCCOc2cccc3ccccc23)c2ccc(Cl)c3c2n1CCCCOCc1nn(CCC=O)c(C)c1-3]

(Rac)-ethyl-4-chloro-2-(3-hydroxypropyl)-3-methyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate (see Intermediate 83, 300 mg, 476 µmol) was dissolved in 10 mL of dichloromethane and a solution of 1,1,1-tris(acetyloxy)-1lambda5,2-benziodoxol-3(1H)-one in dichloromethane (1.4 mL, 15% purity, 710 µmol) was added. The reaction mixture was stirred overnight at rt. A solution of 1,1,1-tris(acetyloxy)-1 lambda5,2-benziodoxol-3(1H)-one in dichloromethane (0.6 mL, 15% purity, 304 µmol) was added and stirring was continued for 18 hours at room temperature. Water was added and the mixture was extracted with dichloromethane. The combined organic layers were dried over sodium sulfate, filtered and concentrated under reduced pressure to give the title compound (399 mg) which was used without further purification.

LC-MS (Method 1): Rt=1.68 min; MS (ESIpos): m/z=628 [M+H]$^+$ $^1$H-NMR (400 MHz, DMSO-d6) δ[ppm]: 0.206 (0.74), 0.883 (0.55), 0.999 (1.17), 1.210 (0.69), 1.302 (2.86), 1.320 (6.07), 1.337 (3.00), 1.866 (8.78), 1.952 (4.22), 2.247 (0.77), 2.263 (0.57), 2.303 (13.53), 2.372 (0.51), 2.568 (1.93), 2.714 (0.50), 3.059 (0.78), 3.063 (0.82), 3.080 (1.03), 3.095 (1.06), 3.109 (0.53), 3.299 (0.55), 3.355 (1.25), 4.214 (1.31), 4.222 (0.69), 4.246 (2.56), 4.252 (1.62), 4.261 (1.29), 4.270 (1.15), 4.279 (1.37), 4.296 (1.03), 4.314 (0.59), 4.332 (0.96), 4.349 (0.91), 4.359 (0.54), 4.377 (0.53), 4.420 (0.54), 4.436 (1.06), 4.445 (1.62), 4.452 (0.81), 4.459 (1.03), 4.477 (1.47), 5.803 (16.00), 6.939 (1.06), 6.957 (1.12), 7.260 (2.10), 7.282 (2.24), 7.415 (0.78), 7.436 (1.47), 7.455 (1.12), 7.498 (1.53), 7.519 (0.88), 7.556 (0.95), 7.561 (1.57), 7.571 (1.97), 7.580 (1.72), 7.585 (1.08), 7.804 (2.09), 7.809 (1.00), 7.826 (3.05), 7.844 (0.82), 7.847 (0.83), 7.905 (1.74), 7.916 (0.59), 7.923 (2.01), 7.929 (0.91), 8.053 (0.71), 8.057 (0.87), 8.071 (0.74), 8.075 (1.03), 8.077 (0.87), 8.092 (0.70), 8.096 (0.90), 8.106 (1.32), 8.110 (1.23), 8.125 (1.08), 8.129 (0.99), 8.252 (0.75), 8.259 (0.63), 8.276 (0.74), 9.788 (1.21), 9.792 (2.51), 9.795 (1.27).

Intermediate 85

(rac)-ethyl 4-chloro-3-methyl-2-[3-(4-methylpiperazin-1-yl) propyl]-7-{3-[(naphthalen-1-yl)oxy]-propyl}-2,10,11,12,13,15-hexahydropyrazolo[4',3':9,10][1,6]oxazacycloundecino[8,7,6-hi]-indole-8-carboxylate

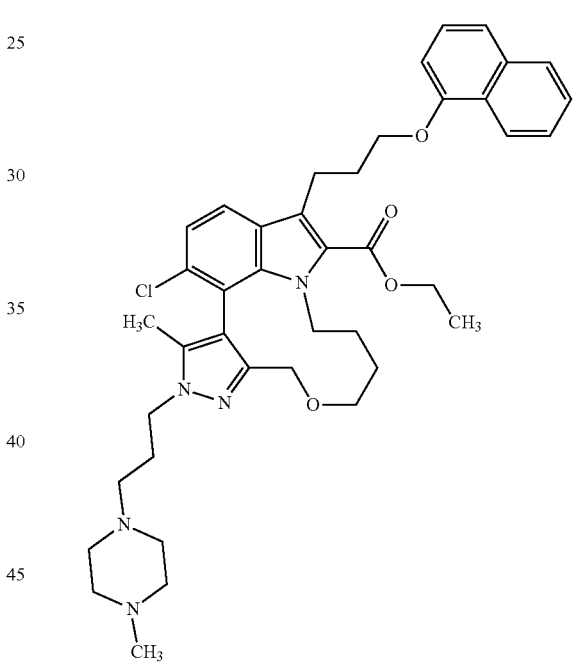

(Rac)-ethyl-4-chloro-3-methyl-7-{3-[(naphthalen-1-yl)oxy]propyl}-2-(3-oxopropyl)-2,10,11,12,13,15-hexahydropyrazolo[4',3':9,10][1,6]oxazacycloundecino[8,7,6-hi]indole-8-carboxylate (see Intermediate 84, 399 mg, 635 µmol) was dissolved in a mixture of 11 mL of ethanol and 2.8 mL of dichloromethane. Acetic acid (73 µL, 1.27 mmol) and 1-methylpiperazine (CAS 109-01-3, 110 µL, 950 µmol) were added. After stirring at room temperature for 15 minutes, sodium cyanoborohydride (79.8 mg, 1.27 mmol) was added and stirring was continued overnight. Water was added and the reaction mixture was concentrated under reduced pressure. The crude product was purified by flash chromatography using amino-substituted silica gel (gradient dichloromethane/ethanol) to give the title compound (174 mg).

LC-MS (Method 2): R$_t$=1.75 min; MS (ESIpos): m/z=712 [M+H]$^+$

¹H-NMR (400 MHz, DMSO-d6) δ[ppm]: 0.000 (0.69), 0.884 (0.93), 0.992 (0.79), 1.010 (0.96), 1.028 (0.59), 1.090 (0.39), 1.134 (0.42), 1.199 (1.08), 1.211 (0.81), 1.217 (1.57), 1.235 (1.30), 1.250 (0.86), 1.275 (1.37), 1.297 (5.74), 1.314 (12.02), 1.331 (5.77), 1.363 (0.56), 1.783 (0.42), 1.846 (16.00), 1.968 (0.52), 1.986 (0.81), 2.003 (1.13), 2.032 (2.50), 2.042 (0.83), 2.060 (0.47), 2.167 (15.14), 2.174 (7.26), 2.195 (2.26), 2.212 (1.42), 2.224 (2.09), 2.251 (2.01), 2.271 (3.66), 2.309 (1.55), 2.326 (1.94), 2.344 (1.74), 2.362 (1.89), 2.367 (2.36), 2.372 (2.70), 2.376 (2.23), 2.563 (4.91), 2.568 (3.41), 2.667 (1.25), 2.676 (0.98), 2.704 (0.59), 2.709 (1.10), 2.714 (1.52), 2.718 (1.06), 2.723 (0.52), 3.133 (0.49), 3.147 (0.81), 3.159 (0.79), 3.173 (0.52), 3.265 (0.54), 3.281 (0.76), 3.298 (1.01), 3.317 (0.64), 3.335 (0.79), 3.356 (1.91), 3.883 (0.44), 3.907 (0.81), 3.932 (0.54), 4.062 (0.44), 4.080 (0.44), 4.116 (0.44), 4.134 (0.74), 4.150 (1.33), 4.158 (1.01), 4.166 (0.98), 4.175 (1.37), 4.191 (1.23), 4.209 (1.35), 4.227 (2.01), 4.244 (4.00), 4.249 (3.98), 4.253 (3.02), 4.261 (2.63), 4.271 (3.04), 4.280 (3.26), 4.289 (2.23), 4.306 (0.74), 4.311 (0.79), 4.329 (2.09), 4.339 (0.47), 4.347 (1.91), 4.356 (1.13), 4.365 (0.56), 4.374 (1.10), 4.470 (2.48), 4.501 (2.01), 6.938 (2.18), 6.955 (2.23), 7.268 (4.91), 7.289 (4.81), 7.414 (1.67), 7.434 (2.99), 7.453 (2.31), 7.498 (3.09), 7.518 (1.79), 7.536 (0.52), 7.541 (0.76), 7.553 (2.11), 7.560 (2.77), 7.569 (4.20), 7.578 (2.72), 7.584 (2.11), 7.597 (0.76), 7.602 (0.42), 7.805 (4.07), 7.826 (3.68), 7.906 (1.84), 7.916 (0.98), 7.924 (1.33), 7.930 (1.50), 8.250 (1.60), 8.257 (1.42), 8.266 (0.81), 8.274 (1.42).

Intermediate 86 ethyl 6-chloro-7-{5-ethyl-3-[(1E)-6-hydroxyhex-1-en-1-yl]-1-methyl-1H-pyrazol-4-yl}-3-{3-[(naphthalen-1-yl)oxy]propyl}-1H-indole-2-carboxylate

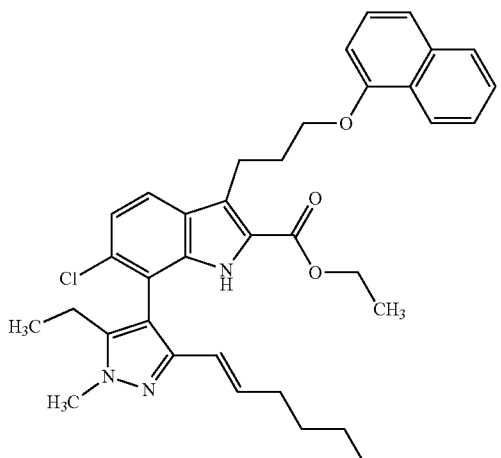

Ethyl-6-chloro-3-{3-[(naphthalen-1-yl)oxy]propyl}-7-(4,4,5,5-tetramethyl-1,3,2-dioxaborolan-2-yl)-1H-indole-2-carboxylate (see Intermediate 7, 2.23 g, 4.18 mmol), 6-(4-bromo-5-ethyl-1-methyl-1H-pyrazol-3-yl)hex-5-en-1-ol (see Intermediate 30, 1.20 g), potassium phosphate (2.13 g, 10.0 mmol) and XPhos Pd G3 (424 mg, 501 µmol) in a degassed mixture of 15 mL of 1,4-dioxane and 5 mL of water were stirred for 30 minutes at 110° C. in a microwave reactor. The aqueous layer of the reaction mixture was separated and the organic layer was concentrated under reduced pressure. The residue was purified by flash chromatography using silica gel (gradient dichloromethane/ethyl acetate) to give the title compound (557 mg) and the Z-isomer (see Intermediate 87, 440 mg).

LC-MS (Method 1): Rt=1.64 min; MS (ESIneg): m/z=612 [M−H]⁻

¹H-NMR (400 MHz, DMSO-d6) δ[ppm]: 0.854 (3.62), 0.872 (8.10), 0.891 (3.74), 1.062 (2.08), 1.066 (1.37), 1.075 (1.02), 1.081 (4.52), 1.100 (2.12), 1.145 (0.96), 1.157 (2.76), 1.164 (1.86), 1.172 (2.17), 1.176 (5.04), 1.183 (2.10), 1.190 (1.47), 1.195 (2.60), 1.223 (2.10), 1.235 (6.30), 1.252 (11.46), 1.270 (5.37), 1.429 (2.45), 1.436 (3.08), 1.445 (2.90), 1.862 (0.76), 1.879 (2.06), 1.896 (2.03), 1.913 (0.74), 1.987 (1.11), 2.147 (0.76), 2.151 (0.78), 2.164 (0.84), 2.182 (0.66), 2.197 (1.17), 2.215 (1.62), 2.233 (1.26), 2.243 (1.00), 2.262 (1.03), 2.281 (1.29), 2.300 (1.03), 2.332 (0.62), 2.365 (1.36), 2.383 (1.75), 2.402 (1.21), 2.421 (0.74), 2.518 (3.81), 2.523 (2.46), 2.560 (0.67), 2.579 (1.48), 2.597 (1.46), 2.606 (0.73), 2.616 (0.62), 2.625 (1.99), 2.644 (1.91), 2.673 (0.65), 3.240 (1.39), 3.255 (3.15), 3.268 (3.31), 3.283 (1.37), 3.296 (1.42), 3.318 (2.53), 3.372 (0.81), 3.377 (0.69), 3.387 (1.73), 3.392 (1.70), 3.401 (1.84), 3.405 (1.65), 3.416 (0.70), 3.638 (0.58), 3.682 (7.62), 3.722 (1.28), 3.762 (10.01), 3.797 (16.00), 4.193 (1.62), 4.208 (3.29), 4.225 (2.64), 4.243 (4.56), 4.259 (6.34), 4.271 (2.13), 4.278 (1.26), 4.342 (0.80), 4.355 (1.54), 4.360 (1.11), 4.368 (0.85), 4.373 (1.97), 4.386 (0.85), 5.501 (0.54), 5.530 (0.60), 5.639 (0.56), 5.657 (1.22), 5.675 (0.62), 5.679 (0.84), 5.697 (1.80), 5.715 (0.78), 5.758 (6.57), 5.869 (2.43), 5.910 (1.66), 6.052 (1.73), 6.144 (0.66), 6.158 (0.80), 6.173 (0.62), 6.198 (1.06), 6.402 (0.82), 6.442 (0.60), 6.897 (2.01), 6.915 (2.14), 7.150 (3.75), 7.172 (3.90), 7.371 (1.36), 7.391 (2.71), 7.410 (2.09), 7.452 (2.91), 7.473 (1.65), 7.494 (0.62), 7.507 (1.64), 7.511 (1.75), 7.514 (2.12), 7.523 (3.53), 7.531 (2.24), 7.539 (1.81), 7.551 (0.63), 7.701 (2.90), 7.723 (2.64), 7.861 (1.65), 7.870 (0.88), 7.879 (1.36), 7.884 (1.40), 8.217 (1.43), 8.224 (1.32), 8.233 (0.73), 8.241 (1.40), 11.012 (3.31).

Intermediate 87 ethyl-6-chloro-7-{5-ethyl-3-[(1Z)-6-hydroxyhex-1-en-1-yl]-1-methyl-1H-pyrazol-4-yl}-3-{3-[(naphthalen-1-yl)oxy]propyl}-1H-indole-2-carboxylate

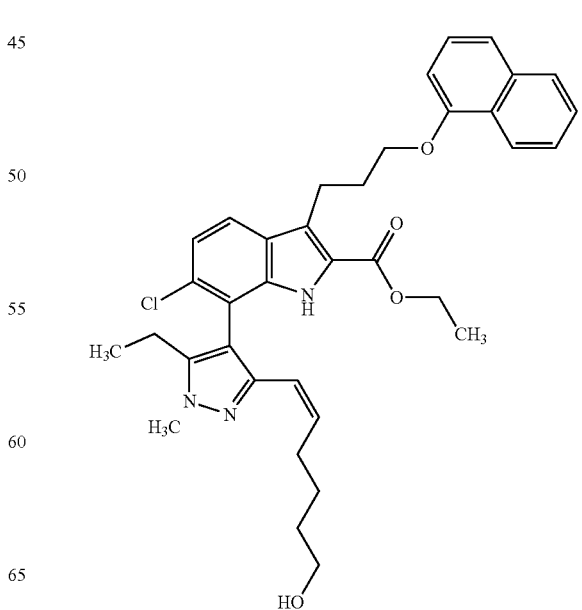

The title compound was isolated in the synthesis of Intermediate 86.

LC-MS (Method 1): Rt=1.70 min; MS (ESIneg): m/z=612 [M−H]⁻

¹H-NMR (400 MHz, DMSO-d6) δ[ppm]: 0.860 (3.84), 0.872 (1.42), 0.879 (8.68), 0.891 (0.92), 0.898 (3.91), 1.074 (0.45), 1.093 (0.85), 1.112 (0.43), 1.154 (0.68), 1.172 (1.26), 1.190 (0.79), 1.233 (5.93), 1.251 (12.29), 1.269 (5.66), 1.299 (0.61), 1.308 (0.95), 1.318 (1.10), 1.335 (1.46), 1.350 (1.71), 1.368 (1.05), 1.376 (1.06), 1.391 (2.13), 1.407 (1.93), 1.423 (1.32), 1.433 (1.15), 1.449 (0.50), 1.987 (1.93), 2.195 (1.17), 2.211 (1.80), 2.228 (1.23), 2.244 (0.50), 2.280 (0.76), 2.299 (1.05), 2.317 (1.57), 2.322 (1.03), 2.327 (1.19), 2.332 (1.01), 2.336 (1.37), 2.383 (0.45), 2.402 (1.12), 2.422 (1.30), 2.440 (1.03), 2.459 (0.81), 2.518 (5.42), 2.523 (3.35), 2.534 (2.00), 2.551 (1.87), 2.569 (0.74), 2.664 (0.92), 2.669 (1.08), 2.673 (0.79), 3.271 (0.41), 3.287 (0.88), 3.295 (1.05), 3.304 (1.77), 3.314 (2.05), 3.350 (1.98), 3.366 (3.32), 3.379 (3.50), 3.395 (1.32), 3.797 (1.46), 3.806 (1.68), 3.846 (16.00), 4.017 (0.49), 4.035 (0.41), 4.199 (1.55), 4.214 (3.24), 4.225 (2.36), 4.242 (4.47), 4.260 (4.13), 4.271 (0.47), 4.277 (1.23), 4.312 (2.11), 4.324 (4.38), 4.338 (2.04), 5.363 (0.59), 5.381 (1.23), 5.392 (0.72), 5.399 (0.56), 5.410 (1.69), 5.428 (0.81), 5.537 (2.22), 5.567 (1.48), 6.908 (1.87), 6.925 (2.02), 7.146 (4.11), 7.167 (4.22), 7.374 (1.41), 7.394 (2.65), 7.413 (2.14), 7.452 (3.01), 7.473 (1.69), 7.487 (0.43), 7.491 (0.65), 7.504 (1.60), 7.509 (1.62), 7.513 (2.05), 7.520 (3.59), 7.528 (2.07), 7.532 (1.96), 7.537 (1.87), 7.549 (0.70), 7.553 (0.43), 7.694 (2.81), 7.716 (2.58), 7.860 (1.66), 7.868 (0.92), 7.878 (1.44), 7.884 (1.44), 8.206 (1.35), 8.212 (1.30), 8.222 (0.77), 8.230 (1.39), 11.035 (2.99).

Intermediate 88 ethyl 6-chloro-7-[5-ethyl-3-(6-hydroxyhexyl)-1-methyl-1H-pyrazol-4-yl]-3-{3-[(naphthalen-1-yl)oxy]propyl}-1H-indole-2-carboxylate

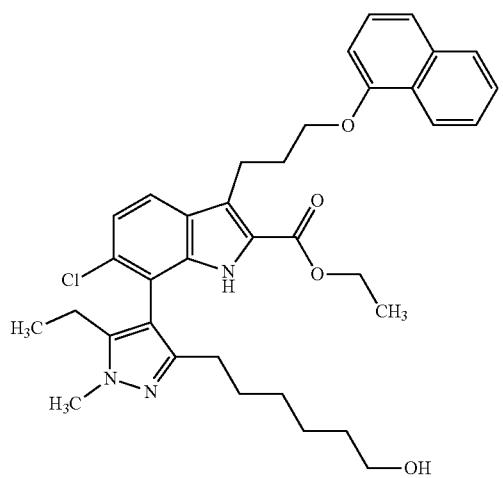 [SMILES: CCOC(=O)c1[nH]c2c(-c3c(CCCCCCO)nn(C)c3CC)c(Cl)ccc2c1CCCOc1cccc2ccccc12]

Ethyl-6-chloro-7-{5-ethyl-3-[(1E)-6-hydroxyhex-1-en-1-yl]-1-methyl-1H-pyrazol-4-yl}-3-{3-[(naphthalen-1-yl)oxy]propyl}-1H-indole-2-carboxylate (see Intermediate 86, 138 mg, 225 μmol) and ethyl-6-chloro-7-{5-ethyl-3-[(1Z)-6-hydroxyhex-1-en-1-yl]-1-methyl-1H-pyrazol-4-yl}-3-{3-[(naphthalen-1-yl)oxy]propyl}-1H-indole-2-carboxylate (see Intermediate 87, 102 mg, 166 μmol) were dissolved in a mixture of 9 mL of ethanol and 9 mL of THF. Tris(triphenylphosphine)rhodium(I) chloride (181 mg, 195 μmol) was added and the mixture was stirred under hydrogen atmosphere until complete conversion. The catalyst was filtered off and the filtrate was concentrated under reduced pressure. The crude material was purified by flash chromatography using silica gel (gradient hexane/ethyl acetate) to give the title compound (143 mg).

LC-MS (Method 1): R$_t$=1.69 min; MS (ESIpos): m/z=616 [M+H]⁺

¹H-NMR (400 MHz, DMSO-d6) δ[ppm]: 0.851 (1.93), 0.870 (4.40), 0.889 (1.97), 1.015 (0.48), 1.032 (0.63), 1.048 (0.86), 1.053 (0.83), 1.066 (0.93), 1.075 (0.69), 1.080 (0.69), 1.098 (0.45), 1.125 (0.55), 1.144 (1.13), 1.154 (4.43), 1.163 (0.76), 1.172 (9.43), 1.182 (0.83), 1.189 (5.03), 1.198 (0.95), 1.216 (0.62), 1.240 (2.72), 1.258 (5.93), 1.275 (3.07), 1.301 (0.62), 1.320 (0.70), 1.339 (0.42), 1.987 (16.00), 2.177 (0.73), 2.184 (0.73), 2.195 (1.28), 2.204 (1.33), 2.214 (1.16), 2.222 (0.90), 2.279 (0.50), 2.297 (0.68), 2.316 (0.60), 2.371 (0.56), 2.390 (0.67), 2.409 (0.55), 2.518 (1.20), 2.523 (1.06), 3.206 (0.57), 3.221 (1.32), 3.236 (1.37), 3.251 (0.58), 3.288 (0.70), 3.309 (1.09), 3.608 (1.87), 3.770 (8.44), 3.999 (1.22), 4.016 (3.58), 4.034 (3.45), 4.053 (1.14), 4.191 (0.78), 4.206 (1.60), 4.213 (1.40), 4.222 (0.93), 4.227 (2.65), 4.239 (1.13), 4.246 (2.30), 4.264 (2.22), 4.282 (0.67), 6.896 (0.95), 6.914 (1.04), 7.139 (2.15), 7.161 (2.19), 7.370 (0.75), 7.390 (1.37), 7.409 (1.11), 7.452 (1.41), 7.472 (0.80), 7.507 (0.86), 7.512 (0.88), 7.515 (1.12), 7.524 (1.83), 7.532 (1.17), 7.534 (0.98), 7.539 (0.95), 7.674 (1.44), 7.696 (1.30), 7.861 (0.81), 7.864 (0.64), 7.870 (0.43), 7.878 (0.65), 7.884 (0.68), 8.226 (0.71), 8.232 (0.63), 8.250 (0.66), 10.964 (1.56).

Intermediate 89 ethyl 7-[3-(6-bromohexyl)-5-ethyl-1-methyl-1H-pyrazol-4-yl]-6-chloro-3-{3-[(naphthalen-1-yl)oxy]propyl}-1H-indole-2-carboxylate

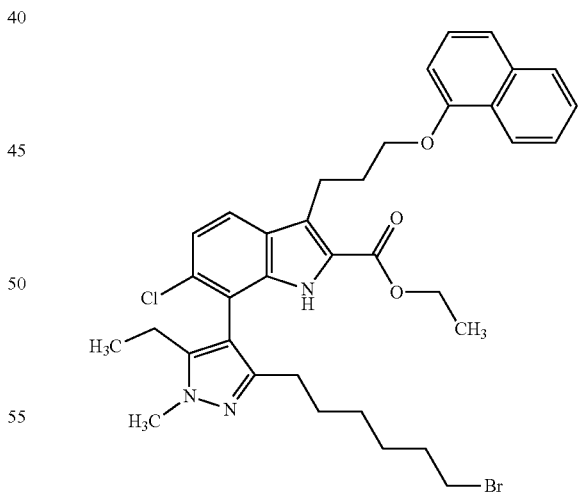

Ethyl-6-chloro-7-[5-ethyl-3-(6-hydroxyhexyl)-1-methyl-1H-pyrazol-4-yl]-3-{3-[(naphthalen-1-yl)oxy]propyl}-1H-indole-2-carboxylate (see Intermediate 88, 140 mg) was dissolved in 5 mL of dichloromethane. Triphenylphosphane (143 mg, 545 μmol) and tetrabromomethane (CAS 558-13-4, 166 mg, 500 μmol) were added. After stirring for 3 hours at room temperature the reaction mixture was concentrated under reduced pressure and purified by flash chromatography twice using silica gel (gradient dichloromethane/ethanol and dichloromethane/ethyl acetate) to give the title compound (121 mg).

LC-MS (Method 2): Rt=1.86 min; MS (ESIpos): m/z=678 [M+H]+

$^1$H-NMR (400 MHz, DMSO-d6) δ[ppm]: 0.852 (3.70), 0.871 (8.39), 0.890 (3.67), 1.075 (2.17), 1.082 (2.20), 1.126 (1.21), 1.145 (2.28), 1.154 (0.75), 1.164 (0.96), 1.172 (1.53), 1.190 (0.78), 1.245 (5.36), 1.263 (11.93), 1.281 (6.11), 1.301 (1.55), 1.319 (1.05), 1.509 (1.13), 1.526 (1.74), 1.542 (1.15), 1.987 (2.79), 2.198 (2.63), 2.217 (3.99), 2.235 (2.33), 2.262 (0.72), 2.281 (0.96), 2.299 (1.29), 2.327 (1.55), 2.331 (1.15), 2.336 (0.72), 2.380 (1.05), 2.391 (0.51), 2.399 (1.26), 2.411 (0.64), 2.417 (1.07), 2.430 (0.51), 2.436 (0.80), 2.518 (5.31), 2.523 (3.81), 2.544 (0.75), 2.673 (1.07), 2.678 (0.48), 3.295 (3.89), 3.312 (9.06), 3.499 (0.54), 3.516 (1.13), 3.532 (0.51), 3.609 (3.67), 3.771 (16.00), 4.017 (0.62), 4.035 (0.64), 4.193 (1.42), 4.208 (2.95), 4.223 (1.39), 4.234 (1.50), 4.252 (4.50), 4.270 (4.42), 4.288 (1.31), 5.801 (0.70), 6.896 (1.80), 6.914 (1.96), 7.144 (4.23), 7.165 (4.34), 7.370 (1.42), 7.391 (2.60), 7.410 (2.12), 7.452 (2.60), 7.472 (1.47), 7.488 (0.43), 7.492 (0.62), 7.505 (1.58), 7.509 (1.45), 7.515 (1.72), 7.522 (3.54), 7.530 (1.77), 7.534 (1.58), 7.538 (1.69), 7.551 (0.67), 7.555 (0.40), 7.682 (2.79), 7.704 (2.52), 7.861 (1.53), 7.869 (0.83), 7.878 (1.42), 7.884 (1.29), 8.222 (1.31), 8.228 (1.23), 8.246 (1.23), 10.998 (2.84).

Intermediate 90

(rac)-ethyl 4-chloro-3-ethyl-2-methyl-7-{3-[(naphthalen-1-yl)oxy]propyl}-10,11,12,13,14,15-hexahydro-2H-pyrazolo[4',3':4,5]azacycloundecino[3,2,1-hi]indole-8-carboxylate

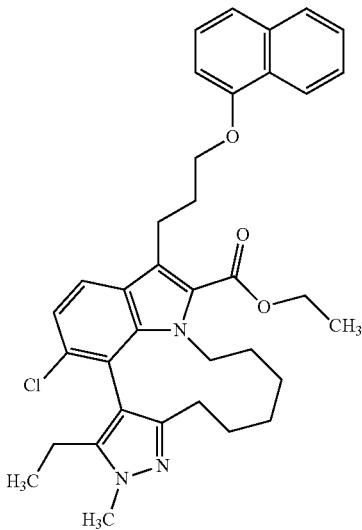 [SMILES: CCOC(=O)c1c(CCCOc2cccc3ccccc23)c2ccc(Cl)c3c2n1CCCCCCc1nn(C)c(CC)c1-3]

Ethyl-7-[3-(6-bromohexyl)-5-ethyl-1-methyl-1H-pyrazol-4-yl]-6-chloro-3-{3-[(naphthalen-1-yl)oxy]propyl}-1H-indole-2-carboxylate (see Intermediate 89, 120 mg, 177 µmol) and cesium carbonate (288 mg, 884 µmol) in 50 mL of DMF were stirred at room temperature for 3.5 hours. The mixture was concentrated and the residue was dissolved in a mixture of dichloromethane and water which was adsorbed on diatomite. The product was eluted with dichloromethane and the filtrate was concentrated under reduced pressure to give the title compound (110 mg).

LC-MS (Method 2): R$_t$=1.85 min; MS (ESIpos): m/z=598 [M+H]+

$^1$H-NMR (400 MHz, DMSO-d6) δ[ppm]: 0.544 (0.41), 0.568 (0.45), 0.795 (0.60), 0.809 (3.39), 0.828 (8.10), 0.847 (4.23), 0.870 (1.10), 0.889 (0.60), 1.001 (0.50), 1.017 (0.50), 1.126 (1.00), 1.145 (2.32), 1.158 (0.79), 1.164 (1.50), 1.185 (0.93), 1.232 (1.46), 1.255 (5.52), 1.273 (11.30), 1.290 (5.44), 1.316 (0.74), 1.337 (0.43), 1.761 (0.64), 1.780 (0.55), 1.798 (0.43), 2.169 (0.53), 2.184 (1.00), 2.215 (2.03), 2.233 (2.22), 2.252 (2.46), 2.271 (1.53), 2.290 (0.69), 2.332 (1.03), 2.336 (0.48), 2.411 (0.43), 2.518 (6.23), 2.522 (3.99), 2.543 (0.69), 2.673 (1.03), 2.678 (0.45), 2.727 (3.56), 2.729 (3.82), 2.888 (4.59), 3.216 (0.45), 3.232 (0.60), 3.249 (0.74), 3.270 (0.45), 3.292 (0.53), 3.313 (1.17), 3.499 (0.50), 3.515 (0.98), 3.532 (0.48), 3.608 (3.53), 3.827 (16.00), 4.013 (0.60), 4.038 (0.43), 4.198 (1.48), 4.202 (1.41), 4.207 (1.27), 4.216 (3.20), 4.225 (2.36), 4.233 (1.58), 4.242 (1.91), 4.260 (0.69), 4.280 (1.72), 4.298 (1.62), 4.307 (0.91), 4.316 (0.50), 4.324 (0.88), 4.450 (0.67), 4.485 (0.62), 5.758 (5.54), 5.801 (0.64), 6.891 (1.74), 6.908 (1.84), 7.216 (4.06), 7.238 (3.87), 7.368 (1.34), 7.388 (2.44), 7.407 (2.01), 7.449 (2.48), 7.469 (1.43), 7.480 (0.50), 7.483 (0.64), 7.497 (1.46), 7.501 (1.34), 7.511 (1.58), 7.516 (2.48), 7.521 (1.67), 7.530 (1.46), 7.534 (1.67), 7.547 (0.69), 7.551 (0.53), 7.763 (3.51), 7.784 (3.06), 7.857 (1.46), 7.863 (0.96), 7.876 (1.58), 7.880 (1.29), 7.951 (0.57), 8.181 (1.29), 8.185 (1.31), 8.203 (1.22), 8.205 (1.27).

Intermediate 91 ethyl 3-(3-{[tert-butyl(dimethyl)silyl]oxy}propyl)-6-chloro-7-{5-ethyl-3-[(1E)-6-hydroxyhex-1-en-1-yl]-1-methyl-1H-pyrazol-4-yl}-1H-indole-2-carboxylate

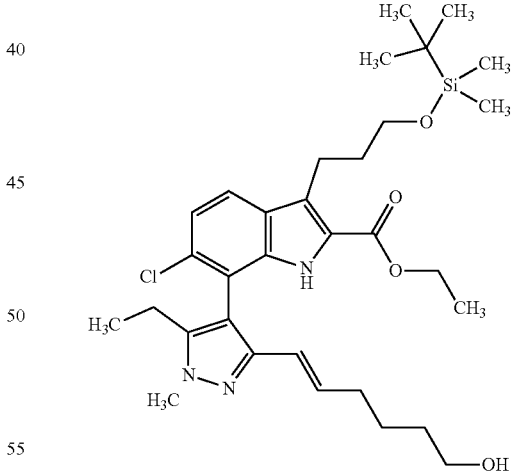

Ethyl-3-(3-{[tert-butyl(dimethyl)silyl]oxy}propyl)-6-chloro-7-(4,4,5,5-tetramethyl-1,3,2-dioxa-borolan-2-yl)-1H-indole-2-carboxylate (see Intermediate 11, 3.00 g, 5.75 mmol), 6-(4-bromo-5-ethyl-1-methyl-1H-pyrazol-3-yl)hex-5-en-1-ol (see Intermediate 30, 1.65 g), potassium phosphate (2.93 g, 13.8 mmol) and XPhos Pd G3 (584 mg, 690 µmol) in a degassed mixture of 15 mL of 1,4-dioxane and 5 mL of water were stirred for 30 minutes at 110° C. in a microwave reactor. The aqueous layer of the reaction mixture was separated and the organic layer was concentrated under reduced pressure. The residue was purified by flash chromatography using silica gel (gradient hexane/ethyl acetate) to give the title compound (820 mg) and the Z-isomer (see Intermediate 92, 921 mg).

LC-MS (Method 1): Rt=1.80 min; MS (ESIpos): m/z=602 [M+H]$^+$ $^1$H-NMR (400 MHz, DMSO-d6) δ[ppm]: −0.007 (0.49), 0.007 (0.76), 0.848 (1.43), 0.856 (16.00), 0.864 (2.97), 0.883 (1.16), 1.059 (0.77), 1.078 (1.79), 1.097 (0.82), 1.168 (0.48), 1.173 (0.47), 1.184 (0.46), 1.224 (0.50), 1.240 (0.45), 1.284 (1.34), 1.301 (2.86), 1.319 (1.36), 1.426 (0.69), 1.433 (0.81), 1.442 (0.74), 1.793 (0.50), 1.878 (0.52), 1.895 (0.53), 2.519 (0.94), 2.622 (0.76), 2.641 (0.74), 3.047 (0.47), 3.053 (0.48), 3.254 (0.80), 3.267 (0.84), 3.390 (0.51), 3.402 (0.50), 3.601 (0.47), 3.617 (1.03), 3.634 (0.51), 3.759 (3.78), 3.790 (4.15), 4.240 (0.47), 4.253 (1.03), 4.259 (0.44), 4.266 (0.53), 4.277 (1.17), 4.295 (1.14), 4.370 (0.69), 5.695 (0.47), 5.755 (1.19), 5.861 (0.63), 5.901 (0.43), 6.194 (0.42), 7.200 (0.97), 7.222 (1.03), 7.649 (0.74), 7.671 (0.66), 10.944 (0.80).

Intermediate 92 ethyl 3-(3-{[tert-butyl(dimethyl)silyl]oxy}propyl)-6-chloro-7-{5-ethyl-3-[(1Z)-6-hydroxyhex-1-en-1-yl]-1-methyl-1H-pyrazol-4-yl}-1H-indole-2-carboxylate

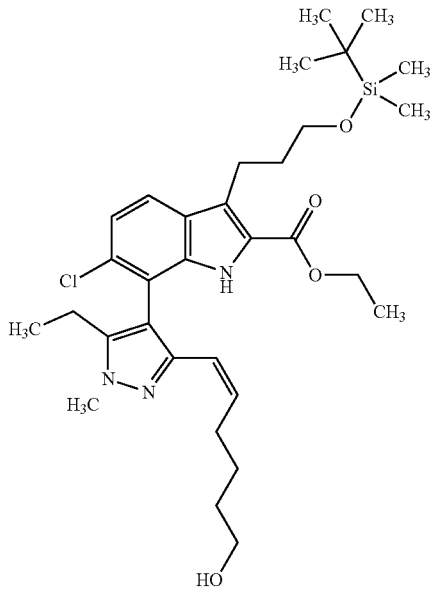

The title compound was isolated in the synthesis of Intermediate 91.

LC-MS (Method 1): Rt=1.86 min; MS (ESIpos): m/z=602 [M+H]$^+$ $^1$H-NMR (400 MHz, DMSO-d6) δ[ppm]: −0.010 (0.88), 0.007 (0.93), 0.850 (15.15), 0.864 (2.45), 0.882 (1.02), 1.052 (16.00), 1.080 (1.08), 1.099 (0.49), 1.142 (1.78), 1.274 (1.31), 1.291 (2.85), 1.308 (1.52), 1.333 (0.44), 1.374 (0.56), 1.390 (0.57), 1.403 (0.60), 1.408 (0.57), 1.412 (0.56), 1.419 (0.54), 1.774 (0.51), 2.305 (0.43), 2.509 (1.43), 2.533 (0.71), 2.630 (0.44), 2.650 (0.60), 3.030 (0.48), 3.036 (0.51), 3.349 (0.93), 3.363 (1.11), 3.377 (0.59), 3.601 (0.49), 3.617 (1.02), 3.633 (0.47), 3.792 (2.26), 3.830 (3.86), 3.924 (2.51), 4.267 (1.15), 4.284 (1.14), 4.295 (0.55), 4.302 (0.43), 4.308 (1.18), 4.322 (0.80), 5.391 (0.40), 5.517 (0.56), 7.181 (0.92), 7.203 (0.97), 7.631 (0.73), 7.653 (0.64), 10.955 (0.76).

Intermediate 93 ethyl 3-(3-{[tert-butyl(dimethyl)silyl]oxy}propyl)-6-chloro-7-[5-ethyl-3-(6-hydroxyhexyl)-1-methyl-1H-pyrazol-4-yl]-1H-indole-2-carboxylate

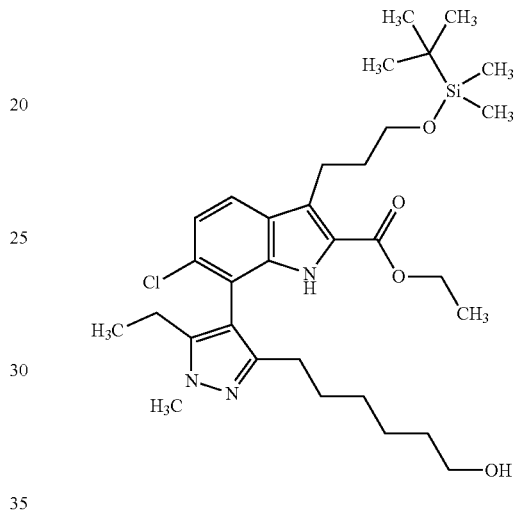

Ethyl-3-(3-{[tert-butyl(dimethyl)silyl]oxy}propyl)-6-chloro-7-{5-ethyl-3-[(1E)-6-hydroxyhex-1-en-1-yl]-1-methyl-1H-pyrazol-4-yl}-1H-indole-2-carboxylate (see Intermediate 91 820 mg) and ethyl 3-(3-{[tert-butyl(dimethyl)silyl]oxy}propyl)-6-chloro-7-{5-ethyl-3-[(1Z)-6-hydroxyhex-1-en-1-yl]-1-methyl-1H-pyrazol-4-yl}-1H-indole-2-carboxylate (see Intermediate 92, 920 mg) were dissolved in a mixture of 30 mL of ethanol and 90 mL of THF. Tris(triphenyl-phosphine)rhodium(I) chloride (1.34 g, 1.44 mmol) was added and the mixture was stirred under hydrogen atmosphere at rt for 8 hours. The crude material was purified by flash chromatography using silica gel (gradient dichloromethane/ethyl acetate) to give the title compound (1.10 g).

LC-MS (Method 1): R$_t$=1.81 min; MS (ESIpos): m/z=604 [M+H]$^+$ $^1$H-NMR (400 MHz, DMSO-d6) δ[ppm]: 0.007 (0.73), 0.844 (1.16), 0.856 (16.00), 0.862 (3.22), 0.881 (1.03), 1.053 (1.03), 1.072 (1.76), 1.091 (0.80), 1.199 (0.45), 1.281 (0.77), 1.288 (1.77), 1.306 (3.05), 1.323 (1.48), 1.789 (0.44), 1.984 (0.53), 2.314 (0.43), 2.402 (0.48), 2.422 (0.51), 2.514 (1.94), 2.519 (1.26), 2.598 (0.60), 2.617 (0.57), 3.045 (0.46), 3.220 (0.65), 3.234 (0.67), 3.352 (0.50), 3.365 (0.51), 3.600 (0.45), 3.616 (0.97), 3.631 (0.44), 3.718 (3.05), 3.764 (3.96), 4.205 (0.46), 4.219 (0.95), 4.231 (0.46), 4.280 (1.10), 4.298 (1.08), 4.324 (0.55), 5.755 (3.90), 7.187 (0.95), 7.208 (1.01), 7.622 (0.72), 7.644 (0.64), 10.885 (0.71).

Intermediate 94 ethyl 7-[3-(6-bromohexyl)-5-ethyl-1-methyl-1H-pyrazol-4-yl]-6-chloro-3-(3-hydroxypropyl)-1H-indole-2-carboxylate

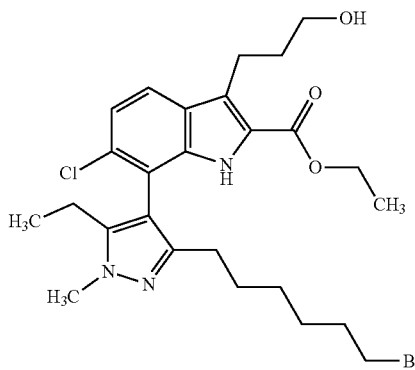

Ethyl-3-(3-{[tert-butyl(dimethyl)silyl]oxy}propyl)-6-chloro-7-[5-ethyl-3-(6-hydroxyhexyl)-1-methyl-1H-pyrazol-4-yl]-1H-indole-2-carboxylate (see Intermediate 93, 1.10 g, 1.82 mmol) was dissolved in 30 mL of dichloromethane and triphenylphosphane (1.15 g, 4.37 mmol) was added at 0° C. After 10 minutes of stirring tetrabromomethane (CAS 558-13-4, 1.33 g, 4.00 mmol) was added and the mixture was stirred for 3 hours. The reaction mixture was purified by flash chromatography using silica gel (gradient hexane/ethylacetate/ethanol) to give the title compound (1.10 g, purity 50%).

LC-MS (Method 1): $R_t$=1.43 min; MS (ESIpos): m/z=552 [M+H]$^+$

Intermediate 95 ethyl 7-[3-(6-bromohexyl)-5-ethyl-1-methyl-1H-pyrazol-4-yl]-3-(3-{[tert-butyl(dimethyl)silyl]oxy}-propyl)-6-chloro-1H-indole-2-carboxylate

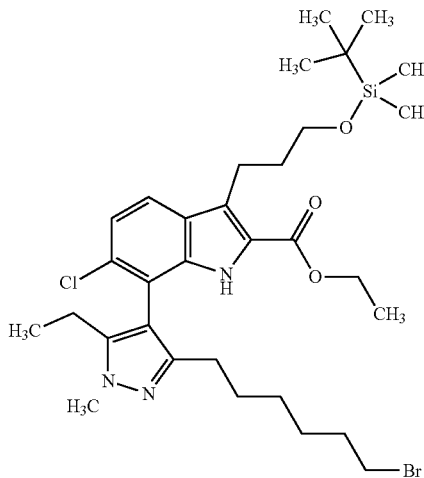

Ethyl-7-[3-(6-bromohexyl)-5-ethyl-1-methyl-1H-pyrazol-4-yl]-6-chloro-3-(3-hydroxypropyl)-1H-indole-2-carboxylate (see Intermediate 94, 1.10 g, 50% purity) was dissolved in 50 mL of THF. 1H-imidazole (102 mg, 1.49 mmol), N,N-dimethylpyridin-4-amine (6.1 mg, 49.7 µmol) and tert-butyl(chloro)dimethylsilane (CAS 18162-48-6, 180 mg, 1.19 mmol) were added and the mixture was stirred for 3 hours at room temperature. Water was added and the mixture was extracted with dichloromethane. The combined organic layers were dried over sodium sulfate, filtered and concentrated under reduced pressure. The residue was stirred in pentane, filtered and the filtrate was concentrated to give the title compound (479 mg) which was used without further purification.

$^1$H-NMR (400 MHz, DMSO-d6) δ[ppm]: −0.051 (12.75), −0.007 (0.43), 0.007 (0.45), 0.825 (0.83), 0.832 (16.00), 0.840 (1.17), 0.845 (0.85), 0.848 (0.96), 0.855 (12.08), 0.860 (2.18), 0.879 (0.72), 1.073 (0.41), 1.080 (0.43), 1.288 (1.07), 1.296 (0.40), 1.305 (2.13), 1.323 (0.98), 1.346 (1.37), 2.211 (0.50), 2.320 (0.41), 2.511 (1.39), 2.516 (0.98), 2.662 (0.40), 3.296 (0.62), 3.313 (1.71), 3.614 (0.70), 3.761 (3.06), 4.279 (0.82), 4.296 (0.81), 5.263 (0.83), 7.186 (0.74), 7.208 (0.75), 7.538 (0.63), 7.540 (0.85), 7.543 (0.77), 7.548 (0.73), 7.551 (0.59), 7.558 (0.95), 7.566 (0.84), 7.584 (0.72), 7.588 (1.20), 7.600 (0.48), 7.602 (0.66), 7.606 (1.00), 7.608 (0.88), 7.615 (1.23), 7.618 (1.21), 7.625 (1.18), 7.631 (0.46), 7.635 (0.76), 7.638 (0.73), 7.646 (0.55), 10.918 (0.47).

Intermediate 96

(rac)-ethyl 7-(3-{[tert-butyl(dimethyl)silyl]oxy}propyl)-4-chloro-3-ethyl-2-methyl-10,11,12,13,14,15-hexahydro-2H-pyrazolo[4',3':4,5]azacycloundecino[3,2,1-hi]indole-8-carboxylate

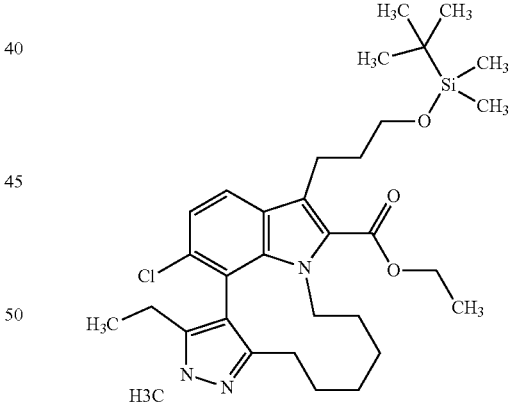

Ethyl-7-[3-(6-bromohexyl)-5-ethyl-1-methyl-1H-pyrazol-4-yl]-3-(3-{[tert-butyl(dimethyl)silyl]oxy}-propyl)-6-chloro-1H-indole-2-carboxylate (see Intermediate 95, 479 mg) was dissolved in 10 mL of DMF and cesium carbonate (1.17 g, 3.59 mmol) was added. After stirring at rt overnight the reaction mixture was poured into water and extracted with ethyl acetate. The combined organic layers were dried over sodium sulfate, filtered and concentrated under reduced pressure to give the title compound (419 mg) which was used without further purification.

LC-MS (Method 1): Rt=1.98 min; MS (ESIpos): m/z=586 [M+H]$^+$

Intermediate 97

(rac)-ethyl 4-chloro-3-ethyl-7-(3-hydroxypropyl)-2-methyl-10,11,12,13,14,15-hexahydro-2H-pyrazolo[4',3':4,5]azacycloundecino[3,2,1-hi]indole-8-carboxylate

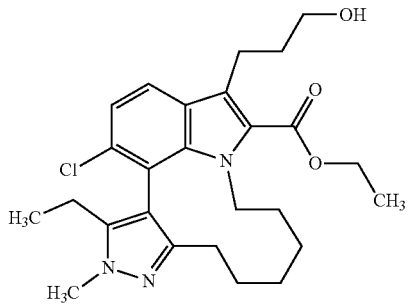 [SMILES: CCOC(=O)c1c(CCCO)c2ccc(Cl)c3c2n1CCCCCCc1nn(C)c(CC)c1-3]

(Rac)-ethyl-7-(3-{[tert-butyl(dimethyl)silyl]oxy}propyl)-4-chloro-3-ethyl-2-methyl-10,11,12,13,14,15-hexahydro-2H-pyrazolo[4',3':4,5]azacycloundecino[3,2,1-hi]indole-8-carboxylate (see Intermediate 96, 419 mg) was dissolved in 20 mL of THF and a solution of N,N,N-tributylbutan-1-aminium fluoride in THF (860 µL, 1.0 M, 860 µmol) was added. The reaction mixture was stirred overnight at room temperature. Water was added and the mixture was extracted with ethyl acetate. The combined organic layers were dried over sodium sulfate, filtered and concentrated under reduced pressure. The crude product was purified by flash chromatography using silica gel (gradient dichloromethane/ethanol) to give the titled compound (233 mg).

LC-MS (Method 1): Rt=1.37 min; MS (ESIpos): m/z=472 [M+H]$^+$ $^1$H-NMR (400 MHz, DMSO-d6) δ[ppm]: 0.000 (3.43), 0.613 (0.46), 0.642 (0.48), 0.842 (0.42), 0.859 (0.74), 0.869 (3.51), 0.883 (6.54), 0.888 (8.32), 0.900 (1.50), 0.907 (3.99), 0.918 (1.12), 0.928 (0.90), 0.937 (0.60), 0.947 (1.34), 0.964 (0.82), 1.007 (0.72), 1.080 (7.16), 1.090 (1.44), 1.097 (13.55), 1.115 (7.52), 1.134 (1.28), 1.179 (0.46), 1.211 (0.96), 1.234 (1.08), 1.269 (1.34), 1.274 (1.38), 1.335 (0.78), 1.355 (5.11), 1.372 (10.65), 1.390 (5.09), 1.757 (0.96), 1.762 (1.02), 1.779 (1.58), 1.795 (1.32), 1.812 (0.80), 2.110 (1.10), 2.235 (0.50), 2.249 (0.54), 2.256 (0.58), 2.274 (1.20), 2.293 (1.74), 2.311 (1.96), 2.327 (1.60), 2.345 (0.72), 2.376 (0.86), 2.562 (4.25), 2.568 (3.19), 2.583 (0.66), 2.989 (0.52), 3.006 (0.66), 3.023 (0.86), 3.044 (0.54), 3.082 (0.56), 3.102 (0.92), 3.120 (0.58), 3.135 (0.50), 3.449 (1.18), 3.462 (1.90), 3.467 (3.57), 3.479 (4.73), 3.484 (3.81), 3.493 (2.07), 3.497 (3.79), 3.501 (1.56), 3.514 (1.12), 3.808 (0.60), 3.814 (0.56), 3.875 (16.00), 4.051 (0.66), 4.076 (0.46), 4.283 (1.00), 4.292 (0.54), 4.300 (1.00), 4.310 (1.62), 4.318 (0.40), 4.327 (1.72), 4.345 (0.60), 4.363 (0.56), 4.381 (1.64), 4.388 (2.19), 4.401 (4.55), 4.408 (1.14), 4.413 (2.01), 4.426 (1.00), 4.492 (0.74), 4.528 (1.92), 4.541 (2.95), 4.554 (1.22), 5.803 (2.71), 7.308 (3.59), 7.330 (3.95), 7.570 (1.74), 7.573 (2.75), 7.577 (2.19), 7.581 (2.63), 7.584 (1.94), 7.591 (6.94), 7.594 (6.40), 7.600 (5.73), 7.602 (4.85), 7.609 (7.84), 7.617 (6.70), 7.636 (5.77), 7.640 (9.78), 7.646 (2.17), 7.654 (5.31), 7.657 (8.26), 7.666 (9.62), 7.669 (10.13), 7.674 (5.37), 7.683 (3.35), 7.686 (5.79), 7.690 (5.43), 7.693 (2.15), 7.759 (3.61), 7.781 (3.23).

Intermediate 98

(rac)-ethyl 7-(3-bromopropyl)-4-chloro-3-ethyl-2-methyl-10,11,12,13,14,15-hexahydro-2H-pyrazolo[4',3':4,5]azacycloundecino[3,2,1-hi]indole-8-carboxylate

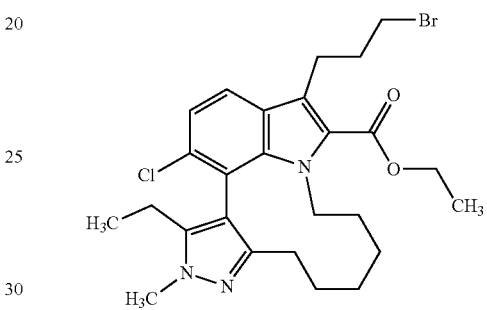

(Rac)-ethyl-4-chloro-3-ethyl-7-(3-hydroxypropyl)-2-methyl-10,11,12,13,14,15-hexahydro-2H-pyrazolo[4',3':4,5]azacycloundecino[3,2,1-hi]indole-8-carboxylate (see Intermediate 97, 230 mg) was dissolved in 10 mL of dichloromethane and triphenylphosphane (141 mg, 536 µmol) and tetrabromomethane (178 mg, 536 µmol) were added. The mixture was stirred at room temperature overnight. The same amounts of triphenylphosphane and tetrabromomethane were added and stirring was continued overnight. The reaction mixture was directly purified by flash chromatography using silica gel (gradient dichloromethane/ethyl acetate) to give the title compound (129 mg).

LC-MS (Method 1): Rt=1.72 min; MS (ESIpos): m/z=534 [M+H]$^+$ $^1$H-NMR (400 MHz, DMSO-d6) δ[ppm]: 0.570 (0.41), 0.598 (0.43), 0.820 (3.33), 0.839 (8.14), 0.858 (3.48), 0.870 (0.59), 0.890 (0.41), 0.915 (0.41), 0.932 (0.46), 1.208 (0.92), 1.230 (0.92), 1.261 (0.59), 1.287 (0.48), 1.323 (5.32), 1.340 (11.17), 1.358 (5.21), 2.105 (0.99), 2.122 (1.45), 2.140 (1.07), 2.188 (0.41), 2.202 (0.43), 2.207 (0.48), 2.226 (1.12), 2.244 (1.70), 2.262 (2.03), 2.280 (1.50), 2.298 (0.66), 2.317 (0.48), 2.518 (2.37), 2.522 (1.76), 2.541 (0.48), 3.062 (0.41), 3.079 (0.61), 3.096 (0.92), 3.117 (0.51), 3.133 (0.53), 3.153 (1.02), 3.171 (0.59), 3.187 (0.43), 3.560 (0.59), 3.568 (0.92), 3.577 (0.43), 3.584 (2.31), 3.601 (2.34), 3.610 (0.43), 3.618 (0.81), 3.626 (0.59), 3.830 (16.00), 4.021 (0.59), 4.030 (0.41), 4.046 (0.41), 4.264 (0.97), 4.274 (0.48), 4.282 (0.94), 4.292 (1.63), 4.309 (1.68), 4.327 (0.56), 4.331 (0.56), 4.349 (1.70), 4.367 (1.65), 4.376 (0.94), 4.385 (0.48), 4.394 (0.92), 4.459 (0.66), 4.495 (0.61), 5.757 (15.72), 7.287 (3.94), 7.309 (3.92), 7.755 (3.61), 7.776 (3.13).

Intermediate 99 ethyl 4-chloro-3-ethyl-7-{3-[(6-fluoronaphthalen-1-yl)oxy]propyl}-2-methyl-10,11,12,13,14,15-hexahydro-2H-pyrazolo[4',3':4,5]azacycloundecino[3,2,1-hi]indole-8-carboxylate

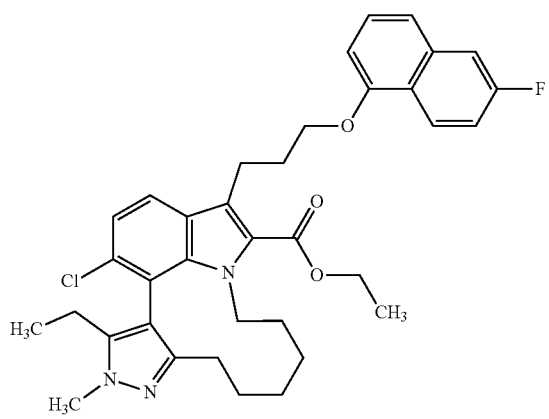 [SMILES: CCOC(=O)c1c(CCCOc2cccc3cc(F)ccc23)c2ccc(Cl)c3c2n1CCCCCCc1nn(C)c(CC)c1-3]

(Rac)-ethyl-7-(3-bromopropyl)-4-chloro-3-ethyl-2-methyl-10,11,12,13,14,15-hexahydro-2H-pyrazolo[4',3':4,5]azacycloundecino[3,2,1-hi]indole-8-carboxylate (see Intermediate 98, 129 mg, 241 µmol) was dissolved in 3 mL of THF and cesium carbonate (471 mg, 1.45 mmol) and 6-fluoronaphthalen-1-ol (CAS 804498-72-4, 78.2 mg, 482 µmol) were added. After stirring at 50 C overnight the reaction mixture was purified by flash chromatography using silica gel (gradient dichloromethane/ethyl acetate) to give the title compound (117 mg, 73% yield).

LC-MS (Method 1): $R_t$=1.87 min; MS (ESIpos): m/z=616 [M+H]$^+$ $^1$H-NMR (400 MHz, DMSO-d6) δ[ppm]: 0.517 (0.39), 0.542 (0.44), 0.806 (3.58), 0.826 (8.44), 0.844 (4.13), 1.154 (1.01), 1.172 (1.40), 1.190 (0.85), 1.204 (0.55), 1.249 (5.66), 1.267 (11.72), 1.285 (5.57), 1.761 (0.42), 1.987 (0.90), 2.173 (0.66), 2.193 (1.53), 2.210 (1.97), 2.229 (2.47), 2.248 (2.51), 2.267 (1.62), 2.285 (0.70), 2.332 (0.90), 2.518 (5.01), 2.522 (3.63), 2.673 (0.90), 3.226 (0.57), 3.244 (0.79), 3.264 (0.48), 3.279 (0.55), 3.300 (0.90), 3.825 (16.00), 4.003 (0.61), 4.017 (0.52), 4.027 (0.42), 4.035 (0.48), 4.193 (1.29), 4.202 (1.66), 4.211 (2.03), 4.216 (2.99), 4.219 (2.84), 4.230 (1.46), 4.237 (1.99), 4.255 (0.63), 4.258 (0.70), 4.277 (1.75), 4.294 (1.66), 4.303 (0.96), 4.312 (0.50), 4.321 (0.96), 4.439 (0.68), 4.465 (0.42), 4.475 (0.66), 5.758 (0.92), 6.864 (1.25), 6.872 (1.27), 6.878 (1.07), 6.885 (1.33), 7.225 (3.96), 7.247 (4.31), 7.355 (0.83), 7.361 (0.96), 7.377 (1.25), 7.384 (1.38), 7.399 (0.92), 7.406 (0.98), 7.430 (2.47), 7.437 (2.62), 7.444 (5.88), 7.644 (1.49), 7.651 (1.55), 7.670 (1.51), 7.677 (1.53), 7.764 (3.72), 7.785 (3.23), 8.195 (1.31), 8.209 (1.38), 8.217 (1.33), 8.233 (1.27).

Intermediate 100 ethyl 1-{4-[bis(tert-butoxycarbonyl)amino]butyl}-6-chloro-3-{3-[(6-fluoronaphthalen-1-yl)oxy]-propyl}-7-[3-(hydroxymethyl)-1,5-dimethyl-1H-pyrazol-4-yl]-1H-indole-2-carboxylate

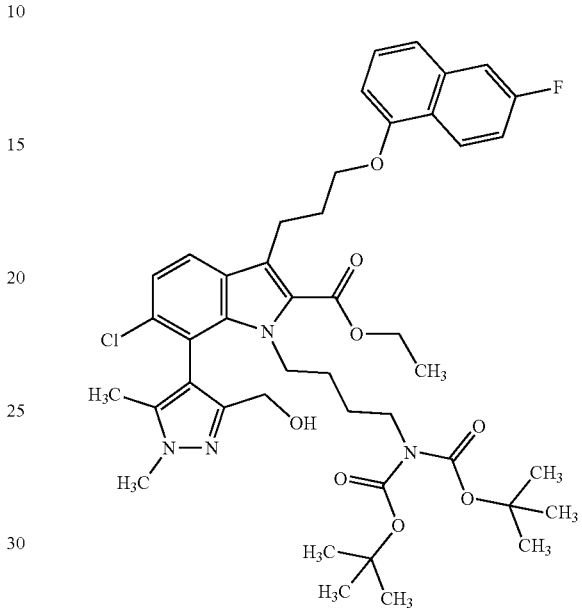

Ethyl 6-chloro-3-{3-[(6-fluoronaphthalen-1-yl)oxy]propyl}-7-[3-(hydroxymethyl)-1,5-dimethyl-1H-pyrazol-4-yl]-1H-indole-2-carboxylate (see Intermediate 47, 3.00 g) was dissolved in 65 mL DMF and treated with the cesium carbonate (8.89 g, 27.3 mmol). It was stirred for 30 minutes under argon atmosphere. Then di-tert-butyl (4-bromobutyl)-2-imidodicarbonate (see Intermediate 2, 2.31 g, 6.55 mmol), dissolved in 6 mL DMF, was added and it was stirred at room temperature for 2 days. Further di-tert-butyl (4-bromobutyl)-2-imidodicarbonate (see Intermediate 2, 1.16 g, 3.27 mmol) was added and it was stirred at room temperature for 5 hours. It was stirred at 60° C. over night. The DMF was removed under vacuum, the residue was diluted with water and ethyl acetate. The aqueous layer was extracted with ethyl acetate three times. The combined organic layers were washed with water and brine once, filtered through a silicone coated filter and concentrated under reduced pressure to provide the crude product which was used without further purification: 6.94 g, 90% pure.

$^1$H-NMR (400 MHz, DMSO-d6) δ[ppm]: 1.154 (2.91), 1.172 (6.20), 1.190 (3.16), 1.243 (0.78), 1.261 (1.69), 1.278 (0.87), 1.375 (16.00), 1.403 (0.70), 1.426 (3.33), 1.435 (9.27), 1.440 (9.36), 1.448 (1.34), 1.987 (11.35), 2.009 (2.26), 2.518 (0.48), 3.252 (0.41), 3.541 (0.46), 3.801 (2.41), 3.999 (0.81), 4.017 (2.43), 4.035 (2.46), 4.053 (0.82), 4.225 (0.62), 4.242 (0.70), 4.258 (0.47), 4.680 (0.42), 7.213 (0.66), 7.235 (0.61), 7.449 (0.66), 7.459 (0.89), 7.741 (0.55), 7.762 (0.50).

Intermediate 101 ethyl 1-{4-[bis(tert-butoxycarbonyl)amino]butyl}-7-[3-(bromomethyl)-1,5-dimethyl-1H-pyrazol-4-yl]-6-chloro-3-{3-[(6-fluoronaphthalen-1-yl)oxy]propyl}-1H-indole-2-carboxylate

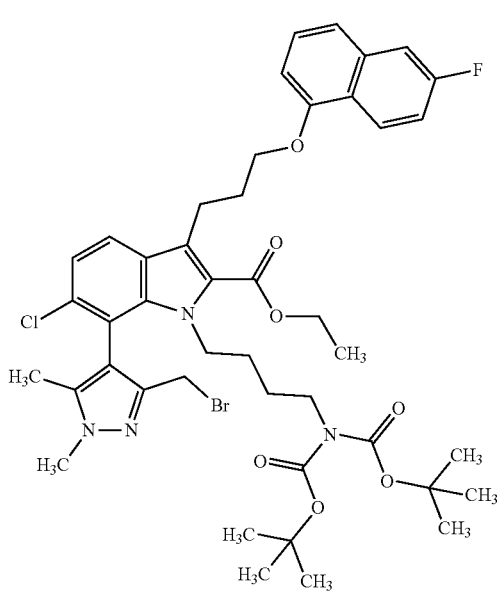 [SMILES: CCOC(=O)c1c(CCCOc2cccc3cc(F)ccc23)c2ccc(Cl)c(-c3c(CBr)nn(C)c3C)c2n1CCCCN(C(=O)OC(C)(C)C)C(=O)OC(C)(C)C]

Ethyl-1-{4-[bis(tert-butoxycarbonyl)amino]butyl}-6-chloro-3-{3-[(6-fluoronaphthalen-1-yl)oxy]-propyl}-7-[3-(hydroxymethyl)-1,5-dimethyl-1H-pyrazol-4-yl]-1H-indole-2-carboxylate (see Intermediate 100, 4.48 g) was dissolved in 110 mL dichloromethane and cooled with an ice bath. Then triphenylphosphine (2.15 g, 8.18 mmol) was added and it was stirred 10 minutes at this temperature. The mixture was allowed to reach room temperature and tetrabromomethane (2.71 g, 8.18 mmol) was added. The reaction mixture was stirred at room temperature under nitrogen atmosphere over night. The reaction mixture was concentrated under reduced pressure and directly purified by flash chromatography (100 g column; silica; snap ultra; hexane/ethyl acetate 0%-100% ethyl acetate) to provide the desired target compound in 99% purity: 861 mg.

$^1$H-NMR (400 MHz, DMSO-d6) b ppm 0.88-1.22 (m, 4H) 1.27 (t, 3H) 1.37 (s, 18H) 2.05 (s, 3H) 2.15-2.24 (m, 2H) 3.25 (br d, 4H) 3.70-3.80 (m, 1H) 3.84 (s, 3H) 4.14-4.31 (m, 7H) 6.86-6.93 (m, 1H) 7.27 (d, 1H) 7.40 (td, 1H) 7.43-7.48 (m, 2H) 7.67 (dd, 1H) 7.82 (d, 1H) 8.25 (dd, 1H)—no OH signal detected.

LC-MS (Method 2): $R_t$=1.90 min; MS (ESIpos): m/z=886 [M+H]$^+$

Intermediate 102 ethyl 1-(4-aminobutyl)-7-[3-(bromomethyl)-1,5-dimethyl-1H-pyrazol-4-yl]-6-chloro-3-{3-[(6-fluoronaphthalen-1-yl)oxy]propyl}-1H-indole-2-carboxylate-hydrochloric acid salt

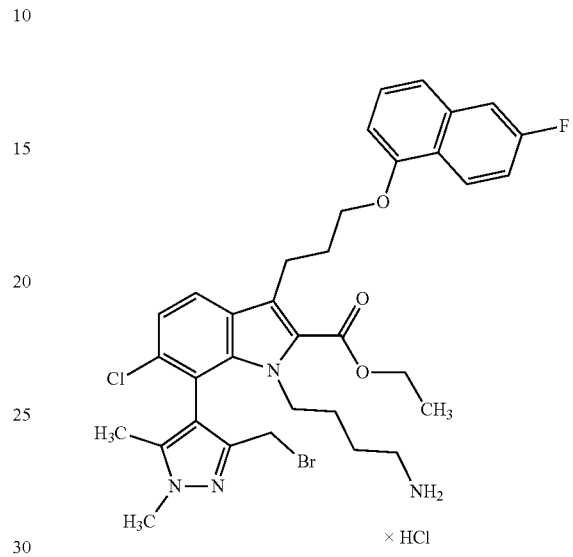

Ethyl 1-{4-[bis(tert-butoxycarbonyl)amino]butyl}-7-[3-(bromomethyl)-1,5-dimethyl-1H-pyrazol-4-yl]-6-chloro-3-{3-[(6-fluoronaphthalen-1-yl)oxy]propyl}-1H-indole-2-carboxylate (see Intermediate 101, 2.41 g, 2.73 mmol) was dissolved in 28 mL methanol and treated with the hydrogen chloride in dioxane (3.4 mL, 4.0 M, 14 mmol). The reaction mixture was stirred at 40° C. for 2 hours under nitrogen atmosphere. The reaction mixture was concentrated under reduced pressure to provide the 77% crude product which was used without further purification: 2.1 g LC-MS (Method 2): $R_t$=1.81 min; MS (ESIpos): m/z=686 [M+H]$^+$ $^1$H-NMR (400 MHz, DMSO-d6) δ[ppm]: 1.267 (1.61), 1.284 (3.44), 1.302 (1.66), 2.061 (2.83), 2.066 (2.71), 2.194 (0.41), 2.518 (0.88), 2.523 (0.70), 3.162 (16.00), 3.279 (0.54), 3.891 (3.15), 3.893 (3.43), 4.219 (0.55), 4.226 (0.84), 4.234 (1.03), 4.253 (0.99), 4.262 (0.70), 4.270 (0.65), 4.280 (0.89), 4.288 (0.56), 4.353 (1.28), 4.897 (1.20), 6.907 (0.45), 7.264 (0.91), 7.285 (0.97), 7.399 (0.42), 7.406 (0.46), 7.445 (0.95), 7.449 (1.03), 7.458 (1.79), 7.654 (0.53), 7.660 (0.52), 7.680 (0.52), 7.686 (0.50), 7.814 (0.72), 7.818 (0.68), 7.836 (0.81), 7.840 (0.83), 7.860 (0.64).

295

Intermediate 103 ethyl 4-chloro-7-{3-[(6-fluoronaphthalen-1-yl)oxy] propyl}-2,3-dimethyl-10,11,12,13,14,15-hexahydro-2H-pyrazolo[3',4':8,9][1,6]diazacycloundecino[10,11,1-hi]indole-8-carboxylate

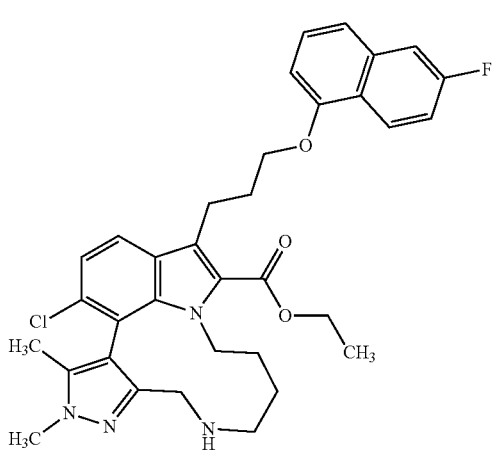 [SMILES: CCOC(=O)c1c(CCCOc2cccc3cc(F)ccc23)c2ccc(Cl)c3c2n1CCCCNCc1nn(C)c(C)c1-3]

Ethyl-1-(4-aminobutyl)-7-[3-(bromomethyl)-1,5-dimethyl-1H-pyrazol-4-yl]-6-chloro-3-{3-[(6-fluoronaphthalen-1-yl)oxy]propyl}-1H-indole-2-carboxylate-hydrochloric acid salt (see Intermediate 102, 2.07 g) was dissolved in 14 mL DMF and treated with cesium carbonate (4.46 g, 13.7 mmol). It was stirred at 60° C. over night under nitrogen atmosphere. The reaction mixture was diluted with water and ethyl acetate. The aqueous layer was extracted with ethyl acetate three times. The combined organic layers were washed with water and brine once, filtered through a silicone coated filter and dried under reduced pressure. The crude product was purified by flash chromatography (55 g column, aminophase; methylene chloride/ethanol 0%-10% ethanol) to provide the desired target compound in 98% purity: 114 mg.

$^1$H-NMR (400 MHz, DMSO-d6) δ[ppm]: 0.919 (0.58), 1.005 (0.63), 1.066 (0.49), 1.105 (0.72), 1.114 (0.85), 1.157 (0.94), 1.161 (0.91), 1.180 (2.24), 1.198 (3.51), 1.216 (1.99), 1.229 (1.30), 1.248 (5.48), 1.266 (11.16), 1.284 (5.23), 1.704 (0.50), 1.758 (0.56), 1.779 (16.00), 1.834 (0.41), 1.863 (0.50), 1.897 (0.94), 1.911 (3.30), 2.067 (0.53), 2.086 (0.67), 2.099 (0.67), 2.117 (0.86), 2.137 (0.70), 2.178 (1.41), 2.195 (1.68), 2.212 (1.25), 2.518 (4.20), 2.523 (2.80), 3.170 (0.74), 3.190 (0.75), 3.206 (0.81), 3.224 (1.24), 3.240 (1.33), 3.259 (0.86), 3.283 (0.97), 3.303 (1.83), 3.447 (0.49), 3.546 (0.42), 3.572 (5.59), 3.642 (0.58), 3.730 (0.59), 3.760 (0.49), 3.770 (0.74), 3.793 (15.41), 3.912 (0.78), 3.921 (3.35), 3.944 (0.72), 4.175 (1.19), 4.192 (3.23), 4.202 (2.72), 4.210 (3.84), 4.219 (3.44), 4.237 (2.88), 4.254 (1.44), 4.275 (2.21), 4.285 (0.80), 4.293 (1.83), 4.302 (1.16), 4.310 (0.55), 4.320 (1.02), 6.862 (0.42), 6.871 (1.71), 6.878 (1.42), 6.885 (1.32), 6.892 (1.41), 7.173 (1.00), 7.198 (4.01), 7.219 (4.12), 7.358 (0.42), 7.378 (1.27), 7.385 (1.27), 7.401 (1.80), 7.407 (1.77), 7.423 (2.02), 7.430 (2.43), 7.435 (2.88), 7.442 (2.96), 7.449 (6.17), 7.463 (0.58), 7.617 (0.56), 7.623 (0.63), 7.642 (0.74), 7.649 (2.11), 7.656 (1.83), 7.675 (1.63), 7.682 (1.63), 7.703 (0.86), 7.725 (4.09), 7.746 (3.24), 8.216 (0.42), 8.231 (0.53), 8.239 (1.74), 8.254 (1.80), 8.262 (1.52), 8.277 (1.35).

296

Intermediate 104 ethyl 4-chloro-7-{3-[(6-fluoronaphthalen-1-yl)oxy] propyl}-2,3-dimethyl-14-(2,2,2-trifluoroethyl)-10,11,12,13,14,15-hexahydro-2H-pyrazolo[3',4':8,9][1,6]diazacycloundecino[10,11,1-hi]indole-8-carboxylate

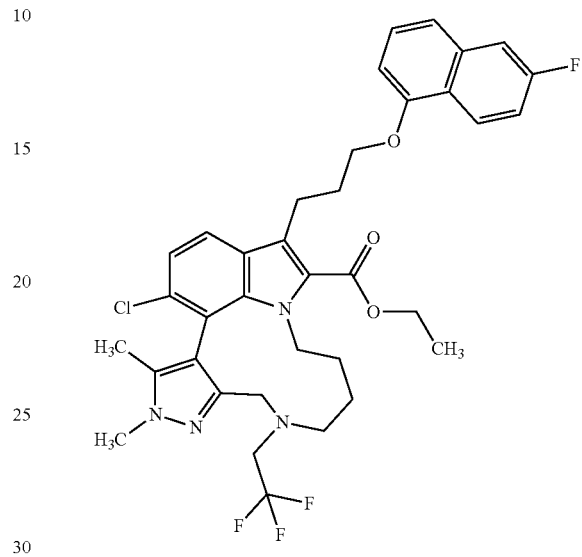

Ethyl-4-chloro-7-{3-[(6-fluoronaphthalen-1-yl)oxy]propyl}-2,3-dimethyl-10,11,12,13,14,15-hexahydro-2H-pyrazolo[3',4':8,9][1,6]diazacycloundecino[10,11,1-hi]indole-8-carboxylate (see Intermediate 103, 114 mg) was dissolved in 730 μL DMF and treated with the N,N-diisopropylethylamine (73 μL, 420 μmol) and 2,2,2-trifluoroethyl trifluoromethanesulfonate (30 μL, 210 μmol). It was stirred at room temperature under argon atmosphere for 2 days. The reaction mixture was diluted with water and dichloromethane. The aqueous layer was extracted with dichloromethane three times. The combined organic layers were washed with water and brine once, filtered through a silicone coated filter and concentrated under reduced pressure. The crude product was purified by HPLC chromatography under basic conditions to provided the desired target compound in 98% purity: 33 mg.

$^1$H-NMR (400 MHz, DMSO-d6): δ [ppm]=0.93-1.01 (m, 1H), 1.05 (br t, 1H), 1.12-1.20 (m, 1H), 1.27 (t, 3H), 1.78 (s, 3H), 2.13-2.24 (m, 2H), 2.25-2.42 (m, 2H), 2.89-3.28 (m, 3H), 3.35-3.45 (2H), 3.58 (d, 1H), 3.73 (d, 1H), 3.78-3.90 (m, 4H), 4.12-4.45 (m, 5H), 6.85 (dd, 1H), 7.20 (d, 1H), 7.34-7.50 (m, 3H), 7.67 (dd, 1H), 7.73 (d, 1H), 8.28 (dd, 1H).

Intermediate 105

4-bromo-3-(bromomethyl)-1,5-dimethyl-1H-pyrazole

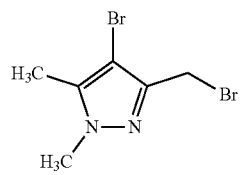

Phosphorus tribromide (12 mL, 122 mmol) was added at 0° C. to (4-bromo-1,5-dimethyl-1H-pyrazol-3-yl)methanol (see Intermediate 15, 25.0 g, 122 mmol) dissolved in 230 mL dichloromethane and stirred at room temperature for 4 hours. The reaction was quenched through addition to aqueous saturated sodium bicarbonate solution, the phases were separated and the organic was washed with brine. The organic phase was dried over magnesium sulfate, filtered through a plug of silica and the solvent was removed under reduced pressure to give 26.8 g of the desired compound without further purification.

LC-MS (Method 3): Rt=1.82 min; MS (ESIpos): m/z=267 [M+H]$^+$ $^1$H-NMR (400 MHz, CDCl$_3$) δ [ppm]=2.23 (s, 3H), 3.77 (s, 3H), 4.42 (s, 2H).

Intermediate 106

2,2-difluoropent-4-en-1-ol

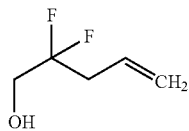

2,2-difluoropent-4-enoic acid (CAS, 55039-89-9, 20.0 g, 147 mmol) was added to a solution of lithium aluminium hydride (11.2 g, 294 mmol) in 400 mL diethyl ether at 0° C., stirred for 30 minutes and then warmed to room temperature and stirred for 2 hours. The reaction was quenched through the addition of water (11 mL), followed by 2-molar aqueous sodium hydroxide (11 mL), followed by a further 30 mL of water and the slurry was stirred overnight, magnesium sulfate was added and the reaction mixture was passed through celite and the solvent was removed under reduced pressure (300 mbar) to give the desired compound which was carried forward to the next step without further purification (27.0 g).

$^1$H-NMR (400 MHz, CDCl$_3$) δ [ppm]=2.68-2.81 (m, 2H), 3.70-3.88 (m, 2H), 5.23-5.29 (m, 2H), 5.76-5.85 (m, 1H)—OH not visible.

$^{19}$F-NMR (376 MHz, CDCl$_3$) δ [ppm]=−107.89 (tt, 1F).

Intermediate 107

4-bromo-3-{[(2,2-difluoropent-4-en-1-yl)oxy]methyl}-1,5-dimethyl-1H-pyrazole

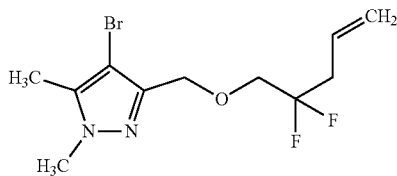 [SMILES: C=CCC(F)(F)COCc1nn(C)c(C)c1Br]

Sodium hydride (8.96 g, 60% purity, 224 mmol) was dissolved in 430 mL of THF at 0° C. under argon, 2,2-difluoropent-4-en-1-ol (see Intermediate 106, 18.9 g, 155 mmol) was added and the reaction was stirred for 10 minutes. 4-Bromo-3-(bromomethyl)-1,5-dimethyl-1H-pyrazole (see Intermediate 105, 32.0 g, 119 mmol) was added and the reaction was warmed to 60° C. and stirred for 4 hours. Upon completion the reaction was cooled to 0° C. and quenched through the addition of water, the reaction was partitioned with ethyl acetate and the organic phase was washed with brine. The organic phases were dried over magnesium sulfate, filtered through a silica plug and the solvent was removed under reduced pressure to give the desired compound which was used in the next step without further purification (37.9 g).

LC-MS (Method 3): Rt=2.26 min; MS (ESIpos): m/z=188.9 [M+H]$^+$ (fragment)

$^1$H-NMR (400 MHz, CDCl$_3$) δ [ppm]=2.24 (s, 3H), 2.71 (tt, 2H), 3.64 (t, 2H), 3.79 (s, 3H), 4.54 (s, 2H), 5.17-5.23 (m, 2H), 5.77 (tt, 1H).

$^{19}$F-NMR (376 MHz, CDCl$_3$) δ [ppm]=−104.11 (tt, 2F).

Intermediate 108

4-[(4-bromo-1,5-dimethyl-1H-pyrazol-3-yl)methoxy]-3,3-difluorobutan-1-ol

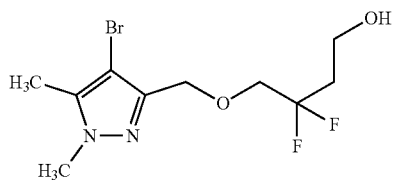 [SMILES: Cc1c(Br)c(COCC(F)(F)CCO)nn1C]

Carried out in two batches: Ozone was passed through a solution of 4-bromo-3-{[(2,2-difluoropent-4-en-1-yl)oxy]methyl}-1,5-dimethyl-1H-pyrazole, batch 1 (see Intermediate 107, 12.0 g, 38.8 mmol), batch 2 (see Intermediate 107, 13.2 g, 42.7 mmol) in dichloromethane, 240/264 mL, and methanol, 240/264 mL, for 55 minutes at −78° C. The reactions were quenched through the addition of sodium borohydride, batch 1 (2.94 g, 77.63 mmol), batch 2 (3.23 g, 85.4 mmol), and allowed to reach room temperature over 18 hours. The reaction mixtures were quenched through the addition of water and the organic solvents were removed under reduced pressure. The residues were combined from both batches and dissolved in ethyl acetate. The organic phase was washed with water, followed by brine, dried over magnesium sulfate, filtered and the solvent was removed under reduced pressure. The crude material was purified by flash chromatography (silica) with 0-70% ethyl acetate in heptane as eluent to give 12.67 g of the desired compound (combined yield).

LC-MS (Method 3): Rt=1.45 min; MS (ESIpos): m/z=188.8 [M+H]$^+$ (fragment)

$^1$H-NMR (400 MHz, CDCl$_3$) δ [ppm]=2.16-2.29 (m, 5H), 2.45 (bs, 1H) 3.69-3.83 (m, 7H), 4.56 (s, 2H).

$^{19}$F-NMR (376 MHz, CDCl$_3$) δ [ppm]=−101.94-102.10 (m, 2F).

Intermediate 109 ethyl 6-chloro-7-{3-[(2,2-difluoro-4-hydroxybutoxy)methyl]-1,5-dimethyl-1H-pyrazol-4-yl}-3-{3-[(naphthalen-1-yl)oxy]propyl}-1H-indole-2-carboxylate

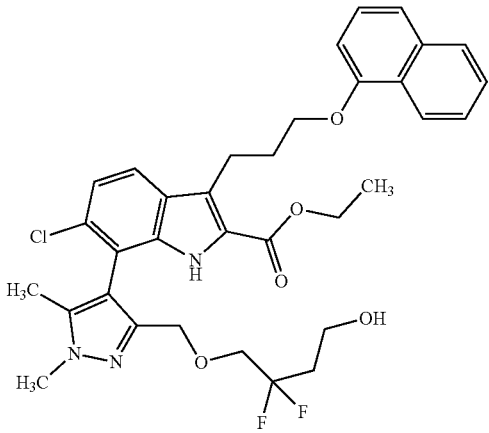 [SMILES: CCOC(=O)c1[nH]c2c(-c3c(COCC(F)(F)CCO)nn(C)c3C)c(Cl)ccc2c1CCCOc1cccc2ccccc12]

Ethyl-6-chloro-3-[3-(1-naphthyloxy)propyl]-7-(4,4,5,5-tetramethyl-1,3,2-dioxaborolan-2-yl)-1H-indole-2-carboxylate (see Intermediate 7, 1.08 g, 2.03 mmol), and 4-[(4-bromo-1,5-dimethyl-1H-pyrazol-3-yl)methoxy]-3,3-difluorobutan-1-ol, (see Intermediate 108, 0.83 g, 2.64 mmol) were dissolved in a mixture of 8.8 mL of 1,4-dioxane and 2.2-molar aqueous potassium carbonate solution (2.76 mL, 6.08 mmol) and degassed for 20 minutes. XPhos Pd G3 (686 mg, 0.81 mmol) was added, the reaction was degassed for 5 minutes and then heated to 110° C. for 20 minutes in a microwave reactor. The crude residue was purified by reverse phase chromatography (C-18) with 10-100% acetonitrile with 0.1% formic acid in water with 0.1% formic acid to give 467 mg of the desired compound.

LC-MS (Method 3): Rt=3.31 min; MS (ESIneg): m/z=637.8 [M–H]⁻

¹H-NMR (400 MHz, CDCl₃): δ [ppm]=1.35 (t, 3H), 1.96-2.09 (m, 5H), 2.30-2.37 (m, 2H), 3.39 (t, 2H), 3.54-3.74 (m, 4H), 3.90 (s, 3H), 4.20 (t, 2H), 4.32-4.37 (m, 3H), 4.41-4.46 (m, 1H), 6.76 (d, 1H), 7.16 (d, 1H), 7.34 (t, 1H), 7.42 (d, 1H), 7.46-7.51 (m, 2H), 7.61 (d, 1H), 7.80 (q, 1H), 8.32-8.34 (m, 1H), 8.79 (s, 1H).

¹⁹F-NMR (376 MHz, CDCl₃): δ [ppm]=–101.43–-103.30 (m, 2F).

Intermediate 110 ethyl 4-chloro-12,12-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate

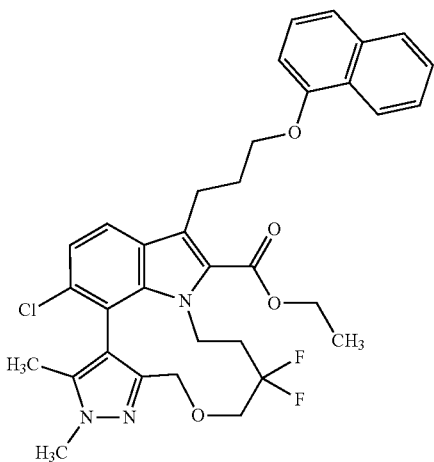 [SMILES: CCOC(=O)c1c(CCCOc2cccc3ccccc23)c2ccc(Cl)c3c2n1CCC(F)(F)COCc1nn(C)c(C)c1-3]

Triphenylphosphine (1.53 g, 5.84 mmol), followed by di-tert-butyl azodicarboxylate (1.34 g, 5.84 mmol) were added to ethyl-6-chloro-7-{3-[(2,2-difluoro-4-hydroxybutoxy)methyl]-1,5-dimethyl-1H-pyrazol-4-yl}-3-[3-(1-naphthyloxy)propyl]-1H-indole-2-carboxylate (see Intermediate 109, 467 mg, 0.73 mmol) in 50 mL of tetrahydrofuran at room temperature and stirred for 16 hours. 2 mL of 4-molar hydrochloric acid in 1,4-dioxane were added to the reaction mixture and stirred for 1 hour. The reaction solvent was removed under reduced pressure and the residue was dissolved in dichloromethane. The organic phase was washed with saturated aqueous sodium bicarbonate solution, followed by brine, dried over magnesium sulfate, filtered and the solvent was removed under reduced pressure. The crude residue was purified by flash chromatography (silica) eluting with 0-50% ethyl acetate in heptane to give the desired compound, 1.50 g (25% purity).

LC-MS (Method 3): Rt=3.75 min, MS (ESIpos): m/z=622.3 [M+H]⁺

¹⁹F-NMR (376 MHz, CDCl₃): δ [ppm]=–106.44–-105.43 (dd, 1F), –90.90–-91.71 (m, 1F).

Intermediate 111 tert-butyl (4-bromobutyl)(2-nitrobenzene-1-sulfonyl)carbamate

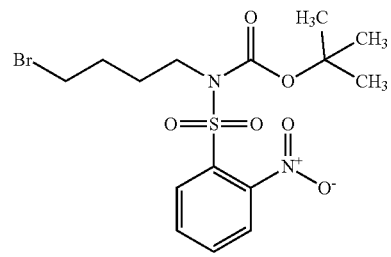 [SMILES: CC(C)(C)OC(=O)N(CCCCBr)S(=O)(=O)c1ccccc1[N+](=O)[O-]]

Tert-butyl (2-nitrobenzene-1-sulfonyl)carbamate (CAS 198572-71-3, 5.0 g) was dissolved in 67 mL THF and 67 mL DMF and treated portion wise with the sodium hydride (662 mg, 60% purity). It was stirred at 65° C. for 2 hours, then 1,4-dibromobutane (CAS 110-52-1, 9.9 mL) was added and it was stirred at the same temperature under Argon atmosphere over night. The reaction mixture was diluted with methyl-tert.butyl-ether and water, it was extracted three times with methyl-tert.butyl-ether, washed with water and brine once, filtered through a silicone coated filter and concentrated under reduced pressure. The crude product was treated with dichloromethane and the precipitate was filtered off. The filtrate was purified by flash chromatography (55 g column, aminophase; dichloromethane/ethanol 0%-10%) to provide the 90% pure target compound: 7.76 g ¹H-NMR (400 MHz, DMSO-d6): δ [ppm]=1.25 (s, 9H), 1.89-1.95 (m, 2H), 3.53-3.61 (m, 4H), 3.72 (t, 2H), 7.90-8.01 (m, 2H), 8.08 (dd, 1H), 8.17 (dd, 1H).

301

Intermediate 112 ethyl 1-{4-[(tert-butoxycarbonyl)(2-nitrobenzene-1-sulfonyl)amino]butyl}-6-chloro-7-[5-ethyl-3-(hydroxymethyl)-1-methyl-1H-pyrazol-4-yl]-3-{3-[(6-fluoronaphthalen-1-yl)oxy]propyl}-1H-indole-2-carboxylate

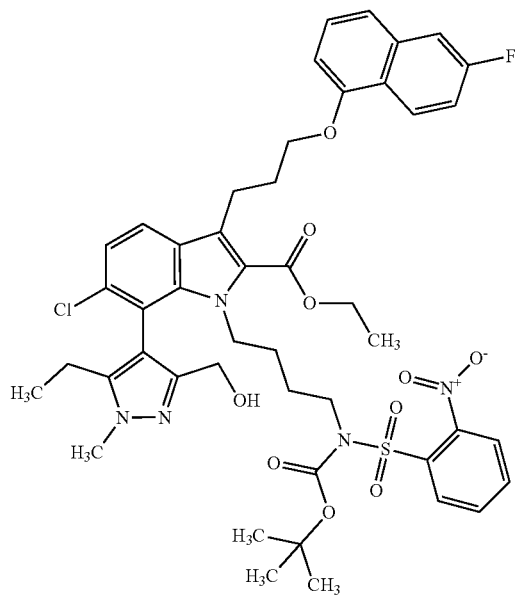 [SMILES: CCOC(=O)c1c(CCCOc2cccc3cc(F)ccc23)c2ccc(Cl)c(-c3c(CO)nn(C)c3CC)c2n1CCCCN(C(=O)OC(C)(C)C)S(=O)(=O)c1ccccc1[N+](=O)[O-]]

Ethyl 6-chloro-7-[5-ethyl-3-(hydroxymethyl)-1-methyl-1H-pyrazol-4-yl]-3-{3-[(6-fluoro-naphthalen-1-yl)oxy]propyl}-1H-indole-2-carboxylate (see Intermediated 34, 6.15 g) was dissolved in 70 mL DMF and treated with the cesium carbonate. It was stirred for 30 minutes under nitrogen atmosphere. Then tert-butyl (4-bromobutyl)(2-nitrobenzene-1-sulfonyl)carbamate (see Intermediate 111, 9.5 g) dissolved in 70 mL DMF was added and it was stirred at room temperature for 3 days. The solvent was removed under reduced pressure and the residue was treated with water and ethyl acetate, the aqueous layer was extracted three times, washed with water and brine once, filtered through a silicone coated filter and evaporated. The crude product was purified by flash chromatography (110 g column, aminophase; hexane/ethyl acetate 20%-100%) to provide the target compound in 88% purity: 2.1 g.

$^1$H-NMR (400 MHz, DMSO-d6) δ[ppm]: 0.958 (0.66), 0.977 (1.36), 0.996 (0.66), 1.066 (3.26), 1.085 (7.13), 1.104 (3.38), 1.171 (0.44), 1.188 (8.44), 1.232 (0.56), 1.259 (0.99), 1.276 (1.96), 1.294 (0.96), 2.518 (0.86), 2.522 (0.55), 2.608 (0.98), 2.627 (3.04), 2.646 (2.98), 2.665 (1.02), 3.266 (0.41), 3.760 (16.00), 3.840 (2.85), 4.212 (0.47), 4.223 (0.53), 4.230 (0.65), 4.241 (0.53), 4.259 (0.86), 4.277 (0.84), 4.287 (3.91), 4.301 (3.91), 4.723 (0.41), 4.940 (0.95), 4.954 (2.07), 4.968 (0.89), 5.758 (3.05), 7.217 (0.73), 7.238 (0.75), 7.445 (0.68), 7.448 (0.71), 7.457 (1.13), 7.751 (0.65), 7.773 (0.59), 7.977 (0.42), 8.061 (0.49), 8.064 (0.47), 8.112 (0.41).

Intermediate 113 ethyl 6-chloro-7-[5-ethyl-3-(hydroxymethyl)-1-methyl-1H-pyrazol-4-yl]-3-{3-[(6-fluoro-naphthalen-1-yl)oxy]propyl}-1-{4-[(2-nitrobenzene-1-sulfonyl)amino]butyl}-1H-indole-2-carboxylate-hydrochloric acid salt

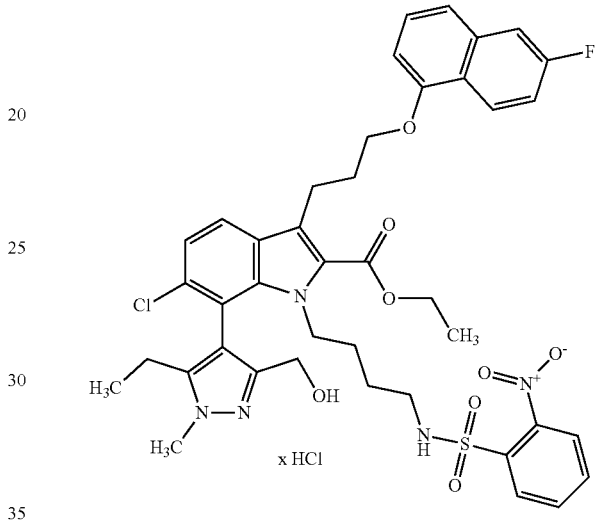

Ethyl 1-{4-[(tert-butoxycarbonyl)(2-nitrobenzene-1-sulfonyl)amino]butyl}-6-chloro-7-[5-ethyl-3-(hydroxymethyl)-1-methyl-1H-pyrazol-4-yl]-3-{3-[(6-fluoronaphthalen-1-yl)oxy]propyl}-1H-indole-2-carboxylate (see Intermediate 112, 2.06 g) was dissolved in 23 mL methanol and treated with hydrochloric acid in dioxane (2.8 mL, 4.0 M). It was stirred at 40° C. over night under nitrogen atmosphere. The reaction mixture was concentrated under reduced pressure. The crude product was used without further purification: 2.1 g $^1$H-NMR (400 MHz, DMSO-d6) δ[ppm]: 0.909 (1.13), 0.928 (2.29), 0.946 (1.19), 0.973 (0.47), 1.063 (5.66), 1.082 (11.99), 1.101 (5.70), 1.184 (2.34), 1.226 (1.46), 1.244 (2.97), 1.262 (1.54), 1.273 (0.64), 1.588 (1.29), 2.172 (0.71), 2.190 (0.72), 2.209 (0.53), 2.468 (0.44), 2.518 (1.19), 2.522 (0.79), 2.605 (1.68), 2.624 (5.26), 2.643 (5.15), 2.662 (1.83), 2.668 (0.72), 2.684 (0.40), 3.162 (5.38), 3.230 (0.48), 3.250 (0.73), 3.267 (0.51), 3.562 (8.70), 3.771 (0.40), 3.789 (4.20), 3.838 (0.51), 3.844 (0.92), 4.089 (0.58), 4.120 (1.02), 4.178 (1.03), 4.208 (1.32), 4.217 (1.32), 4.225 (1.77), 4.242 (1.35), 4.256 (0.51), 4.293 (16.00), 5.781 (2.41), 6.891 (0.43), 6.901 (0.61), 6.913 (0.47), 7.201 (1.05), 7.222 (1.10), 7.400 (0.51), 7.407 (0.59), 7.422 (0.41), 7.429 (0.53), 7.437 (1.27), 7.447 (1.81), 7.453 (0.65), 7.641 (0.49), 7.648 (0.61), 7.667 (0.50), 7.674 (0.59), 7.735 (1.00), 7.757 (0.95), 7.831 (0.74), 7.835 (0.62), 7.842 (1.01), 7.849 (0.73), 7.852 (0.92), 7.855

(0.91), 7.935 (0.75), 7.942 (0.52), 7.946 (0.69), 7.952 (0.52), 7.959 (0.97), 7.965 (0.50), 7.971 (0.60), 7.976 (0.49), 7.983 (0.50), 8.087 (0.56), 8.232 (0.44), 8.246 (0.47), 8.255 (0.48), 8.270 (0.42).

Intermediate 114

(rac)-ethyl 4-chloro-3-ethyl-7-{3-[(6-fluoronaphthalen-1-yl)oxy]propyl}-2-methyl-14-(2-nitro-benzene-1-sulfonyl)-10,11,12,13,14,15-hexahydro-2H-pyrazolo[3',4':8,9][1,6]diazacycloundecino[10,11,1-hi]indole-8-carboxylate

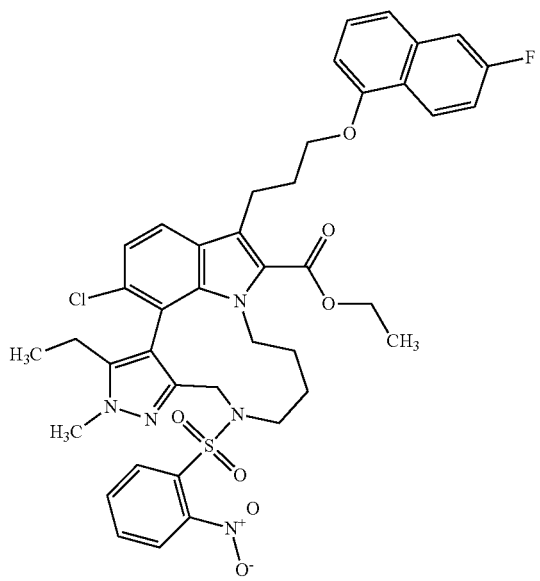

Ethyl 6-chloro-7-[5-ethyl-3-(hydroxymethyl)-1-methyl-1H-pyrazol-4-yl]-3-{3-[(6-fluoro-naphthalen-1-yl)oxy]propyl}-1-{4-[(2-nitrobenzene-1-sulfonyl)amino]butyl}-1H-indole-2-carboxylate-hydrochloric acid (see Intermediate 113, 2.06 g) and triphenylphosphine (5.04 g, 19.2 mmol) were dissolved in 98 mL THF and treated with the di-tert-butyl azodicarboxylate (4.43 g, 19.2 mmol). It was stirred at room temperature under nitrogen atmosphere. The reaction mixture was treated with aqueous hydrochloric acid and extracted with ethyl acetate thrice, washed with water and brine once, filtered through a silicone coated filter and concentrated under reduced pressure. The crude product was purified by flash chromatography (25 g column, silica ULTRA; hexane/ethyl acetate 50%-100%/ethyl acetate/ethanol 0%-20% ethanol). The product fractions were treated with methyl tert-butylether and were sonicated. The recipitate was filtered off and the filtrate was concentrated under reduced pressure to provide the target compound which was still contaminated with triphenylphosphineoxide: 1.01 g. The product was used without further purification.

$^1$H-NMR (400 MHz, DMSO-d6) δ[ppm]: 0.790 (1.59), 0.808 (3.51), 0.827 (1.70), 0.899 (0.41), 0.945 (0.45), 0.956 (0.41), 1.075 (0.48), 1.097 (0.97), 1.238 (2.72), 1.256 (5.05), 1.274 (2.54), 1.331 (0.63), 1.380 (2.27), 1.417 (2.86), 2.192 (1.00), 2.211 (0.86), 2.230 (0.73), 2.248 (0.66), 2.269 (0.61), 2.289 (0.57), 2.308 (0.43), 2.518 (2.67), 3.246 (0.63), 3.266 (0.50), 3.285 (0.59), 3.674 (0.48), 3.751 (0.61), 3.806 (0.68), 3.840 (7.34), 3.985 (0.88), 4.020 (0.95), 4.187 (1.13), 4.205 (1.99), 4.214 (1.54), 4.232 (1.20), 4.245 (0.52), 4.250 (0.54), 4.262 (0.86), 4.280 (0.79), 4.289 (0.48), 4.306 (0.43), 4.470 (1.27), 4.506 (1.09), 5.753 (16.00), 6.858 (0.68), 6.863 (0.70), 6.875 (0.73), 6.880 (0.79), 7.255 (1.59), 7.275 (1.63), 7.370 (0.48), 7.376 (0.52), 7.391 (0.79), 7.399 (1.04), 7.421 (1.63), 7.438 (2.74), 7.524 (2.81), 7.531 (2.90), 7.542 (7.71), 7.544 (7.61), 7.550 (6.57), 7.560 (8.59), 7.568 (7.57), 7.590 (10.97), 7.597 (2.72), 7.608 (9.54), 7.617 (10.81), 7.620 (12.03), 7.637 (6.75), 7.640 (6.69), 7.668 (0.93), 7.674 (0.86), 7.809 (1.90), 7.830 (2.24), 7.848 (1.38), 7.852 (1.50), 7.868 (0.95), 7.871 (1.02), 7.887 (0.50), 7.932 (1.34), 7.935 (1.13), 7.950 (0.97), 7.954 (0.88), 8.113 (0.95), 8.117 (0.97), 8.132 (0.75), 8.135 (0.79), 8.235 (0.75), 8.249 (0.75), 8.258 (0.73), 8.273 (0.63).

Intermediate 115

(rac)-ethyl 4-chloro-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylate

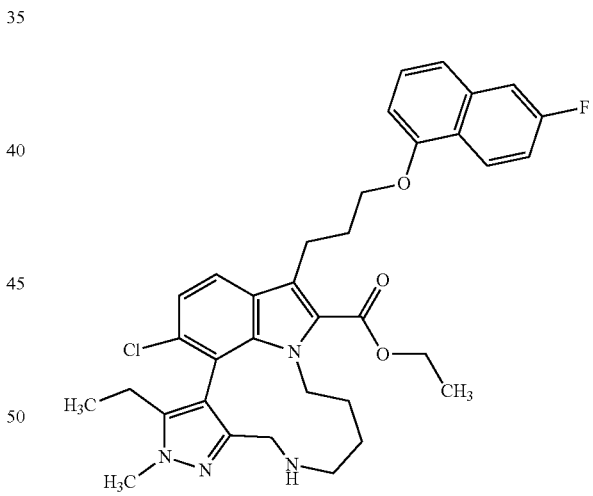

(rac)-Ethyl 4-chloro-3-ethyl-7-{3-[(6-fluoronaphthalen-1-yl)oxy]propyl}-2-methyl-14-(2-nitro-benzene-1-sulfonyl)-10,11,12,13,14,15-hexahydro-2H-pyrazolo[3',4':8,9][1,6]diazacycloundecino[10,11,1-hi]indole-8-carboxylate (see Intermediate 114, 175 mg) was dissolved in 1.2 mL acetonitrile and treated with the potassium carbonate (142 mg, 436 μmol). Then thiophenole (45 μl) was added. It was stirred at room temperature under Argon atmosphere for 2 hours. The precipitate was filtered off and washed with acetonitrile. The filtrate was extracted with ethyl acetate thrice, washed with water and brine once, filtered through a silicone coated filter

Intermediate 116

(rac)-ethyl 4-chloro-3-ethyl-7-{3-[(6-fluoronaphthalen-1-yl)oxy]propyl}-2-methyl-14-(2,2,2-tri-fluoroethyl)-10,11,12,13,14,15-hexahydro-2H-pyrazolo[3',4':8,9][1,6]diazacycloundecino-[10,11,1-hi]indole-8-carboxylate

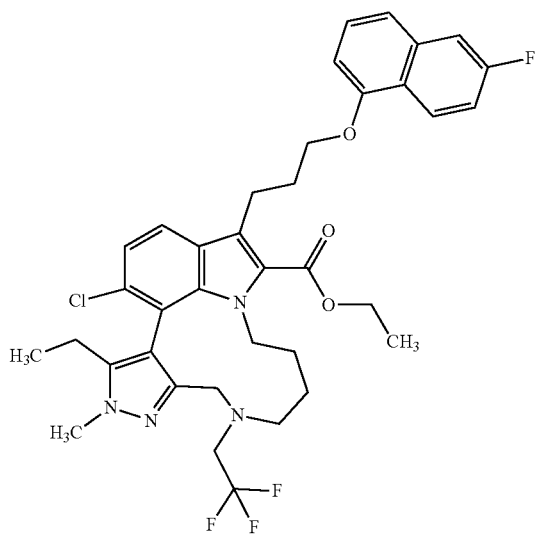 [SMILES: CCOC(=O)c1c(CCCOc2cccc3cc(F)ccc23)c2ccc(Cl)c3c2n1CCCCN(CC(F)(F)F)Cc1nn(C)c(CC)c1-3]

(rac)-Ethyl 4-chloro-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylate (see Intermediate 115, 75.0 mg) was dissolved in 470 µL DMF and treated with the N,N-diisopropylethylamine (47 µl) and 2,2,2-trifluoroethyl trifluoromethanesulfonate (19 µl). It was stirred at room temperature under Argon atmosphere for 2.5 hours. The reaction mixture was diluted with water and methylene chloride, it was stirred for a few minutes, filtered through a silicone coated filter and concentrated under reduced pressure. The crude product was combined with the crude product of a batch started from 50 mg starting material, purified by HPLC chromatography under basic conditions to provide the target compound with 92% purity: 48 mg LC-MS (Method 2): $R_t$=1.82 min; MS (ESIpos): m/z=771 [M+H]$^+$ $^1$H-NMR (400 MHz, DMSO-d6): δ [ppm]=0.80 (t, 3H), 0.90-0.98 (m, 1H), 0.99-1.10 (m, 3H), 1.17 (br dd, 1H), 1.20-1.33 (m, 4H), 2.11-2.22 (m, 3H), 2.24-2.42 (m, 2H), 2.89-3.11 (m, 2H), 3.16-3.34 (m, 2H), 3.53-3.59 (m, 1H), 3.72 (d, 1H), 3.82 (s, 3H), 4.09-4.33 (m, 4H), 4.42 (t, 1H), 6.82 (dd, 1H), 7.19 (d, 1H), 7.34-7.49 (m, 3H), 7.66 (dd, 1H), 7.72 (d, 1H), 8.28 (dd, 1H).

Intermediate 117 ethyl 4-chloro-14-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylate

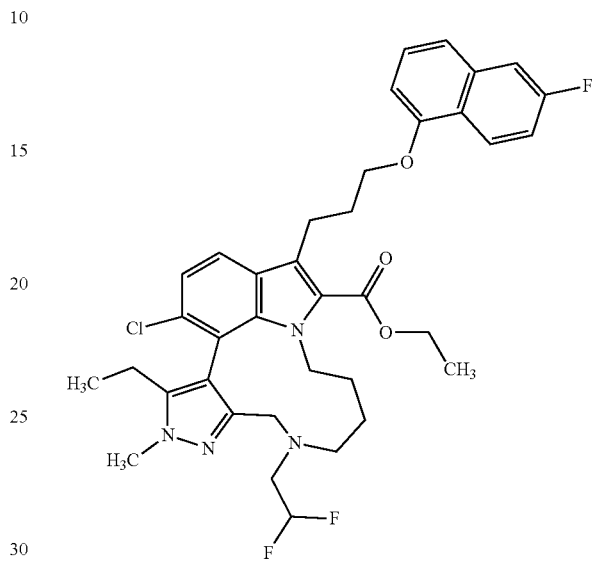

(rac)-Ethyl 4-chloro-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylate (see Intermediate 115, 75.0 mg) was dissolved in 470 µL DMF and treated with the N,N-diisopropylethylamine (47 µl) and 2,2-difluoroethyl trifluoromethanesulfonate (18 µl). It was stirred at room temperature under Argon atmosphere for 2.5 hours The reaction mixture was diluted with water and methylene chloride, it was stirred for a few minutes, filtered through a silicone coated filter and concentrated under reduced pressure. The crude product was purified by HPLC chromatography under basic conditions. To provide the target compound in 90% purity: 32 mg.

LC-MS (Method 2): $R_t$=1.79 min; MS (ESIpos): m/z=683 [M+H]$^+$ $^1$H-NMR (400 MHz, DMSO-d6) δ[ppm]: 0.783 (1.28), 0.790 (0.64), 0.802 (3.20), 0.814 (0.64), 0.821 (1.60), 1.031 (7.04), 1.048 (12.80), 1.066 (7.04), 1.222 (0.64), 1.237 (2.24), 1.255 (4.48), 1.273 (2.24), 2.150 (0.64), 2.158 (0.64), 2.169 (0.96), 2.177 (0.96), 2.195 (0.64), 2.202 (0.96), 2.214 (0.64), 2.261 (0.32), 2.518 (4.16), 2.523 (2.88), 3.236 (0.32), 3.295 (0.64), 3.313 (0.64), 3.330 (0.64), 3.372 (1.28), 3.401 (5.44), 3.419 (16.00), 3.494 (2.56), 3.511 (1.28), 3.520 (0.96), 3.524 (0.96), 3.548 (0.64), 3.597 (0.96), 3.629 (0.64), 3.725 (0.32), 3.816 (6.72), 3.834 (0.64), 4.168 (0.96), 4.186 (0.96), 4.195 (0.64), 4.204 (0.64), 4.213 (0.96), 4.230 (0.64), 4.261 (0.64), 4.278 (0.64), 4.409 (1.92), 4.421 (3.52), 4.434 (1.92), 5.465 (0.32), 6.822 (0.64), 6.825 (0.64), 6.839 (0.64), 6.843 (0.64), 7.188 (1.60), 7.209 (1.60), 7.387 (0.64), 7.390 (0.32), 7.402 (0.64), 7.411 (1.28), 7.431 (1.28), 7.434 (1.28), 7.437 (1.28), 7.642 (0.64), 7.649 (0.64), 7.668 (0.64), 7.675 (0.64), 7.718 (1.60), 7.739 (1.28), 8.265 (0.64), 8.279 (0.64), 8.288 (0.64), 8.303 (0.64).

Intermediate 118

(1R, 2S)-cyclobutane-1,2-diyldimethanol

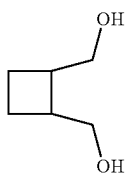

To a solution of 3-oxabicyclo[3.2.0]heptane-2,4-dione (CAS 4462-96-8, 750 mg, 5.95 mmol) in 18 mL THF at Rt was added lithium aluminum hydride (711 mg, 18.7 mmol) portionwise. The reaction mixture was stirred for 30 min at RT. Then 1.1 mL of aqueous sodiumhydroxide solution (2M) and then sodium sulfate as solid was added and stirred for 30 min then filtered. The Residue was washed with ethyl acetate. The collected organic layers were concentrated under vacuum. The crude product was purified by flash chromatography (Biotage Isolera 30 g; ZIP Sphere cartridge) using ethyl acetate and heptane (0:100 to 100:0) to provide the target compound: 565 mg $^1$H-NMR (400 MHz, CHLOROFORM-D) δ 1.57-1.52 (m, 2H), 2.06-1.96 (m, 2H), 2.85-2.65 (m, 4H), 3.60 (dd, 2H), 3.85 (t, 2H).

Intermediate 119

[(1R,2S and 1S,2R)-2-{[(4-bromo-1,5-dimethyl-1H-pyrazol-3-yl)methoxy]methyl}cyclobutyl]-methanol

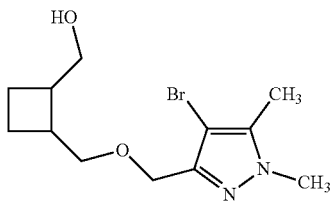 [SMILES: Cc1c(Br)c(COCC2CCC2CO)nn1C]

To a stirred suspension of sodium hydride (214 mg, 60% purity, 5.36 mmol) in THF (26 mL) was added (1R,2S)-cyclobutane-1,2-diyldimethanol (see Intermediate 118, 566 mg) as a solution in THF (2 mL). After 10 minutes of stirring 4-bromo-3-(bromomethyl)-1,5-dimethyl-1H-pyrazole (see Intermediate 105, 1.31 g) was added dissolved in THF (2 mL). The reaction mixture was heated at 60° C. for 18 hours under argon. Saturated ammonium chloride solution was added and the mixture was extracted with ethyl acetate. The combined organics were dried with sodium sulfate and concentrated under reduced pressure. The crude product was purified by flash chromatography (Biotage Isolera 30 g; ZIP Sphere cartridge) using ethyl acetate and heptane (0:100 to 100:0) to give the target compound: 801 mg.

$^1$H-NMR (400 MHz, CHLOROFORM-D) δ 1.63-1.45 (m, 2H), 2.07-1.89 (m, 2H), 2.23 (s, 3H), 2.64-3.10 (m, 3H), 3.51-3.40 (m, 2H), 3.81-3.70 (m, 5H), 4.48 (s, 2H).

Intermediate 120 ethyl 6-chloro-7-[3-({[(1S,2R and 1R,2S)-2-(hydroxymethyl)cyclobutyl]methoxy}methyl)-1,5-dimethyl-1H-pyrazol-4-yl]-3-{3-[(naphthalen-1-yl)oxy]propyl}-1H-indole-2-carboxylate

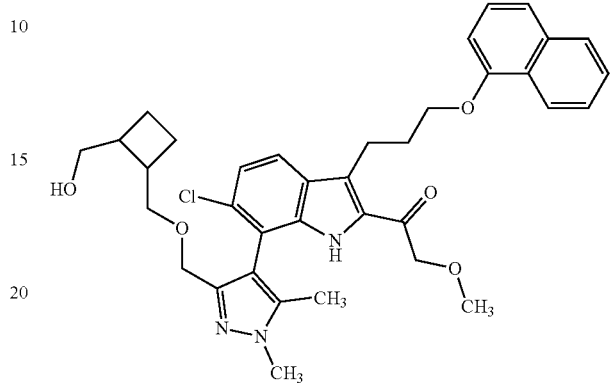

Ethyl 6-chloro-3-{3-[(naphthalen-1-yl)oxy]propyl}-7-(4,4,5,5-tetramethyl-1,3,2-dioxaborolan-2-yl)-1H-indole-2-carboxylate (see Intermediate 7, 1.06 g) and [(1S,2R and 1R,2S)-2-{[(4-bromo-1,5-dimethyl-1H-pyrazol-3-yl)methoxy]methyl}cyclobutyl]methanol (see Intermediate 119, 600 mg) were coupled under conditions described in Intermediate 109 to provide the target compound: 680 mg. The crude product was used without further purification

Intermediate 121 ethyl (9aS,11aR or 9aR,11aS)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]oxazacycloundecino-[8,7,6-hi]indole-14-carboxylate—Stereoisomer 1

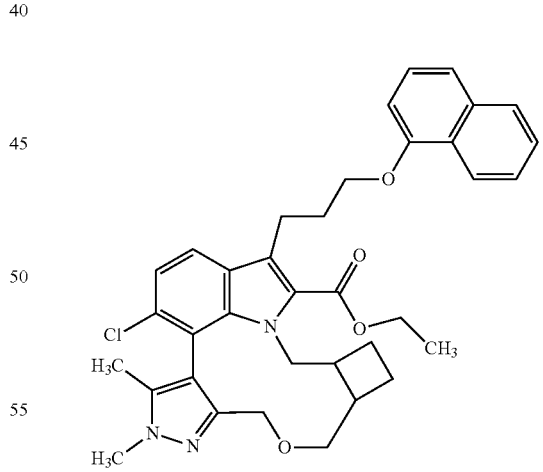

Di-tert-butyl azodicarboxylate: (1.68 g, 7.30 mmol) was added to ethyl 6-chloro-7-[3-({[(1S,2R and 1R,2S)-2-(hydroxymethyl)cyclobutyl]methoxy}methyl)-1,5-dimethyl-1H-pyrazol-4-yl]-3-{3-[(naphthalen-1-yl)oxy]propyl}-1H-indole-2-carboxylate (see Intermediate 120, 575 mg) and triphenylphosphine (1.91 g, 7.30 mmol) were dissolved in 63 mL THF and stirred overnight at room temperature. UPLC analysis of the reaction mixture showed two peaks with the correct mass. The reaction mixture solvent was combined with that from a batch starting with 100 mg of 6-chloro-7-[3-({[(1S,2R or 1R,2S)-2-(hydroxymethyl)cyclobutyl]methoxy}methyl)-1,5-dimethyl-1H-pyrazol-4-yl]-3-{3-[(naphthalen-1-yl)oxy]propyl}-1H-indole-2-carboxylate, then diluted with ethyl acetate (125 mL), washed with water (150 mL) and brine (150 mL), dried over magnesiums sulfate and evaporated to a thick brown oil. This was purified via flash chromatography, eluting with 19:1 heptane/ethyl acetate, 8:2 heptane/ethyl acetate, 7:3 heptane/ethyl acetate and finally 1:1 heptane/ethyl acetate, giving the desired product (434 mg) as a mixture of the two isomers. This mixture was purified through a 60 g C18 cartridge, eluting with a gradient of 30% to 100% acetonitrile in water (+0.1% formic acid), to give Stereoisomer 1 (86 mg, Intermediate 121), and Stereoisomer 2 (140 mg, Intermediate 122).

Intermediate 121

$^1$H NMR (CHLOROFORM-D, 400 MHz): 8.35-8.39 (m, 1H), 7.78-7.82 (m, 1H), 7.56 (d, 1H), 7.46-7.52 (m, 2H), 7.33-7.43 (m, 2H), 7.11 (d, 1H), 6.78 (d, 1H), 4.52 (d, 1H), 4.32 (q, 2H), 4.13-4.26 (m, 4H), 3.92 (s, 3H), 3.88-3.93 (m, 1H), 3.66 (dd, 2H), 3.28-3.42 (m, 2H), 3.25-3.27 (m, 1H), 2.45-2.54 (m, 1H), 2.19-2.34 (m, 3H), 1.95 (s, 3H), 1.85-1.93 (m, 1H), 1.50-1.60 (m, 1H, underwater peak), 1.36 (t, 3H), 1.11-1.21 (m, 1H).

LC-MS (Method 3): Rt=2.65 min, MS (ESIpos): 612 [M+H]$^+$.

Intermediate 122

$^1$H NMR (CHLOROFORM-D, 400 MHz): 8.35-8.39 (m, 1H), 7.78-7.82 (m, 1H), 7.56 (d, 1H), 7.47-7.52 (m, 2H), 7.32-7.43 (m, 2H), 7.12 (d, 1H), 6.75 (d, 1H), 4.71 (d, 1H), 4.34 (q, 2H), 4.05-4.28 (m, 5H), 3.87 (s, 3H), 3.50 (s, 2H), 3.25-3.31 (m, 2H), 2.85-2.95 (m, 1H), 2.10-2.42 (m, 3H), 1.86 (s, 3H), 1.70-1.77 (m, 1H), 1.49-1.60 (m, 1H, underwater peak), 1.36 (t, 3H), 1.00-1.20 (m, 1H), 0.80-0.87 (m, 1H).

LC-MS (Method 3): Rt=2.96 min, MS (ESIpos): 612 [M+H]$^+$.

Intermediate 122 ethyl (9aS,11aR or 9aR, 11aS)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]oxazacycloundecino-[8,7,6-hi]indole-14-carboxylate—Stereoisomer 2

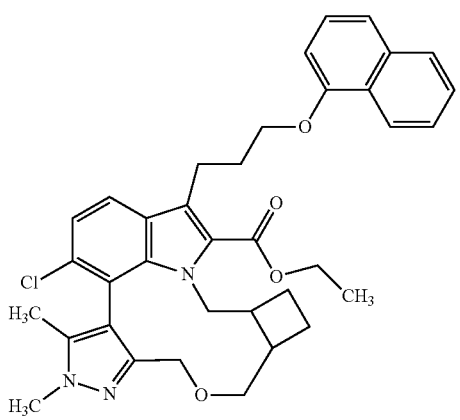 [SMILES: CCOC(=O)c1c(CCCOc2cccc3ccccc23)c2ccc(Cl)c3c2n1CC1CCC1COCc1nn(C)c(C)c1-3]

See Intermediate 121

Intermediate 123

(1R,2S)-cyclopropane-1,2-diyldimethanol

To a solution of dimethyl (1R,2S)-cyclopropane-1,2-dicarboxylate (5.00 g, 31.6 mmol) in 45 mL THF at 0° C. was added Lithium aluminum hydride (2.40 g, 63.2 mmol). The reaction mixture was allowed to warm to RT overnight. Then 0.3 mL water 0.3 mL aqueous sodium hydroxide solution (2.0 M), and 3 mL water were added. The residue was extracted with ethyl acetate. The organic layer was dried over solid sodium sulfate and concentrated under reduced pressure. The crude product was purified by flash chromatography (Biotage Isolera 30 g; ZIP Sphere cartridge) using ethyl acetate and heptane (0:100 to 100:0) to give the desired target compound: 2.25 g.

$^1$H-NMR (400 MHz, CHLOROFORM-D) δ [ppm]=0.21 (q, 1H), 0.77-0.83 (m, 1H), 1.37-1.25 (m, 2H), 2.56 (s, 2H), 3.20-3.30 (m, 2H), 4.10 (dd, 2H).

Intermediate 124

[(1R,2S and 1S,2R)-2-{[(4-bromo-1,5-dimethyl-1H-pyrazol-3-yl)methoxy]methyl}cyclopropyl]-methanol

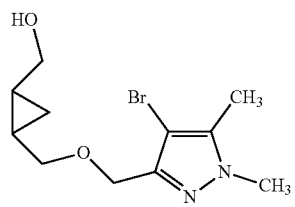 [SMILES: Cc1c(Br)c(COCC2CC2CO)nn1C]

To a stirred suspension of sodium hydride (176 mg, 60% purity, 4.39 mmol) in THF (8 mL) was added (1R,2S)-cyclopropane-1,2-diyldimethanol (see Intermediate 123, 408 mg, 3.99 mmol) as a solution in THF (3 mL). After 10 mins 4-bromo-3-(bromomethyl)-1,5-dimethyl-1H-pyrazole (see Intermediate 105, 1.07 g, 3.99 mmol) was added dissolved in THF (4 mL). The reaction mixture was heated overnight at 60° C. The reaction mixture was quenched with saturated ammonium chloride solution and extracted with dichloromethane twice. The collected organic layers were dried over magnesium sulfate and concentrated under vacuum. The crude product was purified by flash chromatography (Biotage Isolera; 120 g ZIP Sphere cartridge) using ethyl acetate and heptane (0:100 to 100:0) to give the target compound: 687 mg.

$^1$H-NMR (400 MHz, CHLOROFORM-D): 0.17 (q, 1H), 0.73-087 (m, 1H), 1.25-1.39 (m, 2H), 2.25 (s, 3H), 3.15-3.24 (m, 2H), 3.78 (s, 3H), 3.89-3.99 (m, 2H), 4.49 (dd, 2H).

Intermediate 125 ethyl 6-chloro-7-[3-({[(1S,2R and 1R,2S)-2-(hydroxymethyl)cyclopropyl]methoxy}methyl)-1,5-dimethyl-1H-pyrazol-4-yl]-3-{3-[(naphthalen-1-yl)oxy]propyl}-1H-indole-2-carboxylate

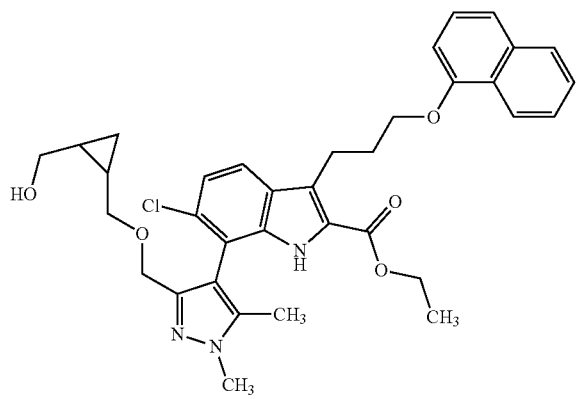 [SMILES: CCOC(=O)c1[nH]c2c(-c3c(COCC4CC4CO)nn(C)c3C)c(Cl)ccc2c1CCCOc1cccc2ccccc12]

Ethyl 6-chloro-3-{3-[(naphthalen-1-yl)oxy]propyl}-7-(4,4,5,5-tetramethyl-1,3,2-dioxaborolan-2-yl)-1H-indole-2-carboxylate (see Intermediate 7, 1.58 g) and [(1S,2R and 1R,2S)-2-{[(4-bromo-1,5-dimethyl-1H-pyrazol-3-yl)methoxy]methyl}cyclopropyl]methanol (see Intermediate 124, 856 mg, 2.96 mmol) were coupled under conditions described in Intermediate 109 with toluene/water instead of dioxane/water as solvent to provide the target compound: 1.3 g.

$^1$HNMR (CHLOROFORM-D, 400 MHz): 8.29-8.36 (m, 1H), 7.75-7.83 (m, 1H), 7.59 (d, 1H), 7.44-7.52 (m, 2H), 7.29-7.42 (m, 2H), 7.16 (dd, 1H), 6.75 (d, 1H), 4.28-4.56 (m, 5H), 4.20 (t, 2H), 3.90-3.97 (m, 1H), 3.77 (s, 3H), 3.39 (t, 1H), 3.10-3.28 (m, 3H), 2.29-2.37 (m, 1H), 2.23 (s, 3H), 1.25-1.43 (m, 6H), 0.75-0.80 (m, 1H), 0.14-0.19 (m, 1H).

LC-MS (Method 3): Rt=3.34 min, 40% and RT=3.38 mins, MS (ESIpos): 616[M+H]$^+$.

Used for Mitsunobu reaction (Intermediate 126) without further purification.

Intermediate 126 ethyl (9aS,10aR or 9aR,10aS)-3-chloro-4,5-dimethyl-14-{3-[(naphthalen-1-yl)oxy]propyl}-5,7,9a,10,10a,11-hexahydro-9H-cyclopropa[3,4]pyrazolo[4',3':9,10][1,6]oxazacycloundecino-[8,7,6-hi]indole-13-carboxylate—Stereoisomer 1

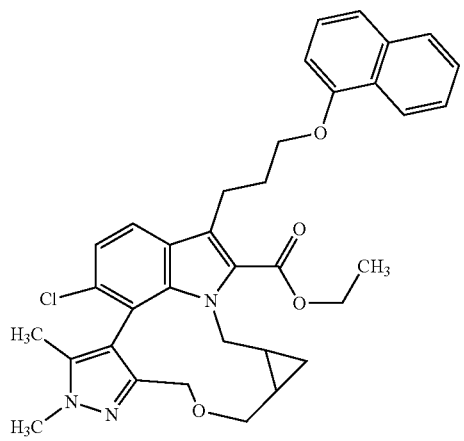 [SMILES: CCOC(=O)c1c(CCCOc2cccc3ccccc23)c2ccc(Cl)c3c2n1CC1CC1COCc1nn(C)c(C)c1-3]

Ethyl 6-chloro-7-[3-({[(1S,2R and 1R,2S)-2-(hydroxymethyl)cyclopropyl]methoxy}methyl)-1,5-dimethyl-1H-pyrazol-4-yl]-3-{3-[(naphthalen-1-yl)oxy]propyl}-1H-indole-2-carboxylate (see Intermediate 125, 1.30 g) were cyclized employing the reaction conditions as described for Intermediate 121 to provide the target compound as separated stereoisomers:

Stereoisomer 1 (Intermediate 126): 125 mg $^1$H NMR (Chloroform-D, 400 MHz): 8.36-8.39 (m, 1H), 7.79-7.83 (m, 1H), 7.59 (d, 1H), 7.48-7.52 (m, 2H), 7.42 (d, 1H), 7.36 (t, 1H), 7.15 (d, 1H), 6.79 (d, 1H), 4.66 (t, 2H), 4.36-4.44 (m, 1H), 4.27-4.35 (m, 1H), 4.19-4.24 (m, 2H), 3.87 (s, 3H), 3.83 (dd, 1H), 3.67 (dd, 1H), 3.35-3.43 (m, 1H), 3.23-3.33 (m, 1H), 2.50 (t, 1H), 2.26-2.34 (m, 2H), 1.88 (s, 3H), 1.41-1.48 (m, 1H), 1.37 (t, 3H), 0.99-1.08 (m, 1H), 0.71-0.81 (m, 1H), 0.60-0.69 (m, 1H), −0.22 (q, 1H).

LC-MS (Method 3): Rt=2.34 min MS (ESIpos): 598. [M+H]$^+$

Stereoisomer 2 (Intermediate 127): 74 mg $^1$H NMR (Chloroform-D, 400 MHz): 8.34-8.38 (m, 1H), 7.78-7.82 (m, 1H), 7.58 (d, 1H), 7.46-7.52 (m, 2H), 7.41 (d, 1H), 7.35 (t, 1H), 7.13 (d, 1H), 6.76 (d, 1H), 4.14-4.47 (m, 6H), 4.03 (dd, 1H), 3.87 (s, 3H), 3.62 (d, 1H), 3.32-3.42 (m, 2H), 3.23-3.32 (m, 1H), 2.27-2.36 (m, 2H), 1.89 (s, 3H), 1.41-1.46 (m, 1H), 1.34 (t, 3H), 1.10-1.20 (m, 1H), 0.84-0.94 (m, 1H), 0.24 (td, 1H), −0.48 (q, 1H).

LC-MS (Method 3): Rt=2.53 min, MS (ESIpos): 598 [M+H]$^+$.

Intermediate 127 ethyl (9aS,10aR or 9aR,10aS)-3-chloro-4,5-dimethyl-14-{3-[(naphthalen-1-yl)oxy]propyl}-5,7,9a,10,10a,11-hexahydro-9H-cyclopropa[3,4]pyrazolo[4',3':9,10][1,6]oxazacycloundecino-[8,7,6-hi]indole-13-carboxylate—Stereoisomer 2

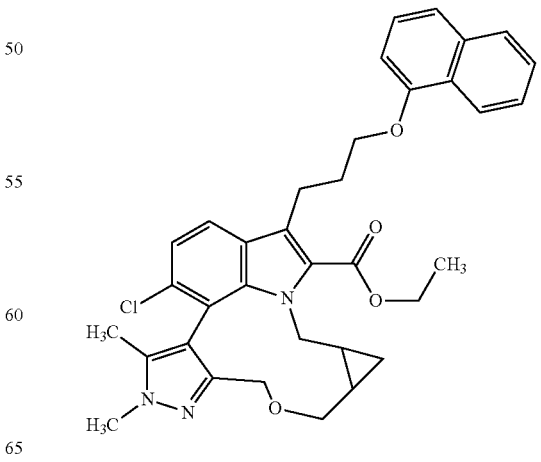

See Intermediate 126

Intermediate 128

4-[(4-bromo-1,5-dimethyl-1H-pyrazol-3-yl)methoxy]-2,2,3,3-tetrafluorobutan-1-ol

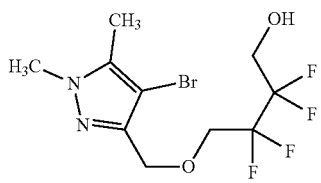 [SMILES: Cc1c(Br)c(COCC(F)(F)C(F)(F)CO)nn1C]

To a stirred solution of 2,2,3,3-tetrafluorobutane-1,4-diol (CAS 425-61-6, 1.00 g, 6.17 mmol) in 30 mL THF was added Sodium hydride (271 mg, 60% purity) on an ice bath and the reaction mixture was stirred for 10 minutes. 4-Bromo-3-(bromomethyl)-1,5-dimethyl-1H-pyrazole (see Intermediate 105, 1.65 g, 6.17 mmol) was added to the reaction mixture dropwise. Then the reaction mixture was warmed up to 20° C. and the stirring continued for 16 hours. Water (10 mL) was slowly added to the reaction mixture and the resulting mixture was washed with ethyl acetate (10 mL×2). The combined organic layers were filtered and concentrated. The crude residue was purified by silica gel column chromatography (percent petroleum ether in 0-100% ethyl acetated) to afford the title compound: 1.28 g.

Intermediate 129 ethyl 6-chloro-7-{1,5-dimethyl-3-[(2,2,3,3-tetrafluoro-4-hydroxybutoxy)methyl]-1H-pyrazol-4-yl}-3-{3-[(naphthalen-1-yl)oxy]propyl}-1H-indole-2-carboxylate

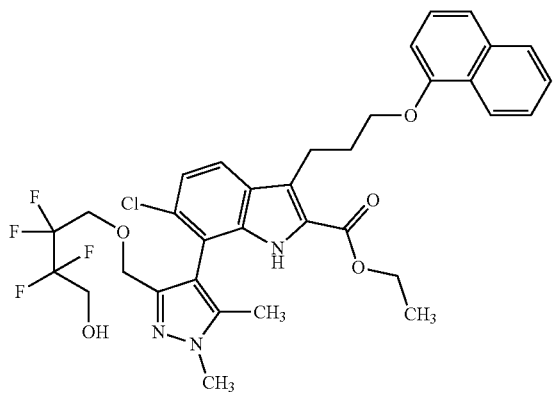 [SMILES: CCOC(=O)c1[nH]c2c(-c3c(COCC(F)(F)C(F)(F)CO)nn(C)c3C)c(Cl)ccc2c1CCCOc1cccc2ccccc12]

Ethyl 6-chloro-3-{3-[(naphthalen-1-yl)oxy]propyl}-7-(4,4,5,5-tetramethyl-1,3,2-dioxaborolan-2-yl)-1H-indole-2-carboxylate (see Intermediate 7, 1.51 g,) and 4-[(4-bromo-1,5-dimethyl-1H-pyrazol-3-yl)methoxy]-2,2,3,3-tetrafluorobutan-1-ol (see Intermediate 128, 1.28 g, 3.67 mmol) were coupled under conditions described in Intermediate 109 to provide the target compound: 1.34 g with 85% purity.

$^1$H NMR (400 MHz, CHLOROFORM-D) δ [ppm]=1.23-1.37 (m, 5H), 2.04 (s, 3H), 2.34 (t, 2H), 3.40 (t, 2H), 3.74-3.91 (m, 7H), 4.19 (t, 2H), 4.31-4.38 (m, 2H), 4.50 (d, 1H), 6.75 (d, 1H), 7.17 (d, 1H), 7.30-7.35 (m, 1H), 7.41 (d, 1H), 7.47-7.50 (m, 2H), 7.62 (d, 1H), 7.77-7.82 (m, 1H), 8.29-8.32 (m, 1H), 8.71 (s, 1H).

$^{19}$F NMR (376 MHz, CHLOROFORM-D) δ [ppm]= −123.68−−124.14 (m, 2F), −121.46−−121.66 (m, 2F)

LCMS (Method 3): Rt=3.40 min., MS (ESIpos): m/z=675.66 (M+H)$^+$.

Intermediate 130 ethyl 6-chloro-7-[1,5-dimethyl-3-({2,2,3,3-tetrafluoro-4-[(methanesulfonyl)oxy]butoxy}methyl)-1H-pyrazol-4-yl]-3-{3-[(naphthalen-1-yl)oxy]propyl}-1H-indole-2-carboxylate

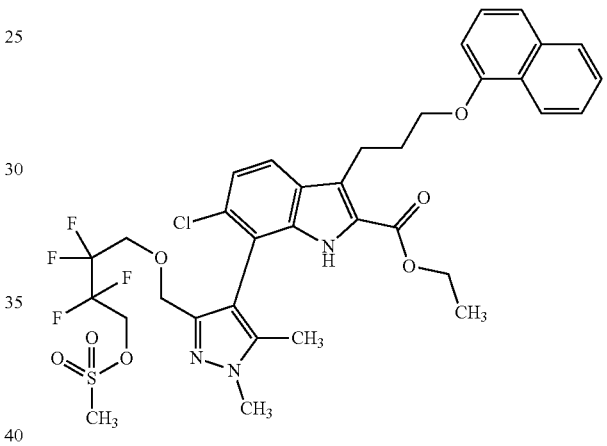

To a solution of ethyl 6-chloro-7-{1,5-dimethyl-3-[(2,2,3,3-tetrafluoro-4-hydroxybutoxy)methyl]-1H-pyrazol-4-yl}-3-{3-[(naphthalen-1-yl)oxy]propyl}-1H-indole-2-carboxylate (see Intermediate 129, 450 mg) in 18 mL dichloromethane was added triethylamine (140 μl, 1000 μmol) and Methanesulfonyl chloride (57 μl, 730 μmol). The reaction mixture was stirred overnight at RT. The reaction mixture was quenched with saturated aqueous sodium hydrogencarbonate solution, and extracted with dichloromethane twice. The organic layers were combined, dried over magnesium sulfate and evaporated. The crude product was purified by flash chromatography, eluting heptane, then 9:1 heptane/ethyl acetate, then 3:1 heptane/ethyl acetate, and finally 1:1 heptane/ethyl acetate. This gave the target compound: 240 mg $^1$H NMR (CHLOROFORM-D, 400 MHz): 8.62 (s, 1H), 8.29-8.34 (m, 1H), 7.78-7.82n (m, 1H), 7.61 (d, 1H), 7.45-7.51 (m, 2H), 7.41 (d, 1H), 7.34 (t, 1H), 7.17 (d, 1H), 6.76 (d, 1H), 4.30-4.53 (m, 6H), 4.20 (t, 1H), 3.91 (s, 3H), 3.79 (t, 2H), 3.39 (t, 1H), 3.05 (s, 3H), 2.29-2.37 (m, 2H), 2.10 (s, 3H), 1.34 (t, 3H).

LC-MS (Method 3): Rt=2.32 min, MS (ESIpos): 754 [M+H]$^+$.

Intermediate 131

(rac)-ethyl 4-chloro-11,11,12,12-tetrafluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate

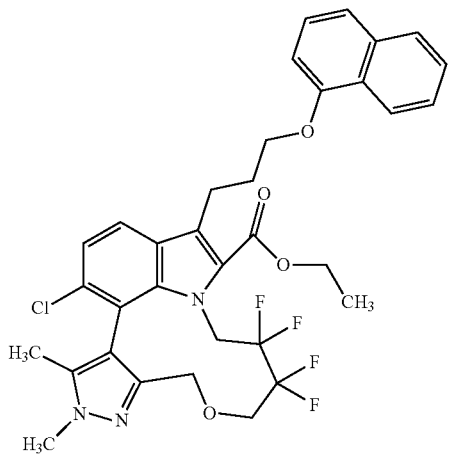 [SMILES: CCOC(=O)c1c(CCCOc2cccc3ccccc23)c2ccc(Cl)c3c2n1CC(F)(F)C(F)(F)COCc1nn(C)c(C)c1-3]

Ethyl 6-chloro-7-[1,5-dimethyl-3-({2,2,3,3-tetrafluoro-4-[(methanesulfonyl)oxy]butoxy}methyl)-1H-pyrazol-4-yl]-3-{3-[(naphthalen-1-yl)oxy]propyl}-1H-indole-2-carboxylate (see Intermediate 130, 240 mg, 318 µmol) and cesium carbonate (518 mg, 1.59 mmol) were dissolved in 150 mL DMF and stirred at 120° C. for 3.5 hour. The reaction mixture was cooled to RT, diluted with ethyl acetate, and filtered through Celite. Filtrate was diluted with water, and the layers separated. The aqueous layer was extracted twice further with ethyl acetate. Combined ethyl acetate extracts were washed with water (×3) and brine, dried over magnesium sulfate, and evaporated. Further purification by 5 g Si SPE cartridge, eluting with 8:2 heptane/ethyl acetate, gave 16 mg of the desired compound.

$^1$H NMR (CHLOROFORM-D, 300 MHz): 1.35 (t, 3H), 1.82 (s, 3H), 2.25-2.39 (m, 2H), 3.26-3.45 (m, 2H), 3.70-3.87 (m, 2H), 3.90 (s, 3H), 4.13-4.25 (m, 2H), 4.34 (q, 2H), 4.47-4.73 (m, 3H), 5.00 (qd, 1H), 6.74 (d, 1H), 7.20 (d, 1H), 7.34 (t, 1H), 7.42 (d, 1H), 7.46-7.53 (m, 2H), 7.63 (d, 1H), 7.77-7.84 (m, 1H), 8.33-8.40 (m, 1H).

LC-MS (Method 3): Rt=2.39 min, MS (ESIpos): 658 [M+H]$^+$.

Intermediate 132

2,2-difluoropent-4-en-1-ol

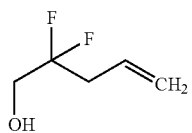

2,2-Difluoropent-4-enoic acid (CAS 55039-89-9, 20.0 g, 147 mmol) was added to a solution of lithium aluminum hydride (11.2 g, 294 mmol) in 400 mL diethyl ether at 0° C., stirred for 30 minutes and then warmed to room temperature and stirred for 2 hours. The reaction was quenched through the addition of water (11 mL), followed by aqueous sodium hydroxide solution (2M, 11 mL) followed by a further 30 mL of water and the slurry was stirred overnight, Magnesium sulfate was added and the reaction mixture was passed through celite and the solvent was removed under reduced pressure (300 mbar) to give the desired compound which was carried forward to the next step without further purification: 27 g.

$^1$H NMR (400 MHz, CHLOROFORM-D) δ [ppm]=2.68-2.81 (m, 2H), 3.70-3.88 (m, 2H), 5.23-5.29 (m, 2H), 5.76-5.85 (m, 1H)—OH not visible $^{19}$F NMR (376 MHz, CHLOROFORM-D) δ [ppm]= −107.89 (tt, 1F)

Intermediate 133 tert-butyl[(2,2-difluoropent-4-en-1-yl)oxy]diphenylsilane

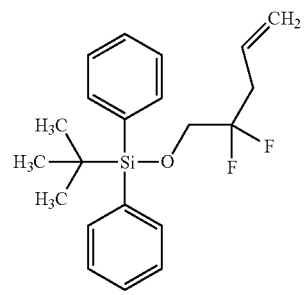 [SMILES: C=CCC(F)(F)CO[Si](c1ccccc1)(c1ccccc1)C(C)(C)C]

Tert-Butylchlorodiphenylsilane (24 ml, 92 mmol) was added to 2,2-difluoropent-4-en-1-ol (see Intermediate 132, 18.0 g), 4-dimethylaminopyridine (450 mg, 3.69 mmol) and N,N-diisopropylethylamine (77 ml, 440 mmol) in 1 L dichloromethane and stirred for 6 days at room temperature, with a further tert-butylchlorodiphenylsilane (24 ml, 92 mmol) added half way through, The reaction mixture was quenched with aqueous sodium bicarbonate and the organic layer was washed with water, dried over magnesium sulfate, filtered and concentrated under reduced pressure. The crude product was purified by flashchromatography (0-20% ethylacetate/heptane). to give 99 g of desired compound which was carried forward to the next step.

Intermediate 134

4-{[tert-butyl(diphenyl)silyl]oxy}-3,3-difluorobutan-1-ol

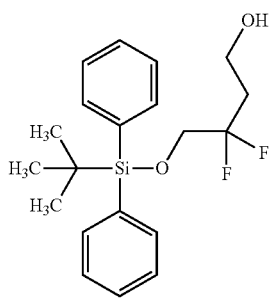 [SMILES: CC(C)(C)[Si](OCC(F)(F)CCO)(c1ccccc1)c1ccccc1]

Ozone was bubbled through a solution of tert-butyl[(2,2-difluoropent-4-en-1-yl)oxy]diphenylsilane (see Intermediate 133, 44.0 g, 50% purity) in 640 mL dichloromethane and 640 mL methanol for 2 hours at −78° C., The reaction mixture was then flushed with oxygen followed by argon and sodium borohydride (4.62 g, 122 mmol) was added to the reaction mixture. The reaction mixture was stirred for 1 hour at −78° C. then warmed to room temperature and stirred overnight. The solvent was removed under reduced pressure, The residue was dissolved in Ethyl acetate, washed with brine, dried over magnesium sulfate, filtered and the solvent was removed under reduced pressure. The residue was purified by flash chromatography (silica 1 kg, with 0-30% ethyl acetate in heptanes as eluent) to give the desired compound in 78% purity: 30 g, $^1$H-NMR (400 MHz, CHLOROFORM-D) δ [ppm]=1.06 (s, 9H), 1.73-2.01 (1H), 2.29 (tt, 2H), 3.79 (t, 2H), 3.89 (t, 2H), 7.38-7.47 (m, 6H), 7.64-7.68 (m, 4H).

$^{19}$F-NMR (376 MHz, CHLOROFORM-D) δ [ppm]= −104.96--105.11 (m, 2F)

Intermediate 135

4-bromo-3-[(4-{[tert-butyl(diphenyl)silyl]oxy}-3,3-difluorobutoxy)methyl]-1,5-dimethyl-1H-pyrazole

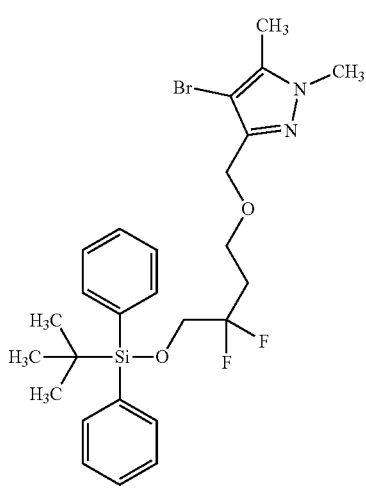 [SMILES: Cc1c(Br)c(COCCC(F)(F)CO[Si](c2ccccc2)(c2ccccc2)C(C)(C)C)nn1C]

Sodium hydride (1.64 g, 60% purity) was added to 4-{[tert-butyl(diphenyl)silyl]oxy}-3,3-difluorobutan-1-ol (see Intermediate 134, 13.0 g) in THF at 0° C. and stirred for 30 mins. 4-bromo-3-(bromomethyl)-1,5-dimethyl-1H-pyrazole (see Intermediate 105, 9.56 g) was added and the reaction was heated to 60° C. for 3 hours. The reaction mixture was cooled to room temperature, quenched by addition of methanol and taken to the next step without further purification.

Intermediate 136

4-[(4-bromo-1,5-dimethyl-1H-pyrazol-3-yl)methoxy]-2,2-difluorobutan-1-ol

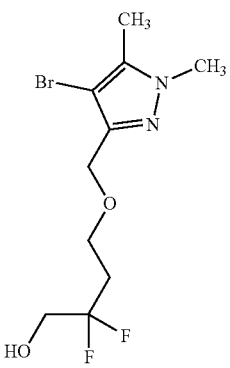 [SMILES: Cc1c(Br)c(COCCC(F)(F)CO)nn1C]

Tetra-n-butylammonium fluoride (71 ml, 1.0 M, 71 mmol) was added to 4-bromo-3-[(4-{[tert-butyl(diphenyl)silyl]oxy}-3,3-difluorobutoxy)methyl]-1,5-dimethyl-1H-pyrazole (see Intermediate 135, 19.7 g) dissolved in THF and stirred overnight at RT. The reaction mixture was heated to 60° C. for 5 hours and left to stand at rt overnight. Aqueous sodium bicarbonate solution was added The aqueous layer was extracted with ethyl acetate and the combined organic fractions were washed with brine, dried over magnesium sulfate and filtered through a plug of silica. The crude material was purified by flash chromatography eluting with 0-50% ethyl acetate in heptanes to give the desired compound: 7.04 g, in 80% purity.

Attempts were made to further purify the compound using the following however no separation was observed: Frist normal phase chromatography (Biotage isolera four, KP-Sil Sphere 120 g) eluting with 0-10% methanol in dichloromethane. And reverse phase chromatography (Biotage isolera one, C-18 60 g) with 10-100% acetonitrile with 0.1% formic acid in water.

All recovered material was combined into a single batch for purification and analysis to give 6.25 g in 81% purity.

$^1$H NMR (400 MHz, CHLOROFORM-D) δ [ppm]=2.19-2.31 (m, 5H), 2.49 (bs, 1H), 3.71-3.88 (m, 7H), 4.60 (s, 2H).

$^{19}$F NMR (376 MHz, CHLOROFORM-D) δ [ppm]= −102.25--102.07 (m, 2F).

Intermediate 137 ethyl 6-chloro-7-{3-[(3,3-difluoro-4-hydroxybutoxy)methyl]-1,5-dimethyl-1H-pyrazol-4-yl}-3-{3-[(naphthalen-1-yl)oxy]propyl}-1H-indole-2-carboxylate

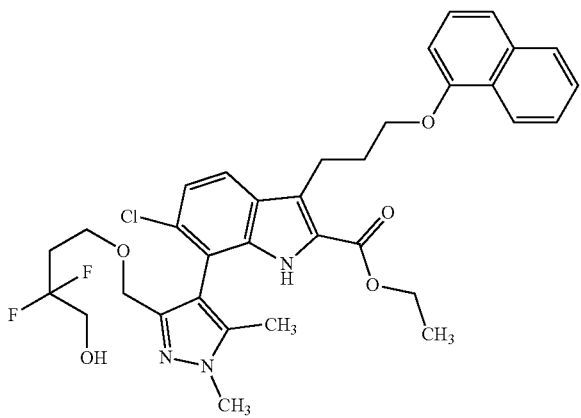 [SMILES: CCOC(=O)c1[nH]c2c(-c3c(COCCC(F)(F)CO)nn(C)c3C)c(Cl)ccc2c1CCCOc1cccc2ccccc12]

Ethyl 6-chloro-3-{3-[(naphthalen-1-yl)oxy]propyl}-7-(4,4,5,5-tetramethyl-1,3,2-dioxaborolan-2-yl)-1H-indole-2-carboxylate (see Intermediate 7, 710 mg) and 4-[(4-bromo-1,5-dimethyl-1H-pyrazol-3-yl)methoxy]-2,2-difluorobutan-1-ol (see Intermediate 136, 500 mg) were coupled under conditions described in Intermediate 109 with toluene/water instead of dioxane/water as solvent to provide the target compound: 280 mg with 96% purity.

$^1$H NMR (400 MHz, CHLOROFORM-D): δ [ppm]=1.38 (t, 3H), 1.98-2.11 (m, 5H), 2.32-2.41 (m, 2H), 2.51-3.20 (brs, 1H), 3.42 (t, 2H), 3.57-3.76 (m, 4H), 3.93 (s, 3H), 4.22 (t, 2H), 4.39-4.55 (m, 3H), 4.46 (d, 1H), 6.79 (d, 1H), 7.21 (d, 1H), 7.37 (t, 1H), 7.44 (d, 1H), 7.51-7.53 (m, 2H), 7.64 (d, 1H), 7.83-7.84 (m, 1H), 8.36 (d, 1H), 8.85 (s, 1H);

LCMS (Method 3): Rt=3.34 min., MS (ESIneg): m/z=638 (M-H)$^-$

Intermediate 138

(rac)-ethyl 4-chloro-11,11-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate

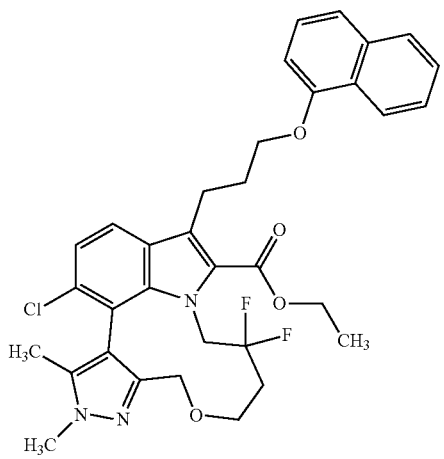 [SMILES: CCOC(=O)c1c(CCCOc2cccc3ccccc23)c2ccc(Cl)c3c2n1CC(F)(F)CCOCc1nn(C)c(C)c1-3]

Triphenylphosphine (918 mg, 3.50 mmol) followed by di-tert-butyl azodicarboxylate (806 mg, 3.50 mmol) was added to ethyl 6-chloro-7-{3-[(3,3-difluoro-4-hydroxybutoxy)methyl]-1,5-dimethyl-1H-pyrazol-4-yl}-3-{3-[(naphthalen-1-yl)oxy]propyl}-1H-indole-2-carboxylate (see intermediate 137, 280 mg) in 30 mL THF at rt and stirred for 96 hours, 4 mL of aqueous hydrochloric acid (4M, in dioxane) added and stirred for 2 hour. Saturated aqueous sodium bicarbonate was added to the reaction mixture. The aqueous layer was, extracted with ethyl acetate and the organic layer was washed with brine, dried over magnesium sulfate, filtered and the solvent was removed und reduced pressure. The crude material was purified by reverse phase chromatography (Biotage Isolera four, 60 g C-18) eluting with 30-100% acetonitrile with 0.1% formic acid in water to give the desired compound in 89% purity: 180 mg $^1$H NMR (400 MHz, CHLOROFORM-D) δ [ppm]=1.35-1.61 (m, 4H), 1.87 (s, 3H), 1.99-2.15 (m, 1H), 2.28-2.41 (m, 2H), 3.31-3.63 (m, 3H), 3.66 (t, 1H), 3.86 (t, 1H), 3.92 (s, 3H), 4.21-4.24 (m, 2H), 4.32-4.46 (m, 3H), 4.56-4.64 (m, 1H), 4.80 (d, 1H), 6.80 (d, 1H), 7.23 (d, 1H), 7.38 (t, 1H), 7.46 (d, 1H), 7.52-7.54 (m, 2H), 7.64 (d, 1H), 7.83-7.86 (m, 1H), 8.37-8.40 (m, 1H);

LCMS (Method 3): Rt=3.79 min., MS (ESIpos): m/z=622.17 (M+H)$^+$.

Intermediate 139

{1-[2-(benzyloxy)ethyl]cyclopropyl}methanol

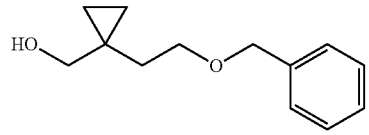 [SMILES: OCC1(CCOCc2ccccc2)CC1]

1-[2-(Benzyloxy)ethyl]cyclopropane-1-carboxylic acid (CAS 1803599-29-2, 2.00 g, 9.08 mmol) was dissolved in 20 mL of tetrahydrofuran, borane tetrahydrofuran complex solution in tetrahydrofuran (15 mL, 1.0 M, 15 mmol) was added dropwise and the mixture was stirred at room temperature for 70 hours. Saturated aqueous ammonium chloride solution was added, the formed precipitate was filtered off and washed with ethyl acetate. The layers of the filtrate were separated and the aqueous layer was extracted with ethyl acetate. The combined organic layers were washed with brine, dried using a water resistant filter and concentrated under reduced pressure to give 1.89 g of the title compound which was used without further purification.

LC-MS (Method 1): R$_t$=1.04 min; MS (ESIpos): m/z=207 [M+H]$^+$ $^1$H-NMR (400 MHz, DMSO-d6) δ[ppm]: 0.249 (1.90), 0.262 (4.42), 0.266 (6.03), 0.273 (5.22), 0.302 (5.27), 0.309 (6.37), 0.313 (4.68), 0.326 (1.97), 0.844 (0.66), 0.861 (1.73), 0.880 (0.90), 1.353 (0.67), 1.593 (3.96), 1.611 (7.79), 1.629 (4.15), 2.518 (1.12), 2.523 (0.71), 3.188 (8.32), 3.202 (8.47), 3.235 (1.29), 3.355 (0.53), 3.368 (0.43), 3.371 (0.66), 3.385 (0.67), 3.500 (5.26), 3.518 (9.63), 3.536 (5.22), 4.326 (0.73), 4.426 (3.13), 4.437 (16.00), 4.454 (2.64), 7.248 (0.40), 7.252 (0.79), 7.257 (0.53), 7.262 (0.58), 7.269 (2.56), 7.275 (0.97), 7.281 (0.92), 7.287 (1.75), 7.291 (2.91), 7.295 (2.81), 7.299 (1.55), 7.305 (1.26), 7.312 (7.73), 7.316 (4.67), 7.324 (5.86), 7.326 (6.75), 7.332 (1.58), 7.341 (3.85), 7.343 (4.86), 7.346 (2.54), 7.358 (0.68), 7.362 (1.54), 7.364 (0.95).

Intermediate 140

4-bromo-3-(bromomethyl)-5-ethyl-1-methyl-1H-pyrazole

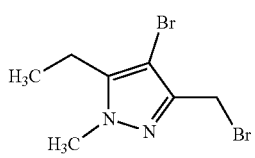

(4-Bromo-5-ethyl-1-methyl-1H-pyrazol-3-yl)methanol (see Intermediate 18, 10.0 g, 45.6 mmol) was dissolved in 100 mL of dichloromethane and phosphorous tribromide (CAS 7789-60-8, 4.3 mL, 45.6 mmol) was added dropwise. After stirring for 2 hours at room temperature the mixture was adjusted to a basic pH using saturated aqueous sodium bicarbonate solution. The layers were separated and the organic layer was washed with brine, dried over sodium sulfate, filtered and concentrated under reduced pressure to give 11.8 g of the title compound which was used without further purification.

LC-MS (Method 1): $R_t$=1.18 min; MS (ESIpos): m/z=281 [M+H]$^+$ $^1$H-NMR (400 MHz, DMSO-d6) δ[ppm]: 1.077 (2.97), 1.086 (0.43), 1.096 (6.96), 1.105 (0.73), 1.115 (3.08), 2.518 (0.69), 2.523 (0.51), 2.619 (0.87), 2.637 (2.81), 2.656 (2.79), 2.676 (0.93), 3.795 (16.00), 3.849 (1.29), 4.499 (9.75), 5.249 (0.69).

Intermediate 141

3-[({1-[2-(benzyloxy)ethyl]cyclopropyl}methoxy)methyl]-4-bromo-5-ethyl-1-methyl-1H-pyrazole

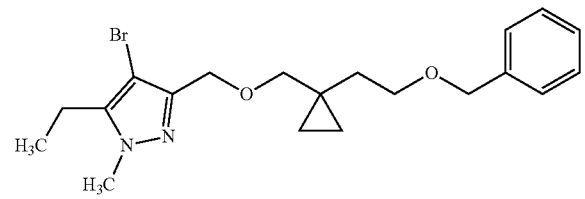 [SMILES: CCc1c(Br)c(COCC2(CCOCc3ccccc3)CC2)nn1C]

{1-[2-(Benzyloxy)ethyl]cyclopropyl}methanol (see Intermediate 139, 1.74 g) was dissolved in 25 mL of tetrahydrofuran and sodium hydride (602 mg, 55% purity, 13.8 mmol) was added portionwise. After three hours of stirring at room temperature N,N,N-tributylbutan-1-aminium iodide (100 mg, 383 μmol) and 4-bromo-3-(bromomethyl)-5-ethyl-1-methyl-1H-pyrazole (see Intermediate 140, 2.40 g) were added and stirring was continued for 72 hours. Water was added and the mixture was extracted with ethyl acetate. The combined organic layers were washed with brine, dried using a water resistant filter and concentrated under reduced pressure. The crude material was purified by flash chromatography using silica gel (gradient dichloromethane/ethanol) to give 3.18 g of the title compound.

LC-MS (Method 1): $R_t$=1.49 min; MS (ESIpos): m/z=407 [M+H]$^+$ $^1$H-NMR (400 MHz, DMSO-d6) δ[ppm]: 0.332 (12.66), 0.845 (0.66), 1.064 (2.97), 1.083 (7.02), 1.088 (1.31), 1.102 (3.13), 1.575 (1.42), 1.593 (3.06), 1.611 (1.81), 2.518 (1.22), 2.522 (0.81), 2.609 (0.89), 2.628 (2.94), 2.634 (0.66), 2.647 (2.87), 2.653 (0.62), 2.666 (0.99), 3.188 (0.43), 3.200 (7.10), 3.379 (0.45), 3.463 (1.64), 3.480 (3.44), 3.498 (1.68), 3.518 (0.46), 3.765 (16.00), 3.774 (1.77), 3.779 (0.73), 4.266 (8.33), 4.407 (6.30), 4.437 (0.87), 7.264 (1.14), 7.271 (0.62), 7.280 (1.86), 7.290 (0.81), 7.297 (3.42), 7.318 (2.91), 7.324 (1.04), 7.333 (1.67), 7.336 (2.14), 7.338 (1.51), 7.354 (0.78), 7.357 (0.56).

Intermediate 142 ethyl 7-{3-[({1-[2-(benzyloxy)ethyl]cyclopropyl}methoxy)methyl]-5-ethyl-1-methyl-1H-pyrazol-4-yl}-6-chloro-3-{3-[(naphthalen-1-yl)oxy]propyl}-1H-indole-2-carboxylate

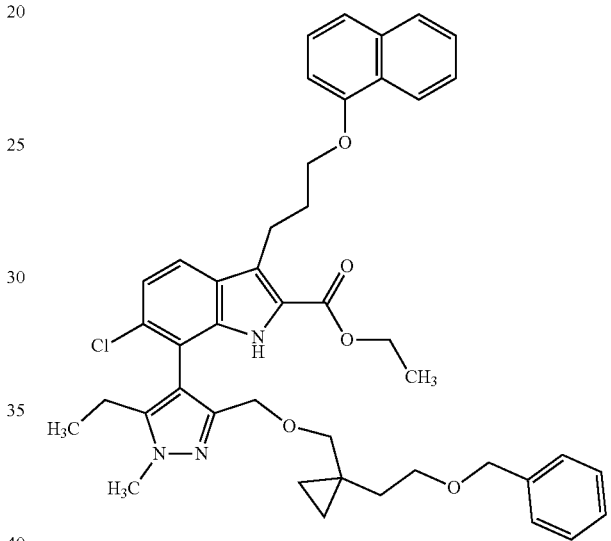

Ethyl-6-chloro-3-{3-[(naphthalen-1-yl)oxy]propyl}-7-(4,4,5,5-tetramethyl-1,3,2-dioxaborolan-2-yl)-1H-indole-2-carboxylate (see Intermediate 7, 1.52 g, 2.85 mmol), 3-[({1-[2-(benzyloxy)ethyl]-cyclopropyl}methoxy)methyl]-4-bromo-5-ethyl-1-methyl-1H-pyrazole (see Intermediate 141, 1.50 g) and potassium phosphate (1.21 g, 5.69 mmol) were suspended in a mixture of 8 mL of 1,4-dioxane and 5 mL of water. The mixture was purged with argon for 5 minutes, RuPhos Pd G3 (131 mg, 156 μmol) was added and the mixture was purged with argon for 5 minutes. The reaction mixture was stirred for 20 minutes at 110° C. in a microwave reactor, was diluted with water and extracted with ethyl acetate. The combined organic layers were washed with brine, dried using a water resistant filter and concentrated under reduced pressure. The crude material was purified by flash chromatography using silica gel (gradient hexane/ethyl acetate) to give 1.32 g of the title compound.

LC-MS (Method 2): $R_t$=1.87 min; MS (ESIpos): m/z=734 [M+H]$^+$ $^1$H-NMR (400 MHz, DMSO-d6) δ[ppm]: −0.077 (0.57), −0.071 (0.50), −0.052 (1.63), −0.026 (2.03), 0.000 (1.00), 0.020 (0.83), 0.043 (4.26), 0.337 (0.60), 0.345 (0.60), 0.614 (0.80), 0.632 (0.40), 0.865 (3.66), 0.884 (8.42), 0.895 (1.46), 0.902 (4.02), 1.082 (11.34), 1.151 (0.63), 1.170 (3.93), 1.188 (6.99), 1.206 (4.46), 1.213 (2.40), 1.230 (1.40), 1.242 (5.22), 1.260 (11.41), 1.273 (1.90), 1.278 (5.46), 1.291 (0.70), 1.608 (0.43), 2.003 (11.41), 2.191 (1.20), 2.207 (1.96), 2.224 (1.43), 2.241 (0.57), 2.313 (0.63), 2.331 (1.03), 2.339 (0.96), 2.343 (1.33), 2.349 (1.90), 2.369 (1.13), 2.422 (1.06), 2.441 (1.30), 2.459 (1.06), 2.478 (0.86), 2.539 (7.98), 2.567 (1.06), 2.586 (0.60), 2.681 (0.83), 2.685 (1.13), 2.690 (0.83), 2.880 (1.40), 2.905 (2.89), 2.937 (2.99), 2.962 (1.36), 3.145 (1.16), 3.151 (1.23), 3.162 (2.36), 3.168 (2.46), 3.179 (1.26), 3.185 (1.23), 3.200 (1.13), 3.264 (0.47), 3.279 (0.83), 3.297 (1.96), 3.315 (2.20), 3.507 (0.57), 3.669 (2.23), 3.824 (16.00), 3.835 (2.20), 3.959 (1.36), 4.016 (0.86), 4.033 (2.53), 4.051 (2.56), 4.069 (0.96), 4.109 (0.67), 4.139 (4.32), 4.144 (4.29), 4.166 (0.43), 4.173 (0.86), 4.187 (1.60), 4.203 (3.39), 4.218 (2.00), 4.232 (1.16), 4.237 (1.26), 4.253 (10.84), 4.267 (2.99), 4.272 (2.79), 4.279 (1.76), 4.284 (1.26), 4.299 (0.47), 4.432 (0.96), 5.962 (0.47), 6.896 (1.96), 6.914 (2.16), 7.154 (3.99), 7.164 (0.53), 7.175 (4.09), 7.186 (0.57), 7.200 (2.73), 7.217 (4.12), 7.220 (3.99), 7.231 (0.70), 7.239 (2.13), 7.245 (0.63), 7.253 (1.40), 7.257 (1.76), 7.281 (3.83), 7.296 (2.59), 7.300 (4.02), 7.316 (1.86), 7.320 (1.23), 7.337 (0.50), 7.378 (1.46), 7.398 (2.69), 7.418 (2.16), 7.463 (2.93), 7.484 (1.76), 7.494 (0.70), 7.498 (0.77), 7.511 (1.63), 7.515 (1.53), 7.526 (1.93), 7.531 (2.79), 7.535 (2.20), 7.545 (1.76), 7.550 (1.93), 7.562 (0.83), 7.566 (0.63), 7.689 (2.83), 7.710 (2.66), 7.874 (1.80), 7.880 (1.20), 7.892 (1.93), 7.897 (1.56), 8.232 (1.56), 8.236 (1.53), 8.254 (1.50), 10.852 (3.16).

Intermediate 143 ethyl 6-chloro-7-[5-ethyl-3-({[1-(2-hydroxyethyl)cyclopropyl]methoxy}methyl)-1-methyl-1H-pyrazol-4-yl]-3-{3-[(naphthalen-1-yl)oxy]propyl}-1H-indole-2-carboxylate

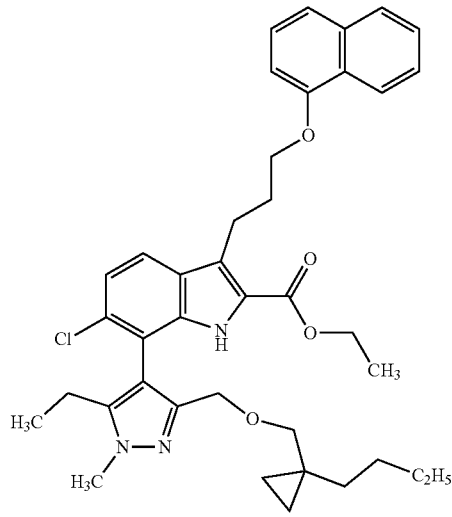 [SMILES: CCCCC1(COCc2nn(C)c(CC)c2-c2c(Cl)ccc3c(CCCOc4cccc5ccccc45)c(C(=O)OCC)[nH]c23)CC1]

Ethyl-7-{3-[({1-[2-(benzyloxy)ethyl]cyclopropyl}methoxy)methyl]-5-ethyl-1-methyl-1H-pyrazol-4-yl}-6-chloro-3-{3-[(naphthalen-1-yl)oxy]propyl}-1H-indole-2-carboxylate (see Intermediate 142, 1.30 g) was dissolved in 20 mL of tetrahydrofuran and palladium on carbon (188 mg, 10% purity, 177 μmol) was added. The mixture was stirred under hydrogen atmosphere for 5.5 hours and was filtered through a celite pad created with water. The layers of the filtrate were separated, the organic layer was dried using a water resistant filter and concentrated under reduced pressure. The crude material was purified by flash chromatography using silica gel (gradient dichloromethane/ethanol) to give 1.15 g of the title compound.

LC-MS (Method 2): $R_t$=1.67 min; MS (ESIpos): m/z=644 [M+H]$^+$ $^1$H-NMR (400 MHz, DMSO-d6) δ[ppm]: 0.000 (0.61), 0.005 (0.48), 0.842 (0.54), 0.861 (1.23), 0.880 (0.56), 1.027 (1.64), 1.044 (3.94), 1.057 (0.96), 1.062 (1.74), 1.233 (0.73), 1.251 (1.60), 1.269 (0.73), 2.075 (0.92), 2.509 (0.55), 2.887 (0.43), 2.913 (0.44), 3.414 (0.63), 3.427 (0.65), 3.431 (0.69), 3.444 (0.70), 3.808 (2.44), 4.089 (0.49), 4.108 (0.48), 4.132 (0.49), 4.196 (0.43), 4.243 (0.57), 4.261 (0.53), 4.349 (0.76), 5.749 (16.00), 7.134 (0.57), 7.155 (0.57), 7.515 (0.51).

Intermediate 144

(rac)-ethyl 4'-chloro-3'-ethyl-2'-methyl-7'-{3-[(naphthalen-1-yl)oxy]propyl}-2',10',11',15'-tetrahydro-13'H-spiro[cyclopropane-1,12'-pyrazolo[4',3':9,10][1,6]oxazacycloundecino[8,7,6-hi]indole]-8'-carboxylate

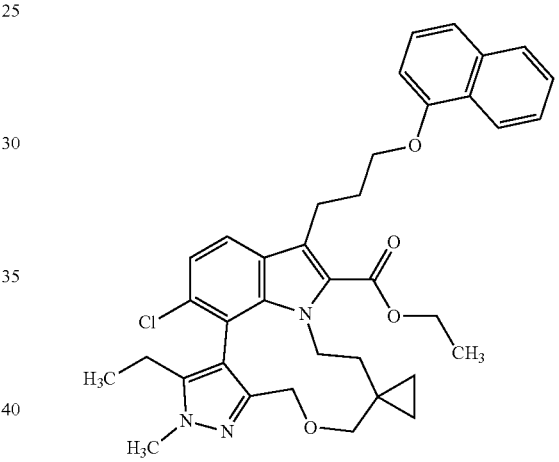

Ethyl-6-chloro-7-[5-ethyl-3-({[1-(2-hydroxyethyl)cyclopropyl]methoxy}methyl)-1-methyl-1H-pyrazol-4-yl]-3-{3-[(naphthalen-1-yl)oxy]propyl}-1H-indole-2-carboxylate (see Intermediate 143, 950 mg) was dissolved in 15 mL of tetrahydrofuran. Diisopropyl azodicarboxylate (2.17 g, 9.44 mmol) and triphenylphosphine (2.48 g, 9.44 mmol) were added and the mixture was stirred for 24 hours at room temperature. The reaction mixture was diluted with water and extracted with ethyl acetate. The combined organic layers were washed with brine, dried using a water resistant filter and concentrated under reduced pressure. The crude material was purified by flash chromatography using silica gel (gradient hexane/ethyl acetate) to give 812 mg of the title compound.

LC-MS (Method 2): $R_t$=1.78 min; MS (ESIpos): m/z=626 [M+H]$^+$ $^1$H-NMR (400 MHz, DMSO-d6) δ[ppm]: 0.000 (0.81), 0.080 (0.40), 0.090 (0.84), 0.104 (1.12), 0.125 (1.06), 0.142 (0.94), 0.153 (0.57), 0.166 (0.83), 0.174 (0.88), 0.187 (0.81), 0.196 (0.45), 0.784 (0.45), 0.798 (0.55), 0.822 (3.38), 0.841 (7.25), 0.860 (3.21), 1.191 (3.64), 1.201 (1.17), 1.209 (6.97), 1.227 (3.32), 1.240 (0.51), 1.270 (4.73), 1.288 (10.27), 1.306 (4.87), 1.350 (0.43), 1.401 (2.18), 1.422 (11.76), 1.447 (1.11), 1.456 (1.35), 1.475 (0.80), 1.536 (0.64), 1.543 (0.43), 2.024 (11.50), 2.124 (0.40), 2.142 (0.71), 2.160 (1.24), 2.169 (0.52), 2.179 (1.17), 2.189 (1.21), 2.207 (1.41), 2.226 (1.43), 2.245 (1.43), 2.263 (0.84), 2.369 (0.68), 2.555 (4.96), 2.559 (2.58), 2.580 (1.72), 2.711 (0.71), 3.281 (0.66), 3.299 (1.04), 3.325 (1.14), 3.344 (0.80), 3.510 (1.23), 3.535 (1.14), 3.897 (16.00), 3.974 (0.43), 4.001 (0.88), 4.028 (0.57), 4.037 (1.20), 4.054 (2.50), 4.072 (2.52), 4.090 (0.84), 4.185 (0.48), 4.203 (3.38), 4.213 (1.24), 4.222 (2.93), 4.234 (4.41), 4.248 (2.90), 4.258 (0.97), 4.266 (1.15), 4.283 (0.54), 4.305 (0.68), 4.323 (1.57), 4.332 (0.43), 4.340 (1.47), 4.350 (1.07), 4.358 (0.48), 4.368 (1.06), 4.513 (2.26), 4.544 (1.93), 6.917 (1.78), 6.935 (1.95), 7.264 (3.93), 7.285 (4.04), 7.401 (1.34), 7.421 (2.50), 7.441 (1.93), 7.489 (2.58), 7.510 (1.55), 7.537 (0.52), 7.550 (1.64), 7.554 (2.95), 7.564 (3.19), 7.573 (3.07), 7.578 (1.92), 7.590 (0.61), 7.800 (3.44), 7.821 (3.04), 7.898 (1.49), 7.902 (1.12), 7.909 (0.78), 7.913 (0.95), 7.916 (1.04), 7.921 (1.26), 8.251 (1.27), 8.259 (0.95), 8.276 (1.21), 8.635 (1.01).

Intermediate 145

(rac)-ethyl 4-chloro-14-(2,2-difluoroethyl)-7-{3-[(6-fluoronaphthalen-1-yl)oxy]propyl}-2,3-dimethyl-10,11,12,13,14,15-hexahydro-2H-pyrazolo[3',4':8,9][1,6]diazacycloundecino[10,11,1-hi]indole-8-carboxylate

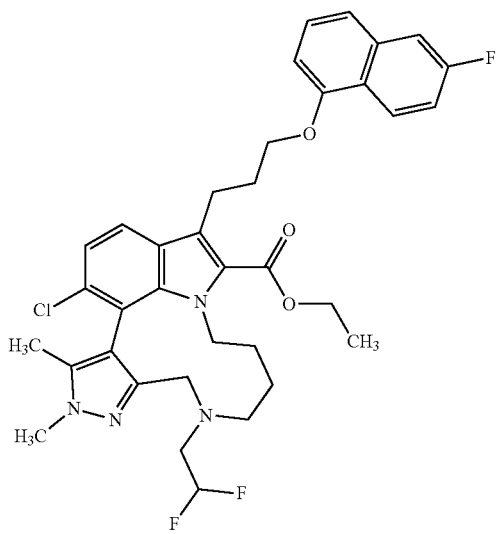 [SMILES: CCOC(=O)c1c(CCCOc2cccc3cc(F)ccc23)c2ccc(Cl)c3c2n1CCCCN(CC(F)F)Cc1nn(C)c(C)c1-3]

(rac)-Ethyl 4-chloro-7-{3-[(6-fluoronaphthalen-1-yl)oxy]propyl}-2,3-dimethyl-10,11,12,13,14,15-hexahydro-2H-pyrazolo[3',4':8,9][1,6]diazacycloundecino[10,11,1-hi]indole-8-carboxylate (see Intermediate 103, 25.0 mg) was dissolved in 160 μL dimethylformamide, treated with N,N-diisopropylethylamine (16 μL, 92 μmol) and the sulfo 2,2-difluoroethyl trifluoromethanesulfonate (6.1 μL, 46 μmol) was added. The reaction mixture was stirred at room temperature under Ar atmosphere for 1.5 hours. The reaction mixture was diluted with water and dichloromethane, stirred, filtered through a silicone coated filter and concentrated under reduced pressure to provide the 80% pure crude product which was used without further purification. 27 mg.

LC-MS (Method 2): $R_t$=1.75 min; MS (ESIpos): m/z=668 [M+H]$^+$

Intermediate 146

4-bromo-3-{[(2,2-difluoropent-4-en-1-yl)oxy]methyl}-5-ethyl-1-methyl-1H-pyrazole

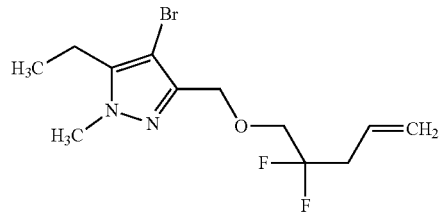 [SMILES: C=CCC(F)(F)COCc1nn(C)c(CC)c1Br]

2,2-Difluoropent-4-en-1-ol (see Intermediate 106, 2.45 g) was dissolved in 50 mL of tetrahydrofuran, sodium hydride (1.21 g, 55% purity, 27.8 mmol) was added portionwise at 0° C. and the mixture was stirred for 10 minutes. 4-Bromo-3-(bromomethyl)-5-ethyl-1-methyl-1H-pyrazole (see Intermediate 140, 4.35 g) was added and the mixture was stirred overnight at 60° C. After cooling to 5° C. water was added and the mixture was extracted with ethyl acetate. The combined organic layers were washed with brine, dried over sodium sulfate, filtered and concentrated under reduced pressure. The crude material was purified by flash chromatography using silica gel (gradient hexane/ethylacetate) to provide 2.36 g of the title compound.

LC-MS (Method 1): $R_t$=1.33 min; MS (ESIpos): m/z=323 [M+H]$^+$ $^1$H-NMR (400 MHz, CHLOROFORM-d) δ [ppm]: 1.092 (3.30), 1.111 (7.35), 1.130 (3.51), 1.191 (0.56), 1.522 (4.59), 1.978 (0.98), 2.580 (1.12), 2.599 (3.82), 2.618 (3.74), 2.637 (1.16), 2.640 (0.86), 2.643 (1.17), 2.658 (0.71), 2.661 (1.11), 2.685 (0.54), 2.702 (0.54), 3.561 (2.11), 3.592 (4.25), 3.622 (2.09), 3.751 (16.00), 4.477 (7.44), 5.104 (0.63), 5.106 (0.79), 5.109 (0.77), 5.129 (1.35), 5.131 (1.48), 5.171 (0.80), 5.174 (0.75), 5.675 (0.69), 5.700 (0.90), 5.718 (0.86), 5.743 (0.57).

Intermediate 147

4-[(4-bromo-5-ethyl-1-methyl-1H-pyrazol-3-yl)methoxy]-3,3-difluorobutan-1-ol

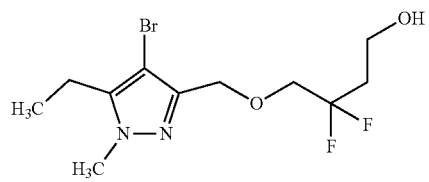 [SMILES: CCc1c(Br)c(COCC(F)(F)CCO)nn1C]

4-Bromo-3-{[(2,2-difluoropent-4-en-1-yl)oxy]methyl}-5-ethyl-1-methyl-1H-pyrazole (see Intermediate 146, 2.36 g) was dissolved in 50 mL of dichloromethane and 50 mL of methanol and the mixture was treated with ozone at −75° C. for 15 minutes. Sodium borohydride (553 mg, 14.6 mmol) was added and the mixture was allowed to warm to room temperature. Water was added and the mixture was concentrated under reduced pressure. The residue was dissolved in ethyl acetate und washed with water. The organic

327 layer was dried over sodium sulfate, filtered and concentrated under reduced pressure to give 2.17 g of the title compound.

LC-MS (Method 1): R$_t$=1.01 min; MS (ESIpos): m/z=327 [M+H]$^+$ $^1$H-NMR (400 MHz, CHLOROFORM-d) δ [ppm]: 1.092 (3.45), 1.111 (7.19), 1.130 (3.43), 1.962 (0.41), 1.978 (0.76), 2.124 (0.46), 2.138 (0.69), 2.153 (0.50), 2.166 (0.88), 2.179 (1.32), 2.195 (0.90), 2.207 (0.45), 2.221 (0.66), 2.236 (0.45), 2.579 (1.13), 2.598 (3.56), 2.617 (3.48), 2.636 (1.04), 3.653 (1.88), 3.684 (3.77), 3.715 (1.89), 3.749 (3.02), 3.755 (16.00), 3.764 (3.30), 3.778 (2.36), 4.512 (7.32).

Intermediate 148 ethyl 6-chloro-7-{3-[(2,2-difluoro-4-hydroxybutoxy)methyl]-5-ethyl-1-methyl-1H-pyrazol-4-yl}-3-{3-[(6-fluoronaphthalen-1-yl)oxy]propyl}-1H-indole-2-carboxylate

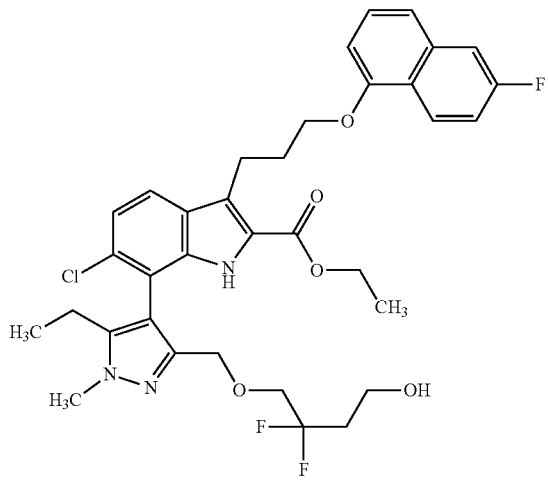 [SMILES: CCOC(=O)c1[nH]c2c(-c3c(COCC(F)(F)CCO)nn(C)c3CC)c(Cl)ccc2c1CCCOc1cccc2cc(F)ccc12]

A first batch of ethyl-6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 9, 100 mg), 4-[(4-bromo-5-ethyl-1-methyl-1H-pyrazol-3-yl)methoxy]-3,3-difluorobutan-1-ol (see Intermediate 147, 65.2 mg) and potassium phosphate (76.9 mg, 0.36 mmol) were suspended in a mixture of 2.5 mL of 1,4-dioxane and 0.5 mL of water. RuPhos Pd G3 (7.6 mg, 9.1 μmol) was added and the mixture was purged with argon for 20 minutes and stirred for 20 minutes at 110° C. in a microwave reactor. A second batch of ethyl-6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 9, 1.00 g), 4-[(4-bromo-5-ethyl-1-methyl-1H-pyrazol-3-yl)methoxy]-3,3-difluorobutan-1-ol (see Intermediate 147, 622 mg) and potassium phosphate (769 mg, 3.62 mmol) were suspended in a mixture of 10 mL of 1,4-dioxane and 2 mL of water. RuPhos Pd G3 (75.8 mg, 90.6 μmol) was added and the mixture was purged with argon for 20 minutes and stirred for 20 minutes at 110° C. in a microwave reactor. The combined mixtures were diluted with water and the organic layer was separated and concentrated under reduced pressure. The crude material was purified by flash chromatography using silica gel (gradient dichloromethane/ethanol) to give 1.16 g of the title compound.

328

LC-MS (Method 1): R$_t$=1.66 min; MS (ESIpos): m/z=672 [M+H]$^+$ $^1$H-NMR (400 MHz, DMSO-d6) δ[ppm]: 0.859 (1.06), 0.878 (2.47), 0.897 (1.09), 1.035 (5.33), 1.053 (12.41), 1.066 (16.00), 1.071 (5.92), 1.078 (1.13), 1.097 (2.49), 1.116 (1.07), 1.156 (2.83), 1.228 (1.54), 1.245 (3.23), 1.263 (1.50), 2.064 (0.61), 2.518 (0.85), 2.523 (0.65), 2.645 (0.98), 2.664 (1.12), 3.304 (0.74), 3.309 (0.62), 3.321 (1.04), 3.327 (1.20), 3.402 (0.53), 3.405 (1.17), 3.418 (1.42), 3.423 (2.83), 3.436 (3.00), 3.440 (2.68), 3.452 (2.84), 3.457 (0.97), 3.470 (0.95), 3.528 (0.45), 3.532 (0.85), 3.546 (0.84), 3.549 (0.43), 3.563 (0.43), 3.638 (0.52), 3.672 (1.17), 3.679 (0.60), 3.706 (0.47), 3.792 (5.60), 3.838 (4.80), 3.940 (2.86), 4.188 (0.42), 4.203 (0.88), 4.221 (0.71), 4.236 (1.89), 4.239 (1.88), 4.257 (1.28), 4.347 (1.95), 4.359 (3.80), 4.372 (1.89), 4.419 (2.41), 4.480 (0.57), 4.492 (1.24), 4.506 (0.54), 4.657 (0.45), 4.670 (0.92), 7.152 (1.23), 7.174 (1.23), 7.401 (0.41), 7.408 (0.46), 7.435 (0.76), 7.442 (0.81), 7.449 (1.76), 7.650 (0.47), 7.656 (0.48), 7.676 (0.48), 7.682 (0.48), 7.690 (0.81), 7.712 (0.72), 8.273 (0.40), 10.954 (0.82).

Intermediate 149

(rac)-ethyl 4-chloro-3-ethyl-12,12-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylate

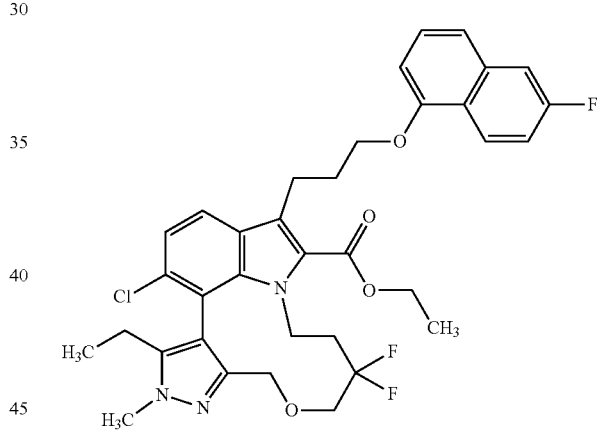

A first batch of ethyl 6-chloro-7-{3-[(2,2-difluoro-4-hydroxybutoxy)methyl]-5-ethyl-1-methyl-1H-pyrazol-4-yl}-3-{3-[(6-fluoronaphthalen-1-yl)oxy]propyl}-1H-indole-2-carboxylate (see Intermediate 148, 200 mg) was dissolved in 25 mL of THF. Triphenylphosphine (624 mg, 2.38 mmol) and di-tert-butyl azodicarboxylate (548 mg, 2.38 mmol) were added and the mixture was stirred at rt for 16 hours. A second batch of ethyl 6-chloro-7-{3-[(2,2-difluoro-4-hydroxybutoxy)methyl]-5-ethyl-1-methyl-1H-pyrazol-4-yl}-3-{3-[(6-fluoronaphthalen-1-yl)oxy]propyl}-1H-indole-2-carboxylate (see Intermediate 148, 910 mg) was dissolved in 60 mL of THF. Triphenylphosphine (2.84 g, 10.8 mmol) and di-tert-butyl azodicarboxylate (2.49 g, 10.8 mmol) were added and the mixture was stirred at rt for 16 hours. The combined reaction mixtures were diluted with water and extracted with ethyl acetate. The combined organic layers were dried over sodium sulfate, filtered and concentrated under reduced pressure. The crude material was purified by flash chromatography using silica gel (gradient hexane/ethylacetate) to give 787 mg of the title compound.

LC-MS (Method 1): R$_t$=1.78 min; MS (ESIpos): m/z=654 [M+H]$^+$ $^1$H-NMR (400 MHz, DMSO-d6) δ[ppm]: 0.762 (1.55), 0.781 (3.71), 0.800 (1.62), 1.074 (0.67), 1.093 (1.49), 1.112 (0.74), 1.154 (4.21), 1.171 (8.78), 1.189 (4.41), 1.264 (2.46), 1.282 (5.21), 1.299 (2.52), 1.360 (1.58), 1.385 (2.16), 1.393 (2.22), 1.407 (3.58), 1.431 (4.80), 1.503 (0.77), 1.506 (0.95), 1.986 (16.00), 2.025 (1.94), 2.135 (0.79), 2.144 (0.73), 2.153 (0.73), 2.162 (0.74), 2.206 (0.50), 2.223 (0.73), 2.239 (0.50), 2.518 (1.08), 2.523 (0.76), 2.536 (1.62), 2.642 (0.71), 2.661 (0.78), 3.285 (0.52), 3.301 (1.04), 3.634 (0.41), 3.642 (0.54), 3.672 (0.46), 3.751 (0.65), 3.791 (3.88), 3.884 (7.74), 3.999 (1.17), 4.017 (3.54), 4.034 (3.52), 4.052 (1.16), 4.198 (0.60), 4.213 (1.22), 4.228 (0.62), 4.233 (0.73), 4.251 (0.49), 4.260 (0.80), 4.278 (0.82), 4.311 (1.04), 4.315 (1.09), 4.329 (0.82), 4.338 (0.52), 4.347 (1.37), 4.355 (0.49), 4.417 (1.09), 4.432 (1.15), 4.555 (0.66), 4.587 (0.52), 6.870 (0.62), 6.876 (0.65), 6.885 (0.59), 6.892 (0.66), 7.292 (1.88), 7.313 (1.98), 7.362 (0.41), 7.369 (0.45), 7.385 (0.67), 7.392 (0.72), 7.407 (0.68), 7.414 (0.52), 7.428 (1.11), 7.439 (1.33), 7.444 (2.67), 7.643 (0.74), 7.649 (0.76), 7.669 (0.74), 7.675 (0.73), 7.818 (1.71), 7.839 (1.51), 8.191 (0.64), 8.206 (0.67), 8.214 (0.65), 8.229 (0.62).

Intermediate 150

3-(bromomethyl)-1,5-dimethyl-1H-pyrazole

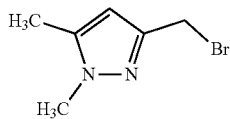

(1,5-Dimethyl-1H-pyrazol-3-yl)methanol (CAS 153912-60-8, 500 mg, 3.96 mmol) was dissolved in 50 mL dichloromethane and cooled to 0° C. At this temperature phosphorous tribromide (5.2 mL, 1.0 M in dichloromethane, 5.2 mmol) was added and the mixture stirred overnight at 0° C. to rt. Further phosphorous tribromide (2 mL, 1.0 M in dichloromethane, 2 mmol) was added and stirred at 35° C. over night. The pH was adjusted to basic by addition of sodium hydroxide solution (2M in water). The aqueous layer was extracted by dichloromethane. The organic layer was washed with water and brine, filtered through a water resistant filter and concentrated under reduced pressure. The crude product (88% pure) was used without further purification: 673 mg.

LC-MS (Method 2): R$_t$=1.88 min; MS (ESIpos): m/z=191 [M+H]$^+$ $^1$H-NMR (400 MHz, DMSO-d6) δ[ppm]: 2.204 (9.19), 2.257 (1.92), 2.280 (1.37), 2.518 (2.66), 2.523 (1.69), 3.674 (16.00), 3.737 (3.22), 3.766 (2.12), 4.517 (9.32), 5.199 (1.72), 5.344 (1.06), 6.080 (2.23), 6.203 (0.50).

Intermediate 151

1,5-dimethyl-3-[(2-{[(2rac)-oxan-2-yl]oxy}ethoxy) methyl]-1H-pyrazole

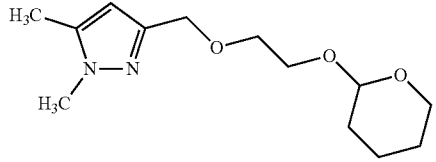 [SMILES: Cc1cc(COCCOC2CCCCO2)nn1C]

2-{[(2rac)-Oxan-2-yl]oxy}ethan-1-ol (CAS: 2162-31-4, 0.2 ml, 8.7 mmol) was dissolved in 11 mL dimethyl formamide and treated with sodium hydride (582 mg, 60% purity, 14.5 mmol). The reaction mixture was stirred for 15 min at rt. 3-(Bromomethyl)-1,5-dimethyl-1H-pyrazole (see Intermediate 150, 550 mg, 2.91 mmol) was added and the reaction mixture was stirred under nitrogen atmosphere at 65° C. over the weekend. The reaction mixture was carefully poured into water and concentrated under reduced pressure. Water was added. The aqueous layer was extracted with ethyl acetate thrice. The combined organic layers were washed with brine, filtered through a water resistant filter and concentrated under reduced pressure. The crude product was purified by flash chromatography (Biotage 50 g ultra silica, 0-5% to 50-100% dichloromethane/ethanol) to provide the target compound in 91% purity: 326 mg.

LC-MS (Method 2): R$_t$=0.90 min; MS (ESIpos): m/z=256 [M+H]$^+$ $^1$H-NMR (400 MHz, DMSO-d6): δ [ppm]=1.33-1.52 (m, 4H), 1.52-1.84 (m, 2H), 2.21 (s, 3H), 3.35-3.57 (m, 4H), 3.61-3.81 (m, 5H), 4.31 (s, 2H), 4.56 (t, 1H), 5.98 (s, 1H).

Intermediate 152

4-bromo-1,5-dimethyl-3-[(2-{[(2rac)-oxan-2-yl] oxy}ethoxy)methyl]-1H-pyrazole

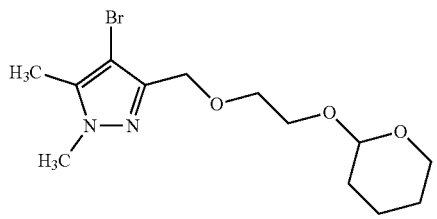 [SMILES: Cc1c(Br)c(COCCOC2CCCCO2)nn1C]

1,5-Dimethyl-3-[(2-{[(2rac)-oxan-2-yl]oxy}ethoxy) methyl]-1H-pyrazole (see Intermediate 151, 300 mg) was dissolved in 2.3 mL dichloroethane and was cooled down to 0° C. N-Bromosuccinimide (210 mg, 1.18 mmol) was added portionwise. The reaction mixture was stirred at 80° C. for 2 h. The reaction mixture was diluted with dichloromethane and aqueous sodium thiosulfate solution (50%) was added. The aqueous layer was extracted with dichloromethane twice. The combined organic layers were washed with water and brine, filtered through a water resistant filter and concentrated under reduced pressure The crude product was purified by basic HPLC (Chromatorex C-18 10 μm; 125*30 mm) to provide the analytically pure target compound: 300 mg.

LC-MS (Method 2): $R_t$=1.08 min; MS (ESIneg): m/z=331 [M−H]⁻

¹H-NMR (400 MHz, DMSO-d6): δ [ppm]=1.38-1.53 (m, 4H), 1.54-1.77 (m, 2H), 2.22 (s, 3H), 3.37-3.43 (m, 1H), 3.43-3.50 (m, 1H), 3.51-3.55 (m, 2H), 3.64-3.78 (m, 5H), 4.33 (s, 2H), 4.56 (t, 1H).

Intermediate 153 ethyl 6-chloro-7-{1,5-dimethyl-3-[(2-{[(2rac)-oxan-2-yl]oxy}ethoxy)methyl]-1H-pyrazol-4-yl}-3-{3-[(naphthalen-1-yl)oxy]propyl}-1H-indole-2-carboxylate

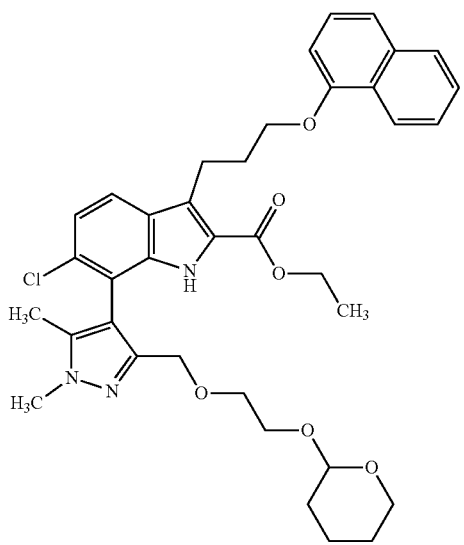 [SMILES: CCOC(=O)c1[nH]c2c(-c3c(COCCOC4CCCCO4)nn(C)c3C)c(Cl)ccc2c1CCCOc1cccc2ccccc12]

Ethyl 6-chloro-3-{3-[(naphthalen-1-yl)oxy]propyl}-7-(4,4,5,5-tetramethyl-1,3,2-dioxaborolan-2-yl)-1H-indole-2-carboxylate (see Intermediate 7, 481 mg), 4-bromo-1,5-dimethyl-3-[(2-{[(2rac)-oxan-2-yl]oxy}ethoxy)methyl]-1H-pyrazole (see Intermediate 152, 300 mg) and potassium phosphate (382 mg, 1.80 mmol) were dissolved in 9 mL toluole and 4 mL water and nitrogen was lead through for 5 minutes. RuPhos-Pd-G3 (41.4 mg, 49.5 μmol) was added and again nitrogen was lead through the solution for 5 minutes. The reaction mixture stirred for 1 h under nitrogen atmosphere at 110° C. The reaction mixture was filtered through a silicone coated filter and the filtrate was concentrated under reduced pressure. The crude product was purified by HPLC (Chromatorex C-18 10 μm; 125*30 mm) to provide the target compound in 94% purity: 222 mg.

LC-MS (Method 2): $R_t$=1.73 min; MS (ESIneg): m/z=661/663 [M−H]⁺

¹H-NMR (400 MHz, DMSO-d6): δ [ppm]=1.17-1.48 (m, 8H), 1.49-1.62 (m, 1H), 1.98 (s, 3H), 2.16-2.27 (m, 2H), 3.09-3.19 (m, 1H), 3.20-3.31 (m, 4H), 3.35-3.60 (m, 3H), 3.80 (s, 3H), 4.10-4.36 (m, 7H), 6.91 (d, 1H), 7.17 (dd, 1H), 7.35-7.42 (m, 1H), 7.44-7.47 (m, 1H), 7.47-7.56 (m, 2H), 7.71 (d, 1H), 7.84-7.93 (m, 1H), 8.15-8.27 (m, 1H), 10.74 (d, 1H).

Intermediate 154 ethyl 6-chloro-7-{3-[(2-hydroxyethoxy)methyl]-1,5-dimethyl-1H-pyrazol-4-yl}-3-{3-[(naphthalen-1-yl)oxy]propyl}-1H-indole-2-carboxylate

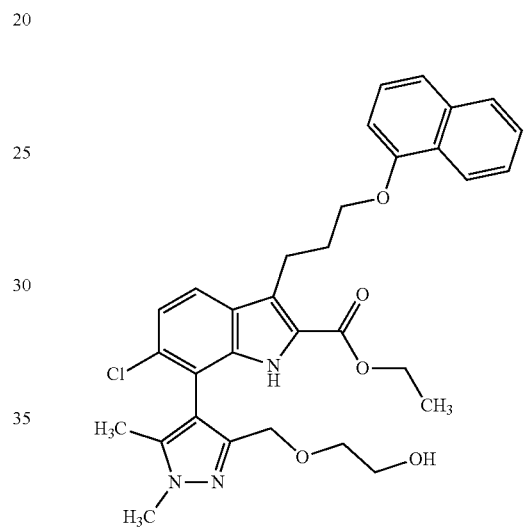

Ethyl 6-Chloro-7-{1,5-dimethyl-3-[(2-{[(2rac)-oxan-2-yl]oxy}ethoxy)methyl]-1H-pyrazol-4-yl}-3-{3-[(naphthalen-1-yl)oxy]propyl}-1H-indole-2-carboxylate (see Intermediate 153, 170 m) was dissolved in 4.2 mL THF and treated with hydrochloric acid (320 μL, 2.0 M in dioxane, 640 μmol). The reaction mixture was stirred at room temperature for 7 hours. The pH was adjusted to 8 by addition of sodium hydroxide solution (2M in water). Then the mixture was diluted with ethyl acetate and it was stirred for a few minutes. The organic layer was filtered through a silicone coated filter and concentrated under reduced pressure. The crude product was combined with the crude product of the former preparation (0.076 mmol starting material) to provide the 171 mg, which were used without further purification.

LC-MS (Method 2): $R_t$=1.57 min; MS (ESIpos): m/z=576 [M+H]⁺

¹H-NMR (400 MHz, DMSO-d6): δ [ppm]=1.26 (t, 3H), 1.55-1.64 (m, 1H), 1.68-1.79 (m, 1H), 1.99 (s, 3H), 2.15-2.27 (m, 2H), 3.17-3.28 (m, 4H), 3.29-3.40 (m, 1H), 3.77-3.88 (m, 2H), 4.11-4.31 (m, 6H), 4.36-4.44 (m, 1H), 6.91 (d, 1H), 7.17 (d, 1H), 7.35-7.43 (m, 1H), 7.44-7.48 (m, 1H), 7.48-7.58 (m, 2H), 7.71 (d, 1H), 7.84-7.91 (m, 1H), 8.22 (dd, 1H), 10.70 (s, 1H).—contains ethyl acetate and 3,4-dihydro-2H-pyran Intermediate 155

(Rac)-ethyl 11-chloro-9,10-dimethyl-1-{3-[(naphthalen-1-yl)oxy]propyl}-4,5,7,9-tetrahydropyrazolo[4',3':7,8][1,4]oxazonino[6,5,4-hi]indole-2-carboxylate

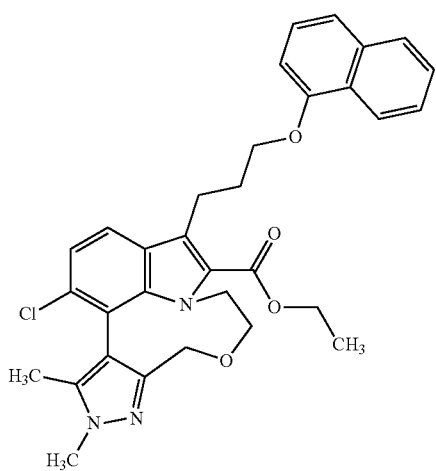 [SMILES: CCOC(=O)c1c(CCCOc2cccc3ccccc23)c2ccc(Cl)c3c2n1CCOCc1nn(C)c(C)c1-3]

Triphenylphosphine (776 mg, 2.96 mmol) followed by di-tert-butyl azodicarboxylte (681 mg, 2.96 mmol) were added to ethyl 6-chloro-7-{3-[(2-hydroxyethoxy)methyl]-1,5-dimethyl-1H-pyrazol-4-yl}-3-{3-[(naphthalen-1-yl)oxy]propyl}-1H-indole-2-carboxylate (see Intermediate 154, 213 mg) in 26 mL THF at rt and stirred for 16 h. Hydrochloric acid (0.8 mL, 4M in dioxane) were added and stirred for 1 h. The reaction mixture was concentrated under reduced pressure. The residue was dissolved in ethyl acetate, washed with saturated aqueous sodium bicarbonate solution and brine, filtered through a silicone coated filter and the solvent was removed under reduced pressure. The crude product was purified by flash chromatography (100 g column, silica phase; dichloromethane/ethanol 9/1) and by HPLC (Chromatorex C-18 10 µm; 125*30 mm) to provide the analytically pure target compound: 137 mg.

LC-MS (Method 2): $R_t$=1.67 min; MS (ESIpos): m/z=559 [M+H]$^+$ $^1$H-NMR (400 MHz, DMSO-d6): δ [ppm]=1.27 (t, 3H), 1.33-1.47 (m, 2H), 2.01 (s, 3H), 2.19 (quin, 2H), 3.24-3.30 (m, 1H), 3.59 (dd, 1H), 3.80 (s, 3H), 3.82-3.92 (m, 1H), 4.11-4.29 (m, 4H), 4.35 (d, 1H), 4.53 (dd, 1H), 4.59 (d, 1H), 6.93 (d, 1H), 7.20 (d, 1H), 7.37-7.44 (m, 1H), 7.45-7.58 (m, 3H), 7.73 (d, 1H), 7.84-7.91 (m, 1H), 8.17-8.25 (m, 1H).—contains ethyl acetate.

Intermediate 156 ethyl 6-chloro-7-{3-[(2,2-difluoro-4-hydroxybutoxy)methyl]-1,5-dimethyl-1H-pyrazol-4-yl}-3-{3-[(6-fluoronaphthalen-1-yl)oxy]propyl}-1H-indole-2-carboxylate

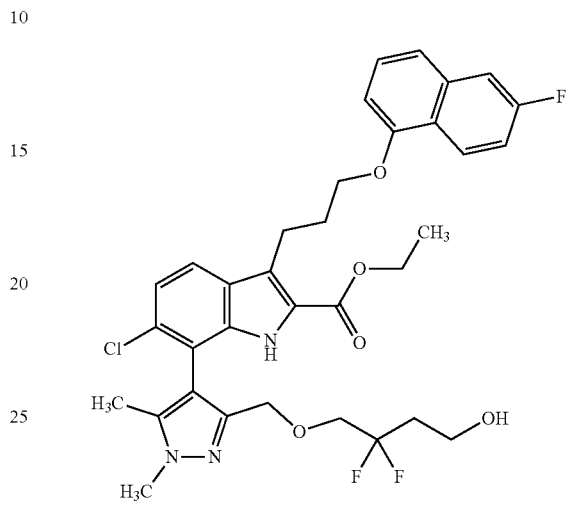

Ethyl-6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 9, 2.70 g), 4-[(4-bromo-1,5-dimethyl-1H-pyrazol-3-yl)methoxy]-3,3-difluorobutan-1-ol (see Intermediate 108, 1.92 g) and potassium phosphate (2.08 g, 9.79 mmol) were dissolved in 49 mL toluene and 20 mL water. The mixture was degassed by bubbling nitrogen through the mixture for 5 minutes. Then the XPhos-Pd-G3 (225 mg, 269 µmol) was added and it was degassed for 5 minutes again. The reaction mixture was stirred at 110° C. for 1 hour. The reaction mixture was filtered through a silicone coated filter and the filtrate was concentrated under reduced pressure. The crude product was purified by flash chromatography (100 g column, silica phase; ethylacetate/ethanol 9/1) to provide the target compound in 96% purity: 3.13 g LC-MS (Method 2): $R_t$=1.60 min; MS (ESIpos): m/z=660 [M+H]$^+$ $^1$H-NMR (400 MHz, DMSO-d6) δ[ppm]: 1.066 (1.36), 1.154 (1.90), 1.172 (2.75), 1.190 (1.42), 1.232 (5.02), 1.249 (11.25), 1.267 (5.14), 1.690 (0.66), 1.717 (0.71), 1.733 (1.31), 1.752 (0.78), 1.777 (0.61), 1.967 (15.64), 1.987 (5.37), 2.019 (0.62), 2.044 (0.65), 2.062 (1.32), 2.079 (0.69), 2.104 (0.56), 2.191 (1.01), 2.208 (1.45), 2.225 (13.28), 2.518 (2.03), 2.523 (1.43), 3.290 (1.31), 3.310 (2.85), 3.356 (0.92), 3.362 (0.81), 3.379 (1.07), 3.387 (1.11), 3.413 (1.97), 3.421 (1.96), 3.447 (0.92), 3.456 (0.90), 3.515 (0.77), 3.528 (0.96), 3.532 (1.67), 3.546 (1.69), 3.549 (0.89), 3.563 (0.76), 3.626 (1.34), 3.660 (2.70), 3.694 (1.20), 3.757 (12.43), 3.808 (16.00), 4.017 (1.12), 4.035 (1.11), 4.187 (1.42), 4.202 (2.91), 4.216 (1.49), 4.226 (1.54), 4.244 (4.34), 4.262 (4.16), 4.287 (7.42), 4.421 (6.25), 4.490 (1.38), 4.503 (2.99), 4.516 (1.30), 4.655 (0.77), 4.667 (1.60), 4.681 (0.74), 5.758 (5.72), 6.876 (1.24), 6.884 (1.28), 6.891 (1.11), 6.898 (1.31), 7.152 (3.74), 7.174 (3.90), 7.373 (0.85), 7.380 (0.97), 7.395 (1.32), 7.402 (1.44), 7.418 (0.96), 7.425 (1.05), 7.435 (2.55), 7.442 (2.73), 7.449 (5.76), 7.649 (1.52), 7.655 (1.58), 7.675 (1.58), 7.681 (1.61), 7.691 (2.91), 7.713 (2.63), 8.245 (1.36), 8.259 (1.39), 8.267 (1.36), 8.283 (1.28), 10.895 (2.70).

Intermediate 157

(rac)-Ethyl 4-chloro-12,12-difluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylate

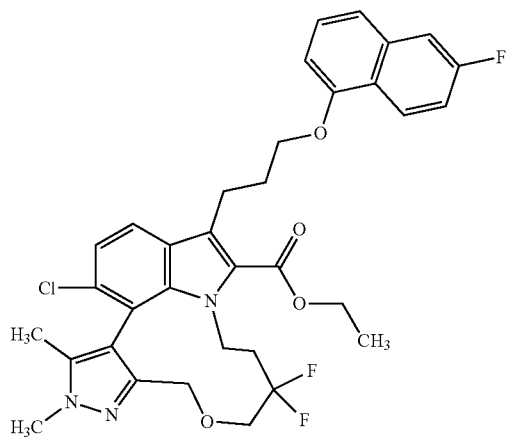 [SMILES: CCOC(=O)c1c(CCCOc2cccc3cc(F)ccc23)c2ccc(Cl)c3c2n1CCC(F)(F)COCc1nn(C)c(C)c1-3]

Triphenylphosphine (8.64 g, 32.9 mmol) followed by di-tert-butyl azodicarboxylate (7.59 g, 32.9 mmol) were added to ethyl 6-chloro-7-{3-[(2,2-difluoro-4-hydroxybutoxy)methyl]-1,5-dimethyl-1H-pyrazol-4-yl}-3-{3-[(6-fluoronaphthalen-1-yl)oxy]propyl}-1H-indole-2-carboxylate (see Intermediate 156, 2.71 g) in 290 mL THF at rt and stirred for 16 h. Hydrochloric acid solution (10.8 mL, 4M in dioxane) was added and stirred for 1 h. The reaction mixture was concentrated under reduced pressure. The residue together with the former preparation (0.35 mmol starting material) was dissolved in dichloromethane, washed with saturated aqueous sodium bicarbonate solution and brine, dried over magnesium sulfate, filtered and concentrated under reduced pressure. The crude product was purified by flash chromatography (340 g column, silica phase; ethylacetate/ethanol 9/1) to provide the target compound: 7.4 g which still contains unknown byproducts, but where used without further purification.

LC-MS (Method 2): $R_t$=1.75 min; MS (ESIpos): m/z=640 [M+H]$^+$ $^1$H-NMR (400 MHz, DMSO-d6) δ[ppm]: 1.283 (0.67), 1.364 (2.65), 1.384 (16.00), 1.409 (2.15), 1.418 (2.63), 1.426 (1.07), 1.436 (1.06), 1.764 (0.91), 2.083 (3.55), 2.518 (0.66), 2.523 (0.53), 3.852 (0.88), 8.596 (1.41).

Intermediate 158 ethyl 6-chloro-7-{3-[(3,3-difluoro-4-hydroxybutoxy)methyl]-1,5-dimethyl-1H-pyrazol-4-yl}-3-{3-[(6-fluoronaphthalen-1-yl)oxy]propyl}-1H-indole-2-carboxylate

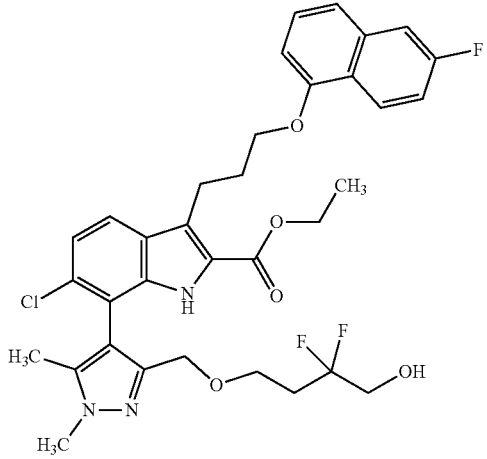 [SMILES: CCOC(=O)c1[nH]c2c(-c3c(COCCC(F)(F)CO)nn(C)c3C)c(Cl)ccc2c1CCCOc1cccc2cc(F)ccc12]

Ethyl-6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 9, 3.00 g), 4-[(4-bromo-1,5-dimethyl-1H-pyrazol-3-yl)methoxy]-2,2-difluorobutan-1-ol (see Intermediate 136, 2.13 g) and potassium phosphate (2.31 g, 10.9 mmol) were dissolved in 54 mL toluene and 22 mL water. The mixture was degassed by bubbling nitrogen through the mixture for 5 minutes. Then the RuPhos-Pd-G3 (250 mg, 299 μmol) was added and it was degassed for 5 minutes again. The reaction mixture stirred at 110° C. for 1 hour under nitrogen atmosphere. The reaction mixture was filtered through a silicone coated filter and the filtrate was concentrated under reduced pressure. The crude product was purified by flash chromatography (100 g column, silica phase; ethylacetate/ethanol 9/1) to provide the target compound in 86% purity: 3.3 g LC-MS (Method 2): $R_t$=1.60 min; MS (ESIpos): m/z=659 [M+H]$^+$ $^1$H-NMR (400 MHz, DMSO-d6) δ[ppm]: 1.153 (4.19), 1.171 (8.55), 1.189 (4.41), 1.231 (3.40), 1.248 (7.35), 1.266 (3.46), 1.691 (0.53), 1.716 (0.57), 1.734 (1.05), 1.752 (0.63), 1.777 (0.50), 1.968 (11.18), 1.986 (16.00), 2.019 (0.44), 2.045 (0.44), 2.062 (0.89), 2.079 (0.48), 2.104 (0.42), 2.169 (0.42), 2.190 (0.87), 2.209 (1.24), 2.215 (1.21), 2.225 (8.22), 2.522 (0.74), 3.290 (1.08), 3.310 (2.23), 3.327 (3.27), 3.357 (0.87), 3.362 (0.70), 3.379 (0.85), 3.387 (0.89), 3.414 (1.53), 3.421 (1.50), 3.448 (0.74), 3.455 (0.70), 3.516 (0.59), 3.529 (0.74), 3.533 (1.20), 3.546 (1.21), 3.550 (0.68), 3.563 (0.53), 3.626 (0.91), 3.660 (1.82), 3.694 (1.10), 3.756 (7.56), 3.808 (11.10), 3.998 (1.25), 4.016 (3.68), 4.034 (3.57), 4.052 (1.19), 4.185 (1.22), 4.200 (2.37), 4.215 (1.24), 4.226 (1.15), 4.243 (3.03), 4.261 (3.05), 4.287 (5.66), 4.421 (4.06), 4.493 (1.13), 4.505 (2.40), 4.519 (1.08), 4.657 (0.57), 4.669 (1.16), 4.683 (0.55), 6.875 (0.95), 6.882 (0.99), 6.889 (0.87), 6.896 (1.01), 7.152 (2.57), 7.174 (2.65), 7.372 (0.62), 7.379 (0.72), 7.395 (1.05), 7.401 (1.10), 7.417 (0.78), 7.424 (0.78), 7.434

(1.98), 7.440 (2.23), 7.448 (4.20), 7.647 (1.17), 7.653 (1.20), 7.673 (1.19), 7.679 (1.22), 7.690 (2.13), 7.712 (1.92), 8.244 (1.00), 8.259 (1.07), 8.267 (1.00), 8.282 (0.94), 10.897 (2.22).

Intermediate 159

(rac)-Ethyl 4-chloro-11,11-difluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylate

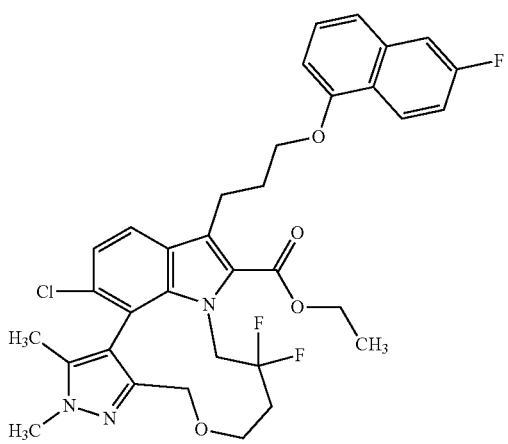 [SMILES: CCOC(=O)c1c(CCCOc2cccc3cc(F)ccc23)c2ccc(Cl)c3c2n1CC(F)(F)CCOCc1nn(C)c(C)c1-3]

Triphenylphosphine (10.5 g, 40.0 mmol) followed by di-tert-butyl azodicarboxylate (9.21 g, 40.0 mmol) added to ethyl 6-chloro-7-{3-[(3,3-difluoro-4-hydroxybutoxy)methyl]-1,5-dimethyl-1H-pyrazol-4-yl}-3-{3-[(6-fluoronaphthalen-1-yl)oxy]propyl}-1H-indole-2-carboxylate (see Intermediate 158, 3.29 g) in 290 mL THF at rt and stirred for 32 h. Hydrochloric acid (10.8 mL, 4M in dioxane) were added and stirred for 1 h. The reaction mixture was concentrated under reduced pressure. The residue was dissolved in ethylacetate, washed with saturated aqueous sodium bicarbonate solution and brine, dried over magnesium sulfate, filtered and concentrated under reduced pressure. The crude product was purified by flash chromatography (340 g column, silica phase; ethylacetate/ethanol 9/1) and HPLC (Chromatorex C-18 10 μm; 125*30 mm) to provide the target compound: 1.5 g.

LC-MS (Method 2): Rt=1.75 min; MS (ESIpos): m/z=640 [M+H]$^+$ $^1$H-NMR (400 MHz, DMSO-d6) δ[ppm]: 1.153 (3.99), 1.170 (7.88), 1.188 (3.78), 1.265 (4.58), 1.282 (10.10), 1.300 (4.69), 1.764 (15.25), 1.964 (0.41), 1.977 (0.50), 1.986 (13.04), 2.199 (0.92), 2.215 (1.43), 2.232 (0.95), 2.518 (1.29), 2.522 (0.80), 3.277 (0.63), 3.295 (1.63), 3.315 (1.76), 3.333 (16.00), 3.595 (0.59), 3.624 (0.68), 3.632 (0.75), 3.661 (0.50), 3.725 (0.42), 3.757 (0.69), 3.789 (0.47), 3.998 (0.98), 4.016 (2.96), 4.034 (2.91), 4.051 (0.92), 4.201 (1.09), 4.217 (2.29), 4.231 (1.90), 4.240 (0.72), 4.248 (0.95), 4.258 (1.61), 4.276 (1.65), 4.294 (0.76), 4.312 (1.99), 4.316 (2.11), 4.330 (1.53), 4.339 (1.06), 4.348 (2.51), 4.357 (1.01), 4.433 (0.50), 4.448 (0.43), 4.458 (0.43), 4.468 (0.43), 4.473 (0.46), 4.569 (1.16), 4.600 (0.93), 6.878 (1.15), 6.884 (1.20), 6.893 (1.03), 6.900 (1.24), 7.294 (3.92), 7.315 (3.90), 7.363 (0.76), 7.370 (0.92), 7.386 (1.18), 7.393 (1.31), 7.408 (0.96), 7.414 (0.94), 7.431 (2.13), 7.440 (2.39), 7.446 (5.48), 7.643 (1.39), 7.650 (1.44), 7.669 (1.41), 7.676 (1.41), 7.817 (3.50), 7.838 (3.20), 8.187 (1.22), 8.202 (1.26), 8.211 (1.25), 8.225 (1.18).

Intermediate 160

4-bromo-3-[(4-{[tert-butyl(diphenyl)silyl]oxy}-3,3-difluorobutoxy)methyl]-5-ethyl-1-methyl-1H-pyrazole

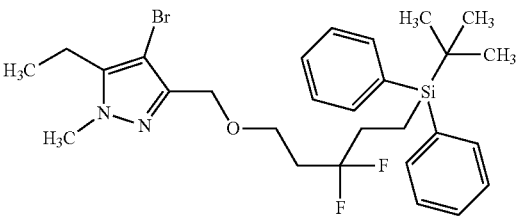 [SMILES: CCc1c(Br)c(COCCC(F)(F)CC[Si](c2ccccc2)(c2ccccc2)C(C)(C)C)nn1C]

4-{[tert-Butyl(diphenyl)silyl]oxy}-3,3-difluorobutan-1-ol (see Intermediate 134, 5.60 g) was dissolved in 250 mL of THF and cooled to 0° C. Sodium hydride (764 mg, 55% purity) was added portionwise and stirred for 1 h at 0° C. 4-Bromo-3-(bromomethyl)-5-ethyl-1-methyl-1H-pyrazole (see Intermediate 140, 4.12 g) was added and the mixture was stirred overnight at 60° C. After cooling to rt, 50 mL of methanol were added to give a solution of the title compound which was used without further purification.

Intermediate 161

4-[(4-bromo-5-ethyl-1-methyl-1H-pyrazol-3-yl)methoxy]-2,2-difluorobutan-1-ol

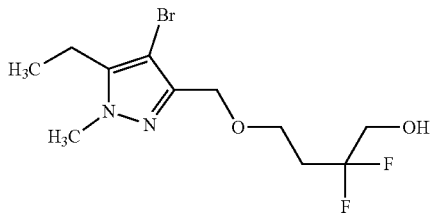 [SMILES: CCc1c(Br)c(COCCC(F)(F)CO)nn1C]

A solution of 4-bromo-3-[(4-{[tert-butyl(diphenyl)silyl]oxy}-3,3-difluorobutoxy)methyl]-5-ethyl-1-methyl-1H-pyrazole (see Intermediate 160) in methanol was treated with a solution of N,N,N-tributylbutan-1-aminium fluoride in THF (29.2 ml, 1.0 M, 29.2 mmol) and was stirred overnight at rt. The reaction mixture was concentrated under reduced pressure and the residue was dissolved in 200 mL of THF, a solution of N,N,N-tributylbutan-1-aminium fluoride in THF (29.2 mL, 1.0 M, 29.2 mmol) was added and stirred for 72 h. The reaction mixture was concentrated under reduced pressure, ethyl acetate was added and the mixture was washed with water and concentrated. The crude product was purified by flash chromatography using silica gel (gradient dichloromethane/ethanol) to provide 790 mg of a mixture of the title compound and the starting material. The material was dissolved in 100 mL of tetrahydrofuran, a solution of N,N,N-tributylbutan-1-aminium fluoride in THF (10 mL, 1.0 M, 10 mmol) was added and the mixture was stirred overnight at 65° C. A solution of N,N,N-tributylbu-

339 tan-1-aminium fluoride in THF (10 mL, 1.0 M, 10 mmol) was added and the mixture was stirred for 20 h at 65° C. The reaction mixture was concentrated under reduced pressure, ethyl acetate was added and the mixture was washed with water. The organic layer was dried over sodium sulfate, filtered and concentrated under reduced pressure. The crude product was purified by flash chromatography using silica gel (gradient dichloromethane/ethanol) to provide 490 mg of the title compound.

LC-MS (Method 1): $R_f$=1.01 min; MS (ESIpos): m/z=327 [M+H]$^+$ $^1$H-NMR (400 MHz, CHLOROFORM-d) δ [ppm]: 1.094 (3.45), 1.113 (7.47), 1.123 (0.57), 1.132 (3.51), 1.801 (1.28), 2.126 (0.43), 2.140 (0.63), 2.155 (0.45), 2.167 (0.86), 2.182 (1.27), 2.196 (0.90), 2.209 (0.42), 2.223 (0.62), 2.237 (0.44), 2.581 (1.04), 2.600 (3.24), 2.619 (3.22), 2.638 (0.99), 3.656 (1.99), 3.687 (3.85), 3.718 (1.85), 3.733 (0.88), 3.750 (2.64), 3.761 (16.00), 3.765 (3.65), 3.775 (0.40), 3.780 (2.36), 4.514 (7.20), 4.524 (0.48).

Intermediate 162 ethyl 6-chloro-7-{3-[(3,3-difluoro-4-hydroxybutoxy)methyl]-5-ethyl-1-methyl-1H-pyrazol-4-yl}-3-{3-[(6-fluoronaphthalen-1-yl)oxy]propyl}-1H-indole-2-carboxylate

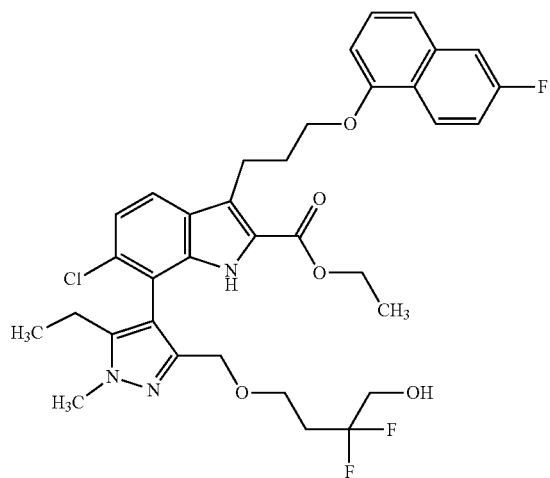 [SMILES: CCOC(=O)c1[nH]c2c(-c3c(COCCC(F)(F)CO)nn(C)c3CC)c(Cl)ccc2c1CCCOc1cccc2cc(F)ccc12]

Ethyl-6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 9, 827 mg, 1.50 mmol) and 4-[(4-bromo-5-ethyl-1-methyl-1H-pyrazol-3-yl)methoxy]-2,2-difluorobutan-1-ol (see Intermediate 161, 490 mg) were dissolved in a mixture of 10 mL of 1,4-dioxane and 2 mL of water and potassium phosphate (636 mg, 3.00 mmol) and RuPhos Pd G3 (62.6 mg, 74.9 µmol) were added. The mixture was purged with argon and stirred for 1 h at 110° C. in a microwave reactor. After filtration the aqueous layer was removed and the organic layer was concentrated under reduced pressure. The crude product was purified by flash chromatography using silica gel (gradient dichloromethane/ethanol) to provide 793 mg of the title compound.

LC-MS (Method 1): $R_f$=1.66 min; MS (ESIpos): m/z=672 [M+H]$^+$ $^1$H-NMR (400 MHz, DMSO-d6) δ[ppm]: 0.859 (2.46), 0.878 (5.57), 0.884 (1.52), 0.897 (2.55), 0.902 (2.25), 0.920 (0.93), 1.035 (5.88), 1.052 (13.89), 1.066 (6.65), 1.070 (7.20), 1.077 (3.02), 1.097 (6.80), 1.115 (3.10), 1.153 (0.46), 1.156 (0.81), 1.171 (0.84), 1.190 (0.51), 1.227 (3.57), 1.236 (0.86), 1.245 (7.72), 1.263 (3.54), 1.704 (0.44), 1.722 (0.66), 1.728 (0.66), 1.739 (0.40), 1.745 (0.46), 2.021 (0.73), 2.038 (0.46), 2.046 (0.75), 2.065 (3.24), 2.080 (0.84), 2.088 (0.40), 2.105 (0.70), 2.190 (0.68), 2.209 (0.90), 2.225 (0.68), 2.301 (0.44), 2.322 (0.90), 2.327 (0.92), 2.331 (0.71), 2.338 (0.92), 2.357 (0.70), 2.407 (0.70), 2.420 (0.62), 2.427 (0.79), 2.438 (0.59), 2.445 (0.70), 2.464 (0.71), 2.518 (3.19), 2.523 (2.07), 2.627 (0.90), 2.646 (2.95), 2.665 (3.45), 2.669 (1.14), 2.673 (0.73), 2.684 (0.84), 3.285 (0.84), 3.292 (0.66), 3.303 (1.76), 3.306 (1.69), 3.308 (1.69), 3.320 (3.10), 3.322 (2.73), 3.349 (1.01), 3.355 (0.79), 3.368 (0.77), 3.385 (0.68), 3.402 (1.23), 3.405 (1.61), 3.417 (2.18), 3.422 (3.56), 3.435 (3.59), 3.440 (3.48), 3.452 (3.94), 3.457 (1.10), 3.470 (0.99), 3.514 (1.21), 3.528 (1.37), 3.532 (2.57), 3.545 (2.55), 3.549 (1.28), 3.562 (1.25), 3.565 (1.50), 3.638 (1.54), 3.672 (3.28), 3.679 (1.52), 3.706 (1.36), 3.792 (16.00), 3.839 (10.78), 3.940 (1.15), 4.189 (1.01), 4.203 (2.11), 4.222 (1.70), 4.235 (4.29), 4.239 (4.05), 4.257 (2.88), 4.274 (0.90), 4.345 (2.18), 4.358 (4.14), 4.370 (2.00), 4.408 (0.64), 4.420 (6.98), 4.479 (1.37), 4.492 (2.73), 4.505 (1.28), 4.656 (1.34), 4.669 (2.84), 4.683 (1.23), 5.758 (8.01), 6.877 (0.82), 6.884 (0.88), 6.892 (0.73), 6.899 (0.90), 7.152 (2.64), 7.174 (2.77), 7.379 (0.64), 7.386 (0.75), 7.402 (0.95), 7.409 (1.08), 7.414 (0.59), 7.424 (0.82), 7.431 (0.93), 7.436 (1.76), 7.443 (1.89), 7.450 (3.85), 7.651 (1.06), 7.657 (1.08), 7.677 (1.10), 7.683 (1.10), 7.690 (1.85), 7.712 (1.61), 8.259 (0.88), 8.273 (0.92), 8.282 (0.90), 8.297 (0.84), 10.957 (1.87).

Intermediate 163

(rac)-ethyl 4-chloro-3-ethyl-11,11-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylate

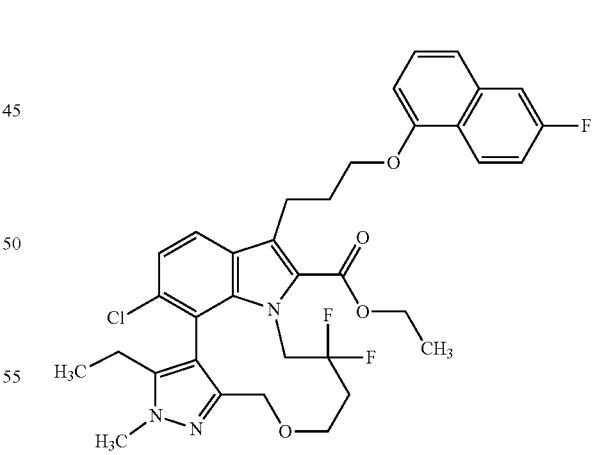

Ethyl 6-chloro-7-{3-[(3,3-difluoro-4-hydroxybutoxy)methyl]-5-ethyl-1-methyl-1H-pyrazol-4-yl}-3-{3-[(6-fluoronaphthalen-1-yl)oxy]propyl}-1H-indole-2-carboxylate (see Intermediate 162, 790 mg) was dissolved in 50 mL of THF, triphenylphosphine (2.47 g, 9.40 mmol) and di-tert-butyl azodicarboxylate (2.17 g, 9.40 mmol) were added and the mixture was stirred for 16 h at rt. The reaction mixture was poured into water and extracted with ethyl acetate. The combined organic layers were dried over sodium sulfate, filtered and concentrated under reduced pressure. The crude product was purified by flash chromatography using silica gel (aminophase, gradient dichloromethane/ethanol) to give 630 mg of the title compound.

LC-MS (Method 1): R$_t$=1.80 min; MS (ESIpos): m/z=654 [M+H]$^+$ $^1$H-NMR (400 MHz, DMSO-d6) δ[ppm]: 0.762 (0.68), 0.781 (1.63), 0.800 (0.71), 1.094 (0.63), 1.172 (0.82), 1.190 (0.43), 1.265 (1.16), 1.282 (2.42), 1.300 (1.14), 1.356 (2.76), 1.364 (2.08), 1.385 (9.81), 1.395 (4.11), 1.410 (8.82), 1.418 (16.00), 1.437 (3.86), 1.987 (1.33), 2.322 (0.41), 2.327 (0.54), 2.331 (0.42), 2.518 (2.01), 2.523 (1.31), 2.664 (0.50), 2.669 (0.58), 2.673 (0.42), 3.302 (0.50), 3.791 (1.50), 3.885 (3.70), 4.215 (0.51), 4.311 (0.48), 4.315 (0.47), 4.346 (0.56), 4.432 (0.72), 7.293 (0.90), 7.315 (0.96), 7.430 (0.46), 7.440 (0.54), 7.446 (1.15), 7.819 (0.78), 7.841 (0.73), 8.598 (0.81), 9.369 (0.61).

Intermediate 164

1-[(4-bromo-5-ethyl-1-methyl-1H-pyrazol-3-yl) methoxy]-4-{[tert-butyl(dimethyl)silyl]oxy}butan-(2-rac)-ol

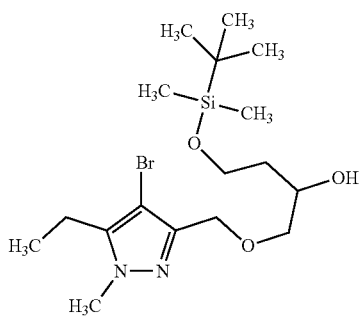 [SMILES: CCc1c(Br)c(COCC(O)CCO[Si](C)(C)C(C)(C)C)nn1C]

4-Bromo-3-(bromomethyl)-5-ethyl-1-methyl-1H-pyrazole (see Intermediate 140, 1.00 g) was dissolved in 30 mL of acetonitrile, cesium carbonate (3.47 g, 3.9 mmol) and (rac)-4-{[tert-butyl(dimethyl)silyl]oxy}butane-1,(2-rac)-diol (see Tetrahedron: Asymmetry 2009, 20, 2635-2638, 860 mg) were added. The mixture was stirred overnight at room temperature and was filtered and concentrated under reduced pressure. The residue was purified by flash chromatography using silica gel (gradient dichloromethane/ethanol) to provide 1.27 g of the title compound.

LC-MS (Method 1): R$_t$=1.52 min; MS (ESIpos): m/z=421 [M+H]$^+$ $^1$H-NMR (400 MHz, DMSO-d6) δ[ppm]: −0.022 (0.65), 0.000 (5.55), 0.003 (5.44), 0.022 (4.69), 0.051 (0.99), 0.821 (0.59), 0.823 (1.20), 0.832 (1.05), 0.840 (16.00), 0.846 (1.30), 0.851 (2.12), 0.855 (7.70), 0.859 (1.24), 0.862 (0.44), 1.067 (1.21), 1.086 (2.85), 1.104 (1.25), 2.626 (0.43), 2.631 (1.22), 2.645 (0.42), 2.650 (1.19), 3.241 (0.42), 3.264 (0.48), 3.278 (0.49), 3.288 (0.47), 3.303 (0.54), 3.619 (0.46), 3.636 (0.69), 3.652 (0.66), 3.666 (0.48), 3.756 (1.24), 3.761 (1.57), 3.771 (5.94), 3.776 (1.40), 4.306 (2.58), 4.316 (0.53), 4.519 (0.71), 4.533 (0.69).

Intermediate 165 ethyl 7-(3-{[(2-rac)-4-{[tert-butyl(dimethyl)silyl] oxy}-2-hydroxybutoxy]methyl}-5-ethyl-1-methyl-1H-pyrazol-4-yl)-6-chloro-3-{3-[(6-fluoronaphthalen-1-yl)oxy]propyl}-1H-indole-2-carboxylate

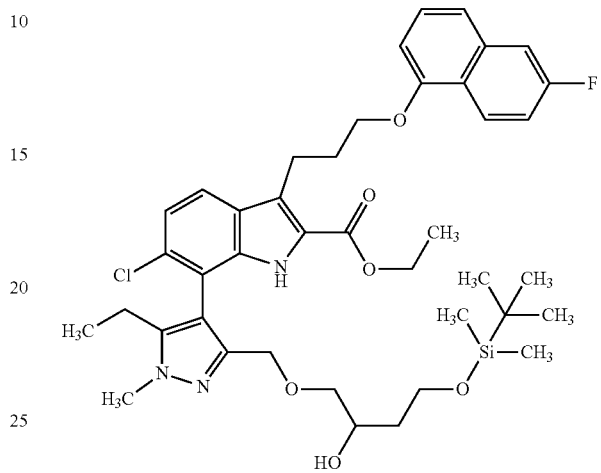

Ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 9, 1.66 g), and 1-[(4-bromo-5-ethyl-1-methyl-1H-pyrazol-3-yl)methoxy]-4-{[tert-butyl(dimethyl)silyl]oxy}butan-(2-rac)-ol (see Intermediate 164, 1.27 g) were dissolved in a mixture of 10 mL of 1,4-dioxane and 3 mL of water and potassium carbonate (1.28 g, 6.03 mmol) and RuPhos Pd G3 (126 mg, 151 μmol) were added. The mixture was purged with argon and stirred for 1 h at 110° C. in a microwave reactor. The aqueous phase was separated and extracted with ethyl acetate. The combined organic layers were dried over sodium sulfate, filtered and concentrated under reduced pressure. The crude material was purified by flash chromatography using silica gel (gradient dichloromethane/methanol) to provide 1.75 g of the title compound, which was formed as a mixture of two racemic diastereomers as a result of atropisomerism at the newly formed bi-heteroaryl bond.

LC-MS (Method 1): R$_t$=1.90 min; MS (ESIpos): m/z=766 [M+H]$^+$ $^1$H-NMR (400 MHz, DMSO-d6) δ[ppm]: −0.218 (0.47), −0.196 (0.51), −0.130 (0.50), −0.111 (0.62), −0.090 (3.23), −0.086 (3.32), −0.080 (4.36), −0.003 (3.90), 0.000 (4.02), 0.003 (2.69), 0.011 (0.55), 0.019 (8.33), 0.031 (0.42), 0.441 (1.11), 0.710 (1.54), 0.744 (0.43), 0.749 (1.63), 0.759 (0.51), 0.770 (10.46), 0.772 (11.02), 0.814 (0.55), 0.817 (0.60), 0.820 (0.68), 0.826 (0.82), 0.829 (0.99), 0.836 (12.33), 0.842 (7.22), 0.852 (15.12), 0.856 (2.95), 0.866 (1.87), 0.868 (2.01), 0.887 (0.91), 1.028 (1.55), 1.046 (2.88), 1.059 (15.32), 1.063 (3.17), 1.082 (2.06), 1.101 (0.95), 1.138 (0.54), 1.149 (0.71), 1.157 (1.12), 1.176 (0.67), 1.224 (0.64), 1.229 (1.91), 1.239 (0.84), 1.246 (3.57), 1.257 (0.46), 1.264 (1.62), 2.199 (0.52), 2.315 (0.42), 2.320 (0.52), 2.325 (0.43), 2.329 (0.44), 2.511 (1.78), 2.516 (1.18), 2.628 (0.76), 2.647 (0.74), 2.657 (0.40), 2.662 (0.55), 2.666 (0.54), 2.999 (0.48), 3.014 (0.46), 3.239 (0.75), 3.254 (0.74), 3.262 (0.58), 3.268 (0.78), 3.275 (0.74), 3.281 (0.67), 3.286 (0.88), 3.300 (0.82), 3.313 (0.94), 3.398 (0.59), 3.411 (0.64), 3.416 (1.12), 3.428 (0.96), 3.433 (0.96), 3.446 (0.82), 3.558 (16.00), 3.633

(0.56), 3.643 (0.76), 3.648 (0.95), 3.654 (2.10), 3.658 (0.74), 3.663 (0.84), 3.667 (0.75), 3.681 (0.58), 3.753 (0.58), 3.757 (0.99), 3.768 (4.00), 3.788 (0.47), 3.816 (4.47), 3.823 (0.94), 3.932 (2.52), 4.118 (0.52), 4.146 (0.59), 4.162 (0.67), 4.167 (0.70), 4.188 (0.95), 4.192 (0.83), 4.196 (0.79), 4.203 (1.31), 4.215 (1.12), 4.234 (1.04), 4.236 (1.00), 4.251 (0.96), 4.295 (0.92), 4.304 (1.81), 4.338 (0.59), 4.351 (1.49), 4.363 (0.99), 4.453 (0.63), 4.518 (0.62), 4.531 (0.56), 5.751 (0.67), 7.129 (0.70), 7.132 (0.68), 7.151 (0.75), 7.154 (0.76), 7.389 (0.44), 7.410 (0.40), 7.430 (0.95), 7.436 (1.12), 7.444 (1.91), 7.643 (0.63), 7.650 (0.63), 7.669 (0.95), 7.675 (0.72), 7.688 (0.46), 7.693 (0.50), 8.262 (0.44), 10.855 (0.70).

Intermediate 166 ethyl 6-chloro-7-(3-{[(2-rac)-2,4-dihydroxybutoxy]methyl}-5-ethyl-1-methyl-1H-pyrazol-4-yl)-3-{3-[(6-fluoronaphthalen-1-yl)oxy]propyl}-1H-indole-2-carboxylate

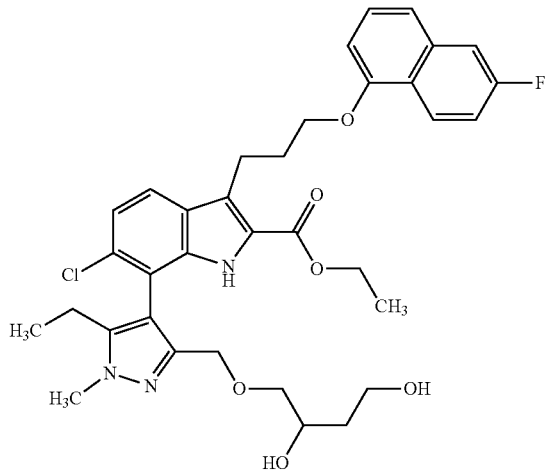 [SMILES: CCOC(=O)c1[nH]c2c(-c3c(COCC(O)CCBr)nn(C)c3CC)c(Cl)ccc2c1CCCOc1cccc2cc(F)ccc12]

Ethyl 7-(3-{[(2-rac)-4-{[tert-butyl(dimethyl)silyl]oxy}-2-hydroxybutoxy]methyl}-5-ethyl-1-methyl-1H-pyrazol-4-yl)-6-chloro-3-{3-[(6-fluoronaphthalen-1-yl)oxy]propyl}-1H-indole-2-carboxylate (see Intermediate 165, 2.89 g) was dissolved in 30 mL of THF, a solution of N,N,N-tributylbutan-1-aminium fluoride in THF (4.5 mL, 1.0 M, 4.5 mmol) was added and the mixture was stirred for 3 h at room temperature. The reaction mixture was poured into water and extracted with ethyl acetate. The combined organic layers were washed with brine, dried over sodium sulfate, filtered and concentrated under reduced pressure. The crude material was purified by flash chromatography using silica gel (gradient dichloromethane/methanol) to provide 1.05 g of the title compound.

LC-MS (Method 1): $R_t$=1.58 min; MS (ESIpos): m/z=652 [M+H]$^+$ $^1$H-NMR (400 MHz, DMSO-d6) δ[ppm]: 0.856 (2.06), 0.875 (4.51), 0.877 (4.28), 0.894 (2.16), 1.035 (0.44), 1.052 (1.01), 1.065 (16.00), 1.120 (0.53), 1.136 (0.49), 1.141 (0.55), 1.158 (0.46), 1.230 (3.88), 1.248 (7.87), 1.265 (3.77), 2.190 (0.84), 2.208 (1.17), 2.226 (0.87), 2.326 (1.18), 2.331 (0.68), 2.343 (0.86), 2.363 (0.90), 2.381 (0.59), 2.412 (0.75), 2.430 (0.83), 2.450 (0.62), 2.469 (0.68), 2.518 (3.49), 2.522 (2.22), 2.664 (0.61), 2.669 (0.84), 2.673 (0.62), 3.025 (1.42), 3.036 (1.32), 3.040 (1.15), 3.050 (0.99), 3.065 (0.83), 3.275 (0.70), 3.291 (1.91), 3.306 (3.23), 3.359 (0.49), 3.422 (0.41), 3.435 (0.46), 3.440 (0.40), 3.452 (0.41), 3.827 (7.76), 3.830 (7.96), 3.940 (2.60), 4.080 (0.67), 4.110 (1.14), 4.115 (0.49), 4.146 (1.30), 4.161 (2.18), 4.170 (0.80), 4.183 (1.82), 4.191 (2.07), 4.196 (1.89), 4.200 (2.58), 4.208 (2.74), 4.223 (2.10), 4.236 (2.23), 4.241 (3.51), 4.248 (2.21), 4.258 (4.32), 4.276 (1.01), 6.887 (0.75), 6.896 (0.89), 6.906 (0.74), 7.146 (1.55), 7.152 (1.61), 7.168 (1.64), 7.174 (1.66), 7.384 (0.53), 7.388 (0.44), 7.405 (0.93), 7.422 (0.47), 7.428 (0.62), 7.439 (2.10), 7.445 (2.29), 7.452 (4.50), 7.652 (1.23), 7.658 (1.29), 7.679 (1.75), 7.685 (2.21), 7.702 (1.02), 7.708 (1.26), 8.251 (0.52), 8.260 (0.56), 8.266 (0.67), 8.275 (1.04), 8.283 (0.62), 8.289 (0.65), 8.298 (0.50), 10.830 (1.12), 10.851 (1.08).

Intermediate 167 ethyl 7-(3-{[(2-rac)-4-bromo-2-hydroxybutoxy]methyl}-5-ethyl-1-methyl-1H-pyrazol-4-yl)-6-chloro-3-{3-[(6-fluoronaphthalen-1-yl)oxy]propyl}-1H-indole-2-carboxylate

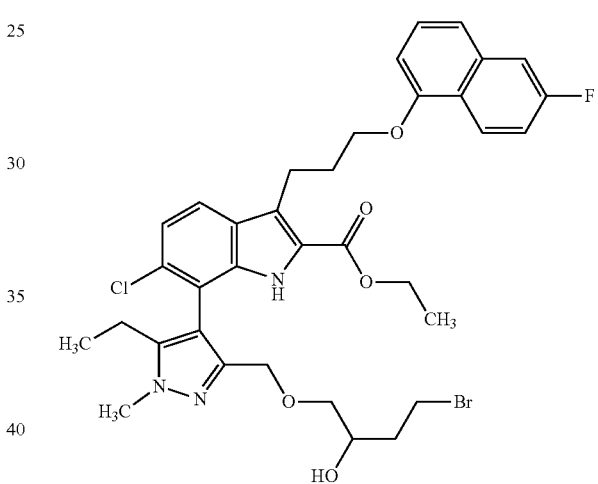

Ethyl 6-chloro-7-(3-{[(2-rac)-2,4-dihydroxybutoxy]methyl}-5-ethyl-1-methyl-1H-pyrazol-4-yl)-3-{3-[(6-fluoronaphthalen-1-yl)oxy]propyl}-1H-indole-2-carboxylate (see Intermediate 166, 650 mg) was dissolved in 15 mL of N,N-dimethylacetamide, triphenylphosphine (3.00 g, 2.39 mmol) and tetrabromomethane (397 mg, 1.20 mmol) were added and the mixture was stirred for 40 min at rt. The reaction mixture was diluted with ethyl acetate, the precipitate was removed and the filtrate was washed water, dried over sodium sulfate, filtered and concentrated under reduced pressure. The crude material was purified by flash chromatography using silica gel (gradient dichloromethane/ethanol) to provide 405 mg of the title compound.

LC-MS (Method 1): $R_t$=1.72 min; MS (ESIpos): m/z=714 [M+H]$^+$ $^1$H-NMR (400 MHz, DMSO-d6) δ[ppm]: 0.857 (0.45), 0.876 (0.97), 0.894 (0.48), 1.237 (0.81), 1.255 (1.59), 1.273 (0.73), 1.955 (11.02), 2.518 (0.81), 2.523 (0.58), 2.782 (10.35), 2.941 (16.00), 3.302 (0.41), 3.823 (2.36), 4.205 (0.42), 4.216 (0.48), 4.231 (0.43), 4.248 (0.62), 4.266 (0.57), 5.759 (0.58), 7.439 (0.50), 7.445 (0.57), 7.453 (0.91).

Intermediate 168

(rac)-ethyl 4-chloro-3-ethyl-7-{3-[(6-fluoronaphthalen-1-yl)oxy]propyl}-(12-rac)-hydroxy-2-methyl-2,10,11,12,13,15-hexahydropyrazolo[4',3':9,10][1,6]oxazacycloundecino[8,7,6-hi]indole-8-carboxylate (Mixture of Four Stereoisomers)

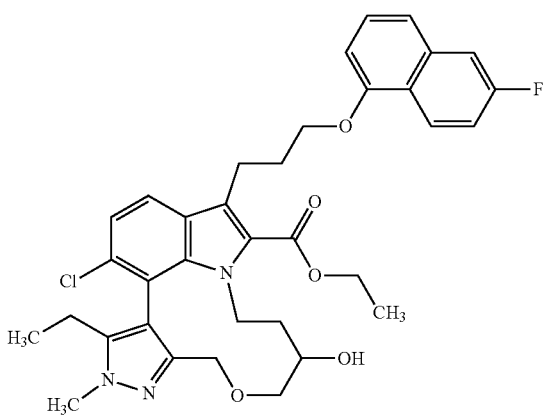 [SMILES: CCOC(=O)c1c(CCCOc2cccc3cc(F)ccc23)c2ccc(Cl)c3c2n1CCC(O)COCc1nn(C)c(CC)c1-3]

Ethyl 7-(3-{[(2-rac)-4-bromo-2-hydroxybutoxy]methyl}-5-ethyl-1-methyl-1H-pyrazol-4-yl)-6-chloro-3-{3-[(6-fluoronaphthalen-1-yl)oxy]propyl}-1H-indole-2-carboxylate (see Intermediate 167, 405 mg) was dissolved in 10 mL of N,N-dimethylformamide, cesium carbonate (923 mg, 2.83 mmol) was added and the mixture was stirred overnight at room temperature and at 50° C. for 4 h. The reaction mixture was filtered and concentrated under reduced pressure. Ethyl acetate was added and the mixture was washed with water. The organic layer was dried over sodium sulfate, filtered and concentrated under reduced pressure to provide 360 mg of the title compound which was used without further purification.

$^1$H NMR (DMSO-d$_6$) δ: 8.16-8.34 (m, 1H), 7.95 (s, 2H), 7.74-7.79 (m, 1H), 7.61-7.72 (m, 2H), 7.38-7.48 (m, 2H), 7.38 (br s, 1H), 7.23 (s, 1H), 6.88 (m, 1H), 4.36-4.59 (m, 1H), 4.07-4.36 (m, 6H), 3.74-3.95 (m, 4H), 3.24-3.31 (m, 2H), 2.89 (s, 7H), 2.73 (s, 7H), 2.07-2.26 (m, 3H), 1.23-1.32 (m, 3H), 0.73-0.94 (m, 4H)

Intermediate 169

[(1S or R,2R or S)-2-{[(4-bromo-5-ethyl-1-methyl-1H-pyrazol-3-yl)methoxy]methyl}cyclopropyl]methanol

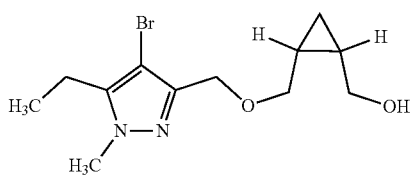 [SMILES: CCc1c(Br)c(COCC2CC2CO)nn1C]

Sodium hydride (746 mg, 60% purity, 18.6 mmol) was suspended in 20 mL THF and treated with [(1R or S,2S or R)-cyclopropane-1,2-diyl]dimethanol (see Intermediate 123, 1.73 g, 16.9 mmol), dissolved in 20 mL THF. It was stirred at room temperature under argon atmosphere for 15 minutes, then 4-bromo-3-(bromomethyl)-5-ethyl-1-methyl-1H-pyrazole (see Intermediate 140, 4.78 g, 16.9 mmol) dissolved in 28 mL THF was added dropwise and it was stirred at 60° C. for 2 days. The reaction mixture was carefully poured into water, diluted with ethyl acetate and extracted with ethyl acetate three times. The combined organic layers were washed with water and brine, filtered through a silicone coated filter and concentrated under reduced pressure. The crude product was purified by flash chromatography (50 g column, silica ULTRA; ethyl acetate/ethanol 0%-15% ethanol; collection mode: lamda all) twice (50 g column, silica ULTRA; hexane/ethyl acetate 0%-100% ethyl acetate/ethyl acetate/ethanol 0%-15% ethanol; collection mode: lamda all) to provide the target compound in 84% purity: 2.1 g.

LC-MS (Method 2): R$_t$=0.97 min; MS (ESIpos): m/z=305 [M+H]$^+$ $^1$H-NMR (400 MHz, DMSO-d6) δ[ppm]: 0.131 (0.58), 0.145 (1.33), 0.157 (1.42), 0.170 (0.63), 0.636 (0.60), 0.648 (0.65), 0.657 (1.33), 0.669 (1.31), 0.678 (0.84), 0.689 (0.79), 1.027 (0.68), 1.029 (0.65), 1.034 (0.42), 1.044 (1.08), 1.047 (0.93), 1.051 (0.72), 1.062 (1.15), 1.066 (1.20), 1.072 (4.69), 1.080 (1.05), 1.088 (4.18), 1.091 (10.21), 1.110 (4.40), 2.518 (0.43), 2.618 (1.21), 2.633 (1.41), 2.637 (4.09), 2.652 (1.40), 2.656 (4.02), 2.675 (1.19), 3.332 (16.00), 3.354 (1.19), 3.357 (1.14), 3.368 (1.63), 3.372 (2.32), 3.375 (1.91), 3.385 (1.63), 3.389 (1.13), 3.394 (0.84), 3.403 (1.42), 3.411 (0.47), 3.421 (1.13), 3.435 (1.49), 3.452 (1.49), 3.461 (0.48), 3.478 (0.46), 4.212 (1.29), 4.226 (2.68), 4.240 (1.23), 4.259 (1.53), 4.263 (1.51), 4.265 (1.57), 4.292 (4.95), 4.302 (5.25), 4.321 (0.45), 4.331 (1.00), 5.758 (1.76).

Intermediate 170 ethyl 6-chloro-7-[5-ethyl-3-({[(1R or S,2S or R)-2-(hydroxymethyl)cyclopropyl]methoxy}methyl)-1-methyl-1H-pyrazol-4-yl]-3-{3-[(6-fluoronaphthalen-1-yl)oxy]propyl}-1H-indole-2-carboxylate

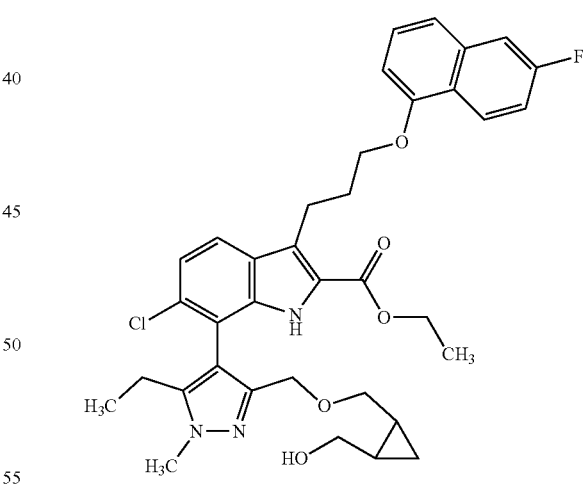

Ethyl-6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 9, 1.00 g, 1.81 mmol), [(1S or R,2R-or-S)-2-{[(4-Bromo-5-ethyl-1-methyl-1H-pyrazol-3yl)methoxy]methyl}cyclopropyl]methanol (see Intermediate 169, 687 mg) and potassium phosphate (1.7 ml, 2.2 M, 3.6 mmol) were dissolved in 18 mL toluene and 7.3 mL water. The mixture was degassed by bubbling argon through the mixture for 5 minutes. Then RuPhos-Pd-G3 (83.4 mg, 99.7 μmol) was added and it was degassed for 5 minutes again. The reaction mixture stirred at 110° C. for 1 hour under argon atmosphere. The reaction mixture was filtered through a silicone coated filter and the filtrate was concentrated under reduced pressure. The crude product was purified by flash chromatography (25 g column, silica ULTRA; ethyl acetate/ethanol 0%-10% ethanol) to provide the target compound in 78% purity: 928 mg, which was formed as a mixture of two racemic diastereomers as a result of atropisomerism at the newly formed bi-heteroaryl bond.

LC-MS (Method 2): $R_t$=1.65 and 1.66 min; MS (ESIpos): m/z=649 [M+H]$^+$ $^1$H-NMR (400 MHz, DMSO-d6) δ[ppm]: 0.131 (0.42), 0.145 (0.96), 0.157 (0.97), 0.170 (0.45), 0.636 (0.43), 0.647 (0.46), 0.657 (0.91), 0.668 (0.90), 0.677 (0.62), 0.688 (0.58), 0.854 (1.25), 0.872 (2.33), 0.891 (1.12), 1.026 (0.56), 1.043 (0.83), 1.046 (0.88), 1.061 (0.88), 1.065 (1.09), 1.071 (3.13), 1.078 (0.78), 1.087 (2.68), 1.090 (6.64), 1.109 (2.89), 1.223 (1.18), 1.225 (1.11), 1.229 (0.45), 1.234 (0.43), 1.241 (2.52), 1.243 (2.34), 1.258 (1.18), 1.260 (1.08), 1.987 (0.66), 2.205 (0.57), 2.327 (0.46), 2.518 (1.74), 2.522 (1.13), 2.618 (0.85), 2.637 (2.69), 2.651 (0.90), 2.655 (2.66), 2.664 (0.43), 2.669 (0.65), 2.674 (1.02), 3.166 (0.40), 3.205 (0.44), 3.210 (0.43), 3.223 (0.50), 3.302 (0.57), 3.312 (0.61), 3.353 (0.94), 3.371 (1.72), 3.374 (1.33), 3.385 (1.20), 3.388 (0.82), 3.394 (0.60), 3.402 (0.99), 3.420 (0.82), 3.434 (1.05), 3.451 (1.05), 3.657 (0.69), 3.661 (0.41), 3.718 (0.47), 3.724 (0.50), 3.775 (16.00), 3.825 (5.98), 4.103 (0.55), 4.136 (0.84), 4.143 (0.80), 4.153 (1.13), 4.168 (0.40), 4.172 (0.53), 4.183 (0.62), 4.201 (0.96), 4.213 (1.45), 4.227 (2.12), 4.238 (1.47), 4.241 (1.20), 4.255 (1.50), 4.258 (1.22), 4.262 (1.14), 4.264 (1.08), 4.272 (0.46), 4.291 (3.61), 4.301 (3.44), 4.330 (0.69), 5.759 (7.18), 6.873 (0.43), 6.880 (0.46), 6.887 (0.40), 6.894 (0.45), 7.153 (0.94), 7.155 (0.78), 7.174 (0.97), 7.177 (0.80), 7.397 (0.42), 7.404 (0.48), 7.435 (0.93), 7.442 (1.11), 7.449 (2.03), 7.650 (0.54), 7.655 (0.53), 7.675 (0.55), 7.682 (0.62), 7.686 (0.75), 7.708 (0.64), 10.811 (0.65).

Intermediate 171

(rac)-ethyl (9aS or R,10aR or S)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]oxazacycloundecino[8,7,6-hi]indole-13-carboxylate (Mixture of Stereoisomers)

Ethyl 6-chloro-7-[5-ethyl-3-({[(1R or S,2S or R)-2-(hydroxymethyl)cyclopropyl]methoxy}methyl)-1-methyl-1H-pyrazol-4-yl]-3-{3-[(6-fluoronaphthalen-1-yl)oxy]propyl}-1H-indole-2-carboxylate (see Intermediate 170, 928 mg) and triphenylphosphine (3.00 g, 11.5 mmol) were dissolved in 58 mL THF and treated with di-tert-butyl azodicarboxylate (2.64 g, 11.5 mmol). It was stirred at room temperature under nitrogen atmosphere over night. The reaction mixture was treated with hydrochloric acid solution (3.6 mL, 4.0 M in dioxane, 14 mmol). The formed precipitate was filtered off. The filtrate was concentrated under reduced pressure and treated with 10 mL ethyl acetate. The formed precipitate was filtered off. The filtrate was purified by flash chromatography (25 g column, silica ULTRA; ethyl acetate/ethanol 0%-10% ethanol) to provide the target compound in stereoisomers: 763 mg.

LC-MS (Method 2): $R_t$=1.73 and 1.77; MS (ESIpos): m/z=631/633 [M+H]$^+$

The title compound (763 mg) was separated into diastereomers by preparative HPLC to give racemate 1 (108 mg, see Intermediate 172) and racemate 2 (136 mg, see Intermediate 173).

Preparative HPLC Method:
Instrument: Waters Autopurification system; Column: Waters XBrigde C18 5μ 100×30 mm;
Eluent A: Water+0.1 Vol-% formic acid (99%), Eluent B: Acetonitrile;
Gradient: 0.00-0.50 min 78% B (35→70 mL/min), 0.51-5.50 min 78-94% B (70 mL/min),
DAD scan: 210-400 nm
Analytical HPLC Method:
Instrument: Waters Acquity UPLCMS SingleQuad; Column: Acquity UPLC BEH C18 1.7 μm, 50×2.1 mm; Eluent A: Water+0.1 Vol-% formic acid (99%), Eluent B: Acetonitriel; Gradient: 0-4.5 min 1-99% B, 4.5-5.0 min 99% B; Flow 0.8 mL/min; Temperature: 60° C.; DAD scan: 210-400 nm Intermediate 172

(rac)-ethyl (9aS or R,10aR or S)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]oxazacycloundecino[8,7,6-hi]indole-13-carboxylate

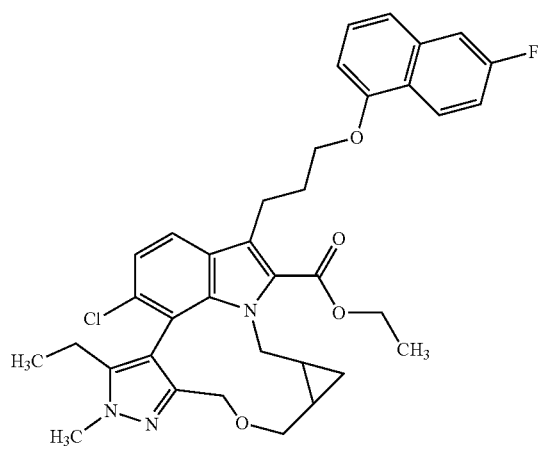 [SMILES: CCOC(=O)c1c(CCCOc2cccc3cc(F)ccc23)c2ccc(Cl)c3c2n1CC1CC1COCc1nn(C)c(CC)c1-3]
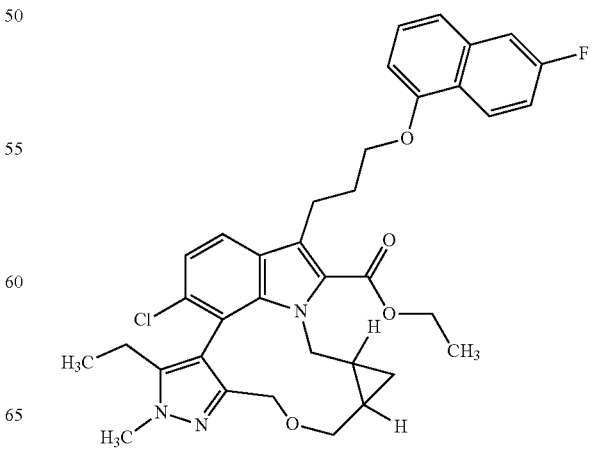

For the preparation of the stereoisomers of title compound see Intermediate 171. Separation of diasteremers by preparative chiral HPLC (method see Intermediate 171) gave the title compound (108 mg).

Analytical HPLC (method see Intermediate 171): R$_t$=1.73 min.

$^1$H-NMR (400 MHz, DMSO-d6) δ[ppm]=−0.28-−0.14 (m, 1H), 0.52-0.64 (m, 2H), 0.81 (t, 3H), 0.87-1.00 (m, 1H), 1.28 (t, 3H), 2.14-2.29 (m, 4H), 2.40 (t, 1H), 3.19-3.28 (m, 2H), 3.58 (br dd, 1H), 3.68 (dd, 1H), 3.83 (s, 3H), 4.06 (d, 1H), 4.15-4.27 (m, 3H), 4.30-4.42 (m, 2H), 4.54 (d, 1H), 6.91 (dd, 1H), 7.24 (d, 1H), 7.37-7.50 (m, 3H), 7.67 (dd, 1H), 7.76 (d, 1H), 8.30 (dd, 1H).

Intermediate 173

(rac)-ethyl (9aS or R,10aR or S)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]oxazacycloundecino[8,7,6-hi]indole-13-carboxylate

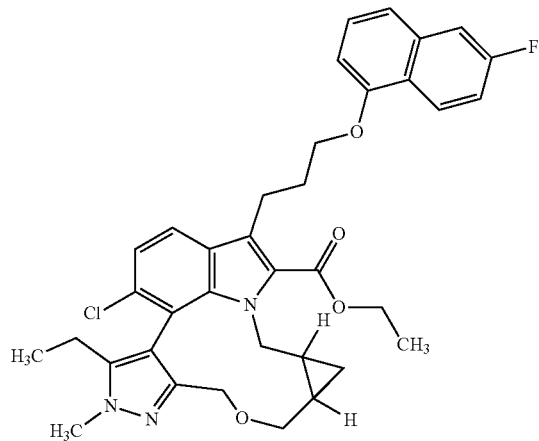 [SMILES: CCOC(=O)c1c(CCCOc2cccc3cc(F)ccc23)c2ccc(Cl)c3c2n1CC1CC1COCc1nn(C)c(CC)c1-3]

For the preparation of the stereoisomers of title compound see Intermediate 171. Separation of diasteremers by preparative chiral HPLC (method see Intermediate 171) gave the title compound (136 mg).

Analytical HPLC (method see Intermediate 171): R$_t$=1.77 min.

$^1$H-NMR (400 MHz, DMSO-d6) δ[ppm]=−0.73-−0.62 (m, 1H), 0.09-0.22 (m, 1H), 0.79-0.94 (m, 4H), 1.06 (br d, 1H), 1.25 (t, 3H), 2.11-2.30 (m, 4H), 3.16-3.30 (m, 3H), 3.42-3.50 (m, 1H), 3.81-3.94 (m, 4H), 4.02-4.35 (m, 7H), 6.86 (dd, 1H), 7.19 (d, 1H), 7.34-7.49 (m, 3H), 7.66 (dd, 1H), 7.74 (d, 1H), 8.27 (dd, 1H).

Intermediate 174 ethyl 7-{3-[({1-[2-(benzyloxy)ethyl]cyclopropyl}methoxy)methyl]-5-ethyl-1-methyl-1H-pyrazol-4-yl}-6-chloro-3-{3-[(6-fluoronaphthalen-1-yl)oxy]propyl}-1H-indole-2-carboxylate

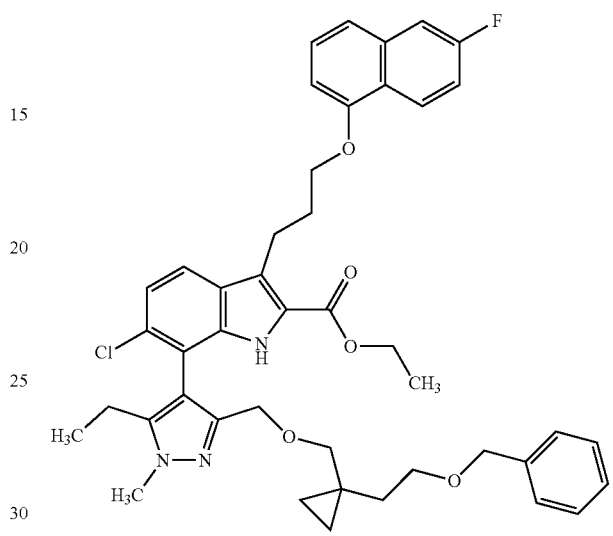

6-Chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 9, 1.56 g), 3-[({1-[2-(benzyloxy)ethyl]cyclopropyl}methoxy)methyl]-4-bromo-5-ethyl-1-methyl-1H-pyrazole (see Intermediate 141, 1.49 g) and potassium phosphate were provided in a mixture of 8 mL of 1,4-dioxane and 3 mL of water and were purged with argon for 5 minutes. RuPhos Pd G3 (130 mg, 155 μmol) was added and the mixture was purged with argon for 5 minutes and stirred at 110° C. for 20 minutes in a microwave reactor. The reaction mixture was diluted with water and extracted with ethyl acetate. The combined organic layers were filtered through a water resistant filter and concentrated under reduced pressure. The crude product was purified by flash chromatography using silica gel (gradient hexane/ethyl acetate) to provide 861 mg of the title compound.

LC-MS (Method 2): R$_t$=1.85 min; MS (ESIpos): m/z=752 [M+H]$^+$ $^1$H-NMR (400 MHz, DMSO-d6) δ[ppm]: −0.120 (0.51), −0.113 (0.45), −0.094 (1.41), −0.067 (1.73), −0.041 (0.90), −0.023 (0.80), 0.000 (3.87), 0.571 (0.49), 0.823 (3.46), 0.843 (7.87), 0.854 (1.00), 0.861 (3.71), 0.905 (0.49), 0.920 (0.49), 1.042 (13.78), 1.064 (0.63), 1.079 (0.55), 1.130 (4.75), 1.148 (10.09), 1.166 (6.24), 1.172 (2.10), 1.192 (5.50), 1.210 (11.23), 1.223 (1.33), 1.228 (5.12), 1.240 (0.45), 1.964 (15.65), 2.147 (1.08), 2.164 (1.69), 2.180 (1.16), 2.269 (0.65), 2.288 (0.98), 2.294 (0.55), 2.299 (1.00), 2.304 (1.55), 2.307 (1.94), 2.326 (1.08), 2.380 (1.02), 2.399 (1.24), 2.417 (1.00), 2.436 (0.94), 2.494 (4.44), 2.499 (2.67), 2.641 (0.80), 2.645 (1.12), 2.650 (0.82), 2.841 (1.24), 2.865 (2.61), 2.898 (2.65), 2.922 (1.22), 3.105 (1.08), 3.110 (1.08), 3.122 (2.16), 3.127 (2.20), 3.139 (1.04), 3.144 (1.04), 3.231

(0.73), 3.249 (1.63), 3.267 (1.67), 3.286 (1.22), 3.629 (0.45), 3.784 (16.00), 3.795 (1.33), 3.917 (2.02), 3.975 (1.14), 3.993 (3.26), 4.011 (3.24), 4.029 (1.16), 4.070 (0.57), 4.099 (3.97), 4.104 (3.93), 4.133 (0.84), 4.145 (1.81), 4.160 (2.93), 4.175 (1.79), 4.184 (1.08), 4.189 (1.18), 4.202 (2.69), 4.211 (8.85), 4.220 (2.81), 4.225 (2.34), 4.237 (1.08), 4.242 (0.82), 5.735 (1.12), 6.831 (1.28), 6.837 (1.37), 6.846 (1.22), 6.852 (1.37), 7.120 (3.95), 7.128 (0.41), 7.141 (3.93), 7.150 (0.67), 7.158 (2.51), 7.175 (3.57), 7.179 (3.36), 7.191 (0.51), 7.199 (1.90), 7.205 (0.51), 7.213 (1.26), 7.217 (1.63), 7.241 (3.63), 7.244 (1.47), 7.255 (2.36), 7.259 (3.49), 7.263 (0.90), 7.272 (0.59), 7.276 (1.35), 7.280 (0.80), 7.334 (0.88), 7.341 (1.02), 7.356 (1.35), 7.363 (1.45), 7.379 (1.22), 7.385 (1.08), 7.391 (0.43), 7.401 (2.32), 7.411 (2.67), 7.417 (5.34), 7.432 (0.59), 7.620 (1.55), 7.627 (1.63), 7.646 (4.20), 7.653 (1.73), 7.669 (2.40), 8.212 (1.33), 8.227 (1.35), 8.235 (1.33), 8.250 (1.22), 10.818 (2.81).

Intermediate 175 ethyl 6-chloro-7-[5-ethyl-3-({[1-(2-hydroxyethyl) cyclopropyl]methoxy}methyl)-1-methyl-1H-pyrazol-4-yl]-3-{3-[(6-fluoronaphthalen-1-yl)oxy]propyl}-1H-indole-2-carboxylate

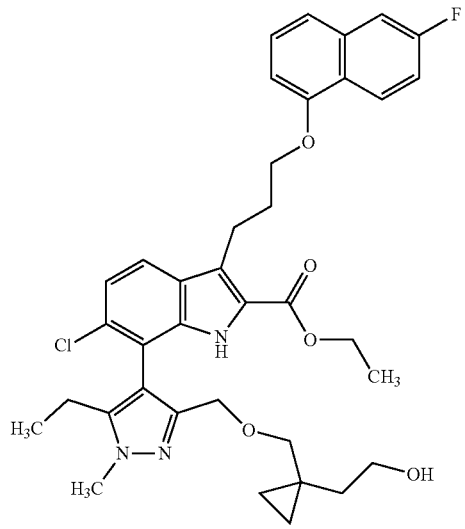 [SMILES: CCOC(=O)c1[nH]c2c(-c3c(COCC4(CCO)CC4)nn(C)c3CC)c(Cl)ccc2c1CCCOc1cccc2cc(F)ccc12]

Ethyl 7-{3-[({1-[2-(benzyloxy)ethyl] cyclopropyl}methoxy)methyl]-5-ethyl-1-methyl-1H-pyrazol-4-yl}-6-chloro-3-{3-[(6-fluoronaphthalen-1-yl)oxy]propyl}-1H-indole-2-carboxylate (see Intermediate 174, 861 mg) was dissolved in 13 mL of THF, palladium (10% on carbon, 122 mg, 0.12 mmol) was added and the mixture was stirred for 6 h at rt under a hydrogen atmosphere. The reaction mixture was filtered through celite with ethyl acetate and through a water resistant filter and was concentrated under reduced pressure. The crude material was purified by flash chromatography using silica gel (gradient dichloromethane/ethanol) to provide 544 mg of the title compound.

LC-MS (Method 2): $R_t$=1.67 min; MS (ESIpos): m/z=662 [M+H]$^+$ $^1$H-NMR (400 MHz, DMSO-d6) δ[ppm]: -0.153 (0.46), -0.147 (0.46), -0.126 (1.54), -0.103 (1.84), -0.076 (0.64), -0.023 (0.42), 0.000 (3.95), 0.005 (3.01), 0.843 (3.39), 0.862 (7.80), 0.881 (3.48), 0.923 (0.48), 0.938 (0.48), 1.047 (0.71), 1.061 (1.51), 1.065 (0.60), 1.082 (0.67), 1.097 (0.54), 1.139 (1.12), 1.144 (1.04), 1.156 (1.92), 1.163 (1.86), 1.175 (1.04), 1.180 (1.11), 1.225 (4.68), 1.243 (10.16), 1.260 (4.68), 2.186 (0.95), 2.203 (1.49), 2.219 (0.98), 2.293 (0.58), 2.312 (1.01), 2.317 (0.63), 2.322 (0.78), 2.330 (1.36), 2.349 (0.96), 2.398 (0.98), 2.417 (1.17), 2.436 (0.96), 2.455 (0.80), 2.513 (2.49), 2.518 (1.57), 2.659 (0.47), 2.664 (0.66), 2.668 (0.48), 2.864 (1.21), 2.889 (2.89), 2.916 (2.92), 2.941 (1.19), 3.184 (0.70), 3.187 (0.78), 3.201 (1.85), 3.205 (1.55), 3.214 (1.59), 3.218 (1.87), 3.232 (0.79), 3.235 (0.74), 3.274 (0.65), 3.293 (1.59), 3.311 (1.82), 3.344 (0.58), 3.811 (16.00), 4.080 (1.90), 4.083 (1.49), 4.092 (4.13), 4.105 (1.88), 4.112 (3.12), 4.134 (3.14), 4.163 (1.28), 4.181 (1.28), 4.196 (2.63), 4.211 (1.33), 4.220 (1.41), 4.237 (3.60), 4.255 (3.33), 4.272 (1.03), 6.864 (1.15), 6.871 (1.20), 6.878 (1.00), 6.886 (1.22), 7.142 (4.12), 7.163 (4.13), 7.371 (0.83), 7.378 (0.95), 7.393 (1.21), 7.401 (1.33), 7.408 (0.46), 7.416 (0.88), 7.422 (1.07), 7.429 (2.29), 7.436 (2.51), 7.443 (5.47), 7.644 (1.40), 7.650 (1.47), 7.670 (1.54), 7.676 (3.93), 7.698 (2.30), 8.246 (1.25), 8.260 (1.30), 8.268 (1.25), 8.283 (1.19), 10.805 (2.70).

Intermediate 176

(rac)-ethyl 4'-chloro-3'-ethyl-7'-{3-[(6-fluoronaphthalen-1-yl)oxy]propyl}-2'-methyl-2',10',11',15'-tetrahydro-13'H-spiro[cyclopropane-1,12'-pyrazolo[4',3':9,10][1,6]oxazacycloundecino[8,7,6-hi]indole]-8'-carboxylate

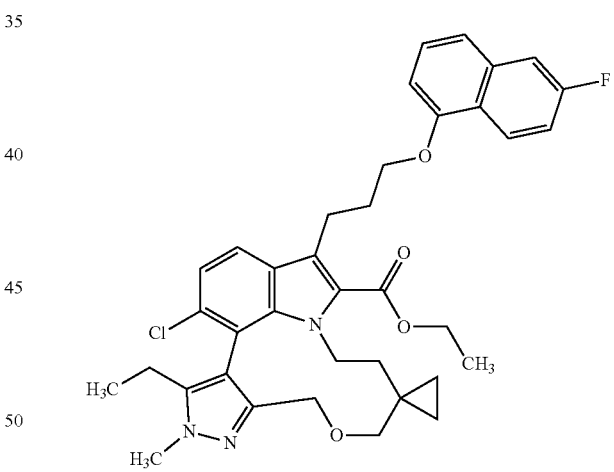

Ethyl 6-chloro-7-[5-ethyl-3-({[1-(2-hydroxyethyl)cyclopropyl]methoxy}methyl)-1-methyl-1H-pyrazol-4-yl]-3-{3-[(6-fluoronaphthalen-1-yl)oxy]propyl}-1H-indole-2-carboxylate (see Intermediate 175, 540 mg) was dissolved in 9.8 mL of THF, triphenylphosphine (1.63 g, 6.20 mmol) and di-tert-butyl-azodicarboxylate (1.43 g, 6.20 mmol) were added and the mixture was stirred for 22 h at rt. The reaction mixture was diluted with water and extracted with ethyl acetate. The combined organic layers were washed with brine, filtered through a water resistant filter and concentrated under reduced pressure. The crude material was purified by flash chromatography using silica gel (gradient hexane/ethyl acetate) to provide 455 mg of the title compound.

LC-MS (Method 2): R$_t$=1.78 min; MS (ESIpos): m/z=644 [M+H]$^+$ $^1$H-NMR (400 MHz, DMSO-d6) δ[ppm]: −0.084 (0.75), 0.011 (0.77), 0.025 (0.96), 0.046 (0.92), 0.064 (0.88), 0.074 (0.52), 0.089 (0.75), 0.096 (0.81), 0.110 (0.77), 0.118 (0.44), 0.695 (0.40), 0.709 (0.50), 0.726 (0.52), 0.743 (3.11), 0.762 (7.09), 0.780 (3.13), 1.106 (0.50), 1.115 (0.86), 1.133 (2.13), 1.151 (0.92), 1.158 (0.42), 1.190 (4.65), 1.208 (10.20), 1.226 (4.74), 1.346 (1.36), 1.385 (0.42), 1.400 (0.73), 1.464 (0.50), 1.467 (0.61), 1.948 (2.79), 2.061 (0.69), 2.080 (1.23), 2.099 (1.09), 2.108 (1.13), 2.127 (1.38), 2.146 (1.38), 2.164 (1.48), 2.183 (0.90), 2.479 (4.24), 2.484 (2.27), 2.503 (1.77), 3.201 (0.67), 3.217 (1.34), 3.235 (1.38), 3.251 (0.63), 3.268 (0.50), 3.433 (1.13), 3.458 (1.06), 3.820 (16.00), 3.922 (0.77), 3.949 (0.50), 3.960 (0.42), 3.978 (0.61), 3.995 (0.61), 4.107 (0.44), 4.125 (1.81), 4.129 (2.50), 4.142 (2.29), 4.152 (2.71), 4.160 (4.15), 4.170 (2.63), 4.187 (1.08), 4.197 (0.58), 4.227 (0.54), 4.244 (1.52), 4.262 (1.40), 4.272 (1.04), 4.281 (0.42), 4.289 (1.02), 4.440 (2.11), 4.472 (1.81), 6.816 (1.25), 6.821 (1.29), 6.832 (1.19), 6.837 (1.31), 7.182 (3.75), 7.204 (4.05), 7.336 (0.79), 7.342 (0.92), 7.358 (1.27), 7.365 (1.73), 7.380 (1.00), 7.387 (2.94), 7.404 (4.63), 7.420 (0.48), 7.605 (1.44), 7.612 (1.48), 7.631 (1.44), 7.638 (1.42), 7.714 (3.52), 7.735 (3.07), 8.165 (1.23), 8.180 (1.31), 8.188 (1.27), 8.202 (1.21).

Intermediate 177 ethyl 1-{3-[(tert-butoxycarbonyl)amino]propyl}-6-chloro-7-[5-ethyl-3-(hydroxymethyl)-1-methyl-1H-pyrazol-4-yl]-3-{3-[(6-fluoronaphthalen-1-yl)oxy]propyl}-1H-indole-2-carboxylate

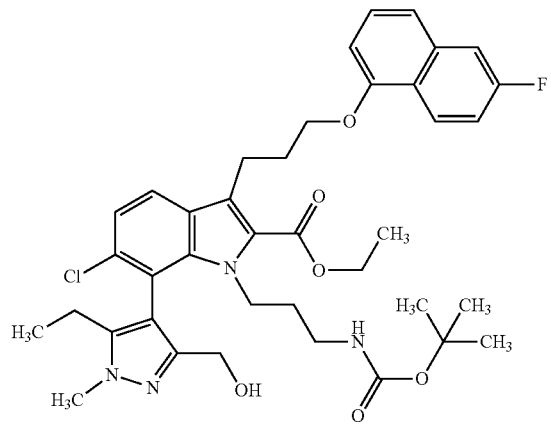 [SMILES: CCOC(=O)c1c(CCCOc2cccc3cc(F)ccc23)c2ccc(Cl)c(-c3c(CO)nn(C)c3CC)c2n1CCCNC(=O)OC(C)(C)C]

Ethyl-6-chloro-7-[5-ethyl-3-(hydroxymethyl)-1-methyl-1H-pyrazol-4-yl]-3-{3-[(6-fluoronaphthalen-1-yl)oxy]propyl}-1H-indole-2-carboxylate (see Intermediate 34, 1.70 g) was dissolved in 20 mL DMF. While stirring at rt tert-butyl (3-bromopropyl)carbamate (CAS 83948-53-2, 789 mg, 3.32 mmol) and cesium carbonate (2.45 g, 7.53 mmol) were added. The reaction mixture was stirred over night at rt. Further tert-butyl (3-bromopropyl)carbamate (300 mg) were added and the reaction mixture was stirred over the weekend at rt. The reaction mixture was quenched with water and concentrated under reduced pressure. It was extracted with dichloromethane twice. The organic layer was washed with brine, filtered through a silicone filter and dried under reduced pressure. The crude product was purified by flash chromatography (Biotage 50 g silica ultra column 0-15% ethyl acetate/ethanol) to provide the target compound in 82% purity: 1.28 g LC-MS (Method 2): R$_t$=1.71 min; MS (ESIpos): m/z=722 [M+H]$^+$ $^1$H-NMR (400 MHz, DMSO-d6) δ[ppm]: 0.923 (0.65), 0.942 (1.41), 0.960 (0.66), 1.066 (0.83), 1.251 (1.02), 1.268 (2.23), 1.286 (1.06), 1.323 (0.41), 1.338 (0.49), 1.357 (5.02), 1.366 (1.67), 3.160 (16.00), 3.173 (15.00), 3.853 (1.88), 4.084 (1.23), 4.097 (3.79), 4.111 (3.56), 4.123 (1.16), 4.200 (0.44), 4.220 (0.67), 4.225 (0.59), 4.231 (0.40), 4.242 (0.89), 4.260 (0.79), 7.202 (0.55), 7.224 (0.56), 7.440 (0.54), 7.445 (0.56), 7.454 (1.15), 7.732 (0.58), 7.754 (0.53).

Intermediate 178 ethyl 1-{3-[(tert-butoxycarbonyl)amino]propyl}-6-chloro-7-[3-(chloromethyl)-5-ethyl-1-methyl-1H-pyrazol-4-yl]-3-{3-[(6-fluoronaphthalen-1-yl)oxy]propyl}-1H-indole-2-carboxylate

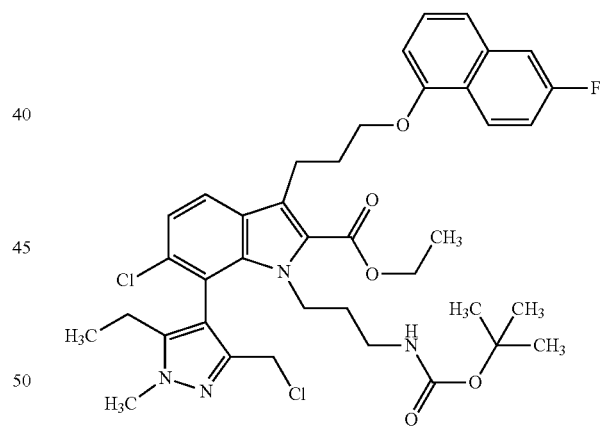

Ethyl 1-{3-[(tert-butoxycarbonyl)amino]propyl}-6-chloro-7-[5-ethyl-3-(hydroxymethyl)-1-methyl-1H-pyrazol-4-yl]-3-{3-[(6-fluoronaphthalen-1-yl)oxy]propyl}-1H-indole-2-carboxylate (see Intermediate 177, 1.28 g), tetrachloromethane (690 µL, 7.1 mmol), pyridine (570 µL, 7.1 mmol) were dissolved in 45 mL acetonitrile and degassed with nitrogen. Triphenylphosphine (1.86 g, 7.10 mmol) was added and stirred under nitrogen atmosphere for 5 h at rt. The reaction mixture was concentrated under reduced pressure and extracted with ethyl acetate and water. The organic layer was concentrated under reduced pressure and purified by flash chromatography (Biotage silica 25 g, Gradient: 0-10% ethyl acetate/ethanol) to provide the target compound in 96% purity: 1.0 g.

LC-MS (Method 2): $R_t$=1.81 min; MS (ESIpos): m/z=741 [M+H]$^+$ $^1$H-NMR (400 MHz, DMSO-d6): δ [ppm]=0.97 (t, 3H), 1.20-1.35 (m, 2H), 1.27 (t, 4H), 1.34-1.39 (m, 11H), 2.14-2.23 (m, 2H), 2.23-2.32 (m, 1H), 2.54-2.65 (m, 1H), 3.26 (br t, 2H), 3.90 (s, 4H), 4.15-4.29 (m, 4H), 4.30-4.42 (m, 2H), 6.68 (br t, 1H), 6.90 (dd, 1H), 7.25 (d, 1H), 7.35-7.49 (m, 3H), 7.67 (dd, 1H), 7.80 (d, 1H), 8.25 (dd, 1H).

Intermediate 179 ethyl 1-(3-aminopropyl)-6-chloro-7-[3-(chloromethyl)-5-ethyl-1-methyl-1H-pyrazol-4-yl]-3-{3-[(6-fluoronaphthalen-1-yl)oxy]propyl}-1H-indole-2-carboxylate

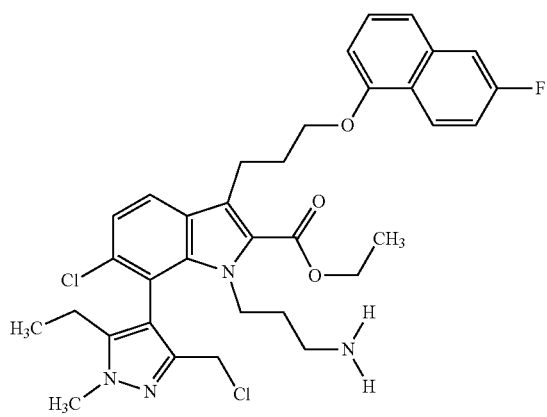 [SMILES: CCOC(=O)c1c(CCCOc2cccc3cc(F)ccc23)c2ccc(Cl)c(-c3c(CCl)nn(C)c3CC)c2n1CCCN]

Ethyl 1-{3-[(tert-butoxycarbonyl)amino]propyl}-6-chloro-7-[3-(chloromethyl)-5-ethyl-1-methyl-1H-pyrazol-4-yl]-3-{3-[(6-fluoronaphthalen-1-yl)oxy]propyl}-1H-indole-2-carboxylate (see Intermediate 178, 1.00 g) was dissolved in 25 mL ethanol. Hydrochloric acid (680 μL, 4.0 M, 2.7 mmol) was added and stirred at rt for 3 h. The reaction mixture was concentrated under red. pressure to provide the crude product in 88% purity, which was used without further purification: 970 mg.

LC-MS (Method 2): $R_t$=1.81 min; MS (ESIpos): m/z=641 [M+H]$^+$ $^1$H-NMR (400 MHz, DMSO-d6): δ [ppm]=0.95 (t, 3H), 1.19-1.26 (m, 2H), 1.29 (t, 3H), 1.44-1.66 (m, 2H), 2.15-2.31 (m, 5H), 2.58-2.65 (m, 1H), 3.25-3.33 (m, 2H), 3.91 (s, 3H), 4.19-4.33 (m, 4H), 4.35-4.50 (m, 2H), 6.91 (dd, 1H), 7.29 (d, 1H), 7.37-7.48 (m, 3H), 7.68 (dd, 1H), 7.76-7.87 (m, 4H), 8.26 (dd, 1H).—as HCl-salt, contains ethanol Intermediate 180

(rac)-ethyl 12-chloro-11-ethyl-1-{3-[(6-fluoronaphthalen-1-yl)oxy]propyl}-10-methyl-4,5,6,7,8,10-hexahydropyrazolo[3',4':7,8][1,5]diazecino[9,10,1-hi]indole-2-carboxylate

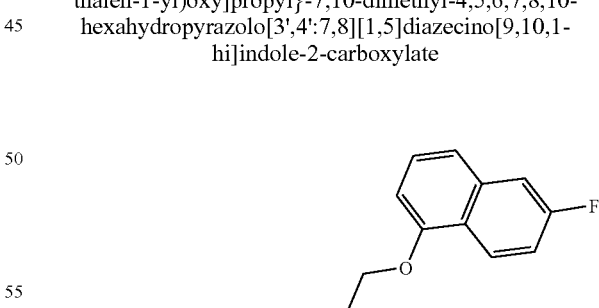

Ethyl 1-(3-aminopropyl)-6-chloro-7-[3-(chloromethyl)-5-ethyl-1-methyl-1H-pyrazol-4-yl]-3-{3-[(6-fluoronaphthalen-1-yl)oxy]propyl}-1H-indole-2-carboxylate (see Intermediate 179, 335 mg) was dissolved in 6.9 mL DMF and treated with the cesium carbonate (853 mg, 2.62 mmol). It was stirred at 65° C. over night under argon atmosphere. The reaction mixture was diluted with water and ethyl acetate. The organic layer was filtered through a silicone coated filter and concentrated under reduced pressure. The crude product was dried by oil pump and used for further reactions without further purification: 218 mg LC-MS (Method 2): $R_t$=1.69 min; MS (ESIpos): m/z=605 [M+H]$^+$ Intermediate 181

(rac)-ethyl 12-chloro-11-ethyl-1-{3-[(6-fluoronaphthalen-1-yl)oxy]propyl}-7,10-dimethyl-4,5,6,7,8,10-hexahydropyrazolo[3',4':7,8][1,5]diazecino[9,10,1-hi]indole-2-carboxylate

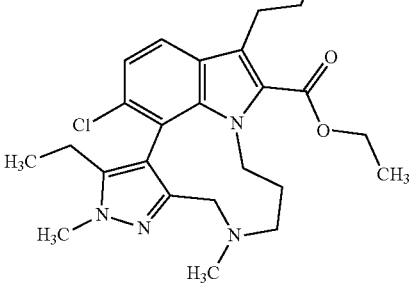

Ethyl 12-chloro-11-ethyl-1-{3-[(6-fluoronaphthalen-1-yl)oxy]propyl}-10-methyl-4,5,6,7,8,10-hexahydropyrazolo[3',4':7,8][1,5]diazecino[9,10,1-hi]indole-2-carboxylate (see Intermediate 180 530 mg) was suspended in 18 mL ethanol and treated with the acetic acid (100 µL, 1.8 mmol) and the formaldehyde (330 µL, 37% purity in water, 4.4 mmol). It was stirred 15 minutes at room temperature under argon atmosphere. Then the sodium cyanoborohydride (110 mg, 1.76 mmol) was added and it was stirred at room temperature over night. Water and ethanol was added and the solvents were removed under reduced pressure. The residue was treated with ethyl acetate and the organic layer was filtered through a silicone coated filter and concentrated under reduced pressure. The crude product was purified by flash chromatography (25 g column, silica; ethyl acetate/ethanol 0%-10%) to provide the target compound in 68% purity: 95 mg.

LC-MS (Method 2): R$_t$=1.64 min; MS (ESIpos): m/z=618 [M+H]$^+$ $^1$H-NMR (400 MHz, DMSO-d6): δ [ppm]=0.90 (t, 3H), 1.22-1.38 (m, 4H), 1.54 (br d, 1H), 1.79 (s, 3H), 1.93-2.03 (m, 1H), 2.13-2.24 (m, 2H), 2.27-2.47 (m, 3H), 3.08 (d, 1H), 3.18-3.31 (m, 3H), 3.76 (br dd, 1H), 3.82 (s, 3H), 4.13-4.31 (m, 4H), 4.52 (br dd, 1H), 6.85 (dd, 1H), 7.14 (d, 1H), 7.37-7.48 (m, 3H), 7.67 (dd, 1H), 7.71 (d, 1H), 8.28 (dd, 1H).

Intermediate 182

(rac)-Ethyl 6-chloro-7-{5-ethyl-1-methyl-3-[(tetrahydro-2H-pyran-2-yloxy)methyl]-1H-pyrazol-4-yl}-3-{3-[(6-fluoro-1-naphthyl)oxy]propyl}-1H-indole-2-carboxylate

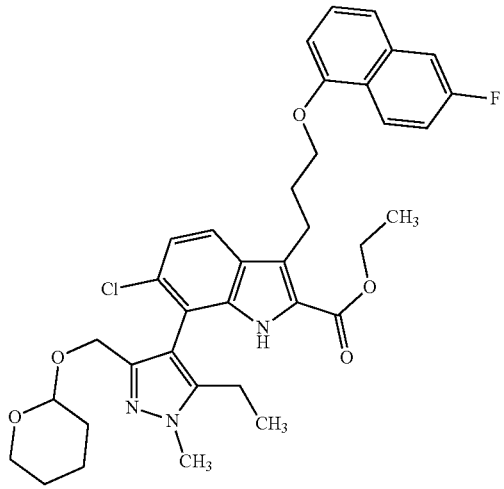 [SMILES: CCOC(=O)c1[nH]c2c(-c3c(COC4CCCCO4)nn(C)c3CC)c(Cl)ccc2c1CCCOc1cccc2cc(F)ccc12]

Ethyl 6-chloro-7-[5-ethyl-3-(hydroxymethyl)-1-methyl-1H-pyrazol-4-yl]-3-{3-[(6-fluoro-1-naphthyl)oxy]propyl}-1H-indole-2-carboxylate (see Intermediate 34, 1.5 g, 2.66 mmol) and 3,4-dihydro-2H-pyran (894 mg, 10.64 mmol) were dissolved in 112 mL anhydrous dichloromethane. 4-Toluenesulfonic acid (51 mg, 266 µmol) was added and the reaction mixture was left to stir and ambient temperature for 19 hours. The mixture was concentrated under reduced pressure and purified by flash chromatography (Biotage isolera, 30 g cartridge) using ethyl acetate and heptane (0:100 to 100:0). Fractions were combined and concentrated under reduced pressure to afford the desired product: 1.64 g (95%), which was formed as a mixture of two racemic diastereomers as a result of atropisomerism at the newly formed bi-heteroaryl bond.

$^1$H NMR (400 MHz, CDCl$_3$) δ [ppm]=1.01 (dt, 3H), 1.34 (t, 3H), 1.36-1.62 (m, 2H), 2.26-2.36 (m, 2H), 2.41-2.58 (m, 2H), 2.84-2.91 (m, 1H), 3.06-3.12 (m, 1H), 3.22-3.28 (m, 1H), 3.33-3.41 (m, 2H), 3.43-3.51 (m, 1H), 3.95 (s, 3H), 4.04-4.21 (m, 4H), 4.24-4.24 (m, 4H), 4.53-4.61 (m, 1H), 6.67-6.72 (m, 1H), 7.14-7.19 (m, 1H), 7.21-7.26 (m, 1H), 8.32-8.38 (m, 1H), 8.56-8.64 (m, 1H).

UPLC4-MS (Method 5): Rt=2.72 & 2.76 min., 96%; MS (ESIpos): m/z=[M+H]$^+$ 564 (fragment)

Intermediate 183

(rac)-Ethyl 1-(4-{[tert-butyl(diphenyl)silyl]oxy}-3,3-difluorobutyl)-6-chloro-7-{3-ethyl-1-methyl-5-[(tetrahydro-2H-pyran-2-yloxy)methyl]-1H-pyrazol-4-yl}-3-{3-[(6-fluoro-1-naphthyl)oxy]propyl}-1H-indole-2-carboxylate

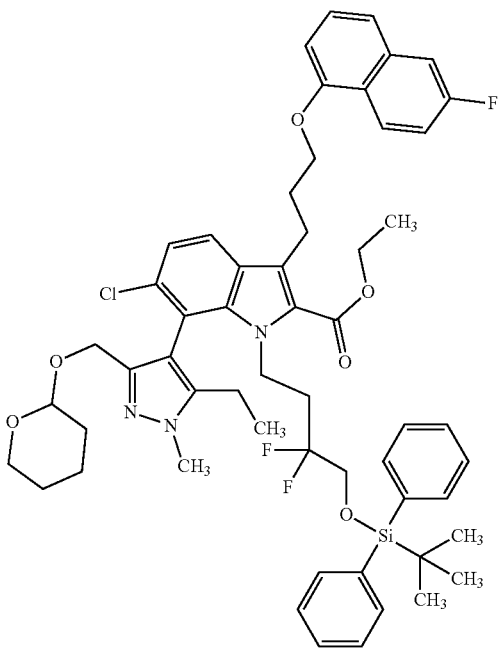 [SMILES: CCOC(=O)c1c(CCCOc2cccc3cc(F)ccc23)c2ccc(Cl)c(-c3c(COC4CCCCO4)nn(C)c3CC)c2n1CCC(F)(F)CO[Si](c1ccccc1)(c1ccccc1)C(C)(C)C]

(rac)-Ethyl 6-chloro-7-{5-ethyl-1-methyl-3-[(tetrahydro-2H-pyran-2-yloxy)methyl]-1H-pyrazol-4-yl}-3-{3-[(6-fluoro-1-naphthyl)oxy]propyl}-1H-indole-2-carboxylate (see Intermediate 182, 890 mg, 1.37 mmol) and 4-{[tert-butyl(diphenyl)silyl]oxy}-3,3-difluorobutan-1-ol (see Intermediate 134, 1.5 g, 4.12 mmol) were dissolved in 18 mL anhydrous toluene in a 10-20 mL microwave vial. Cyanomethyltributylphosphorane (994 mg, 4.12 mmol) was added and the mixture was subjected to microwave irradiation at 120° C. for 1 hour. The reaction mixture was concentrated under reduced pressure and purified by flash chromatography (Biotage isolera, 80 g column) using ethyl acetate and heptane (0:100 to 100:0). Fractions were combined and concentrated under reduced pressure to afford the desired product: 820 mg (60%).

$^1$H NMR (400 MHz, CDCl-3) d [ppm]=1.02 (s, 9H), 1.12 (t, 3H), 1.33 (t, 3H), 1.40-2.00 (m, 4H), 2.22.2.32 (m, 3H), 2.36-2.63 (m, 3H), 2.98-3.21 (m, 1H), 3.24-3.40 (m, 3H). 3.62 (dd, 2H), 3.78-3.88 (m, 4H), 4.11-4.24 (m, 4H), 4.27-4.37 (m, 3H), 4.40-4.54 (m, 3H), 6.73 (dd, 1H), 7.21 (dd, 1H), 7.24-7.30 (m, 1H), 7.31-7.47 (m, 8H), 7.53-7.69 (m, 6H), 8.38 (dd, 1H).

$^{19}$F NMR (400 MHz, CDCl-3) d [ppm]=–115.0 (m, 1H), –111.1--107.5 (m, 2H).

UPLC4-MS (Method 4): Rt=3.74 min., 45%; MS (ESI-pos): m/z=[M+H]$^+$ 910 (Fragment).

Intermediate 184

Ethyl 1-(4-{[tert-butyl(diphenyl)silyl]oxy}-3,3-difluorobutyl)-6-chloro-7-[5-ethyl-3-(hydroxymethyl)-1-methyl-1H-pyrazol-4-yl]-3-{3-[(6-fluoro-1-naphthyl)oxy]propyl}-1H-indole-2-carboxylate

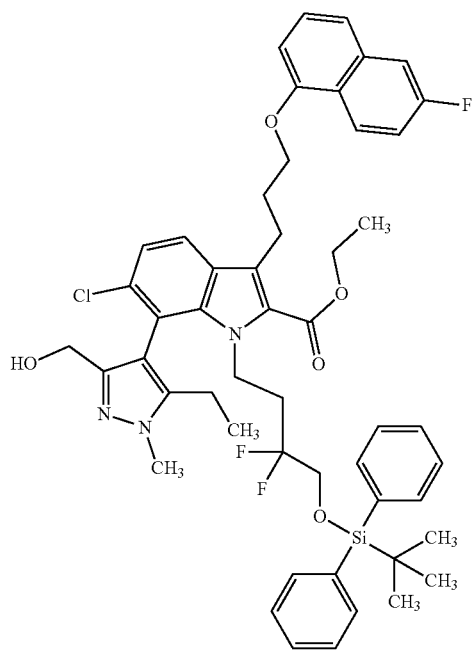 [SMILES: CCOC(=O)c1c(CCCOc2cccc3cc(F)ccc23)c2ccc(Cl)c(-c3c(CO)nn(C)c3CC)c2n1CCC(F)(F)CO[Si](c1ccccc1)(c1ccccc1)C(C)(C)C]

To a solution of ethyl 1-(4-{[tert-butyl(diphenyl)silyl]oxy}-3,3-difluorobutyl)-6-chloro-7-{3-ethyl-1-methyl-5-[(tetrahydro-2H-pyran-2-yloxy)methyl]-1H-pyrazol-4-yl}-3-{3-[(6-fluoro-1-naphthyl)oxy]propyl}-1H-indole-2-carboxylate (see Intermediate 183, 760 mg, 90% pure, 688 µmol) in 50 mL industrial methylated spirit was added 4-toluenesulfonic acid (13 mg, 69.0 µmol). The mixture was heated to 60° C. for 8 hours, then concentrated under reduced pressure and purified by flash chromatography (Biotage Isolera 80 g; ZIP Sphere cartridge) using ethyl acetate and heptane (0:100 to 100:0). Fractions were combined and concentrated under reduced pressure to afford the desired product: 650 mg (94%).

$^1$H NMR (400 MHz, CDCl-3) d [ppm]=1.04 (s, 9H), 1.07 (t, 3H), 1.37 (t, 3H), 1.97-2.22 (m, 2H), 2.27-2.37 (m, 2H), 2.38-2.54 (m, 2H), 3.36 (t, 2H), 3.63 (dd, 2H), 3.85 (d, 3H), 4.23 (t, 2H), 4.30-4.51 (m, 6H), 6.75 (dd, 1H), 7.22 (d, 1H), 7.24-7.28 (m, 1H), 7.35-7.47 (m, 9H), 7.60-7.68 (m, 5H), 8.37 (dd, 1H).

$^{19}$F NMR (400 MHz, CDCl-3) d [ppm]=–114.8 (m, 1H), –110.5--107.8 (dm, 2H).

UPLC4-MS (Method 4): Rt=3.27 min., 97%; MS (ESI-pos): m/z=[M+H]$^+$ 910.

Intermediate 185

Ethyl 7-[3-({(tert-butoxycarbonyl)[(2-nitrophenyl)sulfonyl]amino}methyl)-5-ethyl-1-methyl-1H-pyrazol-4-yl]-1-(4-{[tert-butyl(diphenyl)silyl]oxy}-3,3-difluorobutyl)-6-chloro-3-{3-[(6-fluoro-1-naphthyl)oxy]propyl}-1H-indole-2-carboxylate

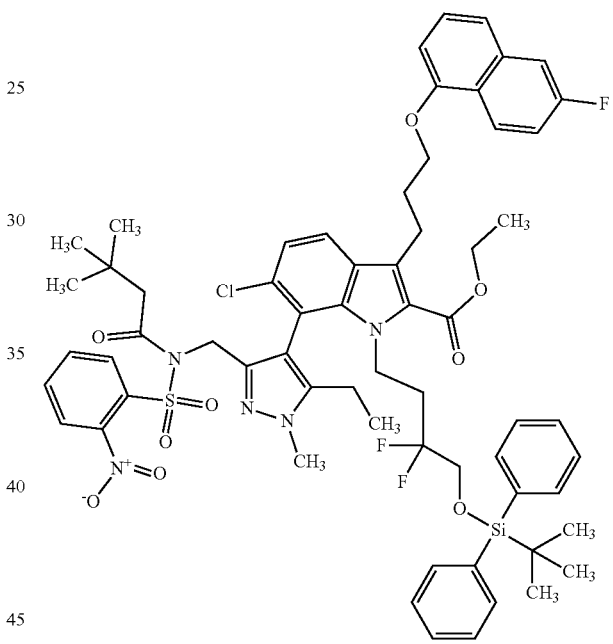

Ethyl 1-(4-{[tert-butyl(diphenyl)silyl]oxy}-3,3-difluorobutyl)-6-chloro-7-[5-ethyl-3-(hydroxymethyl)-1-methyl-1H-pyrazol-4-yl]-3-{3-[(6-fluoro-1-naphthyl)oxy]propyl}-1H-indole-2-carboxylate (see Intermediate 184, 650 mg 91% purity, 0.650 mmol), N-(tert-butoxycarbonyl)-2-nitrobenzenesulfonamide (393 mg, 1.30 mmol) and triphenylphosphine (682 mg, 2.60 mmol) were dissolved in 60 mL anhydrous tetrahydrofuran. To the mixture was added di-tert-butyl azodicarboxylate (598 mg, 2.60 mmol) and the resulting reaction mixture was stirred and ambient temperature for 3 hours. The reaction mixture was concentrated under reduced pressure and purified by flash chromatography (Biotage Isolera 80 g; ZIP Sphere cartridge) using ethyl acetate and heptane (0:100 to 100:0). Fractions were combined and concentrated under reduced pressure to afford the desired product: 1.32 g (85%).

UPLC4-MS (Method 4): Rt=3.73 min., 62%; MS (ESI-pos): m/z=[M+H]⁺ 1194.

Intermediate 186

Ethyl 1-(4-{[tert-butyl(diphenyl)silyl]oxy}-3,3-difluorobutyl)-6-chloro-7-[5-ethyl-1-methyl-3-({[(2-nitrophenyl)sulfonyl]amino}methyl)-1H-pyrazol-4-yl]-3-{3-[(6-fluoro-1-naphthyl)oxy]propyl}-1H-indole-2-carboxylate hydrochloride salt

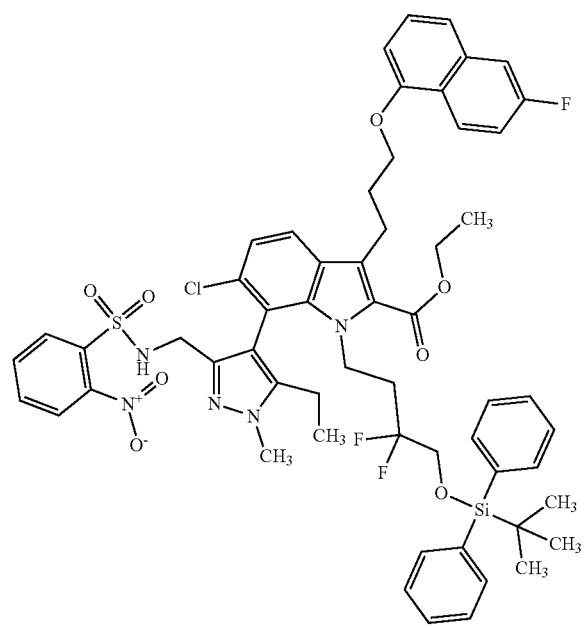 [SMILES: CCOC(=O)c1c(CCCOc2cccc3cc(F)ccc23)c2ccc(Cl)c(-c3c(CNS(=O)(=O)c4ccccc4[N+](=O)[O-])nn(C)c3CC)c2n1CCC(F)(F)CO[Si](c1ccccc1)(c1ccccc1)C(C)(C)C]

Ethyl 7-[3-({(tert-butoxycarbonyl)[(2-nitrophenyl)sulfonyl]amino}methyl)-5-ethyl-1-methyl-1H-pyrazol-4-yl]-1-(4-{[tert-butyl(diphenyl)silyl]oxy}-3,3-difluorobutyl)-6-chloro-3-{3-[(6-fluoro-1-naphthyl)oxy]propyl}-1H-indole-2-carboxylate (see Intermediate 185, 650 mg, 544 µmol) was dissolved in 90 mL dichloromethane and 10 mL trifluoroacetic acid. The mixture was left to stir at ambient temperature for 24 hours. The mixture was concentrated under reduced pressure and taken to the next synthetic step with no further purification: 360 mg (58%).

UPLC4-MS (Method 4): Rt=3.45 min., 49%; MS (ESI-pos): m/z=[M+H]⁺ 1094.

Intermediate 187

Ethyl 6-chloro-1-(3,3-difluoro-4-hydroxybutyl)-7-[5-ethyl-1-methyl-3-({[(2-nitrophenyl)sulfonyl]amino}methyl)-1H-pyrazol-4-yl]-3-{3-[(6-fluoro-1-naphthyl)oxy]propyl}-1H-indole-2-carboxylate

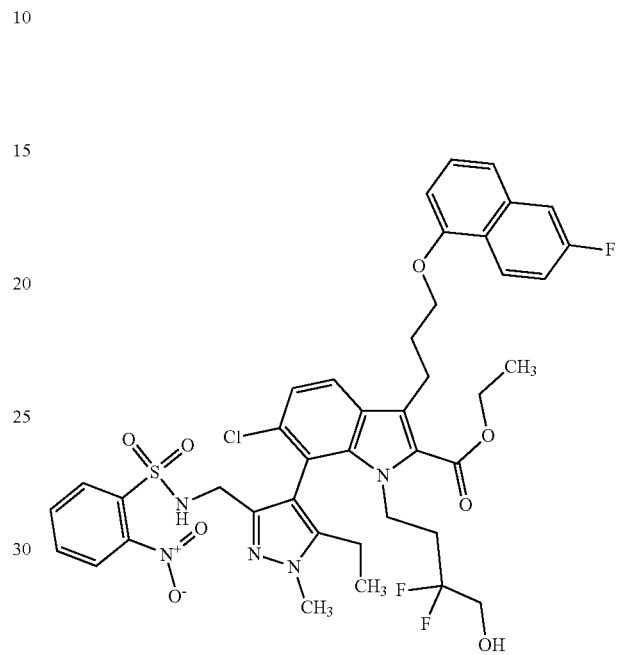

Ethyl 1-(4-{[tert-butyl(diphenyl)silyl]oxy}-3,3-difluorobutyl)-6-chloro-7-[5-ethyl-1-methyl-3-({[(2-nitrophenyl)sulfonyl]amino}methyl)-1H-pyrazol-4-yl]-3-{3-[(6-fluoro-1-naphthyl)oxy]propyl}-1H-indole-2-carboxylate salt (see Intermediate 186, 360 mg, 329 µmol), was dissolved in tetra-n-butylammonium fluoride (20 mL, 1M in tetrahydrofuran) and left to stir at ambient temperature for 15 minutes. The reaction mixture was concentrated under reduced pressure. The crude was partitioned between water and dichloromethane. The aqueous layer was extracted with dichloromethane, the organic layers were combined and concentrated under reduced pressure. Material was purified by flash chromatography (Biotage isolera, 45 g cartridge) using ethyl acetate and heptane (0:100 to 100:0). Fractions were combined and concentrated under reduced pressure to afford the desired product: 180 mg (64% yield).

UPLC4-MS (Method 4): Rt=1.67 min., 68%; MS (ESI-pos): m/z=[M+H]⁺ 856.

363

Intermediate 188

(rac)-Ethyl 4-chloro-3-ethyl-12,12-difluoro-7-{3-[(6-fluoro-1-naphthyl)oxy]propyl}-2-methyl-14-[(2-nitrophenyl)sulfonyl]-10,11,12,13,14,15-hexahydro-2H-pyrazolo[3',4':8,9][1,6]diazacycloundecino[10,11,1-hi]indole-8-carboxylate

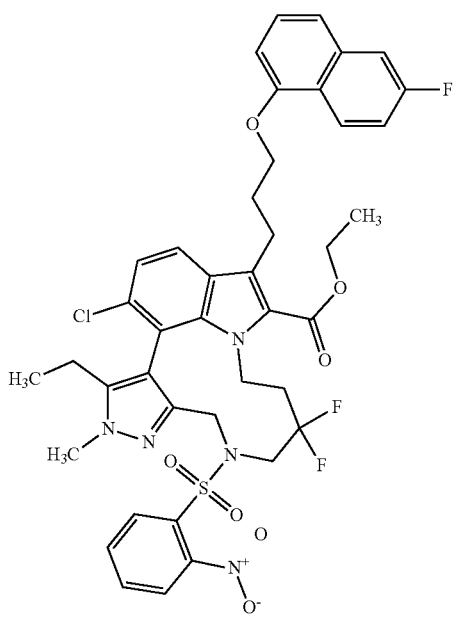

Ethyl 6-chloro-1-(3,3-difluoro-4-hydroxybutyl)-7-[5-ethyl-1-methyl-3-({[(2-nitrophenyl)sulfonyl]amino}methyl)-1H-pyrazol-4-yl]-3-{3-[(6-fluoro-1-naphthyl)oxy]propyl}-1H-indole-2-carboxylate (see Intermediate 187, 60 mg, 70.0 µmol) was dissolved in 4 mL anhydrous toluene. Cyanomethyltributylphosphorane (101 mg, 420 µmol) was added and the mixture was submitted to microwave irradiation at 150° C. for 1 hour 30 minutes. This material was combined with a second reaction batch using ethyl 6-chloro-1-(3,3-difluoro-4-hydroxybutyl)-7-[5-ethyl-1-methyl-3-({[(2-nitrophenyl)sulfonyl]amino}methyl)-1H-pyrazol-4-yl]-3-{3-[(6-fluoro-1-naphthyl)oxy]propyl}-1H-indole-2-carboxylate, (see Intermediate 187, 120 mg, 140 µmol) and cyanomethyltributylphosphorane (101 mg, 420 µmol) in 4 mL anhydrous toluene at 150° C. for 1 hour. The resulting combined reaction mixture was subjected to microwave irradiations at 150° C. for 45 minutes. The mixture was concentrated under reduced pressure and purified by flash chromatography (Biotage isolera, 30 g cartridge) using ethyl acetate and heptane (0:100 to 100:0). Fractions were combined and concentrated under reduced pressure to afford the desired product: 140 mg (80%).

364

UPLC4-MS (Method 4): Rt=2.22 min., 62%; MS (ESI-pos): m/z=[M+H]+ 838.

Intermediate 189

(rac)-Ethyl 4-chloro-3-ethyl-12,12-difluoro-7-{3-[(6-fluoro-1-naphthyl)oxy]propyl}-2-methyl-10,11,12,13,14,15-hexahydro-2H-pyrazolo[3',4':8,9][1,6]diazacycloundecino[10,11,1-hi]indole-8-carboxylate

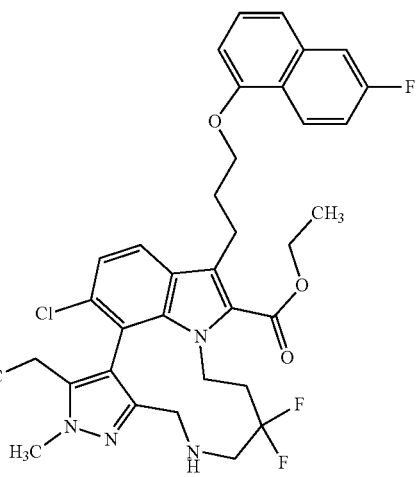

Ethyl 4-chloro-3-ethyl-12,12-difluoro-7-{3-[(6-fluoro-1-naphthyl)oxy]propyl}-2-methyl-14-[(2-nitrophenyl)sulfonyl]-10,11,12,13,14,15-hexahydro-2H-pyrazolo[3',4':8,9][1,6]diazacycloundecino[10,11,1-hi]indole-8-carboxylate, (see Intermediate 188, 130 mg, 80% purity, 124 µmol) was dissolved in 10 mL acetonitrile in a 10-20 mL microwave vial. Cesium carbonate (101 mg, 310 µmol) was added followed by thiophenol (34 µL, 310 µmol). The reaction mixture was topped with a balloon of nitrogen and left to stir at ambient temperature for 3 hours. The mixture was concentrated under reduced pressure and purified through SCX-2 (5 g) (eluent: methanol-10% ammonia in methanol 1:0, 0:1). This isolated flush fraction was concentrated under reduced pressure to afford the desired product: 78 mg (96%).

UPLC4-MS (Method 4): Rt=1.94 min., 72%; MS (ESI-pos): m/z=[M+H]+ 653.

Intermediate 190

(rac)-Ethyl 4-chloro-3-ethyl-12,12-difluoro-7-{3-[(6-fluoro-1-naphthyl)oxy]propyl}-2,14-dimethyl-10,11,12,13,14,15-hexahydro-2H-pyrazolo[3',4':8,9][1,6]diazacycloundecino[10,11,1-hi]indole-8-carboxylate

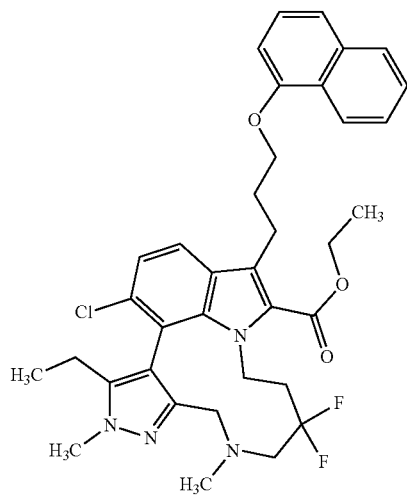

To a solution of ethyl 4-chloro-3-ethyl-12,12-difluoro-7-{3-[(6-fluoro-1-naphthyl)oxy]propyl}-2-methyl-10,11,12,13,14,15-hexahydro-2H-pyrazolo[3',4':8,9][1,6]diazacycloundecino[10,11,1-hi]indole-8-carboxylate (see Intermediate 189, 45 mg, 69.0 µmol) in 3 mL industrial methylated spirit at ambient temperature was added acetic acid (16 µL, 276 µmol) and formaldehyde (56 µL, 689 µmol, 37% aqueous solution). The solution was left to stir at ambient temperature for 15 minutes and sodium cyanoborohydride (43 mg, 689 µmol) was added at once. This was combined with a second reaction batch of ethyl 4-chloro-3-ethyl-12,12-difluoro-7-{3-[(6-fluoro-1-naphthyl)oxy]propyl}-2-methyl-10,11,12,13,14,15-hexahydro-2H-pyrazolo[3',4':8,9][1,6]diazacycloundecino[10,11,1-hi]indole-8-carboxylate (see Intermediate 189, 15 mg, 23.0 µmol), acetic acid, (5 µL, 92.0 µmol) and formaldehyde (18 µL, 689 µmol, 37% aqueous solution) in 1 mL industrial methylated spirit. The combined mixture was left to stir at ambient temperature for 30 minutes. The mixture was purified through SCX-2 (5 g) (eluent: methanol-10% ammonia in methanol 1:0, 0:1). This isolated flush fraction was concentrated under reduced pressure to afford the desired product: 54 mg (89%).

UPLC4-MS (Method 5): Rt=3.24 min., 77%; MS (ESIpos): m/z=[M+H]⁺ 667.

Intermediate 191 tert-butyl [(4-bromo-5-ethyl-1-methyl-1H-pyrazol-3-yl)methyl](2-nitrobenzene-1-sulfonyl)carbamate

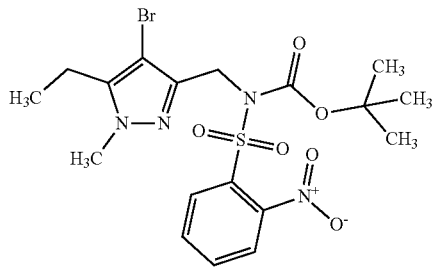 [SMILES: CCc1c(Br)c(CN(C(=O)OC(C)(C)C)S(=O)(=O)c2ccccc2[N+](=O)[O-])nn1C]

Tert-butyl (2-nitrobenzene-1-sulfonyl)carbamate (CAS 198572-71-3, 788 mg, 2.61 mmol) was dissolved in 6 mL THF and 6 mL DMF and treated portion wise with sodium hydride (104 mg, 60% purity, 2.61 mmol). It was stirred at 65° C. for 2 hours, then 4-bromo-3-(bromomethyl)-5-ethyl-1-methyl-1H-pyrazole (see Intermediate 140, 735 mg, 2.61 mmol), dissolved in 5 mL THF and 5 mL DMF was added and it was stirred at the same temperature under argon atmosphere. The reaction mixture was diluted with methyl tert.-butyl ether and water, it was extracted with methyl tert.-butyl ether three times, washed with water and brine once, filtered through a silicone coated filter and concentrated under reduced pressure. The crude product was purified by flash chromatography (10 g column, silica ULTRA, hexane/ethyl acetate 0%-50%) to provide the desired product in 83% purity: 399 mg (fraction A) and in 100% purity: 169 mg (fraction B).

LC-MS (Method 2): $R_t$=1.39 min; MS (ESIpos): m/z=505 [M+H]⁺

Fraction A: 1H-NMR (400 MHz, DMSO-d6): δ [ppm]= 1.10 (t, 3H), 1.19 (s, 9H), 2.66 (q, 2H), 3.79 (s, 3H), 4.79 (s, 2H), 7.90-8.01 (m, 2H), 8.06-8.11 (m, 1H), 8.33-8.39 (m, 1H).—contains some 4-bromo-3-(bromomethyl)-5-ethyl-1-methyl-1H-pyrazole Fraction B: 1H-NMR (400 MHz, DMSO-d6): δ [ppm]= 1.10 (t, 3H), 1.19 (s, 9H), 2.66 (q, 2H), 3.80 (s, 3H), 4.79 (s, 2H), 7.90-8.01 (m, 2H), 8.06-8.11 (m, 1H), 8.33-8.39 (m, 1H).—contains further nosyl-protons

Intermediate 192

N-[(4-bromo-5-ethyl-1-methyl-1H-pyrazol-3-yl)methyl]-2-nitrobenzene-1-sulfonamide-hydrogen chloride salt

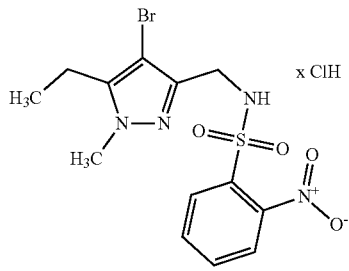 [SMILES: CCc1c(Br)c(CNS(=O)(=O)c2ccccc2[N+](=O)[O-])nn1C]

Tert-butyl [(4-bromo-5-ethyl-1-methyl-1H-pyrazol-3-yl)methyl](2-nitrobenzene-1-sulfonyl)carbamate (see Intermediate 191, 78.0 mg) was dissolved in 1.6 mL methanol and treated with the hydrochloric acid in dioxane (190 µl, 4.0 M, 770 µmol). It was stirred at 40° C. for 2 days under nitrogen atmosphere The reaction mixture was concentrated under reduced pressure to provide the crude product with 74% purity, which was used without further purification: 79 mg LC-MS (Method 2): $R_t$=1.05 min; MS (ESIpos): m/z=403/405 [M+H]$^+$ $^1$H-NMR (400 MHz, DMSO-d6): δ [ppm]=1.00 (t, 3H), 3.65 (s, 3H), 4.03 (d, 2H), 7.71-7.94 (m, 4H), 8.47 (t, 1H).—HCl-salt, 1×CH2 not detectable Intermediate 193

N-[(4-bromo-5-ethyl-1-methyl-1H-pyrazol-3-yl)methyl]-N-(4-{[tert-butyl(diphenyl)silyl]oxy}-3,3-difluorobutyl)-2-nitrobenzene-1-sulfonamide

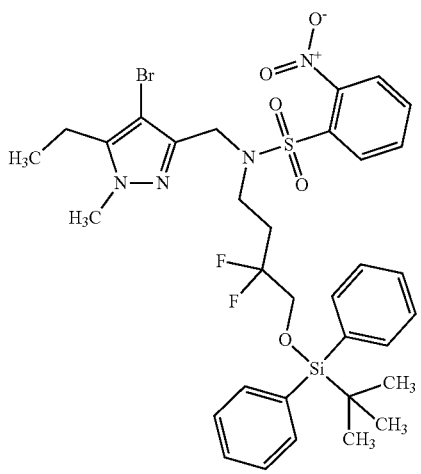 [SMILES: CCc1c(Br)c(CN(CCC(F)(F)CO[Si](c2ccccc2)(c2ccccc2)C(C)(C)C)S(=O)(=O)c2ccccc2[N+](=O)[O-])nn1C]

4-{[tert-butyl(diphenyl)silyl]oxy}-3,3-difluorobutan-1-ol (see Intermediate 134, 65.5 mg, 180 µmol), N-[(4-bromo-5-ethyl-1-methyl-1H-pyrazol-3-yl)methyl]-2-nitrobenzene-1-sulfonamide hydrogen chloride salt (see Intermediate 192 79.0 mg) and triphenylphosphine (377 mg, 1.44 mmol) were dissolved in 7.3 mL THF and treated with di-tert-butyl azodicarboxylte (331 mg, 1.44 mmol). It was stirred at room temperature under argon atmosphere over night. The reaction mixture was treated with hydrochloric acid (450 µL, 4.0 M in dioxane, 1.8 mmol), ethyl acetate and water were added and the organic layer was filtered through a silicone coated filter and concentrated under reduced pressure. The crude product was purified by flash chromatography (10 g column, silica ULTRA; hexane/ethyl acetate 50%-100%/ ethyl acetate/ethanol 0%-10%) to provide the target compound in 76% purity: 89 mg LC-MS (Method 2): $R_t$=1.75 min; MS (ESIpos): m/z=752 [M+H]$^+$ $^1$H-NMR (400 MHz, DMSO-d6): δ [ppm]=0.96 (s, 9H), 1.02 (t, 3H), 2.15-2.31 (m, 2H), 2.54-2.62 (m, 2H), 3.50-3.58 (m, 2H), 3.66 (s, 3H), 3.71-3.81 (m, 2H), 4.45 (s, 2H), 7.37-7.50 (m, 6H), 7.56-7.61 (m, 4H), 7.73-7.79 (m, 1H), 7.82-7.91 (m, 2H), 7.96 (dd, 1H).

Intermediate 194

N-[(4-bromo-5-ethyl-1-methyl-1H-pyrazol-3-yl)methyl]-N-(3,3-difluoro-4-hydroxybutyl)-2-nitrobenzene-1-sulfonamide

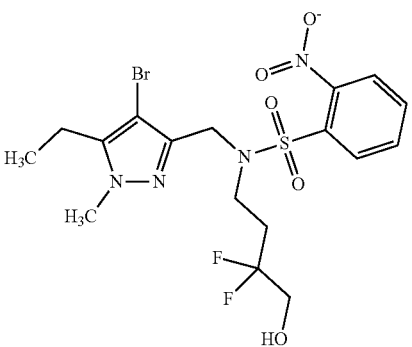

N-[(4-bromo-5-ethyl-1-methyl-1H-pyrazol-3-yl)methyl]-N-(4-{[tert-butyl(diphenyl)silyl]oxy}-3,3-difluorobutyl)-2-nitrobenzene-1-sulfonamide (see Intermediate 193, 590 mg) dissolved in 1.6 mL THF was treated with the tetrabutylammonium fluoride solution (1.6 ml, 1.0 M in THF, 1.6 mmol) and the reaction mixture was stirred at 60° C. under argon atmosphere. The reaction mixture was quenched with saturated sodium hydrogen carbonate solution and diluted with ethyl acetate. It was stirred for a few minutes, the organic layer was filtered through a silicone coated filter and concentrated under reduced pressure. The crude product was purified by flash chromatography (25 g column, silica; methylene chloride/ethanol 0%-10%) to provide the target compound with 82% purity: 439 mg LC-MS (Method 2): $R_t$=1.16 min; MS (ESIpos): m/z=511/513 [M+H]$^+$ $^1$H-NMR (400 MHz, DMSO-d6): δ [ppm]=1.00-1.07 (m, 3H), 2.01-2.22 (m, 2H), 2.56-2.63 (m, 2H), 3.43-3.56 (m, 4H), 3.71 (s, 3H), 4.42 (s, 2H), 5.50 (t, 1H), 7.73-7.81 (m, 1H), 7.83-7.91 (m, 2H), 7.93-8.01 (m, 1H).

Intermediate 195 ethyl 6-chloro-7-(3-{[(3,3-difluoro-4-hydroxybutyl)(2-nitrobenzene-1-sulfonyl)amino]methyl}-5-ethyl-1-methyl-1H-pyrazol-4-yl)-3-{3-[(6-fluoronaphtha-len-1-yl)oxy]propyl}-1H-indole-2-carboxylate

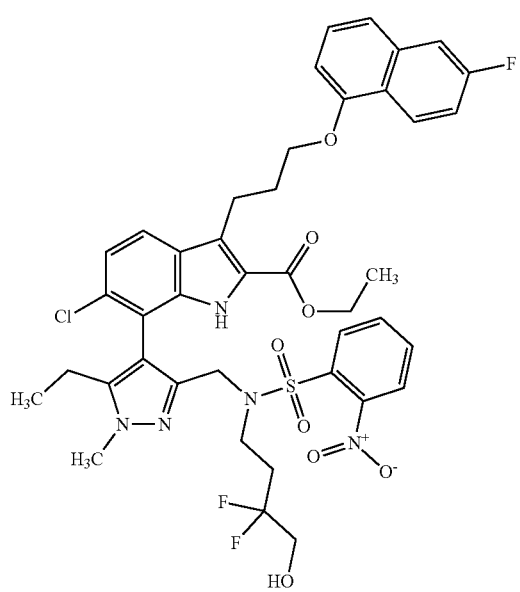 [SMILES: CCOC(=O)c1[nH]c2c(-c3c(CN(CCC(F)(F)CO)S(=O)(=O)c4ccccc4[N+](=O)[O-])nn(C)c3CC)c(Cl)ccc2c1CCCOc1cccc2cc(F)ccc12]

Ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 9, 150 mg, 272 µmol), N-[(4-bromo-5-ethyl-1-methyl-1H-pyrazol-3-yl)methyl]-N-(3,3-difluoro-4-hydroxybutyl)-2-nitrobenzene-1-sulfonamide (see Intermediate 194, 174 mg, 340 µmol) and potassium phosphate (250 µL, 2.2 M in water, 540 µmol) were dissolved in 2.7 mL toluole and 1.1 mL water. The mixture was degassed by bubbling argon through the mixture for 5 minutes. Then RuPhos Pd G3 (12.5 mg, 14.9 µmol) was added and it was degassed for 5 minutes again. The reaction mixture was put in a to 180° C. preheated aluminium block. The temperature was set down to 110° C. and it was stirred for 1 hour under argon atmosphere. The reaction mixture was filtered through a silicone coated filter and concentrated under reduced pressure. The crude product was purified by HPLC chromatography under basic conditions to provide the analytically pure target compound 25 mg and 29 mg (88% pure).

LC-MS (Method 2): $R_t$=1.65 min; MS (ESIpos): m/z=856 [M+H]$^+$ $^1$H-NMR (400 MHz, DMSO-d6): δ [ppm]=0.85 (t, 3H), 1.25 (t, 3H), 1.78-2.01 (m, 2H), 2.14-2.25 (m, 2H), 2.27-2.46 (m, 2H), 3.29 (br t, 2H), 3.34-3.48 (m, 3H), 3.77 (s, 3H), 4.13-4.32 (m, 6H), 5.43 (t, 1H), 6.87 (dd, 1H), 7.09 (d, 1H), 7.36-7.49 (m, 3H), 7.62-7.70 (m, 3H), 7.75-7.89 (m, 3H), 8.29 (dd, 1H), 11.05 (s, 1H).—1H not detectable

Intermediate 196 ethyl 6-chloro-7-(3-{[{3,3-difluoro-4-[(trifluoromethanesulfonyl)oxy]butyl}(2-nitrobenzene-1-sulfonyl)amino]methyl}-5-ethyl-1-methyl-1H-pyrazol-4-yl)-3-{3-[(6-fluoronaphthalen-1-yl)oxy]propyl}-1H-indole-2-carboxylate

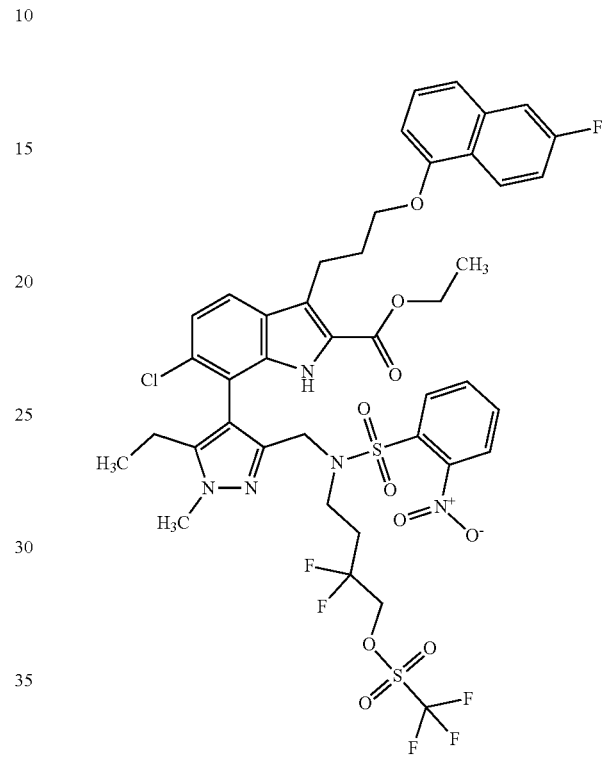

Ethyl 6-chloro-7-(3-{[(3,3-difluoro-4-hydroxybutyl)(2-nitrobenzene-1-sulfonyl)amino]methyl}-5-ethyl-1-methyl-1H-pyrazol-4-yl)-3-{3-[(6-fluoronaphthalen-1-yl)oxy]propyl}-1H-indole-2-carboxylate (see Intermediate 195, 25.0 mg) was dissolved in 140 µL dichloromethane and cooled down with an ice bath. Trifluormethane sulfonic acid anhydride (5.4 µL, 32 µmol) was added. Then triethylamine (12 µL, 88 µmol) was added drop wise and the reaction mixture was stirred at room temperature over night under argon atmosphere. The reaction mixture was diluted with dichloromethane and water, stirred for a few minutes, filtered through a silicone coated filter and concentrated under reduced pressure. The crude product was purified by HPLC chromatography under basic condition to provide analytically pure target compound: 12 mg LC-MS (Method 2): $R_t$=1.76 min; MS (ESIpos): m/z=988 [M+H]$^+$ $^1$H-NMR (400 MHz, DMSO-d6): δ [ppm]=0.85 (t, 3H), 1.20-1.32 (m, 4H), 1.99-2.14 (m, 2H), 2.15-2.23 (m, 2H), 2.25-2.33 (m, 1H), 3.22-3.32 (m, 2H), 3.37-3.47 (m, 2H), 3.77 (s, 3H), 4.10-4.34 (m, 6H), 4.97 (t, 2H), 6.87 (dd, 1H), 7.09 (d, 1H), 7.31-7.47 (m, 3H), 7.61-7.71 (m, 3H), 7.75-7.89 (m, 3H), 8.28 (dd, 1H), 11.06 (s, 1H).

Intermediate 197

(rac)-ethyl 4-chloro-3-ethyl-11,11-difluoro-7-{3-[(6-fluoronaphthalen-1-yl)oxy]propyl}-2-methyl-14-(2-nitrobenzene-1-sulfonyl)-10,11,12,13,14,15-hexahydro-2H-pyrazolo[3',4':8,9][1,6]diazacycloundecino[10,11,1-hi]indole-8-carboxylate

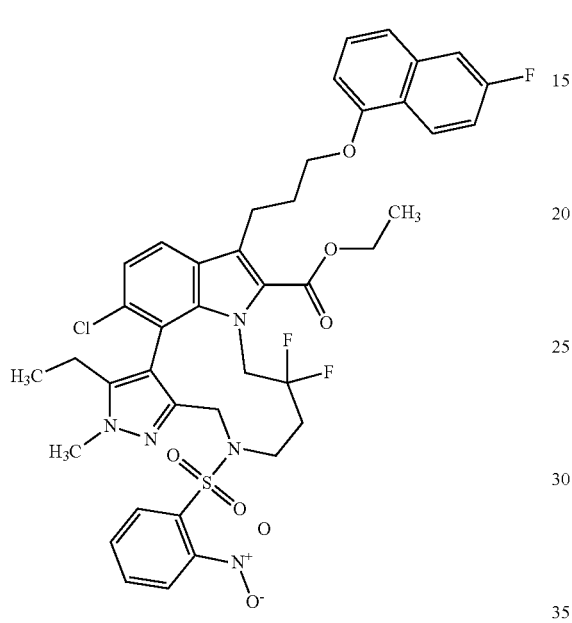

Ethyl 6-chloro-7-(3-{[{3,3-difluoro-4-[(trifluoromethanesulfonyl)oxy]butyl}(2-nitrobenzene-1-sulfonyl)amino]methyl}-5-ethyl-1-methyl-1H-pyrazol-4-yl)-3-{3-[(6-fluoronaphthalen-1-yl)oxy]propyl}-1H-indole-2-carboxylate (see Intermediate 196, 20.0 mg, 20.2 µmol) was dissolved in 78 µL DMF and treated with sodium hydride (2.02 mg, 60% purity, 50.6 µmol). It was stirred at room temperature under nitrogen atmosphere for 1.5 hours. The reaction mixture was diluted with water and dichloromethane, stirred, filtered through a silicone coated filter and concentrated under reduced pressure. The crude product was purified by HPLC chromatography under basic conditions to provide the analytically pure target compound: 7 mg.

LC-MS (Method 2): $R_t$=1.72 min; MS (ESIpos): m/z=839/840 [M+H]$^+$ $^1$H-NMR (400 MHz, DMSO-d6): δ [ppm]=0.79 (t, 3H), 1.18-1.30 (m, 3H), 1.36-1.59 (m, 1H), 1.75-1.93 (m, 1H), 2.12-2.25 (m, 3H), 2.27-2.40 (m, 1H), 2.59-2.70 (m, 1H), 3.14-3.32 (m, 2H), 3.42 (dt, 1H), 3.86 (s, 3H), 4.10-4.52 (m, 7H), 4.95 (dt, 1H), 6.85 (dd, 1H), 7.30-7.47 (m, 4H), 7.66 (dd, 1H), 7.81-7.95 (m, 3H), 7.96-8.03 (m, 1H), 8.16 (dd, 1H), 8.25 (dd, 1H).—contains dichloromethane The crude product was combined with the crude product of BRAL 330-3 and used for further reaction. see BRAL 349-1/FP 2593-1

Intermediate 198

(rac)-ethyl 4-chloro-3-ethyl-11,11-difluoro-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylate

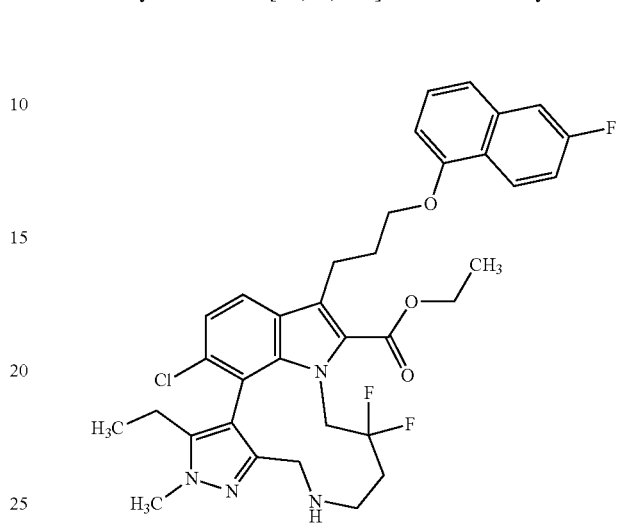

(rac)-Ethyl 4-chloro-3-ethyl-11,11-difluoro-7-{3-[(6-fluoronaphthalen-1-yl)oxy]propyl}-2-methyl-14-(2-nitrobenzene-1-sulfonyl)-10,11,12,13,14,15-hexahydro-2H-pyrazolo[3',4':8,9][1,6]diazacycloundecino[10,11,1-hi]indole-8-carboxylate (see Intermediate 197, 30.0 mg) was dissolved in 200 µL acetonitrile and treated with cesium carbonate (23.3 mg, 71.6 µmol). Then thiophenole (7.3 µL, 72 µmol) was added. After a few minutes the mixture turned cloudy. The reaction mixture was stirred at room temperature under argon atmosphere over night. The reaction mixture was diluted with ethyl acetate and water, stirred for a few minutes, filtered through a silicone coated filter and concentrated under reduced pressure to provide the crude product which was used without further purification: 32 mg.

Intermediate 199

(rac)-ethyl 4-chloro-3-ethyl-11,11-difluoro-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylate

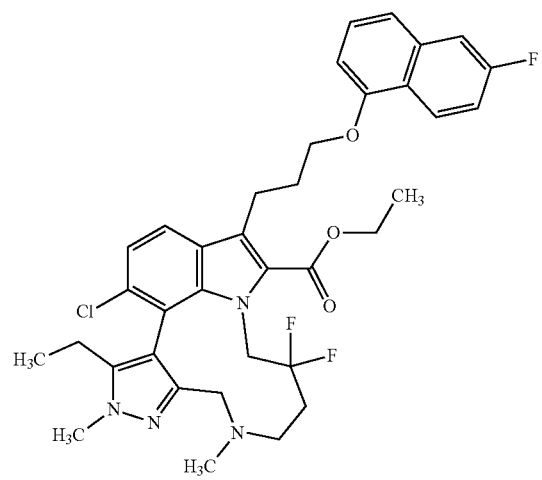 [SMILES: CCOC(=O)c1c(CCCOc2cccc3cc(F)ccc23)c2ccc(Cl)c3c2n1CC(F)(F)CCN(C)Cc1nn(C)c(CC)c1-3]

(rac)-Ethyl 4-chloro-3-ethyl-11,11-difluoro-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylate (see Intermediate 198, 23.0 mg) was suspended in 710 μL ethanol and treated with the acetic acid (4.0 μL, 70 μmol) and form aldehyde (13 μL, 37% purity in water, 180 μmol). The reaction mixture was stirred 15 minutes at room temperature under argon atmosphere. Then the sodium cyanoborohydride (4.43 mg, 70.4 μmol) was added and it was stirred at room temperature over night. The reaction mixture was combined with the reaction mixture starting from ethyl 4-chloro-3-ethyl-11,11-difluoro-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylate (see Intermediate 198, 18 mg), quenched carefully with water and diluted with ethyl acetate. It was stirred for a few minutes, filtered through a silicone coated filter and concentrated under reduced pressure. The crude product was purified by HPLC chromatography under to provide the target compound in 98% purity: 12 mg and in 63% purity: 6 mg.

LC-MS (Method 2): $R_t$=1.76 min; MS (ESIpos): m/z=669 [M+H]$^+$

Intermediate 200

(rac)-ethyl 4-chloro-3-ethyl-7-{3-[(6-fluoronaphthalen-1-yl)oxy]propyl}-14-(2-methoxyethyl)-2-methyl-10,11,12,13,14,15-hexahydro-2H-pyrazolo[3',4':8,9][1,6]diazacycloundecino[10,11,1-hi]indole-8-carboxylate

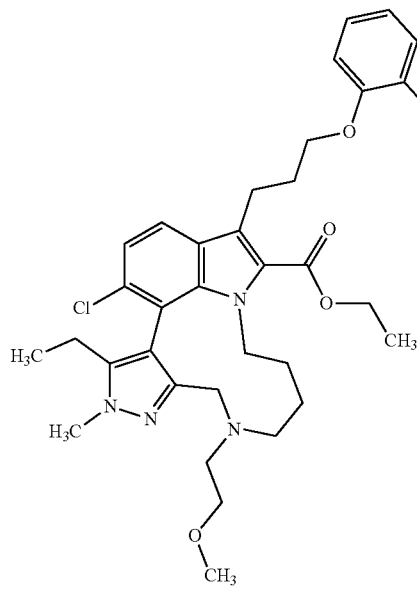

(rac)-Ethyl 4-chloro-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylate (see Intermediate 115, 50.0 mg), 1-bromo-2-methoxyethane (8.4 μL, 89 μmol) and cesium carbonate (132 mg, 405 μmol) were dissolved in 410 μL DMF and the reaction mixture was stirred at 60° C. in a sealed vessel under nitrogen atmosphere. The reaction mixture was diluted with water and dichloromethane, stirred for a few minutes, filtered through a silicone coated filter and concentrated under reduced pressure. The crude product was purified by HPLC chromatography to provide the analytically pure target compound: 28 mg.

LC-MS (Method 2): $R_t$=1.80 min; MS (ESIpos): m/z=677 [M+H]$^+$ $^1$H-NMR (400 MHz, DMSO-d6): δ [ppm]=0.81 (t, 3H), 0.87-0.98 (m, 1H), 1.08 (ddd, 2H), 1.13-1.23 (m, 2H), 1.27 (t, 3H), 2.00-2.10 (m, 1H), 2.11-2.38 (m, 6H), 2.79-2.87 (m, 5H), 3.16-3.30 (m, 3H), 3.70 (d, 1H), 3.80 (s, 3H), 3.83-3.90 (m, 1H), 4.03-4.12 (m, 1H), 4.13-4.36 (m, 4H), 6.85 (dd, 1H), 7.20 (d, 1H), 7.37-7.48 (m, 3H), 7.67 (dd, 1H), 7.72 (d, 1H), 8.30 (dd, 1H).

Intermediate 201

(rac)-8-ethyl 14-(2-methoxyethyl) 4-chloro-3-ethyl-7-{3-[(6-fluoronaphthalen-1-yl)oxy]propyl}-2-methyl-2,10,11,12,13,15-hexahydro-14H-pyrazolo[3',4':8,9][1,6]diazacycloundecino[10,11,1-hi]indole-8,14-dicarboxylate As side product of the reaction to Intermediate 200 the target compound was isolated in 90% purity: 4 mg.

LC-MS (Method 2): $R_t$=1.72 min; MS (ESIpos): m/z=720 [M+H]$^+$ $^1$H-NMR (400 MHz, DMSO-d6): δ [ppm]=0.76-0.97 (m, 4H), 1.08 (br d, 2H), 1.16-1.39 (m, 5H), 2.13-2.31 (m, 4H), 2.36-2.46 (m, 1H), 3.10-3.30 (m, 4H), 3.36-3.50 (m, 2H), 3.80-3.94 (m, 4H), 3.96-4.10 (m, 2H), 4.14-4.36 (m, 4H), 4.42-4.55 (m, 2H), 6.87 (dd, 1H), 7.26 (br d, 1H), 7.34-7.49 (m, 3H), 7.66 (dd, 1H), 7.81 (d, 1H), 8.24 (dd, 1H).—2H not detectable

Intermediate 202

(rac)-ethyl 4-chloro-3-ethyl-7-{3-[(6-fluoronaphthalen-1-yl)oxy]propyl}-2-methyl-14-[2-(oxan-4-yl)ethyl]-10,11,12,13,14,15-hexahydro-2H-pyrazolo[3',4':8,9][1,6]diazacycloundecino[10,11,1-hi]indole-8-carboxylate

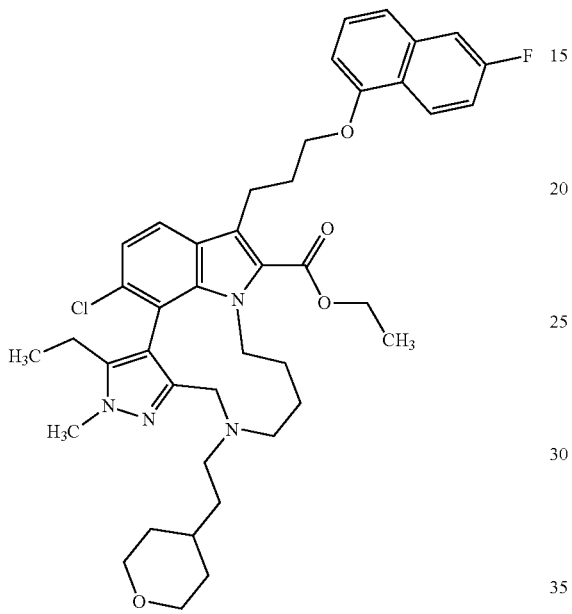

(rac)-Ethyl 4-chloro-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylate (see Intermediate 115, 50.0 mg, 81.0 µmol), 4-(2-bromoethyl)oxane (17.2 mg, 89.1 µmol) and cesiumcarbonate (132 mg, 405 µmol) were dissolved in 410 µL DMF and the reaction mixture was stirred at 60° C. in a sealed vessel under nitrogen atmosphere. The reaction mixture was diluted with water and dichloromethane, stirred for a few minutes, filtered through a silicone coated filter and concentrated under reduced pressure. The crude product was purified by HPLC chromatography under basic conditions to provide the target compound in 99% purity: 23 mg.

LC-MS (Method 2): $R_t$=1.85 min; MS (ESIpos): m/z=730 [M+H]$^+$ $^1$H-NMR (400 MHz, DMSO-d6): δ [ppm]=0.55-0.74 (m, 1H), 0.75-0.96 (m, 7H), 1.00-1.13 (m, 3H), 1.13-1.32 (m, 7H), 1.83-1.93 (m, 2H), 2.03-2.27 (m, 4H), 2.35-2.47 (m, 2H), 2.88 (td, 1H), 2.97 (d, 1H), 3.19-3.31 (m, 2H), 3.50 (br d, 1H), 3.59 (br dd, 1H), 3.72-3.93 (m, 5H), 4.04-4.16 (m, 1H), 4.17-4.39 (m, 4H), 6.90 (dd, 1H), 7.24 (d, 1H), 7.37-7.50 (m, 3H), 7.67 (dd, 1H), 7.75 (d, 1H), 8.30 (dd, 1H).

Intermediate 203

(rac)-8-ethyl 14-[2-(oxan-4-yl)ethyl] 4-chloro-3-ethyl-7-{3-[(6-fluoronaphthalen-1-yl)oxy]propyl}-2-methyl-2,10,11,12,13,15-hexahydro-14H-pyrazolo[3',4':8,9][1,6]diazacycloundecino[10,11,1-hi]indole-8,14-dicarboxylate As side product of the reaction to Intermediate 202 the target compound was isolated in 98% purity: 12 mg.

LC-MS (Method 2): $R_t$=1.77 min; MS (ESIpos): m/z=774 [M+H]$^+$ $^1$H-NMR (400 MHz, DMSO-d6): δ [ppm]=0.83 (t, 3H), 0.91 (br d, 2H), 0.98-1.17 (m, 4H), 1.18-1.31 (m, 5H), 1.32-1.56 (m, 5H), 2.13-2.31 (m, 4H), 3.08-3.31 (m, 4H), 3.75 (br dd, 2H), 3.80-3.98 (m, 6H), 3.99-4.35 (m, 5H), 4.36-4.53 (m, 2H), 6.86 (dd, 1H), 7.25 (br d, 1H), 7.34-7.49 (m, 3H), 7.66 (dd, 1H), 7.80 (d, 1H), 8.24 (dd, 1H).

Intermediate 204

(rac)-ethyl 4-chloro-3-ethyl-7-{3-[(6-fluoronaphtha-len-1-yl)oxy]propyl}-14-(3-hydroxypropyl)-2-methyl-10,11,12,13,14,15-hexahydro-2H-pyrazolo[3',4':8,9][1,6]diazacycloundecino[10,11,1-hi]indole-8-carboxylate

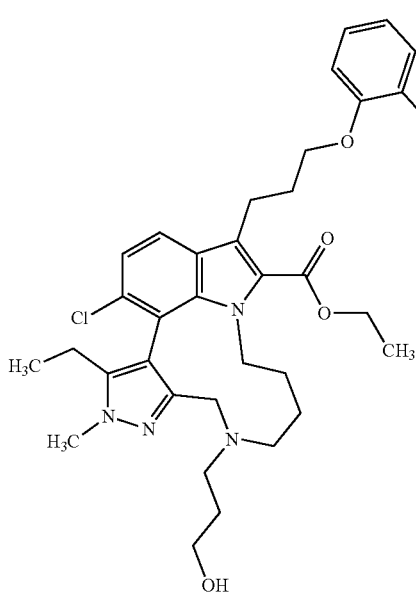

(rac)-Ethyl 4-chloro-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylate (see Intermediate 115, 50.0 mg), 3-bromopropan-1-ol (8.1 µL, 89 µmol) and cesium carbonate (132 mg, 405 µmol) were dissolved in 410 µL DMF and the reaction mixture was stirred at 60° C. in a sealed vessel under nitrogen atmosphere. The reaction mixture was diluted with water and dichloromethane, stirred for a few minutes, filtered through a silicone coated filter and concentrated under reduced pressure. The crude product was purified by HPLC under basic conditions to provide the desired compound in 97% purity: 20 mg LC-MS (Method 2): $R_t$=1.69 min; MS (ESIpos): m/z=676 [M+H]$^+$ $^1$H-NMR (400 MHz, DMSO-d6): δ [ppm]=0.80 (t, 3H), 0.86-0.96 (m, 1H), 0.97-1.13 (m, 3H), 1.13-1.38 (m, 5H), 1.94-2.07 (m, 2H), 2.09-2.26 (m, 4H), 2.27-2.41 (m, 2H), 2.81-2.91 (m, 1H), 2.97 (br d, 1H), 3.11 (d, 1H), 3.18-3.27 (m, 1H), 3.28-3.38 (m, 1H), 3.61 (d, 1H), 3.81 (s, 3H), 3.84-3.94 (m, 1H), 4.02-4.35 (m, 6H), 6.86 (dd, 1H), 7.18 (d, 1H), 7.36-7.47 (m, 3H), 7.64-7.75 (m, 2H), 8.31 (dd, 1H).

Intermediate 205 and Intermediate 206

3-(5-ethyl-1-methyl-1H-pyrazol-3-yl)propanoic acid and 3-(3-ethyl-1-methyl-1H-pyrazol-5-yl)propanoic acid

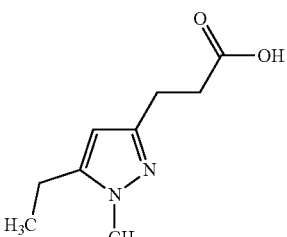

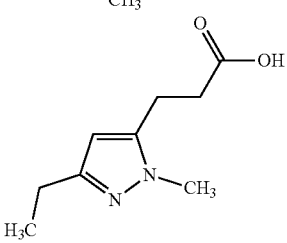

A stirred suspension of sodium hydride (16 g, 60% in oil, 400 mmol) in ethyl propionate (100 mL) was treated with the dropwise addition of a solution of levulenic acid (20 g, 172 mmol) in ethyl propionate (100 mL) over 45 minutes, the resulting mixture was heated to 50° C. for 2 hours, diluted with additional ethyl propionate (80 mL), and warmed to 70° C. for 14 hours. The mixture was cooled to room temperature, and slowly diluted with HCl (3M, aqueous, 200 mL) and ethyl acetate (300 mL), layers were separated and the organic phase washed with saturated aqueous sodium chloride. Combined aqueous phases were back extracted with ethyl acetate, combined organic phases were dried over sodium sulfate, treated with a small amount of charcoal, filtered through a small pad of silica gel, and volatiles were removed under reduced pressure. The residue was dissolved in acetic acid (100 mL) treated with methyl hydrazine (9 mL) and warmed to 50° C. for 15 hours. Volatiles were removed under reduced pressure and the residue was dissolved in HCl (3M, aqueous, 200 mL), washed with diethyl ether (3×100 mL), saturated with sodium chloride and further washed ethyl acetate (3×100 mL), the aqueous phase was concentrated to % volume, diluted with acetonitrile (100 mL) and the resulting solids were removed by filtration. The filtrate was concentrated under reduced pressure and the residue purified by flash chromatography on silica gel eluting with a gradient of ethyl acetate in hexanes, followed by a gradient of 0-10% methanol in dichloromethane to give an early eluting mixture of acid isomers, containing trace methyl and ethyl esters as an amber gum (8 g). Later eluting mixture of acids was dissolved in hot acetonitrile, and upon cooling a small amount of 3-(5-ethyl-1-methyl-1H-pyrazol-3-yl)propanoic acid HCl salt (2.1 g) was isolated by filtration as a white solid. The filtrate was concentrated to give a mixture of acids as a thick amber syrup (9.52 g) which was used in the next step without further manipulation.

3-(5-ethyl-1-methyl-1H-pyrazol-3-yl)propanoic acid (HCl Salt)

LC-MS (Method 7): $R_t$=1.3 min; MS (ESIpos): m/z=183 [M+H]$^+$

¹H NMR (400 MHz, Chloroform-d) δ=6.22 (s, 1H), 4.09 (s, 3H), 3.12 (t, J=7.1 Hz, 2H), 2.90 (t, J=7.1 Hz, 2H), 2.68 (q, J=7.6 Hz, 2H), 1.34 (t, J=7.5 Hz, 3H).

HSQC

13C NMR (101 MHz, CDCl3) δ 104.99, 34.95, 21.04, 32.32, 18.60, 11.61

1H NMR (400 MHz, CDCl3) δ 6.24, 4.11, 3.14, 2.93, 2.71, 1.36.

HMBC

13C NMR (101 MHz, CDCl3) δ 147.01, 149.86, 149.87, 105.27, 173.50, 146.38, 32.28, 21.16, 173.37, 147.60, 105.11, 11.64, 149.73, 149.91, 18.49

1H NMR (400 MHz, CDCl3) δ 6.25, 6.24, 4.11, 3.15, 3.14, 3.14, 3.14, 2.93, 2.93, 2.93, 2.71, 2.70, 2.70, 1.36, 1.36.

15N HMBC

15N NMR (41 MHz, CDCl3) δ 207.72, 182.49, 182.58, 208.97, 208.83

1H NMR (400 MHz, CDCl3) δ 6.25, 6.25, 4.11, 4.11, 3.14

Intermediate 207 and Intermediate 208

3-(5-ethyl-1-methyl-1H-pyrazol-3-yl)propan-1-ol AND 3-(3-ethyl-1-methyl-1H-pyrazol-5-yl)propan-1-ol

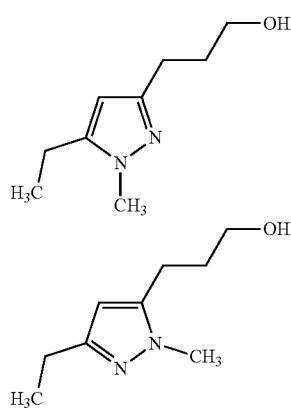

To a solution of a mixture of 3-(5-ethyl-1-methyl-1H-pyrazol-3-yl)propanoic acid and 3-(3-ethyl-1-methyl-1H-pyrazol-5-yl)propanoic acid (9.5 g, 52.1 mmol, see Intermediate 205 and Intermediate 206) in tetrahydrofuran (100 mL) was slowly added borane dimethyl sulfide complex (10 mL) and the solution was stirred at 35° C. for 20 hours. The reaction was cooled to rt and slowly quenched by the addition of methanol (5 mL) dropwise, volatiles were removed under reduced pressure, and the residue was stripped from methanol (3×50 mL), to give an amber gum (7.6 g) which was used in the next step without further manipulation.

LC-MS (Method 7): R$_t$=0.94 min/1.12 min; MS (ESIpos): m/z=169 [M+H]$^+$

Intermediate 209

3-(4-bromo-5-ethyl-1-methyl-1H-pyrazol-3-yl)propan-1-ol and

Intermediate 210

3-(4-bromo-3-ethyl-1-methyl-1H-pyrazol-5-yl)propan-1-ol 3-(4-bromo-5-ethyl-1-methyl-1H-pyrazol-3-yl) propan-1-ol AND 3-(4-bromo-3-ethyl-1-methyl-1H-pyrazol-5-yl) propan-1-ol

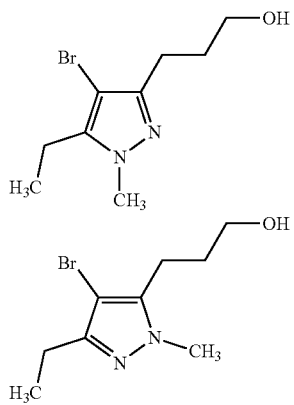

To a mixture of 3-(5-ethyl-1-methyl-1H-pyrazol-3-yl)propan-1-ol AND 3-(3-ethyl-1-methyl-1H-pyrazol-5-yl)propan-1-ol (7.6 g, 42 mmol, see Intermediate 207 and Intermediate 208), dichcloromethane (100 mL) and sodium hydroxide (100 mL, 1N) was added dibromodimethylhydantoin (17.4 g, 60.9 mmol) and the mixture stirred at rt for 17 hours, volume was reduced by half under reduced pressure and the residue was extracted with ethyl acetate (4×100 mL), combined organic phase was dried over sodium sulfate, filtered to remove insoluble materials, and volatiles were removed under reduced pressure, the residue was purified by flash chromatography on silica gel eluting with a gradient of acetone in hexanes (20-60%) to give the title compound as a pale yellow gum, mixture of isomers (6.2 g) (Intermediate 209 AND Intermediate 210) which was used without further manipulation in the next step, as well as some of the more polar 3-(4-bromo-5-ethyl-1-methyl-1H-pyrazol-3-yl)propan-1-ol as a pale amber gum (1.73 g). (Intermediate 210)

3-(4-bromo-5-ethyl-1-methyl-1H-pyrazol-3-yl)propan-1-ol, (Intermediate 209)

LC-MS (Method 6): R$_t$=2.07 min; MS (ESIpos): m/z=247/249 [M+H]$^+$

¹H NMR (300 MHz, Chloroform-d) δ=3.77 (s, 3H), 3.70 (t, J=6.0 Hz, 2H), 2.70 (t, J=7.0 Hz, 2H), 2.65 (q, J=7.6 Hz, 2H), 1.91 (tt, J=7.0, 5.9 Hz, 2H), 1.47 (s, 1H), 1.16 (t, J=7.6 Hz, 3H).
HSQC
13C NMR (101 MHz, CDCl3) δ 36.94, 62.61, 23.82, 18.25, 30.95, 12.85
1H NMR (400 MHz, CDCl3) δ 3.79, 3.72, 2.72, 2.67, 1.94, 1.19.

Intermediate 211

4-bromo-5-(3-{2-[(tert-butyldimethylsilyl)oxy]ethoxy}propyl)-3-ethyl-1-methyl-1H-pyrazole

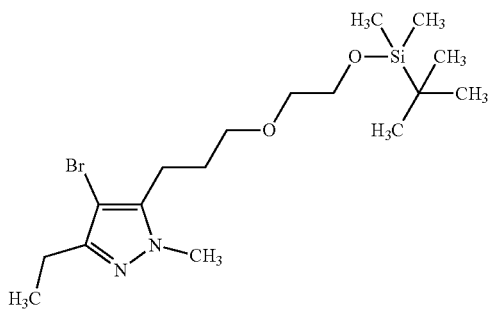 [SMILES: CCc1nn(C)c(CCCOCCO[Si](C)(C)C(C)(C)C)c1Br]

And

Intermediate 212

4-bromo-3-(3-{2-[(tert-butyldimethylsilyl)oxy]ethoxy}propyl)-5-ethyl-1-methyl-1H-pyrazole

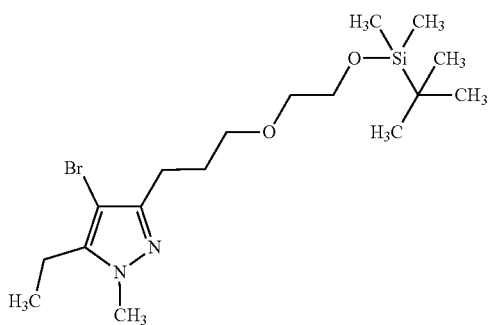 [SMILES: CCc1c(Br)c(CCCOCCO[Si](C)(C)C(C)(C)C)nn1C]

Step A

To a solution of Tertbutyldimethylsilyl chloride (5.09 g, 33.8 mmol) and imidazole (3.2 g, 47 mmol) in dichloromethane (100 mL) was added 2-bromoethanol (3 mL, 5.28 g, 42.2 mmol) and the white suspension was stirred for 20 hours at room temperature. The organics were washed with sodium hydroxide (1M, 100 mL), HCl (3N, aqueous, 40 mL), dried over sodium sulfate, filtered through a short pad of silica gel, washing with dichloromethane (150 mL), and volatiles removed under reduced pressure to give (2-bromoethoxy)(tert-butyl)dimethylsilane) as a colorless oil (7.08 g).
¹H NMR (300 MHz, Chloroform-d) δ=3.89 (t, J=6.5 Hz, 2H), 3.40 (t, J=6.5 Hz, 2H), 0.91 (s, 9H), 0.09 (s, 6H).
Step B
A solution of -(4-bromo-5-ethyl-1-methyl-1H-pyrazol-3-yl)propan-1-ol AND 3-(4-bromo-3-ethyl-1-methyl-1H-pyrazol-5-yl)propan-1-ol (6 g, 24.2 mmol, see Intermediate 209 and Intermediate 210) in dimethyl formamide (20 mL) was treated with sodium hydride (1.5 g, 60% in oil, 36.3 mmol), and stirred at room temperature for 50 minutes, at which time the product of step A (7.06 g) was added and the mixture heated to 50° C. for 17 hours, cool to room temperature, treated with acetic acid (5 mL), water (100 mL), ethyl acetate (50 mL) and hexanes (50 mL), layers separated, organic phase was washed with water, saturated sodium chloride (aqueous) dried over sodium sulfate, insoluble material removed by filtration, and volatiles removed to give a red gum which was purified by flash chromatography on silica gel eluting with a gradient of ethyl acetate in hexanes (0-50%) to give 4-bromo-5-(3-{2-[(tert-butyldimethylsilyl)oxy]ethoxy}propyl)-3-ethyl-1-methyl-1H-pyrazole (940 mg) followed by 4-bromo-3-(3-{2-[(tert-butyldimethylsilyl)oxy]ethoxy}propyl)-5-ethyl-1-methyl-1H-pyrazole (300 mg) as pale yellow oils.

4-bromo-5-(3-{2-[(tert-butyldimethylsilyl)oxy]ethoxy}propyl)-3-ethyl-1-methyl-1H-pyrazole LC-MS (Method 8): $R_t$=1.86 min; MS (ESIpos): m/z=407 [M+H]⁺
¹H NMR (300 MHz, Chloroform-d) δ 3.80-3.73 (m, 5H), 3.50 (dd, J=5.6, 4.8 Hz, 2H), 3.45 (t, J=6.0 Hz, 2H), 2.73 (dd, J=8.1, 6.9 Hz, 2H), 2.59 (q, J=7.6 Hz, 2H), 1.91-1.76 (m, 2H), 1.23 (t, J=7.6 Hz, 3H), 0.90 (s, 9H), 0.07 (s, 6H).
HSQC
13C NMR (101 MHz, CDCl3) δ 36.99, 62.73, 72.39, 69.71, 21.36, 20.54, 28.21, 13.18, 26.11
1H NMR (400 MHz, CDCl3) δ 3.80, 3.79, 3.53, 3.47, 2.75, 2.61, 1.86, 1.26, 0.92.

4-bromo-3-(3-{2-[(tert-butyldimethylsilyl)oxy]ethoxy}propyl)-5-ethyl-1-methyl-1H-pyrazole LC-MS (Method 8): $R_t$=1.86 min; MS (ESIpos): m/z=407 [M+H]⁺
¹H NMR (300 MHz, Chloroform-d) δ=3.82-3.68 (m, 5H), 3.58-3.46 (m, 4H), 2.73-2.56 (m, 4H), 2.00-1.84 (m, 2H), 1.16 (t, J=7.6 Hz, 3H), 0.89 (s, 9H), 0.07 (s, 6H).
HSQC
13C NMR (101 MHz, CDCl3) δ 36.90, 62.76, 70.91, 18.31, 23.54, 28.71, 12.81, 26.12, −5.05
1H NMR (400 MHz, CDCl3) δ 3.79, 3.78, 3.54, 2.66, 2.64, 1.95, 1.18, 0.92, 0.10.

Intermediate 213 ethyl 7-[5-(3-{2-[(tert-butyldimethylsilyl)oxy]ethoxy}propyl)-3-ethyl-1-methyl-1H-pyrazol-4-yl]-6-chloro-3-{3-[(6-fluoronaphthalen-1-yl)oxy]propyl}-1H-indole-2-carboxylate

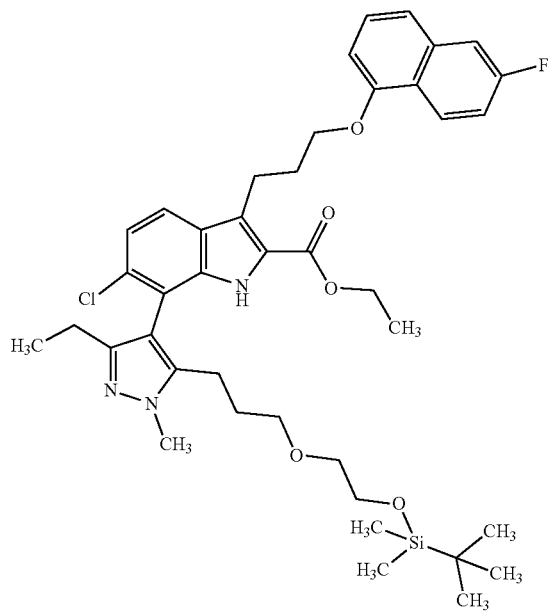 [SMILES: CCOC(=O)c1[nH]c2c(-c3c(CC)nn(C)c3CCCOCCO[Si](C)(C)C(C)(C)C)c(Cl)ccc2c1CCCOc1cccc2cc(F)ccc12]

A room temperature mixture of 4-bromo-5-(3-{2-[(tert-butyldimethylsilyl)oxy]ethoxy}propyl)-3-ethyl-1-methyl-1H-pyrazole (940 mg, 2.31 mmol, see Intermediate 211) ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (600 mg, 1.08 mmol, Intermediate 9), RuPhos Pd G3 (50 mg, 0.05978 mmol), under vacuum was treated with toluene (20 mL) and potassium phosphate tribasic (1 M, 4 mL) and held under vacuum for 2 minutes, then heated to 60° C., after 1 minute mixture was placed under positive nitrogen pressure and continued heating for 2 hours. The mixture was cooled to room temperature, volatiles removed under reduced pressure, and the residue partitioned between ethyl acetate and water, organics then washed with saturated sodium hydrogen carbonate (aqueous) and saturated sodium chloride (aqueous), combined aqueous washes were back extracted with ethyl acetate, combined organics dried over magnesium sulfate, insoluble materials removed by filtration, volatiles removed under reduced pressure and the residue purified by flash chromatography on silica gel eluting with a gradient of ethyl acetate in hexanes (0-50%) to give the title compound as a brown oil (480 mg).

LC-MS (Method 7): $R_t$=6.66 min; MS (ESIpos): m/z=751 [M+H]$^+$ $^1$H NMR (300 MHz, Chloroform-d) δ=8.43 (s, 1H), 8.35 (dd, J=9.2, 5.8 Hz, 1H), 7.58 (dd, J=8.6, 0.6 Hz, 1H), 7.40 (dd, J=10.0, 2.6 Hz, 1H), 7.37-7.31 (m, 2H), 7.24 (td, J=9.2, 8.4, 2.5 Hz, 1H), 7.18 (d, J=8.6 Hz, 1H), 6.71 (dd, J=6.5, 2.1 Hz, 1H), 4.36 (q, J=7.1 Hz, 2H), 4.21 (t, J=6.1 Hz, 2H), 3.91 (s, 3H), 3.62 (t, J=5.2 Hz, 2H), 3.43-3.35 (m, 2H), 3.35-3.17 (m, 4H), 2.75-2.23 (m, 6H), 1.79-1.49 (m, 2H), 1.35 (t, J=7.1 Hz, 3H), 1.05 (t, J=7.6 Hz, 3H), 0.86 (s, 9H), 0.01 (s, 6H).

HSQC
13C NMR (101 MHz, CDCl3) δ 124.77, 120.81, 110.48, 127.38, 119.42, 115.15, 122.06, 103.98, 60.92, 67.56, 36.47, 62.60, 21.54, 72.14, 69.70, 21.43, 21.20, 20.72, 30.57, 28.56, 14.67, 13.70, 26.11, -4.88

1H NMR (400 MHz, CDCl3) δ 8.38, 7.60, 7.42, 7.37, 7.36, 7.26, 7.21, 6.73, 4.38, 4.23, 3.93, 3.64, 3.41, 3.32, 3.29, 2.64, 2.51, 2.44, 2.37, 1.62, 1.37, 1.08, 0.88, 0.02.

Intermediate 214 ethyl 6-chloro-7-{3-ethyl-5-[3-(2-hydroxyethoxy)propyl]-1-methyl-1H-pyrazol-4-yl}-3-{3-[(6-fluoronaphthalen-1-yl)oxy]propyl}-1H-indole-2-carboxylate

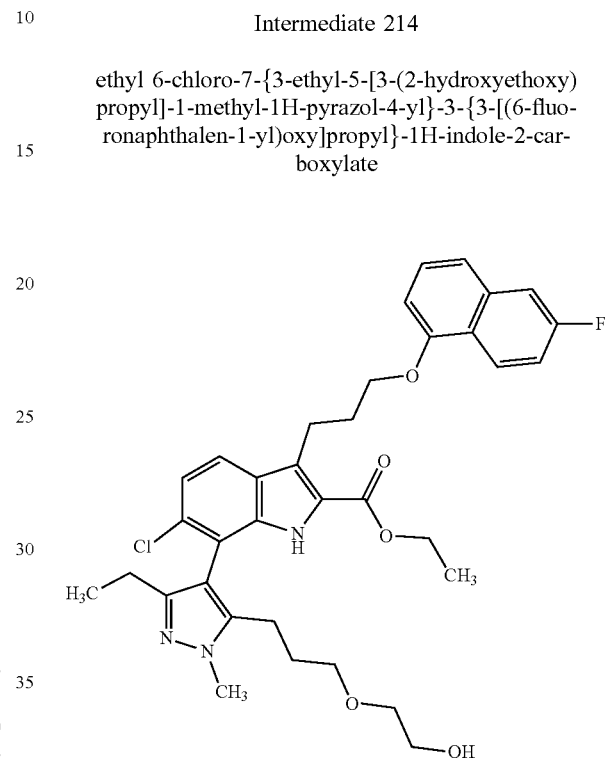

A solution of ethyl 7-[5-(3-{2-[(tert-butyldimethylsilyl)oxy]ethoxy}propyl)-3-ethyl-1-methyl-1H-pyrazol-4-yl]-6-chloro-3-{3-[(6-fluoronaphthalen-1-yl)oxy]propyl}-1H-indole-2-carboxylate, 480 mg, 0.6396 mmol, see Intermediate 213) in ethanol (95%, 75 mL) was treated with HCl (12 M, aqu, 0.5 mL) and stirred at room temperature for 2 hours, volatiles removed, and the residue was dissolved in dichloromethane (40 mL), treated with ammonia methanol (7M, 1 mL), volatiles removed, and the residue was purified by flash chromatography on silica gel eluting with a gradient of 0-100% ethyl acetate in hexanes to give the title compound as a white gum (354 mg).

LC-MS (Method 7): $R_t$=4.75 min; MS (ESIneg): m/z=634 [M−H]$^-$ $^1$H NMR (300 MHz, Chloroform-d) δ=8.85 (s, 1H), 8.34 (dd, J=9.2, 5.8 Hz, 1H), 7.58 (d, J=8.6 Hz, 1H), 7.39 (dd, J=10.0, 2.6 Hz, 1H), 7.36-7.27 (m, 2H), 7.23 (ddd, J=9.3, 8.4, 2.6 Hz, 1H), 7.17 (d, J=8.6 Hz, 1H), 6.70 (dd, J=6.6, 2.1 Hz, 1H), 4.34 (q, J=7.1 Hz, 2H), 4.20 (t, J=6.1 Hz, 2H), 3.89 (s, 3H), 3.60-3.50 (m, 2H), 3.42-3.22 (m, 6H), 2.69-2.44 (m, 2H), 2.36 (dddd, J=14.5, 12.8, 7.8, 3.9 Hz, 4H), 1.72-1.54 (m, 2H), 1.34 (t, J=7.1 Hz, 3H), 1.03 (t, J=7.6 Hz, 4H).

$^{13}$C NMR (101 MHz, Chloroform-d) δ=162.21, 161.24 (d, J=245.9 Hz), 154.93, 152.15, 141.92, 136.95, 135.66, 135.57, 132.22, 127.41, 126.45, 124.84 (d, J=9.1 Hz), 124.34, 124.18, 122.71, 122.04, 120.82, 119.46 (d, J=4.3 Hz), 116.91, 115.13 (d, J=24.9 Hz), 110.63 (d, J=20.7 Hz), 103.96, 71.89, 69.95, 67.61, 61.71, 61.01, 36.53, 30.46, 28.08, 21.78, 21.59, 20.47, 14.49, 13.53.

19F NMR (376 MHz, Chloroform-d) 5-114.83.

HSQC

13C NMR (101 MHz, CDCl3) δ 124.76, 120.91, 110.51, 127.39, 119.40, 115.18, 121.94, 103.99, 60.96, 67.56, 36.55, 61.67, 21.58, 71.89, 69.95, 21.84, 21.64, 20.63, 30.56, 28.00, 14.62, 13.64

1H NMR (400 MHz, CDCl3) δ 8.36, 7.60, 7.41, 7.36, 7.35, 7.25, 7.19, 6.73, 4.36, 4.21, 3.91, 3.57, 3.40, 3.32, 3.31, 2.62, 2.55, 2.41, 2.36, 1.65, 1.36, 1.05.

Intermediate 215 ethyl 7-[3-(3-{2-[(tert-butyldimethylsilyl)oxy]ethoxy}propyl)-5-ethyl-1-methyl-1H-pyrazol-4-yl]-6-chloro-3-{3-[(6-fluoronaphthalen-1-yl)oxy]propyl}-1H-indole-2-carboxylate

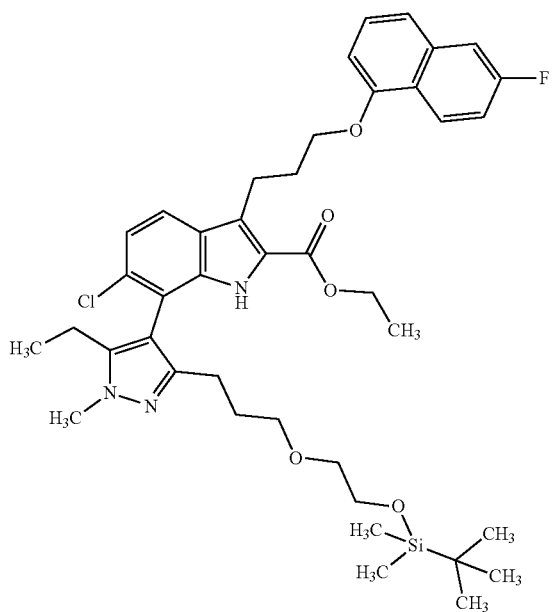 [SMILES: CCOC(=O)c1[nH]c2c(-c3c(CCCOCCO[Si](C)(C)C(C)(C)C)nn(C)c3CC)c(Cl)ccc2c1CCCOc1cccc2cc(F)ccc12]

A room temperature mixture of 4-bromo-3-(3-{2-[(tert-butyldimethylsilyl)oxy]ethoxy}propyl)-5-ethyl-1-methyl-1H-pyrazole (300 mg, 0.74 mmol, see Intermediate 212), ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (500 mg, 0.906 mmol, Intermediate 9), RuPhos Pd G3 (50 mg, 0.05978 mmol), under vacuum was treated with toluene (20 mL) and potassium phosphate tribasic (1M, 4 mL) and held under vacuum for 2 minutes, then heated to 60° C., after 1 minute mixture was placed under positive nitrogen pressure and continued heating for 90 minutes. The mixture was cooled to room temperature, diluted with ethyl acetate and water, layers separated, organics washed with saturated sodium chloride (aqueous), combined aqeuous phases back extracted with ethyl acetate, combined organics dried over sodium sulfate, insoluble materials removed by filtration, volatiles removed under reduced pressure and the residue purified by flash chromatography on silica gel eluting with a gradient of ethyl acetate in hexanes (0-100%) to give the title compound as a pale amber gum (350 mg).

LC-MS (Method 7): R$_f$=6.64 min; MS (ESIneg): m/z=748 [M−H]$^-$ $^1$H NMR (300 MHz, Chloroform-d) δ=8.48 (s, 1H), 8.37 (dd, J=9.2, 5.8 Hz, 1H), 7.60 (dd, J=8.7, 0.6 Hz, 1H), 7.42 (dd, J=9.9, 2.6 Hz, 1H), 7.39 (s, 2H), 7.31-7.22 (m, 1H), 7.20 (d, J=8.6 Hz, 1H), 6.74 (dd, J=6.6, 2.1 Hz, 1H), 4.37 (q, J=7.1 Hz, 2H), 4.23 (t, J=6.1 Hz, 2H), 3.90 (s, 3H), 3.69-3.55 (m, 2H), 3.48-3.27 (m, 6H), 2.61-2.23 (m, 6H), 1.77 (dqd, J=8.5, 6.8, 4.4 Hz, 2H), 1.37 (t, J=7.1 Hz, 3H), 1.01 (t, J=7.6 Hz, 3H), 0.86 (s, 9H), 0.00 (s, 6H).

$^{13}$C NMR (101 MHz, CDCl3) δ=162.48, 162.08, 160.03, 154.95, 150.19, 143.48, 136.90, 135.68, 135.59, 132.40, 127.42, 126.40, 124.91, 124.82, 124.29, 124.20, 122.74, 122.14, 120.80, 119.49, 119.44, 116.87, 115.26, 115.01, 110.73, 110.53, 110.25, 103.99, 77.16, 71.90, 70.91, 67.62, 62.67, 60.98, 36.40, 30.48, 28.99, 25.96, 24.91, 23.92, 21.58, 18.19, 14.51, 13.09,-5.24.

HSQC

13C NMR (101 MHz, CDCl3) δ 124.76, 120.87, 110.26, 127.39, 119.37, 115.12, 122.01, 103.95, 60.92, 67.55, 36.40, 62.66, 21.56, 70.91, 71.88, 23.91, 18.16, 30.49, 28.91, 14.52, 13.16, 26.08,-4.75

1H NMR (400 MHz, CDCl3) δ 8.36, 7.59, 7.42, 7.37, 7.35, 7.25, 7.19, 6.73, 4.36, 4.22, 3.90, 3.62, 3.40, 3.38, 3.33, 2.45, 2.43, 2.36, 1.77, 1.36, 1.00, 0.86, −0.00.

Intermediate 216 ethyl 6-chloro-7-{5-ethyl-3-[3-(2-hydroxyethoxy)propyl]-1-methyl-1H-pyrazol-4-yl}-3-{3-[(6-fluoronaphthalen-1-yl)oxy]propyl}-1H-indole-2-carboxylate

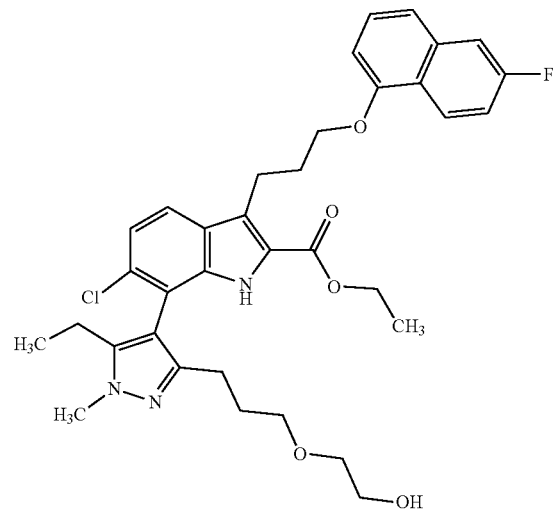 [SMILES: CCOC(=O)c1[nH]c2c(-c3c(CCCOCCO)nn(C)c3CC)c(Cl)ccc2c1CCCOc1cccc2cc(F)ccc12]

To a solution of ethyl 7-[3-(3-{2-[(tert-butyldimethylsilyl)oxy]ethoxy}propyl)-5-ethyl-1-methyl-1H-pyrazol-4-yl]-6-chloro-3-{3-[(6-fluoronaphthalen-1-yl)oxy]propyl}-1H-indole-2-carboxylate (350 mg, 0.4664 mmol, see Intermediate 215) in ethanol (50 mL, 95%) was added HCl (12 M, 0.5 mL, aqueous), and the resulting solution stirred at room temperature for 24 hours. Volatiles were removed and the residue partitioned between ethyl acetate and saturated sodium bicarbonate (aqueous), the organic phase was washed with saturated sodium chloride (aqueous), combined aqueous phases were back extracted with ethyl acetate, and combined organics were dried over sodium sulfate, insoluble material was removed by filtration, and volatiles were removed under reduced pressure. The pale amber residue (300 mg) was used without further manipulation.

LC-MS (Method 8): $R_t$=1.78 min; MS (ESIneg): m/z=634 [M−H]⁻

$^1$H NMR (400 MHz, Chloroform-d) δ=8.82 (s, 1H), 8.34 (dd, J=9.3, 5.8 Hz, 1H), 7.58 (d, J=8.7 Hz, 1H), 7.41 (dt, J=10.1, 2.0 Hz, 1H), 7.38-7.31 (m, 2H), 7.28-7.20 (m, 1H), 7.18 (dd, J=8.6, 1.4 Hz, 1H), 6.80-6.67 (m, 1H), 4.35 (q, J=7.1 Hz, 2H), 4.20 (t, J=6.2 Hz, 2H), 3.88 (d, J=1.4 Hz, 3H), 3.59 (d, J=4.5 Hz, 2H), 3.55-3.33 (m, 6H), 2.45 (dddd, J=50.6, 29.8, 14.3, 7.1 Hz, 7H), 1.65 (qp, J=13.5, 6.4 Hz, 2H), 1.35 (td, J=7.1, 1.4 Hz, 3H), 1.03-0.92 (m, 3H).

$^{13}$C NMR (101 MHz, Chloroform-d) δ=162.35, 161.32 (d, J=245.9 Hz), 155.01, 150.09, 143.85, 137.17, 135.69 (d, J=9.3 Hz), 132.48, 127.46, 126.54, 124.89 (d, J=9.1 Hz), 124.41, 124.26, 122.79, 122.10, 120.96, 119.54 (d, J=4.9 Hz), 116.88, 115.22 (d, J=24.9 Hz), 110.61, 104.02, 100.10, 71.77, 69.75, 67.68, 61.46, 61.12, 36.30, 30.54, 28.36, 23.87, 21.68, 18.22, 14.56, 13.10.

$^{19}$F NMR (376 MHz, Chloroform-d) δ=−114.87.

HSQC

13C NMR (101 MHz, CDCl3) δ 124.68, 120.93, 110.59, 127.29, 119.41, 115.08, 121.74, 103.97, 60.98, 67.57, 36.26, 61.36, 71.65, 69.65, 71.65, 21.56, 23.71, 23.87, 18.08, 30.57, 28.24, 14.65, 13.01

1H NMR (400 MHz, CDCl3) δ 8.36, 7.61, 7.43, 7.37, 7.37, 7.26, 7.20, 6.74, 4.37, 4.23, 3.90, 3.61, 3.51, 3.45, 3.42, 3.40, 2.56, 2.51, 2.44, 2.36, 1.67, 1.37, 1.01.

Intermediate 217

N-{2-[(tert-butyldimethylsilyl)oxy]ethyl}-2-nitrobenzene-1-sulfonamide

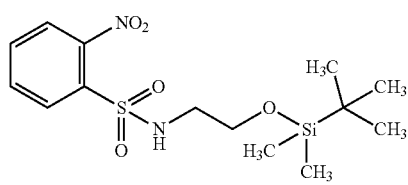 [SMILES: CC(C)(C)[Si](C)(C)OCCNS(=O)(=O)c1ccccc1[N+](=O)[O-]]

To a solution of amino ethanol (10.7 g, 175 mmol) and imidazole (24 g, 352 mmol) in dichloromethane (100 mL) at room temperature was added tert-butyl(chloro)dimethylsilane (27 g, 179 mmol). After stirring for 90 minutes at room temperature was added ethylbis(propan-2-yl)amine (30.4 mL, 175 mmol) and nitrobenzenesulfonylchloride (12.5 g, 56.4 mmol) to give a red solution which was stirred at room temperature for 17 hours. The mixture was diluted with saturated sodium hydrogen carbonate (aqueous, 200 mL) layers separated and organic phase extracted with dichloromethane twice, combined organics were dried over sodium sulfate, and insoluble materials were removed by filtration to give 40 g of an amber gum which was purified by flash chromatography on silica gel eluting with a gradient of dichloromethane in hexanes (0-100%) to give the title compound as a pink oil (12.7 g).

LC-MS (Method 7): $R_t$=4.21 min; MS (ESIneg): m/z=359 [M−H]⁻

$^1$H-NMR (300 MHz, Chloroform-d) δ=8.20-8.08 (m, 1H), 7.94-7.83 (m, 1H), 7.81-7.66 (m, 2H), 5.78 (t, J=5.9 Hz, 1H), 3.69 (dd, J=5.6, 4.6 Hz, 2H), 3.20 (td, J=5.7, 4.7 Hz, 2H), 0.84 (s, 9H), −0.00 (s, 6H).

Intermediate 218

N-[3-(4-bromo-5-ethyl-1-methyl-1H-pyrazol-3-yl)propyl]-N-{2-[(tert-butyldimethylsilyl)oxy]ethyl}-2-nitrobenzene-1-sulfonamide

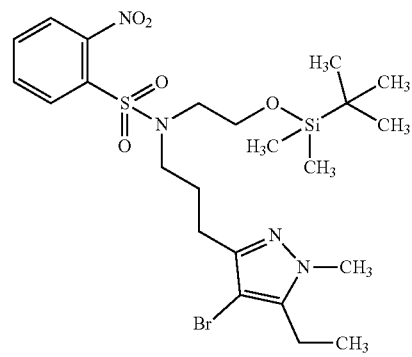 [SMILES: CCc1c(Br)c(CCCN(CCO[Si](C)(C)C(C)(C)C)S(=O)(=O)c2ccccc2[N+](=O)[O-])nn1C]

To a mixture of 3-(4-bromo-5-ethyl-1-methyl-1H-pyrazol-3-yl)propan-1-ol (3.1 g, 12.5 mmol, see Intermediate 209), N-{2-[(tert-butyldimethylsilyl)oxy]ethyl}-2-nitrobenzene-1-sulfonamide (7 g, 19.4 mmol, see Intermediate 217) and triphenylphosphine (4 g, 15.2 mmol), in 100 mL THF was added (E)-N-{[(tert-butoxy)carbonyl]imino}(tert-butoxy)formamide (3.3 g, 14.3 mmol), and the mixture stirred at room temperature for 17 hours. Volatiles were removed under reduced pressure and the residue purified by flash chromatography on silica gel eluting with a gradient of ethyl acetate in hexanes (25-75%) to give the title compound as an amber gum (5.77 g).

LC-MS (Method 7): $R_t$=5.23 min; MS (ESIpos): m/z=593 [M+H]$^+$ $^1$H NMR (300 MHz, Chloroform-d) δ=8.07-8.00 (m, 1H), 7.70-7.54 (m, 3H), 3.82-3.67 (m, 5H), 3.54-3.36 (m, 4H), 2.63 (q, J=7.6 Hz, 2H), 2.47 (t, J=7.6 Hz, 2H), 1.90 (p, J=7.8 Hz, 2H), 1.15 (t, J=7.6 Hz, 3H), 0.86 (s, 9H), 0.02 (s, 6H).

Intermediate 219 ethyl 7-{3-[3-(N-{2-[(tert-butyldimethylsilyl)oxy]ethyl}2-nitrobenzenesulfonamido)propyl]-5-ethyl-1-methyl-1H-pyrazol-4-yl}-6-chloro-3-{3-[(6-fluoronaphthalen-1-yl)oxy]propyl}-1H-indole-2-carboxylate

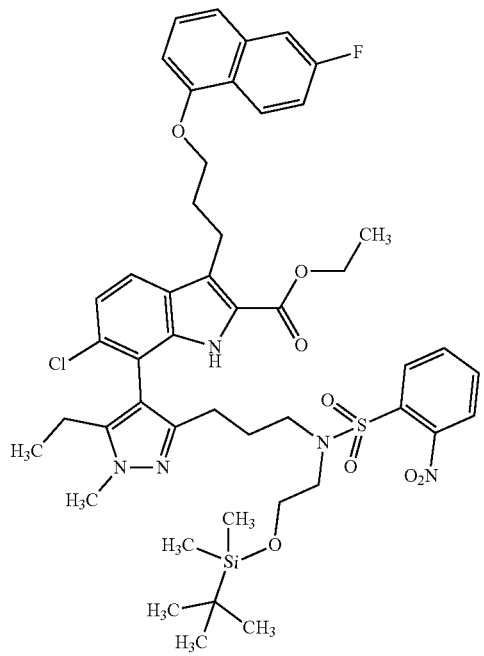 [SMILES: CCOC(=O)c1[nH]c2c(-c3c(CCCN(CCO[Si](C)(C)C(C)(C)C)S(=O)(=O)c4ccccc4[N+](=O)[O-])nn(C)c3CC)c(Cl)ccc2c1CCCOc1cccc2cc(F)ccc12]

A mixture of N-[3-(4-bromo-5-ethyl-1-methyl-1H-pyrazol-3-yl)propyl]-N-{2-[(tert-butyldimethylsilyl)oxy]ethyl}-2-nitrobenzene-1-sulfonamide (780 mg, 1.32 mmol, see Intermediate 218), ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (500 mg, 0.906 mmol, Intermediate 9), tripotassium phosphate (395 mg, 1.86 mmol), and RuPhos Pd G3 (40 mg, 0.0478 mmol) was placed under vacuum, treated with toluene (10 mL) and water (2 mL). Held under vacuum at room temperature for 1 minute, then placed in a preheated aluminum block at 110° C., after 1 minute placed under nitrogen atmosphere, after 1 hour, cooled to room temperature. Mixture was diluted with ethyl acetate (100 mL) and water (100 mL), filtered through a pad of celite to remove insoluble materials, further diluted with ethyl acetate (100 mL) and the layers separated, the organic phase was washed with saturated sodium chloride (aqueous), dried over sodium sulfate, filtered to remove insoluble materials, volatiles removed under reduced pressure, and the residue purified by flash chromatography on silica gel eluting with a gradient of ethyl acetate in hexanes to give the title compound as an amber gum (530 mg).

LC-MS (Method 7): $R_t$=6.64 min; MS (ESIpos): m/z=935 [M+H]$^+$ $^1$H-NMR (400 MHz, Chloroform-d) δ=8.39 (d, J=10.8 Hz, 2H), 7.96-7.88 (m, 1H), 7.66-7.51 (m, 3H), 7.49 (d, J=7.1 Hz, 1H), 7.46-7.32 (m, 3H), 7.30-7.22 (m, 1H), 7.17 (dd, J=8.6, 1.8 Hz, 1H), 6.75 (d, J=7.1 Hz, 1H), 4.37 (q, J=7.2 Hz, 2H), 4.24 (t, J=6.2 Hz, 2H), 3.88 (d, J=1.8 Hz, 3H), 3.64 (t, J=6.0 Hz, 2H), 3.48-3.38 (m, 2H), 3.32 (dd, J=14.8, 7.7 Hz, 3H), 3.21 (dt, J=14.4, 6.2 Hz, 1H), 2.60-2.32 (m, 4H), 2.18 (tt, J=15.0, 7.5 Hz, 2H), 1.75 (q, J=6.9 Hz, 2H), 1.37 (td, J=7.1, 1.8 Hz, 3H), 0.99 (td, J=7.6, 1.9 Hz, 3H), 0.85 (d, J=1.9 Hz, 9H), 0.00 (d, J=1.9 Hz, 6H).

Intermediate 220 ethyl 6-chloro-7-(5-ethyl-3-{3-[N-(2-hydroxyethyl)2-nitrobenzenesulfonamido]propyl}-1-methyl-1H-pyrazol-4-yl)-3-{3-[(6-fluoronaphthalen-1-yl)oxy]propyl}-1H-indole-2-carboxylate

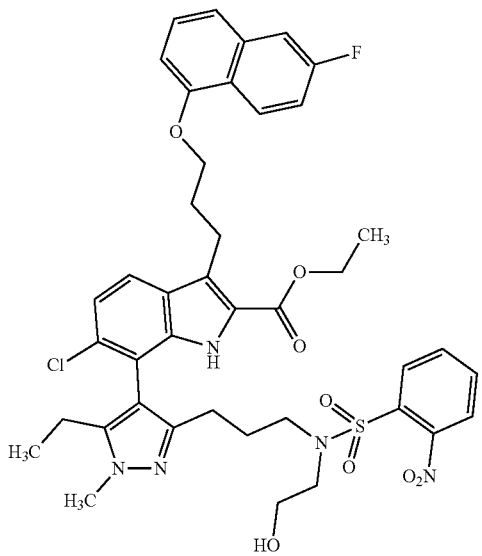 [SMILES: CCOC(=O)c1[nH]c2c(-c3c(CCCN(CCO)S(=O)(=O)c4ccccc4[N+](=O)[O-])nn(C)c3CC)c(Cl)ccc2c1CCCOc1cccc2cc(F)ccc12]

A solution of ethyl 7-{3-[3-(N-{2-[(tert-butyldimethylsilyl)oxy]ethyl}2-nitrobenzenesulfonamido)propyl]-5-ethyl-1-methyl-1H-pyrazol-4-yl}-6-chloro-3-{3-[(6-fluoronaphthalen-1-yl)oxy]propyl}-1H-indole-2-carboxylate (530 mg, 0.5670 mmol, see Intermediate 219) in ethanol (100 mL, 95%) was treated with HCl (1 mL, 12M, aqueous) and Intermediate 221 ethyl 6-chloro-7-[5-ethyl-3-(3-{N-[2-(methanesulfonyloxy)ethyl]2-nitrobenzenesulfonamido}propyl)-1-methyl-1H-pyrazol-4-yl]-3-{3-[(6-fluoronaphthalen-1-yl)oxy]propyl}-1H-indole-2-carboxylate

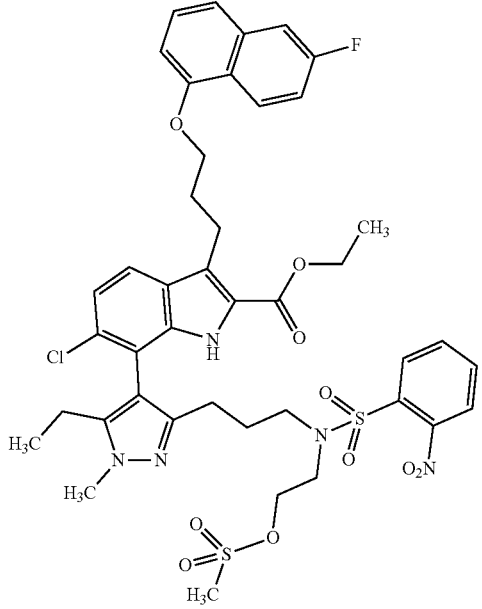 [SMILES: CCOC(=O)c1[nH]c2c(-c3c(CCCN(CCOS(C)(=O)=O)S(=O)(=O)c4ccccc4[N+](=O)[O-])nn(C)c3CC)c(Cl)ccc2c1CCCOc1cccc2cc(F)ccc12]

To a 0° C. solution of ethyl 6-chloro-7-(5-ethyl-3-{3-[N-(2-hydroxyethyl)2-nitrobenzenesulfonamido]propyl}-1-methyl-1H-pyrazol-4-yl)-3-{3-[(6-fluoronaphthalen-1-yl)oxy]propyl}-1H-indole-2-carboxylate (465 mg 0.5688 mmol, see Intermediate 220) and ethylbis(propan-2-yl)amine (1 mL, 5.74 mmol) was added methanesulfonyl chloride (0.15 mL, 1.92 mmol) and stirred at that temperature for 30 minutes, at which time volatiles were removed under reduced pressure, the residue was portioned between ethyl acetate and saturated sodium hydrogen carbonate, layers separated, and the organic phase washed sequentially with sodium hydroxide (1N, aqueous) and saturated sodium chloride (aqueous), combined aqueous phases were back extracted with ethyl acetate, combined organics were dried over sodium sulfate, insoluble materials removed by filtration and volatiles were removed under reduced pressure to give the title compound as a tan gum (680 mg), which was used without further manipulation.

LC-MS (Method 6): R$_t$=1.96 min; MS (ESIpos): m/z=820 [M+H]$^+$

Intermediate 222

(rac)-ethyl 13-chloro-12-ethyl-1-(3-((6-fluoronaphthalen-1-yl)oxy)propyl)-11-methyl-6-((2-nitrophenyl)sulfonyl)-5,6,7,8,9,11-hexahydro-4H-pyrazolo[3',4':8,9][1,4]diazacycloundecino[10,11,1-h,]indole-2-carboxylate

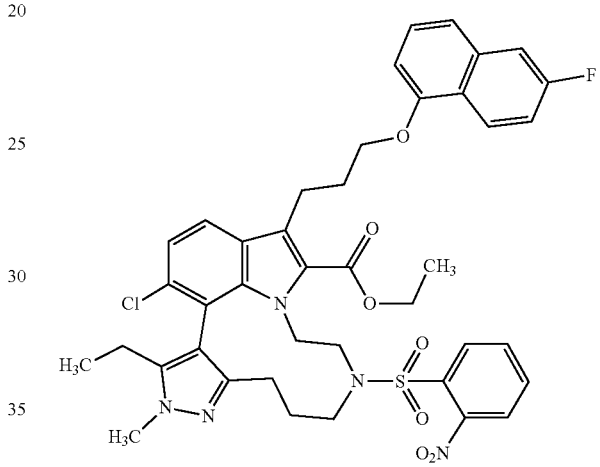

A solution of ethyl 6-chloro-7-[5-ethyl-3-(3-{N-[2-(methanesulfonyloxy)ethyl]2-nitrobenzenesulfonamido}propyl)-1-methyl-1H-pyrazol-4-yl]-3-{3-[(6-fluoronaphthalen-1-yl)oxy]propyl}-1H-indole-2-carboxylate (509 mg 0.5665 mmol, see Intermediate 221, Intermediate 5) in N,N-dimethylformamide (10 mL) was added sodium hydride (50 mg, 60% in oil, 1.25 mmol), and the resulting mixture heated to 40° C. for 16 hours. The mixture was cooled to room temperature, treated with acetic acid (1 mL), volatiles were removed under reduced pressure and the residue was purified by flash chromatography on silica gel eluting with a gradient of ethyl acetate in hexanes (0-100%) to provide the title as an off-white gum (320 mg).

LC-MS (Method 7): R$_t$=5.57 min; MS (ESIpos): m/z=803 [M+H]$^+$ $^1$H NMR (300 MHz, Chloroform-d) δ 8.39 (dd, J=9.2, 5.8 Hz, 1H), 8.03-7.96 (m, 1H), 7.64-7.55 (m, 3H), 7.55-7.34 (m, 3H), 7.29-7.18 (m, 1H), 7.09 (d, J=8.6 Hz, 1H), 6.70 (dd, J=6.4, 2.2 Hz, 1H), 4.56 (dt, J=14.7, 3.0 Hz, 1H), 4.45-4.28 (m, 3H), 4.12 (dq, J=10.7, 7.1, 6.5 Hz, 2H), 3.88 (s, 3H), 3.80-3.61 (m, 2H), 3.45-3.27 (m, 2H), 3.19 (dt, J=14.5, 4.3 Hz, 1H), 2.83-2.56 (m, 4H), 2.34 (q, J=7.6 Hz, 4H), 2.07-1.93 (m, 2H), 1.39 (t, J=7.1 Hz, 3H), 0.94 (t, J=7.6 Hz, 3H).

LC-MS (Method 7): R$_t$=5.45 min; MS (ESIpos): m/z=898 [M+H]$^+$

Intermediate 223

(rac)-ethyl 13-chloro-12-ethyl-1-(3-((6-fluoronaphthalen-1-yl)oxy)propyl)-11-methyl-5,6,7,8,9,11-hexahydro-4H-pyrazolo[3',4':8,9][1,4]diazacycloundecino[10,11,1-h]indole-2-carboxylate

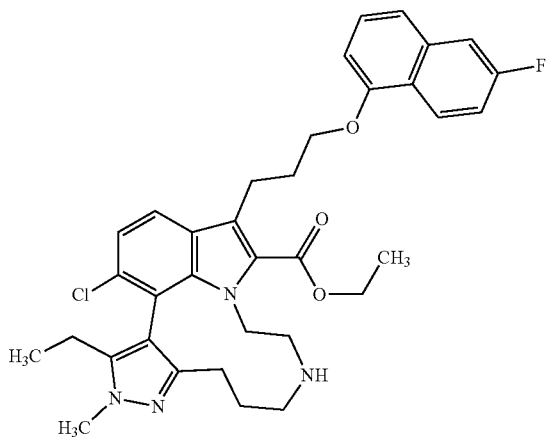 [SMILES: CCOC(=O)c1c(CCCOc2cccc3cc(F)ccc23)c2ccc(Cl)c3c2n1CCNCCCc1nn(C)c(CC)c1-3]

To a mixture of (rac)-ethyl 13-chloro-12-ethyl-1-(3-((6-fluoronaphthalen-1-yl)oxy)propyl)-11-methyl-6-((2-nitrophenyl)sulfonyl)-5,6,7,8,9,11-hexahydro-4H-pyrazolo[3',4':8,9][1,4]diazacycloundecino[10,11,1-hi]indole-2-carboxylate (309 mg, 0.3851 mmol, see Intermediate 222) and potassium carbonate (300 mg, 2.17 mmol) in acetonitrile (35 mL) and water (1 mL) was added thiophenol (0.4 mL, 3.9 mmol) and stirred for 40 hours at room temperature. The mixture was diluted with ethyl acetate (100 mL), insoluble materials were removed by filtration, volatiles removed under reduced pressure and the residue purified by flash chromatography on silica gel eluting with a gradient of methanol in dichloromethane (0-10%) to provide the title compound as an off-white foam (200 mg).

LC-MS (Method 7): $R_t$=3.89 min; MS (ESIpos): m/z=617 [M+H]$^+$ $^1$H NMR (400 MHz, Chloroform-d) δ=8.42-8.31 (m, 1H), 7.62 (dd, J=8.5, 2.0 Hz, 1H), 7.42 (dd, J=10.0, 2.4 Hz, 1H), 7.38 (d, J=8.4 Hz, 2H), 7.26 (t, J=8.9 Hz, 1H), 7.21 (dd, J=8.5, 2.0 Hz, 1H), 6.74 (d, J=7.0 Hz, 1H), 4.57 (d, J=14.3 Hz, 1H), 4.36 (hd, J=8.0, 7.5, 4.4 Hz, 2H), 4.23 (t, J=6.3 Hz, 3H), 3.93 (d, J=2.1 Hz, 3H), 3.39 (ddt, J=27.0, 13.8, 7.6 Hz, 2H), 2.66 (ddd, J=35.2, 17.1, 12.2 Hz, 4H), 2.51 (td, J=13.6, 5.5 Hz, 1H), 2.36 (dt, J=10.3, 6.8 Hz, 4H), 2.17 (t, J=12.3 Hz, 1H), 2.04-1.90 (m, 1H), 1.63 (d, J=14.0 Hz, 1H), 1.39 (td, J=7.2, 1.9 Hz, 3H), 0.97 (td, J=7.6, 2.0 Hz, 3H).

$^{13}$C NMR (101 MHz, Chloroform-d) δ=162.61, 161.27 (d, J=245.9 Hz), 154.96, 148.98, 142.28, 139.41, 135.64 (d, J=9.2 Hz), 135.11, 127.44, 126.45, 126.29, 125.44, 124.86 (d, J=9.1 Hz), 122.75, 121.53, 120.78, 119.49 (d, J=5.0 Hz), 117.18, 115.17 (d, J=24.9 Hz), 114.94, 110.66 (d, J=20.4 Hz), 104.04 (d, J=2.0 Hz), 67.76, 60.76, 52.14, 45.63, 44.25, 36.55, 30.61, 26.69, 22.25, 21.67, 18.11, 14.39, 12.38.

HSQC $^{13}$C NMR (101 MHz, CDCl$_3$) δ 124.76, 120.82, 110.23, 127.40, 119.39, 115.19, 121.51, 103.99, 44.27, 60.73, 44.22, 67.69, 36.66, 22.20, 22.12, 45.49, 52.07, 21.69, 52.11, 21.56, 30.67, 45.48, 26.67, 26.67, 14.57, 12.38.

$^1$H NMR (400 MHz, CDCl$_3$) δ 8.37, 7.62, 7.42, 7.38, 7.36, 7.26, 7.20, 6.74, 4.56, 4.35, 4.25, 4.23, 3.93, 3.40, 3.34, 2.72, 2.69, 2.64, 2.62, 2.50, 2.35, 2.17, 1.96, 1.61, 1.38, 0.97.

15N HMBC $^{15}$N NMR (41 MHz, CDCl$_3$) δ 28.34, 297.92, 194.96, 138.76, 298.18, 194.88

$^1$H NMR (400 MHz, CDCl$_3$) δ 4.58, 3.92, 3.92, 2.63, 2.51, 2.36.

Intermediate 224

(rac)-ethyl 13-chloro-12-ethyl-1-(3-((6-fluoronaphthalen-1-yl)oxy)propyl)-6,11-dimethyl-5,6,7,8,9,11-hexahydro-4H-pyrazolo[3',4':8,9][1,4]diazacycloundecino[10,11,1-h]indole-2-carboxylate

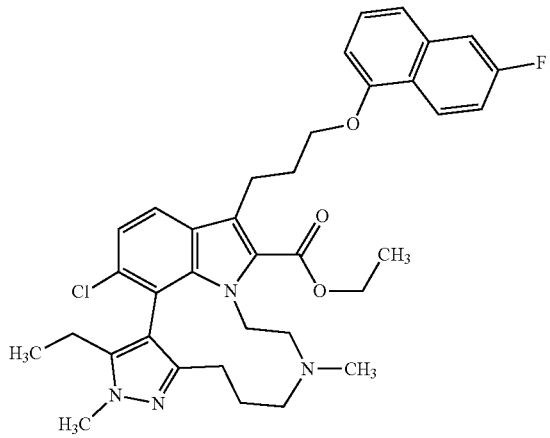 [SMILES: CCOC(=O)c1c(CCCOc2cccc3cc(F)ccc23)c2ccc(Cl)c3c2n1CCN(C)CCCc1nn(C)c(CC)c1-3]

To a solution of (rac)-ethyl 13-chloro-12-ethyl-1-(3-((6-fluoronaphthalen-1-yl)oxy)propyl)-11-methyl-5,6,7,8,9,11-hexahydro-4H-pyrazolo[3',4':8,9][1,4]diazacycloundecino[10,11,1-h]indole-2-carboxylate (200 mg, 0.324 mmol, see Intermediate 223) in tetrahydrofuran (20 mL) was added formaldehyde solution (1 mL, 37% in water with 10-15% methanol, 13.4 mmol) and stirred at room temperature for 15 minutes at which time was added triacetoxyborohydride (240 mg, 1.27 mmol) and the mixture stirred for an additional 2 hours at room temperature, at which time volatiles were removed and the residue (330 mg) as an amber gum was used in the next step without further manipulation.

LC-MS (Method 7): $R_t$=4.74 min; MS (ESIpos): m/z=632 [M+H]$^+$

Intermediate 225

(rac)-ethyl 13-chloro-6-(2,2-difluoroethyl)-12-ethyl-1-(3-((6-fluoronaphthalen-1-yl)oxy)propyl)-11-methyl-5,6,7,8,9,11-hexahydro-4H-pyrazolo[3',4':8,9][1,4]diazacycloundecino[10,11,1-hi]indole-2-carboxylate

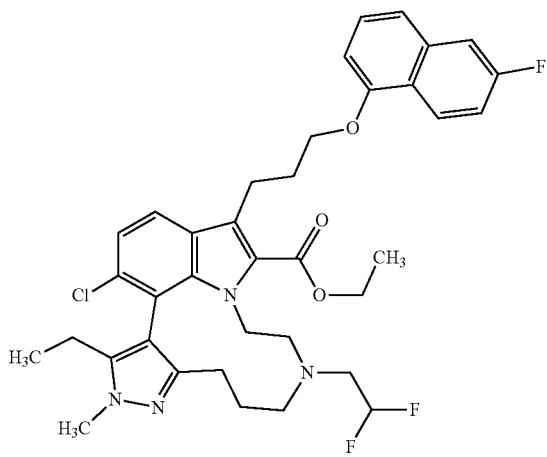 [SMILES: CCOC(=O)c1c(CCCOc2cccc3cc(F)ccc23)c2ccc(Cl)c3c2n1CCN(CC(F)F)CCCc1nn(C)c(CC)c1-3]

and

Intermediate 226

(rac)-ethyl 13-chloro-12-ethyl-1-(3-((6-fluoronaphthalen-1-yl)oxy)propyl)-6-(4-hydroxybutyl)-11-methyl-5,6,7,8,9,11-hexahydro-4H-pyrazolo[3',4':8,9][1,4]diazacycloundecino[10,11,1-hi]indole-2-carboxylate

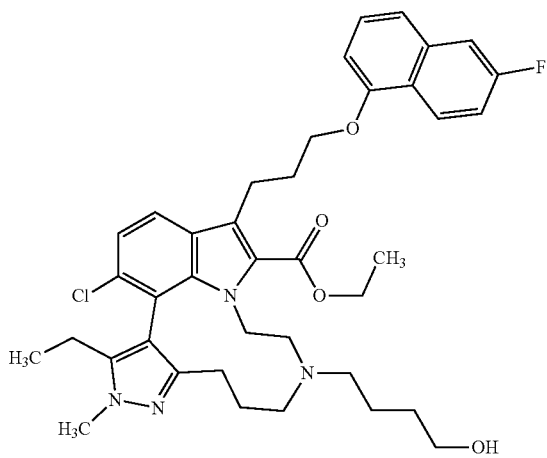 [SMILES: CCOC(=O)c1c(CCCOc2cccc3cc(F)ccc23)c2ccc(Cl)c3c2n1CCN(CCCCO)CCCc1nn(C)c(CC)c1-3]

To a solution of (rac)-ethyl 13-chloro-12-ethyl-1-(3-((6-fluoronaphthalen-1-yl)oxy)propyl)-11-methyl-5,6,7,8,9,11-hexahydro-4H-pyrazolo[3',4':8,9][1,4]diazacycloundecino[10,11,1-hi]indole-2-carboxylate (300 mg, 0.486 mmol, see Intermediate 223) in tetrahydrofuran (14 mL) was added difluoroacetaldehyde ethyl hemiacetal (0.4 mL, 3.86 mmol) followed sodium triacetoxy borohydride (400 mg, 2.11 mmol) and the mixture stirred at room temperature for 20 hours, then warmed to 60° C. and treated with additional difluoroacetaldehyde ethyl hemiacetal (0.3 mL, 2.94 mmol) and held at that temperature for 4 hours, then volatiles were removed under reduced pressure and the residue suspended in tetrahydrofuran (10 mL) and treated with additional sodium triacetoxy borohydride (400 mg, 2.11 mmol) and difluoroacetaldehyde ethyl hemiacetal (0.2 mL, 1.93 mmol) and stirred at room temperature for 18 hours, mixture diluted with toluene (100 ml) and treated with additional difluoroacetaldehyde ethyl hemiacetal (0.3 mL, 2.94 mmol), and heated to reflux for 2 hours, at which time the volatiles were removed under reduced pressure and the residue was suspended in tetrahydrofuran (30 mL) and treated with further sodium triacetoxy borohydride (400 mg, 2.11 mmol), after 20 hours at room temperature the volatiles were removed, and the residue partitioned between ethyl acetate (100 mL), saturated sodium hydrogen carbonate (100 mL, aqueous), and water (30 mL), layers were separated and the organic phase washed with saturated sodium chloride (aqueous), dried over sodium sulfate, insoluble materials were removed by filtration, volatiles removed under reduced pressure and the residue purified by flash chromatography on silica gel eluting with a gradient of ethyl acetate in hexanes to provide ethyl 13-chloro-6-(2,2-difluoroethyl)-12-ethyl-1-(3-((6-fluoronaphthalen-1-yl)oxy)propyl)-11-methyl-5,6,7,8,9,11-hexahydro-4H-pyrazolo[3',4':8,9][1,4]diazacycloundecino[10,11,1-h,]indole-2-carboxylate (100 mg) as a color less film and ethyl 13-chloro-12-ethyl-1-(3-((6-fluoronaphthalen-1-yl)oxy)propyl)-6-(4-hydroxybutyl)-11-methyl-5,6,7,8,9,11-hexahydro-4H-pyrazolo[3',4':8,9][1,4]diazacycloundecino[10,11,1-h,]indole-2-carboxylate (34 mg) as a pale yellow film.

Intermediate 225

LC-MS (Method 7): $R_t$=6.01 min; MS (ESIpos): m/z=682 [M+H]$^+$ $^1$H-NMR (400 MHz, Chloroform-d) δ=8.43 (dd, J=9.3, 5.8 Hz, 1H), 7.60 (dd, J=8.6, 1.3 Hz, 1H), 7.44 (dt, J=10.2, 2.1 Hz, 1H), 7.39 (d, J=7.8 Hz, 2H), 7.29 (tt, J=8.6, 2.0 Hz, 1H), 7.16 (dd, J=8.6, 1.4 Hz, 1H), 6.75 (d, J=6.8 Hz, 1H), 4.61-4.08 (m, 7H), 3.92 (s, 3H), 3.39 (t, J=7.4 Hz, 2H), 2.67-2.16 (m, 12H), 2.00-1.84 (m, 1H), 1.70 (ddt, J=19.0, 12.0, 5.3 Hz, 1H), 1.39 (t, J=7.1 Hz, 3H), 0.97 (t, J=7.5 Hz, 3H).

$^{19}$F-NMR (376 MHz, Chloroform-d) δ=−114.95, −117.68 (d, J=284.3 Hz), −118.90 (d, J=284.5 Hz).

HSQC
$^{13}$C NMR (101 MHz, CDCl$_3$) δ=124.77, 120.68, 110.51, 127.41, 119.40, 115.16, 121.43, 104.04, 44.26, 116.03, 60.68, 67.47, 44.17, 36.49, 22.15, 21.26, 60.16, 55.36, 60.20, 21.16, 17.99, 30.82, 52.33, 55.33, 25.15, 25.08, 14.54, 12.42.

$^1$H NMR (400 MHz, CDCl$_3$) δ=8.43, 7.60, 7.45, 7.39, 7.38, 7.29, 7.16, 6.75, 4.51, 4.40, 4.36, 4.22, 4.15, 3.92, 3.39, 2.57, 2.51, 2.49, 2.45, 2.44, 2.36, 2.33, 2.29, 2.26, 1.92, 1.72, 1.39, 0.97. $^{Proton\ coupled\ 19}$F NMR (376 MHz, Chloroform-d) δ=−114.95 (td, J=9.4, 5.8 Hz), −117.68 (ddt, J=284.4, 56.1, 14.2 Hz), −118.90 (dddd, J=284.2, 56.4, 18.5, 12.0 Hz).

Intermediate 226

LC-MS (Method 7): $R_t$=3.86 min; MS (ESIpos): m/z=690 [M+H]$^+$ $^1$H-NMR (400 MHz, Chloroform-d) δ=8.38 (dd, J=9.4, 5.7 Hz, 1H), 7.60 (dd, J=8.5, 1.3 Hz, 1H), 7.47-7.34 (m, 3H), 7.32-7.24 (m, 1H), 7.20 (dd, J=8.6, 1.4 Hz, 1H), 6.76 (d, J=7.0 Hz, 1H), 4.47 (d, J=14.2 Hz, 1H), 4.43-4.28 (m, 2H), 4.24 (t, J=6.2 Hz, 2H), 4.20-4.10 (m, 3H), 3.92 (s, 3H), 3.43 (dt, J=14.5, 7.5 Hz, 1H), 3.31 (dt, J=14.1, 7.5 Hz, 1H), 3.14 (t, J=6.5 Hz, 2H), 2.56 (dd, J=14.0, 5.2 Hz, 1H), 2.44 (td, J=13.4, 5.3 Hz, 1H), 2.33 (h, J=10.3, 9.1 Hz, 5H), 2.24-2.10

(m, 3H), 1.93-1.67 (m, 3H), 1.39 (td, J=7.1, 1.3 Hz, 3H), 1.20-0.70 (m, 5H), 0.61 (tt, J=13.3, 6.8 Hz, 1H), 0.38 (dq, J=17.6, 8.4 Hz, 1H).

$^{13}$C-NMR (101 MHz, Chloroform-d) δ=162.74, 161.36 (d, J=246.0 Hz), 155.03, 149.44, 142.14, 140.03, 135.77, 135.67, 134.97, 127.48, 126.29, 126.07, 125.71, 124.92 (d, J=9.1 Hz), 122.79, 121.38, 119.62 (d, J=4.9 Hz), 117.96, 115.31 (d, J=24.9 Hz), 115.05, 110.75 (d, J=20.4 Hz), 104.10, 67.88, 62.89, 60.85, 52.84, 52.70, 44.30, 36.56, 30.81, 30.48, 25.04, 23.92, 22.22, 21.85, 18.13, 14.47, 12.54.

HSQC $^{13}$C NMR (101 MHz, CDCl$_3$) δ 124.75, 120.24, 110.45, 127.35, 119.50, 115.19, 121.27, 104.00, 44.17, 60.72, 67.74, 44.19, 36.49, 22.14, 22.00, 62.74, 21.88, 21.69, 17.97, 30.78, 58.36, 52.62, 58.37, 52.59, 52.66, 21.19, 25.10, 52.76, 25.07, 14.54, 12.46, 30.60, 23.76, 30.40, 23.84.

$^1$H NMR (400 MHz, CDCl$_3$) δ 8.38, 7.59, 7.43, 7.39, 7.37, 7.27, 7.20, 6.76, 4.45, 4.35, 4.24, 4.15, 3.92, 3.41, 3.31, 3.14, 2.54, 2.44, 2.34, 2.33, 2.30, 2.20, 2.18, 2.14, 2.08, 2.06, 1.85, 1.76, 1.73, 1.39, 0.96, 0.82, 0.78, 0.61, 0.39.

Intermediate 227

(rac)-ethyl 13-chloro-12-ethyl-1-(3-((6-fluoronaphthalen-1-yl)oxy)propyl)-11-methyl-6-(2,2,3,3-tetrafluoropropyl)-5,6,7,8,9,11-hexahydro-4H-pyrazolo[3',4':8,9][1,4]diazacycloundecino[10,11,1-h,]indole-2-carboxylate

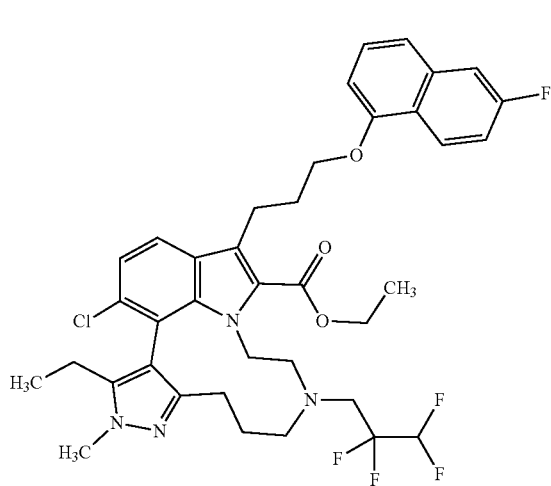 [SMILES: CCOC(=O)c1c(CCCOc2cccc3cc(F)ccc23)c2ccc(Cl)c3c2n1CCN(CC(F)(F)C(F)F)CCCc1nn(C)c(CC)c1-3]

A solution of (rac)-ethyl 13-chloro-12-ethyl-1-(3-((6-fluoronaphthalen-1-yl)oxy)propyl)-11-methyl-5,6,7,8,9,11-hexahydro-4H-pyrazolo[3',4':8,9][1,4]diazacycloundecino[10,11,1-h]indole-2-carboxylate (300 mg, 0.48 mmol, see Intermediate 223)), ethylbis(propan-2-yl)amine (0.6 mL, 3.4 mmol) in tetrahydrofuran (20 mL) was treated with 2,2,3,3-tetrafluoropropyl trifluoromethanesulfonate (0.2 mL, 1.2 mmol) and warmed to 45° C. for 17 hours, then treated with additional 2,2,3,3-tetrafluoropropyl trifluoromethanesulfonate (0.1 mL, 0.6 mmol) and continued heating for an additional 23 hours. Volatiles were removed under reduced pressure and the residue was purified by flash chromatography on silica gel eluting with a gradient of ethyl acetate in hexanes to provide the title compound as an amber foam (320 mg).

LC-MS (Method 8): R$_t$=1.90 min; MS (ESIpos): m/z=731 [M+H]$^+$ $^1$H-NMR (300 MHz, Chloroform-d) δ=8.40 (dd, J=9.2, 5.8 Hz, 1H), 7.62 (d, J=8.6 Hz, 1H), 7.45-7.31 (m, 3H), 7.25 (ddd, J=9.5, 8.6, 2.7 Hz, 1H), 7.20 (d, J=8.6 Hz, 1H), 6.75 (dd, J=7.0, 1.7 Hz, 1H), 4.54 (ddd, J=14.7, 3.1, 1.6 Hz, 1H), 4.32 (qd, J=7.1, 2.3 Hz, 2H), 4.21 (q, J=4.9, 4.2 Hz, 3H), 3.89 (s, 3H), 3.48-3.22 (m, 2H), 2.84-2.53 (m, 3H), 2.52-2.09 (m, 10H), 1.96-1.77 (m, 1H), 1.66 (t, J=13.8 Hz, 1H), 1.35 (t, J=7.1 Hz, 3H), 0.93 (t, J=7.6 Hz, 3H).

$^{19}$F=NMR (376 MHz, Chloroform-d) δ=−114.94, −119.34 (ddd, J=270.1, 12.1, 5.5 Hz), −124.34 (ddd, J=270.2, 13.6, 7.8 Hz), −137.67 (ddd, J=297.0, 13.6, 5.6 Hz), −145.41 (ddd, J=297.1, 12.2, 7.7 Hz).

HSQC $^{13}$C NMR (101 MHz, CDCl$_3$) δ 124.68, 120.95, 110.58, 127.50, 119.38, 115.14, 121.60, 104.16, 43.71, 60.69, 43.65, 67.60, 108.59, 36.52, 22.17, 53.75, 21.54, 60.40, 60.55, 54.02, 30.60, 17.99, 21.39, 30.59, 53.79, 53.76, 25.06, 24.90, 14.52, 12.36.

$^1$H NMR (400 MHz, CDCl$_3$) δ 8.42, 7.64, 7.44, 7.39, 7.37, 7.28, 7.22, 6.77, 4.55, 4.34, 4.25, 4.25, 4.02, 3.92, 3.37, 2.70, 2.65, 2.64, 2.46, 2.43, 2.35, 2.35, 2.35, 2.31, 2.29, 2.20, 1.90, 1.69, 1.37, 0.95.

Intermediate 228

(rac)-ethyl 4-chloro-3-ethyl-7-{3-[(6-fluoronaphthalen-1-yl)oxy]propyl}-14-(3-hydroxy-3-methylbutyl)-2-methyl-10,11,12,13,14,15-hexahydro-2H-pyrazolo[3',4':8,9][1,6]diazacycloundecino[10,11,1-hi]indole-8-carboxylate

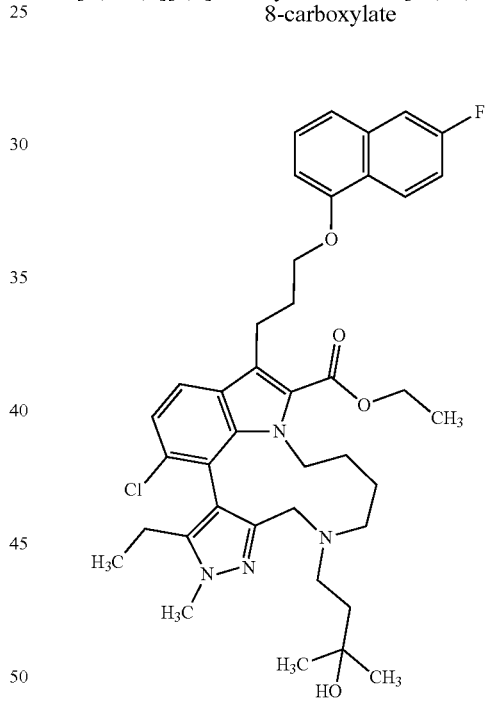

(rac)-Ethyl 4-chloro-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylate (see Intermediate 115, 205 mg, 332 μmol) was dissolved in 5.1 mL DMF. Cesium carbonate (433 mg, 1.33 mmol) and 4-bromo-2-methylbutan-2-ol (45 μL, 365 μmol) were added and the reaction mixture was stirred over night at rt. After 17 h sodium iodide (49.8 mg, 332 μmol) was added and the reaction mixture was stirred for 5 h at 50° C. Then 4-bromo-2-methylbutan-2-ol (39 μL, 332 μmol) was added again and the reaction mixture was stirred for 1 h at 50° C. N,N-Diisopropylethylamine (289 μL, 1.66 mmol) was added and the reaction mixture was stirred for 1 h at 90° C. and at rt over the weekend. The reaction mixture was concentrated under vacuo, dissolved in a small amount of dichloromethane and water and purified by chromatography (dichloromethane/ethanol 0-20%, 25 g 25µ-silica gel) to provide the target compound: 130 mg, 56% yield.

LC-MS (Method 2): $R_t$=1.78 min; MS (ESIpos): m/z=703 [M+H]$^+$ $^1$H-NMR (400 MHz, DMSO-d6) δ[ppm]: 0.726 (0.57), 0.797 (5.70), 0.816 (15.24), 0.835 (5.64), 0.875 (6.35), 0.904 (1.44), 0.922 (0.98), 1.035 (1.50), 1.042 (1.50), 1.052 (2.13), 1.070 (1.55), 1.078 (11.61), 1.231 (1.69), 1.246 (7.85), 1.263 (16.00), 1.281 (7.82), 1.534 (0.57), 1.552 (0.84), 1.570 (0.55), 1.597 (0.44), 2.105 (0.98), 2.169 (2.62), 2.187 (3.00), 2.204 (2.26), 2.221 (1.36), 2.238 (0.84), 2.283 (1.20), 2.318 (1.31), 2.322 (1.69), 2.327 (1.96), 2.331 (1.53), 2.336 (0.90), 2.518 (6.98), 2.523 (4.28), 2.659 (0.55), 2.664 (1.17), 2.669 (1.61), 2.673 (1.17), 2.678 (0.52), 3.161 (0.55), 3.187 (0.90), 3.203 (0.87), 3.220 (0.98), 3.237 (1.12), 3.257 (0.68), 3.273 (0.71), 3.292 (1.23), 3.310 (1.14), 3.431 (0.49), 3.487 (0.82), 3.500 (1.12), 3.506 (0.98), 3.518 (0.90), 3.523 (0.95), 3.536 (0.76), 3.816 (9.02), 3.853 (0.52), 3.873 (0.63), 3.885 (0.95), 3.906 (0.76), 3.920 (0.49), 4.090 (0.74), 4.177 (2.32), 4.193 (3.63), 4.203 (2.15), 4.212 (2.62), 4.220 (2.81), 4.229 (2.13), 4.238 (2.64), 4.253 (1.09), 4.271 (2.62), 4.281 (0.55), 4.289 (2.40), 4.298 (1.44), 4.304 (1.06), 4.306 (0.79), 4.316 (1.74), 4.334 (0.41), 5.759 (0.55), 6.852 (1.66), 6.857 (1.69), 6.868 (1.69), 6.874 (1.74), 7.193 (2.40), 7.214 (2.53), 7.387 (1.23), 7.393 (1.47), 7.408 (2.64), 7.416 (2.15), 7.429 (3.30), 7.438 (2.51), 7.446 (6.46), 7.462 (0.82), 7.652 (2.21), 7.659 (2.26), 7.678 (2.26), 7.685 (2.26), 7.710 (1.61), 7.732 (1.50), 8.273 (1.88), 8.288 (2.02), 8.296 (2.02), 8.311 (1.83).

Intermediate 229

(rac)-ethyl 4-chloro-3-ethyl-7-{3-[(6-fluoronaphthalen-1-yl)oxy]propyl}-2-methyl-14-[2-(morpholin-4-yl)ethyl]-10,11,12,13,14,15-hexahydro-2H-pyrazolo[3',4':8,9][1,6]diazacycloundecino[10,11,1-hi]indole-8-carboxylate

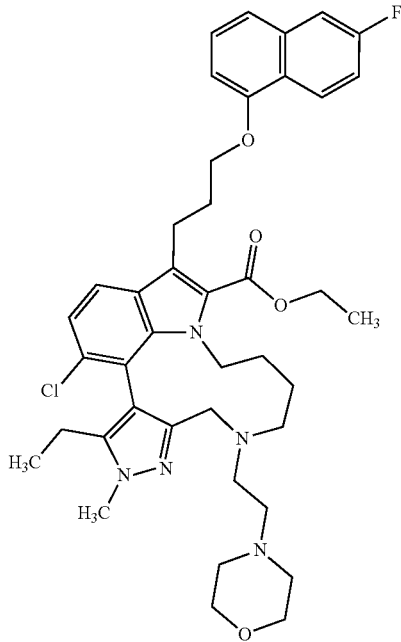 [SMILES: CCOC(=O)c1c(CCCOc2cccc3cc(F)ccc23)c2ccc(Cl)c3c2n1CCCCN(CCN1CCOCC1)Cc1nn(C)c(CC)c1-3]

(rac)-Ethyl 4-chloro-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylate (see Intermediate 115, 205 mg, 332 µmol) was dissolved in 5.1 mL DMF. Cesium carbonate (433 mg, 1.33 mmol) and 4-(2-chloroethyl)morpholine-hydrogen chloride (1/1) (124 mg, 664 µmol) were added and the reaction mixture was stirred over night at rt. After 17 h sodium iodide (49.8 mg, 332 µmol) was added and the reaction mixture was stirred for 6 h at 50° C. N,N-Diisopropylethylamine (289 µL, 1.66 mmol) was added and the reaction mixture was stirred for 1 h at 90° C. and at rt over the weekend. The reaction mixture was concentrated under vacuo, dissolved in a small amount of dichloromethane and water and purified by chromatography (dichloromethane/ethanol 0-15%, 25 g 25µ-silica gel) to provide the target compound: 88 mg, 36% yield.

LC-MS (Method 2): $R_t$=1.77 min; MS (ESIpos): m/z=731 [M+H]$^+$ $^1$H-NMR (400 MHz, DMSO-d6) δ[ppm]: 0.786 (3.00), 0.795 (0.66), 0.805 (7.08), 0.824 (3.20), 1.006 (0.58), 1.019 (0.75), 1.034 (0.80), 1.048 (0.53), 1.084 (0.66), 1.154 (0.51), 1.230 (0.80), 1.249 (5.13), 1.259 (1.09), 1.266 (10.67), 1.284 (5.02), 1.646 (0.75), 1.662 (0.73), 1.677 (0.89), 1.694 (0.42), 1.885 (0.42), 1.901 (0.91), 1.915 (1.26), 1.940 (2.28), 1.948 (2.04), 1.987 (1.00), 2.005 (0.66), 2.019 (0.58), 2.066 (0.62), 2.085 (0.89), 2.103 (1.04), 2.121 (1.49), 2.140 (1.93), 2.160 (1.40), 2.178 (0.91), 2.197 (1.09), 2.216 (1.04), 2.231 (0.66), 2.259 (0.44), 2.276 (0.78), 2.292 (0.64), 2.309 (0.62), 2.323 (1.16), 2.327 (1.51), 2.332 (1.09), 2.336 (0.73), 2.354 (0.46), 2.518 (4.37), 2.523 (3.02), 2.665 (0.75), 2.669 (1.09), 2.673 (0.76), 3.122 (1.55), 3.153 (1.64), 3.221 (0.60), 3.238 (0.80), 3.263 (2.97), 3.275 (4.88), 3.286 (3.42), 3.304 (0.76), 3.720 (1.55), 3.752 (1.38), 3.804 (16.00), 3.866 (0.62), 3.889 (0.46), 4.067 (0.58), 4.085 (0.51), 4.100 (0.44), 4.162 (0.46), 4.170 (0.64), 4.187 (1.57), 4.199 (1.69), 4.203 (1.67), 4.216 (1.44), 4.226 (1.97), 4.234 (0.42), 4.244 (1.86), 4.261 (0.95), 4.280 (1.75), 4.297 (1.58), 4.307 (0.96), 4.315 (0.46), 4.324 (0.96), 5.759 (0.78), 6.846 (1.24), 6.852 (1.29), 6.863 (1.22), 6.868 (1.35), 7.185 (4.02), 7.207 (4.22), 7.386 (0.80), 7.393 (0.98), 7.408 (1.75), 7.416 (1.40), 7.430 (2.48), 7.437 (1.24), 7.445 (3.88), 7.464 (0.55), 7.653 (1.44), 7.660 (1.49), 7.679 (1.46), 7.686 (1.47), 7.702 (3.39), 7.724 (3.17), 8.282 (1.24), 8.297 (1.31), 8.305 (1.29), 8.320 (1.20).

EXAMPLES

Example 1

(rac)-(11Z)-4-chloro-1,3-dimethyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid

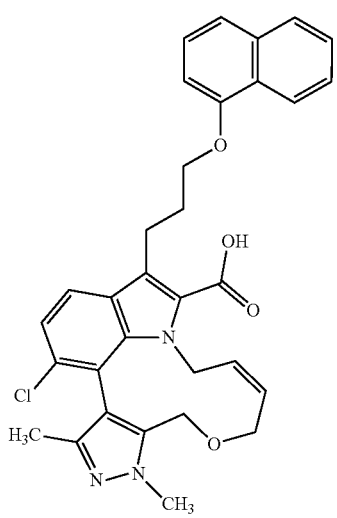 [SMILES: Cc1nn(C)c2c1-c1c(Cl)ccc3c(CCCOc4cccc5ccccc45)c(C(=O)O)n(c13)C/C=C\COC2]

To a solution of (rac)-ethyl (11Z)-4-chloro-1,3-dimethyl-7-[3-(naphthalen-1-yloxy)propyl]-1,10,13,15-tetrahydropyrazolo[4',3':9,10][1,6]oxazacycloundecino[8,7,6-hi]indole-8-carboxylate (see Intermediate 32, 20.0 mg, 34.2 µmol) in THF (1.7 mL) and ethanol (800 µL) was added a solution of lithium hydroxide in water (680 µL, 1.0 M, 680 µmol). The reaction mixture was stirred for 32 hours at 50° C. For work-up, the reaction mixture was concentrated under reduced pressure and the residue was purified by flash chromatography (dichloromethane/methanol gradient, 3.5%→10% methanol) to give the title compound (5.9 mg) as a racemic mixture.

LC-MS (Method 2): Rt=0.89 min; MS (ESIpos): m/z=556 [M+H]$^+$ $^1$H-NMR (400 MHz, DMSO-d6) δ[ppm]: 0.847 (1.95), 1.165 (2.98), 1.227 (16.00), 1.469 (0.91), 1.667 (12.33), 2.240 (4.00), 2.328 (0.85), 2.667 (0.78), 3.476 (1.44), 3.506 (2.32), 3.535 (1.51), 3.751 (2.11), 3.778 (1.98), 3.875 (12.36), 4.090 (2.23), 4.123 (2.47), 4.214 (5.20), 4.509 (1.07), 4.542 (1.66), 4.571 (1.42), 4.683 (2.32), 4.716 (2.16), 4.824 (2.22), 5.060 (2.09), 5.099 (2.98), 6.887 (2.53), 6.903 (2.71), 7.245 (2.58), 7.264 (2.78), 7.386 (2.77), 7.402 (2.40), 7.440 (3.75), 7.459 (3.65), 7.474 (3.44), 7.498 (3.66), 7.520 (2.95), 7.783 (2.68), 7.802 (2.65), 7.849 (2.79), 7.866 (2.59), 8.138 (2.56), 8.155 (2.47).

Example 2 rac-4-chloro-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

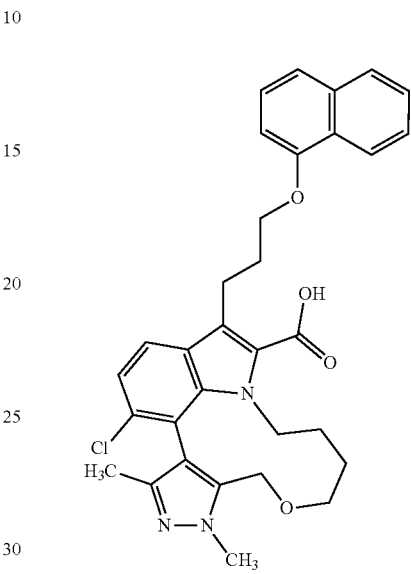

To a solution of (rac)-ethyl 4-chloro-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 33, 105 mg, 179 µmol) in THF (8.7 mL) and ethanol (4.2 mL) was added a solution of lithium hydroxide in water (3.6 mL, 1.0 M, 3.6 mmol). The reaction mixture was stirred for 24 hours at 60° C. For work-up, the reaction mixture was concentrated under reduced pressure and the residue was purified by flash chromatography (dichloromethane/isopropanol gradient, 2.5%→10% methanol) to give the title compound (60 mg) as a racemic mixture.

LC-MS (Method 2): Rt=0.92 min; MS (ESIpos): m/z=558 [M+H]$^+$

The title compound (60 mg) was separated into enantiomers by preparative chiral HPLC to give enantiomer 1 (25 mg, Example 3 and enantiomer 2 (24 mg, Example 4).

Preparative chiral HPLC method: Instrument: Labomatic HD5000, Labocord-5000; Gilson GX-241, Labcol Vario 4000, column: Chiralpak ID 5µ 250×30 mm; eluent A: hexane+0.1 Vol-% TFA (99%); eluent B: isopropanol; gradient: 20-50% B in 20 min; flow 40.0 mL/min; UV 254 nm Analytical chiral HPLC method: Instrument: Agilent HPLC 1260; column: Chiralpak ID3µ 100×4.6 mm; eluent A: hexane+0.1 Vol-% TFA (99%); eluent B: isopropanol; Gradient: 20-50% B in 7 min; flow 1.4 mL/min; temperature: 25° C.; DAD 254 nm

403

Example 3

4-chloro-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 1)

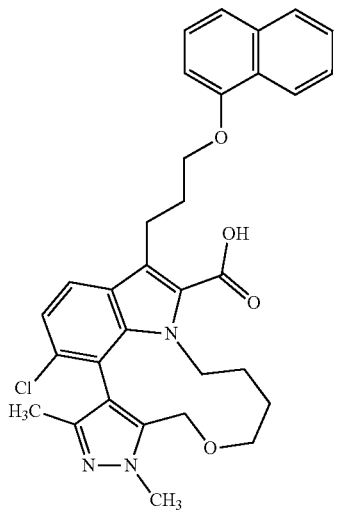 [SMILES: Cc1nn(C)c2c1-c1c(Cl)ccc3c(CCCOc4cccc5ccccc45)c(C(=O)O)n(c13)CCCCOC2]

For the preparation of the racemic title compound see Example 2. Separation of enantiomers by preparative chiral HPLC (method see Example 2), gave the title compound (25 mg).

Analytical Chiral HPLC (method see Example 2): $R_t$=2.64 min.

$^1$H-NMR (400 MHz, DMSO-d6) δ[ppm]: 0.845 (0.43), 0.962 (0.42), 1.041 (1.55), 1.066 (1.61), 1.083 (2.46), 1.103 (2.81), 1.132 (1.62), 1.150 (3.25), 1.168 (1.73), 1.225 (2.81), 1.737 (16.00), 2.183 (1.25), 2.200 (1.81), 2.217 (1.33), 2.323 (0.61), 2.665 (0.61), 2.822 (0.88), 2.833 (0.65), 2.851 (0.94), 2.869 (0.41), 2.898 (0.45), 2.916 (0.62), 2.929 (0.61), 2.947 (0.43), 3.242 (0.57), 3.257 (0.75), 3.275 (1.16), 3.295 (0.66), 3.306 (0.66), 3.325 (1.19), 3.343 (0.78), 3.349 (0.78), 3.359 (0.67), 3.366 (1.29), 3.384 (1.23), 3.401 (0.57), 3.408 (0.51), 3.423 (1.04), 3.437 (0.89), 3.452 (0.97), 3.467 (0.47), 3.900 (1.00), 3.917 (1.30), 3.935 (1.26), 3.952 (1.28), 3.969 (0.76), 4.157 (2.24), 4.175 (1.89), 4.190 (5.76), 4.206 (1.84), 4.464 (1.02), 4.477 (0.62), 4.487 (0.57), 4.499 (0.95), 4.630 (2.34), 4.664 (2.11), 6.874 (2.09), 6.892 (2.26), 7.206 (3.68), 7.226 (3.79), 7.360 (1.33), 7.380 (2.73), 7.399 (2.10), 7.438 (3.01), 7.459 (1.67), 7.478 (0.70), 7.491 (1.63), 7.495 (1.56), 7.506 (1.85), 7.511 (2.86), 7.514 (2.01), 7.525 (1.65), 7.529 (1.81), 7.542 (0.76), 7.765 (3.40), 7.787 (3.15), 7.848 (1.82), 7.866 (1.80), 7.870 (1.55), 8.186 (1.63), 8.189 (1.74), 8.208 (1.64).

404

Example 4

4-chloro-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (Enantiomer 2)

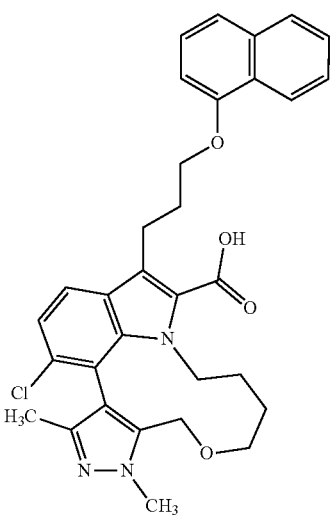 [SMILES: Cc1nn(C)c2c1-c1c(Cl)ccc3c(CCCOc4cccc5ccccc45)c(C(=O)O)n(c13)CCCCOC2]

For the preparation of the racemic title compound see Example 2. Separation of enantiomers by preparative chiral HPLC (method see Example 2), gave the title compound (25 mg).

Analytical Chiral HPLC (method see Example 2): $R_t$=4.20 min.

$^1$H-NMR (400 MHz, DMSO-d6) δ[ppm]: 0.848 (0.44), 0.966 (0.41), 1.047 (1.84), 1.069 (2.43), 1.087 (3.79), 1.105 (2.54), 1.107 (2.89), 1.137 (0.58), 1.144 (0.53), 1.154 (0.90), 1.173 (0.64), 1.227 (2.80), 1.742 (16.00), 2.188 (1.45), 2.205 (2.08), 2.221 (1.54), 2.808 (0.45), 2.827 (0.98), 2.837 (0.77), 2.855 (1.03), 2.872 (0.47), 3.247 (0.64), 3.262 (0.86), 3.280 (1.27), 3.300 (0.72), 3.311 (0.75), 3.330 (1.30), 3.352 (1.18), 3.369 (2.01), 3.387 (1.92), 3.404 (0.81), 3.411 (0.58), 3.427 (1.11), 3.441 (0.99), 3.456 (1.03), 3.470 (0.49), 3.905 (0.71), 3.922 (1.14), 3.939 (1.20), 3.957 (1.30), 3.974 (0.84), 4.038 (0.54), 4.161 (2.59), 4.179 (2.37), 4.195 (6.27), 4.209 (2.26), 4.470 (1.15), 4.482 (0.73), 4.492 (0.69), 4.505 (1.04), 4.634 (2.43), 4.669 (2.17), 6.878 (2.26), 6.896 (2.41), 7.209 (3.44), 7.230 (3.66), 7.363 (1.32), 7.383 (2.79), 7.402 (2.08), 7.442 (3.18), 7.463 (1.81), 7.482 (0.77), 7.495 (1.75), 7.498 (1.72), 7.514 (3.17), 7.528 (1.82), 7.532 (1.89), 7.546 (0.80), 7.769 (3.37), 7.791 (3.05), 7.851 (2.01), 7.869 (1.88), 7.873 (1.69), 8.195 (1.86), 8.213 (1.75).

Example 5

(rac)-4-chloro-3-ethyl-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid

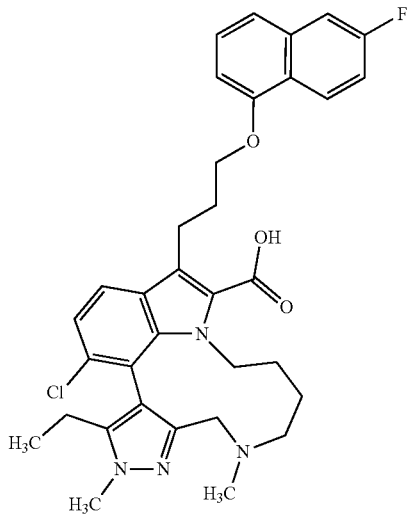 [SMILES: CCc1c2c(nn1C)CN(C)CCCCn1c(C(=O)O)c(CCCOc3cccc4cc(F)ccc34)c3ccc(Cl)c-2c31]

(rac)-Ethyl-4-chloro-3-ethyl-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylate (see Intermediate 38, 27.0 mg) was dissolved in a mixture of 690 µL THF and 620 µL ethanol and aqueous lithium hydroxide solution (960 µL, 1.0 M, 960 µmol) was added. It was stirred at 65° C. overnight. The organic solvents were removed under reduced pressure. The aqueous residue (pH 10) was acidified using about 0.12 mL acetic acid (conc.) till pH value 5 (exothermic). It was extracted with dichloromethane/isopropanole (7:3) three times. The combined organic layers were dried using a water resistant filter and the clear filtrate was concentrated under reduced pressure to obtain the title compound (16.3 mg, 97% purity) as a racemic mixture. Residue of acetic acid were removed by lyophilisation.

LC-MS (Method 2): $R_t$=0.92 min; MS (ESIpos): m/z=603 [M+H]$^+$ $^1$H-NMR (400 MHz, DMSO-d6) δ[ppm]: 0.774 (0.70), 0.793 (1.65), 0.812 (0.73), 1.026 (2.47), 1.042 (2.54), 1.902 (16.00), 2.047 (2.16), 2.125 (0.49), 2.144 (0.53), 2.518 (0.64), 2.523 (0.42), 3.267 (0.45), 3.298 (0.57), 3.420 (0.53), 4.170 (0.44), 7.056 (0.63), 7.077 (0.66), 7.399 (0.55), 7.416 (1.04), 7.522 (0.51), 7.543 (0.45).

The title compound (66 mg) was separated into enantiomers by preparative chiral HPLC to provide enantiomer 1 (21 mg, see Example 6) and enantiomer 2 (17 mg, see Example 7).

Preparative Chiral HPLC Method:
Instrument: Sepiatec: Prep SFC100; Column: Chiralpak IG 5 µm 250×30 mm; Eluent A: CO$_2$, Eluent B: Ethanol+0.2 Vol-% aqueous ammonia (32%); Isokratic: 21% B; Flow 100.0 mL/min Temperature: 40° C.; BPR: 150 bar; MWD @ 220 nm Analytical Chiral HPLC Method:
Instrument: Agilent: 1260, Aurora SFC-Modul; Column: Chiralpak IG 5 µm 100×4.6 mm; Eluent A: CO$_2$, Eluent B: Ethanol+0.2 Vol-% aqueous ammonia (32%); Isokratic: 21% B; Flow 4.0 mL/min; Temperature: 37.5° C.; BPR: 100 bar; MWD @ 220 nm

Example 6

4-chloro-3-ethyl-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid (Enantiomer 1)

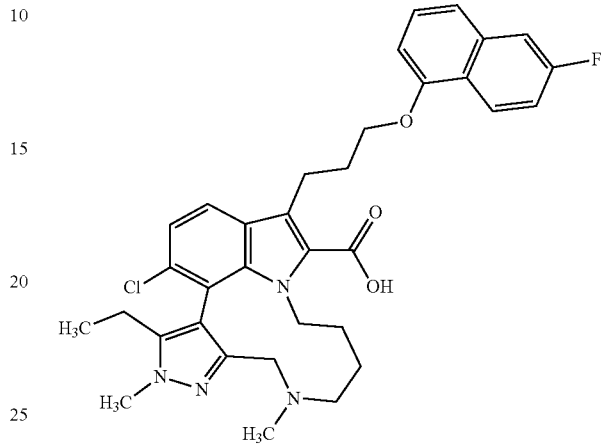

For the preparation of the racemic title compound see Example 5. Separation of enantiomers by preparative chiral HPLC (method see Example 5) provided the target compound (21 mg).

Analytical Chiral HPLC (method see Example 5): $R_t$=1.95 min.

Specific Optical Rotation (Method O1): 36.5° (c=10 mg/mL, chloroform)

$^1$H-NMR (400 MHz, DMSO-d6) δ[ppm]=0.79 (t, 3H), 0.93-1.07 (m, 2H), 1.09-1.32 (m, 3H), 1.79-1.91 (m, 1H), 2.03 (s, 3H), 2.07-2.25 (m, 4H), 3.14-3.28 (m, 4H), 3.39-3.54 (m, 2H), 3.81 (s, 3H), 4.18 (br t, 2H), 4.30 (td, 1H), 6.85 (dd, 1H), 7.16 (d, 1H), 7.33-7.48 (m, 3H), 7.66 (dd, 2H), 8.29 (dd, 1H).

Example 7

4-chloro-3-ethyl-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid (Enantiomer 2)

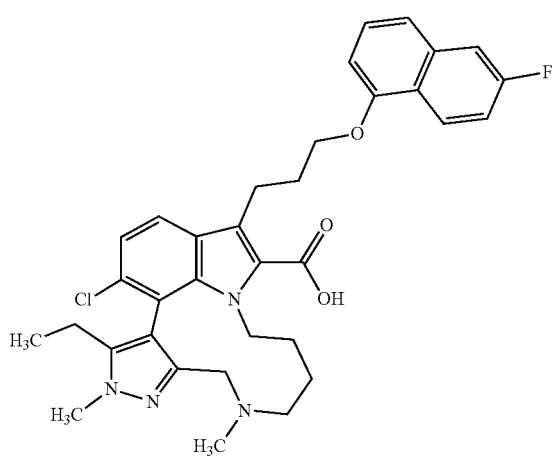 [SMILES: CCc1c2c(nn1C)CN(C)CCCCn1c(C(=O)O)c(CCCOc3cccc4cc(F)ccc34)c3ccc(Cl)c-2c31]

For the preparation of the racemic title compound see Example 5. Separation of enantiomers by preparative chiral HPLC (method see Example 5) provided the target compound (17 mg).

Analytical Chiral HPLC (method see Example 5: $R_t$=3.42 min.

Specific Optical Rotation (Method O1): −32.1° (c=10 mg/mL, chloroform)

$^1$H-NMR (400 MHz, DMSO-d6) δ[ppm]=0.79 (t, 3H), 0.98-1.07 (m, 2H), 1.09-1.18 (m, 6H), 1.80-1.92 (m, 1H), 2.06-2.23 (m, 3H), 2.34-2.43 (m, 1H), 3.16-3.28 (m, 3H), 3.39-3.52 (m, 3H), 3.81 (s, 3H), 4.12-4.22 (m, 2H), 4.24-4.36 (m, 1H), 6.85 (dd, 1H), 7.16 (d, 1H), 7.32-7.48 (m, 3H), 7.61-7.71 (m, 2H), 8.23-8.36 (m, 1H).

Example 8

(rac)-4-chloro-3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid

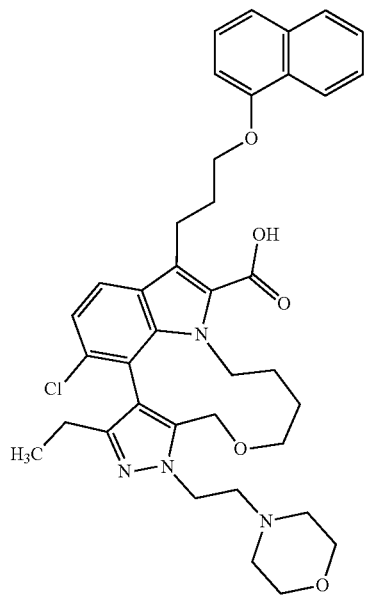 [SMILES: CCc1nn(CCN2CCOCC2)c2c1-c1c(Cl)ccc3c(CCCOc4cccc5ccccc45)c(C(=O)O)n(c13)CCCCOC2]

To a solution of (rac)-ethyl 4-chloro-3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylate (see Intermediate 41, 190 mg, 272 μmol) in a mixture of THF (20 mL) and ethanol (10 mL) was added an aqueous solution of lithium hydroxide (10 mL, 1.0 M, 10 mmol). The resulting mixture was stirred at 40° C. for three days. After removal of all volatiles the residue was subjected to flash chromatography (Biotage SNAP cartridge silica, dichloromethane/ethanol gradient, 0%→30% ethanol) to give the title compound (142 mg).

LC-MS (Method 2): Rt=0.89 min; MS (ESIpos): m/z=672 [M+H]$^+$ $^1$H-NMR (400 MHz, DMSO-d6) δ[ppm]: 0.829 (4.73), 0.848 (10.80), 0.866 (5.20), 1.007 (0.82), 1.035 (3.21), 1.052 (5.63), 1.070 (2.89), 1.144 (0.51), 1.232 (3.17), 1.257 (1.53), 2.075 (1.17), 2.094 (3.68), 2.113 (3.56), 2.132 (1.10), 2.188 (1.10), 2.206 (1.60), 2.222 (1.17), 2.337 (1.56), 2.356 (1.25), 2.369 (1.84), 2.380 (1.02), 2.518 (16.00), 2.523 (10.68), 2.678 (0.86), 2.732 (0.98), 2.748 (1.88), 2.763 (2.15), 2.780 (0.86), 2.795 (0.43), 2.914 (0.74), 2.926 (0.55), 2.943 (0.78), 3.238 (0.43), 3.252 (0.63), 3.270 (1.02), 3.291 (1.10), 3.423 (0.86), 3.434 (1.29), 3.440 (0.98), 3.447 (1.02), 3.460 (0.86), 3.527 (3.56), 3.538 (6.26), 3.550 (3.76), 3.961 (0.51), 3.978 (0.59), 3.995 (0.59), 4.177 (2.58), 4.186 (3.25), 4.202 (1.72), 4.212 (2.31), 4.248 (1.29), 4.266 (2.07), 4.284 (0.98), 4.356 (0.51), 4.448 (0.67), 4.482 (0.63), 4.665 (1.92), 4.699 (1.76), 5.760 (10.48), 6.868 (2.00), 6.887 (2.11), 7.187 (2.58), 7.208 (2.70), 7.359 (1.41), 7.379 (2.70), 7.399 (2.19), 7.441 (2.89), 7.462 (1.64), 7.479 (0.51), 7.483 (0.70), 7.497 (1.60), 7.500 (1.45), 7.510 (1.72), 7.515 (2.97), 7.520 (1.84), 7.530 (1.64), 7.533 (1.84), 7.547 (0.78), 7.550 (0.55), 7.745 (1.88), 7.766 (1.72), 7.852 (1.68), 7.858 (1.10), 7.871 (1.76), 7.875 (1.49), 8.196 (1.49), 8.201 (1.56), 8.220 (1.45).

The title compound (137 mg) was separated into enantiomers by preparative chiral HPLC to give enantiomer 1 (62 mg, see Example 9) and enantiomer 2 (61 mg, see Example 10).

Preparative chiral HPLC method: Instrument: Labomatic HD5000, Labocord-5000; Gilson GX-241, Labcol Vario 4000, column: Chiralpak IE 5μ 250×30 mm; Eluent A: Hexane+0.1 Vol-% N-ethylethanamine (99%); Eluent B: Ethanol; isocratic 60% A+40% B; flow 40.0 mL/min; UV 220 nm Analytical chiral HPLC method Instrument: Agilent HPLC 1260; column: Chiralpak IE 3μ 100×4.6 mm; Eluent A: Hexane+0.1 Vol-% N-ethylethanamine (99%); Eluent B: ethanol; Gradient: 20-50% B in 7 min; Flow 1.4 mL/min; Temperature: 25° C.; DAD 220 nm Example 9

4-chloro-3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 1)

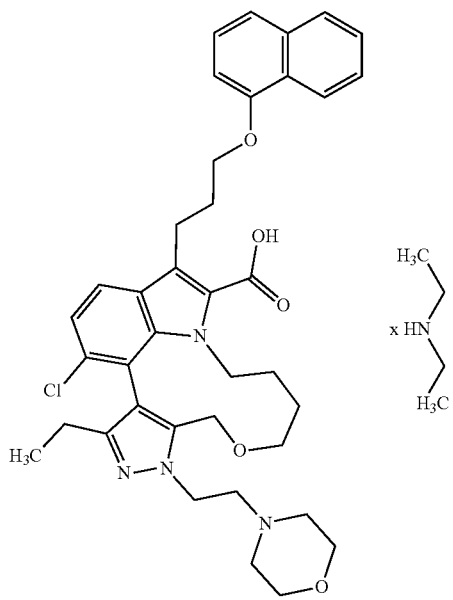

For the preparation of the racemic title compound see Example 8. Separation of enantiomers by preparative chiral HPLC (method see Example 8) gave the title compound (62 mg).

Analytical Chiral HPLC (method see Example 8): $R_t$=5.83 min.

LC-MS (Method 2): Rt=0.88 min; MS (ESIpos): m/z=672 [M+H]$^+$

Specific Optical Rotation (Method O1): 52.2° (c=10 mg/mL, DMSO)

$^1$H-NMR (400 MHz, DMSO-d6) δ[ppm]: 0.776 (0.69), 0.795 (1.67), 0.813 (0.93), 0.819 (0.48), 0.836 (0.63), 0.845 (5.01), 0.864 (11.49), 0.883 (4.99), 0.973 (0.69), 1.001 (1.31), 1.005 (2.39), 1.034 (0.99), 1.084 (1.34), 1.134 (7.61), 1.152 (16.00), 1.170 (7.94), 1.204 (0.42), 1.232 (1.40), 1.259 (1.76), 1.393 (0.57), 1.405 (0.57), 1.421 (0.66), 1.440 (0.48), 1.444 (0.45), 2.093 (1.10), 2.112 (3.04), 2.130 (2.78), 2.149 (1.07), 2.172 (1.04), 2.190 (1.52), 2.208 (1.10), 2.336 (1.10), 2.347 (1.07), 2.363 (1.10), 2.375 (1.67), 2.387 (0.87), 2.518 (7.49), 2.522 (5.49), 2.678 (0.60), 2.719 (0.48), 2.734 (0.93), 2.751 (1.34), 2.760 (0.84), 2.765 (0.81), 2.777 (1.43), 2.795 (0.75), 2.809 (0.54), 2.851 (1.97), 2.869 (6.00), 2.887 (6.18), 2.905 (2.21), 3.135 (0.48), 3.150 (0.54), 3.169 (0.75), 3.231 (0.51), 3.249 (0.99), 3.266 (0.81), 3.283 (0.99), 3.399 (0.60), 3.416 (0.93), 3.427 (0.69), 3.444 (0.81), 3.528 (3.40), 3.540 (5.70), 3.551 (3.37), 3.836 (0.54), 4.145 (1.94), 4.154 (1.34), 4.171 (2.66), 4.179 (2.54), 4.234 (1.31), 4.251 (2.27), 4.269 (0.99), 4.602 (0.54), 4.634 (0.51), 4.665 (1.85), 4.699 (1.70), 6.852 (1.85), 6.870 (2.03), 7.080 (1.91), 7.101 (2.00), 7.343 (1.49), 7.364 (2.63), 7.383 (2.15), 7.429 (2.69), 7.449 (1.58), 7.471 (0.51), 7.476 (0.69), 7.489 (1.70), 7.492 (1.43), 7.495 (0.81), 7.501 (1.88), 7.507 (3.22), 7.513 (1.76), 7.521 (1.64), 7.525 (1.79), 7.538 (0.78), 7.542 (0.48), 7.596 (1.28), 7.617 (1.16), 7.844 (1.64), 7.851 (0.93), 7.863 (1.79), 7.867 (1.34), 8.199 (1.43), 8.204 (1.37), 8.221 (1.31), 8.224 (1.31).

Example 10

4-chloro-3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (Enantiomer 2)

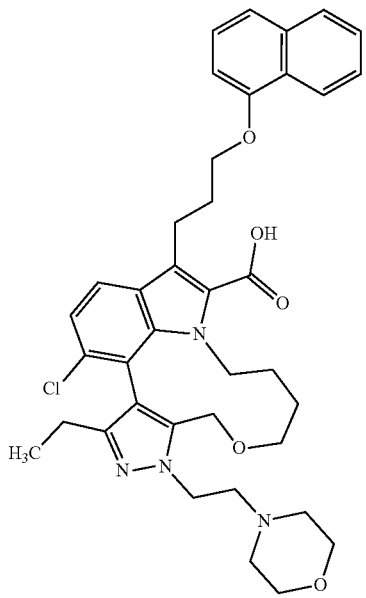

For the preparation of the racemic title compound see Example 8. Separation of enantiomers by preparative chiral HPLC (method see Example 8) gave the title compound (61 mg).

Analytical Chiral HPLC (method see Example 8): $R_t$=7.04 min.

LC-MS (Method 2): Rt=0.88 min; MS (ESIpos): m/z=672 [M+H]$^+$

Specific Optical Rotation (Method O1): −48.9° (c=10 mg/mL, DMSO)

$^1$H-NMR (400 MHz, DMSO-d6) δ[ppm]: 0.776 (0.70), 0.791 (0.44), 0.795 (1.59), 0.813 (0.96), 0.819 (0.49), 0.836 (0.73), 0.844 (5.01), 0.863 (11.35), 0.882 (5.03), 0.973 (0.63), 1.005 (2.39), 1.034 (1.01), 1.084 (1.22), 1.137 (7.42), 1.155 (16.00), 1.173 (7.58), 1.204 (0.42), 1.232 (1.38), 1.259 (1.75), 1.381 (0.49), 1.392 (0.58), 1.404 (0.56), 1.421 (0.61), 1.425 (0.56), 1.440 (0.44), 1.444 (0.42), 2.092 (1.10), 2.111 (3.04), 2.130 (2.83), 2.148 (1.01), 2.174 (1.01), 2.192 (1.47), 2.209 (1.08), 2.332 (1.33), 2.336 (0.98), 2.347 (1.05), 2.363 (1.08), 2.375 (1.64), 2.387 (0.84), 2.518 (5.87), 2.522 (4.26), 2.673 (1.05), 2.678 (0.49), 2.719 (0.44), 2.734 (0.87), 2.751 (1.26), 2.759 (0.80), 2.765 (0.75), 2.777 (1.33), 2.794 (0.73), 2.808 (0.54), 2.855 (1.96), 2.872 (5.99), 2.891 (5.99), 2.909 (1.99), 3.140 (0.47), 3.155 (0.54), 3.174 (0.75), 3.235 (0.51), 3.254 (0.98), 3.271 (0.80), 3.287 (0.96), 3.399 (0.56), 3.415 (0.91), 3.428 (0.65), 3.444 (0.77), 3.528 (3.25), 3.540 (5.52), 3.551 (3.25), 3.844 (0.51), 4.147 (1.85), 4.154 (1.36), 4.171 (2.57), 4.180 (2.41), 4.235 (1.26), 4.252 (2.18), 4.269 (0.96), 4.597 (0.54), 4.630 (0.51), 4.665 (1.75), 4.699 (1.61), 6.852 (1.80), 6.869 (1.94), 7.084 (1.94), 7.106 (2.06), 7.343 (1.43), 7.364 (2.60), 7.383 (2.08), 7.429 (2.60), 7.450 (1.50), 7.471 (0.47), 7.475 (0.65), 7.489 (1.52), 7.492 (1.40), 7.501 (1.78), 7.507 (3.04), 7.513 (1.68), 7.521 (1.57), 7.525 (1.71), 7.538 (0.73), 7.542 (0.51), 7.603 (1.33), 7.624 (1.24), 7.844 (1.57), 7.851 (0.91), 7.863 (1.73), 7.867 (1.33), 8.199 (1.33), 8.203 (1.36), 8.221 (1.26), 8.223 (1.31).

Example 11

(rac)-4-chloro-2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid

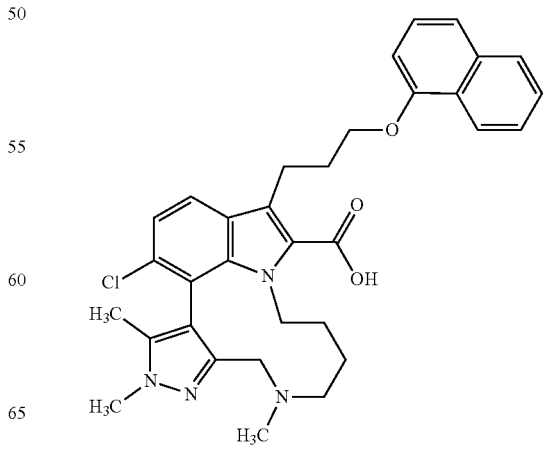

(rac)-Ethyl-4-chloro-2,3,14-trimethyl-7-[3-(naphthalen-1-yloxy)propyl]-10,11,12,13,14,15-hexa-hydro-2H-pyrazolo[3',4':8,9][1,6]diazacycloundecino[10,11,1-hi]indole-8-carboxylate (see Intermediate 46, 730 mg) was dissolved in a mixture of 15 mL of THF and 5 mL of ethanol and aqueous lithium hydroxide solution (2.4 mL, 1.0 M, 2.4 mmol) was added. The mixture was stirred at 65° C. overnight. Aqueous lithium hydroxide solution (1 mL, 1.0 M, 1 mmol) was added and stirring was continued at 65° C. for 72 hours. After concentration, water and a saturated, aqueous solution of citric acid were added until an acidic pH value was reached. The precipitated material was isolated by filtration and was purified by preparative HPLC (Method P4) to give the title compound (140 mg).

LC-MS (Method 1): $R_t$=1.15 min; MS (ESIneg): m/z=569 [M−H]$^-$ $^1$H-NMR (400 MHz, DMSO-d6) δ[ppm]: 1.030 (0.91), 1.044 (0.91), 1.101 (0.50), 1.154 (2.45), 1.172 (4.83), 1.190 (2.53), 1.233 (0.71), 1.753 (15.12), 1.872 (0.56), 1.907 (0.85), 1.980 (1.47), 1.987 (7.87), 2.059 (7.60), 2.153 (0.50), 2.171 (1.21), 2.188 (1.80), 2.205 (1.18), 2.223 (0.44), 2.318 (0.77), 2.322 (1.41), 2.327 (2.03), 2.332 (1.65), 2.336 (1.00), 2.518 (8.75), 2.523 (5.48), 2.539 (1.27), 2.660 (0.59), 2.664 (1.21), 2.669 (1.74), 2.673 (1.27), 2.900 (0.50), 2.912 (0.56), 2.924 (0.53), 3.188 (0.80), 3.206 (1.27), 3.221 (1.36), 3.239 (1.89), 3.259 (1.68), 3.313 (4.24), 3.328 (4.04), 3.344 (4.92), 3.484 (2.36), 3.515 (1.77), 3.634 (0.68), 3.646 (0.68), 3.658 (0.62), 3.793 (16.00), 3.810 (2.09), 3.834 (0.53), 4.000 (0.59), 4.017 (1.77), 4.035 (1.80), 4.053 (0.65), 4.173 (1.53), 4.188 (3.30), 4.204 (1.59), 4.299 (0.53), 4.318 (0.50), 4.333 (0.53), 6.874 (1.89), 6.891 (1.97), 7.158 (3.65), 7.180 (4.04), 7.359 (1.41), 7.380 (2.62), 7.399 (2.12), 7.444 (2.98), 7.464 (1.71), 7.492 (0.62), 7.505 (1.74), 7.510 (1.89), 7.512 (2.30), 7.521 (3.80), 7.530 (2.48), 7.536 (1.94), 7.549 (0.71), 7.553 (0.41), 7.670 (3.21), 7.691 (2.83), 7.853 (1.68), 7.862 (0.88), 7.871 (1.33), 7.877 (1.47), 8.172 (10.96), 8.231 (1.41), 8.238 (1.30), 8.247 (0.74), 8.255 (1.36).

The title compound (140 mg) was separated into enantiomers by preparative chiral HPLC to give enantiomer 1 (63 mg, see Example 12) and enantiomer 2 (69 mg, see Example 13).

Preparative chiral HPLC method: Instrument: Labomatic HD5000, Labocord-5000; Gilson GX-241, Labcol Vario 4000, column: Chiralpak IE 5μ 250×30 mm; Eluent A: Hexane+0.1 Vol-% N-ethylethanamine (99%); Eluent B: ethanol; gradient: 20-50% B in 20 min; flow 40.0 mL/min; UV 220 nm Analytical chiral HPLC method Instrument: Agilent HPLC 1260; column: Chiralpak ID 3μ 100×4.6 mm; Eluent A: Hexane+0.1 Vol-% N-ethylethanamine (99%); Eluent B: ethanol; Gradient: 20-50% B in 7 min; Flow 1.4 mL/min; Temperature: 25° C.; DAD 220 nm Example 12

(+)-4-chloro-2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid-N-ethylethanamine salt (Enantiomer 1)

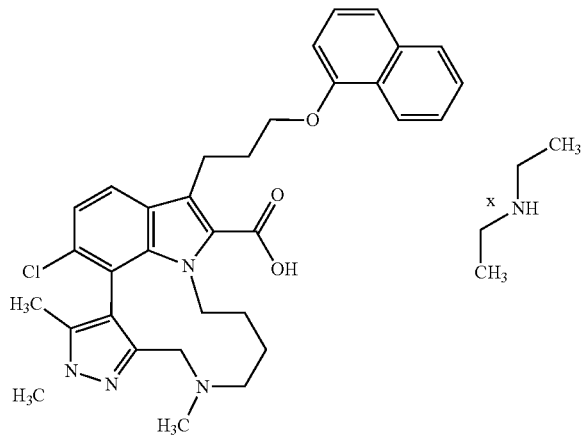

For the preparation of the racemic title compound see Example 11. Separation of enantiomers by preparative chiral HPLC (method see Example 11) gave the title compound (63 mg).

Analytical Chiral HPLC (method see Example 11): $R_t$=2.05 min.

LC-MS (Method 1): $R_t$=1.21 min; MS (ESIneg): m/z=569 [M−H]$^-$

Specific Optical Rotation (Method O1): +33.4° (c=10 mg/mL, chloroform)

$^1$H-NMR (400 MHz, DMSO-d6) δ[ppm]: 1.134 (1.32), 1.152 (2.75), 1.170 (1.33), 1.751 (5.13), 1.891 (0.51), 2.045 (2.50), 2.166 (0.44), 2.183 (0.69), 2.200 (0.48), 2.323 (0.78), 2.327 (1.02), 2.332 (0.80), 2.518 (6.93), 2.523 (5.16), 2.540 (16.00), 2.665 (0.61), 2.669 (0.86), 2.673 (0.61), 2.882 (1.01), 2.900 (0.99), 3.288 (0.79), 3.457 (0.66), 3.488 (0.50), 3.788 (5.43), 4.166 (0.48), 4.181 (1.02), 4.197 (0.53), 6.866 (0.66), 6.884 (0.72), 7.117 (0.63), 7.138 (0.64), 7.353 (0.45), 7.373 (0.88), 7.393 (0.67), 7.439 (1.01), 7.459 (0.59), 7.502 (0.61), 7.509 (0.78), 7.518 (1.20), 7.527 (0.86), 7.533 (0.64), 7.615 (0.47), 7.636 (0.44), 7.851 (0.57), 7.868 (0.45), 7.874 (0.48), 8.230 (0.50), 8.236 (0.44), 8.254 (0.45).

Example 13

(−)-4-chloro-2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid-N-ethylethanamine salt (Enantiomer 2)

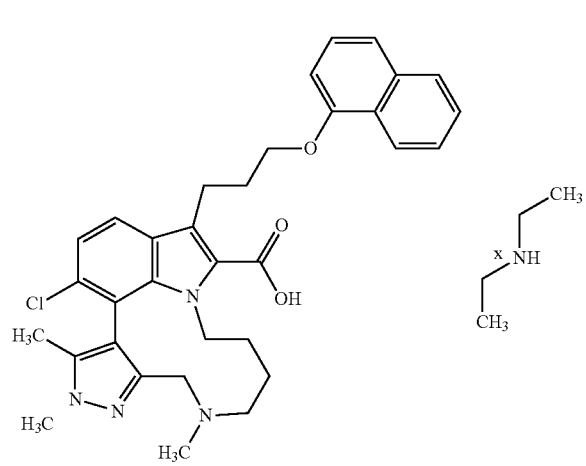

For the preparation of the racemic title compound see Example 11. Separation of enantiomers by preparative chiral HPLC (method see Example 11) gave the title compound (69 mg).

Analytical Chiral HPLC (method see Example 11): $R_t$=3.38 min.

LC-MS (Method 1): $R_t$=1.20 min; MS (ESIpos): m/z=571 [M+H]$^+$

Specific Optical Rotation (Method O1):−24.2° (c=10 mg/mL, chloroform)

$^1$H-NMR (400 MHz, DMSO-d6) δ[ppm]: 0.797 (1.36), 0.802 (0.77), 0.814 (1.63), 0.821 (1.68), 0.834 (0.91), 0.840 (1.15), 0.852 (1.39), 0.886 (0.77), 0.904 (1.42), 0.922 (0.83), 0.973 (0.59), 0.991 (0.72), 1.006 (0.80), 1.049 (0.91), 1.068 (0.93), 1.083 (0.91), 1.131 (6.94), 1.149 (14.50), 1.167 (7.51), 1.204 (1.18), 1.236 (3.23), 1.258 (0.69), 1.754 (15.89), 1.864 (0.61), 1.890 (0.85), 1.904 (1.15), 1.974 (1.76), 2.055 (9.67), 2.161 (1.47), 2.178 (2.16), 2.195 (1.47), 2.210 (0.64), 2.294 (0.61), 2.323 (1.52), 2.327 (2.08), 2.331 (1.47), 2.478 (4.35), 2.518 (7.19), 2.522 (4.51), 2.539 (1.58), 2.665 (1.15), 2.669 (1.60), 2.673 (1.18), 2.836 (1.87), 2.854 (5.77), 2.872 (5.61), 2.890 (1.76), 3.114 (0.40), 3.133 (0.77), 3.146 (0.88), 3.165 (1.34), 3.184 (0.75), 3.252 (1.07), 3.276 (2.80), 3.308 (5.64), 3.435 (2.38), 3.466 (1.68), 3.695 (0.53), 3.711 (0.67), 3.725 (0.59), 3.785 (16.00), 3.801 (2.70), 4.132 (0.75), 4.156 (1.55), 4.170 (3.37), 4.188 (1.60), 4.200 (0.67), 4.424 (0.56), 4.441 (0.56), 4.457 (0.53), 5.759 (2.11), 6.855 (1.98), 6.873 (2.16), 6.887 (0.43), 6.905 (0.43), 7.041 (0.64), 7.062 (0.99), 7.067 (2.46), 7.088 (2.59), 7.343 (1.42), 7.363 (2.94), 7.382 (2.54), 7.402 (0.43), 7.432 (2.99), 7.452 (1.76), 7.480 (0.43), 7.485 (0.67), 7.497 (1.87), 7.504 (2.51), 7.513 (4.27), 7.521 (2.70), 7.528 (2.14), 7.536 (0.80), 7.541 (0.96), 7.550 (2.03), 7.571 (1.76), 7.847 (1.76), 7.855 (1.10), 7.864 (1.44), 7.870 (1.66), 8.227 (1.63), 8.234 (1.52), 8.244 (0.88), 8.251 (1.58).

Example 14

(rac)-4-chloro-7-{3-[(6-fluoronaphthalen-1-yl)oxy]propyl}-2,3-dimethyl-2,10,11,12,13,15-hexahydro-pyrazolo[4',3':9,10][1,6]oxazacycloundecino[8,7,6-hi]indole-8-carboxylic acid

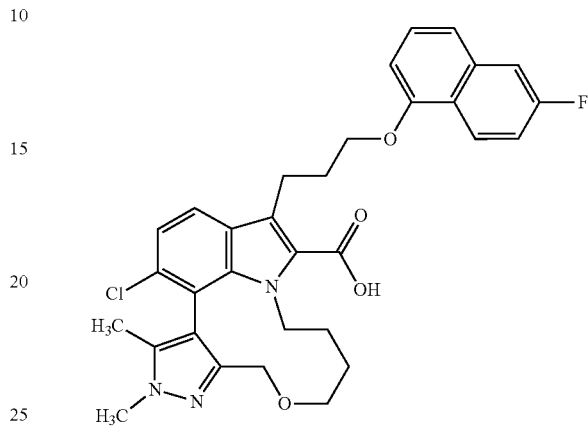

(rac)-Ethyl-4-chloro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylate (see Intermediate 49, 351 mg) was dissolved in a mixture of 3 mL of THF and 1 mL of ethanol and aqueous lithium hydroxide solution (1.2 mL, 1.0 M, 1.2 mmol) was added. The reaction mixture was stirred at 70° C. for 72 hours. Aqueous lithium hydroxide solution (1.2 mL, 1.0 M, 1.2 mmol) was added and stirring was continued at 70° C. for 3 days. The mixture was acidified using an aqueous, saturated solution of citric acid and was extracted with ethyl acetate. The combined organic layers were dried using sodium sulfate, were filtered and were concentrated under reduced pressure. The crude material was purified by preparative HPLC (Method P2) to give the title compound (126 mg).

LC-MS (Method 1): $R_t$=1.54 min; MS (ESIpos): m/z=576 [M+H]$^+$ $^1$H-NMR (400 MHz, DMSO-d6) δ[ppm]: 0.961 (0.54), 1.154 (2.75), 1.172 (5.67), 1.189 (3.48), 1.309 (0.58), 1.773 (15.42), 1.987 (8.68), 2.074 (0.41), 2.178 (1.29), 2.195 (1.93), 2.212 (1.33), 2.322 (0.97), 2.326 (1.25), 2.331 (0.90), 2.522 (6.29), 2.665 (0.99), 2.669 (1.25), 3.112 (0.90), 3.126 (0.84), 3.151 (0.43), 3.236 (0.54), 3.252 (0.90), 3.270 (1.80), 3.292 (2.43), 3.785 (0.54), 3.820 (16.00), 3.999 (0.71), 4.016 (1.98), 4.035 (1.93), 4.053 (0.67), 4.170 (1.48), 4.186 (3.07), 4.193 (3.26), 4.224 (2.60), 4.255 (0.69), 4.275 (0.71), 4.290 (0.58), 4.425 (2.38), 4.456 (1.95), 6.853 (1.37), 6.860 (1.44), 6.868 (1.31), 6.875 (1.44), 7.191 (3.22), 7.212 (3.44), 7.357 (0.82), 7.363 (0.94), 7.379 (1.46), 7.386 (1.57), 7.402 (1.01), 7.408 (1.25), 7.427 (2.71), 7.434 (3.14), 7.441 (5.76), 7.455 (0.52), 7.640 (1.59), 7.646 (1.59), 7.666 (1.63), 7.672 (1.52), 7.718 (2.88), 7.740 (2.64), 8.222 (1.40), 8.237 (1.48), 8.245 (1.44), 8.260 (1.31).

The title compound (116 mg) was separated into enantiomers by preparative chiral HPLC to give enantiomer 1 (65 mg, see Example 15) and enantiomer 2 (65 mg, see Example 17).

Preparative Chiral HPLC Method:

Instrument: Labomatic HD5000, Labocord-5000; Gilson GX-241, Labcol Vario 4000, Column: YMC Amylose SA 5μ 250×30 mm; Eluent A: Hexane+0.1 Vol-% Diethylamine (99%); Eluent B: Ethanol; Gradient: 20-50% B in 15 min; Flow 40.0 mL/min; UV 254 nm Analytical Chiral HPLC Method:

Instrument: Agilent HPLC 1260; Column: YMC Amylose SA 3μ 100×4.6 mm; Eluent A: Hexane+0.1 Vol-% Diethylamine (99%)/2-Propanol 75:25; Flow 1.4 mL/min; Temperature: 25° C.; DAD 254 nm Example 15

(+)-4-chloro-7-{3-[(6-fluoronaphthalen-1-yl)oxy] propyl}-2,3-dimethyl-2,10,11,12,13,15-hexahydro-pyrazolo[4',3':9,10][1,6]oxazacycloundecino[8,7,6-hi]indole-8-carboxylic acid-N-ethylethanamine salt (Enantiomer 1)

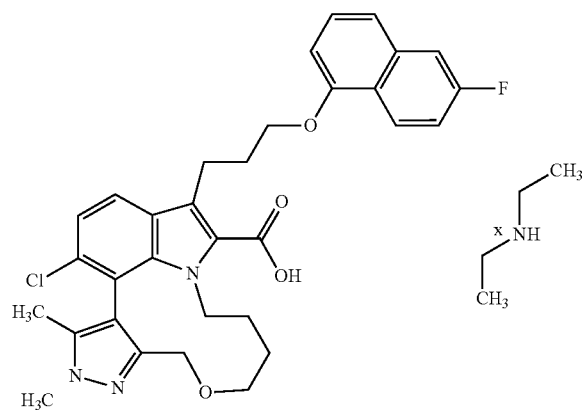

For the preparation of the racemic title compound see Example 14. Separation of enantiomers by preparative chiral HPLC (method see Example 14) gave the title compound (65 mg).

Analytical Chiral HPLC (method see Example 14): $R_t$=1.80 min.

LC-MS (Method 1): $R_t$=1.52 min; MS (ESIpos): m/z=576 [M+H]$^+$

Specific Optical Rotation (Method O1): +39.1° (c=10 mg/mL, chloroform)

$^1$H-NMR (400 MHz, DMSO-d6) δ[ppm]: 0.852 (0.48), 1.088 (0.60), 1.118 (5.69), 1.136 (12.07), 1.154 (5.64), 1.237 (1.11), 1.259 (0.46), 1.292 (0.46), 1.777 (10.19), 2.164 (0.71), 2.181 (1.14), 2.198 (0.80), 2.336 (0.60), 2.518 (16.00), 2.522 (10.51), 2.660 (0.51), 2.819 (1.22), 2.837 (3.81), 2.855 (3.79), 2.873 (1.20), 3.102 (0.48), 3.116 (0.46), 3.127 (0.46), 3.138 (0.51), 3.153 (0.43), 3.172 (0.57), 3.228 (0.68), 3.247 (0.57), 3.261 (0.63), 3.813 (10.14), 4.141 (0.46), 4.157 (1.08), 4.171 (1.11), 4.188 (1.77), 4.219 (1.65), 4.378 (1.42), 4.409 (1.37), 6.829 (0.77), 6.836 (0.85), 6.845 (0.80), 6.852 (0.88), 7.064 (1.00), 7.085 (1.08), 7.355 (0.54), 7.361 (0.65), 7.377 (0.85), 7.384 (1.00), 7.399 (0.68), 7.409 (1.45), 7.419 (1.68), 7.425 (3.53), 7.546 (0.71), 7.567 (0.65), 7.630 (0.97), 7.637 (1.02), 7.656 (0.97), 7.663 (0.97), 8.240 (0.83), 8.255 (0.88), 8.264 (0.88), 8.278 (0.83).

Example 16

(−)-4-chloro-7-{3-[(6-fluoronaphthalen-1-yl)oxy] propyl}-2,3-dimethyl-2,10,11,12,13,15-hexahydro-pyrazolo[4',3':9,10][1,6]oxazacycloundecino[8,7,6-hi]indole-8-carboxylic acid (Enantiomer 1)

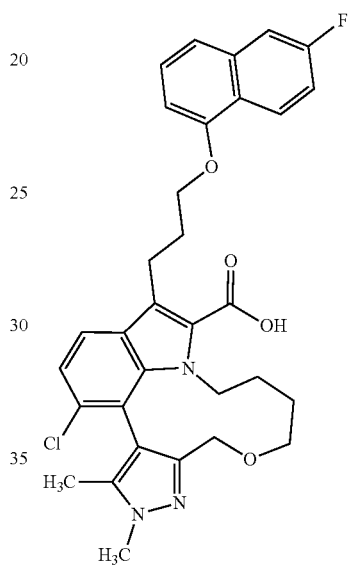

4.50 g of a batch of 4-chloro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi] indole-8-carboxylic acid-N-ethylethanamine (enantiomer 1, see Example 15) containing triphenylphosphine oxide were purified by acidic preparative HPLC.

Preparative HPLC Method:

Labomatic HD3000, Knauer Pump 100, Labcol Vario 4000 Plus, Knauer DAD 2600; column: Waters XBrigde C18 5μ 100×50 mm; Eluent A: water+0.1 Vol-% formic acid (99%), Eluent B: Acetonitril; Isokratic: 70% B, 150 mL/min, DAD @ 220 nm 4.00 g of the obtained material were purified by flash chromatography using an amino-substituted silica gel (gradient dichloromethane/methanol) and using silica gel (gradient dichloromethane/ethyl acetate). The obtained material was dissolved in 25 mL of ethanol and 50 mL of water. The ethanol was removed under reduced pressure and the remaining mixture was dried by lyophilization to give the title compound (1.95 g).

LC-MS (Method 2): $R_t$=0.93 min; MS (ESIpos): m/z=576 [M+H]$^+$

Specific Optical Rotation (Method O1): +50.3° (c=10 mg/mL, chloroform)

¹H-NMR (400 MHz, DMSO-d6) δ[ppm]: 1.175 (0.86), 1.188 (0.89), 1.200 (0.86), 1.211 (0.57), 1.230 (0.46), 1.302 (0.42), 1.774 (15.52), 2.179 (0.97), 2.196 (1.50), 2.212 (0.99), 2.518 (4.24), 2.523 (2.91), 3.113 (0.68), 3.127 (0.63), 3.137 (0.46), 3.252 (0.61), 3.271 (1.33), 3.293 (1.67), 3.820 (16.00), 4.171 (1.07), 4.187 (2.34), 4.194 (2.72), 4.225 (2.34), 4.256 (0.49), 4.275 (0.53), 4.295 (0.42), 4.425 (2.17), 4.457 (1.77), 6.853 (1.16), 6.861 (1.22), 6.868 (1.07), 6.875 (1.26), 7.192 (3.63), 7.213 (3.61), 7.357 (0.78), 7.364 (0.93), 7.380 (1.22), 7.386 (1.35), 7.402 (0.88), 7.408 (1.14), 7.428 (2.24), 7.435 (2.47), 7.442 (5.56), 7.640 (1.43), 7.647 (1.46), 7.666 (1.45), 7.673 (1.45), 7.719 (2.97), 7.741 (2.61), 8.222 (1.27), 8.237 (1.29), 8.246 (1.29), 8.260 (1.24).

Example 17

(−)-4-chloro-7-{3-[(6-fluoronaphthalen-1-yl)oxy]propyl}-2,3-dimethyl-2,10,11,12,13,15-hexahydro-pyrazolo[4',3':9,10][1,6]oxazacycloundecino[8,7,6-hi]indole-8-carboxylic acid-N-ethylethanamine salt (Enantiomer 2)

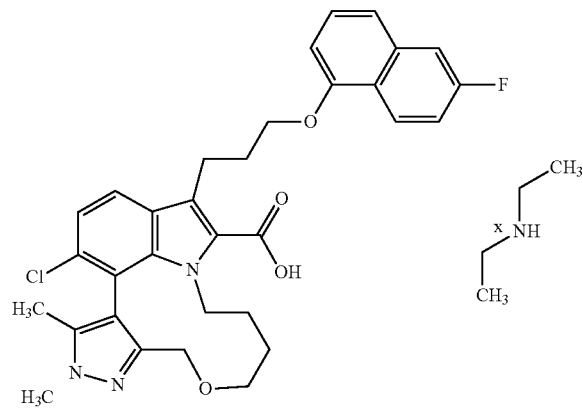

For the preparation of the racemic title compound see Example 14. Separation of enantiomers by preparative chiral HPLC (method see Example 14) gave the title compound (65 mg).

Analytical Chiral HPLC (method see Example 14): $R_t$=3.07 min.

LC-MS (Method 1): $R_t$=1.54 min; MS (ESIpos): m/z=576 [M+H]⁺

Specific Optical Rotation (Method O1): −33.0° (c=10 mg/mL, chloroform)

¹H-NMR (400 MHz, DMSO-d6) δ[ppm]: 1.088 (0.67), 1.125 (7.25), 1.144 (16.00), 1.161 (7.19), 1.234 (0.82), 1.295 (0.48), 1.777 (13.16), 2.166 (0.91), 2.183 (1.43), 2.200 (1.00), 2.336 (0.46), 2.518 (11.98), 2.522 (8.45), 2.827 (1.69), 2.845 (5.25), 2.863 (5.28), 2.881 (1.67), 3.103 (0.61), 3.116 (0.52), 3.126 (0.61), 3.142 (0.61), 3.157 (0.54), 3.176 (0.78), 3.214 (0.46), 3.233 (0.91), 3.250 (0.69), 3.266 (0.80), 3.672 (0.48), 3.812 (13.53), 4.142 (0.61), 4.157 (1.39), 4.171 (1.41), 4.188 (2.28), 4.219 (2.13), 4.379 (1.89), 4.410 (1.72), 4.435 (0.43), 5.759 (1.06), 6.828 (1.04), 6.834 (1.06), 6.844 (1.00), 6.850 (1.13), 7.067 (1.69), 7.088 (1.80), 7.354 (0.72), 7.361 (0.82), 7.376 (1.11), 7.383 (1.28), 7.399 (0.85), 7.407 (1.91), 7.419 (2.15), 7.425 (4.32), 7.440 (0.48), 7.549 (1.19), 7.570 (1.11), 7.630 (1.24), 7.637 (1.28), 7.656 (1.26), 7.663 (1.26), 8.240 (1.06), 8.255 (1.15), 8.263 (1.13), 8.278 (1.06).

Example 18

(rac)-(11Z)-4-chloro-3-ethyl-2-methyl-7-[3-(naphthalen-1-yloxy)propyl]-2,10,13,15-tetrahydropyrazolo[4',3':9,10][1,6]oxazacycloundecino[8,7,6-hi]indole-8-carboxylic acid

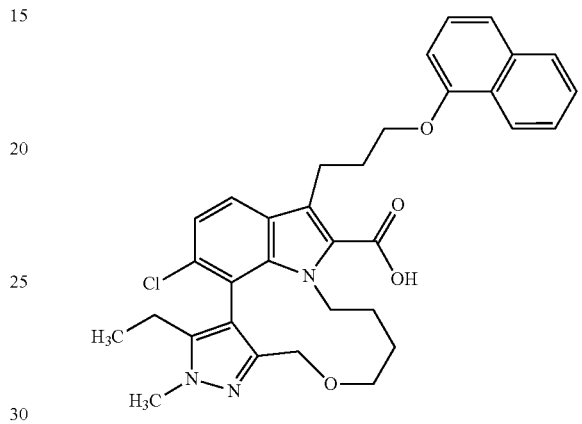

(rac)-Ethyl-(11Z)-4-chloro-3-ethyl-2-methyl-7-[3-(naphthalen-1-yloxy)propyl]-2,10,13,15-tetrahydropyrazolo[4',3':9,10][1,6]oxazacycloundecino[8,7,6-hi]indole-8-carboxylate (see Intermediate 51, 50.0 mg, 83.6 μmol) was dissolved in a mixture of 4.5 mL THF and 1.8 mL ethanol and the aqueous lithium hydroxide solution (1.7 mL, 1.0 M, 1.7 mmol) was added. It was stirred at 65° C. overnight in a heating block. The mixture was diluted with water and it was acidified using 1-molar hydrochloric acid and buffer-solution (pH6). It was extracted with dichloromethane/methanol (9:1). The combined organic layers were dried using sodium sulfate and the clear filtrate was concentrated under reduced pressure. The crude material was purified by preparative HPLC (Method P2) to give the titled compound (23.2 mg, 95% purity) as a racemic mixture.

LC-MS (Method 1): $R_t$=1.67 min; MS (ESIpos): m/z=570 [M+H]⁺

¹H-NMR (400 MHz, DMSO-d6) δ[ppm]: 0.784 (3.10), 0.803 (7.24), 0.822 (3.41), 1.231 (1.00), 1.907 (0.40), 2.141 (0.67), 2.159 (1.52), 2.179 (1.98), 2.198 (1.67), 2.216 (1.40), 2.222 (1.22), 2.235 (1.06), 2.245 (0.88), 2.336 (0.55), 2.518 (6.69), 2.522 (4.56), 2.539 (13.26), 2.678 (0.55), 3.290 (1.83), 3.311 (4.29), 3.558 (0.58), 3.571 (0.70), 3.589 (0.91), 3.601 (0.82), 3.740 (0.79), 3.768 (1.22), 3.797 (0.64), 3.886 (16.00), 4.149 (1.98), 4.181 (2.56), 4.193 (1.46), 4.208 (2.86), 4.223 (1.34), 4.354 (2.46), 4.386 (1.98), 4.573 (0.49), 4.600 (0.58), 4.611 (0.67), 4.638 (0.70), 4.927 (0.76), 4.965 (0.61), 5.001 (0.55), 5.007 (0.43), 5.028 (0.97), 5.035 (0.88), 5.055 (0.52), 5.061 (0.49), 5.249 (0.40), 5.264 (0.64), 5.276 (0.64), 6.887 (1.73), 6.904 (1.89), 7.219 (2.95), 7.240 (3.16), 7.367 (1.34), 7.387 (2.46), 7.406 (2.01), 7.445 (2.62), 7.466 (1.43), 7.473 (0.61), 7.476 (0.67), 7.490 (1.43), 7.493 (1.37), 7.508 (2.74), 7.513 (2.92), 7.528 (1.40), 7.532 (1.61), 7.544 (0.70), 7.549 (0.55), 7.752 (2.34), 7.774 (2.10), 7.852 (1.58), 7.872 (1.67), 7.875 (1.34), 8.179 (1.37), 8.183 (1.43), 8.202 (1.31).

Example 19

(rac)-4-chloro-3-ethyl-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid

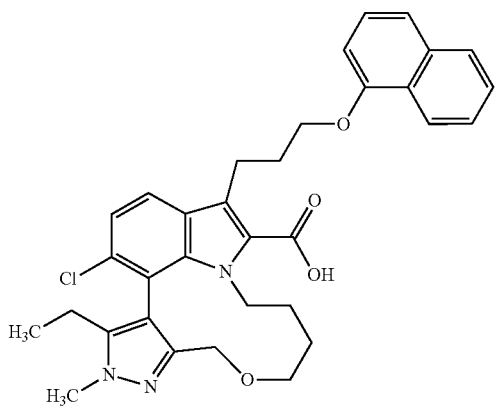 [SMILES: CCc1c2c(nn1C)COCCCCn1c(C(=O)O)c(CCCOc3cccc4ccccc34)c3ccc(Cl)c-2c31]

(rac)-Ethyl-4-chloro-3-ethyl-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylate (see Intermediate 52, 238 mg, 397 μmol) was dissolved in a mixture of 22 mL THF and 9 mL ethanol and the aqueous lithium hydroxide solution (7.9 mL, 1.0 M, 7.9 mmol) was added. It was stirred at 50° C. overnight in a heating block. Because of incomplete reaction stirring was continued at 80° C. for 6 hours and at 60° C. for 72 hours. The mixture was diluted with water and it was acidified using 1-molar hydrochloric acid and buffer-solution (pH6). It was extracted with dichloromethane/methanol (9:1). The combined organic layers were dried using sodium sulfate and the clear filtrate was concentrated under reduced pressure. The crude material was purified by preparative HPLC (Method P2) to give the titled compound (114 mg, 95% purity) as a racemic mixture.

LC-MS (Method 1): $R_t$=1.71 min; MS (ESIpos): m/z=572 [M+H]$^+$ $^1$H-NMR (400 MHz, DMSO-d6) δ[ppm]: 0.789 (3.12), 0.808 (7.26), 0.827 (3.21), 0.961 (0.42), 1.210 (0.90), 1.222 (0.81), 1.232 (0.87), 1.353 (1.71), 1.907 (0.57), 2.118 (0.69), 2.136 (1.29), 2.155 (1.20), 2.162 (1.26), 2.182 (1.95), 2.200 (1.74), 2.218 (1.32), 2.237 (0.45), 2.331 (1.26), 2.337 (0.57), 2.518 (7.89), 2.523 (5.31), 2.540 (1.77), 2.674 (1.26), 2.678 (0.57), 3.125 (0.72), 3.139 (0.66), 3.150 (0.45), 3.256 (0.75), 3.273 (1.32), 3.287 (1.44), 3.849 (16.00), 4.168 (0.99), 4.183 (2.13), 4.187 (2.88), 4.219 (2.58), 4.239 (0.51), 4.258 (0.51), 4.272 (0.42), 4.415 (2.25), 4.446 (1.83), 5.760 (1.23), 6.869 (1.89), 6.887 (1.95), 7.183 (2.82), 7.204 (2.85), 7.360 (1.38), 7.381 (2.52), 7.400 (1.98), 7.446 (2.58), 7.467 (1.50), 7.497 (0.54), 7.509 (1.56), 7.515 (2.43), 7.524 (3.36), 7.533 (2.79), 7.539 (1.80), 7.551 (0.60), 7.717 (2.16), 7.739 (1.98), 7.856 (1.47), 7.859 (1.11), 7.866 (0.75), 7.873 (1.05), 7.879 (1.26), 8.225 (1.32), 8.232 (1.08), 8.241 (0.60), 8.249 (1.23).

The titled compound (121 mg) was separated into enantiomers by preparative chiral HPLC to give enantiomer 1 (39 mg, see Example 20) and enantiomer 2 (39 mg, see Example 21).

Preparative chiral HPLC method: Instrument: Sepiatec: Prep SFC100; column: Chiralpak IG 5 μm 250×30 mm; Eluent A: CO$_2$, Eluent B: Ethanol; Isocratic: 15% B; Flow 100.0 mL/min Temperature: 40° C.; BPR: 150 bar; MWD @ 220 nm Analytical chiral HPLC method: Instrument: Agilent: 1260, Aurora SFC-Modul; column: Chiralpak IG 5 μm 100×4.6 mm; Eluent A: CO$_2$, Eluent B: Ethanol; Isocratic: 15% B; Flow 4.0 mL/min; Temperature: 37.5° C.; BPR: 100 bar; MWD @ 220 nm

Example 20

4-chloro-3-ethyl-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (Enantiomer 1)

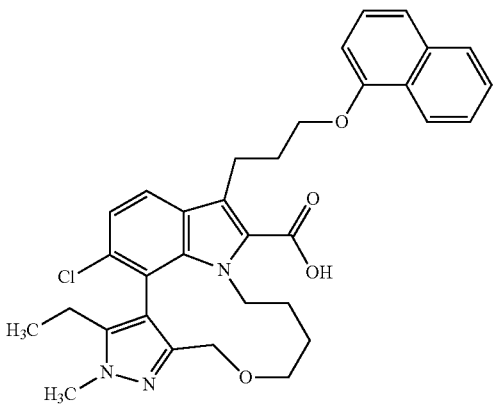

For the preparation of the racemic titled compound see Example 19. Separation of enantiomers by preparative chiral HPLC (method see Example 19) gave the titled compound (39 mg).

Analytical Chiral HPLC (method see Example 19): $R_t$=5.05 min.

Specific Optical Rotation (Method O1): 23.5° (c=10 mg/mL, chloroform)

$^1$H-NMR (400 MHz, DMSO-d6) δ[ppm]: 0.788 (3.09), 0.797 (1.97), 0.807 (7.32), 0.814 (2.35), 0.821 (2.41), 0.826 (3.32), 0.840 (0.93), 0.886 (0.85), 0.904 (1.76), 0.922 (0.99), 0.949 (0.42), 0.971 (0.44), 1.209 (0.91), 1.221 (0.89), 1.235 (0.72), 1.324 (0.44), 2.117 (0.70), 2.135 (1.27), 2.154 (1.21), 2.162 (1.27), 2.169 (0.80), 2.181 (1.78), 2.202 (1.74), 2.217 (1.31), 2.236 (0.44), 2.332 (0.87), 2.518 (6.24), 2.522 (4.13), 2.673 (0.91), 2.678 (0.42), 3.124 (0.74), 3.138 (0.68), 3.149 (0.49), 3.256 (0.87), 3.274 (1.57), 3.287 (1.86), 3.848 (16.00), 4.167 (1.02), 4.182 (2.22), 4.187 (2.90), 4.218 (2.65), 4.236 (0.55), 4.254 (0.53), 4.270 (0.44), 4.415 (2.24), 4.446 (1.86), 6.868 (1.80), 6.885 (1.93), 7.183 (3.15), 7.205 (3.13), 7.359 (1.33), 7.380 (2.48), 7.399 (1.90), 7.445 (2.56), 7.466 (1.50), 7.495 (0.53), 7.508 (1.61), 7.514 (2.46), 7.523

(3.39), 7.532 (2.73), 7.538 (1.80), 7.550 (0.59), 7.719 (2.56), 7.740 (2.26), 7.855 (1.48), 7.858 (1.12), 7.865 (0.76), 7.872 (1.04), 7.878 (1.27), 8.224 (1.29), 8.231 (1.06), 8.240 (0.61), 8.248 (1.23).

Example 21

4-chloro-3-ethyl-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (Enantiomer 2)

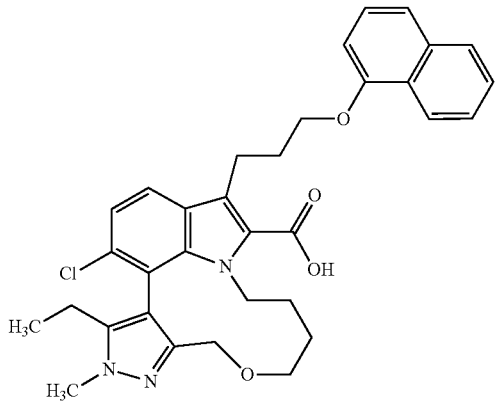 [SMILES: CCc1c2c(nn1C)COCCCCn1c(C(=O)O)c(CCCOc3cccc4ccccc34)c3ccc(Cl)c-2c31]

For the preparation of the racemic titled compound see Example 19. Separation of enantiomers by preparative chiral HPLC (method see Example 19) gave the titled compound (39 mg).

Analytical Chiral HPLC (method see Example 19): $R_t$=6.71 min.

Specific Optical Rotation (Method O1): −24.9° (c=10 mg/mL, chloroform)

$^1$H-NMR (400 MHz, DMSO-d6) δ[ppm]: 0.788 (3.22), 0.807 (7.32), 0.826 (3.41), 0.948 (0.50), 0.959 (0.50), 1.209 (1.05), 1.221 (0.92), 1.325 (0.50), 2.117 (0.75), 2.135 (1.37), 2.154 (1.31), 2.162 (1.40), 2.181 (1.95), 2.202 (1.99), 2.217 (1.46), 2.237 (0.52), 2.322 (0.63), 2.326 (0.86), 2.331 (0.63), 2.522 (3.03), 2.664 (0.65), 2.668 (0.86), 2.673 (0.65), 3.112 (0.44), 3.124 (0.84), 3.138 (0.78), 3.149 (0.58), 3.164 (0.43), 3.242 (0.49), 3.257 (1.09), 3.275 (1.92), 3.288 (2.29), 3.812 (0.43), 3.848 (16.00), 4.166 (1.21), 4.181 (2.52), 4.187 (3.13), 4.218 (2.82), 4.236 (0.65), 4.254 (0.63), 4.271 (0.52), 4.415 (2.39), 4.447 (1.95), 6.867 (1.96), 6.885 (2.11), 7.184 (3.29), 7.206 (3.35), 7.359 (1.33), 7.380 (2.58), 7.399 (1.96), 7.445 (2.77), 7.466 (1.62), 7.495 (0.56), 7.508 (1.68), 7.513 (2.58), 7.523 (3.28), 7.532 (2.89), 7.538 (1.82), 7.550 (0.61), 7.719 (2.86), 7.741 (2.61), 7.855 (1.61), 7.864 (0.84), 7.872 (1.15), 7.878 (1.34), 8.224 (1.40), 8.231 (1.17), 8.239 (0.69), 8.248 (1.31).

Example 22

(rac)-4-chloro-3-ethyl-2,14-dimethyl-7-[3-(naphthalen-1-yloxy)propyl]-10,11,12,13,14,15-hexa-hydro-2H-pyrazolo[3',4':8,9][1,6]diazacycloundecino[10,11,1-hi]indole-8-carboxylic acid

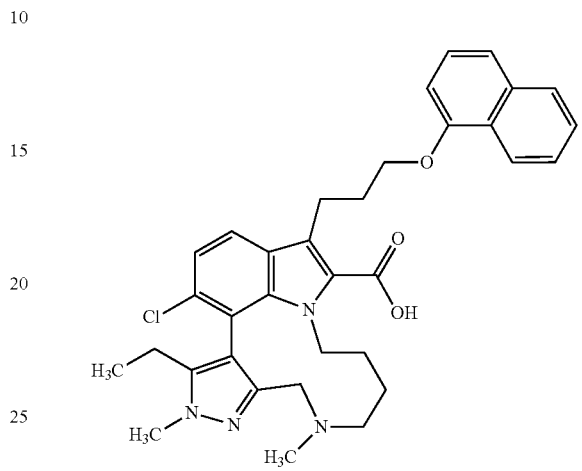

(rac)-Ethyl 4-chloro-3-ethyl-2,14-dimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylate (see Intermediate 56, 622 mg, 85% purity, 862 µmol) was dissolved in a mixture of 40 mL THF and 20 mL ethanol and the aqueous lithium hydroxide solution (17 mL, 1.0 M, 17 mmol) was added. It was stirred at 65° C. overnight in a heating block. The mixture was diluted with water and it was acidified using 1-molar hydrochloric acid and buffer-solution (pH6). It was extracted with dichloromethane/methanol (9:1). The combined organic layers were dried using sodium sulfate and the clear filtrate was concentrated under reduced pressure. The crude material was purified by preparative HPLC (Method P3). Received product fractions were again purified by flash chromatography, gradient dichloromethane/methanol (10-70%) to give the titled compound (276 mg, 95% purity).

$^1$H-NMR (400 MHz, DMSO-d6) δ[ppm]: 0.773 (3.11), 0.792 (7.14), 0.811 (3.26), 0.832 (0.42), 1.024 (1.02), 1.112 (0.48), 1.232 (0.75), 1.865 (0.44), 1.878 (0.48), 1.907 (0.46), 2.034 (7.87), 2.096 (0.66), 2.114 (1.35), 2.127 (1.31), 2.133 (1.33), 2.146 (1.41), 2.171 (1.27), 2.189 (1.74), 2.206 (1.25), 2.224 (0.44), 2.322 (1.08), 2.326 (1.47), 2.332 (1.14), 2.336 (0.68), 2.362 (0.48), 2.518 (4.52), 2.522 (3.03), 2.660 (0.42), 2.664 (0.91), 2.669 (1.20), 2.673 (0.89), 3.165 (0.60), 3.183 (0.93), 3.197 (1.12), 3.216 (1.66), 3.246 (1.74), 3.271 (3.49), 3.447 (3.03), 3.478 (2.12), 3.693 (0.52), 3.812 (16.00), 3.944 (0.73), 4.162 (1.31), 4.178 (2.68), 4.194 (1.41), 4.324 (0.42), 4.355 (0.42), 6.855 (1.74), 6.872 (1.89), 7.112 (2.18), 7.133 (2.35), 7.345 (1.37), 7.365 (2.53), 7.384 (1.99), 7.435 (2.72), 7.456 (1.64), 7.488 (0.60), 7.501 (1.85), 7.506 (2.45), 7.516 (3.69), 7.525 (2.80), 7.531 (1.83), 7.543 (0.66), 7.608

(1.76), 7.630 (1.60), 7.848 (1.62), 7.858 (0.81), 7.866 (1.18), 7.872 (1.37), 8.234 (1.43), 8.241 (1.16), 8.249 (0.71), 8.258 (1.27).

The titled compound (269 mg) was separated into enantiomers by preparative chiral HPLC to give enantiomer 1 (95 mg, see Example 23) and enantiomer 2 (107 mg, see Example 24).

Preparative chiral HPLC method: Instrument: Labomatic HD5000, Labocord-5000; Gilson GX-241, Labcol Vario 4000, column: Chiralpak IE 5μ 250×30 mm; Eluent A: Hexane+0.1 Vol-% N-ethylethanamine (99%); Eluent B: Ethanol; Isocratic: 65% A+35% B; Flow 50.0 mL/min; UV 220 nm Analytical chiral HPLC method: Instrument: Agilent HPLC 1260; column: Chiralpak IE 3μ 100×4.6 mm; Eluent A: Hexane+0.1 Vol-% N-ethylethanamine (99%); Eluent B: Ethanol; Isocratic: 65% A+35% B; Flow 1.4 mL/min; Temperature: 25° C.; DAD 220 nm

Example 23

4-chloro-3-ethyl-2,14-dimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid (Enantiomer 1)

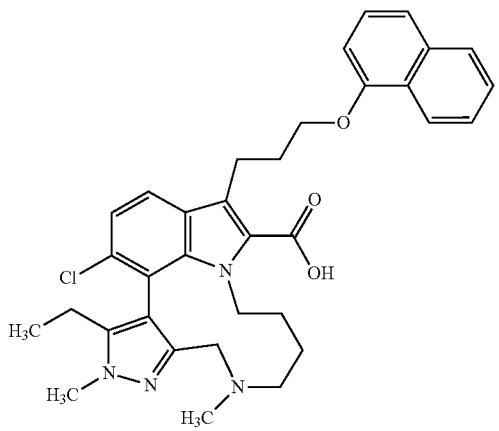 [SMILES: CCc1c2c(nn1C)CN(C)CCCCn1c(C(=O)O)c(CCCOc3cccc4ccccc34)c3ccc(Cl)c-2c31]

For the preparation of the racemic titled compound see Example 22. Separation of enantiomers by preparative chiral HPLC (method see Example 22) gave the titled compound (95 mg).

Analytical Chiral HPLC (method see Example 22): $R_t$=3.23 min.

Specific Optical Rotation (Method O1): 41.7° (c=10 mg/mL, chloroform)

$^1$H-NMR (400 MHz, DMSO-d6) δ[ppm]: 0.776 (3.47), 0.795 (8.00), 0.814 (3.77), 1.026 (0.84), 1.138 (1.25), 1.156 (1.79), 1.174 (0.92), 1.233 (0.84), 1.255 (0.73), 1.907 (0.76), 2.059 (3.85), 2.098 (0.89), 2.116 (1.60), 2.136 (2.12), 2.156 (1.76), 2.177 (1.76), 2.195 (2.28), 2.213 (1.57), 2.323 (1.19), 2.327 (1.65), 2.331 (1.22), 2.352 (0.41), 2.386 (0.65), 2.523 (7.00), 2.665 (1.19), 2.669 (1.63), 2.673 (1.19), 2.929 (0.43), 3.207 (0.43), 3.225 (0.76), 3.240 (1.00), 3.258 (1.63), 3.278 (1.74), 3.295 (2.71), 3.484 (1.90), 3.515 (1.38), 3.822 (16.00), 3.865 (0.84), 3.889 (0.57), 3.939 (0.60), 4.174 (1.76), 4.189 (3.53), 4.205 (1.79), 4.257 (0.57), 4.274 (0.57), 6.868 (2.17), 6.886 (2.33), 7.172 (3.47), 7.193 (3.80), 7.358 (1.55), 7.378 (2.93), 7.397 (2.17), 7.445 (3.15), 7.466 (1.87), 7.490 (0.49), 7.495 (0.68), 7.507 (2.03), 7.514 (2.71), 7.523 (4.01), 7.531 (2.87), 7.538 (2.17), 7.550 (0.76), 7.555 (0.43), 7.688 (3.04), 7.710 (2.77), 7.855 (1.84), 7.864 (1.03), 7.873 (1.46), 7.878 (1.60), 8.238 (1.65), 8.244 (1.46), 8.254 (0.92), 8.262 (1.55).

Example 24

4-chloro-3-ethyl-2,14-dimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid (Enantiomer 2)

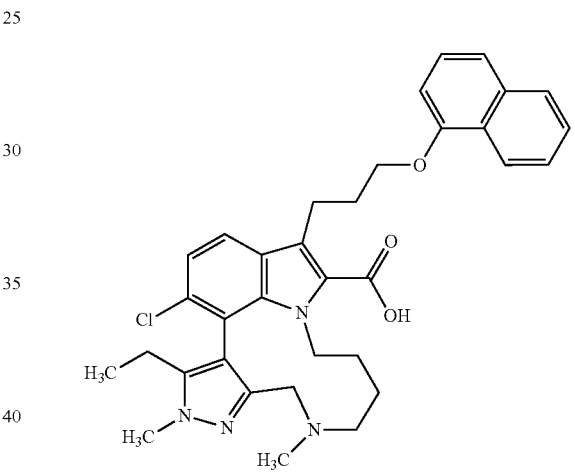

For the preparation of the racemic titled compound see Example 22. Separation of enantiomers by preparative chiral HPLC (method see Example 22) gave the titled compound (107 mg).

Analytical Chiral HPLC (method see Example 22): $R_t$=3.93 min.

Specific Optical Rotation (Method O1): −33.7° (c=10 mg/mL, chloroform)

$^1$H-NMR (400 MHz, DMSO-d6) δ[ppm]: 0.778 (3.81), 0.797 (8.58), 0.815 (4.14), 0.841 (0.48), 1.041 (0.94), 1.073 (0.96), 1.137 (1.54), 1.156 (2.29), 1.173 (1.18), 1.232 (0.94), 1.256 (0.89), 1.907 (0.48), 1.954 (0.43), 2.090 (3.49), 2.125 (2.05), 2.144 (2.48), 2.162 (2.29), 2.180 (2.43), 2.196 (2.72), 2.213 (1.83), 2.323 (1.08), 2.327 (1.47), 2.331 (1.13), 2.354 (0.46), 2.387 (0.72), 2.408 (0.65), 2.665 (1.11), 2.669 (1.47), 2.673 (1.13), 2.913 (0.60), 2.931 (0.60), 3.209 (0.58), 3.227 (0.99), 3.242 (1.33), 3.260 (2.12), 3.280 (2.48), 3.497 (2.00), 3.528 (1.35), 3.828 (16.00), 3.866 (1.01), 3.941 (1.11), 4.175 (2.00), 4.190 (4.00), 4.205 (2.07), 4.272 (0.63), 4.291 (0.65), 6.869 (2.39), 6.887 (2.58), 7.177 (3.83), 7.198 (3.88), 7.358

(1.54), 7.379 (3.11), 7.398 (2.39), 7.445 (3.47), 7.466 (2.10), 7.494 (0.80), 7.507 (2.14), 7.514 (2.99), 7.523 (4.43), 7.531 (3.16), 7.538 (2.51), 7.550 (0.89), 7.555 (0.55), 7.696 (3.23), 7.717 (2.94), 7.855 (2.05), 7.864 (1.25), 7.873 (1.69), 7.878 (1.83), 8.237 (1.83), 8.244 (1.66), 8.253 (1.11), 8.261 (1.76).

Example 25

(rac)-4-chloro-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid

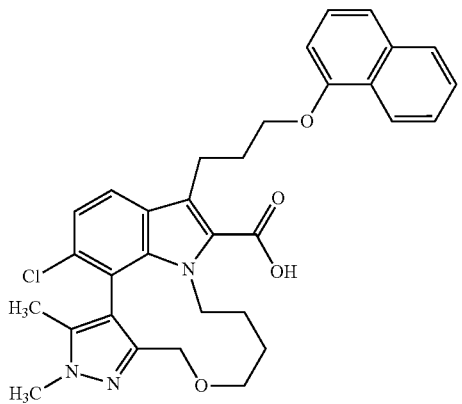 [SMILES: Cc1c2c(nn1C)COCCCCn1c(C(=O)O)c(CCCOc3cccc4ccccc34)c3ccc(Cl)c-2c31]

(rac)-Ethyl-4-chloro-2,3-dimethyl-7-[3-(naphthalen-1-yloxy)propyl]-2,10,11,12,13-hexahydropyrazolo[4',3':9,10][1,6]oxazacycloundecino[8,7,6-hi]indole-8-carboxylate (see Intermediate 58, 175 mg) was dissolved in a mixture of 3 mL of THF and 1 mL of ethanol and aqueous lithium hydroxide solution (600 μL, 1.0 M, 600 μmol) was added. The mixture was stirred at 65° C. overnight. Aqueous lithium hydroxide solution (250 μL, 1.0 M, 250 μmol) was added and stirring was continued at 65° C. for 14 hours. After concentration, water was added and the mixture was acidified using an aqueous, saturated solution of citric acid and was extracted with ethyl acetate. The combined organic layers were dried using sodium sulfate and were concentrated under reduced pressure. The crude material was purified by preparative HPLC (Method P3) to give the title compound (128 mg).

LC-MS (Method 1): $R_t$=1.54 min; MS (ESIpos): m/z=558 [M+H]$^+$ $^1$H-NMR (400 MHz, DMSO-d6) δ[ppm]: 1.177 (0.84), 1.191 (0.75), 1.202 (0.69), 1.351 (16.00), 1.740 (0.45), 1.752 (0.69), 1.757 (1.38), 1.776 (11.98), 2.180 (2.85), 2.197 (1.23), 2.214 (0.84), 2.518 (6.96), 2.523 (4.65), 2.539 (0.81), 3.112 (0.60), 3.127 (0.54), 3.235 (0.51), 3.250 (0.72), 3.269 (1.17), 3.287 (1.38), 3.582 (0.48), 3.598 (1.05), 3.615 (0.42), 3.819 (12.43), 4.167 (0.84), 4.184 (1.77), 4.191 (2.19), 4.222 (1.86), 4.258 (0.42), 4.279 (0.42), 4.421 (1.71), 4.452 (1.44), 6.654 (0.78), 6.868 (1.38), 6.876 (1.44), 6.894 (1.47), 7.187 (2.58), 7.208 (2.67), 7.363 (0.99), 7.384 (1.95), 7.403 (1.56), 7.446 (2.01), 7.467 (1.17), 7.495 (0.42), 7.507 (1.23), 7.514 (1.71), 7.523 (2.55), 7.531 (1.83), 7.538 (1.35), 7.550 (0.48), 7.723 (2.16), 7.743 (1.95), 7.855 (1.14), 7.864 (0.60), 7.873 (0.87), 7.878 (0.99), 8.218 (1.02), 8.225 (0.90), 8.234 (0.48), 8.242 (0.96).

The title compound (126 mg) was separated into enantiomers by preparative chiral HPLC to give enantiomer 1 (47 mg, see Example 26) and enantiomer 2 (47 mg, see Example 27).

Preparative chiral HPLC method: Instrument: Sepiatec: Prep SFC100; column: Chiralpak IG 5 μm 250×30 mm; Eluent A: $CO_2$, Eluent B: 2-Propanole+0.4 Vol-% N-ethylethanamine (99%); Isocratic: 27% B; Flow 100.0 mL/min Temperature: 40° C.; BPR: 150 bar; MWD @ 220 nm Analytical chiral HPLC method: Instrument: Agilent: 1260, Aurora SFC-Modul; column: Chiralpak IG 5 μm 100×4.6 mm; Eluent A: $CO_2$, Eluent B: 2-Propanole+0.2 Vol-% N-ethylethanamine (99%); Isocratic: 27% B; Flow 4.0 mL/min; Temperature: 37.5° C.; BPR: 100 bar; MWD @ 220 nm

Example 26

4-chloro-2,3-dimethyl-7-[3-(naphthalen-1-yloxy) propyl]-2,10,11,12,13,15-hexahydropyrazolo-[4',3':9,10][1,6]oxazacycloundecino[8,7,6-hi]indole-8-carboxylic acid-N-ethylethanamine salt (Enantiomer 1)

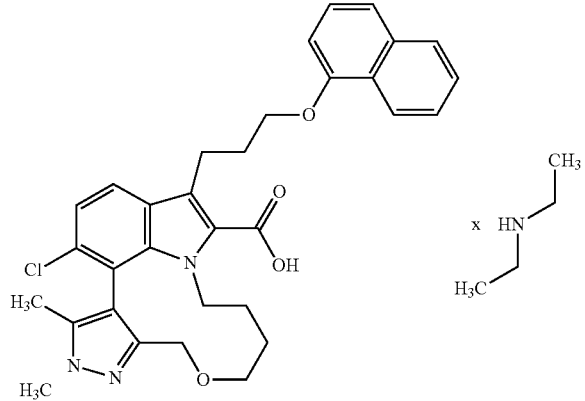

For the preparation of the racemic title compound see Example 25. Separation of enantiomers by preparative chiral HPLC (method see Example 25) gave the title compound (47 mg).

Analytical Chiral HPLC (method see Example 25): $R_t$=2.01 min.

LC-MS (Method): $R_t$=1.53 min; MS (ESIpos): m/z=558 [M+H]$^+$ $^1$H-NMR (400 MHz, DMSO-d6) δ[ppm]: 1.026 (0.52), 1.042 (0.57), 1.088 (0.90), 1.134 (3.48), 1.150 (6.17), 1.165 (3.27), 1.303 (0.57), 1.781 (15.83), 2.170 (1.26), 2.187 (1.93), 2.204 (1.34), 2.221 (0.42), 2.322 (0.75), 2.326 (1.07), 2.331 (0.82), 2.522 (4.01), 2.664 (0.78), 2.669 (1.09), 2.673 (0.86), 2.848 (2.26), 2.864 (2.26), 3.105 (0.86), 3.129 (0.80), 3.142 (0.97), 3.156 (0.78), 3.175 (1.13), 3.193 (0.61), 3.228 (0.78), 3.246 (1.47), 3.264 (1.38), 3.279 (2.14), 3.648 (0.44), 3.673 (0.67), 3.694 (0.48), 3.813 (16.00), 4.129 (0.52), 4.137 (0.76), 4.153 (1.95), 4.168 (1.93), 4.187 (2.62), 4.219 (2.60), 4.377 (2.45), 4.408 (1.99), 4.431 (0.59), 4.450 (0.55), 4.465 (0.57), 6.852 (1.93), 6.870 (2.05), 7.059 (2.64), 7.080 (2.79), 7.343 (1.30), 7.364 (2.56), 7.383 (1.99), 7.431 (2.70), 7.451 (1.61), 7.485 (0.55), 7.497 (1.57), 7.504 (2.22), 7.513 (3.50), 7.522 (2.31), 7.528 (1.91), 7.541 (0.76), 7.550 (2.18), 7.571 (1.89), 7.847 (1.53), 7.856 (0.84), 7.864 (1.22), 7.870 (1.38), 8.222 (1.34), 8.229 (1.26), 8.237 (0.69), 8.246 (1.36).

Example 27

4-chloro-2,3-dimethyl-7-[3-(naphthalen-1-yloxy)propyl]-2,10,11,12,13,15-hexahydropyrazolo-[4',3':9,10][1,6]oxazacycloundecino[8,7,6-hi]indole-8-carboxylic acid-N-ethylethanamine salt (Enantiomer 2)

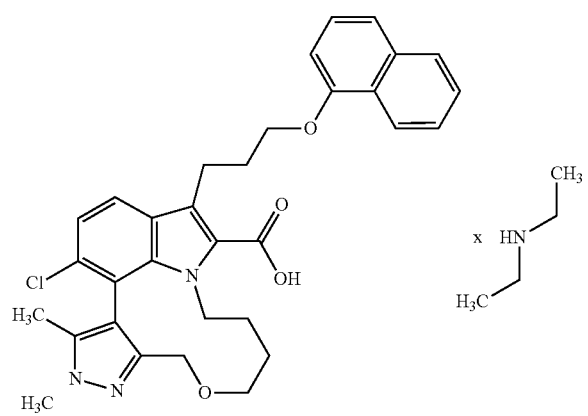

For the preparation of the racemic title compound see Example 25. Separation of enantiomers by preparative chiral HPLC (method see Example 25) gave the title compound (47 mg).

Analytical Chiral HPLC (method see Example 25): $R_t$=3.67 min.

LC-MS (Method 1): $R_t$=1.53 min; MS (ESIpos): m/z=558 [M+H]$^+$ $^1$H-NMR (400 MHz, DMSO-d6) δ[ppm]: 1.027 (3.78), 1.042 (4.04), 1.088 (0.74), 1.112 (3.26), 1.129 (5.83), 1.146 (2.91), 1.299 (0.39), 1.352 (16.00), 1.781 (13.61), 2.166 (0.87), 2.181 (3.09), 2.200 (0.96), 2.332 (1.74), 2.336 (0.78), 2.518 (9.43), 2.522 (6.35), 2.539 (0.52), 2.673 (1.78), 2.678 (0.78), 2.820 (1.91), 2.837 (1.87), 3.103 (0.61), 3.129 (0.78), 3.144 (0.57), 3.163 (0.70), 3.216 (0.43), 3.234 (0.87), 3.253 (0.65), 3.268 (0.83), 3.660 (0.39), 3.813 (13.52), 4.136 (0.57), 4.152 (1.48), 4.168 (1.43), 4.187 (2.00), 4.218 (2.09), 4.374 (1.83), 4.406 (1.52), 6.655 (0.61), 6.854 (1.43), 6.871 (1.96), 7.050 (1.39), 7.071 (1.48), 7.345 (1.13), 7.366 (2.09), 7.385 (1.70), 7.430 (2.09), 7.451 (1.22), 7.486 (0.48), 7.498 (1.35), 7.505 (1.87), 7.514 (2.96), 7.523 (2.04), 7.529 (1.57), 7.540 (1.22), 7.559 (0.87), 7.846 (1.22), 7.856 (0.61), 7.864 (0.87), 7.870 (1.00), 8.222 (1.13), 8.229 (0.91), 8.238 (0.52), 8.247 (1.00).

Example 28

(rac)-12-chloro-10,11-dimethyl-1-[3-(naphthalen-1-yloxy)propyl]-4,5,6,7,8,10-hexahydropyrazolo[3',4':7,8][1,5]diazecino[9,10,1-hi]indole-2-carboxylic acid-formic acid salt

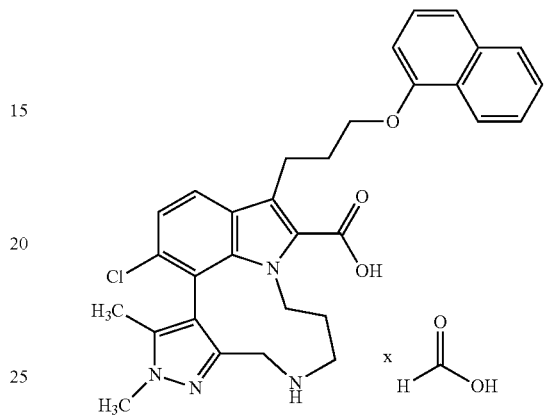

(rac)-Ethyl-12-chloro-10,11-dimethyl-1-[3-(naphthalen-1-yloxy)propyl]-4,5,6,7,8,10-hexahydropyrazolo[3',4':7,8][1,5]diazecino[9,10,1-hi]indole-2-carboxylate (see Intermediate 62, 100 mg) was dissolved in a mixture of 2 mL of THF and 1 mL of ethanol and aqueous lithium hydroxide solution (350 μL, 1.0 M, 350 μmol) was added. The mixture was stirred at 70° C. for 72 hours. Aqueous lithium hydroxide solution (200 μL, 1.0 M, 200 μmol) was added and stirring was continued at 70° C. for 2 days. After concentration, water was added and the mixture was acidified using an aqueous, saturated solution of citric acid and was extracted with ethyl acetate. The combined organic layers were dried using sodium sulfate, were filtered and were concentrated under reduced pressure. The crude material was purified by preparative HPLC (Method P4) to give the title compound (35 mg).

LC-MS (Method 1): $R_t$=1.17 min; MS (ESIneg): m/z=541 [M−H]$^−$ $^1$H-NMR (400 MHz, DMSO-d6) δ[ppm]: 1.561 (1.15), 1.812 (1.00), 1.934 (15.82), 1.952 (0.66), 1.976 (0.55), 2.152 (1.02), 2.169 (1.60), 2.188 (1.94), 2.204 (0.52), 2.336 (0.55), 2.518 (6.61), 2.522 (4.22), 2.539 (7.45), 2.659 (0.55), 2.718 (0.55), 2.753 (0.55), 3.135 (1.63), 3.170 (2.12), 3.180 (1.21), 3.198 (1.44), 3.218 (1.15), 3.276 (2.02), 3.295 (2.91), 3.313 (2.96), 3.328 (3.25), 3.346 (3.02), 3.703 (0.52), 3.723 (0.66), 3.740 (0.55), 3.757 (0.42), 3.831 (16.00), 3.855 (1.18), 4.160 (1.47), 4.176 (3.07), 4.192 (1.55), 4.610 (0.73), 4.646 (0.68), 5.759 (3.17), 6.877 (1.86), 6.895 (1.97), 7.138 (3.70), 7.159 (3.70), 7.360 (1.39), 7.380 (2.60), 7.399 (2.10), 7.438 (2.73), 7.458 (1.50), 7.478 (0.45), 7.481 (0.68), 7.494 (1.52), 7.498 (1.50), 7.506 (1.84), 7.512 (3.30), 7.518 (1.84), 7.526 (1.65), 7.530 (1.76), 7.543 (0.68), 7.547 (0.50), 7.674

(2.91), 7.696 (2.62), 7.848 (1.57), 7.855 (1.00), 7.866 (1.65), 7.871 (1.39), 8.182 (9.50), 8.206 (1.39), 8.211 (1.36), 8.230 (1.36).

Example 29

(rac)-12-chloro-7,10,11-trimethyl-1-[3-(naphthalen-1-yloxy)propyl]-4,5,6,7,8,10-hexahydropyrazolo[3',4':7,8][1,5]diazecino[9,10,1-hi]indole-2-carboxylic acid

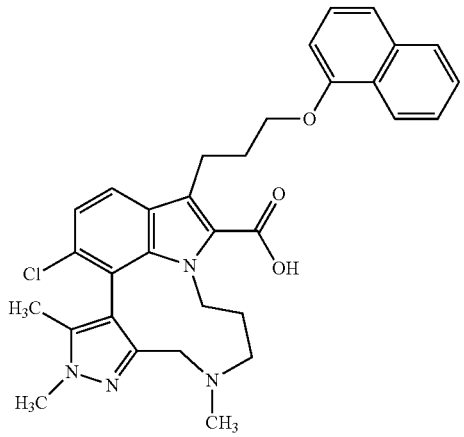 [SMILES: Cc1c2c(nn1C)CN(C)CCCn1c(C(=O)O)c(CCCOc3cccc4ccccc34)c3ccc(Cl)c-2c31]

(rac)-Ethyl-12-chloro-7,10,11-trimethyl-1-[3-(naphthalen-1-yloxy)propyl]-4,5,6,7,8,10-hexahydropyrazolo[3',4':7,8][1,5]diazecino[9,10,1-hi]indole-2-carboxylate (see Intermediate 63, 57.6 mg) was dissolved in a mixture of 2 mL of THF and 1 mL of ethanol and aqueous lithium hydroxide solution (200 µL, 1.0 M, 200 µmol) was added. The mixture was stirred at 70° C. for 72 hours. After concentration, water was added and the mixture was acidified using an aqueous, saturated solution of citric acid and was extracted with ethyl acetate. The combined organic layers were dried using sodium sulfate, were filtered and were concentrated under reduced pressure to give the title compound (52 mg).

LC-MS (Method 1): $R_t$=1.37 min; MS (ESIpos): m/z=557 [M+H]$^+$ $^1$H-NMR (400 MHz, CHLOROFORM-d) δ [ppm]: 0.000 (1.44), 0.007 (0.89), 0.010 (1.00), 0.025 (0.55), 0.104 (0.86), 1.103 (0.44), 1.154 (1.50), 1.184 (1.61), 1.212 (0.64), 1.249 (0.50), 1.265 (0.53), 1.289 (2.30), 1.306 (4.77), 1.324 (2.38), 1.353 (0.64), 1.380 (0.55), 1.410 (1.08), 1.557 (1.30), 1.741 (3.52), 1.933 (1.75), 1.985 (16.00), 2.015 (1.22), 2.023 (1.11), 2.037 (1.36), 2.106 (0.69), 2.230 (1.58), 2.247 (2.00), 2.265 (1.55), 2.966 (2.02), 3.063 (0.55), 3.269 (0.44), 3.287 (0.83), 3.306 (1.30), 3.329 (1.69), 3.348 (1.08), 3.605 (0.67), 3.624 (0.61), 3.641 (0.58), 3.857 (1.86), 3.879 (12.37), 3.961 (1.11), 4.108 (1.25), 4.122 (1.77), 4.135 (1.41), 4.149 (1.28), 4.164 (0.64), 4.231 (0.64), 4.249 (1.77), 4.267 (1.75), 4.284 (0.58), 5.233 (8.98), 6.709 (1.30), 6.726 (1.36), 6.734 (0.78), 6.754 (0.80), 6.929 (1.55), 7.100 (3.94), 7.122 (4.10), 7.156 (0.58), 7.220 (0.44), 7.267 (1.08), 7.288 (1.97), 7.292 (0.97), 7.306 (1.69), 7.313 (1.28), 7.335 (2.16), 7.355 (1.22), 7.366 (1.30), 7.378 (0.92), 7.386 (1.16), 7.396 (1.53), 7.399 (1.33), 7.403 (1.58), 7.415 (1.58), 7.422 (2.91), 7.434 (2.94), 7.440 (1.86), 7.444 (2.66), 7.452 (2.55), 7.458 (1.66), 7.467 (1.00), 7.470 (0.92), 7.485 (0.80), 7.489 (0.83), 7.503 (0.42), 7.507 (0.44), 7.575 (1.16), 7.579 (1.39), 7.596 (1.25), 7.599 (1.08), 7.602 (1.69), 7.605 (1.28), 7.609 (1.36), 7.620 (2.52), 7.623 (2.02), 7.641 (2.11), 7.716 (0.58), 7.728 (1.28), 7.739 (1.22), 7.750 (1.36), 7.762 (0.55), 7.772 (0.50), 8.289 (1.03), 8.295 (1.00), 8.303 (1.08), 8.313 (1.05).

Example 30

(rac)-4-chloro-7-{3-[(6-fluoronaphthalen-1-yl)oxy]propyl}-2,3,14-trimethyl-10,11,12,13,14,15-hexahydro-2H-pyrazolo[3',4':8,9][1,6]diazacycloundecino[10,11,1-hi]indole-8-carboxylic acid

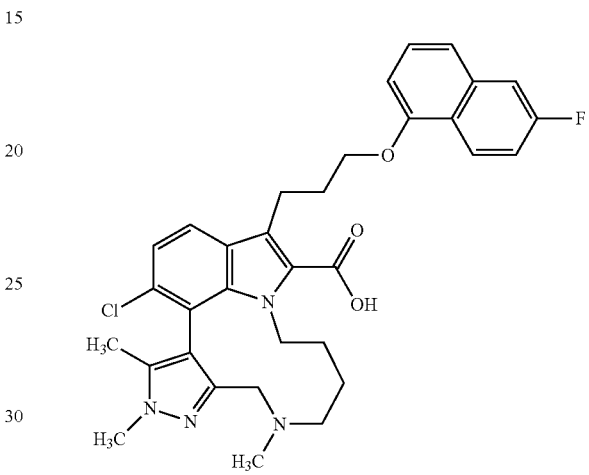

(rac)-Ethyl-4-chloro-7-{3-[(6-fluoronaphthalen-1-yl)oxy]propyl}-2,3,14-trimethyl-10,11,12,13,14,15-hexahydro-2H-pyrazolo[3',4':8,9][1,6]diazacycloundecino[10,11,1-hi]indole-8-carboxylate (see Intermediate 67, 163 mg, 264 µmol) was dissolved in a mixture of 2 mL of THF and 1 mL of ethanol and aqueous lithium hydroxide solution (530 µL, 1.0 M, 530 µmol) was added. The mixture was stirred at 70° C. for 48 hours and was poured into water. The precipitated material was isolated by filtration and purified by preparative HPLC (Method P4) to give the title compound (52 mg, 33% yield).

LC-MS (Method 1): $R_t$=1.24 min; MS (ESIneg): m/z=587 [M−H]$^-$ $^1$H-NMR (400 MHz, DMSO-d6) δ[ppm]: 1.044 (0.95), 1.235 (0.59), 1.754 (14.98), 1.839 (0.83), 1.907 (0.61), 1.979 (0.44), 1.999 (0.41), 2.071 (6.12), 2.167 (1.20), 2.183 (1.85), 2.200 (1.24), 2.318 (0.76), 2.323 (1.24), 2.327 (1.76), 2.332 (1.44), 2.336 (0.90), 2.370 (0.44), 2.518 (5.44), 2.523 (3.88), 2.539 (11.15), 2.660 (0.51), 2.665 (1.07), 2.669 (1.44), 2.673 (1.02), 2.678 (0.46), 3.190 (0.80), 3.209 (1.27), 3.223 (1.37), 3.242 (2.07), 3.262 (1.98), 3.305 (4.66), 3.492 (2.27), 3.523 (1.66), 3.683 (0.90), 3.795 (16.00), 3.812 (0.90), 3.840 (0.61), 4.174 (1.59), 4.189 (3.22), 4.205 (1.59), 4.297 (0.56), 4.314 (0.54), 4.328 (0.51), 5.758 (3.27), 6.853 (1.39), 6.859 (1.46), 6.868 (1.29), 6.874 (1.44), 7.173 (3.76), 7.195 (4.00), 7.361 (0.90), 7.367 (1.12), 7.383 (1.44), 7.390 (1.61), 7.405 (1.44), 7.411 (1.12), 7.425 (2.46), 7.435 (3.20), 7.441 (5.88), 7.456 (0.54), 7.642 (1.73), 7.649 (1.76), 7.668 (1.83), 7.675 (2.12), 7.679 (3.41), 7.700 (2.93), 8.161 (7.59), 8.262 (1.44), 8.276 (1.54), 8.285 (1.49), 8.300 (1.39).

The title compound (90 mg) was separated into enantiomers by preparative chiral HPLC to give enantiomer 1 (36 mg, see Example 31) and enantiomer 2 (34 mg, see Example 32).

Preparative Chiral HPLC Method:
Instrument: Labomatic HD5000, Labocord-5000; Gilson GX-241, Labcol Vario 4000, Column: Chiralpak ID 5μ 250×30 mm; Eluent: Hexane+0.1 Vol-% Diethylamine (99%)/Ethanol 80:20; Flow 50.0 mL/min; UV 254 nm Analytical Chiral HPLC Method:
Instrument: Agilent HPLC 1260; Column: Chiralpak ID 3μ 100×4.6 mm; Eluent A: Hexane+0.1 Vol-% Diethylamine (99%); Eluent B: Ethanol; Gradient: 20-50% B in 7 min; Flow 1.4 mL/min; Temperature: 25° C.; DAD 254 nm

Example 31

(+)-4-chloro-7-{3-[(6-fluoronaphthalen-1-yl)oxy] propyl}-2,3,14-trimethyl-10,11,12,13,14,15-hexahydro-2H-pyrazolo[3',4':8,9][1,6]diazacycloundecino[10,11,1-hi]indole-8-carboxylic acid-N-ethylethanamine salt (Enantiomer 1)

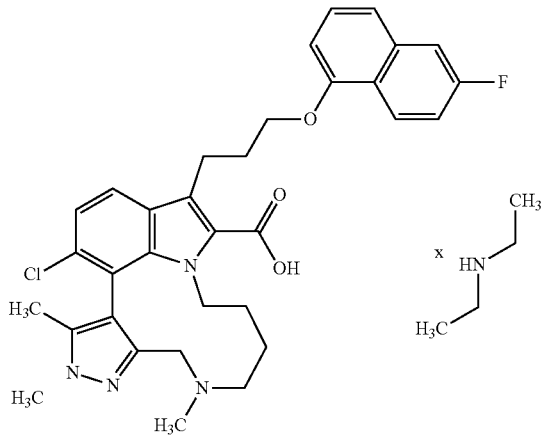

For the preparation of the racemic title compound see Example 30. Separation of enantiomers by preparative chiral HPLC (method see Example 30) gave the title compound (36 mg).

Analytical Chiral HPLC (method see Example 30): $R_t$=2.19 min.

LC-MS (Method 1): $R_t$=1.20 min; MS (ESIpos): m/z=589 [M+H]$^+$

Specific Optical Rotation (Method O1): +16° (c=10 mg/mL, DMSO)

$^1$H-NMR (400 MHz, DMSO-d6) δ[ppm]: 0.797 (0.68), 0.814 (0.75), 0.821 (0.72), 0.840 (0.44), 0.904 (0.77), 0.922 (0.42), 0.993 (0.66), 1.035 (2.85), 1.052 (4.83), 1.070 (2.98), 1.136 (7.29), 1.154 (16.00), 1.172 (7.79), 1.203 (0.72), 1.229 (0.99), 1.750 (15.93), 1.861 (0.99), 1.888 (0.77), 1.905 (1.12), 2.052 (9.22), 2.142 (0.46), 2.159 (1.34), 2.176 (2.02), 2.193 (1.38), 2.210 (0.55), 2.301 (0.59), 2.322 (1.36), 2.326 (1.65), 2.331 (1.40), 2.518 (5.29), 2.522 (3.40), 2.539 (0.44), 2.664 (0.97), 2.669 (1.29), 2.673 (0.97), 2.854 (2.15), 2.872 (6.47), 2.890 (6.34), 2.908 (1.98), 3.128 (0.42), 3.147 (0.72), 3.162 (0.75), 3.181 (1.10), 3.200 (0.61), 3.255 (1.14), 3.281 (2.88), 3.312 (5.90), 3.334 (7.40), 3.411 (1.16), 3.428 (1.45), 3.445 (3.16), 3.463 (0.70), 3.476 (1.73), 3.732 (0.68), 3.752 (0.61), 3.880 (0.66), 4.159 (1.45), 4.175 (2.94), 4.191 (1.49), 4.396 (0.59), 4.413 (0.59), 4.429 (0.53), 5.759 (1.98), 6.834 (1.40), 6.839 (1.47), 6.850 (1.40), 6.855 (1.49), 7.093 (2.50), 7.115 (2.68), 7.356 (0.83), 7.363 (0.99), 7.379 (1.47), 7.385 (1.73), 7.401 (1.08), 7.409 (2.70), 7.427 (5.14), 7.443 (0.68), 7.573 (2.00), 7.594 (1.87), 7.634 (1.65), 7.640 (1.76), 7.660 (1.67), 7.666 (1.69), 8.260 (1.43), 8.275 (1.49), 8.283 (1.65), 8.297 (1.38).

Example 32

(−)-4-chloro-7-{3-[(6-fluoronaphthalen-1-yl)oxy] propyl}-2,3,14-trimethyl-10,11,12,13,14,15-hexahydro-2H-pyrazolo[3',4':8,9][1,6]diazacycloundecino[10,11,1-hi]indole-8-carboxylic acid-N-ethylethanamine salt (Enantiomer 2)

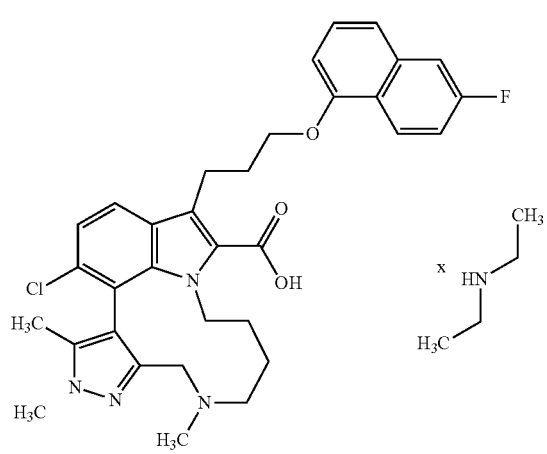

For the preparation of the racemic title compound see Example 30. Separation of enantiomers by preparative chiral HPLC (method see Example 30) gave the title compound (34 mg).

Analytical Chiral HPLC (method see Example 30): $R_t$=3.27 min.

LC-MS (Method 1): $R_t$=1.17 min; MS (ESIpos): m/z=589 [M+H]$^+$

Specific Optical Rotation (Method O1): −14.2° (c=10 mg/mL, DMSO)

$^1$H-NMR (400 MHz, DMSO-d6) δ[ppm]: 0.797 (0.74), 0.814 (0.86), 0.821 (0.82), 0.840 (0.55), 0.885 (0.41), 0.904 (0.84), 0.922 (0.46), 0.973 (0.55), 0.991 (0.65), 1.006 (0.79), 1.035 (4.08), 1.052 (7.10), 1.070 (4.22), 1.083 (0.94), 1.134 (5.57), 1.152 (12.45), 1.170 (6.00), 1.190 (0.67), 1.203 (0.72), 1.230 (0.86), 1.259 (0.46), 1.750 (16.00), 1.860 (1.08), 1.888 (0.70), 1.905 (1.20), 2.051 (9.00), 2.140 (0.43), 2.157 (1.27), 2.175 (1.97), 2.192 (1.37), 2.209 (0.55), 2.300 (0.58), 2.322 (1.39), 2.326 (1.75), 2.331 (1.51), 2.518 (6.57), 2.522 (3.93), 2.664 (1.06), 2.669 (1.42), 2.673 (1.06), 2.850 (1.58), 2.867 (4.85), 2.886 (4.75), 2.903 (1.44), 3.144 (0.67), 3.158 (0.70), 3.176 (1.01), 3.195 (0.55), 3.252 (0.98), 3.270 (1.97), 3.279 (2.61), 3.310 (5.35), 3.333 (7.87), 3.410 (1.22), 3.428 (1.78), 3.444 (2.93), 3.463 (0.79), 3.474 (1.68), 3.728 (0.65), 3.745 (0.55), 3.879 (0.77), 4.158 (1.39), 4.174 (2.81), 4.189 (1.44), 4.395 (0.58), 4.412 (0.58), 4.429 (0.50), 5.759 (2.06), 6.833 (1.37), 6.839 (1.44), 6.849 (1.37), 6.855 (1.46), 7.090 (2.30), 7.112 (2.45), 7.356 (0.89), 7.362 (1.01), 7.378 (1.44), 7.385 (1.73), 7.400 (1.08), 7.408 (2.71), 7.426 (5.04), 7.443 (0.62), 7.569 (1.80), 7.590 (1.70), 7.633 (1.66), 7.640 (1.75), 7.659 (1.68), 7.666 (1.66), 8.260 (1.42), 8.275 (1.49), 8.283 (1.51), 8.298 (1.34).

Example 33

(rac)-4-chloro-3-ethyl-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid

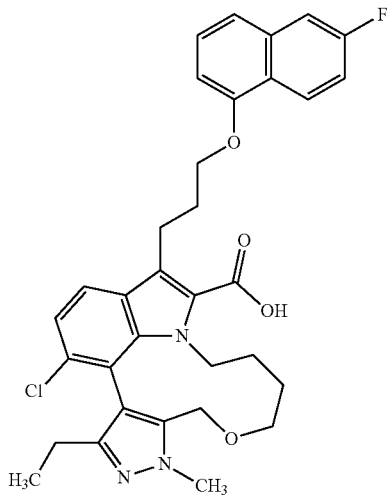 [SMILES: CCc1nn(C)c2c1-c1c(Cl)ccc3c(CCCOc4cccc5cc(F)ccc45)c(C(=O)O)n(c13)CCCCOC2]

(Rac)-ethyl-4-chloro-3-ethyl-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylate (see Intermediate 70, 1.50 g, 2.43 mmol) was dissolved in a mixture of 20 mL of THF and 10 mL of ethanol and aqueous lithium hydroxide solution (10 mL, 1.0 M, 10 mmol) was added. The mixture was stirred at 45° C. for 23 hours, at 60° C. for 6 hours and at 50° C. for 16 hours and was concentrated under reduced pressure. The crude material was purified by flash chromatography twice using silica gel (first time gradient dichloromethane/ethanol, second time ethyl acetate/acetone) to give the title compound (1.44 g, 95% yield).

LC-MS (Method 2): $R_t$=0.95 min; MS (ESIpos): m/z=590 [M+H]$^+$ $^1$H-NMR (400 MHz, DMSO-d6) δ[ppm]: 0.838 (3.99), 0.857 (9.33), 0.876 (4.18), 1.029 (0.95), 1.154 (4.45), 1.172 (8.81), 1.189 (4.29), 1.231 (1.88), 1.249 (1.43), 1.987 (16.00), 2.059 (0.63), 2.068 (0.55), 2.078 (1.54), 2.087 (1.56), 2.097 (1.56), 2.106 (1.47), 2.116 (0.52), 2.124 (0.55), 2.184 (0.80), 2.202 (1.18), 2.219 (0.86), 2.518 (4.54), 2.522 (2.79), 2.825 (0.59), 2.836 (0.43), 2.854 (0.64), 3.257 (0.54), 3.275 (0.89), 3.295 (0.72), 3.307 (1.27), 3.442 (0.68), 3.457 (0.57), 3.471 (0.63), 3.877 (13.25), 3.922 (0.45), 3.941 (0.54), 3.958 (0.52), 3.999 (1.09), 4.017 (3.34), 4.035 (3.36), 4.053 (1.14), 4.165 (1.66), 4.174 (1.23), 4.189 (2.45), 4.199 (2.29), 4.445 (0.64), 4.480 (0.57), 4.629 (1.73), 4.662 (1.59), 6.847 (1.02), 6.855 (1.05), 6.861 (0.93), 6.868 (1.13), 7.205 (3.00), 7.226 (3.02), 7.343 (0.68), 7.350 (0.77), 7.365 (1.05), 7.372 (1.16), 7.388 (0.70), 7.394 (0.80), 7.424 (2.00), 7.431 (2.25), 7.438 (4.86), 7.639 (1.25), 7.645 (1.34), 7.665 (1.27), 7.671 (1.31), 7.759 (2.36), 7.780 (2.15), 8.213 (1.11), 8.227 (1.16), 8.236 (1.13), 8.251 (1.07).

The title compound (1.44 g) was separated into enantiomers by preparative chiral HPLC to give enantiomer 1 (656 mg, see Example 34) and enantiomer 2 (635 mg, see Example 35).

Preparative Chiral HPLC Method:
Instrument: Sepiatec: Prep SFC100; Column: Chiralpak IG 5 µm 250×30 mm; Eluent A: CO$_2$, Eluent B: Ethanol+0.2 Vol-% aqueous ammonia (32%); Isokratic: 17% B; Flow 100.0 mL/min Temperature: 40° C.; BPR: 150 bar; MWD @ 220 nm Analytical Chiral HPLC Method:
Instrument: Agilent: 1260, Aurora SFC-Modul; Column: Chiralpak IG 5 µm 100×4.6 mm; Eluent A: CO$_2$, Eluent B: Ethanol+0.2 Vol-% aqueous ammonia (32%); Isokratic: 25% B; Flow 4.0 mL/min; Temperature: 37.5° C.; BPR: 100 bar; MWD @ 220 nm

Example 34

(+)-4-chloro-3-ethyl-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid (Enantiomer 1)

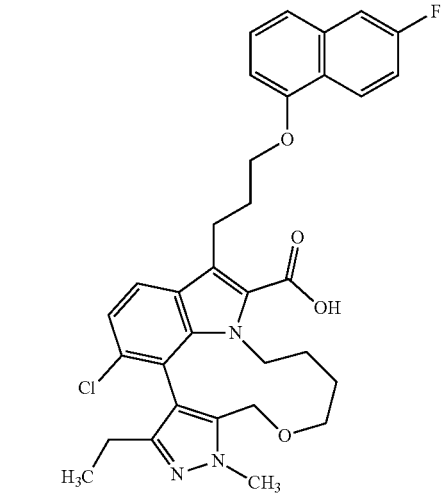 [SMILES: CCc1nn(C)c2c1-c1c(Cl)ccc3c(CCCOc4cccc5cc(F)ccc45)c(C(=O)O)n(c13)CCCCOC2]

For the preparation of the racemic title compound see Example 33. Separation of enantiomers by preparative chiral HPLC (method see Example 33) gave the title compound (656 mg).

Analytical Chiral HPLC (method see Example 33): $R_t$=1.14 min.

LC-MS (Method 2): $R_t$=0.94 min; MS (ESIpos): m/z=590 [M+H]$^+$

Specific Optical Rotation (Method O1): +40.4° (c=10 mg/mL, DMSO)

$^1$H-NMR (400 MHz, DMSO-d6) δ[ppm]: 0.838 (4.96), 0.857 (11.78), 0.876 (5.15), 1.035 (1.11), 1.053 (0.64), 1.231 (1.56), 2.060 (0.76), 2.069 (0.66), 2.078 (1.91), 2.088 (1.92), 2.097 (1.89), 2.107 (1.81), 2.116 (0.62), 2.125 (0.66), 2.185 (0.95), 2.202 (1.42), 2.219 (1.01), 2.518 (4.06), 2.523 (2.96), 2.826 (0.70), 2.836 (0.49), 2.843 (0.47), 2.855 (0.74), 3.242 (0.41), 3.257 (0.62), 3.276 (1.07), 3.295 (0.84), 3.308 (1.50), 3.442 (0.82), 3.456 (0.68), 3.471 (0.78), 3.877 (16.00), 3.924 (0.56), 3.941 (0.64), 3.958 (0.62), 4.166 (2.06), 4.175 (1.50), 4.190 (2.99), 4.199 (2.76), 4.445 (0.78), 4.458 (0.45), 4.467 (0.41), 4.480 (0.72), 4.629 (2.12), 4.663 (1.94), 6.847 (1.28), 6.855 (1.28), 6.862 (1.13), 6.869 (1.36), 7.206 (3.77), 7.226 (3.83), 7.343 (0.86), 7.349 (0.95), 7.365 (1.30), 7.372 (1.42), 7.387 (0.87), 7.394 (0.99), 7.403 (0.41), 7.425 (2.45), 7.431 (2.74), 7.438 (6.07), 7.639 (1.54), 7.646 (1.59), 7.665

(1.56), 7.672 (1.54), 7.759 (3.15), 7.780 (2.84), 8.213 (1.36), 8.227 (1.44), 8.236 (1.40), 8.251 (1.30).

Example 35

(−)-4-chloro-3-ethyl-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid (Enantiomer 2)

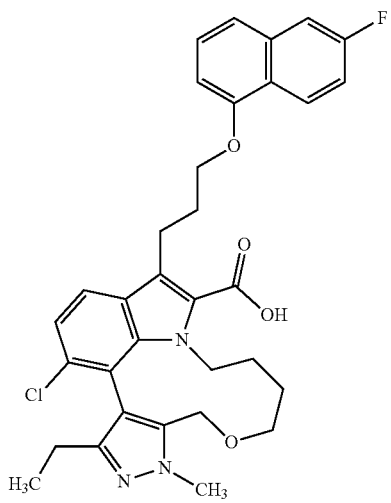 [SMILES: CCc1nn(C)c2c1-c1c(Cl)ccc3c(CCCOc4cccc5cc(F)ccc45)c(C(=O)O)n(c13)CCCCOC2]

For the preparation of the racemic title compound see Example 33. Separation of enantiomers by preparative chiral HPLC (method see Example 33) gave the title compound (635 mg).

Analytical Chiral HPLC (method see Example 33): $R_t$=2.15 min.

LC-MS (Method 2): $R_t$=0.93 min; MS (ESIpos): m/z=590 [M+H]$^+$

Specific Optical Rotation (Method O1): −50.6° (c=10 mg/mL, DMSO)

$^1$H-NMR (400 MHz, DMSO-d6) δ[ppm]: 0.838 (6.75), 0.857 (16.00), 0.875 (6.93), 0.883 (0.49), 0.901 (0.65), 1.009 (0.83), 1.035 (1.69), 1.043 (1.44), 1.053 (1.26), 1.070 (0.47), 1.171 (0.51), 1.229 (2.12), 1.244 (1.66), 1.987 (0.81), 2.060 (1.06), 2.065 (1.11), 2.068 (0.95), 2.078 (2.54), 2.087 (2.62), 2.097 (2.58), 2.106 (2.44), 2.116 (0.83), 2.125 (0.90), 2.143 (0.40), 2.167 (0.46), 2.185 (1.28), 2.202 (1.90), 2.219 (1.34), 2.235 (0.47), 2.518 (2.59), 2.523 (1.76), 2.809 (0.40), 2.827 (0.96), 2.838 (0.66), 2.845 (0.61), 2.855 (1.01), 2.874 (0.40), 3.245 (0.53), 3.259 (0.82), 3.278 (1.45), 3.290 (0.97), 3.298 (1.04), 3.309 (1.78), 3.332 (13.05), 3.427 (0.49), 3.442 (1.13), 3.456 (0.91), 3.471 (1.02), 3.486 (0.40), 3.911 (0.43), 3.927 (0.71), 3.945 (0.90), 3.962 (0.81), 3.981 (0.44), 4.166 (2.83), 4.175 (2.01), 4.190 (3.98), 4.200 (3.76), 4.430 (0.46), 4.442 (1.09), 4.455 (0.62), 4.464 (0.57), 4.477 (1.00), 4.489 (0.42), 4.629 (2.88), 4.663 (2.63), 6.846 (1.75), 6.853 (1.76), 6.861 (1.51), 6.868 (1.86), 7.207 (5.97), 7.229 (6.02), 7.342 (1.18), 7.349 (1.33), 7.364 (1.76), 7.372 (1.94), 7.387 (1.19), 7.393 (1.34), 7.403 (0.56), 7.424 (3.30), 7.431 (3.60), 7.438 (8.12), 7.452 (0.53), 7.638 (2.07), 7.645 (2.14), 7.664 (2.09), 7.671 (2.09), 7.762 (5.03), 7.784 (4.50), 8.212 (1.82), 8.227 (1.88), 8.236 (1.88), 8.250 (1.81).

Example 36

(rac)-4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid

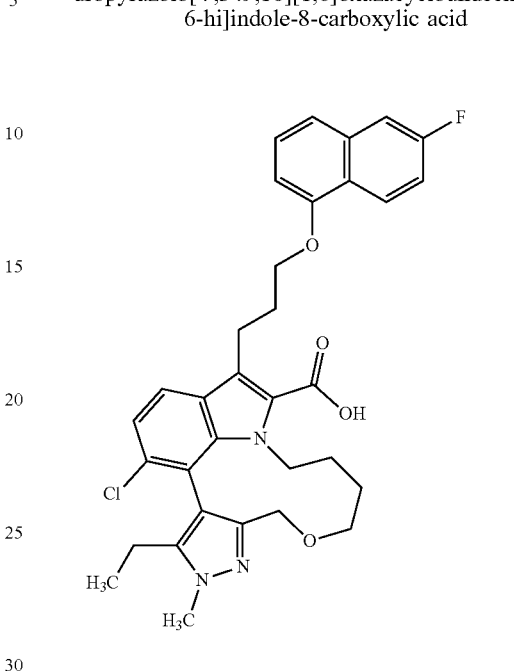

(Rac)-ethyl-4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylate (see Intermediate 72, 745 mg, 1.21 mmol) was dissolved in a mixture of 20 mL of THF and 10 mL of ethanol and aqueous lithium hydroxide solution (10 mL, 1.0 M, 10 mmol) was added. The mixture was stirred at 45° C. for one day and at 60° C. for one day, was neutralized with an aqueous solution of hydrogen chloride (2 M) and was concentrated under reduced pressure. The crude material was purified by flash chromatography twice using silica gel (first time gradient dichloromethane/ethanol, second time ethyl acetate/acetone) to give the title compound (572 mg, 75% yield).

LC-MS (Method 2): $R_t$=0.95 min; MS (ESIpos): m/z=590 [M+H]$^+$ $^1$H-NMR (400 MHz, DMSO-d6) δ[ppm]: 0.785 (2.94), 0.804 (6.78), 0.823 (3.08), 1.154 (3.02), 1.172 (6.36), 1.189 (3.63), 1.208 (0.88), 1.220 (0.78), 1.231 (0.76), 1.248 (0.44), 1.328 (0.43), 1.987 (10.21), 2.112 (0.69), 2.130 (1.19), 2.139 (0.46), 2.149 (1.11), 2.158 (1.15), 2.168 (0.73), 2.178 (1.52), 2.195 (1.53), 2.214 (1.15), 2.234 (0.43), 2.331 (0.50), 2.518 (2.83), 2.522 (1.68), 2.673 (0.47), 3.124 (0.68), 3.138 (0.65), 3.150 (0.45), 3.258 (1.10), 3.278 (1.87), 3.297 (1.42), 3.565 (4.34), 3.847 (16.00), 3.999 (0.75), 4.016 (2.20), 4.035 (2.11), 4.053 (0.72), 4.168 (1.05), 4.184 (2.30), 4.189 (2.80), 4.221 (2.42), 4.246 (0.53), 4.263 (0.44), 4.268 (0.43), 4.420 (2.17), 4.451 (1.76), 6.845 (1.17), 6.851 (1.21), 6.861 (1.12), 6.867 (1.28), 7.189 (3.65), 7.210 (3.71), 7.357 (0.77), 7.363 (0.89), 7.379 (1.22), 7.386 (1.34), 7.402 (1.12), 7.408 (0.97), 7.424 (2.08), 7.434 (2.46), 7.440 (5.35), 7.454 (0.46), 7.640 (1.40), 7.646 (1.50), 7.666 (1.43), 7.672 (1.47), 7.717 (3.11), 7.739 (2.80), 8.225 (1.26), 8.239 (1.29), 8.248 (1.28), 8.263 (1.20).

The title compound (570 mg) was separated into enantiomers by preparative chiral HPLC to give enantiomer 1 (270 mg, see Example 37) and enantiomer 2 (255 mg, see Example 38).

437

Preparative Chiral HPLC Method:

Instrument: Labomatic HD5000, Labocord-5000; Gilson GX-241, Labcol Vario 4000, Column: Amylose SA 5μ 250×30 mm; Eluent A: Hexane+0.1 Vol-% Diethylamine (99%); Eluent B: Ethanol; Isokratic: 75% A+25% B; Flow 50.0 mL/min; UV 254 nm Analytical Chiral HPLC Method:

Instrument: Agilent HPLC 1260; Column: Amylose SA 3μ 100×4.6 mm; Eluent A: Hexane+0.1 Vol-% Diethylamine (99%); Eluent B: Ethanol; Isokratic: 75% A+25% B; Flow 1.4 mL/min; Temperature: 25° C.; DAD 254 nm Example 37

(+)-4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (Enantiomer 1)

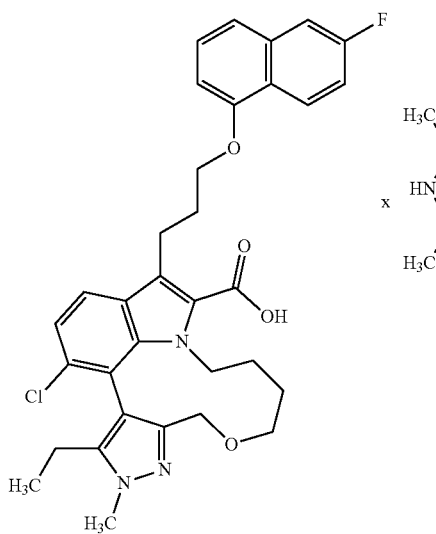

For the preparation of the racemic title compound see Example 36. Separation of enantiomers by preparative chiral HPLC (method see Example 36) gave the title compound (270 mg).

Analytical Chiral HPLC (method see Example 36): $R_t$=2.91 min.

Specific Optical Rotation (Method O1): +9.4° (c=10 mg/mL, DMSO)

Water was added to the obtained material. The mixture was dried by lyophilization and further purified by flash chromatography twice using silica gel (first time: gradient dichloromethane/acetone, second time: dichloromethane/ethanol). The obtained material was triturated with a mixture of ethyl acetate and hexane and stirred for 15 minutes at rt. The solid material was isolated by decantation, was washed with hexane and dried. Water was added to the obtained material and the mixture was dried by lyophilization to give 121 mg of the title compound.

LC-MS (Method 2): $R_t$=0.92 min; MS (ESIpos): m/z=590 [M+H]$^+$

438

$^1$H-NMR (400 MHz, DMSO-d6) δ[ppm]: 0.791 (2.32), 0.810 (5.39), 0.829 (2.45), 1.132 (7.02), 1.150 (16.00), 1.168 (7.39), 1.230 (0.45), 1.307 (0.47), 2.129 (0.52), 2.147 (1.31), 2.151 (1.26), 2.171 (1.61), 2.193 (1.65), 2.210 (1.02), 2.332 (0.68), 2.518 (3.57), 2.523 (2.45), 2.836 (1.81), 2.854 (5.80), 2.872 (5.46), 2.890 (1.71), 3.112 (0.61), 3.125 (0.55), 3.137 (0.44), 3.150 (0.40), 3.184 (0.58), 3.202 (1.26), 3.218 (1.29), 3.235 (0.68), 3.250 (0.50), 3.700 (0.50), 3.840 (11.53), 4.141 (0.58), 4.157 (1.39), 4.171 (1.42), 4.182 (1.99), 4.195 (0.44), 4.213 (2.02), 4.383 (2.07), 4.414 (1.79), 6.819 (0.97), 6.824 (1.02), 6.836 (0.98), 6.840 (1.03), 7.072 (2.02), 7.093 (2.08), 7.353 (0.58), 7.360 (0.66), 7.376 (1.02), 7.382 (1.49), 7.398 (0.89), 7.404 (2.05), 7.419 (3.23), 7.438 (0.45), 7.558 (1.45), 7.578 (1.32), 7.630 (1.11), 7.636 (1.15), 7.656 (1.11), 7.662 (1.10), 8.240 (0.95), 8.255 (1.02), 8.263 (0.98), 8.278 (0.92).

Example 38

(−)-4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (Enantiomer 2)

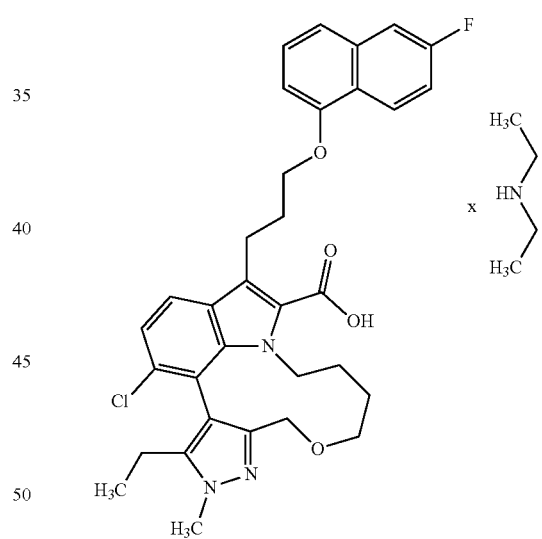

For the preparation of the racemic title compound see Example 36. Separation of enantiomers by preparative chiral HPLC (method see Example 36) gave the title compound (255 mg).

Analytical Chiral HPLC (method see Example 36): $R_t$=5.92 min.

LC-MS (Method 2): $R_t$=0.93 min; MS (ESIpos): m/z=590 [M+H]$^+$

Specific Optical Rotation (Method O1): −8.6° (c=10 mg/mL, DMSO)

$^1$H-NMR (400 MHz, DMSO-d6) δ[ppm]: 0.791 (2.75), 0.797 (0.71), 0.810 (6.69), 0.821 (0.73), 0.828 (2.81), 1.124

(7.32), 1.142 (16.00), 1.160 (7.45), 1.300 (0.47), 1.317 (0.42), 2.130 (0.60), 2.148 (1.55), 2.171 (2.02), 2.190 (1.84), 2.208 (1.08), 2.327 (1.47), 2.331 (1.08), 2.336 (0.47), 2.518 (5.64), 2.523 (3.83), 2.669 (1.52), 2.673 (1.10), 2.678 (0.50), 2.826 (1.78), 2.844 (5.32), 2.862 (5.35), 2.881 (1.60), 3.111 (0.66), 3.124 (0.58), 3.136 (0.47), 3.178 (0.60), 3.195 (1.31), 3.211 (1.31), 3.228 (0.66), 3.243 (0.47), 3.693 (0.47), 3.840 (14.92), 4.132 (0.42), 4.140 (0.63), 4.156 (1.52), 4.171 (1.57), 4.182 (2.15), 4.195 (0.47), 4.213 (2.23), 4.381 (2.12), 4.412 (1.81), 6.820 (1.13), 6.825 (1.15), 6.837 (1.10), 6.841 (1.18), 7.068 (1.70), 7.089 (1.78), 7.354 (0.76), 7.361 (0.84), 7.376 (1.18), 7.383 (1.76), 7.399 (1.02), 7.405 (2.44), 7.421 (3.54), 7.439 (0.47), 7.551 (1.18), 7.573 (1.08), 7.630 (1.34), 7.636 (1.34), 7.656 (1.34), 7.663 (1.29), 8.241 (1.15), 8.256 (1.21), 8.264 (1.15), 8.279 (1.13).

Example 39

(rac)-4-chloro-3-ethyl-7-{3-[(6-fluoronaphthalen-1-yl)oxy]propyl}-1,14-dimethyl-10,11,12,13,14,15-hexahydro-1H-pyrazolo[3',4':8,9][1,6]diazacycloundecino[10,11,1-hi]indole-8-carboxylic acid

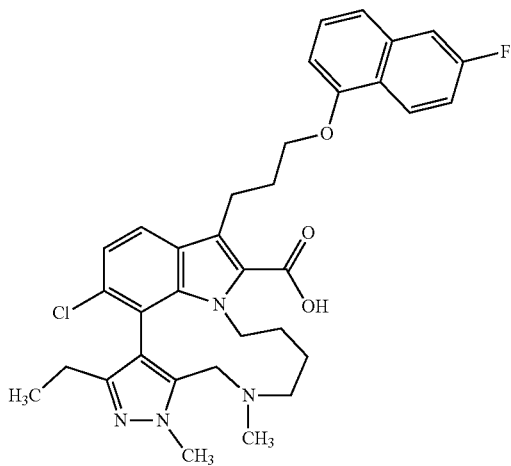 [SMILES: CCc1nn(C)c2c1-c1c(Cl)ccc3c(CCCOc4cccc5cc(F)ccc45)c(C(=O)O)n(c13)CCCCN(C)C2]

Ethyl-4-chloro-3-ethyl-7-{3-[(6-fluoronaphthalen-1-yl)oxy]propyl}-1,14-dimethyl-10,11,12,13,14,15-hexahydro-1H-pyrazolo[3',4':8,9][1,6]diazacycloundecino[10,11,1-hi]indole-8-carboxylate (see Intermediate 76, 395 mg) was dissolved in 10 mL THF and 9.1 mL ethanol and treated with the lithium hydroxide-solution in water (14 mL, 1.0 M, 14 mmol). It was stirred at 60° C. under nitrogen atmosphere for 4 hours. The reaction mixture was concentrated under reduced pressure. The pH was adjusted to 5 by addition of acetic acid. Then the aqueous layer was extracted with dichloromethane/isopropanole (7:3) twice. The combined organic layers were washed with water and brine once, filtered through a silicone coated filter and dried under reduced pressure. The crude product was purified by HPLC to provide the 97% pure target compound: 184 mg.

LC-MS (Method 2): $R_t$=0.93 min; MS (ESIpos): m/z=604 [M+H]$^+$ $^1$H-NMR (400 MHz, DMSO-d6): δ [ppm]=0.68-0.80 (m, 1H), 0.85 (t, 3H), 0.90-1.02 (m, 1H), 1.05-1.16 (m, 1H), 1.21-1.35 (m, 1H), 1.87-2.24 (m, 8H), 2.37-2.47 (m, 1H), 3.08-3.30 (m, 3H), 3.68 (br d, 1H), 3.84-3.98 (m, 4H), 4.20 (t, 2H), 4.46-4.65 (m, 1H), 6.87 (dd, 1H), 7.21 (d, 1H), 7.31-7.49 (m, 3H), 7.66 (dd, 1H), 7.76 (d, 1H), 8.27 (dd, 1H), 13.30 (br s, 1H).

The title compound (184 mg) was separated into enantiomers by preparative chiral HPLC to provide enantiomer 1 (56 mg, see Example 40) and enantiomer 2 (57 mg, see Example 41).

Preparative Chiral HPLC Method:
Instrument: Sepiatec: Prep SFC100; Column: Chiralpak IG 5 μm 250×30 mm; Eluent A: CO$_2$,
Eluent B: Ethanol+0.2 Vol-% aqueous ammonia (32%); Isokratic: 21% B; Flow 100.0 mL/min
Temperature: 40° C.; BPR: 150 bar; MWD @ 220 nm
Analytical Chiral HPLC Method:
Instrument: Agilent: 1260, Aurora SFC-Modul; Column: Chiralpak IG 5 μm 100×4.6 mm; Eluent A: CO$_2$, Eluent B: Ethanol+0.2 Vol-% aqueous ammonia (32%); Isokratic: 21% B; Flow 4.0 mL/min; Temperature: 37.5° C.; BPR: 100 bar; MWD @ 220 nm Example 40

4-chloro-3-ethyl-7-{3-[(6-fluoronaphthalen-1-yl)oxy]propyl}-1,14-dimethyl-10,11,12,13,14,15-hexahydro-1H-pyrazolo[3',4':8,9][1,6]diazacycloundecino[10,11,1-hi]indole-8-carboxylic acid
(Enantiomer 1)

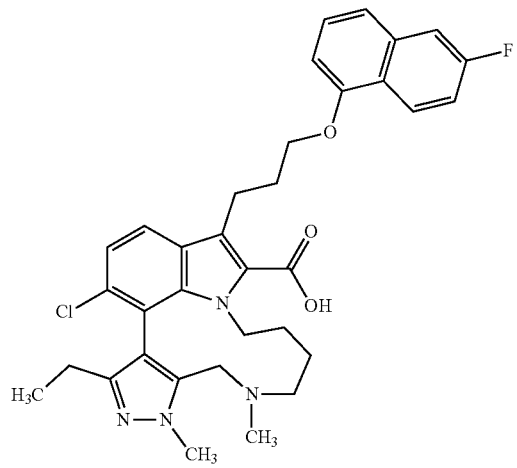 [SMILES: CCc1nn(C)c2c1-c1c(Cl)ccc3c(CCCOc4cccc5cc(F)ccc45)c(C(=O)O)n(c13)CCCCN(C)C2]

For the preparation of the racemic title compound see Example 39. Separation of enantiomers by preparative chiral HPLC (method see Example 39) provided the target compound (56 mg).

Analytical Chiral HPLC (method see Example 39): $R_t$=1.72 min.

Specific Optical Rotation (Method O1): 46.5° (c=10 mg/mL, chloroform)

$^1$H-NMR (500 MHz, DMSO-d6) δ[ppm]=0.71-0.80 (m, 1H), 0.86 (t, 3H), 0.92-1.01 (m, 1H), 1.03-1.13 (m, 1H), 1.31 (br dd, 1H), 1.88-1.98 (m, 1H), 2.01-2.27 (m, 8H), 2.37-2.47 (m, 1H), 3.15 (d, 1H), 3.20-3.28 (m, 1H), 3.29-3.41 (m, 1H), 3.67 (d, 1H), 3.81-3.95 (m, 4H), 4.20 (t, 2H), 4.51-4.65 (m, 1H), 6.86 (dd, 1H), 7.20 (d, 1H), 7.31-7.48 (m, 3H), 7.65 (dd, 1H), 7.73 (d, 1H), 8.27 (dd, 1H).

Example 41

4-chloro-3-ethyl-7-{3-[(6-fluoronaphthalen-1-yl)oxy]propyl}-1,14-dimethyl-10,11,12,13,14,15-hexahydro-1H-pyrazolo[3',4':8,9][1,6]diazacycloundecino[10,11,1-hi]indole-8-carboxylic acid (Enantiomer 2)

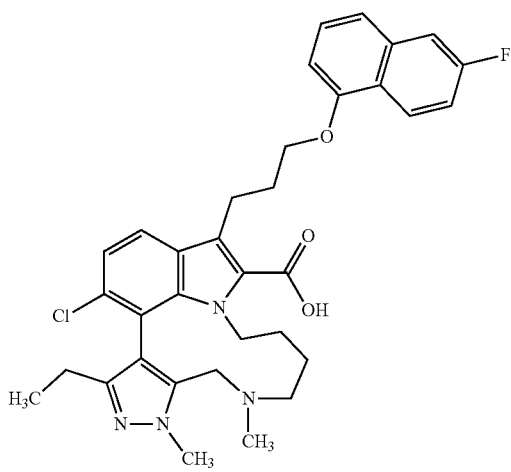 [SMILES: CCc1nn(C)c2c1-c1c(Cl)ccc3c(CCCOc4cccc5cc(F)ccc45)c(C(=O)O)n(c13)CCCCN(C)C2]

For the preparation of the racemic title compound see Example 39. Separation of enantiomers by preparative chiral HPLC (method see Example 39) provided the target compound (57 mg).

Analytical Chiral HPLC (method see Example 39): $R_t$=3.53 min.

Specific Optical Rotation (Method O1): −40.6° (c=10 mg/mL, chloroform)

$^1$H-NMR (500 MHz, DMSO-d6) δ[ppm]=0.68-0.78 (m, 1H), 0.86 (t, 3H), 0.92-1.01 (m, 1H), 1.04-1.14 (m, 1H), 1.27-1.38 (m, 1H), 1.94 (br t, 1H), 2.00-2.26 (m, 8H), 2.37-2.47 (m, 1H), 3.15 (d, 1H), 3.19-3.28 (m, 1H), 3.29-3.38 (m, 1H), 3.66 (d, 1H), 3.84-3.94 (m, 4H), 4.20 (t, 2H), 4.51-4.64 (m, 1H), 6.86 (dd, 1H), 7.19 (d, 1H), 7.27-7.49 (m, 3H), 7.65 (dd, 1H), 7.73 (d, 1H), 8.27 (dd, 1H).

Example 42

(rac)-(11Z)-4-chloro-3-ethyl-14-methyl-1-[2-(morpholin-4-yl)ethyl]-7-{3-[(naphthalen-1-yl)oxy]-propyl}-10,13,14,15-tetrahydro-1H-pyrazolo[3',4':8,9][1,6]diazacycloundecino[10,11,1-hi]indole-8-carboxylic acid

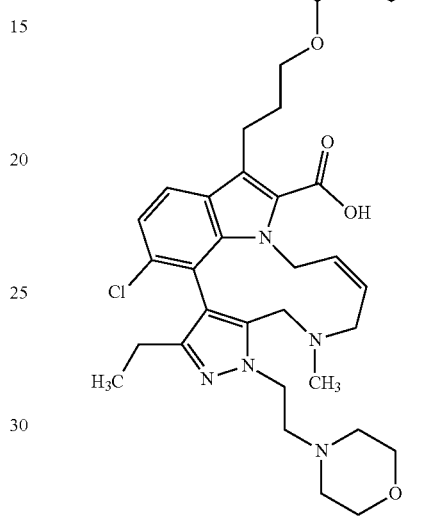

(Rac)-ethyl-(11Z)-4-chloro-3-ethyl-14-methyl-1-[2-(morpholin-4-yl)ethyl]-7-{3-[(naphthalen-1-yl)oxy]propyl}-10,13,14,15-tetrahydro-1H-pyrazolo[3',4':8,9][1,6]diazacycloundecino[10,11,1-hi]indole-8-carboxylate (see Intermediate 78, 90.0 mg, 127 μmol) was dissolved in a mixture of 6 mL of ethanol and 3 mL of THF and aqueous lithium hydroxide solution (2.2 mL, 1.0 M, 2.2 mmol) was added. The mixture was stirred at 45° C. for three days and was concentrated under reduced pressure. The crude material was purified by flash chromatography using silica gel (gradient dichloromethane/ethanol) to give the title compound (62 mg, 70% yield).

LC-MS (Method 2): $R_t$=1.00 min; MS (ESIpos): m/z=682 [M+H]$^+$ $^1$H-NMR (400 MHz, DMSO-d6) δ[ppm]: 0.756 (6.85), 0.775 (16.00), 0.794 (7.31), 1.035 (3.72), 1.052 (9.15), 1.070 (3.99), 1.968 (1.35), 1.984 (3.29), 1.987 (3.35), 2.003 (3.16), 2.006 (2.98), 2.022 (1.04), 2.220 (1.35), 2.235 (1.78), 2.255 (1.38), 2.272 (0.55), 2.327 (1.87), 2.331 (1.50), 2.336 (0.89), 2.357 (15.08), 2.371 (2.03), 2.388 (1.75), 2.400 (2.43), 2.411 (1.35), 2.518 (7.28), 2.523 (4.98), 2.669 (1.87), 2.673 (1.50), 2.678 (0.98), 2.690 (0.61), 2.696 (0.61), 2.708 (1.23), 2.721 (0.98), 2.727 (1.11), 2.739 (0.71), 2.772 (0.71), 2.790 (1.66), 2.808 (1.50), 2.821 (1.20), 2.840 (1.47), 2.957 (1.01), 2.988 (1.20), 3.025 (0.71), 3.141 (2.24), 3.174 (2.33), 3.300 (2.86), 3.406 (0.40), 3.423 (0.71), 3.433 (0.71), 3.441 (0.68), 3.451 (0.64), 3.556 (4.98), 3.568 (8.91), 3.579 (4.85), 3.677 (2.15), 3.710 (1.97), 4.193 (2.00), 4.208 (4.02), 4.223 (1.90), 4.242 (0.61), 4.255 (0.71), 4.260 (0.74), 4.274 (1.11), 4.288 (0.83), 4.294 (0.89), 4.307 (0.61), 4.357 (0.43), 4.493 (0.71), 4.518 (1.20), 4.533 (2.24), 4.550 (1.20), 4.559 (1.32), 4.566 (1.29), 4.584 (0.52), 4.733 (0.80), 4.762 (1.38), 4.792

(0.71), 4.993 (1.17), 5.031 (1.04), 5.258 (0.49), 5.277 (0.89), 5.306 (0.46), 6.881 (2.61), 6.899 (2.79), 7.223 (5.50), 7.245 (5.44), 7.364 (2.09), 7.384 (3.75), 7.403 (3.13), 7.442 (3.90), 7.463 (2.24), 7.471 (1.20), 7.484 (2.18), 7.487 (2.18), 7.491 (1.17), 7.504 (2.61), 7.507 (3.50), 7.511 (2.64), 7.524 (1.20), 7.527 (2.21), 7.531 (2.33), 7.544 (1.17), 7.548 (0.92), 7.751 (4.27), 7.772 (3.96), 7.850 (2.40), 7.870 (2.46), 7.873 (2.06), 8.161 (2.15), 8.165 (2.21), 8.182 (1.84), 8.184 (2.09).

The title compound (56 mg) was separated into enantiomers by preparative chiral HPLC to give enantiomer 1 (22 mg, see Example 43) and enantiomer 2 (21 mg, see Example 44).

Preparative Chiral HPLC Method:

Instrument: Sepiatec: Prep SFC100; Column: Chiralpak IG 5 μm 250×30 mm; Eluent A: $CO_2$, Eluent B: Ethanol+0.2 Vol-% aqueous ammonia (32%); Isokratic: 30% B; Flow 100.0 mL/min Temperature: 40° C.; BPR: 150 bar; MWD @ 220 nm Analytical Chiral HPLC Method:

Instrument: Agilent: 1260, Aurora SFC-Modul; Column: Chiralpak IG 5 μm 100×4.6 mm; Eluent A: $CO_2$, Eluent B: Ethanol+0.2 Vol-% aqueous ammonia (32%); Isokratic: 30% B; Flow 4.0 mL/min; Temperature: 37.5° C.; BPR: 100 bar; MWD @ 220 nm

Example 43

(11Z)-4-chloro-3-ethyl-14-methyl-1-[2-(morpholin-4-yl)ethyl]-7-{3-[(naphthalen-1-yl)oxy]propyl}-10,13,14,15-tetrahydro-1H-pyrazolo[3',4':8,9][1,6]diazacycloundecino[10,11,1-hi]indole-8-carboxylic acid-ammonia salt (Enantiomer 1)

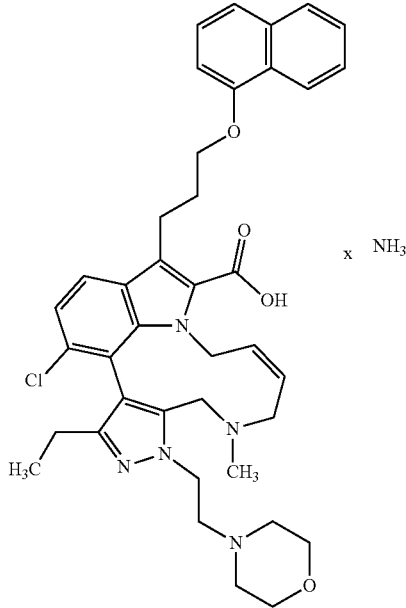

For the preparation of the racemic title compound see Example 42. Separation of enantiomers by preparative chiral HPLC (method see Example 42) gave the title compound (22 mg).

Analytical Chiral HPLC (method see Example 42): $R_t$=2.10 min.

LC-MS (Method 2): $R_t$=0.99 min; MS (ESIpos): m/z=682 $[M+H]^+$ $^1$H-NMR (400 MHz, DMSO-d6) δ[ppm]: 0.755 (6.72), 0.774 (15.16), 0.793 (7.09), 0.814 (0.75), 0.821 (0.75), 0.840 (0.51), 0.854 (0.56), 0.864 (0.75), 0.881 (0.56), 0.904 (0.65), 1.035 (0.47), 1.052 (0.93), 1.070 (0.56), 1.142 (0.42), 1.157 (0.42), 1.231 (1.26), 1.964 (1.31), 1.982 (3.22), 1.986 (3.17), 2.001 (3.03), 2.005 (2.89), 2.019 (1.07), 2.214 (1.63), 2.230 (2.24), 2.249 (1.63), 2.327 (2.99), 2.331 (2.38), 2.336 (1.49), 2.354 (16.00), 2.369 (2.33), 2.386 (2.10), 2.399 (2.94), 2.409 (1.73), 2.518 (13.67), 2.522 (8.82), 2.539 (2.05), 2.669 (2.94), 2.673 (2.43), 2.692 (0.79), 2.705 (1.45), 2.723 (1.21), 2.737 (0.84), 2.769 (0.84), 2.787 (1.87), 2.805 (1.77), 2.818 (1.45), 2.838 (1.73), 2.958 (1.17), 2.989 (1.40), 3.025 (0.84), 3.146 (2.47), 3.179 (2.66), 3.283 (3.17), 3.302 (5.92), 3.428 (0.65), 3.445 (0.56), 3.555 (5.64), 3.566 (9.89), 3.578 (5.41), 3.667 (2.33), 3.700 (2.10), 4.187 (2.29), 4.203 (4.48), 4.218 (2.15), 4.241 (0.70), 4.259 (0.84), 4.273 (1.26), 4.293 (1.03), 4.305 (0.70), 4.456 (0.70), 4.483 (0.93), 4.495 (0.93), 4.521 (1.21), 4.532 (1.63), 4.548 (1.12), 4.566 (1.21), 4.584 (0.56), 4.752 (0.84), 4.782 (1.49), 4.807 (0.79), 5.050 (1.03), 5.088 (0.93), 5.244 (0.61), 5.263 (1.03), 5.292 (0.56), 6.875 (2.85), 6.894 (3.03), 7.190 (3.13), 7.212 (3.27), 7.359 (1.91), 7.379 (3.83), 7.399 (3.08), 7.438 (4.15), 7.459 (2.38), 7.466 (1.07), 7.469 (1.12), 7.483 (2.29), 7.486 (2.24), 7.504 (3.73), 7.508 (3.59), 7.524 (2.29), 7.528 (2.43), 7.541 (1.12), 7.545 (0.93), 7.707 (2.38), 7.728 (2.15), 7.849 (2.66), 7.867 (2.61), 7.870 (2.19), 8.168 (2.80), 8.187 (2.24).

Example 44

(11Z)-4-chloro-3-ethyl-14-methyl-1-[2-(morpholin-4-yl)ethyl]-7-{3-[(naphthalen-1-yl)oxy]propyl}-10,13,14,15-tetrahydro-1H-pyrazolo[3',4':8,9][1,6]diazacycloundecino[10,11,1-hi]indole-8-carboxylic acid-ammonia salt (Enantiomer 2)

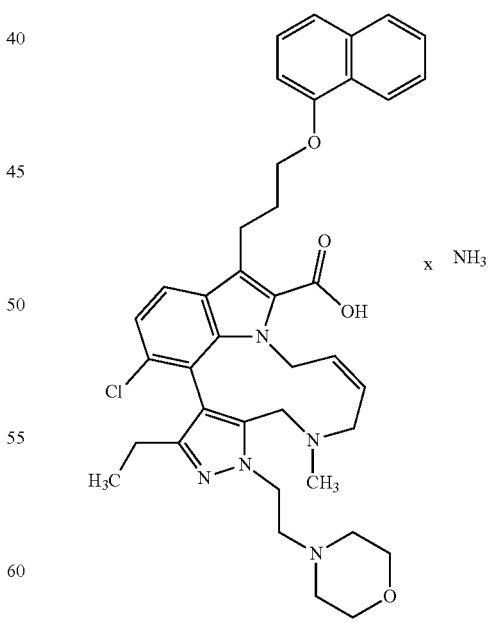

For the preparation of the racemic title compound see Example 42. Separation of enantiomers by preparative chiral HPLC (method see Example 42) gave the title compound (21 mg).

Analytical Chiral HPLC (method see Example 42): R$_t$=3.69 min.

LC-MS (Method 2): R$_t$=0.99 min; MS (ESIpos): m/z=682 [M+H]$^+$ $^1$H-NMR (400 MHz, DMSO-d6) δ[ppm]: 0.731 (0.54), 0.756 (6.88), 0.775 (16.00), 0.794 (7.17), 0.797 (2.49), 0.803 (1.07), 0.814 (1.95), 0.821 (2.05), 0.840 (1.27), 0.852 (0.93), 0.858 (1.12), 0.870 (1.07), 0.877 (0.68), 0.882 (1.12), 0.886 (1.85), 0.904 (2.15), 0.923 (0.98), 1.055 (0.68), 1.143 (0.73), 1.152 (0.83), 1.159 (0.78), 1.167 (0.93), 1.232 (1.46), 1.255 (0.49), 1.966 (1.27), 1.983 (3.12), 1.986 (3.12), 2.002 (3.07), 2.006 (2.88), 2.021 (1.02), 2.216 (1.37), 2.231 (1.95), 2.253 (1.37), 2.327 (3.02), 2.331 (2.39), 2.336 (1.37), 2.356 (15.17), 2.370 (2.20), 2.388 (1.95), 2.399 (2.63), 2.407 (1.51), 2.412 (1.61), 2.518 (11.71), 2.523 (8.24), 2.539 (3.22), 2.669 (3.02), 2.673 (2.44), 2.678 (1.22), 2.687 (0.73), 2.693 (0.73), 2.706 (1.37), 2.719 (1.07), 2.725 (1.12), 2.737 (0.83), 2.770 (0.83), 2.788 (1.76), 2.806 (1.61), 2.819 (1.37), 2.838 (1.46), 2.958 (1.07), 2.989 (1.27), 3.025 (0.78), 3.143 (2.29), 3.177 (2.39), 3.292 (2.73), 3.556 (5.12), 3.567 (9.02), 3.578 (4.88), 3.673 (2.20), 3.706 (1.95), 4.191 (2.00), 4.206 (4.00), 4.221 (1.90), 4.241 (0.63), 4.254 (0.73), 4.260 (0.78), 4.274 (1.12), 4.293 (0.93), 4.306 (0.63), 4.477 (0.68), 4.503 (0.93), 4.514 (1.46), 4.532 (1.56), 4.542 (1.27), 4.566 (1.17), 4.584 (0.54), 4.742 (0.78), 4.770 (1.37), 4.798 (0.68), 5.019 (1.02), 5.056 (0.93), 5.251 (0.54), 5.272 (0.93), 5.299 (0.49), 6.879 (2.59), 6.896 (2.78), 7.208 (4.05), 7.230 (4.20), 7.362 (2.10), 7.382 (3.71), 7.402 (3.07), 7.441 (3.90), 7.462 (2.20), 7.466 (1.12), 7.470 (1.17), 7.484 (2.15), 7.487 (2.15), 7.490 (1.12), 7.504 (2.68), 7.506 (3.12), 7.511 (2.73), 7.526 (2.20), 7.530 (2.34), 7.543 (1.17), 7.547 (0.93), 7.731 (3.02), 7.752 (2.68), 7.849 (2.44), 7.868 (2.49), 7.872 (2.00), 8.163 (2.15), 8.166 (2.20), 8.185 (2.05).

Example 45

(rac)-4-chloro-3-ethyl-14-methyl-1-[2-(morpholin-4-yl)ethyl]-7-{3-[(naphthalen-1-yl)oxy]propyl}-10,11,12,13,14,15-hexahydro-1H-pyrazolo[3',4':8,9][1,6]diazacycloundecino[10,11,1-hi]indole-8-carboxylic acid

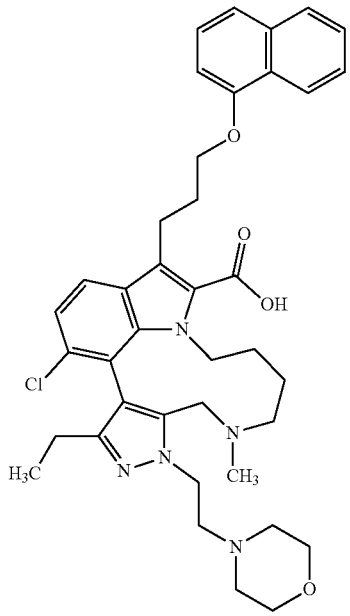 [SMILES: CCc1nn(CCN2CCOCC2)c2c1-c1c(Cl)ccc3c(CCCOc4cccc5ccccc45)c(C(=O)O)n(c13)CCCCN(C)C2]

(Rac)-ethyl-4-chloro-3-ethyl-14-methyl-1-[2-(morpholin-4-yl)ethyl]-7-{3-[(naphthalen-1-yl)oxy]-propyl}-10,11,12,13,14,15-hexahydro-1H-pyrazolo[3',4':8,9][1,6]diazacycloundecino-[10,11,1-hi]indole-8-carboxylate (see Intermediate 79, 134 mg, 188 μmol) was dissolved in a mixture of 3.1 mL of THF and 1.6 mL of ethanol and aqueous lithium hydroxide solution (1.6 mL, 1.0 M, 1.6 mmol) was added. The material was stirred at 40° C. for 4 hours and at 70° C. for 20 hours, was neutralized with a solution of hydrogen chloride (1 M) and was concentrated under reduced pressure. The crude material was purified by flash chromatography using silica gel (gradient dichloromethane/ethanol) to give the title compound (109 mg, 83% yield).

LC-MS (Method 2): R$_t$=0.96 min; MS (ESIpos): m/z=684 [M+H]$^+$ $^1$H-NMR (400 MHz, DMSO-d6) δ[ppm]: 0.717 (0.59), 0.745 (0.67), 0.830 (6.90), 0.849 (16.00), 0.868 (7.22), 0.953 (0.47), 0.979 (0.59), 1.006 (0.44), 1.035 (2.40), 1.052 (5.70), 1.070 (2.63), 1.097 (0.70), 1.127 (0.44), 1.231 (0.44), 1.321 (0.56), 1.986 (0.61), 2.016 (0.91), 2.045 (0.61), 2.057 (0.79), 2.076 (1.17), 2.093 (2.63), 2.112 (3.19), 2.130 (2.75), 2.152 (13.40), 2.166 (1.58), 2.180 (1.55), 2.198 (2.11), 2.215 (1.46), 2.232 (0.56), 2.327 (1.73), 2.331 (1.29), 2.336 (0.64), 2.364 (1.40), 2.380 (1.55), 2.393 (2.52), 2.404 (1.43), 2.415 (0.91), 2.438 (0.82), 2.518 (6.76), 2.523 (4.21), 2.669 (1.73), 2.673 (1.26), 2.678 (0.59), 2.706 (0.53), 2.711 (0.53), 2.724 (1.20), 2.737 (0.97), 2.742 (1.02), 2.755 (0.73), 2.768 (0.76), 2.787 (1.64), 2.805 (0.91), 2.818 (0.85), 3.124 (1.84), 3.157 (1.90), 3.212 (0.44), 3.231 (0.79), 3.245 (0.91), 3.264 (1.49), 3.284 (1.08), 3.381 (0.85), 3.423 (0.47), 3.433 (0.47), 3.441 (0.44), 3.450 (0.41), 3.547 (4.71), 3.559 (8.19), 3.570 (4.68), 3.719 (1.90), 3.752 (1.76), 3.912 (0.53), 3.941 (0.94), 3.969 (0.59), 4.184 (2.34), 4.200 (4.48), 4.215 (2.72), 4.230 (0.94), 4.235 (0.97), 4.248 (0.61), 4.378 (0.67), 4.396 (1.37), 4.414 (0.94), 4.430 (1.02), 4.448 (0.44), 4.547 (0.91), 4.582 (0.82), 6.880 (2.49), 6.898 (2.72), 7.187 (5.47), 7.208 (5.41), 7.364 (2.02), 7.384 (3.66), 7.403 (3.01), 7.447 (3.71), 7.467 (2.11), 7.488 (0.56), 7.492 (0.85), 7.505 (2.25), 7.509 (2.08), 7.514 (2.66), 7.521 (5.06), 7.530 (2.66), 7.533 (2.34), 7.538 (2.49), 7.550 (0.97), 7.555 (0.56), 7.740 (4.15), 7.761 (3.77), 7.854 (2.14), 7.858 (1.73), 7.863 (1.17), 7.872 (1.90), 7.878 (1.84), 8.224 (1.90), 8.230 (1.76), 8.241 (0.94), 8.246 (1.61), 8.248 (1.78).

The title compound (102 mg) was separated into enantiomers by preparative chiral HPLC to give enantiomer 1 (49 mg, see Example 46) and enantiomer 2 (53 mg, see Example 47).

Preparative Chiral HPLC Method:

Instrument: Sepiatec: Prep SFC100; Column: Chiralpak IG 5 μm 250×30 mm; Eluent A: CO$_2$, Eluent B: Ethanol+0.2 Vol-% aqueous ammonia (32%); Isokratic: 28% B; Flow 100.0 mL/min Temperature: 40° C.; BPR: 150 bar; MWD @ 220 nm Analytical Chiral HPLC Method:

Instrument: Agilent: 1260, Aurora SFC-Modul; Column: Chiralpak IG 5 µm 100×4.6 mm; Eluent A: $CO_2$, Eluent B: Ethanol+0.2 Vol-% aqueous ammonia (32%); Isokratic: 28% B; Flow 4.0 mL/min; Temperature: 37.5° C.; BPR: 100 bar; MWD @ 220 nm

Example 46

4-chloro-3-ethyl-14-methyl-1-[2-(morpholin-4-yl)ethyl]-7-{3-[(naphthalen-1-yl)oxy]propyl}-10,11,12,13,14,15-hexahydro-1H-pyrazolo[3',4':8,9][1,6]diazacycloundecino[10,11,1-hi]indole-8-carboxylic acid (Enantiomer 1)

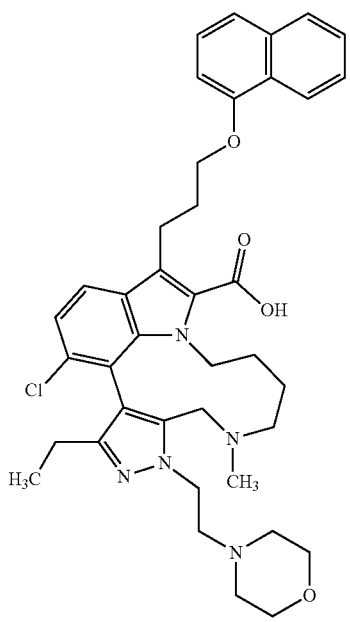 [SMILES: CCc1nn(CCN2CCOCC2)c2c1-c1c(Cl)ccc3c(CCCOc4cccc5ccccc45)c(C(=O)O)n(c13)CCCCN(C)C2]

For the preparation of the racemic title compound see Example 45. Separation of enantiomers by preparative chiral HPLC (method see Example 45) gave the title compound (49 mg).

Analytical Chiral HPLC (method see Example 45): $R_t$=1.95 min.

Water was added to the obtained material and the mixture was dried by lyophilisation. The residue was purified by flash chromatography using silica gel (gradient dichloromethane/ethanol) to give 27 mg (26% yield) of the title compound.

LC-MS (Method 2): $R_t$=0.96 min; MS (ESIpos): m/z=684 $[M+H]^+$ $^1$H-NMR (400 MHz, DMSO-d6) δ[ppm]: 0.715 (0.63), 0.745 (0.73), 0.798 (0.59), 0.815 (0.68), 0.822 (0.78), 0.833 (6.88), 0.852 (16.00), 0.870 (7.12), 0.886 (0.44), 0.905 (0.73), 0.922 (0.49), 0.966 (0.59), 1.043 (0.44), 1.066 (0.78), 1.086 (0.54), 1.105 (0.49), 1.232 (0.78), 1.352 (0.63), 1.984 (0.63), 2.012 (0.93), 2.040 (0.73), 2.059 (0.68), 2.078 (1.12), 2.095 (2.63), 2.114 (3.46), 2.132 (2.83), 2.151 (14.00), 2.167 (1.41), 2.177 (1.56), 2.195 (2.10), 2.212 (1.51), 2.230 (0.59), 2.332 (2.10), 2.336 (0.98), 2.363 (1.37), 2.378 (1.51), 2.392 (2.49), 2.413 (0.83), 2.438 (0.63), 2.518 (13.56), 2.523 (8.63), 2.673 (2.05), 2.678 (0.93), 2.709 (0.49), 2.722 (1.22), 2.735 (0.98), 2.740 (1.02), 2.753 (0.73), 2.767 (0.73), 2.786 (1.66), 2.804 (0.93), 2.817 (0.83), 3.119 (1.90), 3.152 (1.95), 3.205 (0.68), 3.220 (0.78), 3.239 (1.17), 3.258 (0.73), 3.547 (4.73), 3.558 (8.29), 3.570 (4.83), 3.713 (2.00), 3.746 (1.90), 3.760 (0.49), 3.874 (0.44), 3.906 (0.78), 3.936 (0.49), 4.180 (2.34), 4.195 (4.49), 4.211 (2.68), 4.232 (0.98), 4.245 (0.63), 4.378 (0.63), 4.396 (1.37), 4.414 (0.98), 4.430 (1.02), 4.449 (0.44), 4.573 (0.73), 4.608 (0.68), 6.876 (2.49), 6.894 (2.63), 7.161 (2.83), 7.183 (2.98), 7.360 (1.90), 7.380 (3.46), 7.400 (2.73), 7.444 (3.66), 7.464 (2.15), 7.486 (0.54), 7.490 (0.83), 7.503 (2.24), 7.508 (2.10), 7.511 (2.73), 7.520 (5.07), 7.527 (2.73), 7.531 (2.39), 7.535 (2.54), 7.548 (0.88), 7.553 (0.54), 7.704 (1.90), 7.725 (1.76), 7.853 (2.10), 7.861 (1.17), 7.870 (1.85), 7.876 (1.85), 8.223 (1.85), 8.229 (1.76), 8.240 (0.93), 8.248 (1.80).

Example 47

4-chloro-3-ethyl-14-methyl-1-[2-(morpholin-4-yl)ethyl]-7-{3-[(naphthalen-1-yl)oxy]propyl}-10,11,12,13,14,15-hexahydro-1H-pyrazolo[3',4':8,9][1,6]diazacycloundecino[10,11,1-hi]indole-8-carboxylic acid (Enantiomer 2)

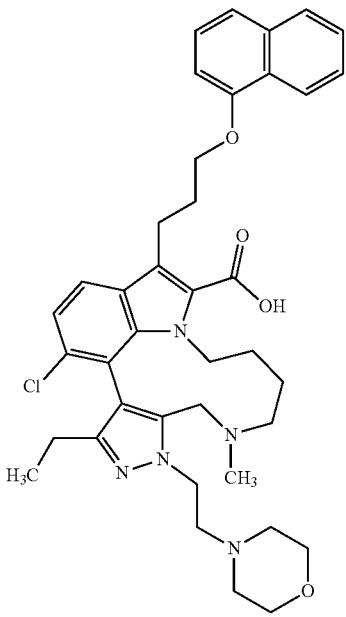 [SMILES: CCc1nn(CCN2CCOCC2)c2c1-c1c(Cl)ccc3c(CCCOc4cccc5ccccc45)c(C(=O)O)n(c13)CCCCN(C)C2]

For the preparation of the racemic title compound see Example 45. Separation of enantiomers by preparative chiral HPLC (method see Example 45) gave the title compound (53 mg). The received product was digested with water and lyophilized.

Analytical Chiral HPLC (method see Example 45): R$_t$=4.04 min.

LC-MS (Method 2): R$_t$=0.96 min; MS (ESIpos): m/z=684 [M+H]$^+$ $^1$H-NMR (400 MHz, DMSO-d6) δ[ppm]: 0.717 (0.74), 0.745 (0.79), 0.775 (0.42), 0.798 (0.95), 0.803 (0.53), 0.815 (1.11), 0.822 (1.27), 0.831 (7.10), 0.850 (16.00), 0.869 (7.31), 0.886 (0.69), 0.893 (0.58), 0.905 (1.17), 0.923 (0.64), 0.974 (0.69), 1.066 (0.74), 1.092 (0.85), 1.124 (0.58), 1.232 (1.22), 1.322 (0.69), 1.352 (0.53), 1.986 (0.69), 2.016 (1.01), 2.044 (0.69), 2.058 (0.79), 2.076 (1.27), 2.094 (2.70), 2.113 (3.44), 2.130 (2.91), 2.152 (14.36), 2.166 (1.64), 2.179 (1.64), 2.197 (2.28), 2.214 (1.59), 2.231 (0.74), 2.318 (1.06), 2.363 (1.48), 2.380 (1.70), 2.393 (2.75), 2.413 (1.01), 2.438 (0.79), 2.518 (13.09), 2.523 (9.01), 2.539 (0.74), 2.678 (1.01), 2.692 (0.42), 2.711 (0.53), 2.724 (1.27), 2.741 (1.11), 2.755 (0.79), 2.769 (0.85), 2.786 (1.75), 2.805 (1.01), 2.818 (0.90), 3.123 (1.96), 3.156 (2.07), 3.208 (0.42), 3.226 (0.74), 3.240 (0.85), 3.259 (1.38), 3.280 (0.95), 3.547 (5.03), 3.559 (8.85), 3.570 (5.09), 3.718 (2.12), 3.750 (1.96), 3.905 (0.53), 3.934 (0.95), 3.963 (0.58), 4.183 (2.44), 4.199 (4.72), 4.214 (2.97), 4.235 (1.06), 4.247 (0.69), 4.378 (0.69), 4.396 (1.43), 4.414 (1.01), 4.430 (1.11), 4.448 (0.48), 4.551 (0.95), 4.587 (0.90), 6.880 (2.60), 6.898 (2.81), 7.183 (4.61), 7.204 (4.66), 7.364 (1.91), 7.384 (3.60), 7.404 (2.81), 7.446 (3.87), 7.467 (2.23), 7.488 (0.48), 7.492 (0.79), 7.505 (2.17), 7.509 (2.12), 7.513 (2.60), 7.521 (5.03), 7.529 (2.70), 7.533 (2.49), 7.537 (2.60), 7.550 (0.95), 7.554 (0.64), 7.734 (3.44), 7.755 (3.18), 7.855 (2.23), 7.863 (1.22), 7.872 (2.01), 7.878 (2.01), 8.224 (1.91), 8.230 (1.85), 8.240 (1.01), 8.248 (1.85).

Example 48

(rac)-4-chloro-3-methyl-2-[3-(4-methylpiperazin-1-yl)propyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid

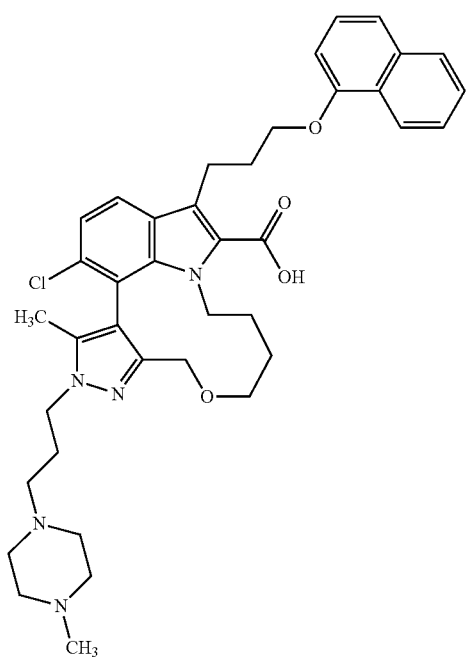 [SMILES: Cc1c2c(nn1CCCN1CCN(C)CC1)COCCCCn1c(C(=O)O)c(CCCOc3cccc4ccccc34)c3ccc(Cl)c-2c31]

(Rac)-ethyl-4-chloro-3-methyl-2-[3-(4-methylpiperazin-1-yl)propyl]-7-{3-[(naphthalen-1-yl)oxy]-propyl}-2,10,11,12,13,15-hexahydropyrazolo[4',3':9,10][1,6]oxazacycloundecino[8,7,6-hi]-indole-8-carboxylate (see Intermediate 85, 172 mg) was dissolved in a mixture of 3.7 mL of THF and 1.9 mL of ethanol and aqueous lithium hydroxide solution (1.9 mL, 1.0 M, 1.9 mmol) was added. The mixture was stirred at 70° C. for one day and at 60° C. for one day and was concentrated under reduced pressure. The crude material was purified by preparative HPLC (Method P1) to give the title compound (101 mg) as a racemic mixture.

LC-MS (Method 1): R$_t$=1.23 min; MS (ESIpos): m/z=684 [M+H]$^+$ $^1$H-NMR (400 MHz, DMSO-d6) δ[ppm]: 0.997 (0.50), 1.144 (0.64), 1.203 (0.50), 1.214 (0.55), 1.230 (0.69), 1.284 (0.47), 1.302 (0.53), 1.798 (16.00), 1.940 (0.69), 1.957 (1.02), 1.983 (0.97), 2.000 (0.77), 2.017 (0.47), 2.131 (1.08), 2.145 (1.66), 2.158 (1.85), 2.187 (12.63), 2.216 (1.49), 2.233 (0.69), 2.318 (1.27), 2.322 (1.96), 2.327 (2.46), 2.332 (2.10), 2.336 (1.55), 2.375 (1.38), 2.518 (7.21), 2.523 (4.53), 2.539 (1.74), 2.660 (0.58), 2.664 (1.19), 2.669 (1.66), 2.673 (1.24), 2.678 (0.61), 3.078 (0.55), 3.089 (0.64), 3.103 (0.99), 3.115 (0.99), 3.129 (0.80), 3.140 (0.69), 3.197 (0.72), 3.216 (1.02), 3.230 (1.24), 3.249 (1.74), 3.268 (1.66), 3.286 (1.96), 3.305 (2.10), 3.320 (2.18), 3.339 (1.77), 3.747 (0.55), 3.770 (0.86), 3.795 (0.58), 4.061 (0.58), 4.079 (0.77), 4.095 (1.22), 4.114 (0.88), 4.131 (1.13), 4.149 (0.97), 4.168 (1.55), 4.176 (2.02), 4.183 (2.10), 4.191 (1.24), 4.203 (2.57), 4.234 (2.38), 4.292 (0.58), 4.309 (0.61), 4.324 (0.50), 4.425 (2.35), 4.456 (1.96), 6.870 (2.02), 6.887 (2.16), 7.161 (4.15), 7.182 (4.01), 7.357 (1.60), 7.378 (2.87), 7.397 (2.29), 7.441 (2.93), 7.462 (1.71), 7.485 (0.41), 7.490 (0.64), 7.502 (1.82), 7.507 (1.71), 7.510 (2.38), 7.518 (3.87), 7.527 (2.38), 7.529 (2.04), 7.534 (2.04), 7.546 (0.69), 7.551 (0.41), 7.684 (3.29), 7.705 (2.96), 7.852 (1.71), 7.861 (0.88), 7.870 (1.38), 7.875 (1.46), 8.174 (2.40), 8.221 (1.52), 8.227 (1.33), 8.238 (0.72), 8.245 (1.41).

The title compound (92 mg) was separated into enantiomers by preparative chiral HPLC to give enantiomer 1 (45 mg, see Example 49) and enantiomer 2 (45 mg, see Example 50).

Preparative Chiral HPLC Method:

Instrument: Labomatic HD5000, Labocord-5000; Gilson GX-241, Labcol Vario 4000, Column: YMC Amylose SA 5μ 250×30 mm; Eluent A: Hexane+0.1 Vol-% Diethylamine (99%); Eluent B: Ethanol; Gradient: 20-50% B in 20 min; Flow 40.0 mL/min; UV 254 nm Analytical Chiral HPLC Method:

Instrument: Agilent HPLC 1260; Column: YMC Amylose SA 3μ 100×4.6 mm; Eluent A: Hexane+0.1 Vol-% Diethylamine (99%); Eluent B: Ethanol; Gradient: 20-50% B in 7 min; Flow 1.4 mL/min; Temperature: 25° C.; DAD 254 nm

Example 49

(+)-4-chloro-3-methyl-2-[3-(4-methylpiperazin-1-yl)propyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (Enantiomer 1)

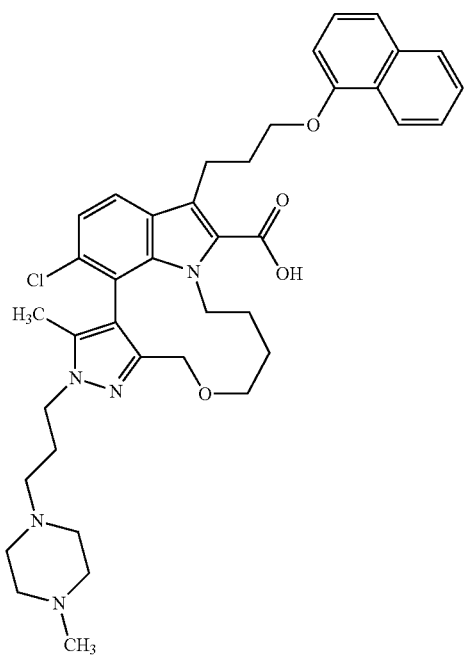 [SMILES: Cc1c2c(nn1CCCN1CCN(C)CC1)COCCCCn1c(C(=O)O)c(CCCOc3cccc4ccccc34)c3ccc(Cl)c-2c31]

For the preparation of the racemic title compound see Example 48. Separation of enantiomers by preparative chiral HPLC (method see Example 48) gave the title compound (45 mg).

Analytical Chiral HPLC (method see Example 48): $R_t$=1.48 min.

LC-MS (Method 2): $R_t$=0.88 min; MS (ESIpos): m/z=684 [M+H]$^+$

Specific Optical Rotation (Method O1): +11.3° (c=10 mg/mL, DMSO)

$^1$H-NMR (400 MHz, DMSO-d6) δ[ppm]: 1.030 (0.48), 1.135 (3.11), 1.154 (6.48), 1.172 (3.11), 1.231 (0.89), 1.292 (0.59), 1.803 (16.00), 1.919 (0.44), 1.937 (0.70), 1.953 (1.00), 1.979 (1.00), 1.995 (0.81), 2.011 (0.48), 2.123 (1.11), 2.138 (1.89), 2.165 (12.78), 2.194 (2.15), 2.211 (1.52), 2.228 (0.74), 2.322 (2.74), 2.327 (3.44), 2.331 (2.89), 2.336 (2.04), 2.518 (8.81), 2.523 (5.93), 2.539 (0.70), 2.659 (0.85), 2.665 (1.67), 2.669 (2.33), 2.673 (1.67), 2.678 (0.81), 2.866 (0.78), 2.884 (2.15), 2.902 (2.11), 2.921 (0.74), 3.101 (1.00), 3.112 (1.00), 3.126 (0.78), 3.186 (1.00), 3.202 (1.19), 3.219 (1.63), 3.249 (1.44), 3.266 (2.15), 3.285 (2.07), 3.300 (2.67), 3.319 (2.89), 3.337 (2.74), 3.738 (0.78), 3.760 (0.56), 4.058 (0.59), 4.078 (0.78), 4.093 (1.19), 4.113 (0.78), 4.130 (1.22), 4.149 (1.26), 4.168 (2.15), 4.178 (1.96), 4.193 (1.04), 4.202 (2.56), 4.233 (2.41), 4.333 (0.56), 4.351 (0.63), 4.368 (0.52), 4.410 (2.26), 4.441 (1.85), 6.865 (2.00), 6.882 (2.15), 7.126 (2.67), 7.147 (2.78), 7.353 (1.56), 7.373 (2.78), 7.393 (2.22), 7.437 (2.89), 7.458 (1.70), 7.484 (0.41), 7.488 (0.67), 7.501 (1.78), 7.505 (1.85), 7.508 (2.41), 7.517 (3.85), 7.525 (2.52), 7.532 (2.00), 7.544 (0.67), 7.636 (2.00), 7.657 (1.81), 7.851 (1.67), 7.859 (0.89), 7.868 (1.30), 7.873 (1.44), 8.222 (1.52), 8.229 (1.33), 8.238 (0.74), 8.246 (1.37).

Example 50

(−)-4-chloro-3-methyl-2-[3-(4-methylpiperazin-1-yl)propyl]-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid (Enantiomer 2)

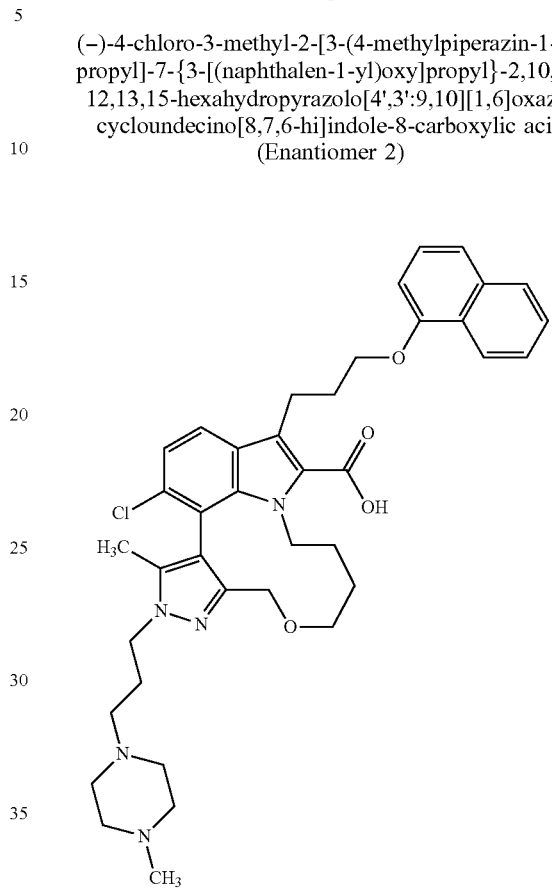

For the preparation of the racemic titled compound see Example 48. Separation of enantiomers by preparative chiral HPLC (method see Example 48) gave the titled compound (45 mg).

Analytical Chiral HPLC (method see Example 48): $R_t$=3.26 min.

LC-MS (Method 2): $R_t$=0.88 min; MS (ESIpos): m/z=684 [M+H]$^+$

Specific Optical Rotation (Method O1): −14.1° (c=10 mg/mL, DMSO)

$^1$H-NMR (400 MHz, DMSO-d6) δ[ppm]: 1.020 (0.48), 1.138 (2.99), 1.156 (6.25), 1.175 (2.80), 1.205 (0.56), 1.231 (0.83), 1.259 (0.48), 1.293 (0.56), 1.802 (16.00), 1.922 (0.43), 1.938 (0.69), 1.956 (0.99), 1.981 (0.99), 1.996 (0.77), 2.012 (0.48), 2.120 (1.12), 2.135 (1.66), 2.148 (1.79), 2.179 (12.23), 2.195 (2.32), 2.212 (1.52), 2.230 (0.75), 2.322 (2.11), 2.327 (2.59), 2.331 (2.22), 2.336 (1.63), 2.370 (1.36), 2.518 (6.17), 2.523 (4.03), 2.659 (0.61), 2.664 (1.23), 2.669 (1.66), 2.673 (1.23), 2.678 (0.59), 2.870 (0.75), 2.888 (2.11), 2.906 (2.11), 2.924 (0.69), 3.087 (0.59), 3.101 (0.93), 3.113 (0.93), 3.126 (0.72), 3.138 (0.61), 3.174 (0.56), 3.192 (0.88), 3.207 (1.04), 3.225 (1.47), 3.250 (1.20), 3.269 (1.74), 3.287 (1.47), 3.302 (1.92), 3.321 (1.90), 3.332 (1.58), 3.716 (0.48), 3.740 (0.77), 3.762 (0.51), 4.056 (0.59), 4.075 (0.72), 4.091 (1.15), 4.107 (0.64), 4.115 (0.64), 4.132 (1.12), 4.150 (1.28), 4.169 (2.16), 4.179 (1.92), 4.194 (1.07), 4.202 (2.43), 4.234 (2.32), 4.331 (0.56), 4.346 (0.61), 4.363 (0.51), 4.416 (2.24), 4.447 (1.84), 6.865 (1.98), 6.882 (2.11), 7.132 (3.05), 7.154

(3.07), 7.353 (1.50), 7.374 (2.78), 7.393 (2.24), 7.438 (2.86), 7.459 (1.68), 7.483 (0.40), 7.488 (0.64), 7.500 (1.82), 7.505 (1.74), 7.508 (2.30), 7.516 (3.82), 7.524 (2.32), 7.527 (1.98), 7.532 (1.95), 7.544 (0.67), 7.644 (2.38), 7.666 (2.11), 7.851 (1.68), 7.859 (0.88), 7.868 (1.36), 7.874 (1.42), 8.223 (1.52), 8.229 (1.34), 8.239 (0.72), 8.247 (1.39).

Example 51

(rac)-4-chloro-3-ethyl-2-methyl-7-{3-[(naphthalen-1-yl)oxy]propyl}-10,11,12,13,14,15-hexa-hydro-2H-pyrazolo[4',3':4,5]azacycloundecino[3,2,1-hi]indole-8-carboxylic acid

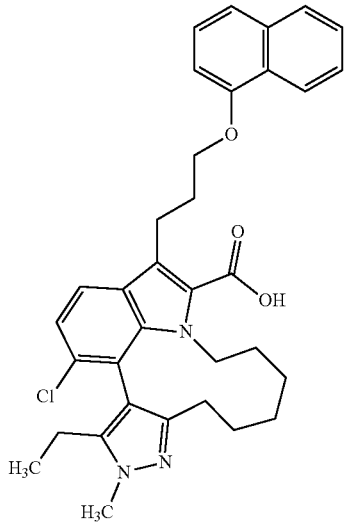 [SMILES: CCc1c2c(nn1C)CCCCCCn1c(C(=O)O)c(CCCOc3cccc4ccccc34)c3ccc(Cl)c-2c31]

(Rac)-ethyl-4-chloro-3-ethyl-2-methyl-7-{3-[(naphthalen-1-yl)oxy]propyl}-10,11,12,13,14,15-hexahydro-2H-pyrazolo[4',3':4,5]azacycloundecino[3,2,1-hi]indole-8-carboxylate (see Intermediate 90, 108 mg, 181 μmol) was dissolved in a mixture of 2.8 mL of THF and 1.4 mL of ethanol and aqueous lithium hydroxide solution (1.4 mL, 1.0 M, 1.4 mmol) was added. The mixture was stirred at 70° C. for 24 hours, was neutralized using an aqueous solution of hydrogen chloride (1 M) and was concentrated under reduced pressure. The crude material was purified by flash chromatography using silica gel (gradient dichloromethane/ethanol) to give the title compound (89 mg).

LC-MS (Method 2): $R_t$=0.98 min; MS (ESIpos): m/z=570 [M+H]$^+$ $^1$H-NMR (400 MHz, DMSO-d6) δ[ppm]: 0.546 (0.44), 0.574 (0.50), 0.797 (0.78), 0.802 (0.64), 0.814 (3.81), 0.821 (1.60), 0.833 (8.30), 0.852 (4.42), 0.871 (0.99), 0.886 (0.55), 0.889 (0.48), 0.904 (0.57), 1.001 (0.48), 1.016 (0.48), 1.035 (1.38), 1.052 (3.32), 1.064 (0.60), 1.070 (1.58), 1.082 (1.05), 1.099 (0.60), 1.125 (1.01), 1.144 (2.02), 1.163 (1.31), 1.189 (0.53), 1.232 (2.04), 1.255 (1.70), 1.273 (2.06), 1.284 (1.19), 1.291 (1.40), 1.762 (0.46), 2.171 (0.66), 2.185 (1.24), 2.201 (1.74), 2.219 (1.95), 2.237 (2.15), 2.243 (1.65), 2.256 (1.56), 2.262 (1.44), 2.275 (0.50), 2.280 (0.60), 2.318 (0.50), 2.322 (0.99), 2.327 (1.33), 2.331 (0.99), 2.336 (0.44), 2.518 (4.97), 2.523 (3.85), 2.543 (0.62), 2.659 (0.44), 2.665 (0.94), 2.669 (1.33), 2.673 (0.96), 2.678 (0.44), 3.223 (0.41), 3.239 (0.60), 3.257 (0.87), 3.285 (0.71), 3.296 (0.87), 3.305 (1.49), 3.312 (2.06), 3.361 (1.03), 3.373 (0.44), 3.379 (0.73), 3.608 (2.98), 3.825 (16.00), 3.970 (0.57), 3.997 (0.46), 4.181 (1.33), 4.196 (2.70), 4.211 (1.31), 4.532 (0.57), 4.566 (0.50), 5.792 (0.55), 6.872 (1.63), 6.889 (1.90), 7.182 (2.96), 7.203 (3.00), 7.360 (1.33), 7.380 (2.38), 7.399 (1.99), 7.440 (2.43), 7.461 (1.38), 7.474 (0.53), 7.478 (0.66), 7.491 (1.44), 7.495 (1.33), 7.507 (1.67), 7.510 (2.11), 7.512 (2.22), 7.515 (1.81), 7.526 (1.38), 7.531 (1.70), 7.543 (0.69), 7.548 (0.55), 7.723 (2.18), 7.744 (1.93), 7.849 (1.47), 7.856 (0.99), 7.868 (1.63), 7.873 (1.26), 8.186 (1.40), 8.191 (1.31), 8.206 (1.01), 8.208 (1.21), 8.210 (1.19).

The title compound (92 mg) was separated into enantiomers by preparative chiral HPLC to give enantiomer 1 (32 mg, see Example 52) and enantiomer 2 (37 mg, see Example 53).

Preparative Chiral HPLC Method:
Instrument: Labomatic HD5000, Labocord-5000; Gilson GX-241, Labcol Vario 4000, Column: YMC Chiralpak IA 5μ 250×30 mm; Eluent A: Hexane+0.1 Vol-% Diethylamine (99%); Eluent B: Ethanol; Gradient: 20-50% B in 15 min; Flow 40.0 mL/min; UV 220 nm Analytical Chiral HPLC Method:
Instrument: Agilent HPLC 1260; Column: Chiralpak IA 3μ 100×4.6 mm; Eluent A: Hexane+0.1 Vol-% Diethylamine (99%); Eluent B: Ethanol; Gradient: 20-50% B in 7 min; Flow 1.4 mL/min; Temperature: 25° C.; DAD 220 nm Example 52

(+)-4-chloro-3-ethyl-2-methyl-7-{3-[(naphthalen-1-yl)oxy]propyl}-10,11,12,13,14,15-hexahydro-2H-pyrazolo[4',3':4,5]azacycloundecino[3,2,1-hi]indole-8-carboxylic acid-N-ethylethanamine salt—Enantiomer 1

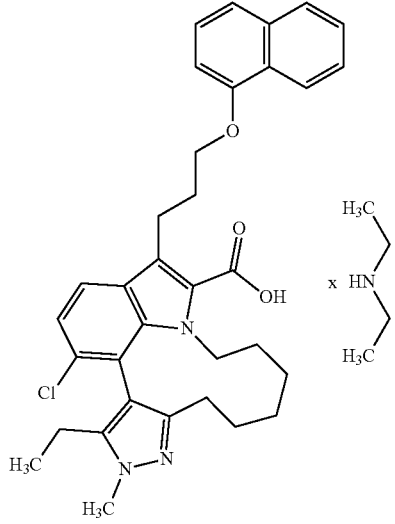

For the preparation of the racemic title compound see Example 51. Separation of enantiomers by preparative chiral HPLC (method see Example 51) gave the title compound (32 mg).

Analytical Chiral HPLC (method see Example 51): $R_t$=3.11 min.

LC-MS (Method 2): $R_t$=0.96 min; MS (ESIpos): m/z=570 [M+H]$^+$

Specific Optical Rotation (Method O1): +16.1° (c=10 mg/mL, DMSO)

$^1$H-NMR (400 MHz, DMSO-d6) δ[ppm]: 0.561 (0.50), 0.588 (0.60), 0.795 (0.70), 0.820 (4.57), 0.839 (8.72), 0.858

(3.90), 0.874 (0.50), 1.066 (0.47), 1.084 (0.67), 1.100 (0.65), 1.138 (6.39), 1.157 (13.52), 1.175 (6.46), 1.205 (0.57), 1.231 (1.59), 1.259 (1.04), 1.297 (0.70), 1.314 (0.70), 1.352 (0.60), 1.763 (0.47), 2.172 (1.09), 2.191 (1.39), 2.202 (1.44), 2.208 (1.59), 2.219 (1.44), 2.238 (1.94), 2.246 (1.59), 2.257 (1.49), 2.265 (1.44), 2.283 (0.62), 2.332 (1.07), 2.336 (0.50), 2.518 (7.38), 2.522 (4.62), 2.673 (1.07), 2.678 (0.50), 2.867 (1.66), 2.884 (5.04), 2.903 (5.07), 2.921 (1.54), 3.148 (0.45), 3.164 (0.55), 3.182 (0.75), 3.201 (0.47), 3.240 (0.60), 3.259 (1.04), 3.276 (1.02), 3.571 (0.42), 3.771 (0.60), 3.821 (16.00), 3.855 (0.52), 3.870 (0.60), 4.168 (1.42), 4.183 (2.96), 4.199 (1.42), 4.612 (0.57), 4.646 (0.52), 6.860 (1.76), 6.878 (1.91), 7.105 (1.81), 7.126 (1.91), 7.348 (1.39), 7.368 (2.56), 7.387 (2.01), 7.431 (2.56), 7.452 (1.54), 7.470 (0.50), 7.474 (0.67), 7.487 (1.52), 7.491 (1.42), 7.501 (1.71), 7.507 (2.58), 7.511 (1.74), 7.521 (1.52), 7.525 (1.71), 7.538 (0.72), 7.542 (0.52), 7.613 (1.24), 7.634 (1.12), 7.844 (1.54), 7.851 (1.02), 7.863 (1.66), 7.868 (1.37), 8.193 (1.34), 8.197 (1.39), 8.215 (1.27), 8.217 (1.29).

Example 53

(−) 4-chloro-3-ethyl-2-methyl-7-{3-[(naphthalen-1-yl)oxy]propyl}-10,11,12,13,14,15-hexahydro-2H-pyrazolo[4',3':4,5]azacycloundecino[3,2,1-hi]indole-8-carboxylic acid-N-ethylethanamine salt—Enantiomer 2

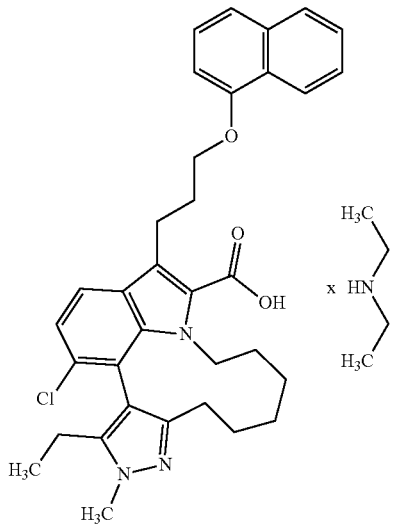

For the preparation of the racemic title compound see Example 51. Separation of enantiomers by preparative chiral HPLC (method see Example 51) gave the title compound (37 mg).

Analytical Chiral HPLC (method see Example 51): $R_t$=4.93 min.

LC-MS (Method 2): $R_t$=0.94 min; MS (ESIpos): m/z=570 $[M+H]^+$

Specific Optical Rotation (Method O1): −5.9° (c=10 mg/mL, DMSO)

$^1$H-NMR (400 MHz, DMSO-d6) δ[ppm]: 0.558 (0.51), 0.585 (0.63), 0.795 (0.71), 0.819 (4.50), 0.829 (2.08), 0.838 (8.48), 0.857 (3.99), 1.084 (0.65), 1.107 (0.60), 1.138 (5.86), 1.156 (11.96), 1.174 (5.84), 1.205 (0.65), 1.231 (1.96), 1.255 (1.00), 1.259 (1.14), 1.273 (1.14), 1.290 (0.94), 1.761 (0.54), 2.202 (1.59), 2.209 (1.62), 2.219 (1.62), 2.238 (2.08), 2.245 (1.74), 2.256 (1.65), 2.264 (1.59), 2.282 (0.71), 2.322 (1.37), 2.326 (1.82), 2.332 (1.31), 2.336 (0.68), 2.518 (7.46), 2.522 (4.58), 2.660 (0.46), 2.664 (1.11), 2.668 (1.59), 2.673 (1.11), 2.678 (0.46), 2.872 (1.45), 2.891 (4.50), 2.909 (4.36), 2.927 (1.31), 3.162 (0.40), 3.179 (0.51), 3.195 (0.71), 3.216 (0.46), 3.249 (0.63), 3.268 (1.08), 3.285 (1.11), 3.822 (16.00), 3.888 (0.54), 4.170 (1.40), 4.186 (2.90), 4.201 (1.42), 4.594 (0.57), 4.629 (0.51), 6.863 (1.77), 6.881 (1.91), 7.119 (1.68), 7.141 (1.74), 7.350 (1.34), 7.371 (2.51), 7.390 (2.08), 7.433 (2.62), 7.454 (1.51), 7.471 (0.57), 7.475 (0.65), 7.488 (1.57), 7.492 (1.37), 7.502 (1.74), 7.508 (2.45), 7.512 (1.74), 7.522 (1.48), 7.526 (1.62), 7.539 (0.68), 7.543 (0.48), 7.634 (1.08), 7.656 (1.00), 7.846 (1.59), 7.851 (0.97), 7.864 (1.71), 7.868 (1.31), 8.191 (1.42), 8.196 (1.42), 8.214 (1.31).

Example 54

(rac)-4-chloro-3-ethyl-7-{3-[(6-fluoronaphthalen-1-yl)oxy]propyl}-2-methyl-10,11,12,13,14,15-hexahydro-2H-pyrazolo[4',3':4,5]azacycloundecino[3,2,1-hi]indole-8-carboxylic acid

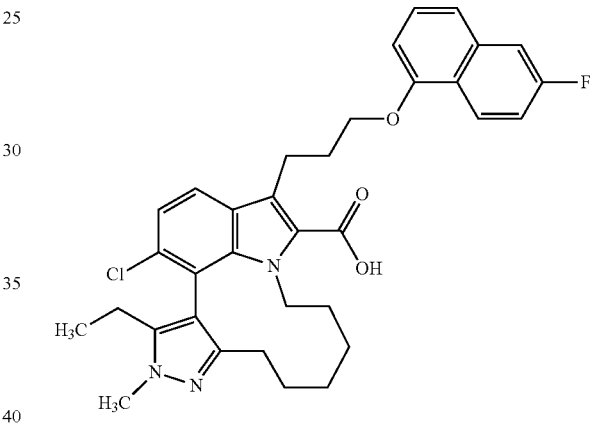

(Rac)-ethyl-4-chloro-3-ethyl-7-{3-[(6-fluoronaphthalen-1-yl)oxy]propyl}-2-methyl-10,11,12,13,14,15-hexahydro-2H-pyrazolo[4',3':4,5]azacycloundecino[3,2,1-hi]indole-8-carboxylate (see Intermediate 99, 113 mg, 183 µmol) was dissolved in a mixture of 4 mL of THF and 1 mL of ethanol and aqueous lithium hydroxide solution (370 µL, 1.0 M, 370 µmol) was added. The mixture was stirred at 70° C. overnight. Aqueous lithium hydroxide solution (370 µL, 1.0 M, 370 µmol) was added and stirring was continued at 70° C. for 14 hours. The mixture was concentrated under reduced pressure. The residue was dissolved in water and acidified using an aqueous, saturated solution of citric acid. The mixture was extracted with ethyl acetate and the combined organic layers were dried using sodium sulfate, were filtered and were concentrated under reduced pressure. The crude material was purified by flash chromatography using silica gel (gradient dichloromethane/ethyl acetate) to give the title compound (63 mg, 55% yield).

LC-MS (Method 1): Rt=1.67 min; MS (ESIpos): m/z=588 $[M+H]^+$ $^1$H-NMR (400 MHz, DMSO-d6) δ[ppm]: 0.522 (0.44), 0.550 (0.53), 0.812 (4.07), 0.831 (8.40), 0.850 (3.86), 1.154 (1.68), 1.172 (3.30), 1.190 (1.77), 1.233 (0.97), 1.907 (0.74), 1.987 (5.24), 2.162 (0.47), 2.197 (1.68), 2.203 (1.59), 2.216 (1.59), 2.233 (1.94), 2.239 (1.83), 2.252 (1.41), 2.258 (1.44), 2.276 (0.59), 2.332 (1.21), 2.336 (0.53), 2.518 (7.10), 2.522

(4.86), 2.673 (1.21), 2.678 (0.53), 3.238 (0.62), 3.256 (0.97), 3.276 (1.06), 3.295 (1.41), 3.824 (16.00), 3.960 (0.59), 3.987 (0.41), 3.999 (0.53), 4.017 (1.12), 4.034 (1.06), 4.181 (1.27), 4.196 (2.68), 4.211 (1.27), 4.522 (0.59), 4.558 (0.56), 5.758 (4.27), 6.845 (1.18), 6.853 (1.24), 6.859 (1.06), 6.867 (1.30), 7.195 (2.98), 7.216 (2.98), 7.332 (0.83), 7.339 (0.91), 7.355 (1.21), 7.362 (1.36), 7.377 (0.83), 7.383 (0.94), 7.422 (2.39), 7.428 (2.56), 7.436 (5.57), 7.636 (1.44), 7.642 (1.50), 7.661 (1.47), 7.668 (1.47), 7.726 (2.21), 7.747 (2.00), 8.198 (1.30), 8.213 (1.33), 8.221 (1.33), 8.236 (1.27).

Example 55

(rac)-4-chloro-12,12-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid

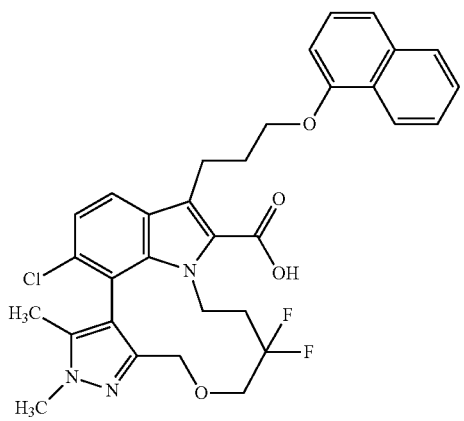 [SMILES: Cc1c2c(nn1C)COCC(F)(F)CCn1c(C(=O)O)c(CCCOc3cccc4ccccc34)c3ccc(Cl)c-2c31]

Ethyl-4-chloro-12,12-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate (see Intermediate 110, 1.50 g, 25% purity, 603 μmol) was dissolved in 14 mL of THF and 14 mL of ethanol. Lithium hydroxide in water (12 mL, 1.0 M, 12 mmol) was added and the reaction was heated to 60° C. overnight. The reaction mixture was neutralised with acetic acid (690 μL, 12 mmol) and the solvent was removed under reduced pressure. The crude residue was dissolved in ethyl acetate and washed with saturated aqueous ammonium chloride solution followed by brine, the organic phase was dried over magnesium sulfate, filtered and the solvent was removed under reduced pressure. The crude material was purified by reverse phase chromatography (C-18) with 50-100% acetonitrile with 0.1% formic acid in water with 0.1% formic acid to give 331 mg of the desired and analytically pure compound as a white solid.

LC-MS (Method 3): Rt=3.41 min; MS (ESIneg): m/z=593.7 [M−H]−

$^1$H-NMR (400 MHz, CDCl$_3$) δ [ppm]=1.39-1.55 (m, 1H), 1.85 (s, 3H), 2.06-2.19 (m, 1H), 2.27-2.37 (m, 2H), 3.36-3.53 (m, 3H), 3.64 (dd, 1H), 3.85 (t, 1H), 3.89 (s, 3H), 4.18 (t, 2H), 4.42 (d, 1H), 4.57-4.65 (m, 1H), 4.79 (d, 1H), 6.75 (d, 1H), 7.23 (t, 1H), 7.34 (t, 1H), 7.41 (d, 1H), 7.45-7.49 (m, 2H), 7.66 (d, 1H), 7.78-7.82 (m, 1H), 8.34-8.38 (m, 1H)—Acid OH signal not observed.

$^{19}$F-NMR (376 MHz, CDCl$_3$) δ [ppm]=−105.82 (dd, 1F), −90.91--91.69 (m, 1F).

Note: A singlet can be seen in the $^1$H-NMR at 1.42 ppm. This is believed to be a by-product from the di-tert-butyl azodicarboxylate used in the Mitsonobu Reaction (Intermediate 110) and is approximately 2.1% w/w.

The title compound (294 mg) was separated into enantiomers by preparative chiral HPLC to give enantiomer 1 (127 mg, see Example 56) and enantiomer 2 (122 mg, see Example 57).

Preparative Chiral HPLC Method:
Instrument: Labomatic HD5000, Labocord-5000; Gilson GX-241, Labcol Vario 4000, Column: YMC Chiralpak IA 5μ 250×30 mm; Eluent A: Hexane+0.1 Vol-% Diethylamine (99%); Eluent B: Ethanol; Isokratisch: 80% A+20% B; Flow 50.0 mL/min; UV 254 nm Analytical Chiral HPLC Method:
Instrument: Agilent HPLC 1260; Column: Chiralpak IA 3μ 100×4.6 mm; Eluent A: Hexane+0.1 Vol-% Diethylamine (99%); Eluent B: Ethanol; Isokratisch: 80% A+20% B; Flow 1.4 mL/min; Temperature: 25° C.; DAD 254 nm Example 56

4-chloro-12,12-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid-N-ethylethanamine salt—Enantiomer 1

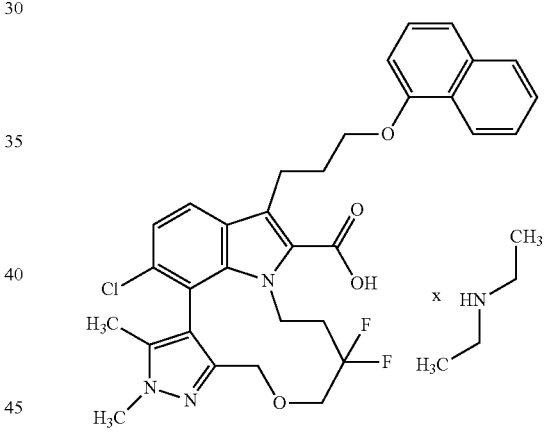

For the preparation of the racemic title compound see Example 55. Separation of enantiomers by preparative chiral HPLC (method see Example 55) gave the title compound (127 mg).

Analytical Chiral HPLC (method see Example 55): R$_t$=1.45 min.

LC-MS (Method 1): R$_t$=1.58 min; MS (ESIpos): m/z=594 [M+H]$^+$

Specific Optical Rotation (Method O1): 0.3° (c=10 mg/mL, DMSO)

$^1$H-NMR (400 MHz, DMSO-d6) δ[ppm]: 0.798 (0.46), 0.814 (0.56), 0.821 (0.51), 0.904 (0.53), 1.084 (0.49), 1.141 (7.16), 1.159 (16.00), 1.178 (7.13), 1.237 (0.44), 1.259 (0.76), 1.765 (11.61), 2.179 (0.86), 2.197 (1.33), 2.214 (0.90), 2.332 (0.43), 2.518 (2.44), 2.523 (1.53), 2.673 (0.45), 2.845 (1.90), 2.864 (6.08), 2.882 (5.83), 2.900 (1.78), 3.195 (0.43), 3.209 (0.58), 3.228 (1.01), 3.239 (0.72), 3.246 (0.74), 3.257 (1.10), 3.275 (0.95), 3.407 (0.61), 3.464 (0.45), 3.495 (0.65), 3.551 (0.54), 3.579 (0.58), 3.587 (0.65), 3.616 (0.42), 3.847 (11.73), 4.134 (0.52), 4.150 (1.32), 4.168 (1.30), 4.184

(0.50), 4.290 (1.50), 4.321 (1.68), 4.554 (0.99), 4.586 (0.79), 6.847 (1.33), 6.865 (1.42), 7.116 (2.34), 7.137 (2.41), 7.338 (0.98), 7.358 (1.82), 7.377 (1.39), 7.429 (1.90), 7.450 (1.14), 7.483 (0.43), 7.496 (1.18), 7.501 (1.15), 7.504 (1.38), 7.513 (2.46), 7.520 (1.46), 7.523 (1.24), 7.528 (1.22), 7.540 (0.46), 7.582 (1.87), 7.603 (1.68), 7.846 (1.13), 7.855 (0.58), 7.863 (0.96), 7.869 (0.95), 8.219 (1.00), 8.226 (0.91), 8.236 (0.50), 8.243 (0.91).

Example 57

4-chloro-12,12-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid-N-ethylethanamine salt—Enantiomer 2

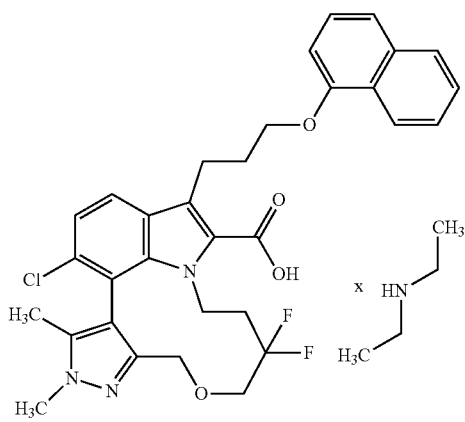

For the preparation of the racemic title compound see Example 55. Separation of enantiomers by preparative chiral HPLC (method see Example 55) gave the title compound (122 mg).

Analytical Chiral HPLC (method see Example 55): $R_t$=2.07 min.

LC-MS (Method 1): $R_t$=1.58 min; MS (ESIpos): m/z=594 [M+H]$^+$

Specific Optical Rotation (Method O1): 2.7° (c=10 mg/mL, DMSO)

$^1$H-NMR (400 MHz, DMSO-d6) δ[ppm]: 0.798 (0.44), 0.814 (0.53), 0.821 (0.47), 0.904 (0.49), 1.084 (0.57), 1.138 (7.15), 1.157 (16.00), 1.175 (7.17), 1.236 (0.44), 1.259 (0.89), 1.765 (11.71), 2.178 (0.83), 2.195 (1.28), 2.212 (0.89), 2.332 (0.57), 2.518 (3.00), 2.523 (2.03), 2.539 (1.65), 2.846 (1.85), 2.864 (5.94), 2.883 (5.76), 2.900 (1.72), 3.207 (0.53), 3.226 (0.93), 3.237 (0.62), 3.244 (0.64), 3.254 (0.99), 3.273 (0.76), 3.287 (0.92), 3.408 (0.49), 3.494 (0.58), 3.551 (0.51), 3.579 (0.56), 3.587 (0.62), 3.616 (0.40), 3.847 (11.55), 4.133 (0.50), 4.150 (1.30), 4.168 (1.29), 4.184 (0.50), 4.290 (1.51), 4.321 (1.71), 4.554 (0.96), 4.586 (0.78), 6.848 (1.32), 6.866 (1.43), 7.117 (2.03), 7.138 (2.18), 7.338 (1.03), 7.359 (1.87), 7.378 (1.42), 7.429 (1.89), 7.450 (1.15), 7.484 (0.40), 7.497 (1.15), 7.501 (1.11), 7.504 (1.42), 7.513 (2.62), 7.521 (1.48), 7.523 (1.22), 7.528 (1.30), 7.541 (0.46), 7.582 (1.55), 7.603 (1.40), 7.846 (1.11), 7.855 (0.58), 7.863 (0.93), 7.869 (0.93), 8.219 (0.99), 8.226 (0.90), 8.236 (0.49), 8.243 (0.92).

Example 58

(rac)-4-chloro-7-{3-[(6-fluoronaphthalen-1-yl)oxy]propyl}-2,3-dimethyl-14-(2,2,2-trifluoroethyl)-10,11,12,13,14,15-hexahydro-2H-pyrazolo[3',4':8,9][1,6]diazacycloundecino[10,11,1-hi]indole-8-carboxylic acid

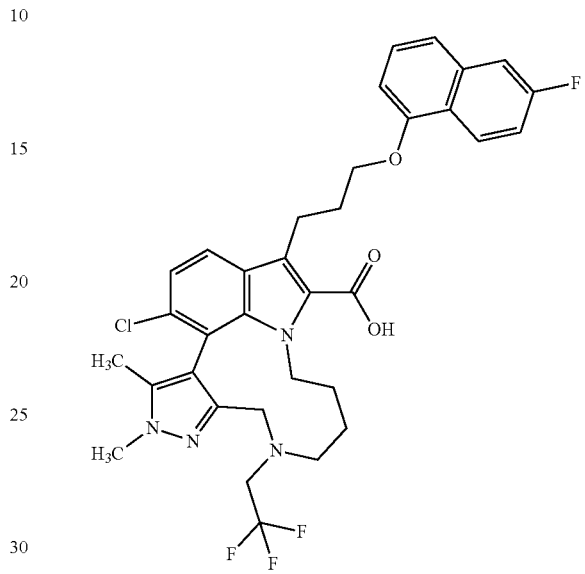

Ethyl 4-chloro-7-{3-[(6-fluoronaphthalen-1-yl)oxy]propyl}-2,3-dimethyl-14-(2,2,2-trifluoroethyl)-10,11,12,13,14,15-hexahydro-2H-pyrazolo[3',4':8,9][1,6]diazacycloundecino[10,11,1-hi]indole-8-carboxylate (see Intermediate 104, 32.0 mg) was dissolved in 760 µL THF and 680 µL ethanol and treated with aqueous lithium hydroxide-solution (1.1 mL, 1.0 M, 1.1 mmol). It was stirred at 60° C. under nitrogen atmosphere over night and at room temperature for three days. The reaction mixture was concentrated under reduced pressure. The pH was adjusted to 5 by addition of acetic acid (60 µL, 1.1 mmol). Then it was extracted three times with dichloromethane/isopropanole 7:3. The combined organic layers were washed with water and brine once, filtered through a silicone coated filter and dried under reduced pressure to provide the analytically pure target compound: 24 mg.

LC-MS (Method 2): $R_t$=0.98 min; MS (ESIpos): m/z=658 [M+H]$^+$ $^1$H-NMR (400 MHz, DMSO-d6): δ [ppm]=0.97-1.10 (m, 3H), 1.11-1.27 (m, 1H), 1.91 (s, 3H), 2.12-2.24 (m, 2H), 2.27-2.38 (m, 2H), 2.90-3.26 (m, 4H), 3.59 (d, 1H), 3.66-3.77 (m, 2H), 3.80 (s, 3H), 4.16 (t, 2H), 4.29-4.46 (m, 1H), 6.83 (dd, 1H), 7.15 (d, 1H), 7.30-7.50 (m, 3H).

The title compound (24 mg) was separated into enantiomers by preparative chiral HPLC to give enantiomer 1 (7 mg, see Example 59) and enantiomer 2 (9 mg, see Example 60).

Preparative Chiral HPLC Method:

Instrument: Sepiatec: Prep SFC100, Column: Chiralpak IG 5 µm 250×30 mm; Eluent A: Carbondioxide; Eluent B: Ethanol+0.2 Vol-% aqueous ammonia (32%); isokratic: 17% B; Flow 100 mL/min; Temperature: 40° C.; BPR: 150 bar; UV 220 nm Analytical Chiral HPLC Method:

Instrument: Agilent HPLC 1260, Aurora SFC-Modul; Column: Chiralpak IG 5 µm 100×4.6 mm; Eluent A: Carbondioxide; Eluent B: Ethanol+0.2 Vol-% aqueous ammonia (32%); Isokratic: 17% B; Flow 4.0 mL/min; Temperature: 37.5° C.; BPR: 100 bar; DAD 254 nm Example 59

4-chloro-7-{3-[(6-fluoronaphthalen-1-yl)oxy]propyl}-2,3-dimethyl-14-(2,2,2-trifluoroethyl)-10,11,12,13,14,15-hexahydro-2H-pyrazolo[3',4':8,9][1,6]diazacycloundecino[10,11,1-hi]indole-8-carboxylic acid—Enantiomer 1

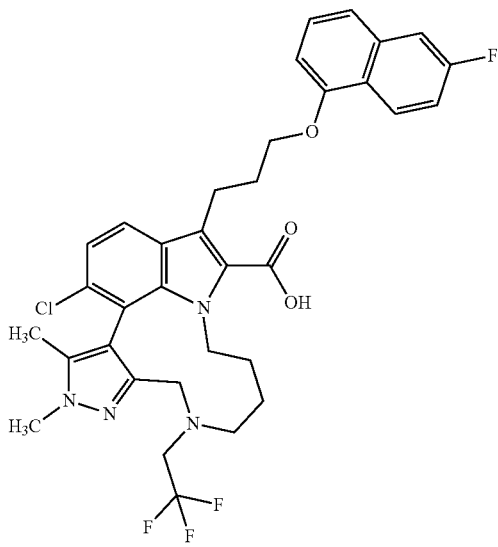 [SMILES: Cc1c2c(nn1C)CN(CC(F)(F)F)CCCCn1c(C(=O)O)c(CCCOc3cccc4cc(F)ccc34)c3ccc(Cl)c-2c31]

For the preparation of the racemic title compound see Example 58. Separation of enantiomers by preparative chiral HPLC (method see Example 58) gave the title compound (7 mg).

Analytical Chiral HPLC (method see Example 58): $R_t$=1.78 min.

$^1$H-NMR (400 MHz, DMSO-d6) δ[ppm]: 0.706 (1.13), 0.724 (2.49), 0.743 (1.29), 0.766 (0.51), 0.776 (1.58), 0.783 (1.02), 0.793 (1.77), 0.798 (2.09), 0.806 (2.03), 0.811 (1.75), 0.815 (2.01), 0.819 (1.94), 0.832 (3.08), 0.841 (3.35), 0.845 (4.21), 0.851 (6.21), 0.861 (10.22), 0.877 (6.27), 0.894 (1.47), 0.897 (1.55), 0.900 (1.50), 0.904 (1.61), 0.912 (1.55), 0.922 (0.97), 0.927 (1.09), 0.965 (2.74), 0.981 (2.22), 0.998 (1.59), 1.041 (4.23), 1.054 (1.29), 1.060 (2.99), 1.066 (1.88), 1.072 (1.34), 1.081 (1.75), 1.092 (1.35), 1.106 (8.49), 1.133 (3.94), 1.138 (4.61), 1.143 (3.87), 1.148 (4.12), 1.154 (4.19), 1.168 (1.18), 1.185 (0.68), 1.197 (1.52), 1.211 (1.77), 1.227 (1.18), 1.253 (0.63), 1.266 (0.59), 1.277 (0.51), 1.292 (0.53), 1.354 (0.55), 1.387 (0.75), 1.417 (0.88), 1.428 (0.79), 1.436 (0.95), 1.447 (1.40), 1.454 (0.77), 1.466 (1.29), 1.485 (0.50), 1.785 (14.45), 1.843 (0.46), 1.907 (0.55), 1.988 (0.47), 2.009 (1.18), 2.029 (0.55), 2.040 (1.40), 2.070 (0.46), 2.083 (0.59), 2.088 (0.49), 2.097 (0.50), 2.103 (0.83), 2.116 (0.56), 2.135 (1.09), 2.171 (1.47), 2.181 (1.79), 2.201 (2.17), 2.282 (1.05), 2.316 (2.56), 2.352 (0.51), 2.461 (0.77), 2.522 (2.18), 2.668 (1.09), 2.776 (0.70), 2.947 (0.66), 2.959 (0.54), 2.973 (0.75), 2.986 (0.96), 3.011 (0.88), 3.038 (0.50), 3.100 (0.67), 3.124 (1.22), 3.149 (1.56), 3.164 (1.59), 3.188 (1.89), 3.203 (1.77), 3.580 (2.39), 3.613 (3.26), 3.665 (2.97), 3.698 (2.28), 3.729 (1.08), 3.803 (16.00), 4.140 (1.59), 4.155 (2.90), 4.170 (1.54), 4.406 (0.60), 4.422 (0.60), 4.440 (0.56), 6.814 (1.51), 6.831 (1.58), 7.112 (2.99), 7.133 (3.14), 7.355 (0.64), 7.361 (0.77), 7.383 (1.92), 7.402 (2.48), 7.421 (4.34), 7.442 (0.77), 7.617 (2.38), 7.632 (1.94), 7.637 (3.74), 7.658 (1.56), 7.663 (1.64), 8.264 (1.05), 8.279 (1.17), 8.286 (1.14), 8.301 (0.98).

Example 60

4-chloro-7-{3-[(6-fluoronaphthalen-1-yl)oxy]propyl}-2,3-dimethyl-14-(2,2,2-trifluoroethyl)-10,11,12,13,14,15-hexahydro-2H-pyrazolo[3',4':8,9][1,6]diazacycloundecino[10,11,1-hi]indole-8-carboxylic acid—Enantiomer 2

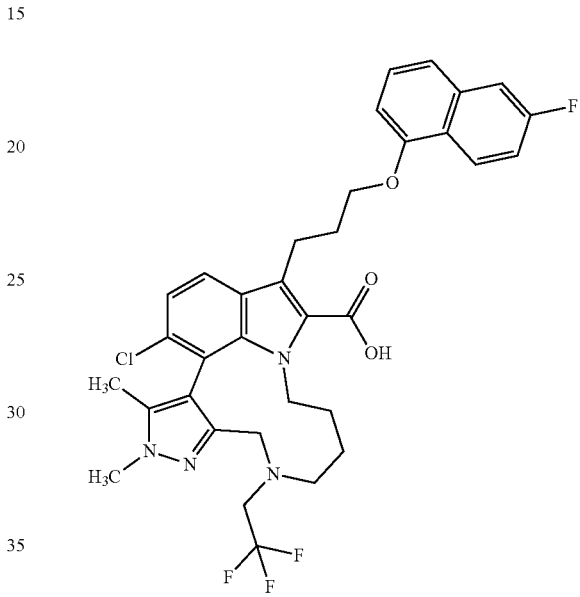

For the preparation of the racemic title compound see Example 58. Separation of enantiomers by preparative chiral HPLC (method see Example 58) gave the title compound (9 mg).

Analytical Chiral HPLC (method see Example 58): $R_t$=2.83 min.

$^1$H-NMR (400 MHz, DMSO-d6) δ[ppm]: 0.704 (1.14), 0.723 (2.69), 0.741 (1.42), 0.748 (0.48), 0.753 (0.53), 0.766 (0.81), 0.771 (1.04), 0.776 (1.45), 0.783 (1.24), 0.794 (2.41), 0.802 (2.43), 0.807 (2.87), 0.811 (2.21), 0.816 (2.48), 0.825 (2.46), 0.832 (3.60), 0.835 (3.45), 0.843 (5.48), 0.852 (10.32), 0.859 (10.07), 0.870 (4.01), 0.875 (6.29), 0.894 (1.95), 0.901 (2.18), 0.910 (2.61), 0.921 (1.50), 0.928 (1.22), 0.961 (2.36), 0.967 (3.35), 0.977 (2.00), 0.981 (2.48), 0.999 (1.75), 1.031 (5.83), 1.060 (3.40), 1.065 (2.64), 1.073 (1.42), 1.080 (1.98), 1.107 (16.00), 1.127 (5.91), 1.132 (3.35), 1.142 (6.80), 1.158 (1.22), 1.164 (1.06), 1.187 (2.26), 1.192 (2.81), 1.208 (0.79), 1.229 (1.65), 1.244 (0.94), 1.263 (0.81), 1.282 (0.61), 1.292 (0.68), 1.354 (0.68), 1.369 (0.46), 1.387 (0.99), 1.412 (1.06), 1.430 (2.21), 1.450 (2.03), 1.469 (0.84), 1.488 (0.43), 1.572 (0.43), 1.581 (0.41), 1.591 (0.46), 1.600 (0.41), 1.760 (0.48), 1.787 (13.24), 1.831 (0.63), 1.906 (0.76), 1.919 (0.43), 1.988 (0.68), 1.998 (1.60), 2.029 (1.67), 2.036 (0.71), 2.073 (5.20), 2.083 (4.74), 2.095 (1.01), 2.102 (0.56), 2.111 (0.53), 2.126 (1.22), 2.138 (0.68), 2.170 (1.55), 2.178 (1.67), 2.195 (2.38), 2.201 (2.03), 2.257 (0.99), 2.289 (1.29), 2.305 (2.08), 2.317 (2.64), 2.322 (2.66), 2.326 (2.74), 2.331 (2.54), 2.451 (0.66), 2.522 (5.12), 2.641 (0.56), 2.665 (1.55), 2.668 (1.75), 2.673 (1.32), 2.743 (1.17), 2.952 (0.61), 2.964 (0.51), 2.977 (0.68), 2.989 (0.89), 3.016 (0.81), 3.042 (0.46), 3.134 (1.22), 3.159 (1.67), 3.174 (1.72), 3.196 (1.93), 3.582 (1.62), 3.614 (2.64), 3.660 (2.46), 3.692 (1.77), 3.719 (0.84), 3.804 (15.01), 4.142 (1.42), 4.156 (2.56), 4.170 (1.39), 4.431 (0.53), 6.818 (1.34), 6.833 (1.39), 7.105 (2.69), 7.127 (2.79), 7.358 (0.68), 7.364 (0.74), 7.386 (1.80), 7.406 (2.41), 7.423 (4.61), 7.444 (0.74), 7.607 (2.00), 7.629 (2.03), 7.634 (2.00), 7.641 (1.67), 7.660 (1.57), 7.667 (1.50), 8.264 (0.94), 8.280 (1.06), 8.288 (1.04), 8.302 (0.89).

Example 61

(rac) 4-chloro-3-ethyl-7-{3-[(6-fluoronaphthalen-1-yl)oxy]propyl}-2-methyl-14-(2,2,2-trifluoroethyl)-10,11,12,13,14,15-hexahydro-2H-pyrazolo[3',4':8,9][1,6]diazacycloundecino[10,11,1-hi]indole-8-carboxylic acid

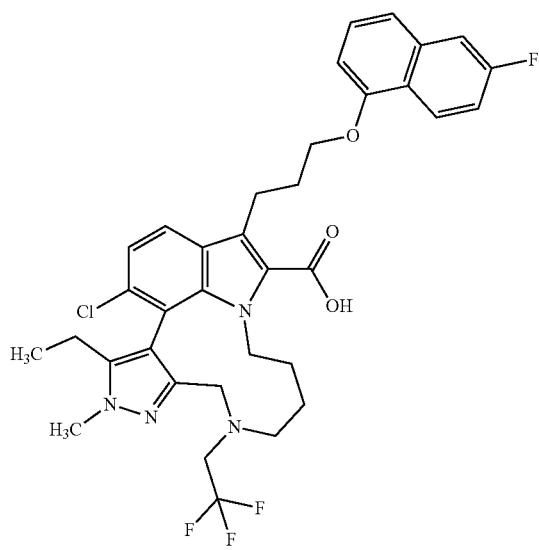 [SMILES: CCc1c2c(nn1C)CN(CC(F)(F)F)CCCCn1c(C(=O)O)c(CCCOc3cccc4cc(F)ccc34)c3ccc(Cl)c-2c31]

The saponification of (rac)-ethyl 4-chloro-3-ethyl-7-{3-[(6-fluoronaphthalen-1-yl)oxy]propyl}-2-methyl-14-(2,2,2-trifluoroethyl)-10,11,12,13,14,15-hexahydro-2H-pyrazolo[3',4':8,9][1,6]diazacycloundecino[10,11,1-hi]indole-8-carboxylate (see Intermediate 116, 46.0 mg) was performed as described in Example 55 to provide the target compound in 88% purity: 10 mg LC-MS Method 2): $R_t$=1.05 min; MS (ESIpos): m/z=673 [M+H]$^+$ $^1$H-NMR (400 MHz, DMSO-d6) δ[ppm]: 0.790 (3.27), 0.809 (7.55), 0.819 (1.27), 0.828 (3.49), 0.837 (0.56), 0.903 (0.46), 0.975 (0.44), 0.993 (0.86), 1.010 (0.66), 1.035 (8.02), 1.052 (16.00), 1.070 (9.03), 1.206 (0.71), 1.225 (1.16), 2.035 (0.83), 2.130 (0.75), 2.148 (1.61), 2.160 (1.72), 2.167 (2.00), 2.179 (2.28), 2.197 (1.85), 2.207 (1.30), 2.214 (1.08), 2.274 (0.51), 2.294 (0.59), 2.308 (0.85), 2.322 (0.65), 2.326 (0.63), 2.331 (0.43), 2.356 (0.41), 2.378 (0.68), 2.392 (0.55), 2.409 (0.46), 2.518 (1.76), 2.522 (1.21), 2.669 (0.44), 2.940 (0.40), 2.966 (0.44), 2.978 (0.70), 3.004 (0.62), 3.062 (0.71), 3.087 (0.72), 3.101 (0.51), 3.126 (0.41), 3.224 (0.50), 3.240 (0.80), 3.258 (1.12), 3.276 (1.18), 3.294 (1.57), 3.329 (2.99), 3.411 (1.25), 3.429 (3.17), 3.446 (3.12), 3.464 (1.08), 3.558 (1.46), 3.589 (1.95), 3.700 (2.06), 3.717 (0.97), 3.732 (2.51), 3.787 (0.51), 3.796 (0.49), 3.810 (0.87), 3.846 (1.11), 4.141 (1.48), 4.157 (3.03), 4.172 (1.49), 4.268 (0.68), 4.285 (0.68), 4.302 (0.66), 4.321 (0.41), 6.805 (1.58), 6.808 (1.54), 6.823 (1.70), 7.159 (3.70), 7.180 (3.81), 7.364 (0.84), 7.371 (1.01), 7.386 (2.15), 7.393 (1.66), 7.408 (2.61), 7.415 (1.18), 7.425 (2.87), 7.431 (3.13), 7.450 (0.83), 7.640 (1.62), 7.647 (1.60), 7.667 (1.66), 7.673 (1.68), 7.682 (3.10), 7.703 (2.78), 8.279 (1.36), 8.293 (1.41), 8.302 (1.35), 8.317 (1.29).

Example 62

(rac)-4-chloro-14-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylic acid

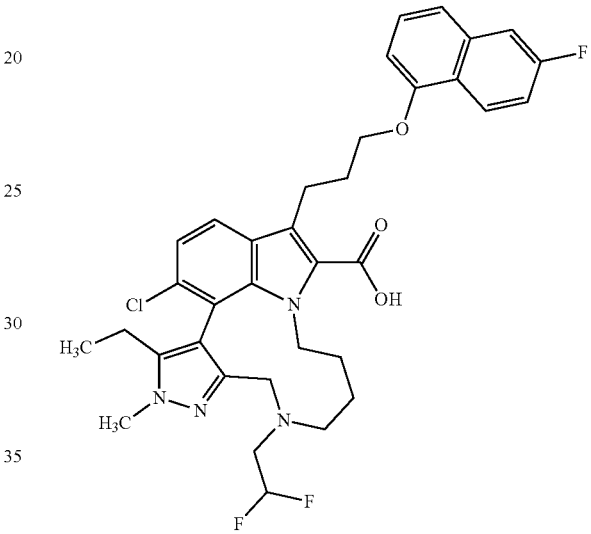

The saponification of (rac)-ethyl 4-chloro-14-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylate (see Intermediate 117, 30.0 mg) was performed as described in Example 55 to provide the target compound in 93% purity: 16 mg LC-MS Method 2): $R_t$=1.01 min; MS (ESIpos): m/z=654 [M+H]$^+$ $^1$H-NMR (400 MHz, DMSO-d6) δ[ppm]: 0.793 (3.80), 0.812 (8.86), 0.818 (2.64), 0.831 (3.76), 0.884 (0.67), 0.902 (1.29), 0.920 (0.71), 0.991 (0.94), 1.034 (8.47), 1.051 (16.00), 1.069 (8.25), 1.226 (1.42), 1.252 (0.62), 1.402 (0.76), 1.418 (0.89), 1.433 (0.58), 1.454 (0.82), 1.471 (0.75), 1.488 (0.48), 1.906 (0.49), 1.980 (0.56), 2.035 (0.41), 2.118 (0.43), 2.137 (0.95), 2.155 (2.09), 2.174 (2.84), 2.188 (3.16), 2.207 (2.52), 2.220 (7.95), 2.272 (1.09), 2.315 (1.03), 2.327 (1.22), 2.369 (0.47), 2.390 (0.41), 2.409 (0.47), 2.555 (0.66), 2.590 (0.72), 2.631 (0.57), 2.664 (1.16), 2.668 (1.16), 2.699 (0.61), 3.216 (1.09), 3.232 (2.02), 3.245 (1.45), 3.257 (1.40), 3.283 (1.24), 3.304 (2.12), 3.405 (0.88), 3.422 (1.80), 3.432 (1.90), 3.440 (1.84), 3.449 (1.73), 3.471 (1.52), 3.504 (1.85), 3.601 (2.15), 3.633 (1.52), 3.716 (0.86), 3.734 (1.13), 3.747 (7.61), 3.824 (15.97), 3.846 (1.10), 3.864 (0.76), 3.879 (0.49), 4.147 (1.70), 4.162 (3.38), 4.177 (1.65), 4.256 (0.82), 4.273 (0.82), 4.290 (0.78), 4.307 (0.44), 4.334 (1.17), 4.362 (1.71), 5.367 (0.46), 5.508 (0.91), 5.648 (0.42), 6.815 (1.68), 6.833 (1.75), 7.171 (3.66), 7.192 (3.85), 7.366 (0.90), 7.373

(1.03), 7.389 (2.05), 7.395 (1.88), 7.411 (2.99), 7.430 (4.28), 7.452 (0.83), 7.642 (1.69), 7.649 (1.67), 7.668 (1.67), 7.675 (1.63), 7.698 (3.24), 7.720 (2.92), 8.279 (1.41), 8.294 (1.49), 8.302 (1.43), 8.317 (1.29).

The title compound (325 mg) was separated into enantiomers by preparative chiral HPLC to give enantiomer 1 (112 mg, see Example 75) and enantiomer 2 (109 mg, see Example 76).

Preparative Chiral HPLC Method:
Instrument: Sepiatec: Prep SFC100, Column: Chiralpak IG 5 μm 250×30 mm; Eluent A: Carbon dioxide; Eluent B: +0.4 Vol-% Diethylamin (99%), Gradient: iscratic, 21% B; Flow 100.0 mL/min; temperature: 40° C., BPR: 150 bar, UV 254 nm.

Analytical Chiral HPLC Method:
Instrument: Agilent HPLC 1260; Column Chiralpak IG 5 μm 100×4.6 mm; Eluent A: carbon dioxide, Eluent B: 2-Propanol+0.2 Vol-% Diethylamin (99%), Gradient: isocratic 21% B; Flow 4.0 mL/min; Temperature: 37.5° C.; BPR 100 bar; DAD 254 nm.

Example 63

(9aS,11aR)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]oxazacycloundecino[8,7,6-hi]indole-14-carboxylic acid—Stereoisomer 1

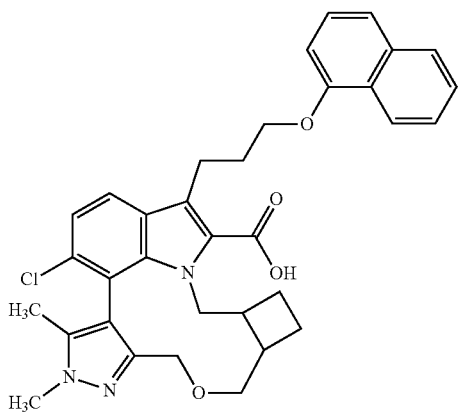 [SMILES: Cc1c2c(nn1C)COCC1CCC1Cn1c(C(=O)O)c(CCCOc3cccc4ccccc34)c3ccc(Cl)c-2c31]

The saponification of ethyl (9aS,11aR or 9aR,11aS)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]oxazacycloundecino[8,7,6-hi]indole-14-carboxylate—Stereoisomer 1 (see Intermediate 121, 86.0 mg) was performed as described in Example 55 to provide the target compound in 99% purity: 50 mg $^1$H NMR (chlororform-d, 400 MHz): 8.33-8.39 (m, 1H), 7.77-7.82 (m, 1H), 7.59 (d, 1H), 7.45-7.50 (m, 2H), 7.41 (d, 1H), 7.34 (t, 1H), 7.14 (d, 1H), 6.76 (d, 1H), 4.54 (d, 1H), 4.16-4.28 (m, 5H), 3.94 (d, 1H), 3.92 (s, 3H), 3.55 (t, 1H), 3.38-3.48 (m, 1H), 3.27-3.37 (m, 2H), 2.54-2.63 (m, 1H), 2.19-2.35 (m, 3H), 1.94 (s, 3H), 1.82-1.94 (m, 1H), 1.55 (t, 1H), 1.10-1.18 (m, 1H).

LCMS (Method 3): Rt=3.32 min, MS (ESIneg): 582[M−H]$^-$.

The title compound (86 mg) was separated into enantiomers by preparative chiral HPLC to give enantiomer 1 (13 mg, see Example 78) and enantiomer 2 (15 mg, see Example 79).

Preparative Chiral HPLC Method:
Instrument: Waters Autopurification System; Column: Chiralpak IA 5 μm 20×250 mm; Eluent A: Heptane; Eluent B: ethanol with 0.1% vol trifluoroacetic acid (99%); Gradient: isocratic, 5% B over 25 min; Flow 18 mL/min; temperature: 25° C., BPR: 100 bar, PAD TP.

Analytical Chiral HPLC Method:
Instrument: Waters Alliance 2695, PDA 2996; Column YMC SA 4.5×250 mm, eluent A: Heptane; eluent B: ethanol with 0.1% vol trifluoroacetic acid (99%), Gradient: isocratic, 5% B; flow 1 ml/min over 30 min; Temperature: 25° C.; PDA 210-350 nm Example 64

(9aR,11aS)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]oxazacycloundecino[8,7,6-hi]indole-14-carboxylic acid—Stereoisomer 2

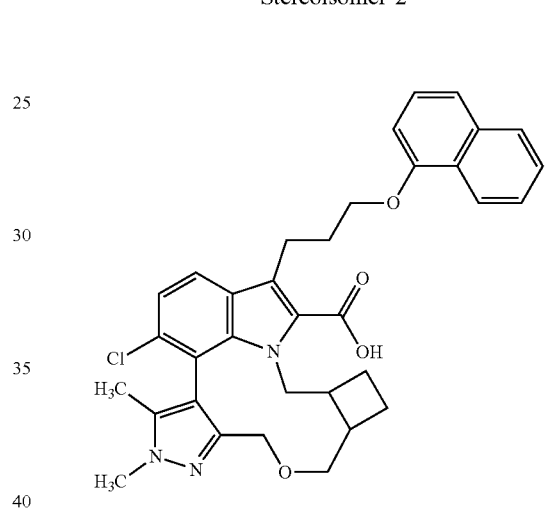

The saponification of ethyl (9aR,11aS or 9aS,11aR)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]oxazacycloundecino[8,7,6-hi]indole-14-carboxylate—Stereoisomer 2 (see Intermediate 122, 140 mg) was performed as described in Example 55 to provide the target compound in 94% purity: 67 mg $^1$H NMR (chloroform-d, 400 MHz): 8.34-8.40 (m, 1H), 7.77-7.81 (m, 1H), 7.60 (d, 1H), 7.45-7.51 (m, 2H), 7.40 (d, 1H), 7.33 (t, 1H), 7.15 (d, 1H), 6.73 (d, 1H), 4.73 (d, 1H), 4.06-4.27 (m, 5H), 3.88 (s, 3H), 3.50 (s, 2H), 3.32-3.41 (m, 2H), 3.03 (sextet, 1H), 2.22-2.38 (m, 2H), 2.12-2.20 (m, 1H), 1.86 (s, 3H), 1.78-1.87 (m, 1H), 1.58 (t, 1H), 1.10 (q, 1H), 0.85 (qn, 1H).

LCMS (Method 3): Rt=3.49 min, MS (ESIneg): 582 [M−H]$^-$.

The title compound (67 mg) was separated into enantiomers by preparative chiral HPLC to give enantiomer 1 (22 mg, see Example 80) and enantiomer 2 (25 mg, see Example 81).

Preparative Chiral HPLC Method:
Instrument: Waters Autopurification System; Column: Chiralpak IA 5 μm 20×250 mm; Eluent A: Heptane; Eluent B: ethanol with 0.1% vol trifluoroacetic acid (99%); Gradient: isocratic, 5% B over 26 min; Flow 18 mL/min; temperature: 25° C., BPR: 100 bar, PAD TP.

Example 65

(9aS,10aR or 9aR,10aS)-3-chloro-4,5-dimethyl-14-{3-[(naphthalen-1-yl)oxy]propyl}-5,7,9a,10,10a,11-hexahydro-9H-cyclopropa[3,4]pyrazolo[4',3':9,10][1,6]oxazacycloundecino-[8,7,6-hi]indole-13-carboxylic acid—Stereoisomer 1

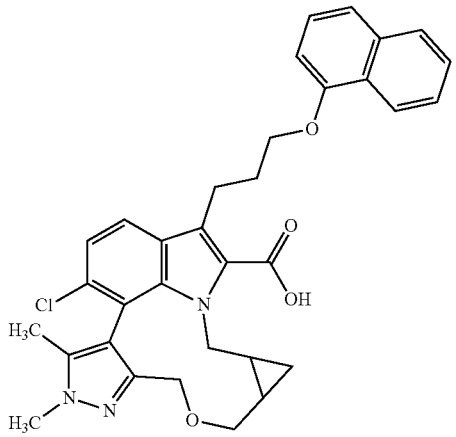 [SMILES: Cc1c2c(nn1C)COCC1CC1Cn1c(C(=O)O)c(CCCOc3cccc4ccccc34)c3ccc(Cl)c-2c31]

The saponification of ethyl (9aS,10aR or 9aR,10aS)-3-chloro-4,5-dimethyl-14-{3-[(naphthalen-1-yl)oxy]propyl}-5,7,9a,10,10a,11-hexahydro-9H-cyclopropa[4',3':9,10][1,6]oxazacycloundecino[8,7,6-hi]indole-13-carboxylate—Stereoisomer 1 (see Intermediate 126, 125 mg) was performed as described in Example 55 to provide the target compound in 100% purity: 65 mg ¹H NMR (CDCl3, 400 MHz): 8.34-8.40 (m, 1H), 7.76-7.82 (m, 1H), 7.62 (d, 1H), 7.45-7.51 (m, 2H), 7.41 (d, 1H), 7.34 (t, 1H), 7.17 (d, 1H), 6.76 (d, 1H), 4.69 (dd, 2H), 4.16-4.29 (m, 3H), 3.87 (s, 3H), 3.82 (dd, 1H), 3.66 (dd, 1H), 3.32-3.49 (m, 2H), 2.49 (t, 1H), 2.26-2.37 (m, 2H), 1.88 (s, 3H), 0.97-1.08 (m, 1H), 0.82 (qn, 1H), 0.60-0.67 (m, 1H), −0.24 (q, 1H).

LCMS (Method 3): Rt=3.14 min, MS (ESIpos): 570 [M+H]⁺.

The title compound (119 mg) was separated into enantiomers by preparative chiral HPLC to give enantiomer 1 (24 mg, see Example 82) and enantiomer 2 (22 mg, see Example 83).

Preparative Chiral HPLC Method:
Instrument: Waters Autopurification System; Column: Chiralpak IA 5 μm 20×250 mm; Eluent A: Heptane; Eluent B: ethanol with 0.1% vol trifluoroacetic acid (99%); Gradient: isocratic, 5% B over 35 min; Flow 18 mL/min; temperature: 25° C., BPR: 100 bar, PAD TP.

Analytical Chiral HPLC Method:
Instrument: Waters Alliance 2695, PDA 2996; Column YMC SA 4.5×250 mm, eluent A: Heptane; eluent B: ethanol with 0.1% vol trifluoroacetic acid (99%), Gradient: isocratic, 5% B; flow 1 ml/min over 30 min; Temperature: 25° C.; PDA 210-350 nm

Example 66

(9aR,10aS or 9aS,10aR)-3-chloro-4,5-dimethyl-14-{3-[(naphthalen-1-yl)oxy]propyl}-5,7,9a,10,10a,11-hexahydro-9H-cyclopropa[3,4]pyrazolo[4',3':9,10][1,6]oxazacycloundecino-[8,7,6-hi]indole-13-carboxylic acid—Stereoisomer 2

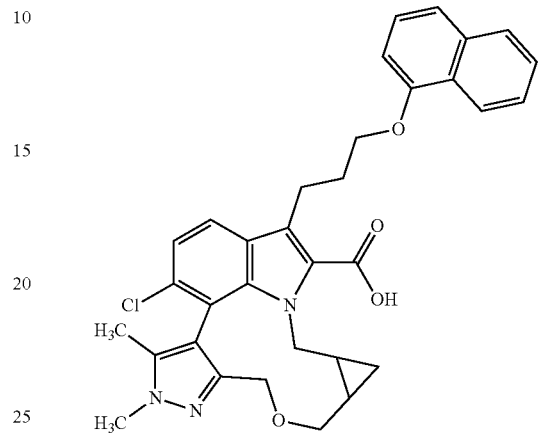

The saponification of ethyl (9aR,10aS or 9aS,10aR)-3-chloro-4,5-dimethyl-14-{3-[(naphthalen-1-yl)oxy]propyl}-5,7,9a,10,10a,11-hexahydro-9H-cyclopropa[3,4]pyrazolo[4',3':9,10][1,6]oxazacycloundecino[8,7,6-hi]indole-13-carboxylate—Stereoisomer 2 (see Intermediate 127, 74.0 mg) was performed as described in Example 55 to provide the target compound in 98% purity: 26 mg ¹H NMR (CHLOROFORM-D, 400 MHz): 8.33-8.39 (m, 1H), 7.76-7.82 (m, 1H), 7.61 (d, 1H), 7.45-7.51 (m, 2H), 7.40 (d, 1H), 7.33 (t, 1H), 7.14 (d, 1H), 6.74 (d, 1H), 4.37-4.47 (m, 2H), 4.24 (d, 1H), 4.12-4.23 (m, 2H), 3.99 (dd, 1H), 3.87 (s, 3H), 3.60 (d, 1H), 3.35-3.48 (m, 3H), 2.28-2.38 (m, 2H), 1.88 (s, 3H), 1.18-1.27 (m, 1H), 0.82-0.93 (m, 1H), 0.19-0.28 (m, 1H), −0.46 (q, 1H).

LCMS (Method 3): Rt=3.22 min, 98.3%. MS (ESIpos): 570 [M+H]⁺.

Example 67

(rac)-4-chloro-11,11,12,12-tetrafluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid

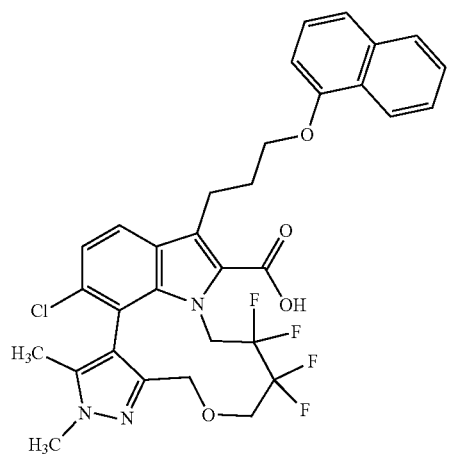 [SMILES: Cc1c2c(nn1C)COCC(F)(F)C(F)(F)Cn1c(C(=O)O)c(CCCOc3cccc4ccccc34)c3ccc(Cl)c-2c31]

(rac)-Ethyl 4-chloro-11,11,12,12-tetrafluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate (see Intermediate 131, 16.0 mg) was performed as described in Example 55 to provide the target compound in 98% purity: 4.5 mg $^1$H NMR (300 MHz, chloroform-d): δ [ppm] 1.82 (s, 3H), 2.30-2.43 (m, 2H), 3.43 (t, 2H), 3.66-3.86 (m, 2H), 3.90 (s, 3H), 4.09-4.24 (m, 2H), 4.51 (d, 1H), 4.52-4.68 (m, 1H, overlapped), 4.68 (d, 1H), 5.02 (qd, 1H), 6.74 (d, 1H), 7.22 (d, 1H), 7.34 (t, 1H), 7.42 (d, 1H), 7.46-7.53 (m, 2H), 7.66 (d, 1H), 7.78-7.84 (m, 1H), 8.35-8.41 (m, 1H).

LCMS (Method 3): Rt=3.21 min, MS (ESIpos): 630 [M+H]$^+$

Example 68

(rac)-4-chloro-11,11-difluoro-2,3-dimethyl-7-[3-(1-naphthyloxy)propyl]-2,10,11,12,13,15-hexahydropyrazolo[4',3':9,10][1,6]oxazacycloundecino[8,7,6-hi]indole-8-carboxylic acid

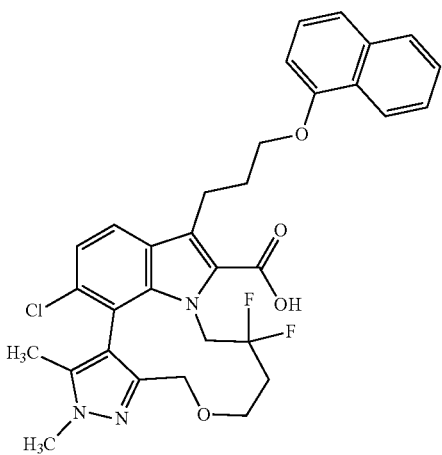 [SMILES: Cc1c2c(nn1C)COCCC(F)(F)Cn1c(C(=O)O)c(CCCOc3cccc4ccccc34)c3ccc(Cl)c-2c31]

(rac)-ethyl 4-chloro-11,11-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylate (see Intermediate 138, 180 mg) was performed as described in Example 55 to provide the target compound: 157 mg in 98% purity.

$^1$H NMR (400 MHz, CHLOROFORM-D) δ [ppm]=1.51 (dt, 1H), 1.88 (s, 3H), 2.07-2.25 (m, 1H), 2.30-2.40 (m, 2H), 3.37-3.59 (m, 3H), 3.67 (dd, 1H), 3.86 (dd, 1H), 3.92 (s, 3H), 4.16-4.28 (m, 2H), 4.44 (d, 1H), 4.58-4.72 (m, 1H), 4.82 (d, 1H), 6.77 (d, 1H), 7.25 (d, 1H), 7.32-7.57 (m, 4H), 7.67 (d, 1H), 7.79-7.86 (m, 1H), 8.35-8.42 (m, 1H)—Acid OH signal not visible;

$^{19}$F NMR (376 MHz, CHLOROFORM-D) δ [ppm]= −106.41−−105.47 (m, 1H), −91.83−−90.88 (m, 1H);

LCMS (Method 3): Rt=3.44 min., MS (ESIneg): m/z=592.2/594.3 (M−H)$^-$.

The title compound (136 mg) was separated into enantiomers by preparative chiral HPLC to give enantiomer 1 (70 mg, see Example 94) and enantiomer 2 (74 mg, see Example 95).

Preparative Chiral HPLC Method:

Instrument: Labomatic HD5000, Labocord-5000; Gilson GX-241, Labcol Vario 4000, Column: Chiralpak IG 5μ 250×30 mm; Eluent A: Hexane+0.1 Vol-% Diethylamine (99%); Eluent B: Ethanol; isokratic: 10% B; Flow 80.0 mL/min; UV 254 nm Analytical Chiral HPLC Method:

Instrument: Agilent HPLC 1260; Column: Amylose SA 3μ 100×4.6 mm; Eluent A: Hexane+0.1 Vol-% Diethylamine (99%); Eluent B: Ethanol; isokratic: 10% B; Flow 1.4 mL/min; Temperature: 25° C.; DAD220 nm.

Example 69

4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (Enantiomer 1)

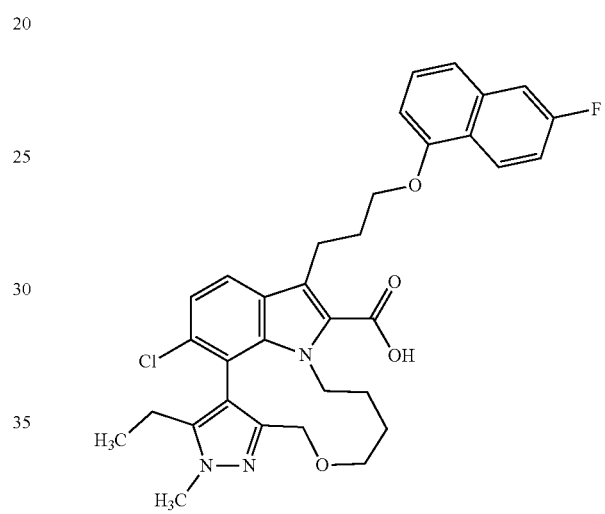

The N-ethylethanamine salt of the title compound (see Example 37, 4.52 g) was purified by flash chromatography using silica gel (gradient dichloromethane/ethanol). The material was dried by lyophilisation to give 3.69 g of the title compound.

LC-MS (Method 2): R$_t$=0.94 min; MS (ESIpos): m/z=590 [M+H]$^+$

Specific Optical Rotation (Method O1): −0.90° (c=10 mg/mL, DMSO)

$^1$H-NMR (400 MHz, DMSO-d6) δ[ppm]: 0.785 (2.95), 0.804 (6.91), 0.823 (3.07), 1.195 (0.72), 1.207 (0.86), 1.219 (0.81), 1.230 (0.74), 1.330 (0.41), 2.111 (0.68), 2.130 (1.21), 2.138 (0.44), 2.149 (1.11), 2.157 (1.13), 2.167 (0.72), 2.176 (1.50), 2.195 (1.49), 2.213 (1.12), 2.233 (0.41), 2.331 (0.44), 2.518 (2.61), 2.523 (1.63), 2.673 (0.45), 3.124 (0.70), 3.137 (0.66), 3.149 (0.47), 3.257 (1.26), 3.277 (2.13), 3.297 (1.95), 3.847 (16.00), 3.870 (0.40), 4.167 (1.05), 4.182 (2.28), 4.189 (2.69), 4.220 (2.41), 4.249 (0.53), 4.262 (0.43), 4.267 (0.43), 4.419 (2.11), 4.450 (1.75), 6.844 (1.19), 6.851 (1.23), 6.860 (1.09), 6.866 (1.28), 7.188 (3.74), 7.210 (3.61), 7.357 (0.80), 7.363 (0.87), 7.379 (1.24), 7.386 (1.36), 7.402 (1.15), 7.408 (0.96), 7.423 (2.08), 7.433 (2.44), 7.439 (5.26), 7.453 (0.43), 7.638 (1.38), 7.645 (1.45), 7.664 (1.40), 7.671 (1.41), 7.717 (3.19), 7.738 (2.82), 8.224 (1.22), 8.239 (1.29), 8.247 (1.28), 8.262 (1.19).

Example 70

(+)-4-chloro-3-ethyl-7-{3-[(6-fluoronaphthalen-1-yl)oxy]propyl}-2-methyl-10,11,12,13,14,15-hexahydro-2H-pyrazolo[4',3':4,5]azacycloundecino[3,2,1-hi]indole-8-carboxylic acid-N-ethylethanamine salt
(Enantiomer 1)

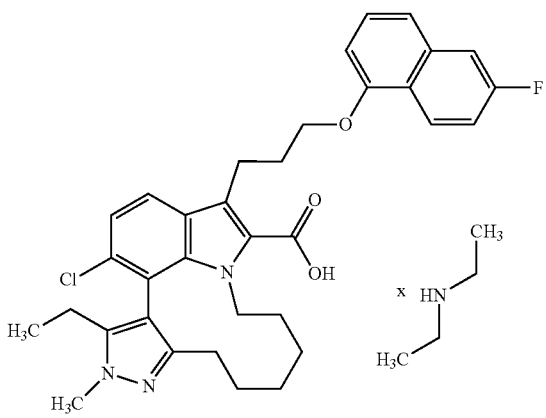

For the preparation of the racemic title compound see Example 54. Separation of enantiomers by preparative chiral HPLC gave the title compound (30 mg).

Preparative Chiral HPLC Method:

Instrument: Labomatic HD5000, Labocord-5000; Gilson GX-241, Labcol Vario 4000, Column: Amylose SA 5μ 250×30 mm; Eluent A: Hexane+0.1 Vol-% Diethylamine (99%); Eluent B: 2-Propanol, Gradient: 20 min, 20%-50% B; Flow 40.0 mL/min; UV 254 nm Analytical Chiral HPLC Method:

Instrument: Agilent HPLC 1260; Column: Amylose SA 3μ 100×4.6 mm; Eluent A: Hexane+0.1 Vol-% Diethylamine (99%), Eluent B: 2-Propanol Gradient: 80:20-50:50, 7 min; Flow 1.4 mL/min; Temperature: 25° C.; DAD 254 nm Analytical Chiral HPLC: $R_t$=1.35 min.

LC-MS (Method 1): $R_t$=1.65 min; MS (ESIpos): m/z=588 [M+H]$^+$

Specific Optical Rotation (Method O1): 16.0° (c=10 mg/mL, DMSO)

$^1$H-NMR (400 MHz, DMSO-d6) δ[ppm]: 0.542 (0.56), 0.570 (0.59), 0.784 (0.87), 0.805 (1.31), 0.819 (3.75), 0.838 (7.58), 0.856 (3.50), 1.057 (0.56), 1.131 (6.55), 1.149 (14.43), 1.167 (6.77), 1.203 (0.64), 1.230 (1.09), 1.258 (0.59), 1.278 (1.57), 1.352 (0.48), 1.371 (0.48), 1.753 (0.45), 2.190 (1.54), 2.214 (1.15), 2.224 (1.12), 2.233 (1.71), 2.242 (1.57), 2.252 (1.40), 2.261 (1.37), 2.280 (0.62), 2.465 (1.34), 2.518 (6.27), 2.523 (4.06), 2.850 (1.79), 2.868 (5.57), 2.886 (5.31), 2.904 (1.68), 3.116 (0.56), 3.130 (0.73), 3.148 (0.92), 3.167 (0.64), 3.207 (0.95), 3.226 (1.48), 3.244 (1.57), 3.261 (1.93), 3.790 (0.56), 3.817 (16.00), 3.847 (0.48), 4.165 (1.40), 4.181 (2.88), 4.197 (1.34), 4.634 (0.62), 4.667 (0.56), 6.829 (1.23), 6.835 (1.23), 6.844 (1.17), 6.850 (1.26), 7.081 (1.90), 7.102 (2.01), 7.333 (0.78), 7.340 (0.87), 7.355 (1.29), 7.362 (1.40), 7.378 (0.90), 7.384 (1.29), 7.405 (2.15), 7.416 (2.60), 7.421 (5.26), 7.436 (0.48), 7.566 (1.34), 7.587 (1.20), 7.626 (1.45), 7.632 (1.51), 7.652 (1.45), 7.658 (1.45), 8.211 (1.26), 8.226 (1.34), 8.234 (1.29), 8.249 (1.20).

Example 71

(−)-4-chloro-3-ethyl-7-{3-[(6-fluoronaphthalen-1-yl)oxy]propyl}-2-methyl-10,11,12,13,14,15-hexahydro-2H-pyrazolo[4',3':4,5]azacycloundecino[3,2,1-hi]indole-8-carboxylic acid-N-ethylethanamine salt
(Enantiomer 2)

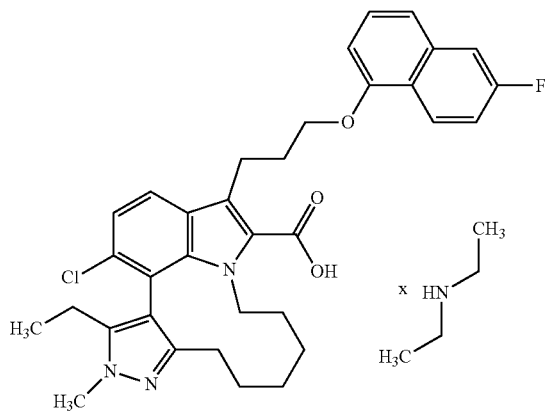

For the preparation of the racemic title compound see Example 54. Separation of enantiomers by preparative chiral HPLC (method see Example 70) gave the title compound (28 mg).

Analytical Chiral HPLC (method see Example 70): $R_t$=2.96 min.

LC-MS (Method 1): $R_t$=1.65 min; MS (ESIpos): m/z=588 [M+H]$^+$

Specific Optical Rotation (Method O1): −13.5° (c=10 mg/mL, DMSO)

$^1$H-NMR (400 MHz, DMSO-d6) δ[ppm]: 0.539 (0.54), 0.566 (0.58), 0.817 (3.92), 0.836 (8.16), 0.855 (3.62), 1.071 (0.56), 1.136 (5.50), 1.154 (12.27), 1.172 (5.64), 1.207 (0.58), 1.230 (0.84), 1.259 (0.51), 1.293 (0.54), 1.311 (0.58), 1.352 (0.54), 1.753 (0.44), 2.172 (1.21), 2.191 (1.63), 2.208 (1.38), 2.225 (1.17), 2.233 (1.75), 2.242 (1.68), 2.252 (1.42), 2.261 (1.42), 2.279 (0.63), 2.318 (0.49), 2.518 (4.59), 2.523 (3.13), 2.539 (0.51), 2.860 (1.45), 2.877 (4.45), 2.896 (4.43), 2.914 (1.33), 3.135 (0.44), 3.150 (0.56), 3.169 (0.77), 3.188 (0.47), 3.220 (0.65), 3.240 (1.07), 3.257 (1.05), 3.273 (1.24), 3.819 (16.00), 3.843 (0.68), 4.167 (1.38), 4.183 (2.89), 4.198 (1.35), 4.617 (0.58), 4.650 (0.56), 6.830 (1.26), 6.836 (1.26), 6.845 (1.17), 6.852 (1.33), 7.101 (1.84), 7.122 (1.98), 7.331 (0.82), 7.338 (0.93), 7.354 (1.31), 7.361 (1.45), 7.376 (0.91), 7.383 (1.00), 7.407 (2.24), 7.417 (2.66), 7.423 (5.60), 7.438 (0.49), 7.594 (1.26), 7.615 (1.19), 7.627 (1.63), 7.634 (1.63), 7.653 (1.54), 7.660 (1.54), 8.208 (1.31), 8.223 (1.38), 8.231 (1.35), 8.247 (1.28).

Example 72

(rac)-4'-chloro-3'-ethyl-2'-methyl-7'-{3-[(naphthalen-1-yl)oxy]propyl}-2',10',11',15'-tetrahydro-13'H-spiro[cyclopropane-1,12'-pyrazolo[4',3':9,10][1,6]oxazacycloundecino[8,7,6-hi]indole]-8'-carboxylic acid

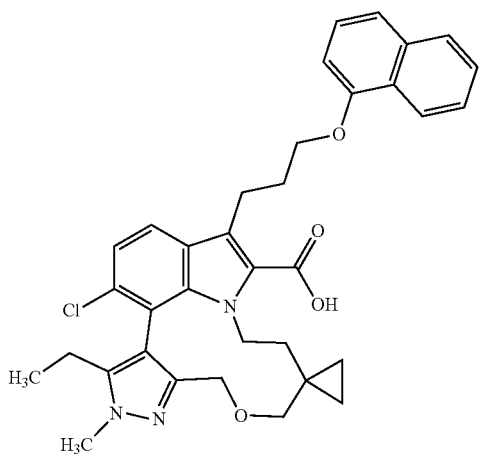 [SMILES: CCc1c2c(nn1C)COCC1(CCn3c(C(=O)O)c(CCCOc4cccc5ccccc45)c4ccc(Cl)c-2c43)CC1]

(Rac)-Ethyl-4'-chloro-3'-ethyl-2'-methyl-7'-{3-[(naphthalen-1-yl)oxy]propyl}-2',10',11',15'-tetrahydro-13'H-spiro[cyclopropane-1,12'-pyrazolo[4',3':9,10][1,6]oxazacycloundecino[8,7,6-hi]indole]-8'-carboxylate (see Intermediate 144, 960 mg) was dissolved in a mixture of 8 mL of THF and 500 µL of ethanol, aqueous lithium hydroxide solution (2.5 mL, 1.0 M, 2.5 mmol) was added and the mixture was stirred at 70° C. under nitrogen atmosphere for 18 hours. Aqueous lithium hydroxide solution (2.5 mL, 1.0 M, 2.5 mmol) was added and the mixture was stirred at 70° C. for 6 days. Again aqueous lithium hydroxide solution (2.5 mL, 1.0 M, 2.5 mmol) was added and the mixture was stirred at 70° C. for 24 hours. The reaction mixture was diluted with water and the pH value was adjusted to 3-4 by addition of a saturated aqueous solution of citric acid. The mixture was extracted with ethyl acetate and the combined organic layers were filtered through a silicone coated filter and concentrated under reduced pressure. The crude product was purified twice by flash chromatography using silica gel (1. gradient dichloromethane/ethanol; 2. gradient hexane/ethyl acetate) to provide 574 mg of the title compound.

LC-MS (Method 2): $R_t$=0.94 min; MS (ESIpos): m/z=598 [M+H]$^+$ $^1$H-NMR (400 MHz, DMSO-d6) δ[ppm]: −0.011 (0.69), 0.000 (0.70), 0.044 (0.53), 0.054 (0.87), 0.066 (0.84), 0.076 (0.51), 0.087 (0.42), 0.121 (0.69), 0.132 (0.98), 0.146 (1.05), 0.153 (1.00), 0.167 (0.68), 0.810 (3.15), 0.829 (6.95), 0.848 (3.21), 1.175 (3.65), 1.192 (8.07), 1.210 (4.30), 1.244 (0.41), 2.008 (13.22), 2.100 (0.45), 2.119 (0.72), 2.137 (1.10), 2.156 (1.02), 2.179 (1.14), 2.198 (1.64), 2.216 (1.72), 2.235 (1.25), 2.254 (0.44), 2.539 (3.94), 2.543 (2.16), 2.564 (1.52), 3.281 (1.11), 3.300 (1.97), 3.318 (1.25), 3.496 (1.16), 3.521 (1.07), 3.879 (16.00), 3.916 (0.42), 3.944 (0.77), 3.971 (0.49), 4.019 (0.99), 4.037 (2.91), 4.055 (2.82), 4.073 (0.92), 4.187 (2.83), 4.197 (1.81), 4.218 (2.46), 4.311 (0.53), 4.326 (0.47), 4.333 (0.48), 4.349 (0.46), 4.498 (2.13), 4.529 (1.84), 6.887 (1.70), 6.904 (1.85), 7.222 (3.58), 7.243 (3.51), 7.379 (1.28), 7.400 (2.33), 7.419 (1.87), 7.467 (2.45), 7.488 (1.47), 7.518 (0.51), 7.530 (1.58), 7.536 (2.53), 7.545 (3.20), 7.554 (2.80), 7.560 (1.74), 7.572 (0.59), 7.753 (3.00), 7.775 (2.79), 7.876 (1.42), 7.886 (0.73), 7.894 (0.99), 7.900 (1.20), 8.245 (1.26), 8.252 (0.99), 8.259 (0.60), 8.269 (1.17).

The title compound (565 mg) was separated into enantiomers by preparative chiral HPLC to give enantiomer 1 (190 mg, see Example 73) and enantiomer 2 (176 mg, see Example 74).

Preparative Chiral HPLC Method:

Instrument: Labomatic HD5000, Labocord-5000; Gilson GX-241, Labcol Vario 4000, Column: Amylose SA 5µ 250×30 mm; Eluent A: Hexane+0.1 Vol-% Diethylamine (99%); Eluent B: Ethanol, Gradient: isokratic, 20% B; Flow 60.0 mL/min; UV 254 nm Analytical Chiral HPLC Method:

Instrument: Agilent HPLC 1260; Column: Amylose SA 3µ 100×4.6 mm; Eluent A: Hexane+0.1 Vol-% Diethylamine (99%), Eluent B: Ethanol Gradient: 20-50% B, 7 min; Flow 1.4 mL/min; Temperature: 25° C.; DAD 254 nm

Example 73

(−)-4'-chloro-3'-ethyl-2'-methyl-7'-{3-[(naphthalen-1-yl)oxy]propyl}-2',10',11',15'-tetrahydro-13'H-spiro[cyclopropane-1,12'-pyrazolo[4',3':9,10][1,6]oxazacycloundecino[8,7,6-hi]indole]-8'-carboxylic acid-N-ethylethanamine salt (Enantiomer 1)

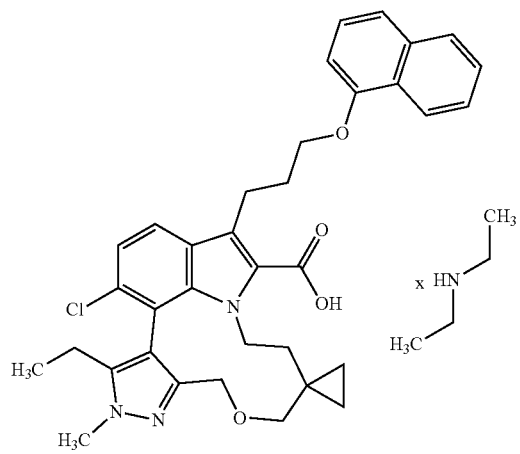

For the preparation of the racemic title compound see Example 72. Separation of enantiomers by preparative chiral HPLC (method see Example 72) gave the title compound (190 mg).

Analytical Chiral HPLC (method see Example 72): R$_t$=1.21 min.

LC-MS (Method 2): R$_t$=0.94 min; MS (ESIpos): m/z=598 [M+H]$^+$

Specific Optical Rotation (Method O1): −34° (c=10 mg/mL, DMSO)

$^1$H-NMR (400 MHz, DMSO-d6) δ[ppm]: 0.000 (0.40), 0.067 (0.45), 0.085 (0.42), 0.092 (0.44), 0.780 (1.49), 0.799 (3.51), 0.818 (1.75), 1.095 (16.00), 1.115 (3.66), 1.133 (8.60), 1.151 (3.93), 1.196 (0.41), 2.113 (0.68), 2.132 (0.76), 2.148 (0.77), 2.166 (0.78), 2.184 (0.85), 2.202 (0.54), 2.505 (2.21), 2.510 (1.30), 2.816 (1.02), 2.834 (3.15), 2.852 (3.12), 2.870 (0.94), 3.177 (0.59), 3.197 (0.95), 3.215 (0.61), 3.472 (0.63), 3.497 (0.57), 3.837 (8.18), 4.125 (0.61), 4.137 (1.32), 4.152 (0.63), 4.168 (1.40), 4.444 (1.12), 4.476 (1.08), 6.822 (0.85), 6.840 (0.92), 7.060 (1.21), 7.081 (1.24), 7.321 (0.66), 7.342 (1.21), 7.361 (0.95), 7.417 (1.20), 7.437 (0.75), 7.486 (0.80), 7.492 (1.11), 7.501 (1.66), 7.510 (1.24), 7.516 (0.89), 7.546 (0.89), 7.567 (0.79), 7.834 (0.70), 7.837 (0.52), 7.852 (0.50), 7.857 (0.60), 8.214 (0.63), 8.221 (0.52), 8.239 (0.59).

Example 74

(+)-4'-chloro-3'-ethyl-2'-methyl-7'-{3-[(naphthalen-1-yl)oxy]propyl}-2',10',11',15'-tetrahydro-13'H-spiro[cyclopropane-1,12'-pyrazolo[4',3':9,10][1,6]oxaza-cycloundecino[8,7,6-hi]indole]-8'-carboxylic acid-N-ethylethanamine salt (Enantiomer 2)

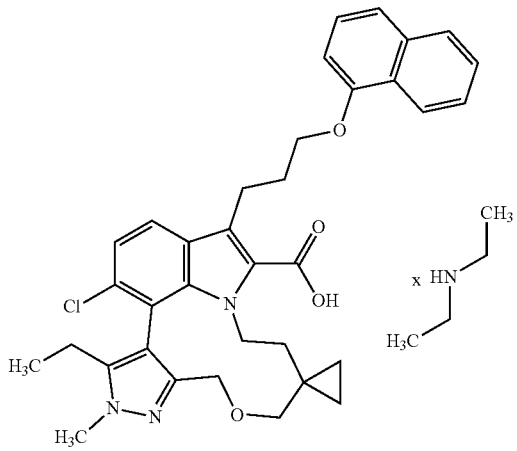

For the preparation of the racemic title compound see Example 72. Separation of enantiomers by preparative chiral HPLC (method see Example 72) gave the title compound (176 mg).

Analytical Chiral HPLC (method see Example 72): R$_t$=1.88 min.

LC-MS (Method 2): R$_t$=0.94 min; MS (ESIpos): m/z=598 [M+H]$^+$

Specific Optical Rotation (Method O1): 35° (c=10 mg/mL, DMSO)

$^1$H-NMR (400 MHz, DMSO-d6) δ[ppm]: 0.780 (1.31), 0.799 (3.10), 0.817 (1.52), 1.094 (16.00), 1.114 (3.35), 1.132 (7.41), 1.150 (3.49), 2.113 (0.58), 2.131 (0.65), 2.148 (0.67), 2.165 (0.68), 2.184 (0.74), 2.201 (0.47), 2.505 (1.96), 2.510 (1.18), 2.814 (0.88), 2.833 (2.81), 2.851 (2.70), 2.869 (0.83), 3.177 (0.51), 3.196 (0.83), 3.213 (0.55), 3.472 (0.56), 3.496 (0.50), 3.836 (7.20), 4.124 (0.54), 4.136 (1.15), 4.151 (0.56), 4.167 (1.22), 4.444 (0.98), 4.475 (0.94), 6.822 (0.74), 6.840 (0.80), 7.059 (1.09), 7.080 (1.13), 7.321 (0.61), 7.342 (1.08), 7.361 (0.84), 7.417 (1.06), 7.437 (0.65), 7.485 (0.71), 7.491 (0.97), 7.501 (1.47), 7.510 (1.09), 7.515 (0.78), 7.545 (0.78), 7.566 (0.70), 7.833 (0.63), 7.836 (0.47), 7.851 (0.45), 7.857 (0.52), 8.214 (0.56), 8.221 (0.46), 8.239 (0.52).

Example 75

(+)-4-chloro-14-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylic acid-N-ethylethanamine salt (Enantiomer 1)

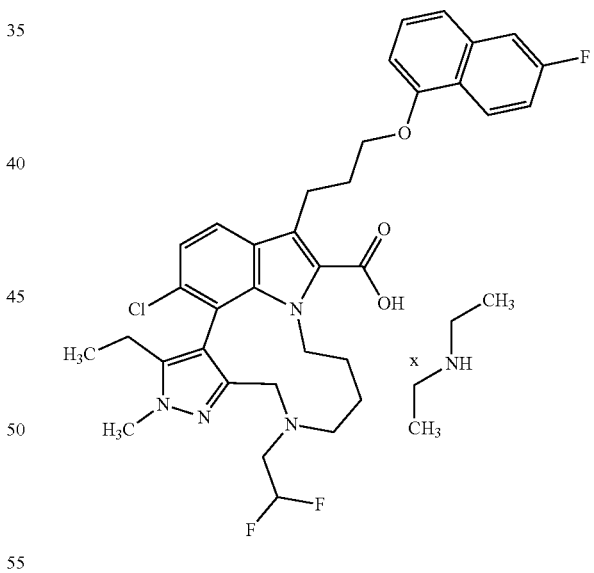

For the preparation of the racemic title compound see Example 62. Separation of enantiomers by preparative chiral HPLC (method see Example 62) gave the title compound (112 mg).

Analytical Chiral HPLC (method see 62): R$_t$=1.93 min.

LC-MS (Method SFC, see Example 62): R$_t$=1.99 min

Specific Optical Rotation (Method O1): 19° (c=10 mg/mL, methanol)

$^1$H-NMR (400 MHz, DMSO-d6): δ [ppm]=0.82 (t, 3H), 0.88-1.07 (m, 2H), 1.12-1.20 (m, 8H), 2.19 (q, 4H), 2.28 (br t, 2H), 2.53-2.65 (m, 1H), 2.77 (br dd, 1H), 2.87 (q, 4H), 3.10-3.20 (m, 2H), 3.21-3.30 (m, 1H), 3.53 (s, 2H), 3.74 (dt, 1H), 3.83 (s, 3H), 4.16 (t, 2H), 4.42-4.56 (m, 1H), 5.61 (tt, 1H), 6.82 (dd, 1H), 7.08 (d, 1H), 7.33-7.46 (m, 3H), 7.57 (d, 1H), 7.65 (dd, 1H), 8.29 (dd, 1H).—as N-ethylethanamine salt.

Example 76

(−)-4-chloro-14-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylic acid N-ethylethanamine salt (Enantiomer 2)

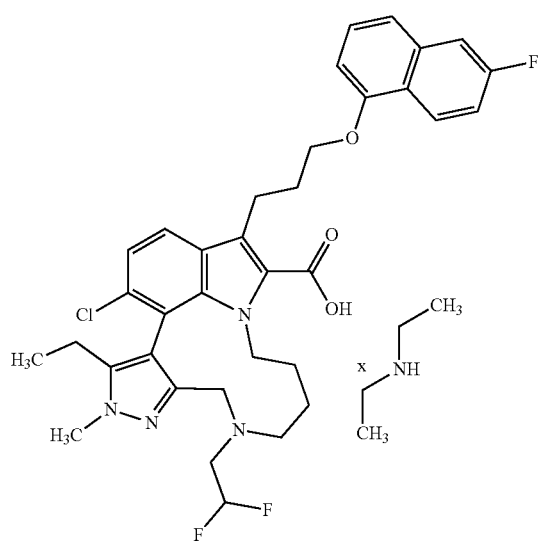

For the preparation of the racemic title compound see Example 62. Separation of enantiomers by preparative chiral HPLC (method see Example 62) gave the title compound (109 mg).

Analytical Chiral HPLC (method see Example 62): $R_t$=4.12 min.

LC-MS (Method SFC, see Example 62): $R_t$=3.74 min

Specific Optical Rotation (Method O1): −20° (c=10 mg/mL, methanol)

¹H-NMR (400 MHz, DMSO-d6): δ [ppm]=0.82 (t, 3H), 0.89-1.07 (m, 2H), 1.07-1.21 (m, 8H), 2.13-2.23 (m, 4H), 2.24-2.32 (m, 2H), 2.60 (br dd, 1H), 2.70-2.82 (m, 1H), 2.87 (q, 4H), 3.10-3.19 (m, 1H), 3.21-3.30 (m, 2H), 3.52 (s, 2H), 3.75 (td, 1H), 3.83 (s, 3H), 4.16 (br t, 2H), 4.38-4.54 (m, 1H), 5.61 (tt, 1H), 6.82 (dd, 1H), 7.08 (d, 1H), 7.34-7.47 (m, 3H), 7.57 (d, 1H), 7.65 (dd, 1H), 8.29 (dd, 1H).—as N-ethylethanamine salt.

Example 77

(rac)-4-chloro-14-(2,2-difluoroethyl)-7-{3-[(6-fluoronaphthalen-1-yl)oxy]propyl}-2,3-dimethyl-10,11,12,13,14,15-hexahydro-2H-pyrazolo[3',4':8,9][1,6]diazacycloundecino[10,11,1-hi]indole-8-carboxylic acid

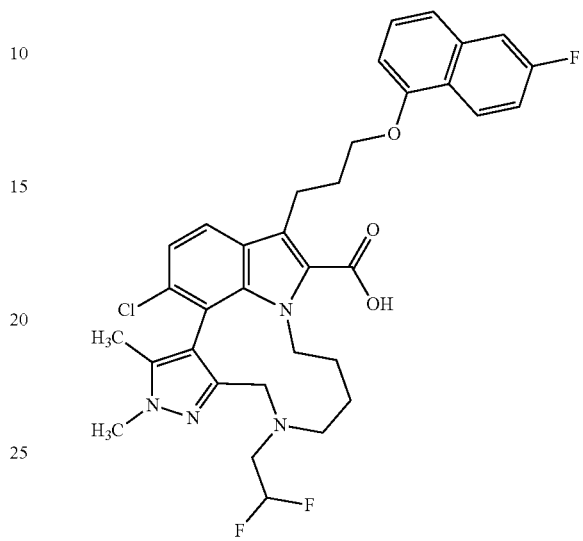

The saponification of (rac)-ethyl 4-chloro-14-(2,2-difluoroethyl)-7-{3-[(6-fluoronaphthalen-1-yl)oxy]propyl}-2,3-dimethyl-10,11,12,13,14,15-hexahydro-2H-pyrazolo[3',4':8,9][1,6]diazacycloundecino[10,11,1-hi]indole-8-carboxylate (see Intermediate 145, 27.0 mg) was performed as described in Example 55 to provide the target compound: 8 mg in 98% purity.

LC-MS (Method 2): $R_t$=0.98 min; MS (ESIpos): m/z=639 [M+H]⁺

¹H-NMR (400 MHz, DMSO-d6): δ [ppm]=0.77-1.01 (m, 1H), 1.23 (s, 3H), 1.79 (s, 2H), 2.13-2.22 (m, 2H), 2.22-2.30 (m, 2H), 2.55-2.81 (m, 2H), 3.14-3.25 (m, 2H), 3.27-3.37 (m, 2H), 3.48-3.65 (m, 2H), 3.70-3.84 (m, 4H), 4.16 (br t, 2H), 4.32-4.47 (m, 1H), 5.38-5.77 (m, 1H), 6.83 (dd, 1H), 7.14 (d, 1H), 7.28-7.52 (m, 3H), 7.61-7.70 (m, 2H), 8.29 (dd, 1H).—contains Ethanol

Example 78

3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]oxazacycloundecino[8,7,6-hi]indole-14-carboxylic acid (Enantiomer 1)

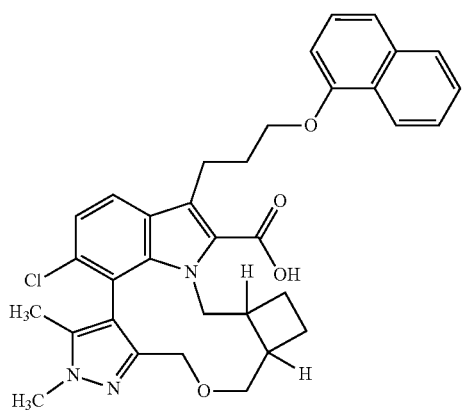 [SMILES: Cc1c2c(nn1C)COCC1CCC1Cn1c(C(=O)O)c(CCCOc3cccc4ccccc34)c3ccc(Cl)c-2c31]

For the preparation of the racemic title compound see Example 63. Separation of enantiomers by preparative chiral HPLC (method see Example 63) gave the title compound (13 mg).

Analytical Chiral HPLC (method see Example 63): $R_t$=15.5 min.

LC-MS (Method 3): $R_t$=3.81 min; MS (ESIpos): m/z=582 [M+H]$^+$ $^1$H-NMR (301 MHz, CHLOROFORM-D) δ=1.31-1.13 (m, 1H), 1.58 (q, 1H), 2.00-1.83 (m, 5H), 2.36-2.16 (m, 3H), 2.67-2.56 (m, 1H), 3.60-3.29 (m, 4H), 3.99-3.87 (m, 4H), 4.30-4.17 (m, 4H), 4.55 (d, 1H), 6.91-6.75 (m, 1H), 7.14 (d, 1H), 7.51-7.29 (m, 4H), 7.60 (d, 1H), 7.81-7.77 (m, 1H), 8.40-8.35 (m, 1H).

Example 79

3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]oxazacycloundecino[8,7,6-hi]indole-14-carboxylic acid (Enantiomer 2)

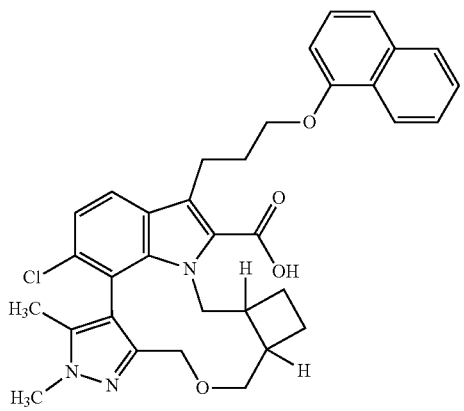 [SMILES: Cc1c2c(nn1C)COCC1CCC1Cn1c(C(=O)O)c(CCCOc3cccc4ccccc34)c3ccc(Cl)c-2c31]

For the preparation of the racemic title compound see Example 63. Separation of enantiomers by preparative chiral HPLC (method see Example 63) gave the title compound (15 mg).

Analytical Chiral HPLC (method see 63): $R_t$=20.3 min.

LC-MS (Method 3): $R_t$=3.81 min; MS (ESIpos): m/z=582 [M+H]$^+$ $^1$H-NMR (300 MHz, CHLOROFORM-D) δ=1.26-1.13 (m, 1H), 1.58 (q, 1H), 1.98-1.83 (m, 5H), 2.36-2.17 (m, 3H), 2.60 (q, 1H), 3.60-3.29 (m, 4H), 3.99-3.92 (m, 4H), 4.30-4.17 (m, 4H), 4.55 (d, 1H), 6.76 (d, 1H), 7.14 (d, 1H), 7.50-7.31 (m, 4H), 7.60 (d, 1H), 7.81-7.77 (m, 1H), 8.37 (q, 1H).

Example 80

3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]oxazacycloundecino[8,7,6-hi]indole-14-carboxylic acid (Enantiomer 4)

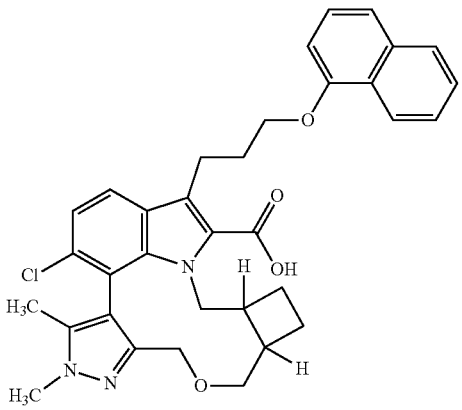 [SMILES: Cc1c2c(nn1C)COCC1CCC1Cn1c(C(=O)O)c(CCCOc3cccc4ccccc34)c3ccc(Cl)c-2c31]

For the preparation of the racemic title compound see Example 64. Separation of enantiomers by preparative chiral HPLC (method see Example 64) gave the title compound (22 mg).

Analytical Chiral HPLC (method see Example 64): $R_t$=15.3 min.

LC-MS (Method 3): $R_t$=2.40 min; MS (ESIpos): m/z=584 [M+H]$^+$ $^1$H-NMR (300 MHz, CHLOROFORM-D) δ=0.94-0.80 (m, 1H), 1.12 (q, 1H), 1.30 (t, OH), 1.62-1.42 (m, 1H), 1.95-1.79 (m, 4H), 2.42-2.05 (m, 3H), 3.06 (td, 1H), 3.41-3.31 (m, 2H), 3.66-3.45 (m, 2H), 3.95-3.82 (m, 3H), 4.28-4.09 (m, 5H), 4.74 (d, 1H), 6.91-6.72 (m, 1H), 7.20-7.12 (m, 1H), 7.52-7.30 (m, 4H), 7.60 (t, 1H), 7.81-7.76 (m, 1H), 8.41-8.36 (m, 1H).

Example 81

3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]oxazacycloundecino[8,7,6-hi]indole-14-carboxylic acid (Enantiomer 4)

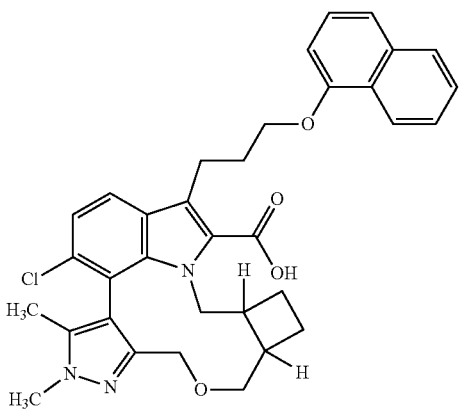 [SMILES: Cc1c2c(nn1C)COCC1CCC1Cn1c(C(=O)O)c(CCCOc3cccc4ccccc34)c3ccc(Cl)c-2c31]

For the preparation of the racemic title compound see Example 64. Separation of enantiomers by preparative chiral HPLC (method see Example 64) gave the title compound (25 mg).

Analytical Chiral HPLC (method see Example 64): $R_t$=18.4 min.

LC-MS (Method 3): $R_t$=2.39 min; MS (ESIpos): m/z=584 [M+H]$^+$ $^1$H-NMR (301 MHz, CHLOROFORM-D) δ=0.86 (t, 1H), 1.12 (s, 1H), 1.60 (d, 1H), 1.84 (d, 4H), 2.35-2.18 (m, 4H), 3.05-3.02 (m, 1H), 3.37 (t, 2H), 3.51 (s, 2H), 3.89 (d, 4H), 4.28-4.07 (m, 5H), 4.73 (d, 1H), 6.74 (d, 1H), 7.15 (d, 1H), 7.26 (s, 8H), 7.51-7.31 (m, 5H), 7.62-7.59 (m, 1H), 7.80 (dd, 1H), 8.39-8.35 (m, 1H).

Example 82

3-chloro-4,5-dimethyl-14-{3-[(naphthalen-1-yl)oxy]propyl}-5,7,9a,10,10a,11-hexahydro-9H-cyclopropa[3,4]pyrazolo[4',3':9,10][1,6]oxazacycloundecino[8,7,6-hi]indole-13-carboxylic acid (Enantiomer 1)

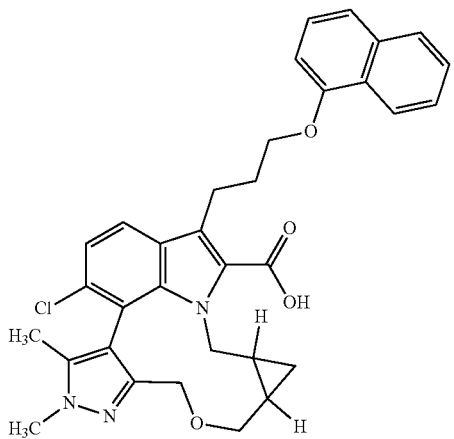 [SMILES: Cc1c2c(nn1C)COCC1CC1Cn1c(C(=O)O)c(CCCOc3cccc4ccccc34)c3ccc(Cl)c-2c31]

For the preparation of the racemic title compound see Example 65. Separation of enantiomers by preparative chiral HPLC (method see Example 65) gave the title compound (24 mg).

Analytical Chiral HPLC (method see Example 65): $R_t$=17.5 min.

LC-MS (Method 3): $R_t$=3.59 min; MS (ESIpos): m/z=568/570 [M+H]$^+$ $^1$H-NMR (400 MHz, CHLOROFORM-D) δ=−0.23 (q, 1H), 0.64-0.70 (m, 1H), 0.79-0.89 (m, 1H), 1.02-1.06 (m, 1H), 1.89 (s, 3H), 2.28-2.38 (m, 2H), 2.51 (t, 1H), 3.32-3.51 (m, 2H), 3.67 (dd, 1H), 3.81-3.87 (m, 4H), 4.19-4.28 (m, 3H), 4.71 (dd, 2H), 6.77 (d, 1H), 7.18 (d, 1H), 7.31-7.42 (m, 2H), 7.44-7.51 (m, 2H), 7.63 (d, 1H), 7.78-7.81 (m, 1H), 8.34-8.41 (m, 1H).

Example 83

3-chloro-4,5-dimethyl-14-{3-[(naphthalen-1-yl)oxy]propyl}-5,7,9a,10,10a,11-hexahydro-9H-cyclopropa[3,4]pyrazolo[4',3':9,10][1,6]oxazacycloundecino[8,7,6-hi]indole-13-carboxylic acid (Enantiomer 2)

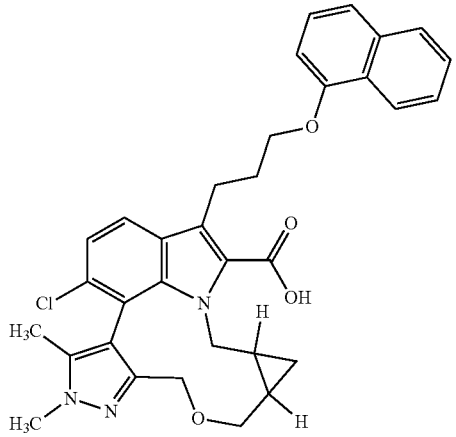 [SMILES: Cc1c2c(nn1C)COCC1CC1Cn1c(C(=O)O)c(CCCOc3cccc4ccccc34)c3ccc(Cl)c-2c31]

For the preparation of the racemic title compound see Example 65. Separation of enantiomers by preparative chiral HPLC (method see Example 65) gave the title compound (22 mg).

Analytical Chiral HPLC (method see Example 65): $R_t$=23.3 min.

LC-MS (Method 3): $R_t$=3.59 min; MS (ESIpos): m/z=568/570 [M+H]$^+$ $^1$H-NMR (400 MHz, CHLOROFORM-D) δ=−0.23 (q, 1H), 0.64-0.70 (m, 1H), 0.79-0.89 (m, 1H), 1.02-1.06 (m, 1H), 1.89 (s, 3H), 2.28-2.38 (m, 2H), 2.51 (t, 1H), 3.32-3.51 (m, 2H), 3.67 (dd, 1H), 3.81-3.87 (m, 4H), 4.19-4.28 (m, 3H), 4.71 (dd, 2H), 6.77 (d, 1H), 7.18 (d, 1H), 7.31-7.42 (m, 2H), 7.44-7.51 (m, 2H), 7.63 (d, 1H), 7.78-7.81 (m, 1H), 8.34-8.41 (m, 1H).

Example 84

(rac)-4-chloro-3-ethyl-12,12-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid

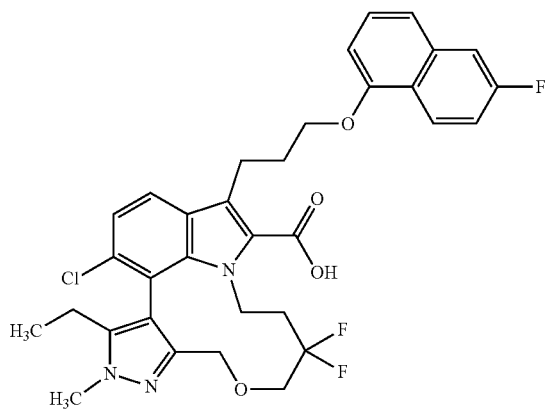 [SMILES: CCc1c2c(nn1C)COCC(F)(F)CCn1c(C(=O)O)c(CCCOc3cccc4cc(F)ccc34)c3ccc(Cl)c-2c31]

(Rac)-ethyl 4-chloro-3-ethyl-12,12-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylate (see Intermediate 149, 787 mg, 1.20 mmol) was dissolved in a mixture of 10 mL of THF and 5 mL of ethanol, an aqueous solution of lithium hydroxide (2.4 ml, 1 M, 2.4 mmol) was added and the mixture was stirred for 17 h at room temperature. The reaction mixture was concentrated under reduced pressure, water was added and the pH value was adjusted to 7 by addition of a saturated aqueous solution of citric acid. The mixture was extracted with ethyl acetate and the combined organic layers were dried over sodium sulfate, filtered and concentrated under reduced pressure to provide 595 mg of crude material. 50 mg of the crude material were purified by flash chromatography using silica gel (gradient dichloromethane/ethanol) and preparative HPLC (Method P3) to give 5.5 mg of the title compound.

LC-MS (Method 2) $R_t$=0.99 min; MS (ESIpos): m/z=626 [M+H]$^+$ $^1$H-NMR (400 MHz, DMSO-d6) δ[ppm]: 0.767 (2.99), 0.786 (7.05), 0.805 (3.16), 1.035 (1.81), 1.053 (3.09), 1.070 (1.86), 1.156 (0.57), 1.174 (0.42), 1.225 (2.07), 1.231 (2.22), 1.348 (2.19), 2.114 (0.64), 2.133 (1.39), 2.151 (1.53), 2.167 (1.32), 2.185 (0.87), 2.195 (0.97), 2.212 (1.27), 2.231 (0.94), 2.318 (0.45), 2.518 (5.42), 2.523 (3.61), 2.539 (0.45), 2.660 (0.42), 3.378 (0.73), 3.394 (0.54), 3.408 (0.64), 3.423 (0.64), 3.600 (0.61), 3.629 (0.71), 3.637 (0.78), 3.665 (0.52), 3.696 (0.42), 3.729 (0.71), 3.760 (0.42), 3.884 (16.00), 4.173 (1.18), 4.188 (2.47), 4.204 (1.18), 4.312 (1.89), 4.343 (2.22), 4.493 (0.49), 4.506 (0.42), 4.517 (0.42), 4.530 (0.45), 4.553 (1.46), 4.586 (1.01), 6.850 (1.18), 6.857 (1.23), 6.866 (1.11), 6.872 (1.27), 7.269 (3.06), 7.290 (3.09), 7.346 (0.80), 7.352 (0.90), 7.368 (1.25), 7.375 (1.34), 7.390 (0.85), 7.397 (0.97), 7.422 (2.10), 7.432 (2.43), 7.438 (5.25), 7.452 (0.42), 7.637 (1.41), 7.644 (1.46), 7.663 (1.41), 7.670 (1.44), 7.785 (2.29), 7.806 (2.05), 8.206 (1.23), 8.221 (1.32), 8.229 (1.27), 8.243 (1.20).

The crude material (545 mg) was separated into enantiomers by preparative chiral HPLC to give enantiomer 1 (144 mg, see Example 85) and enantiomer 2 (147 mg, see Example 86).

Preparative Chiral HPLC Method:
Instrument: Sepiatec: Prep SFC100; Column: Chiralpak IG 5μ 250×30 mm; Eluent A: Carbondioxide; Eluent B: Methanol; Isokratic: 15% B; Flow: 100 mL/min; Temperature 40° C.; BPR: 150 bar; UV: 220 nm Analytical Chiral HPLC Method:
Instrument: Agilent: 1260, Aurora SFC-Modul; Column: Chiralpak IG 5μ 100×4.6 mm; Eluent A: Carbondioxide; Eluent B: Methanol; Isokratic: 15% B; Flow: 4 mL/min; Temperature: 37.5° C.; BPR: 100 bar; DAD: 220 nm.

Example 85

(−)-4-chloro-3-ethyl-12,12-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (Enantiomer 1)

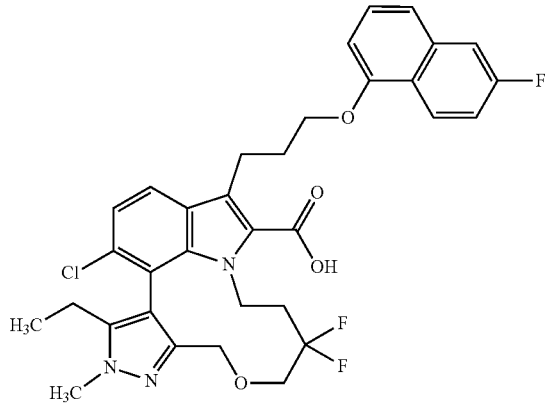 [SMILES: CCc1c2c(nn1C)COCC(F)(F)CCn1c(C(=O)O)c(CCCOc3cccc4cc(F)ccc34)c3ccc(Cl)c-2c31]

For the preparation of the racemic title compound see Example 84. Separation of enantiomers by preparative chiral HPLC (method see Example 84) gave the title compound (144 mg).

Analytical Chiral HPLC (method see Example 84): $R_t$=2.10 min.

LC-MS (Method 1): $R_t$=1.63 min; MS (ESIpos): m/z=626 [M+H]$^+$

Specific Optical Rotation (Method O1): −12.0° (c=10 mg/mL, DMSO)

$^1$H NMR (DMSO-$d_6$) δ: 8.23 (dd, J=9.3, 6.0 Hz, 1H), 7.80 (d, J=8.6 Hz, 1H), 7.66 (dd, J=10.4, 2.5 Hz, 1H), 7.40-7.49 (m, 2H), 7.38 (td, J=8.9, 2.7 Hz, 1H), 7.29 (d, J=8.4 Hz, 1H), 6.80-6.93 (m, 1H), 4.57 (d, J=13.2 Hz, 1H), 4.44-4.55 (m, 1H), 4.33 (d, J=12.4 Hz, 1H), 4.12-4.27 (m, 3H), 3.89 (s, 3H), 3.57-3.81 (m, 2H), 2.09-2.28 (m, 4H), 1.88-2.04 (m, 1H), 1.11 (s, 5H), 0.79 (t, J=7.6 Hz, 3H)

Example 86

(+)-4-chloro-3-ethyl-12,12-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (Enantiomer 2)

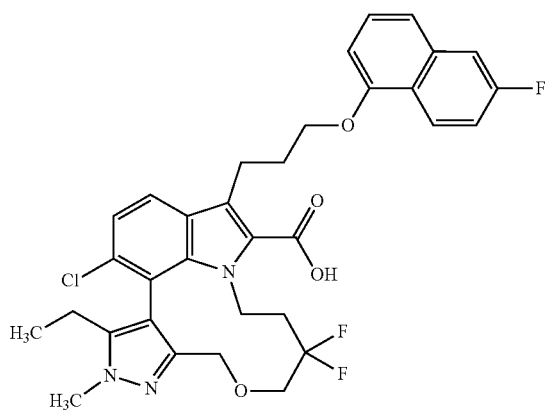 [SMILES: CCc1c2c(nn1C)COCC(F)(F)CCn1c(C(=O)O)c(CCCOc3cccc4cc(F)ccc34)c3ccc(Cl)c-2c31]

For the preparation of the racemic title compound see Example 84. Separation of enantiomers by preparative chiral HPLC (method see Example 84) gave the title compound (147 mg).

Analytical Chiral HPLC (method see Example 84): R$_t$=3.06 min.

LC-MS (Method 1): R$_t$=1.63 min; MS (ESIpos): m/z=626 [M+H]$^+$

Specific Optical Rotation (Method O1): 15.2° (c=10 mg/mL, DMSO)

$^1$H NMR (DMSO-d$_6$) δ: 8.22 (dd, J=9.3, 6.0 Hz, 1H), 7.79 (d, J=8.4 Hz, 1H), 7.65 (dd, J=10.4, 2.8 Hz, 1H), 7.32-7.49 (m, 3H), 7.28 (d, J=8.4 Hz, 1H), 6.86 (dd, J=6.2, 2.4 Hz, 1H), 4.40-4.63 (m, 2H), 4.32 (d, J=12.7 Hz, 1H), 4.07-4.25 (m, 3H), 3.88 (s, 3H), 3.52-3.79 (m, 2H), 2.07-2.27 (m, 4H), 1.10 (s, 5H), 0.78 (t, J=7.5 Hz, 3H)

Example 87

(rac)-11-chloro-9,10-dimethyl-1-{3-[(naphthalen-1-yl)oxy]propyl}-4,5,7,9-tetrahydropyrazolo[4',3':7,8][1,4]oxazonino[6,5,4-hi]indole-2-carboxylic acid

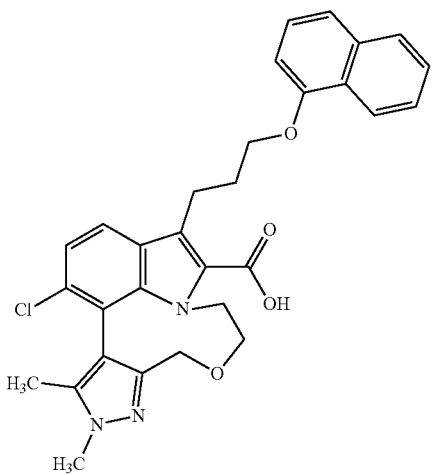 [SMILES: Cc1c2c(nn1C)COCCn1c(C(=O)O)c(CCCOc3cccc4ccccc34)c3ccc(Cl)c-2c31]

(rac)-Ethyl-11-chloro-9,10-dimethyl-1-{3-[(naphthalen-1-yl)oxy]propyl}-4,5,7,9-tetrahydropyrazolo[4',3':7,8][1,4]oxazonino[6,5,4-hi]indole-2-carboxylate (see Intermediate 155, 137 mg) was dissolved in 4 mL THF and 3.6 mL ethanol and treated with the lithium hydroxide solution (4.9 mL, 1.0 M in water, 4.9 mmol). The reaction mixture was stirred for 16 h at 60° C. under nitrogen atmosphere. The pH was adjusted to 5 by addition of acetic acid (280 µL, 4.9 mmol). The reaction mixture was concentrated under reduced pressure. The residue was dissolved in ethyl acetate and washed with saturated aqueous ammonium chloride solution followed by brine, the organic layer was filtered through a silicone coated filter and the solvent was removed under reduced pressure to provide the analytically pure target compound: 130 mg.

LC-MS (Method 2): R$_t$=0.87 min; MS (ESIpos): m/z=530 [M+H]$^+$ $^1$H NMR (DMSO-d$_6$) δ: 8.22 (m, 1H), 7.80 (d, 1H), 7.65 (m, 1H), 7.40-7.45 (m, 2H), 7.32-7.41 (m, 1H), 7.28 (d, 1H), 6.82-6.89 (m, 1H), 4.49-4.61 (m, 1H), 4.44-4.54 (m, 1H), 4.32 (d, 1H), 4.14-4.23 (m, 3H), 3.88 (s, 3H), 3.58-3.81 (m, 2H), 2.08-2.26 (m, 4H), 1.10 (s, 5H), 0.78 (m, 3H)

The title compound (130 mg) was separated into enantiomers by preparative chiral HPLC to give enantiomer 1 (46 mg, see Example 88) and enantiomer 2 (42 mg, see Example 89).

Preparative Chiral HPLC Method:
Instrument: Agilent HPLC 1260; Column: Cellulose SB 3µ 100×4.6 mm; Eluent A: Hexane+0.1 Vol-% trifluoroacidic acid; Eluent B: 2-Propanol; Isokratic: 80% A+20% B; Flow 1.4 mL/min; Temperature: 25° C.; DAD 220 nm Analytical Chiral HPLC Method:
Instrument: Labomatic HD5000, Labocord-5000; Gilson GX-241, Labcol Vario 4000, Column: Cellulose SB 5µ 250×30 mm; Eluent A: Hexan+0.1 Vol-% Trifluoroacidic acid; Eluent B: 2-Propanol; Isokratic: 80% A+20% B; Flow 50.0 mL/min; UV 220 nm.

Example 88

11-chloro-9,10-dimethyl-1-{3-[(naphthalen-1-yl)oxy]propyl}-4,5,7,9-tetrahydropyrazolo[4',3':7,8][1,4]oxazonino[6,5,4-hi]indole-2-carboxylic acid (Enantiomer 1)

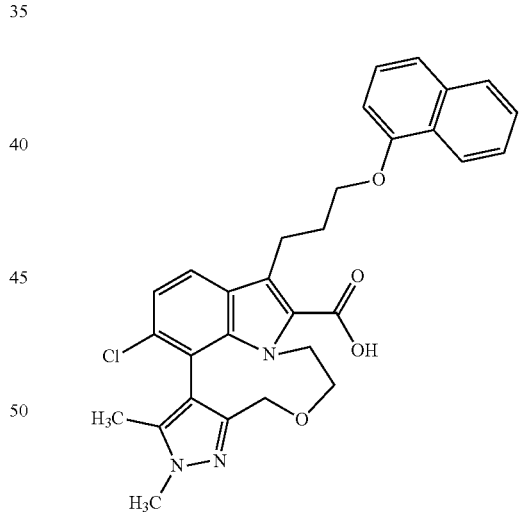

For the preparation of the racemic title compound see Example 87. Separation of enantiomers by preparative chiral HPLC (method see Example 87) gave the title compound (46 mg).

Analytical Chiral HPLC (method see Example 87): R$_t$=1.93 min.

$^1$H NMR (DMSO-d$_6$) δ: 8.22 (m, 1H), 7.79 (d, 1H), 7.65 (m, 1H), 7.32-7.49 (m, 3H), 7.28 (d, 1H), 6.86 (m, 1H), 4.40-4.63 (m, 2H), 4.32 (d, 1H), 4.07-4.25 (m, 3H), 3.88 (s, 3H), 3.52-3.79 (m, 2H), 2.07-2.27 (m, 4H), 1.10 (s, 5H), 0.78 (m, 3H)

Example 89

11-chloro-9,10-dimethyl-1-{3-[(naphthalen-1-yl)oxy]propyl}-4,5,7,9-tetrahydropyrazolo[4',3':7,8][1,4]oxazonino[6,5,4-hi]indole-2-carboxylic acid (Enantiomer 2)

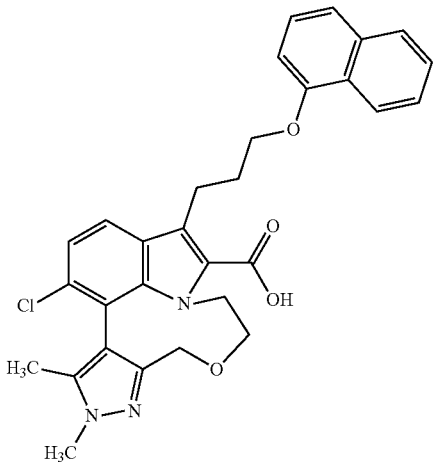 [SMILES: Cc1c2c(nn1C)COCCn1c(C(=O)O)c(CCCOc3cccc4ccccc34)c3ccc(Cl)c-2c31]

For the preparation of the racemic title compound see Example 87. Separation of enantiomers by preparative chiral HPLC (method see Example 87) gave the title compound (42 mg).

Analytical Chiral HPLC (method see Example 87): $R_t$=2.60 min.

$^1$H-NMR (400 MHz, DMSO-d6) δ[ppm]: 2.01 (s, 3H), 2.14-2.23 (m, 2H), 3.30 (oct, 2H), 3.57-3.66 (m, 2H), 3.80 (s, 3H), 3.84-3.94 (m, 1H), 4.10-4.26 (m, 3H), 4.35 (d, 1H), 4.56-4.69 (m, 2H), 6.92 (d, 1H), 7.17 (d, 1H), 7.35-7.43 (m, 1H), 7.44-7.48 (m, 1H), 7.48-7.58 (m, 2H), 7.71 (d, 1H), 7.84-7.91 (m, 1H), 8.19-8.28 (m, 1H).—contains TFA.

Example 90

(rac)-4-Chloro-12,12-difluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid

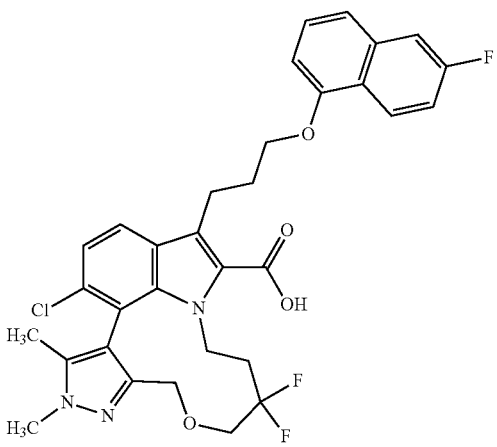 [SMILES: Cc1c2c(nn1C)COCC(F)(F)CCn1c(C(=O)O)c(CCCOc3cccc4cc(F)ccc34)c3ccc(Cl)c-2c31]

(rac)-Ethyl 4-Chloro-12,12-difluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylate (see Intermediate 157, 7.36 g) was dissolved in 190 mL THF and 170 mL ethanol and treated with the aqueous lithium hydroxide solution (230 mL, 1.0 M, 230 mmol). It was stirred for 16 h at 60° C. under nitrogen atmosphere. The pH was adjusted to 5 by addition of acetic acid (13 mL, 230 mmol). The reaction mixture was concentrated under reduced pressure. The crude residue was dissolved in ethyl acetate and washed with saturated aqueous ammonium chloride solution followed by brine. The organic layer was filtered through a silicone coated filter and the solvent was removed under reduced pressure. The crude product was purified by HPLC to provide the target compound: 726 mg.

LC-MS (Method 2): $R_t$=0.93 min; MS (ESIpos): m/z=612 [M+H]$^+$ $^1$H-NMR (400 MHz, DMSO-d6) δ[ppm]: 1.154 (4.26), 1.171 (9.10), 1.189 (4.54), 1.767 (15.49), 1.986 (16.00), 2.074 (6.53), 2.190 (0.97), 2.207 (1.42), 2.224 (1.03), 2.297 (0.47), 2.518 (2.11), 2.523 (1.47), 3.587 (0.70), 3.616 (0.80), 3.623 (0.89), 3.653 (0.78), 3.692 (0.79), 3.724 (0.49), 3.852 (15.87), 3.998 (1.13), 4.017 (3.41), 4.034 (3.44), 4.052 (1.14), 4.175 (1.24), 4.190 (2.59), 4.206 (1.24), 4.312 (1.98), 4.343 (2.23), 4.523 (0.54), 4.539 (0.46), 4.548 (0.48), 4.566 (1.56), 4.598 (1.06), 6.855 (1.24), 6.862 (1.28), 6.871 (1.13), 6.878 (1.33), 7.266 (3.51), 7.287 (3.46), 7.344 (0.82), 7.351 (0.96), 7.367 (1.30), 7.373 (1.42), 7.389 (0.88), 7.395 (0.96), 7.401 (0.50), 7.423 (2.31), 7.431 (2.63), 7.437 (5.83), 7.451 (0.46), 7.635 (1.51), 7.641 (1.55), 7.661 (1.52), 7.667 (1.54), 7.777 (2.81), 7.799 (2.51), 8.204 (1.32), 8.219 (1.38), 8.227 (1.35), 8.242 (1.27).

The title compound (726 mg) was separated into enantiomers by preparative chiral HPLC to give enantiomer 1 (135 mg, see Example 91) and enantiomer 2 (40 mg, see Example 92).

Preparative Chiral HPLC Method:
Instrument: Labomatic HD5000, Labocord-5000; Gilson GX-241, Labcol Vario 4000, Column: Chiralpak IG 5μ 250×30 mm; Eluent A: Hexane+0.1 Vol-% Diethylamine (99%); Eluent B: Ethanol; isokratic: 10% B; Flow 80.0 mL/min; UV 254 nm Analytical Chiral HPLC Method:
Instrument: Agilent HPLC 1260; Column: Chiralpak IG 3μ 100×4.6 mm; Eluent A: Hexane+0.1 Vol-% Diethylamine (99%); Eluent B: Ethanol; Gradient: 20-50% B in 7 min; Flow 1.4 mL/min; Temperature: 25° C.; DAD 254 nm

Example 91

4-chloro-12,12-difluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid-N-ethylethanamine salt (Enantiomer 1)

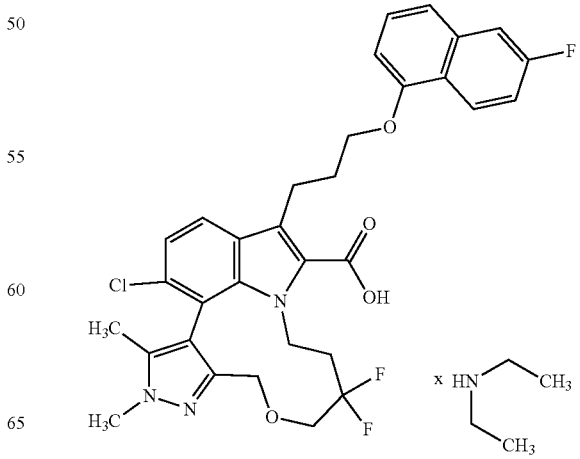

For the preparation of the racemic title compound see Example 90. Separation of enantiomers by preparative chiral HPLC (method see Example 90) gave the title compound (135 mg).

Analytical Chiral HPLC (method see Example 90): $R_t$=1.41 min.

$^1$H-NMR (400 MHz, DMSO-d6) δ[ppm]=1.15 (t, 6H), 1.76 (s, 3H), 1.98-2.11 (m, 1H), 2.12-2.26 (m, 2H), 2.87 (q, 4H), 3.18-3.27 (m, 3H), 3.27-3.42 (m, 2H), 3.49 (br t, 1H), 3.58 (dd, 1H), 3.85 (s, 3H), 4.10-4.23 (m, 2H), 4.31 (d, 1H), 4.57 (d, 1H), 4.70-4.84 (m, 1H), 6.83 (dd, 1H), 7.13 (d, 1H), 7.32-7.46 (m, 3H), 7.58 (d, 1H), 7.64 (dd, 1H), 8.25 (dd, 1H).—contains tBuOH.

Example 92

4-chloro-12,12-difluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid (Enantiomer 2)

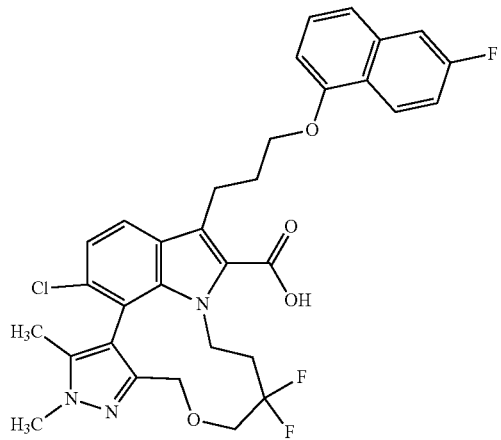 [SMILES: Cc1c2c(nn1C)COCC(F)(F)CCn1c(C(=O)O)c(CCCOc3cccc4cc(F)ccc34)c3ccc(Cl)c-2c31]

For the preparation of the racemic title compound see Example 90. Separation of enantiomers by preparative chiral HPLC (method see Example 90) gave the title compound (40 mg).

Analytical Chiral HPLC (method see Example 90): $R_t$=1.87 min.

$^1$H-NMR (400 MHz, DMSO-d6) δ[ppm]=1.23 (br s, 1H), 1.77 (s, 3H), 1.88-1.97 (m, 2H), 2.21 (quin, 2H), 3.18-3.29 (m, 1H), 3.37 (br s, 1H), 3.56-3.76 (m, 2H), 3.85 (s, 3H), 4.19 (br t, 2H), 4.33 (d, 1H), 4.46-4.65 (m, 2H), 6.87 (dd, 1H), 7.28 (d, 1H), 7.33-7.49 (m, 3H), 7.65 (dd, 1H), 7.79 (d, 1H), 8.22 (dd, 1H), 13.46 (br s, 1H).—contains ethyl acetate.

Example 93

(rac)-4-Chloro-11,11-difluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid

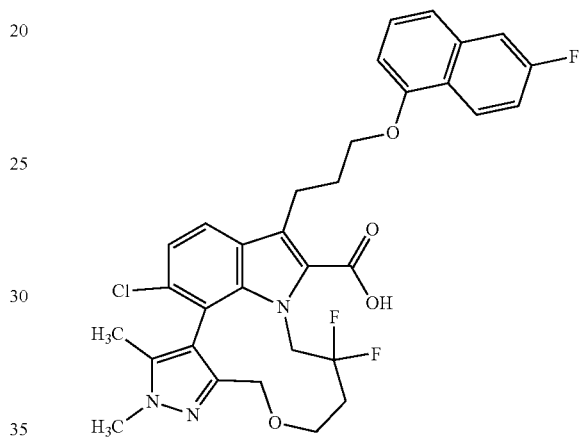

(rac)-Ethyl 4-chloro-11,11-difluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylate (see Intermediate 159, 1.54 g) was dissolved in 39 mL THF and 35 mL ethanol and treated with aqueous lithium hydroxide solution (48 mL, 1.0 M, 48 mmol). It was stirred for 16 h at 60° C. under nitrogen atmosphere. The pH was adjusted to 5 by addition of acetic acid (2.8 mL, 48 mmol). The reaction mixture was concentrated under reduced pressure. The crude residue was dissolved in ethyl acetate and washed with saturated aqueous ammonium chloride solution followed by brine, the organic layer was filtered through a silicone coated filter and the solvent was removed under reduced pressure to provide the analytically pure target compound: 1.6 g.

LC-MS (Method 2): $R_t$=0.99 min; MS (ESIpos): m/z=612 [M+H]$^+$ $^1$H-NMR (400 MHz, DMSO-d6): δ [ppm]=1.20-1.40 (m, 1H), 1.91 (s, 3H), 1.95 (br d, 1H), 2.16-2.27 (m, 2H), 3.28-3.32 (m, 2H), 3.36-3.45 (m, 1H), 3.56-3.77 (m, 2H), 3.85 (s, 3H), 4.19 (t, 2H), 4.33 (d, 1H), 4.47-4.65 (m, 2H), 6.87 (dd, 1H), 7.29 (d, 1H), 7.33-7.49 (m, 3H), 7.65 (dd, 1H), 7.80 (d, 1H), 8.22 (dd, 1H), 13.18 (br s, 1H).

Example 94

4-chloro-11,11-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid N-ethylethanamine salt (Enantiomer 1)

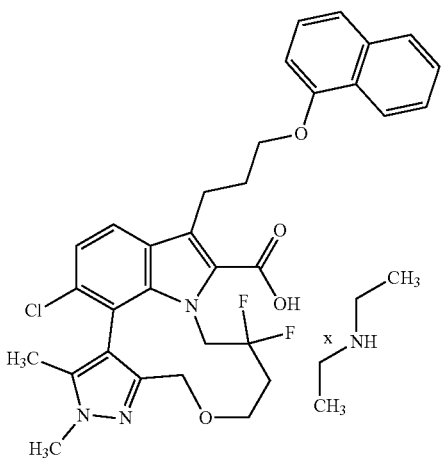

For the preparation of the racemic title compound see Example 68. Separation of enantiomers by preparative chiral HPLC (method see Example 68) gave the title compound (70 mg).

Analytical Chiral HPLC (method see Example 68): $R_t$=2.16 min.

Specific Optical Rotation (Method O1): 27.8° (c=10 mg/mL, methanol)

$^1$H-NMR (400 MHz, DMSO-d6) δ[ppm]=1.21-1.31 (m, 1H), 1.77 (s, 3H), 2.05 (br d, 1H), 2.20 (quin, 2H), 3.18-3.29 (m, 2H), 3.47-3.69 (m, 2H), 3.85 (s, 3H), 4.11-4.23 (m, 2H), 4.31 (d, 1H), 4.57 (d, 1H), 4.66-4.81 (m, 1H), 6.86 (d, 1H), 7.14 (d, 1H), 7.33-7.40 (m, 1H), 7.42-7.46 (m, 1H), 7.47-7.56 (m, 2H), 7.62 (d, 1H), 7.81-7.90 (m, 1H), 8.16-8.29 (m, 1H).—as diethylamine salt.

Example 95

4-chloro-11,11-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid N-ethylethanamine salt (Enantiomer 2)

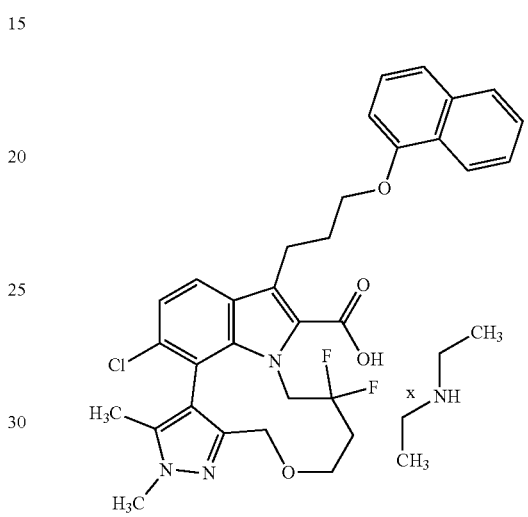

For the preparation of the racemic title compound see Example 68. Separation of enantiomers by preparative chiral HPLC (method see Example 68) gave the title compound (74 mg).

Analytical Chiral HPLC (method see Example 68): $R_t$=3.27 min.

Specific Optical Rotation (Method O1): −27.9° (c=10 mg/mL, methanol)

$^1$H-NMR (400 MHz, DMSO-d6) δ[ppm]=1.21-1.31 (m, 1H), 1.77 (s, 3H), 2.05 (br d, 1H), 2.20 (quin, 2H), 3.18-3.29 (m, 2H), 3.47-3.69 (m, 2H), 3.85 (s, 3H), 4.11-4.23 (m, 2H), 4.31 (d, 1H), 4.57 (d, 1H), 4.66-4.81 (m, 1H), 6.86 (d, 1H), 7.14 (d, 1H), 7.33-7.40 (m, 1H), 7.42-7.46 (m, 1H), 7.47-7.56 (m, 2H), 7.62 (d, 1H), 7.81-7.90 (m, 1H), 8.16-8.29 (m, 1H).—as diethylamine salt.

Example 96

(rac)-4-chloro-3-ethyl-11,11-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid

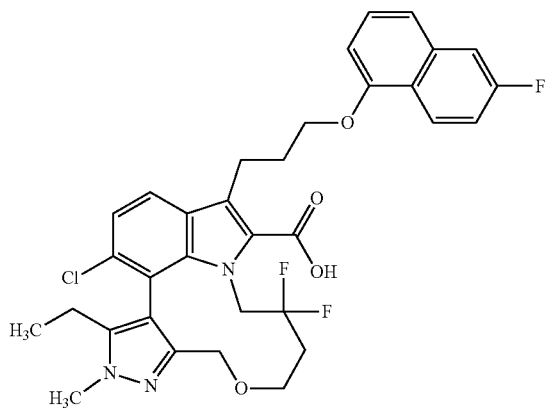 [SMILES: CCc1c2c(nn1C)COCCC(F)(F)Cn1c(C(=O)O)c(CCCOc3cccc4cc(F)ccc34)c3ccc(Cl)c-2c31]

(rac)-Ethyl 4-chloro-3-ethyl-11,11-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylate (see Intermediate 163, 626 mg) was dissolved in a mixture of 20 mL of THF and 5 mL of ethanol, an aqueous solution of lithium hydroxide (1.9 mL, 1.0 M, 1.9 mmol) was added and the mixture was stirred at 65° C. for 4 days. The reaction mixture was concentrated under reduced pressure, water was added and the pH value was adjusted to 4 by addition of saturated aqueous solution of citric acid. The precipitate was isolated by filtration and washed with water. The crude product was purified by flash chromatography using silica gel (gradient dichloromethane/ethanol). The resulted mixture of starting material and title compound was dissolved in a mixture of 20 mL of THF and 5 mL of ethanol, an aqueous solution of lithium hydroxide (1.9 mL, 1.0 M, 1.9 mmol) was added and the mixture was stirred overnight at 65° C. The reaction mixture was concentrated under reduced pressure, water was added and the pH value was adjusted to 4 by addition of a saturated aqueous solution of citric acid. The precipitate was isolated by filtration and washed with water. The crude material was purified by preparative HPLC (Method P2) to provide 205 mg of the title compound.

LC-MS (Method 1): $R_t$=1.63 min; MS (ESIpos): m/z=626 [M+H]$^+$ $^1$H-NMR (400 MHz, DMSO-d6) δ[ppm]: 0.766 (3.00), 0.786 (6.95), 0.804 (3.14), 1.352 (1.75), 1.358 (0.53), 2.114 (0.64), 2.132 (1.42), 2.150 (1.65), 2.168 (1.37), 2.185 (0.94), 2.195 (1.03), 2.211 (1.30), 2.230 (0.98), 2.327 (1.00), 2.331 (0.72), 2.518 (3.79), 2.523 (2.40), 2.669 (1.03), 2.673 (0.72), 3.294 (1.55), 3.379 (0.50), 3.393 (0.45), 3.409 (0.43), 3.602 (0.64), 3.630 (0.74), 3.638 (0.81), 3.667 (0.55), 3.704 (0.46), 3.734 (0.74), 3.767 (0.46), 3.884 (16.00), 4.174 (1.22), 4.189 (2.56), 4.204 (1.24), 4.312 (1.87), 4.344 (2.15), 4.486 (0.52), 4.500 (0.45), 4.510 (0.45), 4.525 (0.50), 4.554 (1.32), 4.585 (1.00), 5.758 (0.94), 6.851 (1.22), 6.858 (1.25), 6.867 (1.24), 6.873 (1.30), 7.273 (3.43), 7.294 (3.45), 7.346 (0.79), 7.353 (0.91), 7.368 (1.25), 7.375 (1.36), 7.391 (0.86), 7.397 (0.94), 7.402 (0.53), 7.422 (2.15), 7.433 (2.54), 7.438 (5.39), 7.453 (0.45), 7.638 (1.42), 7.644 (1.49), 7.664 (1.46), 7.670 (1.46), 7.790 (2.80), 7.812 (2.58), 8.205 (1.25), 8.220 (1.32), 8.228 (1.29), 8.243 (1.22).

The title compound (201 mg) was separated into enantiomers by preparative chiral HPLC to give enantiomer 1 (68 mg, see Example 97).

Preparative Chiral HPLC Method:
Instrument: PrepCon Labomatic HPLC; Column: Chiralpak IG 5µ 250×30; Eluent A: Water+0.1% trifluoroacetic acid; Eluent B: Acetonitrile; Isokratic: 30% A+70% B; Flow: 60 mL/min; Temperature: 25° C.; UV: 254 nm Analytical Chiral HPLC Method:
Instrument: Agilent 1260 HPLC; Column: Chiralpak IG 3µ 100×4.6; Eluent A: Water+0.1% Phosporic acid; Eluent B: Acetonitril; Isokratic; Flow: 1.4 mL/min; Temperature: 25° C.; UV: 254 nm

Example 97

(−)-4-chloro-3-ethyl-11,11-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid
(Enantiomer 1)

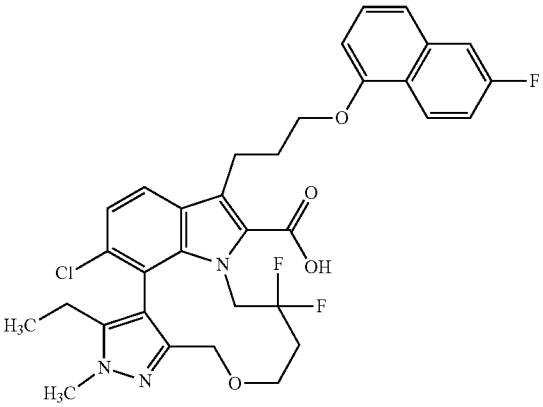 [SMILES: CCc1c2c(nn1C)COCCC(F)(F)Cn1c(C(=O)O)c(CCCOc3cccc4cc(F)ccc34)c3ccc(Cl)c-2c31]

For the preparation of the racemic title compound see Example 96. Separation of enantiomers by preparative chiral HPLC (method see Example 96) gave the title compound (68 mg).

Analytical Chiral HPLC (method see Example 96): $R_t$=5:30 min.

LC-MS (Method 1): $R_t$=1.61 min; MS (ESIpos): m/z=626 [M+H]$^+$

Specific Optical Rotation (Method O1): −6.7° (c=10 mg/mL, DMSO)

$^1$H-NMR (400 MHz, DMSO-d6) δ[ppm]: 0.766 (3.02), 0.785 (6.89), 0.804 (3.19), 1.026 (0.44), 1.042 (0.43), 1.138 (0.91), 1.156 (1.61), 1.174 (1.01), 1.232 (0.68), 1.262 (2.26), 2.084 (6.66), 2.114 (0.72), 2.132 (1.49), 2.144 (2.09), 2.149 (1.68), 2.167 (1.41), 2.185 (0.95), 2.195 (1.06), 2.212 (1.41), 2.230 (1.04), 2.332 (0.83), 2.518 (4.20), 2.523 (2.90), 2.817 (0.52), 2.915 (0.54), 2.933 (0.54), 3.161 (0.97), 3.169 (0.97), 3.409 (0.58), 3.421 (0.46), 3.599 (0.70), 3.628 (0.79), 3.635 (0.87), 3.665 (0.60), 3.696 (0.44), 3.729 (0.75), 3.759 (0.46), 3.883 (16.00), 4.173 (1.22), 4.188 (2.44), 4.202 (1.22), 4.311 (2.03), 4.343 (2.34), 4.497 (0.48), 4.509 (0.43), 4.519 (0.43), 4.532 (0.48), 4.554 (1.64), 4.585 (1.12), 6.850 (1.12), 6.855 (1.14), 6.865 (1.12), 6.871 (1.18), 7.268 (2.92), 7.289 (3.02), 7.345 (0.75), 7.352 (0.81), 7.367 (1.26), 7.374 (1.33), 7.390 (0.79), 7.397 (0.91), 7.421 (2.01), 7.431 (2.61), 7.437 (4.84), 7.452 (0.48), 7.636 (1.45), 7.643 (1.51), 7.662 (1.47), 7.669 (1.45), 7.783 (2.22), 7.804 (2.01), 8.205 (1.18), 8.220 (1.24), 8.228 (1.20), 8.243 (1.10).

Example 98

(+)-4-chloro-3-ethyl-11,11-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (Enantiomer 2)

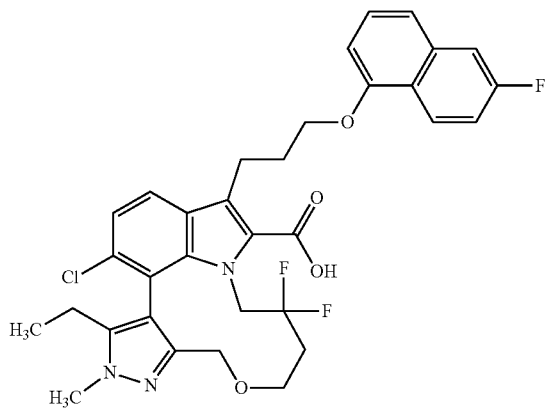 [SMILES: CCc1c2c(nn1C)COCCC(F)(F)Cn1c(C(=O)O)c(CCCOc3cccc4cc(F)ccc34)c3ccc(Cl)c-2c31]

For the preparation of the racemic title compound see Example 96. Separation of enantiomers by preparative chiral HPLC (method see Example 96) and a second preparative chiral HPLC gave the title compound (54 mg).

Second Preparative Chiral HPLC Method:

Instrument: Sepiatec: Prep SFC100; Column: Chiralpak IG 5µ 250×30 mm; Eluent A: carbon dioxide; Eluent B: Ethanol+0.2 Vol-% aqueous ammonia (32%); Isokratic: 15% B; Flow: 100 mL/min; Temperature: 40° C.; BPR: 150 bar; UV: 254 nm Analytical Chiral HPLC Method:

Instrument: Agilent: 1260, Aurora SFC-Modul; Column: Chiralpak IG 5µ 100×4.6 mm; Eluent A: carbon dioxide; Eluent B: Ethanol+0.1 Vol-% aqueous ammonia (32%); Isokratic: 15% B; Flow: 4 mL/min; Temperature: 37.5° C.; BPR: 100 bar; UV: 254 nm Analytical Chiral HPLC: $R_t$=3.22 min.

LC-MS (Method 1): $R_t$=1.63 min; MS (ESIpos): m/z=626 [M+H]$^+$

Specific Optical Rotation (Method O1): 10.6° (c=10 mg/mL, DMSO)

$^1$H-NMR (400 MHz, DMSO-d6) δ[ppm]: 0.766 (3.02), 0.785 (6.89), 0.804 (3.19), 1.026 (0.44), 1.042 (0.43), 1.138 (0.91), 1.156 (1.61), 1.174 (1.01), 1.232 (0.68), 1.262 (2.26), 2.084 (6.66), 2.114 (0.72), 2.132 (1.49), 2.144 (2.09), 2.149 (1.68), 2.167 (1.41), 2.185 (0.95), 2.195 (1.06), 2.212 (1.41), 2.230 (1.04), 2.332 (0.83), 2.518 (4.20), 2.523 (2.90), 2.817 (0.52), 2.915 (0.54), 2.933 (0.54), 3.161 (0.97), 3.169 (0.97), 3.409 (0.58), 3.421 (0.46), 3.599 (0.70), 3.628 (0.79), 3.635 (0.87), 3.665 (0.60), 3.696 (0.44), 3.729 (0.75), 3.759 (0.46), 3.883 (16.00), 4.173 (1.22), 4.188 (2.44), 4.202 (1.22), 4.311 (2.03), 4.343 (2.34), 4.497 (0.48), 4.509 (0.43), 4.519 (0.43), 4.532 (0.48), 4.554 (1.64), 4.585 (1.12), 6.850 (1.12), 6.855 (1.14), 6.865 (1.12), 6.871 (1.18), 7.268 (2.92), 7.289 (3.02), 7.345 (0.75), 7.352 (0.81), 7.367 (1.26), 7.374 (1.33), 7.390 (0.79), 7.397 (0.91), 7.421 (2.01), 7.431 (2.61), 7.437 (4.84), 7.452 (0.48), 7.636 (1.45), 7.643 (1.51), 7.662 (1.47), 7.669 (1.45), 7.783 (2.22), 7.804 (2.01), 8.205 (1.18), 8.220 (1.24), 8.228 (1.20), 8.243 (1.10).

Example 99

4-chloro-3-ethyl-7-{3-[(6-fluoronaphthalen-1-yl)oxy]propyl}-12-hydroxy-2-methyl-2,10,11,12,13,15-hexahydropyrazolo[4',3':9,10][1,6]oxazacycloundecino[8,7,6-hi]indole-8-carboxylic acid-N-ethylethanamine salt (Stereoisomer 1)

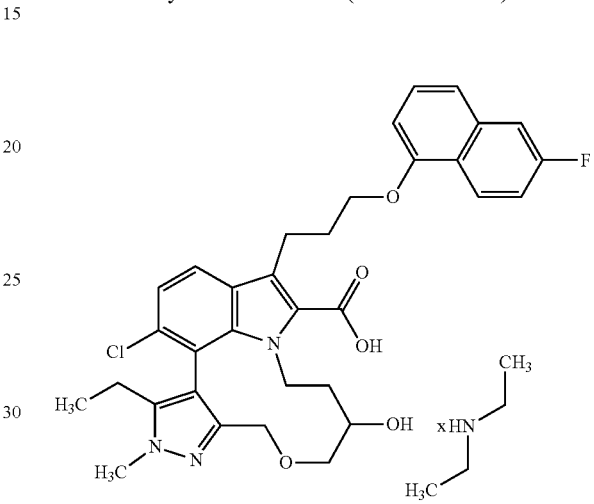

The mixture of the four stereoisomers of (rac)-ethyl 4-chloro-3-ethyl-7-{3-[(6-fluoronaphthalen-1-yl)oxy]propyl}-(12-rac)-hydroxy-2-methyl-2,10,11,12,13,15-hexahydropyrazolo[4',3':9,10][1,6]oxazacycloundecino[8,7,6-hi]indole-8-carboxylate (see Intermediate 168, 260 mg) was dissolved in a mixture of 2 mL of THF and 1 mL of ethanol, an aqueous solution of lithium hydroxide (820 µL, 1.0 M, 820 µmol) was added and the mixture was stirred for 16 h at 60° C. An aqueous solution of lithium hydroxide (400 µL, 1.0 M, 400 µmol) was added and the mixture was stirred for 72 h at 60° C. The reaction mixture was concentrated under reduced pressure, water was added and the pH value was adjusted to 7 by addition of a saturated aqueous solution of citric acid. The precipitate was isolated by filtration and washed with water. The material (86.1 mg) was separated into four stereoisomers by preparative chiral HPLC to give stereoisomer 1 (18.5 mg, Example 99), stereoisomer 2 (17.8 mg, see Example 100), stereoisomer 3 (19.5 mg, see Example 101) and stereoisomer 4 (17.1 mg, see Example 102).

Preparative Chiral HPLC Method:

Instrument: Labomatic HD5000, Labocord-5000; Gilson GX-241, Labcol Vario 4000, column: Chiralpak IG 5µ 250×30 mm; eluent A: hexane+0.1 Vol-% diethylamine (99%); eluent B: ethanol; gradient: 20-50% B in 20 min; flow 40.0 mL/min; UV 254 nm Analytical Chiral HPLC Method:

Instrument: Agilent HPLC 1260; column: Chiralpak IG 3µ 100×4.6 mm; eluent A: hexane+0.1 Vol-% diethylamine (99%); eluent B: ethanol; gradient: 20-50% B in 7 min; flow 1.4 mL/min; temperature: 25° C.; UV 254 nm Analytical Chiral HPLC: $R_t$=2.14 min.

LC-MS (Method 1): $R_t$=1.50 min; MS (ESIpos): m/z=606 [M+H]$^+$ $^1$H-NMR (400 MHz, DMSO-d6) δ[ppm]: 0.792 (2.14), 0.811 (4.85), 0.830 (2.23), 1.125 (7.11), 1.137 (1.35), 1.144 (16.00), 1.154 (0.85), 1.161 (7.14), 1.172 (0.79), 1.231 (0.59), 1.987 (1.16), 2.126 (0.48), 2.145 (0.99), 2.154 (1.02), 2.164 (1.04), 2.173 (1.47), 2.192 (1.47), 2.209 (0.99), 2.327 (1.61), 2.331 (1.19), 2.336 (0.54), 2.518 (6.63), 2.523 (4.12), 2.669 (1.66), 2.673 (1.24), 2.678 (0.56), 2.834 (1.75), 2.853 (5.47), 2.871 (5.22), 2.889 (1.64), 2.952 (0.45), 2.974 (0.85), 2.997 (0.54), 3.176 (0.45), 3.193 (0.76), 3.203 (0.96), 3.216 (1.13), 3.226 (1.38), 3.241 (1.02), 3.260 (0.62), 3.834 (0.87), 3.857 (11.23), 4.149 (0.65), 4.165 (1.16), 4.175 (1.16), 4.191 (0.62), 4.200 (1.64), 4.231 (1.61), 4.395 (1.50), 4.426 (1.19), 4.607 (0.68), 4.619 (0.68), 5.759 (4.09), 6.833 (0.85), 6.839 (0.90), 6.849 (0.85), 6.855 (0.93), 7.085 (1.10), 7.106 (1.16), 7.355 (0.54), 7.362 (0.68), 7.378 (0.87), 7.385 (0.99), 7.389 (0.51), 7.400 (0.68), 7.410 (1.47), 7.427 (3.44), 7.569 (0.79), 7.590 (0.73), 7.633 (1.04), 7.639 (1.10), 7.659 (1.04), 7.665 (1.04), 8.244 (0.85), 8.259 (0.90), 8.267 (0.96), 8.282 (0.90).

Example 100

4-chloro-3-ethyl-7-{3-[(6-fluoronaphthalen-1-yl)oxy]propyl}-12-hydroxy-2-methyl-2,10,11,12,13,15-hexahydropyrazolo[4',3':9,10][1,6]oxazacycloundecino[8,7,6-hi]indole-8-carboxylic acid-N-ethylethanamine salt (Stereoisomer 2)

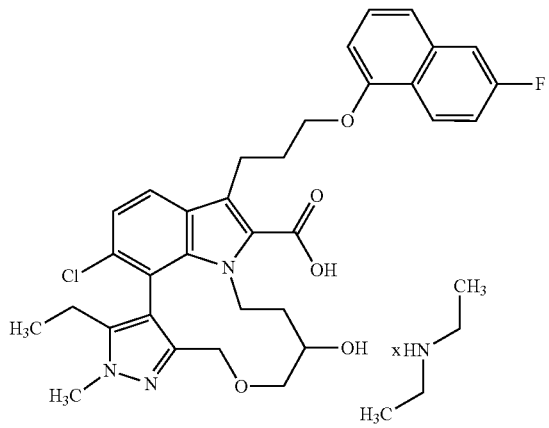

For the preparation of the mixture of four stereoisomers of the title compound see Example 99. Separation of stereoisomers by preparative chiral HPLC (method see Example 99) gave the title compound (17.8 mg).

Analytical Chiral HPLC (method see Example 99): $R_t$=2.48 min.

LC-MS (Method 1): $R_t$=1.46 min; MS (ESIpos): m/z=606 [M+H]$^+$ $^1$H-NMR (400 MHz, DMSO-d6) δ[ppm]: 0.768 (2.78), 0.787 (6.44), 0.806 (3.02), 0.851 (0.46), 0.885 (0.81), 0.913 (0.74), 1.132 (6.96), 1.137 (1.79), 1.150 (16.00), 1.168 (7.42), 1.232 (0.88), 1.259 (0.42), 1.526 (0.56), 1.556 (0.53), 2.093 (0.60), 2.111 (1.41), 2.116 (1.55), 2.130 (1.27), 2.136 (1.30), 2.154 (0.67), 2.173 (0.60), 2.188 (1.09), 2.206 (1.44), 2.223 (1.02), 2.327 (2.00), 2.331 (1.48), 2.336 (0.67), 2.518 (7.77), 2.523 (5.03), 2.539 (0.67), 2.669 (2.07), 2.673 (1.51), 2.678 (0.67), 2.850 (1.83), 2.869 (5.52), 2.886 (5.45), 2.905 (1.69), 3.170 (0.67), 3.177 (0.81), 3.197 (1.20), 3.205 (1.30), 3.214 (1.30), 3.233 (1.97), 3.252 (1.34), 3.268 (2.07), 3.295 (2.67), 3.835 (14.87), 3.858 (1.05), 4.149 (2.29), 4.171 (1.76), 4.181 (3.09), 4.199 (0.81), 4.409 (0.95), 4.420 (1.02), 4.474 (2.25), 4.505 (1.79), 5.759 (0.91), 6.844 (1.13), 6.851 (1.20), 6.858 (1.05), 6.866 (1.16), 7.113 (1.20), 7.134 (1.27), 7.369 (0.77), 7.376 (0.95), 7.392 (1.30), 7.399 (1.58), 7.414 (1.13), 7.421 (3.13), 7.428 (2.81), 7.436 (5.20), 7.599 (0.91), 7.619 (0.81), 7.638 (1.55), 7.645 (1.51), 7.664 (1.48), 7.671 (1.41), 8.264 (1.27), 8.280 (1.41), 8.288 (1.27), 8.302 (1.20).

Example 101

4-chloro-3-ethyl-7-{3-[(6-fluoronaphthalen-1-yl)oxy]propyl}-12-hydroxy-2-methyl-2,10,11,12,13,15-hexahydropyrazolo[4',3':9,10][1,6]oxazacycloundecino[8,7,6-hi]indole-8-carboxylic acid-N-ethylethanamine salt (Stereoisomer 3)

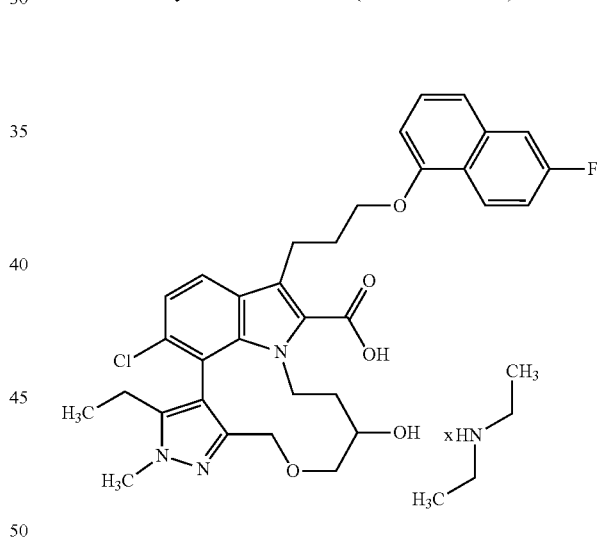

For the preparation of mixture of four stereoisomers of the title compound see Example 99. Separation of enantiomers by preparative chiral HPLC (method see Example 99) gave the title compound (19.5 mg).

Analytical Chiral HPLC (method see Example 99): $R_t$=3.20 min.

LC-MS (Method 1): $R_t$=1.46 min; MS (ESIpos): m/z=606 [M+H]$^+$ $^1$H-NMR (400 MHz, DMSO-d6) δ[ppm]: 0.768 (2.51), 0.787 (5.70), 0.806 (2.76), 0.831 (0.50), 0.861 (0.50), 0.886 (0.83), 0.915 (0.72), 1.127 (7.21), 1.144 (16.00), 1.163 (7.57), 1.231 (1.00), 1.259 (0.50), 1.533 (0.54), 1.562 (0.47), 2.093 (0.65), 2.114 (1.69), 2.132 (1.54), 2.152 (0.72), 2.187 (1.11), 2.204 (1.43), 2.221 (1.04), 2.327 (2.04), 2.331 (1.54), 2.518 (9.47), 2.522 (5.85), 2.669 (2.12), 2.673 (1.58), 2.837 (1.90), 2.855 (5.52), 2.873 (5.45), 2.891 (1.76), 3.177 (0.83), 3.205 (2.01), 3.224 (1.94), 3.242 (1.36), 3.263 (2.08), 3.290 (2.55), 3.834 (12.34), 3.857 (1.33), 4.148 (2.15), 4.167 (1.69), 4.180 (3.16), 4.400 (0.93), 4.413 (0.90), 4.472 (2.08), 4.503 (1.83), 5.759 (5.74), 6.841 (1.08), 6.849 (1.11), 6.855 (1.04), 6.863 (1.08), 7.096 (1.18), 7.117 (1.26), 7.369 (0.68), 7.376 (0.83), 7.391 (1.18), 7.398 (1.54), 7.421 (2.76), 7.427 (2.83), 7.434 (4.59), 7.576 (0.93), 7.597 (0.86), 7.637 (1.36), 7.643 (1.33), 7.663 (1.36), 7.669 (1.29), 8.266 (1.15), 8.282 (1.22), 8.290 (1.15), 8.304 (1.08).

Example 102

4-chloro-3-ethyl-7-{3-[(6-fluoronaphthalen-1-yl)oxy]propyl}-12-hydroxy-2-methyl-2,10,11,12,13,15-hexahydropyrazolo[4',3':9,10][1,6]oxazacycloundecino[8,7,6-hi]indole-8-carboxylic acid-N-ethylethanamine salt (Stereoisomer 4)

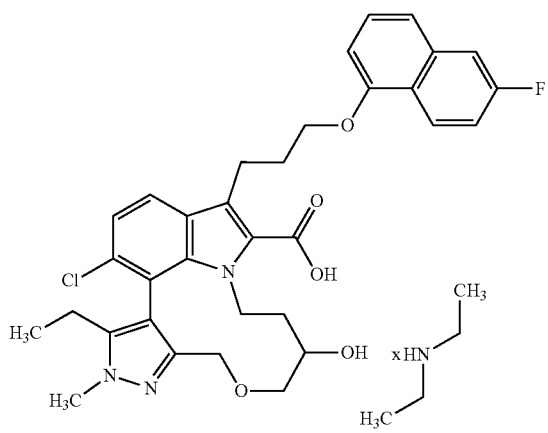

For the preparation of the mixture of four stereoisomers of the title compound see Example 99. Separation of enantiomers by preparative chiral HPLC (method see Example 99) gave the title compound (17.1 mg).

Analytical Chiral HPLC (method see Example 99): R$_t$=3.69 min.

LC-MS (Method 1): R$_t$=1.50 min; MS (ESIpos): m/z=606 [M+H]$^+$ $^1$H-NMR (400 MHz, DMSO-d6) δ[ppm]: 0.792 (2.92), 0.811 (6.29), 0.830 (3.14), 0.851 (0.47), 0.877 (0.55), 0.896 (0.83), 0.915 (0.41), 0.991 (0.74), 1.006 (0.63), 1.133 (7.83), 1.151 (16.00), 1.169 (8.06), 1.190 (0.50), 1.231 (1.38), 1.259 (0.58), 1.481 (0.55), 1.505 (0.72), 1.516 (0.63), 1.987 (0.88), 2.115 (0.61), 2.124 (0.72), 2.142 (1.43), 2.161 (1.77), 2.175 (2.18), 2.194 (2.21), 2.211 (1.60), 2.322 (1.24), 2.327 (1.63), 2.331 (1.24), 2.522 (5.79), 2.665 (1.27), 2.669 (1.66), 2.673 (1.24), 2.851 (1.93), 2.869 (5.54), 2.888 (5.46), 2.905 (1.79), 2.948 (0.72), 2.971 (1.32), 2.994 (0.83), 3.174 (0.55), 3.189 (0.80), 3.209 (1.85), 3.223 (2.01), 3.234 (2.04), 3.248 (1.57), 3.269 (1.19), 3.681 (0.63), 3.809 (0.41), 3.828 (1.79), 3.858 (13.27), 4.151 (1.16), 4.167 (1.79), 4.177 (1.77), 4.200 (2.21), 4.231 (2.15), 4.400 (2.07), 4.431 (1.63), 4.483 (0.47), 4.502 (0.52), 4.619 (0.97), 5.759 (4.41), 6.834 (1.21), 6.839 (1.30), 6.850 (1.24), 6.856 (1.24), 7.101 (1.68), 7.122 (1.77), 7.355 (0.72), 7.361 (0.86), 7.377 (1.32), 7.384 (1.46), 7.391 (0.74), 7.400 (0.94), 7.412 (2.21), 7.428 (4.99), 7.444 (0.61), 7.592 (1.27), 7.612 (1.16), 7.633 (1.46), 7.640 (1.54), 7.659 (1.43), 7.666 (1.49), 8.241 (1.10), 8.256 (1.21), 8.264 (1.27), 8.278 (1.21).

Example 103

(rac)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]oxazacycloundecino[8,7,6-hi]indole-13-carboxylic acid (Racemante 1)

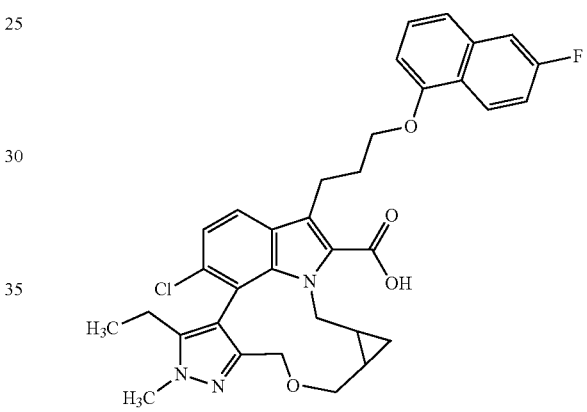

(rac)-Ethyl-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]oxazacycloundecino[8,7,6-hi]indole-13-carboxylate (see Intermediate 172, 225 mg) was dissolved in 5.8 mL THF and 5.2 mL ethanol and treated with the aqueous lithium hydroxide solution (8.0 mL, 1.0 M, 8.0 mmol). The reaction mixture was stirred at 60° C. under argon atmosphere over night and at 75° C. a further night. The pH was adjusted to 5 by addition of acetic acid (460 µL, 8.0 mmol). The reaction mixture was concentrated under reduced pressure and extracted with dichloromethane thrice. The combined organic layers were washed with water and brine, filtered through a silicone coated filter and concentrated under reduced pressure to provide the analytically pure target compound: 272 mg.

LC-MS (Method 2): R$_t$=0.94 min; MS (ESIpos): m/z=603/604 [M+H]$^+$ $^1$H-NMR (400 MHz, DMSO-d6): δ [ppm]=−0.23 (q, 1H), 0.51-0.61 (m, 1H), 0.62-0.74 (m, 1H), 0.81 (t, 3H), 0.87-0.99 (m, 1H), 2.10-2.29 (m, 4H), 2.40 (t, 1H), 3.20-3.30 (m, 2H), 3.51 (br dd, 1H), 3.68 (dd, 1H), 3.83 (s, 3H), 4.06 (d, 1H), 4.22 (t, 2H), 4.37 (d, 1H), 4.64 (d, 1H), 6.90 (dd, 1H), 7.20 (d, 1H), 7.36-7.50 (m, 3H), 7.64-7.76 (m, 2H), 8.30 (dd, 1H), 13.38 (br s, 1H).

The title compound (225 mg) was separated into enantiomers by preparative chiral HPLC to give enantiomer 1 (109 mg, see Example 104) and enantiomer 2 (98 mg, see Example 105).

Preparative Chiral HPLC Method:

Instrument: Labomatic HD5000, Labocord-5000; Gilson GX-241, Labcol Vario 4000, Column: Amylose SA 5μ 250×30 mm; Eluent A: Hexane+0.1 Vol-% Diethylamine (99%); Eluent B: Ethanol; Isokratic: 80% A+20% B; Flow 50.0 mL/min; UV 254 nm Analytical Chiral HPLC Method:

Instrument: Agilent HPLC 1260; Column: Amylose SA 3μ 100×4.6 mm; Eluent A: Hexane+0.1 Vol-% Diethylamine (99%); Eluent B: Ethanol; Isokratic: 80% A+20% B; Flow 1.4 mL/min; Temperature: 25° C.; DAD 254 nm.

Example 104

(+)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]oxazacycloundecino[8,7,6-hi]indole-13-carboxylic acid N-ethylethanamine salt (Enantiomer 1)

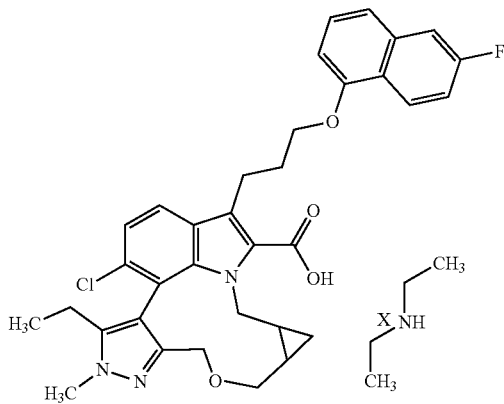

For the preparation of the racemic title compound see Example 103. Separation of enantiomers by preparative chiral HPLC (method see Example 103) gave the title compound (109 mg).

Analytical Chiral HPLC (method see Example 103): $R_t$=1.18 min.

Specific Optical Rotation (Method O1): 6.7° (c=10 mg/mL, methanol)

$^1$H-NMR (400 MHz, DMSO-d6) δ[ppm]=−0.31 (q, 1H), 0.50 (td, 1H), 0.82 (t, 3H), 0.86-0.94 (m, 2H), 2.11-2.28 (m, 4H), 2.36-2.45 (m, 1H), 3.08-3.26 (m, 2H), 3.39 (br s, 2H), 3.64 (dd, 1H), 3.82 (s, 3H), 4.03 (d, 1H), 4.20 (t, 2H), 4.34 (d, 1H), 4.78 (d, 1H), 6.88 (dd, 1H), 7.06 (d, 1H), 7.35-7.46 (m, 3H), 7.53 (d, 1H), 7.66 (dd, 1H), 8.31 (dd, 1H).—as diethylamine salt.

Example 105

(−)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]oxazacycloundecino[8,7,6-hi]indole-13-carboxylic acid N-ethylethanamine salt (Enantiomer 2)

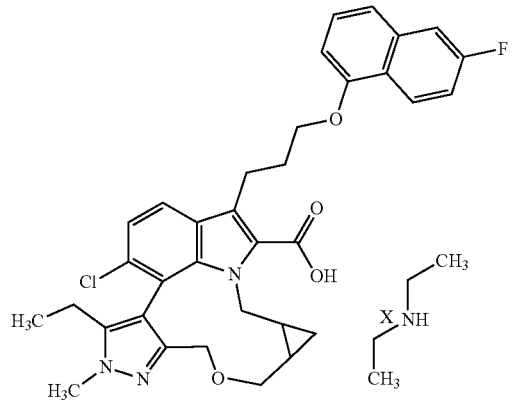

For the preparation of the racemic title compound see Example 103. Separation of enantiomers by preparative chiral HPLC (method see Example 103) gave the title compound (98 mg).

Analytical Chiral HPLC (method see Example 103): $R_t$=1.68 min.

Specific Optical Rotation (Method O1): −4.2° (c=10 mg/mL, methanol)

$^1$H-NMR (400 MHz, DMSO-d6) δ[ppm]=−0.30 (q, 1H), 0.51 (td, 1H), 0.77-0.95 (m, 5H), 2.11-2.29 (m, 4H), 2.40 (t, 1H), 3.08-3.27 (m, 3H), 3.39 (br s, 1H), 3.65 (dd, 1H), 3.82 (s, 3H), 4.03 (d, 1H), 4.20 (t, 2H), 4.34 (d, 1H), 4.77 (d, 1H), 6.88 (dd, 1H), 7.08 (d, 1H), 7.35-7.47 (m, 3H), 7.54 (d, 1H), 7.66 (dd, 1H), 8.31 (dd, 1H).—as diethylamine salt (75%).

Example 106

(rac)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]oxazacycloundecino[8,7,6-hi]indole-13-carboxylic acid (Racemate 2)

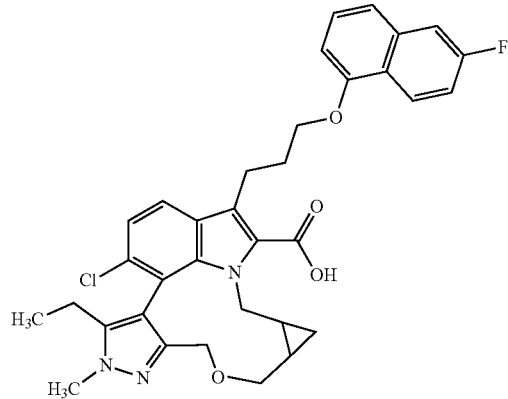 [SMILES: CCc1c2c(nn1C)COCC1CC1Cn1c(C(=O)O)c(CCCOc3cccc4cc(F)ccc34)c3ccc(Cl)c-2c31]

(rac)-Ethyl-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]oxazacycloundecino[8,7,6-hi]indole-13-carboxylate (see Intermediate 173, 230 mg) was dissolved in 5.9 mL THF and 5.3 mL ethanol and treated with the aqueous lithium hydroxide solution (8.2 mL, 1.0 M, 8.2 mmol). The reaction mixture was stirred at 60° C. under argon atmosphere over night. The solvent was evaporated. 5.9 mL THF and 5.3 mL ethanol were added and it was stirred at 75° C. over night. Aqueous lithium hydroxide solution (8.2 mL, 1.0 M, 8.2 mmol) was added and it was stirred for 2 days. The pH was adjusted to 5 by addition of acetic acid (470 µL, 8.2 mmol). The mixture was concentrated under reduced pressure and extracted with dichloromethane thrice. The combined organic layers were washed with water and brine, filtered through a silicone coated filter and concentrated under reduced pressure to provide the crude product which was analytically pure: 217 mg.

LC-MS (Method 2) $R_t$=0.95 min; MS (ESIpos): m/z=603/604 [M+H]$^+$ $^1$H-NMR (400 MHz, DMSO-d6) δ[ppm]: −0.684 (0.71), −0.672 (0.75), 0.138 (0.43), 0.150 (0.63), 0.161 (0.69), 0.173 (0.43), 0.804 (2.35), 0.823 (5.47), 0.842 (2.79), 1.129 (0.44), 1.150 (0.43), 1.166 (0.77), 1.907 (16.00), 2.146 (0.61), 2.164 (0.90), 2.183 (0.89), 2.193 (0.76), 2.200 (0.83), 2.213 (1.03), 2.219 (1.20), 2.229 (0.81), 2.238 (1.02), 2.256 (0.65), 2.518 (1.97), 2.523 (1.41), 3.252 (0.98), 3.271 (1.62), 3.290 (1.66), 3.439 (1.11), 3.464 (0.78), 3.819 (0.59), 3.840 (12.04), 3.855 (0.71), 3.870 (0.61), 4.069 (1.08), 4.101 (1.77), 4.153 (2.19), 4.169 (0.96), 4.185 (1.49), 4.192 (1.00), 4.207 (0.48), 4.342 (0.52), 4.362 (0.63), 4.378 (0.60), 4.399 (0.48), 5.758 (1.09), 6.838 (0.89), 6.845 (0.92), 6.853 (0.79), 6.860 (0.95), 7.150 (2.77), 7.171 (2.66), 7.359 (0.61), 7.365 (0.72), 7.381 (0.91), 7.388 (1.03), 7.403 (0.90), 7.410 (0.71), 7.425 (1.66), 7.433 (1.85), 7.440 (4.14), 7.641 (1.09), 7.648 (1.13), 7.667 (1.10), 7.674 (1.11), 7.697 (2.27), 7.719 (2.04), 8.259 (0.96), 8.274 (1.00), 8.282 (0.98), 8.297 (0.93).

The title compound (217 mg) was separated into enantiomers by preparative chiral HPLC to give enantiomer 1 (86 mg, see Example 107) and enantiomer 2 (84 mg, see Example 108).

Preparative Chiral HPLC Method:

Instrument: Sepiatec: Prep SFC100; Column: Chiralpak IG 5µ 250×30 mm; Eluent A: carbon dioxide; Eluent B: Ethanol+0.2 Vol-% aqueous ammonia (32%); Isokratic: 25% B; Flow: 100 mL/min; Temperature: 40° C.; BPR: 150 bar; UV: 254 nm;

Analytical Chiral HPLC Method:

Instrument: Agilent: 1260, Aurora SFC-Modul; Column: Chiralpak IG 5µ 100×4.6 mm; Eluent A: carbon dioxide; Eluent B: Ethanol+0.1 Vol-% aqueous ammonia (32%); Isokratic: 25% B; Flow: 4 mL/min; Temperature: 37.5° C.; BPR: 100 bar; UV: 254 nm;

Example 107

(+)-(3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]oxazacycloundecino[8,7,6-hi]indole-13-carboxylic acid (Enantiomer 3)

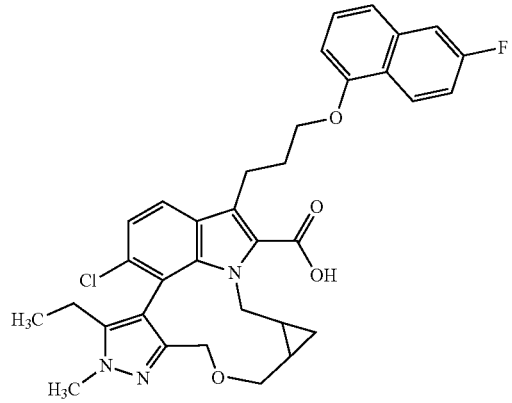 [SMILES: CCc1c2c(nn1C)COCC1CC1Cn1c(C(=O)O)c(CCCOc3cccc4cc(F)ccc34)c3ccc(Cl)c-2c31]

For the preparation of the racemic title compound see Example 106. Separation of enantiomers by preparative chiral HPLC (method see Example 106) gave the title compound (86 mg).

Analytical Chiral HPLC (method see Example 106): $R_t$=1.63 min.

Specific Optical Rotation (Method O1): 66.9° (c=10 mg/mL, methanol)

$^1$H-NMR (400 MHz, DMSO-d6) δ[ppm]=−0.72−−0.63 (m, 1H), 0.16 (dt, 1H), 0.78-0.92 (m, 4H), 1.08-1.20 (m, 4H), 2.11-2.29 (m, 3H), 3.21-3.31 (m, 3H), 3.45 (d, 1H), 3.80-3.91 (m, 4H), 4.04-4.27 (m, 3H), 4.37 (dd, 1H), 6.85 (dd, 1H), 7.16 (d, 1H), 7.34-7.49 (m, 3H), 7.66 (dd, 1H), 7.71 (d, 1H), 8.28 (dd, 1H).

Example 108

(−)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]oxazacycloundecino[8,7,6-hi]indole-13-carboxylic acid (Enantiomer 4)

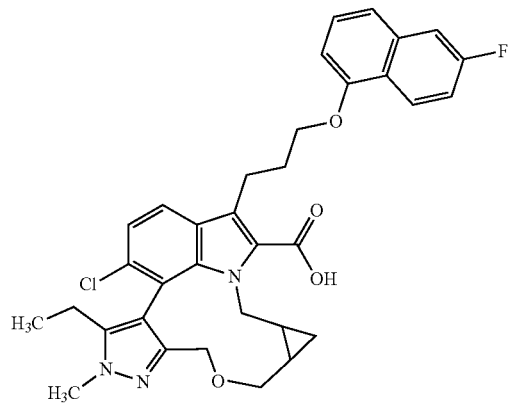 [SMILES: CCc1c2c(nn1C)COCC1CC1Cn1c(C(=O)O)c(CCCOc3cccc4cc(F)ccc34)c3ccc(Cl)c-2c31]

For the preparation of the racemic title compound see Example 106. Separation of enantiomers by preparative chiral HPLC (method see Example 106) gave the title compound (84 mg).

Analytical Chiral HPLC (method see Example 106): $R_t$=2.79 min.

Specific Optical Rotation (Method O1): −72.7° (c=10 mg/mL, methanol)

$^1$H-NMR (400 MHz, DMSO-d6) δ[ppm]=−0.71--−0.63 (m, 1H), 0.16 (td, 1H), 0.78-0.89 (m, 4H), 1.09-1.19 (m, 4H), 2.09-2.31 (m, 3H), 3.22-3.33 (m, 3H), 3.46 (s, 1H), 3.79-3.90 (m, 4H), 4.02-4.24 (m, 3H), 4.37 (dd, 1H), 6.85 (dd, 1H), 7.16 (d, 1H), 7.33-7.49 (m, 3H), 7.66 (dd, 1H), 7.71 (d, 1H), 8.28 (dd, 1H).

Example 109

(rac)-4'-chloro-3'-ethyl-7'-{3-[(6-fluoronaphthalen-1-yl)oxy]propyl}-2'-methyl-2',10',11',15'-tetrahydro-13'H-spiro[cyclopropane-1,12'-pyrazolo[4',3':9,10][1,6]oxazacycloundecino[8,7,6-hi]indole]-8'-carboxylic acid

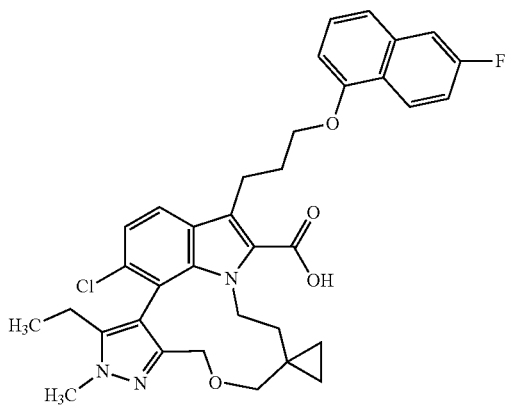 [SMILES: CCc1c2c(nn1C)COCC1(CCn3c(C(=O)O)c(CCCOc4cccc5cc(F)ccc45)c4ccc(Cl)c-2c43)CC1]

(Rac)-ethyl 4'-chloro-3'-ethyl-7'-{3-[(6-fluoronaphthalen-1-yl)oxy]propyl}-2'-methyl-2',10',11',15'-tetrahydro-13'H-spiro[cyclopropane-1,12'-pyrazolo[4',3':9,10][1,6]oxazacycloundecino[8,7,6-hi]indole]-8'-carboxylate (see Intermediate 176, 450 mg) was dissolved in 4 mL of tetrahydrofurane, an aqueous solution of lithium hydroxide (1.3 mL, 1.0 M, 1.3 mmol) and 400 µL of ethanol were added and the mixture was stirred for 22 h at 70° C. An aqueous solution of lithium hydroxide (1.3 mL, 1.0 M, 1.3 mmol) was added and the mixture was stirred for six days at 70° C. The reaction mixture was diluted with water, adjusted to pH 3-4 by addition of a saturated aqueous solution of citric acid and extracted with ethyl acetate. The combined organic layers were filtered using a water resistant filter and concentrated. The crude material was purified by flash chromatography using silica gel (gradient dichloromethane/ethanol) to provide 380 mg of the title compound.

LC-MS (Method 2): $R_t$=0.99 min; MS (ESIpos): m/z=616 [M+H]$^+$ $^1$H-NMR (400 MHz, DMSO-d6) δ[ppm]: −0.060 (0.67), −0.049 (0.70), 0.000 (0.46), 0.009 (0.82), 0.023 (0.84), 0.033 (0.52), 0.043 (0.41), 0.078 (0.65), 0.090 (0.96), 0.104 (1.01), 0.111 (0.98), 0.125 (0.70), 0.736 (0.43), 0.751 (0.53), 0.769 (3.42), 0.779 (1.22), 0.788 (6.99), 0.807 (3.20), 0.865 (2.05), 0.883 (4.66), 0.902 (2.37), 0.973 (0.72), 0.991 (0.64), 1.017 (0.64), 1.035 (1.24), 1.052 (0.65), 1.074 (0.46), 1.146 (0.67), 1.159 (0.60), 1.170 (0.70), 1.195 (0.41), 1.211 (0.50), 1.229 (0.41), 2.047 (6.22), 2.058 (0.50), 2.073 (0.79), 2.077 (0.76), 2.095 (1.13), 2.114 (1.07), 2.136 (1.12), 2.155 (1.48), 2.173 (1.60), 2.192 (1.27), 2.211 (0.46), 2.314 (0.74), 2.383 (0.45), 2.402 (1.27), 2.419 (1.24), 2.437 (0.53), 2.500 (5.00), 2.505 (2.84), 2.522 (1.62), 3.234 (1.25), 3.253 (1.99), 3.271 (1.44), 3.457 (1.20), 3.482 (1.10), 3.840 (16.00), 3.868 (0.43), 3.895 (0.72), 3.923 (0.43), 4.150 (2.82), 4.156 (2.01), 4.181 (2.49), 4.272 (0.48), 4.286 (0.43), 4.295 (0.46), 4.310 (0.46), 4.461 (2.11), 4.493 (1.80), 5.740 (0.69), 6.823 (1.24), 6.829 (1.27), 6.840 (1.19), 6.845 (1.31), 7.181 (3.39), 7.203 (3.66), 7.339 (0.82), 7.346 (0.89), 7.361 (1.25), 7.368 (1.37), 7.384 (1.27), 7.391 (1.01), 7.404 (2.08), 7.416 (2.56), 7.420 (4.98), 7.436 (0.48), 7.621 (1.43), 7.627 (1.53), 7.647 (1.43), 7.653 (1.46), 7.705 (2.75), 7.726 (2.54), 8.201 (1.27), 8.215 (1.32), 8.223 (1.32), 8.239 (1.20).

The title compound (371 mg) was separated into enantiomers by preparative chiral HPLC to give enantiomer 1 (161 mg, see Example 110) and enantiomer 2 (173 mg, see Example 111).

Preparative Chiral HPLC Method:

Instrument: Labomatic HD5000, Labocord-5000; Gilson GX-241, Labcol Vario 4000, Column: Amylose SA 5µ 250×30 mm; Eluent A: Hexane+0.1 Vol-% Diethylamine (99%); Eluent B: Ethanol; Isokratic: 80% A+20% B; Flow 50.0 mL/min; UV 254 nm Analytical Chiral HPLC Method:

Instrument: Agilent HPLC 1260; Column: Amylose SA 3µ 100×4.6 mm; Eluent A: Hexane+0.1 Vol-% Diethylamine (99%); Eluent B: Ethanol; Isokratic: 80% A+20% B; Flow 1.4 mL/min; Temperature: 25° C.; DAD 254 nm.

Example 110

(−)-4'-chloro-3'-ethyl-7'-{3-[(6-fluoronaphthalen-1-yl)oxy]propyl}-2'-methyl-2',10',11',15'-tetrahydro-13'H-spiro[cyclopropane-1,12'-pyrazolo[4',3':9,10][1,6]oxazacycloundecino[8,7,6-hi]indole]-8'-carboxylic acid-N-ethylethanamine salt (Enantiomer 1)

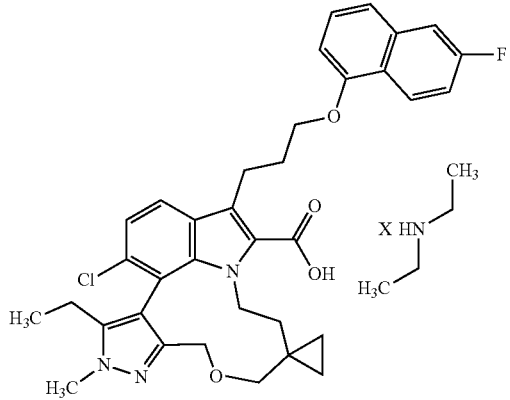

For the preparation of the racemic title compound see Example 109. Separation of enantiomers by preparative chiral HPLC (method see Example 109) gave the title compound (161 mg).

Analytical Chiral HPLC (method Example 109): $R_t$=1.20 min.

Specific Optical Rotation (Method O1): −32.1° (c=10 mg/mL, DMSO)

LC-MS (Method 2): $R_t$=0.94 min; MS (ESIpos): m/z=616 $[M+H]^+$ $^1$H-NMR (400 MHz, DMSO-d6) δ[ppm]: −0.079 (0.69), −0.068 (0.67), −0.023 (0.42), −0.013 (0.78), 0.000 (0.78), 0.011 (0.48), 0.021 (0.62), 0.046 (0.70), 0.058 (0.91), 0.068 (0.69), 0.077 (0.84), 0.083 (0.92), 0.097 (0.76), 0.106 (0.41), 0.771 (3.12), 0.780 (1.54), 0.790 (7.22), 0.796 (2.13), 0.803 (2.06), 0.809 (3.63), 0.821 (0.91), 0.833 (0.53), 0.868 (0.53), 0.886 (1.13), 0.904 (0.55), 1.109 (2.90), 1.127 (6.47), 1.144 (3.11), 1.182 (0.74), 1.212 (0.84), 1.229 (0.63), 2.086 (0.63), 2.103 (1.40), 2.122 (1.58), 2.138 (1.51), 2.157 (1.50), 2.175 (1.78), 2.192 (1.27), 2.211 (0.46), 2.500 (3.86), 2.505 (2.23), 2.812 (0.90), 2.829 (2.46), 2.847 (2.44), 2.864 (0.85), 3.167 (1.22), 3.186 (1.99), 3.204 (1.22), 3.465 (1.25), 3.490 (1.12), 3.731 (0.67), 3.830 (16.00), 3.840 (1.22), 4.098 (0.57), 4.106 (0.64), 4.122 (1.29), 4.132 (2.62), 4.147 (1.34), 4.163 (2.79), 4.439 (2.23), 4.451 (0.53), 4.471 (2.14), 4.483 (0.48), 6.790 (1.27), 6.794 (1.34), 6.807 (1.36), 6.811 (1.37), 7.056 (2.67), 7.077 (2.76), 7.335 (0.81), 7.342 (0.94), 7.358 (1.93), 7.364 (1.50), 7.379 (2.59), 7.386 (1.19), 7.396 (3.79), 7.401 (2.81), 7.418 (0.69), 7.531 (1.97), 7.552 (1.79), 7.610 (1.43), 7.616 (1.47), 7.636 (1.46), 7.642 (1.40), 8.223 (1.25), 8.237 (1.29), 8.246 (1.27), 8.260 (1.19).

Example 111

(+)-4'-chloro-3'-ethyl-7'-{3-[(6-fluoronaphthalen-1-yl)oxy]propyl}-2'-methyl-2',10',11',15'-tetrahydro-13'H-spiro[cyclopropane-1,12'-pyrazolo[4',3':9,10][1,6]oxazacycloundecino[8,7,6-hi]indole]-8'-carboxylic acid-N-ethylethanamine salt (Enantiomer 2)

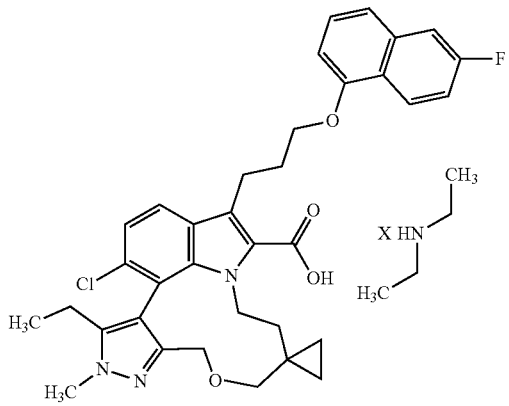

For the preparation of the racemic title compound see Example 109. Separation of enantiomers by preparative chiral HPLC (method see Example 109) gave the title compound (173 mg).

Analytical Chiral HPLC (method Example 109): $R_t$=1.83 min.

Specific Optical Rotation (Method O1): 29.5° (c=10 mg/mL, DMSO)

LC-MS (Method 2): $R_t$=0.94 min; MS (ESIpos): m/z=616 $[M+H]^+$ $^1$H-NMR (400 MHz, DMSO-d6) δ[ppm]: −0.078 (0.66), −0.069 (0.65), −0.023 (0.43), −0.013 (0.80), 0.000 (0.80), 0.022 (0.62), 0.047 (0.68), 0.058 (0.89), 0.068 (0.65), 0.076 (0.82), 0.083 (0.89), 0.097 (0.73), 0.771 (3.09), 0.780 (1.65), 0.790 (7.28), 0.796 (2.31), 0.803 (2.15), 0.809 (3.56), 0.821 (0.98), 0.868 (0.68), 0.886 (1.37), 0.904 (0.65), 1.109 (3.06), 1.126 (6.82), 1.144 (3.29), 1.182 (0.72), 1.209 (0.51), 2.086 (0.61), 2.103 (1.38), 2.122 (1.52), 2.138 (1.47), 2.156 (1.48), 2.175 (1.70), 2.192 (1.22), 2.211 (0.44), 2.500 (4.10), 2.505 (2.35), 2.521 (13.85), 2.811 (0.93), 2.828 (2.63), 2.847 (2.59), 2.864 (0.90), 3.166 (1.25), 3.185 (2.02), 3.203 (1.26), 3.465 (1.27), 3.489 (1.15), 3.731 (0.66), 3.830 (16.00), 4.097 (0.57), 4.106 (0.64), 4.122 (1.27), 4.132 (2.59), 4.147 (1.27), 4.163 (2.67), 4.439 (2.23), 4.470 (2.15), 6.790 (1.27), 6.794 (1.34), 6.807 (1.31), 6.811 (1.34), 7.056 (2.59), 7.077 (2.66), 7.335 (0.82), 7.342 (0.93), 7.358 (1.88), 7.365 (1.43), 7.379 (2.51), 7.386 (1.09), 7.397 (3.81), 7.401 (2.71), 7.418 (0.62), 7.531 (1.98), 7.552 (1.76), 7.610 (1.45), 7.616 (1.45), 7.636 (1.41), 7.643 (1.38), 8.222 (1.20), 8.237 (1.27), 8.246 (1.25), 8.260 (1.19).

Example 112

(rac)-12-chloro-11-ethyl-1-{3-[(6-fluoronaphthalen-1-yl)oxy]propyl}-7,10-dimethyl-4,5,6,7,8,10-hexahydropyrazolo[3',4':7,8][1,5]diazecino[9,10,1-hi]indole-2-carboxylic acid

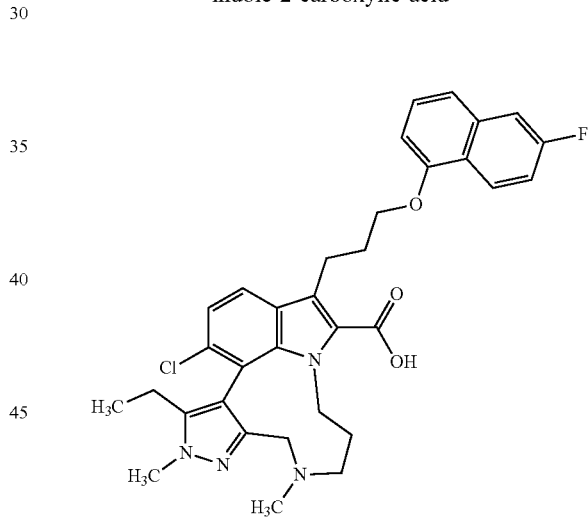

Ethyl 12-chloro-11-ethyl-1-{3-[(6-fluoronaphthalen-1-yl)oxy]propyl}-7,10-dimethyl-4,5,6,7,8,10-hexahydropyrazolo[3',4':7,8][1,5]diazecino[9,10,1-hi]indole-2-carboxylate (see Intermediate 181, 95 mg) was dissolved in 0.9 mL THF and 0.8 mL ethanol and treated with lithium hydroxide solution (308 µL, 1.0 M in water, 308 µmol). It was stirred at 70° C. under argon atmosphere for 2 days The reaction mixture was concentrated under reduced pressure. The residue was treated with water and saturated citric acid. dichloromethane was added, it was stirred for a few minutes, the organic layer was filtered through a silicone coated filter and concentrated under reduced pressure to provide the crude product which was purified by flash chromatography to provide the target compound in 95% purity: 31 mg.

LC-MS (Method 2): $R_t$=0.92 min; MS (ESIpos): m/z=590 $[M+H]^+$

¹H-NMR (400 MHz, DMSO-d6): δ [ppm]=0.90 (t, 3H), 1.30-1.42 (m, 1H), 1.50-1.64 (m, 1H), 1.83 (s, 3H), 1.92-2.04 (m, 1H), 2.17 (quin, 2H), 2.25-2.47 (m, 3H), 3.08 (d, 1H), 3.15-3.29 (m, 3H), 3.72 (br dd, 1H), 3.82 (s, 3H), 4.16 (br t, 2H), 4.61 (br dd, 1H), 6.83 (dd, 1H), 7.11 (d, 1), 7.33-7.51 (m, 3H), 7.62-7.75 (m, 2H), 8.29 (dd, 1H), 12.47-13.85 (m, 1H).

Another batch of the title compound (95 mg) was separated into enantiomers by preparative chiral HPLC to give enantiomer 1 (45 mg, see Example 113) and enantiomer 2 (40 mg, see Example 114).

Preparative Chiral HPLC Method:
Instrument: Sepiatec: Prep SFC100; Column: Chiralpak ID 5μ 250×30 mm; Eluent A: carbon dioxide; Eluent B: 2-Propanol+0.4% Diethylamine (99%); Isokratic: 25% B; Flow: 100 mL/min; Temperature: 40° C.; BPR: 150 bar; UV: 254 nm;

Analytical Chiral HPLC Method:
Instrument: Agilent: 1260, Aurora SFC-Modul; Column: Chiralpak ID 5μ 100×4.6 mm; Eluent A: carbon dioxide; Eluent B: 2-Propanol+0.2% Diethylamine (99%); Isokratic: 25% B; Flow: 4 mL/min; Temperature: 37.5° C.; BPR: 100 bar; UV: 254 nm;

Example 113

(+)-12-chloro-11-ethyl-1-{3-[(6-fluoronaphthalen-1-yl)oxy]propyl}-7,10-dimethyl-4,5,6,7,8,10-hexahydropyrazolo[3',4':7,8][1,5]diazecino[9,10,1-hi]indole-2-carboxylic acid N-ethylethanamine salt (Enantiomer 1)

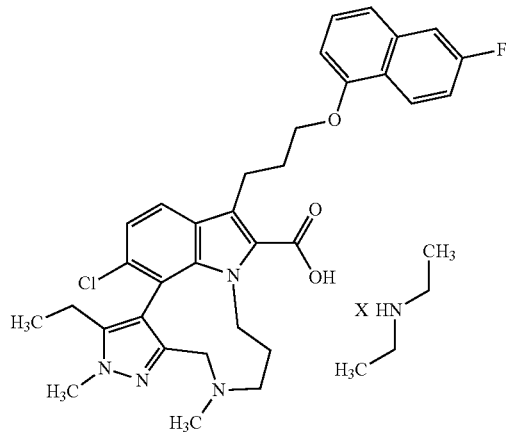

For the preparation of the racemic title compound see Example 112. Separation of enantiomers by preparative chiral HPLC (method see Example 112) gave the title compound (45 mg).

Analytical Chiral HPLC (method see Example 112): R$_t$=1.95 min.

Specific Optical Rotation (Method O1): 64.6° (c=10 mg/mL, Methanol)

¹H-NMR (400 MHz, DMSO-d6) δ[ppm]=0.91 (t, 3H), 1.35-1.57 (m, 2H), 1.87 (s, 3H), 1.90-1.99 (m, 1H), 2.17 (quin, 2H), 2.35-2.45 (m, 2H), 3.06 (d, 1H), 3.10-3.19 (m, 1H), 3.21-3.28 (m, 2H), 3.53-3.64 (m, 1H), 3.82 (s, 3H), 4.08-4.23 (m, 2H), 4.71 (br dd, 1H), 6.82 (dd, 1H), 7.04 (d, 1H), 1H), 7.33-7.46 (m, 3H), 7.56 (d, 1H), 7.65 (dd, 1H), 8.28 (dd, 1H).—as diethylamine salt.

Example 114

(−)-2-chloro-11-ethyl-1-{3-[(6-fluoronaphthalen-1-yl)oxy]propyl}-7,10-dimethyl-4,5,6,7,8,10-hexahydropyrazolo[3',4':7,8][1,5]diazecino[9,10,1-hi]indole-2-carboxylic acid salt (Enantiomer 2)

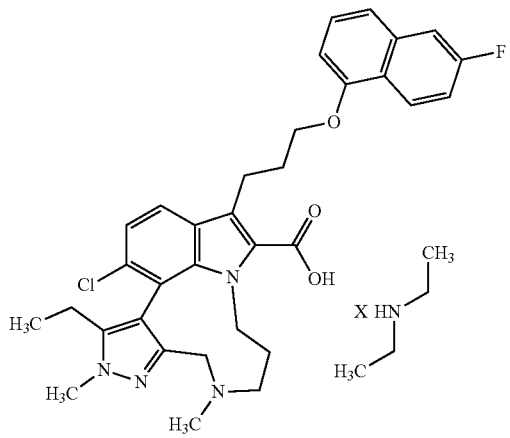

For the preparation of the racemic title compound see Example 112. Separation of enantiomers by preparative chiral HPLC (method see Example 112) gave the title compound (40 mg).

Analytical Chiral HPLC (method see Example 112): R$_t$=2.62 min.

Specific Optical Rotation (Method O1): −43.8° (c=10 mg/mL, Methanol)

¹H-NMR (400 MHz, DMSO-d6) δ[ppm]=0.91 (t, 3H), 1.39-1.54 (m, 2H), 1.87 (s, 3H), 1.91-1.99 (m, 1H), 2.17 (br t, 2H), 2.35-2.45 (m, 2H), 3.06 (d, 1H), 3.10-3.20 (m, 1H), 3.22-3.29 (m, 2H), 3.54-3.66 (m, 1H), 3.82 (s, 3H), 4.08-4.25 (m, 2H), 4.71 (br dd, 1H), 6.82 (dd, 1H), 7.04 (d, 1H), 7.34-7.48 (m, 3H), 7.56 (d, 1H), 7.65 (dd, 1H), 8.28 (dd, 1H).—as diethylamine salt, two further signals at 7.15 and 7.25 with 26%

Example 115

(rac)-4-chloro-3-ethyl-7-{3-[(6-fluoronaphthalen-1-yl)oxy]propyl}-2,12-dimethyl-10,11,12,13,14,15-hexahydro-2H-pyrazolo[3',4':8,9][1,4]diazacycloundecino[10,11,1-hi]indole-8-carboxylic acid

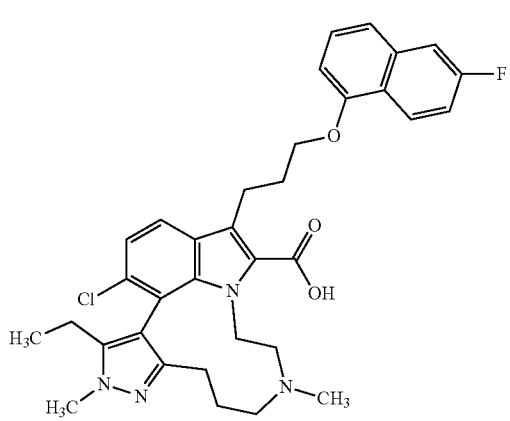 [SMILES: CCc1c2c(nn1C)CCCN(C)CCn1c(C(=O)O)c(CCCOc3cccc4cc(F)ccc34)c3ccc(Cl)c-2c31]

To a mixture of crude (rac)-ethyl 13-chloro-12-ethyl-1-(3-((6-fluoronaphthalen-1-yl)oxy)propyl)-6,11-dimethyl-5,6,7,8,9,11-hexahydro-4H-pyrazolo[3',4':8,9][1,4]diazacycloundecino[10,11,1-hi]indole-2-carboxylate (330 mg, 0.316 mmol theory, Intermediate 224) in ethanol (50 mL, 95%) was added NaOH (10 mL, 1N, aqueous) and the mixture was heated to reflux for 16 hours. The mixture was cooled to room temperature, volatiles removed under reduced pressure, the residue was diluted with acetonitrile (10 ml) and HCl (10 mL, 3N, aqueous) and adsorbed onto celite, purified by reverse phase chromatography on HP C18 eluting with a gradient of acetonitrile in water (containing 0.1% formic acid) to give the title compound as a white powder (172 mg).

LC-MS (Method 7): $R_t$=3.42 min; MS (ESIpos): m/z=604 [M+H]$^+$ $^1$H NMR (400 MHz, DMSO-d6) δ=10.15 (s, 1H), 8.76 (s, 1H), 8.27 (dt, J=21.5, 7.6 Hz, 1H), 7.89-7.82 (m, 1H), 7.68 (d, J=10.4 Hz, 1H), 7.46 (d, J=3.6 Hz, 1H), 7.44-7.28 (m, 2H), 6.90 (s, 1H), 4.77 (d, J=15.7 Hz, 2H), 4.62-4.01 (m, 9H), 3.86 (s, 3H), 3.36 (d, J=20.0 Hz, 3H), 3.00 (s, 2H), 2.96-2.79 (m, 1H), 2.69 (d, J=3.6 Hz, 2H), 2.61 (t, J=6.8 Hz, 3H), 2.51 (d, J=2.4 Hz, 11H), 2.20 (dd, J=22.3, 7.8 Hz, 4H), 2.11-1.69 (m, 3H), 0.80 (q, J=9.1, 8.6 Hz, 3H).

The title compound (166 mg) was separated into enantiomers by preparative chiral HPLC to give enantiomer 1 (58 mg, see Example 116) and enantiomer 2 (68 mg, see Example 117).

Preparative Chiral HPLC Method:
Instrument: PrepCon Labomatic HPLC; Column: YMC Amylose SA 5μ 250×30; Eluent A: Hexane+0.1% diethylamine; Eluent B: 2-Propanol; Gradient: 20-50% B in 15 min; Flow: 40 mL/min; Temperature: 25° C.; UV: 254 nm Analytical Chiral HPLC Method:
Instrument: Agilent 1260 HPLC; Column: YMC Amylose SA 3μ 100×4.6; Eluent A: Hexane+0.1% diethylamine; Eluent B: 2-Propanol; Gradient: 20-50% B in 7 min; Flow: 1.4 mL/min; Temperature: 25° C.; UV: 254 nm Example 116

(+)-4-chloro-3-ethyl-7-{3-[(6-fluoronaphthalen-1-yl)oxy]propyl}-2,12-dimethyl-10,11,12,13,14,15-hexahydro-2H-pyrazolo[3',4':8,9][1,4]diazacycloundecino[10,11,1-hi]indole-8-carboxylic acid (Enantiomer 1)

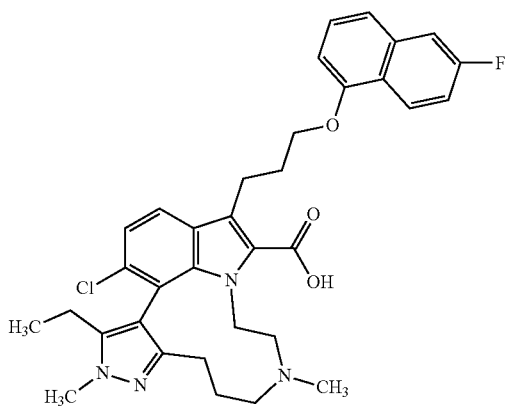 [SMILES: CCc1c2c(nn1C)CCCN(C)CCn1c(C(=O)O)c(CCCOc3cccc4cc(F)ccc34)c3ccc(Cl)c-2c31]

For the preparation of the racemic title compound see Example 115. Separation of enantiomers by preparative chiral HPLC (method see Example 115) gave the title compound (58 mg).

Analytical Chiral HPLC (method see Example 115): $R_t$=2.26 min.

Specific Optical Rotation (Method O1): 22.1° (c=10 mg/mL, DMSO)

LC-MS (Method 1): $R_t$=1.21 min; MS (ESIpos): m/z=603 [M+H]$^+$ $^1$H-NMR (400 MHz, DMSO-d6) δ[ppm]: 0.833 (1.77), 0.852 (4.23), 0.871 (1.76), 1.065 (0.45), 1.107 (16.00), 1.140 (4.72), 1.158 (10.18), 1.176 (4.90), 1.656 (5.02), 2.156 (0.45), 2.176 (0.82), 2.192 (1.62), 2.209 (0.96), 2.231 (0.96), 2.250 (1.53), 2.270 (1.61), 2.288 (0.53), 2.322 (0.52), 2.327 (0.67), 2.331 (0.49), 2.518 (2.61), 2.523 (1.69), 2.664 (0.47), 2.669 (0.67), 2.673 (0.48), 2.864 (1.31), 2.882 (4.18), 2.900 (4.16), 2.919 (1.22), 3.220 (0.59), 3.229 (0.46), 3.247 (0.68), 3.266 (0.55), 3.281 (0.63), 3.813 (8.64), 4.166 (0.63), 4.182 (0.44), 4.192 (0.75), 6.830 (0.66), 6.835 (0.67), 6.846 (0.63), 6.851 (0.68), 7.066 (1.04), 7.087 (1.12), 7.356 (0.45), 7.363 (0.51), 7.378 (0.69), 7.386 (0.96), 7.401 (0.56), 7.407 (1.53), 7.425 (2.20), 7.577 (0.71), 7.598 (0.63), 7.633 (0.77), 7.640 (0.81), 7.659 (0.77), 7.666 (0.76), 8.263 (0.67), 8.278 (0.70), 8.286 (0.68), 8.301 (0.64).

Example 117

(−)-4-chloro-3-ethyl-7-{3-[(6-fluoronaphthalen-1-yl)oxy]propyl}-2,12-dimethyl-10,11,12,13,14,15-hexahydro-2H-pyrazolo[3',4':8,9][1,4]diazacycloundecino[10,11,1-hi]indole-8-carboxylic acid (Enantiomer 2)

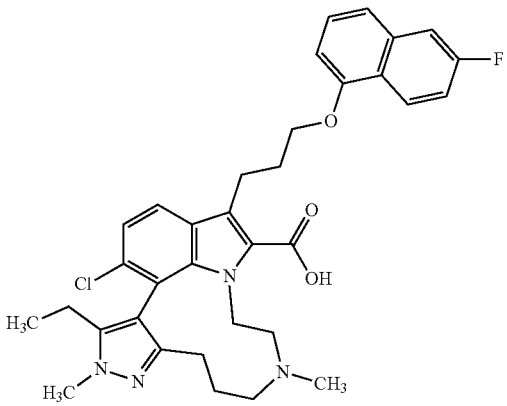 [SMILES: CCc1c2c(nn1C)CCCN(C)CCn1c(C(=O)O)c(CCCOc3cccc4cc(F)ccc34)c3ccc(Cl)c-2c31]

For the preparation of the racemic title compound see Example 115. Separation of enantiomers by preparative chiral HPLC (method see Example 115) gave the title compound (68 mg).

Analytical Chiral HPLC (method see Example 115): $R_t$=3.55 min.

Specific Optical Rotation (Method O1): −19.0° (c=10 mg/mL, DMSO)

LC-MS (Method 1): $R_t$=1.22 min; MS (ESIpos): m/z=603 [M+H]$^+$ $^1$H-NMR (400 MHz, DMSO-d6) δ[ppm]: 0.834 (0.75), 0.853 (1.75), 0.872 (0.77), 1.107 (16.00), 1.137 (1.87), 1.155 (4.16), 1.173 (1.91), 1.656 (2.22), 2.173 (0.51), 2.190 (0.46), 2.230 (0.41), 2.250 (0.79), 2.268 (0.77), 2.518 (1.00), 2.522 (0.63), 2.539 (1.31), 2.853 (0.50), 2.872 (1.60), 2.890 (1.51), 2.908 (0.47), 3.811 (3.50), 7.043 (0.53), 7.064 (0.54), 7.382 (0.41), 7.402 (0.49), 7.419 (0.90).

Example 118

(rac)-4-chloro-12-(2,2-difluoroethyl)-3-ethyl-7-{3-[(6-fluoro-1-naphthyl)oxy]propyl}-2-methyl-10,11,12,13,14,15-hexahydro-2H-pyrazolo[3',4':8,9][1,4]diazacycloundecino[10,11,1-hi]indole-8-carboxylic acid

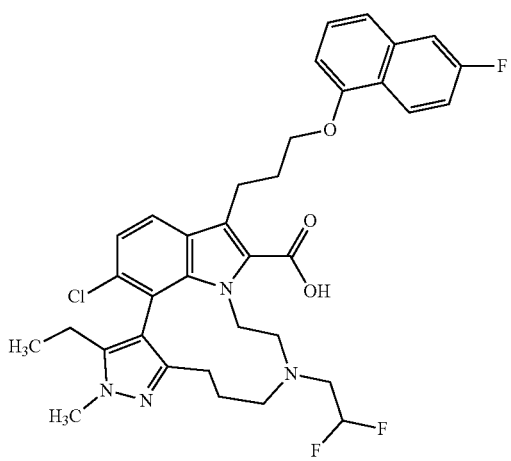 [SMILES: CCc1c2c(nn1C)CCCN(CC(F)F)CCn1c(C(=O)O)c(CCCOc3cccc4cc(F)ccc34)c3ccc(Cl)c-2c31]

A mixture of (rac)-ethyl 13-chloro-6-(2,2-difluoroethyl)-12-ethyl-1-(3-((6-fluoronaphthalen-1-yl)oxy)propyl)-11-methyl-5,6,7,8,9,11-hexahydro-4H-pyrazolo[3',4':8,9][1,4]diazacycloundecino[10,11,1-hi]indole-2-carboxylate (134 mg, 0.197 mmol, Intermediate 225) and sodium hydroxide (3 mL, 1N, aqueous) in ethanol (50 mL, 95%) was heated to reflux for 16 hours, cooled to room temperature, volatiles removed, and the residue was partitioned between ethyl acetate (100 mL) and HCl (50 mL, 0.6 M, aqueous), layers separated and the organic phase washed with saturated sodium chloride (aqueous), combined aqueous phases were back extracted with ethyl acetate, combined organics dried over sodium sulfate, insoluble materials removed by filtration, volatiles removed under reduced pressure, and the residue purified by flash chromatography on silica gel eluting with a gradient of methanol in dichloromethane (0-10%) to provide the title compound as a white solid (101 mg).

LC-MS (Method 7): $R_t$=5.06 min; MS (ESIpos): m/z=654 [M+H]$^+$ $^1$H NMR (300 MHz, Chloroform-d) δ=12.52 (s, 1H), 8.41 (dd, J=9.2, 5.8 Hz, 1H), 7.62 (d, J=8.6 Hz, 1H), 7.40 (dd, J=10.0, 2.6 Hz, 1H), 7.37-7.30 (m, 2H), 7.28-7.18 (m, 1H), 7.15 (d, J=8.6 Hz, 1H), 6.72 (dd, J=6.8, 1.9 Hz, 1H), 4.64-4.52 (m, 1H), 4.41-4.16 (m, 3H), 4.15-4.03 (m, 1H), 3.95 (s, 3H), 3.57-3.34 (m, 2H), 2.65-2.09 (m, 12H), 2.02-1.83 (m, 1H), 1.66 (d, J=9.0 Hz, 1H), 0.95 (t, J=7.6 Hz, 3H).

$^{13}$C NMR (101 MHz, Chloroform-d) δ=165.89, 161.18 (d, J=245.8 Hz), 155.01, 149.01, 142.51, 139.99, 135.55 (d, J=9.2 Hz), 135.04, 128.32, 127.46, 126.42, 125.00, 124.91 (d, J=9.1 Hz), 122.72, 121.45, 120.82, 119.33 (d, J=4.8 Hz), 116.94, 116.10 (t, J=242.0 Hz), 115.21, 115.18, 114.96, 110.55 (d, J=20.4 Hz), 103.96 (d, J=1.7 Hz), 67.49, 60.29, 55.26 (t, J=25.2 Hz), 52.23, 44.23, 36.19, 30.72, 24.76, 22.17, 21.07, 17.95, 12.31.

$^{19}$F NMR (376 MHz, Chloroform-d) δ=-114.97, -117.81 (d, J=284.3 Hz), -119.05 (d, J=284.3 Hz).

HSQC $^{13}$C NMR (101 MHz, CDCl3) δ=124.89, 120.93, 110.54, 127.44, 119.30, 115.09, 121.46, 104.00, 44.26, 113.57, 115.93, 118.33, 67.49, 44.25, 36.26, 22.08, 21.13, 60.35, 21.05, 55.36, 30.84, 17.95, 52.25, 55.34, 25.15, 24.84, 12.33

1H NMR (400 MHz, CDCl3) δ 8.43, 7.64, 7.42, 7.38, 7.35, 7.25, 7.17, 6.74, 4.60, 4.54, 4.40, 4.26, 4.23, 4.12, 3.97, 3.50, 2.61, 2.49, 2.47, 2.44, 2.38, 2.38, 2.27, 2.22, 1.96, 1.69, 0.98.

19F Proton Coupled $^{19}$F NMR (376 MHz, Chloroform-d) δ=-114.97 (td, J=9.1, 5.8 Hz), -117.81 (ddt, J=284.4, 56.2, 14.7 Hz), -119.05 (dddd, J=284.4, 56.5, 17.8, 11.8 Hz).

The title compound (81 mg) was separated into enantiomers by preparative chiral HPLC to give enantiomer 1 (16.0 mg, see Example 119) and enantiomer 2 (19.7 mg, see Example 120).

Preparative Chiral HPLC Method:
Instrument: Labomatic HD5000, Labocord-5000; Gilson GX-241, Labcol Vario 4000, Column: Amylose SA 5μ 250×30 mm; Eluent A: Hexane+0.1 Vol-% Diethylamine (99%); Eluent B: 2-Propanol; Gradient: 20-50% B in 20 min; Flow 40.0 mL/min; UV 254 nm Analytical Chiral HPLC Method:
Instrument: Agilent HPLC 1260; Column: Amylose SA 3μ 100×4.6 mm; Eluent A: Hexane+0.1 Vol-% Diethylamine (99%); Eluent B: 2-Propanol; Gradient: 20-50% B in 7 min; Flow 1.4 mL/min; Temperature: 25° C.; DAD 254 nm.

Example 119

(+)-4-chloro-12-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,4]diazacycloundecino[10,11,1-hi]indole-8-carboxylic acid N-ethylethanamine salt (Enantiomer 1)

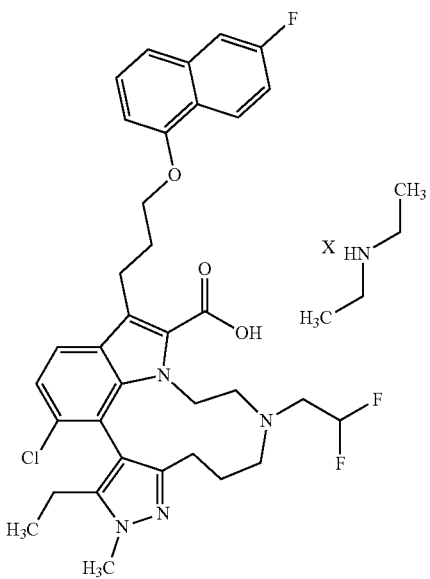

For the preparation of the racemic title compound see Example 118. Separation of enantiomers by preparative chiral HPLC (method see Example 118) gave the title compound (16.0 mg).

Analytical Chiral HPLC (method see Example 118): R_t=2.02 min.
Specific Optical Rotation (Method O1): 34.3° (c=10 mg/mL, DMSO)
LC-MS (Method 1): R_t=1.59 min; MS (ESIpos): m/z=653 [M+H]+
¹H-NMR (400 MHz, DMSO-d6) δ[ppm]: 0.858 (3.10), 0.877 (7.28), 0.895 (3.19), 1.132 (6.97), 1.150 (16.00), 1.168 (6.88), 1.231 (0.57), 1.635 (0.73), 1.905 (0.47), 2.098 (0.52), 2.109 (0.52), 2.128 (0.40), 2.142 (0.54), 2.179 (0.80), 2.211 (1.80), 2.251 (1.89), 2.268 (1.80), 2.287 (2.60), 2.307 (2.22), 2.318 (0.83), 2.322 (1.51), 2.326 (2.20), 2.331 (1.39), 2.336 (0.71), 2.376 (0.66), 2.414 (1.35), 2.435 (0.85), 2.518 (5.62), 2.522 (3.52), 2.539 (2.48), 2.659 (0.47), 2.664 (1.04), 2.669 (1.42), 2.673 (1.04), 2.678 (0.47), 2.850 (1.89), 2.869 (5.96), 2.886 (5.70), 2.905 (1.77), 3.125 (0.52), 3.143 (0.66), 3.162 (0.40), 3.183 (0.45), 3.202 (0.66), 3.218 (0.66), 3.234 (0.54), 3.816 (14.87), 4.167 (0.92), 4.181 (1.87), 4.198 (0.99), 4.462 (0.90), 4.496 (0.92), 4.519 (0.45), 6.844 (1.11), 6.853 (1.25), 6.866 (1.18), 7.000 (1.54), 7.021 (1.61), 7.378 (0.80), 7.385 (0.90), 7.401 (1.21), 7.407 (1.51), 7.427 (2.79), 7.431 (3.07), 7.440 (5.18), 7.510 (1.06), 7.531 (0.97), 7.643 (1.37), 7.649 (1.47), 7.669 (1.42), 7.675 (1.39), 8.301 (1.25), 8.315 (1.30), 8.323 (1.28), 8.339 (1.23).

Example 120

(−)-4-chloro-12-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,4]diazacycloundecino[10,11,1-hi]indole-8-carboxylic acid N-ethylethanamine salt (Enantiomer 2)

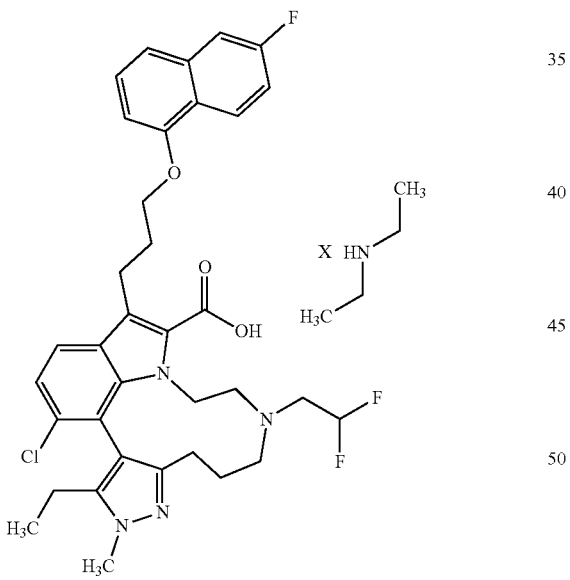

For the preparation of the racemic title compound see Example 118. Separation of enantiomers by preparative chiral HPLC (method see Example 118) gave the title compound (19.7 mg).
Analytical Chiral HPLC (method see Example 118): R_t=3.66 min.
Specific Optical Rotation (Method O1): −29.3° (c=10 mg/mL, DMSO)
LC-MS (Method 1): R_t=1.59 min; MS (ESIpos): m/z=653 [M+H]+
¹H-NMR (400 MHz, DMSO-d6) δ[ppm]: 0.858 (3.26), 0.877 (7.53), 0.896 (3.36), 1.026 (0.67), 1.042 (0.69), 1.135 (7.16), 1.153 (16.00), 1.171 (7.28), 1.636 (0.78), 1.905 (0.48), 2.099 (0.55), 2.109 (0.55), 2.129 (0.43), 2.143 (0.59), 2.163 (0.52), 2.178 (0.86), 2.209 (1.81), 2.242 (1.86), 2.251 (1.97), 2.268 (1.74), 2.288 (2.76), 2.307 (2.34), 2.318 (0.74), 2.323 (1.24), 2.326 (1.88), 2.331 (1.16), 2.377 (0.76), 2.414 (1.41), 2.436 (0.90), 2.463 (1.00), 2.518 (4.17), 2.522 (2.53), 2.664 (0.74), 2.669 (1.03), 2.673 (0.74), 2.849 (1.97), 2.867 (6.16), 2.885 (5.91), 2.903 (1.83), 3.110 (0.45), 3.124 (0.57), 3.142 (0.76), 3.161 (0.43), 3.184 (0.50), 3.200 (0.74), 3.219 (0.71), 3.232 (0.59), 3.253 (0.57), 3.767 (0.40), 3.816 (15.59), 4.167 (0.95), 4.181 (1.91), 4.198 (1.02), 4.469 (0.95), 4.503 (1.28), 6.842 (1.17), 6.851 (1.29), 6.856 (1.07), 6.865 (1.24), 6.997 (2.02), 7.018 (2.10), 7.377 (0.81), 7.384 (0.95), 7.400 (1.28), 7.406 (1.55), 7.426 (2.84), 7.430 (3.24), 7.439 (5.57), 7.506 (1.43), 7.528 (1.31), 7.642 (1.47), 7.648 (1.52), 7.668 (1.47), 7.674 (1.47), 8.300 (1.31), 8.315 (1.34), 8.323 (1.31), 8.338 (1.26).

Example 121

(rac)-12-(4-acetoxybutyl)-4-chloro-3-ethyl-7-{3-[(6-fluoro-1-naphthyl)oxy]propyl}-2-methyl-10,11,12,13,14,15-hexahydro-2H-pyrazolo[3',4':8,9][1,4]diazacycloundecino[10,11,1-hi]indole-8-carboxylic acid

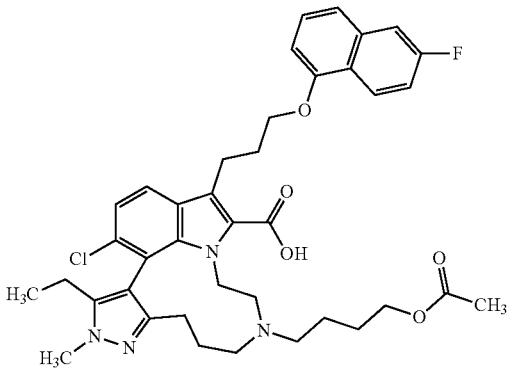 [SMILES: CCc1c2c(nn1C)CCCN(CCCCOC(C)=O)CCn1c(C(=O)O)c(CCCOc3cccc4cc(F)ccc34)c3ccc(Cl)c-2c31]

and

Example 122

(rac)-4-chloro-3-ethyl-7-{3-[(6-fluoro-1-naphthyl)oxy]propyl}-12-(4-hydroxybutyl)-2-methyl-10,11,12,13,14,15-hexahydro-2H-pyrazolo[3',4':8,9][1,4]diazacycloundecino[10,11,1-hi]indole-8-carboxylic acid

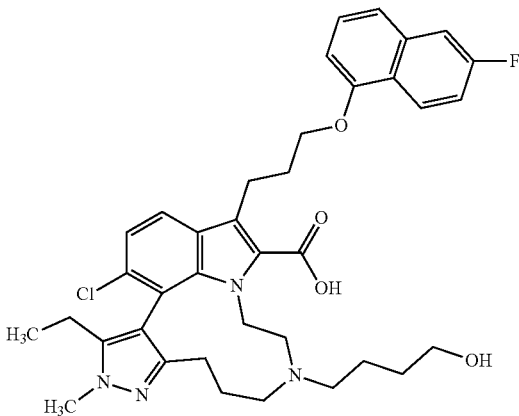 [SMILES: CCc1c2c(nn1C)CCCN(CCCCO)CCn1c(C(=O)O)c(CCCOc3cccc4cc(F)ccc34)c3ccc(Cl)c-2c31]

A mixture of (rac)-ethyl 13-chloro-12-ethyl-1-(3-((6-fluoronaphthalen-1-yl)oxy)propyl)-6-(4-hydroxybutyl)-11-methyl-5,6,7,8,9,11-hexahydro-4H-pyrazolo[3',4':8,9][1,4]diazacycloundecino[10,11,1-hi]indole-2-carboxylate (30 mg, 0.197 mmol, Intermediate 226) and sodium hydroxide (3 mL, 1N, aqueous) in ethanol (50 mL, 95%) was heated to reflux for 5 hours, cooled to room temperature, volatiles removed under reduced pressure and the residue treated with acetic acid (2 mL), water (20 mL), and ethyl acetate (50 mL), the layers were separated and the aqueous phase was extracted with ethyl acetate, combined organics were dried over sodium sulfate, insoluble materials removed by filtration, and volatiles removed under reduced pressure, the residue was then adsorbed onto celite and purified by reverse phase chromatography on HP C18 eluting with a gradient of acetonitrile in water (30-100%) containing 01% formic acid to give Example 122 as a white solid (15 mg) and Example 121 as a white solid (8 mg).

Example 121

LC-MS (Method 8): $R_t$=1.49 min; MS (ESIpos): m/z=703 [M+H]$^+$ $^1$H-NMR (400 MHz, Chloroform-d) δ=8.27 (s, 1H), 7.61 (d, J=8.5 Hz, 1H), 7.44-7.28 (m, 3H), 7.21 (d, J=7.6 Hz, 2H), 6.71 (d, J=7.1 Hz, 1H), 4.64 (s, 1H), 4.19 (d, J=6.3 Hz, 2H), 3.91 (s, 3H), 3.74 (s, 2H), 3.40 (t, J=7.6 Hz, 2H), 2.63 (s, 2H), 2.56-2.08 (m, 10H), 1.97 (s, 3H), 1.93-1.59 (m, 4H), 1.36-0.70 (m, 7H).

Example 122

LC-MS (Method 8): $R_t$=1.44 min; MS (ESIpos): m/z=661 [M+H]$^+$ $^1$H-NMR (400 MHz, DMSO-d6) δ=13.15 (s, 1H), 8.33 (dd, J=9.3, 5.9 Hz, 1H), 7.72-7.63 (m, 2H), 7.46 (d, J=4.2 Hz, 2H), 7.44-7.38 (m, 1H), 7.15 (d, J=8.5 Hz, 1H), 6.92 (q, J=4.5 Hz, 1H), 4.43 (d, J=13.9 Hz, 1H), 4.23 (t, J=6.2 Hz, 2H), 4.13-3.89 (m, 2H), 3.83 (d, J=1.3 Hz, 3H), 3.31 (d, J=13.5 Hz, 2H), 3.07-2.82 (m, 2H), 2.24 (dq, J=28.9, 7.5, 6.8 Hz, 7H), 2.15-1.89 (m, 4H), 1.66 (s, 3H), 0.94-0.82 (m, 3H), 0.82-0.61 (m, 2H), 0.55 (s, 1H), 0.22 (s, 1H).

HSQC $^{13}$C-NMR (101 MHz, DMSO) δ=124.77, 120.53, 110.38, 119.19, 127.60, 115.01, 120.40, 104.38, 43.51, 67.55, 43.40, 36.14, 21.40, 60.40, 60.36, 39.52, 21.11, 17.26, 57.96, 30.48, 57.96, 52.14, 51.92, 24.67, 52.27, 12.18, 23.38, 29.73, 29.69, 23.47

$^1$H-NMR (400 MHz, DMSO) δ=8.34, 7.68, 7.67, 7.46, 7.46, 7.40, 7.15, 6.91, 4.43, 4.23, 3.96, 3.83, 3.29, 2.97, 2.92, 2.50, 2.31, 2.28, 2.25, 2.21, 2.10, 2.07, 1.97, 1.67, 1.66, 0.87, 0.76, 0.66, 0.54, 0.22.

Example 123

(rac)-4-chloro-3-ethyl-7-{3-[(6-fluoro-1-naphthyl)oxy]propyl}-2-methyl-12-(2,2,3,3-tetrafluoropropyl)-10,11,12,13,14,15-hexahydro-2H-pyrazolo[3',4':8,9][1,4]diazacycloundecino[10,11,1-hi]indole-8-carboxylic acid

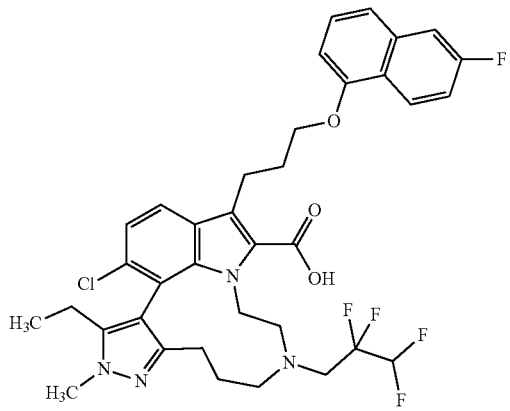 [SMILES: CCc1c2c(nn1C)CCCN(CC(F)(F)C(F)F)CCn1c(C(=O)O)c(CCCOc3cccc4cc(F)ccc34)c3ccc(Cl)c-2c31]

A mixture of (rac)-ethyl 13-chloro-12-ethyl-1-(3-((6-fluoronaphthalen-1-yl)oxy)propyl)-11-methyl-6-(2,2,3,3-tetrafluoropropyl)-5,6,7,8,9,11-hexahydro-4H-pyrazolo[3',4':8,9][1,4]diazacycloundecino[10,11,1-hi]indole-2-carboxylate (320 mg, 0.437 mmol, Intermediate 227) and sodium hydroxide (4 mL, 1 N) in ethanol (25 mL, 95%) was heated to reflux for 18 hours, cooled to room temperature, volatiles removed under reduced pressure and the residue partitioned between ethyl acetate (100 mL) and HCl (3N, aqueous, 50 mL), the layers were separated and the organic phase washed with saturated sodium chloride (aqueous), combined aqueous phases were back extracted with ethyl acetate, combined organics were dried over sodium sulfate, insoluble materials were removed by filtration, volatiles removed under reduced pressure and the residue was purified by flash chromatography on silica gel eluting with a gradient of methanol in dichloromethane (0-10%) to afford the title compound as an off-white solid (271 mg).

LC-MS (Method 8): $R_t$=1.77 min; MS (ESIpos): m/z=703 [M+H]$^+$

LC-MS (Method 7): $R_t$=5.24 min; MS (ESIpos): m/z=704 [M+H]$^+$ $^1$H-NMR (400 MHz, DMSO-d6) δ=12.84 (s, 1H), 8.33 (dd, J=9.3, 5.9 Hz, 1H), 7.77 (d, J=8.6 Hz, 1H), 7.67 (dd, J=10.4, 2.6 Hz, 1H), 7.46 (d, J=4.3 Hz, 2H), 7.41 (td, J=9.0, 2.4 Hz, 1H), 7.25 (d, J=8.5 Hz, 1H), 6.91 (q, J=4.7 Hz, 1H), 4.50 (d, J=14.3 Hz, 1H), 4.37-4.14 (m, 3H), 4.05 (dq, J=13.8, 7.6, 6.6 Hz, 1H), 3.84 (s, 3H), 3.35 (ddd, J=14.7, 9.4, 5.9 Hz, 2H), 3.23 (dq, J=14.0, 7.7, 6.9 Hz, 1H), 2.89-2.04 (m, 12H), 1.68 (d, J=13.5 Hz, 2H), 0.85 (t, J=7.5 Hz, 3H).

$^{19}$F-NMR (376 MHz, DMSO-d6) δ=−114.68 (ddd, J=294.9, 13.9, 3.9 Hz), −118.79 (ddd, J=266.7, 12.4, 3.9 Hz), −123.61 (ddd, J=266.8, 13.7, 7.2 Hz), −137.97 (ddd, J=294.6, 12.6, 4.4 Hz), −143.95 (ddd, J=294.3, 11.9, 7.1 Hz).

HSQC $^{13}$C-NMR (101 MHz, DMSO) δ=125.22, 121.40, 110.84, 128.16, 119.72, 115.59, 121.28, 104.90, 43.71, 68.10, 108.89, 43.69, 36.69, 22.08, 22.00, 53.26, 53.12, 40.27, 60.53, 21.24, 17.76, 21.25, 30.78, 53.18, 25.18, 12.70

¹H-NMR (400 MHz, DMSO) δ=8.33, 7.77, 7.67, 7.46, 7.46, 7.41, 7.25, 6.90, 4.50, 4.24, 4.17, 4.06, 3.83, 3.34, 3.23, 2.72, 2.57, 2.50, 2.46, 2.42, 2.27, 2.19, 2.17, 2.15, 1.64, 0.84.

Non-Decoupled 19F

¹⁹F-NMR (376 MHz, DMSO-d6) δ=−114.68 (td, J=9.4, 5.9 Hz), −118.79 (ddt, J=266.8, 26.4, 13.1 Hz), −123.07--124.30 (m), −137.91 (ddd, J=294.7, 52.4, 13.9 Hz), −143.96 (ddd, J=293.9, 53.6, 7.3 Hz).

Example 124

(rac)-4-chloro-3-ethyl-7-{3-[(6-fluoro-1-naphthyl)oxy]propyl}-2-methyl-2,10,11,13,14,15-hexahydro-pyrazolo[4',3':7,8][1,4]oxazacycloundecino[6,5,4-hi]indole-8-carboxylic acid

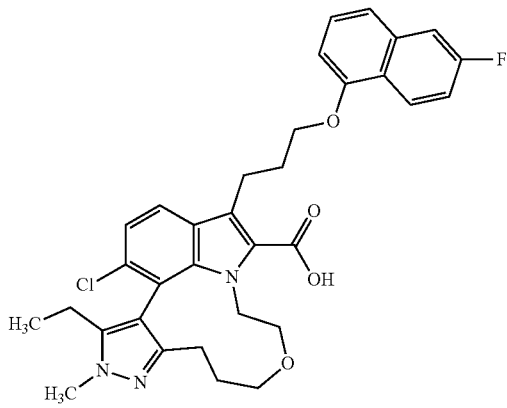 [SMILES: CCc1c2c(nn1C)CCCOCCn1c(C(=O)O)c(CCCOc3cccc4cc(F)ccc34)c3ccc(Cl)c-2c31]

To a solution of (rac)-ethyl 6-chloro-7-{3-ethyl-5-[3-(2-hydroxyethoxy)propyl]-1-methyl-1H-pyrazol-4-yl}-3-{3-[(6-fluoronaphthalen-1-yl)oxy]propyl}-1H-indole-2-carboxylate (300 mg, 0.475 mmol, Intermediate 216) in dichloromethane (20 mL) and DIPEA (0.4 mL, 2.29 mmol) at 0° C. was added methane sulfonyl chloride (0.1 mL, 1.28 mmol), after 1 hour, volatiles were removed under reduced pressure and the residue was portioned between ethyl acetate and sodium hydroxide (1M, aqueous), layers were separated and the organic phase washed sequentially with sodium hydroxide (1M, aqueous), saturated sodium hydrogen carbonate (aqueous) and saturated sodium chloride (aqueous), the combined aqueous phases were back extracted with ethyl acetate and combined organics were dried over sodium sulfate, insoluble material was removed by filtration, and the volatiles removed under reduced pressure. The amber residue was dissolved in N,N-dimethyl formamide (10 mL), placed in an ice water bath, and treated with sodium hydride (45 mg, 60% in oil, 1.1 mmol), and then warmed to 40° C. for 18 hours, additional sodium hydride (45 mg, 60% in oil, 1.1 mmol) was added and heating continued for 6 hours. The mixture was then treated with sodium hydroxide (4 mL, 1N) and warmed to 70° C. for 18 hours. Majority of the volatiles were removed under reduced pressure and the residue portioned between ethyl acetate and HCl (1N, aqueous), layers separated and the aqueous phase extracted with ethyl acetate (twice), combined organics were washed with saturate sodium chloride (aqueous), dried over sodium sulfate, insoluble materials were removed by filtration, and volatiles removed under reduced pressure. The residue was purified by flash chromatography silica gel eluting with a gradient of 0-10% methanol in dichloromethane, to give the title compound as an off-white solid (177 mg).

LC-MS (Method 8): R$_t$=1.73 min; MS (ESIpos): m/z=590 [M+H]⁺

¹H NMR (400 MHz, Chloroform-d) δ=11.18 (s, 1H), 8.37 (dd, J=9.2, 5.8 Hz, 1H), 7.63 (d, J=8.6 Hz, 1H), 7.43-7.30 (m, 3H), 7.24-7.16 (m, 2H), 6.71 (dd, J=6.9, 1.8 Hz, 1H), 4.62 (dd, J=14.4, 2.6 Hz, 1H), 4.38 (dd, J=14.7, 9.5 Hz, 1H), 4.21 (t, J=6.0 Hz, 2H), 3.96 (s, 3H), 3.63 (dd, J=13.4, 9.5 Hz, 1H), 3.52-3.38 (m, 3H), 3.33-3.22 (m, 1H), 3.08 (ddd, J=12.2, 9.0, 3.0 Hz, 1H), 2.74-2.63 (m, 1H), 2.47 (ddd, J=14.5, 12.6, 6.1 Hz, 1H), 2.43-2.27 (m, 4H), 2.03-1.76 (m, 2H), 0.97 (t, J=7.6 Hz, 3H).

¹³C NMR (101 MHz, Chloroform-d) δ=166.40, 161.29 (d, J=245.7 Hz), 155.07, 148.91, 142.75, 139.47, 135.69, 135.67 (d, J=9.2 Hz), 128.46, 127.52, 126.78, 124.97 (d, J=9.1 Hz), 124.50, 122.81, 121.72, 121.24, 119.49 (d, J=4.8 Hz), 116.58, 115.22, 115.21 (d, J=24.9 Hz), 110.68 (d, J=20.3 Hz), 104.23-103.83 (m), 72.92, 67.77, 67.65, 44.47, 36.30, 30.76, 26.78, 22.39, 20.99, 18.10, 12.41.

HSQC

13C NMR (101 MHz, CDCl3) δ 124.82, 121.20, 110.57, 127.43, 119.34, 115.21, 121.63, 104.02, 44.44, 44.37, 67.63, 36.24, 72.79, 22.23, 67.51, 72.81, 67.52, 21.03, 20.94, 18.02, 30.77, 26.71, 26.76, 12.37

1H NMR (400 MHz, CDCl3) δ 8.39, 7.65, 7.42, 7.37, 7.35, 7.24, 7.21, 6.73, 4.64, 4.40, 4.23, 3.98, 3.65, 3.46, 3.44, 3.28, 3.10, 2.69, 2.49, 2.40, 2.36, 1.97, 1.86, 1.00.

15N HMBC

15N NMR (41 MHz, CDCl3) δ 194.04, 289.38, 137.73, 137.44, 289.77, 193.89

1H NMR (400 MHz, CDCl3) δ 3.99, 3.99, 3.68, 3.28, 2.49, 2.40.

Example 125

(rac)-4-chloro-3-ethyl-7-{3-[(6-fluoro-1-naphthyl)oxy]propyl}-1-methyl-1,10,11,13,14,15-hexahydro-pyrazolo[4',3':7,8][1,4]oxazacycloundecino[6,5,4-hi]indole-8-carboxylic acid

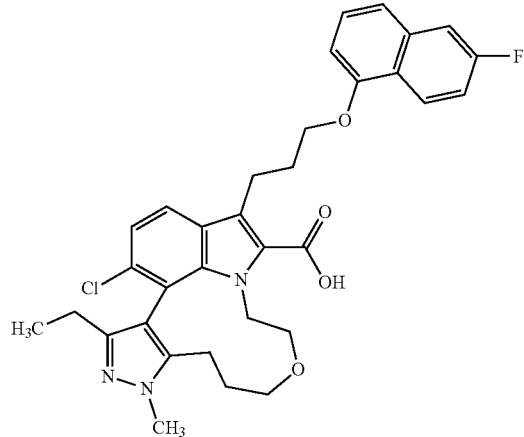 [SMILES: CCc1nn(C)c2c1-c1c(Cl)ccc3c(CCCOc4cccc5cc(F)ccc45)c(C(=O)O)n(c13)CCOCCC2]

To a solution of (rac)-ethyl 6-chloro-7-{3-ethyl-5-[3-(2-hydroxyethoxy)propyl]-1-methyl-1H-pyrazol-4-yl}-3-{3-[(6-fluoronaphthalen-1-yl)oxy]propyl}-1H-indole-2-carboxylate (354 mg, 0.5564 mmol, Intermediate 214) in dichloromethane (20 mL) at 0° C. was added DIPEA (0.4 mL, 2.29 mmol) followed by methane sulfonyl chloride (0.1 mL, 1.28 mmol), after 1 hour at that temperature, volatiles were removed under reduced pressure and the residue was portioned between ethyl acetate and sodium hydroxide (1M, aqueous), layers were separated and the organic phase washed sequentially with sodium hydroxide (1M, aqueous), saturated sodium hydrogen carbonate (aqueous) and saturated sodium chloride (aqueous), the combined aqueous phases were back extracted with ethyl acetate and combined organics were dried over sodium sulfate, insoluble material was removed by filtration, and the volatiles removed under reduced pressure. The amber residue was dissolved in N,N-dimethyl formamide (10 mL), placed in an ice water bath, and treated with sodium hydride (45 mg, 60% in oil, 1.1 mmol), and then warmed to 40° C. for 18 hours, additional sodium hydride (45 mg, 60% in oil, 1.1 mmol) was added and heating continued for 6 hours. The mixture was then treated with sodium hydroxide (4 mL, 1N) and warmed to 60° C. for 18 hours. Majority of the volatiles were removed under reduced pressure and the residue portioned between ethyl acetate and HCl (1N, aqueous), layers separated and the aqueous phase extracted with ethyl acetate (twice), combined organics were washed with saturate sodium chloride (aqueous), dried over sodium sulfate, insoluble materials were removed by filtration, and volatiles removed under reduced pressure. The residue was purified by flash chromatography silica gel eluting with a gradient of 0-5% methanol in dichloromethane, to give the title compound as an off-white solid (250 mg).

LC-MS (Method 8): $R_t$=1.72 min; MS (ESIneg): m/z=591 $[M+H]^+$ $^1$H-NMR (400 MHz, Chloroform-d) δ=11.54 (s, 1H), 8.38 (dd, J=9.3, 5.8 Hz, 1H), 7.62 (d, J=8.6 Hz, 1H), 7.42-7.27 (m, 3H), 7.22 (td, J=8.8, 2.6 Hz, 1H), 7.17 (d, J=8.5 Hz, 1H), 6.71 (dd, J=7.0, 1.6 Hz, 1H), 4.74 (dd, J=14.8, 2.7 Hz, 1H), 4.45 (dd, J=14.9, 9.6 Hz, 1H), 4.20 (t, J=6.1 Hz, 2H), 3.90 (s, 3H), 3.66 (dd, J=13.4, 9.6 Hz, 1H), 3.57-3.26 (m, 4H), 2.90 (d, J=19.5 Hz, 1H), 2.80-2.55 (m, 2H), 2.36 (ddq, J=29.0, 14.7, 7.4 Hz, 4H), 1.82 (dh, J=6.6, 3.4 Hz, 2H), 1.01 (t, J=7.6 Hz, 3H).

$^{13}$C-NMR (101 MHz, Chloroform-d) δ 165.04, 161.15 (d, J=245.6 Hz), 154.98, 151.70, 140.62, 138.91, 135.51 (d, J=9.3 Hz), 134.67, 127.43, 127.05, 126.68, 125.19, 124.96 (d, J=9.1 Hz), 122.70, 121.35, 120.93, 119.25 (d, J=4.8 Hz), 116.57, 115.04 (d, J=24.9 Hz), 114.96, 110.47 (d, J=20.4 Hz), 103.97 (d, J=2.2 Hz), 73.00, 67.74, 67.64, 44.31, 36.74, 30.61, 24.86, 22.15, 20.35, 20.09, 13.01.

Alternate Solvent $^1$H-NMR (400 MHz, DMSO-d6) δ=13.26 (s, 1H), 8.30 (dd, J=9.2, 5.9 Hz, 1H), 7.74 (d, J=8.6 Hz, 1H), 7.67 (dd, J=10.4, 2.6 Hz, 1H), 7.49-7.43 (m, 2H), 7.40 (td, J=8.9, 2.7 Hz, 1H), 7.20 (d, J=8.6 Hz, 1H), 6.90 (dd, J=5.2, 3.5 Hz, 1H), 4.61 (dd, J=14.8, 2.4 Hz, 1H), 4.34-4.23 (m, 1H), 4.23 (t, J=6.1 Hz, 2H), 3.80 (s, 3H), 3.46-3.22 (m, 5H), 2.75 (d, J=5.8 Hz, 1H), 2.72-2.63 (m, 1H), 2.44-2.32 (m, 1H), 2.22 (q, J=7.8, 7.3 Hz, 2H), 2.18-2.03 (m, 2H), 1.95-1.78 (m, 1H), 1.77-1.60 (m, 1H), 0.88 (t, J=7.6 Hz, 3H).

$^{19}$F NMR (376 MHz, DMSO-d6) δ=–114.69.

HSQC

13C NMR (101 MHz, CDCl3) δ 124.93, 121.05, 110.46, 127.46, 119.22, 115.13, 121.42, 104.03, 44.44, 44.33, 67.72, 36.84, 73.00, 22.12, 67.64, 73.02, 67.67, 67.60, 20.32, 20.62, 30.74, 20.56, 25.02, 13.07

1H NMR (400 MHz, CDCl3) δ 8.38, 7.62, 7.39, 7.34, 7.32, 7.22, 7.17, 6.71, 4.74, 4.45, 4.20, 3.90, 3.66, 3.44, 3.37, 3.33, 2.90, 2.90, 2.65, 2.39, 2.35, 2.32, 1.82, 1.01.

15 N HSQC

15N NMR (41 MHz, CDCl3) δ 107.33, 192.14, 290.88, 137.74, 138.25, 106.63, 192.58, 291.06

1H NMR (400 MHz, CDCl3) δ 8.02, 3.90, 3.90, 3.69, 3.34, 2.90, 2.66, 2.32.

15N NMR (41 MHz, CDCl3) δ 192.14, 290.88, 137.74, 138.25, 192.58, 291.06

1H NMR (400 MHz, CDCl3) δ 3.90, 3.90, 3.69, 3.34, 2.66, 2.32.

HSQC DMSO

13C NMR (101 MHz, DMSO) δ 125.23, 121.35, 110.88, 119.67, 128.11, 115.68, 121.35, 104.91, 43.98, 43.82, 68.10, 37.13, 22.05, 72.45, 67.62, 67.51, 20.02, 40.34, 19.95, 30.91, 20.78, 20.65, 24.77, 24.55, 13.42

1H NMR (400 MHz, DMSO) δ 8.29, 7.75, 7.67, 7.45, 7.45, 7.40, 7.20, 6.90, 4.59, 4.28, 4.22, 3.79, 3.31, 3.31, 3.29, 2.74, 2.68, 2.50, 2.38, 2.19, 2.17, 2.08, 1.85, 1.66, 0.87.

Example 126

(rac)-4-Chloro-3-ethyl-12,12-difluoro-7-{3-[(6-fluoro-1-naphthyl)oxy]propyl}-2,14-dimethyl-10,11,12,13,14,15-hexahydro-2H-pyrazolo[3',4':8,9][1,6]diazacycloundecino[10,11,1-hi]indol-14-ium-8-carboxylate

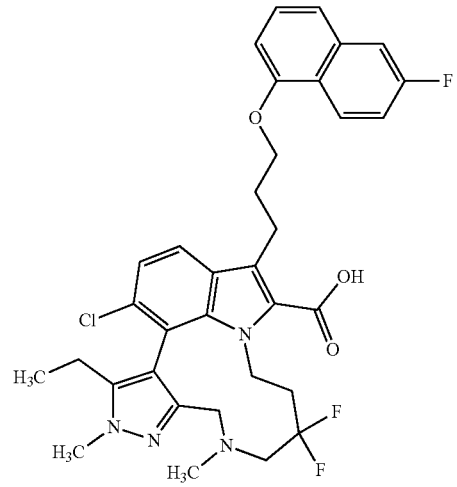 [SMILES: CCc1c2c(nn1C)CN(C)CC(F)(F)CCn1c(C(=O)O)c(CCCOc3cccc4cc(F)ccc34)c3ccc(Cl)c-2c31]

Ethyl 4-chloro-3-ethyl-12,12-difluoro-7-{3-[(6-fluoro-1-naphthyl)oxy]propyl}-2,14-dimethyl-10,11,12,13,14,15-hexahydro-2H-pyrazolo[3',4':8,9][1,6]diazacycloundecino[10,11,1-hi]indole-8-carboxylate (see Intermediate 190, 53 mg, 79.0 μmol) was dissolved in 4 mL tetrahydrofuran, and 4 mL industrial methylated spirit. Lithium hydroxide monohydrate (1.6 mL, 159 mmol, 1 N in water) was added and the mixture was heated at 70° C. for 10 hours. The reaction was cooled to ambient temperature and purified by reversed phase chromatography (Biotage isolera, 30 g, SNAP C18 cartridge) using acetonitrile containing 0.1% formic acid and water containing 0.1% formic acid buffer (3:97 to 100:0). Desired fractions were combined and concentrated under reduced pressure and co-evaporated with acetonitrile. This material was combined with a purified reaction mixture resulting from the reaction of ethyl 4-chloro-3-ethyl-12,12-difluoro-7-{3-[(6-fluoro-1-naphthyl)oxy]propyl}-2,14-dimethyl-10,11,12,13,14,15-hexahydro-2H-pyrazolo[3',4':8,9][1,6]diazacycloundecino[10,11,1-hi]indole-8-carboxylate (see Intermediate 190, 12 mg, 0.018 mmol) in 1 mL tetrahydrofuran and 1 mL industrial methylated spirit with lithium hydroxide monohydrate (1N in water, 0.36 mL, 360 μmol), and heated at 70° C. for 10 hours. This was cooled to ambient temperature and purified by reversed phase chromatography (Biotage isolera, 30 g, SNAP C18 cartridge) using acetonitrile containing 0.1% formic acid and water containing 0.1% formic acid buffer (3:97 to 100:0). The combination of the 2 batches of this reaction was subsequently freeze dried to afford the desired product: 49 mg (79%).

$^1$H-NMR (400 MHz, CDCl3): δ [ppm]=0.82 (t, 3H), 1.38-1.54 (m, 1H), 2.16 (s, 3H), 2.17-2.35 (6H+water), 2.91 (ddd, 1H), 3.33-3.48 (m, 3H), 3.67 (d, 1H), 3.84 (s, 3H), 3.89 (t, 1H), 4.20 (t, 2H), 4.43-4.54 (m, 1H), 6.80-6.83 (m, 1H), 7.23 (d, 1H), 7.34 (td, 1H), 7.40-7.47 (m, 2H), 7.54 (dd, 1H), 7.73 (d, 1H), 8.39 (dd, 1H).

$^{19}$F NMR (400 MHz, CDCl¬3) d [ppm]=−116.63-−116.53 (m, 1H), −100.0 (dd, 1H), −84.8 (d, 1H).

UPLC-MS (CSH C18 Long Acidic, 50-95%): Rt=2.61 min., >99%;

MS (ESIpos): m/z=[M+H]$^+$ 639.

The title compound (42 mg) was separated into enantiomers by preparative chiral HPLC to give enantiomer 1 (18 mg, see Example 127) and enantiomer 2 (19 mg, see Example 128).

Preparative Chiral HPLC Method:
Instrument: Labomatic HD5000, Labocord-5000; Gilson GX-241, Labcol Vario 4000, Column: Chiralpak ID 5μ 250×30 mm; Eluent A: Water+0.1 Vol-% TFA (99%); Eluent B: Acetonitrile; Isocratic: 50% B; Flow 30.0 mL/min; UV 220 nm Analytical Chiral HPLC Method:
Instrument: Agilent HPLC 1260; Column: Chiralpak ID 3μ 100×4.6 mm; Eluent A: Water+0.1 Vol-% TFA (99%); Eluent B: Acetonitrile; Isocratisc: 50% B; Flow 1.4 mL/min; Temperature: 25° C.; DAD 220 nm Example 127

4-chloro-3-ethyl-12,12-difluoro-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid (Enantiomer 1)

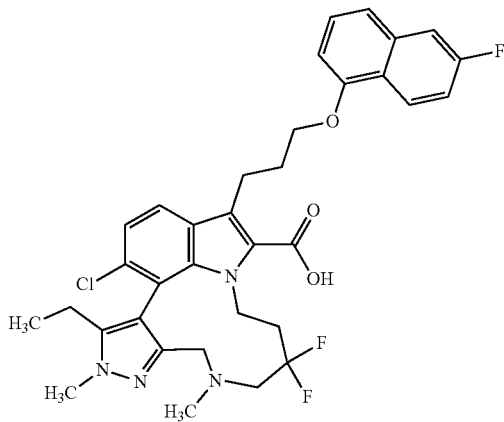 [SMILES: CCc1c2c(nn1C)CN(C)CC(F)(F)CCn1c(C(=O)O)c(CCCOc3cccc4cc(F)ccc34)c3ccc(Cl)c-2c31]

For the preparation of the racemic title compound see Example 126. Separation of stereoisomers by preparative chiral HPLC (method see Example 126) gave the 99% pure title compound (18 mg, 99% ee).

Analytical Chiral HPLC (method see Example 126): R$_t$=3.05 min.

$^1$H-NMR (400 MHz, DMSO-d6) δ[ppm]=0.77 (t, 3H), 1.32-1.53 (m, 1H), 1.86-2.02 (m, 1H), 2.06-2.16 (m, 5H), 2.20 (br t, 2H), 2.25-2.36 (m, 1H), 2.71-2.96 (m, 1H), 3.23-3.33 (m, 4H), 3.58 (br d, 1H), 3.79 (br d, 1H), 3.84 (s, 3H), 4.19 (t, 2H), 4.45 (br d, 1H), 6.86 (dd, 1H), 7.28 (d, 1H), 7.34-7.48 (m, 3H), 7.66 (dd, 1H), 7.78 (d, 1H), 8.28 (dd, 1H).

Example 128

4-chloro-3-ethyl-12,12-difluoro-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid (Enantiomer 2)

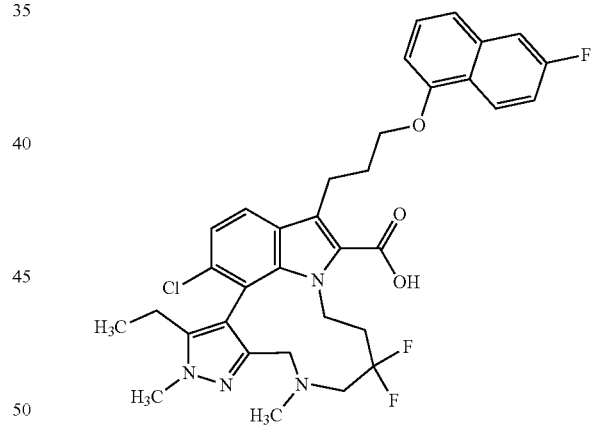

For the preparation of the racemic title compound see Example 126. Separation of stereoisomers by preparative chiral HPLC (method see Example 126) gave the 95% pure title compound (19 mg, 91% ee).

Analytical Chiral HPLC (method see Example 126): R$_t$=3.58 min.

$^1$H-NMR (400 MHz, DMSO-d6) δ[ppm]=0.77 (t, 3H), 1.34-1.58 (m, 1H), 1.97 (br s, 1H), 2.06-2.25 (m, 7H), 2.35-2.42 (m, 1H), 2.76-2.97 (m, 1H), 3.28-3.36 (m, 2H), 3.61 (br d, 3H), 3.76-3.90 (m, 4H), 4.20 (br t, 2H), 4.39-4.56 (m, 1H), 6.86 (dd, 1H), 7.27 (d, 1H), 7.34-7.47 (m, 3H), 7.66 (dd, 1H), 7.78 (d, 1H), 8.28 (dd, 1H).

Example 129

(rac)-4-chloro-3-ethyl-11,11-difluoro-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid

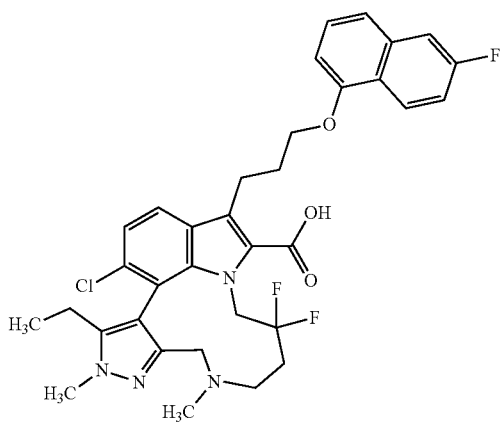 [SMILES: CCc1c2c(nn1C)CN(C)CCC(F)(F)Cn1c(C(=O)O)c(CCCOc3cccc4cc(F)ccc34)c3ccc(Cl)c-2c31]

(rac)-Ethyl-4-chloro-3-ethyl-11,11-difluoro-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylate (see Intermediate 199, 6.00 mg) was dissolved in 47 μL THF and 94 μL ethanol and treated with the aqueous lithium hydroxide solution (18 μL, 1.0 M, 18 μmol). The reaction mixture was stirred at 70° C. under argon atmosphere over night. Aqueous lithium hydroxide solution (18 μL, 1.0 M, 18 μmol) was added and it was stirred at 70° C. for over night. The reaction mixture was combined with the reaction mixture starting from rac-Ethyl 4-chloro-3-ethyl-11,11-difluoro-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylate (see Intermediate 199, 12 mg) and diluted with water and dichloromethane. The pH was adjusted to 3 by addition of acetic acid. It was stirred for a few minutes, the organic layer was filtered through a silicone coated filter and concentrated under reduced pressure. The crude product was purified by HPLC under basic conditions to provide the target compound in 89% purity: 7 mg LC-MS (Method 2): $R_t$=0.93 min; MS (ESIpos): m/z=641 [M+H]$^+$ $^1$H-NMR (400 MHz, DMSO-d6): δ [ppm]=0.73-0.83 (m, 3H), 0.83-0.90 (m, 1H), 1.09-1.37 (m, 1H), 1.63-1.85 (m, 1H), 2.03 (s, 3H), 2.10-2.24 (m, 5H), 2.24-2.30 (m, 1H), 3.18-3.29 (m, 2H), 3.37-3.49 (m, 2H), 3.84 (s, 3H), 4.12-4.25 (m, 2H), 4.30-4.46 (m, 1H), 4.74-4.95 (m, 1H), 6.83 (dd, 1H), 7.24 (d, 1H), 7.34-7.47 (m, 3H), 7.66 (dd, 1H), 7.73 (d, 1H), 8.28 (dd, 1H).

Example 130

(rac)-4-chloro-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylic acid

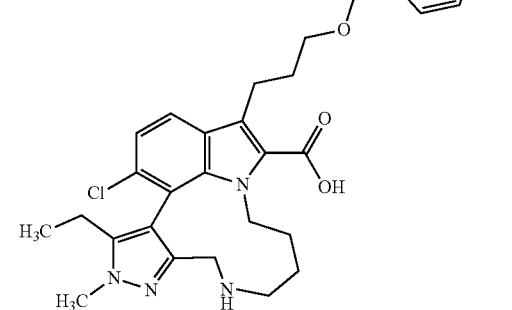

(rac)-Ethyl-4-chloro-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylate (see Intermediate 115, 200 mg) was dissolved in 1.7 mL THF and 3.4 mL ethanol and treated with aqueous lithium hydroxide solution (650 μL, 1.0 M, 650 μmol). It was stirred at 70° C. under argon atmosphere over night. The reaction mixture was concentrated under reduced pressure. The residue was treated with water and acetic acid. Dichloromethane was added, it was stirred for a few minutes, the organic layer was filtered through a silicone coated filter and concentrated under reduced pressure. The crude product was treated with DMF and undissolved precipitate was filtered off and dried at 50° C. under vacuo to provide the target compound with 89% purity: 58 mg.

LC-MS (Method 2): $R_t$=0.89 min; MS (ESIpos): m/z=589 [M+H]$^+$ $^1$H-NMR (400 MHz, DMSO-d6): δ [ppm]=0.83 (t, 3H), 1.04-1.20 (m, 2H), 1.28-1.41 (m, 1H), 2.08-2.30 (m, 4H), 3.05-3.20 (m, 1H), 3.54 (br d, 1H), 3.67-3.80 (m, 1H), 3.88 (s, 3H), 4.17 (br t, 2H), 4.49-4.69 (m, 1H), 6.85 (dd, 1H), 7.08-7.20 (m, 1H), 7.34-7.46 (m, 3H), 7.58-7.70 (m, 2H), 8.28 (dd, 1H).—6H not detectable, contains DMF.

Example 131

(rac)-4-chloro-3-ethyl-7-{3-[(6-fluoronaphthalen-1-yl)oxy]propyl}-14-(2-methoxyethyl)-2-methyl-10,11,12,13,14,15-hexahydro-2H-pyrazolo[3',4':8,9][1,6]diazacycloundecino[10,11,1-hi]indole-8-carboxylic acid

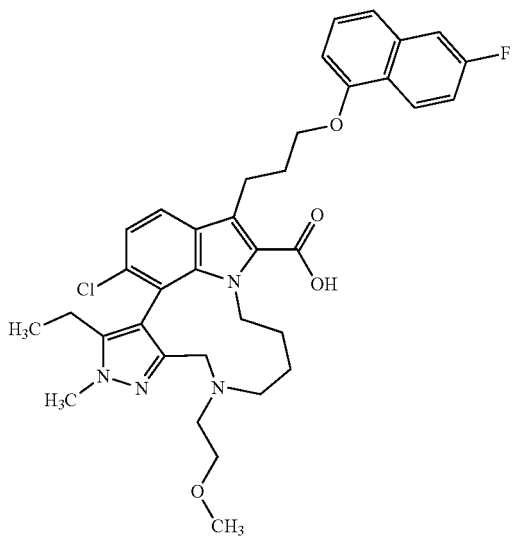 [SMILES: CCc1c2c(nn1C)CN(CCOC)CCCCn1c(C(=O)O)c(CCCOc3cccc4cc(F)ccc34)c3ccc(Cl)c-2c31]

(rac)-Ethyl 4-chloro-3-ethyl-7-{3-[(6-fluoronaphthalen-1-yl)oxy]propyl}-14-(2-methoxyethyl)-2-methyl-10,11,12,13,14,15-hexahydro-2H-pyrazolo[3',4':8,9][1,6]diazacycloundecino[10,11,1-hi]indole-8-carboxylate (see Intermediate 200, 22.0 mg) was dissolved in 170 μL THF and 340 μL ethanol and treated with aqueous lithium hydroxide solution (65 μL, 1.0 M, 65 μmol). The reaction mixture was stirred at 70° C. under argon atmosphere overnight. The reaction mixture was concentrated under reduced pressure. The residue was dissolved in dichloromethane and treated with water and acetic acid. It was stirred for a few minutes, the organic layer was filtered through a silicone coated filter and concentrated under reduced pressure to provide the product in 86% purity: 20 mg.

LC-MS (Method 2): $R_t$=0.96 min; MS (ESIpos): m/z=649 [M+H]$^+$ $^1$H-NMR (400 MHz, DMSO-d6): δ [ppm]=0.81 (t, 3H), 0.91-1.12 (m, 4H), 2.02-2.26 (m, 6H), 2.27-2.39 (m, 2H), 2.78-2.92 (m, 5H), 3.15-3.31 (m, 4H), 3.68 (d, 1H), 3.75-3.87 (m, 4H), 4.11-4.26 (m, 3H), 6.82 (dd, 1H), 7.15 (d, 1H), 7.35-7.47 (m, 3H), 7.62-7.70 (m, 2H), 8.31 (dd, 1H).

A further batch of the title compound (81 mg) was separated into enantiomers by preparative chiral HPLC to give enantiomer 1 (31 mg, see Example 132) and enantiomer 2 (36 mg, see Example 133).

Preparative Chiral HPLC Method:

Instrument: Labomatic HD5000, Labocord-5000; Gilson GX-241, Labcol Vario 4000, Column: Chiralpak IG 5μ 250×30 mm; Eluent A: Hexan+0.1 Vol-% Diethylamine (99%); Eluent B: Ethanol; Gradient: 20-50% B in 20 min; Flow 50.0 mL/min; UV 220 nm.

Analytical Chiral HPLC Method:

Instrument: Agilent HPLC 1260; Column: Chiralpak IG 3μ 100×4.6 mm; Eluent A: Hexan+0.1 Vol-% Diethylamine (99%); Eluent B: Ethanol; Gradient: 20-50% B in 7 min; Flow 1.4 mL/min; Temperature: 25° C.; DAD 254 nm.

Example 132

4-chloro-3-ethyl-7-{3-[(6-fluoronaphthalen-1-yl)oxy]propyl}-14-(2-methoxyethyl)-2-methyl-10,11,12,13,14,15-hexahydro-2H-pyrazolo[3',4':8,9][1,6]diazacycloundecino[10,11,1-hi]indole-8-carboxylic acid (Enantiomer 1)

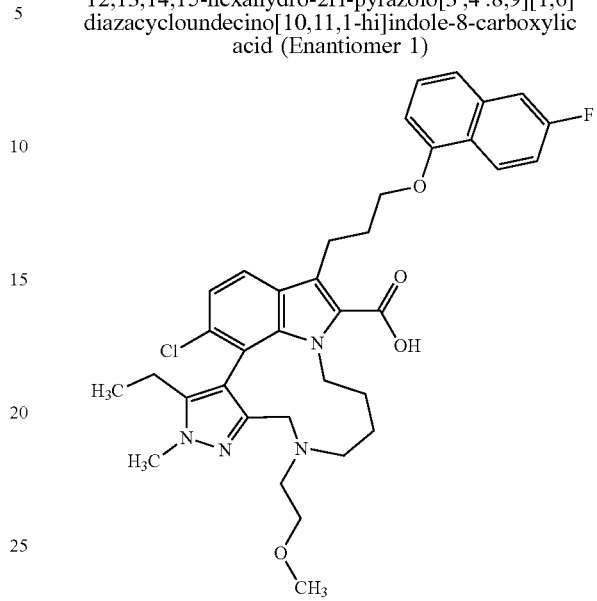

For the preparation of the racemic title compound see Example 131. Separation of stereoisomers by preparative chiral HPLC (method see Example 131) gave the pure title compound (31 mg).

Analytical Chiral HPLC (method see Example 131): $R_t$=1.67 min.

$^1$H-NMR (400 MHz, DMSO-d6) δ[ppm]=0.81 (t, 3H), 0.95-1.09 (m, 3H), 1.18-1.28 (m, 1H), 2.05-2.36 (m, 8H), 2.80-2.97 (m, 4H), 3.14-3.28 (m, 4H), 3.64 (d, 1H), 3.71-3.84 (m, 4H), 4.16 (ddt, 2H), 4.24-4.37 (m, 1H), 6.82 (dd, 1H), 7.11 (d, 1H), 7.34-7.46 (m, 3H), 7.60 (d, 1H), 7.65 (dd, 1H), 8.30 (dd, 1H).—30% diethylamine salt.

Example 133

4-chloro-3-ethyl-7-{3-[(6-fluoronaphthalen-1-yl)oxy]propyl}-14-(2-methoxyethyl)-2-methyl-10,11,12,13,14,15-hexahydro-2H-pyrazolo[3',4':8,9][1,6]diazacycloundecino[10,11,1-hi]indole-8-carboxylic acid N-ethylethanamine salt (Enantiomer 2)

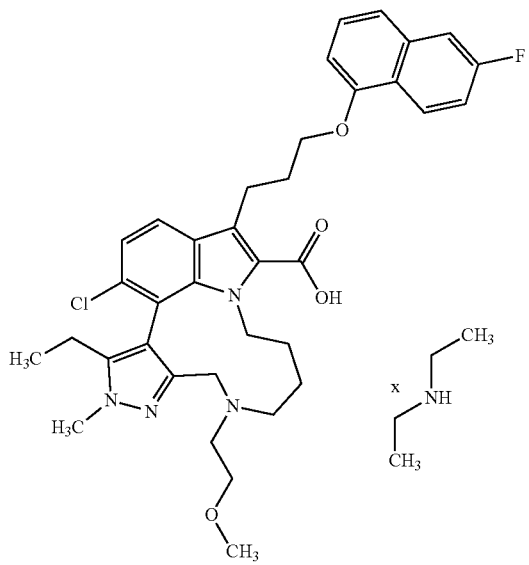

For the preparation of the racemic title compound see Example 131. Separation of stereoisomers by preparative chiral HPLC (method see Example 131) gave the pure title compound (36 mg).

Analytical Chiral HPLC (method see Example 131): $R_t$=3.32 min.

$^1$H-NMR (400 MHz, DMSO-d6) δ[ppm]=0.82 (t, 3H), 0.95-1.04 (m, 3H), 1.21-1.29 (m, 1H), 2.05-2.32 (m, 8H), 2.88-2.97 (m, 4H), 3.09-3.25 (m, 4H), 3.60 (br d, 1H), 3.67-3.77 (m, 1H), 3.80 (s, 3H), 4.10-4.21 (m, 2H), 4.34 (dtd, 1H), 6.82 (dd, 1H), 7.07 (d, 1H), 7.33-7.47 (m, 3H), 7.52-7.59 (m, 1H), 7.65 (dd, 1H), 8.24-8.34 (m, 1H).—65% diethylamine salt Example 134

(rac)-4-chloro-3-ethyl-7-{3-[(6-fluoronaphthalen-1-yl)oxy]propyl}-14-[(2-methoxyethoxy)carbonyl]-2-methyl-10,11,12,13,14,15-hexahydro-2H-pyrazolo[3',4':8,9][1,6]diazacycloundecino[10,11,1-hi]indole-8-carboxylic acid

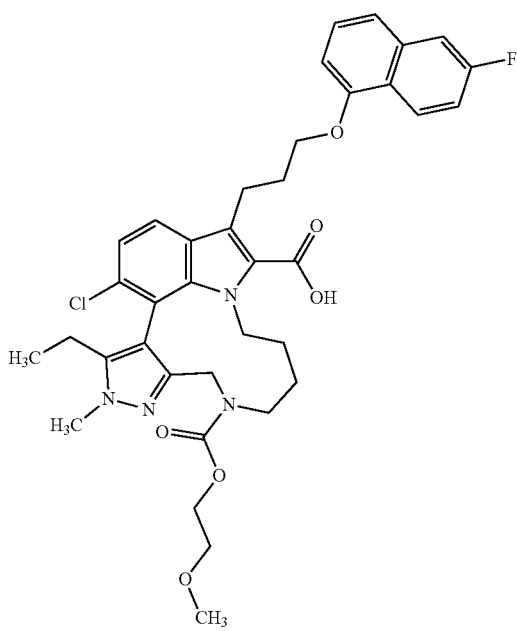 [SMILES: CCc1c2c(nn1C)CN(C(=O)OCCOC)CCCCn1c(C(=O)O)c(CCCOc3cccc4cc(F)ccc34)c3ccc(Cl)c-2c31]

(rac)-8-Ethyl 14-(2-methoxyethyl) 4-chloro-3-ethyl-7-{3-[(6-fluoronaphthalen-1-yl)oxy]propyl}-2-methyl-2,10,11,12,13,15-hexahydro-14H-pyrazolo[3',4':8,9][1,6]diazacycloundecino[10,11,1-hi]indole-8,14-dicarboxylate (see Intermediate 201, 3.00 mg) was dissolved in 22 μL THF and 44 μL ethanol and treated with aqueous lithium hydroxide solution (8.3 μL, 1.0 M, 8.3 μmol). It was stirred at 70° C. under argon atmosphere over night. The reaction mixture was concentrated under reduced pressure. The residue was dissolved in dichloromethane and treated with water and acetic acid. It was stirred for a few minutes, the organic layer was filtered through a silicone coated filter and concentrated under reduced pressure to provide the target compound with 95% purity: 3 mg.

LC-MS (Method 2): $R_t$=0.94 min; MS (ESIpos): m/z=692 [M+H]$^+$ $^1$H-NMR (400 MHz, DMSO-d6) δ[ppm]: 0.816 (4.54), 0.835 (9.86), 0.854 (5.47), 1.167 (2.27), 1.231 (8.88), 1.907 (1.14), 2.182 (2.12), 2.230 (1.03), 2.249 (1.60), 2.268 (1.55), 2.296 (1.29), 2.331 (2.58), 2.518 (15.33), 2.522 (9.39), 2.539 (2.58), 2.673 (2.27), 3.157 (3.87), 3.221 (3.41), 3.259 (1.50), 3.456 (1.45), 3.810 (1.24), 3.881 (16.00), 3.940 (1.03), 4.018 (1.50), 4.160 (1.81), 4.175 (3.35), 4.190 (1.70), 4.487 (0.88), 4.521 (0.77), 4.611 (0.62), 6.829 (1.50), 6.835 (1.60), 6.845 (1.55), 6.851 (1.65), 7.158 (1.19), 7.181 (1.24), 7.338 (0.83), 7.344 (0.98), 7.360 (1.50), 7.367 (1.65), 7.388 (1.39), 7.408 (2.74), 7.418 (3.51), 7.424 (6.40), 7.625 (1.96), 7.632 (2.06), 7.651 (2.06), 7.657 (2.12), 7.677 (1.03), 7.699 (0.93), 8.240 (1.03).

Example 135

(rac)-4-chloro-3-ethyl-7-{3-[(6-fluoronaphthalen-1-yl)oxy]propyl}-2-methyl-14-[2-(oxan-4-yl)ethyl]-10,11,12,13,14,15-hexahydro-2H-pyrazolo[3',4':8,9][1,6]diazacycloundecino[10,11,1-hi]indole-8-carboxylic acid

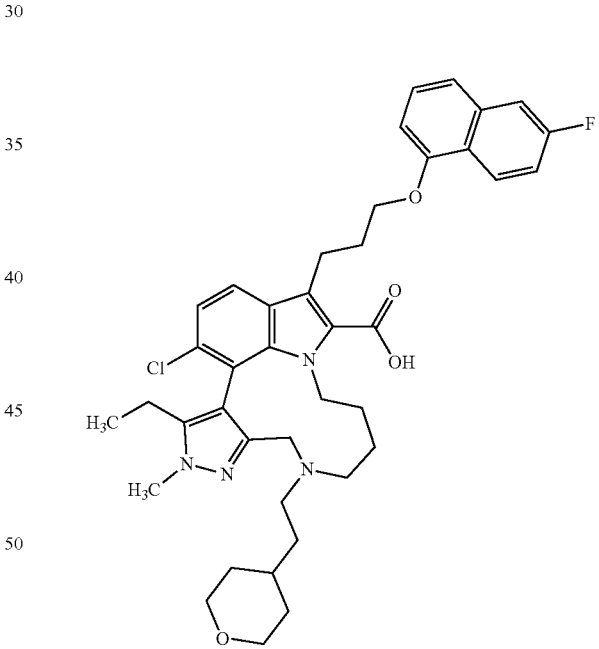

(rac)-Ethyl 4-chloro-3-ethyl-7-{3-[(6-fluoronaphthalen-1-yl)oxy]propyl}-2-methyl-14-[2-(oxan-4-yl)ethyl]-10,11,12,13,14,15-hexahydro-2H-pyrazolo[3',4':8,9][1,6]diazacycloundecino[10,11,1-hi]indole-8-carboxylate (see Intermediate 202, 23.0 mg) was dissolved in 170 μL THF and 330 μL ethanol and treated with aqueous lithium hydroxide solution (63 μL, 1.0 M, 63 μmol). It was stirred at 70° C. under argon atmosphere over night. The reaction mixture was concentrated under reduced pressure. The residue was dissolved in dichloromethane and treated with water and acetic acid. It was stirred for a few minutes, the organic layer was filtered through a silicone coated filter and concentrated under reduced pressure to provide the target compound in 87% purity: 22 mg.

LC-MS (Method 2): $R_t$=1.01 min; MS (ESIpos): m/z=703 [M+H]$^+$ $^1$H-NMR (400 MHz, DMSO-d6): δ [ppm]=0.59-0.74 (m, 2H), 0.79 (t, 3H), 0.83-0.97 (m, 3H), 0.98-1.13 (m, 3H), 1.15-1.31 (m, 4H), 1.81-1.96 (m, 2H), 2.04-2.15 (m, 2H), 2.16-2.27 (m, 2H), 2.34-2.46 (m, 2H), 2.85-2.93 (m, 1H), 2.95-3.03 (m, 1H), 3.18-3.30 (m, 2H), 3.48 (br d, 1H), 3.55-3.64 (m, 1H), 3.74-3.86 (m, 5H), 4.13-4.29 (m, 3H), 6.82-6.92 (m, 1H), 7.18 (d, 1H), 7.34-7.47 (m, 3H), 7.62-7.71 (m, 2H), 8.30 (dd, 1H), 12.80 (br s, 1H).

A further batch of the title compound (288 mg) was separated into enantiomers by preparative chiral HPLC to give enantiomer 1 (122 mg, see Example 136) and enantiomer 2 (134 mg, see Example 137).

Preparative Chiral HPLC Method:

Instrument: Labomatic HD5000, Labocord-5000; Gilson GX-241, Labcol Vario 4000, Column: Chiralpak IE 5μ 250×50 mm; Eluent A: Hexane+0.1 Vol-% Diethylamine (99%); Eluent B: Ethanol; Isocratic: 60% A+40% B; Flow 100.0 mL/min; UV 220 nm Analytical Chiral HPLC Method:

Instrument: Agilent HPLC 1260; Column: Chiralpak IE 3μ 100×4.6 mm; Eluent A: Hexane+0.1 Vol-% Diethylamine (99%); Eluent B: Ethanol; Isocratic: 60% A+40% B; Flow 1.4 mL/min; Temperature 25° C.; DAD 220 nm Example 136

4-chloro-3-ethyl-7-{3-[(6-fluoronaphthalen-1-yl)oxy]propyl}-2-methyl-14-[2-(oxan-4-yl)ethyl]-10,11,12,13,14,15-hexahydro-2H-pyrazolo[3',4':8,9][1,6]diazacycloundecino[10,11,1-hi]indole-8-carboxylic acid N-ethylethanamine salt (Enantiomer 1)

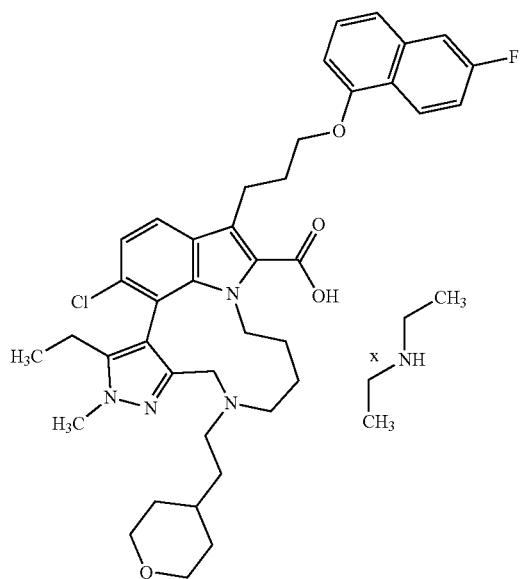

For the preparation of the racemic title compound see Example 135. Separation of stereoisomers by preparative chiral HPLC (method see Example 135) gave the pure title compound (122 mg).

Analytical Chiral HPLC (method see Example 135): $R_t$=2.41 min.

$^1$H-NMR (400 MHz, DMSO-d6) δ[ppm]=0.61-0.74 (m, 2H), 0.79 (t, 3H), 0.82-0.96 (m, 2H), 0.96-1.02 (m, 2H), 1.03-1.12 (m, 2H), 1.18-1.29 (m, 3H), 1.83-1.97 (m, 2H), 2.05-2.15 (m, 2H), 2.16-2.26 (m, 2H), 2.34-2.45 (m, 2H), 2.83-2.95 (m, 1H), 2.99 (d, 1H), 3.14-3.28 (m, 4H), 3.46 (br d, 1H), 3.58 (br dd, 1H), 3.67-3.78 (m, 2H), 3.80 (s, 3H), 4.12-4.26 (m, 2H), 4.26-4.40 (m, 1H), 6.86 (dd, 1H), 7.12 (d, 1H), 7.33-7.46 (m, 3H), 7.60 (d, 1H), 7.65 (dd, 1H), 8.30 (dd, 1H).—as diethylamine salt (50%)

Example 137

4-chloro-3-ethyl-7-{3-[(6-fluoronaphthalen-1-yl)oxy]propyl}-2-methyl-14-[2-(oxan-4-yl)ethyl]-10,11,12,13,14,15-hexahydro-2H-pyrazolo[3',4':8,9][1,6]diazacycloundecino[10,11,1-hi]indole-8-carboxylic acid N-ethylethanamine (Enantiomer 2)

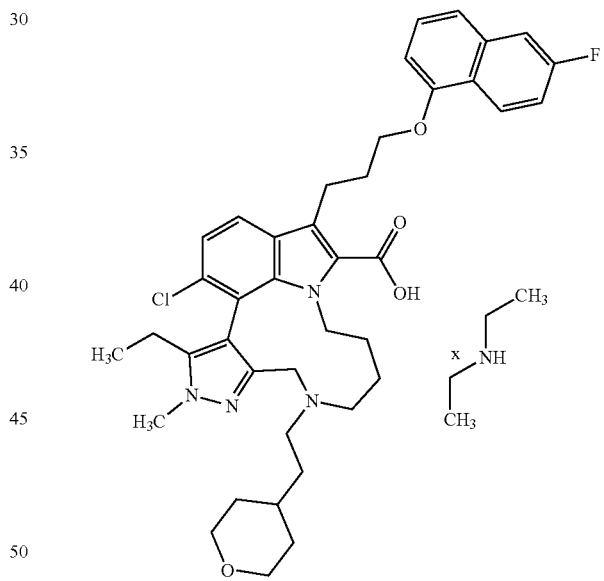

For the preparation of the racemic title compound see Example 135. Separation of stereoisomers by preparative chiral HPLC (method see Example 135) gave the pure title compound (134 mg).

Analytical Chiral HPLC (method see Example 135): $R_t$=4.29 min.

$^1$H-NMR (400 MHz, DMSO-d6) δ[ppm]: 0.64-0.75 (m, 2H), 0.79 (t, 3H), 0.83-0.94 (m, 2H), 1.00-1.12 (m, 4H), 1.20-1.29 (m, 3H), 1.84-1.97 (m, 2H), 2.05-2.15 (m, 2H), 2.16-2.26 (m, 2H), 2.34-2.44 (m, 2H), 2.90-2.95 (m, 1H), 2.99 (d, 1H), 3.15-3.28 (m, 4H), 3.46 (br d, 1H), 3.58 (br dd, 1H), 3.70-3.83 (m, 5H), 4.10-4.38 (m, 3H), 6.86 (dd, 1H), 7.14 (d, 1H), 7.32-7.48 (m, 3H), 7.59-7.70 (m, 2H), 8.30 (dd, 1H).—as diethylamine salt (50%)

Example 138

(rac)-4-chloro-3-ethyl-7-{3-[(6-fluoronaphthalen-1-yl)oxy]propyl}-2-methyl-14-{[2-(oxan-4-yl)ethoxy]carbonyl}-10,11,12,13,14,15-hexahydro-2H-pyrazolo[3',4':8,9][1,6]diazacycloundecino[10,11,1-hi]indole-8-carboxylic acid

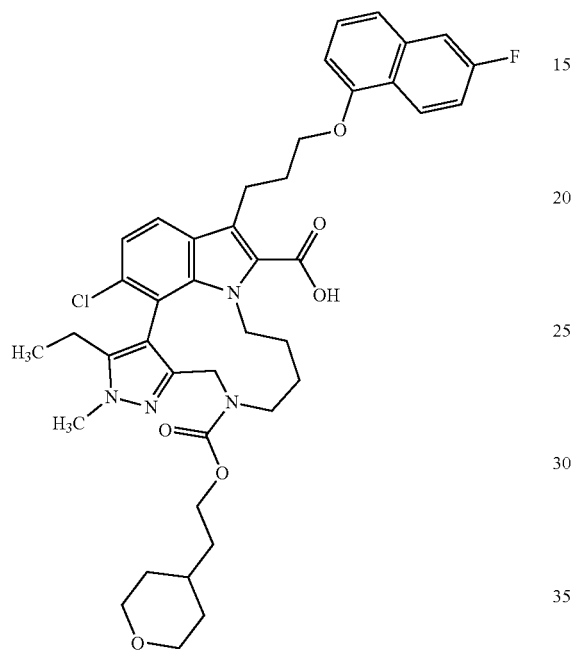

(rac)-8-Ethyl 14-[2-(oxan-4-yl)ethyl] 4-chloro-3-ethyl-7-{3-[(6-fluoronaphthalen-1-yl)oxy]propyl}-2-methyl-2,10,11,12,13,15-hexahydro-14H-pyrazolo[3',4':8,9][1,6]diazacycloundecino[10,11,1-hi]indole-8,14-dicarboxylate (see Intermediate 203, 10.0 mg) was dissolved in 68 μL THF and 140 μL ethanol and treated with aqueous lithium hydroxide solution (26 μL, 1.0 M, 26 μmol). The reaction mixture was stirred at 70° C. under argon atmosphere over night. The reaction mixture was concentrated under reduced pressure. The residue was dissolved in dichloromethane and treated with water and acetic acid. It was stirred for a few minutes, the organic layer was filtered through a silicone coated filter and concentrated under reduced pressure to provide the target compound in 92% purity: 10 mg.

LC-MS (Method 2): $R_t$=0.98 min; MS (ESIpos): m/z=746 [M+H]$^+$ $^1$H-NMR (400 MHz, DMSO-d6): δ [ppm]=0.77-0.97 (m, 5H), 1.02-1.21 (m, 8H), 1.33-1.56 (m, 6H), 2.12-2.30 (m, 4H), 3.12-3.23 (m, 3H), 3.70-3.79 (m, 3H), 3.88 (s, 3H), 3.90-3.99 (m, 2H), 4.17 (br t, 2H), 4.38-4.51 (m, 1H), 4.55-4.69 (m, 1H), 6.83 (dd, 1H), 7.18 (br d, 1H), 7.32-7.45 (m, 3H), 7.60-7.74 (m, 2H), 8.24 (dd, 1H).

Example 139

(rac)-4-chloro-3-ethyl-7-{3-[(6-fluoronaphthalen-1-yl)oxy]propyl}-14-(3-hydroxypropyl)-2-methyl-10,11,12,13,14,15-hexahydro-2H-pyrazolo[3',4':8,9][1,6]diazacycloundecino[10,11,1-hi]indole-8-carboxylic acid

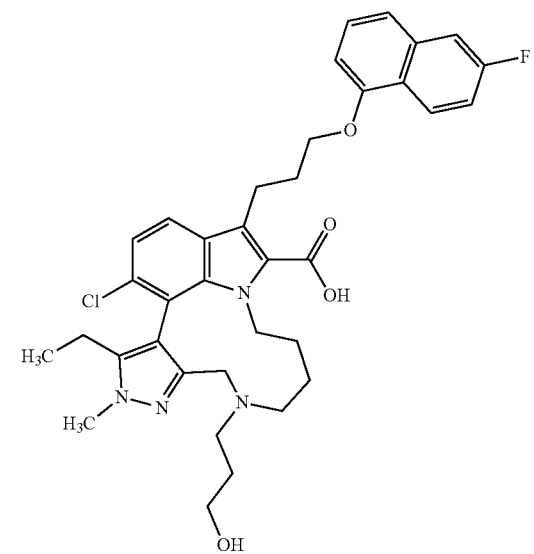 [SMILES: CCc1c2c(nn1C)CN(CCCO)CCCCn1c(C(=O)O)c(CCCOc3cccc4cc(F)ccc34)c3ccc(Cl)c-2c31]

(rac)-Ethyl 4-chloro-3-ethyl-7-{3-[(6-fluoronaphthalen-1-yl)oxy]propyl}-14-(3-hydroxypropyl)-2-methyl-10,11,12,13,14,15-hexahydro-2H-pyrazolo[3',4':8,9][1,6]diazacycloundecino[10,11,1-hi]indole-8-carboxylate (see Intermediate 204, 19.0 mg) was dissolved in 150 μL THF and 290 μL ethanol and treated with the aqueous lithium hydroxide solution (56 μL, 1.0 M, 56 μmol). The reaction mixture was stirred at 70° C. under argon atmosphere over night. The reaction mixture was concentrated under reduced pressure. The residue was dissolved in dichloromethane and treated with water and acetic acid. It was stirred for a few minutes, the organic layer was filtered through a silicone coated filter and concentrated under reduced pressure. The crude product was purified by HPLC under basic conditions to provide the desired target compound with 93% purity: 13 mg LC-MS (Method 2): $R_t$=0.92 min; MS (ESIpos): m/z=649 [M+H]$^+$ $^1$H-NMR (400 MHz, DMSO-d6): δ [ppm]=0.81 (t, 3H), 0.90-1.15 (m, 4H), 1.16-1.27 (m, 2H), 1.28-1.40 (m, 1H), 1.98-2.25 (m, 6H), 2.28-2.42 (m, 2H), 2.87-2.97 (m, 1H), 2.97-3.07 (m, 1H), 3.13-3.27 (m, 3H), 3.60 (d, 1H), 3.77-3.92 (m, 4H), 4.16 (t, 2H), 4.20-4.33 (m, 1H), 6.84 (dd, 1H), 7.14 (d, 1H), 7.35-7.49 (m, 3H), 7.62-7.73 (m, 2H), 8.31 (dd, 1H).—1H not detectable.

Example 140

4-chloro-3-ethyl-7-{3-[(6-fluoronaphthalen-1-yl)oxy]propyl}-14-(3-hydroxy-3-methylbutyl)-2-methyl-10,11,12,13,14,15-hexahydro-2H-pyrazolo[3',4':8,9][1,6]diazacycloundecino[10,11,1-hi]indole-8-carboxylic acid (Enantiomer 1)

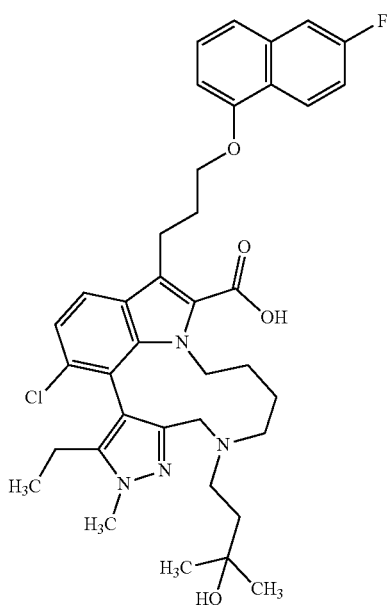 [SMILES: CCc1c2c(nn1C)CN(CCC(C)(C)O)CCCCn1c(C(=O)O)c(CCCOc3cccc4cc(F)ccc34)c3ccc(Cl)c-2c31]

(rac)-Ethyl 4-chloro-3-ethyl-7-{3-[(6-fluoronaphthalen-1-yl)oxy]propyl}-14-(3-hydroxy-3-methylbutyl)-2-methyl-10,11,12,13,14,15-hexahydro-2H-pyrazolo[3',4':8,9][1,6]diazacycloundecino[10,11,1-hi]indole-8-carboxylate (see Intermediate 228, 305 mg, 434 μmol) was dissolved in 6.9 mL THF and 3.4 mL ethanol. Aqueous lithiumhydroxide solution (3.4 mL, 1.0 M, 3.4 mmol) was added and the reaction mixture was stirred for 21 h at 70° C. The reaction mixture was concentrated in vacuo dissolved in a small amount of dichloromethane and water and purified by column chromatography (dichloromethane/ethanol 0-100%, 25 g 25μ-silica gel) to provide the target compound: 312 mg.

LC-MS (Method 2): R$_t$=0.97 min; MS (ESIpos): m/z=675 [M+H]$^+$ $^1$H-NMR (400 MHz, DMSO-d6) δ[ppm]: 0.808 (0.86), 0.814 (0.48), 0.821 (0.54), 0.827 (1.98), 0.845 (0.95), 0.909 (3.14), 0.922 (0.43), 0.941 (3.05), 1.034 (4.91), 1.051 (9.23), 1.069 (5.26), 1.660 (16.00), 2.170 (0.67), 2.189 (0.98), 2.209 (0.88), 2.326 (0.61), 2.331 (0.43), 2.345 (0.59), 2.518 (1.43), 2.522 (0.92), 3.331 (0.79), 3.340 (0.82), 3.410 (1.69), 3.428 (4.64), 3.445 (4.47), 3.462 (1.63), 3.816 (4.07), 4.156 (0.48), 4.172 (0.49), 6.979 (0.94), 7.000 (0.98), 7.377 (0.46), 7.384 (0.40), 7.396 (0.60), 7.414 (1.21), 7.430 (1.06), 7.451 (0.80), 7.631 (0.40).

The racemic compound (306 mg) was separated into enantiomers by preparative chiral HPLC followed by a column chromatography to give the target compound (enantiomer 1, 99 mg) and enantiomer 2 (92 mg, see Example 141).

Analytical Chiral HPLC: R$_t$=2.19 min.

LC-MS (Method 2): R$_t$=0.99 min; MS (ESIpos): m/z=675 [M+H]$^+$ $^1$H-NMR (400 MHz, DMSO-d6) δ[ppm]: 0.798 (1.63), 0.805 (3.57), 0.814 (2.05), 0.824 (7.93), 0.842 (3.74), 0.886 (2.02), 0.896 (11.14), 0.904 (3.46), 0.923 (2.70), 0.931 (11.95), 1.035 (2.70), 1.052 (4.86), 1.070 (2.81), 1.109 (0.76), 1.124 (0.76), 1.142 (0.76), 1.160 (1.01), 1.231 (2.02), 1.339 (0.45), 1.360 (0.73), 1.375 (0.67), 1.394 (0.59), 1.901 (7.00), 2.156 (1.32), 2.171 (2.28), 2.183 (3.88), 2.202 (4.27), 2.221 (1.77), 2.322 (2.31), 2.327 (2.95), 2.331 (2.39), 2.518 (7.06), 2.523 (4.39), 2.659 (0.56), 2.664 (1.21), 2.669 (1.69), 2.673 (1.24), 2.678 (0.56), 3.084 (0.48), 3.098 (0.56), 3.116 (0.70), 3.183 (0.51), 3.202 (0.96), 3.219 (0.76), 3.235 (0.76), 3.253 (0.59), 3.428 (0.70), 3.445 (0.59), 3.663 (0.51), 3.678 (0.62), 3.694 (0.53), 3.815 (16.00), 4.139 (0.84), 4.156 (1.72), 4.167 (1.72), 4.183 (0.84), 4.510 (0.51), 4.543 (0.51), 6.815 (1.24), 6.819 (1.21), 6.831 (1.27), 6.836 (1.27), 7.006 (2.08), 7.027 (2.19), 7.354 (0.87), 7.360 (1.01), 7.376 (1.91), 7.382 (1.63), 7.398 (2.39), 7.405 (1.57), 7.413 (4.22), 7.431 (0.65), 7.467 (1.55), 7.488 (1.38), 7.625 (1.60), 7.631 (1.69), 7.651 (1.63), 7.657 (1.63), 8.265 (1.32), 8.280 (1.41), 8.288 (1.38), 8.303 (1.27).

Preparative Chiral HPLC Method:
Instrument: Labomatic HD5000, Labocord-5000; Gilson GX-241, Labcol Vario 4000, Column: Amylose SA 5μ 250×30 mm; Eluent A: Methyl tertbytyl ether+0.1 Vol-% Diethylamine (99%); Eluent B: Ethanol; Isokratic 80% A+20% B; Flow 40.0 mL/min; UV 254 nm Analytical Chiral HPLC Method:
Instrument: Agilent HPLC 1260; Column: Amylose SA 3μ 100×4.6 mm; Eluent A: Methyl tertbytyl ether+0.1 Vol-% Diethylamine (99%); Eluent B: Ethanol; Gradient: 2-60% B in 7 min; Flow 1.4 mL/min; Temperature: 25° C.; DAD 254 nm.

Example 141

4-chloro-3-ethyl-7-{3-[(6-fluoronaphthalen-1-yl)oxy]propyl}-14-(3-hydroxy-3-methylbutyl)-2-methyl-10,11,12,13,14,15-hexahydro-2H-pyrazolo[3',4':8,9][1,6]diazacycloundecino[10,11,1-hi]indole-8-carboxylic acid (Enantiomer 2)

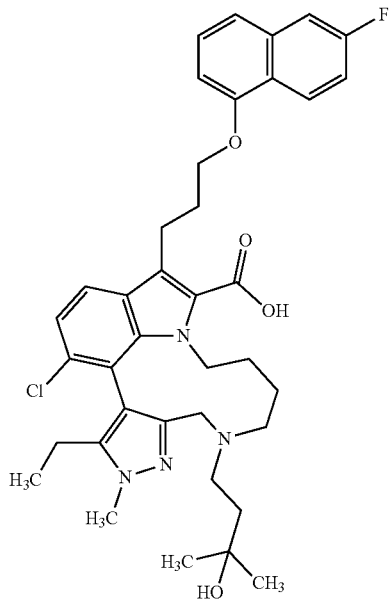 [SMILES: CCc1c2c(nn1C)CN(CCC(C)(C)O)CCCCn1c(C(=O)O)c(CCCOc3cccc4cc(F)ccc34)c3ccc(Cl)c-2c31]

For the preparation of the racemic title compound and their separation of enantiomers by preparative chiral HPLC see Example 140. Enantiomer 2: 92 mg.

Analytical Chiral HPLC (method Example 140): Rt=3.18 min.

LC-MS (Method 2): Rt=0.97 min, MS (ESIpos): m/z=675 [M+H]+

$^1$H-NMR (400 MHz, DMSO-d6) δ[ppm]: 0.798 (2.91), 0.806 (3.51), 0.814 (3.48), 0.821 (4.55), 0.825 (7.73), 0.840 (2.55), 0.844 (3.75), 0.877 (0.90), 0.886 (2.40), 0.904 (14.17), 0.923 (2.61), 0.937 (11.27), 1.035 (2.43), 1.052 (4.67), 1.070 (2.94), 1.090 (1.14), 1.108 (0.99), 1.123 (0.84), 1.142 (0.81), 1.160 (1.08), 1.231 (1.62), 1.255 (0.99), 1.270 (0.72), 1.274 (0.75), 1.288 (0.54), 1.346 (0.42), 1.365 (0.84), 1.382 (0.66), 1.399 (0.66), 1.890 (10.67), 2.152 (1.23), 2.170 (2.61), 2.187 (4.13), 2.205 (4.01), 2.223 (1.59), 2.322 (2.25), 2.327 (2.49), 2.331 (2.19), 2.337 (2.10), 2.358 (1.29), 2.373 (0.60), 2.388 (0.54), 2.394 (0.57), 2.406 (0.54), 2.412 (0.69), 2.518 (6.53), 2.523 (4.22), 2.659 (0.60), 2.664 (1.26), 2.669 (1.80), 2.673 (1.32), 2.678 (0.60), 3.067 (0.48), 3.083 (0.54), 3.100 (0.69), 3.173 (0.48), 3.192 (0.90), 3.209 (0.72), 3.224 (0.72), 3.242 (0.48), 3.428 (0.60), 3.445 (0.51), 3.639 (0.48), 3.659 (0.63), 3.677 (0.48), 3.815 (16.00), 4.138 (0.78), 4.154 (1.62), 4.167 (1.65), 4.183 (0.78), 4.543 (0.60), 4.560 (0.48), 4.576 (0.57), 6.814 (1.20), 6.818 (1.17), 6.830 (1.23), 6.835 (1.23), 6.989 (2.40), 7.010 (2.52), 7.354 (0.84), 7.361 (0.96), 7.376 (1.77), 7.383 (1.56), 7.396 (2.07), 7.413 (4.07), 7.431 (0.72), 7.444 (1.83), 7.465 (1.62), 7.624 (1.56), 7.631 (1.62), 7.650 (1.56), 7.657 (1.59), 8.264 (1.26), 8.279 (1.38), 8.287 (1.32), 8.302 (1.23).

Example 142

4-chloro-3-ethyl-7-{3-[(6-fluoronaphthalen-1-yl)oxy]propyl}-2-methyl-14-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid (Enantiomer 1)

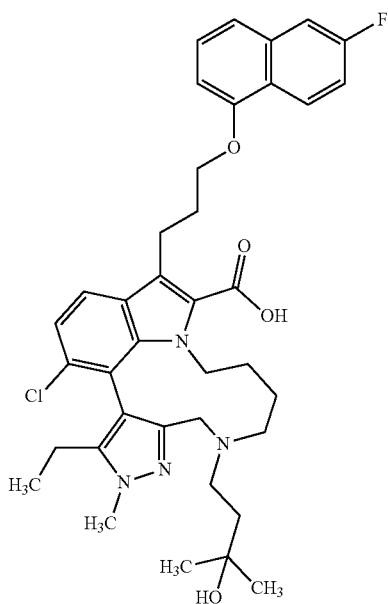 [SMILES: CCc1c2c(nn1C)CN(CCC(C)(C)O)CCCCn1c(C(=O)O)c(CCCOc3cccc4cc(F)ccc34)c3ccc(Cl)c-2c31]

(rac)-Ethyl 4-chloro-3-ethyl-7-{3-[(6-fluoronaphthalen-1-yl)oxy]propyl}-2-methyl-14-[2-(morpholin-4-yl)ethyl]-10,11,12,13,14,15-hexahydro-2H-pyrazolo[3',4':8,9][1,6]diazacycloundecino[10,11,1-hi]indole-8-carboxylate (see Intermediate 229, 86.0 mg, 118 μmol) was dissolved in 1.9 mL THF and 930 μL ethanol. Aqueous lithiumhydroxide solution (930 μL, 1.0 M, 930 μmol) was added and the reaction mixture was stirred for 21 h at 70° C. The reaction mixture was concentrated in vacuo dissolved in a small amount of dichloromethane and water and purified by column chromatography (dichloromethane/ethanol 0-100%, 10 g 25μ-silica gel) to provide the target compound as lithium salt: 82 mg.

LC-MS (Method 2): R$_t$=0.94 min; MS (ESIpos): m/z=702 [M+H]+

$^1$H-NMR (400 MHz, DMSO-d6) δ[ppm]: 0.792 (3.46), 0.797 (5.35), 0.802 (2.80), 0.811 (7.99), 0.814 (6.97), 0.821 (5.59), 0.830 (3.79), 0.840 (2.66), 0.850 (0.67), 0.886 (2.57), 0.904 (5.04), 0.922 (2.73), 1.018 (1.04), 1.035 (1.82), 1.052 (2.31), 1.070 (1.44), 1.090 (0.40), 1.108 (0.53), 1.123 (0.69), 1.142 (1.04), 1.160 (1.13), 1.179 (1.00), 1.203 (1.07), 1.229 (2.51), 1.255 (1.02), 1.269 (0.55), 1.274 (0.58), 1.288 (0.42), 1.738 (0.69), 1.754 (0.71), 1.769 (0.89), 1.785 (0.55), 1.904 (14.58), 1.946 (0.53), 1.964 (1.04), 1.998 (3.82), 2.056 (0.78), 2.126 (1.13), 2.145 (2.55), 2.164 (2.82), 2.170 (2.84), 2.190 (2.82), 2.209 (1.84), 2.230 (0.91), 2.269 (0.82), 2.286 (1.35), 2.302 (1.18), 2.318 (1.42), 2.322 (1.75), 2.326 (1.78), 2.331 (1.33), 2.336 (0.89), 2.358 (0.71), 2.373 (0.82), 2.388 (0.98), 2.394 (1.00), 2.399 (0.53), 2.406 (0.95), 2.412 (1.26), 2.518 (5.68), 2.522 (3.60), 2.659 (0.49), 2.664 (0.98), 2.669 (1.35), 2.673 (1.00), 2.678 (0.49), 3.148 (0.49), 3.172 (2.04), 3.180 (1.44), 3.204 (2.93), 3.222 (0.93), 3.237 (0.80), 3.280 (4.22), 3.291 (6.28), 3.302 (5.04), 3.410 (0.69), 3.428 (0.82), 3.445 (0.71), 3.626 (1.46), 3.657 (1.46), 3.676 (0.58), 3.693 (0.62), 3.709 (0.55), 3.799 (16.00), 4.122 (0.64), 4.129 (0.71), 4.146 (1.26), 4.161 (0.91), 4.174 (1.29), 4.191 (0.71), 4.198 (0.64), 4.346 (0.49), 4.360 (0.53), 6.807 (1.22), 6.811 (1.24), 6.824 (1.31), 6.828 (1.31), 7.034 (1.80), 7.055 (1.91), 7.351 (0.84), 7.358 (0.98), 7.375 (1.75), 7.381 (1.66), 7.396 (2.66), 7.403 (1.42), 7.414 (4.44), 7.433 (0.67), 7.506 (1.33), 7.527 (1.22), 7.627 (1.60), 7.633 (1.64), 7.653 (1.60), 7.659 (1.58), 8.271 (1.31), 8.286 (1.35), 8.294 (1.33), 8.309 (1.22).

The racemic compound (240 mg—from two different batches) was separated into enantiomers by preparative chiral HPLC followed by a column chromatography to give the target compound (enantiomer 1, 68 mg) and enantiomer 2 (49 mg, see Example 143).

Analytical Chiral HPLC: R$_t$=2.55 min.

LC-MS (Method 2): R$_t$=0.93 min; MS (ESIpos): m/z=702 [M+H]+

$^1$H-NMR (400 MHz, DMSO-d6) δ[ppm]: 0.697 (0.68), 0.745 (0.52), 0.765 (0.52), 0.788 (3.30), 0.798 (1.13), 0.807 (7.42), 0.826 (3.60), 0.840 (0.74), 0.851 (1.00), 0.859 (0.62), 0.878 (0.55), 0.904 (0.62), 0.984 (0.49), 0.999 (0.49), 1.018 (0.49), 1.035 (1.33), 1.042 (1.04), 1.052 (2.43), 1.068 (1.65), 1.070 (1.72), 1.154 (2.56), 1.232 (4.96), 1.293 (0.68), 1.323 (0.55), 1.360 (0.45), 1.681 (0.55), 1.697 (0.58), 1.713 (0.65), 1.907 (1.00), 1.928 (1.17), 1.944 (1.85), 1.957 (2.49), 2.023 (0.68), 2.085 (0.65), 2.103 (1.00), 2.121 (1.68), 2.140 (1.78), 2.163 (1.55), 2.181 (1.62), 2.200 (1.75), 2.218 (1.10), 2.251 (0.49), 2.293 (0.68), 2.318 (1.10), 2.322 (1.98), 2.326 (2.56), 2.331 (1.91), 2.336 (1.07), 2.518 (8.03), 2.523 (5.02), 2.659 (0.65), 2.664 (1.39), 2.669 (1.94), 2.673 (1.43), 2.678 (0.65), 3.145 (0.84), 3.176 (0.94), 3.224 (0.45), 3.240 (0.87), 3.268 (3.56), 3.278 (6.41), 3.290 (3.95), 3.712 (1.43), 3.743 (1.33), 3.804 (16.00), 3.850 (0.42), 4.171 (1.88), 4.180 (1.94), 4.194 (1.17), 5.758 (9.26), 6.829 (1.26), 6.833 (1.30), 6.845 (1.26), 6.849 (1.33), 7.151 (2.82), 7.172 (2.85), 7.366 (0.84), 7.373 (0.97), 7.388 (1.26), 7.396 (1.46), 7.411 (0.94), 7.421

(2.14), 7.438 (4.02), 7.455 (0.55), 7.645 (1.49), 7.652 (1.59), 7.662 (2.27), 7.671 (1.65), 7.678 (1.75), 7.683 (2.11), 8.285 (1.26), 8.300 (1.36), 8.308 (1.33), 8.323 (1.23).

Preparative Chiral HPLC Method:

Instrument: Sepiatec: Prep SFC100; Column: Chiralpak IG 5µ 250×30 mm; Eluent A: carbon dioxide; Eluent B: 2-Propanol+0.4% Diethylamine (99%); Isokratic: 25% B; Flow: 100 mL/min; Temperature: 40° C.; BPR: 150 bar; UV: 254 nm.

Analytical Chiral HPLC Method:

Instrument: Agilent: 1260, Aurora SFC-Modul; Column: Chiralpak IG 5µ 100×4.6 mm; Eluent A: carbon dioxide; Eluent B: 2-Propanol+0.2% Diethylamine (99%); Isokratic: 25% B; Flow: 4 mL/min; Temperature: 37.5° C.; BPR: 100 bar; UV: 254 nm.

Example 143

4-chloro-3-ethyl-7-{3-[(6-fluoronaphthalen-1-yl)oxy]propyl}-2-methyl-14-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid (Enantiomer 2)

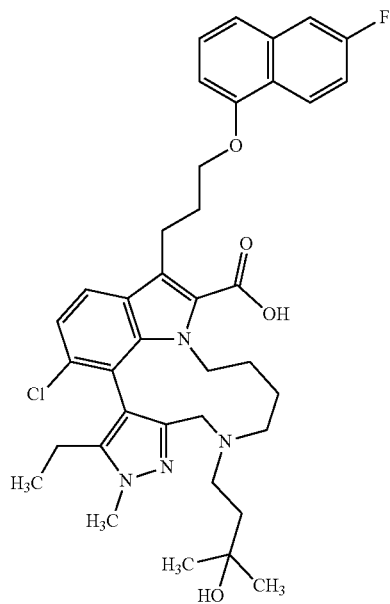 [SMILES: CCc1c2c(nn1C)CN(CCC(C)(C)O)CCCCn1c(C(=O)O)c(CCCOc3cccc4cc(F)ccc34)c3ccc(Cl)c-2c31]

For the preparation of the racemic title compound and their separation of enantiomers by preparative chiral HPLC see Example 142. Enantiomer 2: 49 mg.

Analytical Chiral HPLC (method Example 142): $R_t$=5.31 min.

LC-MS (Method 2): $R_t$=0.92 min; MS (ESIpos): m/z=702 [M+H]$^+$ $^1$H-NMR (400 MHz, DMSO-d6) δ[ppm]: 0.697 (1.27), 0.797 (2.53), 0.806 (1.01), 0.816 (5.87), 0.834 (3.14), 0.851 (1.37), 0.859 (0.71), 0.878 (0.56), 0.984 (1.37), 0.999 (1.27), 1.035 (0.46), 1.052 (0.46), 1.068 (0.71), 1.158 (1.42), 1.232 (6.73), 1.294 (0.86), 1.324 (0.61), 1.353 (0.56), 1.359 (0.61), 1.383 (0.41), 1.766 (0.51), 1.783 (0.51), 1.798 (0.61), 1.900 (1.42), 1.983 (0.76), 2.017 (2.78), 2.074 (0.61), 2.133 (0.66), 2.151 (2.18), 2.169 (2.73), 2.185 (2.13), 2.202 (1.42), 2.252 (0.76), 2.271 (0.86), 2.289 (0.96), 2.303 (0.86), 2.318 (1.37), 2.322 (2.63), 2.327 (3.14), 2.331 (2.33), 2.336 (1.22), 2.518 (16.00), 2.523 (10.08), 2.659 (0.96), 2.664 (2.13), 2.669 (2.99), 2.673 (2.18), 2.678 (1.01), 3.127 (0.41), 3.145 (0.76), 3.171 (0.81), 3.187 (1.47), 3.218 (1.32), 3.287 (2.53), 3.299 (3.95), 3.310 (3.95), 3.590 (0.86), 3.622 (1.06), 3.800 (12.71), 4.113 (0.51), 4.120 (0.51), 4.137 (0.86), 4.157 (0.56), 4.175 (0.91), 4.191 (0.51), 4.199 (0.51), 6.803 (0.91), 6.808 (0.96), 6.820 (0.96), 6.825 (1.01), 6.985 (0.96), 7.006 (1.01), 7.354 (0.66), 7.361 (0.76), 7.376 (1.32), 7.383 (1.22), 7.395 (1.57), 7.405 (1.22), 7.412 (3.19), 7.430 (0.61), 7.442 (0.76), 7.462 (0.66), 7.625 (1.16), 7.632 (1.22), 7.651 (1.16), 7.658 (1.16), 8.269 (0.96), 8.283 (1.01), 8.292 (1.01), 8.306 (0.96).

Experimental Section—Biological Assays

Examples were tested in selected biological assays one or more times. When tested more than once, data are reported as either average values, median values or as geometric mean values, wherein
- the average value, also referred to as the arithmetic mean value, represents the sum of the values obtained divided by the number of times tested,
- the median value represents the middle number of the group of values when ranked in ascending or descending order. If the number of values in the data set is odd, the median is the middle value. If the number of values in the data set is even, the median is the arithmetic mean of the two middle values, and
- the geometric mean value represents the nth root of the product of n numbers.

Examples were synthesized one or more times. When synthesized more than once, data from biological assays represent average values or median values calculated utilizing data sets obtained from testing of one or more synthetic batch.

An empty field in any of the following tables means that the respective compound has not been tested in that Assay.

The in vitro activity of the compounds of the present invention can be demonstrated in the following assays.

Assay 1

Protein-Protein Interaction Assay: MCL-1/Noxa BH3 Peptide (MCL-1 Assay)

The dose-dependent inhibition by the compounds described in this invention of the interaction between MCL-1 and the BH3 domain of Noxa (both human) was determined using a steady state binding competition assay with time-resolved fluorescence energy transfer (TR-FRET) readout. For that purpose MCL-1 (amino acids 173-321, N-terminal fused to Maltose Binding Protein (MBP) SEQ ID 1) and a synthetic Noxa BH3-derived peptide of sequence Biotin-PEG2-PEG2-PAELEVE-Nva-ATQLRRFGDKLN-FRQKLL-amide (SEQ ID 2) served as protein receptor and tracer ligand respectively. The MBP-MCL-1 was purchased from Beryllium (Bedford, Mass., USA). The expression and purification of this protein construct has been described elsewhere (DOI:10.1371/journal.pone.0125010). The Noxa BH3-derived peptide can be obtained from e.g. Biosyntan (Berlin, Germany), 50812.1.

In the assay 11 different concentrations of each compound (0.1 nM, 0.33 nM, 1.1 nM, 3.8 nM, 13 nM, 44 nM, 0.15 µM, 0.51 µM, 1.7 µM, 5.9 µM and 20 µM) were typically measured as duplicates in the same microtiter plate. For that, 100-fold concentrated DMSO solutions were prepared by serial dilutions (1:3.4) of a 2 mM stock solution in a clear, 384-well microtiter plate (Greiner Bio-One, Frickenhausen, Germany). From there, 50 nl were transferred in a dark test plate (Greiner Bio-One, Frickenhausen, Germany). The assay was initiated by addition of 2 μL of a 2.5-fold concentrated MBP-MCL-1 solution (usually for a 1 nM end concentration in 5 μL reaction volume) in aqueous assay buffer [50 mM Tris/HCl pH 7, 100 mM sodium chloride (NaCl), 50 mM potassium fluoride (KF), 0.005% Tween-20, 2 mM DTT, 0.1% bovine gamma globulin (BGG)] to the compounds in the assay plate. This was followed by a 10-minute incubation step at 22° C. for pre-equilibration of the putative complex between MBP-MCL-1 and the compounds. After that, 3 μL of a 1.67-fold concentrated solution (in assay buffer) consisting of Noxa BH3-derived peptide (1 nM end concentration) and TR-FRET detection reagents [1.67 nM anti-MBP-Eu cryptate and 1.67 nM streptavidin-XL665 (both from Cisbio Bioassays, Codolet, France)], were added.

The mixture was incubated in the dark for one hour at 22° C. and then overnight at 4° C. The formation of MCL-1/Noxa complexes was determined by measuring the resonance energy transfer of the anti-MBP-Eu-cryptate antibody to the streptavidin-XL665 present in the reaction. For that purpose, the fluorescence emission at 620 nm and 665 nm after excitation at 330-350 nm was measured in a TR-FRET measuring instrument, for instance a Rubystar or a Pherastar (both from BMG Lab Technologies, Offenburg, Germany) or a Viewlux (Perkin-Elmer). The ratio of the emission at 665 nm and at 622 nm was used as indicator of the amount of MCL-1/NOXA complexes present.

The resulting data (ratio) were normalized, taking 0% inhibition as the mean value of control measurements (usually 32 data points) where all reagents were included. In this case 50 nl DMSO were used instead of compounds. A 100% inhibition corresponded to the mean value of control measurements (usually 32 data points) where all reagents except MCL-1 were included. $IC_{50}$ values were determined by regression analysis based on a 4 parameter equation (minimum, maximum, $IC_{50}$, Hill; $Y=Max+(Min-Max)/(1+(X/IC_{50})^{Hill})$ using the Screener Software (Genedata).

```
SEQ ID 1:
GKIEEGKLVIWINGDKGYNGLAEVGKKFEKDTGIKVTVEHPDKLEEKFPQ

VAATGDGPDIIFWAHDRFGGYAQSGLLAEITPDKAFQDKLYPFTWDAVRY

NGKLIAYPIAVEALSLIYNKDLLPNPPKTWEEIPALDKELKAKGKSALMF

NLQEPYFTWPLIAADGGYAFKYENGKYDIKDVGVDNAGAKAGLTFLVDLI

KNKHMNADTDYSIAEAAFNKGETAMTINGPWAWSNIDTSKVNYGVTVLPT

FKGQPSKPFVGVLSAGINAASPNKELAKEFLENYLLTDEGLEAVNKDKPL

GAVALKSYEEELAKDPRIAATMENAQKGEIMPNIPQMSAFWYAVRTAVIN

AASGRQTVDEALKDAQTGSSELYRQSLEIISRYLREQATGAADTAPMGAS

GATSRKALETLRRVGDGVQRNHETAFQGMLRKLDIKNEDDVKSLSRVMIH

VFSDGVTNWGRIVTLISFGAFVAKHLKTINQESCIEPLAESITDVLVRTK

RDWLVKQRGWDGFVEFFHV

SEQ ID 2
Biotin-PEG2-PEG2-PAELEVE-Nva-ATQLRRFGDKLNFRQKLLamide
```

Assay 2
Protein-Protein Interaction Assay: BCL-XL/Bad BH3 Peptide (BCL-XL Assay)

The dose-dependent inhibition by the compounds described in this invention of the interaction between BCL-XL and the BH3 domain of Bad (both human) was determined using a steady state binding competition assay with time-resolved fluorescence energy transfer (TR-FRET) readout. For that purpose BCL-XL (amino acids 1-212, C-terminal fused to a hexahistidine (6×His) tag (SEQ ID 3) and a synthetic Bad BH3-derived peptide of sequence Biotin-PEG2-PEG2-NLWAAQRYGRELRR-Nle-SDEFVDSFKK-amide (SEQ ID 4) served as protein receptor and tracer ligand respectively. The recombinant BCL-XL protein (expressed in *E. coli*) was purchased from BPS Bioscience (San Diego, Calif., USA). The Bad BH3-derived peptide can be obtained from e.g. Biosyntan (Berlin, Germany).

In the assay 11 different concentrations of each compound (0.1 nM, 0.33 nM, 1.1 nM, 3.8 nM, 13 nM, 44 nM, 0.15 μM, 0.51 μM, 1.7 μM, 5.9 μM and 20 μM) were typically measured as duplicates in the same microtiter plate. For that, 100-fold concentrated DMSO solutions were prepared by serial dilutions (1:3.4) of a 2 mM stock solution in a clear, 384-well microtiter plate (Greiner Bio-One, Frickenhausen, Germany). From there, 50 nl were transferred in a dark test plate (Greiner Bio-One, Frickenhausen, Germany). The assay was initiated by addition of 2 μL of a 2.5-fold concentrated His-BCL-XL solution (usually for a 1 nM end concentration in 5 μL reaction volume) in aqueous assay buffer [50 mM Tris/HCl pH 7, 100 mM sodium chloride (NaCl), 50 mM potassium fluoride (KF), 0.005% Tween-20, 2 mM DTT, 0.1% bovine gamma globulin (BGG)] to the compounds in the assay plate. This was followed by a 10-minute incubation step at 22° C. for pre-equilibration of the putative complex between His-BCL-XL and the compounds. After that, 3 μL of a 1.67-fold concentrated solution (in assay buffer) consisting of Bad BH3-derived peptide (1 nM end concentration) and TR-FRET detection reagents [1.67 nM anti-His-Eu cryptate and 1.67 nM streptavidin-XL665 (both from Cisbio Bioassays, Codolet, France)], were added.

The mixture was incubated in the dark for one hour at 22° C. and then overnight at 4° C. The formation of BCL-XL/Bad complexes was determined by measuring the resonance energy transfer of the anti-His-Eu-cryptate antibody to the streptavidin-XL665 present in the reaction. For that purpose, the fluorescence emission at 620 nm and 665 nm after excitation at 330-350 nm was measured in a TR-FRET measuring instrument, for instance a Rubystar or a Pherastar (both from BMG Lab Technologies, Offenburg, Germany) or a Viewlux (Perkin-Elmer). The ratio of the emission at 665 nm and at 622 nm was used as indicator of the amount of BCL-XL/Bad complexes present.

The resulting data (ratio) were normalized, taking 0% inhibition as the mean value of control measurements (usually 32 data points) where all reagents were included. In this case 50 nl DMSO were used instead of compounds. A 100% inhibition corresponded to the mean value of control measurements (usually 32 data points) where all reagents except BCL-XL were included. $IC_{50}$ values were determined by regression analysis based on a 4 parameter equation (minimum, maximum, $IC_{50}$, Hill; $Y=Max+(Min-Max)/(1+(X/IC_{50})^{Hill})$ using the Screener Software (Genedata).

```
                                                SEQ ID 3
MSQSNRELVV DFLSYKLSQK GYSWSQFSDV EENRTEAPEG

TESEMETPSA INGNPSWHLA DSPAVNGATG HSSSLDAREV

IPMAAVKQAL REAGDEFELR YRRAFSDLTS QLHITPGTAY
```

-continued
QSFEQVVNEL FRDGVNWGRI VAFFSFGGAL CVESVDKEMQ

VLVSRIAAWM ATYLNDHLEP WIQENGGWDT FVELYGNNAA

AESRKGQERF NR

SEQ ID 4
Biotin-PEG2-PEG2-NLWAAQRYGRELRR-Nle-SDEFVDSFKKamide

Assay 3

Protein-Protein Interaction Assay: BCL-2/Bad BH3 Peptide (BCL-2 Assay)

The dose-dependent inhibition by the compounds described in this invention of the interaction between BCL-2 and the BH3 domain of Bad (both human) was determined using a steady state binding competition assay with time-resolved fluorescence energy transfer (TR-FRET) readout. For that purpose BCL-2 (amino acids 1-211, C-terminal fused to a hexahistidine (6×His) tag (SEQ ID 5) and a synthetic Bad BH3-derived peptide of sequence Biotin-PEG2-PEG2-NLWAAQRYGRELRR-Nle-SDEFVDSFKK-amide (SEQ ID 4) served as protein receptor and tracer ligand respectively. The recombinant BCL-2 protein (expressed in *E. coli*) was purchased from BPS Bioscience (San Diego, Calif., USA). The Bad BH3-derived peptide can be obtained from e.g. Biosyntan (Berlin, Germany).

In the assay 11 different concentrations of each compound (0.1 nM, 0.33 nM, 1.1 nM, 3.8 nM, 13 nM, 44 nM, 0.15 µM, 0.51 µM, 1.7 µM, 5.9 µM and 20 µM) were typically measured as duplicates in the same microtiter plate. For that, 100-fold concentrated DMSO solutions were prepared by serial dilutions (1:3.4) of a 2 mM stock solution in a clear, 384-well microtiter plate (Greiner Bio-One, Frickenhausen, Germany). From there, 50 nl were transferred in a dark test plate (Greiner Bio-One, Frickenhausen, Germany). The assay was initiated by addition of 2 µL of a 2.5-fold concentrated His-BCL-2 solution (usually for a 1 nM end concentration in 5 µL reaction volume) in aqueous assay buffer [50 mM Tris/HCl pH 7, 100 mM sodium chloride (NaCl), 50 mM potassium fluoride (KF), 0.005% Tween-20, 2 mM DTT, 0.1% bovine gamma globulin (BGG)] to the compounds in the assay plate. This was followed by a 10-minute incubation step at 22° C. for pre-equilibration of the putative complex between His-BCL-2 and the compounds. After that, 3 µL of a 1.67-fold concentrated solution (in assay buffer) consisting of Bad BH3-derived peptide (1 nM end concentration) and TR-FRET detection reagents [1.67 nM anti-His-Eu cryptate and 1.67 nM streptavidin-XL665 (both from Cisbio Bioassays, Codolet, France)], were added.

The mixture was incubated in the dark for one hour at 22° C. and then overnight at 4° C. The formation of BCL-2/Bad complexes was determined by measuring the resonance energy transfer of the anti-His-Eu-cryptate antibody to the streptavidin-XL665 present in the reaction. For that purpose, the fluorescence emission at 620 nm and 665 nm after excitation at 330-350 nm was measured in a TR-FRET measuring instrument, for instance a Rubystar or a Pherastar (both from BMG Lab Technologies, Offenburg, Germany) or a Viewlux (Perkin-Elmer). The ratio of the emission at 665 nm and at 622 nm was used as indicator of the amount of BCL-2/Bad complexes present.

The resulting data (ratio) were normalized, taking 0% inhibition as the mean value of control measurements (usually 32 data points) where all reagents were included. In this case 50 nl DMSO were used instead of compounds. A 100% inhibition corresponded to the mean value of control measurements (usually 32 data points) where all reagents except BCL-2 were included. $IC_{50}$ values were determined by regression analysis based on a 4 parameter equation (minimum, maximum, $IC_{50}$, Hill; $Y = Max + (Min - Max)/(1 + (X/IC_{50})^{Hill})$ using the Screener Software (Genedata).

SEQ ID 5:
MAHAGRTGYD NREIVMKYIH YKLSQRGYEW DAGDVGAAPP

GAAPAPGIFS SQPGHTPHPA ASRDPVARTS PLQTPAAPGA

AAGPALSPVP PVVHLTLRQA GDDFSRRYRR DFAEMSSQLH

LTPFTARGRF ATVVEELFRD GVNWGRIVAF FEFGGVMCVE

SVNREMSPLV DNIALWMTEY LNRHLHTWIQ DNGGWDAFVE

LYGPSMRPLF D

TABLE 2

$IC_{50}$ values of selected examples in biochemical MCL-1 assay (Assay 1) and

| Example | MCL-1 Assay [M] (median) | BCL-2 Assay [M] (median) | BCL-XL Assay [M] (median) |
|---|---|---|---|
| 1 | 6.1E-9 | >2.0E-5 | >2.0E-5 |
| 2 | 1.6E-9 | >2.0E-5 | >2.0E-5 |
| 3 | 1.1E-9 | >2.0E-5 | >2.0E-5 |
| 4 | 3.8E-8 | 1.6E-5 | >2.0E-5 |
| 5 | 1.2E-9 | >2.0E-5 | >2.0E-5 |
| 6 |  | >2.0E-5 | >2.0E-5 |
| 7 | 1.7E-8 | >2.0E-5 | >2.0E-5 |
| 8 |  | >2.0E-5 | >2.0E-5 |
| 9 |  | >2.0E-5 | >2.0E-5 |
| 10 | 1.2E-8 | >2.0E-5 | 1.9E-5 |
| 11 | 1.1E-9 | >2.0E-5 | >2.0E-5 |
| 12 |  | >2.0E-5 | >2.0E-5 |
| 13 | 2.6E-8 | >2.0E-5 | >2.0E-5 |
| 14 | 1.0E-9 | >2.0E-5 | >2.0E-5 |
| 15 |  | >2.0E-5 | >2.0E-5 |
| 16 | 5.2E-9 | >2.0E-5 | >2.0E-5 |
| 17 |  | >2.0E-5 | >2.0E-5 |
| 18 | 1.3E-9 | >2.0E-5 | >2.0E-5 |
|  |  | 1.9E-5 |  |
|  |  | 2.0E-5 |  |
| 19 |  | >2.0E-5 | >2.0E-5 |
| 20 |  | >2.0E-5 | >2.0E-5 |
| 21 | 8.9E-9 | 1.5E-5 | 1.4E-5 |
| 22 | 1.5E-9 | >2.0E-5 | >2.0E-5 |
| 23 |  | >2.0E-5 | >2.0E-5 |
| 24 | 1.5E-8 | >2.0E-5 | >2.0E-5 |
| 25 | 1.2E-9 | >2.0E-5 | >2.0E-5 |
| 26 |  | >2.0E-5 | >2.0E-5 |
| 27 | 1.8E-8 | >2.0E-5 | >2.0E-5 |
| 28 | 1.3E-9 | >2.0E-5 | >2.0E-5 |
| 29 | 1.5E-9 | >2.0E-5 | >2.0E-5 |
| 30 |  | >2.0E-5 | >2.0E-5 |
| 31 |  | >2.0E-5 | >2.0E-5 |
| 32 | 2.6E-8 | >2.0E-5 | >2.0E-5 |
| 33 | 1.7E-9 | 1.8E-5 | >2.0E-5 |
| 34 |  | >2.0E-5 | >2.0E-5 |
| 35 | 2.2E-8 | 1.2E-5 | 1.6E-5 |
| 36 |  | 1.7E-5 | >2.0E-5 |
| 37 |  | >2.0E-5 | >2.0E-5 |
| 38 | 1.6E-8 | 2.0E-5 | >2.0E-5 |
| 39 |  | 2.0E-5 | >2.0E-5 |
| 40 |  | >2.0E-5 | >2.0E-5 |
| 41 | 1.3E-9 | >2.0E-5 | >2.0E-5 |
| 42 | 1.2E-8 | >2.0E-5 | >2.0E-5 |
| 43 | 4.0E-9 | >2.0E-5 | >2.0E-5 |
| 44 | 1.4E-8 | >2.0E-5 | >2.0E-5 |
| 45 | 4.1E-8 | >2.0E-5 | >2.0E-5 |
| 46 | 1.3E-9 | >2.0E-5 | >2.0E-5 |
| 47 | 4.4E-8 | >2.0E-5 | 1.9E-5 |
| 48 |  | >2.0E-5 | >2.0E-5 |

TABLE 2-continued

IC$_{50}$ values of selected examples in biochemical MCL-1 assay (Assay 1) and

| Example | MCL-1 Assay [M] (median) | BCL-2 Assay [M] (median) | BCL-XL Assay [M] (median) |
|---|---|---|---|
| 49 | 1.7E−9 | >2.0E−5 | >2.0E−5 |
| 50 |  | >2.0E−5 | >2.0E−5 |
| 51 | 1.5E−8 | >2.0E−5 | >2.0E−5 |
| 52 | 3.3E−9 | >2.0E−5 | >2.0E−5 |
| 53 |  |  |  |
| 54 | 2.1E−8 | >2.0E−5 | >2.0E−5 |
| 55 | 1.3E−9 | >2.0E−5 | >2.0E−5 |
| 56 |  |  |  |
| 57 | 7.2E−9 | 2.0E−5 | >2.0E−5 |
| 58 | 2.3E−9 | 1.9E−5 | >2.0E−5 |
| 59 |  | 1.4E−5 | >2.0E−5 |
| 60 | 2.3E−8 | 1.6E−5 | >2.0E−5 |
| 61 | 1.5E−9 | >2.0E−5 | >2.0E−5 |
| 62 | 1.5E−9 | 1.9E−5 | >2.0E−5 |
| 63 | 5.0E−8 | >2.0E−5 | >2.0E−5 |
| 64 | 2.4E−9 | >2.0E−5 | >2.0E−5 |
| 65 | 2.7E−9 | 1.9E−5 | >2.0E−5 |
| 66 |  |  |  |
| 67 | 2.2E−8 | >2.0E−5 | 1.9E−5 |
| 68 | 1.5E−9 | >2.0E−5 | >2.0E−5 |
| 069 | 4.9E−9 | >2.0E−5 | >2.0E−5 |
| 070 |  | >2.0E−5 | >2.0E−5 |
| 071 | 2.5E−8 | >2.0E−5 | >2.0E−5 |
| 072 | 1.8E−9 | >2.0E−5 | >2.0E−5 |
| 073 | 1.1E−7 | >2.0E−5 | >2.0E−5 |
| 074 |  | >2.0E−5 | >2.0E−5 |
| 075 | 1.7E−9 | >2.0E−5 | >2.0E−5 |
| 076 |  | >2.0E−5 | >2.0E−5 |
| 077 | 1.3E−8 | >2.0E−5 | >2.0E−5 |
| 078 | 1.3E−9 | 1.1E−5 | >2.0E−5 |
| 079 | 1.6E−9 | 1.0E−5 | 1.9E−5 |
| 080 | 1.1E−9 | 1.3E−5 | >2.0E−5 |
| 081 | 6.4E−8 | 1.5E−5 | >2.0E−5 |
| 082 | 1.6E−9 | 1.8E−5 | 2.0E−5 |
| 083 |  | 1.7E−5 | >2.0E−5 |
| 084 | 5.2E−8 |  | 1.4E−5 |
| 085 | 1.1E−9 | >2.0E−5 | >2.0E−5 |
| 086 | 1.0E−9 | 1.3E−5 | >2.0E−5 |
| 087 |  | 1.2E−5 | >2.0E−5 |
| 088 | 1.3E−8 | 9.0E−6 | 1.6E−5 |
| 089 | 1.0E−8 | 1.8E−5 | >2.0E−5 |
| 090 | 3.5E−9 | >2.0E−5 | >2.0E−5 |
| 091 | 2.4E−8 | >2.0E−5 | >2.0E−5 |
| 092 | 1.1E−9 | 1.4E−5 | >2.0E−5 |
| 093 |  | 1.3E−5 | 1.8E−5 |
| 094 | 1.1E−8 | 1.3E−5 | >2.0E−5 |
| 095 | 1.2E−9 | 1.5E−5 | >2.0E−5 |
| 096 | 1.3E−9 |  | 1.2E−5 |
| 097 |  | 1.2E−5 | >2.0E−5 |
| 098 | 2.0E−8 | 1.0E−5 | >2.0E−5 |
| 99 |  | >2.0E−5 | >2.0E−5 |
| 100 |  |  |  |
| 101 | 6.9E−9 | >2.0E−5 | >2.0E−5 |
| 102 | 1.1E−8 | >2.0E−5 | >2.0E−5 |
| 103 |  | 1.4E−5 | 1.8E−5 |
| 104 | 1.4E−9 | >2.0E−5 | >2.0E−5 |
| 105 |  | 1.6E−5 | >2.0E−5 |
| 106 | 5.6E−9 | 1.5E−5 | >2.0E−5 |
| 107 |  | 2.0E−5 | >2.0E−5 |
| 108 | 7.6E−9 | 2.0E−5 | >2.0E−5 |
| 109 | 1.2E−9 | >2.0E−5 | >2.0E−5 |
| 110 |  | 1.6E−5 | >2.0E−5 |
| 111 | 1.9E−8 | 1.6E−5 | 1.8E−5 |
| 112 | 1.2E−9 | >2.0E−5 | >2.0E−5 |
| 113 |  | >2.0E−5 | >2.0E−5 |
| 114 | 7.4E−9 | >2.0E−5 | >2.0E−5 |
| 115 |  | >2.0E−5 | >2.0E−5 |
| 116 | 1.1E−9 | >2.0E−5 | >2.0E−5 |
| 117 | 6.7E−9 | >2.0E−5 | >2.0E−5 |
| 118 | 2.3E−9 | >2.0E−5 | >2.0E−5 |
| 119 |  |  |  |
| 120 | 3.9E−8 | >2.0E−5 | >2.0E−5 |
| 121 | 3.1E−9 | >2.0E−5 | >2.0E−5 |
| 122 | 2.1E−9 | >2.0E−5 | >2.0E−5 |
| 123 | 5.6E−9 | >2.0E−5 | 1.9E−5 |
| 124 | 1.2E−9 | >2.0E−5 | >2.0E−5 |
| 125 | 1.4E−9 | >2.0E−5 | >2.0E−5 |
| 126 | 1.2E−9 | 1.0E−5 | >2.0E−5 |
| 127 | 1.0E−9 |  |  |
| 128 | 1.5E−8 |  |  |
| 129 | 3.1E−9 | >2.0E−5 | >2.0E−5 |
| 130 | 2.4E−9 | >2.0E−5 | >2.0E−5 |
| 131 | 1.1E−9 | >2.0E−5 | >2.0E−5 |
| 132 | 2.3E−8 |  |  |
| 133 |  |  |  |
| 134 | 1.6E−9 | >2.0E−5 | >2.0E−5 |
| 135 | 1.7E−9 | >2.0E−5 | >2.0E−5 |
| 136 |  |  |  |
| 137 | 5.2E−8 |  |  |
| 138 | 3.6E−9 | >2.0E−5 | >2.0E−5 |
| 139 | 2.0E−9 | >2.0E−5 | >2.0E−5 |
| 140 |  |  |  |
| 141 | 1.5E−8 |  |  |
| 142 |  |  |  |
| 143 | 6.2E−8 |  |  |

Biochemical BCL-2 (Assay 3) and, BCL-XL Assay (Assay 2)

One aspect of the invention are compounds of formula (I) having an IC$_{50}$ in the MCL-1 Assay which is 1 E-9 or less.

Cellular Assays

Assay 4

Induction of Caspase-3/7 Activity Upon Treatment of Cells with Selected Compounds The BH3-domain of MCL-1 sequesters pro-apoptotic proteins, thereby inhibiting apoptosis. In contrast, MCL-1 inhibitors are expected to antagonize this effect leading to an increase in apoptosis, which can be determined by measuring the activity of caspase-3/7.

The activity of caspase-3/7 was determined in DLBCL (Diffuse large B-cell lymphoma) cell lines (SUDHL5 and SUDHL10) upon treatment with different compounds, using the Caspase-Glo® 3/7 reagent from Promega (G8092).

The different cell lines were plated in culture medium (RPMI 1640 [GIBCO #22400-089] supplemented with 10% Fetal Bovine Serum) at a density of 3,300 cells in 30 µL/well in a sterile, solid black, flat bottom, polystyrene, TC-treated 384-well microplate (Corning #3571) using Multidrop Combi Reagent Dispenser. As a control, medium without cells was also added to the plate. Cells were incubated in a humidified incubator at 37° C. overnight.

On the next day, the cells were treated with compounds (stock solution, 10 mM in DMSO) using the HP D300 Digital Dispenser in a concentration range of 3.3×10e-5 M (33 µM) to 5×10e-9 M (5 nM) in a single-dot curve with at least 16 dilutions and a DMSO concentration of 0.33%. Rim wells were excluded. The cells were incubated for 3 h hours in a humidified incubator at 37° C. After this incubation, 30 µL of Caspase-Glo® 3/7 reagent (Promega G8092) was added to each well using the Multidrop Combi Reagent Dispenser, followed by 1 h incubation at 37° C. Finally, luminescence was read at 0.1 ms, with a gain of 3000 using the PHERAstar FS microplate reader (BMG Labtech).

For the evaluation of the results, the background measured with "medium-only" was subtracted from all other values. Then, the values were normalized to DMSO-only treated cells (every value was divided by the mean of the DMSO control). The Bella DRC Master Sheet was used to calculate EC$_{50}$s, with fixed C0=1 and CI=plateau/max induction for the reference compound.

TABLE 3

EC$_{50}$ values of selected examples in cellular caspase induction assay 4

| Example | Caspase SUDHL5 [M] (median) | Caspase SUDHL10 [M] (median) |
|---|---|---|
| 1 | 2.9E−6 | 5.5E−6 |
| 2 | 9.5E−7 | 3.8E−6 |
| 3 | 7.1E−7 | 1.6E−6 |
| 4 | | |
| 5 | 2.7E−7 | 6.1E−7 |
| 6 | | 2.2E−7 |
| 7 | 8.0E−6 | |
| 8 | 2.9E−7 | 3.6E−7 |
| 9 | 2.7E−7 | 3.3E−7 |
| 10 | 6.6E−6 | |
| 11 | 1.4E−7 | 2.6E−7 |
| 12 | | |
| 13 | | |
| 14 | 2.5E−7 | 4.1E−7 |
| 15 | 1.2E−7 | 1.5E−7 |
| 16 | 3.6E−6 | 5.2E−6 |
| 17 | 2.90E−07 | 3.8E−7 |
| 18 | 1.1E−6 | 1.3E−6 |
| 19 | 3.4E−7 | 3.2E−7 |
| 20 | 1.4E−7 | 3.9E−7 |
| 21 | 4.6E−6 | |
| 22 | 1.4E−7 | 2.7E−7 |
| 23 | | 1.8E−7 |
| 24 | 4.5E−6 | |
| 25 | 3.9E−7 | 1.2E−6 |
| 26 | 2.5E−7 | 4.1E−7 |
| 27 | | |
| 28 | 2.9E−6 | 5.8E−6 |
| 29 | 1.2E−6 | 3.7E−6 |
| 30 | 1.8E−7 | 3.7E−7 |
| 31 | | |
| 32 | | |
| 33 | 6.7E−7 | 5.7E−6 |
| 34 | 3.8E−7 | 9.3E−7 |
| 35 | 7.6E−6 | |
| 36 | 3.0E−7 | 4.5E−7 |
| 37 | | 3.3E−7 |
| 38 | 5.4E−6 | |
| 39 | | 1.5E−7 |
| 40 | 2.0E−7 | 3.9E−7 |
| 41 | | 3.1E−7 |
| 42 | 2.8E−6 | 9.4E−6 |
| 43 | 5.4E−7 | 1.3E−6 |
| 44 | 6.2E−7 | 1.6E−6 |
| 45 | 9.4E−6 | |
| 46 | 2.9E−7 | 4.6E−7 |
| 47 | | |
| 48 | 1.6E−7 | 4.0E−7 |
| 49 | 5.9E−7 | 5.9E−7 |
| 50 | 3.6E−7 | 4.5E−7 |
| 51 | | |
| 52 | 8.0E−7 | 1.9E−6 |
| 53 | 6.60E−07 | 7.0E−7 |
| 54 | 3.5E−6 | |
| 55 | 6.0E−7 | 5.2E−7 |
| 56 | 1.3E−7 | 3.1E−7 |
| 57 | 3.2E−6 | 8.0E−6 |
| 58 | 5.1E−7 | 1.5E−6 |
| 59 | 3.5E−7 | 1.0E−6 |
| 60 | 7.6E−6 | |
| 61 | 3.3E−7 | 4.4E−7 |
| 62 | | 3.8E−7 |
| 63 | 9.0E−6 | |
| 64 | 3.3E−7 | |
| 65 | 2.7E−7 | |
| 66 | | |
| 67 | | |
| 68 | 1.4E−6 | 3.1E−6 |
| 069 | 1.8E−6 | 8.3E−6 |
| 070 | 7.1E−7 | 1.3E−6 |
| 071 | | |
| 072 | 7.30E−07 | 2.8E−6 |
| 073 | | |
| 074 | 1.4E−7 | 5.7E−7 |
| 075 | 5.5E−7 | 3.5E−6 |
| 076 | 2.4E−7 | 2.6E−7 |
| 077 | | |
| 078 | 6.70E−07 | 3.8E−6 |
| 079 | 5.8E−7 | 1.4E−6 |
| 080[#] | 4.9E−7 | 4.5E−7 |
| 081 | 7.4E−6 | 6.2E−6 |
| 082 | 4.9E−7 | 1.1E−6 |
| 083 | 2.2E−7 | 4.1E−7 |
| 084 | | |
| 085 | 1.8E−7 | 3.2E−7 |
| 086 | 4.7E−7 | 6.2E−7 |
| 087 | 1.7E−7 | 2.1E−7 |
| 088 | 7.4E−6 | 4.3E−6 |
| 089 | | |
| 090 | 8.5E−6 | |
| 091 | | |
| 092 | 2.8E−7 | 5.9E−7 |
| 093 | | 2.2E−7 |
| 094 | 1.6E−6 | 3.1E−6 |
| 095 | 5.5E−7 | 8.7E−7 |
| 096 | 4.8E−7 | 2.1E−7 |
| 097 | 3.2E−7 | 4.5E−7 |
| 098 | 6.2E−6 | 5.0E−6 |
| 99 | 1.9E−7 | 1.8E−7 |
| 100 | 2.20E−07 | 1.2E−7 |
| 101 | 5.9E−6 | 6.1E−6 |
| 102 | | 7.8E−6 |
| 103 | | 5.0E−7 |
| 104 | 8.1E−7 | 1.5E−6 |
| 105 | 1.3E−7 | 1.2E−7 |
| 106 | 2.4E−6 | 4.6E−6 |
| 107 | 3.9E−7 | 4.7E−7 |
| 108 | 6.3E−6 | 7.8E−6 |
| 109 | 4.4E−7 | 2.9E−7 |
| 110 | 1.2E−7 | 1.6E−7 |
| 111 | 5.0E−6 | 4.9E−6 |
| 112 | 6.0E−7 | 8.6E−7 |
| 113 | 2.7E−7 | 3.6E−7 |
| 114 | 4.3E−6 | 6.3E−6 |
| 115 | 1.6E−7 | 1.4E−6 |
| 116 | 2.9E−7 | 2.9E−7 |
| 117 | 2.4E−6 | 2.6E−6 |
| 118 | 3.3E−7 | 5.1E−7 |
| 119 | 1.1E−7 | 2.1E−7 |
| 120 | 1.0E−5 | |
| 121 | 1.2E−6 | 1.7E−6 |
| 122 | 9.2E−7 | 7.5E−7 |
| 123 | 4.7E−7 | 1.1E−6 |
| 124 | 9.5E−7 | 1.8E−6 |
| 125 | 1.4E−6 | 4.6E−6 |
| 126 | 4.2E−7 | 7.2E−7 |
| 127 | 2.8E−7 | 4.8E−7 |
| 128 | 2.1E−6 | 3.4E−6 |
| 129 | 3.0E−7 | 7.4E−7 |
| 130 | 7.3E−6 | |
| 131 | | 1.3E−7 |
| 132 | 9.3E−6 | |
| 133 | | |
| 134 | 1.3E−7 | 2.4E−7 |
| 135 | | 1.4E−7 |
| 136 | | |
| 137 | | |
| 138 | 2.8E−7 | 3.8E−7 |
| 139 | | |
| 140 | | |
| 141 | 3.0E−6 | 3.6E−6 |
| 142 | | |
| 143 | | |

[#]single value

A further aspect of the invention are compounds which show an EC$_{50}$ < 3 × E−7 in the Caspase SUDHL5 assay.

Assay 5
PIxEL: Protein-Protein Interaction in Permeabilized Cells by ELISA

Most MCL1 protein molecules are localized at the mitochondria outer membrane and sequester pro-apoptotic proteins through binding of their BCL2 homology domain 3 (BH3 domain). MEB buffer (150 mM mannitol, 10 mM HEPES pH 7.5, 50 mM KCl, 20 µM EDTA, 20 µM EGTA, 5 mM potassium succinate, 0.1% protease-free BSA (SIGMA) with low dose digitonin (0.002%) permeabilizes plasma membrane while leaves live mitochondria, where MCL1 maintains its native localization and conformation. Unlike biophysical assays (e.g. TR-FRET) that use truncated recombinant MCL1 protein, this assay uses full length endogenous MCL1 protein at mitochondria outer membrane. It measures the interaction between MCL1 protein and biotinylated BIM BH3 peptide. Compounds can compete with BIM BH3 peptide to bind to MCL1 protein. This serum free assay measures the affinity between MCL1 protein and compound in permeabilized cells, therefore it is not affected by serum binding and cell permeability, and can measure the intrinsic compound affinity.

On day 1, RKO colon cancer cell line cells were plated at 0.8 million cells/ml, 100 µl/well in 96-well flat bottom TC plates (Corning). MCL1 antibody (Santa Cruz sc-12756) were diluted at 200 fold (final concentration 1 µg/ml) in carbonate buffer (Thermo Fisher Scientific, pH 9.6), and 50 µl of diluted antibody was added to each well of high bind ELISA plates (SARSTEDT). Each plate was tapped to make sure liquid covering entire bottom of wells and incubate at 37° C. overnight.

On the second day, MCL1 antibody was washed from ELISA plate. 250 µl Odyssey® Blocking Buffer (PBS) (Li-Cor) was added to each well, incubated at room temperature for at least 1 hour, then washed once with 250 µl 1×PBST. Plates with RKO cells were gently washed once with 100 µl/well PBS, once with 100 µl/well MEB buffer without digitonin, then 100 µl of MEB buffer with 0.002% digitonin was gently added to each well. Compounds were added with HP Tecan compound dispenser in 3-fold dilution series, highest dose 30 µM, 10-dose per compound in quadruplicates. Biotin-BIM peptide (synthesized by 21st Century) was added with HP Tecan compound dispenser at 0.2 µM immediately after the addition of compounds. Plates were rocked for 1 hour at room temperature. Then MEB buffer was aspirated and 50 µl of CHAPS buffer (50 mM Tris-Cl, pH 7.4, 150 mM NaCl, 1% CHAPS, 1 mM EDTA, 1 mM EGTA, cOmplete protease inhibitors (Roche), PhosSTOP (Roche)) was added to each well. Plates were rocked for 1 hour at 4° C., then 45 µl cell lysate from each well were transferred to ELISA plates coated with MCL1 antibody. Plates were incubated overnight in the cold room with rocking.

On the third day, ELISA plates were washed once with 250 µl 1×PBST. Streptavidin-poly-HRP (Thermo Fisher Scientific) was diluted to 20 ng/ml in Odyssey blocking buffer plus 0.05% Triton-100, and 100 µl was added to each well of the ELISA plate. Plates were incubated at RT from 1 hour with rocking, then washed with 100 µL 1×PBST for 3 times. Each SuperSignal ELISA Femto Maximum Sensitivity substrate was added to a 50-ml tube and mixed, then 100 µl of mixed substrate was added to each well. Plates were shaken for 1 minute then luminescence was measured by Envision plate reader (HP). Signal of each well were normalized by no-compound control and no-cell control. $IC_{50}$ was calculated using Graphic Pad PRISM software.

Table 4 shows the results of the protein-protein interaction in permeabilized cells by ELISA assay (Assay 5).

TABLE 4

$IC_{50}$ values of selected examples in protein-protein interaction in permeabilized cells by ELISA assay (Assay 5)

| Example | PIxEL [M] (median) |
|---|---|
| 1 | |
| 2 | |
| 3 | 2.86E−06 |
| 4 | |
| 5 | |
| 6 | 1.28E−07 |
| 7 | |
| 8 | |
| 9 | 2.79E−07 |
| 10 | |
| 11 | |
| 12 | 1.53E−07 |
| 13 | |
| 14 | |
| 15 | 3.32E−07 |
| 16 | 1.24E−07 |
| 17 | |
| 18 | |
| 19 | |
| 20 | 3.96E−07 |
| 21 | |
| 22 | |
| 23 | 2.20E−07 |
| 24 | |
| 25 | |
| 26 | |
| 27 | |
| 28 | 2.39E−06 |
| 29 | 1.71E−06 |
| 30 | 2.27E−07 |
| 31 | |
| 32 | 1.91E−05 |
| 33 | |
| 34 | 8.52E−07 |
| 35 | |
| 36 | |
| 37 | 1.72E−07 |
| 38 | |
| 39 | |
| 40 | 5.76E−08 |
| 41 | |
| 42 | |
| 43 | 6.84E−07 |
| 44 | |
| 45 | |
| 46 | 1.41E−07 |
| 47 | |
| 48 | |
| 49 | 4.36E−07 |
| 50 | |
| 51 | |
| 52 | 2.39E−07 |
| 53 | |
| 54 | |
| 55 | |
| 56 | 5.79E−07 |
| 57 | |
| 58 | |
| 59 | |
| 60 | |
| 61 | |
| 62 | |
| 63 | 2.15E−06 |
| 64 | 2.76E−06 |
| 65 | 7.52E−07 |
| 66 | 1.74E−06 |
| 67 | 1.54E−05 |
| 68 | |
| 69 | 1.94E−07 |
| 70 | 7.36E−08 |

TABLE 4-continued

IC$_{50}$ values of selected examples in protein-protein interaction in permeabilized cells by ELISA assay (Assay 5)

| Example | PIxEL [M] (median) |
|---|---|
| 71 | |
| 72 | |
| 73 | 3.67E−07 |
| 74 | |
| 75 | 1.54E−08 |
| 76 | |
| 77 | |
| 78 | 1.01E−06 |
| 79 | |
| 80 | 9.39E−07 |
| 81 | |
| 82 | 2.25E−07 |
| 83 | |
| 84 | |
| 85 | 1.13E−07 |
| 86 | |
| 87 | |
| 88 | |
| 89 | |
| 90 | |
| 91 | 2.41E−07 |
| 92 | |
| 93 | |
| 94 | 3.90E−07 |
| 95 | |
| 96 | |
| 97 | 5.57E−08 |
| 98 | 8.62E−07 |
| 99 | 1.39E−07 |
| 100 | 2.86E−07 |
| 101 | |
| 102 | |
| 103 | |
| 104 | 1.53E−07 |
| 105 | 2.29E−06 |
| 106 | |
| 107 | 1.52E−07 |
| 108 | |
| 109 | |
| 110 | 1.18E−07 |
| 111 | |
| 112 | |
| 113 | 2.03E−07 |
| 114 | |
| 115 | |
| 116 | 3.79E−07 |
| 117 | |
| 118 | 1.57E−07 |
| 119 | 5.42E−07 |
| 120 | |
| 121 | 1.27E−06 |
| 122 | 1.16E−06 |
| 123 | 8.99E−08 |
| 124 | 5.15E−07 |
| 125 | 1.57E−08 |
| 126 | |
| 127 | 2.36E−07 |
| 128 | |
| 129 | |
| 130 | |
| 131 | |
| 132 | 5.61E−08 |
| 133 | |
| 134 | |
| 135 | |
| 136 | |
| 137 | |
| 138 | |
| 139 | |
| 140 | |
| 141 | |
| 142 | |
| 143 | |

Assay 6

Induction of Cytotoxicity Upon Treatment of Cells with Selected Compounds

In principle, compounds that induce apoptosis will concomitantly induce cell cytotoxicity. Therefore, cytotoxicity assays were run in parallel in SUDHL5 and SUDHL10 cells.

The different cell lines were plated in culture medium (RPMI 1640 [GIBCO #22400-089] supplemented with 10% Fetal Bovine Serum) at a density of 3,300 cells in 30 μL/well in a sterile, solid black, flat bottom, polystyrene, TC-treated 384-well microplate (Corning #3571) using Multidrop Combi Reagent Dispenser. As a control, medium without cells was also added to the plate. Cells were incubated in a humidified incubator at 37° C. overnight. On the next day, the cells were treated with compounds (stock solution, 10 mM in DMSO) using the HP D300 Digital Dispenser in a concentration range of 3.3×10e-5 M (33 μM) to 5×10e-9 M (5 nM) in a single-dot curve with at least 16 dilutions and a DMSO concentration of 0.33%. Rim wells were excluded. The cells were incubated for 5 h hours in a humidified incubator at 37° C. After this incubation, 30 μL of CellTiter-Glo® Luminescent Cell Viability reagent (Promega, G7573) was added to each well using the Multidrop Combi Reagent Dispenser, followed by 15 min incubation on a shaker at room temperature. Finally, luminescence was read at 0.1 ms, with a gain of 3000 using the PHERAstar FS microplate reader (BMG Labtech).

For the evaluation of the results, each value was normalized to DMSO-only treated cells (every value was divided by the mean of the DMSO control). The Bella DRC Master Sheet was used to calculate IC$_{50}$s, with fixed C1=0 and C0=1.

Assay 7

Assessment of the Anti-Proliferative Effect of Compounds in Different Cell Lines The impact of compounds on the proliferation of different cell lines was assessed using the CellTiter-Glo® Luminescent Cell Viability reagent from Promega (G7573). The cell lines used for the proliferation assays are examples of tumor indications and listed in the table below.

TABLE 5 cell lines, sources and indications

| Cell line | Source | Indication |
|---|---|---|
| SUDHL5 | DSMZ | B-cell lymphoma (GC-DLBCL) |
| SUDHL10 | DSMZ | B-cell lymphoma (GC-DLBCL) |
| MV-4-11 | ATCC | Acute monocytic leukemia |
| HMC-1-8 | JCRB | Triple-negative Breast Cancer |
| T47D | ATCC | ER+-positive Breast Cancer |
| SK-BR-3 | ATCC | Her2-positive Breast Cancer |
| AMO-1 | DSMZ | Multiple Myeloma |
| A2058 | ATCC | Melanoma |
| NCI-H23 | ATCC | Non-Small Cell Lung Cancer |
| KYSE-180 | DSMZ | Esophageal cancer |
| SNU-389 | ATCC | Liver Cancer |
| DMS-114 | ATCC | Small Cell Lung Cancer |

The different cell lines were plated in culture medium (RPMI 1640 [Biochrom; #FG 1215] supplemented with 10% Fetal Calf Serum [Biochrom; #S 0415]) at a density of 3,300 cells (for suspension cells) or 800 cells (for adherent cells) in 30 μL/well in a sterile, solid black, flat bottom, polystyrene, TC-treated 384-well microplate (Corning #3571) using Multidrop Combi Reagent Dispenser. In parallel, cells were plated in a reference (day 0) plate for time zero determination. Cells were incubated in a humidified incubator at 37° C. overnight.

On the next day, cells were treated with compounds (stock solution, 10 mM in DMSO) using the HP D300 Digital Dispenser in a concentration range of 3.3×10e-5 M (33 µM) to 5×10e-9 M (5 nM) in a single-dot curve with at least 16 dilutions and a DMSO concentration of 0.33%. Rim wells were excluded. The cells were incubated for 72 h hours in a humidified incubator at 37° C. The day 0 plate was measured by adding 30 µL/well of CTG solution (CellTiter-Glo® Luminescent Cell Viability reagent, Promega G7573) to time zero wells in the reference plate followed by a 10 minutes incubation and luminescence reading at 0.1 ms. using the PHERAstar FS microplate reader (BMG Labtech).

After 72 h incubation, the treated plates were measured in the same way as the day 0 plate mentioned above. The Bella DRC Master Sheet was used to calculate $IC_{50}$s, with CI=day 0 values and C0=DMSO control values.

Table 6 shows the results of the SUDHL5 and SUDHL10 cytotoxicity and antiproliferation assays.

TABLE 6

$IC_{50}$ values of selected examples in cellular cytotoxicity induction assay 6 and antiproliferation assay 7

| Example PCT | Cytotox SUDHL5 [M] (median) | Cytotox SUDHL10 [M] (median) | Antiproli SUDHL5 [M] (median) | Antiproli SUDHL10 [M] (median) |
|---|---|---|---|---|
| 1 | 2.9E−6 | 6.1E−6 | 5.7E−6 | 5.7E−6 |
| 2 | 1.1E−6 | 3.0E−6 | 2.8E−6 | 2.4E−6 |
| 3 | 6.5E−7 | 1.5E−6 | 1.6E−6 | 1.7E−6 |
| 4 | | | | 1.2E−5 |
| 5 | 2.9E−7 | 5.3E−7 | 3.3E−7 | 2.8E−7 |
| 6 | 1.5E−7 | 3.6E−7 | 2.3E−7 | nd |
| 7 | 6.1E−6 | 9.3E−6 | 4.2E−6 | nd |
| 8 | 3.5E−7 | 4.5E−7 | 4.7E−7 | nd |
| 9 | 2.9E−7 | 3.4E−7 | 3.7E−7 | 2.7E−7 |
| 10 | 5.2E−6 | | 4.9E−6 | nd |
| 11 | 1.8E−7 | 3.7E−7 | 3.0E−7 | nd |
| 12 | | 1.4E−7 | 1.7E−7 | 1.4E−7 |
| 13 | 6.9E−6 | | 6.4E−6 | nd |
| 14 | 3.9E−7 | 6.1E−7 | 5.1E−7 | 4.2E−7 |
| 15 | 1.4E−7 | 2.3E−7 | 1.9E−7 | 2.0E−7 |
| 16 | 3.3E−6 | 4.9E−6 | 1.5E−6 | nd |
| 17 | 2.2E−7 | 6.6E−7 | 2.1E−7 | nd |
| 18 | 1.2E−6 | 1.3E−6 | 1.4E−6 | nd |
| 19 | 4.8E−7 | 4.4E−7 | 5.7E−7 | nd |
| 20 | 1.7E−7 | 6.9E−7 | 2.2E−7 | 4.5E−7 |
| 21 | 3.7E−6 | | 3.3E−6 | nd |
| 22 | 1.6E−7 | 4.0E−7 | 2.8E−7 | nd |
| 23 | 1.4E−7 | 3.1E−7 | 1.5E−7 | nd |
| 24 | 4.7E−6 | 7.4E−6 | 3.4E−6 | nd |
| 25 | 5.3E−7 | 9.3E−7 | 5.6E−7 | nd |
| 26 | 4.6E−7 | 5.0E−7 | 5.8E−7 | nd |
| 27 | | | 7.8E−6 | nd |
| 28 | 3.3E−6 | 5.6E−6 | 3.0E−6 | nd |
| 29 | 1.5E−6 | 3.2E−6 | 1.5E−6 | nd |
| 30 | 2.1E−7 | 3.4E−7 | 1.7E−7 | 1.5E−7 |
| 31 | | | | nd |
| 32 | 9.3E−6 | | 6.0E−6 | nd |
| 33 | 1.0E−6 | 2.0E−6 | 1.2E−6 | nd |
| 34 | 5.3E−7 | 1.3E−6 | 6.2E−7 | nd |
| 35 | 6.3E−6 | | 6.1E−6 | nd |
| 36 | 3.0E−7 | 6.4E−7 | 3.4E−7 | nd |
| 37 | 2.0E−7 | 4.3E−7 | 2.8E−7 | nd |
| 38 | 4.3E−6 | | 1.8E−6 | nd |
| 39 | 1.5E−7 | 2.4E−7 | 1.3E−7 | nd |
| 40 | 2.3E−7 | 4.1E−7 | 2.0E−7 | nd |
| 41 | 1.1E−7 | 2.9E−7 | 1.5E−7 | nd |
| 42 | 4.0E−6 | | 2.7E−6 | nd |
| 43 | 6.0E−7 | 1.6E−6 | 2.2E−7 | nd |
| 44 | 7.0E−6 | 1.2E−6 | 9.5E−6 | nd |
| 45 | 8.1E−6 | | 7.2E−6 | nd |
| 46 | 4.0E−7 | 7.5E−7 | 5.3E−7 | nd |
| 47 | 1.0E−5 | | 8.0E−6 | nd |
| 48 | 1.8E−7 | 3.0E−7 | 2.0E−7 | nd |
| 49 | 5.9E−7 | 1.0E−6 | 5.7E−7 | nd |
| 50 | 4.4E−7 | 6.2E−7 | 4.8E−7 | nd |
| 51 | 8.4E−6 | 8.6E−6 | 6.7E−6 | nd |
| 52 | 8.4E−7 | 2.0E−6 | 1.6E−6 | |
| 53 | 4.8E−7 | 9.7E−7 | 7.4E−7 | |
| 54 | 2.5E−6 | | | nd |
| 55 | 6.7E−7 | 7.4E−7 | 4.3E−7 | nd |
| 56 | 2.2E−7 | 3.3E−7 | 3.4E−7 | |
| 57 | 4.9E−6 | | 3.9E−6 | |
| 58 | 8.4E−7 | 2.0E−6 | 6.2E−7 | nd |
| 59 | 8.0E−7 | 1.2E−6 | 1.1E−6 | |
| 60 | 6.9E−6 | | 3.9E−6 | |
| 61 | 3.4E−7 | 5.3E−7 | 2.5E−7 | |
| 62 | 3.1E−7 | 3.6E−7 | 3.4E−7 | |
| 63 | | | | |
| 64 | 5.4E−7 | | 5.0E−7 | |
| 65 | 3.3E−7 | | 2.7E−7 | |
| 66 | | 1.4E−7 | | |
| 67 | | | | |
| 68 | 1.5E−6 | 3.3E−6 | 2.6E−6 | |
| 069 | 2.3E−6 | 7.3E−6 | 4.2E−6 | |
| 070 | 1.0E−6 | 1.7E−6 | 1.5E−6 | |
| 071 | | | | |
| 072 | 1.0E−6 | 2.5E−6 | 8.8E−7 | |
| 073 | | | | |
| 074 | 4.1E−7 | 4.0E−7 | 7.6E−7 | |
| 075 | 9.1E−7 | 1.4E−6 | 1.6E−6 | |
| 076 | 3.0E−7 | 4.0E−7 | 3.2E−7 | |
| 077 | | | | |
| 078 | 8.2E−7 | 3.1E−6 | | |
| 079 | 7.7E−7 | 1.6E−6 | 1.3E−6 | |
| 080 | 5.8E−7 | 8.1E−7 | 2.2E−7 | |
| 081 | 5.8E−6 | 8.4E−6 | | |
| 082 | 4.9E−7 | 1.4E−6 | 8.1E−7 | |
| 083 | 5.8E−7 | 5.9E−7 | 5.2E−7 | |
| 084 | | | | |
| 085 | 3.0E−7 | 9.8E−7 | 3.6E−7 | |
| 086 | 6.3E−7 | 9.7E−7 | 9.3E−7 | |
| 087 | 2.9E−7 | 2.6E−7 | 5.5E−7 | |
| 088 | 5.1E−6 | 4.0E−6 | | |
| 089 | 8.9E−6 | | 9.0E−6 | |
| 090 | 9.9E−6 | | | |
| 091 | | | | |
| 092 | 3.4E−7 | 8.1E−7 | 8.2E−7 | |
| 093 | 3.5E−7 | 4.3E−7 | 1.8E−7 | |
| 094 | 2.9E−6 | 4.5E−6 | | |
| 095 | 7.7E−7 | 4.5E−7 | 1.0E−6 | |
| 096 | 4.7E−7 | 3.5E−7 | 3.1E−7 | |
| 097 | 4.4E−7 | 4.2E−7 | 5.5E−7 | |
| 098 | 7.3E−6 | 6.3E−6 | 2.2E−6 | |
| 99 | 2.7E−7 | 2.3E−7 | 2.6E−7 | |
| 100 | 1.8E−7 | 1.8E−7 | 1.9E−7 | |
| 101 | 7.3E−6 | 7.7E−6 | | |
| 102 | 8.4E−6 | 8.2E−6 | | |
| 103 | 5.7E−7 | 7.0E−7 | 5.5E−7 | |
| 104 | 9.7E−7 | 1.5E−6 | 1.0E−6 | |
| 105 | 1.6E−7 | 2.2E−7 | | |
| 106 | 2.8E−6 | 5.8E−6 | 2.1E−6 | |
| 107 | 4.6E−7 | 5.9E−7 | 7.2E−7 | |
| 108 | 7.0E−7 | | 1.0E−5 | |
| 109 | 5.9E−7 | 2.8E−7 | 5.5E−7 | |
| 110 | 1.6E−7 | 2.8E−7 | 2.1E−7 | |
| 111 | 6.0E−6 | 6.7E−6 | 3.1E−7 | |
| 112 | 6.1E−7 | 1.2E−6 | 1.5E−6 | |
| 113 | 3.0E−7 | 6.5E−7 | 2.1E−6 | |
| 114 | 5.7E−6 | 5.9E−6 | | |
| 115 | 4.4E−7 | 1.4E−6 | 7.8E−7 | |
| 116 | 4.1E−7 | 3.4E−7 | 3.4E−7 | |
| 117 | 2.6E−7 | 2.3E−7 | 3.4E−6 | |
| 118 | 5.5E−7 | 6.4E−7 | 5.5E−7 | |
| 119 | 1.4E−7 | 2.9E−7 | 3.1E−7 | |
| 120 | | | 7.0E−6 | |
| 121 | 1.3E−6 | 1.9E−6 | 9.0E−7 | |
| 122 | 1.1E−6 | 1.1E−6 | 6.8E−7 | |

TABLE 6-continued

IC$_{50}$ values of selected examples in cellular cytotoxicity induction assay 6 and antiproliferation assay 7

| Example PCT | Cytotox SUDHL5 [M] (median) | Cytotox SUDHL10 [M] (median) | Antiproli SUDHL5 [M] (median) | Antiproli SUDHL10 [M] (median) |
|---|---|---|---|---|
| 123 | 6.6E−7 | 1.2E−6 | 2.2E−6 | |
| 124 | 1.1E−6 | 2.4E−6 | 4.4E−6 | |
| 125 | 1.3E−6 | 5.4E−6 | 7.9E−6 | |
| 126 | 5.0E−7 | 8.7E−7 | 8.8E−7 | |
| 127 | 2.4E−7 | 3.8E−7 | 4.3E−7 | |
| 128 | 2.3E−6 | 3.6E−6 | 4.1E−6 | |
| 129 | 3.3E−7 | 8.9E−7 | 4.5E−7 | |
| 130 | 7.1E−6 | | 7.5E−6 | |
| 131 | | 1.5E−7 | | |
| 132 | 8.2E−6 | | | |
| 133 | | | | |
| 134 | 1.8E−7 | 3.4E−7 | 2.3E−7 | |
| 135 | | 1.5E−7 | 1.2E−7 | |
| 136 | | | | |
| 137 | 8.2E−6 | 7.7E−6 | 5.1E−6 | |
| 138 | 2.4E−7 | 6.0E−7 | 3.5E−7 | |
| 139 | | | | |
| 140 | | | | |
| 141 | 2.6E−6 | 3.6E−6 | 1.6E−6 | |
| 142 | | | | |
| 143 | | | 9.4E−6 | |

A further aspect of the invention are compounds which show an IC$_{50}$ of <5×E-7 in the antiprolferation SUDHL5 assay Table 7 shows the results of the MV-4-11, AMO-1, HMC-1-8, SK-BR-3 and T47D antiproliferation assays 7.

TABLE 7

IC$_{50}$ values of selected examples in antiproliferation assay

| Example | Antiproli MV-4-11 [M] median | Antiproli AMO-1 [M] median | Antiproli HMC-1-8 [M] median | Antiproli SK-BR-3 [M] median | Antiproli T4713 [M] median |
|---|---|---|---|---|---|
| 1 | | | | | |
| 2 | 1.61E−6 | 4.9E−6 | | 8.27E−6 | |
| 3 | 7.66E−7 | 2.5E−6 | 8.3E−6 | 7.37E−6 | |
| 4 | | | | | |
| 5 | 7.01E−7 | 6.1E−7 | | | |
| 6 | 7.94E−8 | 2.4E−7 | 3.4E−6 | | |
| 7 | 8.63E−6 | 6.6E−6 | | | |
| 8 | 1.10E−6 | 1.2E−6 | | 3.00E−6 | |
| 9 | 8.23E−7 | 8.7E−7 | | 1.08E−6 | |
| 10 | 1.09E−5 | | | | |
| 11 | 4.42E−7 | 7.3E−7 | 4.2E−6 | 1.48E−6 | |
| 12 | 4.41E−7 | 3.3E−7 | 1.6E−6 | 6.67E−7 | 7.10E−6 |
| 13 | 1.22E−5 | | | | |
| 14 | 1.23E−6 | 7.4E−7 | | | |
| 15 | 4.61E−7 | 5.3E−7 | 1.4E−6 | | 1.19E−5 |
| 16 | 5.24E−7 | 8.9E−6 | | | |
| 17 | 6.70E−6 | 5.2E−7 | 1.2E−6 | | |
| 18 | 4.71E−6 | | | | |
| 19 | 1.65E−6 | 1.5E−6 | | 3.26E−6 | |
| 20 | 9.07E−7 | 8.7E−7 | 2.5E−6 | 2.52E−6 | |
| 21 | 1.49E−5 | | | | |
| 22 | 6.92E−7 | 6.6E−7 | | 8.94E−7 | |
| 23 | 3.87E−7 | 6.1E−7 | 5.2E−6 | | |
| 24 | 6.72E−6 | | | | |
| 25 | 2.78E−6 | 1.3E−6 | 6.5E−6 | 1.29E−5 | |
| 26 | 1.81E−6 | 1.0E−6 | 2.9E−6 | 3.30E−6 | |
| 27 | 1.61E−5 | | | | |
| 28 | 8.08E−6 | | | | |
| 29 | 2.68E−6 | | | | |
| 30 | 2.93E−7 | 4.2E−7 | 1.6E−6 | | |
| 31 | 2.75E−7 | 1.7E−7 | 1.9E−6 | | |
| 32 | 1.40E−5 | | | | |
| 33 | 1.70E−6 | 1.6E−6 | | | |
| 34 | 1.26E−6 | 1.4E−6 | 2.0E−6 | | |
| 35 | 8.59E−6 | | | | |

TABLE 7-continued

IC$_{50}$ values of selected examples in antiproliferation assay

| Example | Antiproli MV-4-11 [M] median | Antiproli AMO-1 [M] median | Antiproli HMC-1-8 [M] median | Antiproli SK-BR-3 [M] median | Antiproli T4713 [M] median |
|---|---|---|---|---|---|
| 36 | 1.01E−6 | 2.9E−7 | | | |
| 37 | 3.77E−7 | 3.6E−7 | 1.6E−6 | | |
| 38 | 1.34E−5 | | | | |
| 39 | 4.42E−7 | 2.4E−7 | 3.3E−6 | | |
| 40 | 9.55E−8 | 3.6E−7 | | | |
| 41 | 4.89E−6 | 5.4E−7 | 7.0E−7 | | |
| 42 | 9.75E−7 | | | | |
| 43 | 1.38E−6 | 1.4E−6 | | | |
| 44 | 1.17E−5 | 1.1E−6 | 2.1E−6 | | |
| 45 | 6.28E−7 | | | | |
| 46 | 4.90E−7 | 5.9E−7 | | | |
| 47 | 5.65E−6 | | | | |
| 48 | 9.18E−7 | 1.8E−7 | 8.2E−7 | | |
| 49 | | 1.5E−6 | | | |
| 50 | | 1.3E−6 | 3.1E−6 | | |
| 51 | 1.71E−6 | | | | |
| 52 | | 2.2E−6 | | | |
| 53 | | 1.5E−6 | 6.9E−6 | | |
| 54 | | | | | |
| 55 | | 1.4E−6 | 2.2E−6 | | |
| 56 | | 4.4E−7 | 3.3E−6 | | |
| 57 | | 7.6E−6 | | | |
| 58 | | 1.7E−6 | 5.8E−6 | | |
| 59 | | 1.5E−6 | | | |
| 60 | | | 8.7E−6 | | |
| 61 | | 6.8E−7 | 1.7E−6 | | |
| 62 | | 2.2E−7 | 2.2E−6 | | |
| 63 | | | | | |
| 64 | | 1.6E−6 | 5.6E−6 | | |
| 65 | | 6.0E−7 | 2.5E−6 | | |
| 66 | | | 1.0E−6 | | |
| 67 | | | | | |
| 68 | | 2.6E−6 | 7.9E−6 | | |
| 069 | | | | | |
| 070 | | 1.1E−6 | | | |
| 071 | | | | | |
| 072 | | 2.8E−6 | | | |
| 073 | | | | | |
| 074 | | 1.3E−6 | 9.4E−6 | | |
| 075 | | 4.8E−6 | | | |
| 076 | | 2.4E−7 | 4.4E−6 | | |
| 077 | | | | | |
| 078 | | 3.0E−6 | | | |
| 079 | | 1.7E−6 | 8.6E−6 | | |
| 080 | | 1.9E−6 | 9.6E−6 | | |
| 081 | | | 5.5E−6 | | |
| 082 | | 2.9E−6 | | | |
| 083 | | 3.8E−7 | 7.4E−6 | | |
| 084 | | | | | |
| 085 | | 4.9E−7 | 3.3E−6 | | |
| 086 | | 1.4E−6 | 6.4E−6 | | |
| 087 | | 3.8E−7 | 4.7E−6 | | |
| 088 | | 6.7E−6 | 4.5E−6 | | |
| 089 | | | | | |
| 090 | | 4.9E−6 | | | |
| 091 | | | | | |
| 092 | | 5.4E−7 | 6.8E−6 | | |
| 093 | | 1.2E−6 | 4.9E−6 | | |
| 094 | | | 6.3E−6 | | |
| 095 | | 9.7E−7 | 7.2E−6 | | |
| 096 | | 4.9E−7 | 5.3E−6 | | |
| 097 | | 2.2E−7 | 2.2E−6 | | |
| 098 | | 6.9E−6 | 5.9E−6 | | |
| 99 | | 5.2E−7 | 5.9E−6 | | |
| 100 | | 6.7E−7 | 5.0E−6 | | |
| 101 | | | | | |
| 102 | | | | | |
| 103 | | 8.2E−7 | 7.1E−6 | | |
| 104 | | 2.4E−6 | 8.5E−6 | | |
| 105 | | 1.8E−7 | 1.6E−6 | | |
| 106 | | 8.1E−6 | | | |
| 107 | | 5.5E−7 | 2.4E−6 | | |
| 108 | | 1.3E−6 | | | |

TABLE 7-continued

IC$_{50}$ values of selected examples in antiproliferation assay

| Example | Antiproli MV-4-11 [M] median | Antiproli AMO-1 [M] median | Antiproli HMC-1-8 [M] median | Antiproli SK-BR-3 [M] median | Antiproli T4713 [M] median |
|---|---|---|---|---|---|
| 109 | | 1.9E−7 | 4.3E−6 | | |
| 110 | | 3.5E−7 | 1.4E−6 | | |
| 111 | | 8.4E−6 | | | |
| 112 | | 9.1E−7 | 7.1E−6 | | |
| 113 | | 3.2E−7 | 3.7E−6 | | |
| 114 | | 4.4E−6 | | | |
| 115 | | 9.1E−7 | 8.0E−6 | | |
| 116 | | 2.1E−7 | 2.3E−6 | | |
| 117 | | 1.2E−6 | | | |
| 118 | | 5.1E−7 | 2.5E−6 | | |
| 119 | | 3.6E−7 | 1.3E−6 | | |
| 120 | | | 7.1E−6 | | |
| 121 | | 1.3E−6 | 9.9E−6 | | |
| 122 | | 5.1E−7 | 6.6E−6 | | |
| 123 | | 7.7E−7 | 3.1E−6 | | |
| 124 | | 8.3E−7 | 7.0E−6 | | |
| 125 | | 1.9E−6 | | | |
| 126 | | 3.7E−7 | 2.2E−6 | | |
| 127 | | 5.8E−7 | 2.2E−6 | | |
| 128 | | 6.5E−6 | | | |
| 129 | | 8.3E−7 | 5.2E−6 | | |
| 130 | | 6.3E−6 | | | |
| 131 | | | 1.3E−6 | | |
| 132 | | | | | |
| 133 | | | 1.0E−6 | | |
| 134 | | 3.4E−7 | 2.1E−6 | | |
| 135 | | 1.2E−7 | 8.7E−7 | | |
| 136 | | | 7.3E−7 | | |
| 137 | | 5.0E−6 | | | |
| 138 | | 4.7E−7 | 3.0E−6 | | |
| 139 | | 4.4E−7 | 5.7E−6 | | |
| 140 | | | 1.4E−6 | | |
| 141 | | 2.4E−6 | | | |
| 142 | | | 7.5E−7 | | |
| 143 | | | | | |

A further aspect of the invention are compounds of general formula (I) which show an IC$_{50}$ of <1.2×E−6 in the Antiproli AMO-1 assay.

A further aspect of the invention are compounds of general formula (I) which show an IC$_{50}$ of 3.5×E or <3.5×E−6 in the Antiproli HMC-1-8 assay.

Yet another aspect of the invention are compounds of general formula (I) which show an IC$_{50}$ of 1.2×E−6 or <1.2×E−6 in the Antiproli AMO-1 assay and/or an IC$_{50}$ of 3.5×E−6 or <3.5×E−6 in the Antiproli HMC-1-8 assay.

Yet another aspect of the invention are compounds of general formula (I) which show an IC$_{50}$ of 1.2×E−6 or <1.2×E−6 in the Antiproli AMO-1 assay and an IC$_{50}$ of 3.5×E−6 or <3.5×E−6 in the Antiproli HMC-1-8 assay.

Yet another aspect of the invention are compounds of general formula (I) which show an IC$_{50}$ of 1.2×E−6 or <1.2×E−6 in the Antiproli AMO-1 assay or an IC$_{50}$ of 3.5×E−6 or <3.5×E−6 in the Antiproli HMC-1-8 assay.

Yet another aspect of the invention are compounds of general formula (I) which show an IC$_{50}$ of <0.5×E−6 in the Antiproli AMO-1 assay and an IC$_{50}$ of <2×E−6 in the Antiproli HMC-1-8 assay.

A further aspect of the invention are compounds of general formula (I) which show an IC$_{50}$ of <5×E−7 in the Antiproli SUDHL5 assay and/or an IC$_{50}$ of <1.2×E−6 in the Antiproli AMO-1 assay and/or an IC$_{50}$ of <3.5×E−6 in the Antiproli HMC-1-8 assay.

A further aspect of the invention are compounds of general formula (I) which show an IC$_{50}$ of <5×E−7 in the Antiproli SUDHL5 assay and an IC$_{50}$ of <1.2×E−6 in the Antiproli AMO-1 assay or an IC$_{50}$ of <3.5×E−6 in the Antiproli HMC-1-8 assay.

A further aspect of the invention are compounds of general formula (I) which show an IC$_{50}$ of <5×E−7 in the Antiproli SUDHL5 assay and an IC$_{50}$ of <3.5×E−6 in the Antiproli HMC-1-8 assay or an IC$_{50}$ of <1.2×E−6 in the Antiproli AMO-1 assay.

A yet further aspect of the invention are compounds of general formula (I) which show an IC$_{50}$ of <5×E−7 in the Antiproli SUDHL5 assay and an IC$_{50}$ of <1.2×E−6 in the Antiproli AMO-1 assay and an IC$_{50}$ of 1-8<3.5×E−6 in the Antiproli HMC-1-8 assay.

Yet another aspect of the invention are compounds of general formula (I) which show an IC$_{50}$ of <0.5×E−6 in the Antiproli AMO-1 assay and an IC$_{50}$ of <2×E−6 in the Antiproli HMC-1-8 assay and an IC$_{50}$<1×E−9 in the MCL-1/Noxa BH3 Peptide (MCL-1 Assay).

Table 8 shows the results of the A2058, NCI-H23, KYSE-180, SNU-389 and DMS-114 antiproliferation assays 7.

TABLE 8

IC$_{50}$ values of selected examples in antiproliferation assay

| Example | Antiproli A2058 [M] median | Antiproli NCI-H23 [M] median | Antiproli KYSE-180 [M] median | Antiproli SNU-389 [M] median | Antiproli DMS-114 [M] median |
|---|---|---|---|---|---|
| 1 | | | | | |
| 2 | >3.00E−05 | 1.46E−5 | | | |
| 3 | >3.00E−05 | 6.12E−6 | | 2.06E−5 | |
| 4 | | | | | |
| 5 | | | | | |
| 6 | | | | 6.96E−7 | 4.97E−7 |
| 7 | | | | | |
| 8 | | | | | |
| 9 | | | | | |
| 10 | | | | | |
| 11 | | | | | |
| 12 | 4.83E−6 | | 3.79E−6 | 7.22E−7 | 1.32E−6 |
| 13 | | | | | |
| 14 | | | | | |
| 15 | 5.86E−6 | | | 9.28E−7 | 6.42E−7 |
| 16 | | | | | |
| 17 | | | | 9.86E−7 | |
| 18 | | | | | |
| 19 | | | | | |
| 20 | | | | | |
| 21 | | | | | |
| 22 | | | | | |
| 23 | | | | 1.70E−6 | 2.06E−6 |
| 24 | | | | | |
| 25 | 2.19E−5 | 6.01E−6 | | | |
| 26 | 1.49E−5 | 2.32E−6 | | 1.66E−6 | 1.76E−6 |
| 27 | | | | | |
| 28 | | | | | |
| 29 | | | | | |
| 30 | | | | | |
| 31 | | | | | |
| 32 | | | | | |
| 33 | | | | | |
| 34 | | | | | |
| 35 | | | | | |
| 36 | | | | | |
| 37 | | | | 1.05E−6 | 1.12E−6 |
| 38 | | | | | |
| 39 | | | | 1.09E−6 | 6.38E−7 |
| 40 | | | | | |
| 41 | | | | 5.56E−7 | 3.65E−7 |
| 42 | | | | | |
| 43 | | | | | |
| 44 | | | | | |
| 45 | | | | | |
| 46 | | | | | |
| 47 | | | | | |

TABLE 8-continued

IC$_{50}$ values of selected examples in antiproliferation assay

| Example | Antiproli A2058 [M] median | Antiproli NCI-H23 [M] median | Antiproli KYSE-180 [M] median | Antiproli SNU-389 [M] median | Antiproli DMS-114 [M] median |
|---|---|---|---|---|---|
| 48 | | | | | |
| 49 | | | | | |
| 50 | | | | | |
| 51 | | | | | |
| 52 | | | | | |
| 53 | | | | | |
| 54 | | | | | |
| 55 | | | | | |
| 56 | | | | 1.23E-6 | 7.79E-7 |
| 57 | | | | | |
| 58 | | | | | |
| 59 | | | | 3.79E-6 | 3.21E-6 |
| 60 | | | | | |
| 61 | | | | | |
| 62 | | | | | |
| 63 | | | | | |
| 64 | | | | | |
| 65 | | | | | |
| 66 | | | | 5.76E-7 | 3.15E-7 |
| 67 | | | | | |
| 68 | | | | | |
| 069 | | | | | |
| 070 | | | | | |
| 071 | | | | | |
| 072 | | | | | |
| 073 | | | | | |
| 074 | | | | | |
| 075 | | | | | |
| 076 | | | | | |
| 077 | | | | | |
| 078 | | | | | |
| 079 | | | | | |
| 080 | | | | | |
| 081 | | | | | |
| 082 | | | | | |
| 083 | | | | | |
| 084 | | | | | |
| 085 | | | | | |
| 086 | | | | | |
| 087 | | | | 1.52E-6 | 1.32E-6 |
| 088 | | | | | |
| 089 | | | | | |
| 090 | | | | | |
| 091 | | | | | |
| 092 | | | | | |
| 093 | | | | | |
| 094 | | | | | |
| 095 | | | | | |
| 096 | | | | | |
| 097 | | | | | |
| 098 | | | | | |
| 99 | | | | | |
| 100 | | | | 1.18E-6 | 1.85E-7 |
| 101 | | | | | |
| 102 | | | | | |
| 103 | | | | | |
| 104 | | | | | |
| 105 | | | | | |
| 106 | | | | | |
| 107 | | | | | |
| 108 | | | | | |
| 109 | | | | | |
| 110 | | | | | |
| 111 | | | | | |
| 112 | | | | | |
| 113 | | | | | |
| 114 | | | | | |
| 115 | | | | | |
| 116 | | | | | |
| 117 | | | | | |
| 118 | | | | | |
| 119 | | | | | |
| 120 | | | | | |
| 121 | | | | | |
| 122 | | | | | |
| 123 | | | | | |
| 124 | | | | | |
| 125 | | | | | |
| 126 | | | | | |
| 127 | | | | | |
| 128 | | | | | |
| 129 | | | | | |
| 130 | | | | | |
| 131 | | | | | |
| 132 | | | | | |
| 133 | | | | 4.97E-7 | 3.85E-7 |
| 134 | | | | | |
| 135 | | | | | |
| 136 | | | | 3.85E-7 | 2.35E-7 |
| 137 | | | | | |
| 138 | | | | | |
| 139 | | | | | |
| 140 | | | | | |
| 141 | | | | | |
| 142 | | | | | |
| 143 | | | | | |

Assay 8

Protein-Compound Interaction Assay (SPR Assay)

The ability of the compounds described in this invention to bind to MCL-1 may be determined using surface plasmon resonance (SPR). This allows for the quantification of binding in terms of the equilibrium dissociation constant (KD [M]), as well as association and dissociation rate constants (kon [1/M 1/s] and koff [1/s], respectively). The measurements may be performed using Biacore® T200 or Biacore® S200 instruments (GE Healthcare).

For SPR measurements, recombinant MCL-1 (amino acids 173-321, N-terminal fused to Maltose Binding Protein (MBP) (SEQ ID 1, supra) purchased from Beryllium (Bedford, Mass., USA)) was immobilized using standard amine coupling (Johnsson B et al, Anal Biochem. 1991 Nov. 1; 198(2):268-77). Briefly, carboxymethylated dextran biosensor chips (Series S Sensor Chip CM5, GE Healthcare) were activated with 1-ethyl-3-(3-dimethylaminopropyl)-carbodiimide hydrochloride (EDC) and N-hydroxysuccinimide (NHS) according to the supplier's instructions. MBP-MCL-1 was diluted in 1×PBS-P+(GE Healthcare) and injected on the activated chip surface. Subsequently, a solution of 1 M ethanolamine-HCl (GE Healthcare) was injected to block unreacted groups, resulting in approximately 400-2500 response units (RU) of immobilized protein. A reference surface was generated by treatment with NHS-EDC and ethanolamine-HCl. Compounds were dissolved in 100% dimethylsulfoxide (DMSO) to a concentration of 10 mM and subsequently diluted in running buffer (1×PBS-P+(GE Healthcare) [generated from PBS-P+ Buffer 10× (GE Healthcare): 0.2 M phosphate buffer with 27 mM KCl, 1.37 M NaCl and 0.5% Surfactant P20 (Tween 20).], 1% v/v DMSO). For SPR binding-measurements, serial dilutions of compound (eight dilution steps, typically ranging from 0.2 nM up to 1 μM) were injected over immobilized protein. Binding affinity and kinetics were measured at 25° C. with a flow rate of 100 μl/min in running buffer. Compounds were injected for 60 s followed by a dissociation time of up to 1000 s.

The double-referenced sensorgrams were fit to a simple reversible Langmuir 1:1 reaction mechanism as implemented in the Biacore® T200 and S200 evaluation software (T200 evaluation software version 2.0 and S200 evaluation software version 1.0, GE Healthcare).

TABLE 9

$K_D$, $k_{on}$ and $k_{off}$ values (geometric mean values) of MCL-1 compound interactions of selected examples as determined in SPR assay 8

| Example | $k_{on}$ [1/M 1/s] | $k_{off}$ [1/s] | $K_D$ [M] |
|---|---|---|---|
| 1 | | | |
| 2 | 1.0E6 | 1.1E−2 | 1.1E−8 |
| 3 | | | |
| 4 | | | |
| 5 | | | |
| 6 | 3.1E7 | 6.7E−3 | 2.2E−10 |
| 7 | | | |
| 8 | | | |
| 9 | 8.7E6 | 9.6E−3 | 1.1E−9 |
| 10 | | | |
| 11 | | | |
| 12 | 1.0E7 | 6.2E−3 | 6.1E−10 |
| 13 | | | |
| 14 | | | |
| 15 | 1.2E7 | 5.1E−3 | 4.4E−10 |
| 16 | 1.5E6 | 3.7E−3 | 2.5E−9 |
| 17 | | | |
| 18 | | | |
| 19 | | | |
| 20 | | | |
| 21 | | | |
| 22 | | | |
| 23 | 1.5E7 | 3.4E−3 | 2.3E−10 |
| 24 | | | |
| 25 | | | |
| 26 | 3.7E6 | 1.1E−2 | 3.1E−9 |
| 27 | | | |
| 28 | | | |
| 29 | | | |
| 30 | | | |
| 31 | 6.5E6 | 2.8E−3 | 4.3E−10 |
| 32 | | | |
| 33 | | | |
| 34 | 8.9E5 | 4.0E−3 | 4.5E−9 |
| 35 | | | |
| 36 | | | |
| 37 | 5.1E6 | 5.9E−3 | 1.2E−9 |
| 38 | | | |
| 39 | | | |
| 40 | 7.8E6 | 8.7E−3 | 1.1E−9 |
| 41 | | | |
| 42 | | | |
| 43 | 7.6E5 | 6.3E−3 | 8.3E−9 |
| 44 | | | |
| 45 | | | |
| 46 | 1.7E6 | 3.3E−3 | 1.9E−9 |
| 47 | | | |
| 48 | | | |
| 49 | 6.2E6 | 1.1E−2 | 1.7E−9 |
| 50 | | | |
| 51 | | | |
| 52 | 1.0E6 | 6.7E−3 | 6.5E−9 |
| 53 | | | |
| 54 | | | |
| 55 | | | |
| 56 | 1.6E6 | 1.3E−2 | 7.8E−9 |
| 57 | | | |
| 58 | | | |
| 59 | | | |
| 60 | | | |
| 61 | | | |
| 62 | | | |
| 63 | | | |
| 64 | | | |
| 65 | 5.5E6 | 2.0E−2 | 3.6E−9 |
| 66 | | | |
| 67 | | | |
| 68 | | | |
| 69 | 3.9E6 | 6.6E−3 | 1.7E9 |
| 70 | 7.9E5 | 4.4E−3 | 5.5E−9 |

TABLE 9-continued $K_D$, $k_{on}$ and $k_{off}$ values (geometric mean values) of MCL-1 compound interactions of selected examples as determined in SPR assay 8

| Example | $k_{on}$ [1/M 1/s] | $k_{off}$ [1/s] | $K_D$ [M] |
|---|---|---|---|
| 71 | | | |
| 72 | | | |
| 73 | 1.7E6 | 7.6E−3 | 4.5E−9 |
| 74 | | | |
| 75 | 9.5E5 | 2.0E−3 | 2.1E−9 |
| 76 | | | |
| 77 | | | |
| 78 | | | |
| 79 | | | |
| 80 | | | |
| 81 | | | |
| 82 | | | |
| 83 | | | |
| 84 | | | |
| 85 | 8.6E5 | 5.6E−3 | 6.5E−9 |
| 86 | | | |
| 87 | | | |
| 88 | | | |
| 89 | | | |
| 90 | | | |
| 91 | 7.8E5 | 4.6E−3 | 5.9E−9 |
| 92 | | | |
| 93 | | | |
| 94 | | | |
| 95 | | | |
| 96 | | | |
| 97 | 3.7E5 | 3.3E−3 | 8.9E−9 |
| 98 | | | |
| 99 | | | |
| 100 | 3.4E5 | 2.8E−3 | 8.3E−9 |
| 101 | | | |
| 102 | | | |
| 103 | | | |
| 104 | | | |
| 105 | | | |
| 106 | | | |
| 107 | | | |
| 108 | | | |
| 109 | | | |
| 110 | | | |
| 111 | | | |
| 112 | | | |
| 113 | | | |
| 114 | | | |
| 115 | | | |
| 116 | | | |
| 117 | | | |
| 118 | | | |
| 119 | | | |
| 120 | | | |
| 121 | | | |
| 122 | | | |
| 123 | | | |
| 124 | | | |
| 125 | | | |
| 126 | | | |
| 127 | | | |
| 128 | | | |
| 129 | | | |
| 130 | | | |
| 131 | | | |
| 132 | 7.8E6 | 2.2E−3 | 2.8E−10 |
| 133 | | | |
| 134 | | | |
| 135 | | | |
| 136 | 2.4E7 | 4.0E−3 | 1.7E−10 |
| 137 | | | |
| 138 | | | |
| 139 | | | |
| 140 | | | |
| 141 | | | |
| 142 | | | |
| 143 | | | |

Assay 9

Equilibrium Shake Flask Solubility Assay

Thermodynamic solubility was determined by an equilibrium shake flask method [Edward H. Kerns and Li Di (2008) Solubility Methods in: Drug-like Properties: Concepts, Structure Design and Methods, p 276-286. Burlington, Mass.: Academic Press].

A saturated solution of the drug was prepared and the solution was mixed for 24 h to ensure that equilibrium has been reached. The solution was centrifuged to remove the insoluble fraction and the concentration of the compound in solution was determined using a standard calibration curve.

To prepare the sample, 2 mg solid compound was weighed in a 4 mL glass vial. 1 mL phosphate buffer pH 6.5 respectively borate Buffer pH 8 was added. The suspension was put on a stirrer and mixed for 24 hours at room temperature. The solution was centrifuged afterwards. To prepare the sample for the standard calibration, 1-2 mg (accurate weight) solid sample was dissolved in acetonitrile/water 50:50 and diluted to 20 mL. Sample and standards were quantified by HPLC with UV-detection. For each sample two injection volumes (5 and 50 µL) in triplicates were made. Three injection volumes (5 µL, 10 µL and 20 µL) were made for the standard.

| Chromatographic conditions were as follows: | |
| --- | --- |
| HPLC column: | Xterra MS C18 2.5 µm 4.6 × 30 mm |
| Injection volume: | Sample: 3 × 5 µl and 3 × 50 µl |
| | Standard: 5 µl, 10 µl, 20 µl |
| Flow: | 1.5 mL/min |
| Mobile phase: | acidic gradient: |
| | A: Water/0.01% trifluoroacidic acid |
| | B: Acetonitrile/0.01% trifluoroacidic acid |
| | 0 min → >95% A 5% B |
| | 0-3 min → >35% A 65% B, linear gradient |
| | 3-5 min → >35% A 65% B, isocratic |
| | 5-6 min → >95% A 5% B, isocratic |
| UV detector: | wavelength near the absorption maximum (between 200 and 400 nm) |

The areas of sample- and standard injections as well as the calculation of the solubility value (in mg/L) were determined by using HPLC software (Waters Empower 2 FR).

Assay 10

CYP Inhibition Assay

The inhibitory potency of the test compounds towards cytochrome P450 dependent metabolic pathways was determined in human liver microsomes applying individual CYP isoform-selective standard probes (phenacetin, coumarin, bupropion, amodiaquine, diclofenac, S-mephenytoin, dextromethorphan, chlorzoxazone, midazolam, testosterone). Reference inhibitors were included as positive controls. Incubation conditions (protein and substrate concentration, incubation time) were optimized with regard to linearity of metabolite formation. The assay was processed by using Genesis Workstation (Tecan, Crailsheim, FRG) in 96-well plates at 37° C. After protein precipitation the metabolite formation was quantified by LC-MS/MS analysis followed by inhibition evaluation and $IC_{50}$ calculation.

The potential of an investigational drug to inhibit CYP enzymes, given by determined $IC_{50}$ values of test compounds in vitro, is a basic requirement in order to assess potential drug-drug interactions (DDI) with comedicated drugs which are relevant substrates of studied CYP isoforms. Such investigations are recommended by pertinent guidelines (i.e. EMA and FDA) for the evaluation of DDIs.

Assay 11

CYP Induction Assay

To evaluate the CYP induction potential in vitro, cultured human hepatocytes from three separate livers were treated once daily for three consecutive days with vehicle control, one of eight concentrations of test compound and known human CYP inducers (e.g. omeprazole, phenobarbital, and rifampin). After treatment, the cells were incubated in situ with the appropriate marker substrates for the analysis of CYP3A4, CYP2B6 and CYP1A2 activity by LC-MS/MS. Following the in situ incubation, the same hepatocytes from the same treatment groups were harvested for RNA isolation and analyzed by qRT-PCR to assess the effect of test compound on CYP1A2, CYP2B6 and CYP3A4 mRNA expression levels.

Assay 12

Caco-2 Permeation Assay

Caco-2 cells (purchased from DSMZ Braunschweig, Germany) were seeded at a density of $4.5 \times 10^4$ cell per well on 24 well insert plates, 0.4 µm pore size, and grown for 15 days in DMEM medium supplemented with 10% fetal bovine serum, 1% GlutaMAX (100×, GIBCO), 100 U/mL penicillin, 100 µg/mL streptomycin (GIBCO) and 1% non essential amino acids (100×). Cells were maintained at 37° C. in a humified 5% $CO_2$ atmosphere. Medium was changed every 2-3 day. Before running the permeation assay, the culture medium was replaced by an FCS-free hepes-carbonate transport puffer (pH 7.2). For assessment of monolayer integrity the transepithelial electrical resistance (TEER) was measured. Test compounds were predissolved in DMSO and added either to the apical or basolateral compartment in final concentration of 2 µM. Before and after 2 h incubation at 37° C. samples were taken from both compartments. Analysis of compound content was done after precipitation with methanol by LC/MS/MS analysis. Permeability (Papp) was calculated in the apical to basolateral (A→B) and basolateral to apical (B→A) directions. The apparent permeability was calculated using following equation:

$$P_{app} = (V_r/P_o)(1/S)(P_2/t)$$

Where $V_r$ is the volume of medium in the receiver chamber, $P_o$ is the measured peak area of the test drug in the donor chamber at t=0, S the surface area of the monolayer, $P_2$ is the measured peak area of the test drug in the acceptor chamber after 2 h of incubation, and t is the incubation time. The efflux ratio basolateral (B) to apical (A) was calculated by dividing the $P_{app}$ B-A by the $P_{app}$ A-B. In addition the compound recovery was calculated. As assay control reference compounds were analyzed in parallel.

Assay 13

Investigation of In Vitro Metabolic Stability in Rat Hepatocytes (Including Calculation of Hepatic In Vivo Blood Clearance (CL))

Hepatocytes from Han Wistar rats were isolated via a 2-step perfusion method. After perfusion, the liver was carefully removed from the rat: the liver capsule was opened and the hepatocytes were gently shaken out into a Petri dish with ice-cold WME. The resulting cell suspension was filtered through sterile gaze in 50 mL falcon tubes and centrifuged at 50×g for 3 min at room temperature. The cell pellet was resuspended in 30 mL WME and centrifuged through a Percoll® gradient for 2 times at 100×g. The hepatocytes were washed again with Williams' medium E (WME) and resuspended in medium containing 5% FCS. Cell viability was determined by trypan blue exclusion.

For the metabolic stability assay liver cells were distributed in WME containing 5% FCS to glass vials at a density of $1.0 \times 10^6$ vital cells/mL. The test compound was added to a final concentration of 1 µM. During incubation, the hepatocyte suspensions were continuously shaken and aliquots were taken at 2, 8, 16, 30, 45 and 90 min, to which equal volumes of cold methanol were immediately added.

Samples were frozen at −20° C. over night, after subsequently centrifuged for 15 minutes at 3000 rpm and the supernatant was analyzed with an Agilent 1200 HPLC-system with LCMS/MS detection.

The half-life of a test compound was determined from the concentration-time plot. From the half-life the intrinsic clearances were calculated. Together with the additional parameters liver blood flow, amount of liver cells in vivo and in vitro. The hepatic in vivo blood clearance (CL) and the maximal oral bioavailability ($F_{max}$) was calculated using the following formulae: CL'intrinsic [mL/(min*kg)]=kel [1/min]/((cellno/volume of incubation [mL])*fu,inc) * (cellno/liver weight [g])*(specific liver weight [g liver/kg body weight]); CLblood well-stirred [L/(h*kg)]=(QH [L/(h*kg)]*fu,blood*CL'intrinsic [L/(h*kg)])/(QH [L/(h*kg)]+fu,blood*CL'intrinsic [L/(h*kg)]); Fmax=1-CLblood/QH. The following parameter values were used: Liver blood flow—4.2 L/h/kg rat; specific liver weight—32 g/kg rat body weight; liver cells in vivo-1.1×10$^8$ cells/g liver, liver cells in vitro—1.0×10$^6$/mL; fu,inc and fu,blood is taken as 1.

Assay 14

Investigation of In Vitro Metabolic Stability in Rat Hepatocytes in Liver Microsomes (Including Calculation of Hepatic In Vivo Blood Clearance (CL) and of Maximal Oral Bioavailability (Fmax)))

The in vitro metabolic stability of test compounds was determined by incubating them at 1 µM in a suspension liver microsomes in 100 mM phosphate buffer, pH7.4 (sodium dihydrogen phosphate monohydrate+disodium hydrogen phosphate dihydrate) and at a protein concentration of 0.5 mg/mL at 37° C. The microsomes were activated by adding a co-factor mix containing 8 mM Glucose-6-Phosphat, 4 mM magnesium chloride2; 0.5 mM NADP and 1 IU/mL G-6-P-Dehydrogenase in phosphate buffer, pH 7.4. The metabolic assay was started shortly afterwards by adding the test compound to the incubation at a final volume of 1 mL. Organic solvent in the incubations was limited to <0.01% dimethylsulfoxide (DMSO) and 51% acetonitril. During incubation, the microsomal suspensions were continuously shaken at 580 rpm and aliquots were taken at 2, 8, 16, 30, 45 and 60 min, to which equal volumes of cold methanol were immediately added. Samples were frozen at −20° C. over night, subsequently centrifuged for 15 minutes at 3000 rpm and the supernatant was analyzed with an Agilent 1200 HPLC-system with LCMS/MS detection.

The half-life of a test compound was determined from the concentration-time plot. From the half-life the intrinsic clearances were calculated. Together with the additional parameters liver blood flow, specific liver weight and microsomal protein content the hepatic in vivo blood clearance (CL) and the maximal oral bioavailability ($F_{max}$) were calculated for the different species. The hepatic in vivo blood clearance (CLblood) and the maximal oral bioavailability ($F_{max}$) was calculated using the following formulae: CL'intrinsic [mL/(min*kg)]=kel [1/min]/((mg protein/volume of incubation [mL])*fu,inc) * (mg protein/liver weight [g])*(specific liver weight [g liver/kg body weight]); CLblood well-stirred [L/(h*kg)]=(QH [L/(h*kg)]*fu,blood*CL'intrinsic [L/(h*kg)])/(QH [L/(h*kg)]+fu,blood*CL'intrinsic [L/(h*kg)]); Fmax=1-CLblood/QH and using the following parameter values: Liver blood flow—1.32 L/h/kg (human), 2.1 L/h/kg (dog), 4.2 L/h/kg (rat); specific liver weight—21 g/kg (human), 39 g/kg (dog), 32 g/kg (rat); microsomal protein content—40 mg/g.; fu,inc and fu,blood is taken as 1.

Assay 15

In Vivo Pharmacokinetics in Rats

For in vivo pharmacokinetic experiments test compounds were administered to male Wistar rats intravenously at doses of 0.3 to 1 mg/kg and intragastral at doses of 0.5 to 10 mg/kg formulated as solutions using solubilizers such as PEG400 in well-tolerated amounts.

For pharmacokinetics after intravenous administration test compounds were given as i.v. bolus and blood samples were taken at 2 min, 8 min, 15 min, 30 min, 45 min, 1 h, 2 h, 4 h, 6 h, 8 h and 24 h after dosing. Depending on the expected half-life additional samples were taken at later time points (e.g., 48 h, 72 h). For pharmacokinetics after intragastral administration test compounds were given intragastral to fasted rats and blood samples were taken at 5 min, 15 min, 30 min, 45 min, 1 h, 2 h, 4 h, 6 h, 8 h and 24 h after dosing. Depending on the expected half-life additional samples were taken at later time points (e.g., 48 h, 72 h). Blood was collected into Lithium-Heparintubes (Monovetten®, Sarstedt) and centrifuged for 15 min at 3000 rpm. An aliquot of 100 µL from the supernatant (plasma) was taken and precipitated by addition of 400 µL cold acetonitril and frozen at −20° C. over night. Samples were subsequently thawed and centrifuged at 3000 rpm, 4° C. for 20 minutes. Aliquots of the supernatants were taken for analytical testing using an Agilent 1200 HPLC-system with LCMS/MS detection. PK parameters were calculated by non-compartmental analysis using a PK calculation software.

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood. PK parameters calculated from concentration time profiles after i.g.: Cmax: Maximal plasma concentration (in mg/L); Cmaxnorm: Cmax divided by the administered dose (in kg/L); Tmax: Time point at which Cmax was observed (in h). Parameters calculated from both, i.v. and i.g. concentration-time profiles: AUCnorm: Area under the concentration-time curve from t=0 h to infinity (extrapolated) divided by the administered dose (in kg*h/L); AUC(0−tlast)norm: Area under the concentration-time curve from t=0 h to the last time point for which plasma concentrations could be measured divided by the administered dose (in kg*h/L); t1/2: terminal half-life (in h); F: oral bioavailability: AUCnorm after intragastral administration divided by AUCnorm after intravenous administration (in %).

Assay 16

In Vivo Pharmacokinetics in Mouse

For in vivo pharmacokinetic experiments test compounds were administered to female CD1 mouse intravenously at doses of 0.3 to 1 mg/kg formulated as solutions using solubilizers such as PEG400 in well-tolerated amounts.

For pharmacokinetics after intravenous administration test compounds were given as i.v. bolus and blood samples were taken at 2 min, 5 min, 15 min, 30 min, 1 h, 2 h, 4 h, 7 h, and 24 h after dosing. Blood was collected via a vena jugularis catheter into Lithium-Heparin coated tubes (Eppendorf) and centrifuged for 15 min at 3000 rpm. An aliquot from the supernatant (plasma) was taken and precipitated by addition of 1:10 (v/v) ice cold methanol and frozen at −20° C. over night. Samples were subsequently thawed and centrifuged at 3000 rpm, 4° C. for 20 minutes. Aliquots of the supernatants were taken for analytical testing using an Agilent 1200 HPLC-system with LCMS/MS detection. PK parameters were calculated by non-compartmental analysis using a PK calculation software.

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood. AUCnorm: Area under the concentration-time curve from t=0 h to infinity (extrapolated) divided by the administered dose (in kg*h/L); AUC(0-tlast)norm: Area under the concentration-time curve from t=0 h to the last time point for which plasma concentrations could be measured divided by the administered dose (in kg*h/L); t1/2: terminal half-life (in h); MRT iv (h): mean residence time.

Assay 17

In Vivo Pharmacokinetics in Dog

For in vivo pharmacokinetic experiments test compounds can be administered to Beagle dogs intravenously at doses of 0.3 to 1 mg/kg formulated as solutions using solubilizers such as PEG400 in well-tolerated amounts.

For pharmacokinetics after intravenous administration test compounds are given in in dogs as short term infusion (10 min). Blood samples are taken e.g. at 5 min, 10 min (end of short term infusion), 15 min, 30 min, 1 h, 2 h, 4 h, 6 h, 8 h and 24 h after dosing from the vena saphena. Blood is collected into K-EDTA (Monovetten®, Sarstedt) and centrifuged for 15 min at 3000 rpm. An aliquot of 100 µL from the supernatant (plasma) is taken and precipitated by addition of 400 µL cold acetonitrile and frozen at −20° C. over night. Samples are subsequently thawed and centrifuged at 3000 rpm, 4° C. for 20 minutes. Aliquots of the supernatants are taken for analytical testing using an Agilent HPLC-system with LCMS/MS detection. PK parameters are calculated by non-compartmental analysis using a PK calculation software (e.g. Phoenix WinNonlin®, Certara USA, Inc.).

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood. AUCnorm: Area under the concentration-time curve from t=0 h to infinity (extrapolated) divided by the administered dose (in kg*h/L); AUC(0-tlast)norm: Area under the concentration-time curve from t=0 h to the last time point for which plasma concentrations could be measured divided by the administered dose (in kg*h/L); t1/2: terminal half-life (in h); MRT iv (h): mean residence time.

Assay 18

Assessment of the Anti-Proliferation Effect of Compounds in Tumor Xenografts

The suitability of the compounds of the present invention for the treatment of hyperproliferative disorders can be demonstrated in animal models of the following cancer types: breast cancer; esophageal cancer; liver cancer; lung cancer; lymphoma including non-Hodgkin-lymphoma type, diffuse large B-cell lymphoma subtype including GC-DLBCL* and ABC-DLBCL** subtypes, and mantle cell lymphoma; acute leukemia, acute myeloid leukemia type, acute monocytic leukemia; melanoma; multiple myeloma; melanoma; ovarian cancer; pancreas cancer. For this purpose, human tumor cells of the respective cancer type were injected subcutaneously or intravenously into immunocompromised mice exemplified in FIG. 1, with HL-60 as an example for an AML xenograft model. Once the primary tumor growth was established the animals were then randomized to receive treatment with either compound at maximum tolerated dose or vehicle control for a certain period of time. The difference between those groups in terms of the tumor growth were used to access the treatment efficacy. The principles of such xenograft studies are summarized in Richmond, A.; Su, Y. (2008). "Mouse xenograft models vs GEM models for human cancer therapeutics". Disease Models and Mechanisms 1 (2-3): 78-82. doi: 10.1242/dmm.000976.

The results are reflected in FIG. 1 which shows a comparison of survival of immunocompromised mice intravenously injected with human HL-60 with untreated animals (Vehicle) and groups treated with MCL-1 inhibitor of Example 16 or irinotecan (n=12 animals/group).

The invention claimed is:
1. A compound of general formula (I):

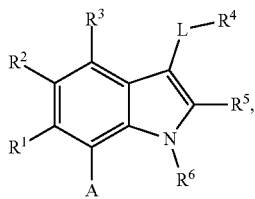

(I)

in which
A is

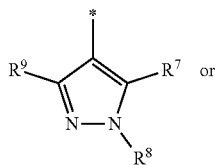

(A1)

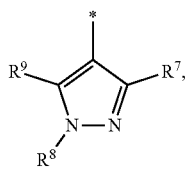

(A2)

wherein $R^6$ and $R^7$, together with two carbon atoms of the pyrazole ring, two carbon atoms of the indole moiety and the nitrogen atom to which $R^6$ is attached, form a 9-membered to 16-membered ring and * is the point of attachment of these moieties to the indole carbon atom bearing the A substituent; or
A is

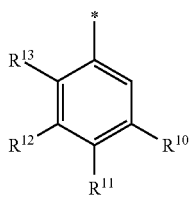

(A3)

wherein optionally one or two of the groups selected from $CR^{11}$, $CR^{12}$ and $CR^{13}$ may be replaced by a nitrogen atom, wherein $R^6$ and $R^{10}$, together with three carbon atoms of the phenyl ring, two carbon atoms of the indole moiety and the nitrogen atom to which $R^6$ is attached, form a 9-membered to 16-membered ring and * is the point of attachment of these moieties to the indole carbon atom bearing the A substituent;
$R^1$ is a chlorine atom;
$R^2$ and $R^3$ are each a hydrogen atom;
$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a C1-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group, and a $C_3$-$C_5$-cycloalkyl group;
L is a group —$(CH_2)_m$-E- wherein any $CH_2$ group is unsubstituted or substituted with one or two substituents and each substituent is independently selected from a halogen atom, a cyano group, a hydroxy group, a $C_1$-$C_3$-alkyl group, and a $C_1$-$C_3$-alkoxy group, or two substituents are optionally taken together with their intervening atoms to form a saturated or partially unsaturated 3-membered to 6-membered cycloalkyl ring, or a 3-membered to 8-membered saturated or partially unsaturated heterocyclic ring having 1-2 heteroatoms independently selected from an oxygen atom, a sulfur atom, a —S(O)— group, a —S(O)$_2$— group, and a —$NR^{14}$— group;
E is a bond, an oxygen atom, a sulfur atom, a —S(O)— group, a —S(O)$_2$— group or a —$NR^{14}$— group and constitutes the connecting element to $R^4$;
m is 2, 3, or 4;
$R^5$ is selected from a COOH group, a

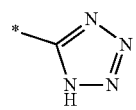

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$($CH_2$)$_s$NHCO($C_1$-$C_6$-alkyl) group, a —C(O)—NHS(O)$_2$($CH_2$)$_s$NHCO($C_3$-$C_6$-cycloalkyl) group, and a —C(O)—NHS(O)$_2$($CH_2$)$_s$NHCO(aryl) group;
—$R^6$-$R^7$— is selected from $^{\#}$—$(CH_2)_n$—(B)$_t$—$(CH_2)_p$—X—$^{\#\#}$, $^{\#}$—($C_2$-$C_6$-alkenylene)-(B)$_t$—$(CH_2)_p$—X—$^{\#\#}$, $^{\#}$—$(CH_2)_n$—(B)$_t$—($C_2$-$C_5$-alkenylene)-X—$^{\#\#}$, and $^{\#}$—$(CH_2)_q$—(B)—$(CH_2)_r$—(B)—$(CH_2)_v$—X—$^{\#\#}$,
wherein $^{\#}$ is the point of attachment with the indole nitrogen atom and $^{\#\#}$ is the point of attachment with the pyrazole carbon atom bearing the $R^7$ substituent; and wherein one or more —CH$_2$— groups may be unsubstituted or substituted with one or more substituents independently selected from a halogen atom, a hydroxy group, a NR$^{16}$R$^{17}$ group, a C$_1$-C$_3$-alkyl group, a C$_1$-C$_3$-haloalkyl group, a C$_1$-C$_3$-alkoxy group, a C$_1$-C$_3$-haloalkoxy group, a C$_3$-C$_6$-cycloalkyl group, and a (heterocycloalkyl)-(C$_1$-C$_3$-alkylene)- group, and wherein optionally, if two such substituents are bound to the same atom, they may form together a 3-membered to 6-membered spiro ring, and wherein a —CH=CH— group in any alkenylene can be replaced by a 1,2-(C$_3$-C$_5$)cycloalkylene group which is unsubstituted or substituted one or two times with a halogen atom or a C$_1$-C$_2$-alkyl group; and where X is an unsubstituted —CH$_2$— group;

—R$^6$-R$^{10}$— is selected from $^{\#}$—(CH$_2$)$_n$—(B)$_t$—(CH$_2$)$_p$—X—$^{\#\#}$, $^{\#}$—(C$_2$-C$_6$-alkenylene)-(B)$_t$—(CH$_2$)$_p$—X—$^{\#\#}$, $^{\#}$—(CH$_2$)$_n$—(B)$_t$—(C$_2$-C$_5$-alkenylene)-X—$^{\#\#}$, and $^{\#}$—(CH$_2$)$_q$—(B)—(CH$_2$)$_r$—(B)—(CH$_2$)$_v$—X—$^{\#\#}$, wherein $^{\#}$ is the point of attachment with the indole nitrogen atom and $^{\#\#}$ is the point of attachment with the carbon atom of the phenyl moiety bearing the R$^{10}$ substituent, wherein one or more —CH$_2$— groups may be unsubstituted or substituted with one or more substituents independently selected from a halogen atom, a hydroxy group, a NR$^{16}$R$^{17}$ group, a C$_1$-C$_3$-alkyl group, a C$_1$-C$_3$-haloalkyl group, a C$_1$-C$_3$-alkoxy group, a C$_1$-C$_3$-haloalkoxy group, a C$_3$-C$_6$-cycloalkyl group, and a (heterocycloalkyl)-(C$_1$-C$_3$-alkylene)- group, wherein a double bond in any alkenylene can be replaced by a 1,2-(C$_1$-C$_6$)cycloalkyl group which is unsubstituted or substituted one or two times with a halogen atom or a C$_1$-C$_2$-alkyl group, and where X is an unsubstituted —CH$_2$— group;

n is 2, 3, 4, 5, 6, 7, 8, or 9;

t is 0 or 1;

p is 0, 1, 2, 3, 4, or 5;

q is 2, 3, 4, 5, or 6;

r is 2, 3, 4, 5, or 6;

v is 0, or 1;

s is 0, 1, 2, or 3;

wherein the integers selected for variables n, t, p, q, r, and v result in forming a 9-membered to 16-membered ring independently from the selection of variable A1, A2 or A3;

B is independently selected from a —C(O)NR$^{15}$— group, a —NR$^{15}$C(O)— group, a —N(R$^{15}$)— group, a —N(R$^{15}$)—C(=O)—N(R$^{15}$)— group, a —O—C(=O)—N(R$^{15}$)— group, a —N(R$^{15}$)—C(=O)—O— group, —O—, —S—, —S(O)—, and —S(O)$_2$—;

R$^8$ is selected from a hydrogen atom,
 a C$_1$-C$_6$-alkyl group, which is unsubstituted or substituted with one or more substituents independently selected from a halogen atom, a hydroxy group, a C$_1$-C$_3$-alkoxy group, a C$_1$-C$_3$-haloalkoxy group, a C$_3$-C$_6$-cycloalkyl group, a heterocycloalkyl group, and a NR$^{20}$R$^{21}$ group;
 a C$_1$-C$_3$-haloalkyl group,
 a C$_3$-C$_6$-cycloalkyl group, and
 a C$_1$-C$_6$-alkyl group in which one or two not directly adjacent carbon atoms are independently replaced by a hetero atom selected from —O— and —NH— and R$^9$ is selected from a hydrogen atom,
 a C$_1$-C$_4$-alkyl group,
 a C$_1$-C$_3$-hydroxyalkyl group,
 a C$_1$-C$_4$-haloalkyl group,
 a C$_1$-C$_4$-haloalkyl-NH—C(O)—O—(C$_1$-C$_3$-alkylene)- group,
 a C$_2$-C$_6$-haloalkenyl group,
 a C$_1$-C$_6$-alkyl-O— group,
 a C$_1$-C$_4$-haloalkoxy group,
 a C$_1$-C$_6$-alkyl-O—(C$_1$-C$_3$-alkylene)- group,
 a (C$_3$-C$_7$)-cycloalkyl group,
 a (C$_3$-C$_7$)-cycloalkyl-O—(C$_1$-C$_3$-alkylene)- group,
 a phenyl-O—(C$_1$-C$_3$-alkylene)- group,
 a phenyl-(C$_1$-C$_3$-alkylene)-O—(C$_1$-C$_3$-alkylene)- group,
 a R$^{18}$-(phenylene)-(C$_1$-C$_3$-alkylene)-O—(C$_1$-C$_3$-alkylene)- group,
 a R$^{18}$-(phenylene)-O—(C$_1$-C$_3$-alkylene)- group,
 a R$^{18}$-(phenylene)-(heteroarylene)-O—(C$_1$-C$_3$-alkylene) group,
 a (R$^{18}$)-(heterocycloalkylene)-(C$_1$-C$_3$-alkylene)- group,
 a (R$^{18}$)-(heterocycloalkylene)-(phenylene)-O—(C$_1$-C$_3$-alkylene)- group,
 a (heterocycloalkenyl)-(phenylene)-O—(C$_1$-C$_3$-alkylene)- group,
 a (R$^{18}$)-(heteroarylene)-(C$_1$-C$_3$-alkylene)-O—(C$_1$-C$_3$-alkylene)- group,
 a (R$^{18}$)-(heteroarylene)-(phenylene)-O—(C$_1$-C$_3$-alkylene)- group,
 a (R$^{19}$)—S(O)$_2$-(phenylene)-O—(C$_1$-C$_3$-alkylene)- group,
 a (R$^{19}$)—S(O)$_2$—NH-(phenylene)-O—(C$_1$-C$_3$-alkylene)- group,
 a (R$^{19}$)—S(O)$_2$—NH-(phenylene)-O—(C$_1$-C$_3$-alkylene)- group,
 a (R$^{19}$)—S(O)$_2$—N(C$_1$-C$_6$-alkyl)-(phenylene)-O—(C$_1$-C$_3$-alkylene)- group,
 a (R$^{19}$)—S(O)$_2$-(heterocycloalkylene)-(phenylene)-O—(C$_1$-C$_3$-alkylene)- group,
 a (R$^{18}$)-(heterocycloalkylene)-(heteroarylene)-O—(C$_1$-C$_3$-alkylene)- group,
 a (R$^{19}$)-(heteroarylene)-O—(C$_1$-C$_3$-alkylene)- group,
 a (R$^{18}$)-(heteroarylene)-O—(C$_1$-C$_3$-alkylene)- group,
 a (R$^{19}$)—S(O)$_2$-(heteroarylene)-O—(C$_1$-C$_3$-alkylene)- group,
 a (R$^{19}$)—S(O)$_2$-(heterocycloalkylene)-(heteroarylene)-O—(C$_1$-C$_3$-alkylene)- group,
 a NR$^{20}$R$^{21}$—(C$_1$-C$_3$-alkylene)- group,
 a (C$_1$-C$_3$-alkyl)-NH—(C$_1$-C$_3$-alkylene)- group,
 a (C$_1$-C$_3$-haloalkyl)-(C$_1$-C$_3$-alkylene)-NH—(C$_1$-C$_3$-alkylene)- group,
 a (C$_1$-C$_3$-haloalkyl)-NH—(C$_1$-C$_3$-alkylene)- group,
 a (C$_1$-C$_3$-alkyl)-NH—C(O)—(C$_1$-C$_3$-alkylene)- group,
 a (C$_1$-C$_3$-alkyl)-NR$^{15}$—C(O)—(C$_1$-C$_3$-alkylene)- group,
 a (C$_1$-C$_3$-alkyl)-C(O)—NH—(C$_1$-C$_3$-alkylene)- group,
 a (C$_1$-C$_3$-alkyl)-C(O)—NR$^{15}$—(C$_1$-C$_3$-alkylene)- group,
 a

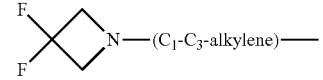

group, and a

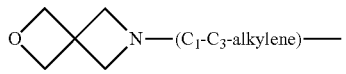

group, wherein the phenyl ring is unsubstituted or substituted with a halogen atom, a hydroxy group, or a $C_1$-$C_3$-alkoxy group and the heterocycloalkyl group is unsubstituted or substituted with an oxo (=O) group or is unsubstituted or substituted with one or more substituents independently selected from a halogen atom, a hydroxy group, a $C_1$-$C_3$-alkyl group, and a $C_1$-$C_3$-alkoxy group, or $R^8$ and $R^9$ together form a 5-membered or 6-membered ring optionally containing one or two heteroatoms selected from —O—, and —$NR^{14}$—;

$R^{11}$ and $R^{13}$ are each independently selected from a hydrogen atom, a halogen atom, a $C_1$-$C_3$-alkyl group, and a $C_1$-$C_3$-alkoxy group;

$R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group, and a $NR^{16}R^{17}$ group;

$R^{14}$ is a hydrogen atom or a $C_1$-$C_3$-alkyl group;

$R^{15}$ is independently selected from a hydrogen atom,
a $C_1$-$C_6$-alkyl group
which is unsubstituted or substituted with one or more substituents selected from a halogen atom, a hydroxy group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a ($C_1$-$C_3$-alkyl)-C(O)—O— group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$-(heterocycloalkylene)-(arylene)-O— group, an (aryl)-(heteroarylene)-O— group, and an (aryl)-(heteroarylene)-O—($C_1$-$C_3$-alkylene)- group;
a $C_1$-$C_3$-alkoxy-($C_1$-$C_6$-alkylene)-O—C(O)— group,
a heterocycloalkyl-($C_1$-$C_6$-alkylene)-O—C(O)— group,
a phenyl group,
a group

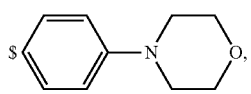

a group

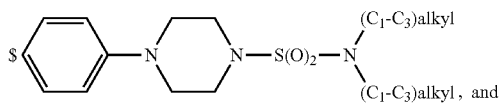

a group

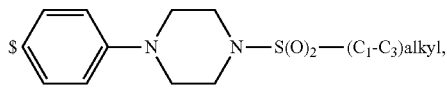

wherein $ is the point of attachment to the nitrogen atom, to which $R^{15}$ is attached;

$R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group, and a $C_1$-$C_3$-alkyl-O—C(=O)— group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a C(O)OR$^{21}$—($C_1$-$C_3$-alkylene)- group, a —C(O)OR$^{21}$ group, a —C(O)NR$^{20}$R$^{21}$ group, a ($C_1$-$C_3$-alkyl)-O—($C_1$-$C_3$-alkylene)-C(O)— group, a ($C_1$-$C_6$-alkyl)-C(O)— group, and a $C_3$-$C_6$-cycloalkyl-C(O)— group;

$R^{19}$ is selected from a $C_1$-$C_3$-alkyl group, a $C_3$-$C_6$-cycloalkyl group, and a NR$^{20}$R$^{21}$ group; and $R^{20}$ and $R^{21}$ are each independently selected from a hydrogen atom or a $C_1$-$C_6$-alkyl group;

or a tautomer, an N-oxide, or a salt thereof, or a salt of a tautomer, or a salt of an N-oxide, or a mixture of same.

2. The compound of general formula (I) according to claim 1, wherein

A is

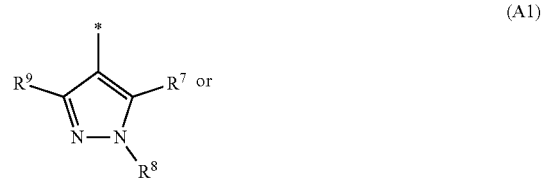

(A1)

(A2)

wherein $R^6$ and $R^7$, together with two carbon atoms of the pyrazole ring, two carbon atoms of the indole moiety and the nitrogen atom to which $R^6$ is attached, form a 9-membered to 16-membered ring and * is the point of attachment of these moieties to the indole carbon atom bearing the A substituent;

$R^1$ is a chlorine atom;

$R^2$ and $R^3$ are each a hydrogen atom;

$R^4$ is selected from an aryl group and a heteroaryl group, each of which is unsubstituted or substituted with one, two, or three, substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, and a ($C_1$-$C_3$)-haloalkyl-S— group, and a $C_3$-$C_5$-cycloalkyl group;

L is a group —(CH$_2$)$_m$-E- wherein any CH$_2$ group is unsubstituted or substituted with one or two substituents and each substituent is independently selected from a halogen atom, a cyano group, a hydroxy group, a $C_1$-$C_3$-alkyl group and a $C_1$-$C_3$-alkoxy group, or two substituents are optionally taken together with their intervening atoms to form a saturated or partially unsaturated 3-membered to 6-membered cycloalkyl ring, or a 3-membered to 8-membered saturated or partially unsaturated heterocyclic ring having 1-2 heteroatoms independently selected from an oxygen atom, a sulfur atom, a —S(O)— group, a —S(O)$_2$— group, and a —NR$^{14}$— group;

E is a bond, an oxygen atom, a sulfur atom, a —S(O)— group, a —S(O)$_2$— group, or a —NR$^{14}$— group and constitutes the connecting element to R$^4$;

m is 2, 3, or 4;

R$^5$ is selected from a COOH group, a

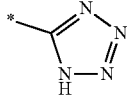

group, a —C(O)—NHS(O)$_2$(C$_1$-C$_6$-alkyl) group, a —C(O)—NHS(O)$_2$(C$_3$-C$_6$-cycloalkyl) group, a —C(O)—NHS(O)$_2$(aryl) group, a —C(O)—NHS(O)$_2$(CH$_2$)$_s$NHCO (C$_1$-C$_6$-alkyl) group, a —C(O)—NHS(O)$_2$(CH$_2$)$_s$NHCO (C$_3$-C$_6$-cycloalkyl) group and a —C(O)—NHS(O)$_2$ (CH$_2$)$_s$NHCO(aryl) group;

—R$^6$-R$^7$— is selected from $^{\#}$—(CH$_2$)$_n$—(B)$_t$—(CH$_2$)$_p$—X—$^{\#\#}$, $^{\#}$—(C$_2$-C$_6$-alkenylene)-(B)$_t$—(CH$_2$)$_p$—X—$^{\#\#}$, $^{\#}$—(CH$_2$)$_n$—(B)$_t$—(C$_2$-C$_5$-alkenylene)-X—$^{\#\#}$, and $^{\#}$—(CH$_2$)$_q$—(B)—(CH$_2$)$_r$—(B)—(CH$_2$)$_v$—X—$^{\#\#}$, wherein $^{\#}$ is the point of attachment with the indole nitrogen atom and $^{\#\#}$ is the point of attachment with the pyrazole carbon atom bearing the R$^7$ substituent; and wherein one or more —CH$_2$— groups may be unsubstituted or substituted with one or more substituents independently selected from a halogen atom, a hydroxy group, a NR$^{16}$R$^{17}$ group, a C$_1$-C$_3$-alkyl group, a C$_1$-C$_3$-haloalkyl group, a C$_1$-C$_3$-alkoxy group, and a C$_1$-C$_3$-haloalkoxy group, and wherein optionally if two such substituents are bound to the same atom they may form together a 3-membered to 6-membered spiro ring, and wherein a —CH=CH— group in any alkenylene can be replaced by a 1,2-(C$_3$-C$_5$)cycloalkylene group which is unsubstituted or substituted one or two times with a halogen atom or a C$_1$-C$_2$-alkyl group, and where X is an unsubstituted —CH$_2$— group;

n is 2, 3, 4, 5, 6, 7, 8, or 9;

p is 0, 1, 2, 3, 4, or 5;

t is 0 or 1;

s is 0, 1, 2, or 3;

wherein the integers selected for variables n, t, and p result in forming a 9-membered to 16-membered ring independently from the selection of variable A1 or A2;

B is independently selected from a —C(O)NR$^{15}$— group, a —NR$^{15}$C(O)— group, a —N(R$^{15}$)— group, a —N(R$^{15}$)—C(=O)—N(R$^{15}$)— group, a —O—C(=O)—N(R$^{15}$)— group, a —N(R$^{15}$)—C(=O)—O— group, —O—, —S—, —S(O)—, and —S(O)$_2$—;

R$^8$ is selected from a hydrogen atom, a C$_1$-C$_6$-alkyl group, which is unsubstituted or substituted with one or more substituents independently selected from a halogen atom, a hydroxy group, a C$_1$-C$_3$-alkoxy group, a C$_1$-C$_3$-haloalkoxy group, a C$_3$-C$_6$-cycloalkyl group, a heterocycloalkyl group, and a NR$^{20}$R$^{21}$ group and R$^9$ is selected from a hydrogen atom, a C$_1$-C$_4$-alkyl group, a C$_1$-C$_3$-hydroxyalkyl group, a C$_1$-C$_4$-haloalkyl group, a C$_1$-C$_4$-haloalkyl-NH—C(O)—O—(C$_1$-C$_3$-alkylene)- group, a C$_2$-C$_6$-haloalkenyl group, a C$_1$-C$_6$-alkyl-O-group, a C$_1$-C$_4$-haloalkoxy group, a C$_1$-C$_6$-alkyl-O—(C$_1$-C$_3$-alkylene)- group, a (C$_3$-C$_7$)-cycloalkyl group, a (C$_3$-C$_7$-cycloalkyl)-O—(C$_1$-C$_3$-alkylene)- group, a phenyl-O—(C$_1$-C$_3$-alkylene)- group, a phenyl-(C$_1$-C$_3$-alkylene)-O—(C$_1$-C$_3$-alkylene)- group, a (R$^{18}$)-(phenylene)-O—(C$_1$-C$_3$-alkylene)- group, a (R$^{18}$)-(phenylene)-(C$_1$-C$_3$-alkylene)-O—(C$_1$-C$_3$-alkylene)- group, a (R$^{18}$)-(phenylene)-(heteroarylene)-O—(C$_1$-C$_3$-alkylene) group, a (R$^{18}$)-(heterocycloalkylene)-(C$_1$-C$_6$-alkylene)- group, a (R$^{18}$)-(heterocycloalkylene)-(phenylene)-O—(C$_1$-C$_3$-alkylene)- group, a (heterocycloalkenyl)-(phenylene)-O—(C$_1$-C$_3$-alkylene)- group, a (R$^{18}$)-(heteroarylene)-(C$_1$-C$_3$-alkylene)-O—(C$_1$-C$_3$-alkylene)- group, a (R$^{18}$)-(heteroarylene)-(phenylene)-O—(C$_1$-C$_3$-alkylene)- group, a (R$^{18}$)-(phenylene)-(C$_1$-C$_3$-alkylene)-O—(C$_1$-C$_3$-alkylene)- group, a (R$^{19}$)—S(O)$_2$-(phenylene)-O—(C$_1$-C$_3$-alkylene)- group, a (R$^{19}$)—S(O)$_2$—NH-(phenylene)-O—(C$_1$-C$_3$-alkylene)- group, a (R$^{19}$)—S(O)$_2$—N(C$_1$-C$_6$-alkyl)-(phenylene)-O—(C$_1$-C$_3$-alkylene)- group, a (R$^{19}$)—S(O)$_2$-(heterocycloalkylene)-(phenylene)-O—(C$_1$-C$_3$-alkylene)- group, a (R$^{18}$)-(heterocycloalkylene)-(heteroarylene)-O—(C$_1$-C$_3$-alkylene)- group, a (R$^{19}$)-(heteroarylene)-O—(C$_1$-C$_3$-alkylene)- group, a (R$^{19}$)—S(O)$_2$-(heteroarylene)-O—(C$_1$-C$_3$-alkylene)- group, a (R$^{19}$)—S(O)$_2$-(heterocycloalkylene)-(heteroarylene)-O—(C$_1$-C$_3$-alkylene)- group, a NR$^{20}$R$^{21}$—(C$_1$-C$_3$-alkylene)- group, a (C$_1$-C$_3$-alkyl)-NH—(C$_1$-C$_3$-alkylene)- group, a (C$_1$-C$_3$-haloalkyl)-(C$_1$-C$_3$-alkylene)-NH—(C$_1$-C$_3$-alkylene)- group, a (C$_1$-C$_3$-haloalkyl)-NH—(C$_1$-C$_3$-alkylene)- group, a (C$_1$-C$_3$-alkyl)-NH—C(O)—(C$_1$-C$_3$-alkylene)- group, a (C$_1$-C$_3$-alkyl)-NR$^{15}$—C(O)—(C$_1$-C$_3$-alkylene)- group, a (C$_1$-C$_3$-alkyl)-C(O)—NH—(C$_1$-C$_3$-alkylene)- group, a (C$_1$-C$_3$-alkyl)-C(O)—NR$^{15}$—(C$_1$-C$_3$-alkylene)- group, a

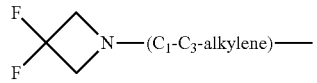

group, and a

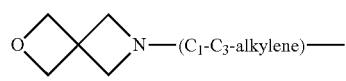

group, wherein the phenyl ring is optionally substituted with a halogen atom, a hydroxy group, or a $C_1$-$C_3$-alkoxy group and the heterocycloalkyl group is optionally substituted with an oxo (=O) group or is optionally substituted with one or more substituents independently selected from a halogen atom, and a $C_1$-$C_3$-alkyl group, or $R^8$ and $R^9$ together form a 5-membered or 6-membered ring optionally containing one or two heteroatoms selected from of —O—, and —$NR^{14}$—;

$R^{14}$ is a hydrogen atom or a $C_1$-$C_3$-alkyl group;

$R^{15}$ is independently selected from a hydrogen atom,
a $C_1$-$C_6$-alkyl group
which is optionally substituted with one or more substituents selected from a halogen atom, a hydroxy group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a ($C_1$-$C_3$-alkyl)-C(O)—O— group, a heterocycloalkyl group, an aryl group, a ($R^{18}$)-(heterocycloalkylene)-(arylene)-O— group, an aryl-O— group, an aryl-($C_1$-$C_3$-alkylene)-O— group, a ($R^{19}$)—S(O)$_2$— arylene-O— group, a ($R^{19}$)S(O)$_2$-heterocycloalkylene-arylene-O— group, and an aryl-heteroarylene-O— group;

a $C_1$-$C_3$-alkoxy-($C_1$-$C_6$-alkylene)-O—C(O)— group,
a heterocycloalkyl-($C_1$-$C_6$-alkylene)-O—C(O)— group,
a phenyl group,
a group

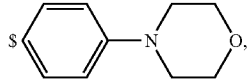

a group

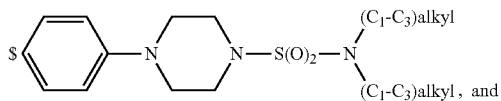

a group

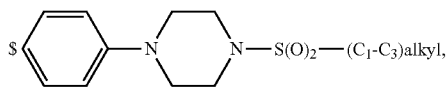

wherein $ is the point of attachment to the nitrogen atom, to which $R^{15}$ is attached, $R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group, and a $C_1$-$C_3$-alkyl-O—C(=O)— group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a C(O)O$R^{21}$—($C_1$-$C_3$-alkylene)- group, a —C(O)O$R^{21}$ group, a —C(O)N$R^{20}R^{21}$ group, a ($C_1$-$C_3$-alkyl)-O—($C_1$-$C_3$-alkylene)-C(O)— group, a ($C_1$-$C_6$-alkyl)-C(O)-group, and a $C_3$-$C_6$-cycloalkyl-C(O)— group;

$R^{19}$ is selected from a $C_1$-$C_3$-alkyl group, a $C_3$-$C_6$-cycloalkyl group, and a N$R^{20}R^{21}$ group; and $R^{20}$ and $R^{21}$ are each independently selected from a hydrogen atom or a $C_1$-$C_6$-alkyl group;

or a tautomer, an N-oxide, or a salt thereof, or a salt of a tautomer, or a salt of an N-oxide, or a mixture of same.

3. The compound of general formula (I) according to claim 1,
in which
A is

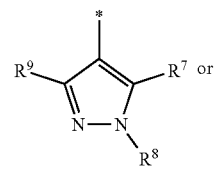

(A1)

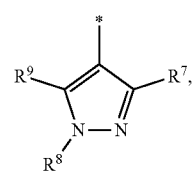

(A2)

wherein $R^6$ and $R^7$, together with two carbon atoms of the pyrazole ring, two carbon atoms of the indole moiety and the nitrogen atom to which $R^6$ is attached, form a 10-membered to 12-membered ring and * is the point of attachment of these moieties to the indole carbon atom bearing the A substituent;

$R^1$ is a chlorine atom;

$R^2$ and $R^3$ are each a hydrogen atom;

$R^4$ is selected from an aryl group and a heteroaryl group, each of which is unsubstituted or substituted with one, two, or three, substituents and each substituent is independently selected from a halogen atom, a $C_1$-$C_3$-alkyl group, and a $C_1$-$C_3$-haloalkyl group;

L is a group —(CH$_2$)$_m$-E-;

E is a bond or an oxygen atom and constitutes the connecting element to $R^4$;

m is 2, 3, or 4;

$R^5$ is a COOH group;

—$R^6$-$R^7$— is selected from $^\#$—(CH$_2$)$_n$—(B)$_t$—(CH$_2$)$_p$—X—$^{\#\#}$, and $^\#$—(C$_2$-C$_6$-alkenylene)-(B)$_t$—(CH$_2$)$_p$—X—$^{\#\#}$, wherein $^\#$ is the point of attachment with the indole nitrogen atom and $^{\#\#}$ is the point of attachment with the pyrazole carbon atom bearing the $R^7$ substituent; and wherein one or more —CH$_2$— groups may be unsubstituted or substituted with one or more substituents independently selected from a halogen atom, a hydroxy group, a N$R^{16}R^{17}$ group, a $C_1$-$C_3$-alkyl group, a $C_1$-$C_3$-haloalkyl group, and a $C_1$-$C_3$-alkoxy group, and wherein optionally if two such substituents are bound to the same atom they may form together a 3-membered to 6-membered spiro ring wherein a —CH=CH— group in any alkenylene can be replaced by a 1,2-($C_3$-$C_5$)cycloalkylene group which is unsubstituted or substituted one or two times with a halogen atom or a $C_1$-$C_2$-alkyl group, and wherein X is an unsubstituted —CH$_2$— group;
n is 3, 4, 5, or 6;
t is 0 or 1;
p is 0;
wherein the integers selected for variables n, t, and p result in forming a 10-membered to 12-membered ring independently from the selection of variable A1 or A2;
B is independently selected from a —N(R$^{15}$)— group and —O— group;
R$^8$ is selected from a hydrogen atom and,
 a C$_1$-C$_4$-alkyl group, which is unsubstituted or substituted with one or more substituents independently selected from a halogen atom, a hydroxy group, a C$_1$-C$_3$-alkoxy group, a C$_1$-C$_3$-haloalkoxy group, a C$_3$-C$_6$-cycloalkyl group, a heterocycloalkyl group, and a NR$^{20}$R$^{21}$ group and
R$^9$ is selected from a hydrogen atom,
 a C$_1$-C$_4$-alkyl group,
 a C$_1$-C$_3$-hydroxyalkyl group,
 a C$_1$-C$_4$-haloalkyl group,
 a C$_2$-C$_6$-haloalkenyl group,
 a C$_1$-C$_6$-alkyl-O—(C$_1$-C$_3$-alkylene)- group,
 a (C$_3$-C$_7$-cycloalkyl) group,
 a phenyl-O—(C$_1$-C$_3$-alkylene)- group,
 a (R$^{18}$)-(phenylene)-O—(C$_1$-C$_3$-alkylene)- group,
 a (R$^{18}$)-(heterocycloalkylene)-(C$_1$-C$_3$-alkylene)- group,
 a (R$^{18}$)-(heteroarylene)-O—(C$_1$-C$_3$-alkylene)- group,
 a (R$^{19}$)—S(O)$_2$-(heteroarylene)-O—(C$_1$-C$_3$-alkylene)- group,
 a NR$^{20}$R$^{21}$—(C$_1$-C$_3$-alkylene)- group, and
 a (C$_1$-C$_3$-alkyl)-NH—(C$_1$-C$_3$-alkylene)- group,
 wherein the phenyl group is unsubstituted or substituted with a halogen atom, a hydroxy group, or a C$_1$-C$_3$-alkoxy group and
 the heterocycloalkylene group is unsubstituted or substituted with a substituent independently selected from an oxo (=O) group and a C$_1$-C$_3$-alkyl group, or
R$^8$ and R$^9$ together form a 6-membered ring optionally containing one or two oxygen atoms;
R$^{15}$ is selected from a hydrogen atom,
 a C$_1$-C$_5$-alkyl group, which is optionally substituted with one or more substituents selected from a halogen atom, a hydroxy group, a C$_1$-C$_3$-alkyl group, a C$_1$-C$_3$-haloalkyl group, a C$_1$-C$_3$-hydroxyalkyl group, a C$_1$-C$_3$-alkoxy group, a (C$_1$-C$_3$-alkyl)-C(O)—O— group, a heterocycloalkyl group, a phenyl group, and a benzyl group;
 a C$_1$-C$_3$-alkoxy-(C$_1$-C$_6$-alkylene)-O—C(O)— group,
 a heterocycloalkyl-(C$_1$-C$_6$-alkylene)-O—C(O)— group,
 a phenyl group,
 a group

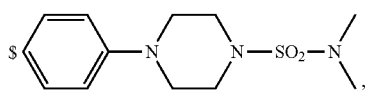

a group

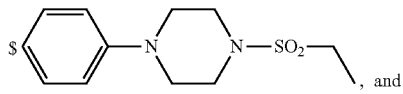

a group

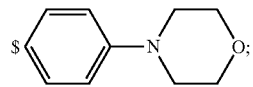

R$^{16}$ and R$^{17}$ are each independently selected from a hydrogen atom, a C$_1$-C$_6$-alkyl group, and a C$_1$-C$_6$-haloalkyl group;
R$^{18}$ is selected from a hydrogen atom, a hydroxy group, a cyano group, a C$_1$-C$_3$-alkyl group, a C$_1$-C$_6$-hydroxyalkyl group, a C$_1$-C$_3$-alkoxy group, a C(O)OR$^{21}$—(C$_1$-C$_3$-alkylene)- group, a —C(O)OR$^{21}$ group, a —C(O)NR$^{20}$R$^{21}$ group, a (C$_1$-C$_3$-alkyl)-O—(C$_1$-C$_3$-alkylene)-C(O)— group, a (C$_1$-C$_3$-alkyl)-C(O)-group, and a C$_3$-C$_6$-cycloalkyl-C(O)— group;
R$^{19}$ is selected from a C$_1$-C$_3$-alkyl group, a C$_3$-C$_6$-cycloalkyl group, and a NR$^{20}$R$^{21}$ group; and
R$^{20}$ and R$^{21}$ are each independently selected from a hydrogen atom and a C$_1$-C$_3$-alkyl group;
 or a tautomer, an N-oxide, or a salt thereof, or a salt of a tautomer, or a salt of an N-oxide, or a mixture of same.

4. The compound of general formula (I) according to claim 1, wherein
A is

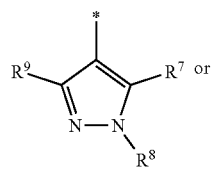

(A1)

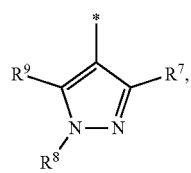

(A2)

wherein R$^6$ and R$^7$, together with two carbon atoms of the pyrazole ring, two carbon atoms of the indole moiety and the nitrogen atom to which R$^6$ is attached, form a 10-membered or 11-membered ring and * is the point of attachment of these moieties to the indole carbon atom bearing the A substituent;
R$^1$ is a chlorine atom;
R$^2$ and R$^3$ are each a hydrogen atom;
R$^4$ is an aryl group which is unsubstituted or substituted with a halogen atom;
L is a group —(CH$_2$)$_m$-E-;
E is an oxygen atom and constitutes the connecting element to R$^4$;
m is 3;
R$^5$ is a COOH group;
—R$^6$-R$^7$— is selected from $^{\#}$—(CH$_2$)$_n$—(B)$_t$—(CH$_2$)$_p$—X—$^{\#\#}$ and $^{\#}$—(C$_2$-C$_6$-alkenylene)-(B)$_t$—(CH$_2$)$_p$—X—$^{\#\#}$, and
 wherein $^{\#}$ is the point of attachment with the indole nitrogen atom and $^{\#\#}$ is the point of attachment with the pyrazole carbon atom bearing the R$^7$ substituent and
 wherein one or more —CH$_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, and a $C_1$-$C_3$-alkoxy group, and wherein optionally if two such substituents are bound to the same atom they may form together a 3-membered to 6-membered spiro ring, and wherein a —CH═CH— group in any alkenylene can be replaced by a 1,2-($C_3$-$C_5$)cycloalkylene group and where X is an unsubstituted —$CH_2$— group;
n is 3 or 4;
t is 1;
p is 0;

wherein the integers selected for variables n, t, and p result in forming a 10-membered to 11-membered ring independently from the selection of variable A1 or A2;

B is independently selected from —O— and —$N(R^{15})$—;
$R^8$ is selected from a hydrogen atom and
a $C_1$-$C_4$-alkyl group, which is unsubstituted or substituted with one or more substituents independently selected from a halogen atom, a hydroxy group, a $C_3$-$C_6$-cycloalkyl group, and a heterocycloalkyl group;

$R^9$ is selected from a $C_1$-$C_4$-alkyl group,
a $C_1$-$C_3$-hydroxyalkyl group,
a $C_1$-$C_3$-haloalkyl group,
a $C_1$-$C_3$-alkyl-O— group,
a $C_1$-$C_3$-haloalkoxy group,
a $C_1$-$C_3$-alkyl-O—($C_1$-$C_3$-alkylene)- group,
a ($C_3$-$C_6$)-cycloalkyl group,
a $R^{18}$-(phenylene)-O—($C_1$-$C_3$-alkylene)- group,
a $NR^{20}R^{21}$—($C_1$-$C_3$-alkylene)- group, and
a ($C_1$-$C_3$-alkyl)-NH—($C_1$-$C_3$-alkylene)- group;

$R^{15}$ is selected from a hydrogen atom, a $C_1$-$C_3$-alkyl group, a $C_1$-$C_3$-haloalkyl group, a $C_1$-$C_5$-hydroxyalkyl group, a ($C_1$-$C_3$-alkyoxy)-($C_1$-$C_3$-alkylene)- group, a ($C_1$-$C_3$-alkyl)-C(O)—O—($C_1$-$C_4$)alkylene- group, a ($C_1$-$C_3$-alkyoxy)-($C_1$-$C_3$-alkylene)-O—C(O)— group, a heterocycloalkyl-($C_1$-$C_3$-alkylene)-O—C(O)— group, and a heterocycloalkyl-($C_1$-$C_3$-alkylene)- group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a —$C(O)OR^{21}$ group, a —$C(O)NR^{20}R^{21}$ group, and a ($C_1$-$C_6$-alkyl)-C(O)-group; and $R^{20}$ and $R^{21}$ are each independently selected from a hydrogen atom and a $C_1$-$C_3$-alkyl group;
or a tautomer, or a salt thereof or a salt of a tautomer or a mixture of same.

5. The compound of general formula (I) according to claim 1, wherein
A is

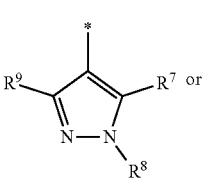
(A1)

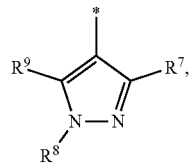
(A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is a chlorine atom;
$R^2$ and $R^3$ are each a hydrogen atom;
$R^4$ is a naphthyl group, which is unsubstituted or substituted with a halogen atom;
L is a group —$(CH_2)_3$—O—;
$R^5$ is a COOH group;
$R^6$-$R^7$— is selected from $^{\#}$—$(CH_2)_n$—(B)$_t$—$(CH_2)_p$—X—$^{\#\#}$ and $^{\#}$—($C_2$-$C_6$-alkenylene)-(B)$_t$—$(CH_2)_p$—X—$^{\#\#}$, and wherein $^{\#}$ is the point of attachment with the indole nitrogen atom and $^{\#\#}$ is the point of attachment with the pyrazole carbon atom bearing the $R^7$ substituent and wherein one or more —$CH_2$— groups may be unsubstituted or substituted with one or more halogen atoms or a hydroxy group, and wherein a —CH═CH— group in any alkenylene can be replaced by a

group or a

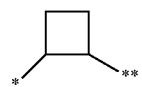

group wherein * is the point of attachment of the ring to the adjacent —$CH_2$— group or to the indole nitrogen atom and ** is the point of attachment to the adjacent —$CH_2$— group or to —(B)$_t$— and wherein optionally if two such substituents are bound to the same atom they may form together a 3-membered to 6-membered spiro ring, and where X is an unsubstituted —$CH_2$— group;
n is 4;
t is 1;
p is 0;

wherein the integers selected for variables n, t, and p result in forming a 11-membered ring independently from the selection of variable A1 or A2;

B is independently selected from —O— and —$N(R^{15})$—;
$R^8$ is a $C_1$-$C_3$-alkyl group, which is unsubstituted or substituted with a heterocycloalkyl group;
$R^9$ is a $C_1$-$C_3$-alkyl group;
$R^{15}$ is selected from a hydrogen atom, a $C_1$-$C_3$-alkyl group, a $C_1$-$C_3$-haloalkyl group, a $C_1$-$C_5$-hydroxyalkyl group, a ($C_1$-$C_3$-alkyoxy)-($C_1$-$C_3$-alkylene)- group, a (C₁-C₃-alkyl)-C(O)—O—(C₁-C₄)alkylene- group, a (C₁-C₃-alkyoxy)-(C₁-C₃-alkylene)-O—C(O)— group, a heterocycloalkyl-(C₁-C₃-alkylene)-O—C(O)— group, and a heterocycloalkyl-(C₁-C₃-alkylene) group; or a tautomer, or a salt thereof or a salt of a tautomer or a mixture of same.

6. The compound of general formula (I) according to claim 1, selected from (rac)-(11Z)-4-chloro-1,3-dimethyl-7-[3-(naphthalen-1-yloxy)propyl]-1,10,13,15-tetrahydropyrazolo[4',3':9,10][1,6]oxazacycloundecino[8,7,6-hi]indole-8-carboxylic acid, rac-4-chloro-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, 4-chloro-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 1), 4-chloro-1,3-dimethyl-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid (enantiomer 2), (rac)-4-chloro-3-ethyl-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid, 4-chloro-3-ethyl-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid (enantiomer 1), 4-chloro-3-ethyl-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid (enantiomer 2), (rac)-4-chloro-3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid, 4-chloro-3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (enantiomer 1), 4-chloro-3-ethyl-1-[2-(morpholin-4-yl)ethyl]-7-[3-(naphthalen-1-yloxy)propyl]-1,10,11,12,13,15-hexahydropyrazolo[4',3':9,10][1,6]oxazacycloundecino[8,7,6-hi]indole-8-carboxylic acid-N-ethylethanamine salt (enantiomer 2), (rac)-4-chloro-2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid, (+)-4-chloro-2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid-N-ethylethanamine salt (enantiomer 1), (−)-4-chloro-2,3,14-trimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid-N-ethylethanamine salt (enantiomer 2), (rac)-4-chloro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid, (+)-4-chloro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid-N-ethylethanamine salt (enantiomer 1), (−)-4-chloro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid (enantiomer 1), (−)-4-chloro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid-N-ethylethanamine salt (enantiomer 2), (rac)-(11Z)-4-chloro-3-ethyl-2-methyl-7-[3-(naphthalen-1-yloxy)propyl]-2,10,13,15-tetrahydropyrazolo[4',3':9,10][1,6]oxazacycloundecino[8,7,6-hi]indole-8-carboxylic acid, (rac)-4-chloro-3-ethyl-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, 4-chloro-3-ethyl-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (enantiomer 1), 4-chloro-3-ethyl-2-methyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid (enantiomer 2), (rac)-4-chloro-3-ethyl-2,14-dimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid, 4-chloro-3-ethyl-2,14-dimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid (enantiomer 1), 4-chloro-3-ethyl-2,14-dimethyl-7-[3-(naphthalen-1-yloxy)propyl]-10,11,12,13,14,15-hexahydro-2H-pyrazolo[3',4':8,9][1,6]diazacycloundecino[10,11,1-hi]indole-8-carboxylic acid (enantiomer 2), (rac)-4-chloro-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid, 4-chloro-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (enantiomer 1), 4-chloro-2,3-dimethyl-7-[3-(naphthalen-1-yloxy)propyl]-2,10,11,12,13,15-hexahydropyrazolo[4',3':9,10][1,6]oxazacycloundecino[8,7,6-hi]indole-8-carboxylic acid-N-ethylethanamine salt (enantiomer 2), (rac)-12-chloro-10,11-dimethyl-1-[3-(naphthalen-1-yloxy)propyl]-4,5,6,7,8,10-hexahydropyrazolo[3',4':7,8][1,5]diazecino[9,10,1-hi]indole-2-carboxylic acid-formic acid salt, (rac)-12-chloro-7,10,11-trimethyl-1-[3-(naphthalen-1-yloxy)propyl]-4,5,6,7,8,10-hexahydropyrazolo[3',4':7,8][1,5]diazecino[9,10,1-hi]indole-2-carboxylic acid, (rac)-4-chloro-7-{3-[(6-fluoronaphthalen-1-yl)oxy]propyl}-2,3,14-trimethyl-10,11,12,13,14,15-hexahydro-2H-pyrazolo[3',4':8,9][1,6]diazacycloundecino[10,11,1-hi]indole-8-carboxylic acid, (+)-4-chloro-7-{3-[(6-fluoronaphthalen-1-yl)oxy]propyl}-2,3,14-trimethyl-10,11,12,13,14,15-hexahydro- 2H-pyrazolo[3',4':8,9][1,6]diazacycloundecino[10,11,1-hi]indole-8-carboxylic acid-N-ethylethanamine salt (enantiomer 1), (−)-4-chloro-7-{3-[(6-fluoronaphthalen-1-yl)oxy]propyl}-2,3,14-trimethyl-10,11,12,13,14,15-hexahydro-2H-pyrazolo[3',4':8,9][1,6]diazacycloundecino[10,11,1-hi]indole-8-carboxylic acid-N-ethylethanamine salt (enantiomer 2), (rac)-4-chloro-3-ethyl-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid (Enantiomer 1), (−)-4-chloro-3-ethyl-7-{3-[(6-fluoronaphthalen-1-yl)oxy]propyl}-1-methyl-1,10,11,12,13,15-hexahydropyrazolo[4',3':9,10][1,6]oxazacycloundecino[8,7,6-hi]indole-8-carboxylic acid (enantiomer 2), (rac)-4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 1), (−)-4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid-N-ethylethanamine salt (enantiomer 2), (rac)-4-chloro-3-ethyl-7-{3-[(6-fluoronaphthalen-1-yl)oxy]propyl}-1,14-dimethyl-10,11,12,13,14,15-hexahydro-1H-pyrazolo[3',4':8,9][1,6]diazacycloundecino[10,11,1-hi]indole-8-carboxylic acid, 4-chloro-3-ethyl-7-{3-[(6-fluoronaphthalen-1-yl)oxy]propyl}-1,14-dimethyl-10,11,12,13,14,15-hexahydro-1H-pyrazolo[3',4':8,9][1,6]diazacycloundecino[10,11,1-hi]indole-8-carboxylic acid (enantiomer 1), 4-chloro-3-ethyl-7-{3-[(6-fluoronaphthalen-1-yl)oxy]propyl}-1,14-dimethyl-10,11,12,13,14,15-hexahydro-1H-pyrazolo[3',4':8,9][1,6]diazacycloundecino[10,11,1-hi]indole-8-carboxylic acid (enantiomer 2), (rac)-(11Z)-4-chloro-3-ethyl-14-methyl-1-[2-(morpholin-4-yl)ethyl]-7-{3-[(naphthalen-1-yl)oxy]propyl}-10,13,14,15-tetrahydro-1H-pyrazolo [3',4':8,9][1,6]diazacycloundecino [10,11,1-hi]indole-8-carboxylic acid, (11Z)-4-chloro-3-ethyl-14-methyl-1-[2-(morpholin-4-yl)ethyl]-7-{3-[(naphthalen-1-yl)oxy]propyl}-10,13,14,15-tetrahydro-1H-pyrazolo [3',4':8,9][1,6]diazacycloundecino [10,11,1-hi]indole-8-carboxylic acid-ammonia salt (enantiomer 1), (11Z)-4-chloro-3-ethyl-14-methyl-1-[2-(morpholin-4-yl)ethyl]-7-{3-[(naphthalen-1-yl)oxy]propyl}-10,13,14,15-tetrahydro-1H-pyrazolo [3',4':8,9][1,6]diazacycloundecino [10,11,1-hi]indole-8-carboxylic acid-ammonia salt (enantiomer 2), (rac)-4-chloro-3-ethyl-14-methyl-1-[2-(morpholin-4-yl)ethyl]-7-{3-[(naphthalen-1-yl)oxy]propyl}-10,11,12,13,14,15-hexahydro-1H-pyrazolo[3',4':8,9][1,6]diazacycloundecino [10,11,1-hi]indole-8-carboxylic acid, 4-chloro-3-ethyl-14-methyl-1-[2-(morpholin-4-yl)ethyl]-7-{3-[(naphthalen-1-yl)oxy]propyl}-10,11,12,13,14,15-hexahydro-1H-pyrazolo[3',4':8,9][1,6]diazacycloundecino[10,11,1-hi]indole-8-carboxylic acid (enantiomer 1), 4-chloro-3-ethyl-14-methyl-1-[2-(morpholin-4-yl)ethyl]-7-{3-[(naphthalen-1-yl)oxy]propyl}-10,11,12,13,14,15-hexahydro-1H-pyrazolo[3',4':8,9][1,6]diazacycloundecino[10,11,1-hi]indole-8-carboxylic acid (enantiomer 2), (rac)-4-chloro-3-methyl-2-[3-(4-methylpiperazin-1-yl)propyl]-7-{3-[(naphthalen-1-yl)oxy]propyl}-2,10,11,12,13,15-hexahydropyrazolo[4',3':9,10][1,6]oxazacycloundecino [8,7,6-hi]indole-8-carboxylic acid, (+)-4-chloro-3-methyl-2-[3-(4-methylpiperazin-1-yl)propyl]-7-{3-[(naphthalen-1-yl)oxy]propyl}-2,10,11,12,13,15-hexahydropyrazolo[4',3':9,10][1,6]oxazacycloundecino [8,7,6-hi]indole-8-carboxylic acid (enantiomer 1), (−)-4-chloro-3-methyl-2-[3-(4-methylpiperazin-1-yl)propyl]-7-{3-[(naphthalen-1-yl)oxy]propyl}-2,10,11,12,13,15-hexahydropyrazolo[4',3':9,10][1,6]oxazacycloundecino [8,7,6-hi]indole-8-carboxylic acid (enantiomer 2), (rac)-4-chloro-3-ethyl-2-methyl-7-{3-[(naphthalen-1-yl)oxy]propyl}-10,11,12,13,14,15-hexahydro-2H-pyrazolo[4',3':4,5]azacycloundecino[3,2,1-hi]indole-8-carboxylic acid, (+)-4-chloro-3-ethyl-2-methyl-7-{3-[(naphthalen-1-yl)oxy]propyl}-10,11,12,13,14,15-hexahydro-2H-pyrazolo[4',3':4,5]azacycloundecino[3,2,1-hi]indole-8-carboxylic acid-N-ethylethanamine salt—(enantiomer 1), (−)$_4$-chloro-3-ethyl-2-methyl-7-{3-[(naphthalen-1-yl)oxy]propyl}-10,11,12,13,14,15-hexahydro-2H-pyrazolo[4',3':4,5]azacycloundecino[3,2,1-hi]indole-8-carboxylic acid-N-ethylethanamine salt—(enantiomer 2), (rac)-4-chloro-3-ethyl-7-{3-[(6-fluoronaphthalen-1-yl)oxy]propyl}-2-methyl-10,11,12,13,14,15-hexahydro-2H-pyrazolo[4',3':4,5]azacycloundecino[3,2,1-hi]indole-8-carboxylic acid, (rac)-4-chloro-12,12-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, 4-chloro-12,12-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid-N-ethylethanamine salt—(enantiomer 1), 4-chloro-12,12-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid-N-ethylethanamine salt—(enantiomer 2), (rac)-4-chloro-7-{3-[(6-fluoronaphthalen-1-yl)oxy]propyl}-2,3-dimethyl-14-(2,2,2-trifluoroethyl)-10,11,12,13,14,15-hexahydro-2H-pyrazolo[3',4':8,9][1,6]diazacycloundecino [10,11,1-hi]indole-8-carboxylic acid, 4-chloro-7-{3-[(6-fluoronaphthalen-1-yl)oxy]propyl}-2,3-dimethyl-14-(2,2,2-trifluoroethyl)-10,11,12,13,14,15-hexahydro-2H-pyrazolo[3',4':8,9][1,6]diazacycloundecino[10,11,1-hi]indole-8-carboxylic acid—(enantiomer 1), 4-chloro-7-{3-[(6-fluoronaphthalen-1-yl)oxy]propyl}-2,3-dimethyl-14-(2,2,2-trifluoroethyl)-10,11,12,13,14,15-hexahydro-2H-pyrazolo[3',4':8,9][1,6]diazacycloundecino[10,11,1-hi]indole-8-carboxylic acid—(enantiomer 2), (rac) 4-chloro-3-ethyl-7-{3-[(6-fluoronaphthalen-1-yl)oxy]propyl}-2-methyl-14-(2,2,2-trifluoroethyl)-10,11,12,13,14,15-hexahydro-2H-pyrazolo[3',4':8,9][1,6]diazacycloundecino [10,11,1-hi]indole-8-carboxylic acid, (rac)-4-chloro-14-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino [10,11,1-hi]indole-8-carboxylic acid, (9aS,11aR)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]oxazacycloundecino [8,7,6-hi]indole-14-carboxylic acid—Stereoisomer 1

(9aR,11aS)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]oxazacycloundecino [8,7,6-hi]indole-14-carboxylic acid— (stereoisomer 2), (9aS,10aR or 9aR,10aS)-3-chloro-4,5-dimethyl-14-{3-[(naphthalen-1-yl)oxy]propyl}-5,7,9a,10,10a,11-hexahydro-9H-cyclopropa[3,4]pyrazolo[4',3':9,10][1,6]-oxazacycloundecino[8,7,6-hi]indole-13-carboxylic acid—(stereoisomer 1), (9aR,10aS or 9aS,10aR)-3-chloro-4,5-dimethyl-14-{3-[(naphthalen-1-yl)oxy]propyl}-5,7,9a,10,10a,11-hexahydro-9H-cyclopropa[3,4]pyrazolo[4',3':9,10][1,6]-oxazacycloundecino[8,7,6-hi]indole-13-carboxylic acid—(stereoisomer 2), (rac)-4-chloro-11,11,12,12-tetrafluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid, (rac)-4-chloro-11,11-difluoro-2,3-dimethyl-7-[3-(1-naphthyloxy)propyl]-2,10,11,12,13,15-hexahydropyrazolo[4',3':9,10][1,6]oxazacycloundecino[8,7,6-hi]indole-8-carboxylic acid, 4-chloro-3-ethyl-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid (enantiomer 1), (+)-4-chloro-3-ethyl-7-{3-[(6-fluoronaphthalen-1-yl)oxy]propyl}-2-methyl-10,11,12,13,14,15-hexahydro-2H-pyrazolo[4',3':4,5]azacycloundecino[3,2,1-hi]indole-8-carboxylic acid-N-ethylethanamine salt (enantiomer 1), (−)-4-chloro-3-ethyl-7-{3-[(6-fluoronaphthalen-1-yl)oxy]propyl}-2-methyl-10,11,12,13,14,15-hexahydro-2H-pyrazolo[4',3':4,5]azacycloundecino[3,2,1-hi]indole-8-carboxylic acid-N-ethylethanamine salt (enantiomer 2), (rac)-4'-chloro-3'-ethyl-2'-methyl-7'-{3-[(naphthalen-1-yl)oxy]propyl}-2',10',11',15'-tetrahydro-13'H-spiro[cyclopropane-1,12'-pyrazolo[4',3':9,10][1,6]oxazacycloundecino [8,7,6-hi]indole]-8'-carboxylic acid, (−)-4'-chloro-3'-ethyl-2'-methyl-7'-{3-[(naphthalen-1-yl)oxy]propyl}-2',10',11',15'-tetrahydro-13'H-spiro[cyclopropane-1,12'-pyrazolo[4',3':9,10][1,6]oxazacycloundecino[8,7,6-hi]indole]-8'-carboxylic acid-N-ethylethanamine salt (enantiomer 1), (+)-4'-chloro-3'-ethyl-2'-methyl-7'-{3-[(naphthalen-1-yl)oxy]propyl}-2',10',11',15'-tetrahydro-13'H-spiro[cyclopropane-1,12'-pyrazolo[4',3':9,10][1,6]oxazacycloundecino [8,7,6-hi]indole]-8'-carboxylic acid-N-ethylethanamine salt (enantiomer 2), (+)-4-chloro-14-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino [10,11,1-hi]indole-8-carboxylic acid-N-ethylethanamine salt, (−)-4-chloro-14-(2,2-difluoroethyl)-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino [10,11,1-hi]indole-8-carboxylic acid N-ethylethanamine salt, (rac)-4-chloro-14-(2,2-difluoroethyl)-7-{3-[(6-fluoronaphthalen-1-yl)oxy]propyl}-2,3-dimethyl-10,11,12,13,14,15-hexahydro-2H-pyrazolo[3',4':8,9][1,6]diazacycloundecino [10,11,1-hi]indole-8-carboxylic acid, (9aS,11aR)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]-oxazacycloundecino[8,7,6-hi]indole-14-carboxylic acid, (9aR,11aS)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]-oxazacycloundecino[8,7,6-hi]indole-14-carboxylic acid, (9aS,11aR)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]-oxazacycloundecino[8,7,6-hi]indole-14-carboxylic acid, (9aR,11aS)-3-chloro-4,5-dimethyl-15-{3-[(naphthalen-1-yl)oxy]propyl}-5,7,9,9a,10,11,11a,12-octahydrocyclobuta[3,4]pyrazolo[4',3':9,10][1,6]-oxazacycloundecino[8,7,6-hi]indole-14-carboxylic acid, (9aS,10aR or 9aR,10aS)-3-chloro-4,5-dimethyl-14-{3-[(naphthalen-1-yl)oxy]propyl}-5,7,9a,10,10a,11-hexahydro-9H-cyclopropa[3,4]pyrazolo[4',3':9,10][1,6]-oxazacycloundecino[8,7,6-hi]indole-13-carboxylic acid, (9aS,10aR or 9aR,10aS)-3-chloro-4,5-dimethyl-14-{3-[(naphthalen-1-yl)oxy]propyl}-5,7,9a,10,10a,11-hexahydro-9H-cyclopropa[3,4]pyrazolo[4',3':9,10][1,6]-oxazacycloundecino[8,7,6-hi]indole-13-carboxylic acid, (rac)-4-chloro-3-ethyl-12,12-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (−)-4-chloro-3-ethyl-12,12-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-12,12-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (rac)-11-chloro-9,10-dimethyl-1-{3-[(naphthalen-1-yl)oxy]propyl}-4,5,7,9-tetrahydropyrazolo[4',3':7,8][1,4]oxazonino[6,5,4-hi]indole-2-carboxylic acid, 11-chloro-9,10-dimethyl-1-{3-[(naphthalen-1-yl)oxy]propyl}-4,5,7,9-tetrahydropyrazolo[4',3':7,8][1,4]oxazonino[6,5,4-hi]indole-2-carboxylic acid, 11-chloro-9,10-dimethyl-1-{3-[(naphthalen-1-yl)oxy]propyl}-4,5,7,9-tetrahydropyrazolo[4',3':7,8][1,4]oxazonino[6,5,4-hi]indole-2-carboxylic acid, (rac)-4-Chloro-12,12-difluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid, 4-chloro-12,12-difluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid-N-ethylethanamine salt, 4-chloro-12,12-difluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid, (rac)-4-Chloro-11,11-difluoro-7-{3-[(6-fluoronaphthalen-1-yl)oxy]propyl}-2,3-dimethyl-2,10,11,12,13,15-hexahydropyrazolo[4',3':9,10][1,6]oxazacycloundecino[8,7,6-hi]indole-8-carboxylic acid, 4-chloro-11,11-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid N-ethylethanamine salt, 4-chloro-11,11-difluoro-2,3-dimethyl-7-{3-[(naphthalen-1-yl)oxy]propyl}-2,10,11,12,13,15-hexahydropyrazolo[4',3':9,10][1,6]oxazacycloundecino[8,7,6-hi]indole-8-carboxylic acid N-ethylethanamine salt, (rac)-4-chloro-3-ethyl-11,11-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (−)-4-chloro-3-ethyl-11,11-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, (+)-4-chloro-3-ethyl-11,11-difluoro-7-{3-[(6-fluoronaphthalen-1-yl)oxy]propyl}-2-methyl-2,10,11,12,13,15-hexahydropyrazolo[4',3':9,10][1,6]oxazacycloundecino[8,7,6-hi]indole-8-carboxylic acid, 4-chloro-3-ethyl-7-{3-[(6-fluoronaphthalen-1-yl)oxy]propyl}-12-hydroxy-2-methyl-2,10,11,12,13,15-hexahydropyrazolo[4',3':9,10][1,6]oxazacycloundecino[8,7,6-hi]indole-8-carboxylic acid-N-ethylethanamine salt (stereoisomer 1), 4-chloro-3-ethyl-7-{3-[(6-fluoronaphthalen-1-yl)oxy]propyl}-12-hydroxy-2-methyl-2,10,11,12,13,15-hexahydropyrazolo[4',3':9,10][1,6]oxazacycloundecino[8,7,6-hi]indole-8-carboxylic acid-N-ethylethanamine salt (stereoisomer 2), 4-chloro-3-ethyl-7-{3-[(6-fluoronaphthalen-1-yl)oxy]propyl}-12-hydroxy-2-methyl-2,10,11,12,13,15-hexahydropyrazolo[4',3':9,10][1,6]oxazacycloundecino[8,7,6-hi]indole-8-carboxylic acid-N-ethylethanamine salt (stereoisomer 3), 4-chloro-3-ethyl-7-{3-[(6-fluoronaphthalen-1-yl)oxy]propyl}-12-hydroxy-2-methyl-2,10,11,12,13,15-hexahydropyrazolo[4',3':9,10][1,6]oxazacycloundecino[8,7,6-hi]indole-8-carboxylic acid-N-ethylethanamine salt (stereoisomer 4), (rac)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid, (+)-(9aS or R,10aR or S)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid N-ethylethanamine salt, (−)-(9aS or R,10aR or S)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid N-ethylethanamine salt, (rac)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid, (+)-(9aS,10aR)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid, (−)-(9aS,10aR)-3-chloro-4-ethyl-14-{3-[(6-fluoronaphthalen-1-yl)oxy]propyl}-5-methyl-5,7,9a,10,10a,11-hexahydro-9H-cyclopropa[3,4]pyrazolo[4',3':9,10][1,6]-oxazacycloundecino[8,7,6-hi]indole-13-carboxylic acid, (rac)-4'-chloro-3'-ethyl-7'-{3-[(6-fluoronaphthalen-1-yl)oxy]propyl}-2'-methyl-2',10',11',15'-tetrahydro-13'H-spiro[cyclopropane-1,12'-pyrazolo[4',3':9,10][1,6]-oxazacycloundecino[8,7,6-hi]indole]-8'-carboxylic acid, (−)-4'-chloro-3'-ethyl-7'-{3-[(6-fluoronaphthalen-1-yl)oxy]propyl}-2'-methyl-2',10',11',15'-tetrahydro-13'H-spiro[cyclopropane-1,12'-pyrazolo[4',3':9,10][1,6]oxazacycloundecino-[8,7,6-hi]indole]-8'-carboxylic acid-N-ethylethanamine salt, (+)-4'-chloro-3'-ethyl-7'-{3-[(6-fluoronaphthalen-1-yl)oxy]propyl}-2'-methyl-2',10',11',15'-tetrahydro-13'H-spiro[cyclopropane-1,12'-pyrazolo[4',3':9,10][1,6]oxazacycloundecino-[8,7,6-hi]indole]-8'-carboxylic acid-N-ethylethanamine salt, (rac)-12-chloro-11-ethyl-1-{3-[(6-fluoronaphthalen-1-yl)oxy]propyl}-7,10-dimethyl-4,5,6,7,8,10-hexahydropyrazolo[3',4':7,8][1,5]diazecino[9,10,1-hi]indole-2-carboxylic acid, (+) 12-chloro-11-ethyl-1-{3-[(6-fluoronaphthalen-1-yl)oxy]propyl}-7,10-dimethyl-4,5,6,7,8,10-hexahydropyrazolo[3',4':7,8][1,5]diazecino[9,10,1-hi]indole-2-carboxylic acid N-ethylethanamine salt, (−)-12-chloro-11-ethyl-1-{3-[(6-fluoronaphthalen-1-yl)oxy]propyl}-7,10-dimethyl-4,5,6,7,8,10-hexahydropyrazolo[3',4':7,8][1,5]diazecino[9,10,1-hi]indole-2-carboxylic acid-salt, (rac)-4-chloro-3-ethyl-7-{3-[(6-fluoronaphthalen-1-yl)oxy]propyl}-2,12-dimethyl-10,11,12,13,14,15-hexahydro-2H-pyrazolo[3',4':8,9][1,4]diazacycloundecino[10,11,1-hi]indole-8-carboxylic acid, (+)-4-chloro-3-ethyl-7-{3-[(6-fluoronaphthalen-1-yl)oxy]propyl}-2,12-dimethyl-10,11,12,13,14,15-hexahydro-2H-pyrazolo[3',4':8,9][1,4]diazacycloundecino[10,11,1-hi]indole-8-carboxylic acid, (−)-4-chloro-3-ethyl-7-{3-[(6-fluoronaphthalen-1-yl)oxy]propyl}-2,12-dimethyl-10,11,12,13,14,15-hexahydro-2H-pyrazolo[3',4':8,9][1,4]diazacycloundecino[10,11,1-hi]indole-8-carboxylic acid, (rac)-4-chloro-12-(2,2-difluoroethyl)-3-ethyl-7-{3-[(6-fluoro-1-naphthyl)oxy]propyl}-2-methyl-10,11,12,13,14,15-hexahydro-2H-pyrazolo[3',4':8,9][1,4]diazacycloundecino [10,11,1-hi]indole-8-carboxylic acid, (+)-4-chloro-12-(2,2-difluoroethyl)-3-ethyl-7-{3-[(6-fluoronaphthalen-1-yl)oxy]propyl}-2-methyl-10,11,12,13,14,15-hexahydro-2H-pyrazolo [3',4':8,9][1,4]diazacycloundecino [10,11,1-hi]indole-8-carboxylic acid N-ethylethanamine salt, (−)-4-chloro-12-(2,2-difluoroethyl)-3-ethyl-7-{3-[(6-fluoronaphthalen-1-yl)oxy]propyl}-2-methyl-10,11,12,13,14,15-hexahydro-2H-pyrazolo [3',4':8,9][1,4]diazacycloundecino [10,11,1-hi]indole-8-carboxylic acid-N-ethylethanamine salt, (rac)-12-(4-acetoxybutyl)-4-chloro-3-ethyl-7-{3-[(6-fluoro-1-naphthyl)oxy]propyl}-2-methyl-10,11,12,13, 14,15-hexahydro-2H-pyrazolo[3',4':8,9][1,4]diazacycloundecino[10,11,1-hi]indole-8-carboxylic acid, (rac)-4-chloro-3-ethyl-7-{3-[(6-fluoro-1-naphthyl)oxy]propyl}-12-(4-hydroxybutyl)-2-methyl-10,11,12,13,14,15-hexahydro-2H-pyrazolo[3',4':8,9][1,4]diazacycloundecino[10,11,1-hi]indole-8-carboxylic acid, (rac)-4-chloro-3-ethyl-7-{3-[(6-fluoro-1-naphthyl)oxy]propyl}-2-methyl-12-(2,2,3,3-tetrafluoropropyl)-10,11,12,13,14,15-hexahydro-2H-pyrazolo[3',4':8,9][1,4]diazacycloundecino[10,11,1-hi]indole-8-carboxylic acid, (rac)-4-chloro-3-ethyl-7-{3-[(6-fluoro-1-naphthyl)oxy]propyl}-2-methyl-2,10,11,13,14,15-hexahydropyrazolo[4',3':7,8][1,4]oxazacycloundecino[6,5,4-hi]indole-8-carboxylic acid, (rac)-4-chloro-3-ethyl-7-{3-[(6-fluoro-1-naphthyl)oxy]propyl}-1-methyl-1,10,11,13,14,15-hexahydropyrazolo[4',3':7,8][1,4]oxazacycloundecino[6,5,4-hi]indole-8-carboxylic acid, (rac)-4-Chloro-3-ethyl-12,12-difluoro-7-{3-[(6-fluoro-1-naphthyl)oxy]propyl}-2,14-dimethyl-10,11,12,13,14,15-hexahydro-2H-pyrazolo[3',4':8,9][1,6]diazacycloundecino[10,11,1-hi]indol-14-ium-8-carboxylate, 4-chloro-3-ethyl-12,12-difluoro-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid, 4-chloro-3-ethyl-12,12-difluoro-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino[10,11,1-hi]indole-8-carboxylic acid, rac-4-chloro-3-ethyl-11,11-difluoro-7-{3-[(6-fluoronaphthalen-1-yl)oxy]propyl}-2,14-dimethyl-10,11,12,13,14,15-hexahydro-2H-pyrazolo[3',4':8,9][1,6]diazacycloundecino [10,11,1-hi]indole-8-carboxylic acid, rac-4-chloro-3-ethyl-7-{3-[(6-fluoronaphthalen-1-yl)oxy]propyl}-2-methyl-10,11,12,13,14,15-hexahydro-2H-pyrazolo[3',4':8,9][1,6]diazacycloundecino[10,11,1-hi]indole-8-carboxylic acid, rac-4-chloro-3-ethyl-7-{3-[(6-fluoronaphthalen-1-yl)oxy]propyl}-14-(2-methoxyethyl)-2-methyl-10,11,12,13,14,15-hexahydro-2H-pyrazolo[3',4':8,9][1,6]diazacycloundecino[10,11,1-hi]indole-8-carboxylic acid, 4-chloro-3-ethyl-7-{3-[(6-fluoronaphthalen-1-yl)oxy]propyl}-14-(2-methoxyethyl)-2-methyl-10,11,12,13,14,15-hexahydro-2H-pyrazolo[3',4':8,9][1,6]diazacycloundecino[10,11,1-hi]indole-8-carboxylic acid, 4-chloro-3-ethyl-7-{3-[(6-fluoronaphthalen-1-yl)oxy]propyl}-14-(2-methoxyethyl)-2-methyl-10,11,12,13,14,15-hexahydro-2H-pyrazolo[3',4':8,9][1,6]diazacycloundecino[10,11,1-hi]indole-8-carboxylic acid N-ethylethanamine salt, rac-4-chloro-3-ethyl-7-{3-[(6-fluoronaphthalen-1-yl)oxy]propyl}-14-[(2-methoxyethoxy)carbonyl]-2-methyl-10,11,12,13,14,15-hexahydro-2H-pyrazolo[3',4':8,9][1,6]diazacycloundecino[10,11,1-hi]indole-8-carboxylic acid, rac-4-chloro-3-ethyl-7-{3-[(6-fluoronaphthalen-1-yl)oxy]propyl}-2-methyl-14-[2-(oxan-4-yl)ethyl]-10,11,12,13,14,15-hexahydro-2H-pyrazolo[3',4':8,9][1,6]diazacycloundecino [10,11,1-hi]indole-8-carboxylic acid, 4-chloro-3-ethyl-7-{3-[(6-fluoronaphthalen-1-yl)oxy]propyl}-2-methyl-14-[2-(oxan-4-yl)ethyl]-10,11,12,13,14,15-hexahydro-2H-pyrazolo[3',4':8,9][1,6]diazacycloundecino[10,11,1-hi]indole-8-carboxylic acid N-ethylethanamine salt, 4-chloro-3-ethyl-7-{3-[(6-fluoronaphthalen-1-yl)oxy]propyl}-2-methyl-14-[2-(oxan-4-yl)ethyl]-10,11,12,13,14,15-hexahydro-2H-pyrazolo[3',4':8,9][1,6]diazacycloundecino[10,11,1-hi]indole-8-carboxylic acid-N-ethylethanamine (1/1), rac-4-chloro-3-ethyl-7-{3-[(6-fluoronaphthalen-1-yl)oxy]propyl}-2-methyl-14-{[2-(oxan-4-yl)ethoxy]carbonyl}-10,11,12,13,14,15-hexahydro-2H-pyrazolo[3',4':8,9][1,6]diaza cycloundecino[10,11,1-hi]indole-8-carboxylic acid, rac-4-chloro-3-ethyl-7-{3-[(6-fluoronaphthalen-1-yl)oxy]propyl}-14-(3-hydroxypropyl)-2-methyl-10,11,12,13,14,15-hexahydro-2H-pyrazolo[3',4':8,9][1,6]diazacycloundecino [10,11,1-hi]indole-8-carboxylic acid, 4-chloro-3-ethyl-7-{3-[(6-fluoronaphthalen-1-yl)oxy]propyl}-14-(3-hydroxy-3-methylbutyl)-2-methyl-10,11,12,13,14,15-hexahydro-2H-pyrazolo[3',4':8,9][1,6]diazacycloundecino [10,11,1-hi]indole-8-carboxylic acid (enantiomer 1), 4-chloro-3-ethyl-7-{3-[(6-fluoronaphthalen-1-yl)oxy]propyl}-14-(3-hydroxy-3-methylbutyl)-2-methyl-10,11,12,13,14,15-hexahydro-2H-pyrazolo[3',4':8,9][1,6]diazacycloundecino [10,11,1-hi]indole-8-carboxylic acid (enantiomer 2), 4-chloro-3-ethyl-7-{3-[(6-fluoronaphthalen-1-yl)oxy]propyl}-2-methyl-14-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid (enantiomer 1) and 4-chloro-3-ethyl-7-{3-[(6-fluoronaphthalen-1-yl)oxy]propyl}-2-methyl-14-[2-(morpholin-4-yl)ethyl]-10,11,12,13,14,15-hexahydro-2H-pyrazolo[3',4':8,9][1,6]diazacycloundecino[10,11,1-hi]indole-8-carboxylic acid (enantiomer 2)

or a tautomer, an N-oxide, or a salt thereof, or a salt of a tautomer, or a salt of an N-oxide, or a mixture of same.

7. A method of preparing a compound of general formula (I) according to claim 1, said method comprising the step of allowing an intermediate compound of general formula (II):

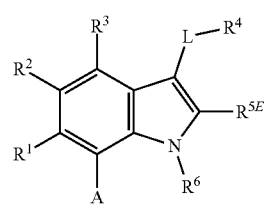

(II)

in which $R^1$, $R^2$, $R^3$, $R^4$, $R^6$, A and L are as defined for the compound of general formula (I) according to claim 1, and $R^{5E}$ represents a carboxylic ester group or a benzyl ester group, to react with an alkali hydroxide in a mixture of water with THF and/or an aliphatic alcohol of formula $C_1$-$C_3$-alkyl-OH, at a temperature between 0° C. and 100° C. including 0° C. and 100° C., to transform the group $R^{5E}$ into a group $R^5$ as defined for the compounds of general formula (I), and subsequently optionally to convert the free acid group $R^5$ into a pharmaceutically acceptable salt thereof to obtain a compound of general formula (I)

(I)

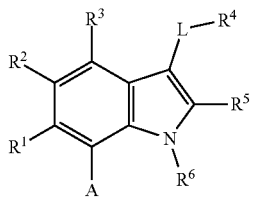

in which $R^1$, $R^2$, $R^3$, $R^4$, $R^5$, $R^6$, A and L are as defined for the compound of general formula (I) according to claim 1 or a stereoisomer, a tautomer, an N-oxide, a hydrate, a solvate, or a salt thereof, or a mixture of same and optionally separating enantiomers by means of preparative HPLC on a chiral stationary phase.

8. A method of inhibiting proliferation of a cell and/or the induction of apoptosis in a cell, comprising contacting the cell with a compound of formula (I) according to claim 1.

9. A method of treating a hyperproliferative disease, comprising administering a compound of general formula (I) according to claim 1.

10. The method according to claim 9 wherein the hyperproliferative disease is cancer.

11. The method according to claim 10, wherein the cancer is selected from breast cancer; endometrial cancer, leukemia, liver cancer, lung cancer; lymphoma, melanoma; and multiple myeloma.

12. A pharmaceutical composition comprising a compound of general formula (I) according to claim 1 and one or more pharmaceutically acceptable excipients.

13. A method of treating cancer, comprising administering a pharmaceutical composition according to claim 12, wherein the cancer is selected from breast cancer; endometrial cancer, leukemia, liver cancer, lung cancer; lymphoma, melanoma; and multiple myeloma.

14. A pharmaceutical combination comprising:
one or more compounds of general formula (I) according to claim 1, and
one or more further anti-cancer agents.

15. An intermediate compound of general formula (II):

(II)

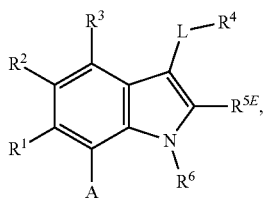

in which
A is (A1)

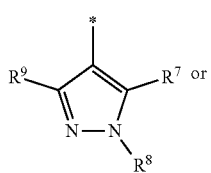

or (A2)

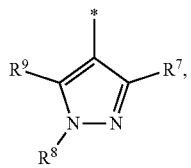

wherein $R^6$ and $R^7$, together with two carbon atoms of the pyrazole ring, two carbon atoms of the indole moiety and the nitrogen atom to which $R^6$ is attached, form a 9-membered to 16-membered ring and * is the point of attachment of these moieties to the indole carbon atom bearing the A substituent: or A is (A3)

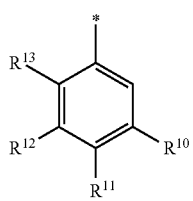

wherein optionally one or two of the groups selected from $CR^{11}$, $CR^{12}$ and $CR^{13}$ may be replaced by a nitrogen atom,
wherein $R^6$ and $R^{10}$, together with three carbon atoms of the phenyl ring, two carbon atoms of the indole moiety and the nitrogen atom to which $R^6$ is attached, form a 9-membered to 16-membered ring and * is the point of attachment of these moieties to the indole carbon atom bearing the A substituent:

$R^1$ is a chlorine atom;
$R^2$ and $R^3$ are each a hydrogen atom;
$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group, and a $C_3$-$C_5$-cycloalkyl group;
L is a group —(CH$_2$)$_m$-E- wherein any CH$_2$ group is unsubstituted or substituted with one or two substituents and each substituent is independently selected from a halogen atom, a cyano group, a hydroxy group, a $C_1$-$C_3$-alkyl group, and a $C_1$-$C_3$-alkoxy group, or two substituents are optionally taken together with their intervening atoms to form a saturated or partially unsaturated 3-membered to 6-membered cycloalkyl ring, or a 3-membered to 8-membered saturated or partially unsaturated heterocyclic ring having 1-2 heteroatoms independently selected from an oxygen atom, a sulfur atom, a —S(O)— group, a —S(O)$_2$— group, and a —NR$^{14}$— group;
E is a bond, an oxygen atom, a sulfur atom, a —S(O)— group, a —S(O)$_2$— group or a —NR$^{14}$— group and constitutes the connecting element to $R^4$;
m is 2, 3, or 4;
$R^{5E}$ represents a carboxylic ester group;
—$R^6$-$R^7$— is selected from $^\#$—(CH$_2$)$_n$—(B)$_t$—(CH$_2$)$_v$—X$^{\#\#}$, $^\#$—(C$_2$-C$_6$-alkenylene)-(B)$_t$—(CH$_2$)$_v$—X—$^{\#\#}$,

—(CH$_2$)$_n$—(B)$_t$—(C$_2$-C$_5$-alkenylene)-X$^{\#\#}$, and
—(CH$_2$)$_q$—(B)—(CH$_2$)$_r$—(B)—(CH$_2$)$_v$—X—$^{\#\#}$,
- wherein $^\#$ is the point of attachment with the indole nitrogen atom and $^{\#\#}$ is the point of attachment with the pyrazole carbon atom bearing the R$^7$ substituent; and
- wherein one or more —CH$_2$— groups may be unsubstituted or substituted with one or more substituents independently selected from a halogen atom, a hydroxy group, a NR$^{16}$R$^{17}$ group, a C$_1$-C$_3$-alkyl group, a C$_1$-C$_3$-haloalkyl group, a C$_1$-C$_3$-alkoxy group, a C$_1$-C$_3$-haloalkoxy group, a C$_3$-C$_6$-cycloalkyl group, and a (heterocycloalkyl)-(C$_1$-C$_3$-alkylene)- group, and wherein optionally, if two such substituents are bound to the same atom, they may form together a 3-membered to 6-membered spiro ring, and
- wherein a —CH=CH— group in any alkenylene can be replaced by a 1,2-(C$_3$-C$_5$)cycloalkylene group which is unsubstituted or substituted one or two times with a halogen atom or a C$_1$-C$_2$-alkyl group; and where X is an unsubstituted —CH$_2$— group;

—R$^6$-R$^{10}$— is selected from $^\#$—(CH$_2$)$_n$—(B)$_t$—(CH$_2$)$_p$—X—$^{\#\#}$, $^\#$—(C$_2$-C$_6$-alkenylene)-(B)$_t$—(CH$_2$)$_p$—X—$^{\#\#}$, $^\#$—(CH$_2$)$_n$—(B)$_t$—(C$_2$-C$_5$-alkenylene)-X—$^{\#\#}$, and $^\#$—(CH$_2$)$_q$—(B)—(CH$_2$)$_r$—(B)—(CH$_2$)$_v$—X—$^{\#\#}$,

- wherein $^\#$ is the point of attachment with the indole nitrogen atom and $^{\#\#}$ is the point of attachment with the carbon atom of the phenyl moiety bearing the R$^{10}$ substituent,
- wherein one or more —CH$_2$— groups may be unsubstituted or substituted with one or more substituents independently selected from a halogen atom, a hydroxy group, a NR$^{16}$R$^{17}$ group, a C$_1$-C$_3$-alkyl group, a C$_1$-C$_3$-haloalkyl group, a C$_1$-C$_3$-alkoxy group, a C$_1$-C$_3$-haloalkoxy group, a C$_3$-C$_6$-cycloalkyl group, and a (heterocycloalkyl)-(C$_1$-C$_3$-alkylene)- group,
- wherein a double bond in any alkenylene can be replaced by a 1,2-(C$_1$-C$_6$)cycloalkyl group which is unsubstituted or substituted one or two times with a halogen atom or a C$_1$-C$_2$-alkyl group, and where X is an unsubstituted —CH$_2$— group;

n is 2,3,4,5,6,7,8, or 9;
t is 0 or 1;
p is 0,1,2,3,4, or 5;
q is 2, 3, 4, 5, or 6;
r is 2, 3, 4, 5, or 6;
v is 0, or 1;
s is 0, 1,2, or 3;

wherein the integers selected for variables n, t, p, q, r, and v result in forming a 9-membered to 16-membered ring independently from the selection of variable A1, A2 or A3;

B is independently selected from a —C(O)NR$^{15}$— group, a —NR$^{15}$C(O)— group, a —N(R$^{15}$)— group, a —N(R$^{15}$)—C(=O)—N(R$^{15}$)— group, a —O—C(=O)—N(R$^{15}$)— group, a —N(R$^{15}$)—C(=O)—O— group, —O—, —S—, —S(O)—, and —S(O)$_2$—;

R$^8$ is selected from a hydrogen atom,
- a C$_1$-C$_6$-alkyl group, which is unsubstituted or substituted with one or more substituents independently selected from a halogen atom, a hydroxy group, a C$_1$-C$_3$-alkoxy group, a C$_1$-C$_3$-haloalkoxy group, a C$_3$-C$_6$-cycloalkyl group, a heterocycloalkyl group, and a NR$^{20}$R$^{21}$ group;
- a C$_1$-C$_3$-haloalkyl group,
- a C$_3$-C$_6$-cycloalkyl group, and
- a C$_1$-C$_6$-alkyl group in which one or two not directly adjacent carbon atoms are independently replaced by a hetero atom selected from —O— and —NH— and R$^9$ is selected from a hydrogen atom,
- a C$_1$-C$_4$-alkyl group,
- a C$_1$-C$_3$-hydroxyalkyl group,
- a C$_1$-C$_4$-haloalkyl group,
- a C$_1$-C$_4$-haloalkyl-NH—C(O)—O—(C$_1$-C$_3$-alkylene)- group,
- a C$_2$-C$_6$-haloalkenyl group,
- a C$_1$-C$_6$-alkyl-O— group,
- a C$_1$-C$_4$-haloalkoxy group,
- a C$_1$-C$_6$-alkyl-O—(C$_1$-C$_3$-alkylene)- group,
- a (C$_3$-C$_7$)-cycloalkyl group,
- a (C$_3$-C$_7$)-cycloalkyl-O—(C$_1$-C$_3$-alkylene)- group,
- a phenyl-O—(C$_1$-C$_3$-alkylene)- group,
- a phenyl-(C$_1$-C$_3$-alkylene)-O—(C$_1$-C$_3$-alkylene)- group,
- a R$^{18}$-(phenylene)-(C$_1$-C$_3$-alkylene)-O—(C$_1$-C$_3$-alkylene)- group,
- a R$^{18}$-(phenylene)-O—(C$_1$-C$_3$-alkylene)- group,
- a R$^{18}$-(phenylene)-(heteroarylene)-O—(C$_1$-C$_3$-alkylene)- group,
- a (R$^{18}$)-(heterocycloalkylene)-(C$_1$-C$_3$-alkylene)- group,
- a (R$^{18}$)-(heterocycloalkylene)-(phenylene)-O—(C$_1$-C$_3$-alkylene)- group,
- a (heterocycloalkenyl)-(phenylene)-O—(C$_1$-C$_3$-alkylene)- group,
- a (R$^{18}$)-(heteroarylene)-(C$_1$-C$_3$-alkylene)-O—(C$_1$-C$_3$-alkylene)- group,
- a (R$^{18}$)-(heteroarylene)-(phenylene)-O—(C$_1$-C$_3$-alkylene)- group,
- a (R$^{19}$)—S(O)$_2$-(phenylene)-O—(C$_1$-C$_3$-alkylene)- group,
- a (R$^{19}$)—S(O)—NH-(phenylene)-O—(C$_1$-C$_3$-alkylene)- group,
- a (R$^{19}$)—S(O)$_2$—NH-(phenylene)-O—(C$_1$-C$_3$-alkylene)- group,
- a (R$^{19}$)—S(O)$_2$—N(C$_1$-C$_6$-alkyl)-(phenylene)-O—(C$_1$-C$_3$-alkylene)- group,
- a (R$^{19}$)—S(O)$_2$-(heterocycloalkylene)-(phenylene)-O—(C$_1$-C$_3$-alkylene)- group,
- a (R$^{18}$)-(heterocycloalkylene)-(heteroarylene)-O—(C$_1$-C$_3$-alkylene)- group,
- a (R$^{19}$)-(heteroarylene)-O—(C$_1$-C$_3$-alkylene)- group,
- a (R$^{18}$)-(heteroarylene)-O—(C$_1$-C$_3$-alkylene)- group,
- a (R$^{19}$)—S(O)$_2$-(heteroarylene)-O—(C$_1$-C$_3$-alkylene)- group,
- a (R$^{19}$)—S(O)$_2$-(heterocycloalkylene)-(heteroarylene)-O—(C$_1$-C$_3$-alkylene)- group,
- a NR$^{20}$R$^{21}$—(C$_1$-C$_3$-alkylene)- group,
- a (C$_1$-C$_3$-alkyl)-NH—(C$_1$-C$_3$-alkylene)- group,
- a (C$_1$-C$_3$-haloalkyl)-(C$_1$-C$_3$-alkylene)-NH—(C$_1$-C$_3$-alkylene)- group,
- a (C$_1$-C$_3$-haloalkyl)-NH—(C$_1$-C$_3$-alkylene)- group,
- a (C$_1$-C$_3$-alkyl)-NH—C(O)—(C$_1$-C$_3$-alkylene)- group,
- a (C$_1$-C$_3$-alkyl)-NR$^{15}$—C(O)—(C$_1$-C$_3$-alkylene)- group,
- a (C$_1$-C$_3$-alkyl)-C(O)—NH—(C$_1$-C$_3$-alkylene)- group,
- a (C$_1$-C$_3$-alkyl)-C(O)—NR$^{15}$-(C$_1$-C$_3$-alkylene)- group,
- a

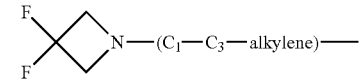

group, and a

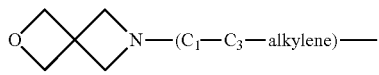

group,
wherein the phenyl ring is unsubstituted or substituted with a halogen atom, a hydroxy group, or a $C_1$-$C_3$-alkoxy group and
the heterocycloalkyl group is unsubstituted or substituted with an oxo (=O) group or is unsubstituted or substituted with one or more substituents independently selected from a halogen atom, a hydroxy group, a $C_1$-$C_3$-alkyl group, and a $C_1$-$C_3$-alkoxy group, or $R^8$ and $R^9$ together form a 5-membered or 6-membered ring optionally containing one or two heteroatoms selected from —O—, and —$NR^{14}$—;

$R^{11}$ and $R^{13}$ are each independently selected from a hydrogen atom, a halogen atom, a $C_1$-$C_3$-alkyl group, and a $C_1$-$C_3$-alkoxy group;

$R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group, and a $NR^{16}R^{17}$ group;

$R^{14}$ is a hydrogen atom or a $C_1$-$C_3$-alkyl group;

$R^{15}$ is independently selected from a hydrogen atom,
a $C_1$-$C_6$-alkyl group
which is unsubstituted or substituted with one or more substituents selected from a halogen atom, a hydroxy group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a ($C_1$-$C_3$-alkyl)-C(O)—O— group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$-(heterocycloalkylene)-(arylene)-O— group, an (aryl)-(heteroarylene)-O— group, and an (aryl)-(heteroarylene)-O—($C_1$-$C_3$-alkylene)- group:
a $C_1$-$C_3$-alkoxy-($C_1$-$C_6$-alkylene)-O—C(O)— group,
a heterocycloalkyl-($C_1$-$C_6$-alkylene)-O—C(O)— group,
a phenyl group, a group

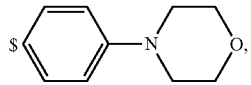

a group

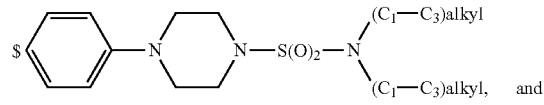

a group

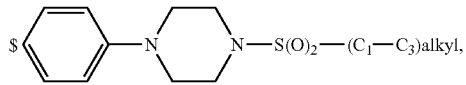

wherein $ is the point of attachment to the nitrogen atom, to which $R^{15}$ is attached;

$R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group, and a $C_1$-$C_3$-alkyl-O—C(=O)— group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a C(O)OR$^{21}$—($C_1$-$C_3$-alkylene)- group, a —C(O)OR$^{21}$ group, a —C(O)NR$^{20}R^{21}$ group, a ($C_1$-$C_3$-alkyl)-O—($C_1$-$C_3$-alkylene)-C(O)— group, a ($C_1$-$C_6$-alkyl)-C(O)-group, and a $C_3$-$C_6$-cycloalkyl-C(O)— group;

$R^{19}$ is selected from a $C_1$-$C_3$-alkyl group, a $C_3$-$C_6$-cycloalkyl group, and a NR$^{20}R^{21}$ group; and $R^{20}$ and $R^{21}$ are each independently selected from a hydrogen atom or a $C_1$-$C_6$-alkyl group;

or a tautomer, an N-oxide, or a salt thereof, or a salt of a tautomer, or a salt of an N-oxide, or a mixture of same.

16. A method of reducing proliferation of a cell, the method comprising contacting the cell with an effective amount of a compound of claim 1.

* * * * *